(12) United States Patent
Ashton et al.

(10) Patent No.: US 8,431,563 B2
(45) Date of Patent: Apr. 30, 2013

(54) COMPOUNDS THAT INTERACT WITH GLUCOKINASE REGULATORY PROTEIN FOR THE TREATMENT OF DIABETES

(75) Inventors: Kate Ashton, Westlake Village, CA (US); Michael David Bartberger, Sherman Oaks, CA (US); Yunxin Bo, Thousand Oaks, CA (US); Marian C. Bryan, West Hills, CA (US); Michael Croghan, Thousand Oaks, CA (US); Christopher Harold Fotsch, Thousand Oaks, CA (US); Clarence Henderson Hale, Camarillo, CA (US); Roxanne Kay Kunz, Santa Monica, CA (US); Longbin Liu, Thousand Oaks, CA (US); Nobuko Nishimura, West Hills, CA (US); Mark H. Norman, Thousand Oaks, CA (US); Lewis Dale Pennington, Ventura, CA (US); Steve Fong Poon, Woodland Hills, CA (US); Markian Myroslaw Stec, Thousand Oaks, CA (US); David Joseph St. Jean, Jr., Camarillo, CA (US); Nuria A. Tamayo, Newbury Park, CA (US); Christopher Michael Tegley, Thousand Oaks, CA (US); Kevin Chao Yang, San Gabriel, CA (US)

(73) Assignee: Amgen Inc., Thousand Oaks, CA (US)

( * ) Notice: Subject to any disclaimer, the term of this patent is extended or adjusted under 35 U.S.C. 154(b) by 21 days.

(21) Appl. No.: 13/215,914

(22) Filed: Aug. 23, 2011

(65) Prior Publication Data
US 2012/0225854 A1 Sep. 6, 2012

Related U.S. Application Data

(60) Provisional application No. 61/376,141, filed on Aug. 23, 2010, provisional application No. 61/492,634, filed on Jun. 2, 2011.

(51) Int. Cl.
| | | |
|---|---|---|
| A61K 31/497 | (2006.01) |
| A61K 31/4965 | (2006.01) |
| A61K 31/435 | (2006.01) |
| A61K 31/105 | (2006.01) |
| A61K 31/535 | (2006.01) |
| A61K 31/54 | (2006.01) |
| A61K 31/445 | (2006.01) |
| A61K 31/501 | (2006.01) |
| A61K 31/50 | (2006.01) |
| A61K 31/495 | (2006.01) |
| A61K 31/10 | (2006.01) |
| A01N 41/12 | (2006.01) |
| A01N 41/10 | (2006.01) |
| C07D 295/00 | (2006.01) |
| C07D 403/00 | (2006.01) |
| C07D 401/00 | (2006.01) |
| C07D 413/00 | (2006.01) |
| C07D 265/36 | (2006.01) |
| C07D 498/02 | (2006.01) |
| C07D 237/00 | (2006.01) |
| C07D 239/00 | (2006.01) |
| C07D 279/12 | (2006.01) |
| C07D 405/00 | (2006.01) |
| C07D 409/00 | (2006.01) |
| C07D 491/00 | (2006.01) |
| C07D 495/00 | (2006.01) |
| C07D 497/00 | (2006.01) |
| C07D 241/02 | (2006.01) |
| C07D 411/00 | (2006.01) |
| C07D 211/70 | (2006.01) |
| C07D 211/82 | (2006.01) |
| C07D 211/54 | (2006.01) |
| C07C 315/00 | (2006.01) |
| C07C 317/00 | (2006.01) |

(52) U.S. Cl.
USPC .............. 514/210.2; 514/252.13; 514/255.03; 514/254.05; 514/253.12; 514/252.14; 514/277; 514/709; 514/254.1; 514/254.02; 514/254.03; 514/235.8; 514/230.5; 514/254.01; 514/227.8; 514/254.08; 514/327; 514/252.02; 514/249; 514/252.11; 514/710; 514/253.04; 544/383; 544/371; 544/360; 544/295; 544/369; 544/121; 544/105; 544/372; 544/370; 544/230; 544/58.2; 544/238; 544/350; 544/357; 544/367; 544/362; 544/379; 546/344; 546/216; 568/32

(58) Field of Classification Search ........................ None
See application file for complete search history.

(56) References Cited

U.S. PATENT DOCUMENTS
2007/0185136 A1 8/2007 Courtemanche

FOREIGN PATENT DOCUMENTS
| WO | WO00/18770 A1 | 4/2000 |
| WO | WO2007/111921 A1 | 10/2007 |
| WO | WO2008/116107 A2 | 9/2008 |
| WO | WO2010/023317 A1 | 3/2010 |

OTHER PUBLICATIONS

International Search Report & Written Opinion, PCT/US2011/048596, Issued Nov. 14, 2011, pp. 1-9.

Primary Examiner — Jeffrey S. Lundgren
Assistant Examiner — William Lee
(74) Attorney, Agent, or Firm — Todd M. Crissey

(57) ABSTRACT

The present invention relates to compounds of Formula I, or pharmaceutically acceptable salts thereof,

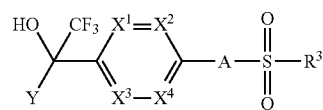

that interact with glucokinase regulatory protein. In addition, the present invention relates to methods of treating type 2 diabetes, and other diseases and/or conditions where glucokinase regulatory protein is involved using the compounds, or pharmaceutically acceptable salts thereof, and pharmaceutical compositions that contain the compounds, or pharmaceutically acceptable salts thereof.

34 Claims, No Drawings

COMPOUNDS THAT INTERACT WITH GLUCOKINASE REGULATORY PROTEIN FOR THE TREATMENT OF DIABETES

CROSS-REFERENCE TO RELATED APPLICATIONS

This application claims priority to U.S. provisional patent application No. 61/376,141, filed Aug. 23, 2010, and U.S. provisional patent application No. 61/492,634, filed Jun. 2, 2011.

FIELD OF THE INVENTION

The present invention relates to compounds of Formula I, or pharmaceutically acceptable salts thereof, as defined herein, that interact with glucokinase regulatory protein. In addition, the present invention relates to methods of treating type 2 diabetes, and other diseases and/or conditions where glucokinase regulatory protein is involved using the compounds, or the pharmaceutically acceptable salts thereof, and pharmaceutical compositions that contain the compounds, or pharmaceutically acceptable salts thereof.

BACKGROUND OF THE INVENTION

Glucokinase (GK) is a member of a family of four hexokinases that are critical in the cellular metabolism of glucose. Specifically GK, also known as hexokinase IV or hexokinase D, facilitates glucose induced insulin secretion from pancreatic β-cells as well as glucose conversion into glycogen in the liver. GK has a unique catalytic activity that enables the enzyme to be active within the physiological range of glucose (from 5 mM glucose to 10 mM glucose).

Genetically modified mouse models support the role of GK playing an important role in glucose homeostasis. Mice lacking both copies of the GK gene die soon after birth from severe hyperglycemia, whereas mice lacking only one copy of the GK gene present with only mild diabetes. Mice that are made to overexpress the GK gene in their livers are hypoglycemic.

Numerous human mutations in the GK gene have been identified, with the vast majority of them resulting in proteins with impaired or absent enzymatic activity. These loss-of-function mutations are thought to contribute to the hyperglycemia seen with maturity-onset diabetes of the young type II (MODY-2). A small fraction of these mutations result in a GK with increased catalytic function. These individuals present with moderate to severe hypoglycemia.

GK activity in the liver is transiently regulated by glucokinase regulatory protein (GKRP). GK catalytic activity is inhibited when GK is bound to GKRP. This interaction is antagonized by increasing concentrations of both glucose and fructose-1-phosphate (F1P). The complex of the two proteins is localized primarily to the nuclear compartment of a cell. Post prandially as both glucose and fructose levels rise, GK released from GKRP translocates to the cytoplasm. Cytoplasmic GK is now free of the inhibitory effects of GKRP and able to kinetically respond to glucose. Evidence from the Zucker diabetic fatty rat (ZDF) indicates that their glucose intolerance may be a result of this mechanism failing to function properly.

A compound that acts directly on GKRP to disrupt its interaction with GK and hence elevate levels of cytoplasmic GK is a viable approach to modulate GK activity. Such an approach would avoid the unwanted hypoglycemic effects of over stimulation of GK catalytic activity, which has been seen in the development of GK activators. A compound having such an effect would be useful in the treatment of diabetes and other diseases and/or conditions in which GKRP and/or GK plays a role. The present invention provides compounds that bind GKRP and disrupts its interaction with GK.

SUMMARY OF THE INVENTION

In embodiment 1, the present invention provides compounds of Formula I, or pharmaceutically acceptable salts thereof,

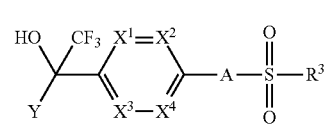

wherein:
Y is —$CF_3$, —$CHF_2$, —$CFH_2$, —$C_{1-6}$alkyl, —$OC_{1-6}$alkyl, —$(CR^cR^c)_nOR^c$, or $C_{3-6}$cycloalkyl;
A is

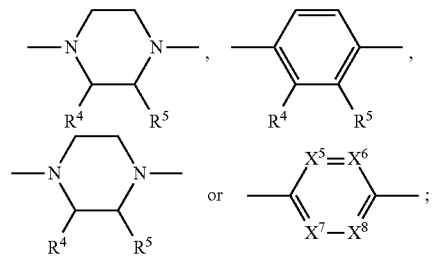

$R^3$ is a five or six membered aryl ring or five or six membered heteroaryl ring containing from 1 to 3 heteroatoms independently selected from N, O or S, which aryl or heteroaryl ring can be optionally substituted with from one to four is substituents independently selected from $C_{1-6}$alkyl, —$OC_{1-6}$alkyl, —$NR^cR^c$, —$CF_3$, —CN, —OH, —$NO_2$ or halo;
each $R^b$ is independently hydrogen, $C_{1-6}$alkyl,
—$S(=O)_2C_{1-6}$alkyl,
—$C(=O)C_{1-6}$alkyl,
—$CD_3$,
—$(CR^cR^c)_nCFH_2$,
—$(CR^cR^c)_nCF_2H$,
—$(CR^cR^c)_nCF_3$,
—$(CR^cR^c)_n$ 5 to 10 membered aryl,
—$(CR^cR^c)_n$ 5 to 10 membered substituted aryl,
—$(CR^cR^c)_n$ 5 to 10 membered heteroaryl containing from 1 to 3 heteroatoms independently selected from N, O or S,
—$(CR^cR^c)_n$ 5 to 10 membered substituted heteroaryl containing from 1 to 3 heteroatoms independently selected from N, O or S,
—$(CR^cR^c)_n$ 3 to 10 membered cycloalkyl,
—$(CR^cR^c)_n$ 3 to 10 membered substituted cycloalkyl,
—$(CR^cR^c)_n$ 3 to 10 membered heterocycloalkyl containing from 1 to 3 heteroatoms independently selected from N, O or S, or
—$(CR^cR^c)_n$ 3 to 10 membered substituted heterocycloalkyl containing from 1 to 3 heteroatoms independently selected from N, O or S, wherein substituted groups can have from one to four substitutents independently selected from —$C_{1-6}$alkyl, —$OC_{1-6}$alkyl, —$NR^cR^c$, —$CF_3$, —CN, —$(CR^cR^c)_nOR^c$, $C_{3-6}$cycloalkyl, halo, —$(CR^cR^c)_nNR^cS(=O)_2R^c$, —$(CR^cR^c)_nC(=O)OR^c$, —$(CR^cR^c)_nC(=O)NR^cR^c$, 5 to 10 membered aryl, or 5 to 10 membered aryl substituted with from one to four substitutents independently selected from —$C_{1-6}$alkyl, —$OC_{1-6}$alkyl, —$NR^cR^c$, —$CF_3$, —CN, —$(CR^cR^c)_nOR^c$, $C_{3-6}$cycloalkyl, halo, —$(CR^cR^c)_nNR^cS(=O)_2R^c$, —$(CR^cR^c)_nC(=O)OR^c$, —$(CR^cR^c)_nC(=O)NR^cR^c$;

each $R^c$ is independently hydrogen or $C_{1-6}$alkyl;

$X^1$, $X^2$, $X^3$ and $X^4$ are each independently selected from $CR^a$ or N;

$X^5$ and $X^6$ are independently selected from N or $CR^a$;

$X^7$ is N or $CR^4$;

$X^8$ is N or $CR^5$;

each $R^a$, $R^4$ and $R^5$ are independently selected from hydrogen,
$C_{1-6}$ alkyl,
halo,
—C≡$CCF_2CH_3$,
—C≡$CCF_2CF_3$,
—$OC_{1-6}$alkyl,
—$(CR^bR^b)_nNR^cR^c$,
—$(CR^bR^b)_nCF_3$,
—$(CR^bR^b)_nOR^c$,
—$(CR^bR^b)_nCN$,
—$(CR^bR^b)_nNR^b(CR^bR^b)_nOR^c$,
—$(CR^bR^b)_nNR^b(CR^bR^b)_n$ 5 to 10 membered aryl,
—$(CR^bR^b)_nNR^b(CR^bR^b)_n$ 5 to 10 membered substituted aryl,
—$(CR^bR^b)_nO(CR^bR^b)_n$ 5 to 10 membered aryl,
—$(CR^bR^b)_nO(CR^bR^b)_n$ 5 to 10 membered substituted aryl,
—$(CR^bR^b)_nO(CR^bR^b)_n$ 5 to 10 membered heteroaryl,
—$(CR^bR^b)_nO(CR^bR^b)_n$ 5 to 10 membered substituted heteroaryl,
—$(CR^bR^b)_nNR^b(CR^bR^b)_n$ 5 to 10 membered heteroaryl,
—$(CR^bR^b)_nNR^b(CR^bR^b)_n$ 5 to 10 membered substituted heteroaryl,
—$(CR^bR^b)_n$ 5 to 10 membered aryl,
—$(CR^bR^b)_n$ 5 to 10 membered substituted aryl,
—$(CR^bR^b)_n$ 5 to 10 membered heteroaryl,
—$(CR^bR^b)_n$ 5 to 10 membered substituted heteroaryl,
—$(CR^bR^b)_n$ 3 to 10 membered cycloalkyl,
—$(CR^bR^b)_n$ 3 to 10 membered substituted cycloalkyl,
—$(CR^bR^b)_n$ 5 to 10 membered heterocycloalkyl,
—$(CR^bR^b)_n$ 5 to 10 membered substituted heterocycloalkyl,
—C≡C—$R^b$,
—C≡C—$(CR^bR^b)_nOR^c$,
—C≡C—$(CR^bR^b)_n$ 3 to 10 membered heterocycloalkyl,
—C≡C—$(CR^bR^b)_n$ 3 to 10 membered substituted heterocycloalkyl,
—$(CR^bR^b)_n$ 3 to 10 membered heterocycloalkyl,
—$(CR^bR^b)_n$ 3 to 10 membered substituted heterocycloalkyl,
—$(CR^bR^b)_nO(CR^bR^b)_n$ 3 to 10 membered cycloalkyl,
—$(CR^bR^b)_nO(CR^bR^b)_n$ 3 to 10 membered substituted cycloalkyl,
—$(CR^bR^b)_nO(CR^bR^b)_n$ 3 to 10 membered heterocycloalkyl,
—$(CR^bR^b)_nO(CR^bR^b)_n$ 3 to 10 membered substituted heterocycloalkyl,
—$(CR^bR^b)_nNR^b(CR^bR^b)_n$ 3 to 10 membered heterocycloalkyl,
—$(CR^bR^b)_nNR^b(CR^bR^b)_n$ 3 to 10 membered substituted heterocycloalkyl,
—C≡C—$(CR^bR^b)_nNR^bC(=O)OR^b$,
—C≡C—$(CR^bR^b)_nNR^bR^b$,
—C≡C—$(CR^bR^b)_nNR^b$—$S(=O)_2R^b$,
—$(CR^bR^b)_nS(CR^bR^b)_n$ 5 to 10 membered aryl,
—$(CR^bR^b)_nS(CR^bR^b)_n$ 5 to 10 membered substituted aryl,
—$(CR^bR^b)_nS(CR^bR^b)_n$ 5 to 10 membered heteroaryl,
—$(CR^bR^b)_nS(CR^bR^b)_n$ 5 to 10 membered substituted heteroaryl,
—$(CR^bR^b)_nS(=O)_2(CR^bR^b)_n$ 5 to 10 membered aryl,
—$(CR^bR^b)_nS(=O)_2(CR^bR^b)_n$ 5 to 10 membered substituted aryl,
—$(CR^bR^b)_nS(=O)_2(CR^bR^b)_n$ 5 to 10 membered heteroaryl,
—$(CR^bR^b)_nS(=O)_2(CR^bR^b)_n$ 5 to 10 membered substituted heteroaryl,
—$(CR^bR^b)_nS(=O)_2(CR^bR^b)_n$ 5 to 10 membered aryl,
—$(CR^bR^b)_nS(=O)_2(CR^bR^b)_n$ 5 to 10 membered substituted aryl,
—$(CR^bR^b)_nNR^bS(=O)_2(CR^bR^b)_n$ 5 to 10 membered aryl,
—$(CR^bR^b)_nNR^bS(=O)_2(CR^bR^b)_n$ 5 to 10 membered substituted aryl,
—$(CR^bR^b)_nNR^bS(=O)_2(CR^bR^b)_n$ 5 to 10 membered heteroaryl,
—$(CR^bR^b)_nNR^bS(=O)_2(CR^bR^b)_n$ 5 to 10 membered substituted heteroaryl,
—$(CR^bR^b)_nNR^b$—$S(=O)_2R^b$,
—$(CR^bR^b)_nNR^b$—$C(=O)R^b$, or
—$(CR^bR^b)_nNR^b$—$S(=O)_2NR^bR^b$, wherein the heteroaryl or heterocycloalkyl groups can have from 1 to 3 heteroatoms independently selected from O, N or S, and wherein substituted groups can have from one to four substitutents independently selected from —$C_{1-6}$alkyl, —$OC_{1-6}$alkyl, —$NR^cR^c$, —$CF_3$, —CN, —$(CR^cR^c)_nOR^c$, $C_{3-6}$cycloalkyl, halo, —$(CR^cR^c)_nNR^cS(=O)_2R^c$, —$(CR^cR^c)_nC(=O)OR^c$, —$(CR^cR^c)_nC(=O)NR^cR^c$, 5 to 10 membered aryl, or 5 to 10 membered aryl substituted with from one to four substitutents independently selected from —$C_{1-6}$alkyl, —$OC_{1-6}$alkyl, —$NR^cR^c$, —$CF_3$, —CN, —$(CR^cR^c)_nOR^c$, $C_{3-6}$cycloalkyl, halo, —$(CR^cR^c)_nNR^cS(=O)_2R^c$, —$(CR^cR^c)_nC(=O)OR^c$, —$(CR^cR^c)_nC(=O)NR^cR^c$, or one or more carbon atoms in any ring group may be replaced with —C(=O)— or —S(=O)_2—; and each n is independently 0, 1 or 2, provided that the compound is not 1,1,1,3,3,3-hexafluoro-2-(4-(4-(2-thiophenylsulfonyl)-1-piperazinyl)phenyl)-2-propanol; 1,1,1,3,3,3-hexafluoro-2-(4-(4-(phenylsulfonyl)-1-piperazinyl)phenyl)-2-propanol; 1,1,1,3,3,3-hexafluoro-2-(4-(4-((2-fluorophenyl)sulfonyl)-1-piperazinyl)phenyl)-2-propanol; 2-(4-(4-(3-chlorophenylsulfonyl)piperazin-1-yl)phenyl)-1,1,1,3,3,3-hexafluoro-2-propanol; or 2-(4-(4-((2-chlorophenyl)sulfonyl)-1-piperazinyl)phenyl)-1,1,1,3,3,3-hexafluoro-2-propanol.

In embodiment 2, the present invention provides compounds of Formula I, or pharmaceutically acceptable salts thereof,

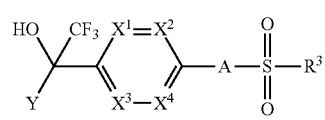

wherein:

Y is —$CF_3$, —$CHF_2$, —$C_{1-6}$alkyl, —$OC_{1-6}$alkyl, —$CH_2OH$, or $C_{3-6}$cycloalkyl;

A is

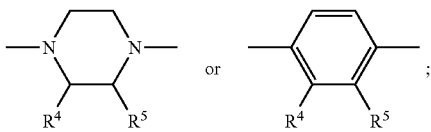

R³ is a five or six membered aryl ring or five or six membered heteroaryl ring containing from 1 to 3 heteroatoms independently selected from N, O or S, which aryl or heteroaryl ring can be optionally substituted with from one to four substituents independently selected from $C_{1-6}$alkyl, —$OC_{1-6}$alkyl, —$NR^bR^b$, —$CF_3$, —CN or halo;

each $R^b$ is independently hydrogen or $C_{1-6}$alkyl;

$X^1$, $X^2$, $X^3$ and $X^4$ are each independently selected from $CR^a$ or N;

each $R^a$, $R^4$ and $R^5$ are independently selected from hydrogen, $C_{1-6}$ alkyl, —$OC_{1-6}$alkyl, —$NR^bR^b$, —$CF_3$, halo, —$(CR^bR^b)_n$OH, —$(CR^bR^b)_n$CN, —$(CR^bR^b)_n$NR^b$(CR^bR^b)_n$OH, —$(CR^bR^b)_n$NR^b$(CR^bR^b)_n$ 5 to 6 membered aryl, —$(CR^bR^b)_n$NR^b$(CR^bR^b)_n$ 5 to 6 membered substituted aryl, —$(CR^bR^b)_n$O$(CR^bR^b)_n$ 5 to 6 membered aryl, —$(CR^bR^b)_n$O$(CR^bR^b)_n$ 5 to 6 membered substituted aryl, —$(CR^bR^b)_n$O$(CR^bR^b)_n$ 5 to 6 membered heteroaryl, —$(CR^bR^b)_n$O$(CR^bR^b)_n$ 5 to 6 membered substituted heteroaryl, —$(CR^bR^b)_n$NR^b$(CR^bR^b)_n$ 5 to 6 membered heteroaryl, —$(CR^bR^b)_n$NR^b$(CR^bR^b)_n$ 5 to 6 membered substituted heteroaryl, —$(CR^bR^b)_n$ 5 to 6 membered aryl, —$(CR^bR^b)_n$ 5 to 6 membered substituted aryl, —$(CR^bR^b)_n$ 5 to 6 membered heteroaryl, —$(CR^bR^b)_n$ 5 to 6 membered substituted heteroaryl, —$(CR^bR^b)_n C_{3-6}$cycloalkyl, —$(CR^bR^b)_n$ substituted $C_{3-6}$cycloalkyl;

—C≡C—$CR^bR^b$OH, —C≡C— 3 to 8 membered heterocycloalkyl,

—C≡C— 3 to 8 membered substituted heterocycloalkyl,

—$(CR^bR^b)_n$ 3 to 8 membered heterocycloalkyl,

—$(CR^bR^b)_n$ 3 to 8 membered substituted heterocycloalkyl, wherein the heteroaryl or heterocycloalkyl groups can have from 1 to 3 heteroatoms independently selected from O, N or S, and wherein substituted groups can have from one to four substitutents independently selected from —$C_{1-6}$ alkyl, —$OC_{1-6}$alkyl, —$NR^bR^b$, —$CF_3$, —CN, —OH or halo; and is each n is independently 0, 1 or 2, provided that the compound is not 1,1,1,3,3,3-hexafluoro-2-(4-(4-(2-thiophenylsulfonyl)-1-piperazinyl)phenyl)-2-propanol; 1,1,1,3,3,3-hexafluoro-2-(4-(4-(phenylsulfonyl)-1-piperazinyl)phenyl)-2-propanol; 1,1,1,3,3,3-hexafluoro-2-(4-(4-((2-fluorophenyl)sulfonyl)-1-piperazinyl)phenyl)-2-propanol; 2-(4-(4-(3-chlorophenylsulfonyl)piperazin-1-yl)phenyl)-1,1,1,3,3,3-hexafluoro-2-propanol; or 2-(4-(4-((2-chlorophenyl)sulfonyl)-1-piperazinyl)phenyl)-1,1,1,3,3,3-hexafluoro-2-propanol.

In embodiment 3, the present invention provides compounds of Formula I, or pharmaceutically acceptable salts thereof,

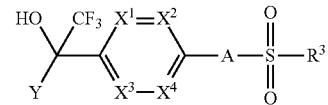

wherein:

Y is —$CF_3$, —$CHF_2$, —$C_{1-6}$alkyl, —$OC_{1-6}$alkyl, —$CH_2$OH, or $C_{3-6}$cycloalkyl;

A is

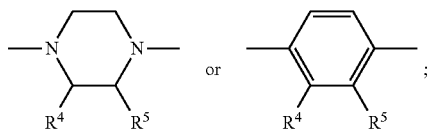

R³ is a five or six membered aryl ring or five or six membered heteroaryl ring containing from 1 to 3 heteroatoms independently selected from N, O or S, which aryl or heteroaryl ring can be optionally substituted with from one to four substituents independently selected from $C_{1-6}$alkyl, —$OC_{1-6}$alkyl, —$NR^bR^b$, —$CF_3$, —CN, —OH, —$NO_2$ or halo;

is each $R^b$ is independently hydrogen, $C_{1-6}$alkyl,

—$(CR^cR^c)_n CF_3$,

—$(CR^cR^c)_n$ 5 to 10 membered aryl,

—$(CR^cR^c)_n$ 5 to 10 membered substituted aryl,

—$(CR^cR^c)_n$ 5 to 10 membered heteroaryl containing from 1 to 3 heteroatoms independently selected from N, O or S, —$(CR^cR^c)_n$ 5 to 10 membered substituted heteroaryl containing from 1 to 3 heteroatoms independently selected from N, O or S, —$(CR^cR^c)_n$ 3 to 10 membered cycloalkyl, —$(CR^cR^c)_n$ 3 to 10 membered substituted cycloalkyl, —$(CR^cR^c)_n$ 3 to 10 membered heterocycloalkyl containing from 1 to 3 heteroatoms independently selected from N, O or S, or —$(CR^cR^c)_n$ 3 to 10 membered substituted heterocycloalkyl containing from 1 to 3 heteroatoms independently selected from N, O or S, wherein substituted groups can have from one to four substitutents independently selected from —$C_{1-6}$alkyl, —$OC_{1-6}$alkyl, —$NR^bR^b$, —$CF_3$, —CN, —$(CR^bR^b)_n$OH, $C_{3-6}$cycloalkyl, halo, —$(CR^bR^b)_n NR^b S(=O)_2 R^b$, —$(CR^bR^b)_n C(=O)OR^b$, —$(CR^bR^b)_n C(=O)NR^bR^b$, 5 to 10 membered aryl, or 5 to 10 membered substituted aryl;

each $R^c$ is independently hydrogen or $C_{1-6}$alkyl;

$X^1$, $X^2$, $X^3$ and $X^4$ are each independently selected from $CR^a$ or N;

each $R^a$, $R^4$ and $R^5$ are independently selected from hydrogen, $C_{1-6}$alkyl, halo, is —$OC_{1-6}$alkyl, —$(CR^bR^b)_n NR^bR^b$, —$(CR^bR^b)_n CF_3$, —$(CR^bR^b)_n$OH, —$(CR^bR^b)_n$CN, —$(CR^bR^b)_n NR^b(CR^bR^b)_n$OH, —$(CR^bR^b)_n NR^b(CR^bR^b)_n$ 5 to 10 membered aryl, —$(CR^bR^b)_n NR^b(CR^bR^b)_n$ 5 to 10 membered substituted aryl, —$(CR^bR^b)_n O(CR^bR^b)_n$ 5 to 10 membered aryl, —(CR$^b$R$^b$)$_n$O(CR$^b$R$^b$)$_n$ 5 to 10 membered substituted aryl,
—(CR$^b$R$^b$)$_n$O(CR$^b$R$^b$)$_n$ 5 to 10 membered heteroaryl,
—(CR$^b$R$^b$)$_n$O(CR$^b$R$^b$)$_n$ 5 to 10 membered substituted heteroaryl,
—(CR$^b$R$^b$)$_n$NR$^b$(CR$^b$R$^b$)$_n$ 5 to 10 membered heteroaryl,
—(CR$^b$R$^b$)$_n$NR$^b$(CR$^b$R$^b$)$_n$ 5 to 10 membered substituted heteroaryl,
—(CR$^b$R$^b$)$_n$ 5 to 10 membered aryl,
—(CR$^b$R$^b$)$_n$ 5 to 10 membered substituted aryl,
—(CR$^b$R$^b$)$_n$ 5 to 10 membered heteroaryl,
—(CR$^b$R$^b$)$_n$ 5 to 10 membered substituted heteroaryl,
—(CR$^b$R$^b$)$_n$ 3 to 10 membered cycloalkyl,
—(CR$^b$R$^b$)$_n$ 3 to 10 membered substituted cycloalkyl,
—C≡C—R$^b$,
—C≡C—(CR$^b$R$^b$)$_n$OR$^b$,
—C≡C— 3 to 10 membered heterocycloalkyl,
—C≡C— 3 to 10 membered substituted heterocycloalkyl,
—(CR$^b$R$^b$)$_n$ 3 to 10 membered heterocycloalkyl,
—(CR$^b$R$^b$)$_n$ 3 to 10 membered substituted heterocycloalkyl,
—(CR$^b$R$^b$)$_n$O(CR$^b$R$^b$)$_n$ 3 to 10 membered cycloalkyl,
—(CR$^b$R$^b$)$_n$O(CR$^b$R$^b$)$_n$ 3 to 10 membered substituted cycloalkyl,
—(CR$^b$R$^b$)$_n$O(CR$^b$R$^b$)$_n$ 3 to 10 membered heterocycloalkyl,
—(CR$^b$R$^b$)$_n$O(CR$^b$R$^b$)$_n$ 3 to 10 membered substituted heterocycloalkyl,
—(CR$^b$R$^b$)$_n$NR$^b$(CR$^b$R$^b$)$_n$ 3 to 10 membered heterocycloalkyl,
—(CR$^b$R$^b$)$_n$NR$^b$(CR$^b$R$^b$)$_n$ 3 to 10 membered substituted heterocycloalkyl,
—C≡C—(CR$^b$R$^b$)$_n$NR$^b$C(=O)OR$^b$,
—C≡C—(CR$^b$R$^b$)$_n$NR$^b$R$^b$,
—C≡C—(CR$^b$R$^b$)$_n$NR$^b$—S(=O)$_2$R$^b$,
—(CR$^b$R$^b$)$_n$S(CR$^b$R$^b$)$_n$ 5 to 10 membered aryl,
—(CR$^b$R$^b$)$_n$S(CR$^b$R$^b$)$_n$ 5 to 10 membered substituted aryl,
—(CR$^b$R$^b$)$_n$S(CR$^b$R$^b$)$_n$ 5 to 10 membered heteroaryl,
—(CR$^b$R$^b$)$_n$S(CR$^b$R$^b$)$_n$ 5 to 10 membered substituted heteroaryl,
—(CR$^b$R$^b$)$_n$S(=O)$_2$(CR$^b$R$^b$)$_n$ 5 to 10 membered aryl,
—(CR$^b$R$^b$)$_n$S(=O)$_2$(CR$^b$R$^b$)$_n$ 5 to 10 membered substituted aryl,
—(CR$^b$R$^b$)$_n$S(=O)$_2$(CR$^b$R$^b$)$_n$ 5 to 10 membered heteroaryl,
—(CR$^b$R$^b$)$_n$S(=O)$_2$(CR$^b$R$^b$)$_n$ 5 to 10 membered substituted heteroaryl,
—(CR$^b$R$^b$)$_n$S(=O)(CR$^b$R$^b$)$_n$ 5 to 10 membered aryl,
—(CR$^b$R$^b$)$_n$S(=O)(CR$^b$R$^b$)$_n$ 5 to 10 membered substituted aryl,
—(CR$^b$R$^b$)$_n$NR$^b$S(=O)$_2$(CR$^b$R$^b$)$_n$ 5 to 10 membered aryl,
—(CR$^b$R$^b$)$_n$NR$^b$S(=O)$_2$(CR$^b$R$^b$)$_n$ 5 to 10 membered substituted aryl,
—(CR$^b$R$^b$)$_n$NR$^b$S(=O)$_2$(CR$^b$R$^b$)$_n$ 5 to 10 membered heteroaryl,
—(CR$^b$R$^b$)$_n$NR$^b$S(=O)$_2$(CR$^b$R$^b$)$_n$ 5 to 10 membered substituted heteroaryl,
—(CR$^b$R$^b$)$_n$NR$^b$—S(=O)$_2$R$^b$,
—(CR$^b$R$^b$)$_n$NR$^b$—C(=O)R$^b$, or
—(CR$^b$R$^b$)$_n$NR$^b$—S(=O)$_2$NR$^b$R$^b$,
wherein the heteroaryl or heterocycloalkyl groups can have from 1 to 3 heteroatoms independently selected from O, N or S, and wherein substituted groups can have from one to four substitutents independently selected from —C$_{1-6}$alkyl, —OC$_{1-6}$alkyl, —NR$^b$R$^b$, —CF$_3$, —CN, —(CR$^b$R$^b$)$_n$OH, C$_{3-6}$cycloalkyl, halo,
—(CR$^b$R$^b$)$_n$NR$^b$S(=O)$_2$R$^b$, —(CR$^b$R$^b$)$_n$C(=O)NR$^b$R$^b$, 5 to 10 membered aryl, or 5 to 10 membered substituted aryl, or a carbon atom in any ring group may be replaced with —C(=O)— or —S(=O)$_2$—; and
each n is independently 0, 1 or 2, provided that the compound is not 1,1,1,3,3,3-hexafluoro-2-(4-(4-(2-thiophenylsulfonyl)-1-piperazinyl)phenyl)-2-propanol; 1,1,1,3,3,3-hexafluoro-2-(4-(4-(phenylsulfonyl)-1-piperazinyl)phenyl)-2-propanol; 1,1,1,3,3,3-hexafluoro-2-(4-(4-((2-fluorophenyl)sulfonyl)-1-piperazinyl)phenyl)-2-propanol; 2-(4-(4-(3-chlorophenylsulfonyl)piperazin-1-yl)phenyl)-1,1,1,3,3,3-hexafluoro-2-propanol; or 2-(4-(4-((2-chlorophenyl)sulfonyl)-1-piperazinyl)phenyl)-1,1,1,3,3,3-hexafluoro-2-propanol.

In embodiment 4, the present invention provides compounds in accordance with any one of embodiments 1 to 3, or pharmaceutically acceptable salts thereof, wherein R$^3$ is thienyl.

In embodiment 5, the present invention provides compounds in accordance with any one of embodiments 1 to 4, or pharmaceutically acceptable salts thereof, wherein A is

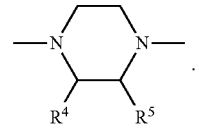

In embodiment 6, the present invention provides compounds in accordance with any one of embodiments 1 to 5, or pharmaceutically acceptable salts thereof, wherein A is

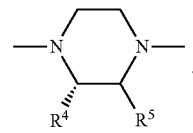

In embodiment 7, the present invention provides compounds in accordance with any one of embodiments 1 to 4, or pharmaceutically acceptable salts thereof, wherein A is

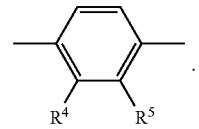

In embodiment 8, the present invention provides compounds in accordance with any one of embodiments 1 to 3, or pharmaceutically acceptable salts thereof, wherein R$^3$ is thienyl, phenyl, pyridyl, pyrazolyl, imidazolyl, furyl, thiazolyl or thiadiazolyl, which can be optionally substituted with from one to four substituents independently selected from C$_{1-6}$alkyl, —OC$_{1-6}$alkyl, —NR$^c$R$^c$, —CF$_3$, —CN or halo.

In embodiment 9, the present invention provides compounds in accordance with any one of embodiments 1 to 8, or pharmaceutically acceptable salts thereof, wherein —CH$_2$OH, —CF$_3$, —CH$_3$ or cyclopropyl.

In embodiment 10, the present invention provides compounds in accordance with any one of embodiments 1 to 8, or pharmaceutically acceptable salts thereof, wherein Y is —CF$_3$.

In embodiment 11, the present invention provides compounds in accordance with any one of embodiments 1 to 8, or pharmaceutically acceptable salts thereof, wherein Y is —CH$_3$.

In embodiment 12, the present invention provides compounds in accordance with any one of embodiments 1 to 3, 4 or 8, or pharmaceutically acceptable salts thereof, wherein A is

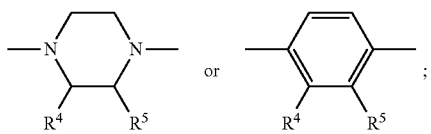

and $R^4$ and $R^5$ are hydrogen.

In embodiment 13, the present invention provides compounds in accordance with any one of embodiments 1 to 12, or pharmaceutically acceptable salts thereof, wherein $X^1$, $X^2$, $X^3$ and $X^4$ are $CR^a$.

In embodiment 14, the present invention provides compounds in accordance with any one of embodiments 1 to 12, or pharmaceutically acceptable salts thereof, wherein $X^1$, $X^2$, $X^3$ and $X^4$ are CH.

In embodiment 15, the present invention provides compounds in accordance with any one of embodiments 1 to 12, or pharmaceutically acceptable salts thereof, wherein $X^1$ and $X^3$ are $CR^a$ and $X^2$ and $X^4$ are N.

In embodiment 16, the present invention provides compounds in accordance with any one of embodiments 1 to 12, or pharmaceutically acceptable salts thereof, wherein at least one of $X^1$, $X^2$, $X^3$ or $X^4$ is N.

In embodiment 17, the present invention provides compounds in accordance with any one of embodiments 1 to 4, or pharmaceutically acceptable salts thereof, wherein A is

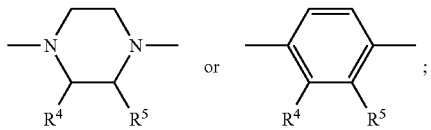

and $R^4$ and $R^5$ are independently hydrogen, halo or —$CH_3$.

In embodiment 18, the present invention provides compounds in accordance with any one of embodiments 1 to 4, or pharmaceutically acceptable salts thereof, wherein A is

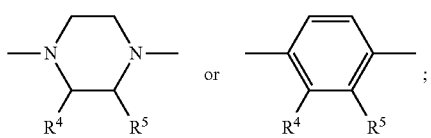

and $R^4$ is hydrogen and $R^5$ is —$CH_3$.

In embodiment 19, the present invention provides compounds in accordance with any one of embodiments 1 to 4, or pharmaceutically acceptable salts thereof, wherein A is

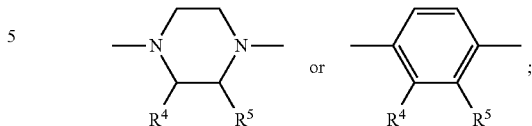

and $R^4$ is hydrogen and $R^5$ is —$CH_2$-morpholino.

In embodiment 20, the present invention provides compounds in accordance with any one of embodiments 1 to 3, or pharmaceutically acceptable salts thereof, wherein
$R^3$ is thienyl, phenyl, pyridyl, pyrazolyl, imidazolyl, furyl, thiazolyl or thiadiazolyl, which can be optionally substituted with from one to four substituents independently selected from $C_{1-6}$alkyl, —$OC_{1-6}$alkyl, —$NR^cR^c$, —$CF_3$, —CN or halo;
A is

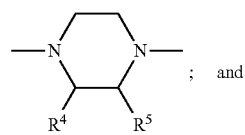
; and

Y is —$CH_2OH$, —$CF_3$, —$CH_3$ or cyclopropyl.

In embodiment 21, the present invention provides compounds in accordance with any one of embodiments 1 to 3, or pharmaceutically acceptable salts thereof, wherein
$R^3$ is thienyl, phenyl, pyridyl, pyrazolyl, imidazolyl, furyl, thiazolyl or thiadiazolyl, which can be optionally substituted with from one to four substituents independently selected from $C_{1-6}$alkyl, —$OC_{1-6}$alkyl, —$NR^cR^c$, —$CF_3$, —CN or halo;
A is

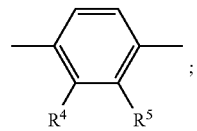

$X^2$ and $X^4$ are N; and

Y is —$CF_3$, —$CH_3$ or cyclopropyl.

In embodiment 22, the present invention provides compounds in accordance with any one of embodiments 20 to 21, or pharmaceutically acceptable salts thereof, wherein Y is —$CF_3$ or —$CH_3$.

In embodiment 23, the present invention provides compounds in accordance with any one of embodiments 1 to 3, or pharmaceutically acceptable salts thereof, wherein
$R^3$ is thienyl, phenyl, pyridyl, pyrazolyl, imidazolyl, furyl, thiazolyl or thiadiazolyl, which can be optionally substituted with from one to four substituents independently selected from $C_{1-6}$alkyl, —$OC_{1-6}$alkyl, —$NR^cR^c$, —$CF_3$, —CN or halo;

A is

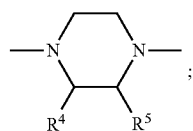

Y is —CF$_3$ or —CH$_3$; and
X$^1$, X$^2$, X$^3$ and X$^4$ are CH or X$^1$ and X$^2$ are CH, and X$^3$ and X$^4$ are N.

In embodiment 24, the present invention provides compounds in accordance with any one of embodiments 1 to 3, or pharmaceutically acceptable salts thereof, wherein R$^3$ is

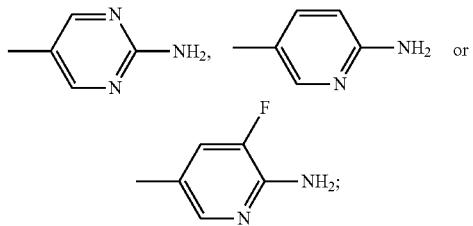

A is

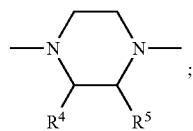

Y is —CF$_3$ or —CH$_3$; and
X$^1$, X$^2$, X$^3$ and X$^4$ are CH or X$^1$ and X$^2$ are CH, and X$^3$ and X$^4$ are N.

In embodiment 25, the present invention provides compounds in accordance with any one of embodiments 1 to 3, or pharmaceutically acceptable salts thereof, wherein R$^3$ is

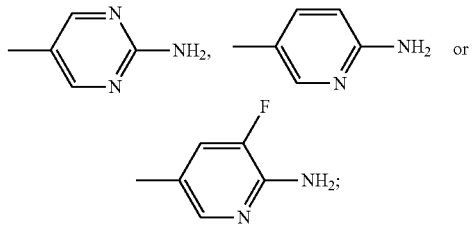

A is

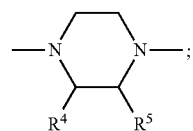

R$^4$ —C≡C—H or —C≡C—C$_{1-6}$alkyl;
R$^5$ is hydrogen;
Y is —CF$_3$ or —CH$_3$; and
X$^1$, X$^2$, X$^3$ and X$^4$ are CH or X$^1$ and X$^2$ are CH, and X$^3$ and X$^4$ are N.

In embodiment 26, the present invention provides compounds in accordance with any one of embodiments 1 to 3, or pharmaceutically acceptable salts thereof, wherein R$^3$ is thienyl, or phenyl, pyridyl, pyrazolyl, imidazolyl, furyl, thiazolyl or thiadiazolyl, which can be optionally substituted with from one to four substituents independently selected from C$_{1-6}$alkyl, —OC$_{1-6}$alkyl, —NR$^c$R$^c$, —CF$_3$, —CN or halo;

A is

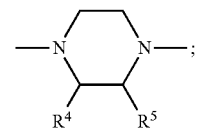

Y is —CF$_3$ or —CH$_3$; and
X$^1$, X$^2$, X$^3$ and X$^4$ are CH or —C—CH$_3$.

In embodiment 27, the present invention provides compounds in accordance with any one of embodiments 1 to 3, or pharmaceutically acceptable salts thereof, wherein R$^3$ is

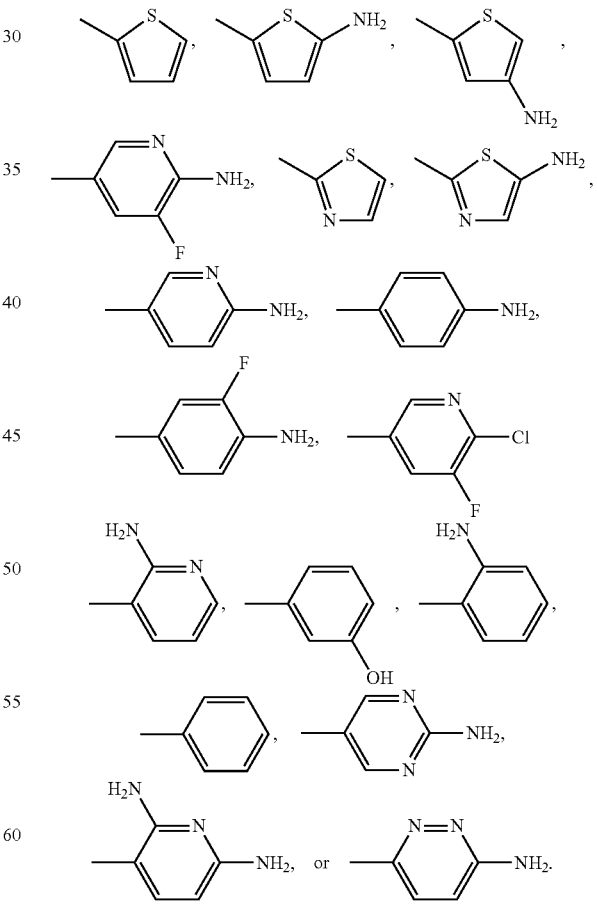

In embodiment 28, the present invention provides compounds in accordance with any one of embodiments 1 to 3, or pharmaceutically acceptable salts thereof, wherein R$^3$ is

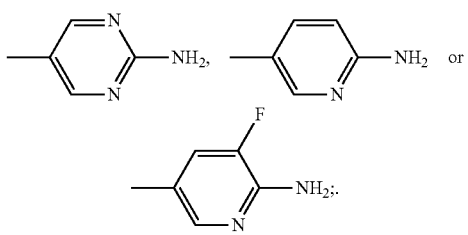

In embodiment 29, the present invention provides the compounds, or pharmaceutically acceptable salts thereof, selected from:
1,1,1,3,3,3-hexafluoro-2-(4-(4-(3-thiophenylsulfonyl)-1-piperazinyl)phenyl)-2-propanol;
1,1,1,3,3,3-hexafluoro-2-(4-(4-((2-methylphenyl)sulfonyl)-1-piperazinyl)phenyl)-2-propanol;
1,1,1,3,3,3-hexafluoro-2-(4-(4-((1-methyl-1h-pyrazol-3-yl)sulfonyl)-1-piperazinyl)phenyl)-2-propanol;
1,1,1,3,3,3-hexafluoro-2-(4-(4-(2-pyridinylsulfonyl)-1-piperazinyl)phenyl)-2-propanol;
1,1,1,3,3,3-hexafluoro-2-(4-(4-((5-methyl-2-thiophenyl)sulfonyl)-1-piperazinyl)phenyl)-2-propanol;
1,1,1,3,3,3-hexafluoro-2-(4-((2S)-2-methyl-4-(2-thiophenylsulfonyl)-1-piperazinyl)phenyl)-2-propanol;
1,1,1,3,3,3-hexafluoro-2-(4-((2S)-2-methyl-4-(phenylsulfonyl)-1-piperazinyl)phenyl)-2-propanol;
2-(4-(2-(2,5-dichlorophenyl)-4-(2-thiophenylsulfonyl)-1-piperazinyl)phenyl)-1,1,1-trifluoro-2-propanol;
2-(4-((3R)-3-cyclopropyl-4-(2-thiophenylsulfonyl)-1-piperazinyl)phenyl)-1,1,1,3,3,3-hexafluoro-2-propanol;
1-cyclopropyl-2,2,2-trifluoro-1-(4-(4-(phenylsulfonyl)-1-piperazinyl)phenyl)ethanol;
1,1,1-trifluoro-2-(2-((2S)-2-methyl-4-(2-thiophenylsulfonyl)-1-piperazinyl)-5-pyrimidinyl)-2-propanol;
(2S)-1,1,1-trifluoro-2-(2-((2S)-2-methyl-4-(2-thiophenylsulfonyl)-1-piperazinyl)-5-pyrimidinyl)-2-propanol;
(2R)-1,1,1-trifluoro-2-(2-((2S)-2-methyl-4-(2-thiophenylsulfonyl)-1-piperazinyl)-5-pyrimidinyl)-2-propanol;
1,1,1,3,3,3-hexafluoro-2-(6-(4-(phenylsulfonyl)phenyl)-3-pyridinyl)-2-propanol;
2-(6-(3-chloro-4-(phenylsulfonyl)phenyl)-3-pyridinyl)-1,1,1-trifluoro-2-propanol;
2-(3'-chloro-4'-(phenylsulfonyl)-4-biphenylyl)-1,1,1-trifluoro-2-propanol;
2-methyl-4-(4-(phenylsulfonyl)-4'-(2,2,2-trifluoro-1-hydroxy-1-methylethyl)-3-biphenylyl)-3-butyn-2-ol;
1,1,1,3,3,3-hexafluoro-2-(4'-(phenylsulfonyl)-4-biphenylyl)-2-propanol;
1,1,1,3,3,3-hexafluoro-2-(6-(4-(phenylsulfonyl)-1-piperazinyl)-3-pyridinyl)-2-propanol;
1,1,1,3,3,3-hexafluoro-2-(2-(4-(phenylsulfonyl)-1-piperazinyl)-5-pyrimidinyl)-2-propanol;
1,1,1-trifluoro-2-(4-(4-(phenylsulfonyl)-1-piperazinyl)phenyl)-2-propanol;
(2R)-1,1,1-trifluoro-2-(4-(4-(phenylsulfonyl)-1-piperazinyl)phenyl)-2-propanol;
(2S)-1,1,1-trifluoro-2-(4-(4-(phenylsulfonyl)-1-piperazinyl)phenyl)-2-propanol;
1,1,1,3,3,3-hexafluoro-2-(4-((3R)-3-methyl-4-(2-thiophenylsulfonyl)-1-piperazinyl)phenyl)-2-propanol;
1,1,1,3,3,3-hexafluoro-2-(4-((3S)-3-methyl-4-(2-thiophenylsulfonyl)-1-piperazinyl)phenyl)-2-propanol;
1,1,1-trifluoro-2-(4-((2S)-2-methyl-4-(2-thiophenylsulfonyl)-1-piperazinyl)phenyl)-2-propanol;
(2R)-1,1,1-trifluoro-2-(4-((2S)-2-methyl-4-(2-thiophenylsulfonyl)-1-piperazinyl)phenyl)-2-propanol;
(2S)-1,1,1-trifluoro-2-(4-((2S)-2-methyl-4-(2-thiophenylsulfonyl)-1-piperazinyl)phenyl)-2-propanol;
1,1,1-trifluoro-2-(4-((2S)-2-methyl-4-(phenylsulfonyl)-1-piperazinyl)phenyl)-2-propanol;
1,1,1-trifluoro-2-(4-(4-(2-thiophenylsulfonyl)-1-piperazinyl)phenyl)-2-propanol;
(2S)-1,1,1-trifluoro-2-(4-(4-(2-thiophenylsulfonyl)-1-piperazinyl)phenyl)-2-propanol;
(2R)-1,1,1-trifluoro-2-(4-(4-(2-thiophenylsulfonyl)-1-piperazinyl)phenyl)-2-propanol;
1,1,1-trifluoro-2-(4-((2S)-4-(3-furanylsulfonyl)-2-methyl-1-piperazinyl)phenyl)-2-propanol;
1,1,1,3,3,3-hexafluoro-2-(4-((2S)-2-methyl-4-(1,3-thiazol-2-ylsulfonyl)-1-piperazinyl)phenyl)-2-propanol;
1,1,1-trifluoro-2-(4-(4-(1,3-thiazol-2-ylsulfonyl)-1-piperazinyl)phenyl)-2-propanol;
1,1,1,3,3,3-hexafluoro-2-(4-(4-(1,3-thiazol-2-ylsulfonyl)-1-piperazinyl)phenyl)-2-propanol;
1,1,1-trifluoro-2-(4-((2S)-2-methyl-4-(1,3-thiazol-2-ylsulfonyl)-1-piperazinyl)phenyl)-2-propanol;
(2S)-1,1,1-trifluoro-2-(4-((2S)-2-methyl-4-(1,3-thiazol-2-ylsulfonyl)-1-piperazinyl)phenyl)-2-propanol;
(2R)-1,1,1-trifluoro-2-(4-((2S)-2-methyl-4-(1,3-thiazol-2-ylsulfonyl)-1-piperazinyl)phenyl)-2-propanol;
2-(4-((2S)-4-((5-amino-1,3,4-thiadiazol-2-yl)sulfonyl)-2-methyl-1-piperazinyl)phenyl)-1,1,1-trifluoro-2-propanol;
1,1,1,3,3,3-hexafluoro-2-(4-(2-(tetrahydro-2H-pyran-4-ylmethyl)-4-(2-thiophenylsulfonyl)-1-piperazinyl)phenyl)-2-propanol;
1,1,1-trifluoro-2-(4-(2-(tetrahydro-2H-pyran-4-ylmethyl)-4-(2-thiophenylsulfonyl)-1-piperazinyl)phenyl)-2-propanol;
(2R)-1,1,1-trifluoro-2-(4-((2R)-2-(tetrahydro-2H-pyran-4-ylmethyl)-4-(2-thiophenylsulfonyl)-1-piperazinyl)phenyl)-2-propanol;
(2R)-1,1,1-trifluoro-2-(4-((2S)-2-(tetrahydro-2H-pyran-4-ylmethyl)-4-(2-thiophenylsulfonyl)-1-piperazinyl)phenyl)-2-propanol;
(2S)-1,1,1-trifluoro-2-(4-((2S)-2-(tetrahydro-2H-pyran-4-ylmethyl)-4-(2-thiophenylsulfonyl)-1-piperazinyl)phenyl)-2-propanol;
(2S)-1,1,1-trifluoro-2-(4-((2R)-2-(tetrahydro-2H-pyran-4-ylmethyl)-4-(2-thiophenylsulfonyl)-1-piperazinyl)phenyl)-2-propanol;
1,1,1-trifluoro-2-(4-(2-(2-fluorobenzyl)-4-(2-thiophenylsulfonyl)-1-piperazinyl)phenyl)-2-propanol;
1,1,1-trifluoro-2-(4-(2-(3-fluorobenzyl)-4-(2-thiophenylsulfonyl)-1-piperazinyl)phenyl)-2-propanol;
1,1,1-trifluoro-2-(4-(2-(4-fluorobenzyl)-4-(2-thiophenylsulfonyl)-1-piperazinyl)phenyl)-2-propanol;
1,1,1-trifluoro-2-(4-(4-(phenylsulfonyl)-2-(tetrahydro-2H-pyran-4-ylmethyl)-1-piperazinyl)phenyl)-2-propanol;
1,1,1,3,3,3-hexafluoro-2-(4-(2-(3-methylbenzyl)-4-(2-thiophenylsulfonyl)-1-piperazinyl)phenyl)-2-propanol;
1,1,1,3,3,3-hexafluoro-2-(4-(2-(4-methylbenzyl)-4-(2-thiophenylsulfonyl)-1-piperazinyl)phenyl)-2-propanol;
1,1,1-trifluoro-2-(4-(2-(hydroxymethyl)-4-(2-thiophenylsulfonyl)-1-piperazinyl)phenyl)-2-propanol;
1,1,1-trifluoro-2-(4-(2-(((3S)-3-methyl-4-morpholinyl)methyl)-4-(2-thiophenylsulfonyl)-1-piperazinyl)phenyl)-2-propanol;
1,1,1-trifluoro-2-(4-(2-(8-oxa-3-azabicyclo[3.2.1]oct-3-ylmethyl)-4-(2-thiophenylsulfonyl)-1-piperazinyl)phenyl)-2-propanol;

2-(4-(2-((2,2-dimethyl-4-morpholinyl)methyl)-4-(2-thiophenylsulfonyl)-1-piperazinyl)phenyl)-1,1,1-trifluoro-2-propanol;
1,1,1-trifluoro-2-(4-(2-((3-(hydroxymethyl)-4-morpholinyl)methyl)-4-(2-thiophenylsulfonyl)-1-piperazinyl)phenyl)-2-propanol;
1,1,1-trifluoro-2-(4-(2-((2-methyl-4-morpholinyl)methyl)-4-(2-thiophenylsulfonyl)-1-piperazinyl)phenyl)-2-propanol;
1,1,1-trifluoro-2-(4-(2-((1R,4R)-2-oxa-5-azabicyclo[2.2.1]hept-5-ylmethyl)-4-(2-thiophenylsulfonyl)-1-piperazinyl)phenyl)-2-propanol;
2-(4-(2-((4,4-difluoro-1-piperidinyl)methyl)-4-(2-thiophenylsulfonyl)-1-piperazinyl)phenyl)-1,1,1-trifluoro-2-propanol;
1,1,1-trifluoro-2-(4-(2-((2-(hydroxymethyl)-4-morpholinyl)methyl)-4-(2-thiophenylsulfonyl)-1-piperazinyl)phenyl)-2-propanol;
1-((4-(2-thiophenylsulfonyl)-1-(4-(2,2,2-trifluoro-1-hydroxy-1-methylethyl)phenyl)-2-piperazinyl)methyl)-3-azetidinol;
2-methyl-2-(((4-(2-thiophenylsulfonyl)-1-(4-(2,2,2-trifluoro-1-hydroxy-1-methylethyl)phenyl)-2-piperazinyl)methyl)amino)-1-propanol;
(4-(2-thiophenylsulfonyl)-1-(4-(2,2,2-trifluoro-1-hydroxy-1-methylethyl)phenyl)-2-piperazinyl)acetonitrile;
(3R)-1-((4-(2-thiophenylsulfonyl)-1-(4-(2,2,2-trifluoro-1-hydroxy-1-methylethyl)phenyl)-2-piperazinyl)methyl)-3-pyrrolidinol;
1,1,1-trifluoro-2-(4-(2-(2-methylpropyl)-4-(2-thiophenylsulfonyl)-1-piperazinyl)phenyl)-2-propanol;
2-(4-(2-(cyclohexylmethyl)-4-(2-thiophenylsulfonyl)-1-piperazinyl)phenyl)-1,1,1-trifluoro-2-propanol;
1,1,1-trifluoro-2-(4-(2-((3-pyridinylmethoxy)methyl)-4-(2-thiophenylsulfonyl)-1-piperazinyl)phenyl)-2-propanol;
1,1,1,3,3,3-hexafluoro-2-(4-(4-(1H-imidazol-4-ylsulfonyl)-1-piperazinyl)phenyl)-2-propanol;
1,1,1-trifluoro-2-(4-(2-(4-morpholinylmethyl)-4-(2-thiophenylsulfonyl)-1-piperazinyl)phenyl)-2-propanol;
2-(4-(2-((benzyl(methyl)amino)methyl)-4-(2-thiophenylsulfonyl)-1-piperazinyl)phenyl)-1,1,1-trifluoro-2-propanol;
2-(4-((2S)-2-ethyl-4-(2-thiophenylsulfonyl)-1-piperazinyl)phenyl)-1,1,1,3,3,3-hexafluoro-2-propanol;
2-(4-((2S)-2-benzyl-4-(2-thiophenylsulfonyl)-1-piperazinyl)phenyl)-1,1,1,3,3,3-hexafluoro-2-propanol;
2-(4-((2S)-2-benzyl-4-(2-thiophenylsulfonyl)-1-piperazinyl)phenyl)-1,1,1-trifluoro-2-propanol;
(2S)-2-(4-((2S)-2-benzyl-4-(2-thiophenylsulfonyl)-1-piperazinyl)phenyl)-1,1,1-trifluoro-2-propanol;
(2R)-2-(4-((2S)-2-benzyl-4-(2-thiophenylsulfonyl)-1-piperazinyl)phenyl)-1,1,1-trifluoro-2-propanol;
3,3,3-trifluoro-2-(4-(4-(2-thiophenylsulfonyl)-1-piperazinyl)phenyl)-1,2-propanediol;
(2S)-3,3,3-trifluoro-2-(4-(4-(2-thiophenylsulfonyl)-1-piperazinyl)phenyl)-1,2-propanediol;
(2R)-3,3,3-trifluoro-2-(4-(4-(2-thiophenylsulfonyl)-1-piperazinyl)phenyl)-1,2-propanediol;
2-(4-((2S)-2-methyl-4-(2-thiophenylsulfonyl)-1-piperazinyl)phenyl)-3,3,3-trifluoro-1,2-propanediol;
2-(4-((2S)-2-benzyl-4-(2-thiophenylsulfonyl)-1-piperazinyl)phenyl)-3,3,3-trifluoro-1,2-propanediol;
1,1,1,3,3,3-hexafluoro-2-(6-(4-(2-thiophenylsulfonyl)-1-piperazinyl)-3-biphenylyl)-2-propanol;
1,1,1,3,3,3-hexafluoro-2-(3'-methoxy-6-(4-(2-thiophenylsulfonyl)-1-piperazinyl)-3-biphenylyl)-2-propanol;
1,1,1,3,3,3-hexafluoro-2-(3'-fluoro-6-(4-(2-thiophenylsulfonyl)-1-piperazinyl)-3-biphenylyl)-2-propanol;
1,1,1,3,3,3-hexafluoro-2-(3-(3-pyridinyl)-4-(4-(2-thiophenylsulfonyl)-1-piperazinyl)phenyl)-2-propanol;
1,1,1,3,3,3-hexafluoro-2-(3-(3-thiophenyl)-4-(4-(2-thiophenylsulfonyl)-1-piperazinyl)phenyl)-2-propanol;
2'-(4-(2-thiophenylsulfonyl)-1-piperazinyl)-5'-(2,2,2-trifluoro-1-hydroxy-1-(trifluoromethyl)ethyl)-4-biphenylol;
1,1,1-trifluoro-2-(3-(3-methyl-3-oxetanyl)ethynyl)-4-(4-(2-thiophenylsulfonyl)-1-piperazinyl)phenyl)-2-propanol; or
1,1,1-trifluoro-2-(4-(2-(4-pyridinylmethyl)-4-(2-thiophenylsulfonyl)-1-piperazinyl)phenyl)-2-propanol.

In embodiment 30, the present invention provides the compounds, or pharmaceutically acceptable salts thereof, selected from:
8-(((2S)-4-(2-thiophenylsulfonyl)-1-(4-(2,2,2-trifluoro-1-hydroxy-1-methylethyl)phenyl)-2-piperazinyl)methyl)-3-oxa-8-azabicyclo[3.2.1]octan-6-ol (endo);
(1R,5R,6R)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol;
(1R,5R,6R)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol;
(1S,5S,6S)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol;
(1S,5S,6S)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol;
8-(((2S)-4-(2-thiophenylsulfonyl)-1-(4-(2,2,2-trifluoro-1-hydroxy-1-methylethyl)phenyl)-2-piperazinyl)methyl)-3-oxa-8-azabicyclo[321]octan-6-ol (exo);
(1S,5S,6R)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol;
(1S,5S,6R)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol;
(1R,5R,6S)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol;
(1R,5R,6S)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol;
8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol;
(1S,5S,6S)-8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol;
(1R,5R,6R)-8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[321]octan-6-ol;
8-(((2S)-4-(phenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol;
8-(((2S)-4-(1,3-thiazol-2-ylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol;
1,1,1,3,3,3-hexafluoro-2-(2-((2S)-2-(((3S)-3-methyl-4-morpholinyl)methyl)-4-(2-thiophenylsulfonyl)-1-piperazinyl)-5-pyrimidinyl)-2-propanol;
3,3,3-trifluoro-2-(4-((2S)-2-(((3S)-3-methyl-4-morpholinyl)methyl)-4-(2-thiophenylsulfonyl)-1-piperazinyl)phenyl)-1,2-propanediol;

(2S)-3,3,3-trifluoro-2-(4-((2S)-2-(((3S)-3-methyl-4-morpholinyl)methyl)-4-(2-thiophenylsulfonyl)-1-piperazinyl)phenyl)-1,2-propanediol;
(2R)-3,3,3-trifluoro-2-(4-((2S)-2-(((3S)-3-methyl-4-morpholinyl)methyl)-4-(2-thiophenylsulfonyl)-1-piperazinyl)phenyl)-1,2-propanediol;
1,1,1-trifluoro-2-(4-((2S)-2-(2-oxa-6-azaspiro[3.3]hept-6-ylmethyl)-4-(2-thiophenylsulfonyl)-1-piperazinyl)phenyl)-2-propanol;
2-(4-((2S)-2-((1,1-dioxido-4-thiomorpholinyl)methyl)-4-(2-thiophenylsulfonyl)-1-piperazinyl)phenyl)-1,1,1-trifluoro-2-propanol;
1,1,1-trifluoro-2-(4-((2S)-2-((3-methyl-1,1-dioxido-4-thiomorpholinyl)methyl)-4-(2-thiophenylsulfonyl)-1-piperazinyl)phenyl)-2-propanol;
2-(4-((2S)-2-((3-cyclopropyl-1,1-dioxido-4-thiomorpholinyl)methyl)-4-(2-thiophenylsulfonyl)-1-piperazinyl)phenyl)-1,1,1-trifluoro-2-propanol;
2-(4-(4-((5-amino-2-thiophenyl)sulfonyl)-1-piperazinyl)phenyl)-1,1,1,3,3,3-hexafluoro-2-propanol;
2-(2-((2S)-4-((5-amino-2-thiophenyl)sulfonyl)-2-methyl-1-piperazinyl)-5-pyrimidinyl)-1,1,1,3,3,3-hexafluoro-2-propanol;
2-(4-(4-((5-amino-2-thiophenyl)sulfonyl)-1-piperazinyl)phenyl)-1,1,1-trifluoro-2-propanol;
2-(4-(4-((6-amino-3-pyridinyl)sulfonyl)-1-piperazinyl)phenyl)-1,1,1,3,3,3-hexafluoro-2-propanol;
2-(4-((2S)-4-((6-amino-3-pyridinyl)sulfonyl)-2-methyl-1-piperazinyl)phenyl)-1,1,1,3,3,3-hexafluoro-2-propanol;
2-(2-((2S)-4-((6-amino-3-pyridinyl)sulfonyl)-2-methyl-1-piperazinyl)-5-pyrimidinyl)-1,1,1,3,3,3-hexafluoro-2-propanol;
1,1,1,3,3,3-hexafluoro-2-(2-((2S)-2-methyl-4-(2-thiophenylsulfonyl)-1-piperazinyl)-5-pyrimidinyl)-2-propanol;
2-(4-(4-((6-amino-3-pyridinyl)sulfonyl)-1-piperazinyl)phenyl)-1,1,1-trifluoro-2-propanol;
2-(4-(4-((2-amino-5-pyrimidinyl)sulfonyl)-1-piperazinyl)phenyl)-1,1,1,3,3,3-hexafluoro-2-propanol;
2-(4-(4-((6-amino-5-fluoro-3-pyridinyl)sulfonyl)-1-piperazinyl)phenyl)-1,1,1,3,3,3-hexafluoro-2-propanol;
9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo);
9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one;
9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo);
9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one;
8-(((2S)-4-(2-thiophenylsulfonyl)-1-(5-(2,2,2-trifluoro-1-hydroxy-1-methylethyl)-2-pyrimidinyl)-2-piperazinyl)methyl)-3-oxa-8-azabicyclo[3.2.1]octan-6-ol (endo);
(1R,5R,6R)-8-(((2S)-4-(2-thiophenylsulfonyl)-1-(5-((1R)-2,2,2-trifluoro-1-hydroxy-1-methylethyl)-2-pyrimidinyl)-2-piperazinyl)methyl)-3-oxa-8-azabicyclo[3.2.1]octan-6-ol (endo);
(1R,5R,6R)-8-(((2S)-4-(2-thiophenylsulfonyl)-1-(5-((1S)-2,2,2-trifluoro-1-hydroxy-1-methylethyl)-2-pyrimidinyl)-2-piperazinyl)methyl)-3-oxa-8-azabicyclo[3.2.1]octan-6-ol (endo);
(1S,5S,6S)-8-(((2S)-4-(2-thiophenylsulfonyl)-1-(5-((1R)-2,2,2-trifluoro-1-hydroxy-1-methylethyl)-2-pyrimidinyl)-2-piperazinyl)methyl)-3-oxa-8-azabicyclo[3.2.1]octan-6-ol (endo);
(1S,5S,6S)-8-(((2S)-4-(2-thiophenylsulfonyl)-1-(5-((1S)-2,2,2-trifluoro-1-hydroxy-1-methylethyl)-2-pyrimidinyl)-2-piperazinyl)methyl)-3-oxa-8-azabicyclo[3.2.1]octan-6-ol (endo);
1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol;
(2R)-1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol;
(2S)-1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol;
1,1,1-trifluoro-2-(4-((2S)-2-(((3S)-3-methyl-4-morpholinyl)methyl)-4-(1,3-thiazol-2-ylsulfonyl)-1-piperazinyl)phenyl)-2-propanol;
2-(4-(4-((4-aminophenyl)sulfonyl)-1-piperazinyl)phenyl)-1,1,1,3,3,3-hexafluoro-2-propanol;
2-(4-(4-((4-amino-3-fluorophenyl)sulfonyl)-1-piperazinyl)phenyl)-1,1,1,3,3,3-hexafluoro-2-propanol;
3-((4-(4-(2,2,2-trifluoro-1-hydroxy-1-(trifluoromethyl)ethyl)phenyl)-1-piperazinyl)sulfonyl)phenol;
9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-one;
9-(((2S)-4-(2-thiophenylsulfonyl)-1-(4-((1R)-2,2,2-trifluoro-1-hydroxy-1-methylethyl)phenyl)-2-piperazinyl)methyl)-3-oxa-9-azabicyclo[3.3.1]nonan-7-one;
9-(((2S)-4-(2-thiophenylsulfonyl)-1-(4-((1S)-2,2,2-trifluoro-1-hydroxy-1-methylethyl)phenyl)-2-piperazinyl)methyl)-3-oxa-9-azabicyclo[3.3.1]nonan-7-one;
9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-ol (endo);
(1R,5S)-7-methyl-9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-ol (endo);
1,1,1-trifluoro-2-(4-((2S)-2-(((1R,5S)-7-methoxy-3-oxa-9-azabicyclo[3.3.1]non-9-yl)methyl)-4-(2-thiophenylsulfonyl)-1-piperazinyl)phenyl)-2-propanol (endo);
1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol;
(2R)-1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol;
(2S)-1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol;
1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol;
(2R)-1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol;
(2S)-1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol;
N-((4-(((2S)-4-(2-thiophenylsulfonyl)-1-(4-(2,2,2-trifluoro-1-hydroxy-1-methylethyl)phenyl)-2-piperazinyl)methyl)-3-morpholinyl)methyl)methanesulfonamide;

N-(((3R)-4-(((2S)-4-(2-thiophenylsulfonyl)-1-(4-((1Rr)-2,2,
2-trifluoro-1-hydroxy-1-methylethyl)phenyl)-2-piperazi-
nyl)methyl)-3-morpholinyl)methyl)methanesulfonamide;
N-(((3S)-4-(((2S)-4-(2-thiophenylsulfonyl)-1-(4-((1S)-2,2,
2-trifluoro-1-hydroxy-1-methylethyl)phenyl)-2-piperazi-
nyl)methyl)-3-morpholinyl)methyl)methane sulfonamide;
N-(((3R)-4-(((2S)-4-(2-thiophenylsulfonyl)-1-(4-((1S)-2,2,
2-trifluoro-1-hydroxy-1-methylethyl)phenyl)-2-piperazi-
nyl)methyl)-3-morpholinyl)methyl)methane sulfonamide;
N-(((3S)-4-(((2S)-4-(2-thiophenylsulfonyl)-1-(4-((1R)-2,2,
2-trifluoro-1-hydroxy-1-methylethyl)phenyl)-2-piperazi-
nyl)methyl)-3-morpholinyl)methyl)methane sulfonamide;
(4-(((2S)-4-(2-thiophenylsulfonyl)-1-(4-(2,2,2-trifluoro-1-
hydroxy-1-methylethyl)phenyl)-2-piperazinyl)methyl)-3-
morpholinyl)acetate;
N,N-dimethyl-2-(4-(((2S)-4-(2-thiophenylsulfonyl)-1-(4-(2,
2,2-trifluoro-1-hydroxy-1-methylethyl)phenyl)-2-piper-
azinyl)methyl)-3-morpholinyl)acetamide;
1,1,1-trifluoro-2-(4-((2S)-2-((3-(4-fluorophenyl)-4-mor-
pholinyl)methyl)-4-(2-thiophenylsulfonyl)-1-piperazinyl)
phenyl)-2-propanol;
(2R)-1,1,1-trifluoro-2-(4-((2S)-2-(((3R)-3-(4-fluorophe-
nyl)-4-morpholinyl)methyl)-4-(2-thiophenylsulfonyl)-1-
piperazinyl)phenyl)-2-propanol;
(2S)-1,1,1-trifluoro-2-(4-((2S)-2-(((3S)-3-(4-fluorophenyl)-
4-morpholinyl)methyl)-4-(2-thiophenylsulfonyl)-1-piper-
azinyl)phenyl)-2-propanol;
(2R)-1,1,1-trifluoro-2-(4-((2S)-2-(((3S)-3-(4-fluorophenyl)-
4-morpholinyl)methyl)-4-(2-thiophenylsulfonyl)-1-piper-
azinyl)phenyl)-2-propanol;
(2S)-1,1,1-trifluoro-2-(4-((2S)-2-(((3R)-3-(4-fluorophenyl)-
4-morpholinyl)methyl)-4-(2-thiophenylsulfonyl)-1-piper-
azinyl)phenyl)-2-propanol;
1,1,1-trifluoro-2-(4-((2R)-2-((2-furanylmethoxy)methyl)-4-
(2-thiophenylsulfonyl)-1-piperazinyl)phenyl)-2-pro-
panol;
1,1,1-trifluoro-2-(4-((2R)-2-(((3-methyl-3-oxetanyl)meth-
oxy)methyl)-4-(2-thiophenylsulfonyl)-1-piperazinyl)phe-
nyl)-2-propanol;
1,1,1-trifluoro-2-(4-((2R)-2-((tetrahydro-2-furanylmethoxy)
methyl)-4-(2-thiophenylsulfonyl)-1-piperazinyl)phenyl)-
2-propanol;
1,1,1-trifluoro-2-(4-((2R)-2-(((1-methyl-1H-imidazol-4-yl)
methoxy)methyl)-4-(2-thiophenylsulfonyl)-1-piperazi-
nyl)phenyl)-2-propanol;
(2R)-1,1,1-trifluoro-2-(4-((2R)-2-(((1-methyl-1H-imidazol-
4-yl)methoxy)methyl)-4-(2-thiophenylsulfonyl)-1-piper-
azinyl)phenyl)-2-propanol;
(2S)-1,1,1-trifluoro-2-(4-((2R)-2-(((1-methyl-1H-imidazol-
4-yl)methoxy)methyl)-4-(2-thiophenylsulfonyl)-1-piper-
azinyl)phenyl)-2-propanol;
1,1,1-trifluoro-2-(4-((2S)-2-((tetrahydro-2H-pyran-4-
ylamino)methyl)-4-(2-thiophenylsulfonyl)-1-piperazinyl)
phenyl)-2-propanol;
1,1,1-trifluoro-2-(4-((2S)-2-((methyl((1-methyl-1H-imida-
zol-4-yl)methyl)amino)methyl)-4-(2-thiophenylsulfo-
nyl)-1-piperazinyl)phenyl)-2-propanol;
1,1,1-trifluoro-2-(4-((2S)-2-(cis-hexahydro-5H-furo[2,3-c]
pyrrol-5-ylmethyl)-4-(2-thiophenylsulfonyl)-1-piperazi-
nyl)phenyl)-2-propanol;
1,1,1-trifluoro-2-(4-((2S)-2-((3aR,6aS)-tetrahydro-1H-furo
[3,4-c]pyrrol-5(3H)-ylmethyl)-4-(2-thiophenylsulfonyl)-
1-piperazinyl)phenyl)-2-propanol;
2-(4-((2S)-4-((6-amino-3-pyridinyl)sulfonyl)-2-(((3S)-3-
methyl-4-morpholinyl)methyl)-1-piperazinyl)phenyl)-1,
1,1,3,3,3-hexafluoro-2-propanol;
125: 2-(4-((2S)-4-((6-amino-3-pyridinyl)sulfonyl)-2-(((3S)-
3-methyl-4-morpholinyl)methyl)-1-piperazinyl)phenyl)-
1,1,1-trifluoro-2-propanol;
(2S)-2-(4-((2S)-4-((6-amino-3-pyridinyl)sulfonyl)-2-(((3R)-
3-methyl-4-morpholinyl)methyl)-1-piperazinyl)phenyl)-
1,1,1-trifluoro-2-propanol;
(2R)-2-(4-((2S)-4-((6-amino-3-pyridinyl)sulfonyl)-2-
(((3R)-3-methyl-4-morpholinyl)methyl)-1-piperazinyl)
phenyl)-1,1,1-trifluoro-2-propanol;
2-(4-((2S)-4-((6-amino-3-pyridinyl)sulfonyl)-2-(tetrahydro-
2H-pyran-4-ylmethyl)-1-piperazinyl)phenyl)-1,1,1,3,3,3-
hexafluoro-2-propanol;
2-(4-((2S)-4-((6-amino-3-pyridinyl)sulfonyl)-2-(tetrahydro-
2H-pyran-4-ylmethyl)-1-piperazinyl)phenyl)-1,1,1-trif-
luoro-2-propanol;
(2R)-2-(4-((2S)-4-((6-amino-3-pyridinyl)sulfonyl)-2-(tet-
rahydro-2H-pyran-4-ylmethyl)-1-piperazinyl)phenyl)-1,
1,1-trifluoro-2-propanol;
(2S)-2-(4-((2S)-4-((6-amino-3-pyridinyl)sulfonyl)-2-(tet-
rahydro-2H-pyran-4-ylmethyl)-1-piperazinyl)phenyl)-1,
1,1-trifluoro-2-propanol;
2-(2-((2S)-4-((6-amino-3-pyridinyl)sulfonyl)-2-(((3S)-3-
methyl-4-morpholinyl)methyl)-1-piperazinyl)-5-pyrim-
idinyl)-1,1,1,3,3,3-hexafluoro-2-propanol;
2-(2-((2S)-4-((6-amino-3-pyridinyl)sulfonyl)-2-(((3S)-3-
methyl-4-morpholinyl)methyl)-1-piperazinyl)-5-pyrim-
idinyl)-1,1,1-trifluoro-2-propanol;
2-(2-((2S)-4-((6-amino-3-pyridinyl)sulfonyl)-2-(tetrahydro-
2H-pyran-4-ylmethyl)-1-piperazinyl)-5-pyrimidinyl)-1,1,
1,3,3,3-hexafluoro-2-propanol;
2-(2-((2S)-4-((6-amino-3-pyridinyl)sulfonyl)-2-(tetrahydro-
2H-pyran-4-ylmethyl)-1-piperazinyl)-5-pyrimidinyl)-1,1,
1,3,3,3-hexafluoro-2-propanol;
1,1,1,3,3,3-hexafluoro-2-(4-((2S)-2-(((3S)-3-methyl-4-mor-
pholinyl)methyl)-4-(2-thiophenylsulfonyl)-1-piperazinyl)
phenyl)-2-propanol;
2-(2-((2S)-4-((5-amino-2-thiophenyl)sulfonyl)-2-(tetrahy-
dro-2H-pyran-4-ylmethyl)-1-piperazinyl)-5-pyrimidi-
nyl)-1,1,1,3,3,3-hexafluoro-2-propanol;
1,1,1,3,3,3-hexafluoro-2-(2-((2S)-2-(tetrahydro-2H-pyran-
4-ylmethyl)-4-(2-thiophenylsulfonyl)-1-piperazinyl)-5-
pyrimidinyl)-2-propanol;
2-(2-((2S)-4-((5-amino-2-thiophenyl)sulfonyl)-2-(tetrahy-
dro-2H-pyran-4-ylmethyl)-1-piperazinyl)-5-pyrimidi-
nyl)-1,1,1-trifluoro-2-propanol;
2-(4-((2S)-4-((5-amino-2-thiophenyl)sulfonyl)-2-benzyl-1-
piperazinyl)phenyl)-1,1,1-trifluoro-2-propanol;
2-(2-((2S)-4-((5-amino-2-thiophenyl)sulfonyl)-2-methyl-1-
piperazinyl)-5-pyrimidinyl)-1,1,1-trifluoro-2-propanol;
2-(4-(4-((4-amino-2-thiophenyl)sulfonyl)-1-piperazinyl)
phenyl)-1,1,1,3,3,3-hexafluoro-2-propanol;
2-(4-((2S)-4-((5-amino-2-thiophenyl)sulfonyl)-2-methyl-1-
piperazinyl)phenyl)-1,1,1-trifluoro-2-propanol;
9-(((2S)-4-(2-thiophenylsulfonyl)-1-(4-(2,2,2-trifluoro-1-
hydroxy-1-methylethyl)phenyl)-2-piperazinyl)methyl)-9-
azabicyclo[3.3.1]nonan-3-one;
9-(((2S)-4-(2-thiophenylsulfonyl)-1-(4-(2,2,2-trifluoro-1-
hydroxy-1-methylethyl)phenyl)-2-piperazinyl)methyl)-9-
azabicyclo[3.3.1]nonan-3-ol (endo);
3-fluoro-9-(((2S)-1-(4-(1,2,2,2-tetrafluoro-1-methylethyl)
phenyl)-4-(2-thiophenylsulfonyl)-2-piperazinyl)methyl)-
9-azabicyclo[3.3.1]nonane (exo);
2-(4-((2S)-2-((3-ethyl-4-morpholinyl)methyl)-4-(2-thiophe-
nylsulfonyl)-1-piperazinyl)phenyl)-1,1,1-trifluoro-2-pro-
panol;

1-(((2S)-4-(2-thiophenylsulfonyl)-1-(4-(2,2,2-trifluoro-1-hydroxy-1-methylethyl)phenyl)-2-piperazinyl)methyl)-4-piperidinone;
(3S)-1-(((2S)-4-(2-thiophenylsulfonyl)-1-(4-(2,2,2-trifluoro-1-hydroxy-1-methylethyl)phenyl)-2-piperazinyl)methyl)-3-piperidinol;
1,1,1,3,3,3-hexafluoro-2-(2-((2S)-2-methyl-4-(1,3-thiazol-2-ylsulfonyl)-1-piperazinyl)-5-pyrimidinyl)-2-propanol;
2-(2-((2S)-4-((2-amino-1,3-thiazol-5-yl)sulfonyl)-2-methyl-1-piperazinyl)-5-pyrimidinyl)-1,1,1,3,3,3-hexafluoro-2-propanol;
1,1,1-trifluoro-2-(4-((2S)-2-(2-(3-oxetanylamino)propyl)-4-(2-thiophenylsulfonyl)-1-piperazinyl)phenyl)-2-propanol;
2-(4-((2S)-4-((5-amino-2-thiophenyl)sulfonyl)-2-methyl-1-piperazinyl)phenyl)-1,1,1,3,3,3-hexafluoro-2-propanol;
4-(2-(4-(2-thiophenylsulfonyl)-1-piperazinyl)-5-(2,2,2-trifluoro-1-hydroxy-1-(trifluoromethyl)ethyl)phenyl)-3-butyn-1-ol;
4-(2-(4-(2-thiophenylsulfonyl)-1-piperazinyl)-5-(2,2,2-trifluoro-1-hydroxy-1-(trifluoromethyl)ethyl)phenyl)-3-butyn-2-ol;
3-(2-(4-(2-thiophenylsulfonyl)-1-piperazinyl)-5-(2,2,2-trifluoro-1-hydroxy-1-(trifluoromethyl)ethyl)phenyl)-2-propyn-1-ol;
1,1,1,3,3,3-hexafluoro-2-(3-(3-methoxyprop-1-ynyl)-4-(4-(thiophen-2-ylsulfonyl)piperazin-1-yl)phenyl)propan-2-ol;
1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol;
1,1,1,3,3,3-hexafluoro-2-(3-(3-methoxy-1-pentyn-1-yl)-4-(4-(2-thiophenylsulfonyl)-1-piperazinyl)phenyl)-2-propanol;
4-methyl-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol;
1,1,1,3,3,3-hexafluoro-2-(3-(3-methoxy-4-methyl-1-pentyn-1-yl)-4-(4-(2-thiophenylsulfonyl)-1-piperazinyl)phenyl)-2-propanol;
tert-butyl (3-(2-(4-(2-thiophenylsulfonyl)-1-piperazinyl)-5-(2,2,2-trifluoro-1-hydroxy-1-(trifluoromethyl)ethyl)phenyl)-2-propyn-1-yl)carbamate;
2-(3-(3-amino-1-propyn-1-yl)-4-(4-(2-thiophenylsulfonyl)-1-piperazinyl)phenyl)-1,1,1,3,3,3-hexafluoro-2-propanol;
N-(3-(2-(4-(2-thiophenylsulfonyl)-1-piperazinyl)-5-(2,2,2-trifluoro-1-hydroxy-1-(trifluoromethyl)ethyl)phenyl)-2-propyn-1-yl)methanesulfonamide;
2-(4'-((6-amino-3-pyridinyl)sulfonyl)-4-biphenylyl)-1,1,1-trifluoro-2-propanol;
1-(2-(4-(phenylsulfonyl)-1-piperidinyl)-5-(2,2,2-trifluoro-1-hydroxy-1-(trifluoromethyl)ethyl)phenyl)-1-pentyn-3-ol;
1,1,1,3,3,3-hexafluoro-2-(3-(3-methoxypent-1-ynyl)-4-(4-(phenylsulfonyl)piperidin-1-yl)phenyl)-2-propanol;
2-(4-(4-(6-aminopyridazin-3-ylsulfonyl)piperazin-1-yl)phenyl)-1,1,1,3,3,3-hexafluoro-2-propanol;
2-(4-(4-(2-aminophenylsulfonyl)piperazin-1-yl)phenyl)-1,1,1,3,3,3-hexafluoro-2-propanol;
2-(4-(4-(2,6-diaminopyridin-3-ylsulfonyl)piperazin-1-yl)phenyl)-1,1,1,3,3,3-hexafluoro-2-propanol;
(S)-2-(2-(4-(2-aminophenylsulfonyl)-2-methylpiperazin-1-yl)pyrimidin-5-yl)-1,1,1,3,3,3-hexafluoro-2-propanol;
(2-(4-((2S)-4-((2-aminophenyl)sulfonyl)-2-methyl-1-piperazinyl)phenyl)-1,1,1,3,3,3-hexafluoro-2-propanol;
2-(4-(4-(4-bromothiophen-3-ylsulfonyl)piperazin-1-yl)phenyl)-1,1,1,3,3,3-hexafluoro-2-propanol;
2-(4-((S)-2-((1h-imidazol-1-yl)methyl)-4-(thiophen-2-ylsulfonyl)piperazin-1-yl)phenyl)-1,1,1-trifluoro-2-propanol;
2-(4-((S)-2-((5H-pyrrolo[2,3-b]pyrazin-5-yl)methyl)-4-(thiophen-2-ylsulfonyl)piperazin-1-yl)phenyl)-1,1,1-trifluoro-2-propanol;
2-(4-((S)-2-((1H-pyrrolo[2,3-b]pyridin-1-yl)methyl)-4-(thiophen-2-ylsulfonyl)piperazin-1-yl)phenyl)-1,1,1-trifluoro-2-propanol;
1,1,1,3,3,3-hexafluoro-2-(4-(2-(3-methoxybenzyl)-4-(thiophen-2-ylsulfonyl)piperazin-1-yl)phenyl)-2-propanol;
1,1,1,3,3,3-hexafluoro-2-(4-(2-(2-methoxybenzyl)-4-(thiophen-2-ylsulfonyl)piperazin-1-yl)phenyl)-2-propanol;
1,1,1,3,3,3-hexafluoro-2-(4-(2-(4-methoxybenzyl)-4-(thiophen-2-ylsulfonyl)piperazin-1-yl)phenyl)-2-propanol;
3-((1-(4-(1,1,1,3,3,3-hexafluoro-2-hydroxypropan-2-yl)phenyl)-4-(thiophen-2-ylsulfonyl)piperazin-2-yl)methyl)phenol;
4-((1-(4-(1,1,1,3,3,3-hexafluoro-2-hydroxypropan-2-yl)phenyl)-4-(thiophen-2-ylsulfonyl)piperazin-2-yl)methyl)phenol;
2-((1-(4-(1,1,1,3,3,3-hexafluoro-2-hydroxypropan-2-yl)phenyl)-4-(thiophen-2-ylsulfonyl)piperazin-2-yl)methyl)phenol;
4-(((2S)-4-(2-thiophensulfonyl)-1-(4-(2,2,2-trifluoro-1-hydroxy-1-methylethyl)phenyl)-2-piperazinyl)methyl)-2-piperazinone;
3,3-dimethyl-4-(((2S)-4-(2-thiophenylsulfonyl)-1-(4-(2,2,2-trifluoro-1-hydroxy-1-methylethyl)phenyl)-2-piperazinyl)methyl)-2-piperazinone;
3-(1-methylethyl)-4-(((2S)-4-(2-thiophenylsulfonyl)-1-(4-(2,2,2-trifluoro-1-hydroxy-1-methylethyl)phenyl)-2-piperazinyl)methyl)-2-piperazinone;
(3S-3-methyl-4-(((2S)-4-(2-thiophenylsulfonyl)-1-(4-(2,2,2-trifluoro-1-hydroxy-1-methylethyl)phenyl)-2-piperazinyl)methyl)-2-piperazinone;
5-methyl-4-(((2S)-4-(2-thiophenylsulfonyl)-1-(4-(2,2,2-trifluoro-1-hydroxy-1-methylethyl)phenyl)-2-piperazinyl)methyl)-2-piperazinone;
4-(((S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone;
(3R)-4-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone;
(3S)-4-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone;
3-(1-methylethyl)-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone;
1,1,1-trifluoro-2-(4-((2R)-2-((phenylsulfanyl)methyl)-4-(2-thiophenylsulfonyl)-1-piperazinyl)phenyl)-2-propanol;
1,1,1-trifluoro-2-(4-((2R)-2-((phenylsulfonyl)methyl)-4-(2-thiophenylsulfonyl)-1-piperazinyl)phenyl)-2-propanol;
(2S)-1,1,1-trifluoro-2-(4-((2R)-2-((phenylsulfonyl)methyl)-4-(2-thiophenylsulfonyl)-1-piperazinyl)phenyl)-2-propanol;
(2R)-1,1,1-trifluoro-2-(4-((2R)-2-((phenylsulfonyl)methyl)-4-(2-thiophenylsulfonyl)-1-piperazinyl)phenyl)-2-propanol;

1,1,1-trifluoro-2-(4-((2R)-2-(((3-fluorophenyl)sulfanyl)methyl)-4-(2-thiophenylsulfonyl)-1-piperazinyl)phenyl)-2-propanol;
1,1,1-trifluoro-2-(4-((2R)-2-(((3-fluorophenyl)sulfonyl)methyl)-4-(2-thiophenylsulfonyl)-1-piperazinyl)phenyl)-2-propanol;
1,1,1-trifluoro-2-(4-((2R)-2-(((3-fluorophenyl)sulfinyl)methyl)-4-(2-thiophenylsulfonyl)-1-piperazinyl)phenyl)-2-propanol;
1,1,1-trifluoro-2-(4-((2R)-2-(((4-fluorophenyl)sulfanyl)methyl)-4-(2-thiophenylsulfonyl)-1-piperazinyl)phenyl)-2-propanol;
1,1,1-trifluoro-2-(4-((2R)-2-(((4-fluorophenyl)sulfanyl)methyl)-4-(2-thiophenylsulfonyl)-1-piperazinyl)phenyl)-2-propanol;
1,1,1-trifluoro-2-(4-((2R)-2-(((4-fluorophenyl)sulfinyl)methyl)-4-(2-thiophenylsulfonyl)-1-piperazinyl)phenyl)-2-propanol;
N-(((2S)-4-(2-thiophenylsulfonyl)-1-(4-(2,2,2-trifluoro-1-hydroxy-1-methylethyl)phenyl)-2-piperazinyl)methyl)-3-pyridinesulfonamide;
N-(((2S)-4-(2-thiophenylsulfonyl)-1-(4-(2,2,2-trifluoro-1-hydroxy-1-methylethyl)phenyl)-2-piperazinyl)methyl) benzenesulfonamide;
2-(4-((2S)-2-((bis(1-methylethyl)amino)methyl)-4-(2-thiophenylsulfonyl)-1-piperazinyl)phenyl)-1,1,1-trifluoro-2-propanol;
N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide;
N-(1-methylethyl)-N-(((2S)-4-(2-thiophenylsulfonyl)-1-(4-(2,2,2-trifluoro-1-hydroxy-1-methylethyl)phenyl)-2-piperazinyl)methyl)acetamide;
N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)benzenesulfonamide;
N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)-3-pyridinesulfonamide;
2-(4-((2S)-2-((cyclopropylamino)methyl)-4-(2-thiophenylsulfonyl)-1-piperazinyl)phenyl)-1,1,1-trifluoro-2-propanol;
N-cyclopropyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide;
N-(2-methylpropyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;
N-(cyclopropylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;
1,1,1-trifluoro-2-(4-((2S)-2-((phenylamino)methyl)-4-(2-thiophenylsulfonyl)-1-piperazinyl)phenyl)-2-propanol;
N-phenyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide;
2-(4-((2S)-2-((di-3-oxetanylamino)methyl)-4-(2-thiophenylsulfonyl)-1-piperazinyl)phenyl)-1,1,1-trifluoro-2-propanol;
1,1,1-trifluoro-2-(4-((2S)-2-((3-oxetanylamino)methyl)-4-(2-thiophenylsulfonyl)-1-piperazinyl)phenyl)-2-propanol;
N-3-oxetanyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide;
N-methyl-N-(((2S)-4-(2-thiophenylsulfonyl)-1-(4-(2,2,2-trifluoro-1-hydroxy-1-methylethyl)phenyl)-2-piperazinyl)methyl)methanesulfonamide;
N,N-dimethyl-N'-(1-methylethyl)-N'-(((2R)-4-(2-thiophenylsulfonyl)-1-(4-(2,2,2-trifluoro-1-hydroxy-1-methylethyl)phenyl)-2-piperazinyl)methyl)sulfamide;
2-methyl-N-(((2S)-4-(2-thiophenylsulfonyl)-1-(4-(2,2,2-trifluoro-1-hydroxy-1-methylethyl)phenyl)-2-piperazinyl)methyl)-1-propanesulfonamide;
2-methyl-N-phenyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide;
N-cyclobutyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide;
N-cyclobutyl-N-(((2R)-4-(2-thiophenylsulfonyl)-1-(4-(2,2,2-trifluoro-1-hydroxy-1-methylethyl)phenyl)-2-piperazinyl)methyl)-3-pyridinesulfonamide;
2,2,2-trifluoro-N-(2-methylpropyl)-N-(((2S)-4-(2-thiophenylsulfonyl)-1-(4-(2,2,2-trifluoro-1-hydroxy-1-methylethyl)phenyl)-2-piperazinyl)methyl)ethanesulfonamide;
N,N-dimethyl-N-(2-methylpropyl)-N-(((2R)-4-(2-thiophenylsulfonyl)-1-(4-(2,2,2-trifluoro-1-hydroxy-1-methylethyl)phenyl)-2-piperazinyl)methyl)sulfamide;
N-((3-methyl-3-oxetanyl)methyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;
N-methyl-N-(((2S)-4-(2-thiophenylsulfonyl)-1-(4-(2,2,2-trifluoro-1-hydroxy-1-methylethyl)phenyl)-2-piperazinyl)methyl)-3-pyridinesulfonamide;
N-(cyclobutylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;
1,1,1-trifluoro-2-(4-((2R)-2-(((2-fluorophenyl)sulfanyl)methyl)-4-(2-thiophenylsulfonyl)-1-piperazinyl)phenyl)-2-propanol;
N-benzyl-N-(((2S)-4-(2-thiophenylsulfonyl)-1-(4-(2,2,2-trifluoro-1-hydroxy-1-methylethyl)phenyl)-2-piperazinyl)methyl)methanesulfonamide;
N-(3-pyridinylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;
N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide;
2-methyl-N-3-pyridinyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide;
N-phenyl-N-(((2S)-4-(2-thiophenylsulfonyl)-1-(4-(2,2,2-trifluoro-1-hydroxy-1-methylethyl)phenyl)-2-piperazinyl)methyl)acetamide;
2-(4-((2S)-4-((5-amino-2-thiophenyl)sulfonyl)-2-(((3S)-3-methyl-4-morpholinyl)methyl)-1-piperazinyl)phenyl)-1,1,1,3,3,3-hexafluoro-2-propanol;
3,3-dimethyl-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone;
(S)-4-((4-((5-aminothiophen-2-yl)sulfonyl)-1-(5-(1,1,1,3,3,3-hexafluoro-2-hydroxypropan-2-yl)pyrimidin-2-yl)piperazin-2-yl)methyl)-3,3-dimethylpiperazin-2-one;
5,5-dimethyl-1-(((2S)-4-(2-thiophenylsulfonyl)-1-(4-(2,2,2-trifluoro-1-hydroxy-1-methylethyl)phenyl)-2-piperazinyl)methyl)-2,4-imidazolidinedione;

N-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-n-(2-methylpropyl)methanesulfonamide;

N-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide;

N-(((2S)-4-((2-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide;

N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide;

N-(((2R)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide;

N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide;

N-(((2R)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide;

4-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone;

5-(((2S)-4-(2-thiophenylsulfonyl)-1-(4-(2,2,2-trifluoro-1-hydroxy-1-methylethyl)phenyl)-2-piperazinyl)methyl)-5,7-diazaspiro[3.4]octane-6,8-dione;

N-(((2S)-4-(thiophen-2-ylsulfonyl)-1-(4-(1,1,1-trifluoro-2-hydroxypropan-2-yl)phenyl)piperazin-2-yl)methyl)propane-2-sulfonamide;

N-(((2S)-4-(2-thiophenylsulfonyl)-1-(4-(2,2,2-trifluoro-1-hydroxy-1-methylethyl)phenyl)-2-piperazinyl)methyl)-2-butanesulfonamide;

1,1,1-trifluoro-2-(2-(2-(prop-1-yn-1-yl)-4-(thiophen-2-ylsulfonyl)piperazin-1-yl)pyrimidin-5-yl)propan-2-ol;

2-(4-(4-((6-amino-3-pyridinyl)sulfonyl)-2-(1-propyn-1-yl)-1-piperazinyl)-5-pyrimidinyl)-1,1,1,3,3,3-hexafluoro-2-propanol;

2-(2-((2R)-4-((6-amino-3-pyridinyl)sulfonyl)-2-(1-propyn-1-yl)-1-piperazinyl)-5-pyrimidinyl)-1,1,1,3,3,3-hexafluoro-2-propanol; or 2-(2-((2S)-4-((6-amino-3-pyridinyl)sulfonyl)-2-(1-propyn-1-yl)-1-piperazinyl)-5-pyrimidinyl)-1,1,1,3,3,3-hexafluoro-2-propanol.

In embodiment 31, the present invention provides the compounds, or pharmaceutically acceptable salts thereof, selected from:

2-(4-(4-((6-amino-3-pyridinyl)sulfonyl)-2-(1-propyn-1-yl)-1-piperazinyl)phenyl)-1,1,1,3,3,3-hexafluoro-2-propanol;

2-(4-((2S)-4-((6-amino-3-pyridinyl)sulfonyl)-2-(1-propyn-1-yl)-1-piperazinyl)phenyl)-1,1,1,3,3,3-hexafluoro-2-propanol;

2-(4-((2R)-4-((6-amino-3-pyridinyl)sulfonyl)-2-(1-propyn-1-yl)-1-piperazinyl)phenyl)-1,1,1,3,3,3-hexafluoro-2-propanol;

5,5-dimethyl-3-(1-methylethyl)-1-(((2S)-4-(2-thiophenylsulfonyl)-1-(4-(2,2,2-trifluoro-1-hydroxy-1-methylethyl)phenyl)-2-piperazinyl)methyl)-2,4-imidazolidinedione;

2-(4-(4-((6-amino-3-pyridinyl)sulfonyl)-2-(1-propyn-1-yl)-1-piperazinyl)phenyl)-1,1,1-trifluoro-2-propanol;

(2S)-2-(4-((2S)-4-((6-amino-3-pyridinyl)sulfonyl)-2-(1-propyn-1-yl)-1-piperazinyl)phenyl)-1,1,1-trifluoro-2-propanol;

(2S)-2-(4-((2R)-4-((6-amino-3-pyridinyl)sulfonyl)-2-(1-propyn-1-yl)-1-piperazinyl)phenyl)-1,1,1-trifluoro-2-propanol;

(2R)-2-(4-((2S)-4-((6-amino-3-pyridinyl)sulfonyl)-2-(1-propyn-1-yl)-1-piperazinyl)phenyl)-1,1,1-trifluoro-2-propanol;

(2R)-2-(4-((2R)-4-((6-amino-3-pyridinyl)sulfonyl)-2-(1-propyn-1-yl)-1-piperazinyl)phenyl)-1,1,1-trifluoro-2-propanol;

2-(2-(4-((6-amino-3-pyridinyl)sulfonyl)-2-(2-hydroxypropyl)-1-piperazinyl)-5-pyrimidinyl)-1,1,1,3,3,3-hexafluoro-2-propanol;

2-(2-(4-((6-amino-3-pyridinyl)sulfonyl)-2-($^2H_3$)-1-propyn-1-yl-1-piperazinyl)-5-pyrimidinyl)-1,1,1,3,3,3-hexafluoro-2-propanol;

2-(2-(4-((6-amino-3-pyridinyl)sulfonyl)-2-(cyclopropylethynyl)-1-piperazinyl)-5-pyrimidinyl)-1,1,1,3,3,3-hexafluoro-2-propanol;

1,1,1,3,3,3-hexafluoro-2-(4-((2S)-4-(phenylsulfonyl)-2-(1-propyn-1-yl)-1-piperazinyl)phenyl)-2-propanol;

2-(4-(4-((5-amino-1,3,4-thiadiazol-2-yl)sulfonyl)-2-(1-propyn-1-yl)-1-piperazinyl)phenyl)-1,1,1,3,3,3-hexafluoro-2-propanol;

2-(4-(4-((5-amino-1,3,4-thiadiazol-2-yl)sulfonyl)-2-(1-propyn-1-yl)-1-piperazinyl)phenyl)-1,1,1,3,3,3-hexafluoro-2-propanol;

2-(4-(4-((6-amino-5-fluoro-3-pyridinyl)sulfonyl)-2-(1-propyn-1-yl)-1-piperazinyl)phenyl)-1,1,1,3,3,3-hexafluoro-2-propanol;

2-(2-(4-((6-amino-3-pyridinyl)sulfonyl)-2-(1-propyn-1-yl)-1-piperazinyl)-5-pyrimidinyl)-1,1,1-trifluoro-2-propanol;

(2S)-2-(2-((2S)-4-((6-amino-3-pyridinyl)sulfonyl)-2-(1-propyn-1-yl)-1-piperazinyl)-5-pyrimidinyl)-1,1,1-trifluoro-2-propanol;

(2R)-2-(2-((2S)-4-((6-amino-3-pyridinyl)sulfonyl)-2-(1-propyn-1-yl)-1-piperazinyl)-5-pyrimidinyl)-1,1,1-trifluoro-2-propanol;

(2S)-2-(2-((2R)-4-((6-amino-3-pyridinyl)sulfonyl)-2-(1-propyn-1-yl)-1-piperazinyl)-5-pyrimidinyl)-1,1,1-trifluoro-2-propanol;

(2R)-2-(2-((2R)-4-((6-amino-3-pyridinyl)sulfonyl)-2-(1-propyn-1-yl)-1-piperazinyl)-5-pyrimidinyl)-1,1,1-trifluoro-2-propanol;

N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

2-methyl-N-3-pyridinyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide;

4-fluoro-N-(((2S)-4-(2-thiophenylsulfonyl)-1-(4-(2,2,2-trifluoro-1-hydroxy-1-methylethyl)phenyl)-2-piperazinyl)methyl)benzenesulfonamide;

N-(4-fluorophenyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

N-(4-fluorophenyl)-N-(((2S)-4-(2-thiophenylsulfonyl)-1-(4-(2,2,2-trifluoro-1-hydroxy-1-methylethyl)phenyl)-2-piperazinyl)methyl)acetamide;

1,1,1,3,3,3-hexafluoro-2-(4-(2-((2-methoxy-3-pyridinyl)methyl)-4-(2-thiophenylsulfonyl)-1-piperazinyl)phenyl)-2-propanol;

1,1,1,3,3,3-hexafluoro-2-(4-(2-((6-methoxy-2-pyridinyl)methyl)-4-(2-thiophenylsulfonyl)-1-piperazinyl)phenyl)-2-propanol;

4-((4-(2-thiophenylsulfonyl)-1-(4-(2,2,2-trifluoro-1-hydroxy-1-(trifluoromethyl)ethyl)phenyl)-2-piperazinyl)methyl)-2(1H)-pyridinone;

2-(4-(4-((4-amino-3-pyridinyl)sulfonyl)-1-piperazinyl)phenyl)-1,1,1,3,3,3-hexafluoro-2-propanol;

2-(4-(4-((2,4-diaminophenyl)sulfonyl)-1-piperazinyl)phenyl)-1,1,1,3,3,3-hexafluoro-2-propanol;

1,1,1,3,3,3-hexafluoro-2-(3-(1-propyn-1-yl)-4-(4-(2-thiophenylsulfonyl)-1-piperazinyl)phenyl)-2-propanol;

1,1,1,3,3,3-hexafluoro-2-(2-(4-(phenylsulfonyl)phenyl)-5-pyrimidinyl)-2-propanol;

2-(2-(4-((6-amino-3-pyridinyl)sulfonyl)phenyl)-5-pyrimidinyl)-1,1,1,3,3,3-hexafluoro-2-propanol;

2-(2-(4-((6-amino-3-pyridinyl)sulfonyl)phenyl)-5-pyrimidinyl)-1,1,1-trifluoro-2-propanol;

2-(6-(4-((6-amino-3-pyridinyl)sulfonyl)phenyl)-3-pyridinyl)-1,1,1,3,3,3-hexafluoro-2-propanol;

2-(2-(6-((6-amino-3-pyridinyl)sulfonyl)-3-pyridinyl)-5-pyrimidinyl)-1,1,1,3,3,3-hexafluoro-2-propanol;

2-(2-(4-((6-amino-3-pyridinyl)sulfonyl)-2-methylphenyl)-5-pyrimidinyl)-1,1,1,3,3,3-hexafluoro-2-propanol;

1,1,1,3,3,3-hexafluoro-2-(2-(2-(1-propyn-1-yl)-4-(2-thiophenylsulfonyl)-1-piperazinyl)-5-pyrimidinyl)-2-propanol;

1,1,1-trifluoro-2-(4-((2S)-4-(2-thiophenylsulfonyl)-2-((3-(trifluoromethyl)-1-piperazinyl)methyl)-1-piperazinyl)phenyl)-2-propanol;

2-(2-((2S)-4-((6-amino-3-pyridinyl)sulfonyl)-2-(3-oxa-8-azabicyclo[3.2.1]oct-8-ylmethyl)-1-piperazinyl)-5-pyrimidinyl)-1,1,1,3,3,3-hexafluoro-2-propanol;

(S)-5-methyl-4-(((S)-4-(tiophen-2-ylsulfonyl)-1-(4-((S)-1,1,1-trifluoro-2-hydroxypropan-2-yl)phenyl)piperazin-2-yl)methyl)morpholin-3-one; or 2-(4-((2R)-4-((6-amino-3-pyridinyl)sulfonyl)-2-((phenylsulfonyl)methyl)-1-piperazinyl)phenyl)-1,1,1,3,3,3-hexafluoro-2-propanol.

In embodiment 32, the present invention provides methods of treating type 2 diabetes, hyperglycemia, impaired glucose tolerance, insulin resistance, retinopathy, nephropathy, neuropathy, cataracts, glaucoma, Syndrome X, or polycystic ovarian syndrome, the method comprising administering to a patient in need thereof a therapeutically effective amount of a compound in accordance with any one of embodiments 1 to 31, or a pharmaceutically acceptable salts thereof.

In embodiment 33, the present invention provides the methods of embodiment 32 wherein the treatment is for type 2 diabetes.

In embodiment 34, the present invention provides pharmaceutical compositions comprising a compound in accordance with any one of embodiments 1 to 31, or a pharmaceutically acceptable salt thereof, and a pharmaceutically acceptable excipient.

DETAILED DESCRIPTION

The present invention provides compounds of Formula I, as defined above, or pharmaceutically acceptable salts thereof. The present invention also provides pharmaceutical compositions comprising a compound of Formula I, or pharmaceutically acceptable salts thereof, and methods of treating diseases and/or conditions, such as diabetes, using compounds of Formula I, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heterotaoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heterotaoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctenyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, —NR$^x$R$^x$, nitro, cyano, halo or perhalo$C_{1-8}$alkyl, $C_{2-8}$alkenyl, $C_{2-8}$alkynyl, —SR$^x$, —S(=O)$_2$R$^x$, —C(=O)OR$^x$, —C(=O)R$^x$, wherein each R$^x$ is independently hydrogen or $C_1$-$C_8$ alkyl. It is noted that when the substituent is —NR$^x$R$^x$, the R$^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of the present invention or a formulation containing a compound of the present invention, or a particular excipient, are suitable for administration to a patient.

The terms "treating", "treat" or "treatment" and the like include preventative (e.g., prophylactic) and palliative treatment.

The term "patient in need thereof" means a patient who has or is at risk of having a GKRP/GK mediated disease or condition, such as type 2 diabetes.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

The compounds of the present invention may be used in the manufacture of a medicament for the treatment of a disease and/or condition mediated by GKRP/GK, such as type 2 diabetes.

The compounds of the present invention may be used in combination with other pharmaceutically active compounds. It is noted that the term "pharmaceutically active compounds" can include biologics, such as proteins, antibodies and peptibodies. Examples of other pharmaceutically active compounds include, but are not limited to: (a) dipeptidyl peptidase IV (DPP-IV) inhibitors such as Vildagliptin (Novartis), Sitagliptin (Merck&Co.), Saxagliptin (BMS) Allogliptin (Takeda); (b) insulin sensitizers including (i) PPARγ agonists such as the glitazones (e.g., troglitazone, pioglitazone, edaglitazone, rosiglitazone, and the like) and other PPAR ligands, including PPARα/γ dual agonists such as muraglitazar (BMS) and tesaglitazar (AstraZeneca), and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors; (c) insulin or insulin mimetics; (d) incretin and incretin mimetics such as (i) Exenatide available from Amylin Pharmaceuticals, (i) amylin and amylin mimetics such as pramlintide acetate, available as Symlin®, (iii) GLP-1, GLP-1 mimetics, and GLP-1 receptor agonists, (iv) GIP, GIP mimetics and GIP receptor agonists; (e) sulfonylureas and other insulin secretagogues, such as tolbutamide, glyburide, gliclazide, glipizide, glimepiride, meglitinides, and repaglinide; (f) α-glucosidase inhibitors (such as acarbose and miglitol); (g) glucagon receptor antagonists; (h) PACAP, PACAP mimetics, and PACAP receptor agonists; (i) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants such as cholestyramine, colestipol and dialkylaminoalkyl derivatives of a cross-linked dextran, (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists such as muraglitazar (BMS) and tesaglitazar (AstraZeneca), (vi) inhibitors of cholesterol absorption, such as beta-sitosterol and ezetimibe, (vii) acyl CoA:cholesterol acyltransferase inhibitors such as avasimibe, and (viii) antioxidants such as probucol; (j) PPARδ agonists such as GW-501516 from GSK; (k) anti-obesity compounds such as fenfluramine, dexfenfluramine, phentemine, sibutramine, orlistat, neuropeptide Y1 or Y5 antagonists, MTP inhibitors, squalene synthase inhibitor, lipoxygenase inhibitor, ACAT inhibitor, Neuropeptide Cannabinoid CB-1 receptor antagonists, CB-1 receptor inverse agonists and antagonists, fatty acid oxidation inhibitors, appetite suppressants (l) adrenergic receptor agonists, melanocortin receptor agonists, in particular—melanocortin-4 receptor agonists, ghrelin antagonists, and melanin-concentrating hormone (MCH) receptor antagonists; (m) ileal bile acid transporter inhibitors; (n) agents intended for use in inflammatory conditions such as aspirin, non steroidal anti-inflammatory drugs, glucocorticoids, azalfidine, and selective cyclooxygenase-2 inhibitors; (o) antihypertensive agents such as ACE inhibitors (enalapril, lisinopril, captopril, quinapril, fosinoprol, ramipril, spirapril, tandolapril), angiotensin-II (AT-1) receptor blockers (losartan, candesartan, irbesartan, valsartan, telmisartan, eprosartan), beta blockers and calcium channel blockers; and (p) glucokinase activators (GKAs); (q) agents which can be used for the prevention, delay of progression or treatment of neurodegenerative disorders, cognitive disorders or a drug for improving memory such as anti-inflammatory drugs, antioxidants, neuroprotective agents, glutamate receptor antagonists, acetylcholine esterase inhibitors, butyrylcholinesterase inhibitors, MAO inhibitors, dopamine agonists or antagonists, inhibitors of gamma and beta secretases, inhibitors of amyloid aggregation, amyloid beta peptide, antibodies to amyloid beta peptide, inhibitors of acetylcholinesterase, glucokinase activators, agents directed at modulating GABA, NMDA, cannabinoid, AMPA, kainate, phosphodiesterase (PDE), PKA, PKC, CREB or nootropic systems; (r) leukocyte growth promotors intended for the treatment and prevention of reduced bone marrow production, infectious diseases, hormone dependent disorders, inflammatory diseases, HIV, allergies, leukocytopenia, and rheumatism; (s) SGLT2 inhibitor; (t) glycogen phosphorylase inhibitor; (u) aP2 inhibitors; (v) aminopeptidase N inhibitor (w) vasopeptidase inhibitors like neprilysin inhibitors and/or ACE inhibitors or dual NEP/ACE inhibitor; (x) growth hormone secretagogue for enhancing growth hormone levels and for treating growth retardation/dwarfism or metabolic disorders or where the disorder is an injury, or a wound in need of healing, or a mammalian patient recovering from surgery; (y) 5-HT 3 or 5-HT 4 receptor modulators (tegaserod, cisapride, nor-cisapride, renzapride, zacopride, mosapride, prucalopride, buspirone, nor-cisapride, cilansetron, ramosetron, azasetron, ondansetron, etc.); (Za) aldose reductase inhibitors; (Zb) sorbitol dehydrogenase inhibitors; (Zc) AGE inhibitors; (Zd) erythropoietin agonist such as EPO, EPO mimetics, and EPO receptor agonists. The compounds of the present invention may also be used in combination with GPR40 agonists.

Examples of glucokinase activators that can be used in combination with the compounds of the present invention include those set forth in published PCT patent application no. WO 2009/042435, published Apr. 2, 2009. Examples of specific compounds, or pharmaceutically acceptable salts thereof, disclosed in the published application that may be used in combination with the compounds of the present invention, or pharmaceutically acceptable salts thereof, include compounds selected from:

(S)-1-(5-(5-bromo-3-(2-methylpyridin-3-yloxy)pyridin-2-ylamino)-1,2,4-thiadiazol-3-yl)ethane-1,2-diol;

(S)-1-(5-(5-trifluoromethyl-3-(2-methylpyridin-3-yloxy)pyridin-2-ylamino)-1,2,4-thiadiazol-3-yl)ethane-1,2-diol;

(S)-1-(5-(5-phenylthio-3-(2-methylpyridin-3-yloxy)pyridin-2-ylamino)-1,2,4-thiadiazol-3-yl)ethane-1,2-diol;

(S)-1-(5-(5-phenylthio-3-(pyridin-3-yloxy)pyridin-2-ylamino)-1,2,4-thiadiazol-3-yl)piperidin-1-yl)ethane-1,2-diol;

(S)-1-(5-(3-(2-methylpyridin-3-yloxy)-5-(pyridin-2-ylthio)pyridin-2-ylamino)-1,2,4-thiadiazol-3-yl)ethane-1,2-diol;

(S)-1-(5-(5(2hydroxyethylthio)-3-(2-methylpyridin-3-yloxy)pyridin-2-ylamino)-1,2,4-thiadiazol-3-yl)ethane-1,2-diol;

(S)-1-(5-(4-fluorophenoxy)-5-pyridin-2-ylthio)pyridin-2-ylamino)-1,2,4-thiadiazol-3-yl)ethane-1,2-diol;

(R)-1-(2-(5-bromo-3-(4-fluorophenoxy)pyridin-2-ylamino)thiazol-4-yl)ethane-1,2-diol;

(S)-1-(2-(5-bromo-3-(4-fluorophenoxy)pyridin-2-ylamino)thiazol-4-yl)ethane-1,2-diol;

(R)-1-(2-(3-(4-fluorophenoxy)-5-(pyridin-2-ylthio)pyridin-2-ylamino)thiazol-4-yl)-ethane-1,2-diol;

(1S)-1-(5-(5-bromo-3-(5,6,7,8-tetrahydroquinolin-5-yloxy)pyridin-2-ylamino)-1,2,4-thiadiazol-3-yl)ethane-1,2-diol;

(S)-1-(5-(5-bromo-3-(1-(2-hydroxyethyl)-1H-pyrazol-4-yloxy)pyridin-2-ylamino)-1,2,4-thiadiazol-3-yl)ethane-1,2-diol;

(R)-1-(2-(5-bromo-3-(2-methylpyridin-3-yloxy)pyridin-2-ylamino)thiazol-4-yl)-ethane-1,2-diol;

(S)-1-(5-(5-(2-hydroxyethylthio)-3-(pyridin-3-yloxy)pyridin-2-ylamino)-1,2,4-thiadiazol-3-yl)ethane-1,2-diol;

(S)-1-(5-(5-bromo-3-(1-methyl-1H-pyrazol-4-yloxy)pyridin-2-ylamino)-1,2,4-thiadiazol-3-yl)ethane-1,2-diol;

(S)-1-(5-(3-(1-methyl-1H-pyrazol-4-yloxy)-5-(2-methylpyridin-3-ylthio)pyridin-2-ylamino)-1,2,4-thiadiazol-3-yl)ethane-1,2-diol;
(S)-1-(5-(5-(2-methylpyridin-3-ylthio)-3-(1,3,5-trimethyl-1H-pyrazol-4-yloxy)-pyridin-2-ylamino)-1,2,4-thiadiazol-3-yl)ethane-1,2-diol;
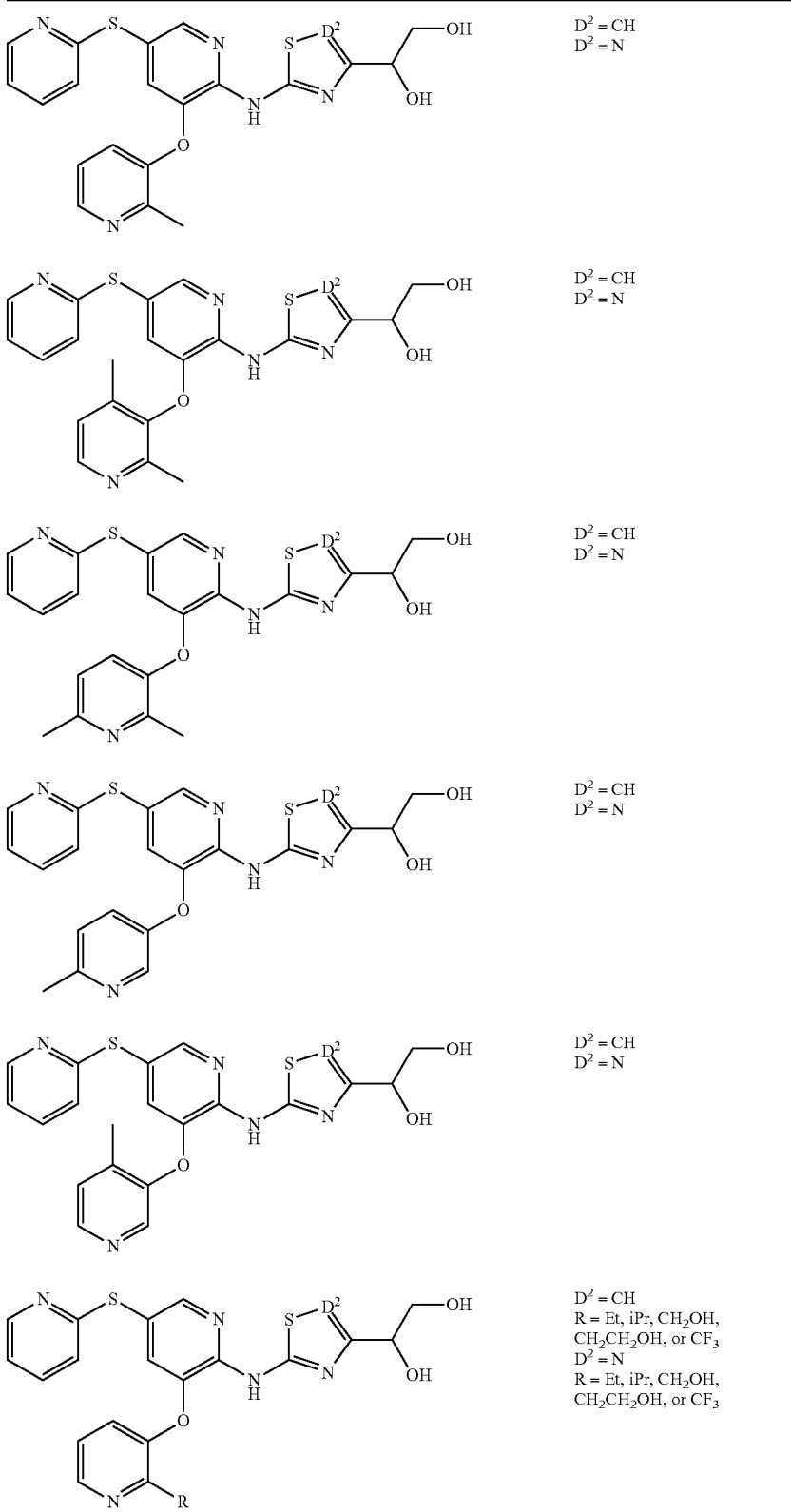

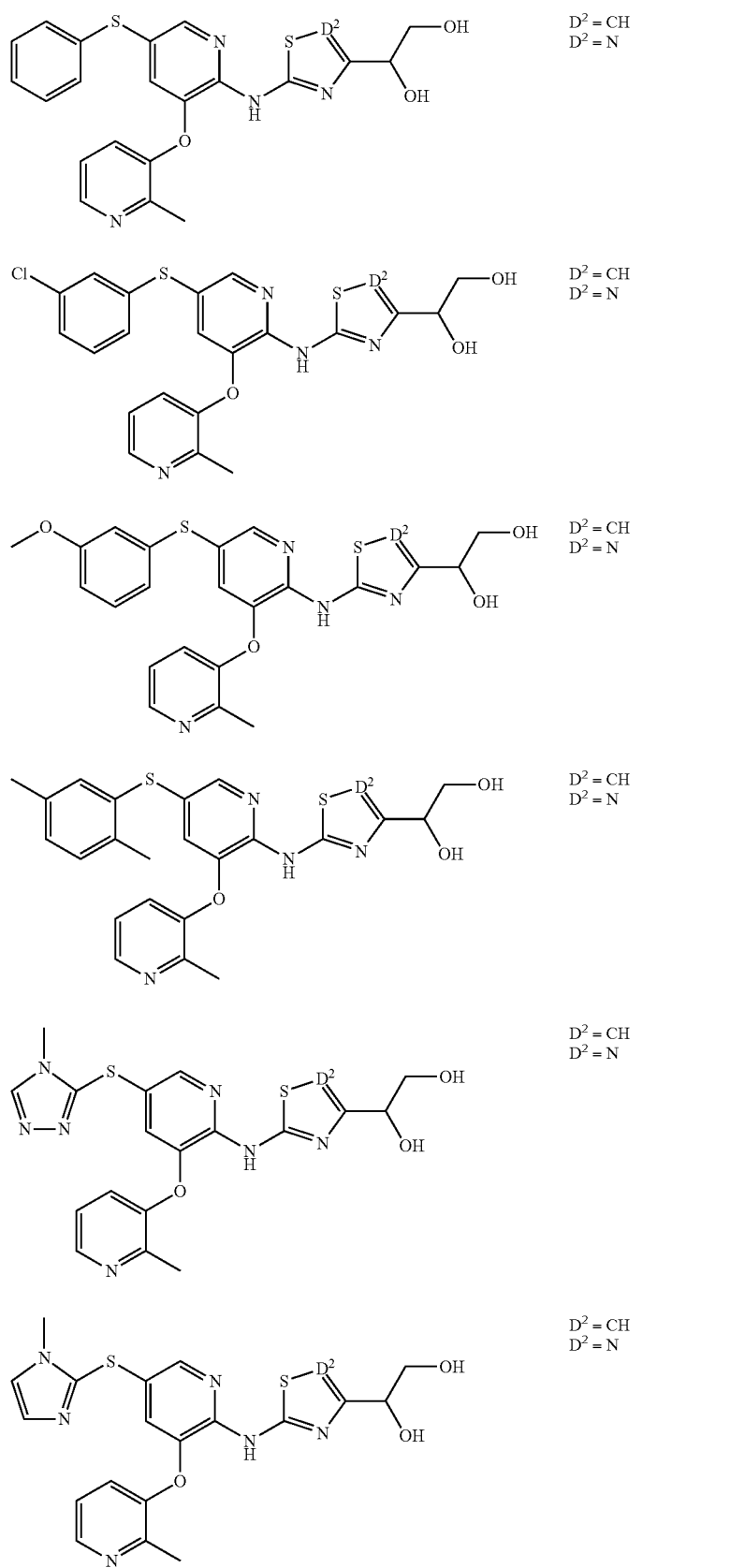

-continued
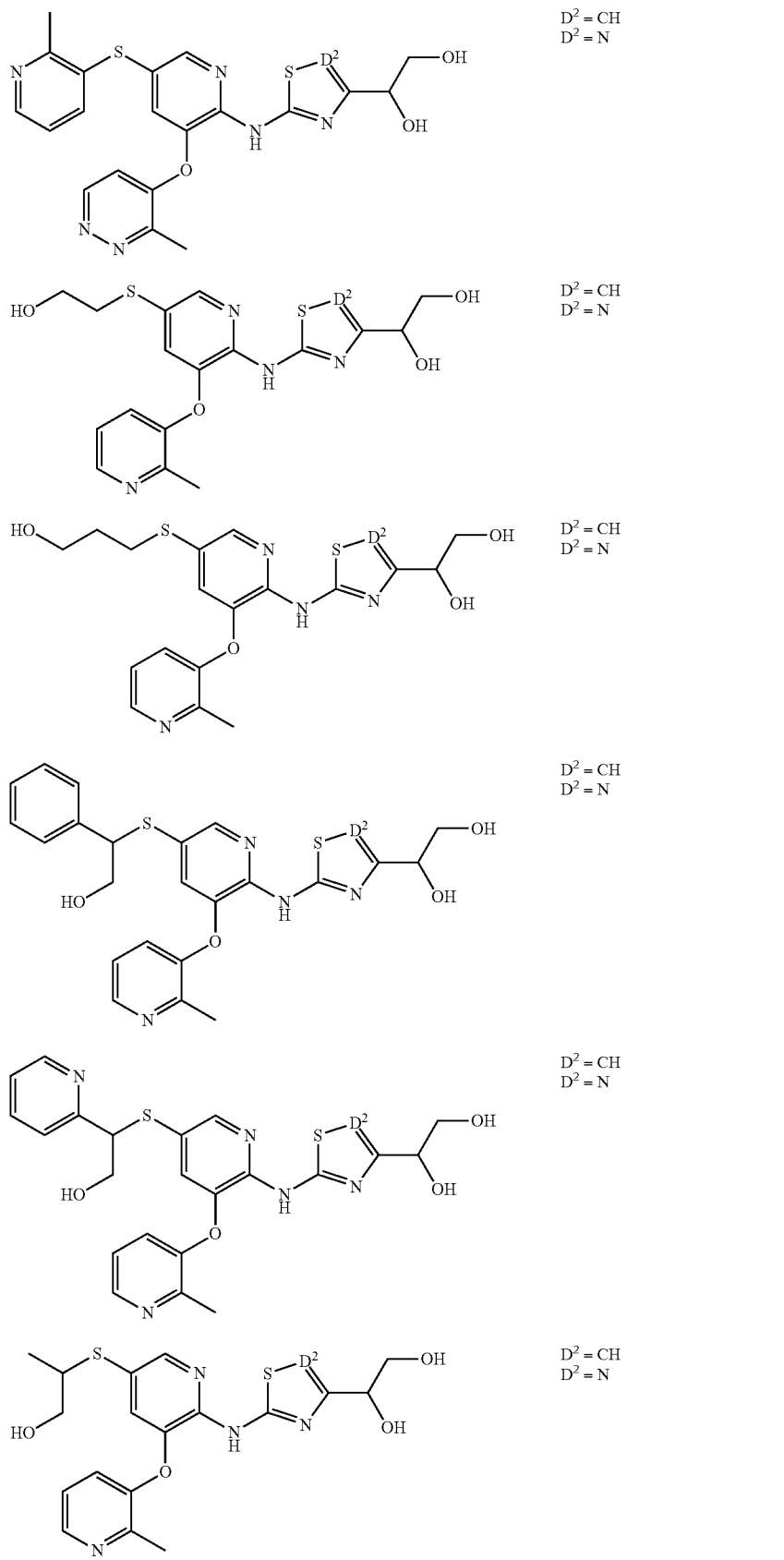
D² = CH
D² = N
D² = CH
D² = N
D² = CH
D² = N
D² = CH
D² = N
D² = CH
D² = N
D² = CH
D² = N -continued
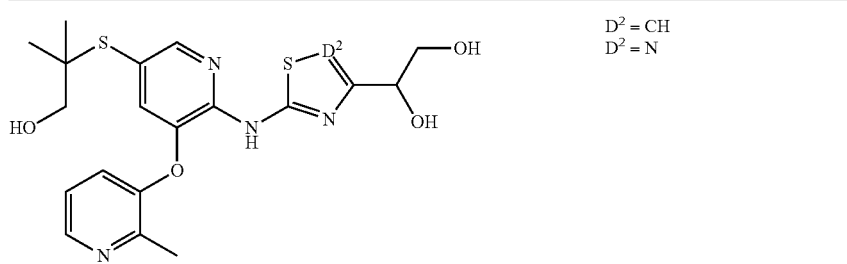
D² = CH
D² = N
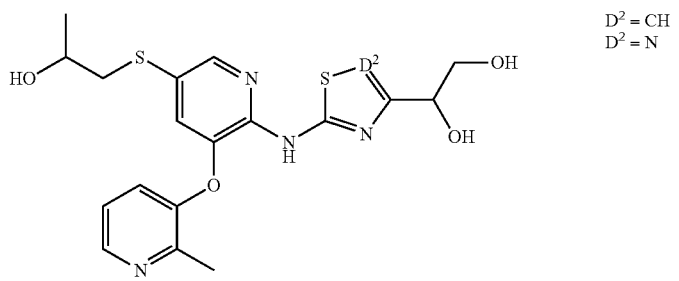
D² = CH
D² = N
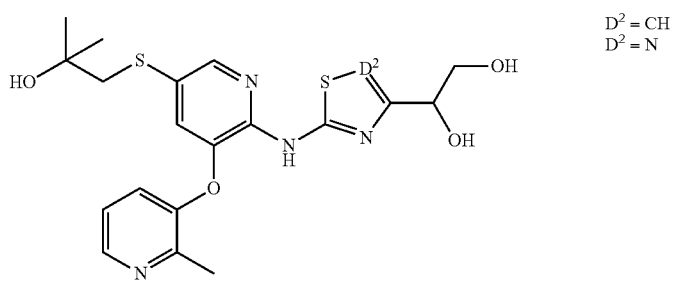
D² = CH
D² = N
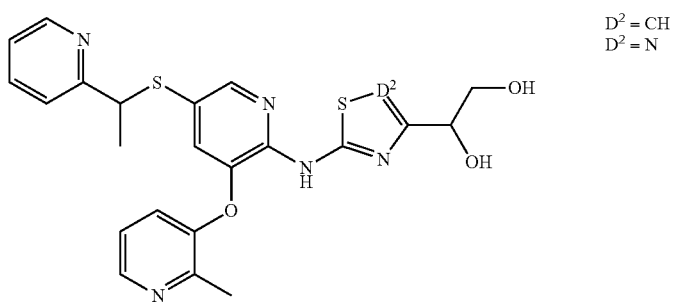
D² = CH
D² = N
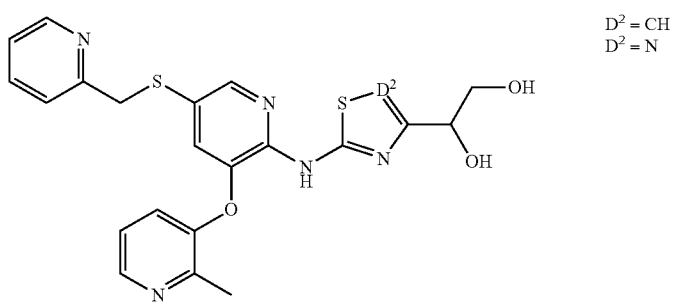
D² = CH
D² = N

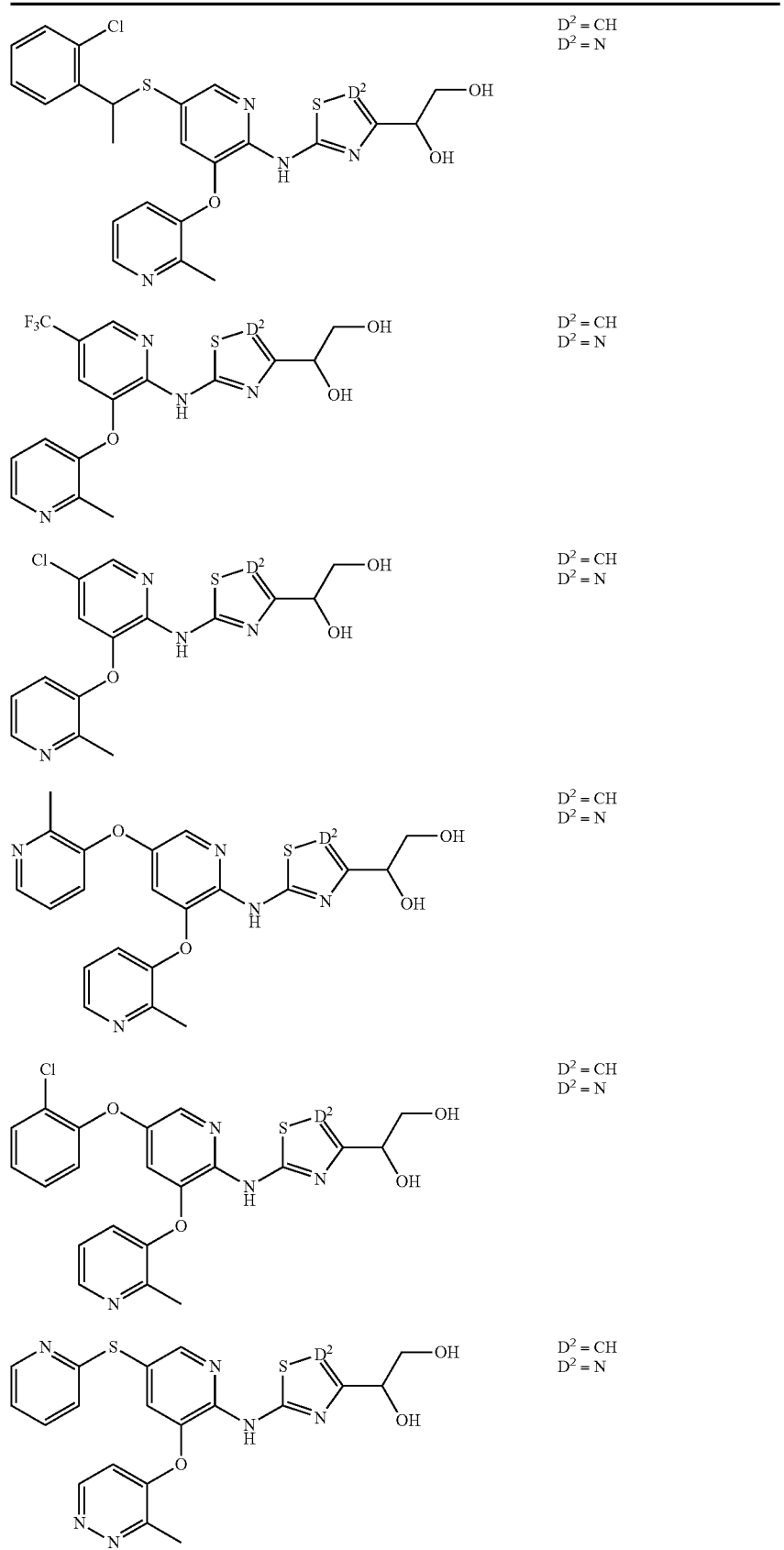

-continued
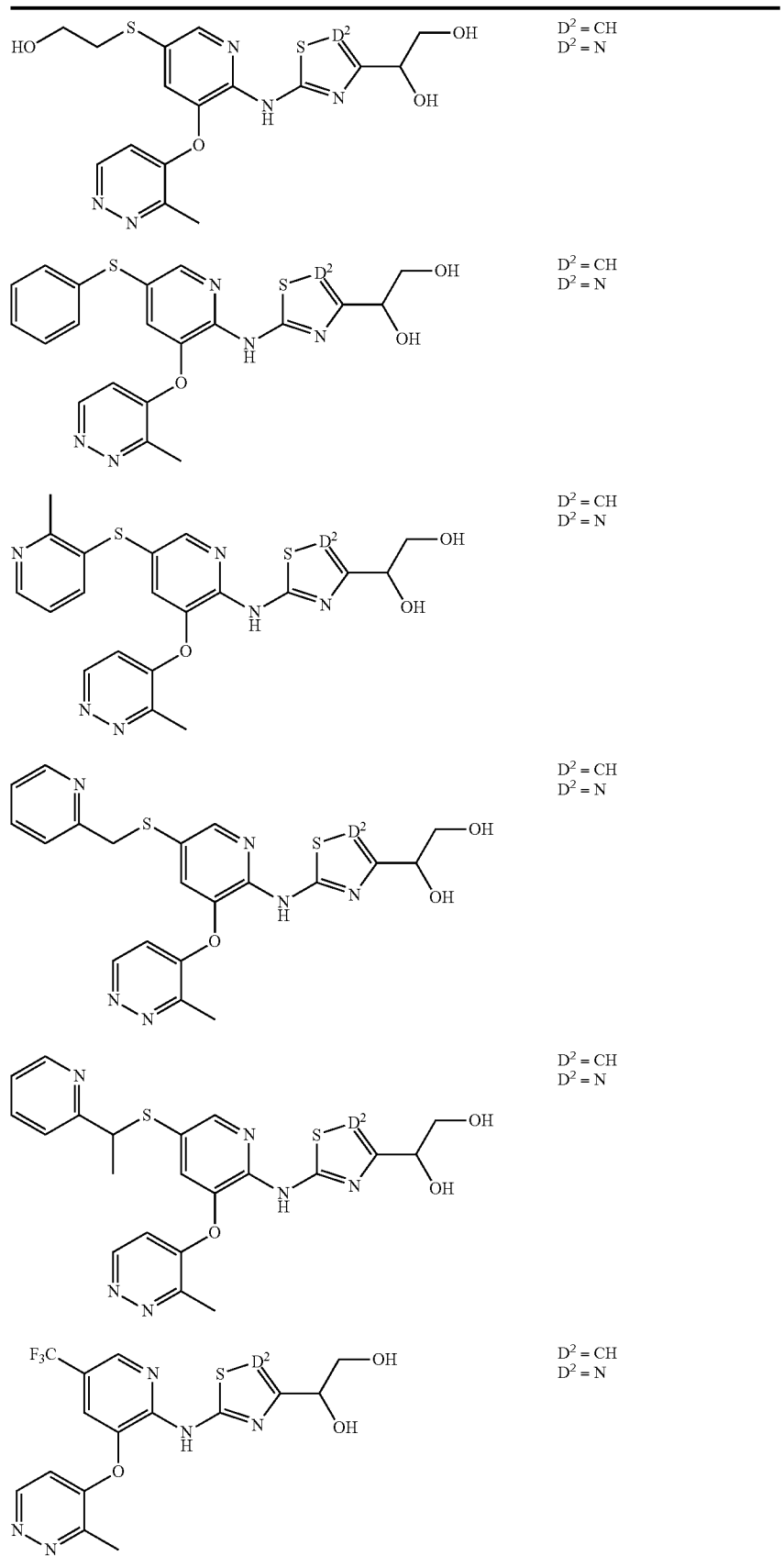
D² = CH
D² = N
D² = CH
D² = N
D² = CH
D² = N
D² = CH
D² = N
D² = CH
D² = N
D² = CH
D² = N -continued
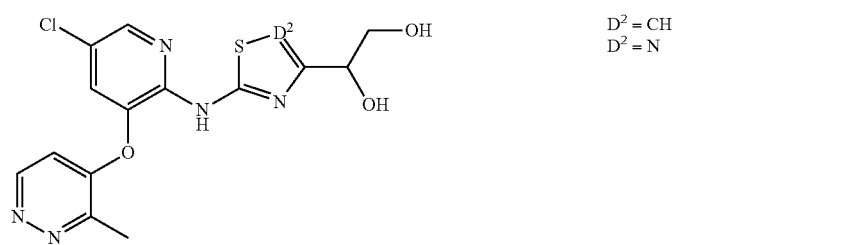 D² = CH
D² = N
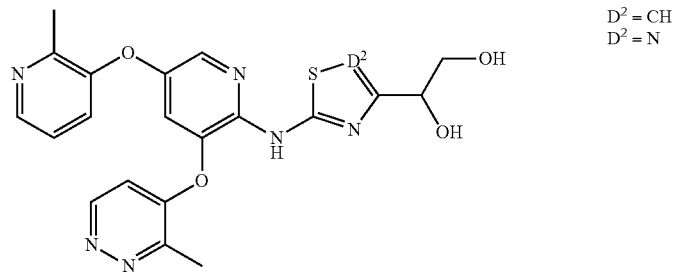 D² = CH
D² = N
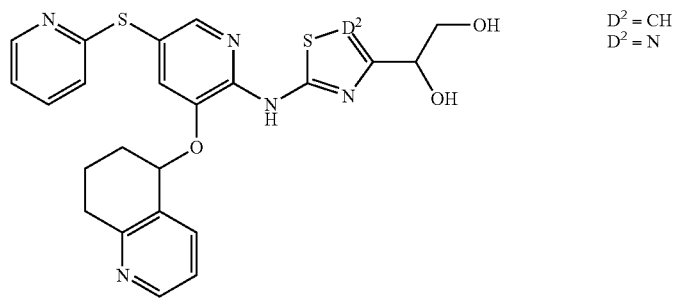 D² = CH
D² = N
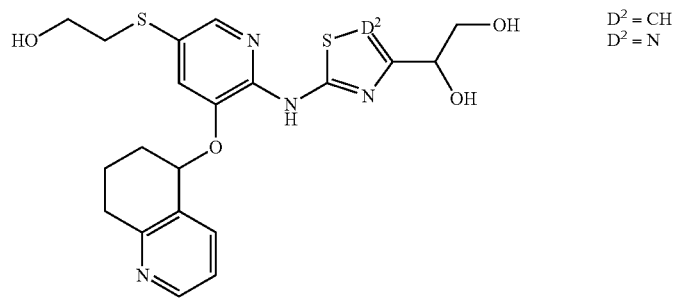 D² = CH
D² = N
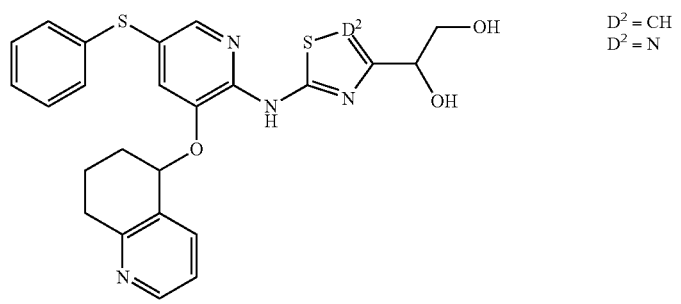 D² = CH
D² = N

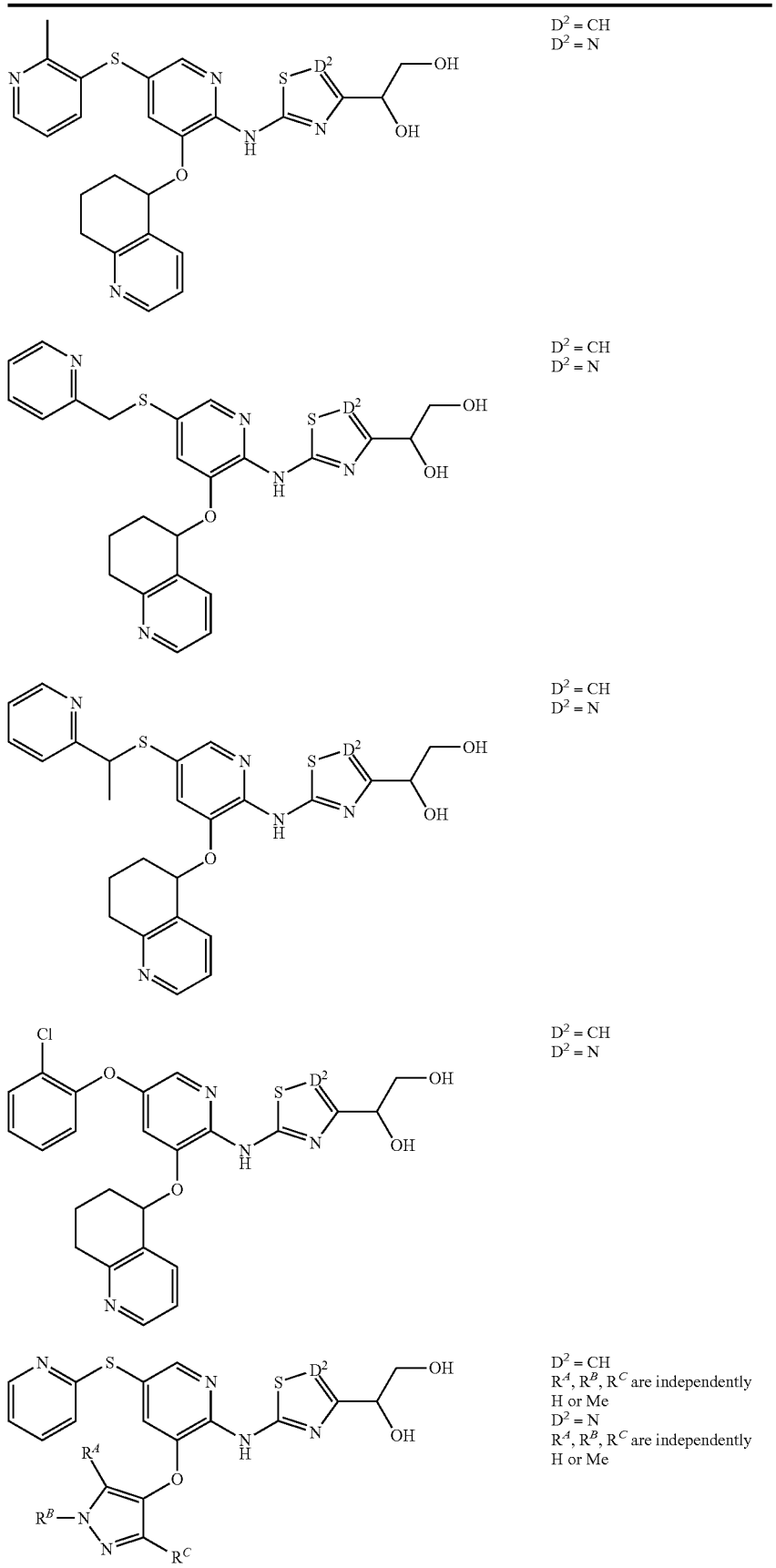

| | |
|---|---|
| 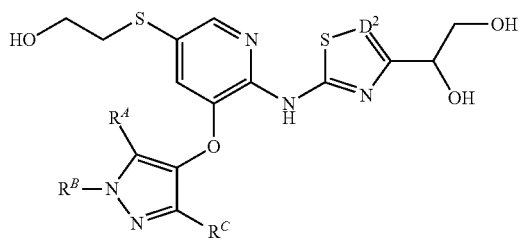 | $D^2$ = CH<br>$R^A, R^B, R^C$ are independently H or Me<br>$D^2$ = N<br>$R^A, R^B, R^C$ are independently H or Me |
| 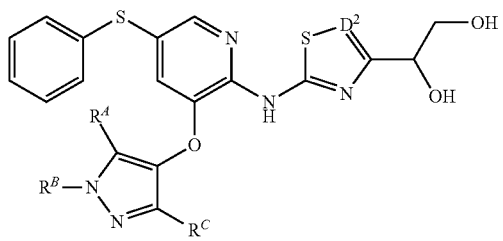 | $D^2$ = CH<br>$R^A, R^B, R^C$ are independently H or Me<br>$D^2$ = N<br>$R^A, R^B, R^C$ are independently H or Me |
| 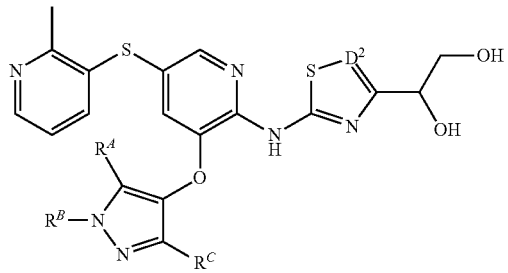 | $D^2$ = CH<br>$R^A, R^B, R^C$ are independently H or Me<br>$D^2$ = N<br>$R^A, R^B, R^C$ are independently H or Me |
| 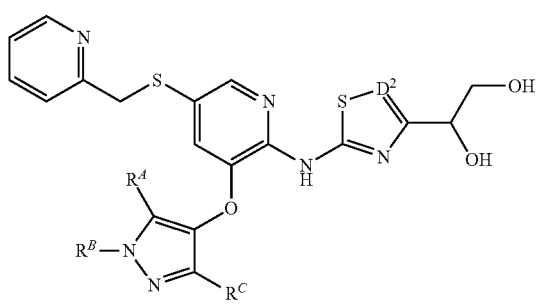 | $D^2$ = CH<br>$R^A, R^B, R^C$ are independently H or Me<br>$D^2$ = N<br>$R^A, R^B, R^C$ are independently H or Me |
| 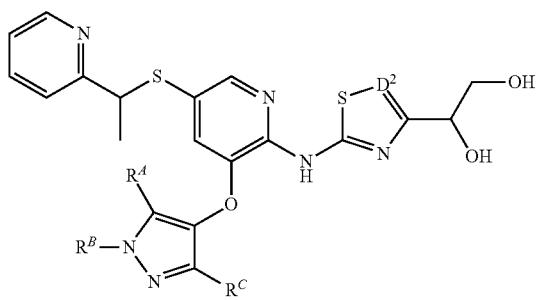 | $D^2$ = CH<br>$R^A, R^B, R^C$ are independently H or Me<br>$D^2$ = N<br>$R^A, R^B, R^C$ are independently H or Me |
| 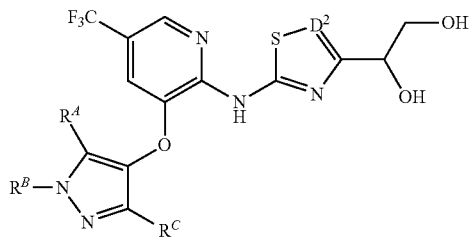 | $D^2$ = CH<br>$R^A, R^B, R^C$ are independently H or Me<br>$D^2$ = N<br>$R^A, R^B, R^C$ are independently H or Me |

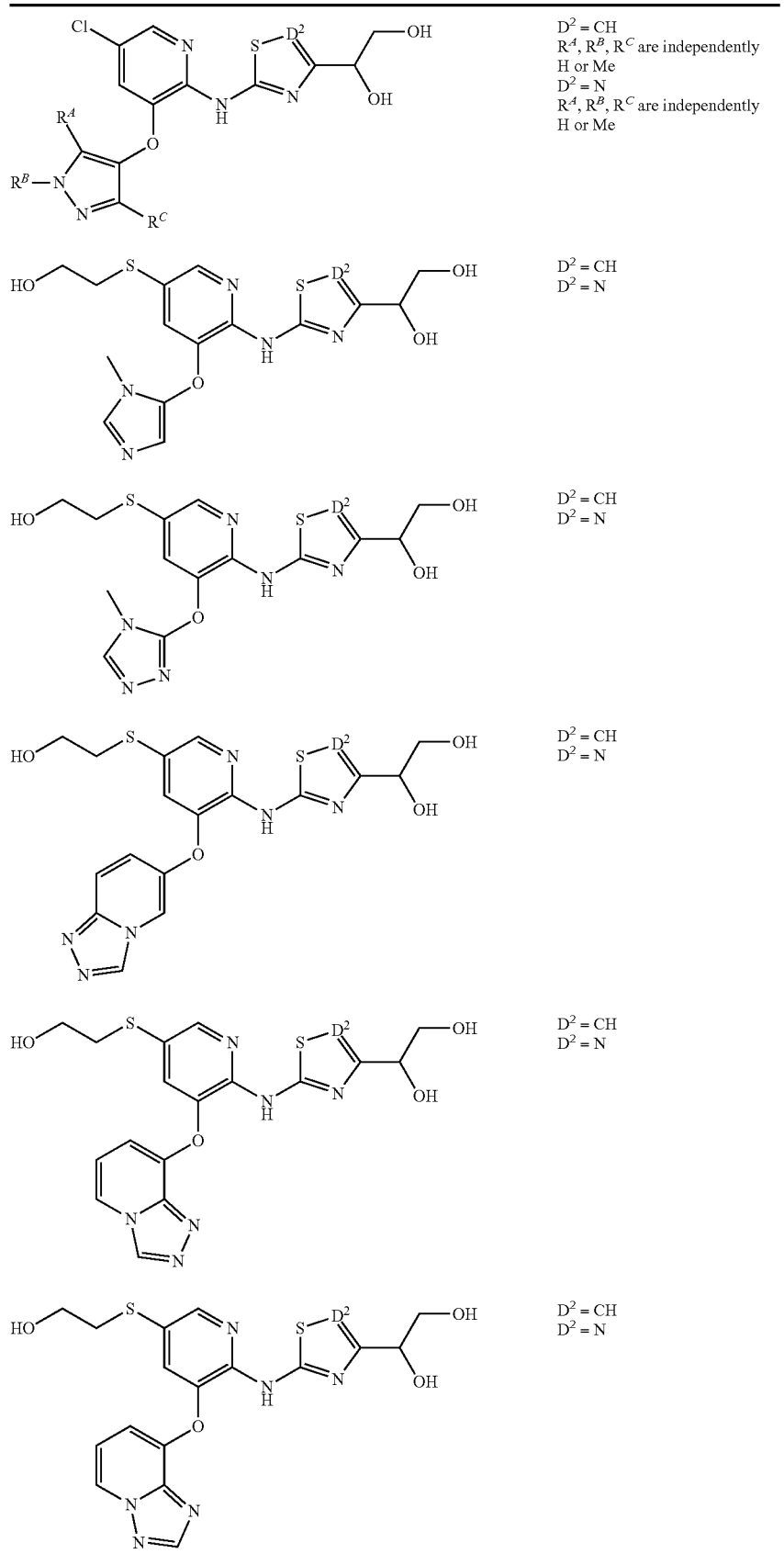

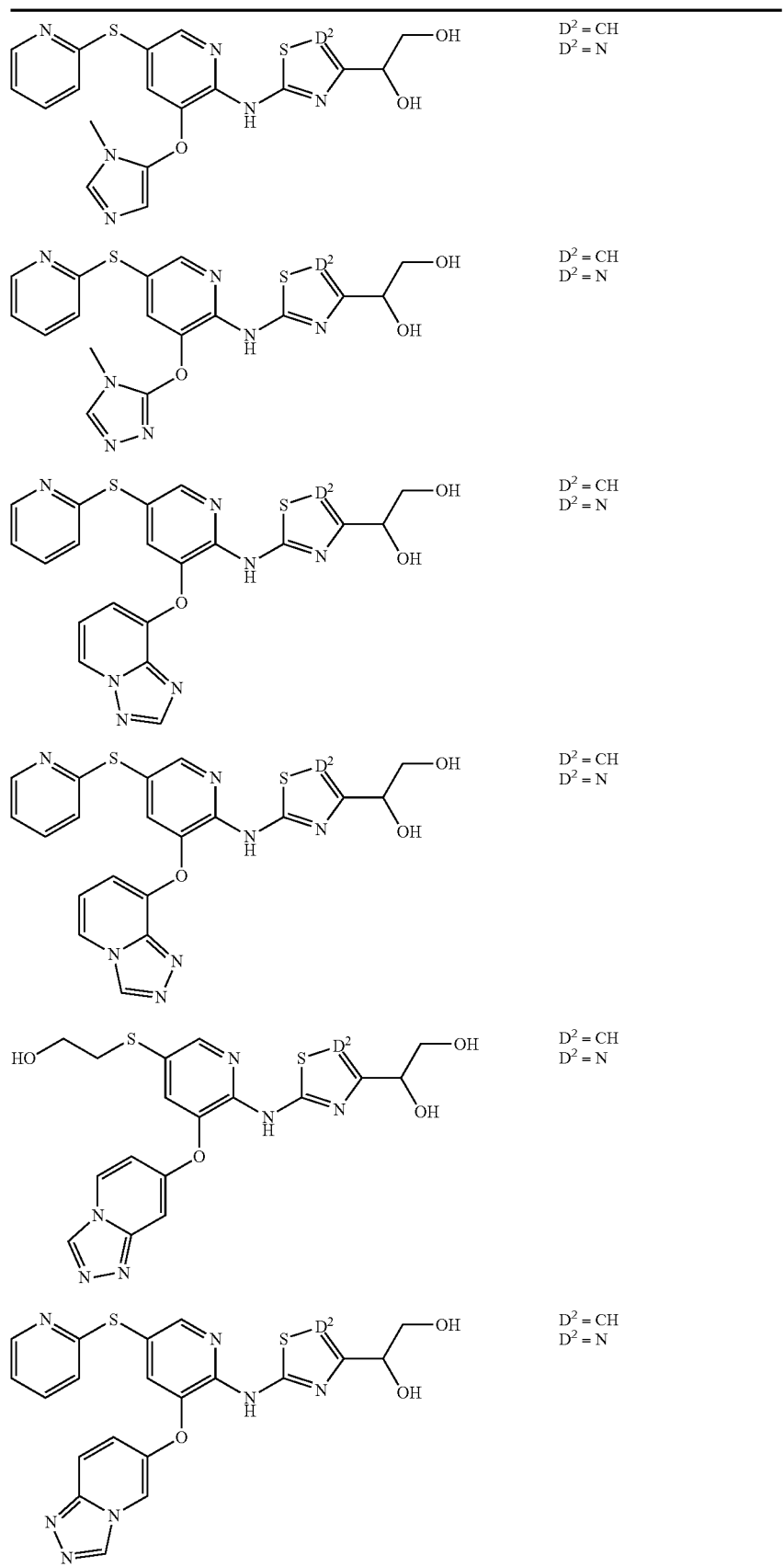

-continued
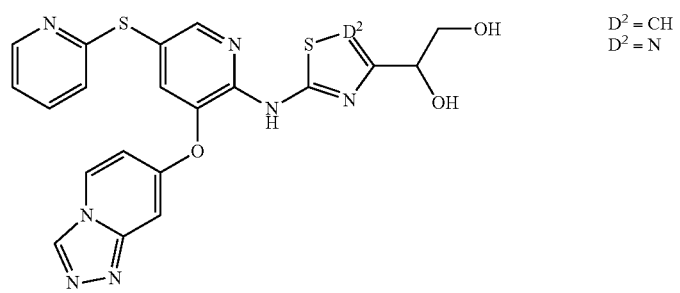
D² = CH
D² = N
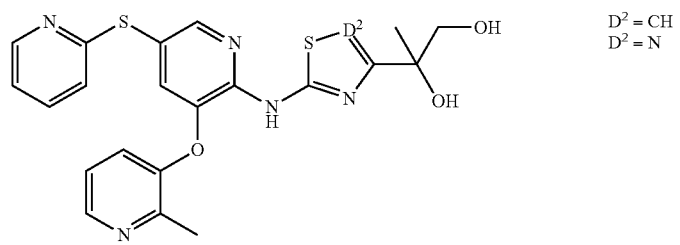
D² = CH
D² = N
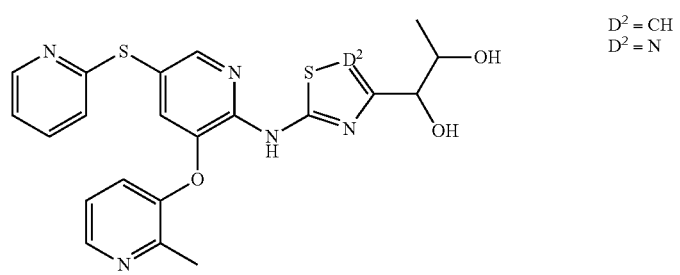
D² = CH
D² = N
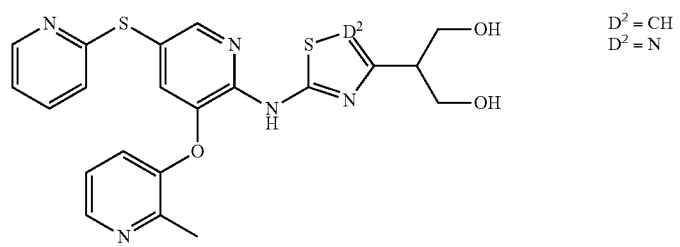
D² = CH
D² = N
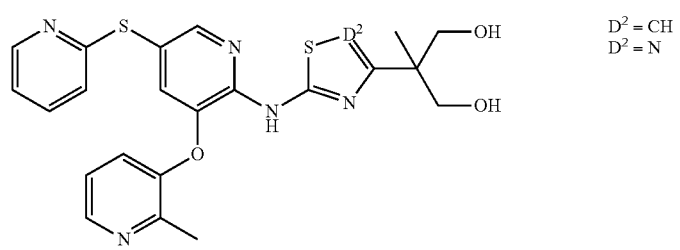
D² = CH
D² = N
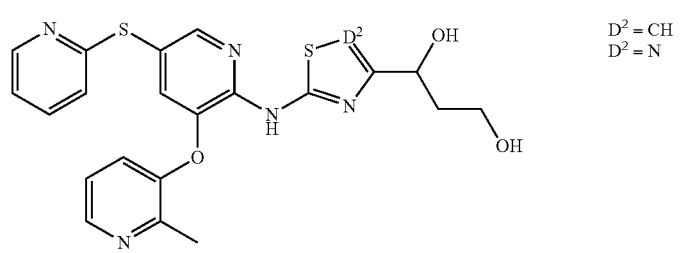
D² = CH
D² = N

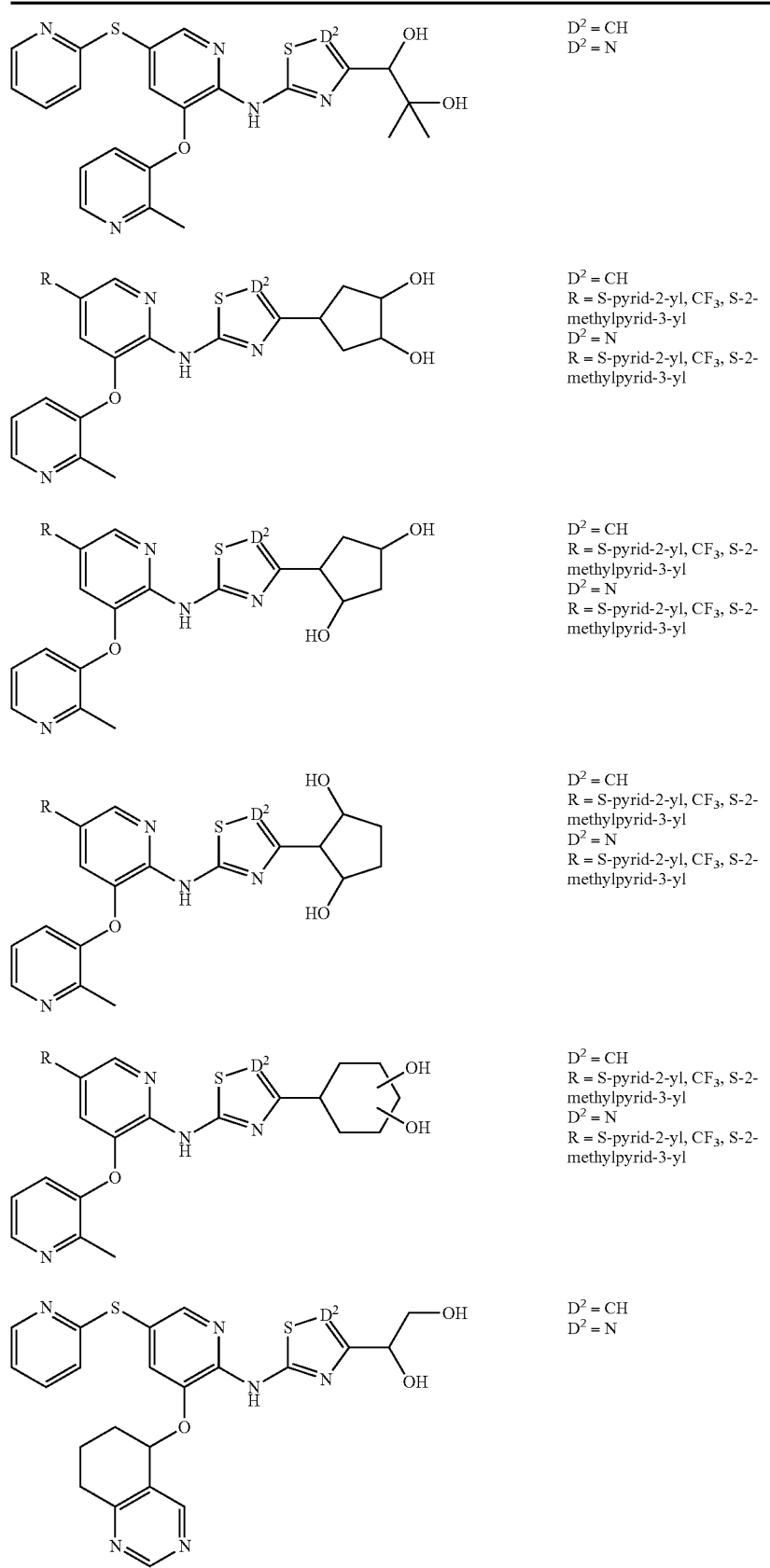

-continued
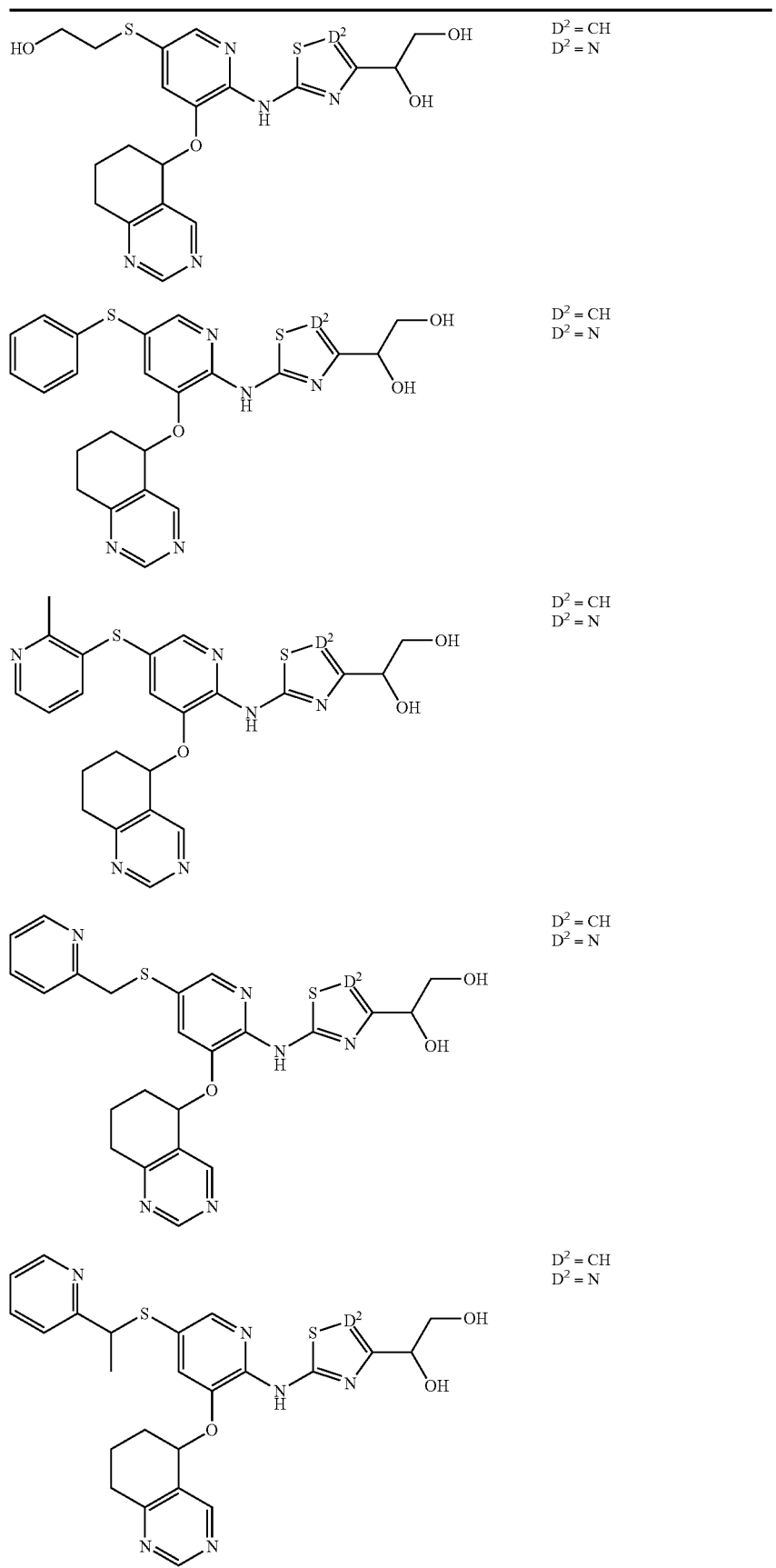

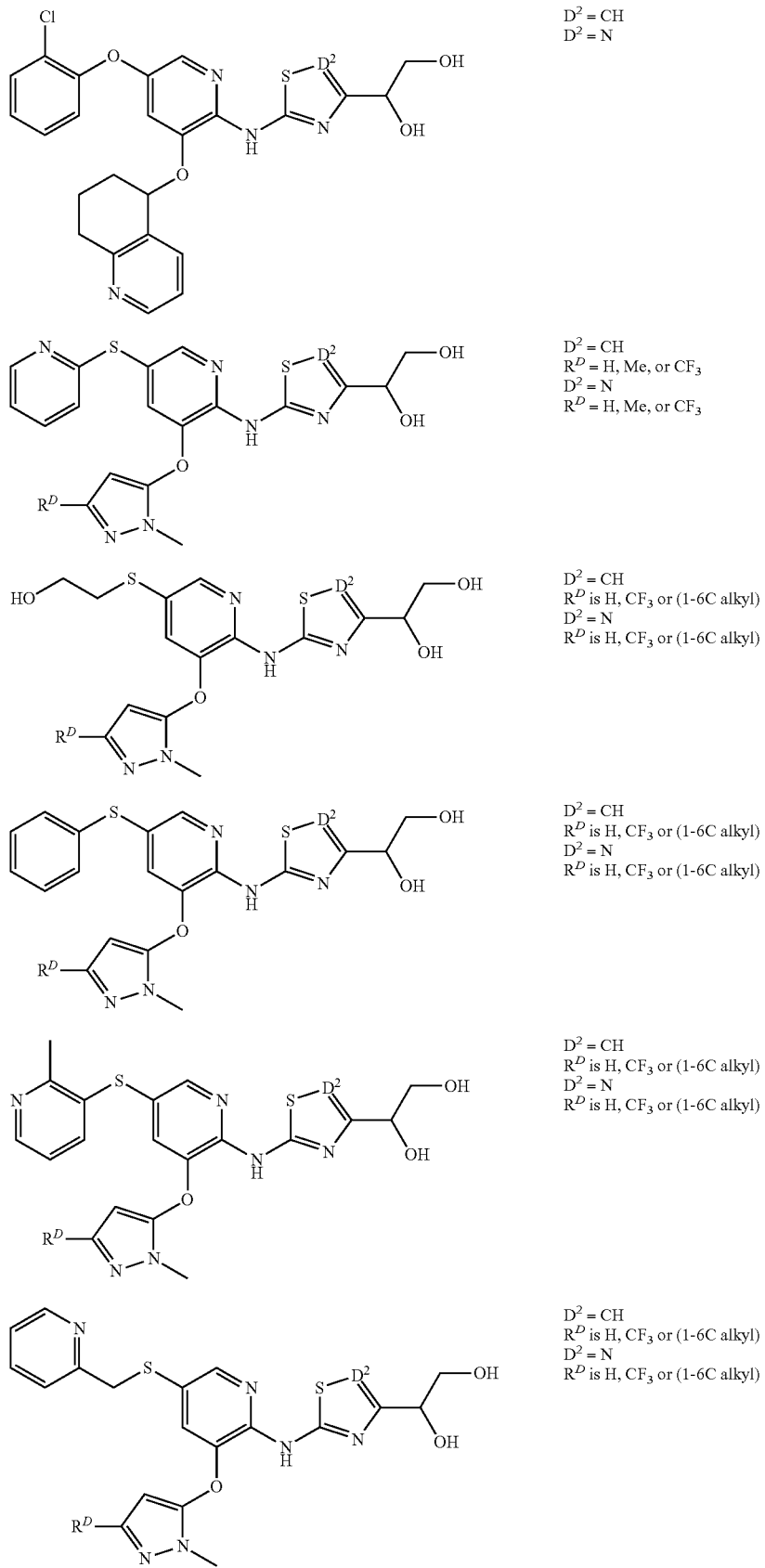
$D^2$ = CH
$D^2$ = N
$D^2$ = CH
$R^D$ = H, Me, or $CF_3$
$D^2$ = N
$R^D$ = H, Me, or $CF_3$
$D^2$ = CH
$R^D$ is H, $CF_3$ or (1-6C alkyl)
$D^2$ = N
$R^D$ is H, $CF_3$ or (1-6C alkyl)
$D^2$ = CH
$R^D$ is H, $CF_3$ or (1-6C alkyl)
$D^2$ = N
$R^D$ is H, $CF_3$ or (1-6C alkyl)
$D^2$ = CH
$R^D$ is H, $CF_3$ or (1-6C alkyl)
$D^2$ = N
$R^D$ is H, $CF_3$ or (1-6C alkyl)
$D^2$ = CH
$R^D$ is H, $CF_3$ or (1-6C alkyl)
$D^2$ = N
$R^D$ is H, $CF_3$ or (1-6C alkyl)

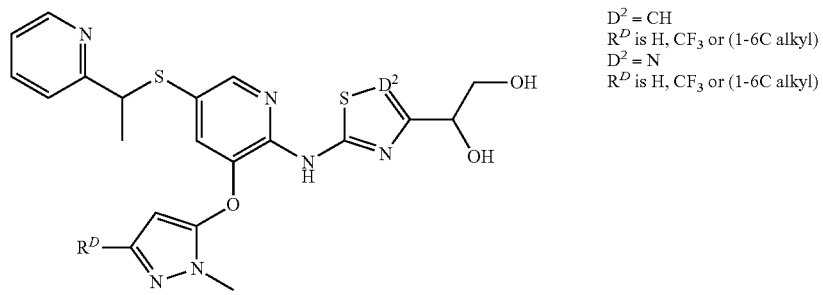
D² = CH
R^D is H, CF₃ or (1-6C alkyl)
D² = N
R^D is H, CF₃ or (1-6C alkyl)
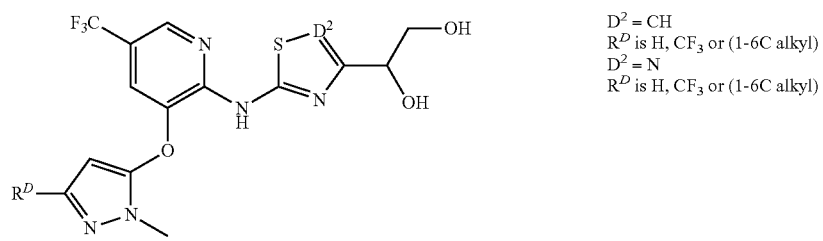
D² = CH
R^D is H, CF₃ or (1-6C alkyl)
D² = N
R^D is H, CF₃ or (1-6C alkyl)
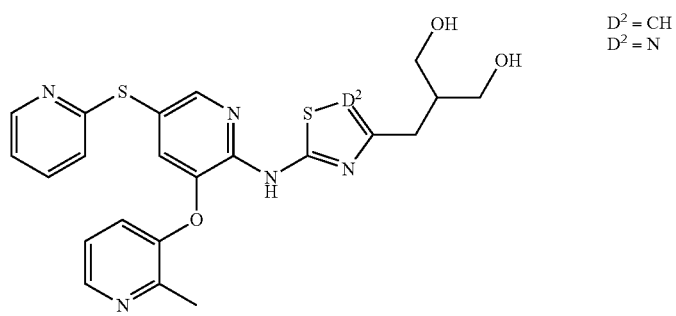
D² = CH
D² = N
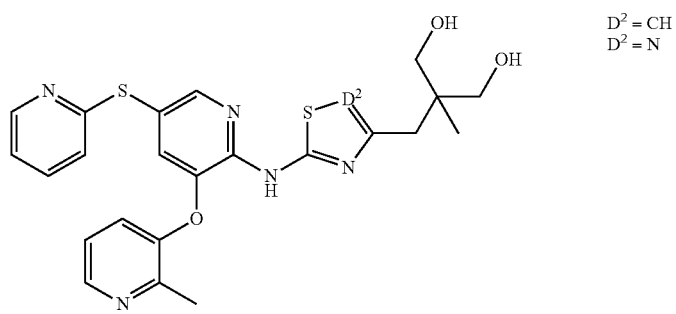
D² = CH
D² = N
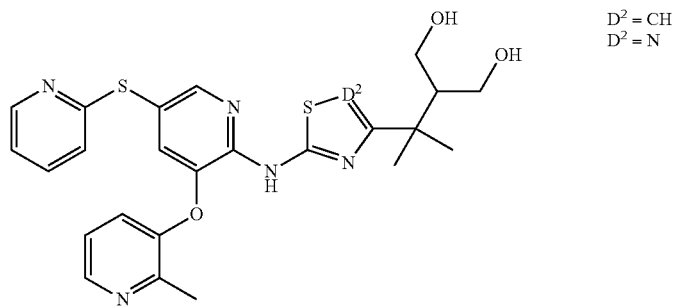
D² = CH
D² = N

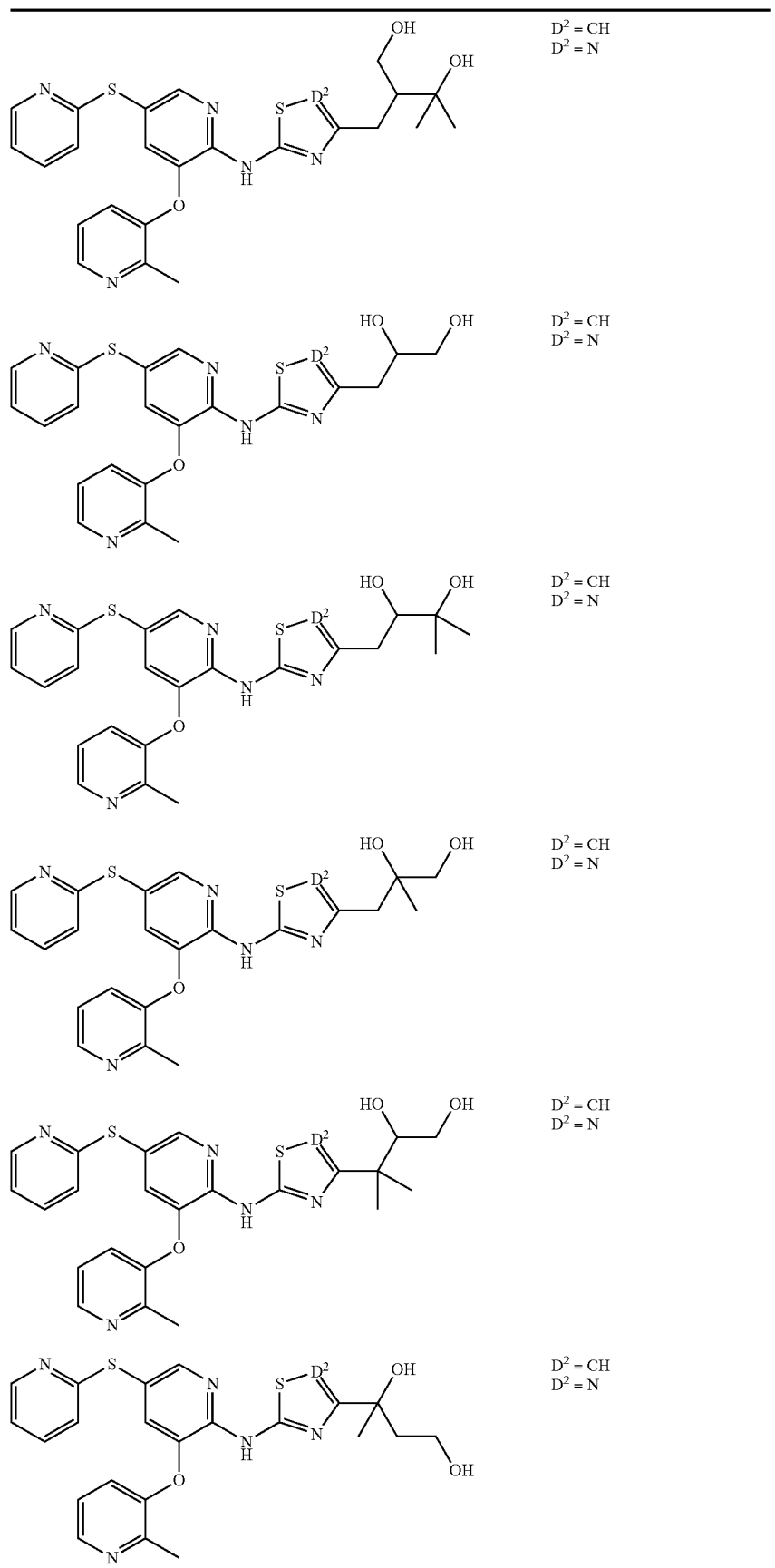

-continued
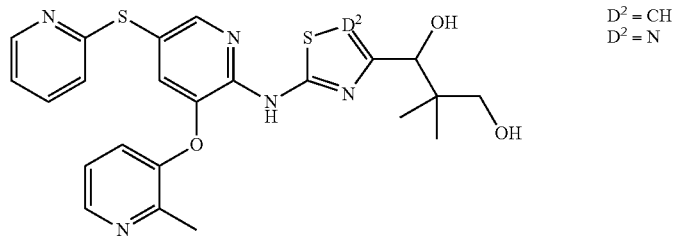
D² = CH
D² = N
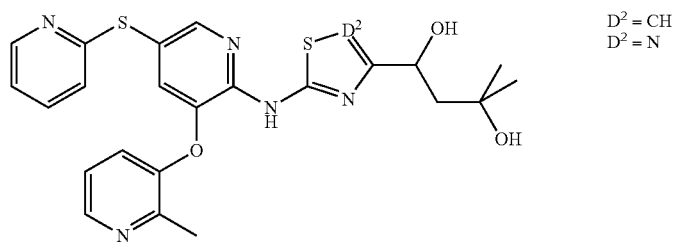
D² = CH
D² = N
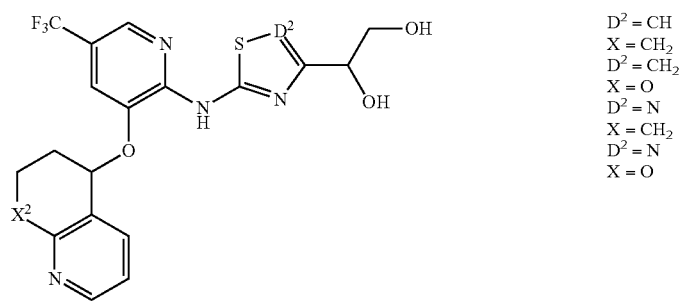
D² = CH
X = CH₂
D² = CH
X = O
D² = N
X = CH₂
D² = N
X = O
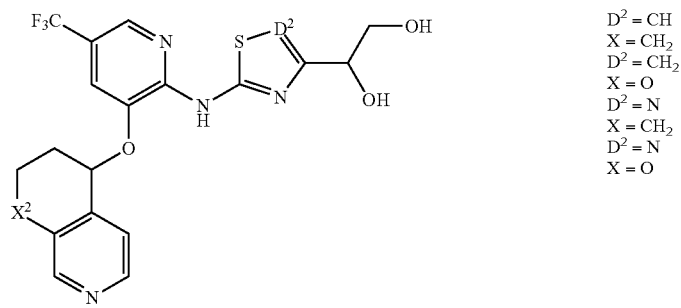
D² = CH
X = CH₂
D² = CH
X = O
D² = N
X = CH₂
D² = N
X = O
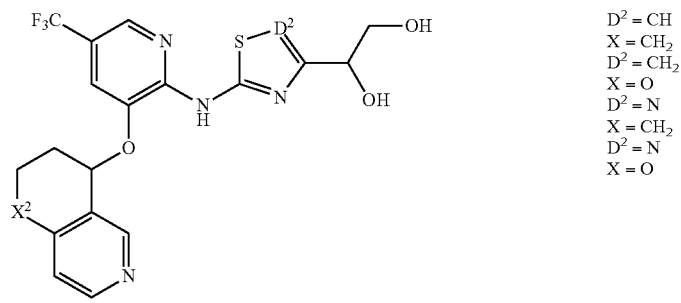
D² = CH
X = CH₂
D² = CH
X = O
D² = N
X = CH₂
D² = N
X = O

D² = CH
X = CH₂
D² = CH₂
X = O
D² = N
X = CH₂
D² = N
X = O
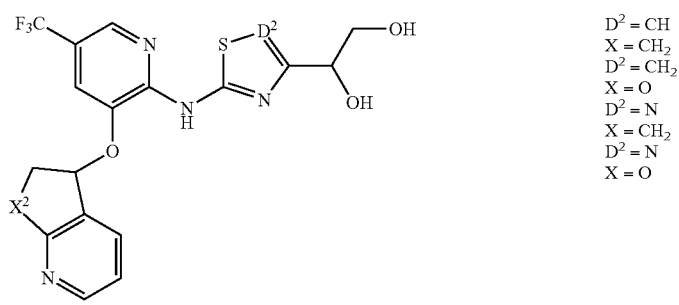
D² = CH
X = CH₂
D² = CH₂
X = O
D² = N
X = CH₂
D² = N
X = O
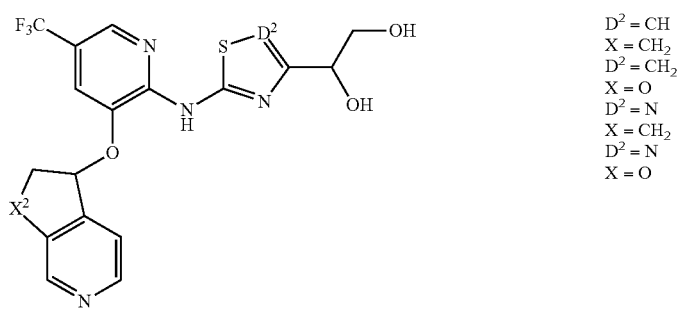
D² = CH
X = CH₂
D² = CH₂
X = O
D² = N
X = CH₂
D² = N
X = O
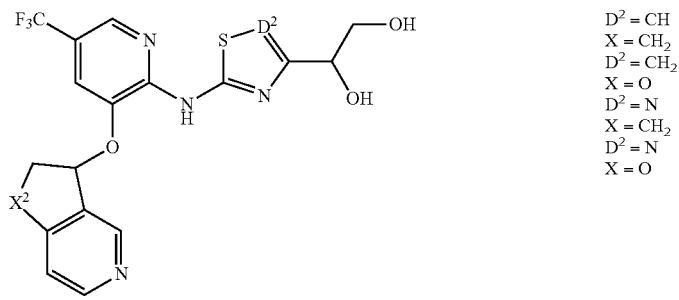
D² = CH
X = CH₂
D² = CH₂
X = O
D² = N
X = CH₂
D² = N
X = O
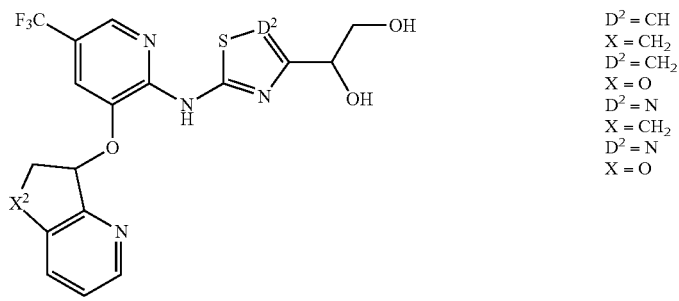
D² = CH
X = CH₂
D² = CH₂
X = O
D² = N
X = CH₂
D² = N
X = O -continued
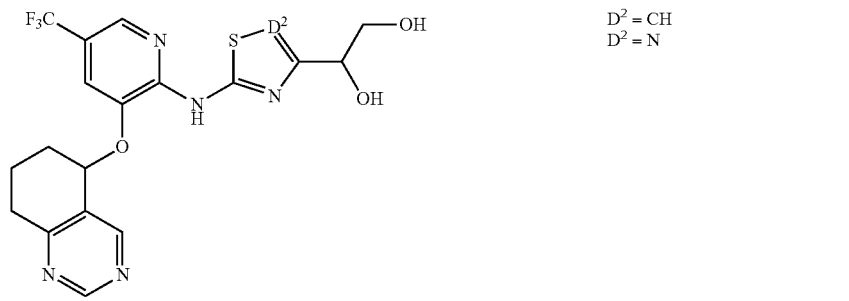 D² = CH
D² = N
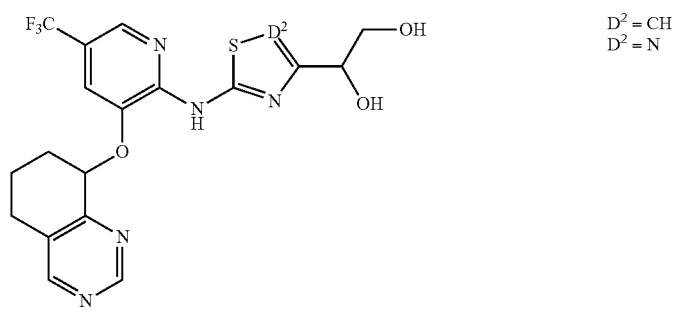 D² = CH
D² = N
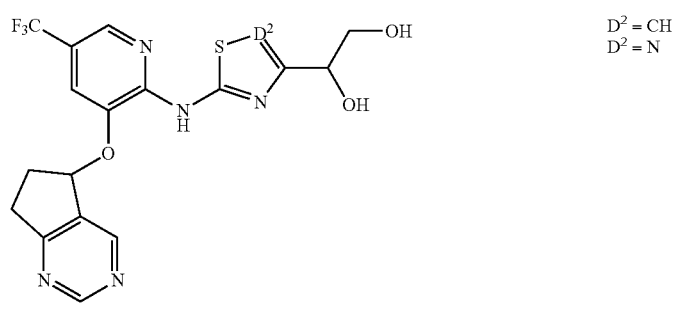 D² = CH
D² = N
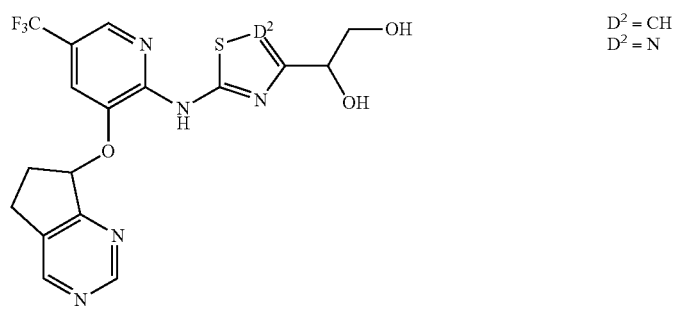 D² = CH
D² = N
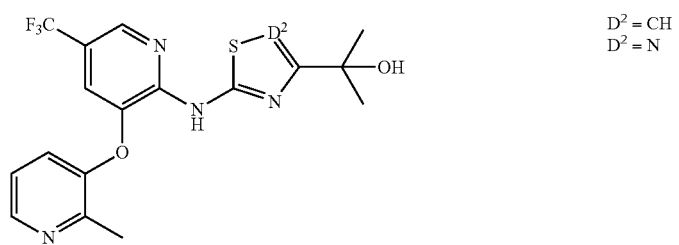 D² = CH
D² = N

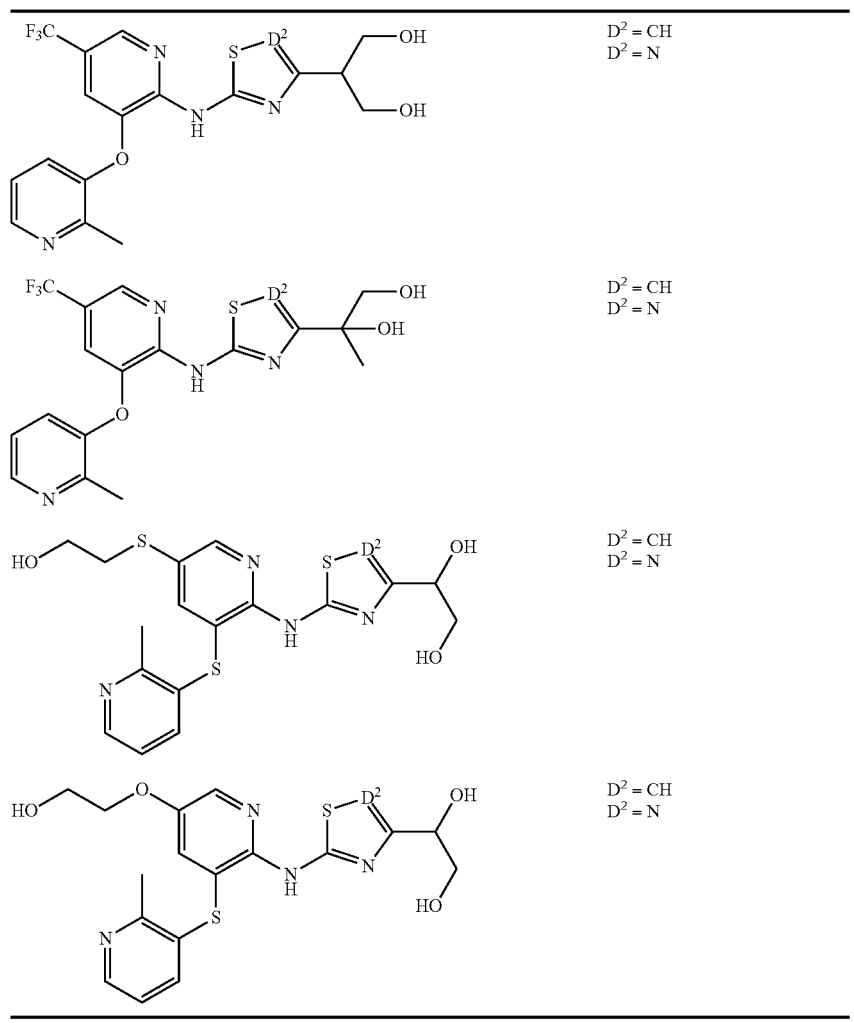

| | |
|---|---|
| | $D^2$ = CH<br>$D^2$ = N |
| | $D^2$ = CH<br>$D^2$ = N |
| | $D^2$ = CH<br>$D^2$ = N |
| | $D^2$ = CH<br>$D^2$ = N |

(S)-1-(5-(3-(2-methylpyridin-3-yloxy)-5-(pyridin-2-ylthio) pyridin-2-ylamino)-1,2,4-thiadiazol-3-yl)ethane-1,2-diol;

(S)-1-(5-(3-(2,6-dimethylpyridin-3-yloxy)-5-(pyridin-2-ylthio)pyridin-2-ylamino)-1,2,4-thiadiazol-3-yl)ethane-1, 2-diol;

(S)-1-(5-(5-(cyclopropylmethylthio)-3-(2-methylpyridin-3-yloxy)pyridin-2-yl-amino)-1,2,4-thiadiazol-3-yl)ethane-1,2-diol;

(S)-1-(5-(3-(2-ethylpyridin-3-yloxy)-5-(pyridin-2-ylthio) pyridin-2-ylamino)-1,2,4-thiadiazol-3-yl)ethane-1,2-diol;

(S)-1-(5-(5-(3-methoxypropylthio)-3-(2-methylpyridin-3-yloxy)pyridin-2-ylamino)-1,2,4-thiadiazol-3-yl)ethane-1, 2-diol;

(S)-1-(5-(3-(1-Ethyl-1H-pyrazol-5-yloxy)-5-(pyridin-2-ylthio)pyridin-2-ylamino)-1,2,4-thiadiazol-3-yl)ethane-1, 2-diol;

(S)-1-(5-(3-(1-ethyl-1H-pyrazol-5-yloxy)-5-(pyridin-2-ylthio)pyridin-2-ylamino)-1,2,4-thiadiazol-3-yl)-2-methylpropane-1,2-diol;

(S)-1-(5-(5-(3-methylpyridin-2-ylthio)-3-(2-methylpyridin-3-yloxy)pyridin-2-yl-amino)-1,2,4-thiadiazol-3-yl) ethane-1,2-diol;

(S)-1-(5-(3-(2,4-dimethylpyridin-3-yloxy)-5-(pyridin-2-ylthio)pyridin-2-ylamino)-1,2,4-thiadiazol-3-yl)ethane-1, 2-diol;

(S)-2-methyl-1-(5-(3-(2-methylpyridin-3-yloxy)-5-(pyridin-2-ylthio)pyridin-2-ylamino)-1,2,4-thiadiazol-3-yl)propane-1,2-diol;

(S)-1-(5-(5-(2-methoxyethylthio)-3-(2-methylpyridin-3-yloxy)pyridin-2-ylamino)-1,2,4-thiadiazol-3-yl)ethane-1, 2-diol;

(1S,2S)-1-(5-(3-(2-ethylpyridin-3-yloxy)-5-(pyridin-2-ylthio)pyridin-2-ylamino)-1,2,4-thiadiazol-3-yl)-3-methoxypropane-1,2-diol;

(S)-2-methyl-1-(5-(5-(pyridin-2-ylthio)-3-(1,3,5-trimethyl-1H-pyrazol-4-yloxy)-pyridin-2-ylamino)-1,2,4-thiadiazol-3-yl)propane-1,2-diol;

(S)-1-(5-(5-(pyridin-2-ylthio)-3-(1,3,5-trimethyl-1H-pyrazol-4-yloxy)pyridin-2-yl-amino)-1,2,4-thiadiazol-3-yl) ethane-1,2-diol;

(S)-1-(5-(5-(2-methoxyethylthio)-3-(1,3,5-trimethyl-1H-pyrazol-4-yloxy)pyridin-2-yl-amino)-1,2,4-thiadiazol-3-yl)ethane-1,2-diol;

(R)-1-(5-(3-(2-methylpyridin-3-yloxy)-5-(pyridin-2-ylthio) pyridin-2-ylamino)-1,2,4-thiadiazol-3-yl)ethane-1,2-diol;

(S)-2-(5-(3-(2-methylpyridin-3-yloxy)-5-(pyridin-2-ylthio) pyridin-2-ylamino)-1,2,4-thiadiazol-3-yl)propane-1,2-diol; or (R)-2-(5-(3-(2-methylpyridin-3-yloxy)-5-(pyridin-2-ylthio) pyridin-2-ylamino)-1,2,4-thiadiazol-3-yl)propane-1,2-diol, or the pharmaceutically acceptable salts thereof.

Other compounds that may be used in combination with the compounds of the present invention include the IL1-R1 compounds set forth in U.S. Pat. No. 7,438,910. A particular disease that can be treated with the combination is type 2 diabetes.

The compounds of the present invention can also be used in combination with FGF-21 compounds, and particularly for the treatment of type 2 diabetes. Examples of FGF-21 compounds are disclosed in U.S. Pat. No. 7,671,180; U.S. Pat. No. 7,667,008; U.S. Pat. No. 7,459,540; U.S. Pat. No. 7,696,172; PCT application publication no. WO 2010/042747; and PCT application publication no. WO 2009/149171.

The compounds of the present invention can be also be used in combination with anakinra, particularly for the treatment of type 2 diabetes.

In one particular aspect, the compounds of the present invention may be used in combination with metformin.

The compounds of the present invention are used in the treatment diseases or symptoms mediated by GKRP and/or GK (GKRP/GK). Examples of diseases or symptoms mediated by GKRP/GK include, but are not limited to, Type II (type 2) diabetes and related disorders, such as hyperglycemia, low or impaired glucose tolerance, insulin resistance, obesity, lipid disorders such as dyslipidemia, hyperlipidemia, hypertriglyceridemia, hypercholesterolernia, low HDL levels, high LDL levels, atherosclerosis, and vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, neuropathy, cataracts, glaucoma, glomerulosclerosis, foot ulcerations and unlcerative colitis, altered gastrointestinal motility, Syndrome X, ovarian hyperandrogenism, polycystic ovarian syndrome, premenstrual syndrome, other disorders where insulin resistance is a component. In Syndrome X, also known as Metabolic Syndrome, obesity is thought to promote insulin resistance, diabetes, dyslipidemia, hypertension, and increased cardiovascular risk, growth hormone deficiency, neutropenia, neuronal disorders, tumor invasion and metastasis, benign prostatic hypertrophy, gingivitis, osteoporosis, frailty of aging, intestinal injury, benign prostatic hypertrophy (BPH), and sperm motility/male contraception.

The compounds of the present invention are also useful for the prevention, delay of progression or the treatment of an early cardiac or early cardiovascular diseases or damages, renal diseases or damages, heart Failure, or heart Failure associated diseases like (i) cardiovascular diseases or damages e.g. cardiac hypertrophy, cardiac remodelling after myocardial infarction, pulmonary congestion and cardiac fibrosis in dilated or in hypertrophic cardiomyopathy, cardiomyopathy such as dilated cardiomyopathy or hypertrophic cardiomyopathy, mesanglial hypertrophy, or diabetic cardiomyopathy, left or right ventricular hypertrophy, arrhythmia, cardiac dysrhythmia, syncopy, angina pectoris, cardiac bypass reocclusion, intermittent claudication, diastolic and/or systolic dysfunction, diabetic myopathy, stroke prevention in congestive heart failure, hypertrophic medial thickening in arteries and/or large vessels, mesenteric vasculature hypertrophy or artherosclerosis, preferably artherosclerosis in mammalian patients with hypertension of diabetes; (ii) renal diseases or damages like renal hyperfiltration such as after portal renal ablation, proteinuria in chronic renal disease, renal arteriopathy as a consequence of hypertension, nephrosclerosis, hypertensive nephrosclerosis or mesanglial hypertrophy; (iii) Heart Failure to be treated is secondary to idiopathic dilated cardiomyopathy and/or coronary ischemic disease.

The compounds of the present invention can also be used for the prevention, the delay of the onset, the delay of progression or the treatment of neurodegenerative disorders, cognitive disorders and for improving memory (both short term and long term) and learning ability wherein the (i) neurodegenerative disorder is dementia, senile dementia, schizophrenia, mild cognitive impairment, Alzheimer related dementia, Huntington's chores, tardive dyskinesia, hyperkinesias, mania, Morbus Parkinson, Steel-Richard syndrome, Down's syndrome, myasthenia gravis, nerve and brain trauma, vascular amyloidosis, cerebral haemorrhage I with amyloidosis, brain inflammation, Friedrich ataxia, acute confusion disorders, acute confusion disorders with apoptotic necrocytosis, amyotrophic lateral sclerosis, glaucoma, and Alzheimer's disease; (ii) cognitive disorders like cognitive deficits associated with schizophrenia, age-induced memory impairment, cognitive deficits associated with psychosis, cognitive impairment associated with diabetes, cognitive deficits associated with post-stroke, memory defects associated hypoxia, cognitive and attention deficits associated with senile dementia, attention deficits disorders, memory problems associated with mild cognitive impairment, impaired cognitece function associated with vascular dementia, cognitive problems associated with brain tumors, Pick's disease, cognitive deficits due to autism, cognitive deficits post electroconvulsive therapy, cognitive deficits associated with traumatic brain injury, amnesic disorders, deliriums, vitamin deficiency, dementias, impaired cognitive function associated with Parkinson's disease, attention-deficit disorders; (iii) prevention of memory impairment as a result of Alzheimer disease, Creutzfeld-Jakob disease, Pick disease, Huntington disease, AIDS, brain injury, brain aneurysm, epilepsy, stroke, toxicant exposure, mental retardation in children, Huntington's disease; (iv) to improve learning speed and potential in educational and rehabilitation contexts.

The compounds of the present invention can also be used for stimulating an immune response in a subject having or at risk of having cancer wherein the cancer is selected from the group consisting of basal cell carcinomas including cancers of the binary tract, bladder, urinary system, bone, brain, breast, cervical, endometrial, ovarian, uterine, choriocarcinoma, central nervous system, colon and rectal cancers, connective tissue cancer, cancer of the digestive system, esophageal, gastric, stomach, larynx, liver, pancreatic, colorectal, renal cancers; cancers of the urinary system; cancers of eye, head and neck, oral cavity, skin, prostate; cancers of biliary tract, testicular, thyroid; intra-epithelial neoplasm, leukemia, acute myeloid leukemia, acute lymphoid leukemia, chronic myeloid leukemia, chronic lymphoid leukemia; and other cancers of the respiratory system, lung, small cell lung, non-small cell lung; lymphoma, Hodgkin's lymphoma, Non-Hodgkin's lymphoma; melanoma, myeloma, neuroblastoma, retinoblastoma, fibrosarcoma (bone or connective tissue sarcoma), rhabdomyosarcoma; and other cancers including neoplastic conditions, adipose cell tumors, adipose cell carcinomas, such as liposarcoma.

The compounds of the present invention can also be used for the treatment or prophylaxis of chronic inflammatory diseases such as autoimmune disorders like rheumatoid arthritis, systemic lupus erythematosus, multiple sclerosis, psoriasis, allergies or asthma.

The compounds of the present invention can also be used in the treatment of pain, neuropathic pain, rheumatoid pain, osteoarthritis pain, anesthesia adjunct in mammalian patients undergoing surgery, chronic pain in advanced cancer, treatment of refractory diarrhea, biliary pain caused by gallstones.

The compounds of the present invention can also be used for the treatment of mammalian patients undergoing islet/pancreas transplantation, for the prevention or the delay of transplant rejection, or allograft rejection in transplantation, for improving pancreatic function by increasing the number and size of pancreatic beta-cells in the treatment of Type 1 diabetes patients, and for improving pancreatic function by increasing the number and size of pancreatic beta-cells in general.

Furthermore, the compounds of the present invention can be used for the treatment of mammalian patients with acne, skin disorders (e.g. pigmentation disorders or psoriasis), scleroderma, mycoses; anxiety, anxiety neurosis, major depression disorder, drug abuse, alcohol addiction, insomnia, chronic fatigue, sleep apnea; anorexia nervosa; epilepsy; migraine; encephalomyelitis; osteoarthritis, osteoporosis, calcitonin-induced osteoporosis; male and female sexual dysfunction, infertility; Type 1 diabetes; immunosuppression, HIV infection; hematopoiesis, anemia; and for weight reduction.

Additionally, the compounds of the present invention are useful for the prevention, delay of progression or treatment of (i) bacterial infections from *Escherichia coli, Staphylococcus, Streptoococcus, Pseudomonas, Clostridium difficile* infection, *Legionella, Pneumococcus, Haemophilus, Klebsiella, Enterobacter, Citrobacter, Neisseria, Shigella, Salmonella, Listeria, Pasteurella, Streptobacillus, Spirillum, Treponema, Actinomyces, Borrelia, Corynebacterium, Nocardia, Gardnerella, Campylobacter, Spirochaeta, Proteus, Bacteriodes, Helicobacter pylori*, and anthrax infection; (ii) mycobacterial infection from tuberculosis and leprosy; (iii) viral infection from HIV, Herpes simplex virus 1, Herpes simplex virus 2, Cytomegalovirus, hepatitis A virus, hepatitis B virus, hepatitis C virus, human papilloma virus, Epstein Barr virus, rotavirus, adenovirus, influenza A virus, respiratory syncytial virus, varicella-zoster virus, small pox, monkey pox and SARS; (iv) fungal infection from candidiasis, ringworm, histoplasmosis, blastomycosis, paracoccidioidomycosis, cryptococcosis, aspergillosis, chromomycosis, mycetoma infections, pseudallescheriasis, Tinea versicolor infection; (v) parasite infection from amebiasis, *Trypanosoma cruzi, Fascioliasis, Leishmaniasis, Plasmodium, Onchocerciasis, Paragonimiasis, Trypanosoma brucei, Pneumocystis, Trichomonas vaginalis, Taenia, Hymenolepsis, Echinococcus, Schistosomiasis, neurocysticerosis, Necator americanus*, and *Trichuris trichuria*.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, is Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents.

Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2Cl_2$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-m (alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

The examples presented below illustrate specific embodiments of the present invention. These examples are meant to be representative and are not intended to limit the scope of the claims in any manner.

EXAMPLES

Biological Assays

GKRP LC MS/MS Biochemical Assay

This assay is used to directly measure the formation of $^{13}$C-glucose-6-phosphate from $^{13}$C-glucose by liquid chromatography-mass spectrometry (LC MS/MS). Begin by preparing the following solutions: Compound Buffer (CB): 50 mM Tris, pH 7.5/4 mM MgCl$_2$/6% DMSO/fresh 10 mM DTT from 1M frozen stock. Enzyme Buffer (EB): 50 mM Tris, pH 7.5/4 mM MgCl$_2$/6% DMSO/fresh 0.1% BSA/fresh 0.01% Brij-35 (10% BSA and 1% Brij-35 stock). GK (Glucokinase) Working Stock (5×): Dilute human His-hepatic GK to 30 nM in EB buffer. Substrate Working Stock (1.47×): Dilute 13C-D-glucose (Sigma-Aldrich, St. Louis, Mo.) to 7.35 mM from 1M stock (1M $^{13}$C-D-glucose=186.11 mg/ml in 50 mM Tris pH 7.5, 4 mM MgCl$_2$) and dilute ATP (EMD Chemical Inc., Gibbstown, N.J.) to 0.3528 mM from frozen 100 mM stock and dilute 20 mM fructose-6-phosphate (F6P) (Sigma-Aldrich, St. Louis, Mo.) to 441 µM in CB buffer. GKRP (Glucokinase Regulatory Protein) (10×): Dilute GKRP to 1 µM from 33.366 mM stock in EB buffer. Combine the following reagents in a 96-well polypropylene plate: 34 µl of Substrate Working Stock (1.47×), 5 µl of 1 µM GKRP (10×), and 1 µl of compound or DMSO. Seal the plate and incubate for 30 minutes at room temperature while mixing. After 30 minutes add 10 µl of GK Working Stock (5×). Re-seal the plate and incubate for another 30 minutes at room temperature while mixing. After the second 30 minutes, stop the reaction by the addition of 50 µl of 100% acetonitrile, seal, and mix for 5-10 minutes. Run 10 µl of this sample through the LC MS/MS (API 3200, Applied Biosystems Inc., Carlsbad, Calif.). Detection settings are for 265.2/78.8 atomic mass units.

GKRP NADPH Coupled Assay

This assay is used as an indirect measure of glucose-6-phosphate (G6P) formed from glucose due to the enzymatic activity of glucokinase. Assay format is the same as for GKRP LC MS/MS Biochemical Assay with the following exceptions. GK Working Stock (5×): Dilute human His-hepatic GK to 20 nM in EB buffer. Stop & Detection Reagent (2×): Dilute β-nicotinamide adenine dinucleotide phosphate sodium salt (β-NADP) (Aldrich-Sigma, St. Louis, Mo.) to 2 mM from 100 mM stock (stock in 10 mM Tris, pH 9.2) and dilute glucose-6-phosphate dehydrogenase (Aldrich-Sigma, St. Louis, Mo.) to 0.04 Unit/µl from 10 Unit/µl (stock in 10 mM Tris pH 7.5/0.05% Brij-35) in 0.2 M Tris, pH 9.2/8% DMSO. After the initial 30 minute incubation add 10 µl of 20 nM GK diluted in EB (5×). Re-seal the plate and incubate for another 1 hour at room temperature while mixing. After 1 hour remove the seal and add 50 µl of Stop & Detection Reagent and incubate for 5 minutes at room temperature while mixing. After 5 minutes read the plate using an Infinite M1000 (Tecan Systems Inc., San Jose Calif.) with the following detection settings: Mode: Fluorescence Top Reading, Excitation Wavelength: 340 nm, Emission Wavelength: 450 nm, Excitation Bandwidth: 20 nm, Emission Bandwidth: 20 nm, Gain: 95, Number of Flashes: 10, Flash Frequency: 400 Hz, Integration Time: 20 µs.

GK-GKRP Binding Assay Protocol

This assay is used to directly measure the interaction between glucokinase (GK) and glucokinase regulatory protein (GKRP). Begin by preparing the following solutions. Assay Buffer: 20 mM Tris, pH 7.5/0.05% BSA/1 mM DTT/1 µM sorbitol-6-phosphate. Assay Procedure: Dilute avi-tagged GKRP to 10.7 nM in assay buffer. Combine the following reagents in a white 96-well half area plate. Pipette 14 µl of the diluted avi-tagged GKRP into each well. Add 1 µl of compound to be tested and incubate at room temperature for 20 minutes. After 20 minutes, add 5 µl of assay buffer containing 6 nM GK-fluorescein. Add 10 µl of AlphaScreen® beads (Perkin Elmer, Waltham Mass.) that have been diluted 1:333 in assay buffer. Incubate in a dark room for 2 hours at room temperature. After 2 hours read the plate using an Envision plate reader (Perkin Elmer, Waltham Mass.).

GKRP LC MS/MS-2 Biochemical Assay

This assay is used to directly measure the formation of $^{13}$C-glucose-6-phosphate from $^{13}$C-glucose by LC MS/MS. Begin by preparing the following solutions: Compound Buffer (CB): 50 mM Tris, pH 7.5/4 mM MgCl$_2$/6% DMSO/fresh 10 mM DTT from 1M frozen stock. Enzyme Buffer (EB): 50 mM Tris, pH 7.5/4 mM MgCl$_2$/6% DMSO/fresh 0.1% BSA/fresh 0.01% Brij-35 (10% BSA and 1% Brij-35 stock). GK (Glucokinase) Working Stock (5×): Dilute human His-hepatic GK to 30 nM in EB buffer. Substrate Working Stock (1.47×): Dilute $^{13}$C-D-glucose (Sigma-Aldrich, St. Louis, Mo.) to 7.35 mM from 1M stock and dilute ATP (EMD Chemical, Gibbstown, N.J.) to 0.3528 mM from frozen 100 mM stock in CB buffer (1M $^{13}$C-D-glucose=186.11 mg/ml in water). Dilute 20 mM fructose-6-phosphate (F6P) (Sigma-Aldrich, St. Louis, Mo.) to 441 µM in the substrate working stock. GKRP (Glucokinase Regulatory Protein) (10×): Dilute GKRP to 280 nM from 33.366 mM stock in EB buffer. Combine the following reagents in a 96-well polypropylene plate: 34 µL of Substrate Working Stock (1.47×), 5 µl of 280 nM GKRP (10×), and 1 µl of compound or DMSO. Seal the plate and incubate for 30 minutes at room temperature while mixing. After 30 minutes add 10 µl of GK Working Stock (5×). Re-seal the plate and incubate for another 30 minutes at room temperature while mixing. After the second 30 minutes, stop the reaction by the addition of 50 µl of 100% acetonitrile, seal, and mix for 5-10 minutes. Run 10 µl of this sample through the LC MS/MS (API 3200, Applied Biosystems, Carlsbad, Calif.). Detection settings are for 265.2/78.8 atomic mass units.

Results for compounds tested in these biological assays are set forth in the numbered examples below.

The following synthetic schemes show generally how to make compounds of the present invention.

General Synthetic Schemes

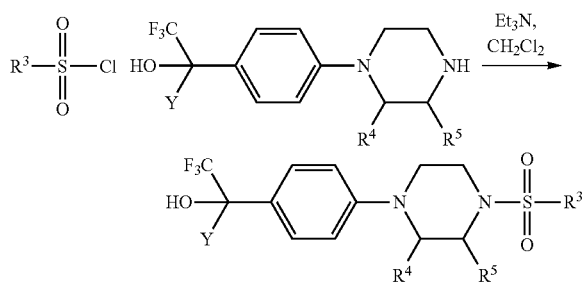

The sulfonamide can be synthesized by the reaction of an amine with a substituted sulfonyl chloride in an anhydrous solvent (such as CH$_2$Cl$_2$, THF or ether) in the presence of a base (either inorganic or amine) such as Et$_3$N, DIPEA, K$_2$CO$_3$, Na$_2$CO$_3$, or NaOH.

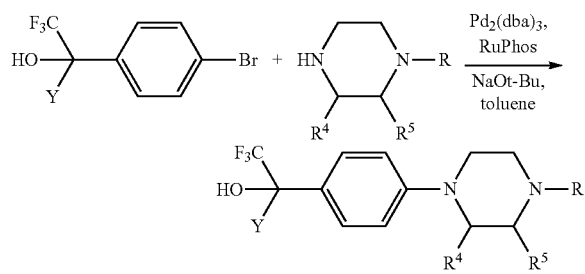

The N-arylation can be conducted using a variety of bases (such as NaOt-Bu, $K_3PO_4$ or LiHMDS), catalyst (such as $Pd_2(dba)_3$, $Pd(OAc)_2$ or $Pd(PPh_3)_4$), catalyst ligands (such as RuPhos, BINAP or SPhos), and solvents (such as toluene or dioxane).

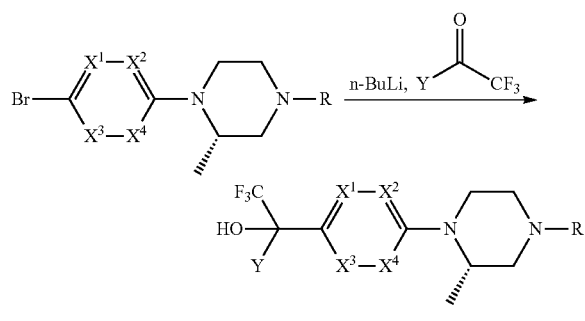

The carbinol functionality can be installed, for example, using n-BuLi (or t-BuLi) with THF or diethyl ether as the reaction solvent.

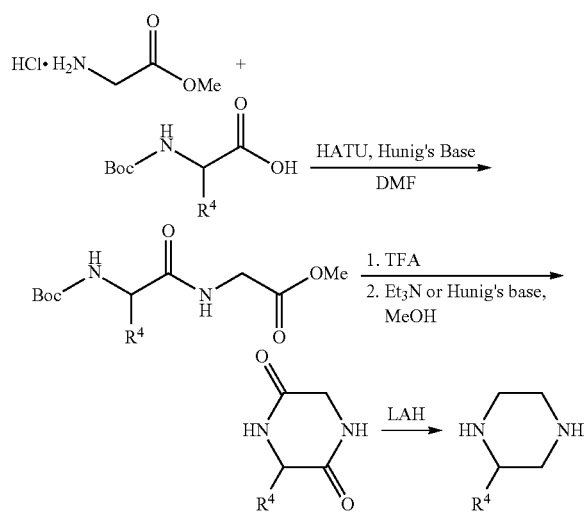

The amine coupling can accomplished using a variety of both coupling reagents (for example, TBTU, HATU or EDC) and solvents (for example, $CH_2Cl_2$, DMF or DMSO). The removal of the Boc protection group can be achieved by a number of conditions including: neat TFA, a $TFA/CH_2Cl_2$ solution or a 4N HCl solution in dioxane. The cyclization proceeds with an amine base (such as $NH_3$, $Et_3N$, or DIPEA) in alcoholic solvent (such as MeOH).

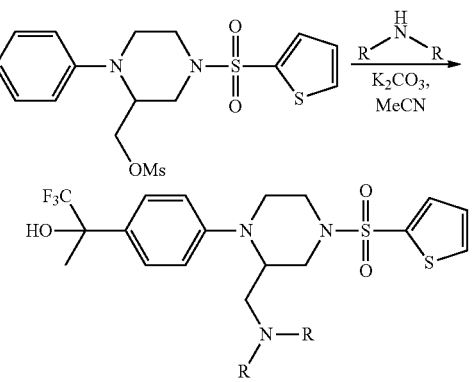

The amine substitution can be accomplished using a variety of inorganic bases (such as $K_2CO_3$, $Na_2CO_3$, or $Cs_2CO_3$) in polar aprotic solvents (such as MeCN, DMF or DMSO).

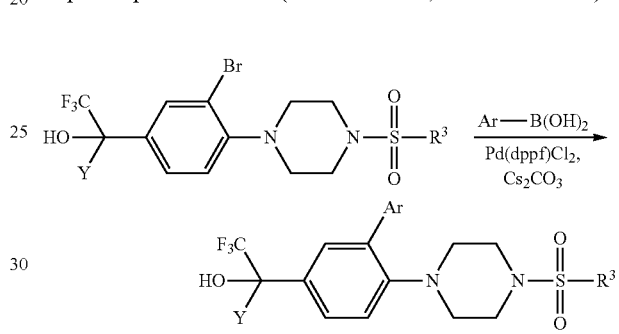

The Suzuki reaction with the aryl bromide can be achieved using a variety of bases (such as $Cs_2CO_3$, $K_2CO_3$, or $Na_2CO_3$), catalysts (such as $Pd(dppf)Cl_2$, or $Pd(PPh_3)_4$), and solvents (such as DME, EtOH, DMF or EtOH)

The following abbreviations may be used herein:
HATU [dimethylamino(triazolo[4,5-b]pyridin-3-yloxy)methylidene]-dimethylazanium
Hünig's base or DIPEA diisopropylethylamine
dppf 1,1'-bis(diphenylphosphanyl)ferrocene
dba 1,5-diphenylpenta-1,4-dien-3-one
LAH lithium aluminum hydride
TMS trimethylsilyl
EDC 3-(ethyliminomethyleneamino)-N,N-dimethyl-propan-1-amine
HOBt 1-hydroxybenzotriazole
TLC thin layer chromatography
MHz megahertz
br. broad
s singlet
d doublet
t triplet
dt doublet of triplet
dd doublet of doublet
quin quintuplet
q quartet
~ about
+ve or pos. ion positive ion
Δ heat
Ac acetyl
AcOH Acetic acid
$Ac_2O$ acetic anhydride
ACN acetonitrile A-phos, Am-Phos (bis[4-di-tert-butylphosphino)-N,N-dimethylaniline]palladium dichloride)
aq aqueous
ATP adenosine 5'-triphosphate
BOC or Boc tert-butyloxycarbonyl
Bu butyl
Bn benzyl
Calcd or Calc'd calculated
Conc. concentrated
DCE 1,2-dichloroethane
DCM dichloromethane
DEA diethylamine
DIEA diisopropylethylamine
DMAP 4-dimethylaminopyridine
DME dimethoxyl ethyl ether
DMF N,N-dimethylformamide
DMSO dimethyl sulfoxide
DTT dithiothreitol
ESI or ES electrospray ionization
Et ethyl
Et$_2$O diethyl ether
Et$_3$N triethylamine
EtOAc ethyl acetate
EtOH ethyl alcohol
FBS fetal bovine serum
g grams
h hour
HCO$_2$H formic acid
Hex hexanes
HOAc acetic acid
HPLC high pressure liquid chromatography
IPA or iPrOH isopropyl alcohol
iPr$_2$NEt N-ethyl diisopropylamine
KOAc potassium acetate
LC MS, LC-MS or LC/MS liquid chromatography mass spectroscopy
LDA lithium diisopropylamide
LHMDS or LiHMDS lithium hexamethyldisilazide
LiTMP lithium tetramethylpiperidide
m/z mass divided by charge
mCPBA or MCPBA m-chloroperoxybenzoic acid
Me methyl
MeCN acetonitrile
MeI iodomethane
MeOH methyl alcohol
mg milligrams
min minutes
mL milliliters
MS mass spectra
MsCl mesylchloride
NaBH$_4$ sodium borohydride
NaHMDS sodium hexamethyldisilazide
NaOtBu sodium tert-butoxide
NBS N-bromosuccinimide
n-BuLi n-butyllithium
NMO N-methylmorpholine-N-oxide
NMP 1-methyl-2-pyrrolidinone
NMR nuclear magnetic resonance
Pd$_2$ dba$_3$ tris(dibenzylideneacetone)dipalladium(0)
PMB paramethoxybenzyl
RT or rt room temperature
Sat. or sat'd or satd saturated
SFC supercritical fluid chromatography
RhPhos 2-dicyclohexyl(2',6'-diisopropoxybiphenyl-2-yl) phosphine chloro(2-dicyclohexylphosphino-2',6'-di-1-propoxy-1,1'-biphenyl)[2-(2-aminoethylphenyl)]palladium(II), methyl-t-
RuPhos Palladacycle butylether adduct
TFA trifluoroacetic acid
THF tetrahydrofuran
Ti(O-iPr)$_4$ titanium isopropoxide
TPAP tetrapropylammonium perruthenate
Tris tris(hydroxymethyl)aminomethane
xantphos (9,9-dimethyl-9H-xanthene-4,5-diyl)bis(diphenylphosphine)
X-Phos 2-Dicyclohexylphosphino-2',4',6'-triisopropyl-1,1'-biphenyl It is noted that when a percent (%) is used with regard to a liquid, it is a percent by volume with respect to the solution. When used with a solid, it is the percent with regard to the solid composition. Throughout the Examples, chromatography columns are used for separations and purifications. Below are some representative suppliers of columns: Phenomenex, Torrance, Calif. (e.g., Gemini); Diacel Inc., Fort Lee, N.J. (e.g., Chiralcel®, Chiralpak®); Krackeler Scientific, Albany, N.Y. (e.g., AccuBOND).

Intermediate A:
(S)-3-(benzyloxymethyl)piperazine-2,5-dione

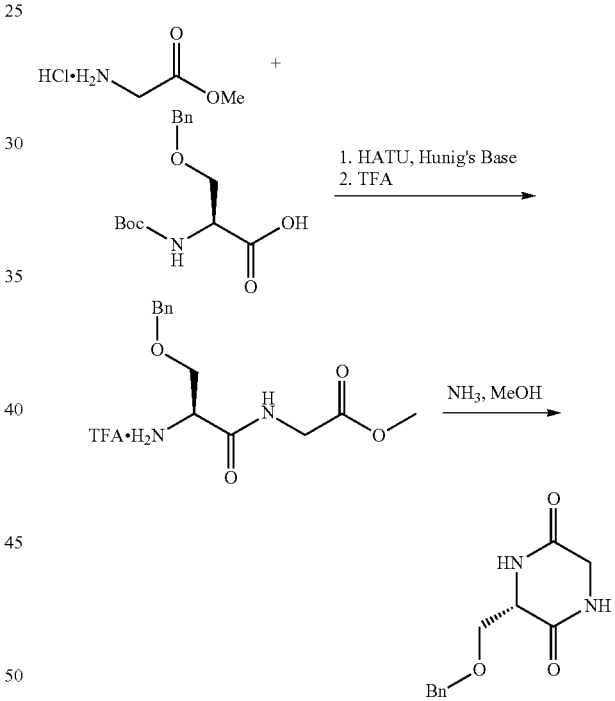

A 1 L round-bottomed flask was charged with O-benzyl-N-(tert-butoxycarbonyl)-L-serine (150 g, 508 mmol, Sigma-Aldrich, St. Louis, Mo.), glycine methyl ester hydrochloride (65.0 g, 518 mmol, Sigma-Aldrich, St. Louis, Mo.), HATU (203 g, 533 mmol, Sigma-Aldrich, St. Louis, Mo.) and DMF (400 mL). Hünig's base (177 mL, 1016 mmol) was added over a period of 1 h. After the addition was complete the mixture was diluted with EtOAc (600 mL) and washed with water (450 mL). The organic layer was then dried (MgSO$_4$) and concentrated. The crude material was dissolved in CH$_2$Cl$_2$ (500 mL) and the precipitate that resulted was filtered off and discarded. TFA (157 mL) was added to the solution over a period of 1 h and after this time the reaction was concentrated to give the TFA salt as an oil. To this salt was added 800 mL of 2 M NH$_3$ in MeOH and the resulting solu- Intermediate B: ((2R)-4-(2-thiophenylsulfonyl)-1-(4-(2,2,2-trifluoro-1-hydroxy-1-methylethyl)phenyl)-2-piperazinyl)methyl methanesulfonate

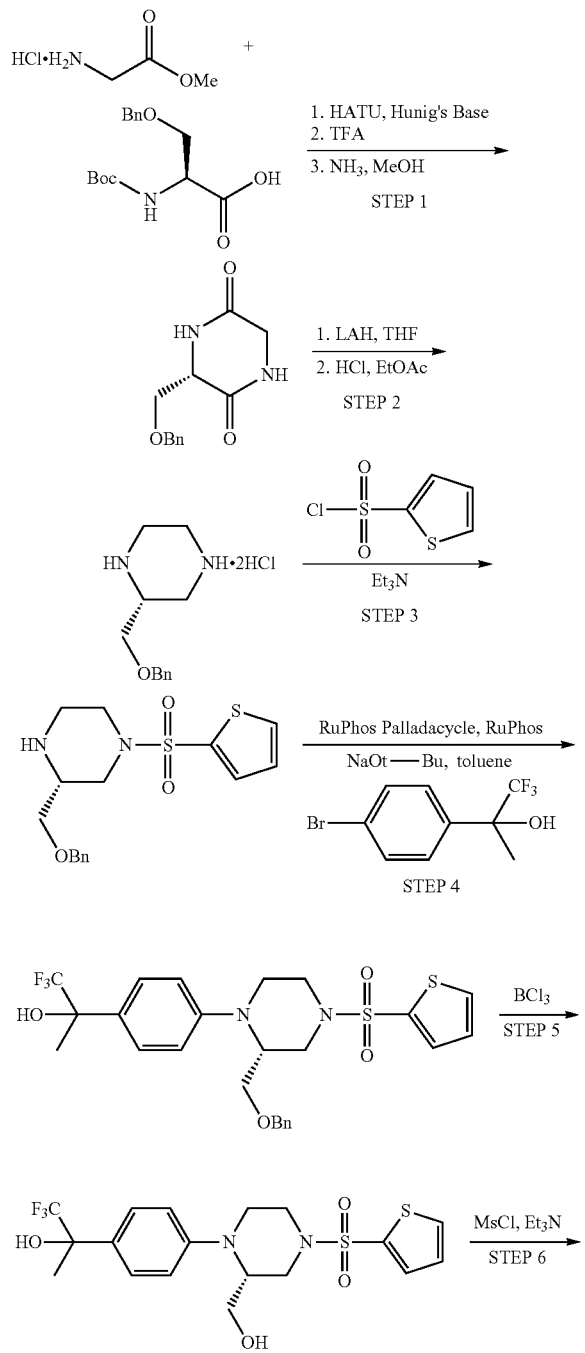

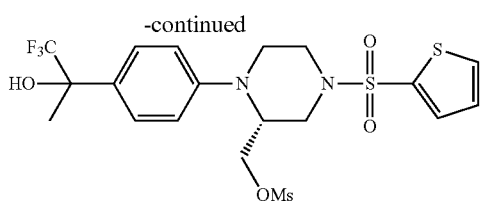

Step 1: (3S)-3-((benzyloxy)methyl)-2,5-piperazinedione

A 1-L round-bottomed flask was charged with O-benzyl-N-(tert-butoxycarbonyl)-L-serine (150 g, 508 mmol, Sigma-Aldrich, St. Louis, Mo.), glycine methyl ester hydrochloride (65.0 g, 518 mmol, Sigma-Aldrich, St. Louis, Mo.), HATU (203 g, 533 mmol, Sigma-Aldrich, St. Louis, Mo.) and DMF (400 mL). At room temperature, Hünig's base (177 mL, 1016 mmol) was added over a period of 1 h. The mixture was then diluted with EtOAc (1000 mL) and washed with water (4×450 mL). The organic extract was then dried (MgSO$_4$), filtered, and concentrated. The crude material was dissolved in CH$_2$Cl$_2$ (500 mL) and the precipitate that formed was filtered off and discarded. TFA (157 mL) was then added to the solution over a period of 1 h. The mixture was concentrated to give the TFA salt as an oil. To this was added 800 mL of 2 M NH$_3$ in MeOH (Sigma-Aldrich, St. Louis, Mo.). The resulting solution was stirred at room temperature for 12 h. After that time, another 500 mL 2M NH$_3$ in MeOH was added and stirring was continued for 4 h. After removing approximately half of the volatiles in vacuo, a white solid precipitated. The solid was collected by filtration and rinsed with 1 L of diethyl ether. The solid was dried overnight under reduced pressure (<1 Torr; 133 Pa) to give (S)-3-(benzyloxymethyl)piperazine-2,5-dione (72.8 g).

Step 2: (2R)-2-((benzyloxy)methyl)piperazine dihydrochloride

A solution of LAH (1.87 g, 49.3 mmol) in THF (50 mL) was chilled to 0° C. To this mixture was added (3S)-3-((benzyloxy)methyl)-2,5-piperazinedione (3.85 g, 16.44 mmol) slowly portion wise. The mixture was allowed to warm to room temperature and then heated at reflux for 1 h. Afterwards, the mixture was chilled to 0° C. and the reaction was quenched with an excess of solid sodium sulfate decahydrate (approximately 50 g). After stirring at room temperature for 1 h, the mixture was filtered. The filtrate was concentrated to give (R)-2-(benzyloxymethyl)piperazine (2.60 g) as a yellow oil. To this was added excess HCl (4M in dioxane) to deliver (2R)-2-((benzyloxy)methyl)piperazine dihydrochloride.

Step 3: (3R)-3-((benzyloxy)methyl)-1-(2-thiophenyl-sulfonyl)piperazine

A 1-L round-bottomed flask was charged with (R)-2-(benzyloxymethyl)piperazine dihydrochloride (55.5 g, 199 mmol) and 300 mL of CH$_2$Cl$_2$. After cooling to 0° C., triethylamine (111 mL, 795 mmol) and 2-thiophenesulfonyl chloride (36.3 g, 199 mmol, Sigma-Aldrich, St. Louis, Mo.) were added. This mixture was stirred at 0° C. for 30 min and then diluted with water. The organics were separated, dried (MgSO$_4$), filtered and concentrated to give a brown oil. Purification via column chromatography on silica gel (25 to 100%

EtOAc in hexanes) gave (3R)-3-((benzyloxy)methyl)-1-(2-thiophenylsulfonyl)piperazine (47.8 g) as a light-brown solid.

Step 4: 2-(4-((2R)-2-((benzyloxy)methyl)-4-(2-thiophenylsulfonyl)-1-piperazinyl)phenyl)-1,1,1-trifluoro-2-propanol A 1-L pressure vessel was charged with 2-(4-bromophenyl)-1,1,1-trifluoropropan-2-ol (43.8 g, 163 mmol, Example 27, Step 1), (3R)-3-((benzyloxy)methyl)-1-(2-thiophenylsulfonyl)piperazine (47.8 g, 136 mmol), 200 mL of toluene, and sodium tert-butoxide (32.6 g, 339 mmol). After bubbling nitrogen gas through the solution for 5 min, chloro(2-dicyclohexylphosphino-2',6'-di-1-propoxy-1,1'-biphenyl)[2-(2-aminoethylphenyl)]palladium(II), methyl-t-butylether adduct (RuPhos Palladacycle) (0.99 g, 1.36 mmol, Strem Chemicals, Newburyport, Mass.) and 2-dicyclohexyl(2',6'-diisopropoxybiphenyl-2-yl)phosphine (RuPhos) (0.63 g, 1.36 mmol, Strem Chemicals, Newburyport, Mass.) were added. The vessel was sealed and heated at 65° C. for 12 h. After that time, the mixture was diluted with water and extracted with EtOAc, dried (MgSO$_4$), filtered, and concentrated. Purification by column chromatography on silica gel (0 to 60% EtOAc in hexanes) gave 2-(4-((2R)-2-((benzyloxy)methyl)-4-(2-thiophenylsulfonyl)-1-piperazinyl)phenyl)-1,1,1-trifluoro-2-propanol (54.4 g) as a yellow foam.

Step 5: 1,1,1-trifluoro-2-(4-((2R)-2-(hydroxymethyl)-4-(2-thiophenylsulfonyl)-1-piperazinyl)phenyl)-2-propanol A 2-L round-bottomed flask was charged with 2-(4-((2R)-2-((benzyloxy)methyl)-4-(2-thiophenylsulfonyl)-1-piperazinyl)phenyl)-1,1,1-trifluoro-2-propanol (54.4 g, 101 mmol) and 200 mL of CH$_2$Cl$_2$. After cooling to 0° C., BCl$_3$ (1M in CH$_2$Cl$_2$, 302 mL, 302 mmol, Sigma-Aldrich, St. Louis, Mo.) was added over 10 min. After 30 min at 0° C., the mixture was carefully diluted with MeOH and then concentrated and purified via column chromatography on silica gel (0 to 3% MeOH in CH$_2$Cl$_2$) to give 1,1,1-trifluoro-2-(4-((2R)-2-(hydroxymethyl)-4-(2-thiophenylsulfonyl)-1-piperazinyl)phenyl)-2-propanol (42.7 g) as a tan foam.

Step 6: ((2R)-4-(2-thiophenylsulfonyl)-1-(4-(2,2,2-trifluoro-1-hydroxy-1-methylethyl)phenyl)-2-piperazinyl)methyl methanesulfonate A 1-L round-bottomed flask was charged with 1,1,1-trifluoro-2-(4-((2R)-2-(hydroxymethyl)-4-(2-thiophenylsulfonyl)-1-piperazinyl)phenyl)-2-propanol (42.7 g, 95 mmol), 200 mL of CH$_2$Cl$_2$, and triethylamine (15.18 mL, 109 mmol). After cooling to 0° C., methanesulfonyl chloride (7.75 g, 99 mmol) was added. After 5 min, another 1 equiv of triethylamine and methanesulfonyl chloride were added. The mixture was then diluted with water and extracted with CH$_2$Cl$_2$. The combined organics were dried (MgSO$_4$), filtered, and concentrated. Purification by column chromatography on silica gel (0 to 50% EtOAc in hexanes) gave ((2R)-4-(2-thiophenylsulfonyl)-1-(4-(2,2,2-trifluoro-1-hydroxy-1-methylethyl)phenyl)-2-piperazinyl)methyl methanesulfonate (35.0 g) as a light-yellow brittle foam.

$^1$H NMR (400 MHz, CDCl$_3$) δ ppm 7.68 (dd, J=4.99, 1.08 Hz, 1H), 7.60 (dd, J=3.81, 1.08 Hz, 1H), 7.47 (d, J=8.61 Hz, 2H), 7.19 (dd, J=4.99, 3.81 Hz, 1H), 6.89 (d, J=8.80 Hz, 2H), 4.38-4.48 (m, 1H), 4.22-4.31 (m, 2H), 3.92 (d, J=11.93 Hz, 1H), 3.84 (d, J=11.15 Hz, 1H), 3.45-3.54 (m, 1H), 3.31 (td, J=11.93, 3.52 Hz, 1H), 2.97 (s, 3H), 2.77 (d, J=11.74 Hz, 1H), 2.65 (td, J=11.15, 3.33 Hz, 1H), 1.74 (s, 3H). m/z (ESI, +ve ion) 529.1 (M+H)$^+$. GK-GKRP IC$_{50}$ (Binding)=0.357 µM; GK-GKRP EC$_{50}$ (LC MS/MS-2)=0.827 µM.

Intermediate C:
(2S)-2-(tetrahydro-2H-pyran-4-ylmethyl)piperazine

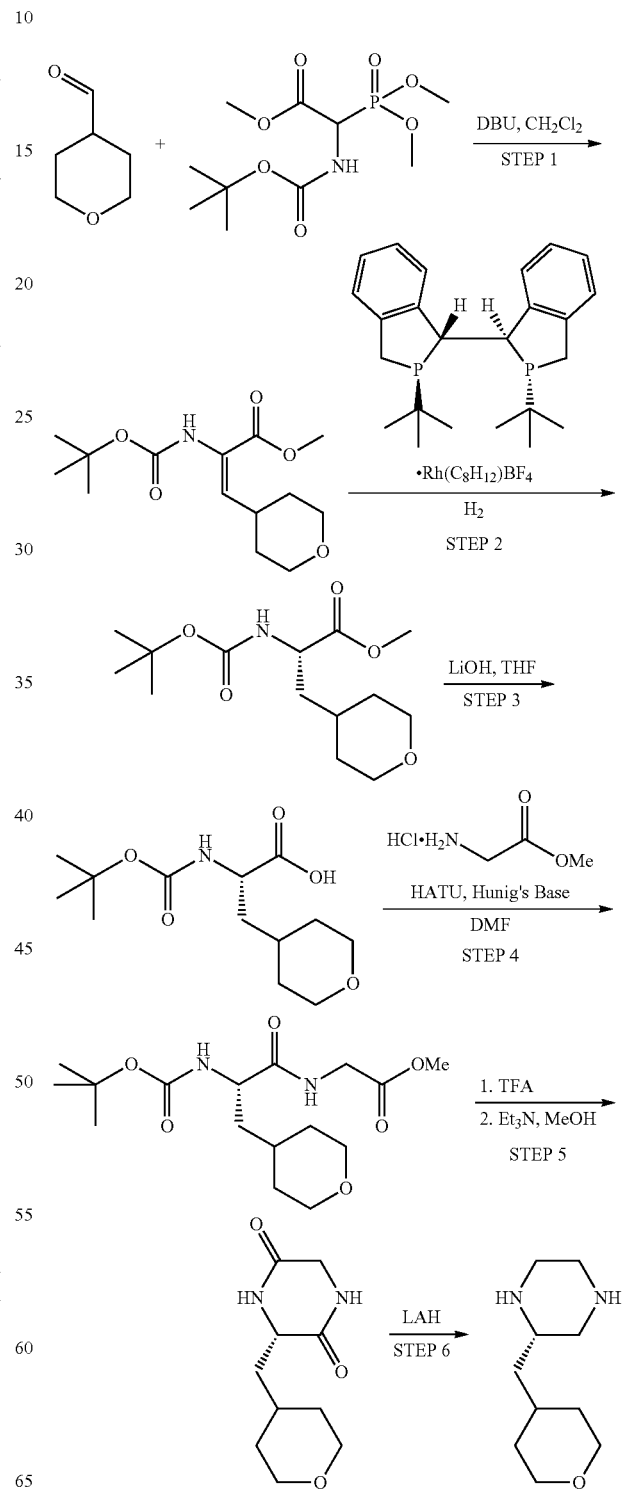

Step 1: methyl (2E)-2-((tert-butoxycarbonyl)amino)-3-(tetrahydro-2H-pyran-4-yl)-2-propenoate To a solution of tetrahydro-2H-pyran-4-carbaldehyde (5.0 g, 43.9 mmol, Frontier Scientific Inc., Logan, Utah) in $CH_2Cl_2$ (100 mL) at room temperature was added (rac)-Boc-α-phosphonoglycine trimethyl ester (14.4 g, 48.3 mmol, Sigma-Aldrich, St. Louis, Mo.) followed by DBU (7.3 mL, 48.3 mmol). The reaction was stirred overnight before being diluted with water (100 mL) and extracted with $CH_2Cl_2$ (2×200 mL). The layers were separated and the organic extracts were washed with water (2×100 mL), dried ($MgSO_4$), filtered, and concentrated. The crude material was purified by silica gel column chromatography (0 to 70% hexanes in EtOAc) to give methyl (2E)-2-((tert-butoxycarbonyl)amino)-3-(tetrahydro-2H-pyran-4-yl)-2-propenoate.

Step 2: methyl N-(tert-butoxycarbonyl)-3-(tetrahydro-2H-pyran-4-yl)-L-alaninate A 250-mL pressure tube was charged with methyl (2E)-2-((tert-butoxycarbonyl)amino)-3-(tetrahydro-2H-pyran-4-yl)-2-propenoate (8.75 g, 30.7 mmol), MeOH (100 mL), and rhodium[(1R,1'R,2R,2'R)-2,2'-bis(1,1-dimethylethyl)-2,2',3,3'-tetrahydro-1,1'-bi-1H-isophosphindole-κP2,κP2'][(1,2,5,6-η)-1,5-cyclooctadiene]tetrafluoroborate (0.209 g, 0.30 mmol, ChiralQuest, Monmouth Junction, N.J.). The mixture was stirred under a 50 psi (344 kilopascal) hydrogen atmosphere for 3 h. The mixture was then filtered through a pad of silica, washing with 1:1 EtOAc in hexanes, and then concentrated to give methyl N-(tert-butoxycarbonyl)-3-(tetrahydro-2H-pyran-4-yl)-L-alaninate.

Step 3: N-(tert-butoxycarbonyl)-3-(tetrahydro-2H-pyran-4-yl)-L-alanine

A 500-mL round-bottomed flask was charged with methyl N-(tert-butoxycarbonyl)-3-(tetrahydro-2H-pyran-4-yl)-L-alaninate (8.81 g, 30.7 mmol), 100 mL of THF, 100 mL of water and lithium hydroxide (2.20 g, 92 mmol). After stirring overnight at room temperature, the mixture was concentrated and acidified to pH 3 with concentrated aqueous HCl. The mixture was then extracted with EtOAc, dried ($MgSO_4$), filtered, and concentrated to give N-(tert-butoxycarbonyl)-3-(tetrahydro-2H-pyran-4-yl)-L-alanine (8.00 g) as a white solid.

Step 4: methyl N-(tert-butoxycarbonyl)-3-(tetrahydro-2H-pyran-4-yl)-L-alanylglycinate A 100-mL round-bottomed flask was charged with N-(tert-butoxycarbonyl)-3-(tetrahydro-2H-pyran-4-yl)-L-alanine (3.11 g, 11.38 mmol), HATU (5.41 g, 14.22 mmol), glycine methyl ester hydrochloride (1.714 g, 13.65 mmol, Sigma-Aldrich, St. Louis, Mo.), and 10 mL of DMF. To this was added Hünig's base (4.37 mL, 25.03 mmol). After 30 min at room temperature, the mixture was diluted with water (100 mL) and extracted with EtOAc (2×200 mL). The layers were separated and the organic extracts were washed with water (2×100 mL) and brine (50 mL), dried ($MgSO_4$), filtered and concentrated to give methyl N-(tert-butoxycarbonyl)-3-(tetrahydro-2H-pyran-4-yl)-L-alanylglycinate (3.00 g) as a yellow oil.

Step 5: (3S)-3-(tetrahydro-2H-pyran-4-ylmethyl)-2,5-piperazinedione

A 250-mL round-bottomed flask was charged with methyl N-(tert-butoxycarbonyl)-3-(tetrahydro-2H-pyran-4-yl)-L-alanylglycinate (3.00 g, 8.71 mmol), 10 mL of $CH_2Cl_2$, and 5 mL of TFA. After 10 min at room temperature, the mixture was concentrated then dissolved in 2N $NH_3$ in MeOH (20 mL) and stirred at room temperature for 4 h. The reaction was then concentrated and triturated with ether to give (3S)-3-(tetrahydro-2H-pyran-4-ylmethyl)-2,5-piperazinedione (1.44 g) as a white solid.

Step 6: (2S)-2-(tetrahydro-2H-pyran-4-ylmethyl)piperazine

A 250-mL round-bottomed flask was charged with (3S)-3-(tetrahydro-2H-pyran-4-ylmethyl)-2,5-piperazinedione (1.44 g, 6.78 mmol), 50 mL of THF, and LAH (1M in THF, 27.1 mL, 27.1 mmol, Sigma-Aldrich, St. Louis, Mo.). After heating at reflux for 2 h, the mixture was allowed to cool to room temperature. Sodium sulfate decahydrate (10 g) was then added and the mixture was stirred at temperature for 1 h. The mixture was filtered and the filtrate was concentrated to give (2S)-2-(tetrahydro-2H-pyran-4-ylmethyl)piperazine (0.950 g, 5.16 mmol) as a colorless oil.

Intermediate D (2-chloro-5-pyrimidinyl)-1,1,1,3,3,3-hexafluoro-2-propanol

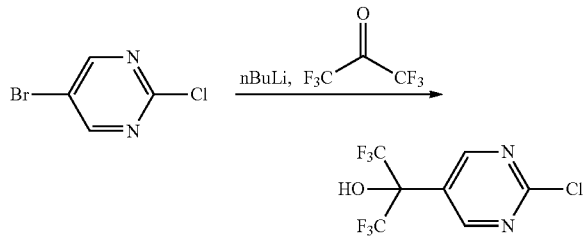

A 500-mL round-bottomed flask was charged with 5-bromo-2-chloropyrimidine (10.0 g, 52 mmol, Combi-Blocks, San Diego, Calif.) and 100 mL of ether. After cooling to −78° C., n-BuLi (2.5 M in hexanes, 22.8 mL, 57 mmol) was added. This mixture was stirred at −78° C. for 10 min, then 1,1,1,3,3,3-hexafluoro-2-propanone (Sigma-Aldrich, St. Louis, Mo.) was bubbled through the solution for 5 min. After stirring for an additional 10 min, the reaction was quenched with saturated aqueous $NH_4Cl$. The solution was extracted with EtOAc, dried ($MgSO_4$), filtered, and concentrated. Purification via column chromatography on silica gel (twice, 0 to 50% EtOAc in hexanes then 0 to 4% MeOH in $CH_2Cl_2$) gave (2-chloro-5-pyrimidinyl)-1,1,1,3,3,3-hexafluoro-2-propanol (3.25 g) as a yellow solid.

Intermediate E: 2-(2-chloro-5-pyrimidinyl)-1,1,1-trifluoro-2-propanol

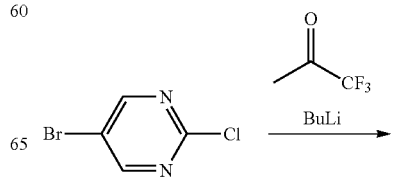

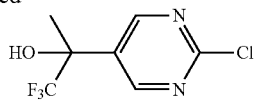

A 500-mL round-bottomed flask was charged with 5-bromo-2-chloropyrimidine (8.53 g, 44.1 mmol, Combi-Blocks, San Diego, Calif.) and 100 mL of ether. After cooling to −78° C., n-BuLi (2.5 M in hexanes, 27.6 mL, 44.1 mmol) was added. This mixture was stirred at −78° C. for 10 min, then 1,1,1,-tri-fluoro-2-propanone (14.82 g, 132 mmol, Sigma-Aldrich, St. Louis, Mo.) was added. After stirring for an additional 10 min at −78° C., the reaction was quenched with saturated aqueous $NH_4Cl$. The solution was extracted with EtOAc, dried ($MgSO_4$), filtered, and concentrated. Purification via column chromatography on silica gel (0 to 85% EtOAc in hexanes) gave 2-(2-chloro-5-pyrimidinyl)-1,1,1-trifluoro-2-propanol (1.70 g) as a white solid.

Example 1

1,1,1,3,3,3-hexafluoro-2-(4-(4-(2-thiophenylsulfonyl)-1-piperazinyl)phenyl)-2-propanol

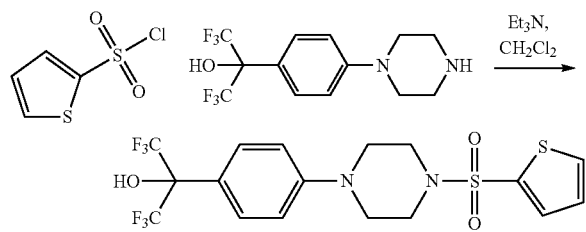

A 100 mL round-bottomed flask was charged with 1,1,1,3,3,3-hexafluoro-2-(4-(1-piperazinyl)phenyl)-2-propanol (2.27 g, 6.92 mmol, published PCT patent application no. WO 2006/094842), 20 mL of $CH_2Cl_2$ and triethylamine (1.45 mL, 10.4 mmol). To this was added 2-thiophenesulfonyl chloride (1.39 mL, 7.61 mmol, Sigma-Aldrich, St. Louis, Mo.) and the mixture was stirred at room temperature for 2 h. After that time, the mixture was diluted with water (50 mL) and extracted with EtOAc (100 mL). The combined extracts were dried ($MgSO_4$) and concentrated. This oil was purified by column chromatography (120 g silica gel, 0 to 50% EtOAc in hexanes) to give 1,1,1,3,3,3-hexafluoro-2-(4-(4-(2-thiophenylsulfonyl)-1-piperazinyl)phenyl)-2-propanol (2.35 g) as a white solid. $^1$H NMR (400 MHz, $CDCl_3$) δ 7.70-7.65 (m, 1H) 7.64-7.56 (m, 3H), 7.23-7.18 (m, 1H), 7.02-6.94 (m, 2H), 3.43-3.36 (m, 4H), 3.33-3.25 (m, 4H). m/z (ESI, +ve ion) 475.0 (M+H)$^+$. GK-GKRP $EC_{50}$ (NADPH-coupled)=0.332 μM; GK-GKRP $EC_{50}$ (LC MS/MS)=0.500 μM.

Example 2

1,1,1,3,3,3-hexafluoro-2-(4-(4-(phenylsulfonyl)-1-piperazinyl)phenyl)-2-propanol

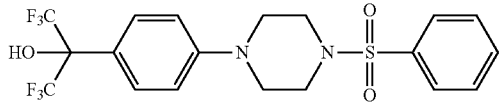 [SMILES: O=S(=O)(c1ccccc1)N1CCN(c2ccc(C(O)(C(F)(F)F)C(F)(F)F)cc2)CC1]

Following the procedure for Example 1, the reaction of 1,1,1,3,3,3-hexafluoro-2-(4-(1-piperazinyl)phenyl)-2-propanol (published PCT patent application no. WO 2006/094842) and benzenesulfonyl chloride (Sigma-Aldrich, St. Louis, Mo.) delivered 1,1,1,3,3,3-hexafluoro-2-(4-(4-(phenylsulfonyl)-1-piperazinyl)phenyl)-2-propanol. $^1$H NMR (400 MHz, $CDCl_3$) δ 7.85-7.77 (m, 2H), 7.67-7.54 (m, 5H), 7.01-6.92 (m, 2H), 3.39-3.28 (m, 4H), 3.27-3.21 (m, 4H). m/z (ESI, +ve ion) 469.0 (M+H)$^+$. GK-GKRP $EC_{50}$ (NADPH-coupled)=0.803 μM; GK-GKRP $EC_{50}$ (LC MS/MS)=1.10 μM.

Example 3

1,1,1,3,3,3-hexafluoro-2-(4-(4-(3-thiophenylsulfonyl)-1-piperazinyl)phenyl)-2-propanol

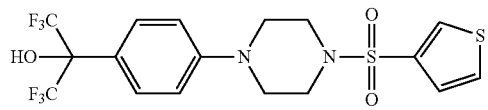

To a solution of 1,1,1,3,3,3-hexafluoro-2-(4-(1-piperazinyl)phenyl)-2-propanol (50 mg, 0.152 mmol, published PCT patent application no. WO 2006/094842) and triethylamine (63.6 μL, 0.457 mmol) in 1,2-dichloroethane (1.5 mL) was added 3-thiophenesulfonyl chloride (1M in dichloroethane, 168 μL, 0.168 mmol, ASDI, Newark, Del.). The reaction was shaken on an orbital shaker for 18 h. The reaction solvent was removed under reduced pressure and the crude product was purified by reverse-phase preparative HPLC using a Sunfire Prep C18 OBD (100×19 mm, 5 μm) column, 0.1% TFA in MeOH/$H_2O$, gradient (65% to 95% over 4.5 min) to provide 1,1,1,3,3,3-hexafluoro-2-(4-(4-(3-thiophenylsulfonyl)-1-piperazinyl)phenyl)-2-propanol. $^1$H NMR (400 MHz, DMSO-$d_6$) δ 8.35-8.27 (m, 1H), 7.85 (dd, J=5.1, 2.9 Hz, 1H), 7.47 (d, J=8.8 Hz, 2H), 7.37 (d, J=5.1 Hz, 1H), 7.02 (d, J=9.0 Hz, 2H), 3.33-3.28 (m, 4H), 3.07-3.01 (m, 4H). m/z (ESI, +ve ion) 475.1 (M+H)$^+$. GK-GKRP $EC_{50}$ (NADPH-coupled)=0.597 μM; GK-GKRP $EC_{50}$ (LC MS/MS)=0.964 μM.

Example 4

1,1,1,3,3,3-hexafluoro-2-(4-(4-((2-methylphenyl)sulfonyl)-1-piperazinyl)phenyl)-2-propanol

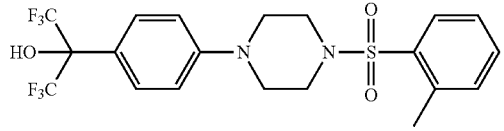 [SMILES: Cc1ccccc1S(=O)(=O)N1CCN(c2ccc(C(O)(C(F)(F)F)C(F)(F)F)cc2)CC1]

Following the procedure reported for Example 3, the reaction of 1,1,1,3,3,3-hexafluoro-2-(4-(1-piperazinyl)phenyl)-2-propanol (published PCT patent application no. WO 2006/094842) and 2-methyl-benzene-1-sulfonyl chloride (ASDI, Newark, Del.) provided 1,1,1,3,3,3-hexafluoro-2-(4-(4-((2-methylphenyl)sulfonyl)-1-piperazinyl)phenyl)-2-propanol. $^1$H NMR (400 MHz, DMSO-$d_6$) δ 7.87-7.80 (m, 1H), 7.64-7.56 (m, 1H), 7.52-7.41 (m, 4H), 7.02 (d, J=9.2 Hz, 2H), 3.32-3.24 (m, 4H), 3.20-3.11 (m, 4H), 2.60 (s, 3H). m/z (ESI, +ve ion) 483.2 (M+H)⁺. GK-GKRP EC$_{50}$ (NADPH-coupled)=1.27 µM; GK-GKRP EC$_{50}$ (LC MS/MS)=1.71 µM.

Example 5

1,1,1,3,3,3-hexafluoro-2-(4-(4-((1-methyl-1H-pyrazol-3-yl)sulfonyl)-1-piperazinyl)phenyl)-2-propanol

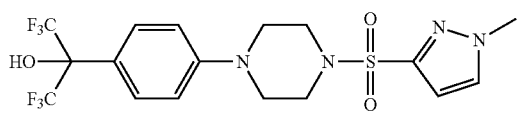

Following the procedure reported for Example 3, the reaction of 1,1,1,3,3,3-hexafluoro-2-(4-(1-piperazinyl)phenyl)-2-propanol (published PCT patent application no. WO 2006/094842) and 1-methyl-1H-pyrazole-3-sulfonyl chloride (Maybridge, Cambridge, UK) provided 1,1,1,3,3,3-hexafluoro-2-(4-(4-((1-methyl-1H-pyrazol-3-yl)sulfonyl)-1-piperazinyl)phenyl)-2-propanol. ¹H NMR (400 MHz, CDCl$_3$) δ 7.58 (d, J=8.6 Hz, 2H), 7.46 (d, J=2.2 Hz, 1H), 6.91 (d, J=9.0 Hz, 2H), 6.69 (d, J=2.2 Hz, 1H), 4.00 (s, 3H), 3.34 (br. s., 8H). m/z (ESI, +ve ion) 473.0 (M+H)⁺. GK-GKRP EC$_{50}$ (NADPH-coupled)=1.58 µM; GK-GKRP EC$_{50}$ (LC MS/MS)=5.38 µM.

Example 6

1,1,1,3,3,3-hexafluoro-2-(4-(4-((2-fluorophenyl)sulfonyl)-1-piperazinyl)phenyl)-2-propanol

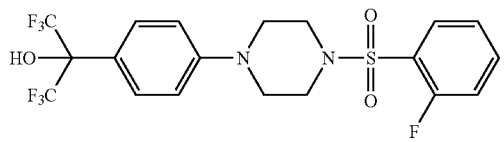 [SMILES: O=S(=O)(c1ccccc1F)N1CCN(c2ccc(C(O)(C(F)(F)F)C(F)(F)F)cc2)CC1]

Following the procedure reported for Example 3, the reaction of 1,1,1,3,3,3-hexafluoro-2-(4-(1-piperazinyl)phenyl)-2-propanol (published PCT patent application no. WO 2006/094842) and 2-fluorobenzene-1-sulfonyl chloride (ASDI, Newark, Del.) provided 1,1,1,3,3,3-hexafluoro-2-(4-(4-((2-fluorophenyl)sulfonyl)-1-piperazinyl)phenyl)-2-propanol. ¹H NMR (400 MHz, CDCl$_3$) δ 7.90-7.84 (m, 1H), 7.63-7.52 (m, 3H), 7.30 (t, J=7.7 Hz, 1H), 7.22 (d, J=9.0 Hz, 1H), 6.92-6.87 (m, 2H), 3.39-3.27 (m, 8H). m/z (ESI, +ve ion) 487.1 (M+H)⁺. GK-GKRP EC$_{50}$ (NADPH-coupled)=1.88 µM; GK-GKRP EC$_{50}$ (LC MS/MS)=1.52 µM.

Example 7

1,1,1,3,3,3-hexafluoro-2-(4-(4-(2-pyridinylsulfonyl)-1-piperazinyl)phenyl)-2-propanol

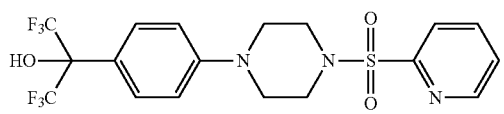

Following the procedure reported for Example 3, the reaction of 1,1,1,3,3,3-hexafluoro-2-(4-(1-piperazinyl)phenyl)-2-propanol (published PCT patent application no. WO 2006/094842) and 2-pyridinesulfonyl chloride hydrochloride (J & W PharmLab, Levittown, Pa.) provided 1,1,1,3,3,3-hexafluoro-2-(4-(4-(2-pyridinylsulfonyl)-1-piperazinyl)phenyl)-2-propanol. ¹H NMR (400 MHz, CDCl$_3$) δ 8.71 (d, J=4.09 Hz, 1H), 8.01-7.88 (m, 2H), 7.57 (d, J=8.5 Hz, 2H), 7.54-7.46 (m, 1H), 6.89 (d, J=8.8 Hz, 2H), 3.59-3.49 (m, 4H), 3.31 (d, J=4.8 Hz, 4H). m/z (ESI, +ve ion) 470.2 (M+H)⁺. GK-GKRP EC$_{50}$ (NADPH-coupled)=3.78 µM; GK-GKRP EC$_{50}$ (LC MS/MS)=3.29 µM.

Example 8

1,1,1,3,3,3-hexafluoro-2-(4-(4-((5-methyl-2-thiophenyl)sulfonyl)-1-piperazinyl)phenyl)-2-propanol

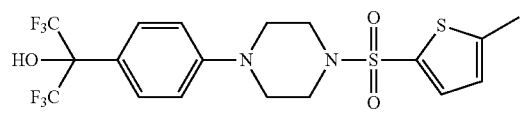 [SMILES: Cc1ccc(S(=O)(=O)N2CCN(c3ccc(C(O)(C(F)(F)F)C(F)(F)F)cc3)CC2)s1]

Following the procedure reported for Example 3, the reaction of 1,1,1,3,3,3-hexafluoro-2-(4-(1-piperazinyl)phenyl)-2-propanol (published PCT patent application no. WO 2006/094842) and 5-methylthiophene-2-sulfonyl chloride (Maybridge, Cambridge, UK) provided 1,1,1,3,3,3-hexafluoro-2-(4-(4-((5-methyl-2-thiophenyl)sulfonyl)-1-piperazinyl)phenyl)-2-propanol. ¹H NMR MHz, CDCl$_3$) δ 7.58 (d, J=8.3 Hz, 2H), 7.37 (d, J=3.5 Hz, 1H), 6.89 (d, J=8.9 Hz, 2H), 6.82 (d, J=2.6 Hz, 1H), 3.32 (d, J=4.8 Hz, 4H), 3.21 (d, J=5.4 Hz, 4H), 2.53 (s, 3H). m/z (ESI, +ve ion) 489.1 (M+H)⁺. GK-GKRP EC$_{50}$ (NADPH-coupled)=4.58 µM; GK-GKRP EC$_{50}$ (LC MS/MS)=11.40 µM.

Example 9

2-(4-(4-(3-chlorophenylsulfonyl)piperazin-1-yl)phenyl)-1,1,1,3,3,3-hexafluoro-2-propanol

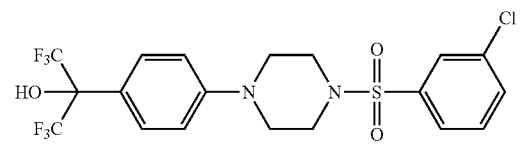 [SMILES: O=S(=O)(c1cccc(Cl)c1)N1CCN(c2ccc(C(O)(C(F)(F)F)C(F)(F)F)cc2)CC1]

Following the procedure reported for Example 3, the reaction of 1,1,1,3,3,3-hexafluoro-2-(4-(1-piperazinyl)phenyl)-2-propanol (published PCT patent application no. WO 2006/094842) and 3-chlorobenzene-1-sulfonyl chloride (ASDI, Newark, Del.) provided 2-(4-(4-(3-chlorophenylsulfonyl)piperazin-1-yl)phenyl)-1,1,1,3,3,3-hexafluoro-2-propanol. ¹H NMR (300 MHz, CDCl$_3$) δ 7.79 (t, J=1.8 Hz, 1H), 7.69 (dt, J=7.8, 1.3 Hz, 1H), 7.63-7.49 (m, 4H), 6.93-6.87 (m, 2H), 3.36-3.31 (m, 4H), 3.24-3.18 (m, 4H). m/z (ESI, +ve ion)

503.1 (M+H)+. GK-GKRP EC$_{50}$ (NADPH-coupled)=4.41 µM; GK-GKRP EC$_{50}$ (LC MS/MS)=3.71 µM.

Example 10

2-(4-(4-((2-chlorophenyl)sulfonyl)-1-piperazinyl)phenyl)-1,1,1,3,3,3-hexafluoro-2-propanol

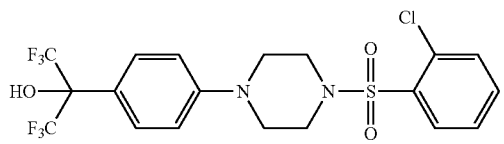 [SMILES: O=S(=O)(c1ccccc1Cl)N1CCN(c2ccc(C(O)(C(F)(F)F)C(F)(F)F)cc2)CC1]

Following the procedure reported for Example 3, the reaction of 1,1,1,3,3,3-hexafluoro-2-(4-(1-piperazinyl)phenyl)-2-propanol (published PCT patent application no. WO 2006/094842) and 2-chlorobenzene-1-sulfonyl chloride (ASDI, Newark, Del.) provided 2-(4-(4-((2-chlorophenyl)sulfonyl)-1-piperazinyl)phenyl)-1,1,1,3,3,3-hexafluoro-2-propanol. $^1$H NMR (300 MHz, CDCl$_3$) δ 8.08 (dd, J=7.8, 1.4 Hz, 1H), 7.60-7.49 (m, 4H), 7.45-7.39 (m, 1H), 6.94-6.88 (m, 2H), 3.48-3.44 (m, 4H), 3.30 (dd, J=6.3, 3.9 Hz, 4H). m/z (ESI, +ve ion) 503.1 (M+H)+. GK-GKRP EC$_{50}$ (NADPH-coupled)=3.95 µM; GK-GKRP EC$_{50}$ (LC MS/MS)=2.60 µM.

Example 11

1,1,1,3,3,3-hexafluoro-2-(4-((2S)-2-methyl-4-(2-thiophenylsulfonyl)-1-piperazinyl)phenyl)-2-propanol

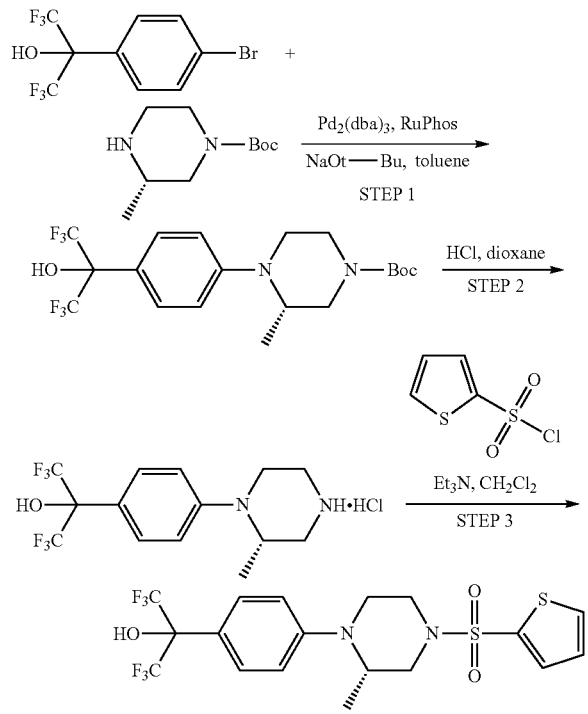

Step 1: (3S)-3-methyl-4-(4-(2,2,2-trifluoro-1-hydroxy-1-(trifluoromethyl)ethyl)phenyl)-1-piperazinecarboxylate A 20 mL vial was charged with 2-(4-bromophenyl)-1,1,1,3,3,3-hexafluoro-2-propanol (0.725 g, 2.24 mmol, Bioorg. Med. Chem. Lett. 2002, 12, 3009), (S)-tert-butyl 3-methylpiperazine-1-carboxylate (0.517 g, 2.58 mmol, Sigma-Aldrich, St. Louis, Mo.), sodium tert-butoxide (0.475 g, 4.94 mmol), and 4 mL of anhydrous toluene. To this was added dicyclohexyl(2',6'-diisopropoxybiphenyl-2-yl)phosphine (RuPhos) (0.016 g, 0.034 mmol, Strem Chemical Inc, Newburyport, Mass.) and tris(dibenzylideneacetone)dipalladium (0) (0.010 g, 0.011 mmol, Strem Chemical Inc, Newburyport, Mass.). The vial was sealed and the mixture was heated at 100° C. for 12 h. After that time, the reaction was diluted with water (5 mL) and extracted with EtOAc (2×20 mL). The organics were separated and dried (MgSO$_4$) to give (3S)-3-methyl-4-(4-(2,2,2-trifluoro-1-hydroxy-1-(trifluoromethyl)ethyl)phenyl)-1-piperazinecarboxylate (0.300 g) as an orange oil which was used without purification.

Step 2: (S)-1,1,1,3,3,3-hexafluoro-2-(4-(2-methylpiperazin-1-yl)phenyl)-2-propanol hydrochloride A 100 mL round-bottomed flask was charged with (3S)-3-methyl-4-(4-(2,2,2-trifluoro-1-hydroxy-1-(trifluoromethyl)ethyl)phenyl)-1-piperazinecarboxylate (0.250 g, 0.565 mmol) and 10 mL of 4N HCl in dioxane. After 2 h at room temperature, the mixture was concentrated to give (S)-1,1,1,3,3,3-hexafluoro-2-(4-(2-methylpiperazin-1-yl)phenyl)-2-propanol hydrochloride as a yellow foam (0.214 g) which was used without purification.

Step 3: 1,1,1,3,3,3-hexafluoro-2-(4-((2S)-2-methyl-4-(2-thiophenylsulfonyl)-1-piperazinyl)phenyl)-2-propanol Following the procedure reported above for Example 1, (S)-1,1,1,3,3,3-hexafluoro-2-(4-(2-methylpiperazin-1-yl)phenyl)-2-propanol hydrochloride and 2-thiophenesulfonyl chloride (Sigma-Aldrich, St. Louis, Mo.) delivered 1,1,1,3,3,3-hexafluoro-2-(4-((2S)-2-methyl-4-(2-thiophenylsulfonyl)-1-piperazinyl)phenyl)-2-propanol. $^1$H NMR (400 MHz, CD$_3$OD) δ 7.92 (dd, J=5.0, 1.3 Hz, 1H), 7.66 (dd, J=3.8, 1.3 Hz, 1H), 7.58 (d, J=8.8 Hz, 2H), 7.28 (dd, J=5.0, 3.8 Hz, 1H), 7.00 (d, J=9.2 Hz, 2H), 4.26-4.17 (m, 1H), 3.77-3.71 (m, 1H), 3.57-3.47 (m, 2H), 3.26 (td, J=11.8, 3.5 Hz, 1H), 2.80 (dd, J=11.3, 3.3 Hz, 1H), 2.64 (td, J=11.2, 3.5 Hz, 1H), 1.18 (J=6.5 Hz, 3H). m/z (ESI, +ve ion) 489.0 (M+H)+. GK-GKRP EC$_{50}$ (NADPH-coupled)=0.217 µM; GK-GKRP EC$_{50}$ (LC MS/MS)=0.371 µM.

Example 12

1,1,1,3,3,3-hexafluoro-2-(4-((2S)-2-methyl-4-(phenylsulfonyl)-1-piperazinyl)phenyl)-2-propanol

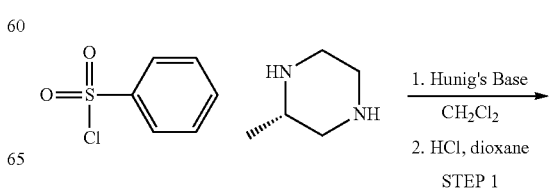

-continued

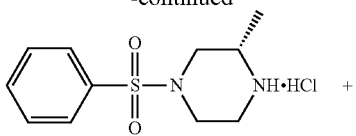

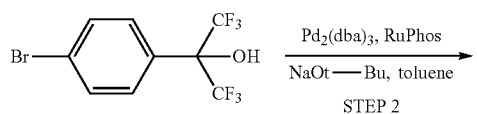

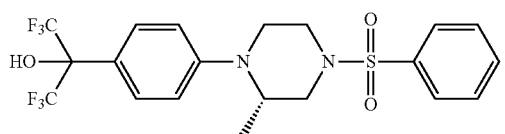

Step 1: (S)-2-methyl-4-(phenylsulfonyl)piperazine hydrochloride

A 500 mL round-bottomed flask was charged with (S)-2-methylpiperazine (5.00 g, 49.9 mmol), 100 mL of $CH_2Cl_2$, and Hünig's base (9.59 mL, 54.9 mmol). After cooling to 0° C., benzenesulfonyl chloride (6.76 mL, 52.4 mmol, Sigma-Aldrich, St. Louis, Mo.) was slowly added. The mixture was stirred at 0° C. for 1 h, then diluted with water (50 mL) and extracted with $CH_2Cl_2$ (2×50 mL). The organic extracts were dried ($MgSO_4$) and concentrated to give an oil. Purification via column chromatography (120 g of silica, 0 to 10% MeOH in $CH_2Cl_2$) gave the free base as an oily solid. This residue was dissolved in EtOAc (100 mL) and acidified with 4N HCl in dioxane (3.5 mL). The resulting white solid was collected by filtration to give (S)-2-methyl-4-(phenylsulfonyl)piperazine hydrochloride (4.25 g).

Step 2: 1,1,1,3,3,3-hexafluoro-2-(4-((2S)-2-methyl-4-(phenylsulfonyl)-1-piperazinyl)phenyl)-2-propanol A 20 mL vial was charged with 2-(4-bromophenyl)-1,1,1,3,3,3-hexafluoro-2-propanol (1.52 g, 4.70 mmol, *Bioorg. Med. Chem. Lett.* 2002, 12, 3009), (S)-2-methyl-4-(phenylsulfonyl)piperazine hydrochloride (1.00 g, 3.61 mmol), sodium tert-butoxide (1.13 g, 11.7 mmol), and 10 mL of anhydrous toluene. To this was added dicyclohexyl(2',6'-diisopropoxybiphenyl-2-yl)phosphine (RuPhos) (0.051 g, 0.11 mmol, Strem Chemical Inc, Newburyport, Mass.) and tris(dibenzylideneacetone)dipalladium (0) (0.033 g, 0.036 mmol, Strem Chemical Inc, Newburyport, Mass.). The vial was sealed and the mixture was heated at 100° C. for 12 h. After that time, the reaction was diluted with water (5 mL) and extracted with EtOAc (2×20 mL). The organics were dried ($MgSO_4$) and concentrated to give an oil that was purified via column chromatography (40 g of silica, 0 to 50% EtOAc in hexanes) to give 1,1,1,3,3,3-hexafluoro-2-(4-((2S)-2-methyl-4-(phenylsulfonyl)-1-piperazinyl)phenyl)-2-propanol (0.310 g). $^1$H NMR (400 MHz, $CD_3OD$) δ 7.83-7.74 (m, 2H), 7.72-7.60 (m, 3H), 7.53 (d, J=8.8 Hz, 2H), 6.94 (d, J=9.2 Hz, 2H), 4.18-4.02 (m, 1H), 3.70 (dd, J=2.4, 11.2 Hz, 1H), 3.56-3.36 (m, 2H), 3.20 (dt, J=3.4, 11.8 Hz, 1H), 2.69 (dd, J=3.4, 11.4 Hz, 1H), 2.53 (dt, J=3.5, 11.2 Hz, 1H), 1.13 (d, J=6.5 Hz, 3H). M/Z (ESI, +ve ion) 483.0 (M+H)$^+$. GK-GKRP $EC_{50}$ (NADPH-coupled)=0.821 µM; GK-GKRP $EC_{50}$ (LC MS/MS)=0.884 µM.

Example 13

2-(4-(2-(2,5-dichlorophenyl)-4-(2-thiophenylsulfonyl)-1-piperazinyl)phenyl)-1,1,1-trifluoro-2-propanol

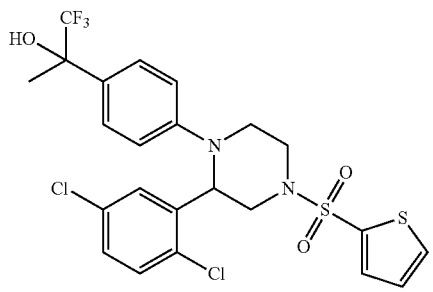 [SMILES: CC(O)(c1ccc(N2CCN(S(=O)(=O)c3cccs3)CC2c2cc(Cl)ccc2Cl)cc1)C(F)(F)F]

To a solution of 2-(2,5-dichlorophenyl)piperazine (316 mg, 1.369 mmol, Ark Pharm, Libertyville, Ill.) in $CH_2Cl_2$ (7.0 mL) was added 2-thiophenesulfonyl chloride (250 mg, 1.369 mmol, Sigma-Aldrich, St. Louis, Mo.) and triethylamine (572 µL, 4.11 mmol). The reaction was stirred at 23° C. for 18 h, after which time the mixture was concentrated to dryness. To this intermediate was added 2-(4-bromophenyl)-1,1,1-trifluoro-2-propanol (368.3 mg, 1.369 mmol, Example 27, step 1), 2-dicyclohexylphosphino-2',6'-diisopropoxybiphenyl (RuPhos) (95.8 mg, 0.734 mmol, Strem Chemical Inc, Newburyport, Mass.) tris(dibenzylideneacetone)dipalladium (0) (62.7 mg, 0.068 mmol, Strem Chemical Inc, Newburyport, Mass.), 10 mL of toluene (9.78 mL) and sodium tert-butoxide (315.7 mg, 3.28 mmol). The reaction was heated to 90° C. and stirred for 20 h. After that time, the mixture was cooled to room temperature, filtered and concentrated. The crude material was absorbed onto a plug of silica gel and purified by silica gel chromatography (50 g of silica, 10 to 40% EtOAc in hexanes) followed by reverse-phase preparative HPLC using a Phemomenex Gemini-NX $C_{18}$ 110A column (150×30 mm), eluting with 0.1% TFA in $CH_3CN/H_2O$ (10% to 90% over 16.5 min) to provide 2-(4-(2-(2,5-dichlorophenyl)-4-(2-thiophenylsulfonyl)-1-piperazinyl)phenyl)-1,1,1-trifluoro-2-propanol as a mixture of 4 isomers.

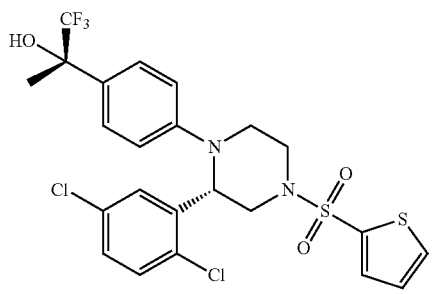

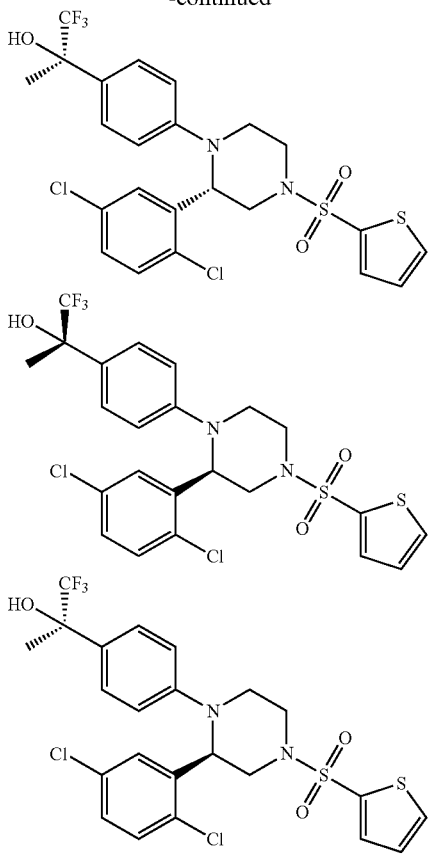

(2S)-2-(4-((2S)-2-(2,5-dichlorophenyl)-4-(2-thiophenylsulfonyl)-1-piperazinyl)phenyl)-1,1,1-trifluoro-2-propanol;
(2S)-2-(4-((2R)-2-(2,5-dichlorophenyl)-4-(2-thiophenylsulfonyl)-1-piperazinyl)phenyl)-1,1,1-trifluoro-2-propanol;
(2R)-2-(4-((2S)-2-(2,5-dichlorophenyl)-4-(2-thiophenylsulfonyl)-1-piperazinyl)phenyl)-1,1,1-trifluoro-2-propanol;
(2R)-2-(4-((2R)-2-(2,5-dichlorophenyl)-4-(2-thiophenylsulfonyl)-1-piperazinyl)phenyl)-1,1,1-trifluoro-2-propanol. $^1$H NMR (300 MHz, CDCl$_3$) δ 7.63 (d, J=5.0 Hz, 1H), 7.55 (dd, J=3.65, 1.0 Hz, 1H), 7.36 (d, J=8.5 Hz, 2H), 7.29 (d, J=1.8 Hz, 1H), 7.24 (s, 1H), 7.14 (dd, J=4.9, 3.9 Hz, 1H), 7.08 (dd, J=8.5, 2.5 Hz, 1H), 6.85 (d, J=8 62 Hz, 2H), 4.84 (dd, J=9.0, 3.4 Hz, 1H), 3.73-3.90 (m, 2H), 3.60 (d, J=12.3 Hz, 1H), 3.19-3.31 (m, 1H), 3.00-3.11 (m, 1H), 2.59-2.71 (m, 1H), 1.68 (d, J=3.5 Hz, 3H). m/z (ESI, +ve ion) 586.8 (M+Na)$^+$. GK-GKRP EC$_{50}$ (NADPH-coupled)=2.64 μM; GK-GKRP EC$_{50}$ (LC MS/MS)=1.96 μM.

Example 14

2-(4-((3R)-3-cyclopropyl-4-(2-thiophenylsulfonyl)-1-piperazinyl)phenyl)-1,1,1,3,3,3-hexafluoro-2-propanol

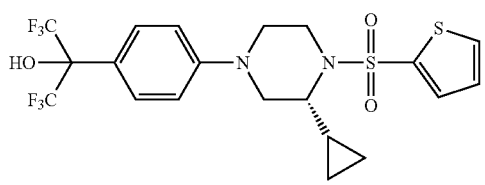 [SMILES: O=S(=O)(c1cccs1)N1CCN(c2ccc(C(O)(C(F)(F)F)C(F)(F)F)cc2)C[C@H]1C1CC1]

A 20 mL vial was charged with toluene (1.2 mL), sodium tert-butoxide (69.2 mg, 720 μmol) were added to (R)-2-cyclopropyl-piperazine (59.7 mg, 300 μmol, Anichem, North Brunswick, N.J.), 2-(4-bromophenyl)-1,1,1,3,3,3-hexafluoro-2-propanol (97 mg, 300 μmol, Bioorg. Med. Chem. Lett. 2002, 12, 3009), dicyclohexyl(2',6'-diisopropoxybiphenyl-2-yl)phosphine (RuPhos), (21.0 mg, 45.0 μmol, Strem Chemical Inc, Newburyport, Mass.) and tris(dibenzylideneacetone)dipalladium (0) (13.7 mg, 15.00 μmol, Strem Chemical Inc, Newburyport, Mass.). The reaction was heated to 90° C. for 40 h, then cooled to 23° C., and diluted with water (15 mL) and extracted with CH$_2$Cl$_2$ (15 mL). The organic layer was loaded onto an AccuBOND II SCX cartridge (Krackeler Scientific, Inc., Albany, N.Y.) (6 g), washed with MeOH (5 mL) and eluted with 2N NH$_3$ in MeOH (10 mL) to give (R)-2-(4-(3-cyclopropylpiperazin-1-yl)phenyl)-1,1,1,3,3,3-hexafluoro-2-propanol. To this was added a solution of 2-thiophenesulfonyl chloride (54.8 mg, 300 μmol, Sigma-Aldrich, St. Louis, Mo.) and Hünig's base (57.5 μL, 330 μmol) in CH$_2$Cl$_2$ (0.6 mL). The reaction was stirred at 23° C. for 18 h and then concentrated to dryness. The crude material was purified by reverse-phase preparative HPLC using a Gemini C$_{18}$ 100 Å column (150×30 mm), eluting with 0.1% TFA in CH$_3$CN/H$_2$O (10% to 90% over 12 min) to give 2-(4-((3R)-3-cyclopropyl-4-(2-thiophenylsulfonyl)-1-piperazinyl)phenyl)-1,1,1,3,3,3-hexafluoro-2-propanol. $^1$H NMR (400 MHz, DMSO-d$_6$) δ 8.49 (s, 1H), 7.93 (dd, J=5.3 1.3 Hz, 1H), 7.71 (dd, J=3.7, 1.1 Hz, 1H), 7.46 (d, J=9.2 Hz, 2H), 7.18 (dd, J=4.8, 4.0 Hz, 1H), 6.95 (d, J=9.7 Hz, 2H), 2.67 (dd, J=12.5, 3.7 Hz, 1H), 2.52-2.60 (m, 4H), 1.30-1.42 (m, 1H), 0.35-0.56 (m, 6H). m/z (ESI, +ve ion) 515.0 (M+H)$^+$. GK-GKRP EC$_{50}$ (NADPH-coupled)=5.0 μM.

Example 15

1-cyclopropyl-2,2,2-trifluoro-1-(4-(4-(phenylsulfonyl)-1-piperazinyl)phenyl)ethanol

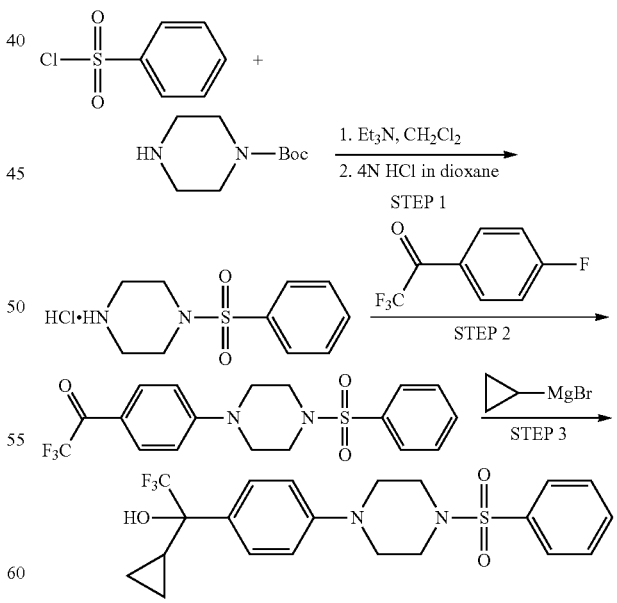

Step 1: 1-(phenylsulfonyl)piperazine hydrochloride

A 500 ml, round-bottomed flask was charged with 1-Boc-piperazine (18.55 g, 100 mmol, Sigma-Aldrich, St. Louis, Mo.), triethylamine (18.05 mL, 129 mmol), and 200 mL of CH$_2$Cl$_2$. To this was added benzenesulfonyl chloride (16.05 mL, 124 mmol, Sigma-Aldrich, St. Louis, Mo.). After 15 min, the mixture was diluted with water (150 mL) and the layers were separated. The organics were dried (MgSO$_4$) and concentrated to give a white solid. This solid was dissolved in EtOAc (300 mL) and 150 mL of 4N HCl in dioxane. After 3 h at 65° C., the white precipitate was filtered to give 1-(phenylsulfonyl)piperazine hydrochloride (21.0 g) as a white solid.

Step 2: 2,2,2-trifluoro-1-(4-(4-(phenylsulfonyl)-1-piperazinyl)phenyl)ethanone

A 125 ml, pressure tube was charged with 2,2,2-trifluoro-1-(4-fluorophenyl)ethanone (7.31 g, 38.1 mmol, Sigma-Aldrich, St. Louis, Mo.), 1-(phenylsulfonyl)piperazine hydrochloride (5.00 g, 19.0 mmol), 20 mL of CH$_3$CN, and triethylamine (7.96 mL, 57.1 mmol). The tube was sealed and heated at 110° C. for 3 h. After that time, the mixture was diluted with EtOAc (100 mL) and water (50 mL). The organics were separated, dried (MgSO$_4$) and concentrated to give a white solid. This solid was slurried with hexane (150 mL) to give 2,2,2-trifluoro-1-(4-(4-(phenylsulfonyl)-1-piperazinyl)phenyl)ethanone (3.85 g) as a bright white solid.

Step 3: 1-cyclopropyl-2,2,2-trifluoro-1-(4-(4-(phenylsulfonyl)-1-piperazinyl)phenyl)ethanol A 100 mL round-bottom flask was charged with 2,2,2-trifluoro-1-(4-(4-(phenylsulfonyl)-1-piperazinyl)phenyl)ethanone (0.50 g, 1.26 mmol) and 10 mL of THF. After cooling to 0° C., cyclopropylmagnesium bromide (5.02 mL, 0.5 M in THF, 2.51 mmol, Sigma-Aldrich, St. Louis, Mo.) was added. After 10 min, the mixture was quenched with saturated aqueous NH$_4$Cl (15 mL), extracted with EtOAc (2×50 mL), dried (MgSO$_4$), and concentrated to give an oil. This oil was purified via column chromatography (40 g of silica, 0 to 40% EtOAc in hexanes) to give 1-cyclopropyl-2,2,2-trifluoro-1-(4-(4-(phenylsulfonyl)-1-piperazinyl)phenyl)ethanol (0.375 g) as a mixture of two enantiomers.

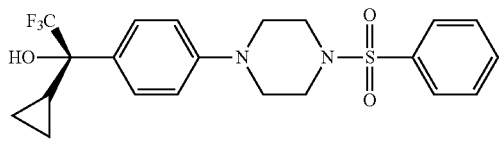

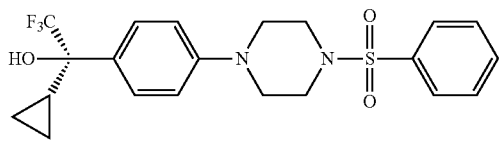

(1R)-1-cyclopropyl-2,2,2-trifluoro-1-(4-(4-(phenylsulfonyl)-1-piperazinyl)phenyl)ethanol; (1S)-1-cyclopropyl-2,2,2-trifluoro-1-(4-(4-(phenylsulfonyl)-1-piperazinyl)phenyl)ethanol. $^1$H NMR (400 MHz, CD$_3$OD) δ 7.88-7.78 (m, 2H), 7.74-7.57 (m, 3H), 7.48 (s, 2H), 6.96-6.83 (m, 2H), 3.28-3.23 (m, 4H), 3.18-3.05 (m, 4H), 1.61-1.48 (m, 1H), 0.76-0.63 (m, 1H), 0.58-0.46 (m, 1H), 0.44-0.34 (m, 1H), 0.30-0.20 (m, 1H). m/z (ESI, +ve ion) 441.0 (M+H)$^+$. GK-GKRP EC$_{50}$ (NADPH-coupled)=2.62 μM; GK-GKRP EC$_{50}$ (LC MS/MS)=2.77 μM.

Example 16

1,1,1-trifluoro-2-(2-((2S)-2-methyl-4-(2-thiophenylsulfonyl)-1-piperazinyl)-5-pyrimidinyl)-2-propanol

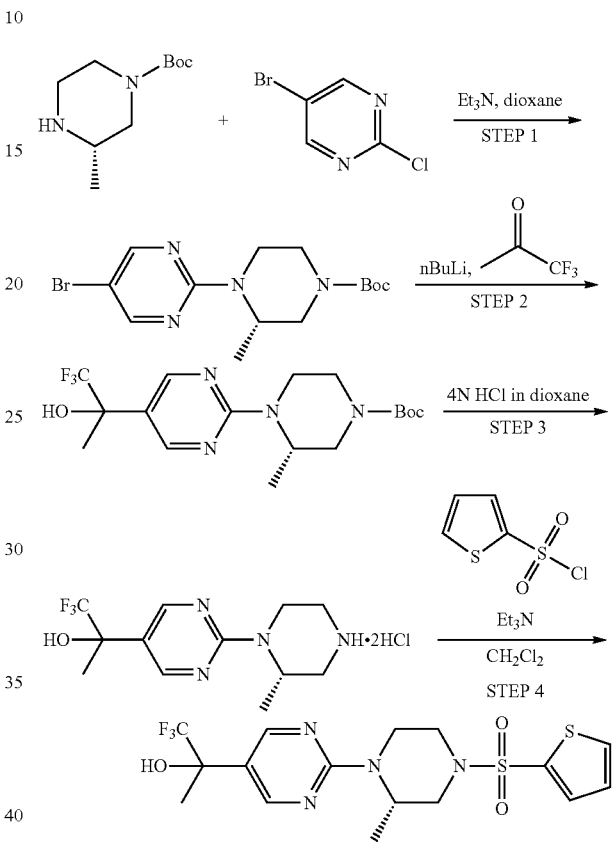

Step 1: tert-butyl (3S)-4-(5-bromo-2-pyrimidinyl)-3-methyl-1-piperazinecarboxylate A 250 mL pressure vessel was charged with (S)-4-(tert-butoxycarbonyl)-2-methylpiperazine (4.17 g, 21.84 mmol, Sigma-Aldrich, St. Louis, Mo.), 5-bromo-2-chloropyrimidine (4.22 g, 21.84 mmol, Combi-Blocks, San Diego, Calif.), triethylamine (6.09 mL, 43.7 mmol), and 50 mL of dioxane. The tube was sealed and heated at 110° C. for 24 h. The mixture was diluted with water (100 mL) and extracted with EtOAc (2×150 mL). The organics were dried (MgSO$_4$) and concentrated to give an oil that was purified via column chromatography (120 g silica, 0 to 30% EA/Hex) to give tert-butyl (3S)-4-(5-bromo-2-pyrimidinyl)-3-methyl-1-piperazinecarboxylate (6.15 g) as a white solid.

Step 2: (3S)-3-methyl-4-(5-(2,2,2-trifluoro-1-hydroxy-1-methylethyl)-2-pyrimidinyl)-1-piperazinecarboxylate A 250 mL round-bottomed flask was charged with tert-butyl (3S)-4-(5-bromo-2-pyrimidinyl)-3-methyl-1-piperazinecarboxylate (4.00 g, 11.2 mmol) and 20 mL of THF. After cooling to −78° C., n-BuLi (5.15 mL, 2.5 M in hexanes, 12.9 mmol) was added. This mixture was stirred at −78° C. for 10 min, then 1,1,1-trifluoro-2-propanone (2.51 mL, 22.4 mmol, Sigma-Aldrich, St. Louis, Mo.) was added. The mixture was stirred at −78° C. for an additional 1 h, then quenched with saturated aqueous NH$_4$Cl (50 mL) and extracted with EtOAc (2×50 mL). The combined organic extracts were dried (MgSO$_4$), concentrated and purified via column chromatography (40 g of silica, 0 to 50% EtOAc in hexanes) to give (3S)-3-methyl-4-(5-(2,2,2-trifluoro-1-hydroxy-1-methylethyl)-2-pyrimidinyl)-1-piperazinecarboxylate (1.12 g) as a white foam.

Step 3: 1,1,1-trifluoro-2-(2-((2S)-2-methyl-1-piperazinyl)-5-pyrimidinyl)-2-propanol dihydrochloride A 100 mL round-bottomed flask was charged with ((3S)-3-methyl-4-(5-(2,2,2-trifluoro-1-hydroxy-1-methylethyl)-2-pyrimidinyl)-1-piperazinecarboxylate (1.12 g, 2.87 mmol), 10 mL of EtOAc, and 3 mL of 4N HCl in dioxane. The mixture was heated at 80° C. for 3 h. The resulting white precipitate was collected by filtration to give 1,1,1-trifluoro-2-(2-((2S)-2-methyl-1-piperazinyl)-5-pyrimidinyl)-2-propanol dihydrochloride (1.05 g)

Step 4: 1,1,1-trifluoro-2-(2-((2S)-2-methyl-4-(2-thiophenylsulfonyl)-1-piperazinyl)-5-pyrimidinyl)-2-propanol A 100 mL round-bottomed flask was charged with 1,1,1-trifluoro-2-(2-((2S)-2-methyl-1-piperazinyl)-5-pyrimidinyl)-2-propanol dihydro chloride (0.250 g, 0.763 mmol) and 10 mL of CH$_2$Cl$_2$. To this was added 2-thiophenesulfonyl chloride (0.153 g, 0.839 mmol, Sigma-Aldrich, St. Louis, Mo.). After 15 min, the mixture was diluted with water (50 mL) and extracted with CH$_2$Cl$_2$ (2×50 mL). The combined extracts were dried (MgSO$_4$), concentrated, and purified via column chromatography (40 g of silica, 0 to 50% EtOAc in hexanes) to give 1,1,1-trifluoro-2-(2-((2S)-2-methyl-4-(2-thiophenylsulfonyl)-1-piperazinyl)-5-pyrimidinyl)-2-propanol (0.125 g) as mixture of two isomers.

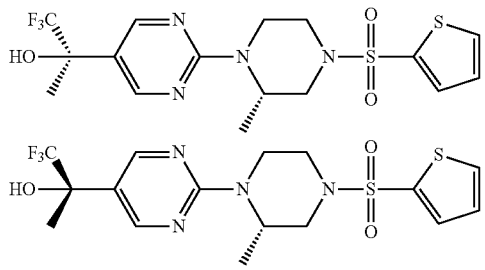

(2S)-1,1,1-trifluoro-2-(2-((2S)-2-methyl-4-(2-thiophenylsulfonyl)-1-piperazinyl)-5-pyrimidinyl)-2-propanol; (2R)-1,1,1-trifluoro-2-(2-((2S)-2-methyl-4-(2-thiophenylsulfonyl)-1-piperazinyl)-5-pyrimidinyl)-2-propanol. $^1$H NMR (400 MHz, CD$_3$OD) δ 8.50 (s, 2H), 7.86 (dd, J=1.2, 5.1 Hz, 1H), 7.63 (dd, J=1.2, 3.7 Hz, 1H), 7.27-7.21 (m, 1H), 5.08 (br. s., 1H), 4.68 (d, J=13.5 Hz, 1H), 3.86-3.74 (m, 1H), 3.68-3.60 (m, 1H), 3.38-3.29 (m, 1H), 2.61-2.56 (m, 1H), 2.43 (dt, J=3.5, 11.8 Hz, 1H), 1.70 (s, 3H), 1.33 (d, J=6.8 Hz, 3H). m/z (ESI, +ve ion) 437.1 (M+H)$^+$. GK-GKRP EC$_{50}$ (NADPH-coupled)=1.00 μM; GK-GKRP EC$_{50}$ (LC MS/MS)=1.10 μM.

This mixture of isomers was resolved using preparative SFC (Chiralcel® OJ-H column (250 mm×21 mm, 5 μm) eluting with 90% liquid CO$_2$ in 10% i-PrOH (0.2% diethylamine) at a flow rate of 70.0 mL/min) to give two products in greater than 95% diastereomeric excess.

First Eluting Peak (Peak #1)
$^1$H NMR (400 MHz, CD$_3$OD) δ 8.49 (s, 2H), 7.85 (d, J=1.0 Hz, 1H), 7.61 (dd, J=1.0, 3.7 Hz, 1H), 7.34-7.12 (m, 1H), 5.06 (s, 1H), 4.67 (d, J=13.7 Hz, 1H), 3.78 (br. s., 1H), 3.62 (s, 1H), 3.39-3.29 (m, 1H), 2.63-2.51 (m, 1H), 2.42 (dt, J=3.5, 11.8 Hz, 1H), 1.69 (s, 3H), 1.31 (d, J=6.7 Hz, 3H). m/z (ESI, +ve ion) 437.1 (M+H)$^+$. GK-GKRP EC$_{50}$ (NADPH-coupled)=0.865 μM; GK-GKRP EC$_{50}$ (LC MS/MS)=1.16 μM.

Second Eluting Peak (Peak #2)
$^1$H NMR (400 MHz, CD$_3$OD) δ 8.48 (s, 2H), 7.89-7.79 (m, 1H), 7.61 (d, J=3.7 Hz, 1H), 7.32-7.02 (m, 1H), 5.06 (s, 1H), 4.66 (d, J=14.7 Hz, 1H), 3.78 (d, J=11.2 Hz, 1H), 3.62 (d, J=11.7 Hz, 1H), 3.42-3.29 (m, 1H), 2.57 (dd, J=3.6, 11.6 Hz, 1H), 2.41 (dt, J=3.6, 11.9 Hz, 1H), 1.68 (s, 3H), 1.30 (d, J=6.7 Hz, 3H). m/z (ESI, +ve ion) 437.1 (M+H)$^+$. GK-GKRP EC$_{50}$ (NADPH-coupled)=0.547 μM; GK-GKRP EC$_{50}$ (LC MS/MS)=0.806 μM.

Example 17

1,1,1,3,3,3-hexafluoro-2-(6-(4-(phenylsulfonyl)phenyl)-3-pyridinyl)-2-propanol

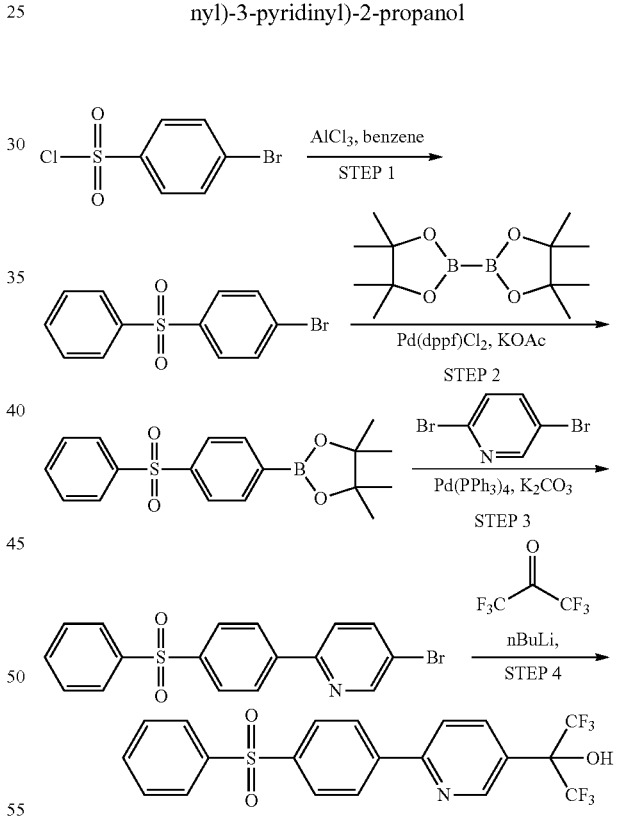

Step 1: 1-bromo-4-(phenylsulfonyl)benzene

A 500 mL round-bottomed flask was charged with 4-bromobenzenesulfonyl chloride (10.00 g, 39.1 mmol, Sigma-Aldrich, St. Louis, Mo.), 100 mL of benzene and aluminum chloride (6.26 g, 47.0 mmol). After stirring at room temperature for 12 h, the mixture was diluted water (100 mL) and extracted with EtOAc (2×100 mL). The organic extracts were dried (MgSO$_4$) and concentrated to give 1-bromo-4-(phenylsulfonyl)benzene (10.50 g) as a white solid.

Step 2: 4,4,5,5-tetramethyl-2-(4-(phenylsulfonyl)phenyl)-1,3,2-dioxaborolane

A 250 mL round-bottomed flask was charged with 1-bromo-4-(phenylsulfonyl)benzene (2.50 g, 8.41 mmol), bis(pinacolato)diboron (2.46 g, 9.67 mmol, Sigma-Aldrich, St. Louis, Mo.), 1,1'bis(diphenylphosphino)ferrocene]dichloropalladium (II) (0.344 g, 0.421 mmol, Sigma-Aldrich, St. Louis, Mo.), potassium acetate (2.48 g, 25.2 mmol), and 50 ml, of dioxane. This mixture was heated at 100° C. for 12 h and then cooled to room temperature. The reaction was diluted with EtOAc (200 mL), filtered, and concentrated to give a dark solid. This solid was slurried with cold (0° C.) MeOH (50 mL) to give 4,4,5,5-tetramethyl-2-(4-(phenylsulfonyl)phenyl)-1,3,2-dioxaborolane (2.20 g) as a gray solid.

Step 3: 5-bromo-2-(4-(phenylsulfonyl)phenyl)pyridine

A 100 ml, pressure vessel was charged with 4,4,5,5-tetramethyl-2-(4-(phenylsulfonyl)phenyl)-1,3,2-dioxaborolane (1.00 g, 2.91 mmol), 2,5-dibromopyridine (0.860 g, 3.63 mmol, Sigma-Aldrich, St. Louis, Mo.), potassium carbonate (1.20 g, 8.72 mmol), tetrakis(triphenylphosphine)palladium (0) (0.168 g, 0.145 mmol, Strem Chemical Inc, Newburyport, Mass.), 16 mL of 1,2-dimethoxyethane, and 4 mL of water. The vessel was sealed and the reaction was heated at 100° C. for 2 h. After cooling to room temperature, the mixture was diluted with EtOAc (30 mL), separated, dried (MgSO$_4$) and concentrated to give an oil. Purification via column chromatography (40 g of silica gel, 0 to 50% EtOAc in hexanes) produced a yellow solid that was slurried with cold (0° C.) MeOH (20 mL) to give 5-bromo-2-(4-(phenylsulfonyl)phenyl)pyridine (0.450 g).

Step 4: 1,1,1,3,3,3-hexafluoro-2-(6-(4-(phenylsulfonyl)phenyl)-3-pyridinyl)-2-propanol A 250 mL round-bottomed flask was charged with 5-bromo-2-(4-(phenylsulfonyl)phenyl)pyridine (0.45 g, 1.20 mmol) and 15 mL of THF. After cooling to −78° C., n-BuLi (0.60 mL, 2.5 M in hexanes, 1.50 mmol) was added dropwise. The resulting black solution was stirred for 15 min at −78° C. and then 1,1,1,3,3,3-hexafluoro-2-propanone (Sigma-Aldrich, St. Louis, Mo.) was bubbled thru the solution for 3 min. The reaction was then quenched with saturated aqueous NH$_4$Cl (20 mL) and extracted with EtOAc (2×40 mL). The combined organic extracts were dried (MgSO$_4$), concentrated, and purified via column chromatography (40 g of silica, 0 to 50% EtOAc in hexanes) to give 1,1,1,3,3,3-hexafluoro-2-(6-(4-(phenylsulfonyl)phenyl)-3-pyridinyl)-2-propanol (0.025 g) as a white solid. $^1$H NMR (400 MHz, CD$_3$OD) δ 8.95 (s, 1H), 8.38-8.15 (m, 3H), 8.13-7.88 (m, 5H), 7.61 (s, 3H). m/z (ESI, +ve ion) 462.0 (M+H)$^+$. GK-GKRP EC$_{50}$ (NADPH-coupled)=1.63 μM; GK-GKRP EC$_{50}$ (LC MS/MS)=1.71 μM.

Example 18

2-(6-(3-chloro-4-(phenylsulfonyl)phenyl)-3-pyridinyl)-1,1,1-trifluoro-2-propanol

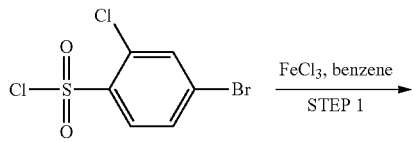

Step 1: 4-bromo-2-chloro-1-(phenylsulfonyl)benzene

A 500 mL round-bottomed flask was charged with 4-bromo-2-chlorobenzene-1-sulfonyl chloride (10.0 g, 34.5 mmol, Sigma-Aldrich, St. Louis, Mo.), ferric chloride (2.80 g, 17.2 mmol), and 200 mL of benzene. The mixture was heated at reflux for 12 h then diluted with water (100 mL) and extracted with CH$_2$Cl$_2$ (2×300 mL). The combined organic layers were dried (MgSO$_4$) and concentrated to give a brown solid that was slurried with EtOH (100 mL) to give 4-bromo-2-chloro-1-(phenylsulfonyl)benzene (7.50 g).

Steps 2, 3 and 4: 2-(6-(3-chloro-4-(phenylsulfonyl)phenyl)-3-pyridinyl)-1,1,1-trifluoro-2-propanol Following the procedure outlined for Example 17 (with 1,1,1-trifluoro-2-propanone replacing 1,1,1,3,3,3-hexafluoro-2-propanone), 4-bromo-2-chloro-1-(phenylsulfonyl)benzene was converted to 2-(6-(3-chloro-4-(phenylsulfonyl)phenyl)-3-pyridinyl)-1,1,1-trifluoro-2-propanol (mixture of two enantiomers).

(2S)-2-(6-(3-chloro-4-(phenylsulfonyl)phenyl)-3-pyridinyl)-1,1,1-trifluoro-2-propanol; (2R)-2-(6-(3-chloro-4-(phenylsulfonyl)phenyl)-3-pyridinyl)-1,1,1-trifluoro-2-propanol. $^1$H NMR (400 MHz, CD$_3$OD) δ 8.95-8.88 (m, 1H), 8.46 (d, J=8.0 Hz, 1H), 8.31-8.21 (m, 2H), 8.19-8.11 (m, 1H), 8.06-

7.95 (m, 3H), 7.74-7.66 (m, 1H), 7.62 (s, 2H), 1.81 (s, 3H). m/z (ESI, +ve ion) 441.8 (M+H)+. GK-GKRP EC$_{50}$ (NADPH-coupled)=3.75 µM; GK-GKRP EC$_{50}$ (LC MS/MS)=3.57 µM.

Example 19

2-(3'-chloro-4'-(phenylsulfonyl)-4-biphenylyl)-1,1,1-trifluoro-2-propanol

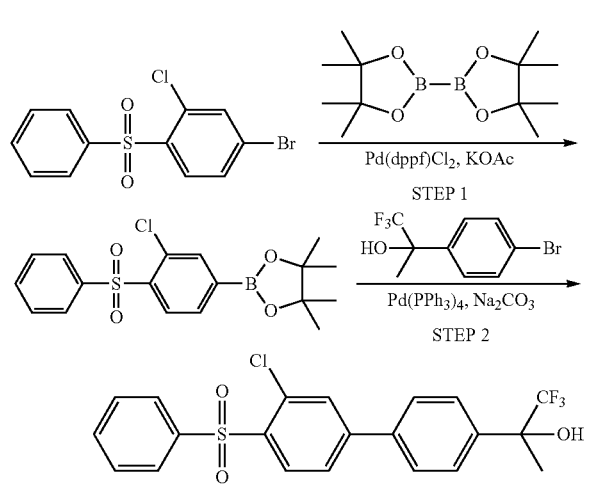

Step 1: 2-(3-chloro-4-(phenylsulfonyl)phenyl)-4,4,5,5-tetramethyl-1,3,2-dioxaborolane Following the procedure described for Example 17 (Step 2), 4-bromo-2-chloro-1-(phenylsulfonyl)benzene provided 2-(3-chloro-4-(phenylsulfonyl)phenyl)-4,4,5,5-tetramethyl-1,3,2-dioxaborolane.

Step 2: 2-(3'-chloro-4'-(phenylsulfonyl)-4-biphenylyl)-1,1,1-trifluoro-2-propanol Following the procedure described for Example 17 (Step 3), 2-(3-chloro-4-(phenylsulfonyl)phenyl)-4,4,5,5-tetramethyl-1,3,2-dioxaborolane coupled with 2-(4-bromophenyl)-1,1,1-trifluoro-2-propanol (example 27, step 1) to deliver 2-(3'-chloro-4'-(phenylsulfonyl)-4-biphenylyl)-1,1,1-trifluoro-2-propanol (mixture of two enantiomers).

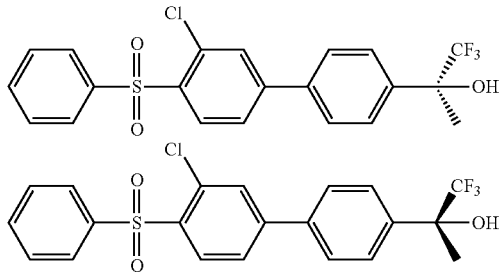

(2R)-2-(3'-chloro-4'-(phenylsulfonyl)-4-biphenylyl)-1,1,1-trifluoro-2-propanol; (2S)-2-(3'-chloro-4'-(phenylsulfonyl)-4-biphenylyl)-1,1,1-trifluoro-2-propanol. ¹H NMR (400 MHz, CD$_3$OD) δ 8.43 (d, J=8.2 Hz, 1H), 8.02-7.81 (m, 4H), 7.79-7.68 (m, 5H), 7.66-7.58 (m, 2H), 1.77 (s, 3H). m/z (ESI, +ve ion) 441.1 (M+H)+. GK-GKRP EC$_{50}$ (NADPH-coupled)=3.58 µM; GK-GKRP EC$_{50}$ (LC MS/MS)=4.23 µM.

Example 20

2-methyl-4-(4-(phenylsulfonyl)-4'-(2,2,2-trifluoro-1-hydroxy-1-methylethyl)-3-biphenylyl)-3-butyn-2-ol

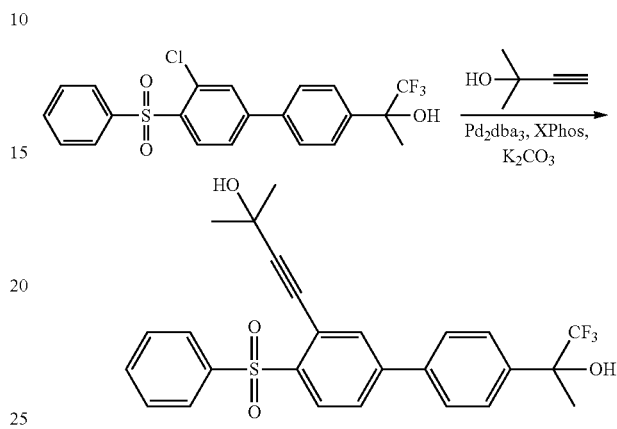

A 20 mL vial was charged with 2-(3'-chloro-4'-(phenylsulfonyl)-4-biphenylyl)-1,1,1-trifluoro-2-propanol (0.300 g, 0.680 mmol, Example 19), 2-methyl-3-butyn-2-ol (0.099 mL, 1.021 mmol, Sigma-Aldrich, St. Louis, Mo.), potassium carbonate (0.235 g, 1.701 mmol), 2 mL of dimethylacetamide, 2-(dicyclohexylphosphino)-2',4',6',-triisopropyl-biphenyl (XPhos) (9.73 mg, 0.020 mmol, Strem Chemical Inc, Newburyport, Mass.), and tris(dibenzylideneacetone)dipalladium (0) (0.021 g, 0.020 mmol, Strem Chemical Inc, Newburyport, Mass.). The vial was sealed and heated at 100° C. for 2 h. After that time, the mixture was concentrated and purified by column chromatography (40 g of silica, 0 to 40% EtOAc in hexane) to give 2-methyl-4-(4-(phenylsulfonyl)-4'-(2,2,2-trifluoro-1-hydroxy-1-methylethyl)-3-biphenylyl)-3-butyn-2-ol (0.035 g) as a mixture of two enantiomers.

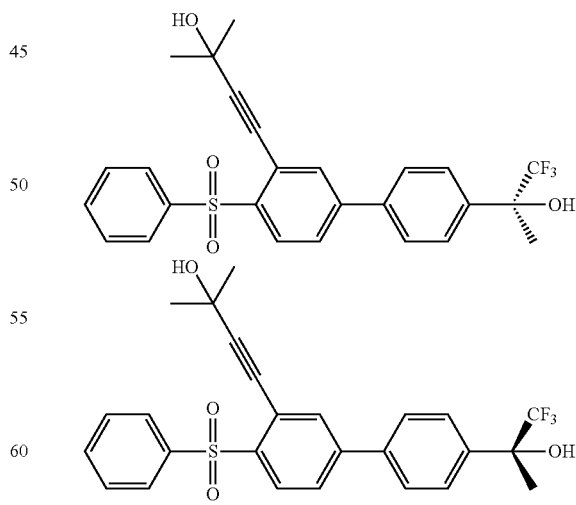

2-methyl-4-(4-(phenylsulfonyl)-4'-((1S)-2,2,2-trifluoro-1-hydroxy-1-methylethyl)-3-biphenylyl)-3-butyn-2-ol; 2-methyl-4-(4-(phenylsulfonyl)-4'-((1R)-2,2,2-trifluoro-1-hydroxy-1-methylethyl)-3-biphenylyl)-3-butyn-2-ol. ¹H NMR (400 MHz, CD$_3$OD) δ 8.34 (d, J=8.2 Hz, 1H), 8.05 (d, J=7.8 Hz, 2H), 7.92-7.81 (m, 2H), 7.79-7.66 (m, 5H), 7.64-7.55 (m, 2H), 1.77 (s, 3H), 1.59 (s, 6H). m/z (ESI, +ve ion) 471.0 (M-OH)$^+$. GK-GKRP EC$_{50}$ (NADPH-coupled)=1.80 μM; GK-GKRP EC$_{50}$ (LC MS/MS)=2.25 μM.

Example 21

1,1,1,3,3,3-hexafluoro-2-(4'-(phenylsulfonyl)-4-biphenylyl)-2-propanol

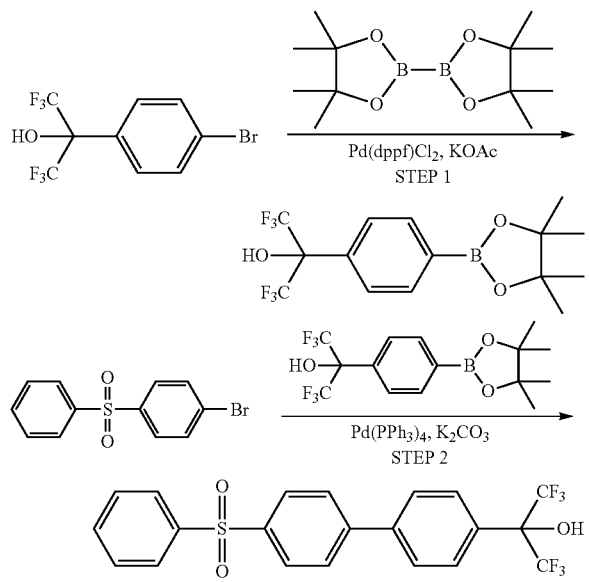

Step 1: 1,1,1,3,3,3-hexafluoro-2-(4-(4,4,5,5-tetramethyl-1,3,2-dioxaborolan-2-yl)phenyl)-2-propanol A 150 ml, pressure vessel was charged with 4 bis(pinacolato)diboron (4.72 g, 18.57 mmol, Sigma-Aldrich, St. Louis, Mo.), 2-(4-bromophenyl)-1,1,1,3,3,3-hexafluoro-2-propanol (5.00 g, 15.48 mmol, Bioorg. Med. Chem. Lett. 2002, 12, 3009), potassium acetate (4.56 g, 46.4 mmol), 1,1' bis(diphenylphosphino)ferrocene]dichloropalladium (II) (0.632 g, 0.774 mmol), and 25 ml, of dioxane. After 3 h at 100° C., the mixture was diluted with EtOAc (100 mL) and filtered. The filtrate was concentrated and purified via column chromatography (0 to 25% EtOAc in hexanes) to give 1,1,1,3,3,3-hexafluoro-2-(4-(4,4,5,5-tetramethyl-1,3,2-dioxaborolan-2-yl)phenyl)-2-propanol (3.50 g) as a white solid.

Step 2: 1,1,1,3,3,3-hexafluoro-2-(4'-(phenylsulfonyl)-4-biphenylyl)-2-propanol A 100 mL pressure vessel was charged with 1-bromo-4-(phenylsulfonyl)benzene (1.00 g, 3.37 mmol, Example 17, step 1), 1,1,1,3,3,3-hexafluoro-2-(4-(4,4,5,5-tetramethyl-1,3,2-dioxaborolan-2-yl)phenyl)-2-propanol (1.62 g, 4.37 mmol), potassium carbonate (1.40 g, 10.10 mmol), tetrakis (triphenylphosphine)palladium (0) (0.194 g, 0.168 mmol), 20 mL of 1,2-dimethoxyethane, and 5 mL of water. The vessel was sealed and the reaction was heated to 100° C. for 2 h. After cooling to room temperature, the mixture was diluted with EtOAc (30 mL), separated, dried (MgSO$_4$) and concentrated to give an oil. Purification via column chromatography (40 g of silica, 0 to 50% EtOAc in hexanes) produced a yellow solid that was slurried with cold (0° C.) MeOH (25 mL) to give 1,1,1,3,3,3-hexafluoro-2-(4'-(phenylsulfonyl)-4-biphenylyl)-2-propanol (0.650 g). $^1$H NMR (400 MHz, CD$_3$OD) δ 8.08-7.95 (m, 4H), 7.91-7.74 (m, 6H), 7.69-7.54 (m, 3H). m/z (ESI, +ve ion) 461.0 (M+H)$^+$. GK-GKRP EC$_{50}$ (NADPH-coupled)=1.66 μM; GK-GKRP EC$_{50}$ (LC MS/MS)=3.96 μM.

Example 22

1,1,1,3,3,3-hexafluoro-2-(6-(4-(phenylsulfonyl)-1-piperazinyl)-3-pyridinyl)-2-propanol

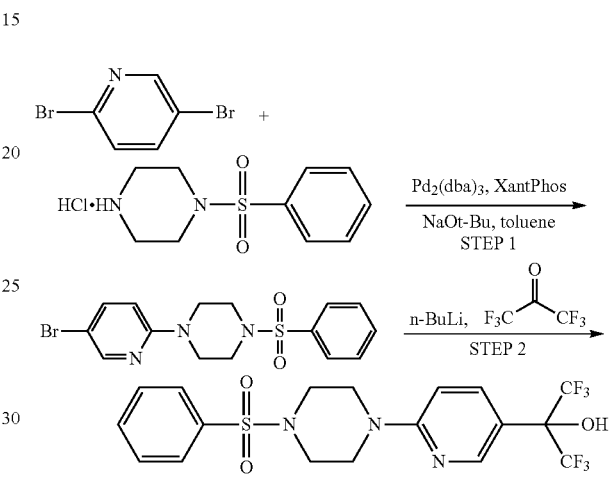

Step 1: 1-(5-bromo-2-pyridinyl)-4-(phenylsulfonyl)piperazine

A 350 ml, pressure vessel was charged with 4-(phenylsulfonyl)piperazine hydrochloride (1.50 g, 5.71 mmol, Example 15, step 1), 2,5-dibromopyridine (1.76 g, 7.42 mmol, Sigma-Aldrich, St. Louis, Mo.), 100 mL of toluene, sodium tert-butoxide (1.37 g, 14.3 mmol), tris(dibenzylideneacetone)dipalladium (0) (0.105 g, 0.114 mmol, Strem Chemical Inc, Newburyport, Mass.), and 4,5-bis(diphenylphosphino)-9,9-dimethylxanthene (XantPhos) (0.198 g, 0.343 mmol, Strem Chemical Inc, Newburyport, Mass.). The tube was sealed and heated at 110° C. for 3 h. After that time, the reaction was cooled to room temperature, diluted with water (20 mL) and extracted with EtOAc (2×50 mL). The organic layer was separated, dried (MgSO$_4$) and concentrated to give a yellow solid. This solid was slurried with cold (0° C.) MeOH (25 mL) to give 1-(5-bromo-2-pyridinyl)-4-(phenylsulfonyl)piperazine (0.957 g) as a light yellow solid.

Step 2: 1,1,1,3,3,3-hexafluoro-2-(6-(4-(phenylsulfonyl)-1-piperazinyl)-3-pyridinyl)-2-propanol A 250 mL round-bottomed flask was charged with 1-(5-bromo-2-pyridinyl)-4-(phenylsulfonyl)piperazine (0.96 g, 2.50 mmol) and 15 mL of THF. After cooling to −78° C., n-BuLi (1.20 mL, 3.0 mmol, 2.5 M in hexanes) was added drop-wise. After stirring at −78° C. for 15 min, 1,1,1,3,3,3-hexafluoro-2-propanone (Sigma-Aldrich, St. Louis, Mo.) was bubbled through the solution for 3 min. The reaction was then quenched with saturated aqueous NH$_4$Cl (20 mL) and extracted with EtOAc (2×40 mL). The combined organic extracts were dried (MgSO$_4$) and concentrated to give an oil that was purified via column chromatography (40 g of silica, 0 to 50% EtOAc in hexanes) to give 1,1,1,3,3,3-hexafluoro-2-(6-(4-(phenylsulfonyl)-1-piperazinyl)-3-pyridinyl)-2-propanol (0.44 g) as a white solid. $^1$H NMR (400 MHz, CD$_3$OD) δ 8.46-8.22 (m, 1H), 7.91-7.46 (m, 6H), 6.93-6.69 (m, 1H), 3.87-3.58 (m, 4H), 3.17-2.96 (m, 4H). m/z (ESI, +ve ion) 470.0 (M+H)$^+$. GK-GKRP EC$_{50}$ (NADPH-coupled)=2.73 μM; GK-GKRP EC$_{50}$ (LC MS/MS)=2.08 μM.

Example 23

1,1,1,3,3,3-hexafluoro-2-(2-(4-(phenylsulfonyl)-1-piperazinyl)-5-pyrimidinyl)-2-propanol

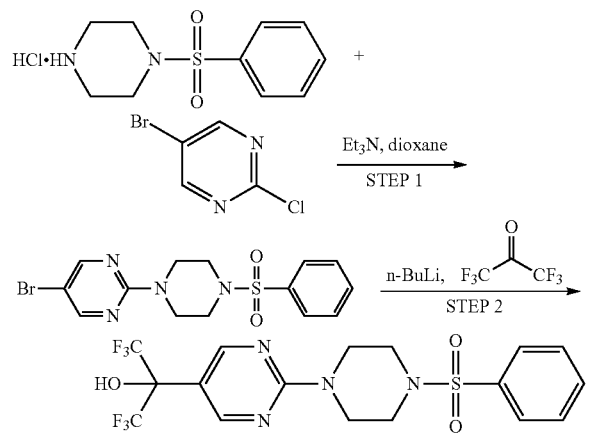

Step 1: 5-bromo-2-(4-(phenylsulfonyl)-1-piperazinyl)pyrimidine

A 250 mL round-bottomed flask was charged with 1-(phenylsulfonyl)piperazine hydrochloride (4.08 g, 15.51 mmol, Example 15, step 1), 5-bromo-2-chloropyrimidine (2.50 g, 12.92 mmol, Sigma-Aldrich, St. Louis, Mo.), and 20 mL of dioxane. To this was added triethylamine (4.50 mL, 32.3 mmol). After stirring at room temperature for 3 h, the mixture was diluted with water (50 mL) and the resulting precipitate was collected by filtration to give 5-bromo-2-(4-(phenylsulfonyl)-1-piperazinyl)pyrimidine (2.50 g) as a white solid.

Step 2: 1,1,1,3,3,3-hexafluoro-2-(2-(4-(phenylsulfonyl)-1-piperazinyl)-5-pyrimidinyl)-2-propanol A 100 mL round-bottomed flask was charged with 5-bromo-2-(4-(phenylsulfonyl)-1-piperazinyl)pyrimidine (1.00 g, 2.61 mmol) and 20 mL of THF. After cooling to −78° C., n-BuLi (1.31 mL, 2.5 M in hexanes, 3.26 mmol) was added. This mixture was stirred at −78° C. for 10 min, and then 1,1,1,3,3,3-hexafluoro-2-propanone (Sigma-Aldrich, St. Louis, Mo.) was bubbled through the solution for 5 min. The mixture was stirred at −78° C. for an additional 30 min, then quenched with saturated aqueous NH$_4$Cl (50 mL) and extracted with EtOAc (2×50 mL). This oil was purified by column chromatography (twice, first with 0 to 40% EtOAc in hexanes (40 g of silica) then 0 to 10% MeOH in CH$_2$Cl$_2$ (40 g of silica)) to give 1,1,1,3,3,3-hexafluoro-2-(2-(4-(phenylsulfonyl)-1-piperazinyl)-5-pyrimidinyl)-2-propanol (0.078 g) as a white solid. $^1$H NMR (400 MHz, CD$_3$OD) δ 8.54 (s, 2H), 7.89-7.79 (m, 2H), 7.74-7.50 (m, 3H), 4.12-3.78 (m, 4H), 3.21-2.92 (m, 4H). m/z (ESI, +ve ion) 470.8 (M+H)$^+$. GK-GKRP EC$_{50}$ (NADPH-coupled)=1.02 μM; GK-GKRP EC$_{50}$ (LC MS/MS)=1.31 μM.

Example 24

1,1,1-trifluoro-2-(4-(4-(phenylsulfonyl)-1-piperazinyl)phenyl)-2-propanol

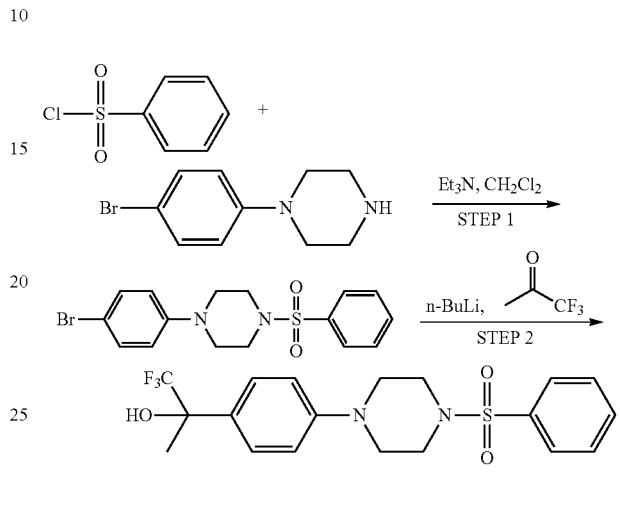

Step 1:
1-(4-bromophenyl)-4-(phenylsulfonyl)piperazine

A 500 mL round-bottomed flask was charged with 1-(4-bromophenyl)piperazine (10.00 g, 41.5 mmol, CombiBlocks, San Diego, Calif.) and 100 mL of CH$_2$Cl$_2$. To this was slowly added triethylamine (6.94 mL, 49.8 mmol) and benzenesulfonyl chloride (6.15 mL, 47.7 mmol). After 15 min at room temperature, the mixture was diluted with water (100 mL) and layers were separated. The organics were dried (MgSO$_4$) and concentrated. The resulting solid was slurried with diethyl ether (200 mL) to give 1-(4-bromophenyl)-4-(phenylsulfonyl)piperazine (15.00 g) as a white solid.

Step 2: 1,1,1-trifluoro-2-(4-(4-(phenylsulfonyl)-1-piperazinyl)phenyl)-2-propanol A 250 mL round-bottomed flask was charged with 1-(4-bromophenyl)-4-(phenylsulfonyl)piperazine (0.50 g, 1.31 mmol) and 20 mL of THF. After cooling to −78° C., n-BuLi (0.603 mL, 2.5 M in hexanes, 1.51 mmol) was slowly added. The mixture was stirred at −78° C. for 30 min, then 1,1,1-trifluoro-2-propanone (0.441 g, 3.93 mmol, Sigma-Aldrich, St. Louis, Mo.) was added. The reaction was stirred at −78° C. for 1 h, and then quenched with saturated aqueous NH$_4$Cl (15 mL). The organics were extracted with EtOAc (2×50 mL), dried (MgSO$_4$), and concentrated to give an oil. Purification via column chromatography (40 g of silica, 0 to 40% EtOAc in hexanes) produced 1,1,1-trifluoro-2-(4-(4-(phenylsulfonyl)-1-piperazinyl)phenyl)-2-propanol (0.215 g) as a mixture of two enantiomers.

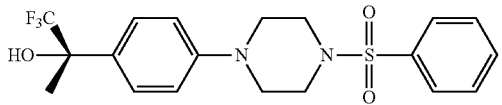

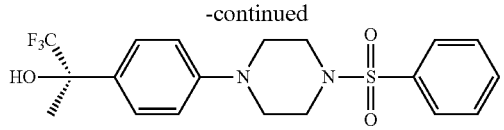

(2R)-1,1,1-trifluoro-2-(4-(4-(phenylsulfonyl)-1-piperazinyl)phenyl)-2-propanol; (2S)-1,1,1-trifluoro-2-(4-(4-(phenylsulfonyl)-1-piperazinyl)phenyl)-2-propanol. $^1$H NMR (400 MHz, CD$_3$OD) δ 7.81 (s, 2H), 7.74-7.58 (m, 3H), 7.47-7.38 (m, 2H), 6.93 (s, 2H), 3.28-3.21 (m, 4H), 3.13 (d, J=5.3 Hz, 4H), 1.66 (s, 3H). m/z (ESI, +ve ion) 415.0 (M+H)$^+$. GK-GKRP EC$_{50}$ (NADPH-coupled)=1.84 μM; GK-GKRP EC$_{50}$ (LC MS/MS)=3.96 μM.

This mixture was resolved using preparative SFC (AD column (210 mm×25 mm, 10 μm) eluting with 65% liquid CO$_2$ and 35% MeOH (0.2% diethylamine) flow rate=65 mL, T=40° C.) which gave two products in greater than 99% enantiomeric excess.

First Eluting Peak (Peak #1)

$^1$H NMR (400 MHz, CD$_3$OD) δ 7.82 (s, 2H), 7.64 (s, 3H), 7.44 (s, 2H), 6.93 (d, J=9.0 Hz, 2H), 3.29-3.23 (m, 4H), 3.17-3.12 (m, 4H), 1.67 (s, 3H). m/z (ESI, +ve ion) 415.1 (M+H)$^+$. GK-GKRP EC$_{50}$ (NADPH-coupled)=2.57 μM; GK-GKRP EC$_{50}$ (LC MS/MS)=2.07 μM.

Second Eluting Peak (Peak #2)

$^1$H NMR (400 MHz, CD$_3$OD) δ 7.86-7.79 (m, 2H), 7.74-7.60 (m, 3H), 7.47-7.41 (m, 2H), 6.94 (m, 2H), 3.26 (d, J=5.5 Hz, 4H), 3.15 (d, J=5.5 Hz, 4H), 1.67 (s, 3H). m/z (ESI, +ve ion) 415.1 (M+H)$^+$. GK-GKRP EC$_{50}$ (LC MS/MS)=3.01 μM.

Example 25

1,1,1,3,3,3-hexafluoro-2-(4-((3R)-3-methyl-4-(2-thiophenylsulfonyl)-1-piperazinyl)phenyl)-2-propanol

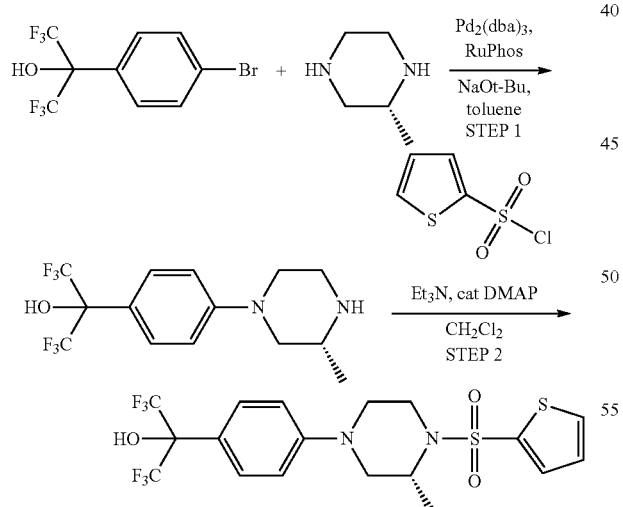

Step 1: 1,1,1,3,3,3-hexafluoro-2-(4-((3R)-3-methyl-1-piperazinyl)phenyl)-2-propanol A 20 mL vial was charged with (R)-2-methylpiperazine (0.357 g, 3.56 mmol, Sigma-Aldrich, St. Louis, Mo.), 2-(4-bromophenyl)-1,1,1,3,3,3-hexafluoropropan-2-ol (1.00 g, 3.10 mmol, *Bioorg. Med. Chem. Lett.* 2002, 12, 3009), sodium tert-butoxide (0.625 g, 6.50 mmol) and 6 mL of toluene. To this was added dicyclohexyl(2',6'-diisopropoxybiphenyl-2-yl)phosphine (RuPhos) (0.022 g, 0.046 mmol, Strem Chemical Inc, Newburyport, Mass.), tris(dibenzylideneacetone)dipalladium (0) (0.014 g, 0.015 mmol, Strem Chemical Inc, Newburyport, Mass.). The vial was sealed in heated at 100° C. for 12 h. After that time, the mixture was diluted with water (20 mL) and extracted with EtOAc (2×50 mL). The combined extracts were dried (MgSO$_4$) and concentrated to give 1,1,1,3,3,3-hexafluoro-2-(4-((3R)-3-methyl-1-piperazinyl)phenyl)-2-propanol (0.950 g) as an oil which was used without purification.

Step 2: 1,1,1,3,3,3-hexafluoro-2-(4-((3R)-3-methyl-4-(2-thiophenylsulfonyl)-1-piperazinyl)phenyl)-2-propanol A 100 mL round-bottomed flask was charged with 1,1,1,3,3,3-hexafluoro-2-(4-((3R)-3-methyl-1-piperazinyl)phenyl)-2-propanol (0.950 g, 2.78 mmol), 5 mL of CH$_2$Cl$_2$, 2-thiophenesulfonyl chloride (0.583 g, 3.19 mmol, Sigma-Aldrich, St. Louis, Mo.), and triethylamine (0.580 mL, 4.16 mmol). After 1 h at room temperature, 0.010 g of DMAP was added. After an additional 30 min, the mixture was concentrated and purified via column chromatography (80 g of silica, 0 to 40% EtOAc in hexanes) to give 1,1,1,3,3,3-hexafluoro-2-(4-((3R)-3-methyl-4-(2-thiophenylsulfonyl)-1-piperazinyl)phenyl)-2-propanol (0.425 g) as an off-white solid. $^1$H NMR (400 MHz, CDCl$_3$) δ=7.70-7.46 (m, 4H), 7.12 (dd, J=3.7, 4.9 Hz, 1H), 6.94 (d, J=9.0 Hz, 2H), 4.30 (m, 1H), 3.83 (td, J=3.0, 13.1 Hz, 1H), 3.66-3.57 (m, 1H), 3.54-3.38 (m, 2H), 3.31 (s, 1H), 3.07 (dd, J=3.5, 12.3 Hz, 1H), 2.95 (dt, J=3.6, 11.6 Hz, 1H), 1.30 (d, J=6.7 Hz, 3H). m/z (ESI, +ve ion) 488.7 (M+H)$^+$. GK-GKRP EC$_{50}$ (NADPH-coupled)=2.36 μM; GK-GKRP EC$_{50}$ (LC MS/MS)=2.57 μM.

Example 26

1,1,1,3,3,3-hexafluoro-2-(4-((3S)-3-methyl-4-(2-thiophenylsulfonyl)-1-piperazinyl)phenyl)-2-propanol

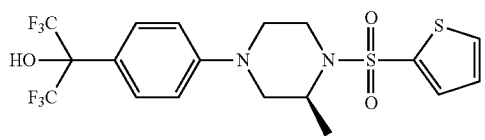 [SMILES: C[C@H]1CN(c2ccc(C(O)(C(F)(F)F)C(F)(F)F)cc2)CCN1S(=O)(=O)c1cccs1]

Following the procedure reported for Example 25, (S)-2-methylpiperazine (Sigma-Aldrich, St. Louis, Mo.) delivered 1,1,1,3,3,3-hexafluoro-2-(4-((3S)-3-methyl-4-(2-thiophenylsulfonyl)-1-piperazinyl)phenyl)-2-propanol. $^1$H NMR (400 MHz, CDCl$_3$) δ=7.65-7.54 (m, 4H), 7.12 (dd, J=3.7, 4.9 Hz, 1H), 6.94 (d, J=9.0 Hz, 2H), 4.30 (m, 1H), 3.83 (td, J=3.0, 13.1 Hz, 1H), 3.68-3.57 (m, 1H), 3.52-3.36 (m, 2H), 3.31 (s, 1H), 3.07 (dd, J=3.7, 12.3 Hz, 1H), 2.95 (dt, J=3.6, 11.6 Hz, 1H), 1.30 (d, J=6.7 Hz, 3H). m/z (ESI, +ve ion) 488.7

(M+H)+. GK-GKRP EC$_{50}$ (NADPH-coupled)=3.42 µM; GK-GKRP EC$_{50}$ (LC MS/MS)=3.22 µM.

Example 27

1,1,1-trifluoro-2-(4-((2S)-2-methyl-4-(2-thiophenyl-sulfonyl)-1-piperazinyl)phenyl)-2-propanol

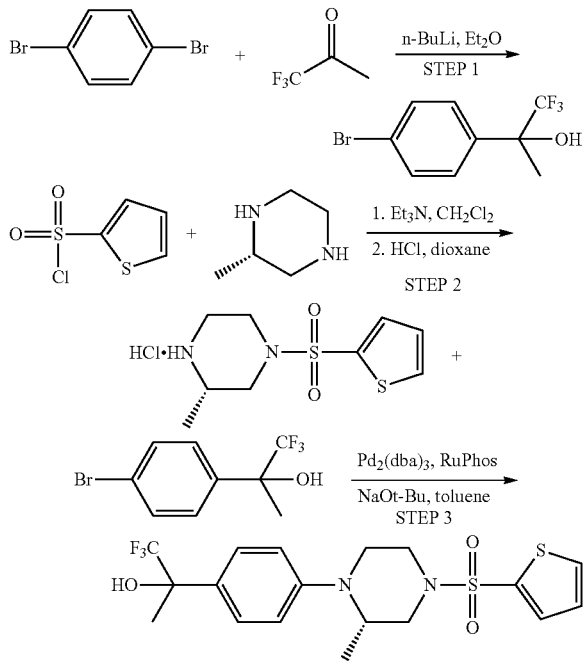

Step 1:
2-(4-bromophenyl)-1,1,1-trifluoro-2-propanol

A 500 mL round-bottomed flask was charged with 1,4-dibromobenzene (30.27 g, 128 mmol, Sigma-Aldrich, St. Louis, Mo.) and 200 mL of ether. After cooling to −78° C., n-BuLi (59.0 mL, 2.5 M in hexanes, 148 mmol) was added. This mixture was stirred for 15 min at −78° C., then 1,1,1-trifluoro-2-propanone (24.2 mL, 257 mmol, Sigma-Aldrich, St. Louis, Mo.) was added. Stirring was continued at −78° C. for 30 min then the mixture was quenched with 100 mL of saturated aqueous NH$_4$Cl. The mixture was extracted with EtOAc (250 mL), dried (MgSO$_4$) and concentrated to give an oil. Purification via column chromatography (330 g of silica, 0 to 30% EtOAc in hexanes) gave 2-(4-bromophenyl)-1,1,1-trifluoro-2-propanol (21.50 g) as a colorless oil.

Step 2:
(S)-2-methyl-4-(2-thiophenylsulfonyl)piperazine hydrochloride

A 500 mL round-bottomed flask was charged with (S)-2-methylpiperazine (10.23 g, 102 mmol, Sigma-Aldrich, St. Louis, Mo.) and 100 mL of CH$_2$Cl$_2$. After cooling to 0° C., 2-thiophenesulfonyl chloride (18.65 g, 102 mmol, Sigma-Aldrich, St. Louis, Mo.) was added. This mixture was stirred at 0° C. for 15 min then diluted with water (100 mL). The layers were separated and the organics were dried (MgSO$_4$) and concentrated to give an oil. To this oil was added 300 mL of EtOAc and 28 mL of 4 M HCl in dioxane. The resulting white precipitate was collected by filtration to give (S)-2-methyl-4-(2-thiophenylsulfonyl)piperazine hydrochloride (26 g).

Step 3: 1,1,1-trifluoro-2-(4-((2S)-2-methyl-4-(2-thiophenylsulfonyl)-1-piperazinyl)phenyl)-2-propanol A 100 mL round-bottomed flask was charged with (S)-2-methyl-4-(2-thiophenylsulfonyl)piperazine hydrochloride (10.0 g, 35.4 mmol), 2-(4-bromophenyl)-1,1,1-trifluoro-2-propanol (16.7 g, 61.9 mmol, Example 27, step 1), sodium tert-butoxide (13.6 g, 141 mmol) and 20 mL of toluene. To this was added dicyclohexyl(2',6'-diisopropoxybiphenyl-2-yl)phosphine (RuPhos) (1.98 g, 4.24 mmol, Strem Chemical Inc, Newburyport, Mass.), tris(dibenzylideneacetone)dipalladium (0) (1.94 g, 0.265 mmol, Strem Chemical Inc, Newburyport, Mass.). The mixture was heated at 100° C. for 12 h. After that time, the reaction was diluted with water (100 mL) and extracted with EtOAc (2×150 mL). The combined extracts were dried (MgSO$_4$) and concentrated and purified by column chromatography (330 g of silica, 0 to 50% EtOAc in hexanes) to give 1,1,1-trifluoro-2-(4-((2S)-2-methyl-4-(2-thiophenylsulfonyl)-1-piperazinyl)phenyl)-2-propanol (13.20 g) as a mixture of two isomers.

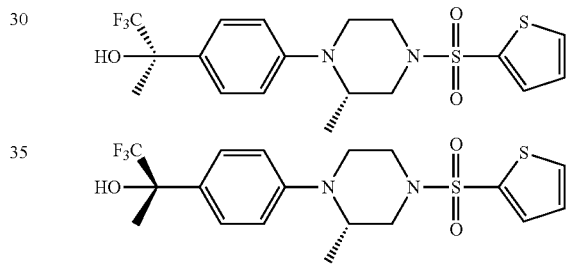

(2R)-1,1,1-trifluoro-2-(4-((2S)-2-methyl-4-(2-thiophenyl-sulfonyl)-1-piperazinyl)phenyl)-2-propanol; (2S)-1,1,1-trifluoro-2-(4-((2S)-2-methyl-4-(2-thiophenylsulfonyl)-1-piperazinyl)phenyl)-2-propanol.

This mixture was resolved using preparative SFC (Chiralcel® OJ-H column (250×30 mm) eluting with 70% liquid CO$_2$ in 30% MeOH (0.2% diethylamine) at a flow rate of 120.0 mL/min) to give two products in greater than 99% diastereomeric excess.

First Eluting Peak (Peak #1)

$^1$H NMR (400 MHz, CD$_3$OD) δ 7.91-7.87 (m, 1H), 7.65 (dd, J=1.2, 3.7 Hz, 1H), 7.47 (d, J=8.6 Hz, 2H), 7.27 (dd, J=3.8, 5.0 Hz, 1H), 6.95 (d, J=8.8 Hz, 2H), 4.11-4.01 (m, 1H), 3.67-3.59 (m, 1H), 3.45-3.35 (m, 2H), 3.27-3.17 (m, 1H), 2.92-2.84 (m, 1H), 2.72 (dt, J=3.5, 10.9 Hz, 1H), 1.69 (s, 3H), 1.11 (d, J=6.5 Hz, 3H). m/z (ESI, +ve ion) 435.0 (M+H)$^+$. GK-GKRP EC$_{50}$ (NADPH-coupled)=0.616 µM; GK-GKRP EC$_{50}$ (LC MS/MS)=0.768 µM.

Second Eluting Peak (Peak #2)

$^1$H NMR (400 MHz, CD$_3$OD) δ 7.89 (dd, J=1.0, 5.1 Hz, 1H), 7.69-7.59 (m, 1H), 7.47 (d, J=8.6 Hz, 2H), 7.31-7.21 (m, 1H), 6.95 (d, J=8.8 Hz, 2H), 4.12-4.01 (m, 1H), 3.63 (dd, J=1.9, 11.2 Hz, 1H), 3.45-3.34 (m, 2H), 3.28-3.18 (m, 1H), 2.95-2.81 (m, 1H), 2.79-2.61 (m, 1H), 1.69 (s, 3H), 1.11 (d,

J=6.7 Hz, 3H). m/z (ESI, +ve ion) 435.0 (M+H)+. GK-GKRP EC$_{50}$ (NADPH-coupled)=0.724 μM; GK-GKRP EC$_{50}$ (LC MS/MS)=0.972 μM Example 28

1,1,1-trifluoro-2-(4-((2S)-2-methyl-4-(phenylsulfonyl)-1-piperazinyl)phenyl)-2-propanol

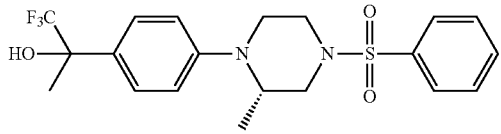 [SMILES: C[C@H]1CN(S(=O)(=O)c2ccccc2)CCN1c1ccc(C(C)(O)C(F)(F)F)cc1]

Following the procedure reported for Example 27 (substituting benzenesulfonyl chloride for 2-thiophenesulfonyl chloride) yielded 1,1,1-trifluoro-2-(4-((2S)-2-methyl-4-(phenylsulfonyl)-1-piperazinyl)phenyl)-2-propanol as a mixture of two isomers.

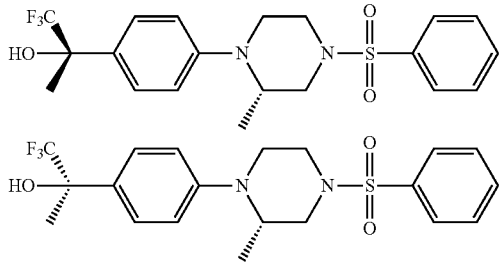

(2R)-1,1,1-trifluoro-2-(4-((2S)-2-methyl-4-(phenylsulfonyl)-1-piperazinyl)phenyl)-2-propanol; (2S)-1,1,1-trifluoro-2-(4-((2S)-2-methyl-4-(phenylsulfonyl)-1-piperazinyl)phenyl)-2-propanol. $^1$H NMR (300 MHz, MeOH) δ 7.72 (d, J=7.3 Hz, 2H), 7.62-7.50 (m, 3H), 7.35 (d, J=8.5 Hz, 2H), 6.81 (d, J=8.6 Hz, 2H), 3.51 (d, J=11.6 Hz, 1H), 3.34-3.26 (m, 3H), 3.15-3.01 (m, 1H), 2.69 (d, J=11.4 Hz, 1H), 2.53 (t, J=8.9 Hz, 1H), 1.57 (s, 3H), 0.98 (d, J=6.4 Hz, 3H). m/z (ESI, +ve ion) 429.0 (M+H)+. GK-GKRP EC$_{50}$ (NADPH-coupled)=3.12 μM; GK-GKRP EC$_{50}$ (LC MS/MS)=4.01 μM Example 29

1,1,1-trifluoro-2-(4-(4-(2-thiophenylsulfonyl)-1-piperazinyl)phenyl)-2-propanol

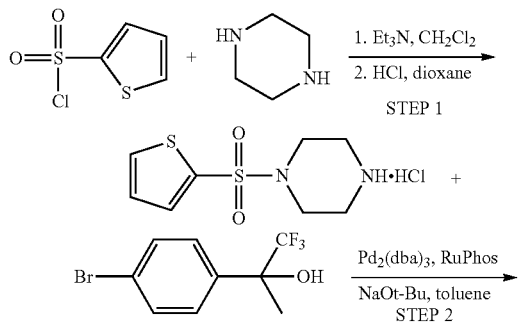

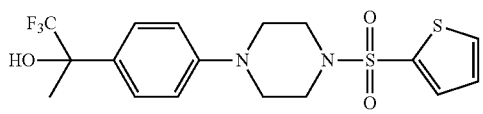

Step 1: 4-(2-thiophenylsulfonyl)piperazine hydrochloride

A 1 L round-bottomed flask was charged with tert-butyl piperazine-1-carboxylate (20.70 g, 111 mmol, Sigma-Aldrich, St. Louis, Mo.), 300 mL of CH$_2$Cl$_2$, and triethylamine (17.81 mL, 128 mmol). After cooling to 0° C., 2-thiophenesulfonyl chloride (21.31 g, 117 mmol, Sigma-Aldrich, St. Louis, Mo.) was added and the reaction was stirred at 0° C. for 30 min. The mixture was diluted with water (200 mL) and the layers were separated, dried (MgSO$_4$) and concentrated to give tert-butyl 4-(thiophen-2-ylsulfonyl)piperazine-1-carboxylate (37.0 g) as a white solid. To this solid was added 300 mL of EtOAc, and 4 N HCl in dioxane (100 mL). The mixture was heated to 65° C. to give a clear solution. Over the course of 2 h, a white precipitate formed. The white precipitate was collected by filtration and dried under reduced pressure to give 4-(thiophen-2-ylsulfonyl)piperazine hydrochloride (26.0 g).

Step 2: 1,1,1-trifluoro-2-(4-(4-(2-thiophenylsulfonyl)-1-piperazinyl)phenyl)-2-propanol A 20 ml, vial was charged with 4-(2-thiophenylsulfonyl)piperazine hydrochloride (70 mg, 0.260 mmol), sodium tert-butoxide (45.7 mg, 0.476 mmol), tris(dibenzylideneacetone)dipalladium (0) (1.1 mg, 1.13 μmol, Strem Chemical Inc, Newburyport, Mass.), dicyclohexyl(2',6'-diisopropoxybiphenyl-2-yl)phosphine (RuPhos) (1.6 mg, 3.40 μmol, Strem Chemical Inc, Newburyport, Mass.) and 2-(4-bromophenyl)-1,1,1-trifluoro-2-propanol (60.9 mg, 0.226 mmol, Example 27, step 1) in toluene (906 μL) was heated to 100° C. for 20 h. The reaction was then cooled to ambient temperature and additional tris(dibenzylideneacetone)dipalladium (0) (1.1 mg, 1.13 μmol, Strem Chemical Inc, Newburyport, Mass.) and dicyclohexyl(2',6'-diisopropoxybiphenyl-2-yl)phosphine (1.6 mg, 3.40 μmol, Strem Chemical Inc, Newburyport, Mass.) were added. The reaction was then heated to 100° C. for an additional 20 h. The reaction was cooled to ambient temperature and diluted with MeOH (2 mL). The reaction was loaded onto a 1 g AccuBOND II SCX cartridge, which was washed with MeOH (5 mL) and eluted with 2 N ammonia in MeOH (5 mL) to give the crude reaction mixture. The crude material was absorbed onto a plug of silica gel and purified by column chromatography (10 g of silica gel, 5%-45% EtOAc in hexanes) to provide 1,1,1-trifluoro-2-(4-(4-(2-thiophenylsulfonyl)-1-piperazinyl)phenyl)-2-propanol as a mixture of two enantiomers.

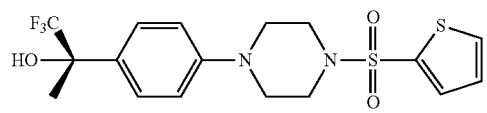

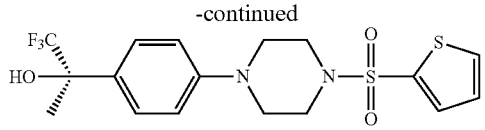

(2S)-1,1,1-trifluoro-2-(4-(4-(2-thiophenylsulfonyl)-1-piperazinyl)phenyl)-2-propanol; (2R)-1,1,1-trifluoro-2-(4-(4-(2-thiophenylsulfonyl)-1-piperazinyl)phenyl)-2-propanol. $^1$H NMR (300 MHz, CDCl$_3$) δ 7.64 (d, J=4.7 Hz, 1H) 7.57 (d, J=2.8 Hz, 1H) 7.45 (d, J=8.5 Hz, 2H) 7.17 (t, J=4.3 Hz, 1H) 6.87 (d, J=8.6 Hz, 2H) 3.26 (m, 8H) 2.47 (m, 1H) 1.73 (s, 3H). m/z (ESI, +ve ion) 421.0 (M+H)$^+$. GK-GKRP EC$_{50}$ (NADPH-coupled)=0.563 μM; GK-GKRP EC$_{50}$ (LC MS/MS)=0.779 μM.

This mixture was resolved using preparative SFC (Chiralcel® OJ-H column (150×4.6 mm, 5 μm) eluting with 60% liquid CO$_2$ in 40% EtOH (0.2% diethylamine) at a flow rate of 4.0 mL/min) to give two products in greater than 99% enantiomeric excess.

First Eluting Peak (Peak #1)
$^1$H NMR (300 MHz, CDCl$_3$) δ 7.64 (d, J=4.4 Hz, 1H), 7.57 (s, 1H), 7.45 (d, J=8.2 Hz, 2H), 7.17 (s, 1H), 6.88 (d, J=8.33 Hz, 2H), 3.27 (m, 8H), 1.74 (s, 3H). m/z (ESI, +ve ion) 421.0 (M+H)$^+$. GK-GKRP EC$_{50}$ (NADPH-coupled)=0.546 μM; GK-GKRP EC$_{50}$ (LC MS/MS)=0.835 μM.

Second Eluting Peak (Peak #2)
$^1$H NMR (300 MHz, CDCl$_3$) δ 7.64 (d, J=4.7 Hz, 1H), 7.58 (d, J=2.9 Hz, 1H), 7.45 (d, J=8.5 Hz, 2H), 7.17 (t, J=4.2 Hz, 1H), 6.88 (d, J=8.8 Hz, 2H), 3.27 (m, 8H), 1.74 (s, 3H). m/z (ESI, +ve ion) 421.0 (M+H)$^+$. GK-GKRP EC$_{50}$ (NADPH-coupled)=0.775 μM; GK-GKRP EC$_{50}$ (LC MS/MS)=1.17 μM.

Example 30

1,1,1-trifluoro-2-(4-((2S)-4-(3-furanylsulfonyl)-2-methyl-1-piperazinyl)phenyl)-2-propanol

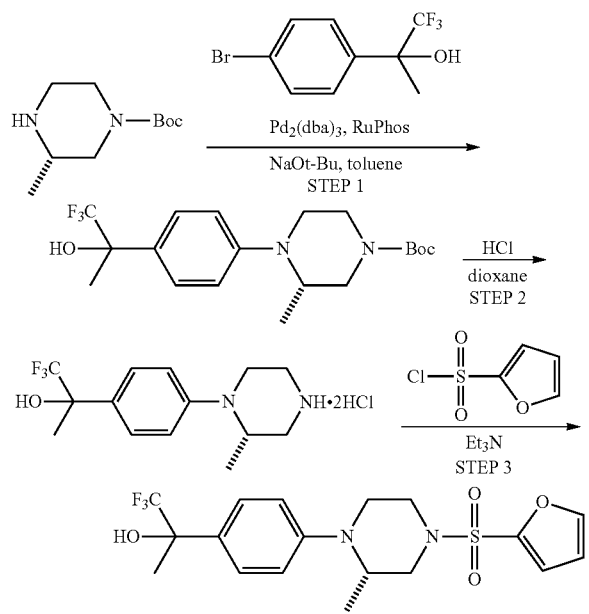

Step 1: tert-butyl (3S)-3-methyl-4-(4-(2,2,2-trifluoro-1-hydroxy-1-methylethyl)phenyl)-1-piperazinecarboxylate A 100 mL round-bottomed flask was charged with tert-butyl (3S)-3-methyl-1-piperazinecarboxylate (10.0 g, 49.9 mmol), 2-(4-bromophenyl)-1,1,1-trifluoro-2-propanol (13.43 g, 49.9 mmol, Example 27, step 1), sodium tert-butoxide (10.56 g, 110 mmol) and 100 mL of toluene. To this was added dicyclohexyl(2',6'-diisopropoxybiphenyl-2-yl)phosphine (RuPhos) (1.864 g, 3.99 mmol, Strem Chemical Inc, Newburyport, Mass.), tris(dibenzylideneacetone)dipalladium (0) (1.83 g, 2.00 mmol, Strem Chemical Inc, Newburyport, Mass.). The mixture was heated at 100° C. for 12 h then diluted with water (100 mL) and extracted with EtOAc (2×200 mL). The combined extracts were dried (MgSO$_4$) and purified by column chromatography (330 g of silica, 0 to 50% EtOAc in hexanes) to give tert-butyl (3S)-3-methyl-4-(4-(2,2,2-trifluoro-1-hydroxy-1-methylethyl)phenyl)-1-piperazinecarboxylate (13.05 g) as a white solid.

Step 2: 1,1,1-trifluoro-2-(4-((2S)-2-methyl-1-piperazinyl)phenyl)-2-propanol dihydrochloride A 500 mL round-bottomed flask was charged with tert-butyl (3S)-3-methyl-4-(4-(2,2,2-trifluoro-1-hydroxy-1-methylethyl)phenyl)-1-piperazinecarboxylate (8.33 g, 21.5 mmol) and 200 mL of EtOAc. To this was added 20 mL of 4N HCl (80 mmol) in dioxane. After 12 h at reflux, the resulting white precipitate was collected and dried under reduced pressure to give 1,1,1-trifluoro-2-(4-((2S)-2-methyl-1-piperazinyl)phenyl)-2-propanol dihydrochloride (5.45 g) as a white solid.

Step 3: 1,1,1-trifluoro-2-(4-((2S)-4-(3-furanylsulfonyl)-2-methyl-1-piperazinyl)phenyl)-2-propanol To a solution of 1,1,1-trifluoro-2-(4-((2S)-2-methyl-1-piperazinyl)phenyl)-2-propanol dihydrochloride (100 mg, 0.277 mmol) and triethylamine (0.115 mL, 0.830 mmol) in CH$_2$Cl$_2$ (4.0 mL) was added 3-furansulfonyl chloride (55.3 mg, 0.332 mmol, Ryan Scientific, Inc., Mt. Pleasant, S.C.). After 30 min at room temperature, the reaction was concentrated and purified via column chromatography (12 g of silica, 0 to 70% EtOAc in hexanes) to yield 1,1,1-trifluoro-2-(4-((2S)-4-(3-furanylsulfonyl)-2-methyl-1-piperazinyl)phenyl)-2-propanol (25 mg) as a mixture of two isomers.

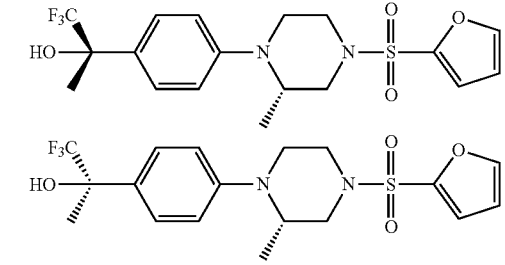

(2S)-1,1,1-trifluoro-2-(4-((2S)-4-(2-furanylsulfonyl)-2-methyl-1-piperazinyl)phenyl)-2-propanol; (2R)-1,1,1-trifluoro-2-(4-((2S)-4-(2-furanylsulfonyl)-2-methyl-1-piperazinyl)phenyl)-2-propanol. $^1$H NMR (400 MHz, CD$_3$OD) δ 8.14 (s, 1H), 7.74-7.71 (m, 1H), 7.46 (d, J=8.9 Hz, 2H), 6.94 (d, J=8.9 Hz, 2H), 6.74-6.72 (m, 1H), 4.08-4.01 (m, 1H), 3.64-3.57 (m, 1H), 3.42-3.33 (m, 2H), 3.24-3.15 (m, 1H), 2.93-2.87 (m, 1H), 2.77-2.69 (m, 1H), 1.68 (ms, 3H), 1.08 (d, J=9.0 Hz, 3H). m/z (ESI, +ve ion) 419.1 (M+H)$^+$. GK-GKRP EC$_{50}$ (NADPH-coupled)=3.12 μM; GK-GKRP EC$_{50}$ (LC MS/MS)=50 μM.

Example 31

1,1,1,3,3,3-hexafluoro-2-(4-((2S)-2-methyl-4-(1,3-thiazol-2-ylsulfonyl)-1-piperazinyl)phenyl)-2-propanol trifluoroacetate

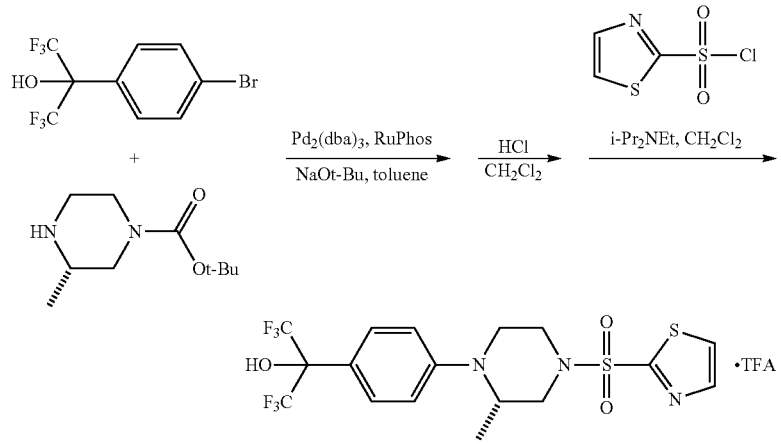

A vial was charged with 2-(4-bromophenyl)-1,1,1,3,3,3-hexafluoro-2-propanol (0.161 g, 0.499 mmol, *Bioorg. Med. Chem. Lett.* 2002, 12, 3009), (S)-tert-butyl 3-methylpiperazine-1-carboxylate (0.100 g, 0.499 mmol, Sigma-Aldrich, St. Louis, Mo.), sodium tert-butoxide (0.115 g, 1.198 mmol), and 2.5 mL of anhydrous toluene. To this was added dicyclohexyl (2',6'-diisopropoxybiphenyl-2-yl)phosphine (RuPhos) (0.035 g, 0.075 mmol, Strem Chemical Inc, Newburyport, Mass.) and tris(dibenzylideneacetone)dipalladium (0) (0.023 g, 0.025 mmol, Strem Chemical Inc, Newburyport, Mass.). The vial was sealed and the mixture was heated at 100° C. for 18 h. After that time, the reaction was partitioned between saturated $NaHCO_3$ (50 mL) and EtOAc (50 mL). The organics were separated, washed with brine (50 mL), and dried ($NaSO_4$) and volatiles were removed in vacuo. The residue was dissolved in 2 mL of $CH_2Cl_2$. To this was added 4 N HCl in dioxane (5 mL) and the mixture was stirred at room temperature for 3 h. The reaction mixture was concentrated and the residue was dissolved with $CH_2Cl_2$ (10 mL). To this was added 1 mL of Hünig's base and 2-thiazolesulfonyl chloride (95 mg, 0.52 mmol, *Bioorg. Med. Chem.*, 2006, 14, 6628). This mixture was stirred at room temperature for 18 h and then concentrated, the residue was dissolved in methanol (3 mL), and filtered through a 0.45 micron filter. The crude material was purified by reverse-phase preparative HPLC using a Phenomenex Gemini $C_{18}$ column (10 μm), 150×30 mm, eluting with a 0.1% TFA in $CH_3CN/H_2O$, gradient (10% to 90% over 20 min) to afford 1,1,1,3,3,3-hexafluoro-2-(4-((2S)-2-methyl-4-(1,3-thiazol-2-ylsulfonyl)-1-piperazinyl)phenyl)-2-propanol trifluoroacetate (41 mg) as an orange oil. $^1$H NMR (300 MHz, MeOH) δ 8.06 (d, J=3.1 Hz, 1H), 7.98 (d, J=2.9 Hz, 1H), 7.56 (d, J=8.8 Hz, 2H), 6.98 (d, J=8.8 Hz, 2H), 4.17 (d, J=3.4 Hz, 1H), 3.83 (s, 1H), 3.64 (d, J=12.1 Hz, 1H), 3.47 (d, J=2.9 Hz, 1H), 3.07-3.27 (m, 2H), 2.87-3.04 (m, 1H), 2.15 (s, 3H). m/z (ESI, +ve ion) 490.1 (M+H)$^+$. GK-GKRP $EC_{50}$ (NADPH-coupled)=0.561 μM; GK-GKRP $EC_{50}$ (LC MS/MS)=0.702 μM.

Example 32

1,1,1-trifluoro-2-(4-(4-(1,3-thiazol-2-ylsulfonyl)-1-piperazinyl)phenyl)-2-propanol trifluoroacetate

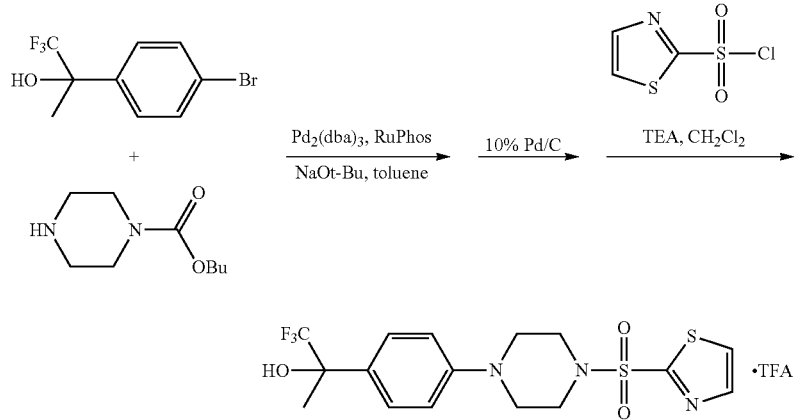

2-(4-Bromophenyl)-1,1,1-trifluoro-2-propanol (330 mg, 1.226 mmol, Example 27, step 1), benzyl 1-piperazinecarboxylate (270 mg, 1.226 mmol, Sigma-Aldrich, St. Louis, Mo.), dicyclohexyl(2',6'-diisopropoxybiphenyl-2-yl)phosphine (RuPhos) (86 mg, 0.184 mmol, Strem Chemical Inc, Newburyport, Mass.), sodium tert-butoxide (283 mg, 2.94 mmol), and tris(dibenzylideneacetone)dipalladium (0) (56.2 mg, 0.061 mmol, Strem Chemical Inc, Newburyport, Mass.) were combined in toluene (5 mL) and stirred in a sealed tube overnight at 100° C. The reaction was poured into saturated aqueous sodium bicarbonate (100 mL) and EtOAc (100 mL). The organic extracts were separated washed with brine (25 mL), dried ($Na_2SO_4$), filtered and concentrated. The residue was dissolved in methanol (10 mL). Under nitrogen, 10% Pd/C (100 mg) was added and the resulting black suspension was placed under a hydrogen atmosphere (1 atm) for 1 h. After that time, the mixture was filtered through a 0.45 micron filter and concentrated. This crude material, 2-thiazolesulfonyl chloride (225 mg, 1.225 mmol, *Bioorg. Med. Chem.*, 2006, 14, 6628), and Hünig's base (214 μL, 1.225 mmol) were combined in $CH_2Cl_2$ (10 mL). This was allowed to stir for at room temperature 3 h. After that time, the reaction was concentrated then dissolved in methanol (3 mL) and filtered through a 0.45 micron filter. The crude material was purified by reverse-phase preparative HPLC using a Phenomenex Gemini ($C_{18}$ column (150×30 mm, 10 μm) eluting with a 0.1% TFA in $CH_3CN/H_2O$, gradient (10% to 90% over 30 min)) to afford 1,1,1-trifluoro-2-(4-(4-(1,3-thiazol-2-ylsulfonyl)-1-piperazinyl)phenyl)-2-propanol trifluoroacetate (120 mg) as a mixture of two enantiomers.

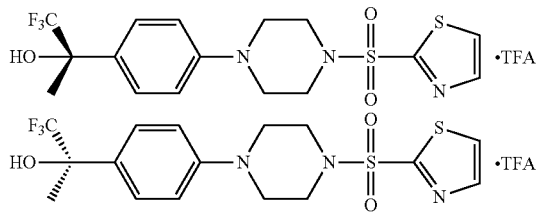

(2S)-1,1,1-trifluoro-2-(4-(4-(1,3-thiazol-2-ylsulfonyl)-1-piperazinyl)phenyl)-2-propanol trifluoroacetate; (2R)-1,1,1-trifluoro-2-(4-(4-(1,3-thiazol-2-ylsulfonyl)-1-piperazinyl)phenyl)-2-propanol. $^1$H NMR (400 MHz, $CDCl_3$) δ 8.03 (d, J=3.1 Hz, 1H), 7.67 (d, J=3.1 Hz, 1H), 7.48 (d, J=8.8 Hz, 2H), 6.94 (d, J=9.0 Hz, 2H), 3.48-3.58 (m, 4H), 3.27-3.38 (m, 4H), 1.76 (s, 3H). m/z (ESI, +ve ion) 421.8 (M+H)$^+$. GK-GKRP $EC_{50}$ (NADPH-coupled)=1.18 μM; GK-GKRP $EC_{50}$ (LC MS/MS)=4.75 μM.

Example 33

1,1,1,3,3,3-hexafluoro-2-(4-(4-(1,3-thiazol-2-ylsulfonyl)-1-piperazinyl)phenyl)-2-propanol trifluoroacetate

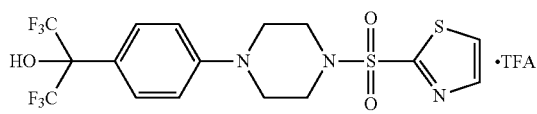

1,1,1,3,3,3-hexafluoro-2-(4-(1-piperazinyl)phenyl)-2-propanol (150 mg, 0.457 mmol, published PCT patent application no. WO 2006/094842) was suspended in 20 mL of $CH_2Cl_2$. To this was added 2-thiazolesulfonyl chloride (84 mg, 0.457 mmol, *Bioorg. Med. Chem.*, 2006, 14, 6628) and Hünig's base (0.2 mL). After stirring for 20 min at room temperature, the reaction was concentrated and then re-dissolved in methanol (3 mL). The crude material was purified by reverse-phase preparative HPLC (Phenomenex Gemini $C_{18}$ column (150×30 mm, 10 μm), eluting with a 0.1% TFA in $CH_3CN/H_2O$, gradient (0% to 100% over 20 min)) to afford 1,1,1,3,3,3-hexafluoro-2-(4-(4-(1,3-thiazol-2-ylsulfonyl)-1-piperazinyl)phenyl)-2-propanol trifluoroacetate (36 mg) as a white powder. $^1$H NMR (300 MHz, $CD_3OD$) δ 8.09 (d, J=3.1 Hz, 1H), 8.01 (d, J=3.1 Hz, 1H), 7.58 (d, J=8.5 Hz, 2H), 7.03 (d, J=8.9 Hz, 2H), 3.44 (m, 4H), 3.35 (m, 4H). m/z (ESI, +ve ion) 476.0 (M+H)$^+$. GK-GKRP $EC_{50}$ (NADPH-coupled)=0.664 μM; GK-GKRP $EC_{50}$ (LC MS/MS)=0.842 μM.

Example 34

1,1,1-trifluoro-2-(4-((2S)-2-methyl-4-(1,3-thiazol-2-ylsulfonyl)-1-piperazinyl)phenyl)-2-propanol trifluoroacetate

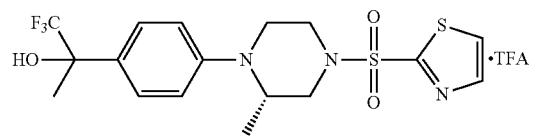

Following the procedure described for Example 33, (S)-1,1,1-trifluoro-2-(4-(2-methylpiperazin-1-yl)phenyl)propan-2-ol (Example 30) provided 1,1,1-trifluoro-2-(4-((2S)-2-methyl-4-(1,3-thiazol-2-ylsulfonyl)-1-piperazinyl)phenyl)-2-propanol trifluoroacetate as a mixture of two isomers.

The mixture was resolved by chiral SFC (Chiralcel® OJ-H column (250 mm×20 mm, 5 μm) eluting with 70% liquid $CO_2$ and 30% MeOH (0.2% diethylamine), EtOH, i-PrOH (1:1:1)) to give two products in greater than 95% diastereomeric excess.

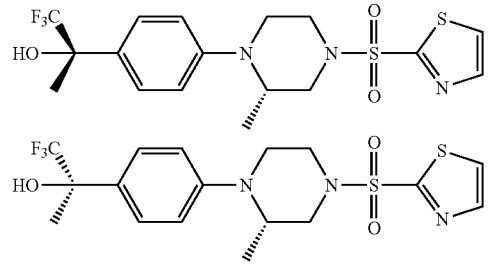

(2S)-1,1,1-trifluoro-2-(4-((2S)-2-methyl-4-(1,3-thiazol-2-ylsulfonyl)-1-piperazinyl)phenyl)-2-propanol; (2R)-1,1,1-trifluoro-2-(4-((2S)-2-methyl-4-(1,3-thiazol-2-ylsulfonyl)-1-piperazinyl)phenyl)-2-propanol.

First Eluting Peak (Peak #1)

$^1$H NMR (300 MHz, MeOH) δ 8.07 (d, J=3.2 Hz, 1H) 7.98 (d, J=3.1 Hz, 1H) 7.46 (d, J=8.6 Hz, 2H), 6.93 (d, J=8.9 Hz, 2H), 4.14-3.95 (m, 1H), 3.77 (dd, J=11.5, 1.7 Hz, 1H), 3.63-3.47 (m, 1H), 3.44-3.33 (m, 1H), 3.26-3.11 (m, 2H), 3.09-2.93 (m, 1H), 1.68 (s, 3H), 1.07 (d, J=6.4 Hz, 3H). m/z (ESI, +ve ion) 436.0 (M+H)$^+$. GK-GKRP $EC_{50}$ (NADPH-coupled)=2.5 μM.

Second Eluting Peak (Peak #2):
$^1$H NMR (300 MHz, MeOH) δ 8.07 (d, J=3.1 Hz, 1H) 7.99 (d, J=3.1 Hz, 1H) 7.46 (d, J=8.6 Hz, 2H), 6.94 (d, J=8.9 Hz, 2H), 4.11-3.97 (m, 1H), 3.83-3.72 (m, 1H), 3.60-3.49 (m, 1H), 3.42-3.33 (m, 1H), 3.27-3.13 (m, 2H), 3.10-2.96 (m, 1H), 1.68 (s, 3H) 1.08 (d, J=6.6 Hz, 3H). m/z (ESI, +ve ion) 436.0 (M+H)$^+$. GK-GKRP EC$_{50}$ (NADPH-coupled)=1.94 µM; GK-GKRP EC$_{50}$ (LC MS/MS)=1.92 µM.

Example 35

2-(4-(((2S)-4-((5-amino-1,3,4-thiadiazol-2-yl)sulfonyl)-2-methyl-1-piperazinyl)phenyl)-1,1,1-trifluoro-2-propanol

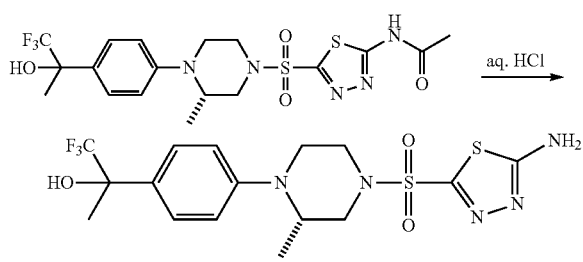

N-(5-(((3S)-3-methyl-4-(4-(2,2,2-trifluoro-1-hydroxy-1-methylethyl)phenyl)-1-piperazinyl)sulfonyl)-1,3,4-thiadiazol-2-yl)acetamide was synthesized following the procedure reported for Example 30, replacing 3-furansulfonyl chloride with 5-(acetylamino)-1,3,4-thiadiazole-2-sulfonyl chloride (*Eur. J. Med. Chem.*, 2006, 41, 918). A solution of N-(5-((3S)-3-methyl-4-(4-(1,1,1-trifluoro-2-hydroxypropan-2-yl)phenyl)piperazin-1-ylsulfonyl)-1,3,4-thiadiazol-2-yl)acetamide (85 mg, 0.172 mmol) in aqueous 5N HCl (5 mL, 5.00 mmol) was heated to 100° C. for 3 h. The mixture was diluted with water (20 mL) and extracted with EtOAc (3×100 mL). The organic layer was separated, dried (Na$_2$SO$_4$), filtered and concentrated. The crude material was purified by column chromatography (12 g of silica, 0 to 100% (10% [2M ammonia in methanol]/CH$_2$Cl$_2$) in CH$_2$Cl$_2$) to yield 2-(4-((2S)-4-((5-amino-1,3,4-thiadiazol-2-yl)sulfonyl)-2-methyl-1-piperazinyl)phenyl)-1,1,1-trifluoro-2-propanol (20 mg) as a mixture of 2 isomers.

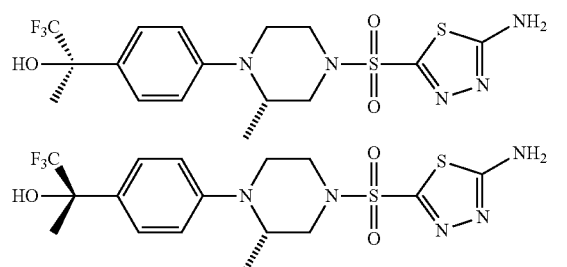

(2S)-2-(4-((2S)-4-((5-amino-1,3,4-thiadiazol-2-yl)sulfonyl)-2-methyl-1-piperazinyl)phenyl)-1,1,1-trifluoro-2-propanol; (2R)-2-(4-((2S)-4-((5-amino-1,3,4-thiadiazol-2-yl)sulfonyl)-2-methyl-1-piperazinyl)phenyl)-1,1,1-trifluoro-2-propanol. $^1$H NMR (400 MHz, CD$_3$OD) δ 7.47 (d, J=8.6 Hz, 2H), 6.98 (d, J=8.6 Hz, 2H), 4.10-4.03 (m, 1H), 3.80-3.74 (m, 1H), 3.57-3.51 (m, 1H), 3.42-3.36 (m, 1H), 3.29-3.17 (m, 2H), 3.15-3.07 (m, 1H), 1.68 (s, 3H), 1.10-1.06 (d, J=6.5 Hz, 3H). m/z (ESI, +ve ion) 452.1 (M+H)$^+$. GK-GKRP EC$_{50}$ (NADPH-coupled)=3.04 µM; GK-GKRP EC$_{50}$ (LC MS/MS)=5.62 µM.

Example 36

1,1,1,3,3,3-hexafluoro-2-(4-(2-(tetrahydro-2H-pyran-4-ylmethyl)-4-(2-thiophenylsulfonyl)-1-piperazinyl)phenyl)-2-propanol

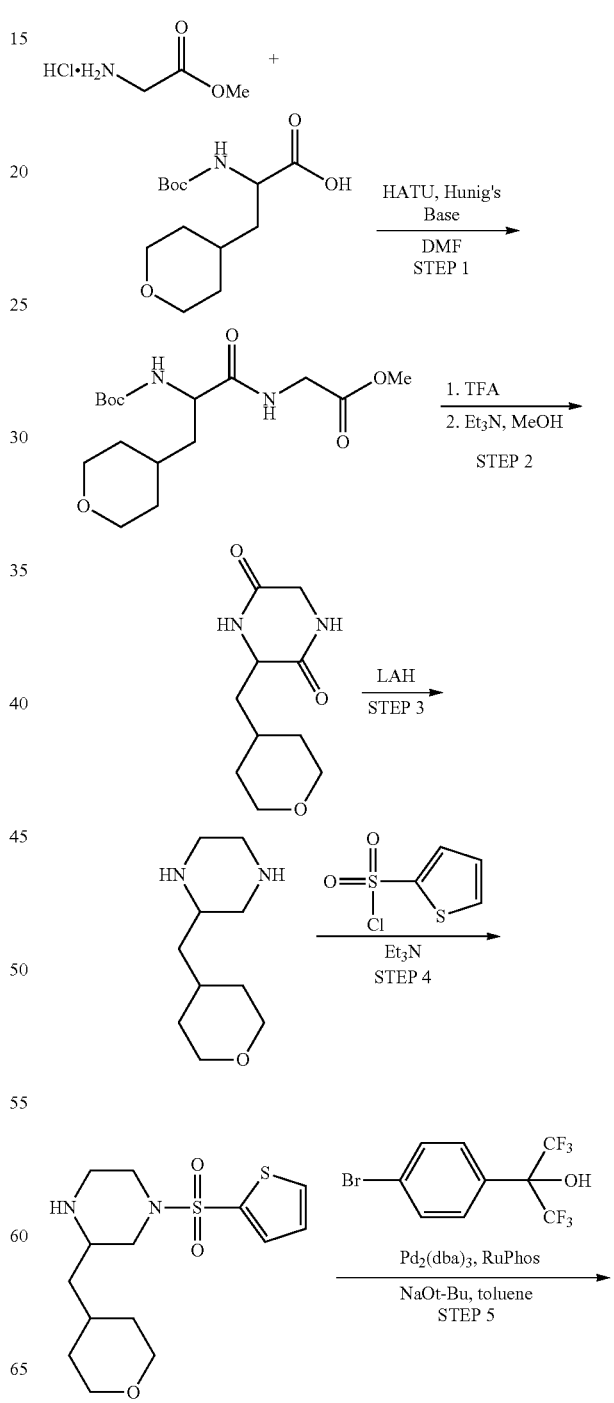

-continued

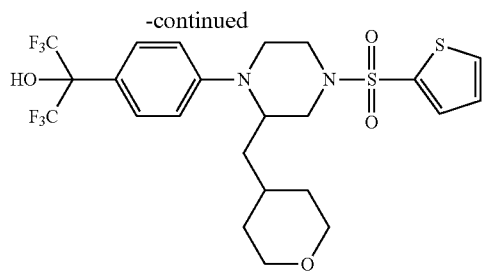

Step 1: methyl N-(tert-butoxycarbonyl)-3-(tetrahydro-2H-pyran-4-yl)-alanylglycinate A 100 mL round-bottomed flask was charged with N-(tert-butoxycarbonyl)-3-(tetrahydro-2H-pyran-4-yl)-alanine (3.11 g, 11.38 mmol, Acros/Fisher Scientific, Waltham, Mass.), HATU (5.41 g, 14.22 mmol, Oakwood, West Columbia, S.C.), glycine methyl ester hydrochloride (1.714 g, 13.65 mmol, Sigma-Aldrich, St. Louis, Mo.), and 10 mL of DMF. To this was added Hünig's base (4.37 mL, 25.03 mmol). After 30 min at room temperature, the mixture was diluted with water (100 mL) and extracted with EtOAc (2×200 mL). The layers were separated and the organic extracts were washed with water (2×100 mL) and brine (50 mL), dried ($MgSO_4$) and concentrated to give methyl N-(tert-butoxycarbonyl)-3-(tetrahydro-2H-pyran-4-yl)-alanylglycinate (3.00 g) as a yellow oil

Step 2: 3-(tetrahydro-2H-pyran-4-ylmethyl)-2,5-piperazinedione

A 250 mL round-bottomed flask was charged with methyl N-(tert-butoxycarbonyl)-3-(tetrahydro-2H-pyran-4-yl)-alanylglycinate (3.00 g, 8.71 mmol), 10 mL of $CH_2Cl_2$, and 5 mL of TFA. After 10 min, the mixture was concentrated then re-dissolved in MeOH (50 mL) and triethylamine (10 mL) and then heated at reflux for 18 h. After that time, the white precipitate formed was collected by filtration to give 3-(tetrahydro-2H-pyran-4-ylmethyl)-2,5-piperazinedione (1.44 g) as a white solid.

Step 3: 2-(tetrahydro-2H-pyran-4-ylmethyl)piperazine

A 250 ml, round-bottomed flask was charged with 3-(tetrahydro-2H-pyran-4-ylmethyl)-2,5-piperazinedione (1.44 g, 6.78 mmol), 50 mL of THF, and lithium aluminum hydride (27.1 mL, 1M in THF, 27.1 mmol). After refluxing for 2 h, the mixture was cooled to room temperature where sodium sulfate decahydrate (10 g) was added. After stirring at room temperature for 1 h, the mixture was filtered and the filtrate was concentrated to give 2-((tetrahydro-2H-pyran-4-yl)methyl)piperazine (0.950 g) as a colorless oil.

Step 4: 3-(tetrahydro-2H-pyran-4-ylmethyl)-1-(2-thiophenylsulfonyl)piperazine hydrochloride A 100 mL round-bottomed flask was charged with 2-((tetrahydro-2H-pyran-4-yl)methyl)piperazine (0.950 g, 5.16 mmol), 20 mL of $CH_2Cl_2$, triethylamine (0.790 mL, 5.67 mmol), and 2-thiophenesulfonyl chloride (0.942 mL, 5.16 mmol, Sigma-Aldrich, St. Louis, Mo.). After 15 min at room temperature, the mixture was diluted with water (50 mL) and $CH_2Cl_2$ (50 mL), the organics were separated, dried ($MgSO_4$) and concentrated to give a dark oil. To this oil was added 50 mL of ether and 10 mL of 1N HCl in ether. The resulting white precipitate was collected by filtration to give 3-(tetrahydro-2H-pyran-4-ylmethyl)-1-(2-thiophenylsulfonyl)piperazine hydrochloride (1.45 g) as an orange solid.

Step 5: 1,1,1,3,3,3-hexafluoro-2-(4-(2-(tetrahydro-2H-pyran-4-ylmethyl)-4-(2-thiophenylsulfonyl)-1-piperazinyl)phenyl)-2-propanol A 100 ml, round-bottomed flask was charged with 3-(tetrahydro-2H-pyran-4-ylmethyl)-1-(2-thiophenylsulfonyl) piperazine hydrochloride (0.250 g, 0.681 mmol), 2-(4-bromophenyl)-1,1,1,3,3,3-hexafluoro-2-propanol (0.330 g, 1.02 mmol, *Bioorg. Med. Chem. Lett.* 2002, 12, 3009), sodium tert-butoxide (0.196 g, 2.04 mmol) and 10 mL of toluene. To this was added dicyclohexyl(2',6'-diisopropoxybiphenyl-2-yl)phosphine (RuPhos) (0.032 g, 0.068 mmol, Strem Chemical Inc, Newburyport, Mass.), tris(dibenzylideneacetone)dipalladium (0) (0.031 g, 0.034 mmol, Strem Chemical Inc, Newburyport, Mass.). The mixture was heated at 100° C. for 12 h and then diluted with water (10 mL) and extracted with EtOAc (2×20 mL). The combined organic extracts were dried ($MgSO_4$), concentrated, and purified by reverse-phase preparative HPLC (Phenomenex Gemini $C_{18}$ column (150×30 mm, 10 μm), eluting with a 0.1% TFA in $CH_3CN/H_2O$ (10% to 90% over 25 min)) to afford 1,1,1,3,3,3-hexafluoro-2-(4-(2-(tetrahydro-2H-pyran-4-ylmethyl)-4-(2-thiophenylsulfonyl)-1-piperazinyl)phenyl)-2-propanol (0.008 g) as a mixture of two enantiomers.

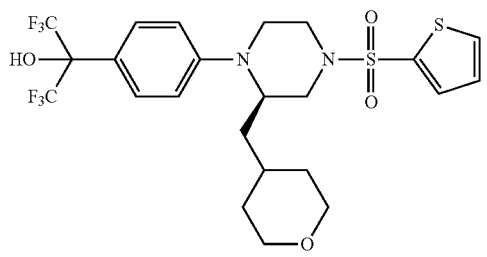

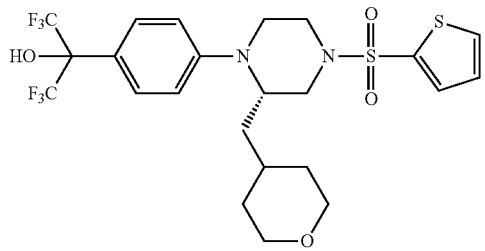

1,1,1,3,3,3-hexafluoro-2-(4-((2R)-2-(tetrahydro-2H-pyran-4-ylmethyl)-4-(2-thiophenylsulfonyl)-1-piperazinyl)phenyl)-2-propanol; 1,1,1,3,3,3-hexafluoro-2-(4-((2S)-2-(tetrahydro-2H-pyran-4-ylmethyl)-4-(2-thiophenylsulfonyl)-1-piperazinyl)phenyl)-2-propanol. $^1$H NMR (400 MHz, $CD_3OD$) δ 7.89 (d, J=4.9 Hz, 1H), 7.70-7.61 (m, 1H), 7.55 (d, J=9.0 Hz, 2H), 7.31-7.23 (m, 1H), 6.96 (d, J=9.2 Hz, 2H), 4.18 (br. s., 1H), 3.95-3.64 (m, 4H), 3.60-3.44 (m, 1H), 3.40-3.23 (m, 2H), 2.70 (dd, J=2.9, 11.7 Hz, 1H), 2.57 (dt, J=3.6, 11.4 Hz, 1H), 1.86-1.65 (m, 2H), 1.65-1.38 (m, 3H), 1.38-

1.08 (m, 3H). m/z (ESI, +ve ion) 573.0 (M+H)⁺. GK-GKRP EC$_{50}$ (NADPH-coupled)=0.169 µM; GK-GKRP EC$_{50}$ (LC MS/MS)=0.281 µM.

Example 37

1,1,1-trifluoro-2-(4-(2-(tetrahydro-2H-pyran-4-ylmethyl)-4-(2-thiophenylsulfonyl)-1-piperazinyl)phenyl)-2-propanol

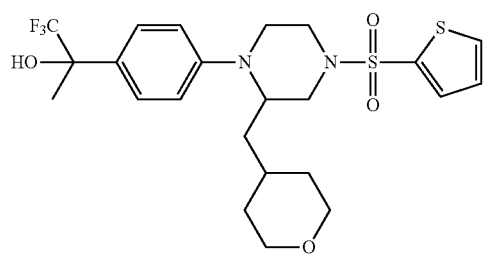 [SMILES: CC(O)(c1ccc(N2CCN(S(=O)(=O)c3cccs3)CC2CC2CCOCC2)cc1)C(F)(F)F]

Following the procedure reported for Example 36, starting from N-(tert-butoxycarbonyl)-3-(tetrahydro-2H-pyran-4-yl)-L-alanine (Acros/Fisher Scientific, Waltham, Mass.) and coupling with 2-(4-bromophenyl)-1,1,1-trifluoro-2-propanol (Example 27, step 1) delivered 1,1,1-trifluoro-2-(4-(-2-(tetrahydro-2H-pyran-4-ylmethyl)-4-(2-thiophenylsulfonyl)-1-piperazinyl)phenyl)-2-propanol as a mixture of four isomers.

This mixture was resolved using chiral SFC (Chiralpak® IA column (250×21 mm, 5 µm) using 30% methanol (0.2% diethylamine) in supercritical CO$_2$, total flow was 65 mL/min). Peaks 1 and 2 were purified a second time using SFC (IC column (250×21 mm, 5 µm), with 25% methanol (0.2% diethylamine) in supercritical CO$_2$ as the eluent). This produced four products with both diastereomeric and enantiomeric excesses over 95%.

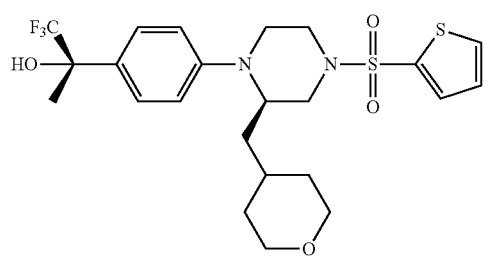

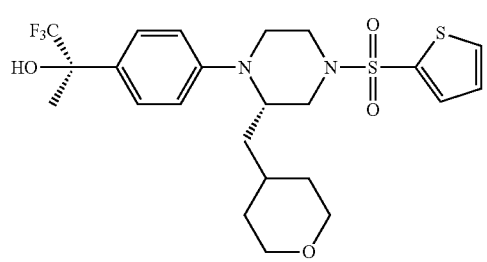

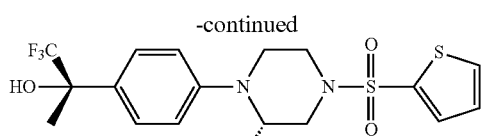

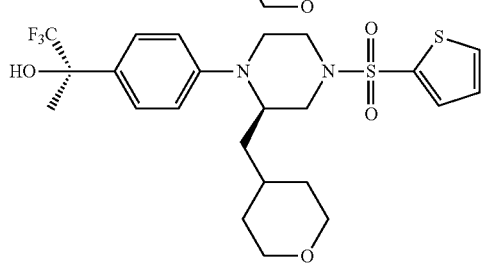

(2R)-1,1,1-trifluoro-2-(4-((2R)-2-(tetrahydro-2H-pyran-4-ylmethyl)-4-(2-thiophenylsulfonyl)-1-piperazinyl)phenyl)-2-propanol; (2R)-1,1,1-trifluoro-2-(4-((2S)-2-(tetrahydro-2H-pyran-4-ylmethyl)-4-(2-thiophenylsulfonyl)-1-piperazinyl)phenyl)-2-propanol; (2S)-1,1,1-trifluoro-2-(4-((2S)-2-(tetrahydro-2H-pyran-4-ylmethyl)-4-(2-thiophenylsulfonyl)-1-piperazinyl)phenyl)-2-propanol; (2S)-1,1,1-trifluoro-2-(4-((2R)-2-(tetrahydro-2H-pyran-4-ylmethyl)-4-(2-thiophenylsulfonyl)-1-piperazinyl)phenyl)-2-propanol.

First Eluting Peak (Peak #1)

$^1$H NMR (400 MHz, CD$_3$OD) δ 7.76 (dd, J=1.3, 5.0 Hz, 1H), 7.53 (dd, J=1.3, 3.8 Hz, 1H), 7.34 (d, J=8.6 Hz, 2H), 7.14 (dd, J=3.9, 4.9 Hz, 1H), 6.79 (d, J=9.0 Hz, 2H), 3.99 (br. s., 1H), 3.84-3.69 (m, 2H), 3.66-3.50 (m, 2H), 3.43-3.23 (m, 1H), 3.18-3.04 (m, 1H), 2.70-2.56 (m, 1H), 2.48 (dt, J=3.5, 11.3 Hz, 1H), 1.75-1.51 (m, 6H), 1.50-0.95 (m, 6H). m/z (ESI, +ve ion) 519.2 (M+H)⁺. GK-GKRP EC$_{50}$ (NADPH-coupled)=0.111 µM; GK-GKRP EC$_{50}$ (LC MS/MS)=0.162 µM.

Second Eluting Peak (Peak #2)

$^1$H NMR (400 MHz, CD$_3$OD) δ 7.76 (dd, J=1.2, 4.9 Hz, 1H), 7.58-7.44 (m, 1H), 7.41-7.23 (m, 2H), 7.21-7.04 (m, 1H), 6.80 (s, 2H), 3.99 (br. s., 1H), 3.85-3.66 (m, 2H), 3.66-3.46 (m, 2H), 3.41-3.26 (m, 2H), 3.18-3.04 (m, 2H), 2.61 (dd, J=3.0, 11.4 Hz, 1H), 2.48 (dt, J=3.6, 11.4 Hz, 1H), 1.66 (m, 1H), 1.57 (m, 4H), 1.51-0.90 (m, 5H). m/z (ESI, +ve ion) 519.2 (M+H)⁺. GK-GKRP EC$_{50}$ (NADPH-coupled)=0.124 µM; GK-GKRP EC$_{50}$ (LC MS/MS)=0.128 µM.

Third Eluting Peak (Peak #3)

$^1$H NMR (400 MHz, CD$_3$OD) δ 7.88 (d, J=4.9 Hz, 1H), 7.66 (s, 1H), 7.47 (s, 2H), 7.27 (d, J=4.7 Hz, 1H), 6.91 (d, J=9.0 Hz, 2H), 4.20-4.02 (m, 1H), 3.93-3.81 (m, 2H), 3.79-3.63 (m, 2H), 3.53-3.36 (m, 2H), 3.31-3.17 (m, 1H), 2.78-2.69 (m, 1H), 2.60 (dt, J=3.6, 11.3 Hz, 1H), 1.78 (m, 1H), 1.71 (m, 4H), 1.61-1.06 (m, 6H). m/z (ESI, +ve ion) 519.2 (M+H)⁺. GK-GKRP EC$_{50}$ (NADPH-coupled)=13.0 µM.

Fourth Eluting Peak (Peak #4)

$^1$H NMR (400 MHz, CD$_3$OD) δ 7.88 (d, J=4.1 Hz, 1H), 7.66 (s, 1H), 7.46 (d, J=8.4 Hz, 2H), 7.32-7.18 (m, 1H), 6.91 (d, J=8.8 Hz, 2H), 4.10 (br. s., 1H), 3.87 (t, J=11.0 Hz, 2H), 3.79-3.61 (m, 2H), 3.57-3.38 (m, 1H), 3.30-3.18 (m, 1H), 2.73 (dd, J=3.3, 11.3 Hz, 1H), 2.66-2.50 (m, 1H), 1.86-1.73 (m, 1H), 1.69 (s, 3H), 1.62-0.87 (m, 8H). m/z (ESI, +ve ion) 519.2 (M+H)⁺. GK-GKRP EC$_{50}$ (NADPH-coupled)=>50 µM.

Example 38

1,1,1-trifluoro-2-(4-(2-(2-fluorobenzyl)-4-(2-thiophenylsulfonyl)-1-piperazinyl)phenyl)-2-propanol

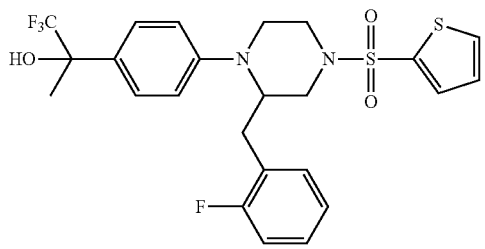

Following the procedure reported for Example 36, starting from (3S)-3-((tert-butoxycarbonyl)amino)-4-(2-fluorophenyl)butanoic acid (Chem-Impex International, Inc., Wood Dale, Ill.) and coupling with 2-(4-bromophenyl)-1,1,1-trifluoro-2-propanol (Example 27, step 1) delivered 1,1,1-trifluoro-2-(4-(-2-(2-fluorobenzyl)-4-(2-thiophenylsulfonyl)-1-piperazinyl)phenyl)-2-propanol as a mixture of four isomers.

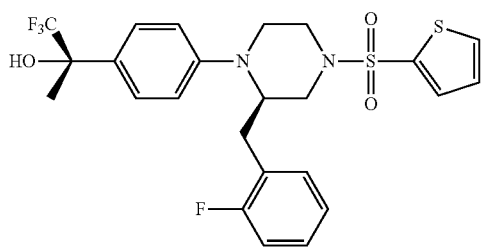 [SMILES: CC(O)(c1ccc(N2CCN(S(=O)(=O)c3cccs3)CC2Cc2ccccc2F)cc1)C(F)(F)F]

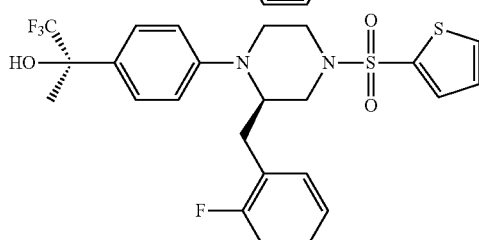

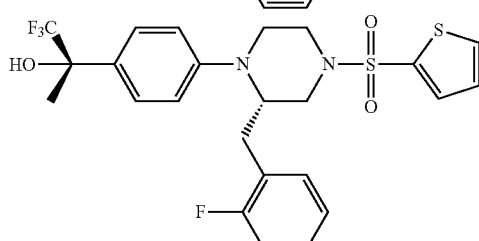

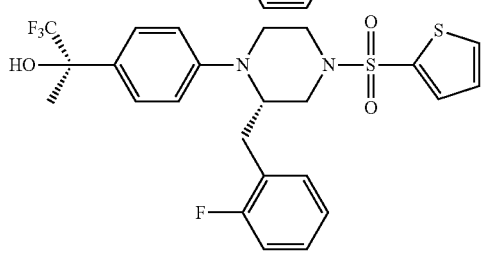

(2R)-1,1,1-trifluoro-2-(4-((2R)-2-(2-fluorobenzyl)-4-(2-thiophenylsulfonyl)-1-piperazinyl)phenyl)-2-propanol;
(2R)-1,1,1-trifluoro-2-(4-((2S)-2-(2-fluorobenzyl)-4-(2-thiophenylsulfonyl)-1-piperazinyl)phenyl)-2-propanol;
(2S)-1,1,1-trifluoro-2-(4-((2R)-2-(2-fluorobenzyl)-4-(2-thiophenylsulfonyl)-1-piperazinyl)phenyl)-2-propanol;
(2S)-1,1,1-trifluoro-2-(4-((2S)-2-(2-fluorobenzyl)-4-(2-thiophenylsulfonyl)-1-piperazinyl)phenyl)-2-propanol. 1H NMR (400 MHz, CD$_3$OD) δ 7.86 (d, J=4.9 Hz, 1H), 7.64-7.54 (m, 1H), 7.45 (d, J=8.8 Hz, 2H), 7.32 (t, J=7.6 Hz, 1H), 7.26-7.16 (m, 2H), 7.14-6.93 (m, 4H), 4.29-4.18 (m, 1H), 3.87-3.76 (m, 1H), 3.61-3.48 (m, 2H), 3.41 (dt, J=3.5, 12.0 Hz, 1H), 3.13-3.01 (m, 1H), 2.85 (dd, J=3.8, 13.2 Hz, 1H), 2.62-2.49 (m, 2H), 1.69 (s, 3H). m/z (ESI, +ve ion) 529.0 (M+H)$^+$. GK-GKRP EC$_{50}$ (NADPH-coupled)=0.515 μM; GK-GKRP EC$_{50}$ (LC MS/MS)=0.850 μM.

Example 39

1,1,1-trifluoro-2-(4-(2-(3-fluorobenzyl)-4-(2-thiophenylsulfonyl)-1-piperazinyl)phenyl)-2-propanol

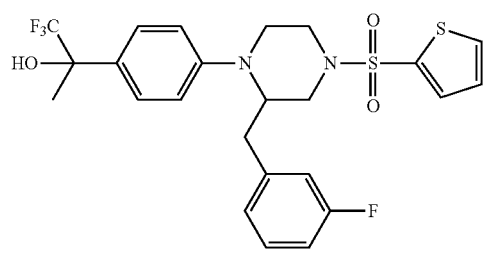 [SMILES: CC(O)(c1ccc(N2CCN(S(=O)(=O)c3cccs3)CC2Cc2cccc(F)c2)cc1)C(F)(F)F]

Following the procedure reported for Example 36, starting from (3S)-3-((tert-butoxycarbonyl)amino)-4-(3-fluorophenyl)butanoic acid (Acros/Fisher Scientific, Waltham, Mass.) and coupling with 2-(4-bromophenyl)-1,1,1-trifluoro-2-propanol (Example 27, step 1) delivered 1,1,1-trifluoro-2-(4-(-2-(3-fluorobenzyl)-4-(2-thiophenylsulfonyl)-1-piperazinyl)phenyl)-2-propanol as a mixture of four isomers.

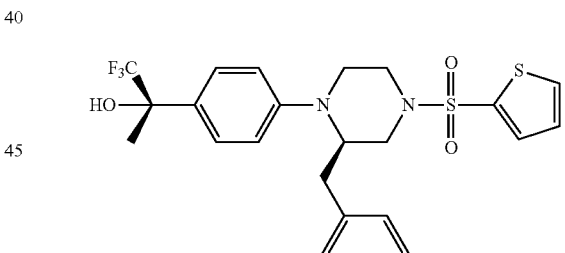

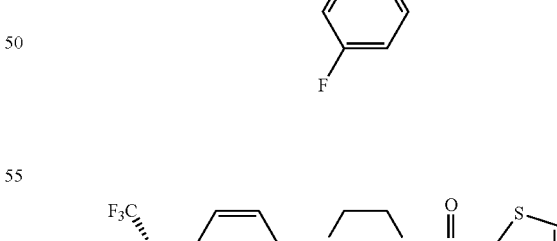

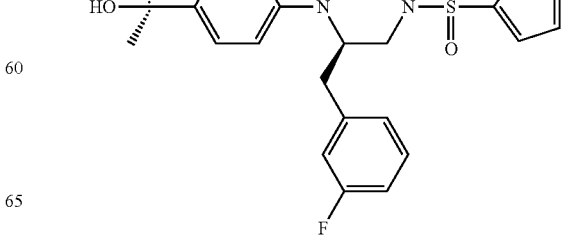

-continued

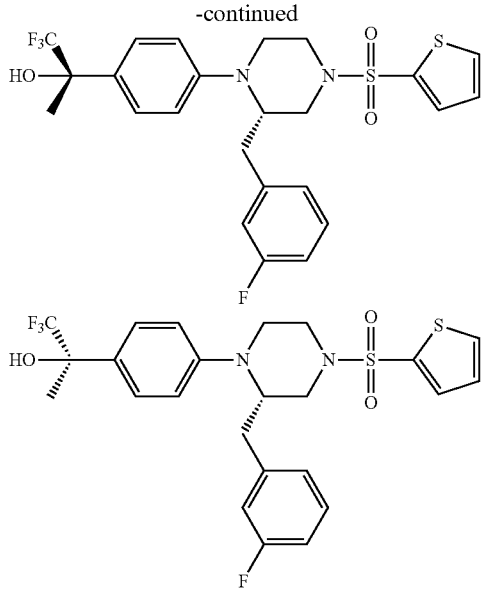

(2R)-1,1,1-trifluoro-2-(4-((2R)-2-(3-fluorobenzyl)-4-(2-thiophenylsulfonyl)-1-piperazinyl)phenyl)-2-propanol;
(2R)-1,1,1-trifluoro-2-(4-((2S)-2-(3-fluorobenzyl)-4-(2-thiophenylsulfonyl)-1-piperazinyl)phenyl)-2-propanol;
(2S)-1,1,1-trifluoro-2-(4-((2R)-2-(3-fluorobenzyl)-4-(2-thiophenylsulfonyl)-1-piperazinyl)phenyl)-2-propanol;
(2S)-1,1,1-trifluoro-2-(4-((2S)-2-(3-fluorobenzyl)-4-(2-thiophenylsulfonyl)-1-piperazinyl)phenyl)-2-propanol. $^1$H NMR (400 MHz, CD$_3$OD) δ 7.86 (dd, J=1.2, 5.1 Hz, 1H), 7.64-7.59 (m, 1H), 7.55-7.48 (m, 2H), 7.36-7.15 (m, 2H), 7.11-6.77 (m, 5H), 4.17-4.09 (m, 1H), 3.84 (d, J=10.0 Hz, 1H), 3.61 (d, J=11.3 Hz, 1H), 3.55-3.43 (m, 1H), 3.42-3.34 (m, 1H), 3.19-3.04 (m, 1H), 2.69-2.48 (m, 3H), 1.70 (s, 3H). m/z (ESI, +ve ion) 529.0 (M+H)$^+$. GK-GKRP EC$_{50}$ (NADPH-coupled)=0.802 μM; GK-GKRP EC$_{50}$ (LC MS/MS)=1.09 μM.

Example 40

1,1,1-trifluoro-2-(4-(2-(4-fluorobenzyl)-4-(2-thiophenylsulfonyl)-1-piperazinyl)phenyl)-2-propanol

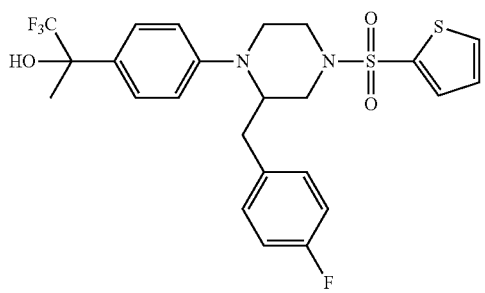 [SMILES: CC(O)(c1ccc(N2CCN(S(=O)(=O)c3cccs3)CC2Cc2ccc(F)cc2)cc1)C(F)(F)F]

Following the procedure reported for Example 36, starting from (3S)-3-((tert-butoxycarbonyl)amino)-4-(4-fluorophenyl)butanoic acid (Acros/Fisher Scientific, Waltham, Mass.) and coupling with 2-(4-bromophenyl)-1,1,1-trifluoro-2-propanol (Example 27, step 1) delivered 1,1,1-trifluoro-2-(4-(-2-(4-fluorobenzyl)-4-(2-thiophenylsulfonyl)-1-piperazinyl)phenyl)-2-propanol as a mixture of four isomers.

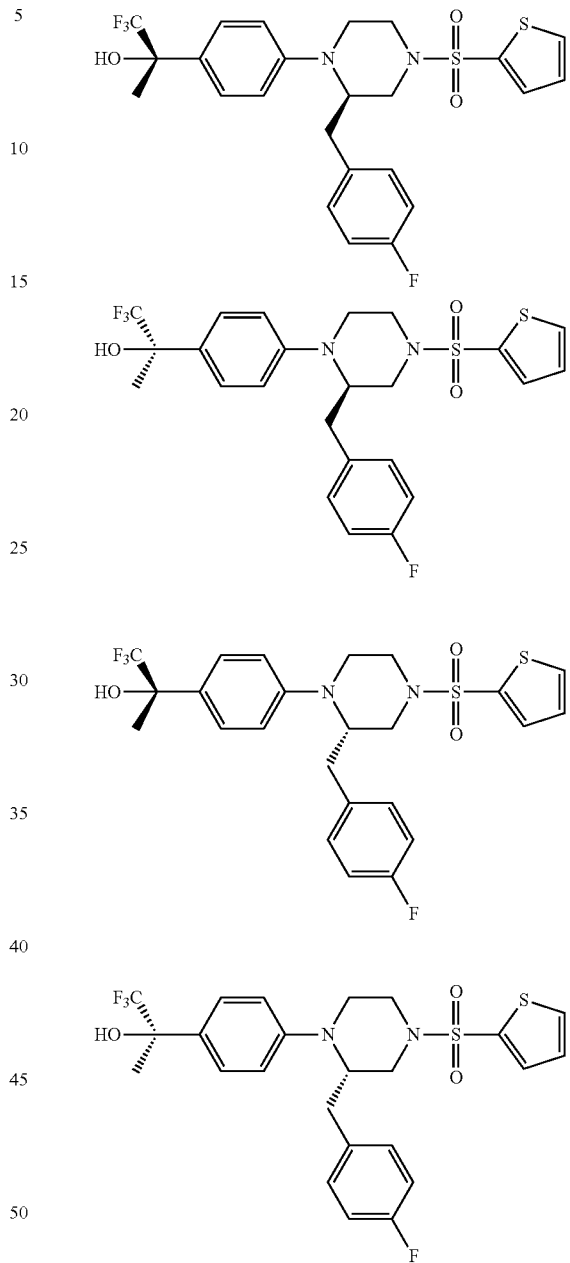

(2R)-1,1,1-trifluoro-2-(4-((2R)-2-(4-fluorobenzyl)-4-(2-thiophenylsulfonyl)-1-piperazinyl)phenyl)-2-propanol;
(2R)-1,1,1-trifluoro-2-(4-((2S)-2-(4-fluorobenzyl)-4-(2-thiophenylsulfonyl)-1-piperazinyl)phenyl)-2-propanol;
(2S)-1,1,1-trifluoro-2-(4-((2R)-2-(4-fluorobenzyl)-4-(2-thiophenylsulfonyl)-1-piperazinyl)phenyl)-2-propanol;
(2S)-1,1,1-trifluoro-2-(4-((2S)-2-(4-fluorobenzyl)-4-(2-thiophenylsulfonyl)-1-piperazinyl)phenyl)-2-propanol. $^1$H NMR (400 MHz, CD$_3$OD) δ 7.93-7.81 (m, 1H), 7.61 (d, J=2.5 Hz, 1H), 7.56-7.43 (m, 2H), 7.30-7.15 (m, 3H), 7.08-6.91 (m, 4H), 4.11 (br. s., 1H), 3.84 (d, J=11.0 Hz, 1H), 3.60 (d, J=11.3 Hz, 1H), 3.55-3.46 (m, 1H), 3.40-3.35 (m, 1H), 3.21-2.96 (m, 1H), 2.72-2.47 (m, 3H), 1.70 (s, 3H). m/z (ESI, +ve ion) 529.0

(M+H)⁺. GK-GKRP EC₅₀ (NADPH-coupled)=0.895 μM; GK-GKRP EC₅₀ (LC MS/MS)=1.25 μM.

Example 41

1,1,1-trifluoro-2-(4-(4-(phenylsulfonyl)-2-(tetrahydro-2H-pyran-4-ylmethyl)-1-piperazinyl)phenyl)-2-propanol

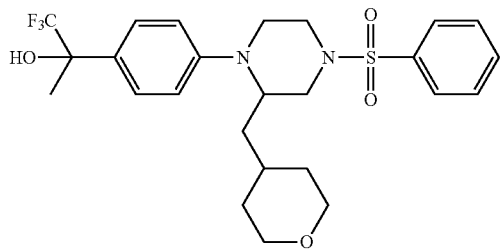 [SMILES: CC(O)(c1ccc(N2CCN(S(=O)(=O)c3ccccc3)CC2CC2CCOCC2)cc1)C(F)(F)F]

Following the procedure reported for Example 36, starting from N-(tert-butoxycarbonyl)-3-(tetrahydro-2H-pyran-4-yl)-L-alanine (Acros/Fisher Scientific, Waltham, Mass.) and coupling with benzenesulfonyl chloride (Sigma-Aldrich, St. Louis, Mo.) and 2-(4-bromophenyl)-1,1,1-trifluoro-2-propanol (Example 27, step 1) and delivered 1,1,1-trifluoro-2-(4-(4-(phenylsulfonyl)-2-(tetrahydro-2H-pyran-4-ylmethyl)-1-piperazinyl)phenyl)-2-propanol as a mixture of four compounds.

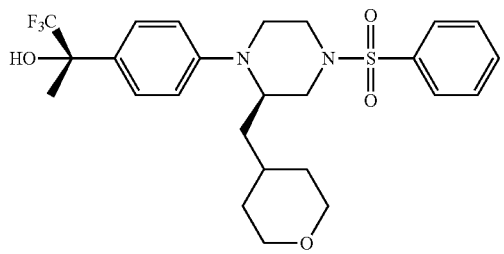

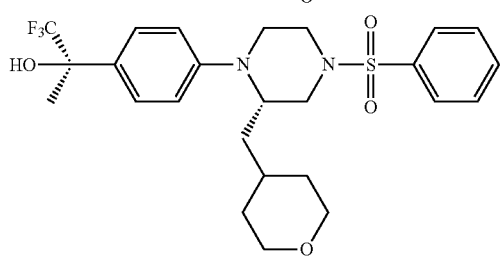

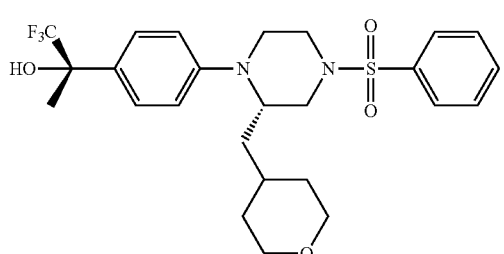

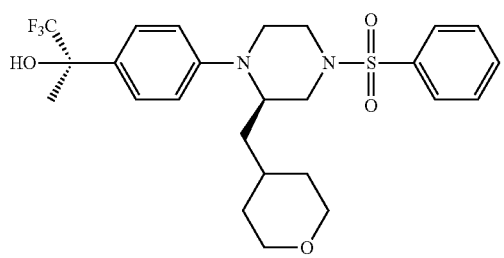

(2R)-1,1,1-trifluoro-2-(4-((2R)-4-(phenylsulfonyl)-2-(tetrahydro-2H-pyran-4-ylmethyl)-1-piperazinyl)phenyl)-2-propanol; (2R)-1,1,1-trifluoro-2-(4-((2S)-4-(phenylsulfonyl)-2-(tetrahydro-2H-pyran-4-ylmethyl)-1-piperazinyl)phenyl)-2-propanol; (2S)-1,1,1-trifluoro-2-(4-((2R)-4-(phenylsulfonyl)-2-(tetrahydro-2H-pyran-4-ylmethyl)-1-piperazinyl)phenyl)-2-propanol; (2S)-1,1,1-trifluoro-2-(4-((2S)-4-(phenylsulfonyl)-2-(tetrahydro-2H-pyran-4-ylmethyl)-1-piperazinyl)phenyl)-2-propanol. ¹H NMR (400 MHz, CD₃OD) δ 7.83 (s, 2H), 7.65 (s, 3H), 7.44 (d, J=8.8 Hz, 2H), 6.89 (d, J=9.0 Hz, 2H), 4.06 (m, 1H), 3.92-3.82 (m, 2H), 3.80-3.72 (m, 1H), 3.67 (d, J=11.5 Hz, 1H), 3.47-3.37 (m, 1H), 3.31-3.19 (m, 1H), 2.65 (dd, J=3.1, 11.5 Hz, 1H), 2.51 (dt, J=3.6, 11.4 Hz, 1H), 1.83-1.73 (m, 1H), 1.68 (s, 4H), 1.60-1.49 (m, 2H), 1.40-1.03 (m, 5H). m/z (ESI, +ve ion) 513.0 (M+H)⁺. GK-GKRP EC₅₀ (NADPH-coupled)=0.785 μM; GK-GKRP EC₅₀ (LC MS/MS)=0.572 μM.

Example 42

1,1,1,3,3,3-hexafluoro-2-(4-(2-(3-methylbenzyl)-4-(2-thiophenylsulfonyl)-1-piperazinyl)phenyl)-2-propanol hydrochloride

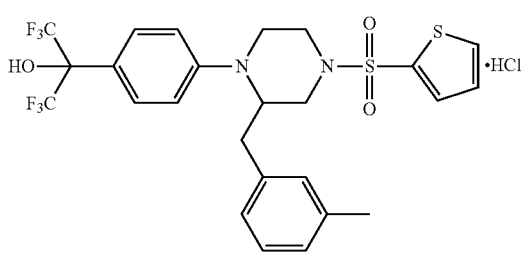 [SMILES: Cc1cccc(CC2CN(S(=O)(=O)c3cccs3)CCN2c2ccc(C(O)(C(F)(F)F)C(F)(F)F)cc2)c1 ; Cl]

Following the procedure reported for Example 36, starting from N-(tert-butoxycarbonyl)-3-methyl-L-phenylalanine (Sigma-Aldrich, St. Louis, Mo.) and coupling with 2-(4-bromophenyl)-1,1,1,3,3,3-hexafluoro-2-propanol (*Bioorg. Med. Chem. Lett.* 2002, 12, 3009) produced the desired product. The free base was acidified with 4 N HCl in dioxane to provide 1,1,1,3,3,3-hexafluoro-2-(4-(2-(3-methylbenzyl)-4-(2-thiophenylsulfonyl)-1-piperazinyl)phenyl)-2-propanol hydrochloride as a mixture of two enantiomers.

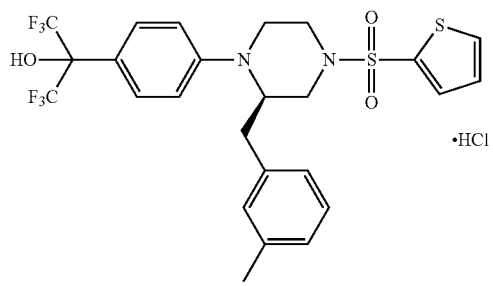

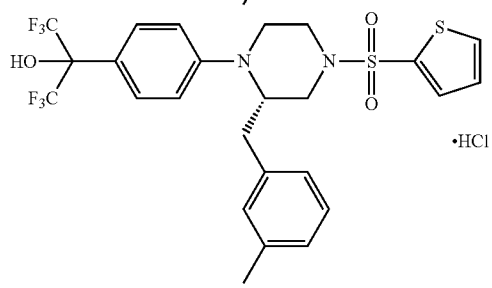

1,1,1,3,3,3-hexafluoro-2-(4-((2R)-2-(3-methylbenzyl)-4-(2-thiophenylsulfonyl)-1-piperazinyl)phenyl)-2-propanol hydrochloride; 1,1,1,3,3,3-hexafluoro-2-(4-((2S)-2-(3-methylbenzyl)-4-(2-thiophenylsulfonyl)-1-piperazinyl)phenyl)-2-propanol hydrochloride. $^1$H NMR (400 MHz, CD$_3$OD) δ 7.87-7.83 (m, 1H), 7.62-7.58 (m, 3H), 7.24-7.21 (m, 1H), 7.19-7.14 (m, 1H), 7.08-6.99 (m, 5H), 4.17-4.11 (m, 1H), 3.88-3.82 (m, 1H), 3.68-3.56 (m, 2H), 3.42-3.34 (m, 1H), 3.12-3.04 (m, 1H), 2.62-2.53 (m, 2H), 2.51-2.46 (m, 1H), 2.31 (s, 3H). m/z (ESI, +ve ion) 578.8 (M+H)$^+$. GK-GKRP EC$_{50}$ (NADPH-coupled)=0.724 μM; GK-GKRP EC$_{50}$ (LC MS/MS)=0.688 μM.

Example 43

1,1,1,3,3,3-hexafluoro-2-(4-(2-(4-methylbenzyl)-4-(2-thiophenylsulfonyl)-1-piperazinyl)phenyl)-2-propanol hydrochloride

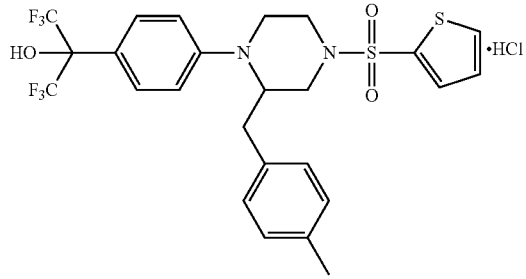 [SMILES: Cc1ccc(CC2CN(S(=O)(=O)c3cccs3)CCN2c2ccc(C(O)(C(F)(F)F)C(F)(F)F)cc2)cc1 ; Cl]

Following the procedure reported for Example 36, starting from N-(tert-butoxycarbonyl)-4-methyl-L-phenylalanine (Sigma-Aldrich, St. Louis, Mo.) and coupling with 2-(4-bromophenyl)-1,1,1,3,3,3-hexafluoro-2-propanol (*Bioorg. Med. Chem. Lett.* 2002, 12, 3009) produced the desired product. The free base was acidified with 4N HCl in dioxane to provide 1,1,1,3,3,3-hexafluoro-2-(4-(2-(4-methylbenzyl)-4-(2-thiophenylsulfonyl)-1-piperazinyl)phenyl)-2-propanol hydrochloride as a mixture of two enantiomers.

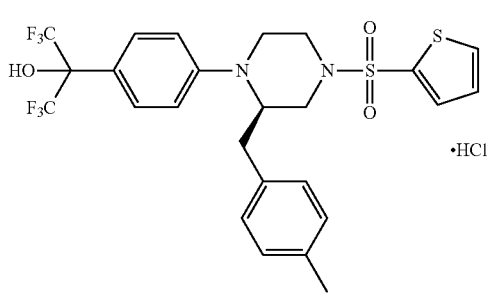

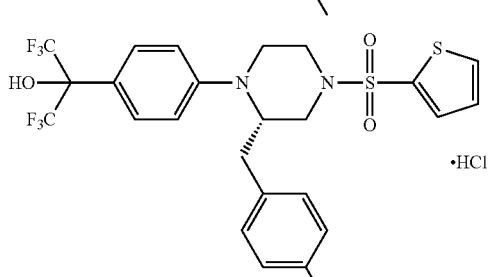

1,1,1,3,3,3-hexafluoro-2-(4-((2S)-2-(4-methylbenzyl)-4-(2-thiophenylsulfonyl)-1-piperazinyl)phenyl)-2-propanol hydrochloride; 1,1,1,3,3,3-hexafluoro-2-(4-((2R)-2-(4-methylbenzyl)-4-(2-thiophenylsulfonyl)-1-piperazinyl)phenyl)-2-propanol hydrochloride. $^1$H NMR (400 MHz, CD$_3$OD) δ 7.86-7.83 (m, 1H), 7.61-7.56 (m, 3H), 7.24-7.20 (m, 1H), 7.13-7.07 (m, 4H), 7.05-7.00 (m, 2H), 4.15-4.08 (m, 1H), 3.86-3.81 (m, 1H), 3.66-3.55 (m, 2H), 3.41-3.33 (m, 1H), 3.10-3.03 (m, 1H), 2.61-2.53 (m, 2H), 2.51-2.46 (m, 1H), 2.29 (s, 3H). m/z (ESI, +ve ion) 578.8 (M+H)$^+$. GK-GKRP EC$_{50}$ (NADPH-coupled)=2.50 μM; GK-GKRP EC$_{50}$ (LC MS/MS)=2.62 μM.

Example 44

1,1,1-trifluoro-2-(4-(2-(hydroxymethyl)-4-(2-thiophenylsulfonyl)-1-piperazinyl)phenyl)-2-propanol

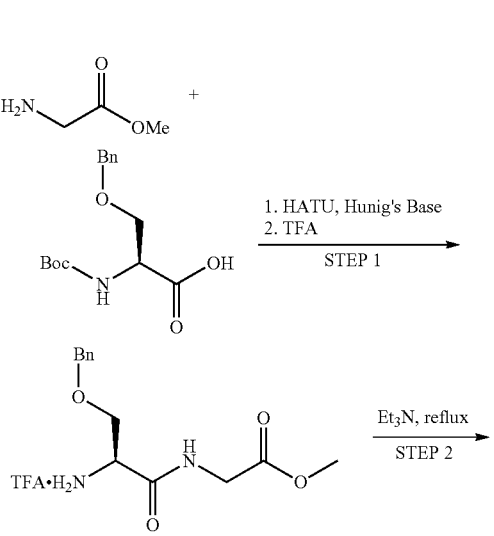

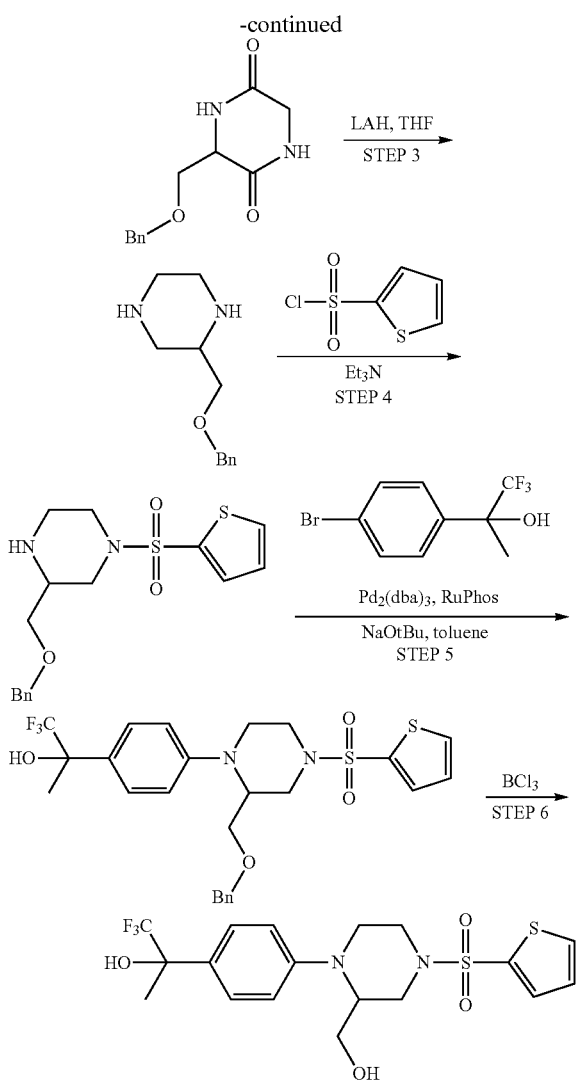

Step 2: 3-((benzyloxy)methyl)-2,5-piperazinedione

A 250 ml, round-bottomed flask was charged with methyl O-benzyl-L-serylglycinate trifluoroacetate (9.37 g, 24.64 mmol) and 3:1 MeOH/triethylamine (50 mL). The mixture was then heated to reflux for 16 h. The reaction was then cooled to room temperature, concentrated, and diluted with ice cold 50% aqueous EtOH (50 mL). The resulting precipitate was collected by filtration and dried under reduced pressure to give 3-(benzyloxymethyl)piperazine-2,5-dione (3.95 g) as a white solid.

Step 3: 2-((benzyloxy)methyl)piperazine

A 250 ml, round-bottomed flask was charged with lithium aluminum hydride (1.871 g, 49.3 mmol) and THF (75 mL). After cooling to 0° C., 3-(benzyloxymethyl)piperazine-2,5-dione (3.85 g, 16.44 mmol) was slowly added. The mixture was warmed to room temperature and then heated at reflux for 1 h. After this time, the mixture was cooled to 0° C. and the reaction was quenched with sodium sulfate decahydrate (20 g) and stirred vigorously for 1 h. The mixture was filtered, and the filtrate was concentrated to give 2-(benzyloxymethyl)piperazine (2.60 g) as a yellow oil. This material was taken to the next step without purification.

Step 4: 3-((benzyloxy)methyl)-1-(2-thiophenylsulfonyl) piperazine

A 250 mL round-bottomed flask was charged with 2-(benzyloxymethyl)piperazine (2.10 g, 10.1 mmol), triethylamine (1.42 mL, 10.2 mmol) and $CH_2Cl_2$ (50 mL). After cooling to 0° C., 2-thiophenesulfonyl chloride (1.84 g, 10.1 mmol, Sigma-Aldrich, St. Louis, Mo.) was added slowly via syringe. After 2 h, the mixture was concentrated and diluted with EtOAc (200 mL). The organic solution was washed with 1 N HCl (2×50 mL) and the combined acidic layers made basic with $Na_2CO_3$. The resulting basic solution was extracted with EtOAc (3×100 mL) and the combined organic layers were dried ($MgSO_4$), filtered and concentrated to give 3-(benzyloxymethyl)-1-(thiophen-2-ylsulfonyl)piperazine (1.79 g) as a yellow tar.

Step 5: 2-(4-(2-((benzyloxy)methyl)-4-(2-thiophenylsulfonyl)-1-piperazinyl)phenyl)-1,1,1-trifluoro-2-propanol A mixture of 3-(benzyloxymethyl)-1-(thiophen-2-ylsulfonyl)piperazine (2.95 g, 8.37 mmol), 2-(4-bromophenyl)-1,1,1-trifluoropropan-2-ol (2.70 g, 10.04 mmol, Example 27, step 1), dicyclohexyl(2',6'-diisopropoxybiphenyl-2-yl)phosphine (RuPhos) (0.156 g, 0.335 mmol, Strem Chemicals, Newburyport, Mass.), tris(dibenzylideneacetone)dipalladium (0) (0.153 g, 0.167 mmol, Strem Chemicals, Newburyport, Mass.), sodium tert-butoxide (2.011 g, 20.92 mmol) and toluene (50 mL) was added to a high-pressure reaction vessel. The vessel was sealed and heated at 100° C. for 16 h. The solution was then diluted with EtOAc (200 mL). The organic solution was washed with water (100 mL) and brine (100 mL) then dried ($MgSO_4$), filtered and concentrated. The crude material was subjected to flash chromatography on silica gel (120 g, 5-80% (10% MeOH-EtOAc) in hexanes) to give 2-(4-(2-((benzyloxy)methyl)-4-(2-thiophenylsulfonyl)-1-piperazinyl)phenyl)-1,1,1-trifluoro-2-propanol (3.95 g) as a mixture of four isomers.

Step 1: methyl O-benzyl-L-serylglycinate trifluoroacetate

A 250 mL round-bottomed flask was charged with O-benzyl-N-(tert-butoxycarbonyl)-L-serine (7.28 g, 24.65 mmol, Sigma-Aldrich, St. Louis, Mo.), glycine methyl ester hydrochloride (3.09 g, 24.65 mmol, Sigma-Aldrich, St. Louis, Mo.), Hünig's base (8.83 mL, 50.5 mmol) and DMF (100 mL). After cooling to 0° C., HATU (9.37 g, 24.65 mmol, Sigma-Aldrich, St. Louis, Mo.) was added. After the addition was complete, the reaction was slowly warmed to room temperature and stirred for 3 h. The mixture was diluted with EtOAc (300 mL) and the organic solution was washed with 0.5 N aqueous HCl (150 mL), saturated aqueous $NaHCO_3$ (150 mL), water (150 mL), and then brine (150 mL). The organic layer was then dried ($MgSO_4$) and concentrated. The crude material was dissolved in a 2:1 $CH_2Cl_2$/TFA solution (100 mL) and stirred for 2 h at room temperature. The mixture was then concentrated and azeotroped with toluene (2×100 mL) to give methyl O-benzyl-L-serylglycinate trifluoroacetate as a yellow tar (9.37 g). The product was taken onto the next step without purification.

145

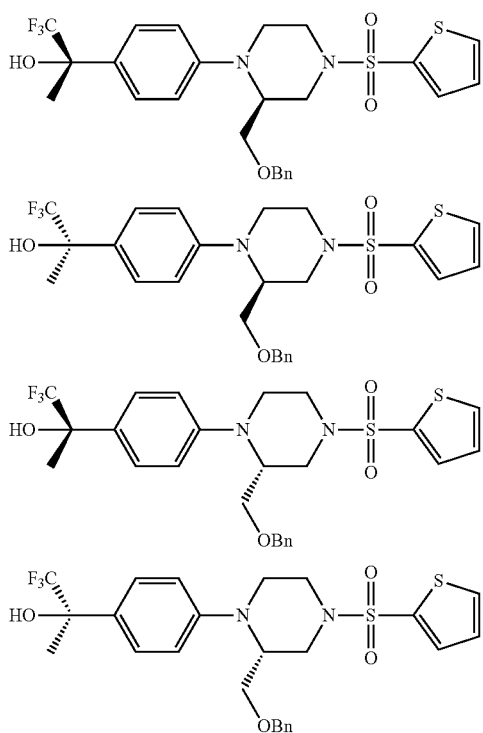

(2R)-2-(4-((2R)-2-((benzyloxy)methyl)-4-(2-thiophenylsulfonyl)-1-piperazinyl)phenyl)-1,1,1-trifluoro-2-propanol;
(2R)-2-(4-((2S)-2-((benzyloxy)methyl)-4-(2-thiophenylsulfonyl)-1-piperazinyl)phenyl)-1,1,1-trifluoro-2-propanol;
(2S)-2-(4-((2R)-2-((benzyloxy)methyl)-4-(2-thiophenylsulfonyl)-1-piperazinyl)phenyl)-1,1,1-trifluoro-2-propanol;
(2S)-2-(4-((2S)-2-((benzyloxy)methyl)-4-(2-thiophenylsulfonyl)-1-piperazinyl)phenyl)-1,1,1-trifluoro-2-propanol. $^1$H NMR (400 MHz, CDCl$_3$) δ 7.64-7.58 (m, 2H), 7.42-7.40 (m, 2H), 7.35-7.26 (m, 5H), 7.17-7.15 (m, 1H), 6.84-6.82 (m, 2H), 4.55-4.45 (m, 2H), 4.06-3.99 (m, 2H), 3.82-3.74 (m, 2H), 3.48-3.44 (m, 2H), 3.23-3.17 (m, 1H), 2.72-2.61 (m, 2H), 1.74 (s, 3H). m/z (ESI, +ve ion) 541.1 (M+H)$^+$. GK-GKRP EC$_{50}$ (NADPH-coupled)=0.420 µM; GK-GKRP EC$_{50}$ (LC MS/MS)=0.617 µM.

Step 6: 1,1,1-trifluoro-2-(4-(2-(hydroxymethyl)-4-(2-thiophenylsulfonyl)-1-piperazinyl)phenyl)-2-propanol A 250 mL round-bottomed flask was charged with 2-(4-(2-((benzyloxy)methyl)-4-(2-thiophenylsulfonyl)-1-piperazinyl)phenyl)-1,1,1-trifluoro-2-propanol (2.93 g, 5.43 mmol) and CH$_2$Cl$_2$ (50 mL) and cooled to −78° C. A 1.0 M solution of BCl$_3$ (1M in CH$_2$Cl$_2$, 7.31 mL, 7.31 mmol, Sigma-Aldrich, St. Louis, Mo.) was added slowly to the mixture and the reaction was stirred for 1 h at −78° C. After this time, MeOH (25 mL) was added and the mixture was warmed to room temperature. After the MeOH was removed in vacuo, diethyl ether (100 mL) was added. The resulting precipitate was collected by filtration, dried under reduced pressure to yield 1,1,1-trifluoro-2-(4-(2-(hydroxymethyl)-4-(2-thiophenylsulfonyl)-1-piperazinyl)phenyl)-2-propanol (2.17 g) as a mixture of four isomers.

146

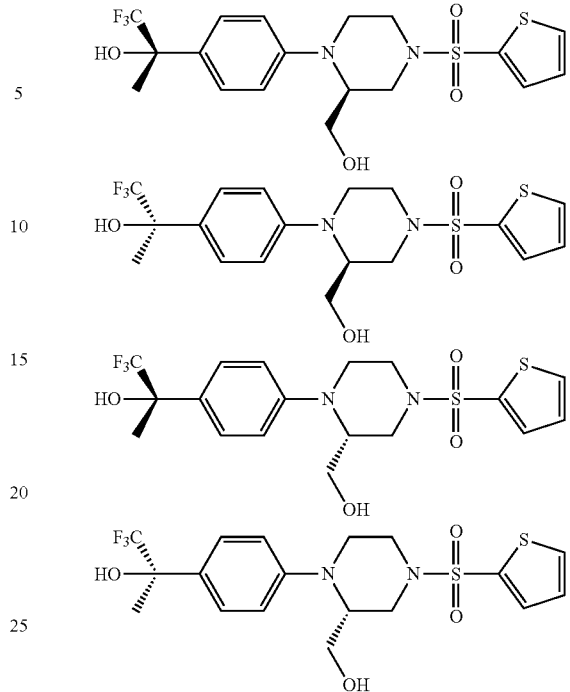

(2R)-1,1,1-trifluoro-2-(4-((2R)-2-(hydroxymethyl)-4-(2-thiophenylsulfonyl)-1-piperazinyl)phenyl)-2-propanol;
(2R)-1,1,1-trifluoro-2-(4-((2S)-2-(hydroxymethyl)-4-(2-thiophenylsulfonyl)-1-piperazinyl)phenyl)-2-propanol;
(2S)-1,1,1-trifluoro-2-(4-((2R)-2-(hydroxymethyl)-4-(2-thiophenylsulfonyl)-1-piperazinyl)phenyl)-2-propanol;
(2S)-1,1,1-trifluoro-2-(4-((2S)-2-(hydroxymethyl)-4-(2-thiophenylsulfonyl)-1-piperazinyl)phenyl)-2-propanol. $^1$H NMR (400 MHz, CDCl$_3$) δ 7.65 (dd, J=1.3, 5.0 Hz, 1H), 7.58 (dd, J=1.4, 3.7 Hz, 1H), 7.44 (d, J=8.8 Hz, 2H), 7.20-7.15 (m, 1H), 6.93-6.85 (m, 2H), 3.97-3.86 (m, 3H), 3.75-3.65 (m, 2H), 3.50-3.46 (m, 1H), 3.33-3.26 (m, 1H), 2.80-2.69 (m, 2H), 1.74 (s, 3H). m/z (ESI, +ve ion) 451.1 (M+H)$^+$ The mixture was resolved using chiral SFC(OJH column, 21×250 mm, 5 µM) using 70% supercritical CO$_2$/30% iPrOH (0.2% diethylamine) at a flow rate of 65 mL/min) to give 4 products with diastereomeric and enantiomeric excesses greater than 95%.

First Eluting Peak (Peak #1)
$^1$H NMR (400 MHz, CDCl$_3$) δ 7.66-7.64 (dd, J=5.0, 1.2 Hz, 1H), 7.59-7.57 (dd, J=3.7, 1.2 Hz, 1H), 7.45-7.42 (d, J=8.8 Hz, 2H), 7.18-7.16 (dd, J=5.0, 3.7 Hz, 1H), 6.90-6.88 (m, 2H), 3.97-3.86 (m, 3H), 3.75-3.67 (m, 2H), 3.50-3.45 (m, 1H), 3.33-3.26 (m, 1H), 2.79-2.68 (m, 2H), 1.74 (s, 3H). m/z (ESI, +ve ion) 451.1 (M+H)$^+$. GK-GKRP EC$_{50}$ (NADPH-coupled)=2.06 µM; GK-GKRP EC$_{50}$ (LC MS/MS)=50 µM.

Second Eluting Peak (Peak #2)
$^1$H NMR (400 MHz, CDCl$_3$) δ 7.66-7.64 (dd, J=5.0, 1.2 Hz, 1H), 7.59-7.57 (dd, J=3.7, 1.2 Hz, 1H), 7.45-7.42 (d, J=8.8 Hz, 2H), 7.18-7.16 (dd, J=5.0, 3.7 Hz, 1H), 6.90-6.88 (m, 2H), 3.97-3.86 (m, 3H), 3.75-3.67 (m, 2H), 3.50-3.45 (m, 1H), 3.33-3.26 (m, 1H), 2.79-2.68 (m, 2H), 1.74 (s, 3H). m/z (ESI, +ve ion) 451.1 (M+H)$^+$. GK-GKRP EC$_{50}$ (NADPH-coupled)=2.06 µM; GK-GKRP EC$_{50}$ (LC MS/MS)=3.38 µM.

Third Eluting Peak (Peak #3)
$^1$H NMR (400 MHz, CDCl$_3$) δ 7.66-7.64 (dd, J=5.0, 1.1 Hz, 1H), 7.59-7.57 (dd, J=3.7, 1.1 Hz, 1H), 7.45-7.42 (d, J=8.6 Hz, 2H), 7.18-7.16 (dd, J=5.0, 3.7 Hz, 1H), 6.90-6.88

(m, 2H), 3.97-3.86 (m, 3H), 3.75-3.67 (m, 2H), 3.50-3.45 (m, 1H), 3.33-3.26 (m, 1H), 2.79-2.68 (m, 2H), 1.73 (s, 3H). m/z (ESI, +ve ion) 451.1 (M+H)+. GK-GKRP $EC_{50}$ (NADPH-coupled)=>50 µM; GK-GKRP $EC_{50}$ (LC MS/MS)=>50 µM. Fourth Eluting Peak (Peak #4)

$^1$H NMR (400 MHz, CDCl$_3$) δ 7.66-7.64 (dd, J=5.0, 1.1 Hz, 1H), 7.59-7.57 (dd, J=3.7, 1.1 Hz, 1H), 7.45-7.42 (d, J=8.6 Hz, 2H), 7.18-7.16 (dd, J=5.0, 3.7 Hz, 1H), 6.90-6.88 (m, 2H), 3.97-3.86 (m, 3H), 3.75-3.67 (m, 2H), 3.50-3.45 (m, 1H), 3.33-3.26 (m, 1H), 2.79-2.68 (m, 2H), 1.73 (s, 3H). m/z (ESI, +ve ion) 451.1 (M+H)+. GK-GKRP $EC_{50}$ (NADPH-coupled)=>50 µM; GK-GKRP $EC_{50}$ (LC MS/MS)=>50 µM.

Example 45

1,1,1-trifluoro-2-(4-(2-(((3S)-3-methyl-4-morpholinyl)methyl)-4-(2-thiophenylsulfonyl)-1-piperazinyl)phenyl)-2-propanol

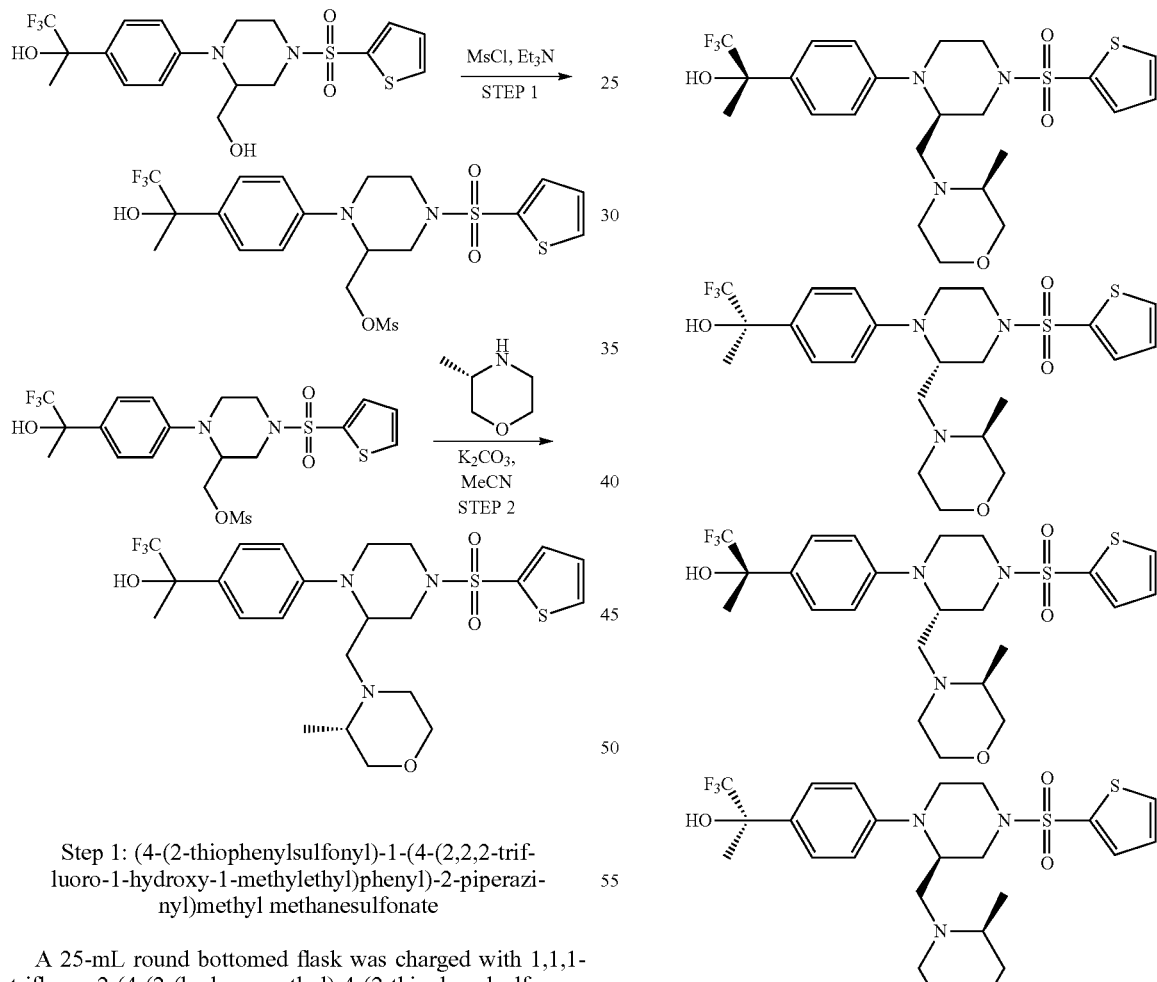

Step 1: (4-(2-thiophenylsulfonyl)-1-(4-(2,2,2-trifluoro-1-hydroxy-1-methylethyl)phenyl)-2-piperazinyl)methyl methanesulfonate A 25-mL round bottomed flask was charged with 1,1,1-trifluoro-2-(4-(2-(hydroxymethyl)-4-(2-thiophenylsulfonyl)-1-piperazinyl)phenyl)-2-propanol (400 mg, 0.888 mmol, Example 44), triethylamine (136 µL, 0.977 mmol) and CH$_2$Cl$_2$ (5 mL). After cooling to 0° C., methanesulfonyl chloride (69.2 µL, 0.888 mmol) was slowly added via syringe. The reaction was then warmed to room temperature and stirred for 3 h. After this time, the mixture was concentrated and the crude material was purified by column chromatography (12 g silica gel, 5%-80% (10% MeOH—CH$_2$Cl$_2$) in CH$_2$Cl$_2$) to give (4-(2-thiophenylsulfonyl)-1-(4-(2,2,2-trifluoro-1-hydroxy-1-methylethyl)phenyl)-2-piperazinyl)methyl methanesulfonate (403 mg) as a colorless foam.

Step 2: 1,1,1-trifluoro-2-(4-(2-(((3S)-3-methyl-4-morpholinyl)methyl)-4-(2-thiophenylsulfonyl)-1-piperazinyl)phenyl)-2-propanol A 20 mL vial was charged with (4-(2-thiophenylsulfonyl)-1-(4-(2,2,2-trifluoro-1-hydroxy-1-methylethyl)phenyl)-2-piperazinyl)methyl methanesulfonate (75 mg, 0.142 mmol), (S)-3-methylmorpholine (28.7 mg, 0.284 mmol Sigma-Aldrich, St. Louis, Mo.), potassium carbonate (39.2 mg, 0.284 mmol), and acetonitrile (4 mL). The vial was sealed and heated at 150° C. for 90 min in a microwave reactor (Emrys Optimizer Automated Microwave Synthesizer, Uppsala, Sweden). After this time, the mixture was filtered and the filtrate was concentrated. The crude material was purified via preparatory silica gel TLC (5% MeOH in CH$_2$Cl$_2$) to give 1,1,1-trifluoro-2-(4-(2-(((3S)-3-methyl-4-morpholinyl)methyl)-4-(2-thiophenylsulfonyl)-1-piperazinyl)phenyl)-2-propanol as a mixture of four isomers.

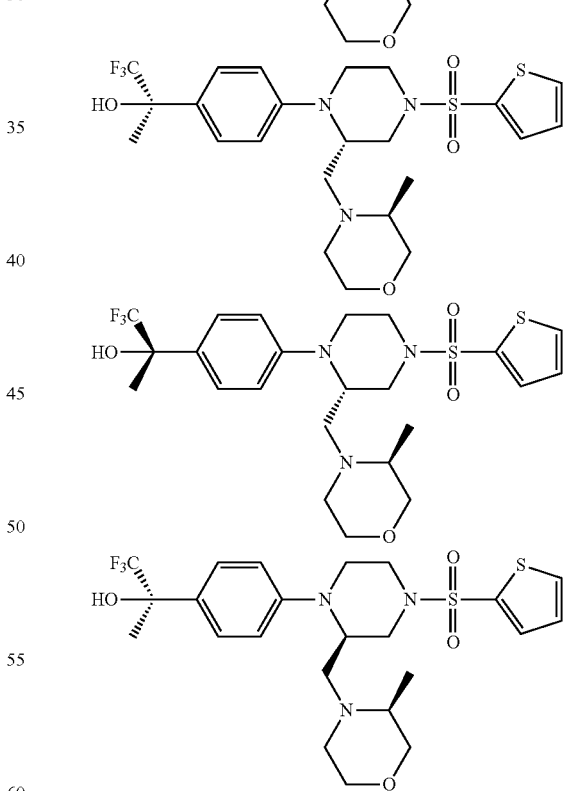

(2R)-1,1,1-trifluoro-2-(4-((2R)-2-(((3S)-3-methyl-4-morpholinyl)methyl)-4-(phenylsulfonyl)-1-piperazinyl)phenyl)-2-propanol; (2R)-1,1,1-trifluoro-2-(4-((2S)-2-(((3S)-3-methyl-4-morpholinyl)methyl)-4-(phenylsulfonyl)-1-piperazinyl)phenyl)-2-propanol; (2S)-1,1,1-trifluoro-2-(4-((2S)-2-(((3S)-3-methyl-4-morpholinyl)methyl)-4-(phenylsulfonyl)-1-piperazinyl)phenyl)-2-propanol; (2S)-1, 1,1-trifluoro-2-(4-((2R)-2-(((3S)-3-methyl-4-morpholinyl)methyl)-4-(phenylsulfonyl)-1-piperazinyl)phenyl)-2-propanol. This mixture was separated using chiral SFC (ADH column, 21×250 mm, 5 μM) using 69% supercritical $CO_2$ and 31% MeOH (0.2% diethylamine) with a flow rate of 65 mL/min) to give four isomers with diastereomeric and enantiomeric excesses greater than 95%.

First Eluting Peak (Peak #1)

$^1$H NMR (400 MHz, $CDCl_3$) δ 7.66-7.64 (dd, J=5.1, 1.2 Hz, 1H), 7.59-7.57 (dd, J=3.7, 1.2 Hz, 1H), 7.45-7.42 (d, J=8.9 Hz, 2H), 7.19-7.16 (m, J=5.0, 3.7 Hz, 1H), 6.82-6.80 (d, J=8.9 Hz, 2H), 4.09-4.04 (m, 1H), 3.89-3.85 (m, 1H), 3.80-3.75 (m, 1H), 3.73-3.69 (m, 1H), 3.65-3.54 (m, 2H), 3.43-3.38 (m, 1H), 3.30-3.20 (m, 3H), 2.76-2.71 (m, 1H), 2.62-2.50 (m, 2H), 2.40-2.34 (m, 1H), 2.21-2.14 (m, 1H), 1.94-1.89 (m, 1H), 1.74 (s, 3H), 1.03-1.02 (d, J=6.1 Hz, 3H). m/z (ESI, +ve ion) 534.2 $(M+H)^+$. GK-GKRP $EC_{50}$ (NADPH-coupled)=0.052 μM; GK-GKRP $EC_{50}$ (LC MS/MS)=0.062 μM.

Second Eluting Peak (Peak #2)

$^1$H NMR (400 MHz, $CDCl_3$) δ 7.66-7.64 (dd, J=5.1, 1.2 Hz, 1H), 7.59-7.57 (dd, J=3.7, 1.2 Hz, 1H), 7.45-7.42 (d, J=8.9 Hz, 2H), 7.19-7.16 (m, J=5.0, 3.7 Hz, 1H), 6.82-6.80 (d, J=8.9 Hz, 2H), 4.09-4.04 (m, 1H), 3.89-3.85 (m, 1H), 3.80-3.75 (m, 1H), 3.73-3.69 (m, 1H), 3.65-3.54 (m, 2H), 3.43-3.38 (m, 1H), 3.30-3.20 (m, 3H), 2.76-2.71 (m, 1H), 2.62-2.50 (m, 2H), 2.40-2.34 (m, 1H), 2.21-2.14 (m, 1H), 1.94-1.89 (m, 1H), 1.74 (s, 3H), 1.03-1.02 (d, J=6.1 Hz, 3H). m/z (ESI, +ve ion) 534.2 $(M+H)^+$. GK-GKRP $EC_{50}$ (NADPH-coupled)=0.068 μM; GK-GKRP $EC_{50}$ (LC MS/MS)=0.071 μM.

Third Eluting Peak (Peak #3)

$^1$H NMR (400 MHz, $CDCl_3$) δ 7.66-7.64 (dd, J=5.1, 1.2 Hz, 1H), 7.59-7.57 (dd, J=3.7, 1.2 Hz, 1H), 7.42-7.40 (d, J=8.9 Hz, 2H), 7.19-7.16 (m, J=5.0, 3.7 Hz, 1H), 6.83-6.80 (d, J=8.9 Hz, 2H), 4.11-4.07 (m, 1H), 3.91-3.88 (m, 1H), 3.82-3.77 (m, 1H), 3.68-3.64 (m, 1H), 3.61-3.49 (m, 2H), 3.37-3.27 (m, 2H), 3.19-3.15 (m, 1H), 2.83-2.78 (m, 1H), 2.68-2.59 (m, 2H), 2.56-2.40 (m, 4H), 1.74 (s, 3H), 0.91-0.89 (d, J=6.3 Hz, 3H). m/z (ESI, +ve ion) 534.2 $(M+H)^+$. GK-GKRP $EC_{50}$ (NADPH-coupled)=15.1 μM.

Fourth Eluting Peak (Peak #4)

$^1$H NMR (400 MHz, $CDCl_3$) δ 7.66-7.64 (dd, J=5.1, 1.2 Hz, 1H), 7.59-7.57 (dd, J=3.7, 1.2 Hz, 1H), 7.42-7.40 (d, J=8.9 Hz, 2H), 7.19-7.16 (m, J=5.0, 3.7 Hz, 1H), 6.83-6.80 (d, J=8.9 Hz, 2H), 4.11-4.07 (m, 1H), 3.91-3.88 (m, 1H), 3.82-3.77 (m, 1H), 3.68-3.64 (m, 1H), 3.61-3.49 (m, 2H), 3.37-3.27 (m, 2H), 3.19-3.15 (m, 1H), 2.83-2.78 (m, 1H), 2.68-2.59 (m, 2H), 2.56-2.40 (m, 4H), 1.74 (s, 3H), 0.91-0.89 (d, J=6.3 Hz, 3H). m/z (ESI, +ve ion) 534.2 $(M+H)^+$. GK-GKRP $EC_{50}$ (NADPH-coupled)=>50 μM.

An alternative synthesis is set forth below.

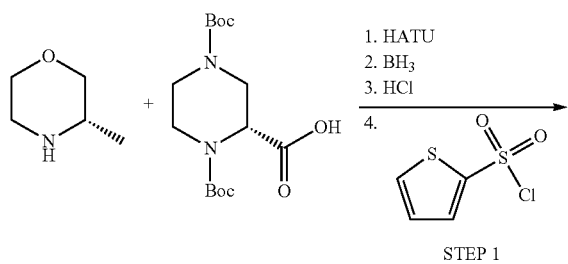

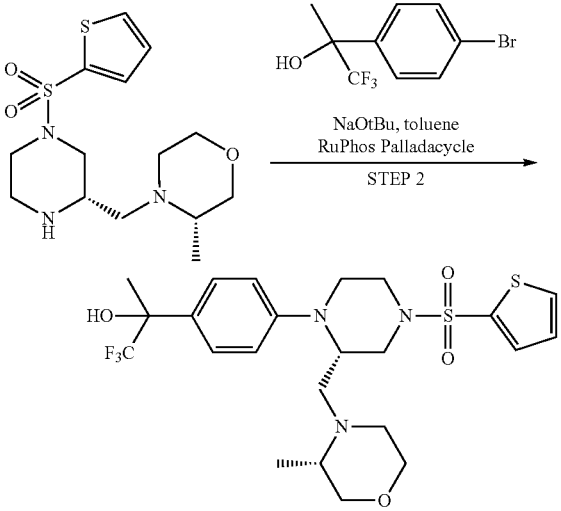

Step 1: (3S)-3-methyl-4-(((2S)-4-(2-thiophenylsulfonyl)-2-piperazinyl)methyl)morpholine A 1-L round-bottomed flask was charged with (R)-1,4-bis(tert-butoxycarbonyl)piperazine-2-carboxylic acid (50.00 g, 151 mmol, ASW MedChem, New Brunswick, N.J.), (S)-3-methylmorpholine (16.84 g, 166 mmol, Synthetech, Albany, Oreg.), 100 mL of DMF, HATU (66.2 g, 174 mmol, Oakwood, West Columbia, S.C.), and Hünig's base (33.0 mL, 189 mmol). After stirring at rt for 1.5 h, 500 mL of water was added and the resulting white precipitate was collected by filtration and dried under vacuum to give the intermediate amide. To this was added 100 mL of THF and $BH_3$.THF complex (1M in THF, 303 mL, 303 mmol, Sigma-Aldrich, St. Louis, Mo.). The mixture was heated at 60° C. for 1 h then cooled to 0° C. where 50 mL of MeOH was slowly added. Once bubbling has ceased, the solvent was removed in vacuo. 200 mL of EtOAc and 200 mL of 4M HCl in dioxane were added. The mixture was heated at 75° C. for 1.5 h then allowed to cool to rt. The solid that had formed was collected by filtration and dried under vacuum, to give the amine trishydrochloride. 500 mL of DCM and triethylamine (211 mL, 1513 mmol) were added. The mixture was cooled to 0° C. and 2-thiophenesulfonyl chloride (27.6 g, 151 mmol, Sigma-Aldrich) was added portion-wise. After 15 min, 250 mL of water was added and the layers were separated. The organics were dried ($MgSO_4$), filtered and concentrated. The resulting oil was purified by column chromatography on silica gel (0 to 10% MeOH/DCM) to give (3S)-3-methyl-4-(((2S)-4-(2-thiophenylsulfonyl)-2-piperazinyl)methyl)morpholine (10.50 g) as a white solid.

Step 2: 1,1,1-trifluoro-2-(4-((2S)-2-(((3S)-3-methyl-4-morpholinyl)methyl)-4-(2-thiophenylsulfonyl)-1-piperazinyl)phenyl)-2-propanol A 1-L pressure vessel was charged with (3S)-3-methyl-4-(((2S)-4-(2-thiophenylsulfonyl)-2-piperazinyl)methyl)morpholine (10.50 g, 30.4 mmol), 100 mL of toluene, (2R)-(4-bromophenyl)-1,1,1-trifluoropropan-2-ol (9.81 g, 36.5 mmol, Example 243, Step 1), and sodium tert-butoxide (7.30 g, 76 mmol). Nitrogen gas through the solution for 3 min then RuPhos Palladacycle (1.107 g, 1.520 mmol) and dicyclohexyl(2',6'-diisopropoxy-[1,1'-biphenyl]-2-yl)phosphine, RuPhos (0.709 g, 1.520 mmol) were added. The vessel was sealed and heated at 60° C. for 12 h. The mixture diluted with water and extracted with EtOAc. The combined organics were dried with MgSO₄, filtered, and concentrated. The residue was purified by column chromatography on silica gel (0-70% EA/Hex) to give a tan foam. To this foam was added 200 mL of IPA and stirred at rt for 1 h. The white solid that had formed was collected by filtration, dissolved in MeOH, then dried under high vac at 70° C. for 1 h to give pure 1,1,1-trifluoro-2-(4-((S)-2-(((S)-3-methylmorpholino)methyl)-4-(thiophen-2-ylsulfonyl)piperazin-1-yl)phenyl)propan-2-ol (8.15 g). This material was identical to peak 2 in example 45.

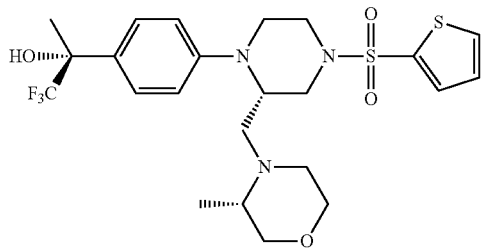 [SMILES: C[C@H]1COCCN1C[C@H]1CN(S(=O)(=O)c2cccs2)CCN1c1ccc([C@@](C)(O)C(F)(F)F)cc1]

Example 46

1,1,1-trifluoro-2-(4-(2-(8-oxa-3-azabicyclo[3.2.1]oct-3-ylmethyl)-4-(2-thiophenylsulfonyl)-1-piperazinyl)phenyl)-2-propanol

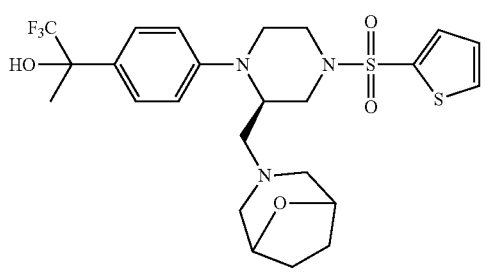 [SMILES: CC(O)(c1ccc(N2CCN(S(=O)(=O)c3cccs3)C[C@H]2CN2CC3CCC(C2)O3)cc1)C(F)(F)F]

Following the procedure reported for Example 45, using 8-oxa-3-azabicyclo[3.2.1]octane hydrochloride (AMRI Fine Chemicals, North Syracuse, N.Y.) and (4-(2-thiophenylsulfonyl)-1-(4-(2,2,2-trifluoro-1-hydroxy-1-methylethyl)phenyl)-2-piperazinyl)methyl methanesulfonate (Example 45, step 1) (using an extra equivalent of potassium carbonate) delivered 1,1,1-trifluoro-2-(4-(2-(8-oxa-3-azabicyclo[3.2.1]oct-3-ylmethyl)-4-(2-thiophenylsulfonyl)-1-piperazinyl)phenyl)-2-propanol as a mixture of four isomers.

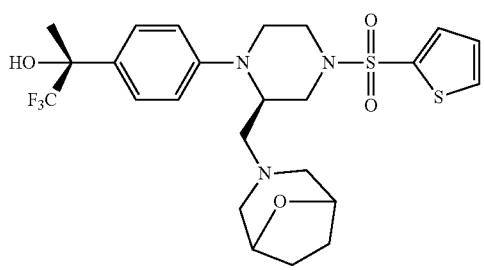

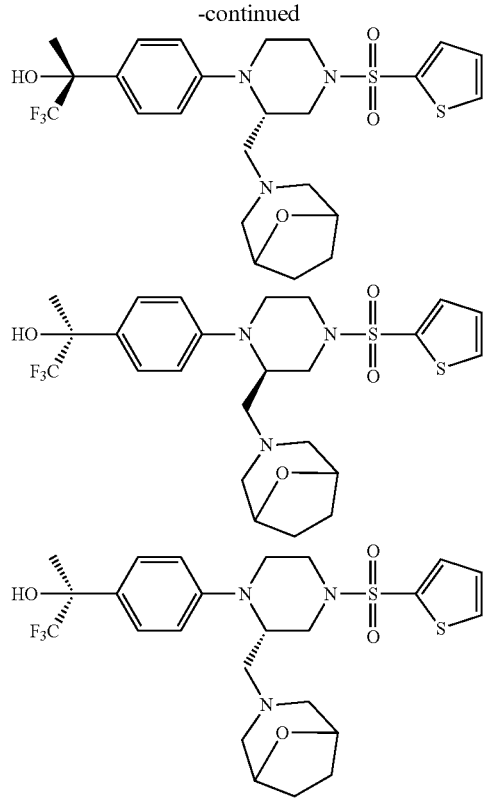

(2R)-1,1,1-trifluoro-2-(4-((2R)-2-(8-oxa-3-azabicyclo[3.2.1]oct-3-ylmethyl)-4-(2-thiophenylsulfonyl)-1-piperazinyl)phenyl)-2-propanol; (2R)-1,1,1-trifluoro-2-(4-((2S)-2-(8-oxa-3-azabicyclo[3.2.1]oct-3-ylmethyl)-4-(2-thiophenylsulfonyl)-1-piperazinyl)phenyl)-2-propanol; (2S)-1,1,1-trifluoro-2-(4-((2R)-2-(8-oxa-3-azabicyclo[3.2.1]oct-3-ylmethyl)-4-(2-thiophenylsulfonyl)-1-piperazinyl)phenyl)-2-propanol; (2S)-1,1,1-trifluoro-2-(4-((2S)-2-(8-oxa-3-azabicyclo[3.2.1]oct-3-ylmethyl)-4-(2-thiophenylsulfonyl)-1-piperazinyl)phenyl)-2-propanol. ¹H NMR (400 MHz, CD₃OD) δ 7.91-7.89 (m, 1H), 7.68-7.66 (m, 1H), 7.47-7.45 (d, J=8.8 Hz, 2H), 7.29-7.17 (m, 1H), 6.93-6.90 (d, J=8.8 Hz, 2H), 4.26-4.20 (m, 2H), 4.11-4.04 (m, 2H), 3.81-3.76 (m, 1H), 3.50-3.45 (m, 1H), 3.26-3.20 (m, 1H), 2.75-2.55 (m, 5H), 2.42-2.39 (m, 1H), 2.28-2.19 (m, 2H), 1.93-1.74 (m, 4H), 1.70 (s, 3H). m/z (ESI, +ve ion) 546.6 (M+H)⁺. GK-GKRP EC₅₀ (NADPH-coupled)=0.154 μM; GK-GKRP EC₅₀ (LC MS/MS)=0.178 μM.

Example 47

2-(4-(2-((2,2-dimethyl-4-morpholinyl)methyl)-4-(2-thiophenylsulfonyl)-1-piperazinyl)phenyl)-1,1,1-trifluoro-2-propanol

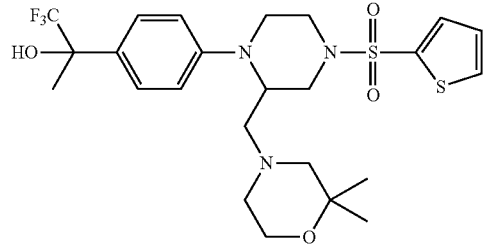 [SMILES: CC1(C)CN(CC2CN(S(=O)(=O)c3cccs3)CCN2c2ccc(C(C)(O)C(F)(F)F)cc2)CCO1]

Following the procedure reported for Example 45, using 2,2-dimethylmorpholine (Chembridge, San Diego, Calif.) produced 2-(4-(2-((2,2-dimethyl-4-morpholinyl)methyl)-4-(2-thiophenylsulfonyl)-1-piperazinyl)phenyl)-1,1,1-trifluoro-2-propanol as a mixture of four isomers.

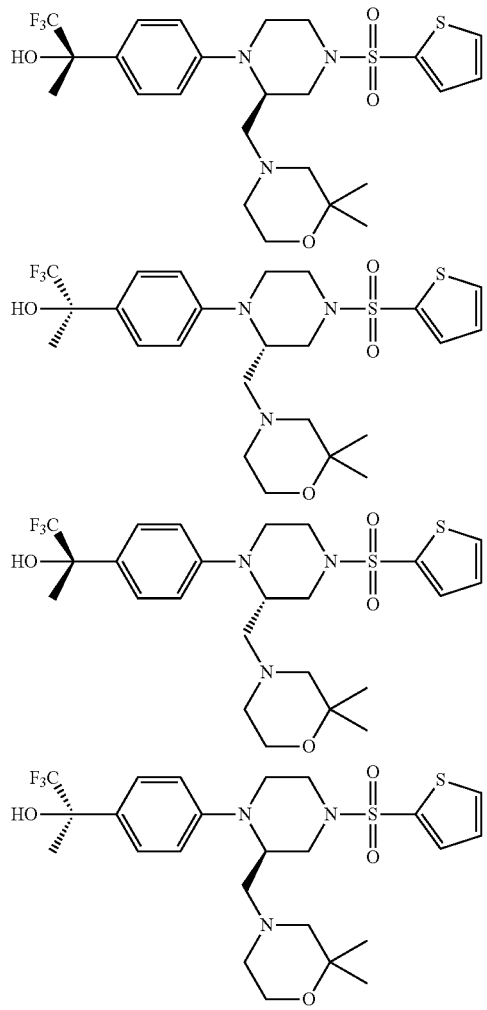

(2R)-2-(4-((2R)-2-((2,2-dimethyl-4-morpholinyl)methyl)-4-(2-thiophenylsulfonyl)-1-piperazinyl)phenyl)-1,1,1-trifluoro-2-propanol; (2R)-2-(4-((2S)-2-((2,2-dimethyl-4-morpholinyl)methyl)-4-(2-thiophenylsulfonyl)-1-piperazinyl)phenyl)-1,1,1-trifluoro-2-propanol; (2S)-2-(4-((2R)-2-((2,2-dimethyl-4-morpholinyl)methyl)-4-(2-thiophenylsulfonyl)-1-piperazinyl)phenyl)-1,1,1-trifluoro-2-propanol; (2S)-2-(4-((2S)-2-((2,2-dimethyl-4-morpholinyl)methyl)-4-(2-thiophenylsulfonyl)-1-piperazinyl)phenyl)-1,1,1-trifluoro-2-propanol. $^1$H NMR (400 MHz, DMSO-d$_6$) δ 8.07-8.05 (m, 1H), 7.68-7.66 (m, 1H), 7.37-7.35 (m, 2H), 7.32-7.29 (m, 1H), 6.88-6.86 (m, 2H), 4.15-4.12 (m, 1H), 3.91-3.88 (m, 1H), 3.46-3.42 (m, 4H), 3.13-3.07 (m, 1H), 2.60-2.55 (m, 1H), 2.49-2.38 (m, 3H), 2.27-2.22 (m, 1H), 2.16-2.05 (m, 3H), 1.61 (s, 3H), 1.11 (s, 3H), 1.07 (s, 3H). m/z (ESI, +ve ion) 548.2 (M+H)$^+$. GK-GKRP EC$_{50}$ (NADPH-coupled)=0.182 μM; GK-GKRP EC$_{50}$ (LC MS/MS)=0.295 μM.

Example 48

1,1,1-trifluoro-2-(4-(2-((3-(hydroxymethyl)-4-morpholinyl)methyl)-4-(2-thiophenylsulfonyl)-1-piperazinyl)phenyl)-2-propanol

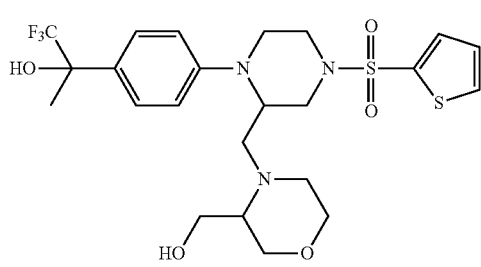 [SMILES: CC(O)(c1ccc(N2CCN(S(=O)(=O)c3cccs3)CC2CN2CCOCC2CO)cc1)C(F)(F)F]

Following the procedure reported for Example 45, using 3-morpholinylmethanol (Tyger Scientific, Ewing, N.J.) produced 1,1,1-trifluoro-2-(4-(2-((3-(hydroxymethyl)-4-morpholinyl)methyl)-4-(2-thiophenylsulfonyl)-1-piperazinyl)phenyl)-2-propanol as a mixture of eight isomers.

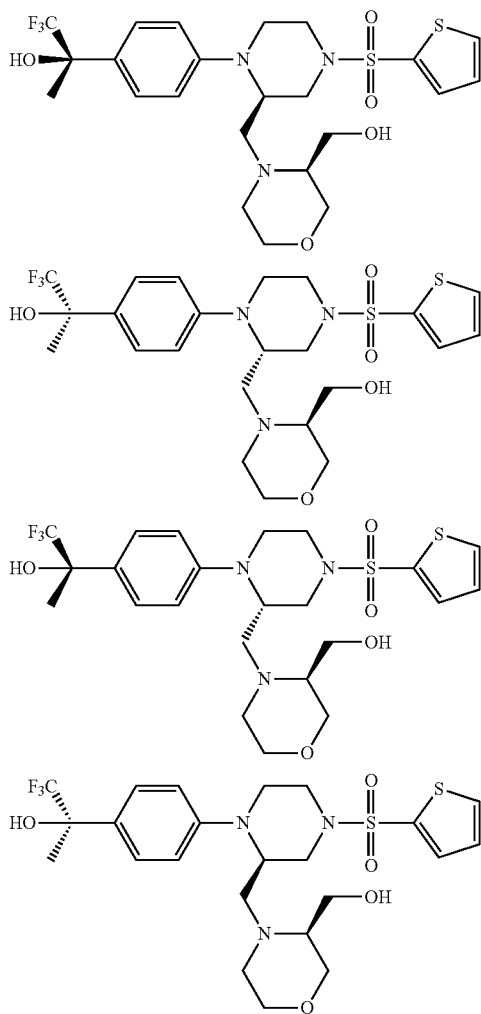

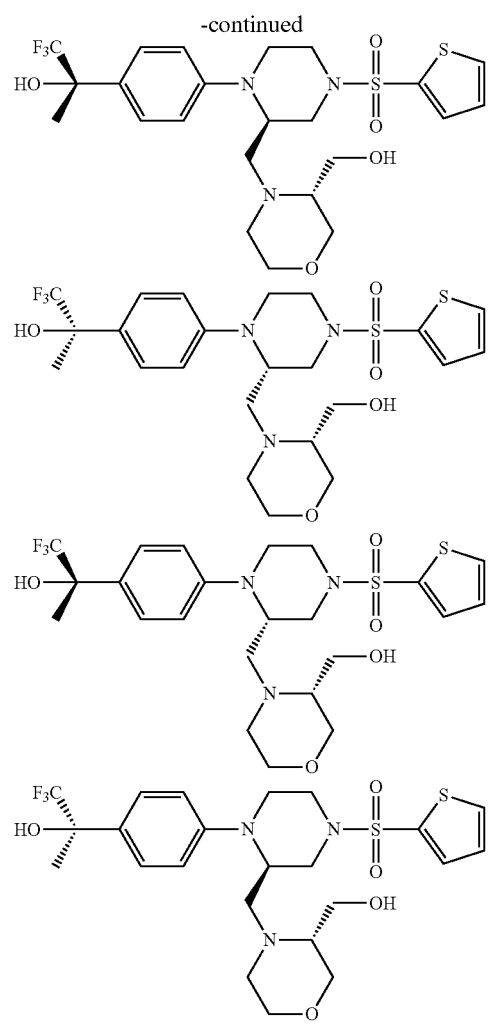

(2R)-1,1,1-trifluoro-2-(4-((2R)-2-(((3R)-3-(hydroxymethyl)-4-morpholinyl)methyl)-4-(2-thiophenylsulfonyl)-1-piperazinyl)phenyl)-2-propanol;
(2R)-1,1,1-trifluoro-2-(4-((2R)-2-(((3S)-3-(hydroxymethyl)-4-morpholinyl)methyl)-4-(2-thiophenylsulfonyl)-1-piperazinyl)phenyl)-2-propanol;
(2R)-1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol;
(2R)-1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol;
(2S)-1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol;
(2S)-1,1,1-trifluoro-2-(4-((2R)-2-(((3S)-3-(hydroxymethyl)-4-morpholinyl)methyl)-4-(2-thiophenylsulfonyl)-1-piperazinyl)phenyl)-2-propanol;
(2S)-1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol;
(2S)-1,1,1-trifluoro-2-(4-((2R)-2-(((3R)-3-(hydroxymethyl)-4-morpholinyl)methyl)-4-(2-thiophenylsulfonyl)-1-piperazinyl)phenyl)-2-propanol.

$^1$H NMR (400 MHz, DMSO-$d_6$) δ 8.06 (m, 1H), 7.69 (m, 1H), 7.38-7.31 (m, 3H), 6.88-6.87 (m, 2H), 4.54-4.52 (m, 1H), 4.13-3.95 (m, 2H), 3.50-3.46 (m, 3H), 3.18-3.15 (m, 2H), 2.88-2.60 (m, 3H), 2.59-2.37 (m, 4H), 2.01-1.95 (m, 1H), 1.63-1.61 (m, 2H), 1.61 (s, 3H). m/z (ESI, +ve ion) 550.2 (M+H)$^+$. GK-GKRP EC$_{50}$ (NADPH-coupled)=0.389 μM; GK-GKRP EC$_{50}$ (LC MS/MS)=0.606 μM.

Example 49

1,1,1-trifluoro-2-(4-(2-((2-methyl-4-morpholinyl)methyl)-4-(2-thiophenylsulfonyl)-1-piperazinyl)phenyl)-2-propanol

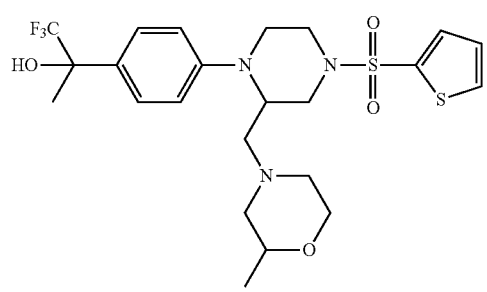 [SMILES: CC1CN(CC2CN(S(=O)(=O)c3cccs3)CCN2c2ccc(C(C)(O)C(F)(F)F)cc2)CCO1]

Following the procedure reported for Example 45, using 2-methylmorpholine (Tyger Scientific, Ewing, N.J.) produced 1,1,1-trifluoro-2-(4-(2-((2-methyl-4-morpholinyl)methyl)-4-(2-thiophenylsulfonyl)-1-piperazinyl)phenyl)-2-propanol as a mixture of eight isomers.

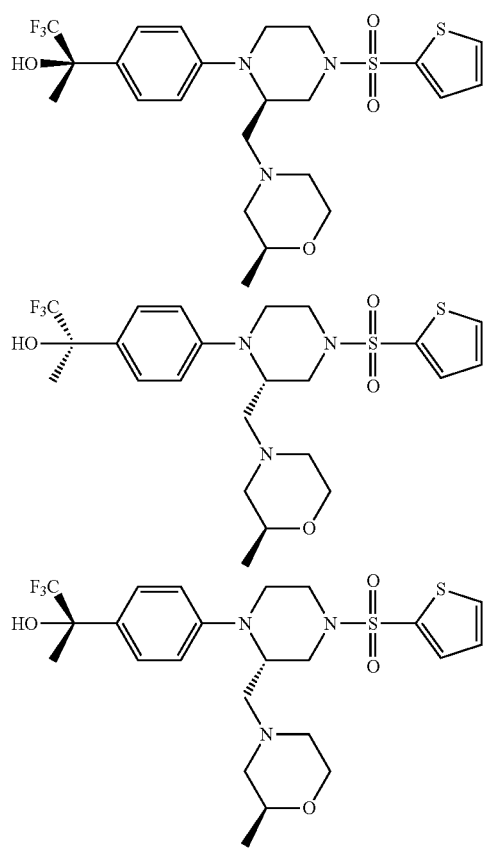

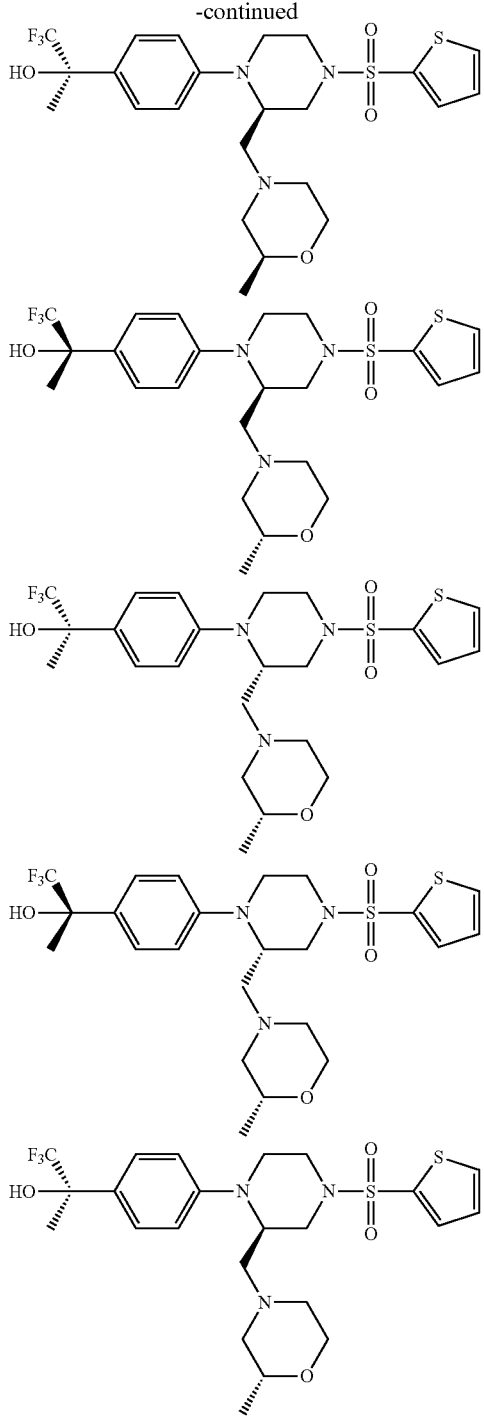

(2R)-1,1,1-trifluoro-2-(4-((2R)-2-(((2R)-2-methyl-4-morpholinyl)methyl)-4-(2-thiophenylsulfonyl)-1-piperazinyl)phenyl)-2-propanol; (2R)-1,1,1-trifluoro-2-(4-((2R)-2-(((2S)-2-methyl-4-morpholinyl)methyl)-4-(2-thiophenylsulfonyl)-1-piperazinyl)phenyl)-2-propanol; (2R)-1,1,1-trifluoro-2-(4-((2S)-2-(((2R)-2-methyl-4-morpholinyl)methyl)-4-(2-thiophenylsulfonyl)-1-piperazinyl)phenyl)-2-propanol; (2R)-1,1,1-trifluoro-2-(4-((2S)-2-(((2S)-2-methyl-4-morpholinyl)methyl)-4-(2-thiophenylsulfonyl)-1-piperazinyl)phenyl)-2-propanol; (2S)-1,1,1-trifluoro-2-(4-((2S)-2-(((2S)-2-methyl-4-morpholinyl)methyl)-4-(2-thiophenylsulfonyl)-1-piperazinyl)phenyl)-2-propanol; (2S)-1,1,1-trifluoro-2-(4-((2R)-2-(((2S)-2-methyl-4-morpholinyl)methyl)-4-(2-thiophenylsulfonyl)-1-piperazinyl)phenyl)-2-propanol; (2S)-1,1,1-trifluoro-2-(4-((2S)-2-(((2R)-2-methyl-4-morpholinyl)methyl)-4-(2-thiophenylsulfonyl)-1-piperazinyl)phenyl)-2-propanol; (2S)-1,1,1-trifluoro-2-(4-((2R)-2-(((2R)-2-methyl-4-morpholinyl)methyl)-4-(2-thiophenylsulfonyl)-1-piperazinyl)phenyl)-2-propanol.

$^1$H NMR (400 MHz, DMSO-d$_6$) δ 8.08-8.06 (m, 1H), 7.71-7.69 (m, 1H), 7.38-7.35 (d, J=9.2 Hz, 2H), 7.31-7.29 (m, 1H), 6.89-6.86 (d, J=9.2 Hz, 2H), 4.13-4.09 (m, 2H), 3.43-3.38 (m, 1H), 3.12-3.06 (m, 1H), 2.85-3.74 (m, 2H), 2.69-2.59 (m, 2H), 2.49-2.40 (m, 3H), 2.13-2.05 (m, 2H), 1.91-1.83 (m, 1H), 1.80-1.71 (m, 1H), 1.61 (s, 3H), 1.60-1.56 (m, 1H), 1.02-0.95 (m, 3H). m/z (ESI, +ve ion) 534.2 (M+H)$^+$. GK-GKRP EC$_{50}$ (NADPH-coupled)=0.647 μM; GK-GKRP EC$_{50}$ (LC MS/MS)=0.707 μM.

Example 50

1,1,1-trifluoro-2-(4-((1R,4R)-2-oxa-5-azabicyclo[2.2.1]hept-5-ylmethyl)-4-(2-thiophenylsulfonyl)-1-piperazinyl)phenyl)-2-propanol

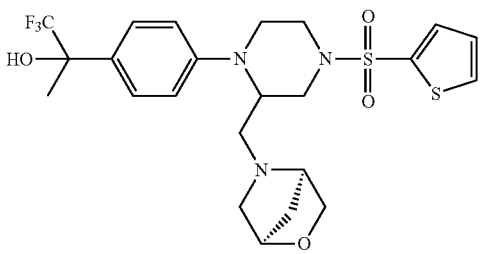 [SMILES: CC(O)(c1ccc(N2CCN(S(=O)(=O)c3cccs3)CC2CN2C[C@H]3C[C@@H]2CO3)cc1)C(F)(F)F]

Following the procedure reported for Example 45, using (R,R)-2-oxa-5-azabicyclo[2.2.1]heptane hydrochloride (Activate Scientific, Ware, UK) produced 1,1,1-trifluoro-2-(4-(2-((1R,4R)-2-oxa-5-azabicyclo[2.2.1]hept-5-ylmethyl)-4-(2-thiophenylsulfonyl)-1-piperazinyl)phenyl)-2-propanol as a mixture of four isomers.

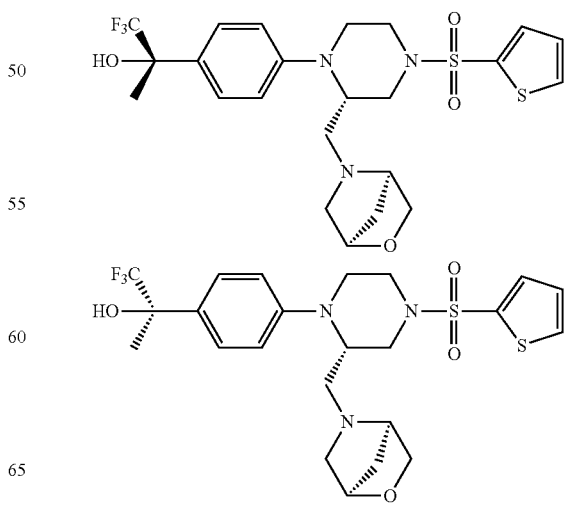

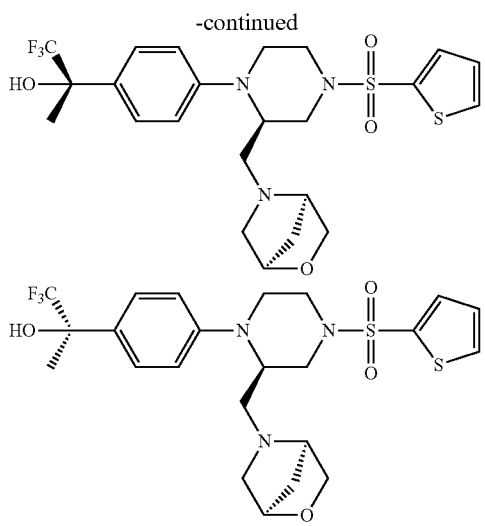

(2R)-1,1,1-trifluoro-2-(4-((2R)-2-((1R,4R)-2-oxa-5-azabicyclo[2.2.1]hept-5-ylmethyl)-4-(2-thiophenylsulfonyl)-1-piperazinyl)phenyl)-2-propanol; (2R)-1,1,1-trifluoro-2-(4-((2S)-2-((1R,4R)-2-oxa-5-azabicyclo[2.2.1]hept-5-ylmethyl)-4-(2-thiophenylsulfonyl)-1-piperazinyl)phenyl)-2-propanol; (2S)-1,1,1-trifluoro-2-(4-((2R)-2-((1R,4R)-2-oxa-5-azabicyclo[2.2.1]hept-5-ylmethyl)-4-(2-thiophenylsulfonyl)-1-piperazinyl)phenyl)-2-propanol; (2S)-1,1,1-trifluoro-2-(4-((2S)-2-((1R,4R)-2-oxa-5-azabicyclo[2.2.1]hept-5-ylmethyl)-4-(2-thiophenylsulfonyl)-1-piperazinyl)phenyl)-2-propanol. $^1$H NMR (400 MHz, CD$_3$OD) δ 7.90 (dd, J=1.0, 5.1 Hz, 1H), 7.67 (d, J=3.5 Hz, 1H), 7.47 (t, J=8.1 Hz, 2H), 7.28 (dd, J=3.8, 5.0 Hz, 1H), 6.99-6.87 (m, 2H), 4.38-4.36 (m, 1H), 4.05-3.90 (m, 2H), 3.80-3.71 (m, 2H), 3.60-3.44 (m, 3H), 3.27-3.20 (m, 1H), 3.06-3.02 (m, 2H), 2.76-2.51 (m, 3H), 2.40-2.38 (m, 1H), 1.84-1.64 (s, 5H). m/z (ESI, +ve ion) 532.2 (M+H)$^+$. GK-GKRP EC$_{50}$ (NADPH-coupled)=0.670 μM; GK-GKRP EC$_{50}$ (LC MS/MS)=0.880 μM.

Example 51

2-(4-(2-((4,4-difluoro-1-piperidinyl)methyl)-4-(2-thiophenylsulfonyl)-1-piperazinyl)phenyl)-1,1,1-trifluoro-2-propanol

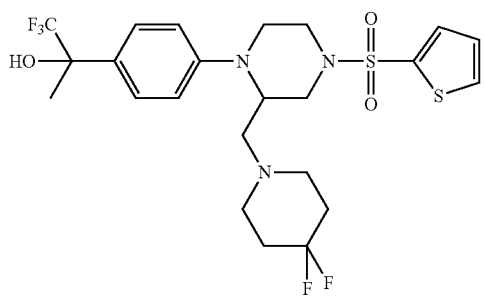 [SMILES: CC(O)(c1ccc(N2CCN(S(=O)(=O)c3cccs3)CC2CN2CCC(F)(F)CC2)cc1)C(F)(F)F]

Following the procedure reported for Example 61, Step 2, 4,4-difluoropiperidine hydrochloride (Sigma-Aldrich, St. Louis, Mo.) was coupled with 4-(2-thiophenylsulfonyl)-1-(4-(2,2,2-trifluoro-1-hydroxy-1-methylethyl)phenyl)-2-piperazinecarbaldehyde to produce 2-(4-(2-((4,4-difluoro-1-piperidinyl)methyl)-4-(2-thiophenylsulfonyl)-1-piperazinyl)phenyl)-1,1,1-trifluoro-2-propanol (mixture of four isomers) following purification by prep HPLC (separation method was as follows: Solvents; A=Water w/0.1% NH$_4$OH B=MeCN w/0.1% NH$_4$OH; 10-90% over 20 min; Column: Phenomenex Gemini-NX C$_{18}$ 110 A 5 μm, 21×100 mm).

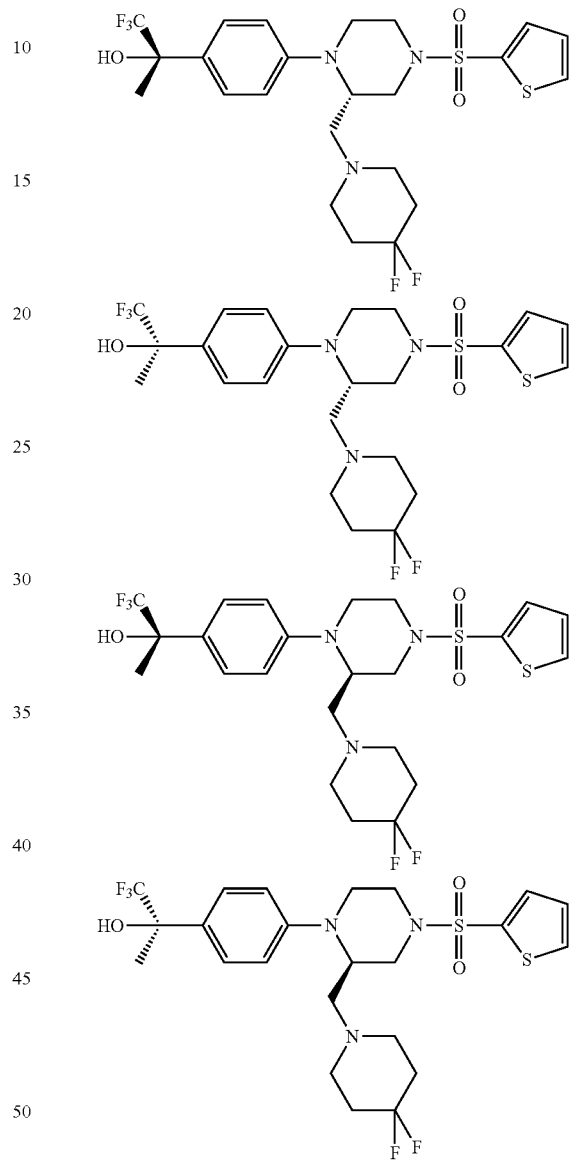

(2R)-2-(4-((2R)-2-((4,4-difluoro-1-piperidinyl)methyl)-4-(2-thiophenylsulfonyl)-1-piperazinyl)phenyl)-1,1,1-trifluoro-2-propanol; (2R)-2-(4-((2S)-2-((4,4-difluoro-1-piperidinyl)methyl)-4-(2-thiophenylsulfonyl)-1-piperazinyl)phenyl)-1,1,1-trifluoro-2-propanol; (2S)-2-(4-((2R)-2-((4,4-difluoro-1-piperidinyl)methyl)-4-(2-thiophenylsulfonyl)-1-piperazinyl)phenyl)-1,1,1-trifluoro-2-propanol; (2S)-2-(4-((2S)-2-((4,4-difluoro-1-piperidinyl)methyl)-4-(2-thiophenylsulfonyl)-1-piperazinyl)phenyl)-1,1,1-trifluoro-2-propanol. $^1$H NMR (400 MHz, DMSO-d$_6$) δ 8.08-8.06 (dd, J=5.1, 1.1 Hz, 1H), 7.70-7.68 (dd, J=3.7, 1.1 Hz, 1H), 7.38-7.34 (d, J=9.2 Hz, 2H), 7.32-7.30 (m, 1H), 6.89-6.87 (d, J=9.2 Hz, 2H), 4.15-4.11 (m, 1H), 3.46-3.38 (m, 3H), 3.15-3.08 (m, 1H), 2.69-2.63 (m, 1H), 2.59-2.52 (m, 2H), 2.46-2.38 (m, 4H), 2.30-2.25 (m, 1H), 1.79-1.73 (m, 4H), 1.61 (s, 3H). m/z (ESI, +ve ion) 554.2 (M+H)⁺. GK-GKRP EC$_{50}$ (NADPH-coupled)=1.05 μM; GK-GKRP EC$_{50}$ (LC MS/MS)=1.53 μM.

Example 52

1,1,1-trifluoro-2-(4-(2-((2-(hydroxymethyl)-4-morpholinyl)methyl)-4-(2-thiophenylsulfonyl)-1-piperazinyl)phenyl)-2-propanol

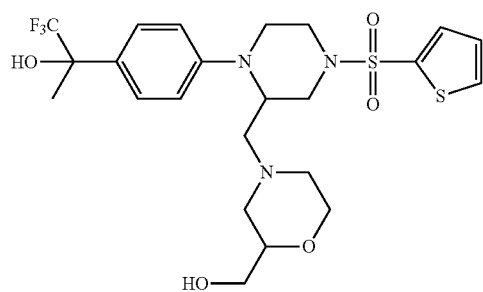 [SMILES: CC(O)(c1ccc(N2CCN(S(=O)(=O)c3cccs3)CC2CN2CCOC(CO)C2)cc1)C(F)(F)F]

Following the procedure reported for Example 45, using 2-morpholinylmethanol (Tyger Scientific, Ewing, N.J.) produced 1,1,1-trifluoro-2-(4-(2-((2-(hydroxymethyl)-4-morpholinyl)methyl)-4-(2-thiophenylsulfonyl)-1-piperazinyl)phenyl)-2-propanol as a mixture of eight isomers.

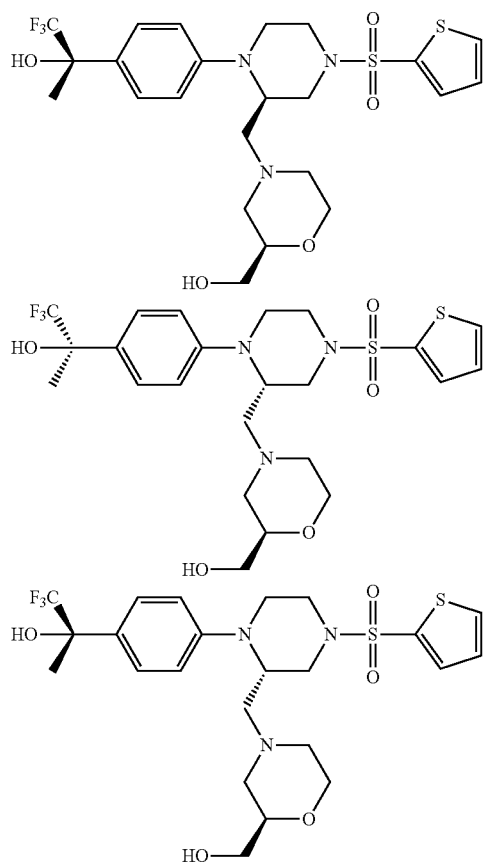

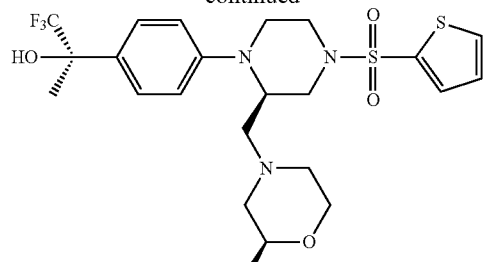

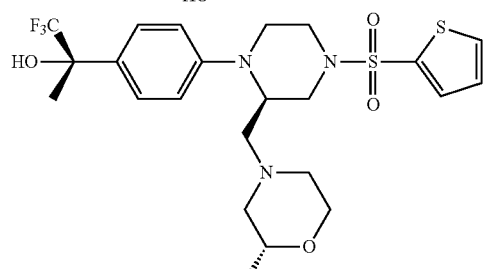

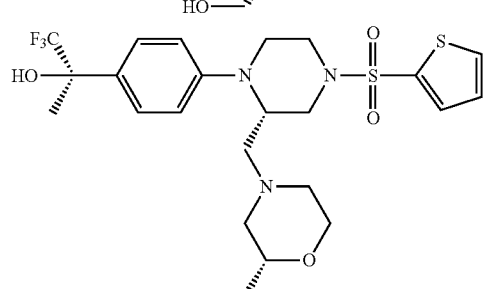

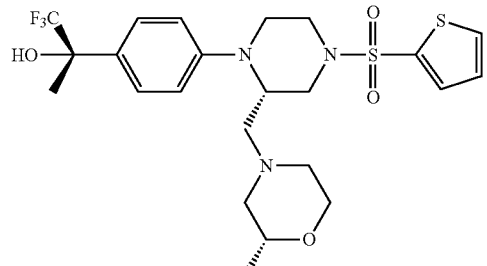

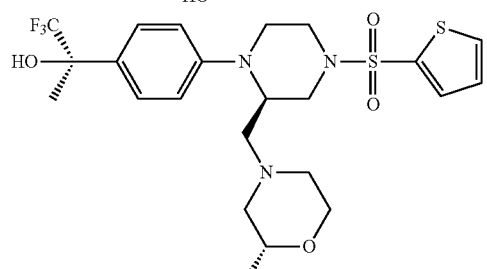

(2R)-1,1,1-trifluoro-2-(4-((2R)-2-(((2R)-2-(hydroxymethyl)-4-morpholinyl)methyl)-4-(2-thiophenylsulfonyl)-1-piperazinyl)phenyl)-2-propanol;

(2R)-1,1,1-trifluoro-2-(4-((2R)-2-(((2S)-2-(hydroxymethyl)-4-morpholinyl)methyl)-4-(2-thiophenylsulfonyl)-1-piperazinyl)phenyl)-2-propanol;

(2R)-1,1,1-trifluoro-2-(4-((2S)-2-(((2R)-2-(hydroxymethyl)-4-morpholinyl)methyl)-4-(2-thiophenylsulfonyl)-1-piperazinyl)phenyl)-2-propanol;

(2R)-1,1,1-trifluoro-2-(4-((2S)-2-(((2S)-2-(hydroxymethyl)-4-morpholinyl)methyl)-4-(2-thiophenylsulfonyl)-1-piperazinyl)phenyl)-2-propanol;

(2S)-1,1,1-trifluoro-2-(4-((2S)-2-(((2S)-2-(hydroxymethyl)-4-morpholinyl)methyl)-4-(2-thiophenylsulfonyl)-1-piperazinyl)phenyl)-2-propanol;

(2S)-1,1,1-trifluoro-2-(4-((2R)-2-(((2S)-2-(hydroxymethyl)-4-morpholinyl)methyl)-4-(2-thiophenylsulfonyl)-1-piperazinyl)phenyl)-2-propanol;

(2S)-1,1,1-trifluoro-2-(4-((2S)-2-(((2R)-2-(hydroxymethyl)-4-morpholinyl)methyl)-4-(2-thiophenylsulfonyl)-1-piperazinyl)phenyl)-2-propanol;

(2S)-1,1,1-trifluoro-2-(4-((2R)-2-(((2R)-2-(hydroxymethyl)-4-morpholinyl)methyl)-4-(2-thiophenylsulfonyl)-1-piperazinyl)phenyl)-2-propanol.

$^1$H NMR (400 MHz, CDCl$_3$) δ 7.65-7.64 (m, 1H), 7.60-7.58 (m, 1H), 7.44-7.42 (d, J=8.6 Hz, 2H), 7.18-7.16 (m, 1H), 6.83-6.78 (m, 2H), 4.05-3.90 (m, 2H), 3.83-3.78 (m, 2H), 3.65-3.46 (m, 4H), 3.43-3.37 (m, 1H), 3.28-3.20 (m, 1H), 2.82-2.56 (m, 5H), 2.47-2.26 (m, 2H), 2.09-1.97 (m, 1H), 1.74 (m, 3H). m/z (ESI, +ve ion) 549.2 (M+H)$^+$. GK-GKRP EC$_{50}$ (NADPH-coupled)=1.62 μM; GK-GKRP EC$_{50}$ (LC MS/MS)=1.17 μM.

Example 53

1-((4-(2-thiophenylsulfonyl)-1-(4-(2,2,2-trifluoro-1-hydroxy-1-methylethyl)phenyl)-2-piperazinyl)methyl)-3-azetidinol

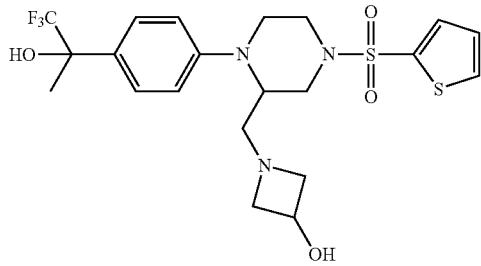 [SMILES: CC(O)(c1ccc(N2CCN(S(=O)(=O)c3cccs3)CC2CN2CC(O)C2)cc1)C(F)(F)F]

Following the procedure reported for Example 61, Step 2, 3-azetidinol hydrochloride (Tyger Scientific, Ewing, N.J.) was coupled with 4-(2-thiophenylsulfonyl)-1-(4-(2,2,2-trifluoro-1-hydroxy-1-methylethyl)phenyl)-2-piperazinecarbaldehyde to produce 1-((4-(2-thiophenylsulfonyl)-1-(4-(2,2,2-trifluoro-1-hydroxy-1-methylethyl)phenyl)-2-piperazinyl)methyl)-3-azetidinol (mixture of four isomers) following purification by prep HPLC (separation method was as follows: Solvents; A=Water w/0.1% NH$_4$OH B=MeCN w/0.1% NH$_4$OH; 10-90% over 20 min; Column: Phenomenex Gemini-NX C18 110 A 5 μm, 21×100 mm).

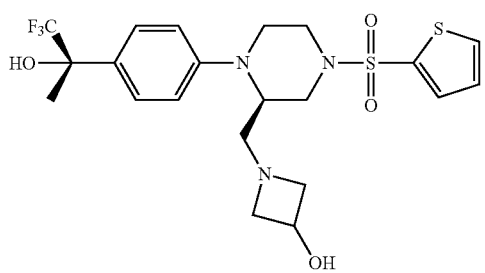

-continued

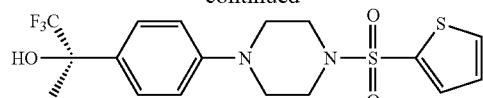

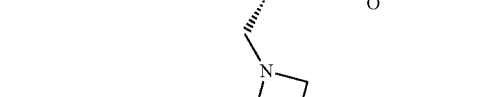

1-(((2R)-4-(2-thiophenylsulfonyl)-1-(4-((1R)-2,2,2-trifluoro-1-hydroxy-1-methylethyl)phenyl)-2-piperazinyl)methyl)-3-azetidinol; 1-(((2R)-4-(2-thiophenylsulfonyl)-1-(4-((1S)-2,2,2-trifluoro-1-hydroxy-1-methylethyl)phenyl)-2-piperazinyl)methyl)-3-azetidinol; 1-(((2S)-4-(2-thiophenylsulfonyl)-1-(4-((1R)-2,2,2-trifluoro-1-hydroxy-1-methylethyl)phenyl)-2-piperazinyl)methyl)-3-azetidinol; 1-(((2S)-4-(2-thiophenylsulfonyl)-1-(4-((1S)-2,2,2-trifluoro-1-hydroxy-1-methylethyl)phenyl)-2-piperazinyl)methyl)-3-azetidinol. $^1$H NMR (400 MHz, DMSO-d$_6$) δ 8.08-8.06 (m, 1H), 7.68-7.66 (m, 1H), 7.40-7.38 (d, J=9.2 Hz, 2H), 7.31-7.29 (m, 1H), 6.86-6.84 (d, J=9.2 Hz, 2H), 4.14-4.10 (m, 1H), 3.44-3.38 (m, 4H), 3.06-2.99 (m, 1H), 2.88-2.82 (m, 1H), 2.73-2.70 (m, 1H), 2.57-2.53 (m, 2H), 2.48-2.38 (m, 3H), 2.07-2.04 (m, 1H), 1.62 (s, 3H). m/z (ESI, +ve ion) 506.2 (M+H)$^+$. GK-GKRP EC$_{50}$ (NADPH-coupled)=2.26 μM; GK-GKRP EC$_{50}$ (LC MS/MS)=1.79 μM.

Example 54

2-methyl-2-(((4-(2-thiophenylsulfonyl)-1-(4-(2,2,2-trifluoro-1-hydroxy-1-methylethyl)phenyl)-2-piperazinyl)methyl)amino)-1-propanol

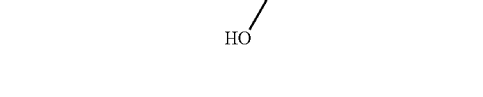

Following the procedure reported for Example 45, 2-amino-2-methyl-1-propanol (Sigma-Aldrich, St. Louis, Mo.) delivered 2-methyl-2-(((4-(2-thiophenylsulfonyl)-1-(4-(2,2,2-trifluoro-1-hydroxy-1-methylethyl)phenyl)-2-piperazinyl)methyl)amino)-1-propanol (mixture of four isomers) after purification by column chromatography (24 g silica gel, 0.5-8% MeOH—CH$_2$Cl$_2$).

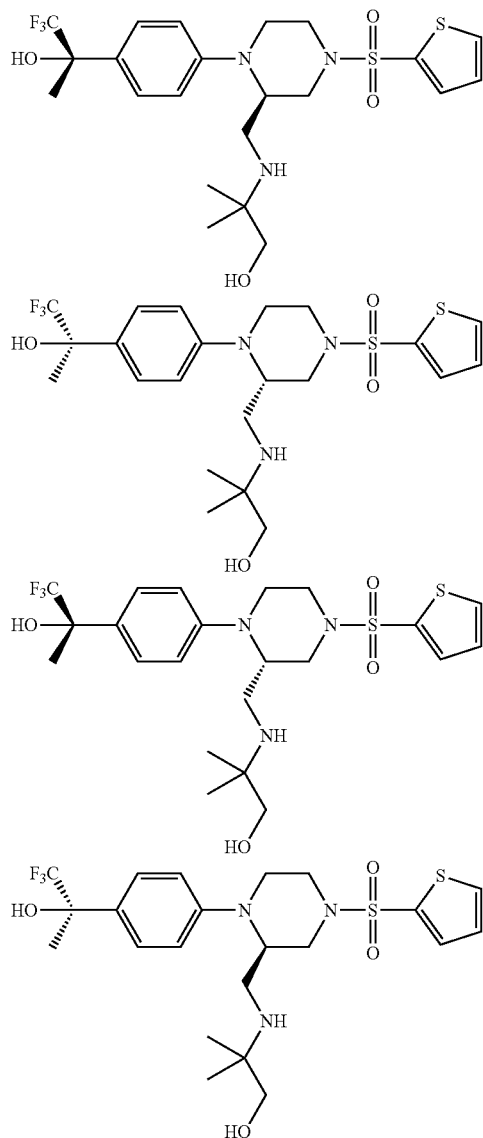

2-methyl-2-((((2R)-4-(2-thiophenylsulfonyl)-1-(4-((1R)-2,2,2-trifluoro-1-hydroxy-1-methylethyl)phenyl)-2-piperazinyl)methyl)amino)-1-propanol; 2-methyl-2-((((2R)-4-(2-thiophenylsulfonyl)-1-(4-((1S)-2,2,2-trifluoro-1-hydroxy-1-methylethyl)phenyl)-2-piperazinyl)methyl)amino)-1-propanol; 2-methyl-2-((((2S)-4-(2-thiophenylsulfonyl)-1-(4-((1R)-2,2,2-trifluoro-1-hydroxy-1-methylethyl)phenyl)-2-piperazinyl)methyl)amino)-1-propanol; 2-methyl-2-((((2S)-4-(2-thiophenylsulfonyl)-1-(4-((1S)-2,2,2-trifluoro-1-hydroxy-1-methylethyl)phenyl)-2-piperazinyl)methyl)amino)-1-propanol. $^1$H NMR (400 MHz, CDCl$_3$) δ 7.65-7.64 (m, 1H), 7.58-7.56 (m, 1H), 7.44-7.42 (d, J=8.6 Hz, 2H), 7.18-7.15 (m, 1H), 6.86-6.83 (d, J=8.6 Hz, 2H), 3.93-3.86 (m, 2H), 3.78-3.73 (m, 1H), 3.51-3.46 (m, 1H), 3.34-3.21 (m, 3H), 2.92-2.87 (m, 1H), 2.72-2.59 (m, 3H), 1.74 (s, 3H), 1.03 (s, 3H), 1.02 (s, 3H). m/z (ESI, +ve ion) 522.2 (M+H)$^+$. GK-GKRP EC$_{50}$ (NADPH-coupled)=2.97 μM; GK-GKRP EC$_{50}$ (LC MS/MS)=2.78 μM Example 55

(4-(2-thiophenylsulfonyl)-1-(4-(2,2,2-trifluoro-1-hydroxy-1-methylethyl)phenyl)-2-piperazinyl)acetonitrile

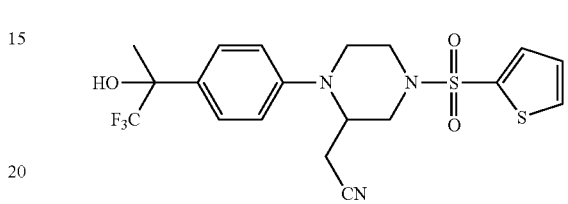

Following the procedure reported for Example 45, using potassium cyanide (Sigma-Aldrich, St. Louis, Mo.) and an extra equivalent of potassium carbonate produced (4-(2-thiophenylsulfonyl)-1-(4-(2,2,2-trifluoro-1-hydroxy-1-methylethyl)phenyl)-2-piperazinyl)acetonitrile as a mixture of four isomers.

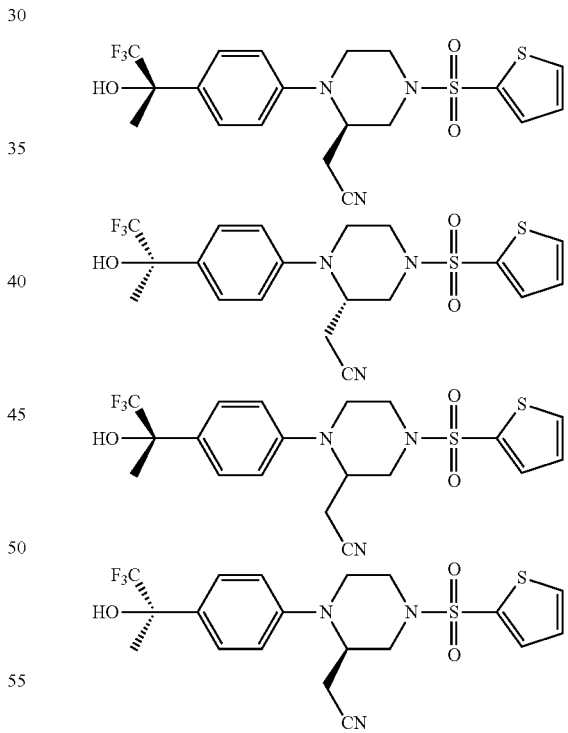

((2R)-4-(2-thiophenylsulfonyl)-1-(4-((1R)-2,2,2-trifluoro-1-hydroxy-1-methylethyl)phenyl)-2-piperazinyl)acetonitrile; ((2R)-4-(2-thiophenylsulfonyl)-1-(4-((1S)-2,2,2-trifluoro-1-hydroxy-1-methylethyl)phenyl)-2-piperazinyl)acetonitrile; ((2S)-4-(2-thiophenylsulfonyl)-1-(4-((1R)-2,2,2-trifluoro-1-hydroxy-1-methylethyl)phenyl)-2-piperazinyl)acetonitrile; ((2S)-4-(2-thiophenylsulfonyl)-1-(4-((1S)-2,2,2-trifluoro-1-hydroxy-1-methylethyl)phenyl)-2-piperazinyl)acetonitrile. $^1$H NMR (400 MHz, CDCl$_3$) δ 7.68-7.66 (m, 1H), 7.62-7.60 (m, 1H), 7.48-7.46 (d, J=8.8 Hz, 2H), 7.19-7.17 (m, 1H), 6.87-6.85 (d, J=8.8 Hz, 2H), 4.11-4.04 (m, 2H), 3.89-3.78 (m, 2H), 3.48-3.41 (m, 2H), 3.27-3.20 (m, 1H), 2.77-2.72 (m, 1H), 2.69-2.61 (m, 1H), 1.74 (s, 3H). m/z (ESI, +ve ion) 460.1 (M+H)+. GK-GKRP $EC_{50}$ (NADPH-coupled)=3.03 μM; GK-GKRP $EC_{50}$ (LC MS/MS)=3.94 μM.

Example 56

(3R)-1-((4-(2-thiophenylsulfonyl)-1-((4-(2,2,2-trifluoro-1-hydroxy-1-methylethyl)phenyl)-2-piperazinyl)methyl)-3-pyrrolidinol

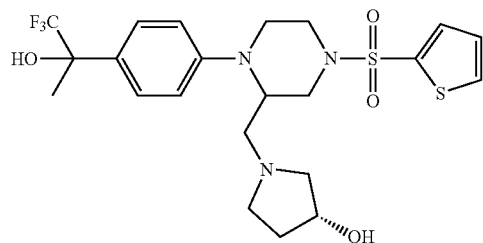 [SMILES: CC(O)(c1ccc(N2CCN(S(=O)(=O)c3cccs3)CC2CN2CC[C@@H](O)C2)cc1)C(F)(F)F]

Following the procedure reported for Example 45, using (3R)-3-pyrrolidinol hydrochloride (Sigma-Aldrich, St. Louis, Mo.) and an extra equivalent of potassium carbonate, produced (3R)-1-((4-(2-thiophenylsulfonyl)-1-(4-(2,2,2-trifluoro-1-hydroxy-1-methylethyl)phenyl)-2-piperazinyl)methyl)-3-pyrrolidinol (mixture of four isomers) after purification by column chromatography (80 g silica gel, 20 to 100% EtOAc in hexanes).

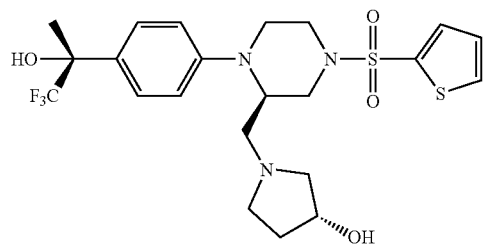

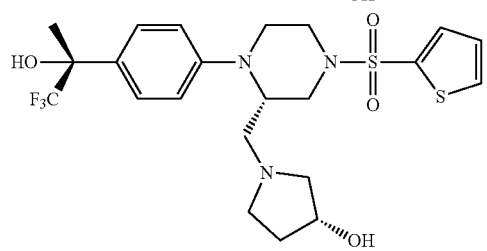

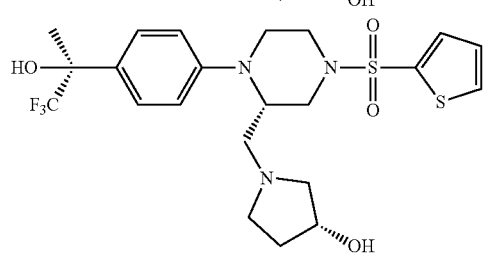

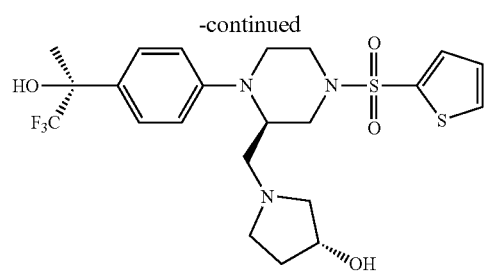

(3R)-1-(((2R)-4-(2-thiophenylsulfonyl)-1-(4-((1R)-2,2,2-trifluoro-1-hydroxy-1-methylethyl)phenyl)-2-piperazinyl)methyl)-3-pyrrolidinol; (3R)-1-(((2R)-4-(2-thiophenylsulfonyl)-1-(4-((1S)-2,2,2-trifluoro-1-hydroxy-1-methylethyl)phenyl)-2-piperazinyl)methyl)-3-pyrrolidinol; (3R)-1-(((2S)-4-(2-thiophenylsulfonyl)-1-(4-((1R)-2,2,2-trifluoro-1-hydroxy-1-methylethyl)phenyl)-2-piperazinyl)methyl)-3-pyrrolidinol; (3R)-1-(((2S)-4-(2-thiophenylsulfonyl)-1-(4-((1S)-2,2,2-trifluoro-1-hydroxy-1-methylethyl)phenyl)-2-piperazinyl)methyl)-3-pyrrolidinol. 1H NMR (400 MHz, DMSO-$d_6$) δ 8.07-8.05 (m, 1H), 7.69-7.67 (m, 1H), 7.38-7.36 (d, J=9.1 Hz, 2H), 7.32-7.29 (m, 1H), 6.90-6.86 (d, J=9.1 Hz, 2H), 4.71-4.67 (m, 1H), 4.17-4.12 (m, 3H), 3.46-3.41 (m, 2H), 3.17-3.04 (m, 1H), 2.99-3.92 (m, 2H), 2.63-2.59 (m, 1H), 2.48-2.38 (m, 3H), 1.95-1.89 (m, 2H), 1.61 (s, 3H), 1.55-1.50 (m, 1H). m/z (ESI, +ve ion) 520.1 (M+H)+. GK-GKRP $EC_{50}$ (NADPH-coupled)=3.50 μM.

Example 57

1,1,1-trifluoro-2-(4-(2-(2-methylpropyl)-4-(2-thiophenylsulfonyl)-1-piperazinyl)phenyl)-2-propanol Following the procedure reported for Example 36, starting from N-(tert-butoxycarbonyl)leucine (Sigma-Aldrich, St. Louis, Mo.) and coupling with 2-(4-bromophenyl)-1,1,1-trifluoro-2-propanol (Example 27, step 1) delivered 1,1,1-trifluoro-2-(4-(2-(2-methylpropyl)-4-(2-thiophenylsulfonyl)-1-piperazinyl)phenyl)-2-propanol (mixture of four isomers) after purification via column chromatography (40 g silica gel, 0.5-8% MeOH—$CH_2Cl_2$).

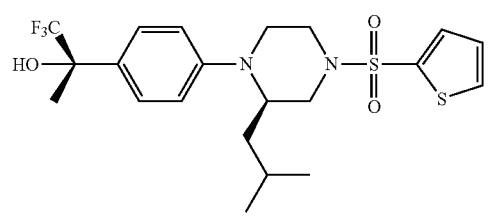

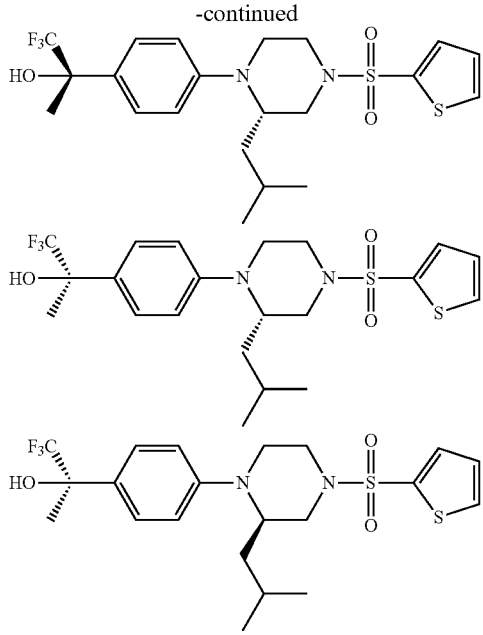

(2R)-1,1,1-trifluoro-2-(4-((2R)-2-(2-methylpropyl)-4-(2-thiophenylsulfonyl)-1-piperazinyl)phenyl)-2-propanol;
(2R)-1,1,1-trifluoro-2-(4-((2S)-2-(2-methylpropyl)-4-(2-thiophenylsulfonyl)-1-piperazinyl)phenyl)-2-propanol;
(2S)-1,1,1-trifluoro-2-(4-((2R)-2-(2-methylpropyl)-4-(2-thiophenylsulfonyl)-1-piperazinyl)phenyl)-2-propanol;
(2S)-1,1,1-trifluoro-2-(4-((2S)-2-(2-methylpropyl)-4-(2-thiophenylsulfonyl)-1-piperazinyl)phenyl)-2-propanol. $^1$H NMR (400 MHz, CDCl$_3$) δ 7.64-7.62 (m, 1H), 7.57-7.55 (m, 1H), 7.43-7.40 (d, J=8.8 Hz, 2H), 7.17-7.14 (m, 1H), 6.81-6.79 (d, J=8.8 Hz, 2H), 3.97-3.90 (m, 1H), 3.75-3.68 (m, 2H), 3.44-3.39 (m, 1H), 3.34-3.27 (m, 1H), 2.71-2.67 (m, 1H), 2.63-2.57 (m, 1H), 1.87-1.79 (m, 1H), 1.65-1.60 (m, 1H), 1.74 (s, 3H), 1.23-1.19 (m, 1H), 0.92-0.88 (m, 6H). m/z (ESI, +ve ion) 477.1 (M+H)$^+$. GK-GKRP EC$_{50}$ (NADPH-coupled)=0.655 μM; GK-GKRP EC$_{50}$ (LC MS/MS)=1.02 μM.

Example 58

2-(4-(2-(cyclohexylmethyl)-4-(2-thiophenylsulfonyl)-1-piperazinyl)phenyl)-1,1,1-trifluoro-2-propanol

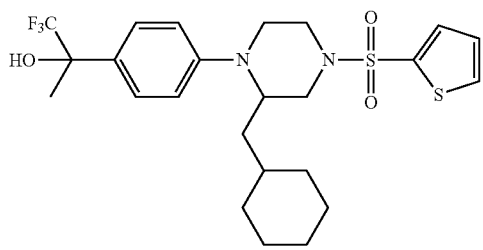 [SMILES: CC(O)(c1ccc(N2CCN(S(=O)(=O)c3cccs3)CC2CC2CCCCC2)cc1)C(F)(F)F]

Following the procedure reported for Example 36, starting from N-(tert-butoxycarbonyl)-3-cyclohexylalanine (Chem-Impex, Wood Dale, Ill.) and coupling with 2-(4-bromophenyl)-1,1,1-trifluoro-2-propanol (Example 27, step 1) delivered 2-(4-(2-(cyclohexylmethyl)-4-(2-thiophenylsulfonyl)-1-piperazinyl)phenyl)-1,1,1-trifluoro-2-propanol (mixture of four isomers) after purification via column chromatography (40 g silica gel, 0.5 to 8% MeOH—CH$_2$Cl$_2$).

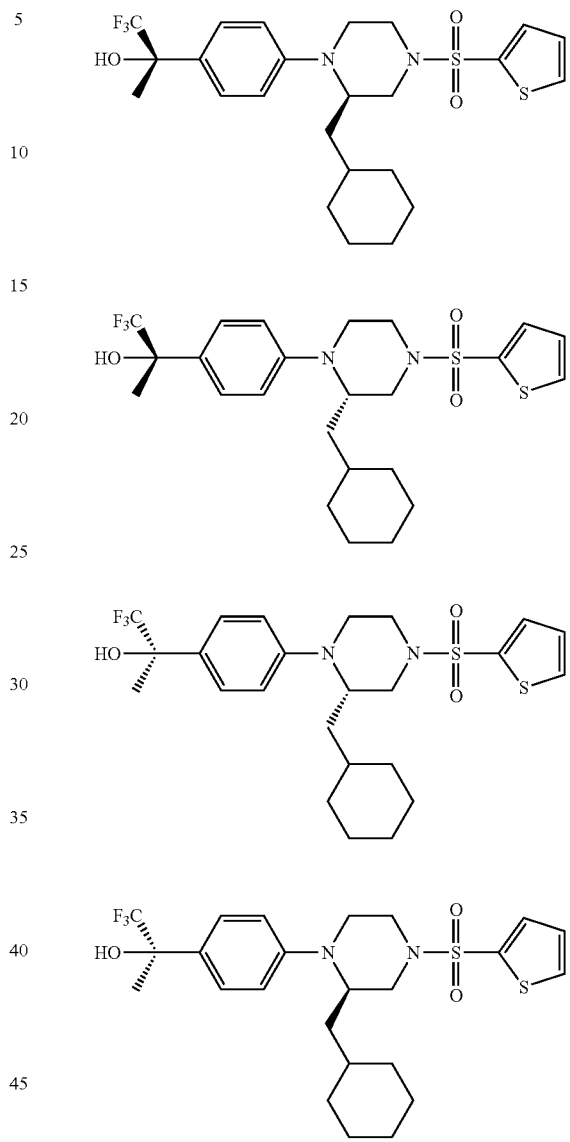

(2R)-2-(4-((2R)-2-(cyclohexylmethyl)-4-(2-thiophenylsulfonyl)-1-piperazinyl)phenyl)-1,1,1-trifluoro-2-propanol;
(2R)-2-(4-((2S)-2-(cyclohexylmethyl)-4-(2-thiophenylsulfonyl)-1-piperazinyl)phenyl)-1,1,1-trifluoro-2-propanol;
(2S)-2-(4-((2R)-2-(cyclohexylmethyl)-4-(2-thiophenylsulfonyl)-1-piperazinyl)phenyl)-1,1,1-trifluoro-2-propanol;
(2S)-2-(4-((2S)-2-(cyclohexylmethyl)-4-(2-thiophenylsulfonyl)-1-piperazinyl)phenyl)-1,1,1-trifluoro-2-propanol. $^1$H NMR (400 MHz, CDCl$_3$) δ 7.64-7.62 (m, 1H), 7.57-7.55 (m, 1H), 7.43-7.40 (d, J=8.6 Hz, 2H), 7.17-7.14 (m, 1H), 6.81-6.79 (d, J=8.6 Hz, 2H), 3.97-3.90 (m, 1H), 3.77-3.65 (m, 2H), 3.44-3.39 (m, 1H), 3.34-3.27 (m, 1H), 2.73-2.67 (m, 1H), 2.63-2.56 (m, 1H), 2.32-2.31 (m, 1H), 1.83-1.74 (m, 2H), 1.74 (s, 3H), 1.69-1.62 (m, 4H), 1.28-1.15 (m, 4H), 0.90-0.84

(m, 2H). m/z (ESI, +ve ion) 517.2 (M+H)⁺. GK-GKRP EC$_{50}$ (NADPH-coupled)=1.00 μM; GK-GKRP EC$_{50}$ (LC MS/MS)=1.32 μM.

Example 59

1,1,1-trifluoro-2-(4-(2-((3-pyridinylmethoxy)methyl)-4-(2-thiophenylsulfonyl)-1-piperazinyl)phenyl)-2-propanol

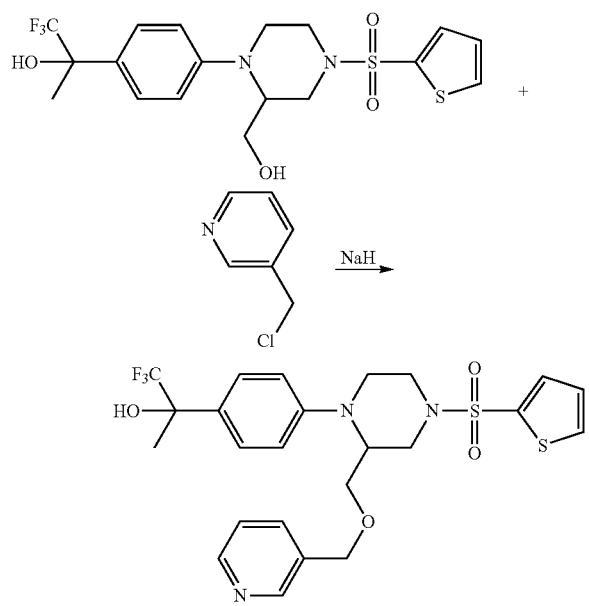

A 25 ml, round-bottomed flask was charged with 1,1,1-trifluoro-2-(4-(2-(hydroxymethyl)-4-(thiophen-2-ylsulfonyl)-1-piperazinyl)phenyl)-2-propanol (25 mg, 0.055 mmol, Example 44) and DMF (5 mL) was cooled to 0° C. To this solution was added sodium hydride (7.3 mg, 60% by weight in mineral oil, 0.18 mmol). The mixture was warmed to room temperature and stirred for 20 min. After cooling to 0° C., 3-(chloromethyl)pyridine hydrochloride (9.1 mg, 0.055 mmol, Sigma-Aldrich, St. Louis, Mo.) was added. The reaction was warmed to room temperature and stirred for 2 h. Saturated aqueous NH$_4$Cl (0.1 mL) was added and the mixture was then purified by silica gel preparatory TLC (2:1 (5% MeOH-EtOAc) in hexanes) to yield 1,1,1-trifluoro-2-(4-(2-((3-pyridinylmethoxy)methyl)-4-(2-thiophenylsulfonyl)-1-piperazinyl)phenyl)-2-propanol (20 mg) as a mixture of four isomers.

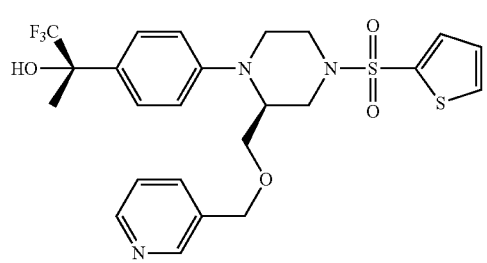

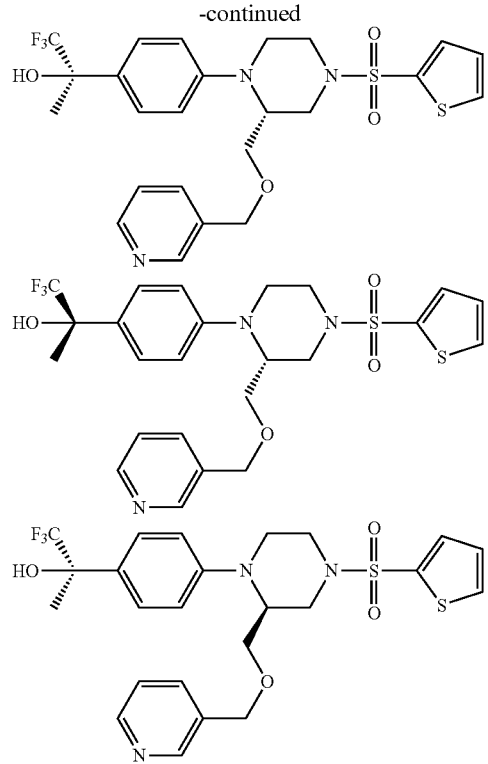

(2R)-1,1,1-trifluoro-2-(4-((2R)-2-((3-pyridinylmethoxy)methyl)-4-(2-thiophenylsulfonyl)-1-piperazinyl)phenyl)-2-propanol; (2R)-1,1,1-trifluoro-2-(4-((2S)-2-((3-pyridinylmethoxy)methyl)-4-(2-thiophenylsulfonyl)-1-piperazinyl)phenyl)-2-propanol; (2S)-1,1,1-trifluoro-2-(4-((2R)-2-((3-pyridinylmethoxy)methyl)-4-(2-thiophenylsulfonyl)-1-piperazinyl)phenyl)-2-propanol; (2S)-1,1,1-trifluoro-2-(4-((2S)-2-((3-pyridinylmethoxy)methyl)-4-(2-thiophenylsulfonyl)-1-piperazinyl)phenyl)-2-propanol. ¹H NMR (400 MHz, CDCl$_3$) δ 8.40-8.38 (m, 1H), 7.67-7.65 (m, 1H), 7.60-7.58 (m, 1H), 7.52-7.46 (m, 3H), 7.45-7.39 (m, 1H), 7.22-7.18 (m, 2H), 6.88-6.86 (m, 2H), 4.45-4.35 (m, 2H), 4.26-4.22 (m, 1H), 3.91-3.77 (m, 3H), 3.73-3.69 (m, 1H), 3.41-3.27 (m, 2H), 2.84-2.79 (m, 1H), 2.69-2.60 (m, 1H), 1.74 (s, 3H). m/z (ESI, +ve ion) 542.1 (M+H)⁺. GK-GKRP EC$_{50}$ (NADPH-coupled)=4.93 μM; GK-GKRP EC$_{50}$ (LC MS/MS)=4.93 μM.

Example 60

1,1,1,3,3,3-hexafluoro-2-(4-(4-(1H-imidazol-4-ylsulfonyl)-1-piperazinyl)phenyl)-2-propanol

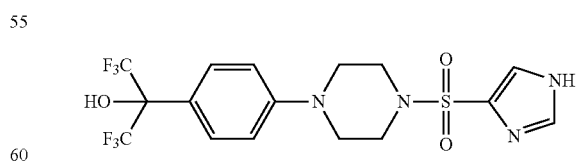

Following the procedure reported for Example 32, using from 1H-imidazole-4-sulfonyl chloride (Chembridge, San Diego, Calif.)), produced 1,1,1,3,3,3-hexafluoro-2-(4-(4-(1H-imidazol-4-ylsulfonyl)-1-piperazinyl)phenyl)-2-propanol. ¹H NMR (400 MHz, DMSO-d$_6$) δ 8.41 (s, 1H), 7.89 (s, 1H), 7.85 (s, 1H), 7.47 (d, J=8.7 Hz, 2H), 7.01 (d, J=8.7 Hz, 1H), 3.32-3.28 (m, 4H), 3.14-3.10 (m, 4H). m/z (ESI, +ve ion) 458.9 (M+H)+. GK-GKRP EC$_{50}$ (NADPH-coupled)=2.34 μM; GK-GKRP EC$_{50}$ (LC MS/MS)=2.32 μM.

Example 61

1,1,1-trifluoro-2-(4-(2-(4-morpholinylmethyl)-4-(2-thiophenylsulfonyl)-1-piperazinyl)phenyl)-2-propanol

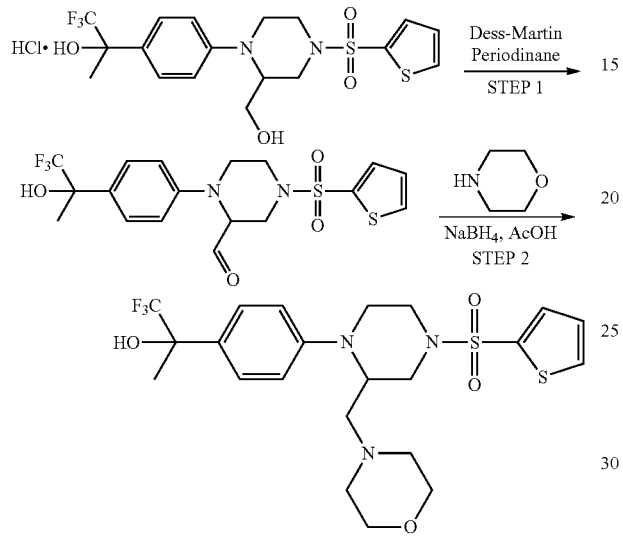

Step 1: 4-(2-thiophenylsulfonyl)-1-(4-(2,2,2-trifluoro-1-hydroxy-1-methylethyl)phenyl)-2-piperazinecarbaldehyde To a suspension of 1,1,1-trifluoro-2-(4-(2-(hydroxymethyl)-4-(thiophen-3-ylsulfonyl)piperazin-1-yl)phenyl)-2-propanol hydrochloride (50 mg, 0.103 mmol, Example 44) in CH$_2$Cl$_2$ (2.0 mL) at room temperature was added solid sodium bicarbonate (17.25 mg, 0.205 mmol) followed by Dess-Martin periodinane (47.9 mg, 0.113 mmol, Sigma-Aldrich, St. Louis, Mo.). The reaction was stirred at this temperature for 30 min and then filtered through a pad of Celite® (diatomaceous earth) eluting with CH$_2$Cl$_2$. The filtrate was concentrated to yield 4-(2-thiophenylsulfonyl)-1-(4-(2,2,2-trifluoro-1-hydroxy-1-methylethyl)phenyl)-2-piperazinecarbaldehyde which was used without purification.

Step 2: 1,1,1-trifluoro-2-(4-(2-(4-morpholinylmethyl)-4-(2-thiophenylsulfonyl)-1-piperazinyl)phenyl)-2-propanol To a solution of 4-(2-thiophenylsulfonyl)-1-(4-(2,2,2-trifluoro-1-hydroxy-1-methylethyl)phenyl)-2-piperazinecarbaldehyde (45 mg, 0.100 mmol) and morpholine (26.2 mg, 0.301 mmol, Aldrich, St. Louis, Mo.) in 1,2-dichloroethane (2.0 mL) was added sodium triacetoxyborohydride (106 mg, 0.502 mmol) and acetic acid (5.74 μL, 0.100 mmol). The reaction was stirred at room temperature for 1 h then quenched with methanol (5 mL) and concentrated. The crude material was dissolved in methanol, filtered and purified using prep HPLC (Phenomenex C18 column (150×30 mm) eluting with TFA in CH$_3$CN/H$_2$O (10% to 90% gradient over 25 min) at a 30 mL/min flow rate) to yield 1,1,1-trifluoro-2-(4-(2-(4-morpholinylmethyl)-4-(2-thiophenylsulfonyl)-1-piperazinyl)phenyl)-2-propanol (5 mg) as a mixture of four isomers.

(2R)-1,1,1-trifluoro-2-(4-((2R)-2-(4-morpholinylmethyl)-4-(2-thiophenylsulfonyl)-1-piperazinyl)phenyl)-2-propanol;
(2R)-1,1,1-trifluoro-2-(4-((2S)-2-(4-morpholinylmethyl)-4-(2-thiophenylsulfonyl)-1-piperazinyl)phenyl)-2-propanol;
(2S)-1,1,1-trifluoro-2-(4-((2R)-2-(4-morpholinylmethyl)-4-(2-thiophenylsulfonyl)-1-piperazinyl)phenyl)-2-propanol;
(2S)-1,1,1-trifluoro-2-(4-((2S)-2-(4-morpholinylmethyl)-4-(2-thiophenylsulfonyl)-1-piperazinyl)phenyl)-2-propanol.
$^1$H NMR (400 MHz, CD$_3$OD) δ 7.89-7.86 (m, 1H), 7.65-7.63 (m, 1H), 7.46-7.41 (m, 2H), 7.27-7.24 (m, 1H), 6.93-6.89 (m, 2H), 4.09-4.03 (m, 1H), 3.99-3.94 (m, 1H), 3.79-3.72 (m, 1H), 3.60-3.55 (m, 4H), 3.50-3.41 (m, 1H), 3.25-3.12 (m, 1H), 2.78-2.71 (m, 1H), 2.68-2.46 (m, 4H), 2.37-2.30 (m, 2H), 2.28-2.21 (m, 1H), 1.67 (s, 3H). m/z (ESI, +ve ion) 519.8

(M+H)⁺. GK-GKRP EC$_{50}$ (NADPH-coupled)=0.230 μM; GK-GKRP EC$_{50}$ (LC MS/MS)=0.355 μM.

Example 62

2-(4-(2-((benzyl(methyl)amino)methyl)-4-(2-thiophenylsulfonyl)-1-piperazinyl)phenyl)-1,1,1-trifluoro-2-propanol

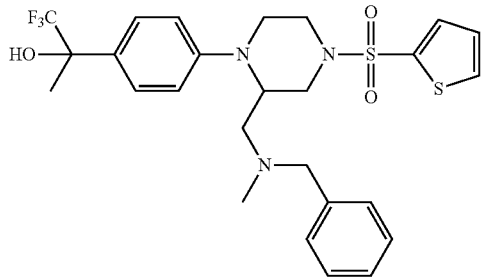 [SMILES: CN(Cc1ccccc1)CC1CN(S(=O)(=O)c2cccs2)CCN1c1ccc(C(C)(O)C(F)(F)F)cc1]

Following the procedure reported for Example 60, the coupling of 4-(2-thiophenylsulfonyl)-1-(4-(2,2,2-trifluoro-1-hydroxy-1-methylethyl)phenyl)-2-piperazinecarbaldehyde with N-benzylmethylamine (Sigma-Aldrich, St. Louis, Mo.) delivered 2-(4-(2-((benzyl(methyl)amino)methyl)-4-(2-thiophenylsulfonyl)-1-piperazinyl)phenyl)-1,1,1-trifluoro-2-propanol as a mixture of four isomers.

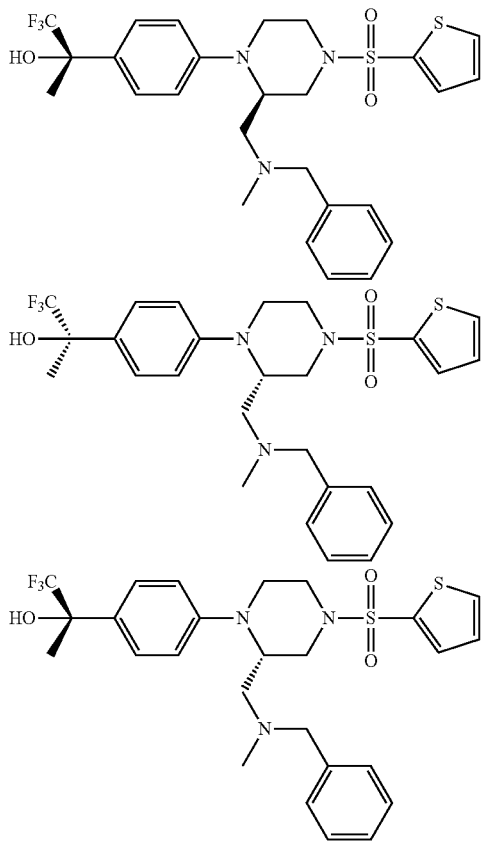

-continued

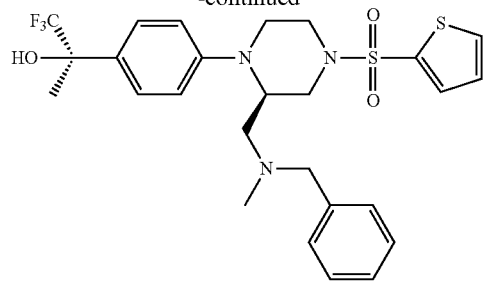

(2R)-2-(4-((2R)-2-((benzyl(methyl)amino)methyl)-4-(2-thiophenylsulfonyl)-1-piperazinyl)phenyl)-1,1,1-trifluoro-2-propanol; (2R)-2-(4-((2S)-2-((benzyl(methyl)amino)methyl)-4-(2-thiophenylsulfonyl)-1-piperazinyl)phenyl)-1,1,1-trifluoro-2-propanol; (2S)-2-(4-((2R)-2-((benzyl(methyl)amino)methyl)-4-(2-thiophenylsulfonyl)-1-piperazinyl)phenyl)-1,1,1-trifluoro-2-propanol; (2S)-2-(4-((2S)-2-((benzyl(methyl)amino)methyl)-4-(2-thiophenylsulfonyl)-1-piperazinyl)phenyl)-1,1,1-trifluoro-2-propanol. ¹H NMR (400 MHz, CD₃OD) δ 7.88-7.86 (m, 1H), 7.66-7.64 (m, 1H), 7.44-7.40 (m, 2H), 7.31-7.21 (m, 6H), 6.86-6.82 (m, 2H), 4.08-3.97 (m, 2H), 3.72-3.66 (m, 1H), 3.53-3.45 (m, 2H), 3.43-3.37 (m, 1H), 3.19-3.11 (m, 1H), 2.95-2.87 (m, 1H), 2.70-2.65 (m, 1H), 2.62-2.54 (m, 1H), 2.25-2.19 (m, 1H), 2.17 (s, 3H), 1.67 (s, 3H). m/z (ESI, +ve ion) 553.8 (M+H)⁺. GK-GKRP EC$_{50}$ (NADPH-coupled)=1.01 μM; GK-GKRP EC$_{50}$ (LC MS/MS)=1.22 μM.

Example 63

2-(4-((2S)-2-ethyl-4-(2-thiophenylsulfonyl)-1-piperazinyl)phenyl)-1,1,1,3,3,3-hexafluoro-2-propanol

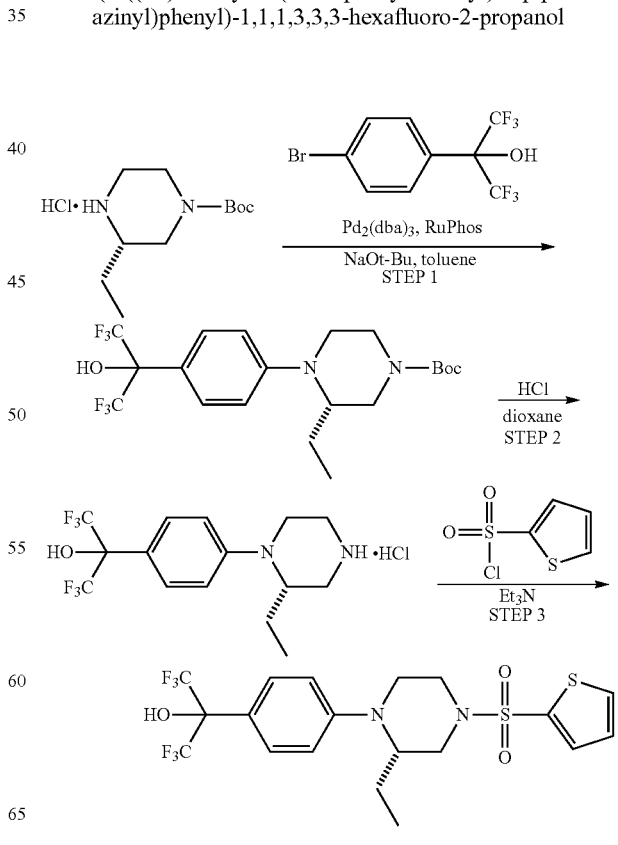

Step 1: tert-butyl (3S)-3-ethyl-4-(4-(2,2,2-trifluoro-1-hydroxy-1-(trifluoromethyl)ethyl)phenyl)-1-piperazinecarboxylate 2-(4-bromophenyl)-1,1,1,3,3,3-hexafluoro-2-propanol (0.50 g, 1.5 mmol, *Bioorg. Med. Chem. Lett.* 2002, 12, 3009), tert-butyl (3S)-3-ethyl-1-piperazinecarboxylate hydrochloride (0.40 g, 1.9 mmol, Acesys Pharmatech, North Brunswick, N.J.), sodium tert-butoxide (0.36 g, 3.7 mmol), dicyclohexyl(2',6'-diisopropoxybiphenyl-2-yl)phosphine (RuPhos) (0.11 g, 0.23 mmol, Strem Chemical Inc, Newburyport, Mass.), tris(dibenzylideneacetone)dipalladium (0) (0.080 g, 0.077 mmol, Strem Chemical Inc, Newburyport, Mass.), and toluene (3.1 mL) were added to a high-pressure reaction vessel. This mixture was sealed and heated at 100° C. for 29 h. After that time, the reaction mixture was allowed to cool to room temperature and then partitioned between EtOAc (25 mL) and saturated aqueous sodium bicarbonate (10 mL). The layers were separated, the organic material was washed sequentially with saturated aqueous sodium bicarbonate (15 mL) and brine (10 mL), dried ($Na_2SO_4$), filtered, and concentrated to give tert-butyl (3S)-3-ethyl-4-(4-(2,2,2-trifluoro-1-hydroxy-1-(trifluoromethyl)ethyl)phenyl)-1-piperazinecarboxylate (0.71 g) as a brown solid. The material was used in the next step without purification.

Step 2: 2-(4-((2S)-2-ethyl-1-piperazinyl)phenyl)-1,1,1,3,3,3-hexafluoro-2-propanol hydrochloride HCl (4.0 M solution with 1,4-dioxane, 3.9 mL, 16 mmol) was added to a stirring solution of tert-butyl (3S)-3-ethyl-4-(4-(2,2,2-trifluoro-1-hydroxy-1-(trifluoromethyl)ethyl)phenyl)-1-piperazinecarboxylate (0.71 g, 1.6 mmol) and $CH_2Cl_2$ (7.8 mL) at room temperature. After 18 h, the reaction mixture was concentrated to give 2-(4-((2S)-2-ethyl-1-piperazinyl)phenyl)-1,1,1,3,3,3-hexafluoro-2-propanol hydrochloride (0.55 g) as a brown solid. The material was used in the next step without purification.

Step 3: 2-(4-((2S)-2-ethyl-4-(2-thiophenylsulfonyl)-1-piperazinyl)phenyl)-1,1,1,3,3,3-hexafluoro-2-propanol 2-Thiophenesulfonyl chloride (0.28 g, 1.5 mmol, Sigma-Aldrich, St. Louis, Mo.) was added to a stirring solution of 2-(4-((2S)-2-ethyl-1-piperazinyl)phenyl)-1,1,1,3,3,3-hexafluoro-2-propanol hydrochloride (0.55 g, 1.5 mmol), Hünig's base (0.81 mL, 4.6 mmol), and DMF (7.7 mL) at room temperature. After 19 h, the reaction mixture was partitioned between EtOAc (20 mL) and saturated aqueous sodium bicarbonate (10 mL). The layers were separated, and the organic material was washed sequentially with saturated aqueous sodium bicarbonate (10 mL) and brine (10 mL), dried ($Na_2SO_4$) and purified via column chromatography (40 g of silica, 20 to 33% EtOAc in hexanes) to give 2-(4-((2S)-2-ethyl-4-(2-thiophenylsulfonyl)-1-piperazinyl)phenyl)-1,1,1,3,3,3-hexafluoro-2-propanol (0.13 g) as an off-white solid. $^1$H NMR (400 MHz, $CDCl_3$): δ 7.63 (d, J=5.1 Hz, 1H), 7.59-7.49 (m, 3H), 7.19-7.13 (m, 1H), 6.83 (d, J=8.0 Hz, 2H), 3.77 (d, J=11.0 Hz, 3H), 3.49 (d, J=12.7 Hz, 1H), 3.32 (dt, J=3.1, 11.9 Hz, 1H), 3.24 (s, 1H), 2.74-2.51 (m, 2H), 1.89 (ddd, J=7.3, 9.3, 14.0 Hz, 1H), 1.60-1.47 (m, 1H), 0.94 (t, J=7.4 Hz, 3H); m/z (ESI, +ve ion) 503.0 (M+H)$^+$. GK-GKRP $EC_{50}$ (NADPH-coupled)=0.679 µM; GK-GKRP $EC_{50}$ (LC MS/MS)=1.37 µM.

Example 64

2-(4-((2S)-2-benzyl-4-(2-thiophenylsulfonyl)-1-piperazinyl)phenyl)-1,1,1,3,3,3-hexafluoro-2-propanol

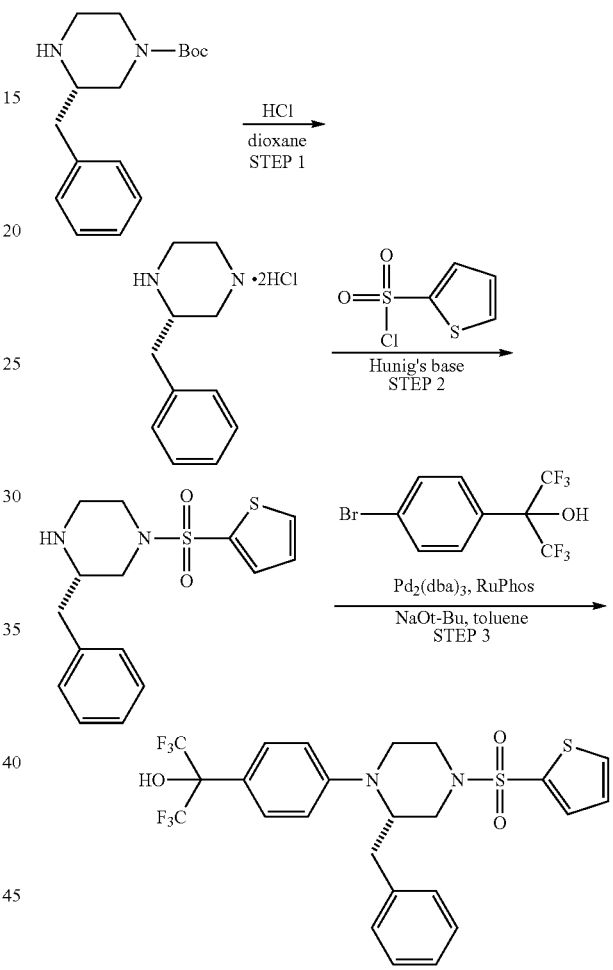

Step 1: (2S)-2-benzylpiperazine dihydrochloride

HCl (4.0 M solution with 1,4-dioxane, 45 mL, 180 mmol) was added to a stirring solution of tert-butyl (3S)-3-benzyl-1-piperazinecarboxylate (5.0 g, 18 mmol, Waterstone Technology, Carmel, Ind.) and $CH_2Cl_2$ (36 mL) at room temperature. After 16 h, the reaction mixture was concentrated to give 4.5 g (2S)-2-benzylpiperazine (4.5 g) as its dihydrochloride salt. The material was used in the next step without purification.

Step 2: (3S)-3-benzyl-1-(2-thiophenylsulfonyl)piperazine

2-Thiophenesulfonyl chloride (2.6 g, 14 mmol, Sigma-Aldrich, St. Louis, Mo.) was added to a stirring solution of (2S)-2-benzylpiperazine hydrochloride (4.5 g, 18 mmol), Hünig's base, (16 mL, 90 mmol), and $CH_2Cl_2$ (90 mL) at room temperature. After 3 h, silica gel (29 g) was added to the reaction mixture and the volatiles were removed in vacuo. The residue was subjected to column chromatography (120 g of silica, 2% MeOH in $CH_2Cl_2$) to give (3S)-3-benzyl-1-(2-thiophenylsulfonyl)piperazine (5.0 g) as a pale yellow solid.

Step 3: 2-(4-((2S)-2-benzyl-4-(2-thiophenylsulfonyl)-1-piperazinyl)phenyl)-1,1,1,3,3,3-hexafluoro-2-propanol 2-(4-bromophenyl)-1,1,1,3,3,3-hexafluoro-2-propanol (0.22 g, 0.68 mmol, Bioorg. Med. Chem. Lett. 2002, 12, 3009), (3S)-3-benzyl-1-(2-thiophenylsulfonyl)piperazine (0.20 g, 0.62 mmol), sodium tert-butoxide (0.19 g, 1.9 mmol), dicyclohexyl(2',6'-diisopropoxybiphenyl-2-yl)phosphine (RuPhos) (0.058 g, 0.12 mmol, Strem Chemical Inc, Newburyport, Mass.), tris(dibenzylideneacetone)dipalladium (0) (0.057 g, 0.062 mmol, Strem Chemical Inc, Newburyport, Mass.), and toluene (2.5 mL) were added to a high-pressure reaction vessel under a nitrogen atmosphere. The vessel was sealed and was heated at 100° C. for 29 h. Then the mixture was allowed to cool to room temperature and then partitioned between EtOAc (15 mL) and saturated aqueous sodium bicarbonate (10 mL). The layers were separated and the organic material was washed sequentially with saturated aqueous sodium bicarbonate (25 mL) and brine (15 mL), dried ($Na_2SO_4$) and filtered. The filtrate was concentrated, and the solution, and the volatiles were removed in vacuo. The residue was subjected purified via column chromatography using silica gel (twice, 100% $CH_2Cl_2$, then 25% EtOAc in hexanes) to give of 2-(4-((2S)-2-benzyl-4-(2-thiophenylsulfonyl)-1-piperazinyl)phenyl)-1,1,1,3,3,3-hexafluoro-2-propanol (0.048 g) as a colorless solid. $^1$H NMR (400 MHz, $CDCl_3$) δ 7.72-7.54 (m, 4H), 7.33-7.14 (m, 6H), 6.94 (d, J=7.2 Hz, 2H), 4.04 (d, J=8.2 Hz, 1H), 3.91 (d, J=9.4 Hz, 1H), 3.75 (d, J=11.2 Hz, 1H), 3.54 (d, J=11.2 Hz, 1H), 3.42 (t, J=10.9 Hz, 1H), 3.31 (br. s., 1H), 3.21 (t, J=11.7 Hz, 1H), 2.67-2.48 (m, 3H); m/z (ESI, +ve ion) 565.0 (M+H)$^+$. GK-GKRP $EC_{50}$ (NADPH-coupled)=0.308 μM; GK-GKRP $EC_{50}$ (LC MS/MS)=0.772 μM.

Example 65

2-(4-((2S)-2-benzyl-4-(2-thiophenylsulfonyl)-1-piperazinyl)phenyl)-1,1,1-trifluoro-2-propanol

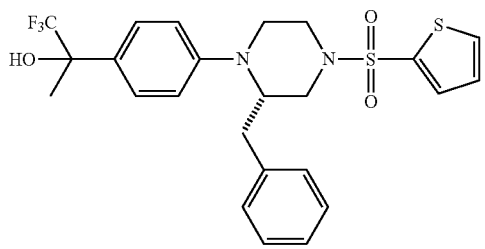 [SMILES: CC(O)(c1ccc(N2CCN(S(=O)(=O)c3cccs3)C[C@@H]2Cc2ccccc2)cc1)C(F)(F)F]

Following the procedure reported for Example 63, the coupling of (3S)-3-benzyl-1-(2-thiophenylsulfonyl)piperazine and 2-(4-bromophenyl)-1,1,1-trifluoropropan-2-ol (Example 27, step 1) delivered 2-(4-((2S)-2-benzyl-4-(2-thiophenylsulfonyl)-1-piperazinyl)phenyl)-1,1,1-trifluoro-2-propanol as a mixture of two isomers.

The mixture was subjected to chiral SFC (Chiralcel OJ-H column, 250 mm×21 mm, 5.0 μm eluting with 60% liquid $CO_2$ and 40% MeOH (0.2% diethylamine)) to give two products in greater than 99% diastereomeric excess.

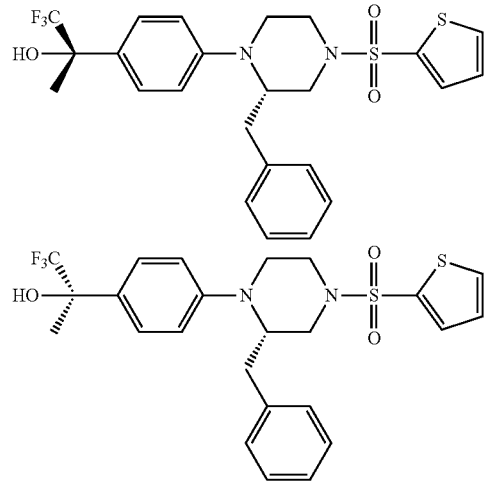

(2S)-2-(4-((2S)-2-benzyl-4-(2-thiophenylsulfonyl)-1-piperazinyl)phenyl)-1,1,1-trifluoro-2-propanol; (2R)-2-(4-((2S)-2-benzyl-4-(2-thiophenylsulfonyl)-1-piperazinyl)phenyl)-1,1,1-trifluoro-2-propanol.

First Eluting Peak (Peak #1)

$^1$H NMR (400 MHz, $CDCl_3$) δ 7.62 (d, J=4.9 Hz, 1H), 7.56-7.46 (m, 3H), 7.37-7.30 (m, 2H), 7.29-7.20 (m, 3H), 7.17-7.11 (m, 1H), 6.91 (d, J=9.0 Hz, 2H), 3.99 (d, J=8.8 Hz, 1H), 3.89 (d, J=10.8 Hz, 1H), 3.72 (d, J=11.3 Hz, 1H), 3.53-3.44 (m, 1H), 3.44-3.33 (m, 1H), 3.25-3.10 (m, 1H), 2.68-2.55 (m, 2H), 2.51 (dd, J=2.7, 11.5 Hz, 1H), 2.34 (br. s., 1H), 1.77 (s, 3H). m/z (ESI, +ve ion) 511.1 (M+H)$^+$. GK-GKRP $EC_{50}$ (NADPH-coupled)=0.367 μM; GK-GKRP $EC_{50}$ (LC MS/MS)=0.643 μM.

Second Eluting Peak (Peak #2)

$^1$H NMR (400 MHz, $CDCl_3$) δ 7.62 (d, J=4.9 Hz, 1H), 7.56-7.47 (m, 3H), 7.36-7.29 (m, 2H), 7.25-7.21 (m, 3H), 7.17-7.12 (m, 1H), 6.94 (br. s., 2H), 3.99 (dd, J=2.7, 10.8 Hz, 1H), 3.89 (d, J=11.2 Hz, 1H), 3.72 (d, J=11.5 Hz, 1H), 3.54-3.33 (m, 2H), 3.17 (t, J=12.0 Hz, 1H), 2.63 (d, J=12.3 Hz, 2H), 2.55 (br. s., 1H), 2.32 (s, 1H), 1.77 (s, 3H). m/z (ESI, +ve ion) 511.1 (M+H)$^+$. GK-GKRP $EC_{50}$ (NADPH-coupled)=0.166 μM; GK-GKRP $EC_{50}$ (LC MS/MS)=0.240 μM.

Example 66

3,3,3-trifluoro-2-(4-(4-(2-thiophenylsulfonyl)-1-piperazinyl)phenyl)-1,2-propanediol

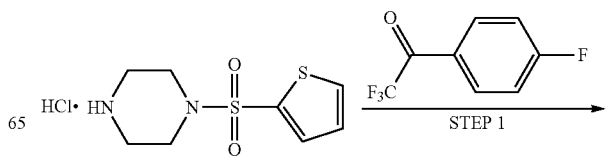

-continued

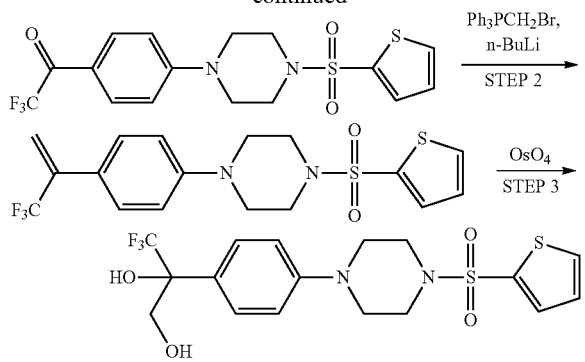

Step 1: 2,2,2-trifluoro-1-(4-(4-(2-thiophenylsulfonyl)-1-piperazinyl)phenyl)ethanone 2,2,2-trifluoro-1-(4-fluorophenyl)ethanone (2.6 g, 13 mmol, Sigma-Aldrich, St. Louis, Mo.), Hünig's base (5.8 mL, 34 mmol), 1-(2-thiophenylsulfonyl)piperazine hydrochloride (3.0 g, 11 mmol, Example 29, step 1), and acetonitrile (22 mL) was added to a high-pressure reaction vessel. The vessel was sealed and heated at 110° C. for 19 h. After cooling to room temperature, the mixture was partitioned between EtOAc (100 mL) and saturated aqueous sodium bicarbonate (50 mL) and the layers were separated. The organic material was washed sequentially with saturated aqueous sodium bicarbonate (50 mL) and brine (50 mL), dried ($Na_2SO_4$) and filtered. The filtrate was concentrated, hexanes (100 mL) was added to the residue and the slurry was filtered to give 2,2,2-trifluoro-1-(4-(4-(2-thiophenylsulfonyl)-1-piperazinyl)phenyl)ethanone (2.5 g) as a light tan solid. The material was used in the next step without purification Step 2: 1-(2-thiophenylsulfonyl)-4-(4-(1-(trifluoromethyl)ethenyl)phenyl)piperazine n-BuLi (0.59 mL, 2.5 M solution in toluene, 1.5 mmol) was added to a stirring mixture of methyltriphenylphosphonium bromide (0.53 g, 1.5 mmol) and THF (3.1 mL) at room temperature under a nitrogen atmosphere. After 30 min, a mixture of 2,2,2-trifluoro-1-(4-(4-(2-thiophenylsulfonyl)-1-piperazinyl)phenyl)ethanone (0.50 g, 1.2 mmol) and THF (3.1 mL) was added. After an additional 1 h, saturated aqueous ammonium chloride (25 mL) was added, the mixture was partitioned between EtOAc (50 mL) and saturated aqueous ammonium chloride (25 mL). The layers were separated, the organic material was washed sequentially with saturated aqueous ammonium chloride (25 mL) and brine (25 mL), and dried ($Na_2SO_4$) purified via column chromatography (10 g of silica, 20% EtOAc in hexanes) to provide 1-(2-thiophenylsulfonyl)-4-(4-(1-(trifluoromethyl)ethenyl)phenyl)piperazine (0.23 g) as an off-white solid.

Step 3: 3,3,3-trifluoro-2-(4-(4-(2-thiophenylsulfonyl)-1-piperazinyl)phenyl)-1,2-propanediol Osmium tetroxide (2.4 mL, 4 wt % solution in water, 0.40 mmol) was added to a stirring solution of 1-(2-thiophenylsulfonyl)-4-(4-(1-(trifluoromethyl)ethenyl)phenyl)piperazine (0.16 g, 0.40 mmol) and pyridine (4.0 mL) at room temperature. After 40 min, water (4.0 mL) and $Na_2SO_3$ (1.5 g, 12 mmol) were added sequentially, the mixture was partitioned between water (10 mL) and chloroform (25 mL). The layers were separated and the aqueous material was washed with chloroform (2×10 mL). The combined organic material was dried ($Na_2SO_4$) and purified via column chromatography (10 g of silica, 1% MeOH in $CH_2Cl_2$). The purified residue was partitioned between water (20 mL) and tert-butanol (20 mL). To this was added sodium sulfite (2.0 g), potassium carbonate (2.0 g), and methanesulfonamide (0.20 g) at room temperature. After 6 h, the reaction mixture was partitioned between EtOAc (50 mL) and saturated aqueous sodium bicarbonate (25 mL) and the layers were separated. The organic material was washed sequentially with saturated aqueous sodium bicarbonate (20 mL) and brine (20 mL), dried ($MgSO_4$), and purified via column chromatography on silica gel (10 g of silica, 1% MeOH in $CH_2Cl_2$) to yield 3,3,3-trifluoro-2-(4-(4-(2-thiophenylsulfonyl)-1-piperazinyl)phenyl)-1,2-propanediol as a mixture of enantiomers (0.088 g).

The mixture was subjected to chiral SFC purification (Chiralpak® AS column, 250 mm×21 mm, 10 μm) eluting with 65% liquid $CO_2$, 35% MeOH (0.2% diethylamine)) to give two products in greater than 99% enantiomeric excess.

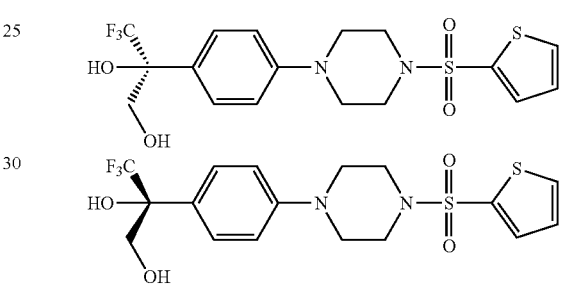

2S)-3,3,3-trifluoro-2-(4-(4-(2-thiophenylsulfonyl)-1-piperazinyl)phenyl)-1,2-propanediol; (2R)-3,3,3-trifluoro-2-(4-(4-(2-thiophenylsulfonyl)-1-piperazinyl)phenyl)-1,2-propanediol.
First Eluting Peak (Peak #1):
$^1$H NMR (400 MHz, $CDCl_3$) δ 7.64 (d, J=4.9 Hz, 1H), 7.58 (d, J=3.3 Hz, 1H), 7.43 (d, J=8.4 Hz, 2H), 7.17 (t, J=4.3 Hz, 1H), 6.89 (d, J=8.8 Hz, 2H), 4.24 (d, J=11.7 Hz, 1H), 3.87 (d, J=11.9 Hz, 1H), 3.36-3.27 (m, 4H), 3.27-3.16 (m, 4H), 1.71 (br. s., 2H). m/z (ESI, +ve ion) 437.0 (M+H)$^+$. GK-GKRP $EC_{50}$ (LC MS/MS)=4.43 μM.
Second Eluting Peak (Peak #2):
$^1$H NMR (400 MHz, $CDCl_3$) δ 7.64 (d, J=4.5 Hz, 1H), 7.61-7.52 (m, 1H), 7.43 (d, J=8.2 Hz, 2H), 7.17 (t, J=3.9 Hz, 1H), 6.89 (d, J=8.4 Hz, 2H), 4.24 (d, J=11.7 Hz, 1H), 3.86 (d, J=11.7 Hz, 1H), 3.35-3.26 (m, 4H), 3.25-3.16 (m, 4H), 1.66 (br. s., 2H). m/z (ESI, +ve ion) 437.0 (M+H)$^+$. GK-GKRP $EC_{50}$ (LC MS/MS)=1.26 μM.

Example 67

2-(4-((2S)-2-methyl-4-(2-thiophenylsulfonyl)-1-piperazinyl)phenyl)-3,3,3-trifluoro-1,2-propanediol

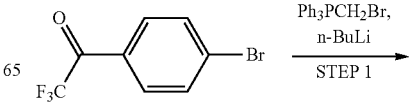

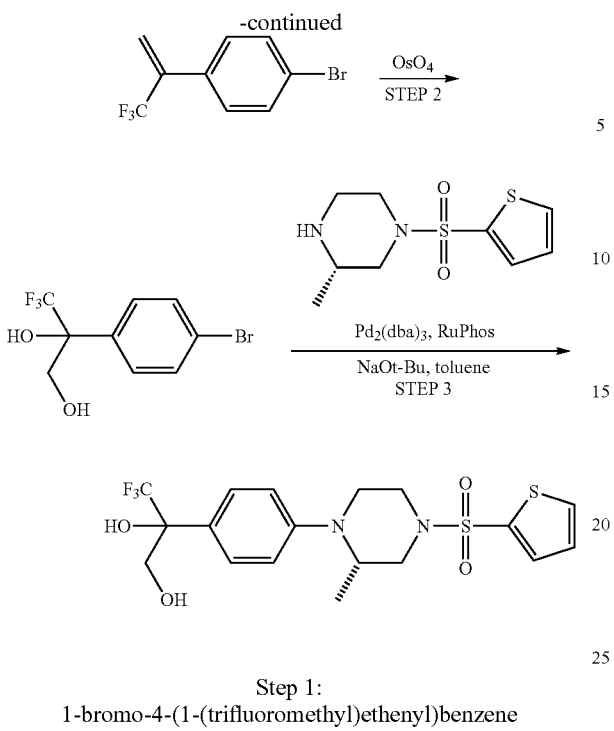

Step 1:
1-bromo-4-(1-(trifluoromethyl)ethenyl)benzene n-BuLi (9.5 mL, 2.5 M solution with toluene, 24 mmol) was added to a stirring mixture of methyltriphenylphosphonium bromide (8.5 g, 24 mmol) and THF (100 mL) at room temperature under a nitrogen atmosphere. After 1 h, 1-(4-bromophenyl)-2,2,2-trifluoroethanone (3.0 mL, 20 mmol, Sigma-Aldrich, St. Louis, Mo.) was added. After an additional 1 h, saturated aqueous ammonium chloride (50 mL) was added. The mixture was partitioned between diethyl ether (100 mL) and saturated aqueous ammonium chloride (50 mL). The layers were separated, the organic material was washed sequentially with saturated aqueous ammonium chloride (50 mL) and brine (50 mL), dried (MgSO$_4$), and purified via column chromatography (35 g of silica, 1% EtOAc in hexanes) to provide 1-bromo-4-(1-(trifluoromethyl)ethenyl)benzene (3.5 g) as an orange oil.

Step 2:
2-(4-bromophenyl)-3,3,3-trifluoro-1,2-propanediol

Osmium tetroxide (4 wt % solution with water, 4.3 mL, 0.70 mmol) was added to a stirring mixture of 1-bromo-4-(1-(trifluoromethyl)ethenyl)benzene (3.5 g, 14 mmol), 4-methylmorpholine N-oxide (1.8 g, 15 mmol), acetone (14 mL), and water (14 mL) at room temperature. After 21 h, Na$_2$SO$_3$ (8.8 g, 70 mmol) was added, the mixture was filtered. Silica gel (20 g) was added to the filtrate, and the volatiles were removed in vacuo. The residue was purified via column chromatography (5% MeOH in CH$_2$Cl$_2$) to afford 2-(4-bromophenyl)-3,3,3-trifluoro-1,2-propanediol (3.0 g) as an off-white solid.

Step 3: 2-(4-((2S)-2-methyl-4-(2-thiophenylsulfonyl)-1-piperazinyl)phenyl)-3,3,3-trifluoro-1,2-propanediol 2-(4-bromophenyl)-3,3,3-trifluoro-1,2-propanediol (0.35 g, 1.2 mmol), (3S)-3-methyl-1-(2-thiophenylsulfonyl)piperazine (0.20 g, 0.81 mmol), sodium tert-butoxide (0.27 g, 2.8 mmol), dicyclohexyl(2',6'-diisopropoxybiphenyl-2-yl)phosphine (RuPhos) (0.076 g, 0.16 mmol, Strem Chemical Inc, Newburyport, Mass.), tris(dibenzylideneacetone)dipalladium (0) (0.074 g, 0.081 mmol, Strem Chemical Inc, Newburyport, Mass.), and toluene (3.3 mL) were added to a high-pressure reaction vessel. The vessel was sealed and heated at 100° C. for 24 h. After cooling to room temperature, was purified via flash chromatography on silica gel (twice, 2% MeOH in CH$_2$Cl$_2$ then 33% EtOAc in hexanes) to afford 2-(4-((2S)-2-methyl-4-(2-thiophenylsulfonyl)-1-piperazinyl)phenyl)-3,3,3-trifluoro-1,2-propanediol (0.017 g) as a mixture of two isomers.

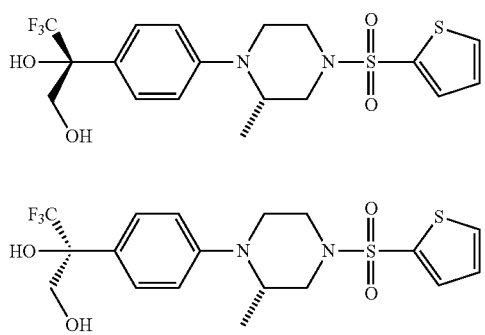 [SMILES: C[C@H]1CN(S(=O)(=O)c2cccs2)CCN1c1ccc([C@@](O)(CO)C(F)(F)F)cc1 ; C[C@H]1CN(S(=O)(=O)c2cccs2)CCN1c1ccc([C@](O)(CO)C(F)(F)F)cc1]

(2R)-3,3,3-trifluoro-2-(4-((2S)-2-methyl-4-(2-thiophenylsulfonyl)-1-piperazinyl)phenyl)-1,2-propanediol; (2S)-3,3,3-trifluoro-2-(4-((2S)-2-methyl-4-(2-thiophenylsulfonyl)-1-piperazinyl)phenyl)-1,2-propanediol. $^1$H NMR (400 MHz, CDCl$_3$) δ 7.64 (dd, J=1.1, 5.0 Hz, 1H), 7.56 (dd, J=1.2, 3.7 Hz, 1H), 7.42 (d, J=8.6 Hz, 2H), 7.16 (dd, J=3.9, 4.9 Hz, 1H), 6.87 (d, J=8.8 Hz, 2H), 4.24 (dd, J=6.3, 11.9 Hz, 1H), 4.05-3.93 (m, 1H), 3.87 (dd, J=7.1, 11.8 Hz, 1H), 3.67 (dd, J=1.8, 11.2 Hz, 1H), 3.59 (s, 1H), 3.45 (dd, J=2.2, 10.9 Hz, 1H), 3.39-3.31 (m, 1H), 3.31-3.19 (m, 1H), 2.89 (dd, J=3.1, 11.2 Hz, 1H), 2.72 (dt, J=3.5, 10.8 Hz, 1H), 1.86 (t, J=6.1 Hz, 1H), 1.16 (d, J=6.5 Hz, 3H). m/z (ESI, +ve ion) 451.1 (M+H)$^+$. GK-GKRP EC$_{50}$ (LC MS/MS)=0.670 μM.

Example 68

2-(4-((2S)-2-benzyl-4-(2-thiophenylsulfonyl)-1-piperazinyl)phenyl)-3,3,3-trifluoro-1,2-propanediol

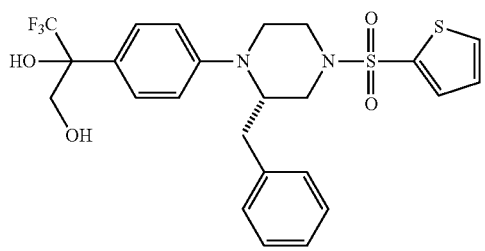 [SMILES: O=S(=O)(c1cccs1)N1CCN(c2ccc(C(O)(CO)C(F)(F)F)cc2)[C@@H](Cc2ccccc2)C1]

Following the procedure reported for Example 66 the coupling of (3S)-3-benzyl-1-(2-thiophenylsulfonyl)piperazine and 2-(4-bromophenyl)-3,3,3-trifluoro-1,2-propanediol delivered 2-(4-((2S)-2-benzyl-4-(2-thiophenylsulfonyl)-1-piperazinyl)phenyl)-3,3,3-trifluoro-1,2-propanediol as a mixture of two isomers.

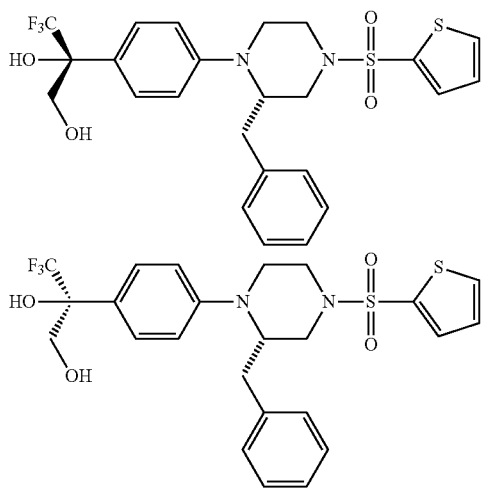

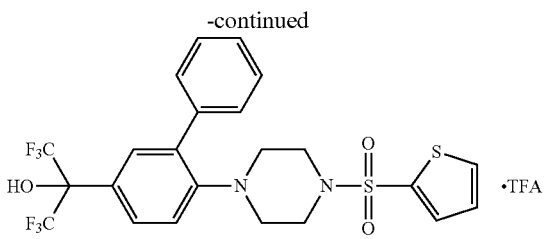

The mixture was resolved via chiral SFC (Chiralpak® AS-H column, 250 mm×21 mm, 5.0 μm) eluting with 73% liquid $CO_2$ and 27% 20 mM $NH_3$ in MeOH) to give to give two products in greater than 95% diastereomeric excess.

First Eluting Peak (Peak #1)

$^1$H NMR (400 MHz, $CDCl_3$) δ 7.62 (d, J=4.9 Hz, 1H), 7.53 (d, J=3.5 Hz, 1H), 7.48 (d, J=8.4 Hz, 2H), 7.37-7.29 (m, 2H), 7.28-7.19 (m, 3H), 7.14 (t, J=4.4 Hz, 1H), 6.93 (d, J=8.8 Hz, 2H), 4.27 (d, J=11.7 Hz, 1H), 4.00 (d, J=9.4 Hz, 1H), 3.90 (d, J=11.9 Hz, 2H), 3.73 (d, J=11.3 Hz, 1H), 3.62 (br. s., 1H), 3.53-3.44 (m, 1H), 3.44-3.33 (m, 1H), 3.24-3.13 (m, 1H), 2.68-2.54 (m, 2H), 2.50 (dd, J=2.7, 11.3 Hz, 1H), 1.85 (br. s., 1H). m/z (ESI, +ve ion) 527.0 (M+H)$^+$. GK-GKRP $EC_{50}$ (LC MS/MS)=0.870 μM.

Second Eluting Peak (Peak #2)

$^1$H NMR (400 MHz, $CDCl_3$) δ 7.62 (d, J=4.9 Hz, 1H), 7.55-7.52 (m, 1H), 7.48 (d, J=8.8 Hz, 2H), 7.36-7.29 (m, 2H), 7.28-7.20 (m, 3H), 7.17-7.11 (m, 1H), 6.92 (d, J=9.0 Hz, 2H), 4.27 (d, J=11.9 Hz, 1H), 4.05-3.96 (m, 1H), 3.90 (d, J=12.5 Hz, 2H), 3.73 (d, J=11.3 Hz, 1H), 3.64 (br. s., 1H), 3.53-3.45 (m, 1H), 3.44-3.33 (m, 1H), 3.18 (dd, J=11.2, 12.7 Hz, 1H), 2.68-2.54 (m, 2H), 2.50 (dd, J=2.5, 11.3 Hz, 1H), 1.59 (br. s., 1H). m/z (ESI, +ve ion) 527.0 (M+H)$^+$. GK-GKRP $EC_{50}$ (LC MS/MS)=0.094 μM.

Example 69

1,1,1,3,3,3-hexafluoro-2-(6-(4-(2-thiophenylsulfonyl)-1-piperazinyl)-3-biphenylyl)-2-propanol trifluoroacetate

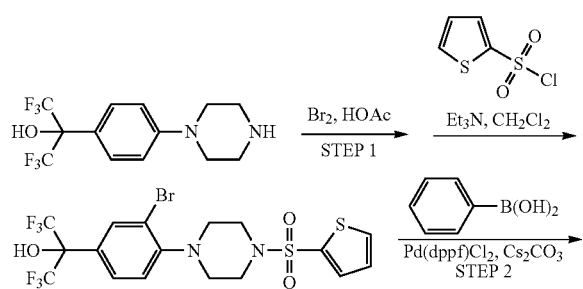

Step 1: 2-(3-bromo-4-(4-(2-thiophenylsulfonyl)-1-piperazinyl)phenyl)-1,1,1,3,3,3-hexafluoro-2-propanol 1,1,1,3,3,3-hexafluoro-2-(4-(1-piperazinyl)phenyl)-2-propanol (1.9 g, 5.8 mmol, published PCT patent application no. WO 2006/094842) was dissolved in acetic acid (10 mL). Bromine (1.9 g, 12 mmol) was added drop wise. The reaction was allowed to stir at room temperature until a solid precipitated. The solid was filtered, dissolved in EtOAc (100 mL) and washed with 1 N NaOH (3×50 mL). The organic layer was separated and washed with water (100 mL), brine (50 mL), dried ($Na_2SO_4$), filtered, and concentrated. The residue was dissolved in $CH_2Cl_2$ (20 mL). To this was added Hünig's base (1.0 mL) and 2-thiophenesulfonyl chloride (1.1 g, 5.8 mmol, Sigma-Aldrich, St. Louis, Mo.) at room temperature. After 3 h, the mixture was purified via column chromatography (40 g of silica, 10% EtOAc in hexanes) to afford 2-(3-bromo-4-(4-(thiophenylsulfonyl)piperazinyl)phenyl)-1,1,1,3,3,3-hexafluoro-2-propanol (1.5 g).

Step 2: 1,1,1,3,3,3-hexafluoro-2-(6-(4-(2-thiophenylsulfonyl)-1-piperazinyl)-3-biphenylyl)-2-propanol trifluoroacetate 2-(3-bromo-4-(4-(2-thiophenylsulfonyl)-1-piperazinyl)phenyl)-1,1,1,3,3,3-hexafluoro-2-propanol (90 mg, 0.163 mmol), phenylboronic acid (23.8 mg, 0.195 mmol, Sigma-Aldrich, St. Louis, Mo.), 1,1' bis(diphenylphosphino)ferrocene]dichloropalladium (II) (13.28 mg, 0.016 mmol, Sigma-Aldrich, St. Louis, Mo.), and cesium carbonate (159 mg, 0.488 mmol) were combined in THF (3 mL) and water (1 mL). The reaction mixture was stirred and heated in a Discover model microwave reactor (CEM, Matthews, N.C.) at 100° C. for 10 min (100 watts, Powermax feature on, ramp time 5 min). The organic layer was separated and filtered through a PTFE (polytetrafluoroethylene) filter (0.45 micron). This crude material was subjected to reverse-phase preparative HPLC using a Phenomenex Gemini $C_{18}$ column (150×30 mm, 10 μm) eluting with 0.1% TFA in $CH_3CN/H_2O$ (10% to 90% over 20 min) to provide 1,1,1,3,3,3-hexafluoro-2-(6-(4-(2-thiophenylsulfonyl)-1-piperazinyl)-3-biphenylyl)-2-propanol trifluoroacetate (43 mg) as a tan oil. $^1$H NMR (300 MHz, $CD_3OD$) δ 7.89 (d, J=4.8 Hz, 1H), 7.68-7.39 (m, 5H), 7.38-7.20 (m, 4H), 7.14 (d, J=8.6 Hz, 1H), 2.93 (br. s, 8H). m/z (ESI, +ve ion) 550.8 (M+H)+. GK-GKRP EC$_{50}$ (NADPH-coupled)=2.12 µM; GK-GKRP EC$_{50}$ (LC MS/MS)=1.75 µM.

Example 70

1,1,1,3,3,3-hexafluoro-2-(3'-methoxy-6-(4-(2-thiophenylsulfonyl)-1-piperazinyl)-3-biphenylyl)-2-propanol trifluoroacetate

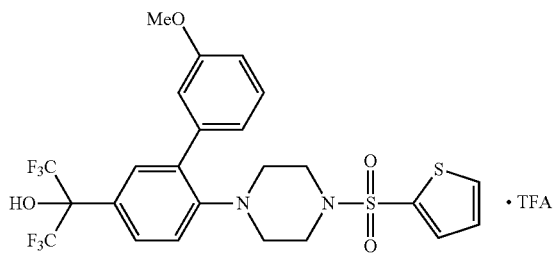 [SMILES: COc1cccc(-c2cc(C(O)(C(F)(F)F)C(F)(F)F)ccc2N2CCN(S(=O)(=O)c3cccs3)CC2)c1]

Following the procedure outlined for Example 69, 3-methoxyphenylboronic acid (26.4 mg, 0.173 mmol, Aldrich, St. Louis, Mo.) was coupled to 2-(3-bromo-4-(4-(2-thiophenylsulfonyl)-1-piperazinyl)phenyl)-1,1,1,3,3,3-hexafluoro-2-propanol to afford 1,1,1,3,3,3-hexafluoro-2-(3'-methoxy-6-(4-(2-thiophenylsulfonyl)-1-piperazinyl)-3-biphenylyl)-2-propanol. $^1$H NMR (400 MHz, CD$_3$OD) δ 7.91 (dd, J=4.9, 1.2 Hz, 1H), 7.61-7.54 (m, 2H), 7.49 (d, J=1.2 Hz, 1H), 7.40 (d, J=8.8 Hz, 2H), 7.28 (dd, J=4.9, 3.9 Hz, 1H), 7.11 (d, J=8.6 Hz, 1H), 6.87 (d, J=8.6 Hz, 2H), 3.81 (s, 3H), 2.95 (br. s, 8H). m/z (ESI, +ve ion) 580.8 (M+H)+. GK-GKRP EC$_{50}$ (NADPH-coupled)=3.34 µM; GK-GKRP EC$_{50}$ (LC MS/MS)=1.82 µM.

Example 71

1,1,1,3,3,3-hexafluoro-2-(3'-fluoro-6-(4-(2-thiophenylsulfonyl)-1-piperazinyl)-3-biphenylyl)-2-propanol

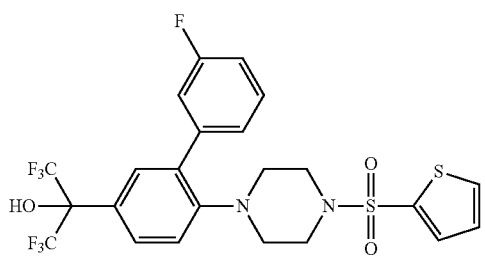 [SMILES: O=S(=O)(c1cccs1)N1CCN(c2ccc(C(O)(C(F)(F)F)C(F)(F)F)cc2-c2cccc(F)c2)CC1]

Following the procedure outlined for Example 69, 3-fluorophenylboronic acid (20.23 mg, 0.145 mmol) was coupled to 2-(3-bromo-4-(4-(2-thiophenylsulfonyl)-1-piperazinyl)phenyl)-1,1,1,3,3,3-hexafluoro-2-propanol to afford 1,1,1,3,3,3-hexafluoro-2-(3'-fluoro-6-(4-(2-thiophenylsulfonyl)-1-piperazinyl)-3-biphenylyl)-2-propanol. $^1$H NMR (300 MHz, CD$_3$OD) δ 7.89 (d, J=4.2 Hz, 1H), 7.66 (s, 1H), 7.58 (d, J=2.6 Hz, 1H), 7.53 (s, 1H), 7.42-7.31 (m, 1H), 7.27 (d, J=4.0 Hz, 3H), 7.17 (d, J=8.6 Hz, 1H), 7.09-6.97 (m, 1H), 2.96 (br. s, 8H). m/z (ESI, +ve ion) 568.8 (M+H)+. GK-GKRP EC$_{50}$ (NADPH-coupled)=3.67 µM; GK-GKRP EC$_{50}$ (LC MS/MS)=1.84 µM.

Example 72

1,1,1,3,3,3-hexafluoro-2-(3-(3-pyridinyl)-4-(4-(2-thiophenylsulfonyl)-1-piperazinyl)phenyl)-2-propanol

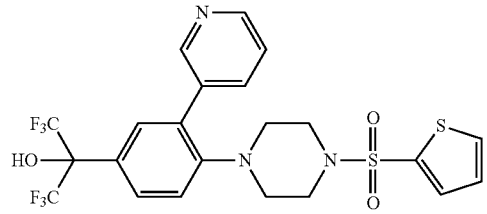 [SMILES: O=S(=O)(c1cccs1)N1CCN(c2ccc(C(O)(C(F)(F)F)C(F)(F)F)cc2-c2cccnc2)CC1]

Following the procedure outlined for Example 69, 3-pyridineboronic acid (21.33 mg, 0.173 mmol) was coupled to 2-(3-bromo-4-(4-(2-thiophenylsulfonyl)-1-piperazinyl)phenyl)-1,1,1,3,3,3-hexafluoro-2-propanol to afford 1,1,1,3,3,3-hexafluoro-2-(3-(3-pyridinyl)-4-(4-(2-thiophenylsulfonyl)-1-piperazinyl)phenyl)-2-propanol. $^1$H NMR (400 MHz, CD$_3$OD) δ 8.67 (d, J=1.6 Hz, 1H), 8.47 (dd, J=4.9, 1.6 Hz, 1H), 8.02-7.94 (m, 1H), 7.89 (dd, J=5.1, 1.2 Hz, 1H), 7.71 (d, J=9.2 Hz, 1H), 7.60-7.53 (m, 2H), 7.43 (dd, J=7.8, 4.9 Hz, 1H), 7.31-7.22 (m, 2H), 2.97 (s, 8H). m/z (ESI, +ve ion) 551.6 (M+H)+. GK-GKRP EC$_{50}$ (NADPH-coupled)=0.775 µM; GK-GKRP EC$_{50}$ (LC MS/MS)=0.783 µM.

Example 73

1,1,1,3,3,3-hexafluoro-2-(3-(3-thiophenyl)-4-(4-(2-thiophenylsulfonyl)-1-piperazinyl)phenyl)-2-propanol

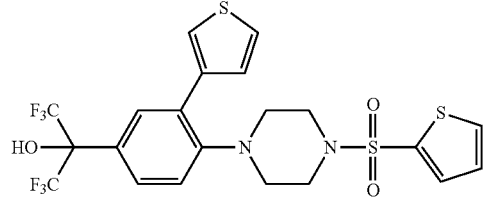 [SMILES: O=S(=O)(c1cccs1)N1CCN(c2ccc(C(O)(C(F)(F)F)C(F)(F)F)cc2-c2ccsc2)CC1]

Following the procedure outlined for Example 69, 3-thiopheneboronic acid (17.8 mg, 0.139 mmol, Sigma-Aldrich, St. Louis, Mo.) was coupled to 2-(3-bromo-4-(4-(2-thiophenylsulfonyl)-1-piperazinyl)phenyl)-1,1,1,3,3,3-hexafluoro-2-propanol, the reaction mixture was filtered, concentrated, and the residue was subjected to reverse-phase preparative HPLC using a Phenomenex Gemini-NX (C$_{18}$ 110 A column (100×21 mm, 5 µm) eluting with 0.1% NH$_4$OH in CH$_3$CN/H$_2$O (5% to 95% over 8 min)) to afford 1,1,1,3,3,3-hexafluoro-2-(3-(3-thiophenyl)-4-(4-(2-thiophenylsulfonyl)-1-piperazinyl)phenyl)-2-propanol. $^1$H NMR (400 MHz, DMSO-d$_6$) δ 8.09 (d, J=6.2 Hz, 1H), 7.69-7.62 (m, 2H), 7.53 (m, 3H), 7.38-7.29 (m, 2H), 7.19 (d, J=9.7 Hz, 1H), 2.99-2.94 (m, 4H), 2.93-2.87 (m, 4H). m/z (ESI, +ve ion) 557.0 (M+H)+. GK-GKRP EC$_{50}$ (NADPH-coupled)=3.50 µM; GK-GKRP EC$_{50}$ (LC MS/MS)=1.90 µM.

Example 74

2'-(4-(2-thiophenylsulfonyl)-1-piperazinyl)-5'-(2,2,2-trifluoro-1-hydroxy-1-(trifluoromethyl)ethyl)-4-biphenylol

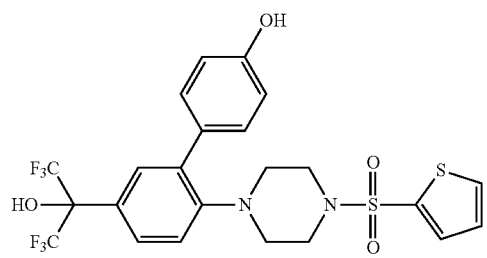 [SMILES: O=S(=O)(c1cccs1)N1CCN(c2ccc(C(O)(C(F)(F)F)C(F)(F)F)cc2-c2ccc(O)cc2)CC1]

Following the procedure outlined for Example 69, 4-hydroxyphenylboronic acid (19.2 mg, 0.139 mmol) was coupled to 2-(3-bromo-4-(4-(2-thiophenylsulfonyl)-1-piperazinyl)phenyl)-1,1,1,3,3,3-hexafluoro-2-propanol, the reaction mixture was filtered, concentrated, and the residue was subjected to reverse-phase preparative HPLC using a Phenomenex Gemini-NX ($C_{18}$ 110 Å column (100×21 mm, 5 μm) eluting with 0.1% $NH_4OH$ in $CH_3CN/H_2O$ (5% to 95% over 8 min)) to afford 2'44-(2-thiophenylsulfonyl)-1-piperazinyl)-5'-(2,2,2-trifluoro-1-hydroxy-1-(trifluoromethyl)ethyl)-4-biphenylol. $^1H$ NMR (400 MHz, DMSO-$d_6$) δ 8.09 (d, J=5.3 Hz, 1H), 7.65 (d, J=4.0 Hz, 1H), 7.53-7.46 (m, 1H), 7.38 (s, 1H), 7.36-7.25 (m, 3H), 7.13 (d, J=8.8 Hz, 1H), 6.72 (d, J=8.8 Hz, 2H), 2.89 (br. s, 8H). m/z (ESI, +ve ion) 567.0 $(M+H)^+$. GK-GKRP $EC_{50}$ (NADPH-coupled)=1.47 μM; GK-GKRP $EC_{50}$ (LC MS/MS)=1.37 μM.

Example 75

1,1,1-trifluoro-2-(3-((3-methyl-3-oxetanyl)ethynyl)-4-(4-(2-thiophenylsulfonyl)-1-piperazinyl)phenyl)-2-propanol

Step 1: tert-butyl 4-(4-(2,2,2-trifluoro-1-hydroxy-1-methylethyl)phenyl)-1-piperazinecarboxylate A 350 mL pressure tube was charged with 2-(4-bromophenyl)-1,1,1-trifluoro-2-propanol (7.22 g, 26.8 mmol, Example 27, step 1), N-Boc-piperazine (5.00 g, 26.8 mmol), sodium tert-butoxide (3.87 g, 40.3 mmol), 50 mL of toluene, dicyclohexyl(2',6'-diisopropoxybiphenyl-2-yl)phosphine (RuPhos) (1.253 g, 2.68 mmol, Strem Chemical Inc, Newburyport, Mass.) and tris(dibenzylideneacetone)dipalladium (0) (1.229 g, 1.342 mmol, Strem Chemical Inc, Newburyport, Mass.). The tube was sealed and heated at 100° C. for 2 h. After that time, the mixture was diluted with water (50 mL) and extracted with EtOAc (2×100 mL) to give a dark oil. Purification via column chromatography (120 g of silica gel, 0 to 40% EtOAc in hexanes) gave tert-butyl 4-(4-(2,2,2-trifluoro-1-hydroxy-1-methylethyl)phenyl)-1-piperazinecarboxylate (8.61 g) as an off-white brittle foam.

Step 2: tert-butyl 4-(2-bromo-4-(2,2,2-trifluoro-1-hydroxy-1-methylethyl)phenyl)-1-piperazinecarboxylate A 500 mL round-bottomed flask was charged with tert-butyl 4-(4-(2,2,2-trifluoro-1-hydroxy-1-methylethyl)phenyl)-1-piperazinecarboxylate (8.61 g, 23.0 mmol) and 100 mL of EtOH. To this was added bromine (1.30 mL, 25.3 mmol). After 15 min, the reaction was concentrated and purified via column chromatography (120 g of silica, 0 to 40% EtOAc in hexanes) to give tert-butyl 4-(2-bromo-4-(2,2,2-trifluoro-1-hydroxy-1-methylethyl)phenyl)-1-piperazinecarboxylate (6.50 g) as a tan foam.

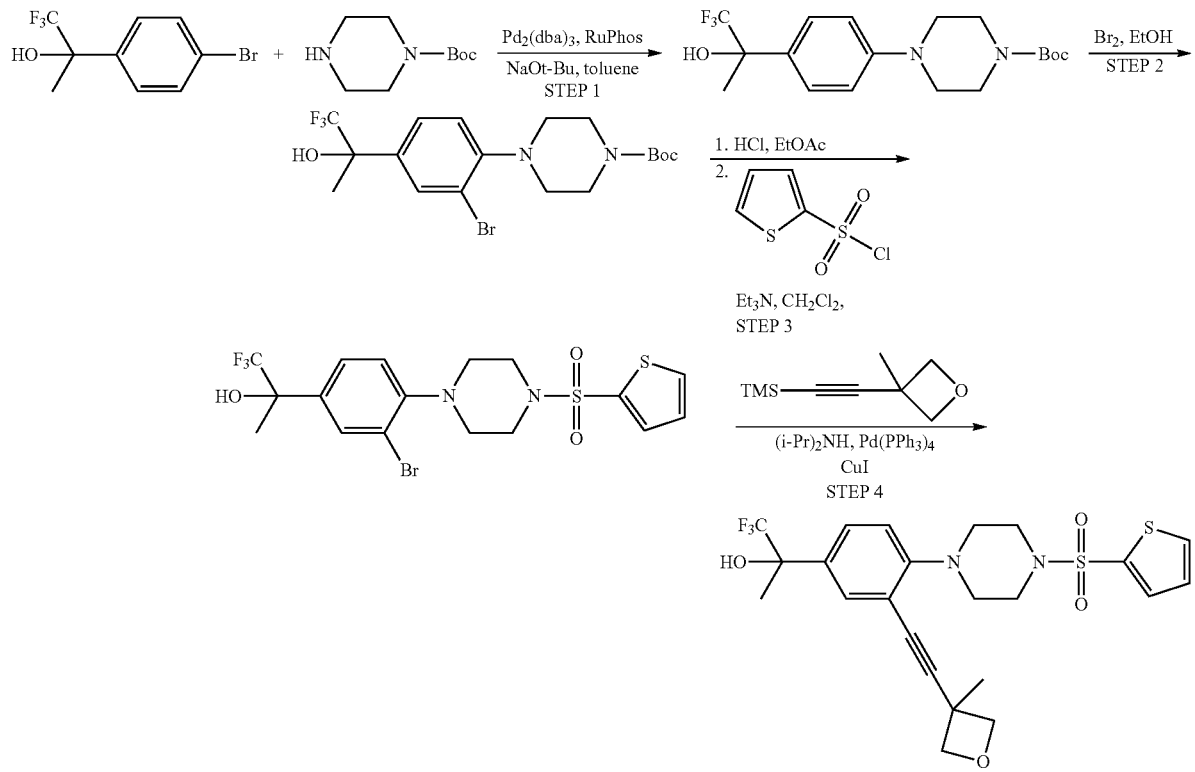

Step 3: 2-(3-bromo-4-(4-(2-thiophenylsulfonyl)-1-piperazinyl)phenyl)-1,1,1-trifluoro-2-propanol A 250 mL round-bottomed flask was charged with tert-butyl 4-(2-bromo-4-(2,2,2-trifluoro-1-hydroxy-1-methylethyl)phenyl)-1-piperazinecarboxylate (3.70 g, 8.16 mmol), 25 mL of EtOAc, and 8 mL of 4M HCl in dioxane (32 mmol). After heating at reflux for 30 min, the mixture was cooled and concentrated. The resulting viscous oil was dissolved in 30 mL of $CH_2Cl_2$ and triethylamine (3.98 mL, 28.6 mmol). At 0° C., 2-thiophenesulfonyl chloride (1.49 g, 8.16 mmol, Sigma-Aldrich, St. Louis, Mo.) was added at 0° C. After 15 min, the mixture was concentrated then re-dissolved in 5 mL of CH$_2$Cl$_2$, filtered, and purified via column chromatography (120 g of silica, 0 to 50% EtOAc in hexanes) to give 2-(3-bromo-4-(4-(thiophen-2-ylsulfonyl)piperazin-1-yl)phenyl)-1,1,1-trifluoro-2-propanol (2.75 g) as a white solid.

Step 4: 1,1,1-trifluoro-2-(3-((3-methyl-3-oxetanyl)ethynyl)-4-(4-(2-thiophenylsulfonyl)-1-piperazinyl)phenyl)-2-propanol A 20 mL vial was charged with 2-(3-bromo-4-(4-(thiophen-2-ylsulfonyl)piperazin-1-yl)phenyl)-1,1,1-trifluoro-2-propanol (0.500 g, 1.00 mmol), diisopropylamine (2.14 mL, 15.0 mmol), 2 mL of DMF, tetrakis(triphenylphosphine)palladium (0) (0.116 g, 0.100 mmol, Strem Chemical Inc, Newburyport, Mass.), copper (I) iodide (0.019 g, 0.100 mmol, Strem Chemical Inc, Newburyport, Mass.), and trimethyl((3-methyloxetan-3-yl)ethynyl)silane (0.506 g, 3.00 mmol, published PCT patent application no. WO2010030954). The vial was sealed and heated at 100° C. for 3 h. After that time, an additional 20 mol % of both tetrakis(triphenylphosphine)palladium (0) and copper (I) iodide were added and heating was continued for an additional 12 h. The mixture was concentrated and purified by column chromatography (40 g of silica, 0 to 60% EtOAc in hexanes) to give 1,1,1-trifluoro-2-(3-((3-methyl-3-oxetanyl)ethynyl)-4-(4-(2-thiophenylsulfonyl)-1-piperazinyl)phenyl)-2-propanol (0.150 g) as a mixture of two enantiomers.

(2R)-1,1,1-trifluoro-2-(3-((3-methyl-3-oxetanyl)ethynyl)-4-(4-(2-thiophenylsulfonyl)-1-piperazinyl)phenyl)-2-propanol; (2S)-1,1,1-trifluoro-2-(3-((3-methyl-3-oxetanyl)ethynyl)-4-(4-(2-thiophenylsulfonyl)-1-piperazinyl)phenyl)-2-propanol. $^1$H NMR (400 MHz, CD$_3$OD) δ 7.92 (dd, J=1.2, 5.1 Hz, 1H), 7.67 (dd, J=1.2, 3.7 Hz, 1H), 7.58 (d, J=2.0 Hz, 1H), 7.50 (s, 1H), 7.29 (dd, J=3.8, 5.0 Hz, 1H), 7.01 (d, J=8.6 Hz, 1H), 4.76 (d, J=5.5 Hz, 2H), 4.48 (d, J=5.5 Hz, 2H), 3.31-3.25 (m, 4H), 3.25-3.15 (m, 4H), 1.71-1.67 (m, 3H), 1.64 (s, 3H).

m/z (ESI, +ve ion) 515.0 (M+H)$^+$. GK-GKRP EC$_{50}$ (NADPH-coupled)=2.90 µM; GK-GKRP EC$_{50}$ (LC MS/MS)=2.80 µM.

Example 76

1,1,1-trifluoro-2-(4-(2-(4-pyridinylmethyl)-4-(2-thiophenylsulfonyl)-1-piperazinyl)phenyl)-2-propanol trifluoroacetate

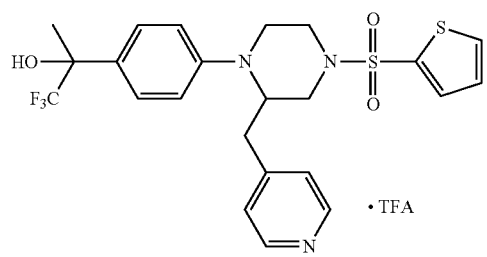 [SMILES: CC(O)(c1ccc(N2CCN(S(=O)(=O)c3cccs3)CC2Cc2ccncc2)cc1)C(F)(F)F]

Following the procedure listed for the Example 76, N-(tert-butoxycarbonyl)-3-(4-pyridinyl)-L-alanine (PepTech Corp., Burlington, Mass.) delivered 1,1,1-trifluoro-2-(4-(2-(4-pyridinylmethyl)-4-(2-thiophenylsulfonyl)-1-piperazinyl)phenyl)-2-propanol trifluoroacetate as a mixture of four isomers.

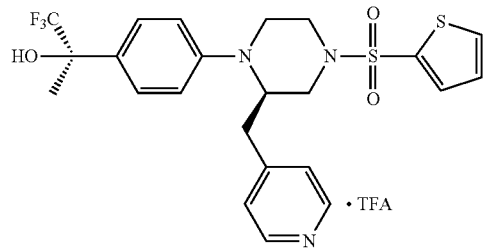

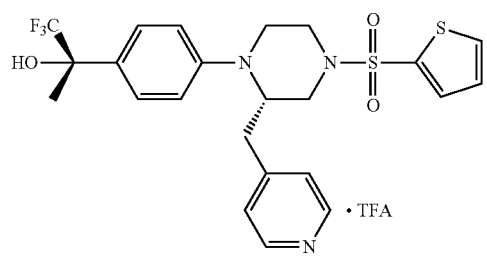

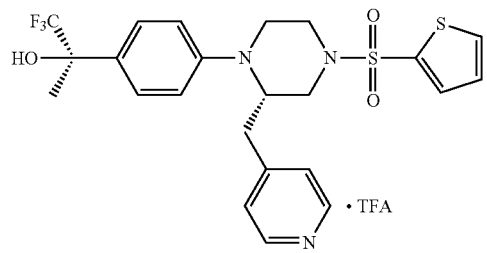

193

-continued

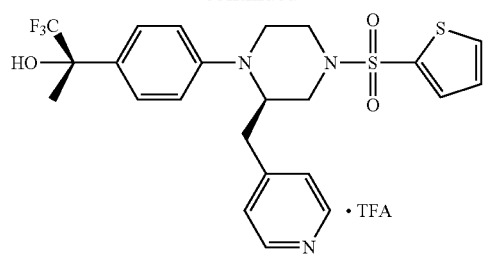

·TFA (2R)-1,1,1-trifluoro-2-(4-((2R)-2-(4-pyridinylmethyl)-4-(2-thiophenylsulfonyl)-1-piperazinyl)phenyl)-2-propanol trifluoroacetate; (2R)-1,1,1-trifluoro-2-(4-((2S)-2-(4-pyridinylmethyl)-4-(2-thiophenylsulfonyl)-1-piperazinyl)phenyl)-2-propanol trifluoroacetate; (2S)-1,1,1-trifluoro-2-(4-((2R)-2-(4-pyridinylmethyl)-4-(2-thiophenylsulfonyl)-1-piperazinyl)phenyl)-2-propanol trifluoroacetate; (2S)-1,1,1-trifluoro-2-(4-((2S)-2-(4-pyridinylmethyl)-4-(2-thiophenylsulfonyl)-1-piperazinyl)phenyl)-2-propanol trifluoroacetate. $^1$H NMR (300 MHz, CD$_3$OD) δ 8.61 (d, J=6.4 Hz, 2H), 7.80-7.93 (m, 3H), 7.62 (dd, J=3.8, 1.2 Hz, 1H), 7.43 (d, J=8.6 Hz, 2H), 7.20-7.29 (m, 1H), 6.95 (d, J=8.9 Hz, 2H), 4.48 (s, 1H), 3.86 (s, 1H), 3.45-3.63 (m, 3H), 3.34-3.45 (m, 1H), 3.16 (dd, J=13.0, 5.7 Hz, 1H), 2.53-2.71 (m, 2H), 1.67 (s, 3H). m/z (ESI, +ve ion) 512.2 (M+H)$^+$. GK-GKRP EC$_{50}$ (NADPH-coupled)=0.207 μM; GK-GKRP EC$_{50}$ (LC MS/MS)=0.522 μM.

Example 77

8-(((2S)-4-(2-thiophenylsulfonyl)-1-(4-(2,2,2-trifluoro-1-hydroxy-1-methylethyl)phenyl)-2-piperazinyl)methyl)-3-oxa-8-azabicyclo[3.2.1]octan-6-ol (endo)

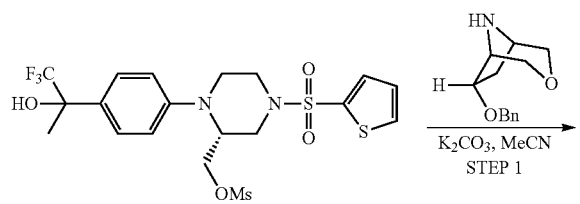

K$_2$CO$_3$, MeCN
STEP 1

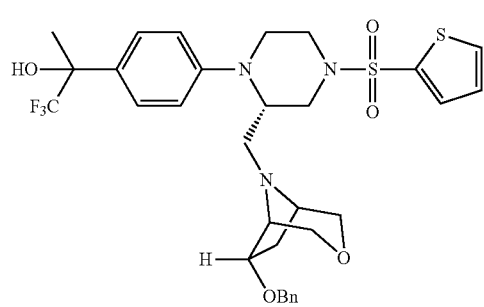

194

-continued

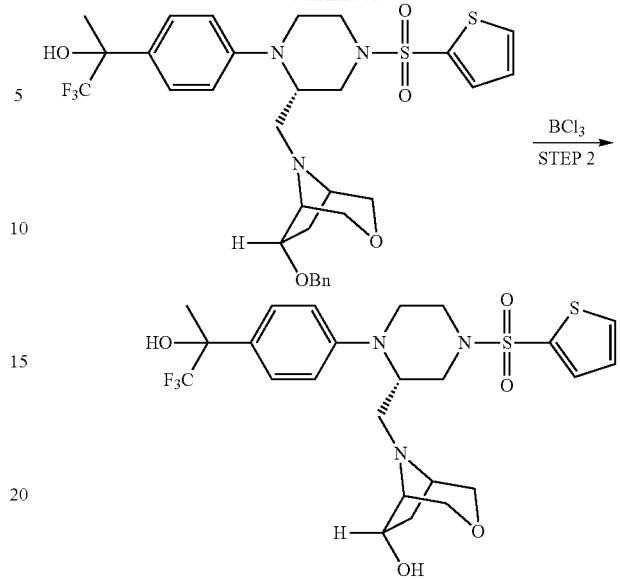

BCl$_3$
STEP 2

Step 1: 2-(4-((2S)-2-((6-(benzyloxy)-3-oxa-8-azabicyclo[3.2.1]oct-8-yl)methyl)-4-(2-thiophenylsulfonyl)-1-piperazinyl)phenyl)-1,1,1-trifluoro-2-propanol (endo)

A 10 mL vial was charged with ((2R)-4-(2-thiophenylsulfonyl)-1-(4-(2,2,2-trifluoro-1-hydroxy-1-methylethyl)phenyl)-2-piperazinyl)methyl methanesulfonate (0.207 g, 0.391 mmol, Intermediate B), 6-(benzyloxy)-3-oxa-8-azabicyclo[3.2.1]octane hydrochloride (endo) (0.100 g, 0.391 mmol, J. Org. Chem. 2010, 75, 1643), potassium carbonate (0.162 g, 1.173 mmol), and 3 mL of MeCN. The tube was sealed and heated in a microwave reactor (Emrys Optimizer Automated Microwave Synthesizer, Uppsala, Sweden) at 150° C. for 1 h. The mixture was diluted with EtOAc, filtered and the filtrate was concentrated and purified via column chromatography on silica gel (0 to 50% EA/Hex) to 2-(4-((2S)-2-((6-(benzyloxy)-3-oxa-8-azabicyclo[3.2.1]oct-8-yl)methyl)-4-(2-thiophenylsulfonyl)-1-piperazinyl)phenyl)-1,1,1-trifluoro-2-propanol as a mixture of four endo isomers (0.130 g).

Step 2: 8-(((2S)-4-(2-thiophenylsulfonyl)-1-(4-(2,2,2-trifluoro-1-hydroxy-1-methylethyl)phenyl)-2-piperazinyl)methyl)-3-oxa-8-azabicyclo[3.2.1]octa-6-ol (endo)

A 100 mL round-bottomed flask was charged with 2-(4-((2S)-2-((6-(benzyloxy)-3-oxa-8-azabicyclo[3.2.1]oct-8-yl)methyl)-4-(2-thiophenylsulfonyl)-1-piperazinyl)phenyl)-1,1,1-trifluoro-2-propanol (0.350 g, 0.537 mmol) and 5 mL of CH$_2$Cl$_2$. After cooling to 0° C., BCl$_3$ (1M in CH$_2$Cl$_2$, 2.15 mL, 2.15 mmol, Sigma-Aldrich, St. Louis, Mo.) was added drop-wise. This mixture was allowed to warm to room temperature then stirred for an additional 15 min. 10 mL of MeOH was added and the mixture was concentrated onto silica gel and purified via column chromatography (0-7% MeOH in CH$_2$Cl$_2$) to give 8-(((2S)-4-(2-thiophenylsulfonyl)-1-(4-(2,2,2-trifluoro-1-hydroxy-1-methylethyl)phenyl)-2-piperazinyl)methyl)-3-oxa-8-azabicyclo[3.2.1]octan-6-ol (endo) (0.210 g) as a mixture of four isomers. $^1$H NMR (400 MHz, CD$_3$OD) δ 7.92 (d, J=4.9 Hz, 1H), 7.67 (d, J=3.5 Hz, 1H), 7.54 (t, J=7.2 Hz, 2H), 7.28 (t, J=5.3 Hz, 1H), 7.06 (t, J=9.1 Hz, 2H), 4.43-4.62 (m, 2H), 3.39-4.24 (m, 13H), 2.66-2.98 (m, 2H), 2.55 (d, J=3.91 Hz, 1H), 1.69 (br. s., 3H). m/z (ESI, +ve ion) 562.1 (M+H)$^+$. GK-GKRP IC$_{50}$ (Binding)=0.028 μM; GK-GKRP EC$_{50}$ (LC MS/MS-2)=0.031 μM.

The individual isomers were isolated using chiral SFC purification (Chrialpak® ASH column (21×250 mm, 5 μm) using 20% ethanol (w/20 mM NH$_3$) in supercritical CO$_2$, total flow was 70 mL/min). This method delivered four products with both diastereomeric and enantiomeric excesses over 95%.

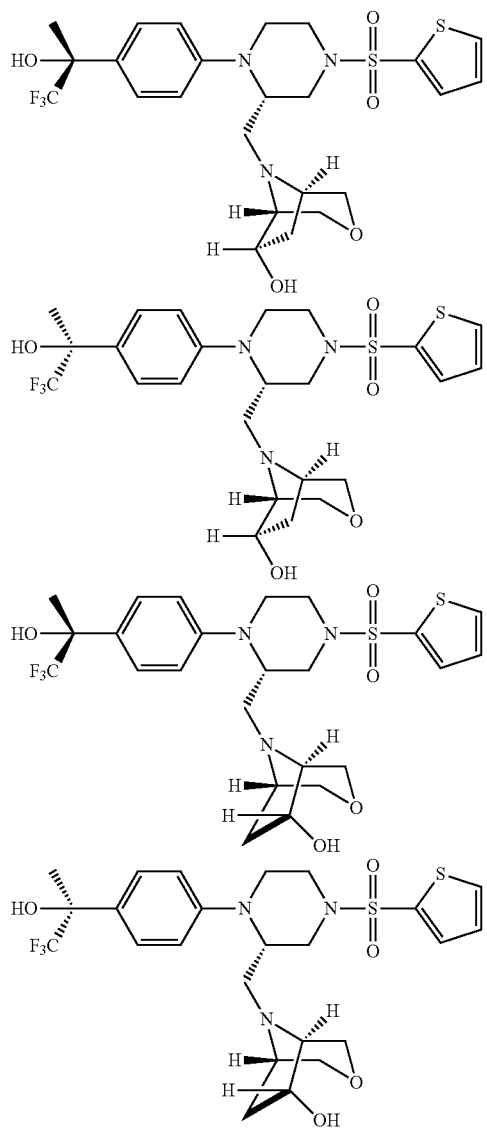

(1R,5R,6R)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol; (1R,5R,6R)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol; (1S,5S,6S)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol; (1S,5S,6S)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol.

First Eluting Peak (Peak #1)

$^1$H NMR (400 MHz, CD$_3$OD) δ=7.78 (d, J=4.9 Hz, 1H), 7.60-7.45 (m, 1H), 7.34 (d, J=8.8 Hz, 2H), 7.16 (t, J=4.4 Hz, 1H), 6.80 (s, 2H), 4.31-4.07 (m, 3H), 3.92 (d, J=11.2 Hz, 2H), 3.81-3.61 (m, 2H), 3.52 (s, 2H), 3.37 (br. s., 1H), 3.10 (d, J=3.5 Hz, 1H), 2.89 (br. s., 1H), 2.79-2.63 (m, 2H), 2.60-2.15 (m, 4H), 1.58 (s, 3H). m/z (ESI, +ve ion) 562.1 (M+H)$^+$. GK-GKRP IC$_{50}$ (Binding)=0.013 μM; GK-GKRP EC$_{50}$ (LC MS/MS-2)=0.038 μM.

Second Eluting Peak (Peak #2)

$^1$H NMR (400 MHz, CD$_3$OD) δ=7.90 (dd, J=1.2, 5.1 Hz, 1H), 7.66 (d, J=2.7 Hz, 1H), 7.46 (d, J=8.8 Hz, 2H), 7.34-7.21 (m, 1H), 6.91 (d, J=8.8 Hz, 2H), 4.42-4.27 (m, 1H), 4.09-3.93 (m, 2H), 3.88 (d, J=10.2 Hz, 1H), 3.79 (d, J=11.3 Hz, 1H), 3.69-3.56 (m, 2H), 3.47 (d, J=12.7 Hz, 1H), 3.39-3.35 (m, 1H), 3.22 (dt, J=3.5, 12.1 Hz, 1H), 3.01 (s, 1H), 2.89-2.74 (m, 2H), 2.70-2.48 (m, 4H), 2.47-2.30 (m, 1H), 1.69 (s, 3H). m/z (ESI, +ve ion) 562.1 (M+H)$^+$. GK-GKRP IC$_{50}$ (Binding)=0.011 μM; GK-GKRP EC$_{50}$ (LC MS/MS-2)=0.019 μM.

Third Eluting Peak (Peak #3)

$^1$H NMR (400 MHz, CD$_3$OD) δ=7.81-7.73 (m, 1H), 7.58-7.50 (m, 1H), 7.34 (d, J=8.6 Hz, 2H), 7.19-7.12 (m, 1H), 6.80 (d, J=8.8 Hz, 2H), 4.35-4.20 (m, 1H), 3.99 (d, J=11.2 Hz, 1H), 3.84-3.58 (m, 4H), 3.45 (d, J=10.6 Hz, 1H), 3.42-3.28 (m, 2H), 3.07 (dt, J=3.1, 12.0 Hz, 1H), 2.83 (d, J=6.8 Hz, 1H), 2.73 (d, J=6.1 Hz, 1H), 2.62 (dd, J=9.9, 12.6 Hz, 1H), 2.57-2.31 (m, 4H), 2.12 (m, 1H), 1.57 (s, 3H). m/z (ESI, +ve ion) 562.1 (M+H)$^+$. GK-GKRP IC$_{50}$ (Binding)=0.029 μM; GK-GKRP EC$_{50}$ (LC MS/MS-2)=0.058 μM.

Fourth Eluting Peak (Peak #4)

$^1$H NMR (400 MHz, CD$_3$OD) δ=7.78 (d, J=4.9 Hz, 1H), 7.55 (d, J=2.7 Hz, 1H), 7.36 (d, J=8.6 Hz, 2H), 7.21-7.08 (m, 1H), 6.82 (d, J=8.6 Hz, 2H), 4.33 (br. s., 1H), 4.01-3.58 (m, 5H), 3.56-3.43 (m, 1H), 3.42-3.30 (m, 2H), 3.16-2.38 (m, 7H), 2.25-2.03 (m, 1H), 1.65-1.44 (m, 4H). m/z (ESI, +ve ion) 562.1 (M+H)$^+$. GK-GKRP IC$_{50}$ (Binding)=0.042 μM; GK-GKRP EC$_{50}$ (LC MS/MS-2)=0.065 μM.

Example 78

8-(((2S)-4-(2-thiophenylsulfonyl)-1-(4-(2,2,2-trifluoro-1-hydroxy-1-methylethyl)phenyl)-2-piperazinyl)methyl)-3-oxa-8-azabicyclo[321]octan-6-ol (exo)

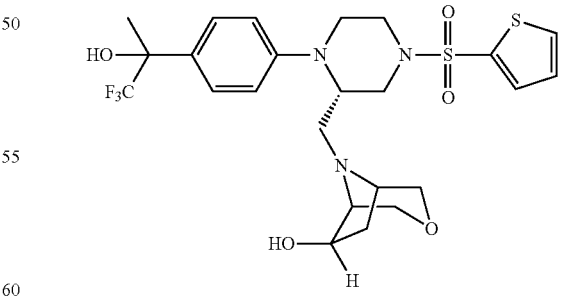

Following the scheme reported for Example 77, 3-oxa-8-azabicyclo[3.2.1]octan-6-ol hydrochloride (exo) (*J. Org. Chem.* 2010, 75, 1643) delivered 8-(((2S)-4-(2-thiophenylsulfonyl)-1-(4-(2,2,2-trifluoro-1-hydroxy-1-methylethyl)phenyl)-2-piperazinyl)methyl)-3-oxa-8-azabicyclo[3.2.1]octan-6-ol (exo, mixture of four isomers) after purification via column chromatography on silica gel (0 to 7% MeOH in CH$_2$Cl$_2$). $^1$H NMR (400 MHz, CD$_3$OD) δ=7.89 (d, J=5.1 Hz, 1H), 7.67 (br. s., 1H), 7.44 (dd, J=8.8, 12.5 Hz, 2H), 7.28 (t, J=4.0 Hz, 1H), 6.92 (dd, J=6.8, 8.8 Hz, 2H), 4.64-4.37 (m, 1H), 4.28-3.72 (m, 3H), 3.62-2.83 (m, 10H), 2.70-2.50 (m, 3H), 2.24-2.03 (m, 1H), 1.76-1.64 (m, 3H). m/z (ESI, +ve ion) 562.1 (M+H)$^+$. GK-GKRP IC$_{50}$ (Binding)=0.042 μM; GK-GKRP EC$_{50}$ (LC MS/MS-2)=0.050 μM.

The individual isomers were isolated using two sequential chiral SFC purifications. The first used a Chiralpak® column (21×250 mm, 5 μm) with 30% methanol (w/20 mM NH$_3$) at a flow rate of 70 mL/min. The second SFC purification used a Chiralcel OJH column (21×250 mm, 5 μm) with 25% MeOH (w/20 mM NH$_3$) and a flow rate of 70 mL/min. This sequence produced the four isomers with both diastereomeric and enantiomeric excesses over 95%.

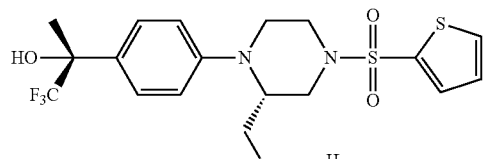

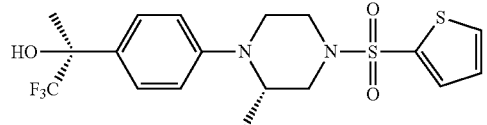

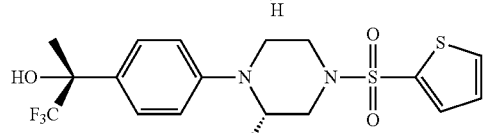

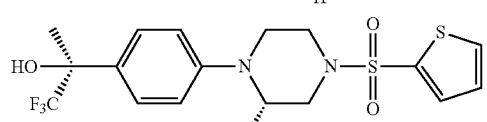

(1S,5S,6R)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol; (1S,5S,6R)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol; (1R,5R,6S)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol; (1R,5R,6S)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol First Eluting Peak (Peak #1)

$^1$H NMR (400 MHz, CD$_3$OD) δ=7.89 (d, J=5.1 Hz, 1H), 7.67 (d, J=2.5 Hz, 1H), 7.46 (d, J=8.8 Hz, 2H), 7.32-7.19 (m, 1H), 6.98-6.87 (m, 2H), 4.48 (dd, J=2.6, 7.1 Hz, 1H), 4.23 (d, J=11.2 Hz, 1H), 3.99-3.90 (m, J=8.4 Hz, 1H), 3.80 (d, J=10.4 Hz, 1H), 3.61-3.35 (m, 5H), 3.28-3.12 (m, 2H), 3.02 (dd, J=10.2, 13.1 Hz, 1H), 2.93 (s, 1H), 2.68-2.52 (m, 3H), 2.20-2.08 (m, 1H), 1.74-1.64 (m, 4H). m/z (ESI, +ve ion) 562.1 (M+H)$^+$. GK-GKRP IC$_{50}$ (Binding)=0.044 μM; GK-GKRP EC$_{50}$ (LC MS/MS-2)=0.146 μM.

Second Eluting Peak (Peak #2)

$^1$H NMR (400 MHz, CD$_3$OD) δ=7.89 (d, J=4.9 Hz, 1H), 7.67 (d, J=3.5 Hz, 1H), 7.46 (d, J=8.6 Hz, 2H), 7.28 (t, J=4.4 Hz, 1H), 6.93 (d, J=8.8 Hz, 2H), 4.48 (dd, J=2.5, 7.0 Hz, 1H), 4.23 (d, J=11.2 Hz, 1H), 3.94 (br. d, J=8.2 Hz, 1H), 3.80 (br. d, J=11.3 Hz, 1H), 3.60-3.35 (m, 5H), 3.27-3.14 (m, 2H), 3.02 (dd, J=10.2, 13.1 Hz, 1H), 2.93 (br. s, 1H), 2.69-2.52 (m, 3H), 2.13 (dd, J=7.2, 13.3 Hz, 1H), 1.74-1.69 (m, 4H). m/z (ESI, +ve ion) 562.1 (M+H)$^+$. GK-GKRP IC$_{50}$ (Binding)=0.049 μM; GK-GKRP EC$_{50}$ (LC MS/MS-2)=0.060 μM.

Third Eluting Peak (Peak #3)

$^1$H NMR (400 MHz, CD$_3$OD) δ=7.89 (d, J=4.9 Hz, 1H), 7.66 (d, J=3.7 Hz, 1H), 7.44 (s, 2H), 7.34-7.17 (m, 1H), 6.91 (d, J=8.8 Hz, 2H), 4.59-4.42 (m, 1H), 4.12 (d, J=11.0 Hz, 1H), 4.05 (br. s., 1H), 3.77 (d, J=9.8 Hz, 1H), 3.58-3.36 (m, 4H), 3.30-3.21 (m, 3H), 3.05-2.97 (m, 1H), 2.95 (s, 1H), 2.91-2.81 (m, 1H), 2.68-2.49 (m, 2H), 2.20 (dd, J=7.4, 13.3 Hz, 1H), 1.91-1.81 (m, 1H), 1.67 (s, 3H). m/z (ESI, +ve ion) 562.1 (M+H)$^+$. GK-GKRP IC$_{50}$ (Binding)=0.033 μM; GK-GKRP EC$_{50}$ (LC MS/MS-2)=0.036 μM Fourth Eluting Peak (Peak #4)

$^1$H NMR (400 MHz, CD$_3$OD) δ=7.77 (d, J=4.9 Hz, 1H), 7.54 (d, J=2.7 Hz, 1H), 7.32 (d, J=8.6 Hz, 2H), 7.22-7.04 (m, 1H), 6.81 (d, J=8.8 Hz, 2H), 4.39 (dd, J=2.9, 7.2 Hz, 1H), 4.10-3.87 (m, 2H), 3.73-3.57 (m, 1H), 3.50-2.72 (m, 10H), 2.58-2.37 (m, 2H), 2.12 (s, 1H), 1.78 (br. s., 1H), 1.61-1.51 (m, 3H). m/z (ESI, +ve ion) 562.1 (M+H)$^+$. GK-GKRP IC$_{50}$ (Binding)=0.04 μM; GK-GKRP EC$_{50}$ (LC MS/MS-2)=0.046 μM.

Example 79

8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol

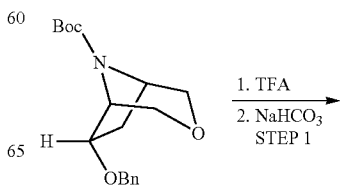

-continued

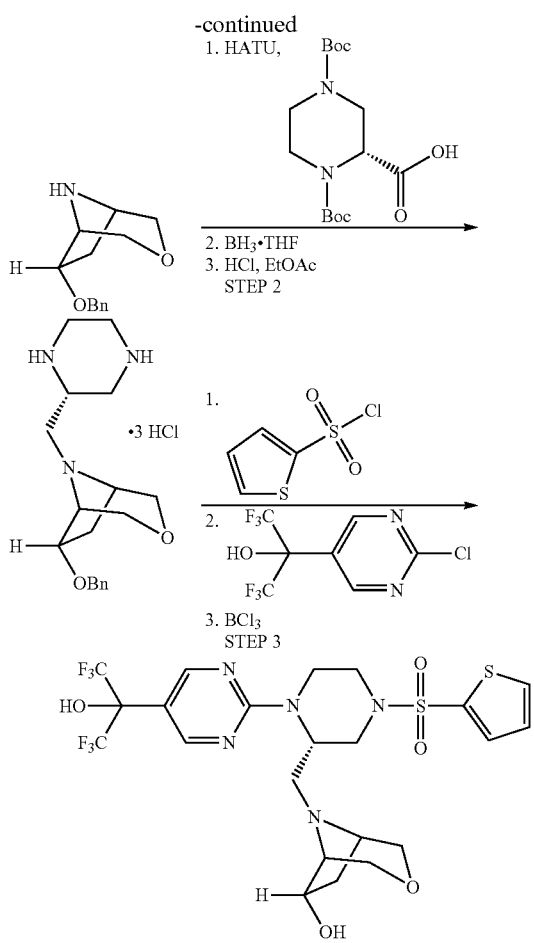

Step 1:
6-(benzyloxy)-3-oxa-8-azabicyclo[3.2.1]octane

A 250-mL round-bottomed flask was charged with tert-butyl 6-(benzyloxy)-3-oxa-8-azabicyclo[3.2.1]octane-8-carboxylate (4.40 g, 13.78 mmol *J. Org. Chem.* 2010, 75, 1643) and 15 mL of $CH_2Cl_2$. To this was added TFA (10.61 mL, 138 mmol). After 2 h at room temperature, the mixture was concentrated and diluted with saturated aqueous $NaHCO_3$ and $CH_2Cl_2$. The layers were separated, the organics were dried ($MgSO_4$), filtered, and concentrated to give a white solid. This solid was slurried with 50 mL of diethyl ether. The resulting white solid was collected by filtration to give 6-(benzyloxy)-3-oxa-8-azabicyclo[3.2.1]octane (3.02 g)

Step 2: 6-(benzyloxy)-8-((2R)-2-piperazinylmethyl)-3-oxa-8-azabicyclo[3.2.1]octane tris-hydrochloride A 100-mL round-bottomed flask was charged with (R)-1,4-bis(tert-butoxycarbonyl)piperazine-2-carboxylic acid (0.83 g, 2.5 mmol, ASW MedChem, New Brunswick, N.J.), 6-(benzyloxy)-3-oxa-8-azabicyclo[3.2.1]octane (0.50 g, 2.3 mmol,) HATU (1.04 g, 2.7 mmol), 5 mL of DMF and Hünig's base (0.60 mL, 3.4 mmol). After stirring at room temperature for 1 h, the mixture was diluted with water and extracted with EtOAc. The combined organics were washed with water, dried with $MgSO_4$, filtered, and concentrated to give (2R)-2-((6-(benzyloxy)-3-oxa-8-azabicyclo[3.2.1]oct-8-yl)carbonyl)-1,4-piperazinedicarboxylate (1.35 g) as a yellow oil. To this was added 20 mL of THF and $BH_3$·THF (1M solution in THF, 12.70 mL, 12.70 mmol, Sigma-Aldrich, St. Louis, Mo.). The mixture was heated at 50° C. for 2 h, then allowed to cool to room temperature and carefully quenched with 10 mL of MeOH. The solvent was removed and replaced with 30 mL of EtOAc. To this was added 10 mL of 4N HCl in dioxane. The mixture was heated at 70° C. for 2 h. The white precipitate which formed was collected by filtration and washed with 100 mL of EtOAc to give 6-(benzyloxy)-8-((2R)-2-piperazinylmethyl)-3-oxa-8-azabicyclo[3.2.1]octane as its tris hydrochloride salt (0.89 g).

Step 3: 8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol A 100-mL round-bottomed flask was charged with (6-(benzyloxy)-8-((2R)-2-piperazinylmethyl)-3-oxa-8-azabicyclo[3.2.1]octane tris hydrochloride (0.40 g, 0.94 mmol), 15 mL of $CH_2Cl_2$, and triethylamine (0.65 mL, 4.7 mmol). To this was added 2-thiophenesulfonyl chloride (0.19 g, 1.03 mmol, Sigma-Aldrich, St. Louis, Mo.). After stirring at room temperature for 15 min, the mixture was diluted with water and extracted with 50 mL of $CH_2Cl_2$. The combined extracts were dried ($MgSO_4$), filtered, and concentrated to give a viscous oil. Purification via column chromatography on silica gel (0 to 8% MeOH in $CH_2Cl_2$) gave the intermediate amine. To this amine was (2-chloro-5-pyrimidinyl)-1,1,1,3,3,3-hexafluoro-2-propanol (0.26 g, 0.94 mmol, Intermediate D), 5 ml, of dioxane, and Hünig's base (0.16 mL, 0.94 mmol). The mixture was heated at 85° C. for 12 h then concentrated and purified via column chromatography on silica gel (0-60% EtOAc in hexane) to give a white solid. This solid was dissolved in 5 mL of $CH_2Cl_2$ and cooled to 0° C. To this was added $BCl_3$ (1M in $CH_2Cl_2$, 0.94 mL, 0.94 mmol, Sigma-Aldrich, St. Louis, Mo.). After stirring at 0° C. for 1.5 h, the mixture was quenched with MeOH (5 mL) and concentrated. Purification via column chromatography on silica gel (0 to 10% MeOH in $CH_2Cl_2$) gave 8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol (0.18 g) as a white solid (mixture of two isomers). $^1H$ NMR (400 MHz, $CD_3OD$) δ=8.56 (s, 2H), 7.87 (d, J=4.9 Hz, 1H), 7.65 (d, J=2.9 Hz, 1H), 7.28-7.20 (m, 1H), 4.97-4.87 (br. s., 1H), 4.75-4.69 (m, 1H), 4.52-4.35 (m, 1H), 4.10-4.00 (m, 1H), 3.95-3.86 (m, 1H), 3.85-3.47 (m, 3H), 3.28-3.10 (m, 2H), 3.03-2.81 (m, 2H), 2.80-2.64 (m, 2H), 2.57-2.34 (m, 3H), 1.67-1.64 (m, 1H). m/z (ESI, +ve ion) 618.0 $(M+H)^+$. GK-GKRP $IC_{50}$ (Binding)=0.039 µM; GK-GKRP $EC_{50}$ (LC MS/MS-2)=0.058 µM.

The individual isomers were isolated using chiral SFC (Chiralpak® AS-H column (21×250 mm, 5 µm) using 30% iPrOH (w/20 mM $NH_3$) in supercritical $CO_2$, total flow was 70 mL/min). This produced two isomers with diastereomeric excess over 99%.

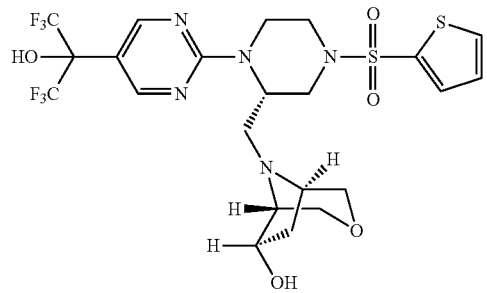

-continued

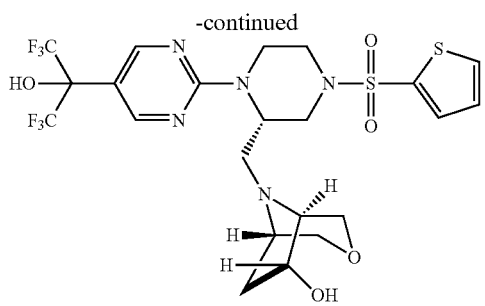

(1S,5S,6S)-8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol; (1R,5R,6R)-8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[321]octan-6-ol First Eluting Peak (Peak #1)

$^1$H NMR (400 MHz, CD$_3$OD) δ=8.55 (s, 2H), 7.87 (d, J=4.9 Hz, 1H), 7.64 (d, J=3.5 Hz, 1H), 7.35-7.17 (m, 1H), 4.94 (br. s., 1H), 4.70 (br. d, J=13.3 Hz, 1H), 4.52-4.35 (m, 1H), 4.00 (d, J=11.5 Hz, 1H), 3.92 (d, J=10.6 Hz, 1H), 3.82 (br. d, J=11.5 Hz, 1H), 3.64-3.47 (m, 2H), 3.40 (d, J=10.2 Hz, 1H), 3.23 (dt, J=3.4, 13.0 Hz, 1H), 3.10 (br. s., 1H), 2.99 (d, J=4.5 Hz, 1H), 2.89 (dd, J=8.1, 12.8 Hz, 1H), 2.80-2.64 (m, 1H), 2.57-2.39 (m, 3H), 1.64 (dd, J=3.7, 13.1 Hz, 1H). m/z (ESI, +ve ion) 618.0 (M+H)$^+$. GK-GKRP IC$_{50}$ (Binding)=0.049 μM; GK-GKRP EC$_{50}$ (LC MS/MS-2)=0.050 μM.

Second Eluting Peak (Peak #2)

$^1$H NMR (400 MHz, CD$_3$OD) δ=8.56 (s, 2H), 7.87 (d, J=4.9 Hz, 1H), 7.65 (d, J=2.9 Hz, 1H), 7.28-7.20 (m, 1H), 4.87 (br. s., 1H), 4.72 (d, J=14.1 Hz, 1H), 4.49 (br. s., 1H), 4.10 (d, J=11.2 Hz, 1H), 3.95-3.86 (m, 1H), 3.85-3.71 (m, 2H), 3.61-3.43 (m, 2H), 3.28-3.10 (m, 2H), 3.03-2.81 (m, 2H), 2.70 (br. s., 1H), 2.57-2.34 (m, 3H), 1.66 (br. d, J=11.2 Hz, 1H). m/z (ESI, +ve ion) 618.0 (M+H)$^+$. GK-GKRP IC$_{50}$ (Binding)=0.032 μM; GK-GKRP EC$_{50}$ (LC MS/MS-2)=0.073 μM.

Example 80

8-(((2S)-4-(phenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol

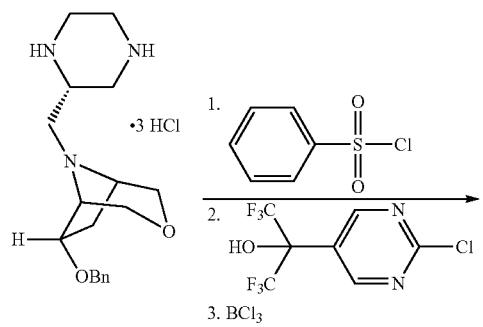

A 100-mL round-bottomed flask was charged with (6-(benzyloxy)-8-((2R)-2-piperazinylmethyl)-3-oxa-8-azabicyclo[3.2.1]octane tris-hydrochloride (0.350 g, 0.820 mmol, Example 79, Step 2), triethylamine (0.514 mL, 3.69 mmol), and 10 mL of CH$_2$Cl$_2$. To this was added benzenesulfonyl chloride (0.106 mL, 0.820 mmol, Sigma-Aldrich, St. Louis, Mo.). After 10 min, the mixture was diluted with water and extracted with CH$_2$Cl$_2$. The combined organics were dried (MgSO$_4$), filtered, concentrated and purified by column chromatography on silica gel (0-6% MeOH/CH$_2$Cl$_2$) to give the intermediate amine. To this was added (2-chloro-5-pyrimidinyl)-1,1,1,3,3,3-hexafluoro-2-propanol (0.35 g, 1.23 mmol), 3 mL of dioxane, and Hünig's base (0.143 mL, 0.820 mmol). This mixture was heated at 85° C. for 12 h then concentrated and purified via column chromatography on silica gel (0 to 60% EtOAc in hexanes) to give the intermediate benzyl protected alcohol (0.215 g). To this oil was dissolved in 10 mL of CH$_2$Cl$_2$. After cooling to 0° C., BCl$_3$ (1M in CH$_2$Cl$_2$, 1.25 mL, 1.25 mmol, Sigma-Aldrich, St. Louis, Mo.) was added. The mixture was stirred at 0° C. for 30 min then 5 mL of MeOH was added. The reaction was concentrated and the resulting solid was slurried with ether. The solid was collected by filtration to give 8-(((2S)-4-(phenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol (0.135 g) as a mixture of two isomers.

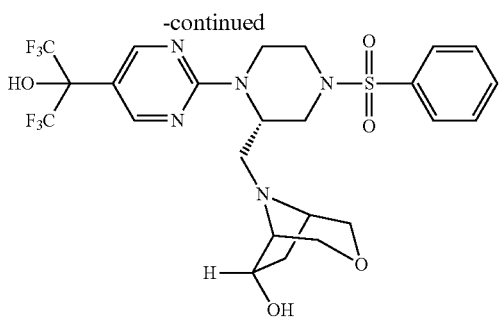

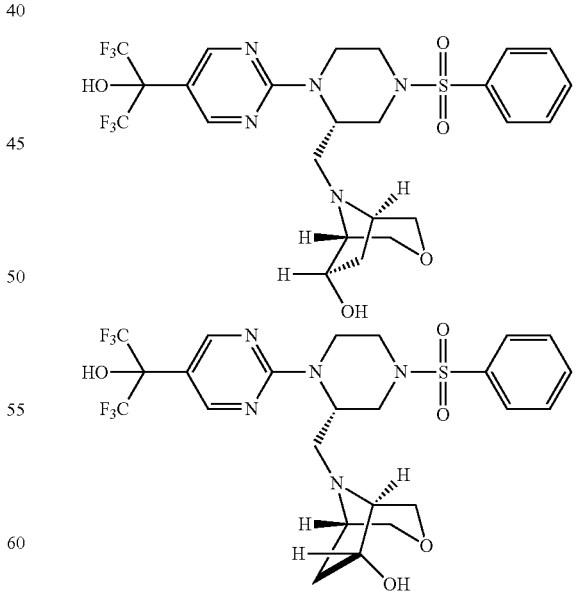

(1R,5R,6R)-8-(((2S)-4-(phenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol and (1S,5S,6S)-8-(((2S)-4-(phenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol. $^1$H NMR (400 MHz, CD$_3$OD) δ=8.66 (s, 2H), 7.90-7.50 (m, 5H), 5.39 (br. s., 1H), 4.92 (s, 2H), 4.57-3.65 (m, 9H), 3.59-3.39 (m, 2H), 3.00-2.71 (m, 1H), 2.67-2.54 (m, 1H), 2.47-2.36 (m, 1H), 2.09-2.01 (m, 1H). m/z (ESI, +ve ion) 612.2 (M+H)$^+$. GK-GKRP IC$_{50}$ (Binding)=0.125 µM; GK-GKRP EC$_{50}$ (LC MS/MS-2)=0.136 µM.

Example 81

8-(((2S)-4-(1,3-thiazol-2-ylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol

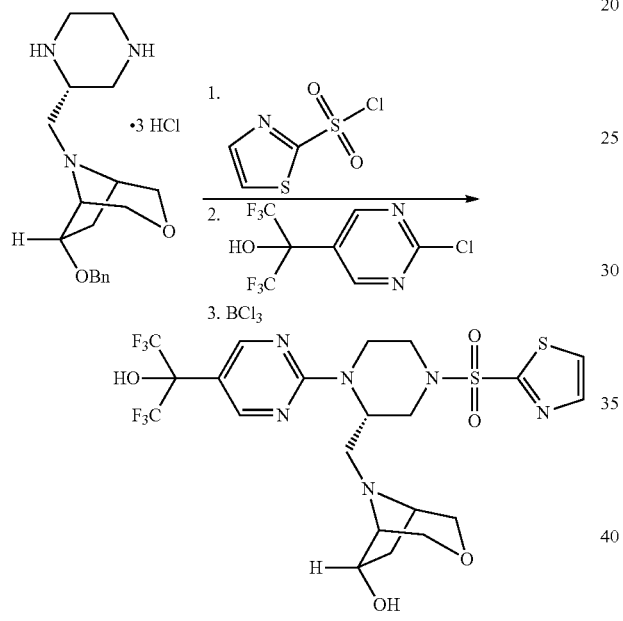

A 100-mL round-bottomed was charged with 6-(benzyloxy)-8-((2R)-2-piperazinylmethyl)-3-oxa-8-azabicyclo[3.2.1]octane tris-hydrochloride (0.400 g, 0.937 mmol, Example 79, Step 2), 10 mL of CH$_2$Cl$_2$, and thiazole-2-sulfonyl chloride (0.210 g, 1.031 mmol, *Bioorg. Med. Chem.*, 2006, 14, 6628). The mixture was diluted with water and extracted with EtOAc. The combined organics were dried (MgSO$_4$), filtered, and concentrated to give an oil. Purification via column chromatography on silica gel (0 to 10% MeOH in CH$_2$Cl$_2$, delivered the intermediate amine. To this was added 2-(2-chloropyrimidin-5-yl)-1,1,1,3,3,3-hexafluoro-2-propanol (0.066 g, 0.23 mmol, Intermediate D), 2 mL of dioxane, and Hünig's base (0.049 mL, 0.281 mmol). The mixture was heated at 85° C. for 12 h then cooled to room temperature and purified by column chromatography on silica gel (0 to 50% EtOAc in hexanes) to give the intermediate benzyl protected alcohol. To this was added 4 mL of CH$_2$Cl$_2$ and BCl$_3$ (1M in CH$_2$Cl$_2$, 0.937 mL, 0.937 mmol, Sigma-Aldrich, St. Louis, Mo.). After 30 min at room temperature, 5 mL of MeOH was added and the mixture was concentrated and purified by column chromatography on silica gel (0 to 10% MeOH in CH$_2$Cl$_2$) to give 8-(((S)-1-(5-(1,1,1,3,3,3-hexafluoro-2-hydroxypropan-2-yl)pyrimidin-2-yl)-4-(thiazol-2-ylsulfonyl)piperazin-2-yl)methyl)-3-oxa-8-azabicyclo[3.2.1]octan-6-ol (0.015 g) as a mixture of two isomers.

(1R,5R,6R)-8-(((2S)-4-(1,3-thiazol-2-ylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol and (1S,5S,6S)-8-(((2S)-4-(1,3-thiazol-2-ylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol.

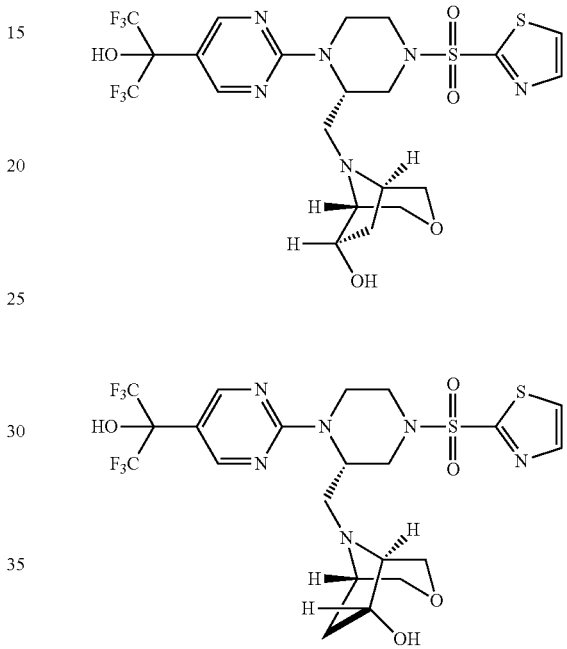

$^1$H NMR (400 MHz, CD$_3$OD) δ=8.45 (s, 2H), 7.96-7.94 (m, 1H), 7.88 (s, 1H), 4.84 (br. s., 1H), 4.61 (br. d, J=12.7 Hz, 1H), 4.44-4.28 (m, 1H), 4.18-3.96 (m, 1H), 3.89-3.58 (m, 2H), 3.53-3.25 (m, 3H), 3.17-2.68 (m, 6H), 2.63-2.49 (m, 1H), 2.42-2.22 (m, 1H), 1.58-1.50 (m 1H). m/z (ESI, +ve ion) 619.1 (M+H)$^+$. GK-GKRP IC$_{50}$ (Binding)=0.177 µM; GK-GKRP EC$_{50}$ (LC MS/MS-2)=0.287 µM.

Example 82

1,1,1,3,3,3-hexafluoro-2-(2-((2S)-2-(((3S)-3-methyl-4-morpholinyl)methyl)-4-(2-thiophenylsulfonyl)-1-piperazinyl)-5-pyrimidinyl)-2-propanol

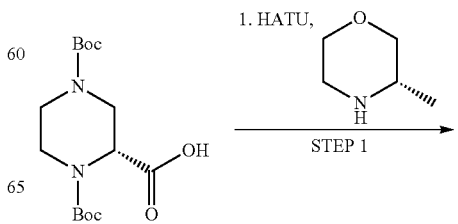

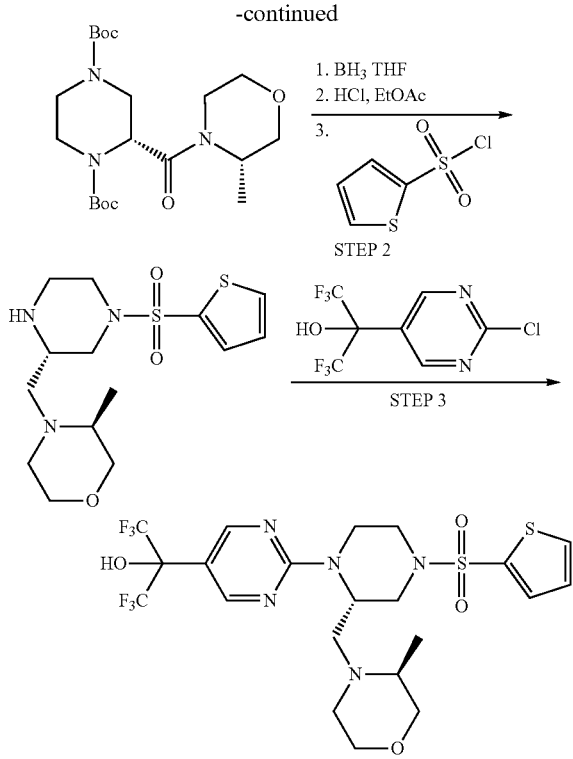

Step 1: (2R)-2-(((3S)-3-methyl-4-morpholinyl)carbonyl)-1,4-piperazinedicarboxylate A 2 L round-bottomed flask was charged with ((S)-3-methylmorpholine (10.10 g, 100 mmol, Synthetech, Albany, Oreg.), HATU (39.7 g, 104 mmol), (R)-1,4-bis(tert-butoxycarbonyl)piperazine-2-carboxylic acid (30.0 g, 91 mmol, ASW MedChem, Inc, New Brunswick, N.J.), and 100 mL of DMF. To this was added Hünig's base (20.3 mL, 114 mmol). After stirring at room temperature for 1 h, the mixture was diluted with water (1 L) and then extracted with 750 mL of ether. The organic layer was separated and washed with water (4×500 mL), saturated is aqueous NaHCO$_3$ (250 mL), brine (250 mL), dried with MgSO$_4$, filtered, and concentrated to give (2R)-2-(((3S)-3-methyl-4-morpholinyl)carbonyl)-1,4-piperazinedicarboxylate (31.83 g) as a white solid.

Step 2: (3S)-3-methyl-4-(((2S)-4-(2-thiophenylsulfonyl)-2-piperazinyl)methyl)morpholine A 1 L round-bottomed flask was charged with ((2R)-2-(((3S)-3-methyl-4-morpholinyl)carbonyl)-1,4-piperazinedicarboxylate (33.76 g, 82 mmol), and 100 mL of THF. To this was added BH$_3$·THF (1M in THF, 327 mL, 327 mmol, Sigma-Aldrich, St. Louis, Mo.). The mixture was heated at 50° C. for 2 h, then cooled to 0° C. and slowly quenched with 100 mL of MeOH. The mixture was concentrated in vacuo and then diluted with 200 mL of EtOAc. To this was added 100 mL of 4N HCl in dioxane. The mixture was heated at 70° C. for 2.5 h and then the resulting white precipitate was collected by filtration to give the amine tris-HCl salt. This solid was suspended in 200 mL of CH$_2$Cl$_2$ and triethylamine (57.0 mL, 408 mmol). After cooling to 0° C., 2-thiophenesulfonyl chloride (14.9 g, 82 mmol, Sigma-Aldrich, St. Louis, Mo.) was added. The mixture was stirred at room temperature for 1 h and then diluted with water and extracted with EtOAc. The combined organics were dried (MgSO$_4$), filtered, and concentrated to give an oil. Purification via column chromatography on silica gel (0 to 10% MeOH in CH$_2$Cl$_2$) gave (3S)-3-methyl-4-(((2S)-4-(2-thiophenylsulfonyl)-2-piperazinyl)methyl)morpholine (20.15 g) as a white solid.

Step 3: 1,1,1,3,3,3-hexafluoro-2-(2-((2S)-2-(((3S)-3-methyl-4-morpholinyl)methyl)-4-(2-thiophenylsulfonyl)-1-piperazinyl)-5-pyrimidinyl)-2-propanol A 20 mL vial was charged with 2-(2-chloropyrimidin-5-yl)-1,1,1,3,3,3-hexafluoropropan-2-ol (0.104 g, 0.370 mmol, Intermediate D), (3S)-3-methyl-4-(425)-4-(2-thiophenylsulfonyl)-2-piperazinyl)methyl)morpholine (0.155 g, 0.450 mmol), 4 mL of dioxane, and triethylamine (0.18 mL, 1.30 mmol). The vial was sealed and heated at 100° C. for 8 h. The mixture was then concentrated and purified by column chromatography on silica gel (twice, 0 to 60% EtOAc in hexanes followed by 0 to 5% MeOH in CH$_2$Cl$_2$) to give 1,1,1,3,3,3-hexafluoro-2-(2-((2S)-2-(((3S)-3-methyl-4-morpholinyl)methyl)-4-(2-thiophenylsulfonyl)-1-piperazinyl)-5-pyrimidinyl)-2-propanol (0.065 g) as an off-white solid. $^1$H NMR (400 MHz, CD$_3$OD) δ=8.65-8.45 (m, 2H), 7.88 (dd, J=1.2, 5.1 Hz, 1H), 7.65 (dd, J=1.2, 3.7 Hz, 1H), 7.37-7.13 (m, 1H), 5.07-4.92 (m, 1H), 4.75 (d, J=13.3 Hz, 1H), 4.11 (d, J=11.3 Hz, 1H), 3.82 (br. s., 1H), 3.76-3.57 (m, 3H), 3.42 (d, J=12.3 Hz, 1H), 3.30-3.18 (m, 2H), 3.17-3.07 (m, 1H), 2.54-2.26 (m, 4H), 2.04 (d, J=9.8 Hz, 1H), 1.10 (d, J=6.3 Hz, 3H). m/z (ESI, +ve ion) 590.1 (M+H)$^+$. GK-GKRP IC$_{50}$ (Binding) =0.015 μM; GK-GKRP EC$_{50}$ (LC MS/MS-2)=0.026 μM.

Example 83

3,3,3-trifluoro-2-(4-((2S)-2-(((3S)-3-methyl-4-morpholinyl)methyl)-4-(2-thiophenylsulfonyl)-1-piperazinyl)phenyl)-1,2-propanediol

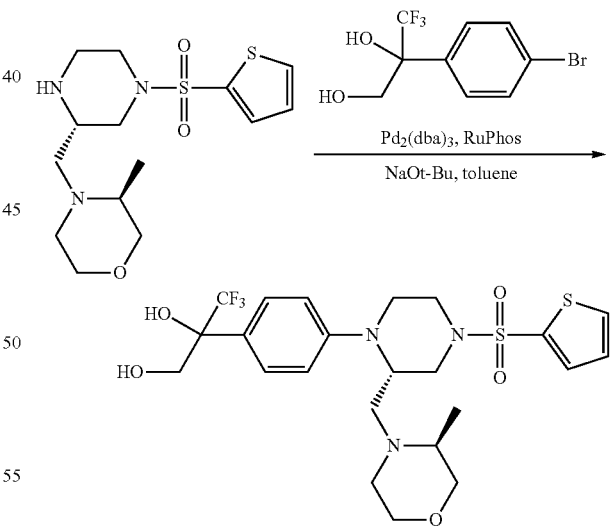

A 20-mL vial was charged with (3S)-3-methyl-4-(((2S)-4-(2-thiophenylsulfonyl)-2-piperazinyl)methyl)morpholine (0.750 g, 2.17 mmol, Example 82), 2-(4-bromophenyl)-3,3,3-trifluoro-1,2-propanediol (0.766 g, 2.69 mmol, Example 67), 6 mL of toluene and sodium tert-butoxide (1.426 mL, 11.65 mmol). After stirring at room temperature for 5 min, dicyclohexyl(2',6'-diisopropoxybiphenyl-2-yl)phosphine (RuPhos) (0.167 g, 0.359 mmol, Strem Chemicals Inc, Newburyport, Mass.) and tris(dibenzylideneacetone)dipalladium (0) (0.164 g, 0.179 mmol, Strem Chemicals Inc, Newburyport, Mass.) were added. The vial was sealed and heated at 100° C. for 1 h. After that time the mixture was cooled to room temperature, diluted with 50 mL MeOH, and filtered. The filtrate was concentrated, re-dissolved in 10 mL of $CH_2Cl_2$ and purified via column chromatography on silica gel (80 g, 0 to 75% EtOAc in hexanes) to give 3,3,3-trifluoro-2-(4-((2S)-2-(((3S)-3-methyl-4-morpholinyl)methyl)-4-(2-thiophenylsulfonyl)-1-piperazinyl)phenyl)-1,2-propanediol as a mixture of two isomers (0.109 g). $^1$H NMR (400 MHz, $CD_3OD$) δ=7.91-7.80 (m, 1H), 7.64 (dd, J=1.2, 3.7 Hz, 1H), 7.45 (d, J=8.8 Hz, 2H), 7.26 (dd, J=3.7, 4.9 Hz, 1H), 6.93 (d, J=9.0 Hz, 2H), 4.09-3.98 (m, 3H), 3.93-3.85 (m, 1H), 3.79-3.37 (m, 6H), 3.26-3.10 (m, 2H), 2.89-2.81 (m, 1H), 2.64-2.45 (m, 2H), 2.37-2.25 (m, 1H), 2.14-1.99 (m, 1H), 1.94-1.81 (m, 1H), 1.00 (d, J=6.3 Hz, 3H). m/z (ESI, +ve ion) 550.1 $(M+H)^+$. GK-GKRP $EC_{50}$ (LC MS/MS-2)=0.019 μM.

This individual isomers were separated using chiral SFC (Chiralpak® AS-H column (21×250 mm, 5 μm) using 30% MeOH (w/20 mM $NH_3$) in supercritical $CO_2$, total flow was 65 mL/min). This produced two isomers with diastereomeric excesses over 99%.

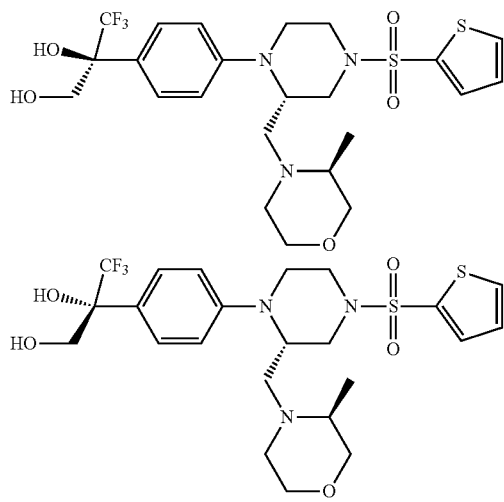

(2S)-3,3,3-trifluoro-2-(4-((2S)-2-(((3S)-3-methyl-4-morpholinyl)methyl)-4-(2-thiophenylsulfonyl)-1-piperazinyl)phenyl)-1,2-propane diol; (2R)-3,3,3-trifluoro-2-(4-((2S)-2-(((3S)-3-methyl-4-morpholinyl)methyl)-4-(2-thiophenylsulfonyl)-1-piperazinyl)phenyl)-1,2-propanediol
First Eluting Peak (Peak #1)
$^1$H NMR (400 MHz, $CD_3OD$) δ=7.88 (dd, J=1.2, 5.1 Hz, 1H), 7.64 (dd, J=1.2, 3.7 Hz, 1H), 7.46 (d, J=8.8 Hz, 2H), 7.27 (dd, J=3.8, 5.0 Hz, 1H), 6.93 (d, J=9.0 Hz, 2H), 4.09-3.98 (m, 3H), 3.93-3.85 (m, 1H), 3.79-3.40 (m, 6H), 3.26-3.10 (m, 2H), 2.89-2.81 (m, 1H), 2.64-2.45 (m, 2H), 2.37-2.25 (m, 1H), 2.14-1.99 (m, 1H), 1.94-1.81 (m, 1H), 1.00 (d, J=6.3 Hz, 3H). m/z (ESI, +ve ion) 550.1 $(M+H)^+$. GK-GKRP $IC_{50}$ (Binding)=0.032 μM; GK-GKRP $EC_{50}$ (LC MS/MS-2)=0.068 μM.
Second Eluting Peak (Peak #2)
$^1$H NMR (400 MHz, $CD_3OD$) δ=7.91-7.80 (m, 1H), 7.64 (dd, J=1.2, 3.7 Hz, 1H), 7.45 (d, J=8.8 Hz, 2H), 7.26 (dd, J=3.7, 4.9 Hz, 1H), 6.93 (d, J=9.0 Hz, 2H), 4.08-3.97 (m, 3H), 3.88 (d, J=11.7 Hz, 1H), 3.80-3.37 (m, 6H), 3.28-3.09 (m, 2H), 2.85 (d, J=11.7 Hz, 1H), 2.64-2.44 (m, 2H), 2.37-2.25 (m, 1H), 2.13-2.00 (m, 1H), 1.89 (br. s., 1H), 1.00 (d, J=6.3 Hz, 3H). m/z (ESI, +ve ion) 550.1 $(M+H)^+$. GK-GKRP $IC_{50}$ (Binding)=0.022 μM; GK-GKRP $EC_{50}$ (LC MS/MS-2)=0.016 μM.

Example 84

1,1,1-trifluoro-2-(4-((2S)-2-(2-oxa-6-azaspiro[3.3]hept-6-ylmethyl)-4-(2-thiophenylsulfonyl)-1-piperazinyl)phenyl)-2-propanol

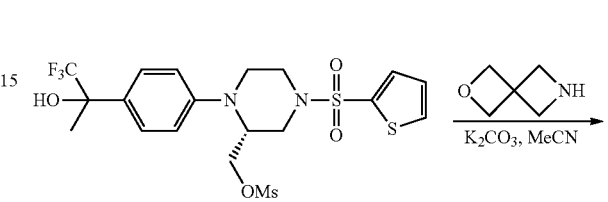

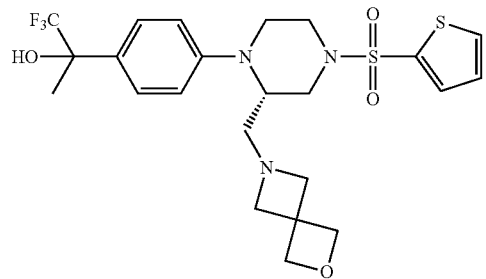

A 10-mL microwave vial was charged with ((2R)-4-(2-thiophenylsulfonyl)-1-(4-(2,2,2-trifluoro-1-hydroxy-1-methylethyl)phenyl)-2-piperazinyl)methyl methanesulfonate (0.140 g, 0.265 mmol, Intermediate B), 2-oxa-6-azaspiro[3.3]heptane (0.026 g, 0.265 mmol. ASW MedChem, Inc. New Brunswick, N.J.), potassium carbonate (0.040 g, 0.291 mmol), and 3 mL of MeCN. The tube was sealed and heated in a microwave (Emrys Optimizer Automated Microwave Synthesizer, Uppsala, Sweden) at 100° C. for 1 h. The mixture was diluted with 5 mL of $CH_2Cl_2$, filtered, and the filtrate was concentrated. The resulting oil was purified by column chromatography on silica gel (20-100% EtOAc in hexanes) to give 1,1,1-trifluoro-2-(4-((2S)-2-(2-oxa-6-azaspiro[3.3]hept-6-ylmethyl)-4-(2-thiophenylsulfonyl)-1-piperazinyl)phenyl)-2-propanol (0.045 g) as a mixture of two isomers:

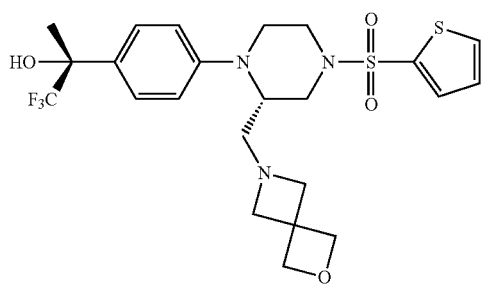

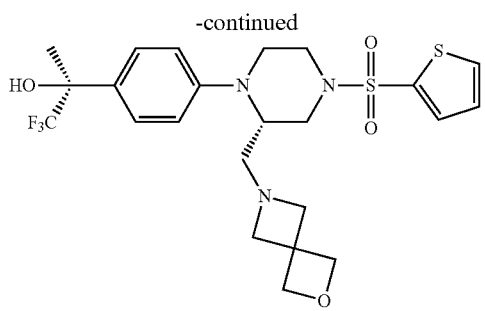

(2R)-1,1,1-trifluoro-2-(4-((2S)-2-(2-oxa-6-azaspiro[3.3]hept-6-ylmethyl)-4-(2-thiophenylsulfonyl)-1-piperazinyl)phenyl)-2-propanol and (2S)-1,1,1-trifluoro-2-(4-((2S)-2-(2-oxa-6-azaspiro[3.3]hept-6-ylmethyl)-4-(2-thiophenylsulfonyl)-1-piperazinyl)phenyl)-2-propanol.

$^1$H NMR (400 MHz, CD$_3$OD) δ=7.89 (d, J=5.1 Hz, 1H), 7.65 (d, J=3.7 Hz, 1H), 7.47 (d, J=8.8 Hz, 2H), 7.33-7.21 (m, 1H), 6.97-6.85 (m, 2H), 4.69 (br. s, 4H), 3.90-3.66 (m, 3H), 3.52-3.38 (m, 3H), 3.27-3.11 (m, 1H), 2.97-2.83 (m, 1H), 2.66 (dd, J=2.8, 11.4 Hz, 1H), 2.57 (dt, J=3.8, 11.4 Hz, 1H), 2.36 (br. d, J=12.1 Hz, 1H), 1.69 (s, 3H), 1.24-1.19 (m, 1H), 1.06-0.99 (m, 1H). m/z (ESI, +ve ion) 532.1 (M+H)$^+$. GK-GKRP IC$_{50}$ (Binding)=0.667 μM; GK-GKRP EC$_{50}$ (LC MS/MS-2)=0.659 μM.

Example 85

2-(4-((2S)-2-((1,1-dioxido-4-thiomorpholinyl)methyl)-4-(2-thiophenylsulfonyl)-1-piperazinyl)phenyl)-1,1,1-trifluoro-2-propanol

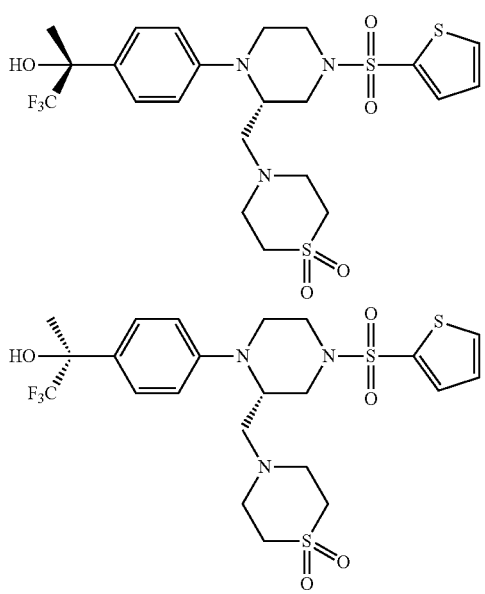

This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and thiomorpholine 1,1-dioxide (Synthech Development Company, Franklin Park, N.J.) followed by purification via column chromatography on silica gel (0-75% EtOAc in hexanes) delivered 2-(4-((2S)-2-((1,1-dioxido-4-thiomorpholinyl)methyl)-4-(2-thiophenylsulfonyl)-1-piperazinyl)phenyl)-1,1,1-trifluoro-2-propanol as a mixture of two isomers. (2R)-2-(4-((2S)-2-((1,1-dioxido-4-thiomorpholinyl)methyl)-4-(2-thiophenylsulfonyl)-1-piperazinyl)phenyl)-1,1,1-trifluoro-2-propanol and (2S)-2-(4-((2S)-2-((1,1-dioxido-4-thiomorpholinyl)methyl)-4-(2-thiophenylsulfonyl)-1-piperazinyl)phenyl)-1,1,1-trifluoro-2-propanol.

$^1$H NMR (400 MHz, CD$_3$OD) δ=7.91 (dd, J=1.3, 5.0 Hz, 1H), 7.68 (dd, J=1.4, 3.7 Hz, 1H), 7.48 (d, J=8.8 Hz, 2H), 7.29 (dd, J=3.7, 5.1 Hz, 1H), 6.98-6.92 (m, 2H), 4.15 (br. s, 1H), 3.98 (br. d, J=11.2 Hz, 1H), 3.83 (br. d, J=11.3 Hz, 1H), 3.47 (d, J=12.5 Hz, 1H), 3.32-3.22 (m, 1H), 3.09-2.75 (m, 9H), 2.74-2.50 (m, 3H), 1.70 (s, 3H). m/z (ESI, +ve ion) 567.8 (M+H)$^+$. GK-GKRP IC$_{50}$ (Binding)=0.350 μM; GK-GKRP EC$_{50}$ (LC MS/MS-2)=0.475 μM.

Example 86

1,1,1-trifluoro-2-(4-((2S)-2-((3-methyl-1,1-dioxido-4-thiomorpholinyl)methyl)-4-(2-thiophenylsulfonyl)-1-piperazinyl)phenyl)-2-propanol

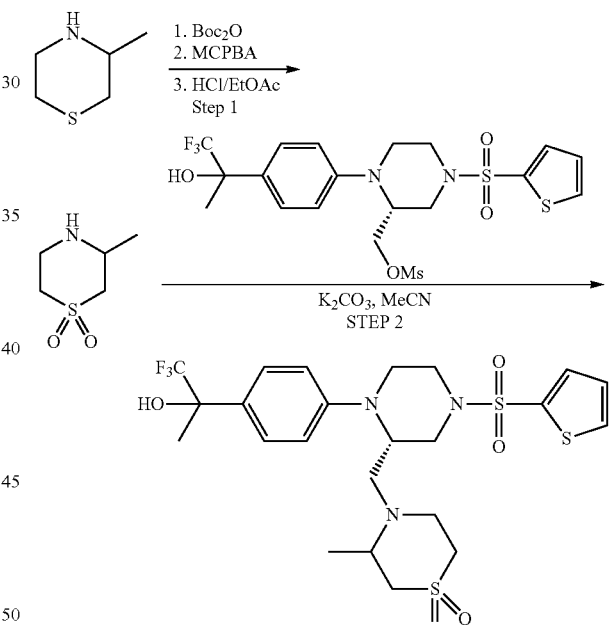

Step 1: 3-methylthiomorpholine 1,1-dioxide

A 250-mL round-bottomed flask was charged with 3-methylthiomorpholine (1.76 g, 15.0 mmol, J. Org. Chem. 1993, 58, 3905), 25 mL of MeOH, and Boc$_2$O (4.10 g, 18.8 mmol, Sigma-Aldrich, St. Louis, Mo.). After stirring at room temperature for 1 h, the mixture was concentrated to give the intermediate Boc-protected sulfide. To this was added 25 mL of CH$_2$Cl$_2$. After cooling to 0° C., mCPBA (70% by weight, 9.25 g, 37.5 mmol, Sigma-Aldrich, St. Louis, Mo.) was slowly added portion wise. After 2 h at 0° C., the mixture was filtered and the filtrate was concentrated. To this oil was added 25 mL of EtOAc and 20 mL of 4 M HCl in dioxane. This mixture was heated to 70° C. for 2 h and the resulting white solid was removed by filtration. The filtrate was diluted with EtOAc and saturated aqueous $K_2CO_3$. After stirring at room temperature for 1 h, the organics were separated, dried ($MgSO_4$), filtered and concentrated to give 3-methylthiomorpholine 1,1-dioxide (1.45 g) as a yellow oil.

Step 2: 1,1,1-trifluoro-2-(4-((2S)-2-((3-methyl-1,1-dioxido-4-thiomorpholinyl)methyl)-4-(2-thiophenylsulfonyl)-1-piperazinyl)phenyl)-2-propanol This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and 3-methylthiomorpholine 1,1-dioxide delivered 1,1,1-trifluoro-2-(4-((2S)-2-((3-methyl-1,1-dioxido-4-thiomorpholinyl)methyl)-4-(2-thiophenylsulfonyl)-1-piperazinyl)phenyl)-2-propanol after purification via column chromatography on silica gel (0-75% EtOAc in hexanes)

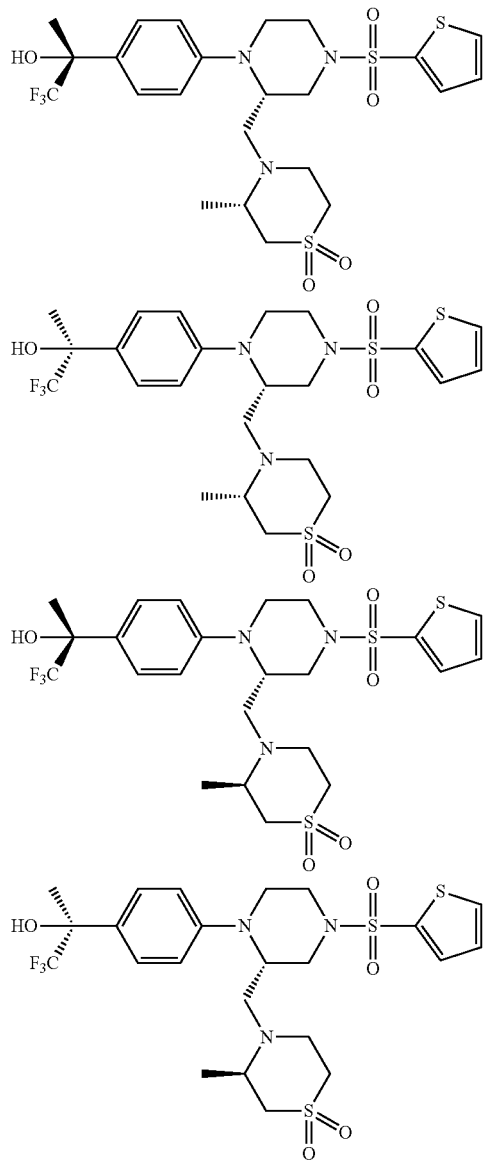

(2R)-1,1,1-trifluoro-2-(4-((2S)-2-(((3R)-3-methyl-1,1-dioxido-4-thiomorpholinyl)methyl)-4-(2-thiophenylsulfonyl)-1-piperazinyl)phenyl)-2-propanol; (2R)-1,1,1-trifluoro-2-(4-((2S)-2-(((3S)-3-methyl-1,1-dioxido-4-thiomorpholinyl)methyl)-4-(2-thiophenylsulfonyl)-1-piperazinyl)phenyl)-2-propanol; (2S)-1,1,1-trifluoro-2-(4-((2S)-2-(((3R)-3-methyl-1,1-dioxido-4-thiomorpholinyl)methyl)-4-(2-thiophenylsulfonyl)-1-piperazinyl)phenyl)-2-propanol; (2S)-1,1,1-trifluoro-2-(4-((2S)-2-(((3S)-3-methyl-1,1-dioxido-4-thiomorpholinyl)methyl)-4-(2-thiophenylsulfonyl)-1-piperazinyl)phenyl)-2-propanol $^1$H NMR (400 MHz, $CD_3OD$) δ=7.90 (dd, J=1.2, 5.1 Hz, 1H), 7.73-7.59 (m, 1H), 7.55-7.37 (m, 2H), 7.27 (dd, J=3.7, 4.9 Hz, 1H), 6.94 (dd, J=2.9, 9.0 Hz, 2H), 4.14-3.97 (m, 2H), 3.79 (d, J=11.0 Hz, 1H), 3.47-3.17 (m, 3H), 3.11-2.73 (m, 7H), 2.65-2.37 (m, 3H), 1.68 (s, 3H), 1.28-1.21 (m, 3H).). m/z (ESI, +ve ion) 581.9 $(M+H)^+$. GK-GKRP $IC_{50}$ (Binding)=0.061 μM; GK-GKRP $EC_{50}$ (LC MS/MS-2)=0.115 μM.

Example 87

2-(4-((2S)-2-((3-cyclopropyl-1,1-dioxido-4-thiomorpholinyl)methyl)-4-(2-thiophenylsulfonyl)-1-piperazinyl)phenyl)-1,1,1-trifluoro-2-propanol

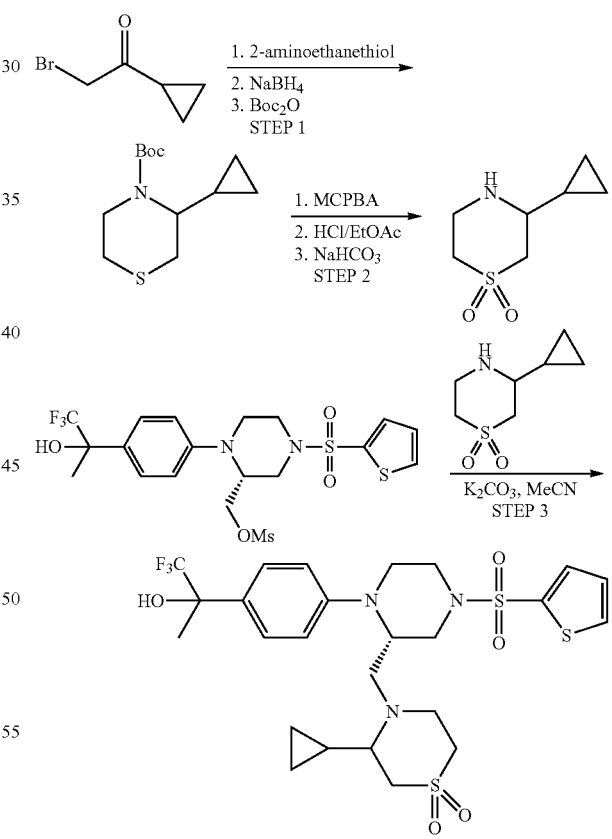

Step 1: tert-butyl 3-cyclopropyl-4-thiomorpholinecarboxylate

A 1 L round-bottomed flask was charged with 2-aminoethanethiol (15.0 g, 194 mmol, Sigma-Aldrich, St. Louis, Mo.) and 200 mL of MeOH. After cooling to 0° C., 2-bromo-1- cyclopropylethanone (31.7 g, 194 mmol, *Tetrahedron*, 1987, 43, 4609) was added drop-wise over 5 min. This mixture was stirred at 0° C. for 30 min, then NaBH$_4$ (7.36 g, 194 mmol) was added portion-wise. After 1 h, Boc$_2$O (42.4 g, 194 mmol, Sigma-Aldrich, St. Louis, Mo.) was added. After stirring at room temperature for 3 h, the mixture was concentrated and diluted with 200 mL EtOAc and 50 mL of water. The organics were separated, dried with MgSO$_4$, filtered and concentrated to give an oil. Purification via column chromatography on silica gel (0-15% EtOAc in hexanes) gave tert-butyl 3-cyclopropyl-4-thiomorpholinecarboxylate (40.0 g) as an oil that slowly solidified.

Step 2: 3-cyclopropylthiomorpholine 1,1-dioxide hydrochloride

A 500 mL round-bottomed flask was charged with tert-butyl 3-cyclopropyl-4-thiomorpholinecarboxylate (14.4 g, 59.2 mmol) and 100 mL of CH$_2$Cl$_2$. After cooling to 0° C., mCPBA (70% by weight, 29.2 g, 118 mmol) was added over 5 min. This mixture was stirred for 1 h and then filtered. The filtrate was concentrated then re-dissolved in 100 mL of EtOAc. To this was added 100 mL of 4M HCl in dioxane. After heating at 80° C. for 2 h, the white solid that precipitated by collected by filtration to give 3-cyclopropylthiomorpholine 1,1-dioxide hydrochloride (12.05 g)

A 100 mL round-bottomed flask was charged with 3-cyclopropylthiomorpholine 1,1-dioxide hydrochloride (1.00 g, 4.72 mmol) and 10 mL of EtOAc. To this was added 15 mL of saturated aqueous NaHCO$_3$. After stirring at room temperature for 15 min, the layers were separated. The organics were dried (MgSO$_4$), filtered, and concentrated to give 3-cyclopropylthiomorpholine 1,1-dioxide (0.800 g) as a colorless oil.

Step 3: 2-(4-((2S)-2-((3-cyclopropyl-1,1-dioxido-4-thiomorpholinyl)methyl)-4-(2-thiophenylsulfonyl)-1-piperazinyl)phenyl)-1,1,1-trifluoro-2-propanol This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and 3-cyclopropylthiomorpholine 1,1-dioxide followed by purification via column chromatography on silica gel (0 to 75% EtOAc in hexanes) delivered 2-(4-((2S)-2-((3-cyclopropyl-1,1-dioxido-4-thiomorpholinyl)methyl)-4-(2-thiophenylsulfonyl)-1-piperazinyl)phenyl)-1,1,1-trifluoro-2-propanol as a mixture of four isomers.

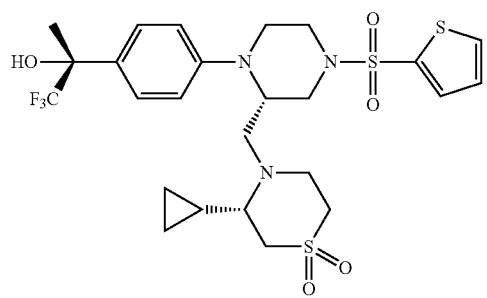

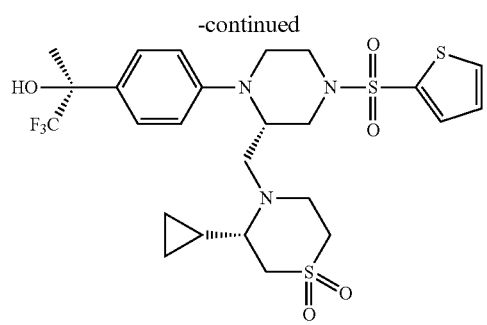

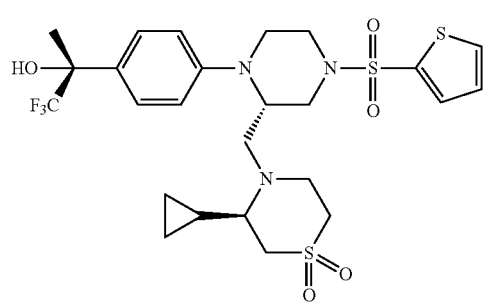

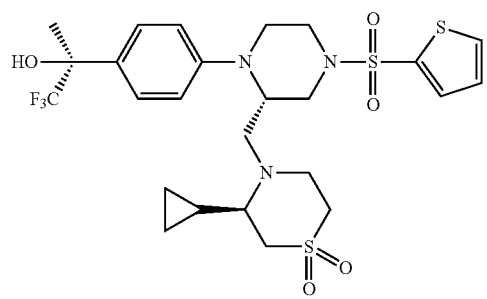

(2R)-2-(4-((2S)-2-(((3S)-3-cyclopropyl-1,1-dioxido-4-thiomorpholinyl)methyl)-4-(2-thiophenylsulfonyl)-1-piperazinyl)phenyl)-1,1,1-trifluoro-2-propanol; (2S)-2-(4-((2S)-2-(((3S)-3-cyclopropyl-1,1-dioxido-4-thiomorpholinyl)methyl)-4-(2-thiophenylsulfonyl)-1-piperazinyl)phenyl)-1,1,1-trifluoro-2-propanol; (2R)-2-(4-((2S)-2-(((3R)-3-cyclopropyl-1,1-dioxido-4-thiomorpholinyl)methyl)-4-(2-thiophenylsulfonyl)-1-piperazinyl)phenyl)-1,1,1-trifluoro-2-propanol; (2S)-2-(4-((2S)-2-(((3R)-3-cyclopropyl-1,1-dioxido-4-thiomorpholinyl)methyl)-4-(2-thiophenylsulfonyl)-1-piperazinyl)phenyl)-1,1,1-trifluoro-2-propanol $^1$H NMR (400 MHz, CD$_3$OD) δ=7.75 (dd, J=1.2, 4.9 Hz, 1H), 7.54-7.47 (m, 1H), 7.30 (d, J=8.4 Hz, 2H), 7.13 (dd, J=3.9, 4.9 Hz, 1H), 6.80 (dd, J=6.7, 8.8 Hz, 2H), 4.08-3.89 (m, 2H), 3.84-3.53 (m, 2H), 3.37-2.32 (m, 7H), 1.97-1.81 (m, 1H), 1.60-1.45 (m, 3H), 1.26-0.60 (m, 6H), 0.56--0.08 (m, 3H). m/z (ESI, +ve ion) 607.8 (M+H)$^+$. GK-GKRP IC$_{50}$ (Binding)=0.229 µM; GK-GKRP EC$_{50}$ (LC MS/MS-2)=0.246 µM.

Example 88

2-(4-(4-((5-amino-2-thiophenyl)sulfonyl)-1-piperazinyl)phenyl)-1,1,1,3,3,3-hexafluoro-2-propanol

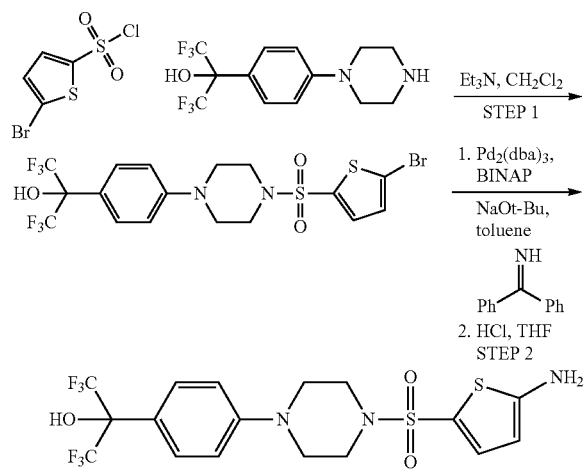

Step 1: 2-(4-(4-((5-bromo-2-thiophenyl)sulfonyl)-1-piperazinyl)phenyl)-1,1,1,3,3,3-hexafluoro-2-propanol A 100-mL round-bottomed was charged with 1,1,1,3,3,3-hexafluoro-2-(4-(1-piperazinyl)phenyl)-2-propanol (0.54 g, 1.65 mmol, published PCT patent application no. WO 2006/094842), 10 mL of $CH_2Cl_2$, and 5-bromo-2-thiophenesulfonyl chloride (0.43 g, 1.65 mmol, Sigma-Aldrich, St. Louis, Mo.). To this was added triethylamine (0.28 mL, 2.06 mmol). After 15 min at room temperature, the mixture was diluted with 10 mL of $CH_2Cl_2$ and filtered. The filtrate was concentrated and purified by column chromatography on silica gel (0-50% EtOAc in hexanes) to give 2-(4-(4-((5-bromo-2-thiophenyl)sulfonyl)-1-piperazinyl)phenyl)-1,1,1,3,3,3-hexafluoro-2-propanol (0.83 g) as a white solid.

Step 2: 2-(4-(4-((5-amino-2-thiophenyl)sulfonyl)-1-piperazinyl)phenyl)-1,1,1,3,3,3-hexafluoro-2-propanol A 20-mL vial was charged with 2-(4-(4-((5-bromo-2-thiophenyl)sulfonyl)-1-piperazinyl)phenyl)-1,1,1,3,3,3-hexafluoro-2-propanol (0.89 g, 1.61 mmol), 1,1-diphenylmethanimine (0.35 g, 1.93 mmol), sodium tert-butoxide (0.37 g, 3.87 mmol), and 6 mL of toluene. To this was added tris(dibenzylideneacetone)dipalladium (0) (0.15 g, 0.16 mmol, Strem Chemical Inc, Newburyport, Mass.) and 2,2'-bis(diphenylphosphino)-1,1'-binaphthyl (BINAP) (0.251 g, 0.403 mmol, Sigma-Aldrich, St. Louis, Mo.). Oxygen free nitrogen gas was bubbled through the solution for 2 min and then the vial was sealed and heated at 80° C. for 12 h. The black mixture was then diluted with EtOAc (10 mL) and filtered. The filtrate was concentrated to give a black tar. Purification via column chromatography on silica gel (0 to 60% EtOAc in hexanes) gave the intermediate imine. To this was added 15 mL of 5M HCl and 15 mL of THF. After 15 min, 15 mL of 5 M NaOH was added and the mixture was extracted with EtOAc (50 mL). The organics were dried ($MgSO_4$), filtered, and collected to give an orange foam. Purification via column chromatography on silica gel (0-70% EtOAc in hexanes) gave an orange oil. 25 mL of ether and 50 mL of hexanes were and added and the resulting white solid was collected by filtration to give 2-(4-(4-((5-amino-2-thiophenyl)sulfonyl)-1-piperazinyl)phenyl)-1,1,1,3,3,3-hexafluoro-2-propanol (0.32 g). $^1$H NMR (400 MHz, $CD_3OD$) δ=7.57 (d, J=8.8 Hz, 2H), 7.22 (d, J=4.1 Hz, 1H), 7.03 (d, J=9.2 Hz, 2H), 6.07 (d, J=4.1 Hz, 1H), 3.39-3.26 (m, 4H), 3.21-3.10 (m, 4H). m/z (ESI, +ve ion) 490.0 (M+H)$^+$. GK-GKRP IC$_{50}$ (Binding)=0.302 μM; GK-GKRP EC$_{50}$ (LC MS/MS-2)=0.150 μM.

Example 89

2-(2-((2S)-4-((5-amino-2-thiophenyl)sulfonyl)-2-methyl-1-piperazinyl)-5-pyrimidinyl)-1,1,1,3,3,3-hexafluoro-2-propanol

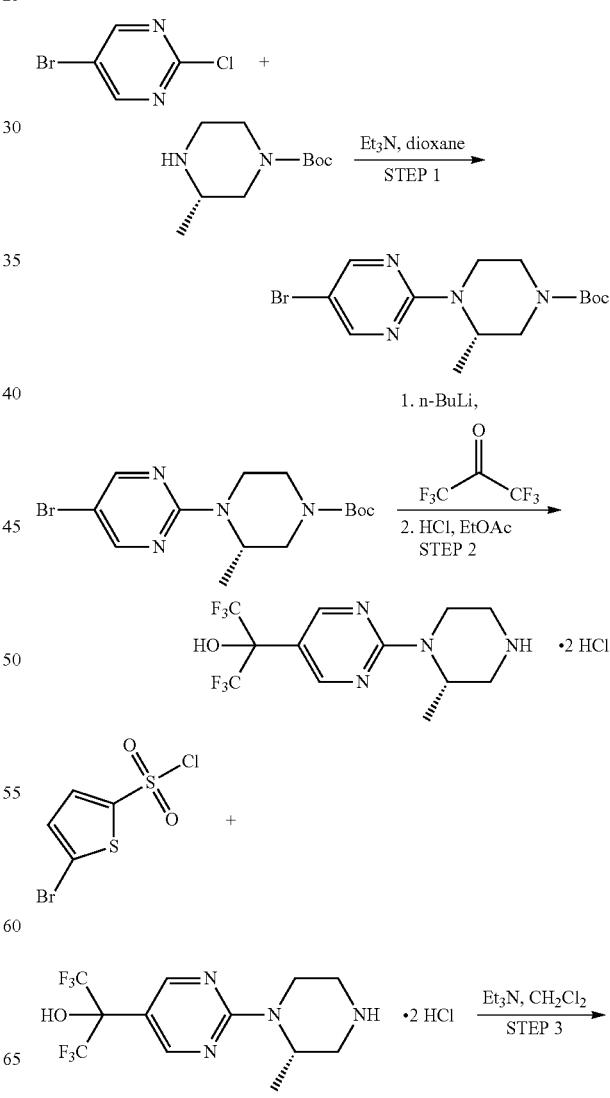

-continued

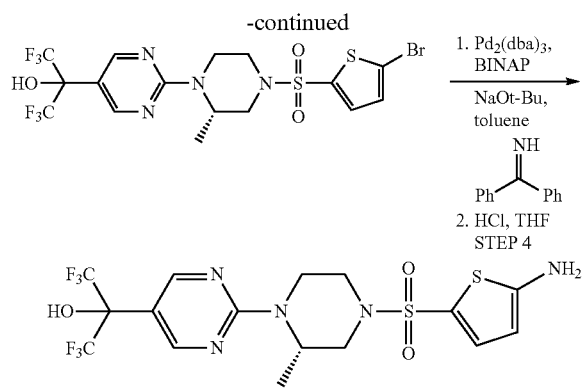

Step 1: (3S)-4-(5-bromo-2-pyrimidinyl)-3-methyl-1-piperazinecarboxylate

A 350-mL pressure vessel was charged with (tert-butyl (3S)-3-methyl-1-piperazinecarboxylate (15.0 g, 74.9 mmol, Sigma-Aldrich, St. Louis, Mo.), 5-bromo-2-chloropyrimidine (14.49 g, 74.9 mmol, Sigma-Aldrich, St. Louis, Mo.), 100 mL of dioxane, and triethylamine (11.48 mL, 82 mmol). The vessel was sealed and heated at 100° C. for 12 h. The mixture was concentrated and then dissolved in 200 mL of EtOAc and 150 mL of water. The organics were separated, dried (MgSO$_4$), filtered, and concentrated to give an oil. Purification via column chromatography on silica gel (0 to 40% EtOAc in hexanes) gave (3S)-4-(5-bromo-2-pyrimidinyl)-3-methyl-1-piperazinecarboxylate (23.5 g) as a white solid.

Step 2: 1,1,1,3,3,3-hexafluoro-2-(2-((2S)-2-methyl-1-piperazinyl)-5-pyrimidinyl)-2-propanol di hydrochloride A 500-mL round-bottomed flask was charged with (3S)-4-(5-bromo-2-pyrimidinyl)-3-methyl-1-piperazinecarboxylate (2.40 g, 6.72 mmol) and 50 mL of diethyl ether. After cooling to −78° C., n-BuLi (2.5 M in hexanes, 5.46 mL, 8.73 mmol) was added. The resulting suspension was stirred for 10 min at −78° C., then 1,1,1,3,3,3-hexafluoro-2-propanone (Sigma-Aldrich, St. Louis, Mo.) was bubbled through the solution for 5 min. After an additional 10 min at −78° C., 100 mL of water was added and the mixture was allowed to warm to room temperature. The organic layer was separated dried (MgSO$_4$), filtered and concentrated. Purification by column chromatography on silica gel (0 to 40% EtOAc in hexanes) gave the amine as an oil. To this was added 15 mL of EtOAc, and hydrochloric acid (4M in dioxane 7.31 mL, 29.3 mmol). After heating at 75° C. for 12 h, the suspension was cooled to room temperature and the white precipitate was collected by filtration to give 1,1,1,3,3,3-hexafluoro-2-(2-((2S)-2-methyl-1-piperazinyl)-5-pyrimidinyl)-2-propanol as its di-hydrochloride salt (1.48 g).

Step 3: 2-(2-((2S)-4-((5-bromo-2-thiophenyl)sulfonyl)-2-methyl-1-piperazinyl)-5-pyrimidinyl)-1,1,1,3,3,3-hexafluoro-2-propanol A 250-mL round-bottomed flask was charged with (1,1,1,3,3,3-hexafluoro-2-(2-((2S)-2-methyl-1-piperazinyl)-5-pyrimidinyl)-2-propanol dihydrochloride (1.48 g, 3.55 mmol), 25 mL of CH$_2$Cl$_2$, and triethylamine (1.48 mL, 10.7 mmol). After cooling to 0° C., 5-bromothiophenesulfonyl chloride (0.93 g, 3.55 mmol. Sigma-Aldrich, St. Louis, Mo.) was added and the solution was stirred for 15 min at 0° C. 100 mL of water was then added and the layers were separated. The organics were dried (MgSO$_4$), filtered, and concentrated to give a tar that was purified by column chromatography on silica gel (0-60% EtOAc in hexanes) to give 2-(2-((2S)-4-((5-bromo-2-thiophenyl)sulfonyl)-2-methyl-1-piperazinyl)-5-pyrimidinyl)-1,1,1,3,3,3-hexafluoro-2-propanol (2.01 g) as an off-white foam.

Step 4: 2-(2-((2S)-4-((5-amino-2-thiophenyl)sulfonyl)-2-methyl-1-piperazinyl)-5-pyrimidinyl)-1,1,1,3,3,3-hexafluoro-2-propanol A 250-mL round-bottomed flask was charged with (2-(2-((2S)-4-((5-bromo-2-thiophenyl)sulfonyl)-2-methyl-1-piperazinyl)-5-pyrimidinyl)-1,1,1,3,3,3-hexafluoro-2-propanol (1.00 g, 1.76 mmol), 1,1-diphenylmethanimine (0.382 g, 2.11 mmol), 30 mL of toluene, sodium tert-butoxide (0.405 g, 4.22 mmol), rac-2,2'-bis(diphenylphosphino)-1,1'-binaphthyl (BINAP) (0.273 mL, 0.439 mmol, Sigma-Aldrich, St. Louis, Mo.), and tris(dibenzylideneacetone)dipalladium (0) (0.101 g, 0.176 mmol, Strem Chemicals, Newburyport, Mass.). The round-bottomed flask was sealed and heated at 90° C. for 15 h. After that time, the mixture was diluted with EtOAc (50 mL) and filtered. The filtrate was concentrated to give a brown oil. To this was added 25 mL of THF and 15 mL of 5M HCl in dioxane. After 15 min, 17 mL of 5M NaOH was added and the mixture was extracted with EtOAc. The layers were separated, the organics were dried (MgSO$_4$), filtered, and concentrated to give an orange oil. Purification via column chromatography on silica gel (120 g of silica, 0 to 65% EtOAc in hexanes) gave 2-(2-((2S)-4-((5-amino-2-thiophenyl)sulfonyl)-2-methyl-1-piperazinyl)-5-pyrimidinyl)-1,1,1,3,3,3-hexafluoro-2-propanol (0.510 g) as a tan solid. $^1$H NMR (400 MHz, CD$_3$OD) δ=8.57 (s, 2H), 7.19 (d, J=4.1 Hz, 1H), 6.04 (d, J=4.1 Hz, 1H), 5.10 (br. s., 1H), 4.71 (d, J=13.7 Hz, 1H), 3.71 (d, J=11.7 Hz, 1H), 3.56 (d, J=11.5 Hz, 1H), 3.31-3.23 (m, 1H), 2.61 (dd, J=3.7, 11.5 Hz, 1H), 2.46 (dt, J=3.5, 11.8 Hz, 1H), 1.32 (d, J=6.8 Hz, 3H). m/z (ESI, +ve ion) 506.0 (M+H)$^+$. GK-GKRP IC$_{50}$ (Binding)=0.252 μM; GK-GKRP EC$_{50}$ (LC MS/MS-2)=0.161 μM.

Example 90

2-(4-(4-((5-amino-2-thiophenyl)sulfonyl)-1-piperazinyl)phenyl)-1,1,1-trifluoro-2-propanol

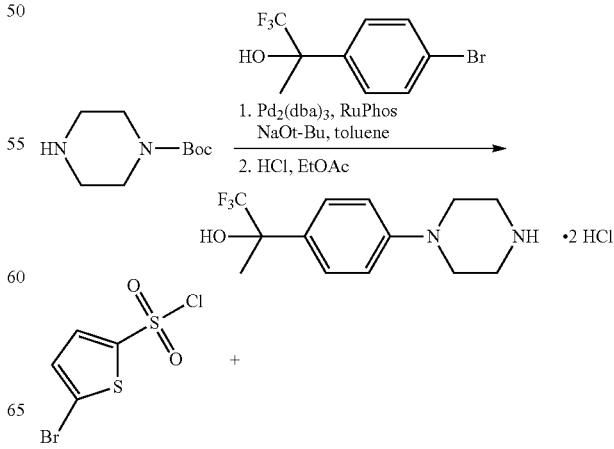

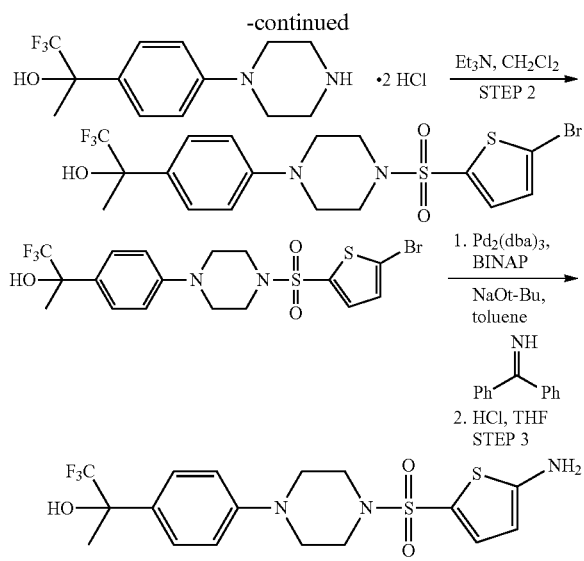

Step 1: 1,1,1-trifluoro-2-(4-(1-piperazinyl)phenyl)-2-propanol dihydrochloride

A 350-mL pressure vessel was charged with tert-butyl 1-piperazinecarboxylate (15.00 g, 81 mmol, Sigma-Aldrich, St. Louis, Mo.), 2-(4-bromophenyl)-1,1,1-trifluoropropan-2-ol (22.75 g, 85 mmol, Example 27, step 1), sodium tert-butoxide (15.48 g, 161 mmol), and 100 mL of toluene. Oxygen-free nitrogen gas was bubbled through the solution for 5 min then 2-dicyclohexyl(2',6'-diisopropoxybiphenyl-2-yl)phosphine (RuPhos) (1.50 g, 3.22 mmol) and tris(dibenzylideneacetone)dipalladium (0) (1.48 g, 1.61 mmol) were added. The vessel was sealed and heated to 90° C. for 2 h. After that time, the mixture was diluted with 150 mL of EtOAc and filtered. The filtrate was concentrated and then 300 mL of EtOAc and 100 mL of 4N HCl in dioxane were added. After 1.5 h at 70° C., the mixture was concentrated. The resulting solid was slurried with diethyl ether and collected by filtration to give 1,1,1-trifluoro-2-(4-(1-piperazinyl)phenyl)-2-propanol dihydrochloride (22.3 g) as an off-white solid.

Step 2: 2-(4-(4-((5-bromo-2-thiophenyl)sulfonyl)-1-piperazinyl)phenyl)-1,1,1-trifluoro-2-propanol A 250-mL round-bottomed flask was charged with 1,1,1-trifluoro-2-(4-(1-piperazinyl)phenyl)-2-propanol dihydrochloride (2.66 g, 7.65 mmol), 5-bromothiophenesulfonyl chloride (2.00 g, 7.65 mmol, Sigma-Aldrich, St. Louis, Mo.), 25 mL of $CH_2Cl_2$, and triethylamine (3.73 mL, 26.8 mmol). After stirring at room temperature for 15 min, the mixture was diluted with $CH_2Cl_2$ (50 mL) and filtered. The filtrate was concentrated and purified by column chromatography on silica gel (0 to 50% EtOAc in hexanes) to give 2-(4-(4-((5-bromo-2-thiophenyl)sulfonyl)-1-piperazinyl)phenyl)-1,1,1-trifluoro-2-propanol (2.10 g) as an off-white solid.

Step 3: 2-(4-(4-((5-amino-2-thiophenyl)sulfonyl)-1-piperazinyl)phenyl)-1,1,1-trifluoro-2-propanol A 20-mL vial was charged with 1,1-diphenylmethanimine (0.44 g, 2.40 mmol), 2-(4-(4-((5-bromo-2-thiophenyl)sulfonyl)-1-piperazinyl)phenyl)-1,1,1-trifluoro-2-propanol (1.00 g, 2.003 mmol), sodium tert-butoxide (0.46 mL, 4.81 mmol), and 10 mL of toluene. To this was added tris(dibenzylideneacetone)dipalladium (0) (0.18 g, 0.20 mmol, Strem Chemicals, Newburyport, Mass.) and rac-2,2'-bis(diphenylphosphino)-1,1'-binaphthyl (BINAP) (0.31 g, 0.50 mmol, Sigma-Aldrich, St. Louis, Mo.). The vial was sealed and heated at 80° C. for 12 h. The mixture was then diluted with EtOAc (10 mL) and filtered. The filtrate was concentrated and the dissolved in 15 mL of THF. To this was added 5 M HCl (15.0 mL, 75 mmol). After stirring at room temperature for 30 min, the pH was adjusted to 12 by 5N NaOH. The mixture was extracted with EtOAc, dried with $MgSO_4$, filtered, and concentrated. Purification via column chromatography on silica gel (0-70% EtOAc in hexanes) gave a white foam. To this was added 25 mL of ether and 25 mL of hexanes. The resulting suspension was stirred at room temperature for 5 min. The white solid was collected by filtration to give 2-(4-(4-((5-amino-2-thiophenyl)sulfonyl)-1-piperazinyl)phenyl)-1,1,1-trifluoro-2-propanol (0.42 g).

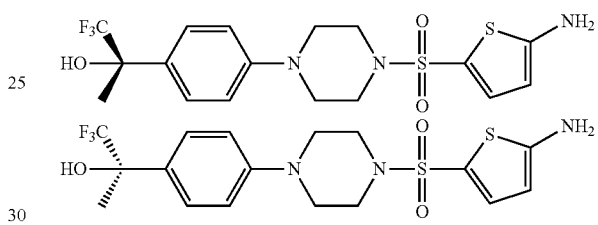

(2S)-2-(4-(4-((5-amino-2-thiophenyl)sulfonyl)-1-piperazinyl)phenyl)-1,1,1-trifluoro-2-propanol; (2R)-2-(4-(4-((5-amino-2-thiophenyl)sulfonyl)-1-piperazinyl)phenyl)-1,1,1-trifluoro-2-propanol. $^1$H NMR (400 MHz, $CD_3OD$) δ=7.48 (d, J=8.8 Hz, 2H), 7.23 (d, J=4.1 Hz, 1H), 7.03-6.91 (m, 2H), 6.08 (d, J=4.1 Hz, 1H), 3.32-3.27 (m, 4H), 3.21-3.15 (m, 4H), 1.70 (s, 3H). m/z (ESI, +ve ion) 436.0 (M+H)$^+$. GK-GKRP $IC_{50}$ (Binding)=0.448 μM; GK-GKRP $EC_{50}$ (LC MS/MS-2)=0.836 μM.

Example 91

2-(4-(4-((6-amino-3-pyridinyl)sulfonyl)-1-piperazinyl)phenyl)-1,1,1,3,3,3-hexafluoro-2-propanol

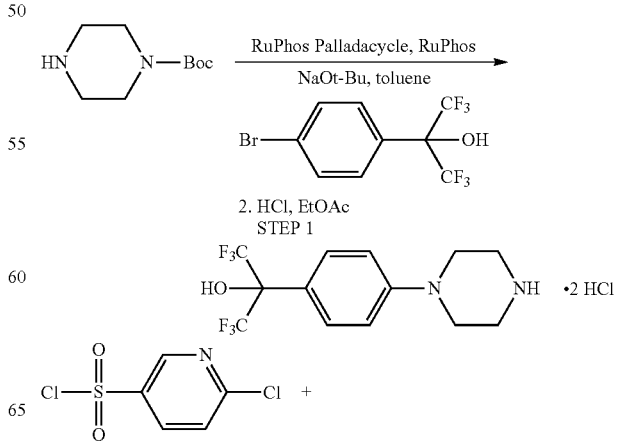

221
-continued

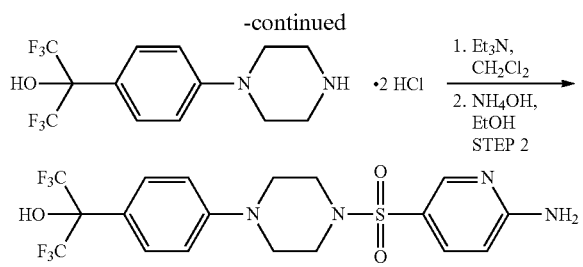

Step 1: 1,1,1,3,3,3-hexafluoro-2-(4-(1-piperazinyl)phenyl)-2-propanol dihydrochloride A 1-L pressure vessel was charged with 2-(4-bromophenyl)-1,1,1,3,3,3-hexafluoropropan-2-ol (70.8 g, 219 mmol, *Bioorg. Med. Chem. Lett.* 2002, 12, 3009), tert-butyl piperazine-1-carboxylate (40.0 g, 215 mmol, Sigma-Aldrich, St. Louis, Mo.), 200 mL of toluene, and sodium tert-butoxide (43.3 g, 451 mmol). Nitrogen gas was bubbled through the solution for 5 min then chloro(2-dicyclohexylphosphino-2',6'-di-1-propoxy-1,1'-biphenyl)[2-(2-aminoethylphenyl)]palladium(II), methyl-t-butylether adduct (RuPhos Palladacycle) (1.57 g, 2.15 mmol, Strem Chemicals Inc, Newburyport, Mass.) and 2-dicyclohexyl(2',6'-diisopropoxybiphenyl-2-yl)phosphine (RuPhos) (2.00 g, 4.30 mmol, Strem Chemicals Inc, Newburyport, Mass.) were added. The vessel was sealed and heated at 65° C. for 2 h. The mixture was then diluted with water and extracted with EtOAc. The combined organic extracts were dried (MgSO₄), filtered, and concentrated to give an oil. To this material was added 200 mL of EtOAc and 200 mL of 4N HCl in dioxane. The solution was heated at 80° C. for 12 h and the resulting suspension was then allowed to cool to room temperature. The solid precipitate was collected by filtration to give 1,1,1,3,3,3-hexafluoro-2-(4-(1-piperazinyl)phenyl)-2-propanol dihydrochloride (76.2 g) as a white solid.

Step 2: 2-(4-(4-(((6-amino-3-pyridinyl)sulfonyl)-1-piperazinyl)phenyl)-1,1,1,3,3,3-hexafluoro-2-propanol A 250-mL round-bottomed flask was charged with 1,1,1,3,3,3-hexafluoro-2-(4-(1-piperazinyl)phenyl)-2-propanol dihydrochloride (2.50 g, 6.23 mmol), 20 mL of CH₂Cl₂, triethylamine (3.47 mL, 24.93 mmol), and 6-chloropyridine-3-sulfonyl chloride (1.32 g, 6.23 mmol, *Organic Process Research & Development* 2009, 13, 875). After stirring at room temperature for 30 min, water was added and the layers were separated. The organics were dried (MgSO₄), filtered, and concentrated to give an oily solid. To this material was added 10 mL of EtOH and concentrated ammonium hydroxide (9.95 mL, 255 mmol). The vessel was sealed and heated at 120° C. for 12 h. After the mixture was allows to cool to room temperature, EtOAc (100 mL) and water (50 mL) were added. The organics were separated, dried (MgSO₄), filtered and concentrated to give an oil. Purification via column chromatography on silica gel (0 to 70% EtOAc in hexanes) delivered 2-(4-(4-(((6-amino-3-pyridinyl)sulfonyl)-1-piperazinyl)phenyl)-1,1,1,3,3,3-hexafluoro-2-propanol (1.65 g) as an off-white solid. ¹H NMR (400 MHz, CD₃OD) δ=8.30 (d, J=2.3 Hz, 1H), 7.74 (dd, J=2.4, 8.9 Hz, 1H), 7.56 (d, J=8.8 Hz, 2H), 7.00 (d, J=9.0 Hz, 2H), 6.64 (d, J=8.8 Hz, 1H), 3.35-3.30 (m, 4H), 3.17-3.11 (m, 4H). m/z (ESI, +ve ion) 484.9 (M+H)⁺. GK-GKRP IC₅₀ (Binding)=0.085 µM; GK-GKRP EC₅₀ (LC MS/MS-2)=0.142 µM.

222

Example 92

2-(4-((2S)-4-(((6-amino-3-pyridinyl)sulfonyl)-2-methyl-1-piperazinyl)phenyl)-1,1,1,3,3,3-hexafluoro-2-propanol

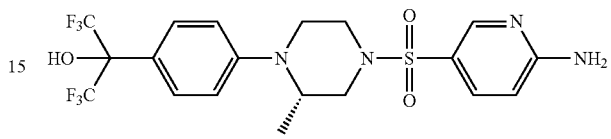

This compound was synthesized following the procedure outlined for Example 91, Step 2. The reaction of (S)-1,1,1,3,3,3-hexafluoro-2-(4-(2-methylpiperazin-1-yl)phenyl)-2-propanol (Example 11) and 6-chloropyridine-3-sulfonyl chloride (*Organic Process Research & Development* 2009, 13, 875) followed by amination with NH₄OH and purification via column chromatography on silica gel (0-70% EtOAc in hexanes) delivered 2-(4-((2S)-4-(((6-amino-3-pyridinyl)sulfonyl)-2-methyl-1-piperazinyl)phenyl)-1,1,1,3,3,3-hexafluoro-2-propanol as a white solid. ¹H NMR (400 MHz, CD₃OD) δ=8.31 (d, J=2.2 Hz, 1H), 7.74 (dd, J=2.4, 8.9 Hz, 1H), 7.56 (d, J=8.6 Hz, 2H), 6.98 (d, J=9.0 Hz, 2H), 6.65 (d, J=9.0 Hz, 1H), 4.22-4.12 (m, 1H), 3.72-3.63 (m, 1H), 3.54-3.42 (m, 2H), 3.21 (dt, J=3.4, 11.7 Hz, 1H), 2.75 (dd, J=3.2, 11.2 Hz, 1H), 2.58 (dt, J=3.2, 11.1 Hz, 1H), 1.15 (d, J=6.5 Hz, 3H). m/z (ESI, +ve ion) 498.8 (M+H)⁺. GK-GKRP IC₅₀ (Binding)=0.205 µM; GK-GKRP EC₅₀ (LC MS/MS-2)=0.233 µM.

Example 93

2-(2-((2S)-4-(((6-amino-3-pyridinyl)sulfonyl)-2-methyl-1-piperazinyl)-5-pyrimidinyl)-1,1,1,3,3,3-hexafluoro-2-propanol

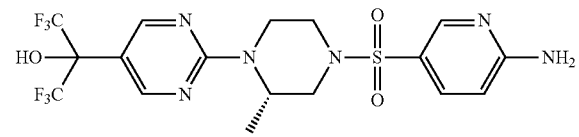 [SMILES: C[C@H]1CN(S(=O)(=O)c2ccc(N)nc2)CCN1c1ncc(C(O)(C(F)(F)F)C(F)(F)F)cn1]

This compound was synthesized following the procedure outlined for Example 91, Step 2. The reaction of (1,1,1,3,3,3-hexafluoro-2-(2-((2S)-2-methyl-1-piperazinyl)-5-pyrimidinyl)-2-propanol (Example 89) and 6-chloropyridine-3-sulfonyl chloride (*Organic Process Research & Development* 2009, 13, 875) followed by amination with NH₄OH and purification via column chromatography on silica gel (0-75% EtOAc in hexanes) delivered 2-(2-((2S)-4-(((6-amino-3-pyridinyl)sulfonyl)-2-methyl-1-piperazinyl)-5-pyrimidinyl)-1,1,1,3,3,3-hexafluoro-2-propanol. ¹H NMR (400 MHz, CD₃OD) δ=8.56 (s, 2H), 8.29 (d, J=2.2 Hz, 1H), 7.72 (dd, J=2.4, 8.9 Hz, 1H), 6.62 (d, J=9.0 Hz, 1H), 5.09 (br. s., 1H), 4.71 (d, J=13.3 Hz, 1H), 3.81-3.71 (m, 1H), 3.61 (d, J=11.5 Hz, 1H), 3.31-3.24 (m, 1H), 2.55 (dd, J=3.7, 11.5 Hz, 1H), 2.39 (dt, J=3.5, 11.8 Hz, 1H), 1.32 (d, J=6.7 Hz, 3H). m/z

Example 94

1,1,1,3,3,3-hexafluoro-2-(2-((2S)-2-methyl-4-(2-thiophenylsulfonyl)-1-piperazinyl)-5-pyrimidinyl)-2-propanol

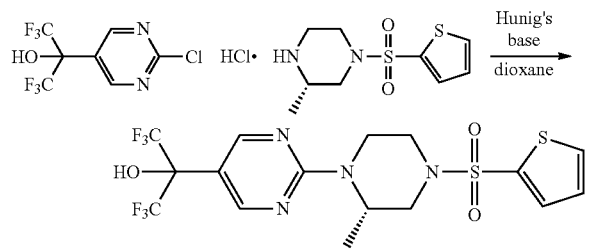

A 20-mL vial was charged with (S)-2-methyl-4-(2-thiophenylsulfonyl)piperazine hydrochloride (0.75 g, 2.6 mmol, Example 27), (2-chloro-5-pyrimidinyl)-1,1,1,3,3,3-hexafluoro-2-propanol (0.92 g, 3.3 mmol, Intermediate D), 15 mL of dioxane, and Hünig's base (1.2 mL, 6.6 mmol). The mixture was heated at 85° C. for 12 h and then concentrated and purified via column chromatography on silica gel (0 to 50% EtOAc in hexanes) delivered 1,1,1,3,3,3-hexafluoro-2-(2-((2S)-2-methyl-4-(2-thiophenylsulfonyl)-1-piperazinyl)-5-pyrimidinyl)-2-propanol (0.360 g). $^1$H NMR (400 MHz, CD$_3$OD) δ=8.58 (s, 2H), 7.87 (d, J=5.1 Hz, 1H), 7.66-7.63 (m, 1H), 7.28-7.23 (m, 1H), 5.14 (br. s., 1H), 4.76 (d, J=13.9 Hz, 1H), 3.83 (d, J=11.3 Hz, 1H), 3.67 (d, J=11.5 Hz, 1H), 3.40 (s, 1H), 2.69-2.58 (m, 1H), 2.47 (dt, J=3.6, 12.0 Hz, 1H), 1.36 (d, J=6.7 Hz, 3H). m/z (ESI, +ve ion) 491.0 (M+H)$^+$. GK-GKRP IC$_{50}$ (Binding)=0.362 μM; GK-GKRP EC$_{50}$ (LC MS/MS-2)=0.470 μM.

Example 95

2-(4-(4-((6-amino-3-pyridinyl)sulfonyl)-1-piperazinyl)phenyl)-1,1,1-trifluoro-2-propanol

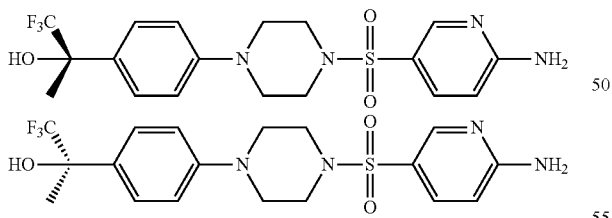

This compound was synthesized following the procedure outlined for Example 91, Step 2. The reaction of 1,1,1-trifluoro-2-(4-(1-piperazinyl)phenyl)-2-propanol (Example 90) and 6-chloropyridine-3-sulfonyl chloride (*Organic Process Research & Development* 2009, 13, 875) followed by amination with NH$_4$OH and purification via column chromatography on silica gel (0 to 75% EtOAc in hexanes) delivered 2-(4-(4-((6-amino-3-pyridinyl)sulfonyl)-1-piperazinyl)phenyl)-1,1,1-trifluoro-2-propanol of two isomers. (2S)-2-(4-(4-((6-amino-3-pyridinyl)sulfonyl)-1-piperazinyl)phenyl)-1,1,1-trifluoro-2-propanol and (2R)-2-(4-(4-((6-amino-3-pyridinyl)sulfonyl)-1-piperazinyl)phenyl)-1,1,1-trifluoro-2-propanol. $^1$H NMR (400 MHz, CD$_3$OD) δ=8.30 (d, J=2.2 Hz, 1H), 7.74 (dd, J=2.4, 8.9 Hz, 1H), 7.46 (d, J=8.8 Hz, 2H), 6.95 (d, J=9.0 Hz, 2H), 6.64 (d, J=9.0 Hz, 1H), 3.30-3.24 (m, 4H), 3.18-3.08 (m, 4H), 1.68 (s, 3H). m/z (ESI, +ve ion) 431.1 (M+H)$^+$. GK-GKRP IC$_{50}$ (Binding)=0.359 μM; GK-GKRP EC$_{50}$ (LC MS/MS-2)=0.605 μM.

Example 96

2-(4-(4-((2-amino-5-pyrimidinyl)sulfonyl)-1-piperazinyl)phenyl)-1,1,1,3,3,3-hexafluoro-2-propanol

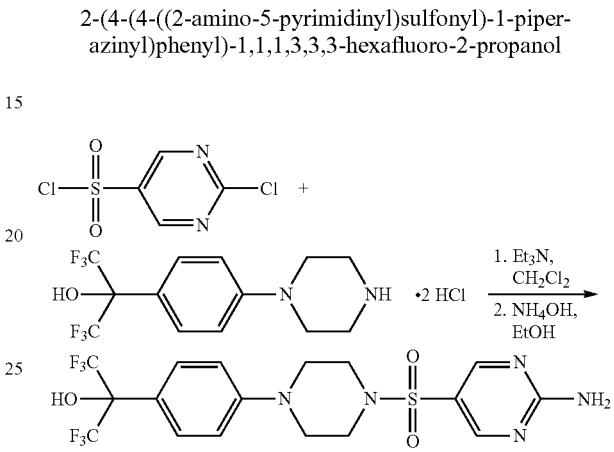

A 100-mL round-bottomed flask was charged with 1,1,1,3,3,3-hexafluoro-2-(4-(1-piperazinyl)phenyl)-2-propanol dihydrochloride (0.45 g, 1.13 mmol, Example 91), 10 mL of CH$_2$Cl$_2$, triethylamine (0.63 mL, 4.51 mmol), and 2-chloro-5-pyrimidinesulfonyl chloride (0.24 g, 1.13 mmol, Matrix Scientific, Columbia, S.C.). After stirring for 15 min at room temperature, the mixture was concentrated then diluted with 10 mL of EtOH and 10 mL of NH$_4$OH. The mixture was stirred at room temperature for an additional 1 h and then diluted with EtOAc. The organics were separated, dried (MgSO$_4$), filtered and concentrated. The residue was purified by column chromatography on silica gel (0 to 65% EtOAc in hexanes) to give 2-(4-(4-((2-amino-5-pyrimidinyl)sulfonyl)-1-piperazinyl)phenyl)-1,1,1,3,3,3-hexafluoro-2-propanol (0.22 g). $^1$H NMR (400 MHz, CD$_3$OD) δ=8.58 (s, 2H), 7.57 (d, J=8.8 Hz, 2H), 7.03 (d, J=9.2 Hz, 2H), 3.38-3.34 (m, 4H), 3.22-3.17 (m, 4H). m/z (ESI, +ve ion) 485.6 (M+H)$^+$. GK-GKRP IC$_{50}$ (Binding)=0.258 μM; GK-GKRP EC$_{50}$ (LC MS/MS-2)=0.518 μM.

Example 97

2-(4-(4-((6-amino-5-fluoro-3-pyridinyl)sulfonyl)-1-piperazinyl)phenyl)-1,1,1,3,3,3-hexafluoro-2-propanol

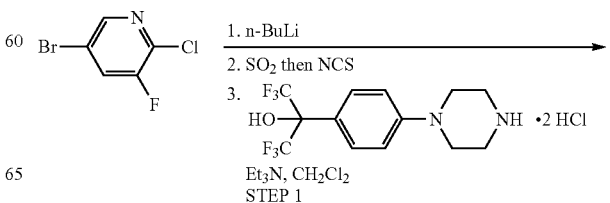

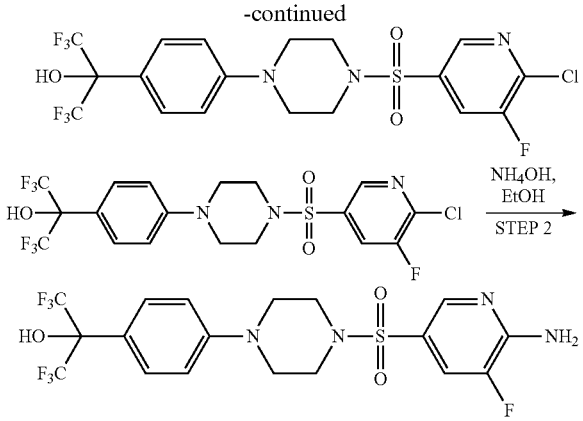

Step 1: 2-(4-(4-((6-chloro-5-fluoro-3-pyridinyl)sulfonyl)-1-piperazinyl)phenyl)-1,1,1,3,3,3-hexafluoro-2-propanol A 250-mL round-bottomed flask was charged with 5-bromo-2-chloro-3-fluoropyridine (0.50 g, 2.38 mmol, Sigma-Aldrich, St. Louis, Mo.) and 20 mL of diethyl ether. After cooling to −78° C., n-BuLi (2.5 M in hexanes, 0.95 mL, 2.38 mmol) was added. After 5 min at −78° C., sulfur dioxide (Sigma-Aldrich, St. Louis, Mo.) was bubbled through the solution for 1 min. The mixture was allowed to warm to room temperature and then concentrated. 20 mL of $CH_2Cl_2$ was then added along with 1-chloro-2,5-pyrrolidinedione (NCS) (0.381 g, 2.85 mmol, Sigma-Aldrich, St. Louis, Mo.). After 30 min at room temperature, 1,1,1,3,3,3-hexafluoro-2-(4-(1-piperazinyl)phenyl)-2-propanol dihydrochloride (0.95 g, 2.38 mmol, Example 91) and triethylamine (1.33 mL, 9.50 mmol) were added. After 10 min, 50 mL of water was added and the layers were separated. The organics were dried ($MgSO_4$), filtered and concentrated. The residue was purified via column chromatography on silica gel (0 to 50% EtOAc in hexanes) to give 2-(4-(4-((6-chloro-5-fluoro-3-pyridinyl)sulfonyl)-1-piperazinyl)phenyl)-1,1,1,3,3,3-hexafluoro-2-propanol (0.750 g) as a white foam.

Step 2: 2-(4-(4-((6-amino-5-fluoro-3-pyridinyl)sulfonyl)-1-piperazinyl)phenyl)-1,1,1,3,3,3-hexafluoro-2-propanol A 100-mL pressure vessel was charged with 2-(4-(4-((6-chloro-5-fluoro-3-pyridinyl)sulfonyl)-1-piperazinyl)phenyl)-1,1,1,3,3,3-hexafluoro-2-propanol (0.725 g, 1.389 mmol), 5 mL of EtOH, and concentrated ammonium hydroxide (10 mL, 257 mmol). The vessel was sealed and the mixture was heated to 125° C. for 18 h. After that time, the mixture was diluted with water and extracted with $CH_2Cl_2$ (3×100 mL). The combined extracts were dried ($MgSO_4$), filtered and concentrated. The residue was purified by column chromatography on silica gel (0 to 70% EtOAc in hexanes) and to give 2-(4-(4-((6-amino-5-fluoro-3-pyridinyl)sulfonyl)-1-piperazinyl)phenyl)-1,1,1,3,3,3-hexafluoro-2-propanol (0.375 g) as a white solid. $^1H$ NMR (400 MHz, $CD_3OD$) δ=8.18 (d, J=1.4 Hz, 1H), 7.62 (dd, J=1.9, 10.5 Hz, 1H), 7.56 (d, J=8.8 Hz, 2H), 7.01 (d, J=9.0 Hz, 2H), 3.35-3.29 (m, 4H), 3.19-3.14 (m, 4H). m/z (ESI, +ve ion) 503.1 $(M+H)^+$. GK-GKRP $IC_{50}$ (Binding)=0.163 μM; GK-GKRP $EC_{50}$ (LC MS/MS-2)=0.299 μM.

Example 98

9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one

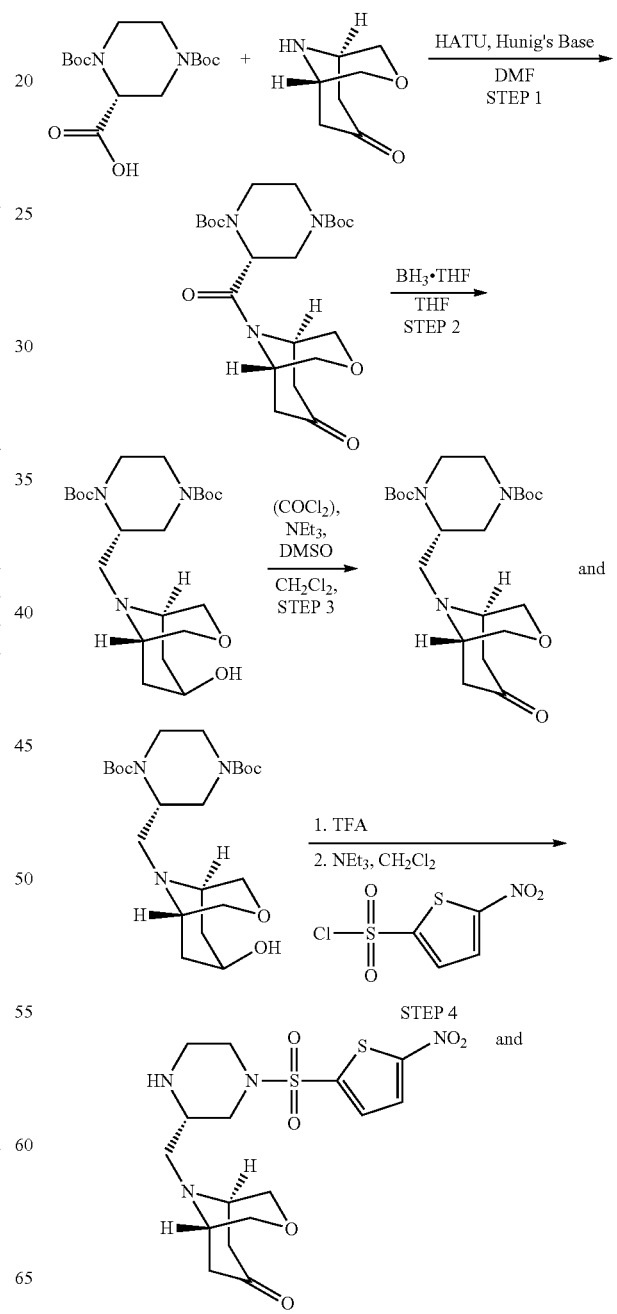

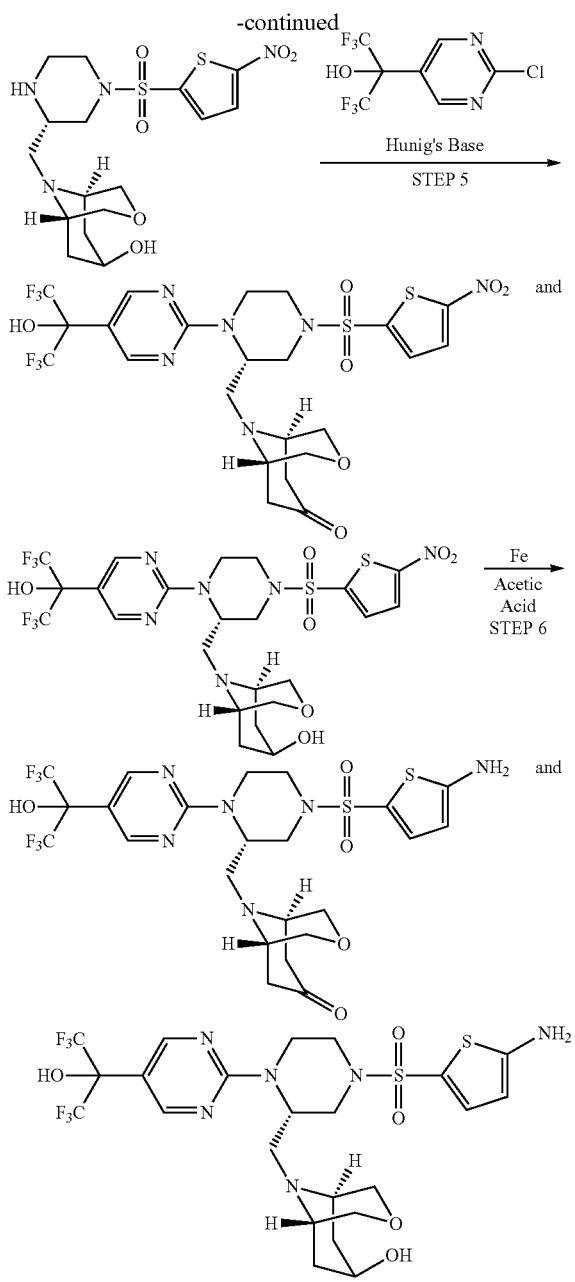

Step 1: (2R)-2-((7-oxa-3-oxa-9-azabicyclo[3.3.1]non-9-yl)carbonyl)-1,4-piperazinedicarboxylate A 100-mL round-bottomed flask was charged with (R)-1,4-bis(tert-butoxycarbonyl)piperazine-2-carboxylic acid (2.86 g, 8.64 mmol, ASW MedChem Inc., New Brunswick, N.J.), 3-oxa-9-azabicyclo[3.3.1]nonan-7-one (1.22 g, 8.64 mmol, published PCT patent application no. WO 2007/022502), HATU (3.61 g, 9.51 mmol, Oakwood Products, Inc., West Columbia, S.C.), Hünig's base (3.06 mL, 17.28 mmol) and DMF (20 mL). After 1 h, the mixture was diluted with water (150 mL) and EtOAc (150 mL) and the layers were separated. The organic layer was washed with water (3×100 mL), dried (Na₂SO₄), filtered, and concentrated to give (2R)-2-((7-oxo-3-oxa-9-azabicyclo[3.3.1]non-9-yl)carbonyl)-1,4-piperazinedicarboxylate (3.9 g) as an oil.

Step 2: (2S)-2-((7-hydroxy-3-oxa-9-azabicyclo[3.3.1]non-9-yl)methyl)-1,4-piperazinedicarboxylate (endo)

A 250-mL round-bottomed flask was charged with (2R)-2-((7-oxo-3-oxa-9-azabicyclo[3.3.1]non-9-yl)carbonyl)-1,4-piperazinedicarboxylate (3.9 g, 8.6 mmol) and THF (50 mL). BH₃·THF (1.0 M in THF, 34.4 mL, 34.4 mmol, Sigma-Aldrich, St. Louis, Mo.) was added carefully at room temperature. After gas evolution ceased the reaction was heated at 50° C. for 2 h, the reaction was then cooled and carefully quenched with MeOH (100 mL). The reaction was concentrated onto silica gel and purified via column chromatography (120 g silica gel, 0 to 100% EtOAc in hexanes) to give (2S)-2-((7-hydroxy-3-oxa-9-azabicyclo[3.3.1]non-9-yl)methyl)-1,4-piperazinedicarboxylate (endo) (1.6 g).

Step 3: (2S)-2-((7-oxo-3-oxa-9-azabicyclo[3.3.1]non-9-yl)methyl)-1,4-piperazinedicarboxylate and (2S)-2-((7-hydroxy-3-oxa-9-azabicyclo[3.3.1]non-9-yl)methyl)-1,4-piperazinedicarboxylate (endo)

A 250-mL round-bottomed flask was charged with oxalyl chloride (5.27 mL, 10.53 mmol, Sigma-Aldrich, St. Louis, Mo.) and CH₂Cl₂ (50 mL) and cooled to −78° C. DMSO (1.5 mL, 21.1 mmol) was added and after gas evolution ceased (5 min) (2S)-2-((7-hydroxy-3-oxa-9-azabicyclo[3.3.1]non-9-yl)methyl)-1,4-piperazinedicarboxylate (endo) (1.6 g, 3.5 mmol) was added as a solution in CH₂Cl₂ (10 mL). The reaction was stirred at this temp for 1 h. Triethylamine (4.89 mL, 35.1 mmol) was added and the reaction was warmed to room temperature for 12 h. Saturated aqueous NaHCO₃ (100 mL) and EtOAc (150 mL) were added and the layers were separated. The organic layer was washed with water (3×100 mL), dried (Na₂SO₄), concentrated and purified via column chromatography (80 g silica gel, 0 to 100% EtOAc in hexanes) to give a 1:1 mixture of (2S)-2-((7-oxo-3-oxa-9-azabicyclo[3.3.1]non-9-yl)methyl)-1,4-piperazinedicarboxylate and (2S)-2-((7-hydroxy-3-oxa-9-azabicyclo[3.3.1]non-9-yl)methyl)-1,4-piperazinedicarboxylate (endo) (0.5 g).

Step 4: 9-(((2S)-4-((5-nitro-2-thiophenyl)sulfonyl)-2-piperazinyl)methyl)-3-oxa-9-azabicyclo[3.3.1]nonan-7-ol (endo) and 9-(((2S)-4-((5-nitro-2-thiophenyl)sulfonyl)-2-piperazinyl)methyl)-3-oxa-9-azabicyclo[3.3.1]nonan-7-one A 100-mL round-bottomed flask was charged with (2S)-2-((7-oxo-3-oxa-9-azabicyclo[3.3.1]non-9-yl)methyl)-1,4-piperazinedicarboxylate and (2S)-2-((7-hydroxy-3-oxa-9-azabicyclo[3.3.1]non-9-yl)methyl)-1,4-piperazinedicarboxylate (endo) (0.5 g) in EtOAc (20 mL) and 4N HCl in dioxane (0.85 mL, 3.4 mmol) was added. The reaction was heated to 70° C. for 2 h and after this time the precipitate was filtered, collected and dried. This material was dissolved in CH₂Cl₂ (10 mL). Triethylamine (0.75 mL, 5.4 mmol) followed by 5-nitrothiophene-2-sulfonyl chloride (0.26 g, 1.13 mmol, Enamine Building Blocks, Kiev, Ukraine) as a solution in CH₂Cl₂ (5 mL) were then added. After 10 min at room temperature, the reaction was concentrated onto silica and purified via column chromatography (40 g silica gel, 0 to 10% MeOH in CH₂Cl₂) to give 9-(((2S)-4-((5-nitro-2-thiophenyl)sulfonyl)-2-piperazinyl)methyl)-3-oxa-9-azabicyclo[3.3.1]nonan-7-ol (endo) and 9-(((2S)-4-((5-nitro-2-thiophenyl)sulfonyl)-2-piperazinyl)methyl)-3-oxa-9-azabicyclo[3.3.1]nonan-7-one (0.54 g).

Step 5: 9-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one A 20-mL vial was charged with 9-(((2S)-4-((5-nitro-2-thiophenyl)sulfonyl)-2-piperazinyl)methyl)-3-oxa-9-azabicyclo[3.3.1]nonan-7-ol (endo) and 9-(((2S)-4-((5-nitro-2-thiophenyl)sulfonyl)-2-piperazinyl)methyl)-3-oxa-9-azabicyclo[3.3.1]nonan-7-one (0.53 g, 1.9 mmol), Hünig's base (0.67 mL, 3.8 mmol), 2-(2-chloropyrimidin-5-yl)-1,1,1,3,3,3-hexafluoropropan-2-ol (0.53 g, 1.88 mmol, Intermediate D) and dioxane (10 mL). The vial was, sealed and heated at 100° C. overnight. The crude reaction was concentrated onto silica gel and purified via column chromatography (40 g silica gel, 0 to 100% EtOAc in hexanes) to give 9-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one (0.46 g) as a 1:1 mixture.

Step 6: 9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one A 50-mL round-bottomed flask was charged with 9-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one (0.10 g, 0.15 mmol), acetic acid (5 mL) and iron filings (0.04 g, 0.74 mmol). The reaction was stirred vigorously at 50° C. for 20 min. Saturated aqueous NaHCO$_3$ (50 mL) was added and the mixture was extracted with EtOAc (3×50 mL). The organic extracts were washed with water (3×100 mL), dried (Na$_2$SO$_4$), filtered, and concentrated. The residue was purified by reverse-phase preparative HPLC using a Phenomenex Gemini C$_{18}$ column (30×150 mm, 10 μm) eluting with 0.1% TFA in CH$_3$CN/H$_2$O (10% to 100% over 15 min) to give and 9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) (0.030 g) and 9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one (0.030 g).

9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo)

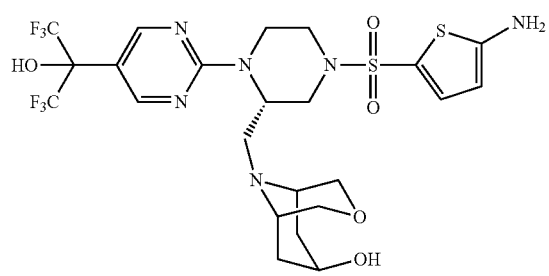 [SMILES: Nc1ccc(S(=O)(=O)N2CCN(c3ncc(C(O)(C(F)(F)F)C(F)(F)F)cn3)[C@@H](CN3C4COCC3CC(O)C4)C2)s1]

$^1$H NMR (400 MHz, CD$_3$OD) δ=8.56 (s, 2H), 7.21 (d, J=4.1 Hz, 1H), 6.03 (d, J=4.1 Hz, 1H), 4.67 (d, J=12.9 Hz, 1H), 3.93 (d, J=11.35 Hz, 1H), 3.85 (br. s., 1H), 3.56-3.81 (m, 5H), 3.30-3.36 (m, 1H), 3.25-3.06 (m, 1H), 3.02-2.89 (m, 1H), 2.82 (d, J=19.2 Hz, 3H), 2.61-2.41 (m, 2H), 2.33-2.12 (m, 2H), 1.54 (t, J=12.8 Hz, 2H). m/z (ESI, +ve ion) 647.4 (M+H)$^+$. GK-GKRP IC$_{50}$ (Binding)=0.002 μM; GK-GKRP EC$_{50}$ (LC MS/MS-2)=0.019 μM.

9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one

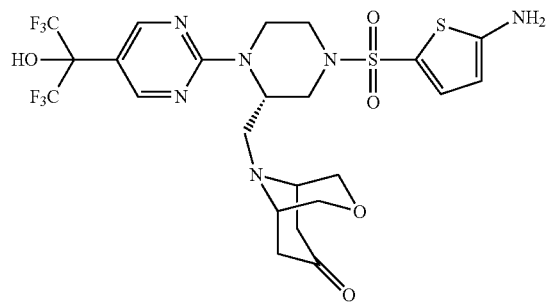 [SMILES: Nc1ccc(S(=O)(=O)N2CCN(c3ncc(C(O)(C(F)(F)F)C(F)(F)F)cn3)[C@@H](CN3C4COCC3CC(=O)C4)C2)s1]

$^1$H NMR (400 MHz, CD$_3$OD) δ=8.42-8.69 (m, 2H), 7.22 (d, J=4.3 Hz, 1H), 6.04 (d, J=4.1 Hz, 1H), 5.06-4.95 (m, 1H), 4.71 (d, J=11.2 Hz, 1H), 3.98 (d, J=11.9 Hz, 1H), 3.81-3.72 (m, 1H), 3.69-3.68 (m, 1H), 3.70-3.54 (m, 3H), 3.52-3.43 (m, 1H), 3.26-3.18 (m, 1H), 3.17-3.01 (m, 2H), 2.97-2.81 (m, 1H), 2.77-2.46 (m, 4H), 2.22 (d, J=15.6 Hz, 2H). m/z (ESI, +ve ion) 645.3 (M+H)$^+$. GK-GKRP IC$_{50}$ (Binding)=0.016 μM; GK-GKRP EC$_{50}$ (LC MS/MS-2)=0.040 μM.

Example 99

9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one Step 1: 9-(((2R)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2R)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one

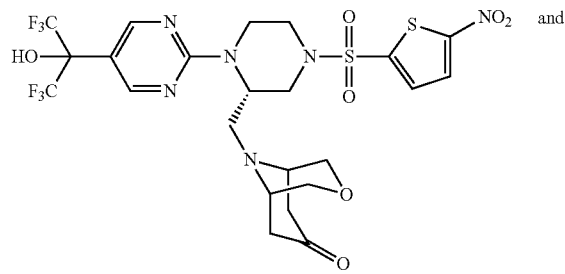

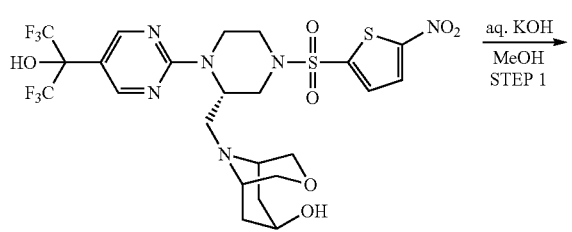

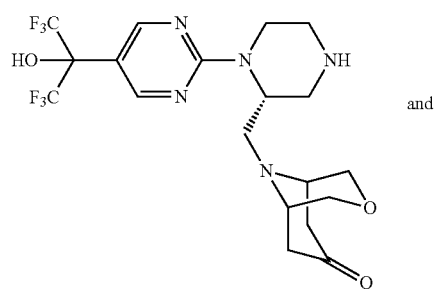

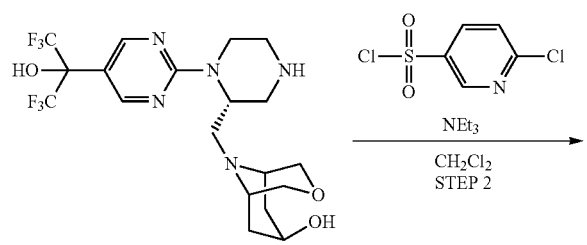

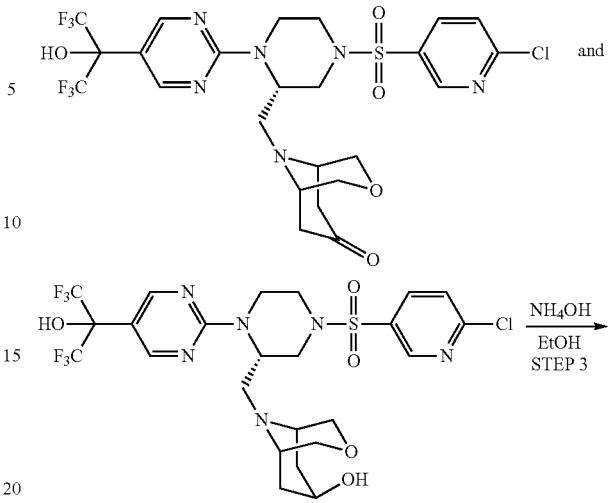

A 25-mL round-bottomed flask was charged with a 1:1 mixture of 9-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one (300 mg, 0.44 mmol, Example 98, Step 5), potassium hydroxide (749 mg, 13.34 mmol), MeOH (5 mL) and water (2 mL) and was stirred at room temperature for 30 min. The solvent was removed in vacuo and then diluted with water (50 mL) and extracted with EtOAc (3×50 mL). The organic layers were dried (Na$_2$SO$_4$), filtered, and concentrated to give 9-(((2R)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2R)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one (215 mg) which were used without purification.

Step 2: 9-(4ZS)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one A 25-mL round-bottomed flask was charged with a 1:1 mixture of 9-(((2R)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2R)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one (215 mg, 0.44 mmol), triethylamine (0.19 mL, 1.33 mmol) and $CH_2Cl_2$ (5 mL). 6-chloropyridine-3-sulfonyl chloride (94 mg, 0.44 mmol, *Organic Process Research & Development* 2009, 13, 875) was added as a solution in $CH_2Cl_2$ (2 mL) and the reaction was stirred at room temperature for 20 min. The reaction was then concentrated onto silica and purified via column chromatography (12 g silica gel, 0 to 100% EtOAc in hexanes) to give 9-(((2S)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one (50 mg).

Step 3: 9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one A 30-mL sealed tube was charged with 9-(((2S)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) and 9-(((2S)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one (50 mg, 0.076 mmol), ammonium hydroxide (266 mg, 7.59 mmol) and EtOH (5 mL) and was heated to 150° C. o/n. The reaction was diluted with water (50 mL) and EtOAc (100 mL) and the organic layer was separated, dried ($Na_2SO_4$), filtered and concentrated. The resulting residue was purified via reverse-phase preparative HPLC using a Phenomenex Gemini $C_{18}$ column (30×150 mm, 10 µm) eluting with 0.1% TFA in $CH_3CN/H_2O$ (10% to 100% over 15 min) to give 9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo) (12 mg) and 9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one (10 mg).

9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo)

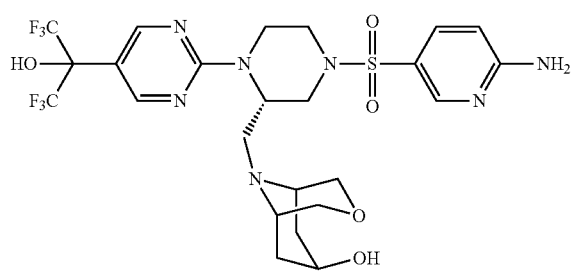 [SMILES: Nc1ccc(S(=O)(=O)N2CCN(c3ncc(C(O)(C(F)(F)F)C(F)(F)F)cn3)[C@@H](CN3C4COCC3CC(O)C4)C2)cn1]

$^1$H NMR (400 MHz, $CD_3OD$) δ=8.50 (s, 2H), 8.24 (s, 1H), 7.73 (d, J=11.2 Hz, 1H), 6.62 (d, J=9.0 Hz, 1H), 4.67 (d, J=14.7 Hz, 1H), 3.96 (d, J=11.7 Hz, 1H), 3.88-3.75 (m, 3H), 3.72-3.59 (m, 3H), 3.25-3.10 (m, 2H), 3.00-2.89 (m, 1H), 2.87-2.70 (m, 3H), 2.59-2.38 (m, 2H), 2.35-2.11 (m, 2H), 1.54 (m, J=12.5 Hz, 2H). m/z (ESI, +ve ion) 642.2 (M+H)$^+$. GK-GKRP $IC_{50}$ (Binding)=0.003 µM; GK-GKRP $EC_{50}$ (LC MS/MS-2)=0.025 µM.

9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one

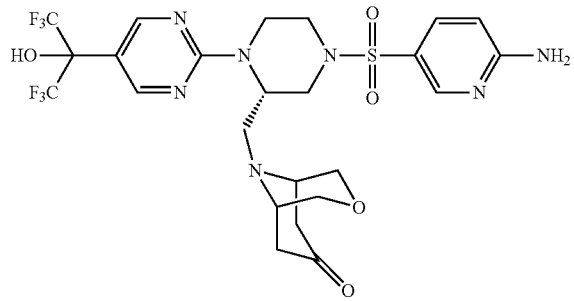 [SMILES: Nc1ccc(S(=O)(=O)N2CCN(c3ncc(C(O)(C(F)(F)F)C(F)(F)F)cn3)[C@@H](CN3C4COCC3CC(=O)C4)C2)cn1]

$^1$H NMR (400 MHz, $CD_3OD$) δ=8.59 (s, 2H), 8.31 (d, J=2.3 Hz, 1H), 7.74 (dd, J=8.9, 2.4 Hz, 1H), 6.62 (d, J=8.8 Hz, 1H), 5.07-4.93 (m, 1H), 4.70 (d, J=14.1 Hz, 1H), 4.02 (d, J=11.9 Hz, 1H), 3.83 (d, J=13.1 Hz, 1H), 3.72-3.54 (m, 3H), 3.52-3.44 (m, 2H), 3.28-3.23 (m, 2H), 3.11-3.00 (m, 1H), 2.99-2.85 (m, 1H), 2.76-2.60 (m, 2H), 2.60-2.38 (m, 2H), 2.22 (d, J=15.6 Hz, 2H). m/z (ESI, +ve ion) 640.3 (M+H)$^+$. GK-GKRP $IC_{50}$ (Binding)=0.075 µM; GK-GKRP $EC_{50}$ (LC MS/MS-2)=0.097 µM.

Example 100

8-(((2S)-4-(2-thiophenylsulfonyl)-1-(5-(2,2,2-trifluoro-1-hydroxy-1-methylethyl)-2-pyrimidinyl)-2-piperazinyl)methyl)-3-oxa-8-azabicyclo[3.2.1]octan-6-ol (endo)

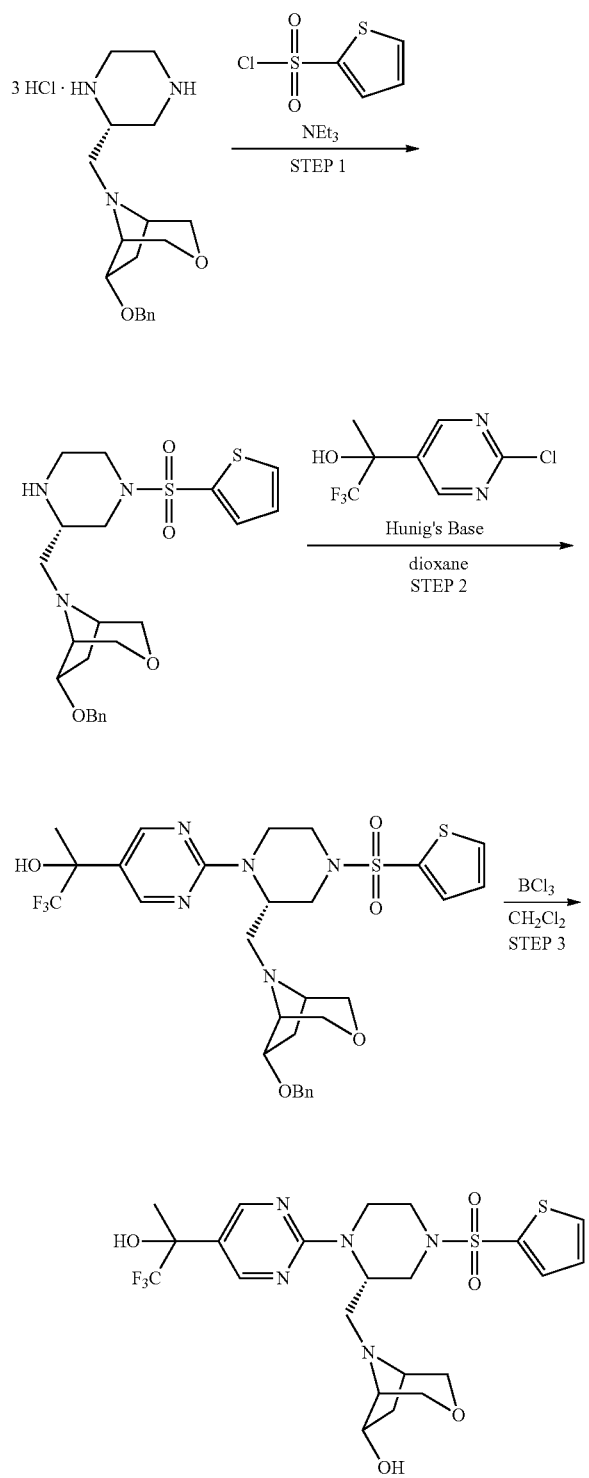

Step 1: 6-(benzyloxy)-8-(((2S)-4-(2-thiophenylsulfonyl)-2-piperazinyl)methyl)-3-oxa-8-azabicyclo[3.2.1]octane (endo)

A 50-mL round-bottomed flask was cooled to 0° C. and charged with 6-(benzyloxy)-8-((R)-piperazin-2-ylmethyl)-3-oxa-8-azabicyclo[3.2.1]octane trihydrochloride (endo) (700 mg, 1.64 mmol, Example 79, Step 3), triethylamine (1.14 mL, 8.20 mmol) and $CH_2Cl_2$ (10 mL). This was followed by thiophene-2-sulfonyl chloride (300 mg, 1.64 mmol, Sigma-Aldrich, St. Louis, Mo.) as a solution in $CH_2Cl_2$ (5 mL). After 10 min, the reaction was concentrated onto silica gel and purified via column chromatography (40 g silica gel, 0 to 10% MeOH in $CH_2Cl_2$) to give 6-(benzyloxy)-8-(((2S)-4-(2-thiophenylsulfonyl)-2-piperazinyl)methyl)-3-oxa-8-azabicyclo[3.2.1]octane (endo) (250 mg) as a mixture of two isomers.

Step 2: 2-(2-((2S)-2-((6-(benzyloxy)-3-oxa-8-azabicyclo[3.2.1]oct-8-yl)methyl)-4-(2-thiophenylsulfonyl)-1-piperazinyl)-5-pyrimidinyl)-1,1,1-trifluoro-2-propanol (endo)

A 20-mL vial was charged with 6-(benzyloxy)-8-(((2S)-4-(2-thiophenylsulfonyl)-2-piperazinyl)methyl)-3-oxa-8-azabicyclo[3.2.1]octane (endo) (250 mg, 0.54 mmol), 2-(2-chloropyrimidin-5-yl)-1,1,1-trifluoropropan-2-ol (244 mg, 1.078 mmol, Intermediate E), Hünig's base (0.29 mL, 1.62 mmol) and dioxane (5 mL). The reaction was heated to 120° C. for 12 h. The mixture was then concentrated onto silica gel and purified via column chromatography (120 g silica gel, 0 to 100% EtOAc in hexanes) to give 2-(2-((2S)-2-((6-(benzyloxy)-3-oxa-8-azabicyclo[3.2.1]oct-8-yl)methyl)-4-(2-thiophenylsulfonyl)-1-piperazinyl)-5-pyrimidinyl)-1,1,1-trifluoro-2-propanol (endo) (170 mg) as a mixture of four isomers.

Step 3: 8-(((2S)-4-(2-thiophenylsulfonyl)-1-(5-(2,2,2-trifluoro-1-hydroxy-1-methylethyl)-2-pyrimidinyl)-2-piperazinyl)methyl)-3-oxa-8-azabicyclo[3.2.1]octan-6-ol (endo)

A 25-mL round-bottomed flask was cooled to 0° C. and charged with 2-(2-((2S)-2-((6-(benzyloxy)-3-oxa-8-azabicyclo[3.2.1]oct-8-yl)methyl)-4-(2-thiophenylsulfonyl)-1-piperazinyl)-5-pyrimidinyl)-1,1,1-trifluoro-2-propanol (endo) (170 mg, 0.26 mmol) and $CH_2Cl_2$ (5 mL). $BCl_3$ (1M in $CH_2Cl_2$, 4.20 mL, 4.20 mmol) was added slowly. After 15 min at 0° C., the reaction was carefully quenched with MeOH and concentrated. The resultant foam was then recrystallized from MeOH/ether to yield an off-white solid which was purified via column chromatography (12 g silica gel, 0 to 10% MeOH in $CH_2Cl_2$) to give 8-(((2S)-4-(2-thiophenylsulfonyl)-1-(5-(2,2,2-trifluoro-1-hydroxy-1-methylethyl)-2-pyrimidinyl)-2-piperazinyl)methyl)-3-oxa-8-azabicyclo[3.2.1]octan-6-ol (120 mg) (endo) as a mixture of four isomers.

This individual isomers were isolated using two separate chiral SFC methods: Chiralpak® ADH column (21×250 mm, 5 µm) using 35% ethanol (w/DEA) in supercritical $CO_2$ (total flow was 70 mL/min) was used to separate peaks 1 and 2 from one another and from peaks 3 and 4 and Chiralpak® ASH column (21×250 mm, 5 µm) using 35% ethanol (w/DEA) in supercritical $CO_2$ (total flow was 70 mL/min) was used to separate peaks 3 and 4 from one another. This produced four isomers with both diastereomeric and enantiomeric excesses over 95%.

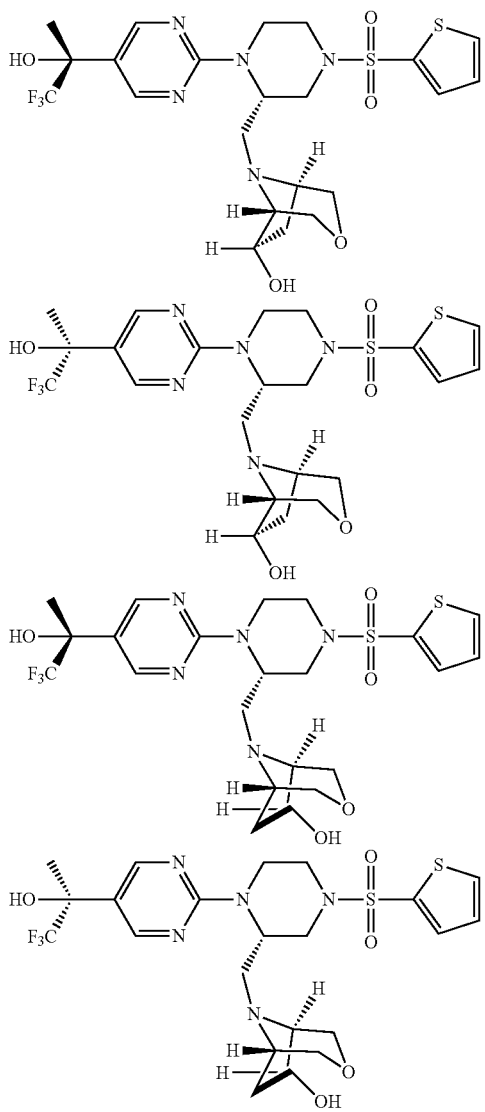

(1R,5R,6R)-8-((((2S)-4-(2-thiophenylsulfonyl)-1-(5-((1R)-2,2,2-trifluoro-1-hydroxy-1-methylethyl)-2-pyrimidinyl)-2-piperazinyl)methyl)-3-oxa-8-azabicyclo[3.2.1]octan-6-ol (endo); (1R,5R,6R)-8-((((2S)-4-(2-thiophenylsulfonyl)-1-(5-((1S)-2,2,2-trifluoro-1-hydroxy-1-methylethyl)-2-pyrimidinyl)-2-piperazinyl)methyl)-3-oxa-8-azabicyclo[3.2.1]octan-6-ol (endo); (1S,5S,6S)-8-(((2S)-4-(2-thiophenylsulfonyl)-1-(5-((1R)-2,2,2-trifluoro-1-hydroxy-1-methylethyl)-2-pyrimidinyl)-2-piperazinyl)methyl)-3-oxa-8-azabicyclo[3.2.1]octan-6-ol (endo); (1S,5S,6S)-8-(((2S)-4-(2-thiophenylsulfonyl)-1-(5-((1S)-2,2,2-trifluoro-1-hydroxy-1-methylethyl)-2-pyrimidinyl)-2-piperazinyl)methyl)-3-oxa-8-azabicyclo[3.2.1]octan-6-ol (endo).

First Eluting Peak (Peak #1)

$^1$H NMR (400 MHz, CD$_3$OD) δ=8.49 (s, 2H), 7.85 (dd, J=5.1, 1.2 Hz, 1H), 7.64 (dd, J=3.7, 1.2 Hz, 1H), 7.23 (dd, J=5.0, 3.8 Hz, 1H), 4.64 (d, J=12.9 Hz, 1H), 4.61-4.40 (m, 1H), 4.15-4.14 (m, 1H), 4.18-4.06 (m, 1H), 3.90 (d, J=11.2 Hz, 1H), 3.84-3.69 (m, 2H), 3.58 (d, J=10.6 Hz, 1H), 3.48 (d, J=11.7 Hz, 1H), 3.23-3.07 (m, 2H), 2.99-2.89 (m, 1H), 2.89-2.75 (m, 1H), 2.68-2.55 (m, 1H), 2.54-2.31 (m, 3H), 1.69 (s, 3H), 1.66-1.57 (m, 1H). m/z (ESI, +ve ion) 564.2 (M+H)$^+$. GK-GKRP IC$_{50}$ (Binding)=0.022 µM; GK-GKRP EC$_{50}$ (LC MS/MS-2)=0.041 µM.

Second Eluting Peak (Peak #2)

$^1$H NMR (400 MHz, CD$_3$OD) δ=8.49 (s, 2H), 7.85 (dd, J=5.1, 1.2 Hz, 1H), 7.63 (dd, J=3.8, 1.1 Hz, 1H), 7.23 (dd, J=5.0, 3.8 Hz, 1H), 4.95-4.86 (m, 1H), 4.64 (d, J=13.3 Hz, 1H), 4.49-4.36 (m, 1H), 3.99 (s, 1H), 3.92 (d, J=10.8 Hz, 1H), 3.79 (d, J=11.3 Hz, 1H), 3.53-3.67 (m, 2H), 3.45-3.37 (m, 1H), 3.25-2.97 (m, 3H), 2.96-2.82 (m, 1H), 2.79-2.60 (m, 1H), 2.59-2.35 (m, 3H), 1.69 (s, 3H), 1.67-1.62 (m, 1H). m/z (ESI, +ve ion) 564.2 (M+H)$^+$. GK-GKRP IC$_{50}$ (Binding)=0.051 µM; GK-GKRP EC$_{50}$ (LC MS/MS-2)=0.057 µM.

Third Eluting Peak (Peak #3)

$^1$H NMR (400 MHz, CD$_3$OD) δ=8.49 (s, 2H), 7.85 (dd, J=5.0, 1.3 Hz, 1H), 7.63 (dd, J=3.7, 1.2 Hz, 1H), 7.23 (dd, J=5.0, 3.8 Hz, 1H), 4.92-4.87 (m, 1H), 4.64 (d, J=13.3 Hz, 1H), 4.51-4.35 (m, 1H), 4.01 (d, J=11.9 Hz, 1H), 3.90 (s, 1H), 3.79 (d, J=10.0 Hz, 1H), 3.60 (m, J=9.0 Hz, 2H), 3.45-3.38 (m, 1H), 3.24-2.98 (m, 3H), 2.94-2.82 (m, 1H), 2.76-2.60 (m, 1H), 2.56-2.28 (m, 3H), 1.69 (s, 3H), 1.66-1.56 (m, 1H). m/z (ESI, +ve ion) 564.2 (M+H)$^+$. GK-GKRP IC$_{50}$ (Binding)=0.031 µM; GK-GKRP EC$_{50}$ (LC MS/MS-2)=0.065 µM.

Fourth Eluting Peak (Peak #4)

$^1$H NMR (400 MHz, CD$_3$OD) δ=8.49 (s, 2H), 7.85 (dd, J=4.9, 1.2 Hz, 1H), 7.63 (dd, J=3.7, 1.2 Hz, 1H), 7.23 (dd, J=5.0, 3.8 Hz, 1H), 4.73-4.59 (m, 1H), 4.59-4.42 (m, 1H), 4.23-4.02 (m, 1H), 4.01-3.85 (m, 1H), 3.85-3.74 (m, 2H), 3.67-3.44 (m, 2H), 3.24-3.09 (m, 3H), 3.03-2.78 (m, 2H), 2.76-2.59 (m, 1H), 2.59-2.31 (m, 3H), 1.60-1.74 (m, 4H). m/z (ESI, +ve ion) 564.2 (M+H)$^+$. GK-GKRP IC$_{50}$ (Binding)=0.088 µM; GK-GKRP EC$_{50}$ (LC MS/MS-2)=0.15 µM.

Example 101

1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol

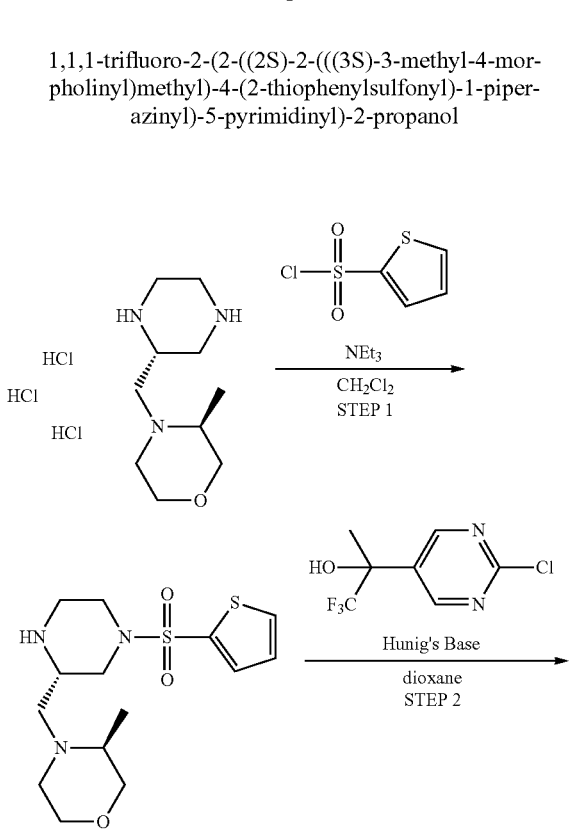

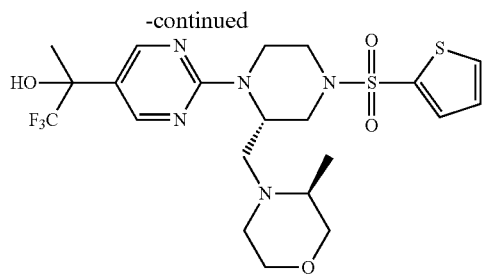

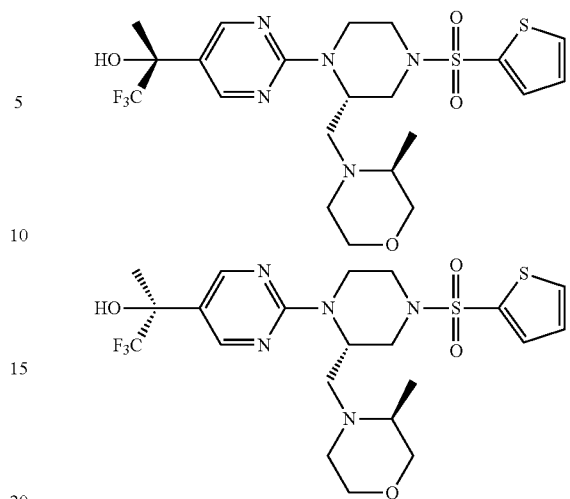

Step 1: (3S)-3-methyl-4-(((2S)-4-(2-thiophenylsulfonyl)-2-piperazinyl)methyl)morpholine A 50-mL round-bottomed flask was cooled to 0° C. and charged with (3S)-3-methyl-4-((2R)-2-piperazinylmethyl)morpholine trihydrochloride (1.0 g, 3.24 mmol, Example 82, Step 2), CH$_2$Cl$_2$ (10 mL) and triethylamine (2.3 mL, 16.2 mmol). 2-Thiophenesulfonyl chloride (0.59 g, 3.24 mmol, Sigma-Aldrich, St. Louis, Mo.) was added as a solution in CH$_2$Cl$_2$ (5 mL) and after 10 min the MeOH (20 mL) was added and concentrated onto silica gel. The crude material was purified via column chromatography (40 g silica gel, 0 to 10% MeOH in CH$_2$Cl$_2$) to give (3S)-3-methyl-4-(((2S)-4-(2-thiophenylsulfonyl)-2-piperazinyl)methyl)morpholine (0.68 g).

Step 2: 1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol A 20 mL vial was charged with (3S)-3-methyl-4-(((2S)-4-(2-thiophenylsulfonyl)-2-piperazinyl)methyl)morpholine (0.68 g, 1.97 mmol), 2-(2-chloropyrimidin-5-yl)-1,1,1-trifluoropropan-2-ol (0.45 g, 1.97 mmol, Example 100, Step 1), Hünig's base (0.69 mL, 3.94 mmol) and dioxane (10 mL) heated at 100° C. for one week. The crude reaction was then concentrated onto silica gel and purified via column chromatography (40 g silica gel, 0 to 10% MeOH in CH$_2$Cl$_2$) and the resultant foam triturated with ether to give 1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol (0.5 g) as a mixture of two isomers.

$^1$H NMR (400 MHz, CD$_3$OD) δ=8.49 (s, 2H), 7.86 (dd, J=1.3, 5.0 Hz, 1H), 7.66-7.58 (m, J=2.5 Hz, 1H), 7.24 (dd, J=3.8, 5.0 Hz, 1H), 4.99-4.90 (m, 1H), 4.68 (d, J=13.7 Hz, 1H), 4.09 (d, J=11.3 Hz, 1H), 3.83-3.55 (m, 4H), 3.45-3.36 (m, 1H), 3.28-3.04 (m, 3H), 2.52-2.16 (m, 4H), 1.97-1.96 (m, 1H), 1.69 (s, 3H), 1.08 (d, J=6.1 Hz, 3H). m/z (ESI, +ve ion) 536.2 (M+H)$^+$. GK-GKRP IC$_{50}$ (Binding)=0.012 µM; GK-GKRP EC$_{50}$ (LC MS/MS-2)=0.032 µM.

The individual isomers were isolated using chiral SFC. The method used was as follows: Chiralpak® ASH column (21× 250 mm, 5 µm) using 15% ethanol (w/DEA) in supercritical CO$_2$ (total flow was 70 mL/min). This produced the two isomers with both diastereomeric and enantiomeric excesses over 95%.

(2R)-1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol; (2S)-1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol.

First Eluting Peak (Peak #1)

$^1$H NMR (400 MHz, CD$_3$OD) δ=8.49 (s, 2H), 7.85 (d, J=4.9 Hz, 1H), 7.68-7.57 (m, 1H), 7.32-7.17 (m, 1H), 4.98-4.90 (m, 1H), 4.68 (d, J=13.7 Hz, 1H), 4.09 (d, J=11.0 Hz, 1H), 3.83-3.54 (m, 4H), 3.44-3.36 (m, 1H), 3.26-2.97 (m, 3H), 2.57-2.19 (m, 4H), 1.98 (d, J=11.5 Hz, 1H), 1.68 (s, 3H), 1.07 (d, J=6.1 Hz, 3H). m/z (ESI, +ve ion) 536.2 (M+H)$^+$. GK-GKRP IC$_{50}$ (Binding)=0.009 µM; GK-GKRP EC$_{50}$ (LC MS/MS-2)=0.02 µM.

Second Eluting Peak (Peak #2)

$^1$H NMR (400 MHz, CD$_3$OD) δ=8.49 (s, 2H), 7.85 (dd, J=1.3, 5.0 Hz, 1H), 7.63 (dd, J=1.2, 3.7 Hz, 1H), 7.24 (dd, J=3.8, 5.0 Hz, 1H), 5.01-4.89 (m, 1H), 4.68 (d, J=13.3 Hz, 1H), 4.09 (d, J=11.3 Hz, 1H), 3.91-3.53 (m, 4H), 3.45-3.35 (m, 1H), 3.27-3.01 (m, 3H), 2.50-2.19 (m, 4H), 2.04-1.91 (m, 1H), 1.69 (s, 3H), 1.07 (d, J=6.3 Hz, 3H). m/z (ESI, +ve ion) 536.2 (M+H)$^+$. GK-GKRP IC$_{50}$ (Binding)=0.019 µM; GK-GKRP EC$_{50}$ (LC MS/MS-2)=0.03 µM.

Example 102

1,1,1-trifluoro-2-(4-((2S)-2-(((3S)-3-methyl-4-morpholinyl)methyl)-4-(1,3-thiazol-2-ylsulfonyl)-1-piperazinyl)phenyl)-2-propanol

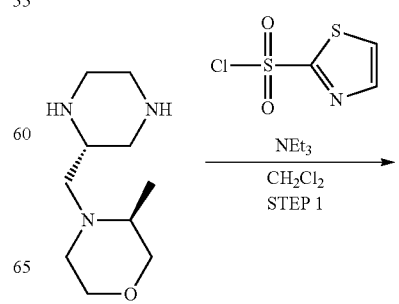

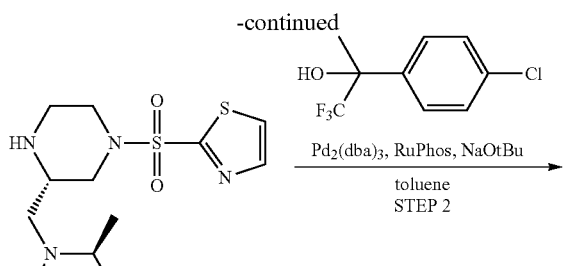

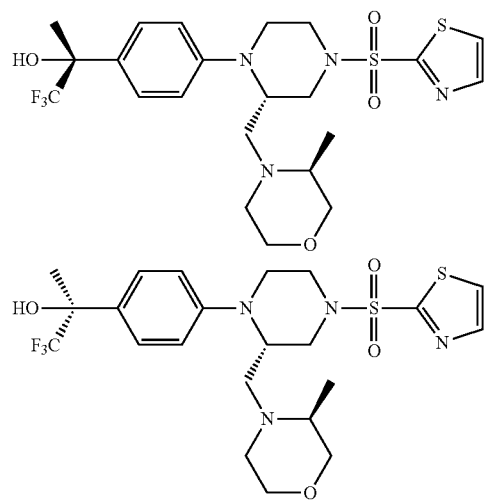

Step 1: (3S)-3-methyl-4-(((2S)-4-(1,3-thiazol-2-yl-sulfonyl)-2-piperazinyl)methyl)morpholine A 50-mL round-bottomed flask was cooled to 0° C. and charged with (3S)-3-methyl-4-((2R)-2-piperazinylmethyl) morpholine (100 mg, 0.5 mmol, Example 82, Step 2), $CH_2Cl_2$ (5 mL) and triethylamine (0.07 mL, 0.5 mmol). Thiazole-2-sulfonyl chloride (92 mg, 0.5 mmol, Bioorg. Med. Chem., 2006, 14, 6628) was added and after 10 min the reaction was concentrated and acidified with 4 N HCl in dioxane (5 mL). The HCl salt was collected after filtration and the crude material was purified via column chromatography (40 g silica gel, 0 to 10% (2M $NH_3$ in MeOH) in $CH_2Cl_2$) to give (3S)-3-methyl-4-(((2S)-4-(1,3-thiazol-2-ylsulfonyl)-2-piperazinyl) methyl)morpholine (210 mg).

Step 2: 1,1,1-trifluoro-2-(4-((2S)-2-(((3S)-3-methyl-4-morpholinyl)methyl)-4-(1,3-thiazol-2-ylsulfonyl)-1-piperazinyl)phenyl)-2-propanol A 20-mL vial was charged with (3S)-3-methyl-4-(((2S)-4-(1,3-thiazol-2-ylsulfonyl)-2-piperazinyl)methyl)morpholine (210 mg, 0.61 mmol), 2-(4-bromophenyl)-1,1,1-trifluoropropan-2-ol (326 mg, 1.21 mmol, Example 27, Step 1), sodium tert-butoxide (175 mg, 1.82 mmol), $Pd_2(dba)_3$ (55.5 mg, 0.061 mmol), dicyclohexyl(2',6'-diisopropoxybiphenyl-2-yl) phosphine (RuPhos) (42.4 mg, 0.091 mmol, Strem Chemicals, Newburyport, Mass.) and toluene (5 mL). the vial was sealed and heated to 100° C. for 3 h. The reaction was filtered, concentrated and purified via reverse-phase preparative HPLC using a Phenomenex Gemini $C_{18}$ column (30×150 mm, 10 μm) eluting with 0.1% TFA in $CH_3CN/H_2O$ (5% to 100% over 15 min) to give 1,1,1-trifluoro-2-(4-((2S)-2-(((3S)-3-methyl-4-morpholinyl)methyl)-4-(1,3-thiazol-2-ylsulfonyl)-1-piperazinyl)phenyl)-2-propanol (20 mg) that was a mixture of two isomers.

(2R)-1,1,1-trifluoro-2-(4-((2S)-2-(((3S)-3-methyl-4-morpholinyl)methyl)-4-(1,3-thiazol-2-ylsulfonyl)-1-piperazinyl)phenyl)-2-propanol, (2S)-1,1,1-trifluoro-2-(4-((2S)-2-(((3S)-3-methyl-4-morpholinyl)methyl)-4-(1,3-thiazol-2-ylsulfonyl)-1-piperazinyl)phenyl)-2-propanol. $^1H$ NMR (400 MHz, $CD_3OD$) δ=8.09 (d, J=3.1 Hz, 1H), 8.01 (d, J=3.1 Hz, 1H), 7.45 (d, J=8.8 Hz, 2H), 6.93 (d, J=8.8 Hz, 2H), 4.13 (d, J=11.5 Hz, 1H), 4.07-3.97 (m, 1H), 3.93-3.80 (m, 1H), 3.70-3.51 (m, 4H), 3.50-3.40 (m, 1H), 3.28-3.15 (m, 2H), 2.97-2.80 (m, 3H), 2.41-2.26 (m, 1H), 2.16-1.98 (m, 1H), 1.92-1.82 (m, 1H), 1.67 (s, 3H), 1.00 (d, J=6.3 Hz, 3H). m/z (ESI, +ve ion) 535.2 $(M+H)^+$. GK-GKRP $IC_{50}$ (Binding)=0.134 μM; GK-GKRP $EC_{50}$ (LC MS/MS-2)=0.137 μM.

Example 103

2-(4-(4-((4-aminophenyl)sulfonyl)-1-piperazinyl) phenyl)-1,1,1,3,3,3-hexafluoro-2-propanol

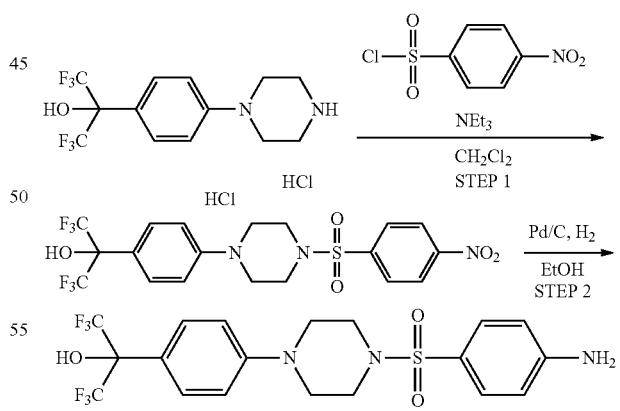

Step 1: 2-(4-(4-((4-nitrophenyl)sulfonyl)-1-piperazinyl)phenyl)-1,1,1,3,3,3-hexafluoro-2-propanol A 25-mL round-bottomed flask was cooled to 0° C. and charged with 1,1,1,3,3,3-hexafluoro-2-(4-(1-piperazinyl) phenyl)-2-propanol dihydrochloride (250 mg, 0.62 mmol, Example 91, Step 1), $CH_2Cl_2$ (5 mL) and triethylamine (0.26 mL, 1.87 mmol). 4-Nitrobenzenesulfonyl chloride (166 mg, 0.75 mmol, Sigma-Aldrich, St. Louis, Mo.) was added. After 10 min at 0° C. the reaction was concentrated onto silica gel and purified via column chromatography (40 g silica gel, 0 to 10% MeOH in $CH_2Cl_2$) to give 2-(4-(4-((4-nitrophenyl)sulfonyl)-1-piperazinyl)phenyl)-1,1,1,3,3,3-hexafluoro-2-propanol (180 mg).

Step 2: 2-(4-(4-((4-aminophenyl)sulfonyl)-1-piperazinyl)phenyl)-1,1,1,3,3,3-hexafluoro-2-propanol A 100-mL round-bottomed flask was charged with 2-(4-(4-((4-nitrophenyl)sulfonyl)-1-piperazinyl)phenyl)-1,1,1,3,3,3-hexafluoro-2-propanol (180 mg) and EtOH (20 mL). The reaction was placed under an atmosphere of argon. 10% Pd/C (37.3 mg, 0.351 mmol, Sigma-Aldrich, St. Louis, Mo.) was added and the reaction stirred under a balloon atmosphere of $H_2$ (0.707 mg, 0.351 mmol) for 12 h. The reaction was carefully filtered through a pad of Celite®(diatomaceous earth), rinsing with EtOH. The crude material was concentrated onto silica gel and purified via column chromatography (40 g silica gel, 0 to 10% MeOH in $CH_2Cl_2$) to give 2-(4-(4-((4-aminophenyl)sulfonyl)-1-piperazinyl)phenyl)-1,1,1,3,3,3-hexafluoro-2-propanol (90 mg). $^1H$ NMR (400 MHz, $CD_3OD$) δ=7.54 (d, J=8.8 Hz, 2H), 7.48 (d, J=8.6 Hz, 2H), 6.98 (d, J=9.0 Hz, 2H), 6.73 (d, J=8.6 Hz, 2H), 3.31-3.26 (m, 4H), 3.11-3.03 (m, 4H). m/z (ESI, +ve ion) 484.1 $(M+H)^+$. GK-GKRP $IC_{50}$ (Binding)=0.582 μM; GK-GKRP $EC_{50}$ (LC MS/MS-2)=0.828 μM.

Example 104

2-(4-(4-((4-amino-3-fluorophenyl)sulfonyl)-1-piperazinyl)phenyl)-1,1,1,3,3,3-hexafluoro-2-propanol

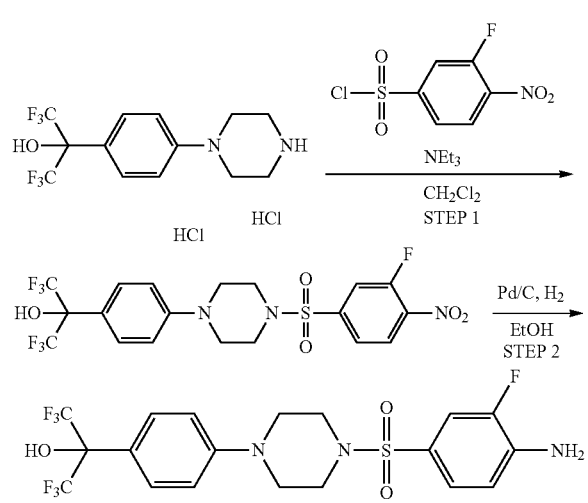

Step 1: 2-(4-(4-((3-fluoro-4-nitrophenyl)sulfonyl)-1-piperazinyl)phenyl)-1,1,1,3,3,3-hexafluoro-2-propanol A 25-mL round-bottomed flask was cooled to 0° C. and charged with 1,1,1,3,3,3-hexafluoro-2-(4-(1-piperazinyl)phenyl)-2-propanol dihydro chloride (500 mg, 1.25 mmol, Example 91, Step 1), $CH_2Cl_2$ (10 mL) and triethylamine (0.52 mL, 3.74 mmol). 3-Fluoro-4-nitrobenzenesulfonyl chloride (328 mg, 1.371 mmol, Matrix Scientific, Columbia, S.C.) was added and after 10 min the reaction was concentrated onto silica gel and purified via column chromatography (40 g silica gel, 0 to 100% hexanes in EtOAc) to give 2-(4-(4-((3-fluoro-4-nitrophenyl)sulfonyl)-1-piperazinyl)phenyl)-1,1,1,3,3,3-hexafluoro-2-propanol (350 mg).

Step 2: 2-(4-(4-((3-fluoro-4-nitrophenyl)sulfonyl)-1-piperazinyl)phenyl)-1,1,1,3,3,3-hexafluoro-2-propanol A 100-mL round-bottomed flask was charged 2-(4-(4-((3-fluoro-4-nitrophenyl)sulfonyl)-1-piperazinyl)phenyl)-1,1,1,3,3,3-hexafluoro-2-propanol (350 mg, 0.66 mmol) and EtOH (40 mL). The reaction was placed under an atmosphere of argon. 10% Pd/C (70.1 mg, 0.66 mmol) was added and the reaction was stirred under a balloon atmosphere of $H_2$ for 12 h. The reaction was carefully filtered through a pad of Celite, rinsing with EtOH. The crude material was concentrated onto silica gel and purified via column chromatography (40 g silica gel, 0 to 10% MeOH in $CH_2Cl_2$) to give 2-(4-(4-((4-amino-3-fluorophenyl)sulfonyl)-1-piperazinyl)phenyl)-1,1,1,3,3,3-hexafluoro-2-propanol (60 mg). $^1H$ NMR (400 MHz, $CD_3OD$) δ=7.54 (d, J=8.6 Hz, 2H), 7.40-7.31 (m, 2H), 7.01-6.95 (m, 2H), 6.94-6.86 (m, 1H), 3.31-3.26 (m, 4H), 3.14-3.00 (m, 4H). m/z (ESI, +ve ion) 502.0 $(M+H)^+$. GK-GKRP $IC_{50}$ (Binding)=0.999 μM; GK-GKRP $EC_{50}$ (LC MS/MS-2)=0.642 μM.

Example 105

3-((4-(4-(2,2,2-trifluoro-1-hydroxy-1-(trifluoromethyl)ethyl)phenyl)-1-piperazinyl)sulfonyl)phenol

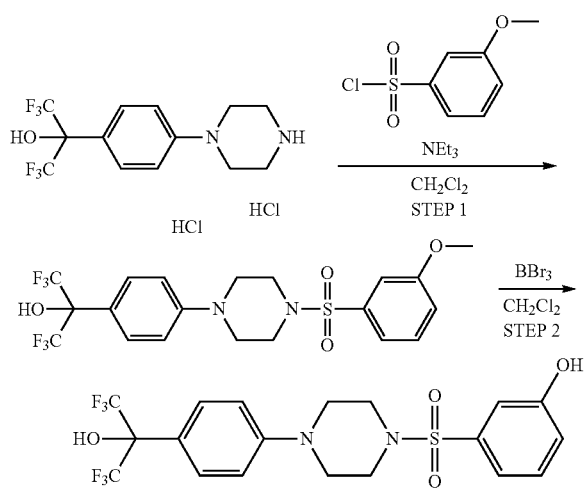

Step 1: 1,1,1,3,3,3-hexafluoro-2-(4-(4-((3-methoxyphenyl)sulfonyl)-1-piperazinyl)phenyl)-2-propanol A 25-mL round-bottomed flask was cooled to 0° C. and charged with 1,1,1,3,3,3-hexafluoro-2-(4-(1-piperazinyl)phenyl)-2-propanol dihydrochloride (200 mg, 0.5 mmol, Example 91, Step 1), $CH_2Cl_2$ (5 mL) and triethylamine (0.35 mL, 2.5 mmol). 3-Methoxybenzenesulfonyl chloride (113 mg, 0.55 mmol, Sigma-Aldrich, St. Louis, Mo.) was added. After 10 min at 0° C., the reaction was concentrated onto silica gel and purified via column chromatography (40 g silica gel, 0 to 100% hexanes in EtOAc) to give 1,1,1,3,3,3-hexafluoro-2-(4-(4-((3-methoxyphenyl)sulfonyl)-1-piperazinyl)phenyl)-2-propanol (120 mg).

Step 2: 3-((4-(4-(2,2,2-trifluoro-1-hydroxy-1-(trifluoromethyl)ethyl)phenyl)-1-piperazinyl)sulfonyl)phenol A 25 ml, round-bottomed flask was charged with 1,1,1,3,3,3-hexafluoro-2-(4-(4-((3-methoxyphenyl)sulfonyl)-1-piperazinyl)phenyl)-2-propanol (80 mg, 0.16 mmol) and $CH_2Cl_2$ (5 mL). $BBr_3$ (1M in $CH_2Cl_2$, 0.48 mL, 0.48 mmol) was added at room temperature. The reaction was stirred at room temperature for 1 h. The mixture was quenched with MeOH (20 mL), concentrated onto silica gel and purified via column chromatography (12 g silica gel, 0 to 10% MeOH in $CH_2Cl_2$) to give 3-((4-(4-(2,2,2-trifluoro-1-hydroxy-1-(trifluoromethyl)ethyl)phenyl)-1-piperazinyl)sulfonyl)phenol.
$^1$H NMR (400 MHz, $CD_3OD$) δ=7.57 (d, J=9.0 Hz, 2H), 7.44 (t, J=8.0 Hz, 1H), 7.25 (d, J=7.4 Hz, 1H), 7.18 (s, 1H), 7.10-7.06 (m, 1H), 7.04 (d, J=9.2 Hz, 2H), 3.37-3.33 (m, 4H), 3.21-3.07 (m, 4H). m/z (ESI, +ve ion) 485.1 (M+H)$^+$. GK-GKRP $IC_{50}$ (Binding)=0.949 μM; GK-GKRP $EC_{50}$ (LC MS/MS-2)=0.74 μM.

Example 106

9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-one

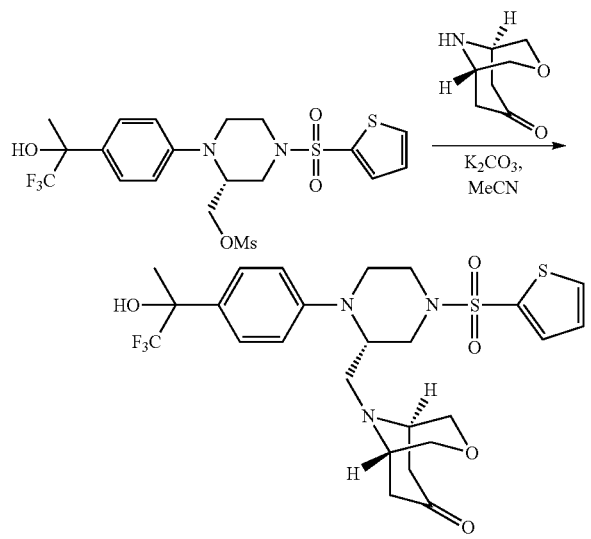

This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and 3-oxa-9-azabicyclo[3.3.1]nonan-7-one (published PCT patent application no. WO 2007/022502) (using an extra equivalent of potassium carbonate) followed by purification via column chromatography on silica gel (0 to 100% EtOAc in hexanes) delivered 9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-one as a mixture of two isomers.

$^1$H NMR (400 MHz, $CD_3OD$) δ=7.92-7.86 (m, 1H), 7.69-7.64 (m, 1H), 7.45 (d, J=8.6 Hz, 2H), 7.32-7.22 (m, 1H), 6.94 (d, J=9.0 Hz, 2H), 4.22-3.98 (m, 2H), 3.83 (d, J=11.7 Hz, 1H), 3.66-3.58 (m, 2H), 3.57-3.44 (m, 3H), 3.30-3.25 (m, 1H), 3.21-3.11 (m, 2H), 3.04-2.92 (m, 1H), 2.92-2.79 (m, 1H), 2.72-2.51 (m, 3H), 2.43 (dd, J=6.0, 15.6 Hz, 1H), 2.24-2.07 (m, 2H), 1.67 (s, 3H). m/z (ESI, +ve ion) 574.1 (M+H)$^+$. GK-GKRP $IC_{50}$ (Binding)=0.035 μM; GK-GKRP $EC_{50}$ (LC MS/MS-2)=0.097 μM.

The individual isomers were isolated using chiral SFC. The method used was as follows: Chiralpak® AD column (21× 250 mm, 5 μm) using 40% iPrOH (w/DEA) in supercritical $CO_2$ (total flow was 70 mL/min). This produced the two isomers with both diastereomeric and enantiomeric excesses over 95%.

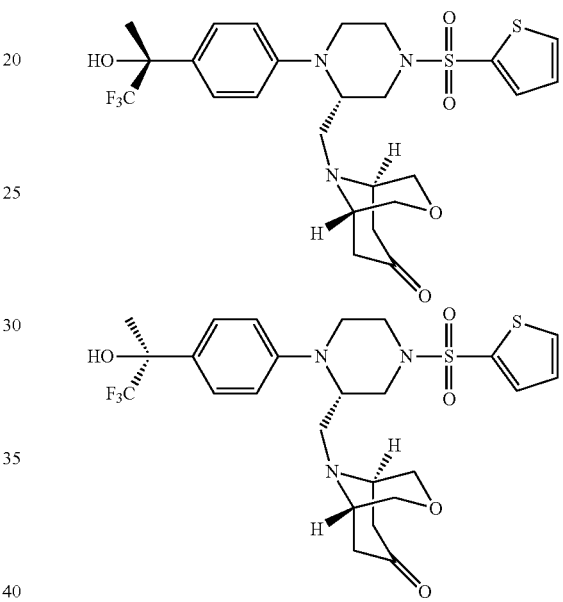

9-(((2S)-4-(2-thiophenylsulfonyl)-1-(4-((1R)-2,2,2-trifluoro-1-hydroxy-1-methylethyl)phenyl)-2-piperazinyl)methyl)-3-oxa-9-azabicyclo[3.3.1]nonan-7-one, 9-(((2S)-4-(2-thiophenylsulfonyl)-1-(4-((1S)-2,2,2-trifluoro-1-hydroxy-1-methylethyl)phenyl)-2-piperazinyl)methyl)-3-oxa-9-azabicyclo[3.3.1]nonan-7-one.

First Eluting Peak (Peak#1)

$^1$H NMR (400 MHz, $CD_3OD$) δ=7.88 (d, J=1.2 Hz, 1H), 7.66 (dd, J=1.3, 3.8 Hz, 1H), 7.44 (d, J=8.8 Hz, 2H), 7.27 (dd, J=3.8, 5.0 Hz, 1H), 6.95 (s, 2H), 4.22-3.99 (m, 2H), 3.89-3.74 (m, 1H), 3.62-3.57 (m, 2H), 3.56-3.43 (m, 3H), 3.30-3.24 (m, 1H), 3.21-3.07 (m, 2H), 2.98 (dd, J=8.8, 13.5 Hz, 1H), 2.87-2.76 (m, J=5.1 Hz, 1H), 2.73-2.51 (m, 3H), 2.42 (dd, J=5.9, 15.6 Hz, 1H), 2.22-2.06 (m, 2H), 1.67 (s, 3H). m/z (ESI, +ve ion) 574.2 (M+H)$^+$. GK-GKRP $IC_{50}$ (Binding)=0.052 μM; GK-GKRP $EC_{50}$ (LC MS/MS-2)=0.088 μM.

Second Eluting Peak (Peak#2)

$^1$H NMR (400 MHz, $CD_3OD$) δ=7.88 (dd, J=1.3, 5.0 Hz, 1H), 7.65 (dd, J=1.4, 3.7 Hz, 1H), 7.43 (d, J=8.8 Hz, 2H), 7.26 (dd, J=3.8, 5.0 Hz, 1H), 6.93 (d, J=9.0 Hz, 2H), 4.19-3.96 (m, 2H), 3.86-3.74 (m, 1H), 3.62-3.56 (m, 2H), 3.55-3.41 (m, 3H), 3.29-3.21 (m, 1H), 3.20-3.10 (m, 2H), 2.97 (dd, J=8.7, 13.4 Hz, 1H), 2.83 (dd, J=5.3, 13.5 Hz, 1H), 2.71-2.51 (m, 3H), 2.42 (dd, J=5.6, 15.6 Hz, 1H), 2.21-2.04 (m, 2H), 1.67 (s,

3H). m/z (ESI, +ve ion) 574.1 (M+H)+. GK-GKRP IC$_{50}$ (Binding)=0.061 μM; GK-GKRP EC$_{50}$ (LC MS/MS-2)=0.142 μM.

Example 107

9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-ol (endo)

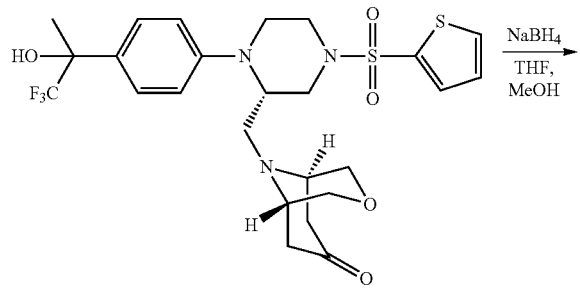

A 25-mL round-bottomed flask was charged with 9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-one (60 mg, 0.11 mmol, Example 106), THF (3 mL) and MeOH (0.5 mL). NaBH$_4$ (39.6 mg, 1.05 mmol) was added and the reaction stirred at room temperature for 20 min. MeOH (50 mL) was added and then the mixture was concentrated onto silica gel and purified via column chromatography (12 g silica gel, 0 to 10% MeOH in CH$_2$Cl$_2$) to give 9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-ol (endo) (10 mg) as a mixture of two isomers.

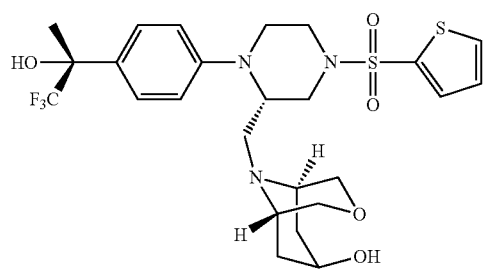

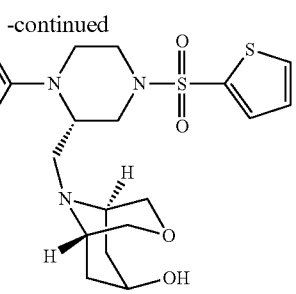

9-(((2S)-4-(2-thiophenylsulfonyl)-1-(4-((1R)-2,2,2-trifluoro-1-hydroxy-1-methylethyl)phenyl)-2-piperazinyl)methyl)-3-oxa-9-azabicyclo[3.3.1]nonan-7-ol (endo), 9-(((2S)-4-(2-thiophenylsulfonyl)-1-(4-((1S)-2,2,2-trifluoro-1-hydroxy-1-methylethyl)phenyl)-2-piperazinyl)methyl)-3-oxa-9-azabicyclo[3.3.1]nonan-7-ol (endo).

$^1$H NMR (400 MHz, CD$_3$OD) δ=7.91-7.82 (m, 1H), 7.67-7.60 (m, 1H), 7.43 (d, J=8.6 Hz, 2H), 7.28-7.20 (m, 1H), 6.90 (d, J=9.0 Hz, 2H), 4.07-3.88 (m, 2H), 3.83-3.74 (m, 3H), 3.71-3.55 (m, 3H), 3.50-3.41 (m, 1H), 3.26-3.18 (m, 1H), 2.88-2.77 (m, 1H), 2.76-2.65 (m, 3H), 2.62-2.45 (m, 2H), 2.25-2.12 (m, 1H), 2.12-1.98 (m, 1H), 1.67 (s, 3H), 1.56-1.35 (m, 2H). m/z (ESI, +ve ion) 576.2 (M+H)+. GK-GKRP IC$_{50}$ (Binding)=0.005 μM; GK-GKRP EC$_{50}$ (LC MS/MS-2)=0.016 μM.

Example 108

(1R,5S)-7-methyl-9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-ol (endo)

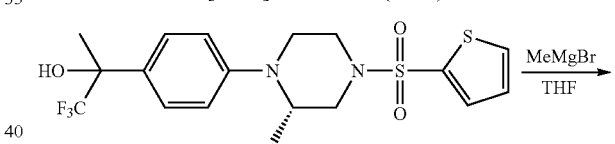

A 25-mL round-bottomed flask was cooled to 0° C. and charged with 9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-one (50 mg, 0.087 mmol, Example 106) and THF (5 mL). Methylmagnesium bromide was added (3.0M in THF, 0.15 mL, 0.44 mmol, Sigma-Aldrich, St. Louis, Mo.) and after 20 min another 0.5 equivalent of methylmagnesium bromide was added. The reaction was then quenched with MeOH (50 mL), concentrated onto silica gel, and purified via column chromatography (12 g silica gel, 0 to 100% hexanes in EtOAc). The material was purified further via reverse-phase preparative HPLC using a Phenomenex Gemini $C_{18}$ column (30×150 mm, 10 μm) eluting with 0.1% TFA in $CH_3CN/H_2O$ (5% to 100% over 15 min) to give (1R,5S)-7-methyl-9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-ol (endo) (10 mg) as a mixture of two isomers.

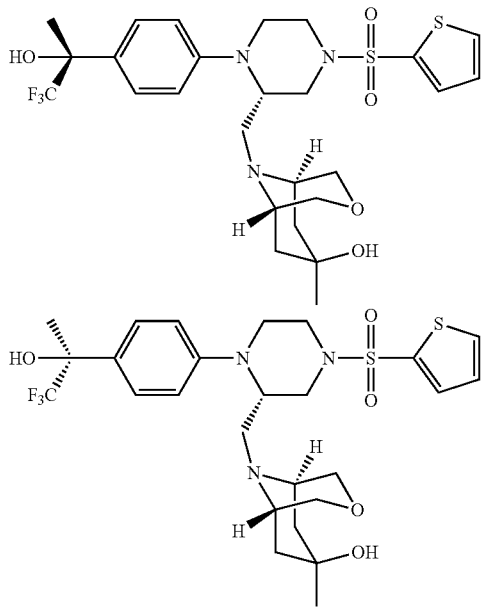

(1R,5S)-7-methyl-9-(((2S)-4-(2-thiophenylsulfonyl)-1-(4-((1R)-2,2,2-trifluoro-1-hydroxy-1-methylethyl)phenyl)-2-piperazinyl)methyl)-3-oxa-9-azabicyclo[3.3.1]nonan-7-ol (endo), (1R,5S)-7-methyl-9-(((2S)-4-(2-thiophenylsulfonyl)-1-(4-((1S)-2,2,2-trifluoro-1-hydroxy-1-methylethyl)phenyl)-2-piperazinyl)methyl)-3-oxa-9-azabicyclo[3.3.1]nonan-7-ol (endo). $^1$H NMR (400 MHz, $CD_3OD$) δ=7.93-7.81 (m, 1H), 7.68-7.59 (m, 1H), 7.50-7.36 (m, 2H), 7.32-7.17 (m, 1H), 7.00-6.73 (m, 2H), 4.08-3.87 (m, 2H), 3.84-3.58 (m, 5H), 3.51-3.39 (m, 1H), 3.26-3.10 (m, 1H), 2.85-2.49 (m, 5H), 2.03-1.94 (m, 1H), 1.85-1.75 (m, 1H), 1.67 (s, 3H), 1.56-1.48 (m, 1H), 1.46-1.39 (m, 1H), 1.36-1.28 (m, 1H), 1.11 (s, 3H). m/z (ESI, +ve ion) 590.2 $(M+H)^+$. GK-GKRP $IC_{50}$ (Binding)=0.027 μM; GK-GKRP $EC_{50}$ (LC MS/MS-2)=0.045 μM.

Example 109

1,1,1-trifluoro-2-(4-((2S)-2-(((1R,5S)-7-methoxy-3-oxa-9-azabicyclo[3.3.1]non-9-yl)methyl)-4-(2-thiophenylsulfonyl)-1-piperazinyl)phenyl)-2-propanol (endo)

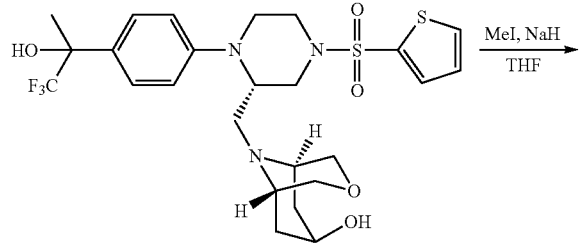

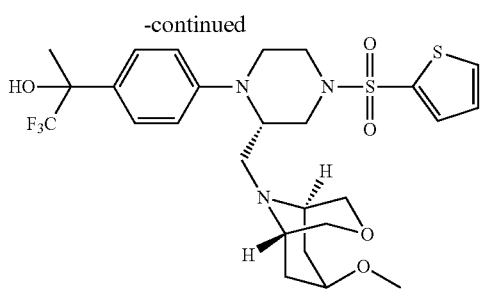

A 25-mL round-bottomed flask was charged with 9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-ol (endo) (50 mg, 0.087 mmol, Example 107) and THF (3 mL). Sodium hydride (60% dispersion in mineral oil, 34.7 mg, 0.869 mmol, Sigma-Aldrich, St. Louis, Mo.) was added at room temperature. After gas evolution had ceased iodomethane (0.054 mL, 0.87 mmol, Sigma-Aldrich, St. Louis, Mo.) was added. The reaction was stirred at room temperature for 20 min, then MeOH (20 mL) was added and then the reaction concentrated onto silica gel and purified via column chromatography (12 g silica gel, 0 to 100% hexanes in EtOAc) to give 1,1,1-trifluoro-2-(4-((2S)-2-(((1R,5S)-7-methoxy-3-oxa-9-azabicyclo[3.3.1]non-9-yl)methyl)-4-(2-thiophenylsulfonyl)-1-piperazinyl)phenyl)-2-propanol (endo) (10 mg) as a mixture of two isomers.

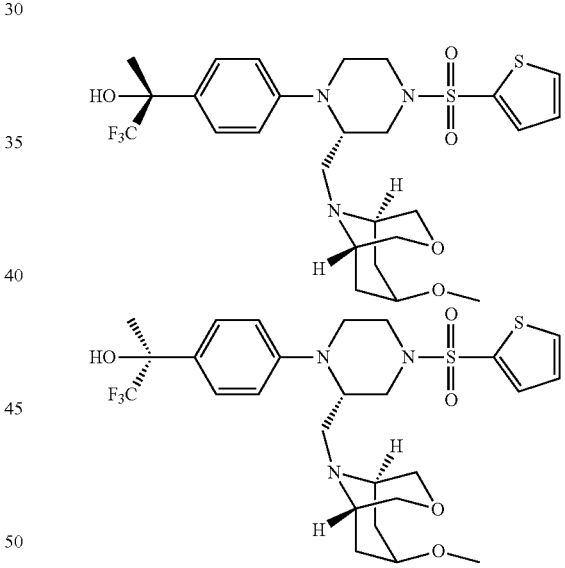

(2R)-1,1,1-trifluoro-2-(4-((2S)-2-(((1R,5S)-7-methoxy-3-oxa-9-azabicyclo[3.3.1]non-9-yl)methyl)-4-(2-thiophenylsulfonyl)-1-piperazinyl)phenyl)-2-propanol (endo), (2S)-1,1,1-trifluoro-2-(4-((2S)-2-(((1R,5S)-7-methoxy-3-oxa-9-azabicyclo[3.3.1]non-9-yl)methyl)-4-(2-thiophenylsulfonyl)-1-piperazinyl)phenyl)-2-propanol (endo).

$^1$H NMR (400 MHz, $CD_3OD$) δ=8.01-7.82 (m, 1H), 7.67-7.62 (m, 1H), 7.39-7.30 (m, 2H), 7.28-7.20 (m, 1H), 7.01-6.81 (m, 2H), 4.10-3.91 (m, 2H), 3.83-3.71 (m, 3H), 3.69-3.56 (m, 3H), 3.53-3.43 (m, 1H), 3.26-3.20 (m, 1H), 3.16 (br. s., 3H), 2.91-2.48 (m, 6H), 2.27-2.13 (m, 1H), 2.13-1.93 (m, 1H), 1.72 (br. s., 3H), 1.56-1.37 (m, 2H). m/z (ESI, +ve ion) 590.2 $(M+H)^+$. GK-GKRP $IC_{50}$ (Binding)=0.072 μM; GK-GKRP $EC_{50}$ (LC MS/MS-2)=0.081 μM.

Example 110

1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol

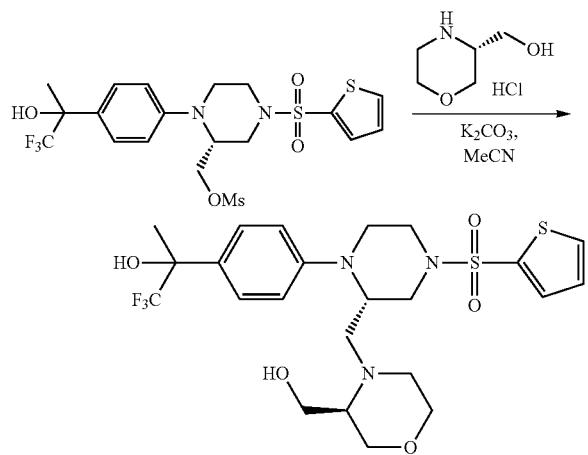

This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and (3R)-3-morpholinylmethanol hydrochloride (Tyger Scientific Inc., Ewing, N.J.) (using an extra equivalent of potassium carbonate) followed by purification via column chromatography on silica gel (0 to 100% EtOAc in hexanes) delivered 1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol as a mixture of two isomers.

The individual isomers were isolated using chiral SFC. The method used was as follows: Chiralpak® OJH column (21× 250 mm, 5 μm) using 0.2% DEA in methanol/ethanol/isopropanol (1:1:1)) in supercritical $CO_2$ (total flow was 65 mL/min). This method delivered the pure isomers with both diastereomeric and enantiomeric excesses over 95%.

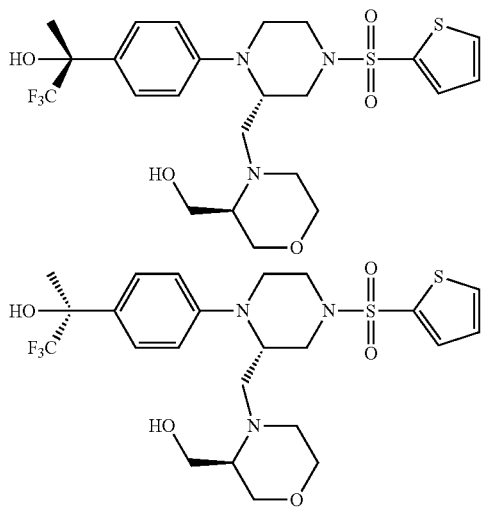

(2R)-1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol;
(2S)-1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol.

First Eluting Peak (Peak #1)
$^1$H NMR (400 MHz, $CD_3OD$) δ=7.87 (dd, J=1.2, 5.1 Hz, 1H), 7.64 (dd, J=1.3, 3.8 Hz, 1H), 7.43 (d, J=8.8 Hz, 2H), 7.26 (dd, J=3.8, 5.0 Hz, 1H), 6.91 (d, J=9.0 Hz, 2H), 4.11-3.99 (m, 2H), 3.76 (d, J=9.8 Hz, 1H), 3.70-3.65 (m, 1H), 3.62-3.52 (m, 5H), 3.45-3.40 (m, 1H), 3.28-3.22 (m, 1H), 2.90-2.73 (m, 2H), 2.68-2.38 (m, 5H), 1.67 (s, 3H). m/z (ESI, +ve ion) 550.2 (M+H)$^+$. GK-GKRP $IC_{50}$ (Binding)=0.101 μM; GK-GKRP $EC_{50}$ (LC MS/MS-2)=0.156 μM.

Second Eluting Peak (Peak #2)
$^1$H NMR (400 MHz, $CD_3OD$) δ=7.87 (dd, J=1.3, 5.0 Hz, 1H), 7.64 (dd, J=1.2, 3.7 Hz, 1H), 7.43 (d, J=8.8 Hz, 2H), 7.26 (dd, J=3.8, 5.0 Hz, 1H), 6.90 (d, J=8.8 Hz, 2H), 4.12-4.00 (m, 2H), 3.81-3.73 (m, 1H), 3.71-3.64 (m, 1H), 3.62-3.51 (m, 5H), 3.45-3.38 (m, 1H), 3.28-3.21 (m, 1H), 2.88-2.75 (m, 2H), 2.65-2.40 (m, 5H), 1.67 (s, 3H). m/z (ESI, +ve ion) 550.2 (M+H)$^+$. GK-GKRP $IC_{50}$ (Binding)=0.079 μM; GK-GKRP $EC_{50}$ (LC MS/MS-2)=0.132 μM.

Example 111

1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol

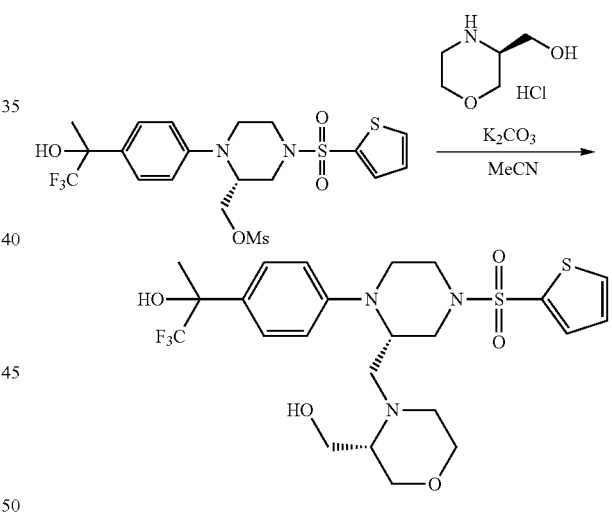

This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and (3S)-3-morpholinylmethanol hydrochloride (Tyger Scientific Inc., Ewing, N.J.) (using an extra equivalent of potassium carbonate) followed by purification via column chromatography on silica gel (0 to 100% EtOAc in hexanes) delivered 1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol as a mixture of two isomers.

The individual isomers were isolated using chiral SFC. The method used was as follows: Chrialpak® ICH column (150× 4.6 mm, 5 um) using 40% methanol (20 nM NH3) in supercritical $CO_2$ (total flow was 70 mL/min). This produced two products with both diastereomeric and enantiomeric excesses over 95%.

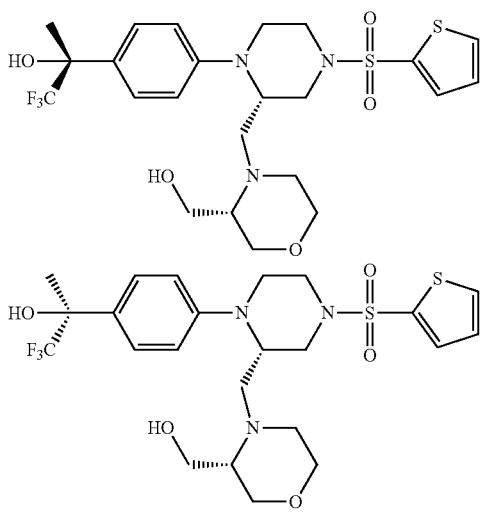

(2R)-1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol, (2S)-1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol.

First Eluting Peak (Peak #1)

¹H NMR (400 MHz, CD₃OD) δ=7.89 (dd, J=1.2, 4.9 Hz, 1H), 7.65 (dd, J=1.2, 3.7 Hz, 1H), 7.44 (d, J=8.8 Hz, 2H), 7.27 (dd, J=3.9, 4.9 Hz, 1H), 6.91 (d, J=9.0 Hz, 2H), 4.13-3.96 (m, 2H), 3.75 (d, J=3.5 Hz, 3H), 3.62-3.37 (m, 5H), 3.28-3.17 (m, 2H), 2.94-2.77 (m, 1H), 2.65-2.46 (m, 2H), 2.44-2.27 (m, 1H), 2.26-2.06 (m, 2H), 1.68 (s, 3H). m/z (ESI, +ve ion) 550.2 (M+H)⁺. GK-GKRP IC₅₀ (Binding)=0.064 μM; GK-GKRP EC₅₀ (LC MS/MS-2)=0.099 μM.

Second Eluting Peak (Peak #2)

¹H NMR (400 MHz, CD₃OD) δ=7.88 (dd, J=1.2, 4.9 Hz, 1H), 7.65 (dd, J=1.3, 3.8 Hz, 1H), 7.44 (d, J=8.6 Hz, 2H), 7.26 (dd, J=3.8, 5.0 Hz, 1H), 6.91 (d, J=8.8 Hz, 2H), 4.16-4.03 (m, 1H), 4.02-3.93 (m, 1H), 3.82-3.69 (m, 3H), 3.62-3.37 (m, 5H), 3.28-3.17 (m, 2H), 2.93-2.78 (m, 1H), 2.66-2.45 (m, 2H), 2.41-2.22 (m, 1H), 2.20-2.04 (m, 2H), 1.67 (s, 3H). m/z (ESI, +ve ion) 550.2 (M+H)⁺. GK-GKRP IC₅₀ (Binding)=0.067 μM; GK-GKRP EC₅₀ (LC MS/MS-2)=0.113 μM.

Example 112

N-((4-(((2S)-4-(2-thiophenylsulfonyl)-1-(4-(2,2,2-trifluoro-1-hydroxy-1-methylethyl)phenyl)-2-piperazinyl)methyl)-3-morpholinyl)methyl) methanesulfonamide

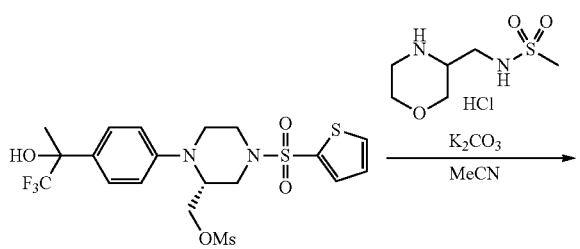

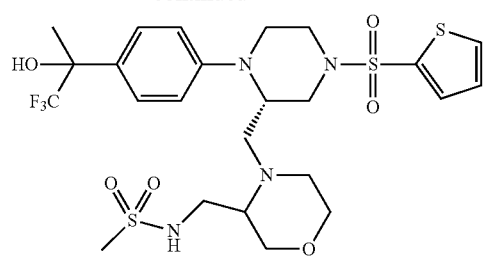

This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and N-(3-morpholinylmethyl)methanesulfonamide hydrochloride (published PCT patent application no. WO 2009/016410) (using an extra equivalent of potassium carbonate) followed by purification via column chromatography on silica gel (0 to 100% EtOAc in hexanes) delivered N-((4-(((2S)-4-(2-thiophenylsulfonyl)-1-(4-(2,2,2-trifluoro-1-hydroxy-1-methylethyl)phenyl)-2-piperazinyl)methyl)-3-morpholinyl)methyl)methanesulfonamide as a mixture of four isomers.

This mixture was partially resolved using reverse-phase preparative HPLC using a Phenomenex Gemini C₁₈ column (30×150 mm, 10 μm) eluting with 0.1% TFA in CH₃CN/H₂O (20% to 50% over 15 min). This separated the compounds into two isolated products that were still a mixture of two isomers.

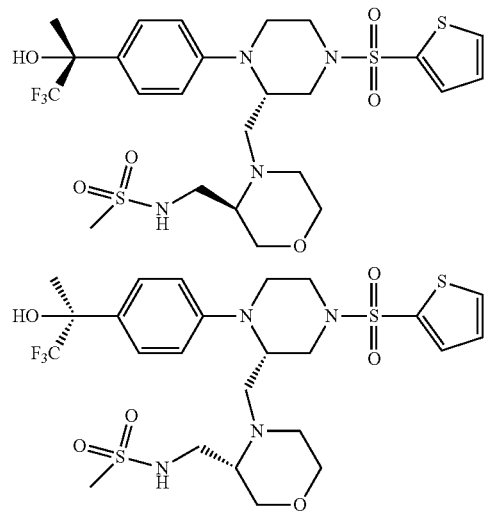

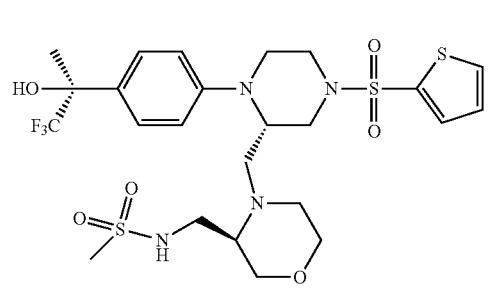

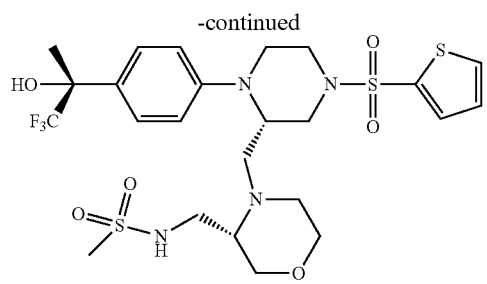

N-(((3R)-4-(((2S)-4-(2-thiophenylsulfonyl)-1-(4-((1R)-2,2,2-trifluoro-1-hydroxy-1-methylethyl)phenyl)-2-piperazinyl)methyl)-3-morpholinyl)methyl)methanesulfonamide;
N-(((3S)-4-(((2S)-4-(2-thiophenylsulfonyl)-1-(4-((1S)-2,2,2-trifluoro-1-hydroxy-1-methylethyl)phenyl)-2-piperazinyl)methyl)-3-morpholinyl)methyl)methanesulfonamide;
N-(((3R)-4-(((2S)-4-(2-thiophenylsulfonyl)-1-(4-((1S)-2,2,2-trifluoro-1-hydroxy-1-methylethyl)phenyl)-2-piperazinyl)methyl)-3-morpholinyl)methyl)methanesulfonamide;
N-(((3S)-4-(((2S)-4-(2-thiophenylsulfonyl)-1-(4-((1R)-2,2,2-trifluoro-1-hydroxy-1-methylethyl)phenyl)-2-piperazinyl)methyl)-3-morpholinyl)methyl)methanesulfonamide.

First Eluting Peak (Peak #1)

$^1$H NMR (400 MHz, CD$_3$OD) δ=7.91-7.85 (m, 1H), 7.67-7.62 (m, 1H), 7.49-7.40 (m, 2H), 7.28-7.24 (m, 1H), 6.98-6.88 (m, 2H), 4.12-3.98 (m, 2H), 3.83-3.73 (m, 1H), 3.60-3.53 (m, 4H), 3.49-3.38 (m, 1H), 3.28-3.12 (m, 3H), 2.95-2.86 (m, 4H), 2.84-2.74 (m, 1H), 2.67-2.37 (m, 5H), 1.67 (s, 3H). m/z (ESI, +ve ion) 627.2 (M+H)$^+$. GK-GKRP IC$_{50}$ (Binding)=0.275 μM; GK-GKRP EC$_{50}$ (LC MS/MS-2)=0.986 μM.

Second Eluting Peak (Peak #2)

$^1$H NMR (400 MHz, CD$_3$OD) δ=7.93-7.84 (m, 1H), 7.72-7.64 (m, 1H), 7.50-7.40 (m, 2H), 7.31-7.21 (m, 1H), 6.96-6.87 (m, 2H), 4.14-3.95 (m, 2H), 3.87-3.74 (m, 2H), 3.65-3.35 (m, 6H), 3.28-3.20 (m, 1H), 3.09-2.88 (m, 5H), 2.64-2.45 (m, 2H), 2.43-2.34 (m, 1H), 2.20-2.03 (m, 2H), 1.67 (s, 3H). m/z (ESI, +ve ion) 627.2 (M+H)$^+$. GK-GKRP IC$_{50}$ (Binding)=0.21 μM; GK-GKRP EC$_{50}$ (LC MS/MS-2)=0.332 μM.

Example 113

(4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetate This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and ethyl 3-morpholinylacetate (Matrix Scientific, Columbia, S.C.) (using an extra equivalent of potassium carbonate) followed by purification via column chromatography on silica gel (0 to 100% EtOAc in hexanes) delivered (4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetate as a mixture of four isomers.

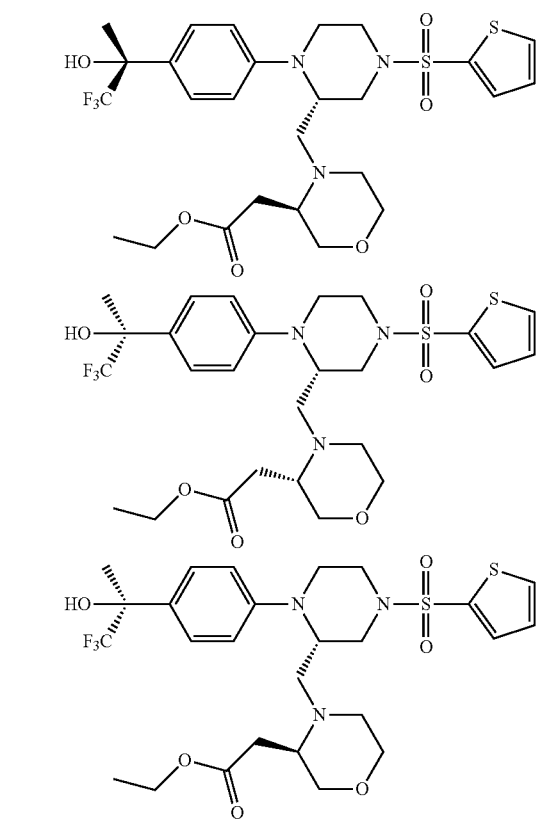

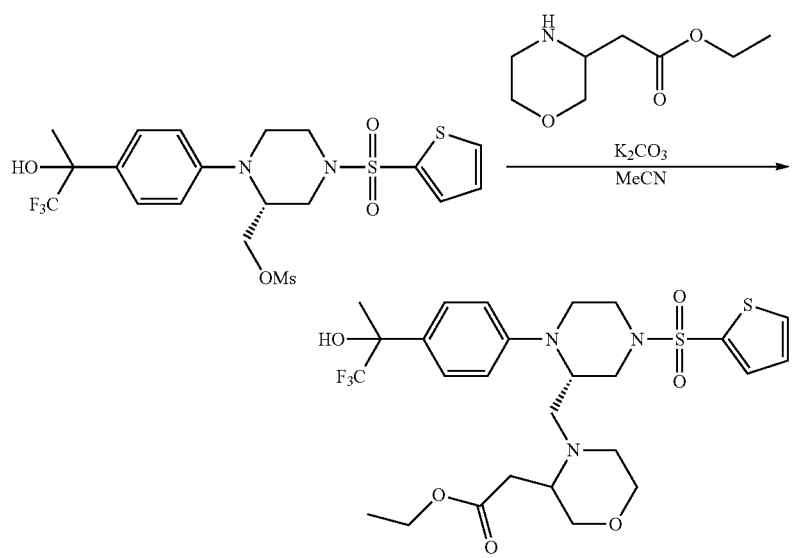

257

-continued

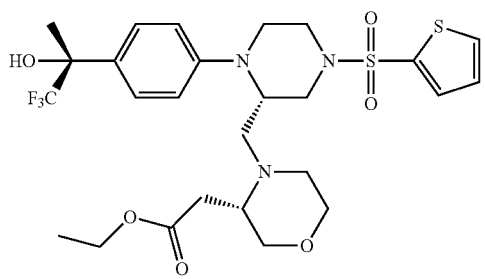

258

-continued

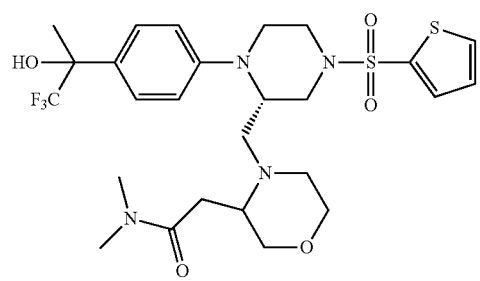

((3R)-4-(((2S)-4-(2-thiophenylsulfonyl)-1-(4-((1R)-2,2,2-trifluoro-1-hydroxy-1-methylethyl)phenyl)-2-piperazinyl)methyl)-3-morpholinyl)acetate, ((3S)-4-(((2S)-4-(2-thiophenylsulfonyl)-1-(4-((1S)-2,2,2-trifluoro-1-hydroxy-1-methylethyl)phenyl)-2-piperazinyl)methyl)-3-morpholinyl)acetate, ((3R)-4-(((2S)-4-(2-thiophenylsulfonyl)-1-(4-((1S)-2,2,2-trifluoro-1-hydroxy-1-methylethyl)phenyl)-2-piperazinyl)methyl)-3-morpholinyl)acetate, ((3S)-4-(((2S)-4-(2-thiophenylsulfonyl)-1-(4-((1R)-2,2,2-trifluoro-1-hydroxy-1-methylethyl)phenyl)-2-piperazinyl)methyl)-3-morpholinyl)acetate.

$^1$H NMR (400 MHz, CD$_3$OD) δ=7.94-7.82 (m, 1H), 7.68-7.60 (m, 1H), 7.44 (d, J=8.6 Hz, 2H), 7.30-7.21 (m, 1H), 6.91 (d, J=8.8 Hz, 2H), 4.19-4.07 (m, 3H), 4.04-3.93 (m, 1H), 3.82-3.72 (m, 1H), 3.62-3.37 (m, 5H), 3.27-3.11 (m, 1H), 3.03-2.68 (m, 3H), 2.64-2.34 (m, 5H), 2.27-2.12 (m, 1H), 1.67 (s, 3H), 1.29-1.22 (m, 3H). m/z (ESI, +ve ion) 606.2 (M+H)$^+$. GK-GKRP IC$_{50}$ (Binding)=0.333 μM; GK-GKRP EC$_{50}$ (LC MS/MS-2)=0.308 μM.

Example 114

N,N-dimethyl-2-(4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetamide

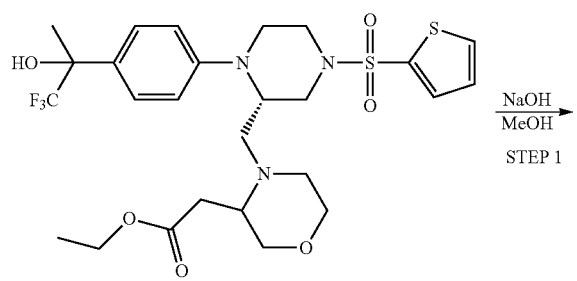

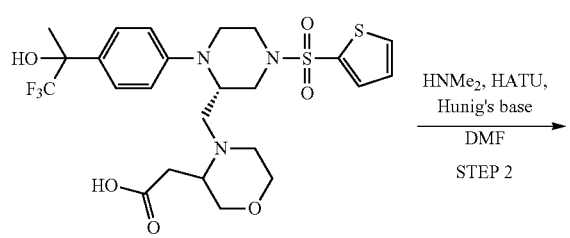

Step 1: (4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetic acid A 25-mL round-bottomed flask was charged with (4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetate (70 mg, 0.116 mmol, Example 113), is aqueous 10 M NaOH (0.5 mL, 5.00 mmol) and MeOH (5 mL) and stirred at room temperature for 2 h. The reaction was concentrated to give (4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetic acid (65 mg) as a mixture of four isomers. This material was used crude in the next reaction.

Step 2: N,N-dimethyl-2-(4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetamide A 25-mL round-bottomed flask was charged with (4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetic acid (65 mg, 0.113 mmol), dimethylamine (2.0 M in MeOH, 1.69 mL, 3.38 mmol, Sigma-Aldrich, St. Louis, Mo.), Hünig's base (0.039 mL, 0.225 mmol), HATU (471 mg, 1.24 mmol) and DMF (3 mL). After stirring at room temperature for 1 h, the reaction was concentrated onto silica gel and purified via column chromatography (12 g silica gel, 0 to 100% hexanes in EtOAc) to give N,N-dimethyl-2-(4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetamide (20 mg) as a mixture of four isomers.

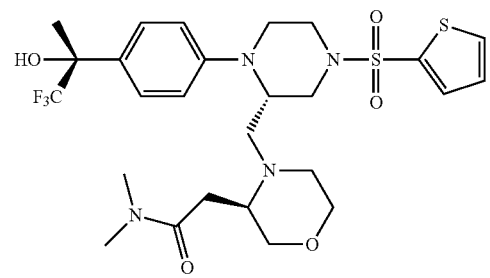

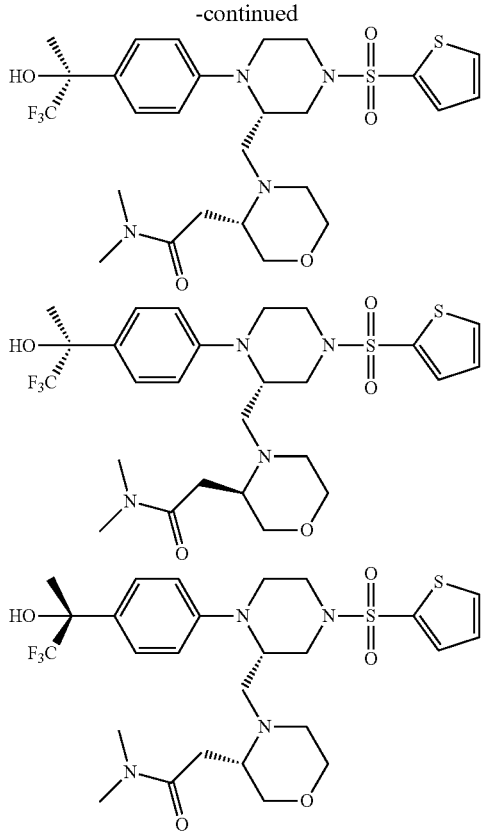

N,N-dimethyl-2-((3R)-4-(((2S)-4-(2-thiophenylsulfonyl)-1-(4-((1R)-2,2,2-trifluoro-1-hydroxy-1-methylethyl)phenyl)-2-piperazinyl)methyl)-3-morpholinyl)acetamide, N,N-dimethyl-2-((3S)-4-(((2S)-4-(2-thiophenylsulfonyl)-1-(4-((1S)-2,2,2-trifluoro-1-hydroxy-1-methylethyl)phenyl)-2-piperazinyl)methyl)-3-morpholinyl)acetamide, N,N-dimethyl-2-((3R)-4-(((2S)-4-(2-thiophenylsulfonyl)-1-(4-((1S)-2,2,2-trifluoro-1-hydroxy-1-methylethyl)phenyl)-2-piperazinyl)methyl)-3-morpholinyl)acetamide, N,N-dimethyl-2-((3S)-4-(((2S)-4-(2-thiophenylsulfonyl)-1-(4-((1R)-2,2,2-trifluoro-1-hydroxy-1-methylethyl)phenyl)-2-piperazinyl)methyl)-3-morpholinyl)acetamide. $^1$H NMR (400 MHz, CD$_3$OD) δ=7.94-7.84 (m, 1H), 7.69-7.61 (m, 1H), 7.49-7.38 (m, 2H), 7.29-7.22 (m, 1H), 7.00-6.85 (m, 2H), 4.12-3.96 (m, 2H), 3.82-3.73 (m, 1H), 3.68-3.51 (m, 3H), 3.48-3.40 (m, 2H), 3.27-3.12 (m, 1H), 3.10-3.03 (m, 4H), 2.95-2.71 (m, 5H), 2.69-2.32 (m, 5H), 2.28-2.05 (m, 1H), 1.67 (s, 3H). m/z (ESI, +ve ion) 605.3 (M+H)$^+$. GK-GKRP IC$_{50}$ (Binding)=0.09 μM; GK-GKRP EC$_{50}$ (LC MS/MS-2)=0.124 μM.

Example 115

1,1,1-trifluoro-2-(4-((2S)-2-((3-(4-fluorophenyl)-4-morpholinyl)methyl)-4-(2-thiophenylsulfonyl)-1-piperazinyl)phenyl)-2-propanol

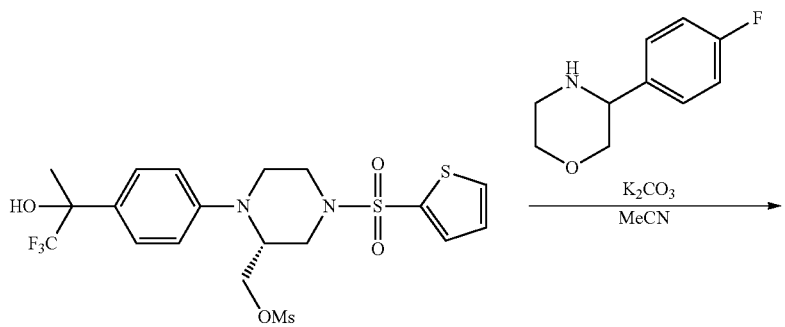

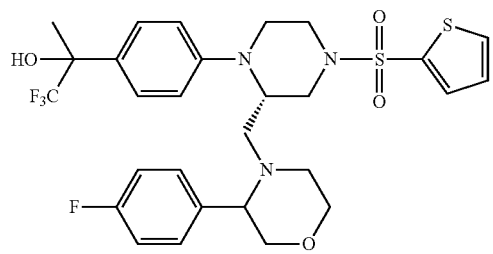

This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and 3-(4-fluorophenyl)morpholine (ASDI, Newark, Del.) (using an extra equivalent of potassium carbonate) delivered 1,1,1-trifluoro-2-(4-((2S)-2-((3-(4-fluorophenyl)-4-morpholinyl)methyl)-4-(2-thiophenylsulfonyl)-1-piperazinyl)phenyl)-2-propanol as a mixture of four isomers. This isomeric mixture was partially resolved using reverse-phase preparative HPLC using a Phenomenex Gemini $C_{18}$ column (150×30 mm, 10 µm) eluting with 0.1% TFA in $CH_3CN/H_2O$ (20% to 60% over 15 min). This separated the compounds into two isolated peaks that were a mixture of two isomers.

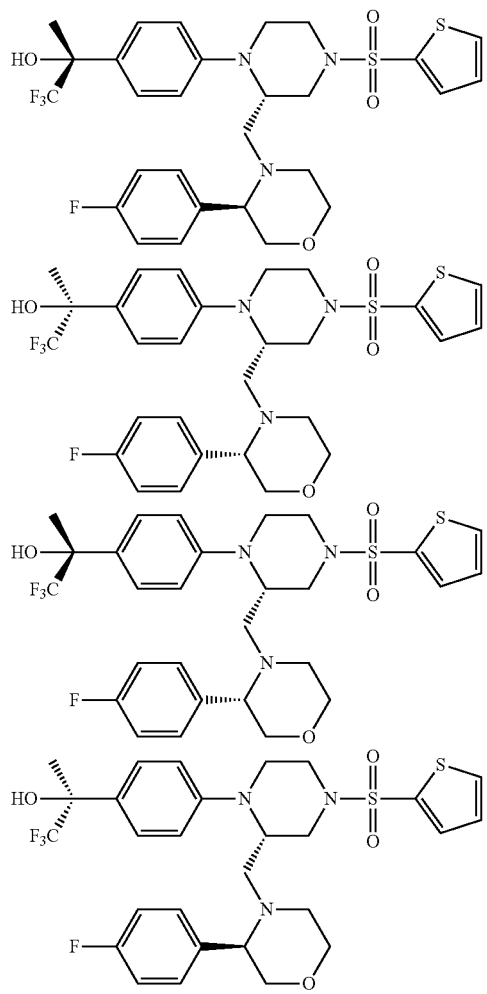

(2R)-1,1,1-trifluoro-2-(4-((2S)-2-(((3R)-3-(4-fluorophenyl)-4-morpholinyl)methyl)-4-(2-thiophenylsulfonyl)-1-piperazinyl)phenyl)-2-propanol,
(2S)-1,1,1-trifluoro-2-(4-((2S)-2-(((3S)-3-(4-fluorophenyl)-4-morpholinyl)methyl)-4-(2-thiophenylsulfonyl)-1-piperazinyl)phenyl)-2-propanol,
(2R)-1,1,1-trifluoro-2-(4-((2S)-2-(((3S)-3-(4-fluorophenyl)-4-morpholinyl)methyl)-4-(2-thiophenylsulfonyl)-1-piperazinyl)phenyl)-2-propanol,
(2S)-1,1,1-trifluoro-2-(4-((2S)-2-(((3R)-3-(4-fluorophenyl)-4-morpholinyl)methyl)-4-(2-thiophenylsulfonyl)-1-piperazinyl)phenyl)-2-propanol.

First Eluting Peak (Peak #1)

$^1$H NMR (400 MHz, $CD_3OD$) δ=7.90-7.83 (m, 1H), 7.65-7.60 (m, 1H), 7.38-7.29 (m, 2H), 7.28-7.23 (m, J=3.9 Hz, 1H), 7.20 (d, J=8.4 Hz, 2H), 7.09 (d, J=16.6 Hz, 2H), 6.28 (dd, J=2.9, 9.0 Hz, 2H), 4.03 (d, J=11.2 Hz, 1H), 3.81 (d, J=11.3 Hz, 1H), 3.72-3.57 (m, 3H), 3.53 (d, J=8.6 Hz, 1H), 3.35 (s, 2H), 3.29-3.24 (m, 1H), 3.21-3.14 (m, 1H), 3.06-2.91 (m, 1H), 2.55-2.33 (m, 5H), 1.64 (d, J=6.1 Hz, 3H). m/z (ESI, +ve ion) 614.2 $(M+H)^+$. GK-GKRP $IC_{50}$ (Binding)=0.589 µM; GK-GKRP $EC_{50}$ (LC MS/MS-2)=0.308 µM.

Second Eluting Peak (Peak #2)

$^1$H NMR (400 MHz, MeOH) δ=7.94-7.84 (m, 1H), 7.68-7.61 (m, 1H), 7.50-7.39 (m, 4H), 7.30-7.24 (m, 1H), 7.09-7.02 (t, J=8.8 Hz, 2H), 6.85 (d, J=8.8 Hz, 2H), 4.28-4.17 (m, 1H), 4.00 (d, J=10.8 Hz, 1H), 3.89 (d, J=10.4 Hz, 1H), 3.81-3.70 (m, 1H), 3.64-3.56 (m, 1H), 3.51-3.43 (m, 1H), 3.40-3.34 (m, 2H), 3.28-3.23 (m, 1H), 3.20-3.08 (m, 2H), 2.95-2.76 (m, 2H), 2.67-2.54 (m, 1H), 2.46-2.32 (m, 1H), 2.25-2.08 (m, 1H), 1.67 (s, 3H). m/z (ESI, +ve ion) 614.2 $(M+H)^+$. GK-GKRP $IC_{50}$ (Binding)=0.836 µM.

Example 116

1,1,1-trifluoro-2-(4-((2R)-2-((2-furanylmethoxy)methyl)-4-(2-thiophenylsulfonyl)-1-piperazinyl)phenyl)-2-propanol

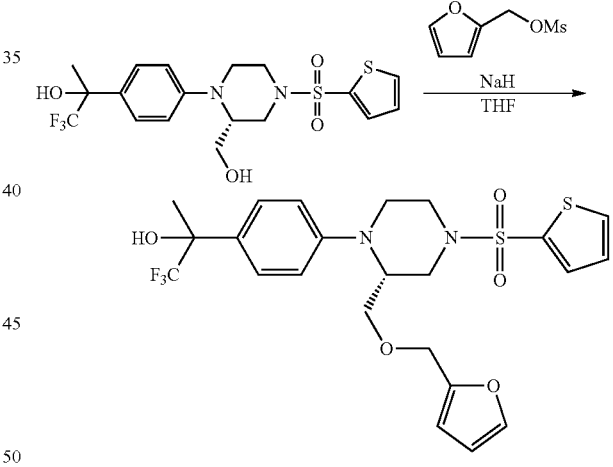

A 10-mL vial was charged with 1,1,1-trifluoro-2-(4-((2R)-2-(hydroxymethyl)-4-(2-thiophenylsulfonyl)-1-piperazinyl)phenyl)-2-propanol (50 mg, 0.11 mmol, Intermediate B synthesis (Step 5)), THF (3 mL) and sodium hydride (60% dispersion in mineral oil, 13.3 mg, 0.33 mmol). After gas evolution ceased, 2-furanylmethyl methanesulfonate (78 mg, 0.44 mmol, US published patent application no. 2008/0153883) was added and the vial was sealed and heated to 80° C. 12 h. MeOH (10 mL) was added and the reaction was filtered, concentrated and purified by reverse-phase HPLC (Phenomenex Gemini-NX $C_{18}$ column, 21×100 mm, 5 µm eluting with A: Water w/0.1% $NH_4OH$ B: Acetonitrile w/0.1% $NH_4OH$) to give 1,1,1-trifluoro-2-(4-((2R)-2-(((2-furanylmethoxy)methyl)-4-(2-thiophenylsulfonyl)-1-piperazinyl)phenyl)-2-propanol as a mixture of two isomers.

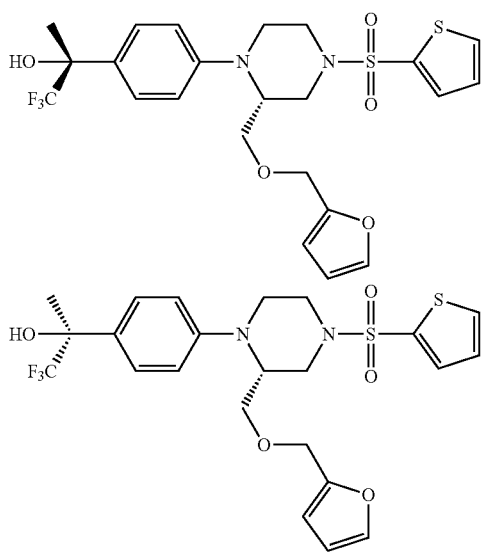

(2R)-1,1,1-trifluoro-2-(4-((2R)-2-((2-furanylmethoxy)methyl)-4-(2-thiophenylsulfonyl)-1-piperazinyl)phenyl)-2-propanol, (2S)-1,1,1-trifluoro-2-(4-((2R)-2-((2-furanylmethoxy)methyl)-4-(2-thiophenylsulfonyl)-1-piperazinyl)phenyl)-2-propanol.

$^1$H NMR (400 MHz, DMSO-d$_6$) δ=8.14-8.01 (m, 1H), 7.76-7.66 (m, 1H), 7.64-7.55 (m, 1H), 7.38 (d, J=8.6 Hz, 2H), 7.33-7.25 (m, 1H), 6.86 (d, J=9.0 Hz, 2H), 6.47-6.25 (m, 2H), 4.13-4.02 (m, 1H), 3.74-3.58 (m, 3H), 3.56-3.48 (m, 1H), 3.32-3.25 (m, 2H), 3.13-2.93 (m, 1H), 2.56-2.53 (m, 2H), 2.47-2.39 (m, 1H), 1.63 (s, 3H). m/z (ESI, +ve ion) 531.2 (M+H)$^+$. GK-GKRP IC$_{50}$ (Binding)=0.284 μM; GK-GKRP EC$_{50}$ (LC MS/MS-2)=0.103 μM.

Example 117

1,1,1-trifluoro-2-(4-((2R)-2-(((3-methyl-3-oxetanyl)methoxy)methyl)-4-(2-thiophenylsulfonyl)-1-piperazinyl)phenyl)-2-propanol

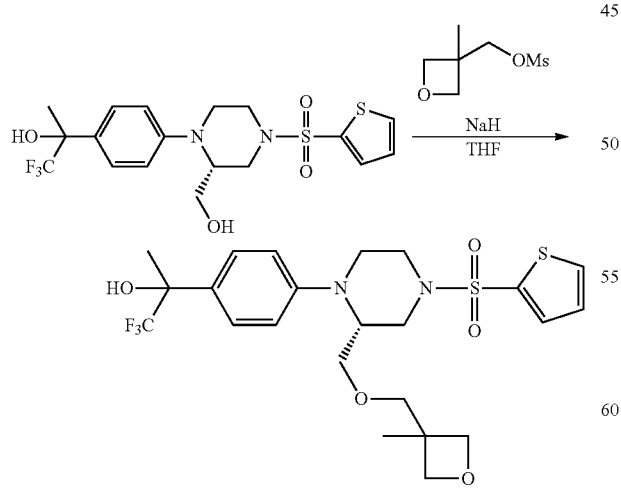

Following the procedure reported for Example 116, using (3-methyl-3-oxetanyl)methyl methanesulfonate (published PCT patent application no. WO 2010/031713) delivered 1,1,1-trifluoro-2-(4-((2R)-2-(((3-methyl-3-oxetanyl)methoxy)methyl)-4-(2-thiophenylsulfonyl)-1-piperazinyl)phenyl)-2-propanol as a mixture of two isomers after purification by reverse phase HPLC (Phenomenex Gemini-NX C$_{18}$ column, 21×100 mm, 5 μm eluting with A: Water w/0.1% NH$_4$OH B: Acetonitrile w/0.1% NH$_4$OH).

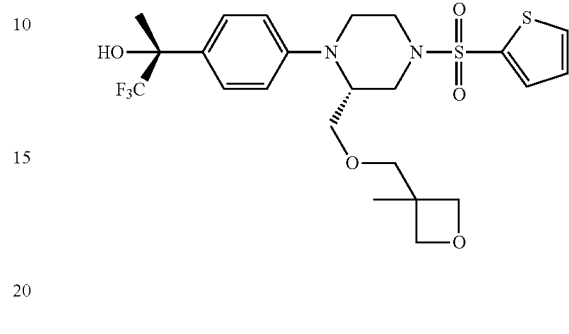

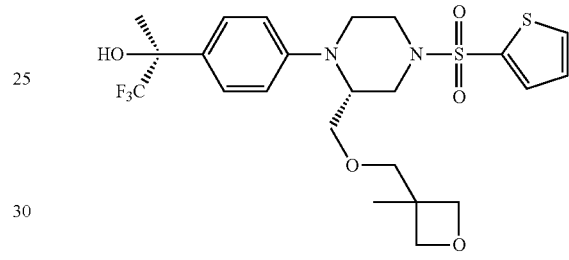

(2R)-1,1,1-trifluoro-2-(4-((2R)-2-(((3-methyl-3-oxetanyl)methoxy)methyl)-4-(2-thiophenylsulfonyl)-1-piperazinyl)phenyl)-2-propanol, (2S)-1,1,1-trifluoro-2-(4-((2R)-2-(((3-methyl-3-oxetanyl)methoxy)methyl)-4-(2-thiophenylsulfonyl)-1-piperazinyl)phenyl)-2-propanol.

$^1$H NMR (400 MHz, DMSO-d$_6$) δ=8.16-7.99 (m, 1H), 7.77-7.64 (m, 1H), 7.37 (d, J=9.0 Hz, 2H), 7.33-7.25 (m, 1H), 6.89 (d, J=9.0 Hz, 2H), 4.38-4.24 (m, 2H), 4.21-4.16 (m, 1H), 4.15-4.03 (m, 2H), 3.80-3.61 (m, 2H), 3.55-3.44 (m, 3H), 3.32-3.27 (m, 1H), 3.20-3.07 (m, 1H), 2.58-2.54 (m, 2H), 2.48-2.40 (m, 1H), 1.61 (s, 3H), 1.15 (s, 3H). m/z (ESI, +ve ion) 535.2 (M+H)$^+$. GK-GKRP IC$_{50}$ (Binding)=0.467 μM; GK-GKRP EC$_{50}$ (LC MS/MS-2)=0.463 μM.

Example 118

1,1,1-trifluoro-2-(4-((2R)-2-((tetrahydro-2-furanylmethoxy)methyl)-4-(2-thiophenylsulfonyl)-1-piperazinyl)phenyl)-2-propanol

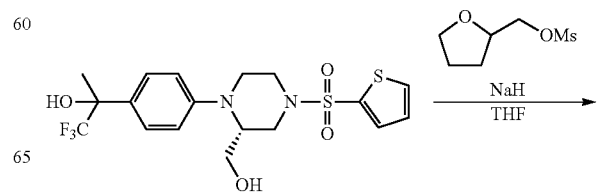

-continued

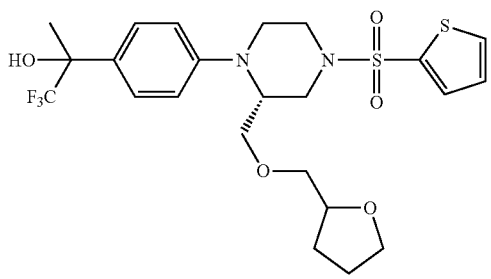

Following the procedure reported for Example 116, using tetrahydro-2-furanylmethyl methanesulfonate (*J. Am. Chem. Soc.,* 1946, 68, 2743) delivered 1,1,1-trifluoro-2-(4-((2R)-2-((tetrahydro-2-furanylmethoxy)methyl)-4-(2-thiophenylsulfonyl)-1-piperazinyl)phenyl)-2-propanol as a mixture of four isomers after purification by reverse phase HPLC (Phenomenex Gemini-NX $C_{18}$ column, 21×100 mm, 5 μm eluting with A: Water w/0.1% $NH_4OH$ B: Acetonitrile w/0.1% $NH_4OH$)

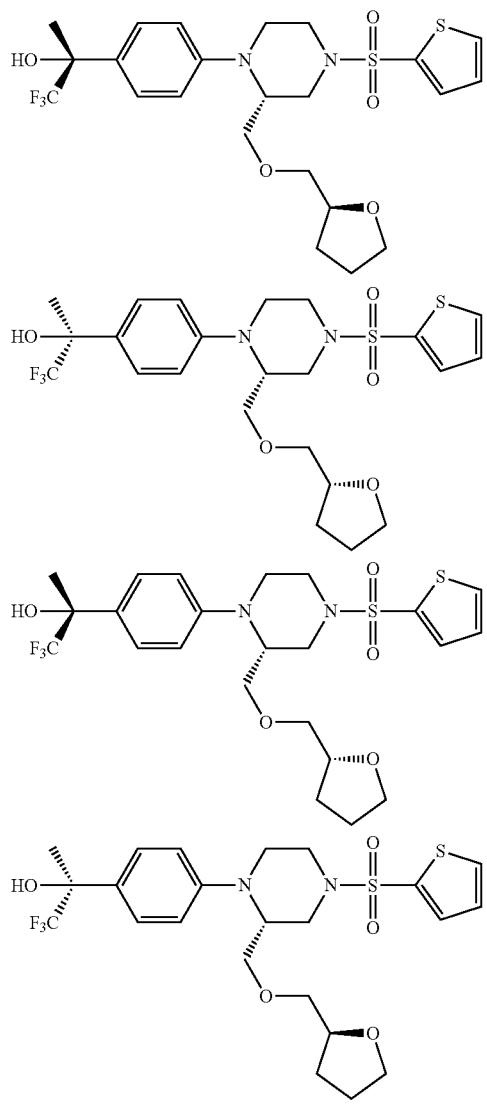

(2R)-1,1,1-trifluoro-2-(4-((2R)-2-(((2S)-tetrahydro-2-furanylmethoxy)methyl)-4-(2-thiophenylsulfonyl)-1-piperazinyl)phenyl)-2-propanol, (2S)-1,1,1-trifluoro-2-(4-((2R)-2-(((2R)-tetrahydro-2-furanylmethoxy)methyl)-4-(2-thiophenylsulfonyl)-1-piperazinyl)phenyl)-2-propanol, (2R)-1,1,1-trifluoro-2-(4-((2R)-2-(((2R)-tetrahydro-2-furanylmethoxy)methyl)-4-(2-thiophenylsulfonyl)-1-piperazinyl)phenyl)-2-propanol, (2S)-1,1,1-trifluoro-2-(4-((2R)-2-(((2S)-tetrahydro-2-furanylmethoxy)methyl)-4-(2-thiophenylsulfonyl)-1-piperazinyl)phenyl)-2-propanol.

$^1$H NMR (400 MHz, DMSO-$d_6$) δ=8.16-7.97 (m, 1H), 7.72-7.64 (m, 1H), 7.41-7.34 (m, 2H), 7.32-7.25 (m, 1H), 6.88 (d, J=9.0 Hz, 2H), 4.16-4.05 (m, 1H), 3.87-3.78 (m, 2H), 3.76-3.47 (m, 6H), 3.30-3.25 (m, 2H), 3.16-3.04 (m, 1H), 2.57-2.54 (m, 2H), 2.48-2.39 (m, 1H), 1.87-1.67 (m, 3H), 1.60 (s, 3H), 1.55-1.40 (m, 1H). m/z (ESI, +ve ion) 535.2 (M+H)$^+$. GK-GKRP $IC_{50}$ (Binding)=0.57 μM; GK-GKRP $EC_{50}$ (LC MS/MS-2)=1.11 μM.

Example 119

1,1,1-trifluoro-2-(4-((2R)-2-(((1-methyl-1H-imidazol-4-yl)methoxy)methyl)-4-(2-thiophenylsulfonyl)-1-piperazinyl)phenyl)-2-propanol

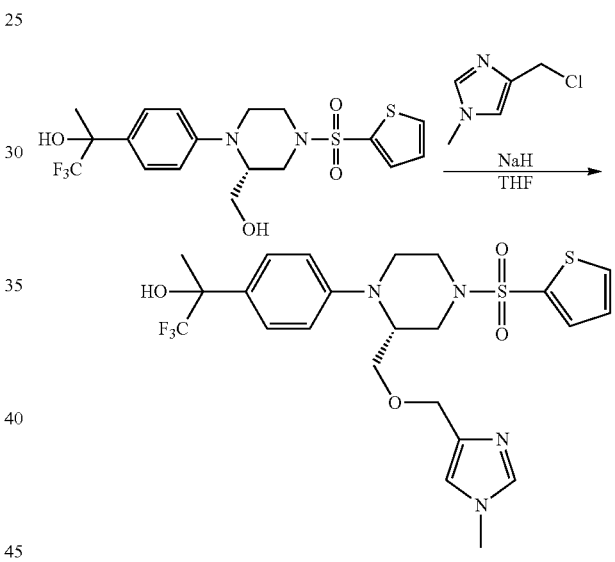

Following the procedure reported for Example 116, using 4-(chloromethyl)-1-methyl-1H-imidazole (Synthonix, Wake Forest, N.C.) and purification via column chromatography (12 g silica gel, 5 to 10% $CH_2Cl_2$ in MeOH) delivered 1,1,1-trifluoro-2-(4-((2R)-2-(((1-methyl-1H-imidazol-4-yl)methoxy)methyl)-4-(2-thiophenylsulfonyl)-1-piperazinyl)phenyl)-2-propanol as a mixture of two isomers after purification by reverse phase HPLC (Phenomenex Gemini-NX $C_{18}$ column, 21×100 mm, 5 μm eluting with A: Water w/0.1% $NH_4OH$ B: Acetonitrile w/0.1% $NH_4OH$) $^1$H NMR (400 MHz, $CD_3OD$) δ=7.90-7.82 (m, 1H), 7.65-7.59 (m, 1H), 7.53-7.48 (m, 1H), 7.42 (d, J=8.8 Hz, 2H), 7.29-7.20 (m, 1H), 7.03-6.97 (m, 1H), 6.88 (d, J=9.0 Hz, 2H), 4.46-4.22 (m, 2H), 4.07-3.95 (m, 1H), 3.88-3.73 (m, 2H), 3.72-3.65 (m, 4H), 3.51-3.44 (m, 1H), 3.40-3.34 (m, 1H), 3.21-3.04 (m, 1H), 2.76-2.64 (m, 1H), 2.63-2.50 (m, 1H), 1.67 (s, 3H). m/z (ESI, +ve ion) 545.3 (M+H)$^+$. GK-GKRP $IC_{50}$ (Binding)=0.392 μM; GK-GKRP $EC_{50}$ (LC MS/MS-2)=0.169 μM.

The individual isomers were separated using chiral SFC. The method used was as follows: Chrialpak® ADH column (15×2 cm, 5 μm) using 20% methanol (0.1% DEA) in supercritical $CO_2$ (total flow was 70 mL/min). This produced both isomers with diastereomeric and enantiomeric excesses over 95%.

267

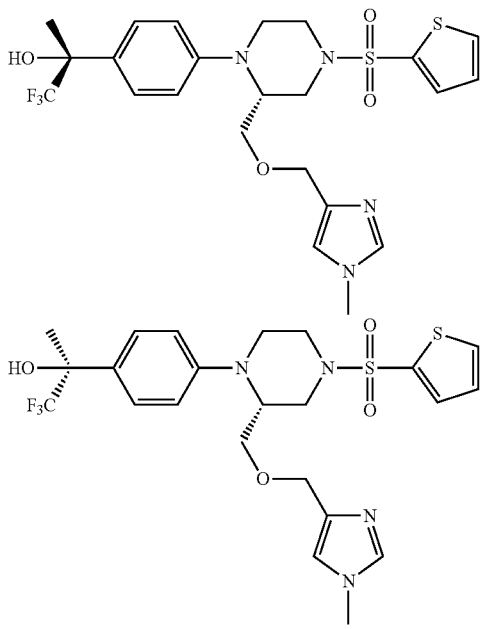

(2R)-1,1,1-trifluoro-2-(4-((2R)-2-(((1-methyl-1H-imidazol-4-yl)methoxy)methyl)-4-(2-thiophenylsulfonyl)-1-piperazinyl)phenyl)-2-propanol, (2S)-1,1,1-trifluoro-2-(4-((2R)-2-(((1-methyl-1H-imidazol-4-yl)methoxy)methyl)-4-(2-thiophenylsulfonyl)-1-piperazinyl)phenyl)-2-propanol.

First Eluting Peak (Peak #1)

$^1$H NMR (400 MHz, CD$_3$OD) δ=7.88 (dd, J=1.2, 4.9 Hz, 1H), 7.64 (dd, J=1.2, 3.7 Hz, 1H), 7.54-7.51 (m, 1H), 7.43 (d, J=8.8 Hz, 2H), 7.26 (dd, J=3.8, 5.0 Hz, 1H), 7.06-6.96 (m, 1H), 6.89 (d, J=9.0 Hz, 2H), 4.48-4.28 (m, 2H), 4.09-3.97 (m, 1H), 3.89-3.74 (m, 2H), 3.72-3.62 (m, 4H), 3.52-3.44 (m, 1H), 3.38-3.35 (m, 1H), 3.20-2.99 (m, 1H), 2.76-2.43 (m, 2H), 1.67 (s, 3H). m/z (ESI, +ve ion) 545.2 (M+H)$^+$. GK-GKRP IC$_{50}$ (Binding)=0.972 μM; GK-GKRP EC$_{50}$ (LC MS/MS-2)=0.235 μM.

Second Eluting Peak (Peak #2)

$^1$H NMR (400 MHz, CD$_3$OD) δ=7.88 (dd, J=1.2, 4.9 Hz, 1H), 7.64 (dd, J=1.2, 3.7 Hz, 1H), 7.54-7.50 (m, 1H), 7.44 (s, 2H), 7.25 (dd, J=3.9, 4.9 Hz, 1H), 7.04-6.99 (m, 1H), 6.89 (d, J=9.0 Hz, 2H), 4.49-4.25 (m, 2H), 4.10-3.97 (m, 1H), 3.90-3.73 (m, 2H), 3.73-3.63 (m, 4H), 3.54-3.43 (m, 1H), 3.38-3.34 (m, 1H), 3.19-3.03 (m, 1H), 2.76-2.64 (m, 1H), 2.63-2.52 (m, 1H), 1.67 (s, 3H). m/z (ESI, +ve ion) 545.2 (M+H)$^+$. GK-GKRP IC$_{50}$ (Binding)=0.979 μM; GK-GKRP EC$_{50}$ (LC MS/MS-2)=0.206 μM.

Example 120

1,1,1-trifluoro-2-(4-((2S)-2-((tetrahydro-2H-pyran-4-ylamino)methyl)-4-(2-thiophenylsulfonyl)-1-piperazinyl)phenyl)-2-propanol

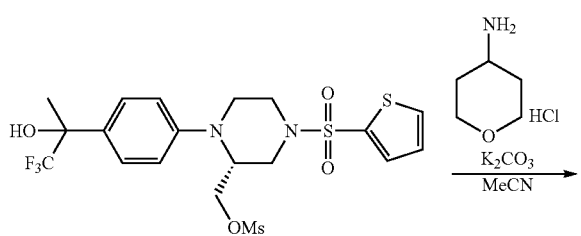

268

-continued

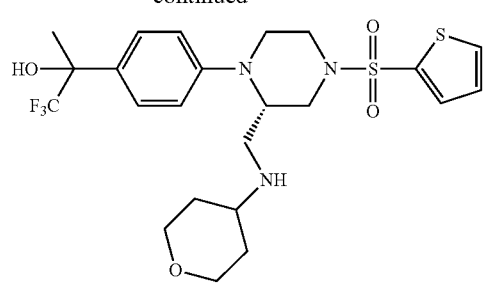

This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and tetrahydro-2H-pyran-4-amine hydrochloride (ASDI, Newark, Del.) using an extra equivalent of potassium carbonate) followed by purification via column chromatography on silica gel (0-10% MeOH in CH$_2$Cl$_2$) delivered 1,1,1-trifluoro-2-(4-((2S)-2-((tetrahydro-2H-pyran-4-ylamino)methyl)-4-(2-thiophenylsulfonyl)-1-piperazinyl)phenyl)-2-propanol as a mixture of two isomers.

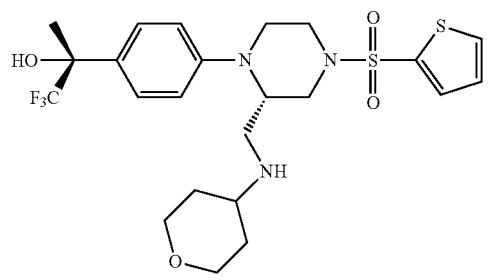

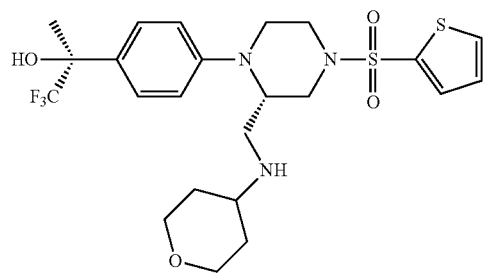

(2R)-1,1,1-trifluoro-2-(4-((2S)-2-((tetrahydro-2H-pyran-4-ylamino)methyl)-4-(2-thiophenylsulfonyl)-1-piperazinyl)phenyl)-2-propanol, (2S)-1,1,1-trifluoro-2-(4-((2S)-2-((tetrahydro-2H-pyran-4-ylamino)methyl)-4-(2-thiophenylsulfonyl)-1-piperazinyl)phenyl)-2-propanol.

$^1$H NMR (400 MHz, MeOH) δ=7.91-7.87 (m, 1H), 7.65-7.60 (m, 1H), 7.53-7.47 (d, J=8.8 Hz, 2H), 7.27-7.23 (m, 1H), 7.03 (d, J=8.8 Hz, 2H), 4.39-4.26 (m, 1H), 4.06-3.95 (m, 2H), 3.78-3.61 (m, 3H), 3.51-3.34 (m, 6H), 2.88-2.76 (m, 1H), 2.66-2.47 (m, 1H), 2.06-1.87 (m, 2H), 1.67 (s, 3H), 1.64-1.54 (m, 2H). m/z (ESI, +ve ion) 534.2 (M+H)$^+$. GK-GKRP IC$_{50}$ (Binding)=0.493 μM; GK-GKRP EC$_{50}$ (LC MS/MS-2)=0.656 μM.

Example 121

1,1,1-trifluoro-2-(4-((2S)-2-((methyl((1-methyl-1H-imidazol-4-yl)methyl)amino)methyl)-4-(2-thiophenylsulfonyl)-1-piperazinyl)phenyl)-2-propanol

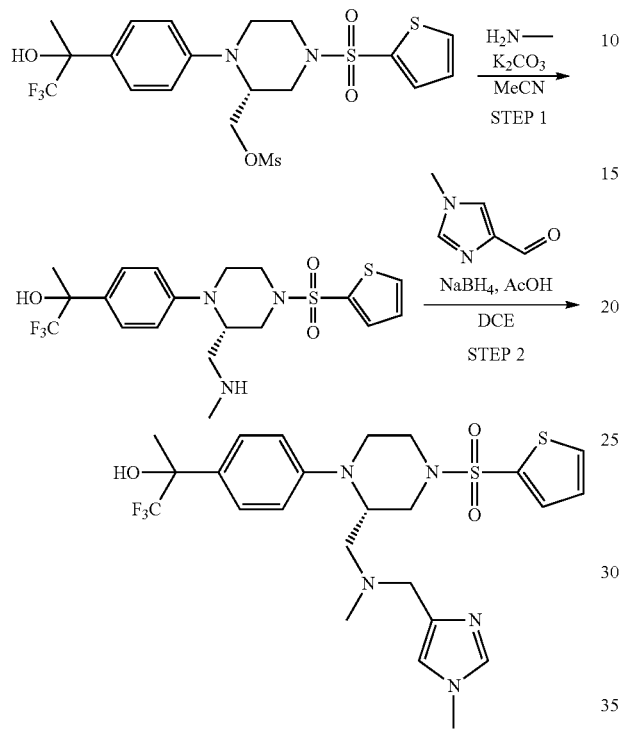

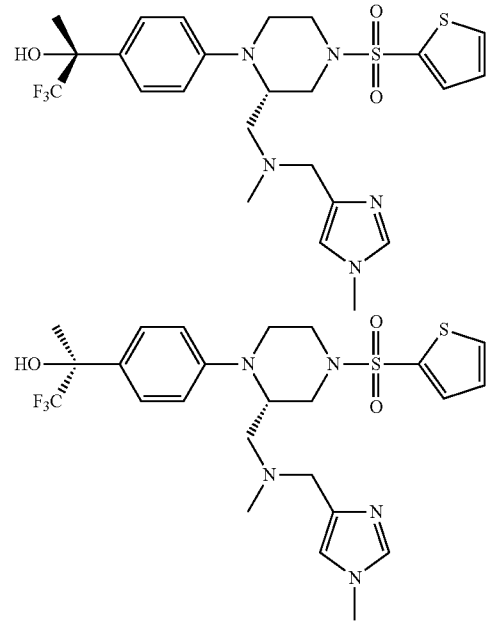

Step 1: 1,1,1-trifluoro-2-(4-((2S)-2-((methylamino)methyl)-4-(2-thiophenylsulfonyl)-1-piperazinyl)phenyl)-2-propanol This compound was synthesized following the procedure outlined for Example 84 The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and methanamine (10 equivalents of a 1.0M solution in THF, Sigma-Aldrich, St. Louis, Mo.) followed by purification via column chromatography on silica gel (0 to 10% MeOH in $CH_2Cl_2$) delivered 1,1,1-trifluoro-2-(4-((2S)-2-((methylamino)methyl)-4-(2-thiophenylsulfonyl)-1-piperazinyl)phenyl)-2-propanol as a mixture of two isomers after column chromatography on silica gel (0-10% MeOH in $CH_2Cl_2$)

Step 2: 1,1,1-trifluoro-2-(4-((2S)-2-((methyl((1-methyl-1H-imidazol-4-yl)methyl)amino)methyl)-4-(2-thiophenylsulfonyl)-1-piperazinyl)phenyl)-2-propanol A 25-mL round-bottomed flask was charged with 1,1,1-trifluoro-2-(4-((2S)-2-((methylamino)methyl)-4-(2-thiophenylsulfonyl)-1-piperazinyl)phenyl)-2-propanol (50 mg, 0.108 mmol), 1-methyl-1H-imidazole-4-carbaldehyde (59.4 mg, 0.539 mmol, ASDI, Newark, Del.), sodium triacetoxyborohydride (114 mg, 0.539 mmol, Sigma-Aldrich, St. Louis, Mo.), AcOH (0.617 µl, 10.79 µmol) and DCE (5 mL). The reaction was stirred at room temperature for 12 h. MeOH (20 mL), was added and the mixture was concentrated onto silica gel and purified via column chromatography (12 g silica gel, 5 to 10% $CH_2Cl_2$ in MeOH) to give 1,1,1-trifluoro-2-(4-((2S)-2-((methyl((1-methyl-1H-imidazol-4-yl)methyl)amino)methyl)-4-(2-thiophenylsulfonyl)-1-piperazinyl)phenyl)-2-propanol (20 mg) as a mixture of two isomers.

(2R)-1,1,1-trifluoro-2-(4-((2S)-2-((methyl((1-methyl-1H-imidazol-4-yl)methyl)amino)methyl)-4-(2-thiophenylsulfonyl)-1-piperazinyl)phenyl)-2-propanol, (2S)-1,1,1-trifluoro-2-(4-((2S)-2-((methyl((1-methyl-1H-imidazol-4-yl)methyl)amino)methyl)-4-(2-thiophenylsulfonyl)-1-piperazinyl)phenyl)-2-propanol.

$^1$H NMR (400 MHz, $CD_3OD$) δ=7.93-7.83 (m, 1H), 7.66-7.59 (m, 1H), 7.52-7.48 (m, 1H), 7.43 (d, J=8.6 Hz, 2H), 7.28-7.20 (m, 1H), 6.95-6.77 (m, 3H), 4.05-3.89 (m, 2H), 3.73-3.63 (m, 4H), 3.61-3.53 (m, 1H), 3.43-3.33 (m, 2H), 3.19-3.07 (m, 1H), 3.04-2.96 (m, 1H), 2.64-2.56 (m, 1H), 2.56-2.43 (m, 1H), 2.27 (s, 3H), 2.10-1.98 (m, 1H), 1.67 (s, 3H). m/z (ESI, +ve ion) 558.2 (M+H)$^+$. GK-GKRP $IC_{50}$ (Binding)=0.521 µM; GK-GKRP $EC_{50}$ (LC MS/MS-2)=0.362 µM.

Example 122

1,1,1-trifluoro-2-(4-((2S)-2-(cis-hexahydro-5H-furo[2,3-c]pyrrol-5-ylmethyl)-4-(2-thiophenylsulfonyl)-1-piperazinyl)phenyl)-2-propanol

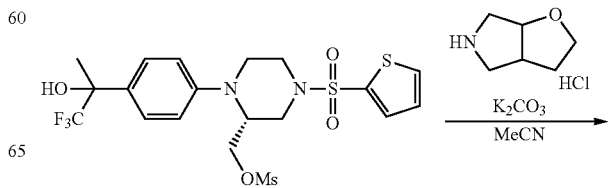

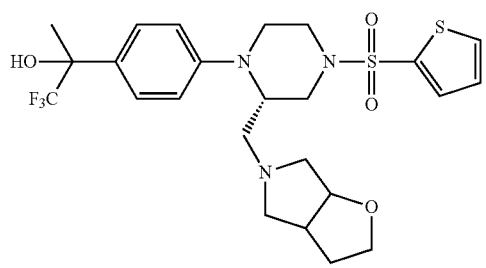
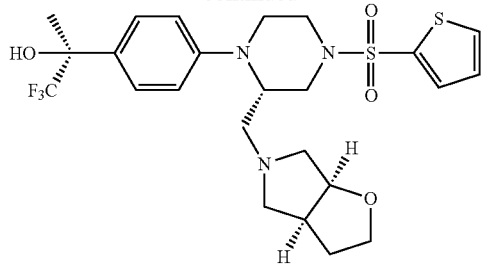

This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and cis-hexahydro-2H-furo[2,3-c]pyrrole hydrochloride (Synthonix, Wake Forest, N.C.) (using an extra equivalent of potassium carbonate and heating at 150° C.) delivered 1,1,1-trifluoro-2-(4-((2S)-2-(cis-hexahydro-5H-furo[2,3-c]pyrrol-5-ylmethyl)-4-(2-thiophenylsulfonyl)-1-piperazinyl)phenyl)-2-propanol as a mixture of four isomers after purification by reverse phase HPLC (Phenomenex Gemini-NX $C_{18}$ column, 21×100 mm, 5 μm eluting with A: Water w/0.1% $NH_4OH$ B: Acetonitrile w/0.1% $NH_4OH$).

(2R)-1,1,1-trifluoro-2-(4-((2S)-2-((3aR,6aR)-hexahydro-5H-furo[2,3-c]pyrrol-5-ylmethyl)-4-(2-thiophenylsulfonyl)-1-piperazinyl)phenyl)-2-propanol, (2S)-1,1,1-trifluoro-2-(4-((2S)-2-((3aR,6aR)-hexahydro-5H-furo[2,3-c]pyrrol-5-ylmethyl)-4-(2-thiophenylsulfonyl)-1-piperazinyl)phenyl)-2-propanol, (2R)-1,1,1-trifluoro-2-(4-((2S)-2-((3aS,6aS)-hexahydro-5H-furo[2,3-c]pyrrol-5-ylmethyl)-4-(2-thiophenylsulfonyl)-1-piperazinyl)phenyl)-2-propanol, (2S)-1,1,1-trifluoro-2-(4-((2S)-2-((3aS,6aS)-hexahydro-5H-furo[2,3-c]pyrrol-5-ylmethyl)-4-(2-thiophenylsulfonyl)-1-piperazinyl)phenyl)-2-propanol.

$^1$H NMR (400 MHz, DMSO-$d_6$) δ=8.09-8.03 (m, 1H), 7.70-7.63 (m, 1H), 6.89-6.82 (m, 2H), 7.39-7.33 (m, 1H), 6.89-6.82 (m, 2H), 4.40-4.30 (m, 1H), 4.14-4.02 (m, 1H), 3.87-3.75 (m, 1H), 3.73-3.46 (m, 5H), 3.13-3.00 (m, 1H), 2.93-2.85 (m, 1H), 2.82-2.55 (m, 3H), 2.45-2.27 (m, 2H), 2.18-1.80 (m, 3H), 1.61 (s, 3H), 1.58-1.42 (m, 1H). m/z (ESI, +ve ion) 546.2 (M+H)$^+$. GK-GKRP $IC_{50}$ (Binding)=0.555 μM; GK-GKRP $EC_{50}$ (LC MS/MS-2)=0.313 μM.

Example 123

1,1,1-trifluoro-2-(4-((2S)-2-((3aR,6aS)-tetrahydro-1H-furo[3,4-c]pyrrol-5(3H)-ylmethyl)-4-(2-thiophenylsulfonyl)-1-piperazinyl)phenyl)-2-propanol

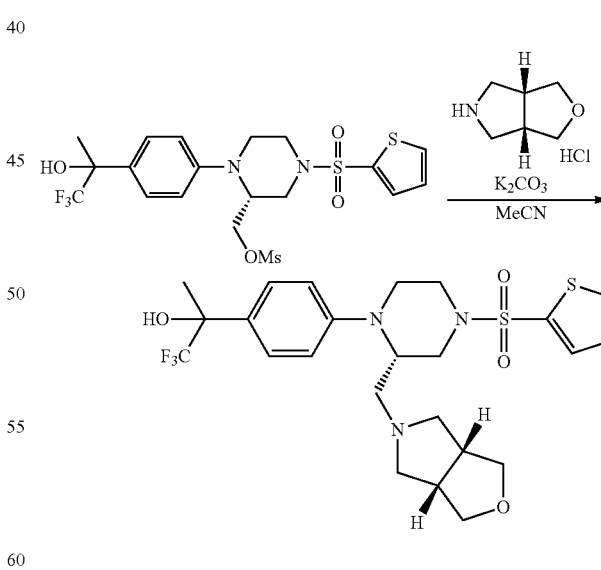

This compound was synthesized following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and (cis)-hexahydro-1H-furo[3,4-c]pyrrole hydrochloride (Synthonix, Wake Forest, N.C.) (using an extra equivalent of potassium carbonate) delivered 1,1,1-trifluoro- 2-(4-((2S)-2-((3aR,6aS)-tetrahydro-1H-furo[3,4-c]pyrrol-5(3H)-ylmethyl)-4-(2-thiophenylsulfonyl)-1-piperazinyl)phenyl)-2-propanol as a mixture of two isomers after purification by reverse phase HPLC (Phenomenex Gemini-NX C$_{18}$ column, 21×100 mm, 5 μm eluting with A: Water w/0.1% NH$_4$OH B: Acetonitrile w/0.1% NH$_4$OH).

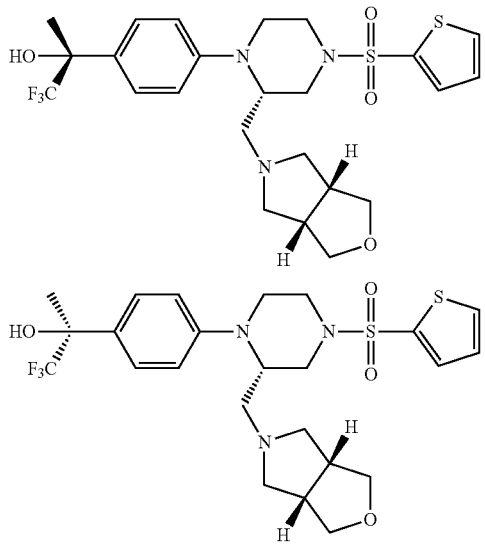

(2R)-1,1,1-trifluoro-2-(4-((2S)-2-((3aR,6aS)-tetrahydro-1H-furo[3,4-c]pyrrol-5(3H)-ylmethyl)-4-(2-thiophenylsulfonyl)-1-piperazinyl)phenyl)-2-propanol, (2S)-1,1,1-trifluoro-2-(4-((2S)-2-((3aR,6aS)-tetrahydro-1H-furo[3,4-c]pyrrol-5(3H)-ylmethyl)-4-(2-thiophenylsulfonyl)-1-piperazinyl)phenyl)-2-propanol.

$^1$H NMR (400 MHz, DMSO-d$_6$) δ=8.13-7.98 (m, 1H), 7.72-7.61 (m, 1H), 7.40-7.33 (m, 2H), 7.32-7.22 (m, 1H), 6.91-6.80 (m, 2H), 4.17-3.99 (m, 1H), 3.87-3.40 (m, 6H), 3.27-3.04 (m, 3H), 2.93-2.82 (m, 1H), 2.68-2.53 (m, 4H), 2.48-2.38 (m, 1H), 2.34-2.19 (m, 2H), 2.13-1.96 (m, 1H), 1.61 (s, 3H). m/z (ESI, +ve ion) 546.0 (M+H)$^+$. GK-GKRP IC$_{50}$ (Binding)=0.671 μM; GK-GKRP EC$_{50}$ (LC MS/MS-2)=0.731 μM.

Example 124

2-(4-((2S)-4-((6-amino-3-pyridinyl)sulfonyl)-2-(((3S)-3-methyl-4-morpholinyl)methyl)-1-piperazinyl)phenyl)-1,1,1,3,3,3-hexafluoro-2-propanol

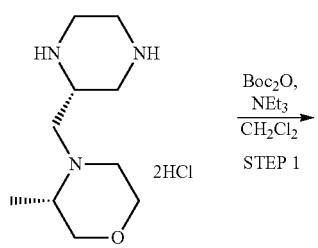

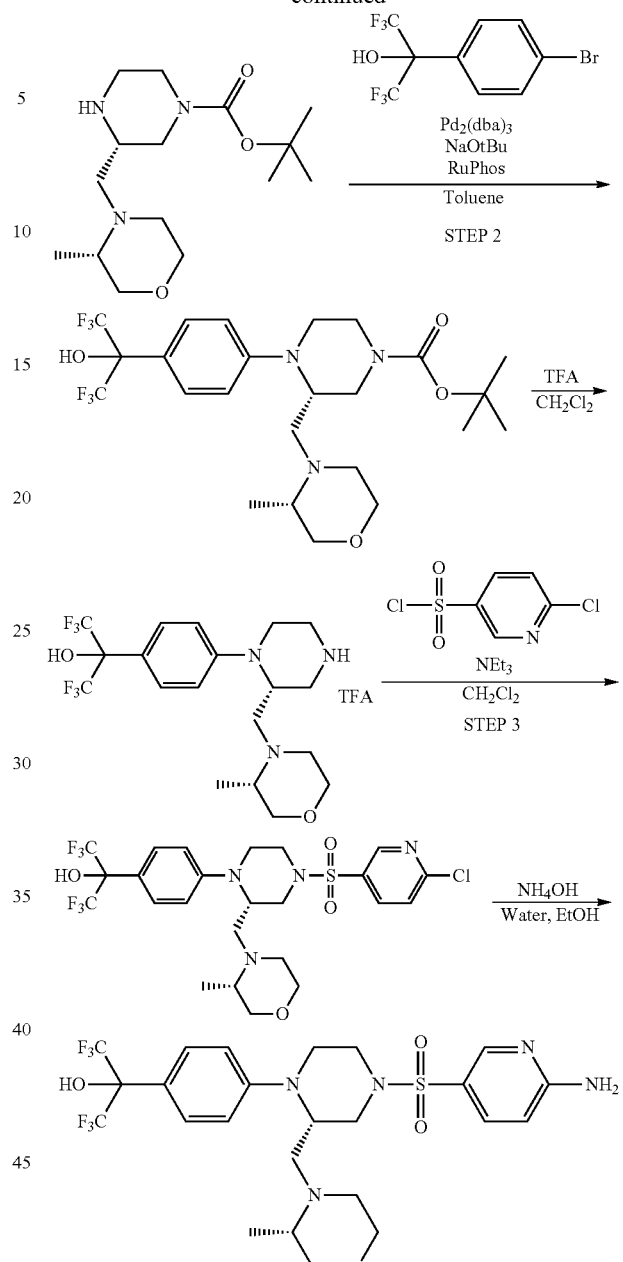

Step 1: (3S)-3-(((3S)-3-methyl-4-morpholinyl)methyl)-1-piperazinecarboxylate (3S)-3-methyl-4-((2R)-2-piperazinylmethyl)morpholine dihydrochloride (1.26, 4.91 mmol, Example 82, Step 2) was suspended in CH$_2$Cl$_2$ (30 mL) and chilled to 0° C. To this mixture was added triethylamine (1.37 mL, 9.82 mmol) followed by Boc$_2$O (1.072 g, 4.91 mmol). The reaction was allowed to gradually warm to room temperature and stirred for 5 h. The mixture was then concentrated and the crude material was purified via column chromatography (40 g silica gel, 0 to 10% MeOH in CH$_2$Cl$_2$) to give (S)-tert-butyl 3-((tetrahydro-2H-pyran-4-yl)methyl)piperazine-1-carboxylate (1.19 g) as a colorless oil.

Step 2: 1,1,1,3,3,3-hexafluoro-2-(4-((2R)-2-(((3S)-3-methyl-4-morpholinyl)methyl)-1-piperazinyl)phenyl)-2-propanol trifluoroacetate In a 20-mL vial, a mixture of (3S)-3-(((3S)-3-methyl-4-morpholinyl)methyl)-1-piperazinecarboxylate (210 mg, 0.738 mmol), 2-(4-bromophenyl)-1,1,1,3,3,3-hexafluoropropan-2-ol (286 mg, 0.886 mmol, Bioorg. Med. Chem. Lett. 2002, 12, 3009), dicyclohexyl(2',6'-diisopropoxy-[1,1'-biphenyl]-2-yl)phosphine (RuPhos) (17.23 mg, 0.037 mmol, Strem Chemicals, Newburyport, Mass.), Pd$_2$(dba)$_3$ (16.90 mg, 0.018 mmol, Strem Chemicals, Newburyport, Mass.) and sodium tert-butoxide (177 mg, 1.846 mmol) in toluene (5 mL) was heated to 100° C. for 16 h. Afterwards, the mixture was diluted with EtOAc (10 mL) and water (20 mL). The layers were separated and washed with water (10 mL) and brine (10 mL). The organic layer was dried over MgSO$_4$, filtered, and concentrated. The crude material was absorbed onto silica gel and purified via column chromatography (40 g silica gel, 0 to 100% EtOAc in hexanes) to give the Boc-protected intermediate.

To this was added 10 mL of CH$_2$Cl$_2$ and 10 mL of TFA. The resulting solution was stirred at room temperature for 3 h. The mixture was then concentrated and dried in vacuo to give 1,1,1,3,3,3-hexafluoro-2-(4-((2R)-2-(((3S)-3-methyl-4-morpholinyl)methyl)-1-piperazinyl)phenyl)-2-propanol trifluoroacetate (45 mg) as a yellow oil.

Step 3: 2-(4-((2S)-4-((6-amino-3-pyridinyl)sulfonyl)-2-(((3S)-3-methyl-4-morpholinyl)methyl)-1-piperazinyl)phenyl)-1,1,1,3,3,3-hexafluoro-2-propanol The 1,1,1,3,3,3-hexafluoro-2-(4-((2R)-2-(((3S)-3-methyl-4-morpholinyl)methyl)-1-piperazinyl)phenyl)-2-propanol trifluoroacetate (115 mg, 0.172 mmol) was dissolved in CH$_2$Cl$_2$ (30 mL) and was chilled to 0° C. To this solution was added triethylamine (96 μl, 0.687 mmol) followed by 6-chloropyridine-3-sulfonyl chloride (40.1 mg, 0.189 mmol, Organic Process Research & Development 2009, 13, 875). The mixture was warmed slowly to room temp and stirred for 2 h. Afterwards, the mixture was concentrated to give 2-(4-((S)-4-((6-chloropyridin-3-yl)sulfonyl)-2-(((R)-3-methylmorpholino)methyl)piperazin-1-yl)phenyl)-1,1,1,3,3,3-hexafluoropropan-2-ol.

The crude chloropyridine derivative was dissolved in 2 mL of EtOH and 2 mL of 30% aqueous ammonium hydroxide. This solution was heated to 140° C. for 60 min. The mixture was concentrated in vacuo and the crude material was purified via column chromatography (40 g silica gel, 0 to 10% MeOH in CH$_2$Cl$_2$) to give 2-(4-((2S)-4-((6-amino-3-pyridinyl)sulfonyl)-2-(((3S)-3-methyl-4-morpholinyl)methyl)-1-piperazinyl)phenyl)-1,1,1,3,3,3-hexafluoro-2-propanol (23 mg) as a foamy solid.

$^1$H NMR (400 MHz, CDCl$_3$) δ 8.45 (m, 1H), 7.76 (m, 1H), 7.55 (d, J=8.6 Hz, 2H), 6.83 (d, J=9 Hz, 2H), 6.54 (d, J=8.6 Hz, 1H), 5.00 (s, 2H), 4.05 (m, 1H), 3.89 (m, 1H), 3.76 (m, 1H), 3.68 (m, 1H), 3.59 (m, 2H), 3.44 (m, 1H), 3.25 (m, 3H), 2.74 (m, 1H), 2.45 (m, 3H), 2.20 (m, 1H), 1.96 (m, 1H), 1.03 (d, J=6.3 Hz, 3H). m/z (ESI, +ve ion) 598.6 (M+H)$^+$. GK-GKRP EC$_{50}$ (NADPH-coupled)=0.001 μM; GK-GKRP EC$_{50}$ (LC MS/MS-2)=0.018 μM.

Example 125

2-(4-((2S)-4-((6-amino-3-pyridinyl)sulfonyl)-2-(((3S)-3-methyl-4-morpholinyl)methyl)-1-piperazinyl)phenyl)-1,1,1-trifluoro-2-propanol

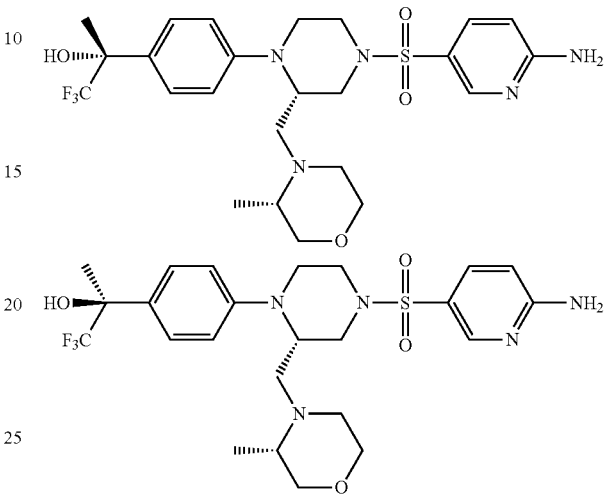

Following the scheme outlined for Example 124, substituting 2-(4-bromophenyl)-1,1,1-trifluoro-2-propanol (Example 27, Step 1) delivered 2-(4-((2S)-4-((6-amino-3-pyridinyl)sulfonyl)-2-(((3S)-3-methyl-4-morpholinyl)methyl)-1-piperazinyl)phenyl)-1,1,1-trifluoro-2-propanol as a mixture of two isomers.

(2S)-2-(4-((2S)-4-((6-amino-3-pyridinyl)sulfonyl)-2-(((3R)-3-methyl-4-morpholinyl)methyl)-1-piperazinyl)phenyl)-1,1,1-trifluoro-2-propanol; (2R)-2-(4-((2S)-4-((6-amino-3-pyridinyl)sulfonyl)-2-(((3R)-3-methyl-4-morpholinyl)methyl)-1-piperazinyl)phenyl)-1,1,1-trifluoro-2-propanol.

$^1$H NMR (400 MHz, CD$_3$OD) δ=8.30 (d, J=2.0 Hz, 1H), 7.73 (dd, J=2.3, 8.8 Hz, 1H), 7.44 (d, J=8.6 Hz, 2H), 6.91 (d, J=8.8 Hz, 2H), 6.64 (d, J=9.0 Hz, 1H), 4.05-3.92 (m, 2H), 3.77-3.51 (m, 4H), 3.40 (d, J=12.1 Hz, 1H), 3.29-3.08 (m, 3H), 2.83 (d, J=11.9 Hz, 1H), 2.58-2.40 (m, 2H), 2.31 (m, 1H), 2.09-1.99 (m, 1H), 1.84 (d, J=12.7 Hz, 1H), 1.67 (s, 3H), 0.99 (d, J=6.3 Hz, 3H). m/z (ESI, +ve ion) 544.6 (M+H)$^+$. GK-GKRP IC$_{50}$ (Binding)=0.003 μM; GK-GKRP EC$_{50}$ (LC MS/MS-2)=0.020 μM.

The individual isomers were separated using chiral SFC. The method used was as follows: Chiralcel® OJ column (21×250 mm, 10 μm) (using 20 mM NH$_3$ in methanol) in supercritical CO$_2$ (total flow was 70 mL/min). This separation yielded two products with both diastereomeric and enantiomeric excesses over 95%.

First Eluting Peak (Peak #1).

$^1$H NMR (400 MHz, CDCl$_3$) δ=8.47 (d, J=2.0 Hz, 1H), 7.76 (dd, J=2.3, 8.8 Hz, 1H), 7.43 (d, J=8.6 Hz, 2H), 6.80 (d, J=8.8 Hz, 2H), 6.53 (d, J=8.8 Hz, 1H), 4.99 (s, 2H), 4.02 (d, J=10.6 Hz, 1H), 3.84 (m, 1H), 3.72 (t, J=10.2 Hz, 2H), 3.66-3.52 (m, 2H), 3.38 (d, J=12.1 Hz, 1H), 3.31-3.14 (m, 3H), 2.73 (d, J=11.7 Hz, 1H), 2.58-2.41 (m, 3H), 2.37 (m, 1H), 1.91 (d, J=12.3 Hz, 1H), 1.74 (s, 3H), 1.03 (d, J=6.1 Hz, 3H). m/z (ESI, +ve ion) 544.6 (M+H)$^+$. GK-GKRP IC$_{50}$ (Binding)=0.004 μM; GK-GKRP EC$_{50}$ (LC MS/MS-2)=0.026 μM.

Second Eluting Peak (Peak #2)

¹H NMR (400 MHz, CDCl₃) δ=8.47 (d, J=2.0 Hz, 1H), 7.76 (dd, J=2.3, 8.8 Hz, 1H), 7.43 (d, J=8.6 Hz, 2H), 6.80 (d, J=8.8 Hz, 2H), 6.53 (d, J=8.8 Hz, 1H), 4.99 (s, 2H), 4.02 (d, J=10.6 Hz, 1H), 3.84 (m, 1H), 3.72 (t, J=10.2 Hz, 2H), 3.66-3.52 (m, 2H), 3.38 (d, J=12.1 Hz, 1H), 3.31-3.14 (m, 3H), 2.73 (d, J=11.7 Hz, 1H), 2.58-2.41 (m, 3H), 2.37 (m, 1H), 1.91 (d, J=12.3 Hz, 1H), 1.74 (s, 3H), 1.03 (d, J=6.1 Hz, 3H). m/z (ESI, +ve ion) 544.6 (M+H)⁺. GK-GKRP IC₅₀ (Binding)=0.007 μM; GK-GKRP EC₅₀ (LC MS/MS-2)=0.018 μM.

Example 126

2-(4-((2S)-4-((6-amino-3-pyridinyl)sulfonyl)-2-(tetrahydro-2H-pyran-4-ylmethyl)-1-piperazinyl)phenyl)-1,1,1,3,3,3-hexafluoro-2-propanol

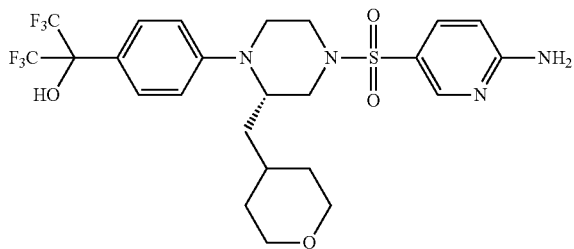 [SMILES: Nc1ccc(S(=O)(=O)N2CCN(c3ccc(C(O)(C(F)(F)F)C(F)(F)F)cc3)[C@@H](CC3CCOCC3)C2)cn1]

Following the scheme reported for Example 124, except using (2S)-2-(tetrahydro-2H-pyran-4-ylmethyl)piperazine dihydrochloride (Intermediate C) delivered 2-(4-((2S)-4-((6-amino-3-pyridinyl)sulfonyl)-2-(tetrahydro-2H-pyran-4-ylmethyl)-1-piperazinyl)phenyl)-1,1,1,3,3,3-hexafluoro-2-propanol.

¹H NMR (400 MHz, CDCl₃) δ ppm 8.44 (d, J=2.2 Hz, 1H), 7.74 (dd, J=8.8, 2.35 Hz, 1H), 7.54 (d, J=8.6 Hz, 2H), 6.80 (d, J=9.0 Hz, 2H), 6.53 (d, J=8.8 Hz, 1H), 4.99 (s, 2H), 4.07-3.81 (m, 3H), 3.74 (d, J=11.4 Hz, 1H), 3.66 (d, J=11.2 Hz, 1H), 3.46 (d, J=12.5 Hz, 1H), 3.39-3.21 (m, 3H), 2.64 (dd, J=11.3, 3.03 Hz, 1H), 2.51 (m, 1H), 1.85 (m, 1H), 1.69-1.34 (m, 5H), 1.33-1.14 (m, 1H). m/z (ESI, +ve ion) 583.6 (M+H)⁺. GK-GKRP IC₅₀ (Binding)=0.022 μM; GK-GKRP EC₅₀ (LC MS/MS-2)=0.037 μM.

Example 127

2-(4-((2S)-4-((6-amino-3-pyridinyl)sulfonyl)-2-(tetrahydro-2H-pyran-4-ylmethyl)-1-piperazinyl)phenyl)-1,1,1-trifluoro-2-propanol

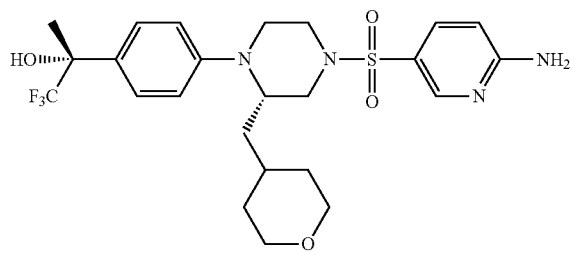

-continued

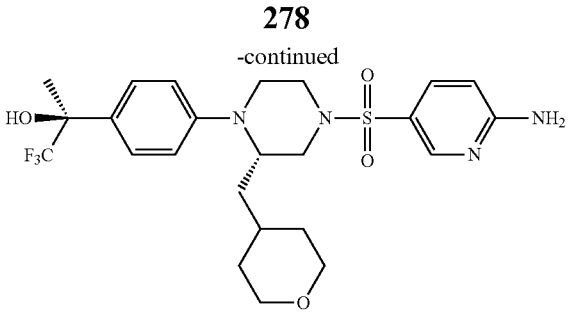

Following the scheme reported for Example 124, except using (2S)-2-(tetrahydro-2H-pyran-4-ylmethyl)piperazine dihydrochloride (Intermediate C) and 2-(4-bromophenyl)-1,1,1-trifluoro-2-propanol (Example 27, Step 1) yielded 2-(4-((2S)-4-((6-amino-3-pyridinyl)sulfonyl)-2-(tetrahydro-2H-pyran-4-ylmethyl)-1-piperazinyl)phenyl)-1,1,1-trifluoro-2-propanol as a mixture of two isomers (2R)-2-(4-((2S)-4-((6-amino-3-pyridinyl)sulfonyl)-2-(tetrahydro-2H-pyran-4-ylmethyl)-1-piperazinyl)phenyl)-1,1,1-trifluoro-2-propanol; (2S)-2-(4-((2S)-4-((6-amino-3-pyridinyl)sulfonyl)-2-(tetrahydro-2H-pyran-4-ylmethyl)-1-piperazinyl)phenyl)-1,1,1-trifluoro-2-propanol.

¹H NMR (400 MHz, CD₃OD) δ=8.20 (d, J=2.0 Hz, 1H), 7.67-7.59 (m, 1H), 7.34 (d, J=8.6 Hz, 2H), 6.78 (d, J=9.0 Hz, 2H), 6.56-6.49 (m, 1H), 4.00-3.93 (m, 1H), 3.80-3.68 (m, 2H), 3.60 (d, J=11.0 Hz, 1H), 3.49 (d, J=11.5 Hz, 1H), 3.31 (d, J=12.5 Hz, 1H), 3.25-3.17 (m, 2H), 3.15-3.07 (m, 1H), 2.57 (dd, J=2.6, 11.4 Hz, 1H), 2.44 (m, 1H), 1.70-1.62 (m, 1H), 1.57 (s, 3H), 1.57-1.53 (m, 1H), 1.42 (d, J=12.9 Hz, 1H), 1.37-1.28 (m, 1H), 1.25-0.93 (m, 3H). m/z (ESI, +ve ion) 531.6 (M+H)⁺. GK-GKRP IC₅₀ (Binding)=0.055 μM; GK-GKRP EC₅₀ (LC MS/MS-2)=0.058 μM.

The individual isomers were separated using chiral SFC. The method used was as follows: Chiralcel® OJ column (21×250 mm, 10 μm) (using 20 mM NH₃ in methanol) in supercritical CO₂ (total flow was 70 mL/min). This separation yielded two products with both diastereomeric and enantiomeric excesses over 95%.

First Eluting Peak (Peak #1)

¹H NMR (400 MHz, CDCl₃) δ=8.45 (d, J=2.2 Hz, 1H), 7.73 (dd, J=2.3, 8.8 Hz, 1H), 7.42 (d, J=8.6 Hz, 2H), 6.78 (d, J=9.0 Hz, 2H), 6.53 (d, J=8.8 Hz, 1H), 5.00 (s, 2H), 3.99-3.84 (m, 3H), 3.70 (d, J=10.8 Hz, 1H), 3.62 (d, J=11.3 Hz, 1H), 3.44-3.21 (m, 4H), 2.71-2.63 (m, 1H), 2.61-2.47 (m, 2H), 1.82 (m, 1H), 1.74 (s, 3H), 1.60-1.41 (m, 3H), 1.40-1.16 (m, 2H). m/z (ESI, +ve ion) 529.6 (M+H)⁺. GK-GKRP IC₅₀ (Binding)=0.051 μM; GK-GKRP EC₅₀ (LC MS/MS-2)=0.098 μM.

Second Eluting Peak (Peak #2)

¹H NMR (400 MHz, CDCl₃) δ=8.45 (d, J=2.2 Hz, 1H), 7.73 (dd, J=2.3, 8.8 Hz, 1H), 7.42 (d, J=8.6 Hz, 2H), 6.78 (d, J=9.0 Hz, 2H), 6.53 (d, J=8.8 Hz, 1H), 5.00 (s, 2H), 3.98-3.84 (m, 3H), 3.70 (d, J=10.8 Hz, 1H), 3.62 (d, J=11.3 Hz, 1H), 3.44-3.21 (m, 4H), 2.70-2.63 (m, 1H), 2.60-2.47 (m, 2H), 1.82 (m, 1H), 1.74 (s, 3H), 1.60-1.41 (m, 3H), 1.40-1.16 (m, 2H). m/z (ESI, +ve ion) 529.6 (M+H)⁺. GK-GKRP IC₅₀ (Binding)=0.048 μM; GK-GKRP EC₅₀ (LC MS/MS-2)=0.072 μM.

Example 128

2-(2-((2S)-4-((6-amino-3-pyridinyl)sulfonyl)-2-(((3S)-3-methyl-4-morpholinyl)methyl)-1-piperazinyl)-5-pyrimidinyl)-1,1,1,3,3,3-hexafluoro-2-propanol

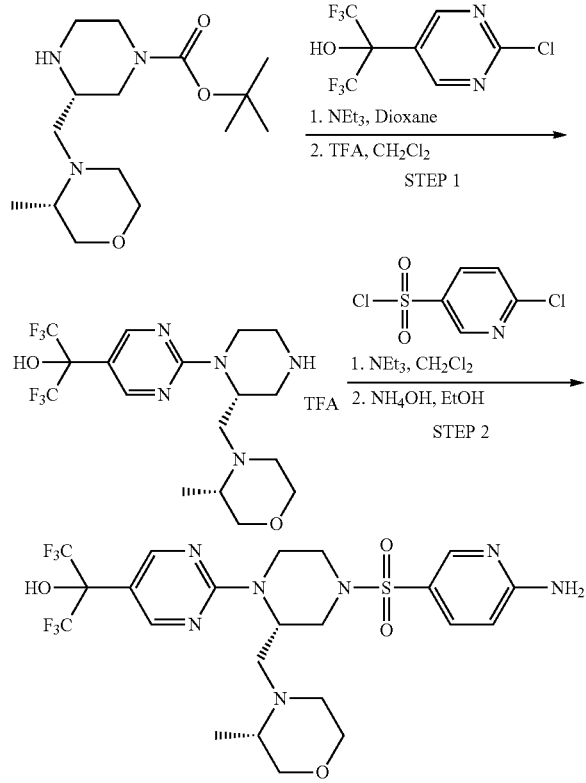

Step 1: 1,1,1,3,3,3-hexafluoro-2-(2-((2R)-2-(((3S)-3-methyl-4-morpholinyl)methyl)-1-piperazinyl)-5-pyrimidinyl)-2-propanol trifluoroacetate In a sealed vial a mixture of (S)-tert-butyl 3-(((R)-3-methylmorpholino)methyl)piperazine-1-carboxylate (114 mg, 0.381 mmol) (Example 124, Step 1), 2-(2-chloropyrimidin-5-yl)-1,1,1,3,3,3-hexafluoropropan-2-ol (139 mg, 0.495 mmol) (Intermediate D), and triethylamine (80 µl, 0.571 mmol) in dioxane (20 mL) was heated to 100° C. for 16 h. After the mixture was allowed to cool to room temperature, the solution was absorbed onto silica gel and purified via column chromatography (24 g silica gel, 0 to 100% EtOAc in hexanes) to give the Boc-protected intermediate.

The intermediate was dissolved in 10 mL of CH$_2$Cl$_2$ and 10 mL of TFA: The solution was stirred at room temperature for 2 h. The mixture was then concentrated and dried in vacuo. The resulting 1,1,1,3,3,3-hexafluoro-2-(2-((R)-2-(((R)-3-methylmorpholino)methyl)piperazin-1-yl)pyrimidin-5-yl)propan-2-ol 2,2,2-trifluoroacetate (165 mg) was used as is in the next step without further purification.

Step 2: 2-(2-((2S)-4-((6-amino-3-pyridinyl)sulfonyl)-2-(((3S)-3-methyl-4-morpholinyl)methyl)-1-piperazinyl)-5-pyrimidinyl)-1,1,1,3,3,3-hexafluoro-2-propanol Following the procedure reported for Example 124, Step 3, the reaction of 1,1,1,3,3,3-hexafluoro-2-(2-((R)-2-(((R)-3-methylmorpholino)methyl)piperazin-1-yl)pyrimidin-5-yl)propan-2-ol 2,2,2-trifluoroacetate and 6-chloropyridine-3-sulfonyl chloride (*Organic Process Research & Development* 2009, 13, 875) followed by amination delivered 2-(2-((2S)-4-((6-amino-3-pyridinyl)sulfonyl)-2-(((3S)-3-methyl-4-morpholinyl)methyl)-1-piperazinyl)-5-pyrimidinyl)-1,1,1,3,3-hexafluoro-2-propanol (55 mg) after purification via column chromatography on silica gel (0 to 10% MeOH in CH$_2$Cl$_2$).

$^1$H NMR (400 MHz, CD$_3$OD) δ=8.54 (s, 2H), 8.28 (d, J=2.0 Hz, 1H), 7.72 (dd, J=2.3, 9.0 Hz, 1H), 6.61 (d, J=8.8 Hz, 1H), 4.94 (d, J=4.5 Hz, 1H), 4.72 (m, 1H), 4.03 (d, J=11.3 Hz, 1H), 3.80-3.53 (m, 4H), 3.42-3.33 (m, 1H), 3.28-3.13 (m, 2H), 3.08 (d, J=12.1 Hz, 1H), 2.51-2.25 (m, 4H), 2.06-1.96 (m, 1H), 1.07 (d, J=6.3 Hz, 3H). m/z (ESI, +ve ion) 600.6 (M+H)$^+$. GK-GKRP IC$_{50}$ (Binding)=0.027 µM; GK-GKRP EC$_{50}$ (LC MS/MS-2)=0.034 µM.

Example 129

2-(2-((2S)-4-((6-amino-3-pyridinyl)sulfonyl)-2-(((3S)-3-methyl-4-morpholinyl)methyl)-1-piperazinyl)-5-pyrimidinyl)-1,1,1-trifluoro-2-propanol

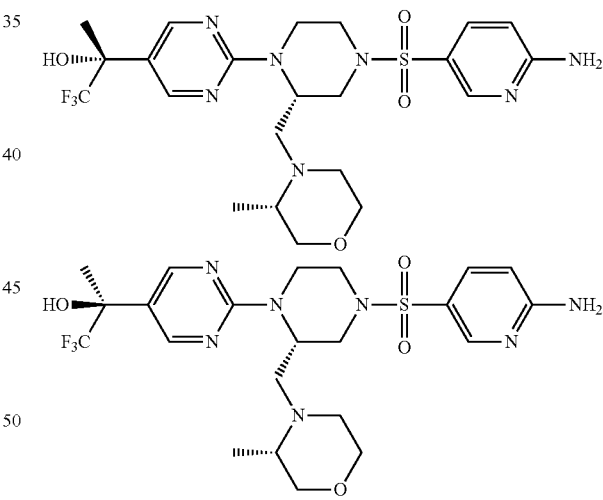

Following the scheme reported for Example 128, the reaction of 2-(2-chloro-5-pyrimidinyl)-1,1,1-trifluoro-2-propanol (Intermediate E) and 1,1,1,3,3,3-hexafluoro-2-(2-((R)-2-(((R)-3-methylmorpholino)methyl)piperazin-1-yl)pyrimidin-5-yl)propan-2-ol 2,2,2-trifluoroacetate (Example 128) delivered 2-(2-((2S)-4-((6-amino-3-pyridinyl)sulfonyl)-2-(((3S)-3-methyl-4-morpholinyl)methyl)-1-piperazinyl)-5-pyrimidinyl)-1,1,1-trifluoro-2-propanol (68 mg) as a mixture of two isomers after purification via column chromatography on silica gel (0 to 10% MeOH in CH$_2$Cl$_2$)

(2R)-2-(2-((2S)-4-((6-amino-3-pyridinyl)sulfonyl)-2-(((3S)-3-methyl-4-morpholinyl)methyl)-1-piperazinyl)-5-pyrimidinyl)-1,1,1-trifluoro-2-propanol; (2S)-2-(2-((2S)-4-

((6-amino-3-pyridinyl)sulfonyl)-2-(((3S)-3-methyl-4-morpholinyl)methyl)-1-piperazinyl)-5-pyrimidinyl)-1,1,1-trifluoro-2-propanol.

$^1$H NMR (400 MHz, CD$_3$OD) δ=8.49 (s, 2H), 8.28 (s, 1H), 7.76-7.67 (m, 1H), 6.61 (d, J=9.0 Hz, 1H), 4.89 (d, J=10.4 Hz, 1H), 4.64 (d, J=13.3 Hz, 1H), 4.03 (d, J=11.3 Hz, 1H), 3.77-3.66 (m, 2H), 3.66-3.55 (m, 2H), 3.42-3.33 (m, 1H), 3.28-3.04 (m, 3H), 2.49-2.23 (m, 4H), 1.97 (d, J=12.1 Hz, 1H), 1.69 (s, 3H), 1.07 (d, J=6.3 Hz, 3H). m/z (ESI, +ve ion) 546.6 (M+H)$^+$. GK-GKRP IC$_{50}$ (Binding)=0.036 μM; GK-GKRP EC$_{50}$ (LC MS/MS-2)=0.099 μM.

Example 130

2-(2-((2S)-4-((6-amino-3-pyridinyl)sulfonyl)-2-(tetrahydro-2H-pyran-4-ylmethyl)-1-piperazinyl)-5-pyrimidinyl)-1,1,1,3,3,3-hexafluoro-2-propanol

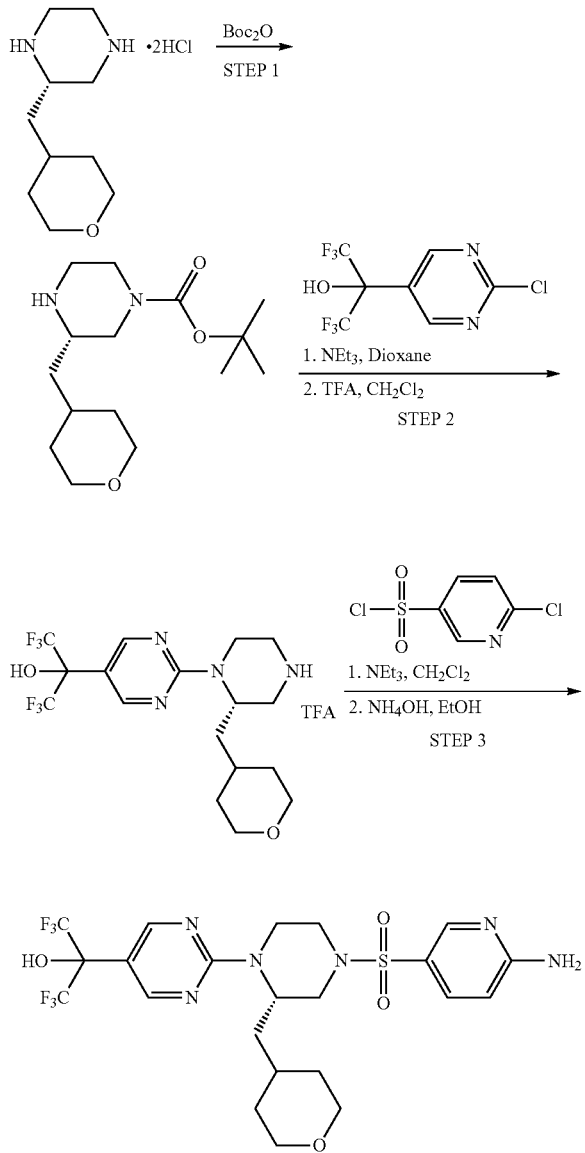

Step 1: tert-butyl (3S)-3-(tetrahydro-2H-pyran-4-ylmethyl)-1-piperazinecarboxylate (2S)-2-(tetrahydro-2H-pyran-4-ylmethyl)piperazine dihydrochloride (1.49 g, 5.77 mmol, Intermediate C) was suspended in CH$_2$Cl$_2$ (30 mL) and chilled to 0° C. To this mixture was added triethylamine (2.41 mL, 17.3 mmol) followed by Boc$_2$O (1.32 g, 6.06 mmol). The reaction was allowed to gradually warm to room temperature and stirred for 3 h. The mixture was then concentrated and the crude material was purified via column chromatography (40 g silica gel, 0 to 10% MeOH in CH$_2$Cl$_2$) to give (S)-tert-butyl 3-((tetrahydro-2H-pyran-4-yl)methyl)piperazine-1-carboxylate (1.355 g) as a colorless oil.

Step 2: 1,1,1,3,3,3-hexafluoro-2-(2-((2S)-2-(tetrahydro-2H-pyran-4-ylmethyl)-1-piperazinyl)-5-pyrimidinyl)-2-propanol ditrifluoroacetate In a 20-mL vial a mixture of (S)-tert-butyl 3-((tetrahydro-2H-pyran-4-yl)methyl)piperazine-1-carboxylate (130 mg, 0.457 mmol), 2-(2-chloropyrimidin-5-yl)-1,1,1,3,3,3-hexafluoro-2-propanol (147 mg, 0.549 mmol, Intermediate D), triethylamine (96 μL, 0.686 mmol) and dioxane (20 mL) was heated at 100° C. for 16 h. The mixture was then concentrated and the crude material was absorbed onto silica gel and purified via column chromatography (24 g silica gel, 0 to 100% EtOAc in hexanes). The desired fractions were combined and concentrated to give the Boc-protected intermediate.

The intermediate was dissolved in 20 mL of a 1:1 TFA:CH$_2$Cl$_2$ solution and was stirred at room temp for 2 h. Afterwards, the mixture was concentrated and dried in vacuo. The resulting 1,1,1,3,3,3-hexafluoro-2-(2-((2S)-2-(tetrahydro-2H-pyran-4-ylmethyl)-1-piperazinyl)-5-pyrimidinyl)-2-propanol ditrifluoroacetate (188 mg) was used as is in the next step without further purification.

Step 3: 2-(2-((2S)-4-((6-amino-3-pyridinyl)sulfonyl)-2-(tetrahydro-2H-pyran-4-ylmethyl)-1-piperazinyl)-5-pyrimidinyl)-1,1,1,3,3,3-hexafluoro-2-propanol Following the procedure reported Example 124, Step 3, the reaction of, 1,1,1,3,3,3-hexafluoro-2-(2-((2S)-2-(tetrahydro-2H-pyran-4-ylmethyl)-1-piperazinyl)-5-pyrimidinyl)-2-propanol ditrifluoroacetate and 6-chloropyridine-3-sulfonyl chloride (*Organic Process Research & Development* 2009, 13, 875) followed by amination delivered 2-(2-((2S)-4-((6-amino-3-pyridinyl)sulfonyl)-2-(tetrahydro-2H-pyran-4-ylmethyl)-1-piperazinyl)-5-pyrimidinyl)-1,1,1,3,3,3-hexafluoro-2-propanol after purification via column chromatography on silica gel (0 to 10% MeOH in CH$_2$Cl$_2$).

$^1$H NMR (400 MHz, CD$_3$OD) δ=8.42 (s, 2H), 8.17 (s, 1H), 7.64-7.56 (m, 1H), 6.50 (d, J=9.0 Hz, 1H), 5.09-4.99 (m, 1H), 4.67 (d, J=13.3 Hz, 1H), 3.84-3.73 (m, 2H), 3.64 (d, J=11.2 Hz, 1H), 3.53 (d, J=11.9 Hz, 1H), 3.33-3.23 (m, 1H), 3.21-3.12 (m, 2H), 2.40 (dd, J=3.5, 11.7 Hz, 1H), 2.27 (m, 1H), 1.74-1.54 (m, 4H), 1.39-1.11 (m, 3H). m/z (ESI, +ve ion) 585.5 (M+H)$^+$. GK-GKRP IC$_{50}$ (Binding)=0.062 μM; GK-GKRP EC$_{50}$ (LC MS/MS-2)=0.134 μM.

Example 131

2-(2-((2S)-4-((6-amino-3-pyridinyl)sulfonyl)-2-(tetrahydro-2H-pyran-4-ylmethyl)-1-piperazinyl)-5-pyrimidinyl)-1,1,1,3,3,3-hexafluoro-2-propanol

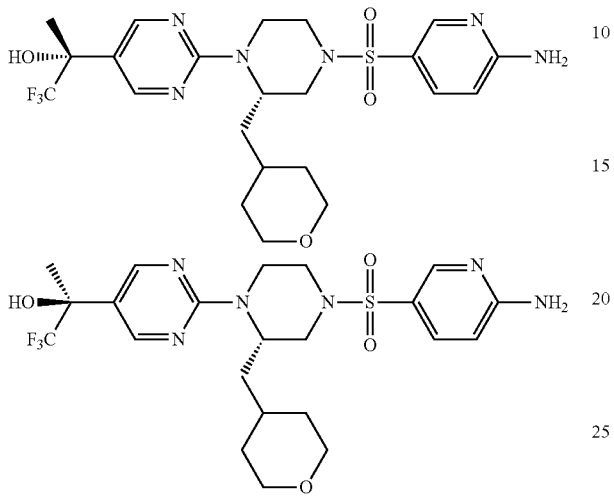

This compound was synthesized following the scheme described for Example 130, except 2-(2-chloro-5-pyrimidinyl)-1,1,1-trifluoro-2-propanol (Intermediate E) was substituted for 2-(2-chloro-5-pyrimidinyl)-1,1,1-trifluoro-2-propanol. This route delivered 2-(2-((2S)-4-((6-amino-3-pyridinyl)sulfonyl)-2-(tetrahydro-2H-pyran-4-ylmethyl)-1-piperazinyl)-5-pyrimidinyl)-1,1,1,3,3,3-hexafluoro-2-propanol as a mixture of two isomers after column chromatography on silica gel (0 to 10% MeOH in $CH_2Cl_2$)

(2R)-2-(2-((2S)-4-((6-amino-3-pyridinyl)sulfonyl)-2-(tetrahydro-2H-pyran-4-ylmethyl)-1-piperazinyl)-5-pyrimidinyl)-1,1,1-trifluoro-2-propanol; (2R)-2-(2-((2S)-4-((6-amino-3-pyridinyl)sulfonyl)-2-(tetrahydro-2H-pyran-4-ylmethyl)-1-piperazinyl)-5-pyrimidinyl)-1,1,1-trifluoro-2-propanol.

$^1$H NMR (400 MHz, $CD_3OD$) δ=8.47 (s, 2H), 8.27 (s, 1H), 7.73-7.63 (m, 1H), 6.60 (d, J=8.8 Hz, 1H), 5.18-5.06 (m, 1H), 4.72 (d, J=13.7 Hz, 1H), 3.89 (t, J=9.9 Hz, 2H), 3.72 (d, J=11.3 Hz, 1H), 3.62 (d, J=11.7 Hz, 1H), 3.42-3.18 (m, 3H), 2.52-2.43 (m, 1H), 2.40-2.28 (m, 1H), 1.84-1.63 (m, 7H), 1.50-1.20 (m, 3H). m/z (ESI, +ve ion) 531.6 (M+H)$^+$. GK-GKRP $IC_{50}$ (Binding)=0.124 µM; GK-GKRP $EC_{50}$ (LC MS/MS-2)=0.102 µM.

Example 132

1,1,1,3,3,3-hexafluoro-2-(4-((2S)-2-(((3S)-3-methyl-4-morpholinyl)methyl)-4-(2-thiophenylsulfonyl)-1-piperazinyl)phenyl)-2-propanol

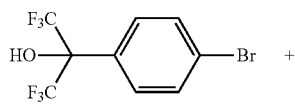 +

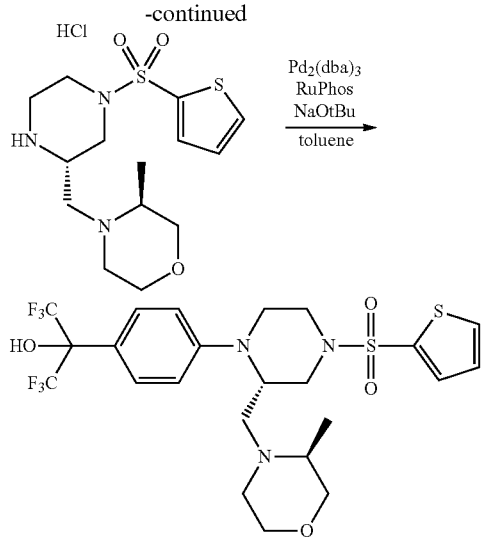

In a pressure tube (3S)-3-methyl-4-(((2S)-4-(2-thiophenylsulfonyl)-2-piperazinyl)methyl)morpholine dihydrochloride (133 mg, 0.318 mmol, Example 82, Step 2), 2-(4-bromophenyl)-1,1,1,3,3,3-hexafluoropropan-2-ol (123 mg, 0.381 mmol, Bioorg. Med. Chem. Lett. 2002, 12, 3009), $Pd_2(dba)_3$ (18.28 mg, 0.032 mmol, Strem Chemicals, Newburyport, Mass.), dicyclohexyl(2',6'-diisopropoxybiphenyl-2-yl)phosphine (RuPhos) (14.83 mg, 0.032 mmol, Strem Chemicals, Newburyport, Mass.), and sodium tert-butoxide (122 mg, 1.272 mmol) were combined and suspended in toluene (5 mL). Nitrogen gas was bubbled through the solution for 5 min. The reaction vial was sealed and heated to 100° C. for 15 h. The reaction mixture was then diluted with water and EtOAc. The aqueous mixture was extracted with EtOAc (2×20 mL). The organic extracts were combined and dried over $MgSO_4$, filtered, and concentrated. The crude material was purified by purified via reverse-phase preparative HPLC using a Phenomenex Gemini $C_{18}$ column (30×150 mm, 10 µm) eluting with 0.1% TFA in $MeCN/H_2O$ (10% to 100% over 15 min) to afford 1,1,1,3,3,3-hexafluoro-2-(4-((2S)-2-(((3S)-3-methyl-4-morpholinyl)methyl)-4-(2-thiophenylsulfonyl)-1-piperazinyl)phenyl)-2-propanol (23 mg).

$^1$H NMR (400 MHz, $CDCl_3$) δ 7.65 (d, J=4.9 Hz, 1H), 7.59 (m, 1H), 7.54 (d, J=8.8 Hz, 2H), 7.17 (m, 1H), 6.83 (d, J=9.0 Hz, 2H), 4.10 (m, 1H), 3.91 (m, 1H), 3.81 (m, 1H), 3.69 (m, 1H), 3.58 (m, 2H), 3.46 (m, 1H), 3.25 (m, 3H), 2.75 (m, 1H), 2.54 (m, 2H), 2.39 (m, 1H), 2.21 (m, 1H), 1.97 (m, 1H), 1.03 (d, J=6.3 Hz, 3H). m/z (ESI, +ve ion) 588.6 (M+H)$^+$. GK-GKRP $IC_{50}$ (Binding)=0.006 µM; GK-GKRP $EC_{50}$ (LC MS/MS-2)=0.009 µM.

Example 133

2-(2-((2S)-4-((5-amino-2-thiophenyl)sulfonyl)-2-(tetrahydro-2H-pyran-4-ylmethyl)-1-piperazinyl)-5-pyrimidinyl)-1,1,1,3,3,3-hexafluoro-2-propanol

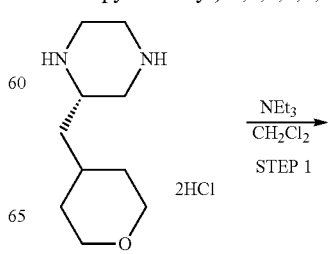

STEP 1

-continued

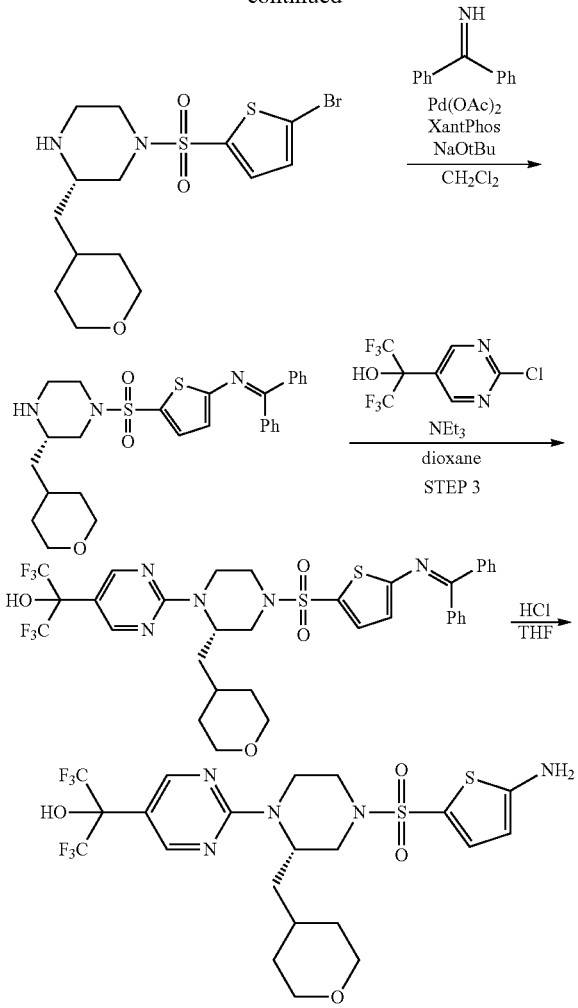

Step 1: (3S)-1-((5-bromo-2-thiophenyl)sulfonyl)-3-(tetrahydro-2H-pyran-4-ylmethyl)piperazine The (S)-2-((tetrahydro-2H-pyran-4-yl)methyl)piperazine dihydrochloride (390 mg, 1.516 mmol, Intermediate C) was dissolved in CH$_2$Cl$_2$ and the solution was chilled to 0° C. To this solution was added triethylamine (634 µL, 4.55 mmol) followed by 5-bromothiophene-2-sulfonyl chloride (497 mg, 1.90 mmol, Sigma-Aldrich, St. Louis, Mo.). The mixture was allowed to slowly warm to room temperature and stirring was continued for 2 h. The mixture was concentrated and the crude material was purified via column chromatography (40 g silica gel, 0 to 10% MeOH in CH$_2$Cl$_2$) to give (3S)-1-((5-bromo-2-thiophenyl)sulfonyl)-3-(tetrahydro-2H-pyran-4-ylmethyl)piperazine (520 mg).

Step 2: N-(diphenylmethylidene)-5-(((3S)-3-(tetrahydro-2H-pyran-4-ylmethyl)-1-piperazinyl)sulfonyl)-2-thiophenamine In a sealed vial (3S)-1-((5-bromo-2-thiophenyl)sulfonyl)-3-(tetrahydro-2H-pyran-4-ylmethyl)piperazine (540 mg, 1.32 mmol), diacetoxypalladium (14.81 mg, 0.066 mmol, Strem Chemicals, Newburyport, Mass.), (9,9-dimethyl-9H-xanthene-4,5-diyl)bis(diphenylphosphine) (XantPhos) (38.2 mg, 0.066 mmol, Strem Chemicals, Newburyport, Mass.), sodium tert-butoxide (279 mg, 2.90 mmol), and diphenylmethanimine (287 mg, 1.58 mmol, Sigma-Aldrich, St. Louis, Mo.) were combined and suspended in toluene (5 mL). Nitrogen gas was bubbled through the solution for 5 min and then the mixture was heated at 100° C. for 16 h. The solution was diluted with EtOAc (20 mL) and then washed with water (15 mL) and brine (15 mL). The organic layer was dried over MgSO$_4$, filtered, and concentrated. The crude material was absorbed onto silica gel and purified via column chromatography (40 g silica gel, 0 to 10% MeOH in CH$_2$Cl$_2$) to give N-(diphenylmethylidene)-5-(((3S)-3-(tetrahydro-2H-pyran-4-ylmethyl)-1-piperazinyl)sulfonyl)-2-thiophenamine (465 mg).

Step 3: 2-(2-((2S)-4-((5-amino-2-thiophenyl)sulfonyl)-2-(tetrahydro-2H-pyran-4-ylmethyl)-1-piperazinyl)-5-pyrimidinyl)-1,1,1,3,3,3-hexafluoro-2-propanol In a 20-mL vial was charged with N-(diphenylmethylidene)-5-(((3S)-3-(tetrahydro-2H-pyran-4-ylmethyl)-1-piperazinyl)sulfonyl)-2-thiophenamine (170 mg, 0.334 mmol)), 2-(2-chloropyrimidin-5-yl)-1,1,1,3,3,3-hexafluoropropan-2-ol (187 mg, 0.667 mmol, Intermediate D), and Hünig's base (175 µL, 1.001 mmol), and dioxane (5 mL). The vial was sealed and heated to 90° C. for 16 h. Afterwards, the mixture was concentrated in vacuo. The crude material was dissolved in THF (20 mL) and 4 N HCl in dioxane (5 mL). The resulting mixture was stirred for 2 h at room temperature. The mixture was concentrated, absorbed onto silica gel, and purified via column chromatography (40 g silica gel, 0 to 10% MeOH in CH$_2$Cl$_2$) to give 2-(2-((2S)-4-((5-amino-2-thiophenyl)sulfonyl)-2-(tetrahydro-2H-pyran-4-ylmethyl)-1-piperazinyl)-5-pyrimidinyl)-1,1,1,3,3,3-hexafluoro-2-propanol (88 mg).

$^1$H NMR (400 MHz, CDCl$_3$) δ=8.52 (s, 2H), 7.17 (d, J=4.1 Hz, 1H), 6.11 (s, 1H), 5.14 (m, 1H), 4.79 (d, J=13.3 Hz, 1H), 4.27 (s, 2H), 3.99-3.86 (m, 2H), 3.76-3.69 (m, 1H), 3.63 (d, J=11.5 Hz, 1H), 3.39-3.22 (m, 3H), 2.57 (dd, J=3.5, 11.5 Hz, 1H), 2.45 (m, 1H), 1.85-1.71 (m, 3H), 1.63-1.60 (m, 2H), 1.49-1.20 (m, 2H). m/z (ESI, +ve ion) 590.6 (M+H)$^+$. GK-GKRP IC$_{50}$ (Binding)=0.047 µM; GK-GKRP EC$_{50}$ (LC MS/MS-2)=0.059 µM.

Example 134

1,1,1,3,3,3-hexafluoro-2-(2-((2S)-2-(tetrahydro-2H-pyran-4-ylmethyl)-4-(2-thiophenylsulfonyl)-1-piperazinyl)-5-pyrimidinyl)-2-propanol

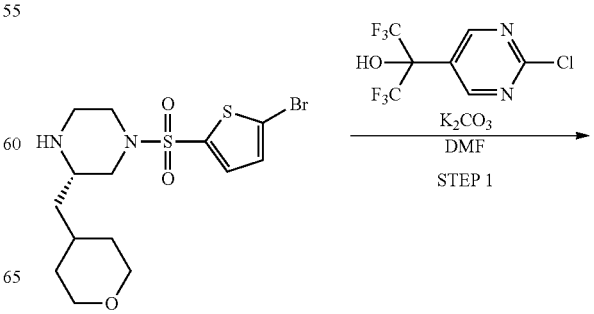

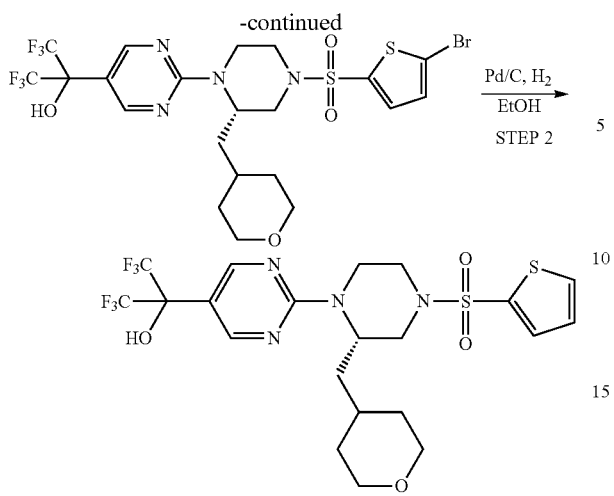

Step 1: 2-(2-((2S)-4-((5-bromo-2-thiophenyl)sulfonyl)-2-(tetrahydro-2H-pyran-4-ylmethyl)-1-piperazinyl)-5-pyrimidinyl)-1,1,1,3,3,3-hexafluoro-2-propanol A mixture of (3S)-1-((5-bromo-2-thiophenyl)sulfonyl)-3-(tetrahydro-2H-pyran-4-ylmethyl)piperazine (190 mg, 0.464 mmol, Example 133, Step 1), 2-(2-chloropyrimidin-5-yl)-1,1,1,3,3,3-hexafluoropropan-2-ol (156 mg, 0.557 mmol, Intermediate D), and potassium carbonate (128 mg, 0.928 mmol) in DMF was heated at 100° C. and stirred for 16 h. The mixture was diluted with water (20 mL) and EtOAc (20 mL). The layers were separated and the organics were washed with water (20 mL) and brine (20 mL). The organic extracts were dried over MgSO$_4$, filtered, and concentrated. The crude material was absorbed onto silica gel and purified via column chromatography (40 g silica gel, 0 to 100% EtOAc in hexanes) to give (S)-2-(2-(4-(5-bromothiophen-2-ylsulfonyl)-2-((tetrahydro-2H-pyran-4-yl)methyl)piperazin-1-yl)pyrimidin-5-yl)-1,1,1,3,3,3-hexafluoropropan-2-ol (140 mg).

Step 2: 1,1,1,3,3,3-hexafluoro-2-(2-((2S)-2-(tetrahydro-2H-pyran-4-ylmethyl)-4-(2-thiophenylsulfonyl)-1-piperazinyl)-5-pyrimidinyl)-2-propanol In a 50-mL round-bottomed flask a mixture of (S)-2-(2-(4-(5-bromothiophen-2-ylsulfonyl)-2-((tetrahydro-2H-pyran-4-yl)methyl)piperazin-1-yl)pyrimidin-5-yl)-1,1,1,3,3,3-hexafluoropropan-2-ol (60 mg, 0.092 mmol) and 10% Pd/C (19.5 mg, 0.018 mmol) in EtOH (10 mL) stirred under 1 atm of H$_2$ for 8 h. Afterwards, the mixture was filtered through a pad of Celite® (diatomaceous earth). The filtrate was concentrated and the crude product was purified by carefully filtering through a plug of silica gel using 5% MeOH in CH$_2$Cl$_2$ as the eluent. Concentration of the filtrate yielded 1,1,1,3,3,3-hexafluoro-2-(2-((2S)-2-(tetrahydro-2H-pyran-4-ylmethyl)-4-(2-thiophenylsulfonyl)-1-piperazinyl)-5-pyrimidinyl)-2-propanol (32 mg).

$^1$H NMR (400 MHz, CDCl$_3$) δ=8.51 (s, 2H), 7.61 (dd, J=1.2, 4.9 Hz, 1H), 7.53 (dd, J=1.3, 3.8 Hz, 1H), 7.14 (dd, J=3.8, 5.0 Hz, 1H), 5.15 (m, 1H), 4.81 (d, J=13.5 Hz, 1H), 3.93 (t, J=10.9 Hz, 2H), 3.82 (m, 1H), 3.72 (s, 1H), 3.41-3.24 (m, 3H), 2.54 (dd, J=3.7, 11.5 Hz, 1H), 2.41 (m, 1H), 1.84-1.74 (m, 2H), 1.67-1.55 (m, 2H), 1.48-1.23 (m, 3H). m/z (ESI, +ve ion) 575.6 (M+H)$^+$. GK-GKRP IC$_{50}$ (Binding)=0.122 µM; GK-GKRP EC$_{50}$ (LC MS/MS-2)=0.079 µM.

Example 135

2-(2-((2S)-4-((5-amino-2-thiophenyl)sulfonyl)-2-(tetrahydro-2H-pyran-4-ylmethyl)-1-piperazinyl)-5-pyrimidinyl)-1,1,1-trifluoro-2-propanol

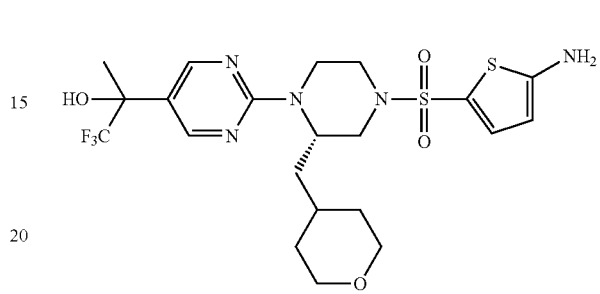

This compound was synthesized according the scheme described for Example 133. For this example racemic 2-(2-chloropyrimidin-5-yl)-1,1,1-trifluoropropan-2-ol (Intermediate E) was used rather than 2-(2-chloropyrimidin-5-yl)-1,1,1,3,3,3-hexafluoropropan-2-ol to yield 2-(2-((2S)-4-((5-amino-2-thiophenyl)sulfonyl)-2-(tetrahydro-2H-pyran-4-ylmethyl)-1-piperazinyl)-5-pyrimidinyl)-1,1,1-trifluoro-2-propanol as a mixture of two isomers. (2S)-2-(4-((2S)-4-((5-amino-2-thiophenyl)sulfonyl)-2-(tetrahydro-2H-pyran-4-ylmethyl)-1-piperazinyl)phenyl)-1,1,1-trifluoro-2-propanol; (2R)-2-(4-((2S)-4-((5-amino-2-thiophenyl)sulfonyl)-2-(tetrahydro-2H-pyran-4-ylmethyl)-1-piperazinyl)phenyl)-1,1,1-trifluoro-2-propanol.

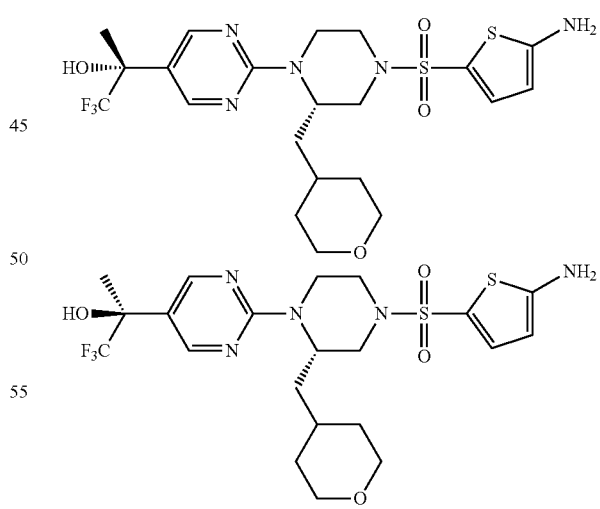

$^1$H NMR (400 MHz, CDCl$_3$) δ=8.43 (s, 2H), 7.16 (d, J=3.9 Hz, 1H), 6.10 (d, J=3.9 Hz, 1H), 5.17-5.09 (m, 1H), 4.82-4.73 (m, 1H), 4.23 (s, 2H), 3.98-3.86 (m, 2H), 3.71 (d, J=11.3 Hz, 1H), 3.65-3.58 (m, 1H), 3.39-3.22 (m, 3H), 2.56 (dd, J=3.6, 11.4 Hz, 1H), 2.48-2.35 (m, 2H), 1.84-1.76 (m, 2H), 1.76-1.70 (m, 3H), 1.63 (d, J=12.7 Hz, 1H), 1.51-1.27 (m, 3H). m/z (ESI, +ve ion) 536.6 (M+H)⁺. GK-GKRP IC$_{50}$ (Binding)=0.055 μM; GK-GKRP EC$_{50}$ (LC MS/MS-2)=0.108 μM.

Example 136

2-(4-((2S)-4-((5-amino-2-thiophenyl)sulfonyl)-2-benzyl-1-piperazinyl)phenyl)-1,1,1-trifluoro-2-propanol

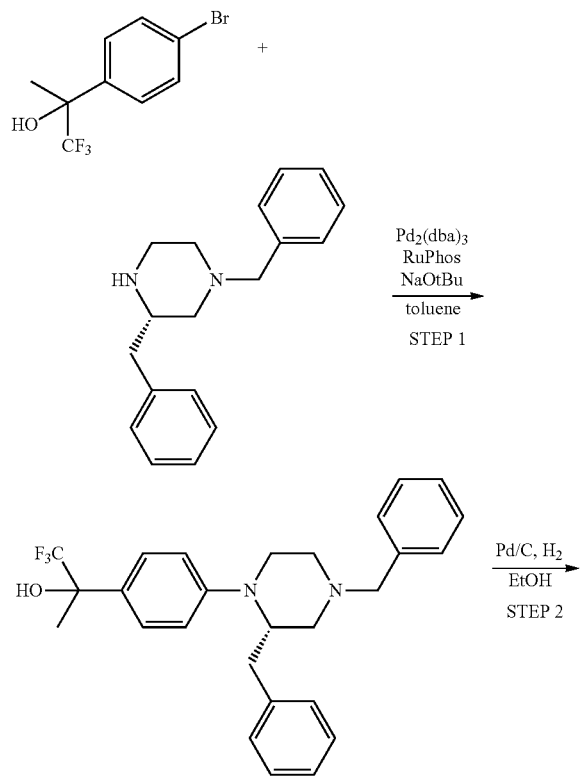

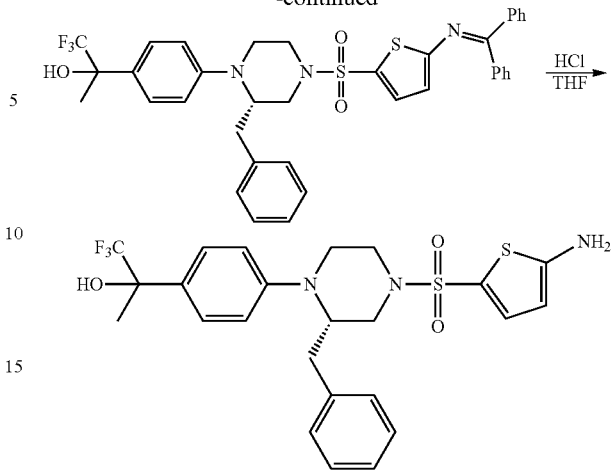

Step 1: 2-(4-((2S)-2,4-dibenzyl-1-piperazinyl)phenyl)-1,1,1-trifluoro-2-propanol In a sealable vial (S)-1,3-dibenzylpiperazine (0.617 g, 2.316 mmol, Alfa Aeser, Ward Hill, Mass.), 2-(4-bromophenyl)-1,1,1-trifluoropropan-2-ol (0.623 g, 2.316 mmol, Example 27, Step 1), dicyclohexyl(2',6'-diisopropoxybiphenyl-2-yl)phosphine (RuPhos) (0.071 g, 0.058 mmol, Strem Chemicals, Newburyport, Mass.), Pd$_2$(dba)$_3$ (0.067 g, 0.116 mmol, Strem Chemicals, Newburyport, Mass.), and sodium tert-butoxide (0.556 g, 5.79 mmol) were combined and suspended in toluene (5 mL). The vial was purged with N$_2$ for 5 min and was then heated at 100° C. for 15 h. The mixture was diluted with EtOAc (20 mL), the layers were separated and the organics were washed with water (10 mL) and brine (10 mL). The organic extracts were dried over MgSO$_4$, filtered, and concentrated. The crude material was absorbed onto silica gel and purified via column chromatography (40 g silica gel, 0 to 100% EtOAc in hexanes) to give 2-(4-((2S)-2,4-dibenzyl-1-piperazinyl)phenyl)-1,1,1-trifluoro-2-propanol (0.355 g).

Step 2: 2-(4-((2S)-2-benzyl-1-piperazinyl)phenyl)-1,1,1-trifluoro-2-propanol In a 100 mL round bottomed flask a mixture of 2-(4-((2S)-2,4-dibenzyl-1-piperazinyl)phenyl)-1,1,1-trifluoro-2-propanol (355 mg, 0.781 mmol) and 10% Pd/C (83 mg) in EtOH (20 mL) was placed under a hydrogen atmosphere (1 atm) 16 h. The mixture was filtered through a pad of Celite® (diatomaceous earth) and then concentrated onto silica gel and purified via column chromatography (40 g, 0 to 10% MeOH in CH$_2$Cl$_2$) to give 2-(4-((2S)-2-benzyl-1-piperazinyl)phenyl)-1,1,1-trifluoro-2-propanol (0.210 g).

Step 3: 2-(4-((2S)-2-benzyl-4-((5-bromo-2-thiophenyl)sulfonyl)-1-piperazinyl)phenyl)-1,1,1-trifluoro-2-propanol The 2-(4-((2S)-2-benzyl-1-piperazinyl)phenyl)-1,1,1-trifluoro-2-propanol (147 mg, 0.404 mmol) was dissolved in CH$_2$Cl$_2$ (10 mL) was cooled to 0° C. To this solution was added triethylamine (124 μL, 0.889 mmol) followed by 5-bromothiophene-2-sulfonyl chloride (127 mg, 0.485 mmol, Sigma-Aldrich, St. Louis, Mo.). The mixture was allowed to slowly warm to room temperature and stirred for 2 h. The mixture was concentrated and absorbed onto silica gel. The crude material was purified via column chromatography (40 g silica gel, 0 to 10% MeOH in $CH_2Cl_2$) to give 2-(4-((2S)-2-benzyl-4-((5-bromo-2-thiophenyl)sulfonyl)-1-piperazinyl)phenyl)-1,1,1-trifluoro-2-propanol (105 mg).

Step 4: 2-(4-((2S)-4-((5-amino-2-thiophenyl)sulfonyl)-2-benzyl-1-piperazinyl)phenyl)-1,1,1-trifluoro-2-propanol In a 25-mL pressure vessel 2-(4-((2S)-2-benzyl-4-((5-bromo-2-thiophenyl)sulfonyl)-1-piperazinyl)phenyl)-1,1,1-trifluoro-2-propanol (105 mg, 0.178 mmol), $Pd(OAc)_2$ (1.999 mg, 8.91 μmol, Strem Chemicals, Newburyport, Mass.), (9,9-dimethyl-9H-xanthene-4,5-diyl)bis(diphenylphosphine) (XantPhos) (5.15 mg, 8.91 μmol, Strem Chemicals, Newburyport, Mass.), sodium tert-butoxide (35.9 mg, 0.374 mmol), and diphenylmethanimine (38.0 mg, 0.214 mmol, Sigma-Aldrich, St. Louis, Mo.) were combined and suspended in toluene (5 mL). The mixture was purged with $N_2$ for 5 min and then heated at 100° C. for 16 h. The solution was diluted with EtOAc (20 mL), the layers were separated. The organic layer was washed with water (10 mL) and brine (10 mL). The combined organic extracts were dried over $MgSO_4$, filtered, and concentrated. The crude material was absorbed onto silica gel, and purified via column chromatography (40 g silica gel, 0 to 10% MeOH in $CH_2Cl_2$) to give the imine intermediate.

To this imine was added 10 mL of THF and 2 mL of 4 M HCl in dioxane (10 mL). After stirring at room temperature for 2 h, the solution was diluted with EtOAc (20 mL) and saturated aqueous $NaHCO_3$. The basic layer was extracted with 2×EtOAc. The combined organic extracts was dried over $MgSO_4$, filtered, and concentrated to give 2-(4-((2S)-4-((5-amino-2-thiophenyl)sulfonyl)-2-benzyl-1-piperazinyl)phenyl)-1,1,1-trifluoro-2-propanol (22 mg) as a mixture of two isomers:

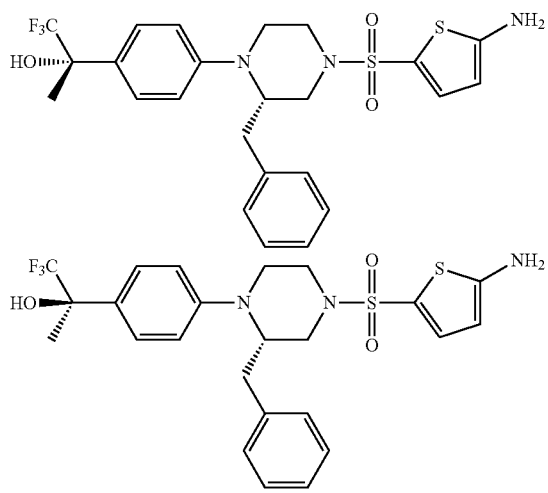

(2R)-2-(4-((2S)-4-((5-amino-2-thiophenyl)sulfonyl)-2-benzyl-1-piperazinyl)phenyl)-1,1,1-trifluoro-2-propanol; (2S)-2-(4-((2S)-4-((5-amino-2-thiophenyl)sulfonyl)-2-benzyl-1-piperazinyl)phenyl)-1,1,1-trifluoro-2-propanol.

$^1$H NMR (400 MHz, $CDCl_3$) δ=7.50 (d, J=8.8 Hz, 2H), 7.35-7.28 (m, 2H), 7.27-7.19 (m, 3H), 7.16 (d, J=4.1 Hz, 1H), 6.92 (d, J=8.8 Hz, 2H), 6.11 (d, J=4.1 Hz, 1H), 4.24 (s, 2H), 3.98 (d, J=8.8 Hz, 1H), 3.81 (d, J=10.8 Hz, 1H), 3.66 (d, J=11.3 Hz, 1H), 3.52-3.43 (m, 1H), 3.36 (m, 1H), 3.22-3.12 (m, 1H), 2.71-2.50 (m, 3H), 1.77 (s, 3H). m/z (ESI, +ve ion) 526.6 (M+H)$^+$. GK-GKRP $IC_{50}$ (Binding)=0.250 μM; GK-GKRP $EC_{50}$ (LC MS/MS-2)=0.146 μM.

Example 137

2-(2-((2S)-4-((5-amino-2-thiophenyl)sulfonyl)-2-methyl-1-piperazinyl)-5-pyrimidinyl)-1,1,1-trifluoro-2-propanol

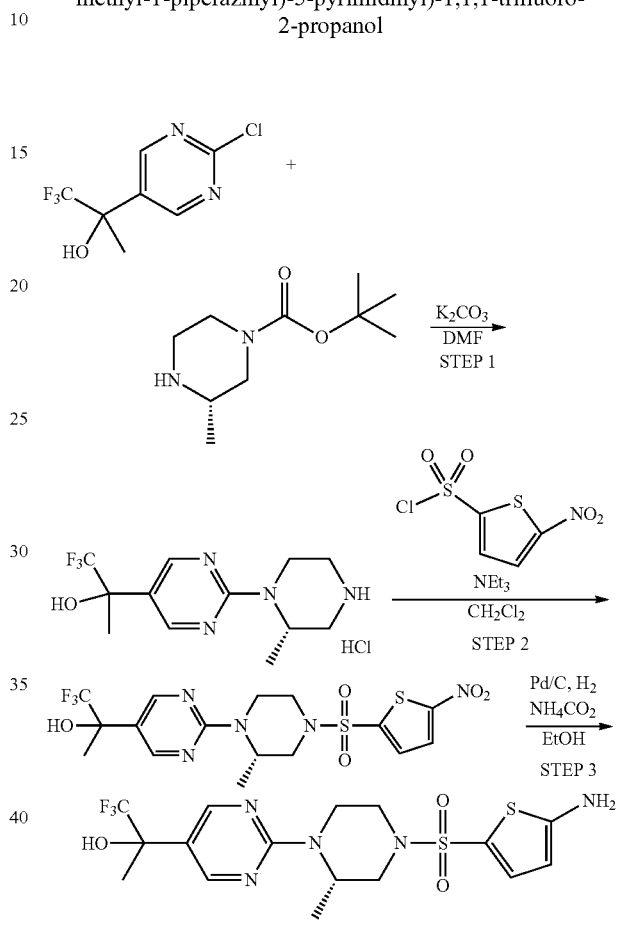

Step 1: 1,1,1-trifluoro-2-(2-((2S)-2-methyl-1-piperazinyl)-5-pyrimidinyl)-2-propanol hydrochloride A mixture of (S)-tert-butyl 3-methylpiperazine-1-carboxylate (250 mg, 1.25 mmol, CNH Technologies, Woburn, Mass.), 2-(2-chloropyrimidin-5-yl)-1,1,1-trifluoropropan-2-ol (339 mg, 1.50 mmol, Intermediate E), and potassium carbonate (362 mg, 2.62 mmol) in DMF (10 mL) was stirred at 100° C. for 16 h. The mixture was diluted with water (20 mL) and EtOAc (30 mL). The layers were separated and the organics were washed with water (20 mL) and brine (20 mL). The combined organic extracts were dried over $MgSO_4$, filtered, and concentrated. The crude material was absorbed onto silica gel and purified via column chromatography (40 g silica gel, 0 to 100% EtOAc in hexanes) to give the Boc-protected product. To this crude intermediate was added 12 mL of EtOAc and 3 mL of 4 M HCl in dioxane. The mixture was heated at reflux for 16 h. The precipitate that had formed was collected by filtration, washed with EtOAc, and to 1,1,1-trifluoro-2-(2-((2S)-2-methyl-1-piperazinyl)-5-pyrimidinyl)-2-propanol hydrochloride (95 mg).

Step 2: 2-(2-((2S)-4-((5-nitro-2-thiophenyl)sulfonyl)-2-methyl-1-piperazinyl)-5-pyrimidinyl)-1,1,1-trifluoro-2-propanol The 1,1,1-trifluoro-2-(2-((2S)-2-methyl-1-piperazinyl)-5-pyrimidinyl)-2-propanol hydrochloride (95 mg, 0.291 mmol) was dissolved in CH$_2$Cl$_2$ (15 mL) was chilled to 0° C. To this solution was added triethylamine (101 µL, 0.727 mmol) followed by 5-nitrothiophene-2-sulfonyl chloride (66.2 mg, 0.291 mmol, Enamine Building Blocks, Kiev, Ukraine). The mixture was warmed slowly to room temperature and stirred for 2 h. Afterwards, the mixture was concentrated onto silica gel and then purified via column chromatography (24 g silica gel, 0 to 10% MeOH in CH$_2$Cl$_2$) to give racemic 2-(2-((2S)-4-((5-nitro-2-thiophenyl)sulfonyl)-2-methyl-1-piperazinyl)-5-pyrimidinyl)-1,1,1-trifluoro-2-propanol (108 mg).

Step 3: 2-(2-((2S)-4-((5-amino-2-thiophenyl)sulfonyl)-2-methyl-1-piperazinyl)-5-pyrimidinyl)-1,1,1-trifluoro-2-propanol In a 50-mL round bottomed flask, a mixture of 2-(2-((2S)-4-((5-nitro-2-thiophenyl)sulfonyl)-2-methyl-1-piperazinyl)-5-pyrimidinyl)-1,1,1-trifluoro-2-propanol (108 mg, 0.224 mmol), ammonium formate (30.1 mg, 0.478 mmol, Sigma-Aldrich, St. Louis, Mo.), and 10% Pd/C (25.4 mg, 0.024 mmol) in EtOH (10 mL) was stirred under an atmosphere of H$_2$ (1 atm) for 18 h. Afterwards, the mixture was filtered through a plug of Celite and the filtrate was concentrated to give the crude product. The crude product was dissolved in CH$_2$Cl$_2$ and filtered through a plug of silica gel. The filtrate was concentrated to give 2-(2-((2S)-4-((5-amino-2-thiophenyl)sulfonyl)-2-methyl-1-piperazinyl)-5-pyrimidinyl)-1,1,1-trifluoro-2-propanol (23 mg) as a mixture of two isomers.

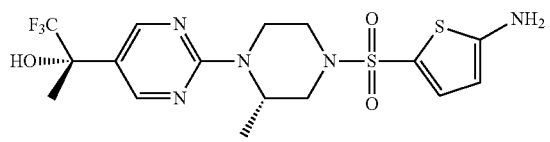

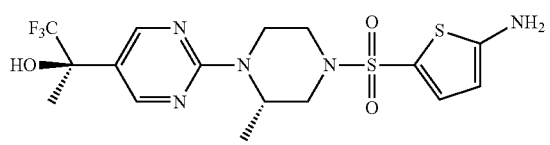

(2S)-2-(2-((2S)-4-((5-amino-2-thiophenyl)sulfonyl)-2-methyl-1-piperazinyl)-5-pyrimidinyl)-1,1,1-trifluoro-2-propanol and (2S)-2-(2-((2S)-4-((5-amino-2-thiophenyl)sulfonyl)-2-methyl-1-piperazinyl)-5-pyrimidinyl)-1,1,1-trifluoro-2-propanol.

$^1$H NMR (400 MHz, CDCl$_3$) δ=8.45 (s, 2H), 7.17 (d, J=3.9 Hz, 1H), 6.11 (d, J=4.1 Hz, 1H), 5.08 (m, 1H), 4.68 (d, J=13.5 Hz, 1H), 4.24 (s, 2H), 3.78-3.68 (m, 1H), 3.57 (d, J=11.2 Hz, 1H), 3.38-3.24 (m, 1H), 2.63 (dd, J=3.7, 11.3 Hz, 1H), 2.47 (dt, J=3.3, 11.7 Hz, 1H), 1.74 (s, 3H), 1.34 (d, J=6.8 Hz, 3H). m/z (ESI, +ve ion) 452.5 (M+H)$^+$. GK-GKRP IC$_{50}$ (Binding)=0.281 µM; GK-GKRP EC$_{50}$ (LC MS/MS-2)=0.658 µM.

Example 138

2-(4-(4-((4-amino-2-thiophenyl)sulfonyl)-1-piperazinyl)phenyl)-1,1,1,3,3,3-hexafluoro-2-propanol

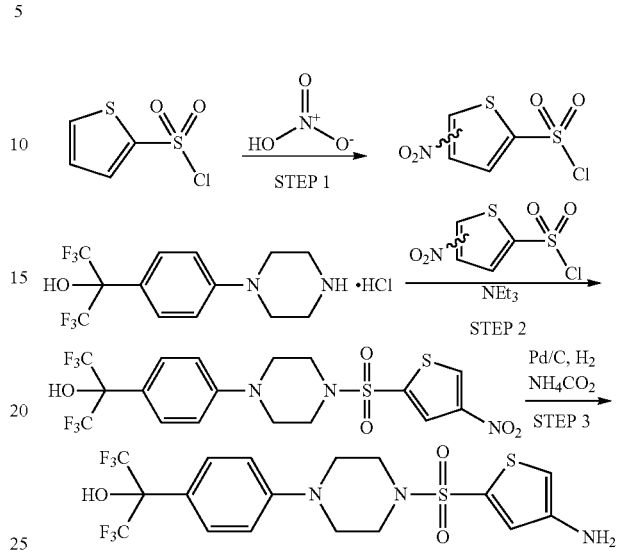

Step 1: 4-nitrothiophene-2-sulfonyl chloride

To a 150-mL round bottomed flask containing fuming nitric acid (100 mL) was slowly added a solution of thiophene-2-sulfonyl chloride (2.20 g, 12.04 mmol, Sigma-Aldrich, St. Louis, Mo.) in CH$_2$Cl$_2$ (30 mL) at 0° C. The mixture was then gradually warmed to 40° C. then stirred for 2 h at that temperature. The mixture was poured over ice and the mixture was extracted with CH$_2$Cl$_2$. The combined organics was dried over MgSO$_4$, filtered, and concentrated give a mixture of 4-nitrothiophene-2-sulfonyl chloride and 5-nitrothiophene-2-sulfonyl chloride (2.05 g) in a 2:1 ratio.

Step 2: 2-(4-(4-((4-nitro-2-thiophenyl)sulfonyl)-1-piperazinyl)phenyl)-1,1,1,3,3,3-hexafluoro-2-propanol The 1,1,1,3,3,3-hexafluoro-2-(4-(1-piperazinyl)phenyl)-2-propanol hydrochloride (306 mg, 0.84 mmol, Example 91, Step 1) was dissolved in CH$_2$Cl$_2$ (20 mL) and the solution was chilled to 0° C. To this solution was added triethylamine (292 µL, 2.10 mmol) followed by 4-nitrothiophene-2-sulfonyl chloride (210 mg, 0.923 mmol). The mixture was allowed to warm to room temperature and stirred for 2 h. Afterwards, the mixture was filtered and concentrated, the filtrate was purified via reverse-phase preparative HPLC using a Phenomenex Gemini C$_{18}$ column (150×30 mm, 10 µm) eluting with 0.1% TFA in CH$_3$CN/H$_2$O (5% to 100% over 15 min) to give 2-(4-(4-((4-nitro-2-thiophenyl)sulfonyl)-1-piperazinyl)phenyl)-1,1,1,3,3,3-hexafluoro-2-propanol (86 mg).

Step 3: 2-(4-(4-((4-amino-2-thiophenyl)sulfonyl)-1-piperazinyl)phenyl)-1,1,1,3,3,3-hexafluoro-2-propanol In a 50 mL round bottomed flask a mixture of 2-(4-(4-((4-nitro-2-thiophenyl)sulfonyl)-1-piperazinyl)phenyl)-1,1,1,3,3,3-hexafluoro-2-propanol (80 mg, 0.154 mmol), ammonium formate (48.6 mg, 0.770 mmol, Sigma-Aldrich, St. Louis, Mo.), and 10% Pd/C (1.639 mg, 0.015 mmol) in EtOH (10 mL) was stirring under an atmosphere of H$_2$ (1 atm) for 18 h.

Afterwards, the reaction mixture was filtered through a plug of Celite® (diatomaceous earth), and the filtrate was concentrated to give the crude product. The crude product was dissolved in CH₂Cl₂ and filtered through a plug of silica gel. The filtrate was concentrated to give 2-(4-(4-((4-amino-2-thiophenyl)sulfonyl)-1-piperazinyl)phenyl)-1,1,1,3,3,3-hexafluoro-2-propanol (23 mg).

¹H NMR (400 MHz, CD₃OD) δ=7.58 (d, J=8.8 Hz, 2H), 7.19 (d, J=2.0 Hz, 1H), 7.03 (d, J=9.0 Hz, 2H), 6.60 (d, J=1.8 Hz, 1H), 3.40-3.35 (m, 4H), 3.23-3.17 (m, 4H). m/z (ESI, +ve ion) 504.5 (M+H)⁺. GK-GKRP IC₅₀ (Binding)=0.310 μM; GK-GKRP EC₅₀ (LC MS/MS-2)=0.272 μM.

Example 139

2-(4-((2S)-4-((5-amino-2-thiophenyl)sulfonyl)-2-methyl-1-piperazinyl)phenyl)-1,1,1-trifluoro-2-propanol

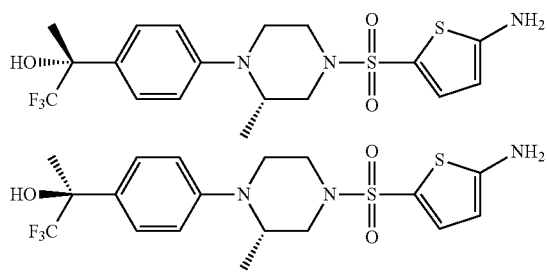

Following the procedure reported for Example 88, 1,1,1-trifluoro-2-(4-((2S)-2-methyl-1-piperazinyl)phenyl)-2-propanol hydrochloride (Example 30, Step 2) delivered 2-(4-((2S)-4-((5-amino-2-thiophenyl)sulfonyl)-2-methyl-1-piperazinyl)phenyl)-1,1,1-trifluoro-2-propanol (43 mg) as a mixture of two isomers after column chromatography on silica gel (0-70% EtOAc in hexanes)

(2R)-2-(4-((2S)-4-((5-amino-2-thiophenyl)sulfonyl)-2-methyl-1-piperazinyl)phenyl)-1,1,1-trifluoro-2-propanol and (2R)-2-(4-((2S)-4-((5-amino-2-thiophenyl)sulfonyl)-2-methyl-1-piperazinyl)phenyl)-1,1,1-trifluoro-2-propanol.

¹H NMR (400 MHz, CDCl₃) δ=7.44 (d, J=8.4 Hz, 2H), 7.20 (d, J=3.9 Hz, 1H), 6.86 (d, J=8.8 Hz, 2H), 6.14 (d, J=4.1 Hz, 1H), 4.27 (s, 2H), 4.02-3.94 (m, 1H), 3.60 (m, 1H), 3.42-3.30 (m, 2H), 3.28-3.19 (m, 1H), 2.92 (dd, J=3.2, 11.1 Hz, 1H), 2.76 (dt, J=3.7, 10.7 Hz, 1H), 1.75 (s, 3H), 1.14 (d, J=6.7 Hz, 3H). m/z (ESI, +ve ion) 450.5 (M+H)⁺. GK-GKRP IC₅₀ (Binding)=0.630 μM; GK-GKRP EC₅₀ (LC MS/MS-2)=0.370 μM.

Example 140

9-(((2S)-4-(2-thiophenylsulfonyl)-1-(4-(2,2,2-trifluoro-1-hydroxy-1-methylethyl)phenyl)-2-piperazinyl)methyl)-9-azabicyclo[3.3.1]nonan-3-one

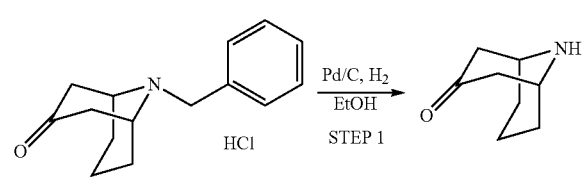

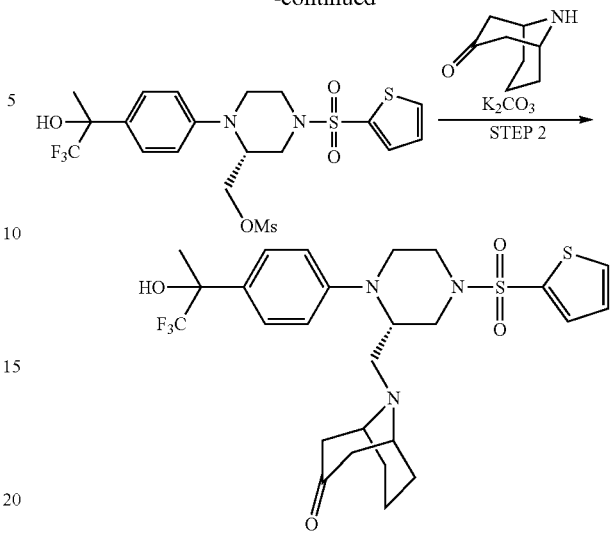

Step 1: 9-azabicyclo[3.3.1]nonan-3-one

A mixture of 9-benzyl-9-azabicyclo[3.3.1]nonan-3-one hydrochloride (295 mg, 1.11 mmol, J & W PharmLab, Levittown, Pa.), a five drops of formic acid, and 10% Pd/C (27.4 mg, 0.257 mmol) in EtOH (20 mL) was subjected to a hydrogen atmosphere (50 psi; 344.7 kilopascal) in a Parr shaker apparatus for 18 h. The mixture was filtered through a pad of Celite® (diatomaceous earth) and then concentrated to give crude 9-azabicyclo[3.3.1]nonan-3-one as the formate salt (180 mg).

Step 2: 9-(((2S)-4-(2-thiophenylsulfonyl)-1-(4-(2,2,2-trifluoro-1-hydroxy-1-methylethyl)phenyl)-2-piperazinyl)methyl)-9-azabicyclo[3.3.1]nonan-3-one This analog was prepared following the procedure outlined for Example 84. The reaction of ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) and crude 9-azabicyclo[3.3.1]nonan-3-one (with one additional equiv of K₂CO₃) delivered 9-(((2S)-4-(2-thiophenylsulfonyl)-1-(4-(2,2,2-trifluoro-1-hydroxy-1-methylethyl)phenyl)-2-piperazinyl)methyl)-9-azabicyclo[3.3.1]nonan-3-one as a mixture of two isomers after purification by reverse-phase preparative HPLC using a Phenomenex Gemini C₁₈ column (150×30 mm, 10 μm) eluting with 0.1% TFA in CH₃CN/H₂O (5% to 100% over 15 min.

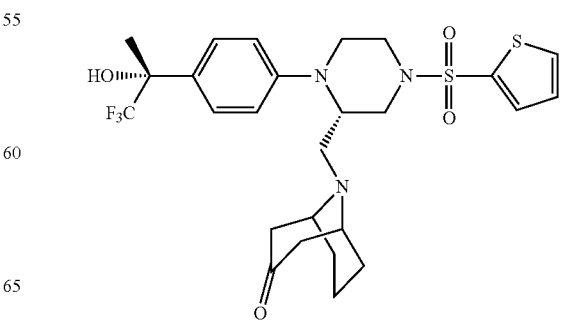

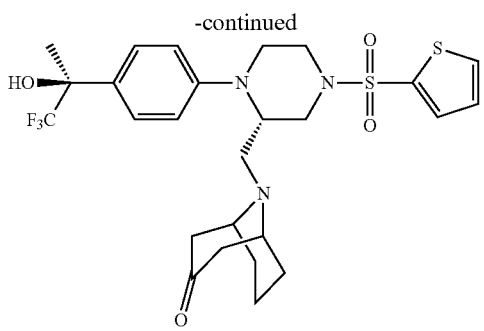

¹H NMR (400 MHz, CDCl₃) δ 7.66 (d, J=5.0 Hz, 1H), 7.59 (m, 1H), 7.54 (d, J=8.8 Hz, 2H), 7.18 (m, 1H), 6.82 (d, J=9.0 Hz, 2H), 4.14 (d, J=11.2 Hz, 1H), 3.91 (m, 1H), 3.86 (m, 2H), 3.48 (m, 1H), 3.27 (m, 3H), 2.95 (m, 1H), 2.73 (m, 1H), 2.62 (m, 2H), 2.48 (m, 2H), 2.34 (d, J=2.9 Hz, 1H), 2.19 (m, 2H), 1.77 (m, 2H), 1.74 (s, 3H), 1.45 (m, 2H). m/z (ESI, +ve ion) 572.7 (M+H)⁺. GK-GKRP IC₅₀ (Binding)=0.007 μM; GK-GKRP EC₅₀ (LC MS/MS-2)=0.015 μM.

Example 141

9-(((2S)-4-(2-thiophenylsulfonyl)-1-(4-(2,2,2-trifluoro-1-hydroxy-1-methylethyl)phenyl)-2-piperazinyl)methyl)-9-azabicyclo[3.3.1]nonan-3-ol (endo)

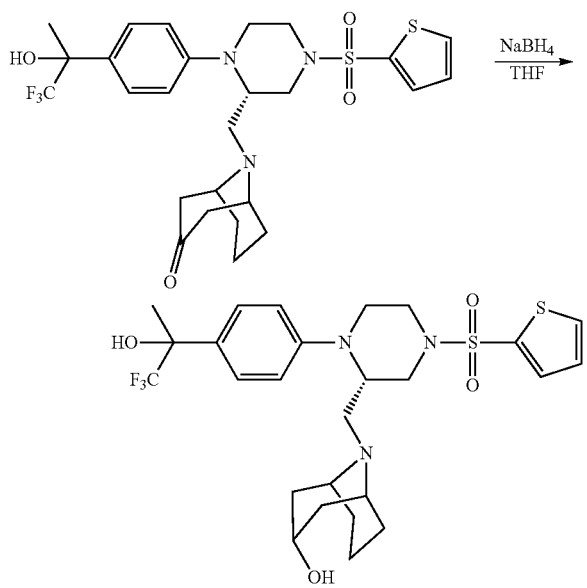

To a solution of racemic 9-(((2S)-4-(2-thiophenylsulfonyl)-1-(4-(2,2,2-trifluoro-1-hydroxy-1-methylethyl)phenyl)-2-piperazinyl)methyl)-9-azabicyclo[331]nonan-3-one (81 mg, 0.142 mmol, Example 140) in 1 mL of THF and 0.3 mL of MeOH was added sodium borohydride (10.72 mg, 0.284 mmol, Sigma-Aldrich, St. Louis, Mo.). The mixture was allowed to gradually warm to room temperature and stirred for 16 h. The crude material was then diluted with EtOAc (10 mL) and water (10 mL). The organic layer was separated and the extracts were washed with water (10 mL) and brine (10 mL). The combined organic extracts were dried over MgSO₄, filtered, and concentrated. The crude material was by purified via reverse-phase preparative HPLC using a Phenomenex Gemini C₁₈ column (150×30 mm, 10 μm) eluting with 0.1% TFA in CH₃CN/H₂O (5% to 100% over 15 min) to give 9-(((2S)-4-(2-thiophenylsulfonyl)-1-(4-(2,2,2-trifluoro-1-hydroxy-1-methylethyl)phenyl)-2-piperazinyl)methyl)-9-azabicyclo[3.3.1]nonan-3-ol (22 mg) as a mixture of two isomers:

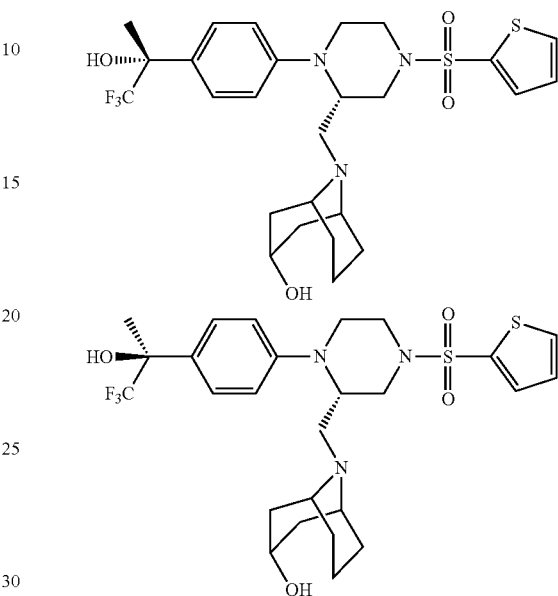

9-(((2S)-4-(2-thiophenylsulfonyl)-1-(4-((1S)-2,2,2-trifluoro-1-hydroxy-1-methylethyl)phenyl)-2-piperazinyl)methyl)-9-azabicyclo[3.3.1]nonan-3-ol (endo) and 9-(((2S)-4-(2-thiophenylsulfonyl)-1-(4-((1R)-2,2,2-trifluoro-1-hydroxy-1-methylethyl)phenyl)-2-piperazinyl)methyl)-9-azabicyclo[3.3.1]nonan-3-ol (endo).

¹H NMR (400 MHz, CDCl₃) δ 7.64 (d, J=5.0 Hz, 1H), 7.58 (m, 1H), 7.42 (d, J=8.6 Hz, 2H), 7.17 (m, 1H), 6.78 (d, J=8.8 Hz, 2H), 3.99 (m, 1H), 3.79 (m, 2H), 3.67 (m, 1H), 3.43 (m, 1H), 3.23 (m, 1H), 2.99 (m, 2H), 2.78 (m, 1H), 2.64 (m, 2H), 2.54 (m, 2H), 2.22 (m, 2H), 2.01 (m, 1H), 1.74 (s, 3H), 1.67 (d, 2H), 1.40 (m, 1H), 1.18 (m, 3H). m/z (ESI, +ve ion) 574.7 (M+H)⁺. GK-GKRP IC₅₀ (Binding)=0.011 μM; GK-GKRP EC₅₀ (LC MS/MS-2)=0.026 μM.

Example 142

3-fluoro-9-(((2S)-1-(4-(1,2,2,2-tetrafluoro-1-methylethyl)phenyl)-4-(2-thiophenylsulfonyl)-2-piperazinyl)methyl)-9-azabicyclo[3.3.1]nonane (exo)

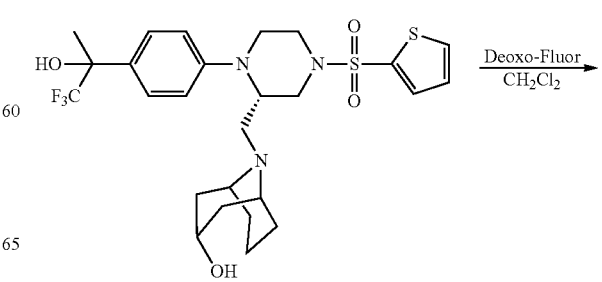

-continued

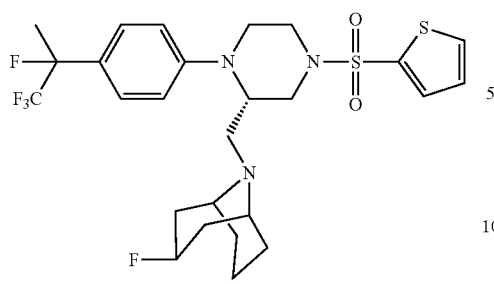

A solution of 9-(((2S)-4-(2-thiophenylsulfonyl)-1-(4-(2,2,2-trifluoro-1-hydroxy-1-methylethyl)phenyl)-2-piperazinyl)methyl)-9-azabicyclo[3.3.1]nonan-3-ol (50 mg, 0.087 mmol, Example 141) in CH$_2$Cl$_2$ was chilled to 0° C. To this solution was added Deoxo-Fluor (64.1 µl, 0.174 mmol, Sigma-Aldrich, St. Louis, Mo.) slowly via syringe. The mixture was allowed to slowly warm to room temperature and stirred for an additional 2 h. Saturated aqueous NaHCO$_3$ was added and the mixture was concentrated and the residue was purified via preparatory TLC eluting with 10% EtOAc in hexanes to yield 3-fluoro-9-(((2S)-1-(4-(1,2,2,2-tetrafluoro-1-methylethyl)phenyl)-4-(2-thiophenylsulfonyl)-2-piperazinyl)methyl)-9-azabicyclo[3.3.1]nonane (15 mg) as a mixture of two isomers:

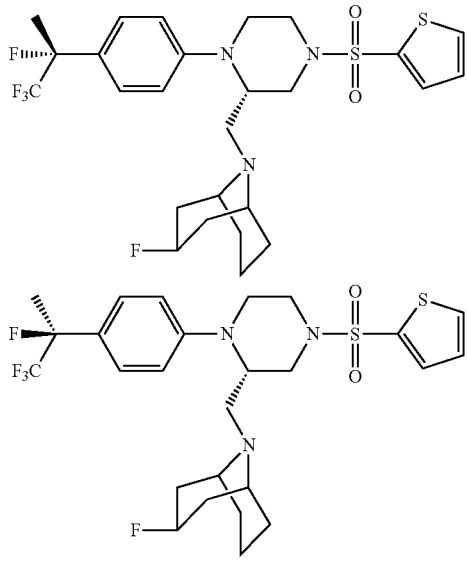

7-fluoro-9-(((2S)-1-(4-((1S)-1,2,2,2-tetrafluoro-1-methylethyl)phenyl)-4-(2-thiophenylsulfonyl)-2-piperazinyl)methyl)-3-oxa-9-azabicyclo[3.3.1]nonane (exo); 7-fluoro-9-(((2S)-1-(4-((1S)-1,2,2,2-tetrafluoro-1-methylethyl)phenyl)-4-(2-thiophenylsulfonyl)-2-piperazinyl)methyl)-3-oxa-9-azabicyclo[3.3.1]nonane (exo).

$^1$H NMR (400 MHz, CDCl$_3$) δ=7.65 (d, J=4.7 Hz, 1H), 7.59 (m, 1H), 7.43 (d, J=8.4 Hz, 2H), 7.17 (m, 1H), 6.82-6.76 (m, 2H), 4.11 (d, J=11.0 Hz, 1H), 3.92-3.71 (m, 3H), 3.69-3.61 (m, 2H), 3.44 (d, J=12.9 Hz, 1H), 3.30-3.19 (m, 1H), 2.91-2.74 (m, 2H), 2.69-2.51 (m, 3H), 1.98 (m, 1H), 1.94-1.84 (m, 1H), 1.84-1.77 (m, 1H), 1.74 (s, 3H), 1.73-1.69 (m, 1H). 1.58 (m, 3H), 1.27 (m, 2H). m/z (ESI, +ve ion) 580.65 (M+H)$^+$. GK-GKRP IC$_{50}$ (Binding)=0.047 µM; GK-GKRP EC$_{50}$ (LC MS/MS-2)=0.189 µM.

Example 143

2-(4-((2S)-2-((3-ethyl-4-morpholinyl)methyl)-4-(2-thiophenylsulfonyl)-1-piperazinyl)phenyl)-1,1,1-trifluoro-2-propanol

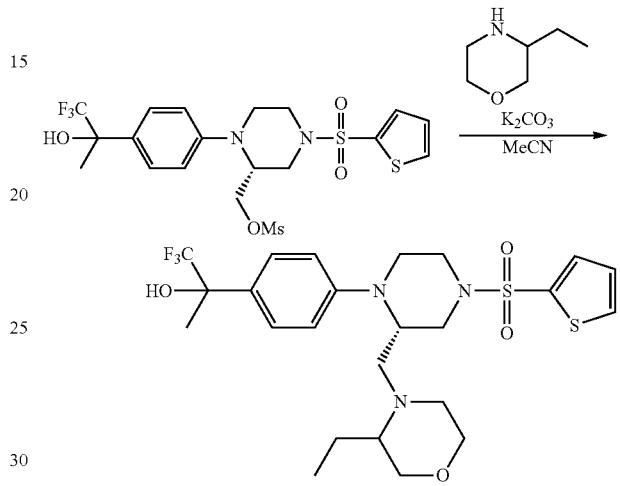

A sealable vial was charged with ((2R)-4-(2-thiophenylsulfonyl)-1-(4-(2,2,2-trifluoro-1-hydroxy-1-methylethyl)phenyl)-2-piperazinyl)methyl methanesulfonate (100 mg, 0.189 mmol, Intermediate B), 3-ethylmorpholine (43.6 mg, 0.378 mmol, ChemBridge Corporation, San Diego, Calif.), potassium carbonate (52.3 mg, 0.378 mmol), and 4 mL of MeCN. The vial was sealed and heated to 150° C. for 90 min. Afterwards, the reaction mixture was filtered and the filtrate was concentrated. The crude material was purified via preparatory TLC using 5% MeOH in CH$_2$Cl$_2$ eluent to yield 2-(4-((2S)-2-((3-ethyl-4-morpholinyl)methyl)-4-(2-thiophenylsulfonyl)-1-piperazinyl)phenyl)-1,1,1-trifluoro-2-propanol (33 mg) as a mixture of four isomers.

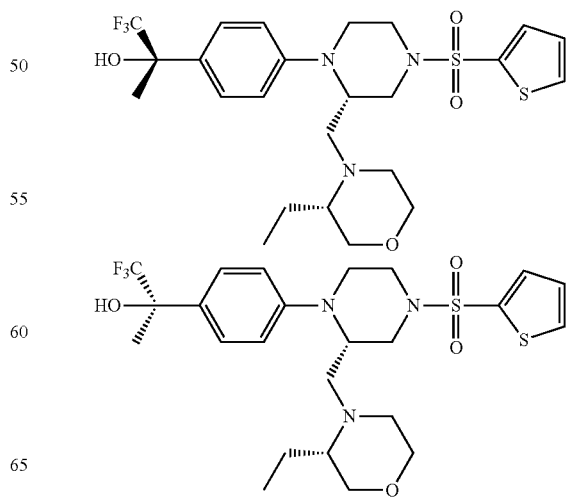

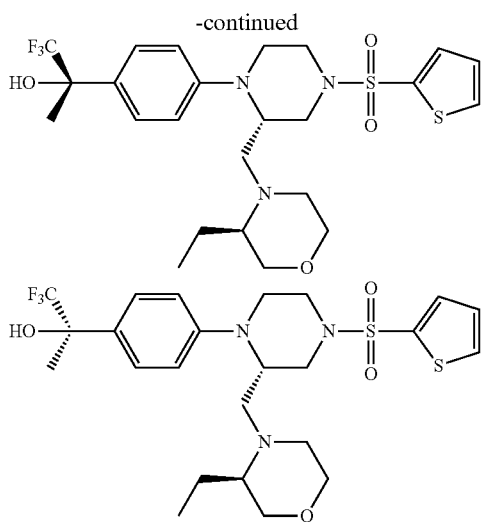

(2S)-2-(4-((2S)-2-(((3R)-3-ethyl-4-morpholinyl)methyl)-4-(2-thiophenylsulfonyl)-1-piperazinyl)phenyl)-1,1,1-trifluoro-2-propanol, (2S)-2-(4-((2S)-2-(((3S)-3-ethyl-4-morpholinyl)methyl)-4-(2-thiophenylsulfonyl)-1-piperazinyl)phenyl)-1,1,1-trifluoro-2-propanol, (2R)-2-(4-((2S)-2-(((3S)-3-ethyl-4-morpholinyl)methyl)-4-(2-thiophenylsulfonyl)-1-piperazinyl)phenyl)-1,1,1-trifluoro-2-propanol, (2R)-2-(4-((2S)-2-(((3R)-3-ethyl-4-morpholinyl)methyl)-4-(2-thiophenylsulfonyl)-1-piperazinyl)phenyl)-1,1,1-trifluoro-2-propanol.

$^1$H NMR (400 MHz, CDCl$_3$) δ=7.65 (dd, J=1.2, 5.1 Hz, 1H), 7.58 (m, 1H), 7.45-7.39 (m, 2H), 7.17 (m, 1H), 6.81 (d, J=8.6 Hz, 2H), 4.10-3.95 (m, 1H), 3.91-3.73 (m, 2H), 3.72-3.52 (m, 3H), 3.44-3.30 (m, 2H), 3.30-3.09 (m, 1H), 2.85-2.67 (m, 1H), 2.66-2.45 (m, 2H), 2.45-2.26 (m, 2H), 2.25-2.04 (m, 1H), 1.74 (s, 3H), 1.63 (d, J=3.1 Hz, 1H), 1.48-1.35 (m, 1H), 1.32-1.23 (m, 1H), 0.89-0.75 (m, 3H). m/z (ESI, +ve ion) 548.7 (M+H)$^+$. GK-GKRP IC$_{50}$ (Binding)=0.080 μM; GK-GKRP EC$_{50}$ (LC MS/MS-2)=0.036 μM.

Example 144

1-(((2S)-4-(2-thiophenylsulfonyl)-1-(4-(2,2,2-trifluoro-1-hydroxy-1-methylethyl)phenyl)-2-piperazinyl)methyl)-4-piperidinone

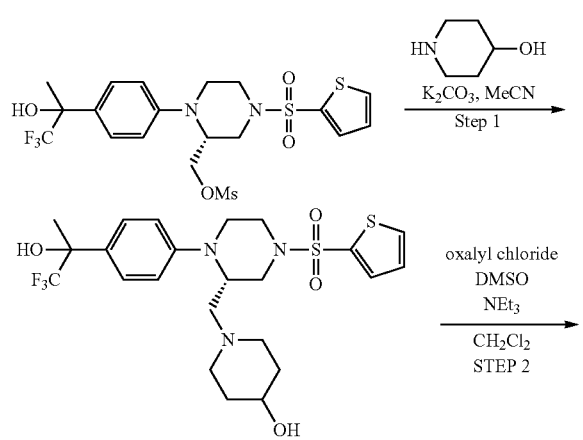

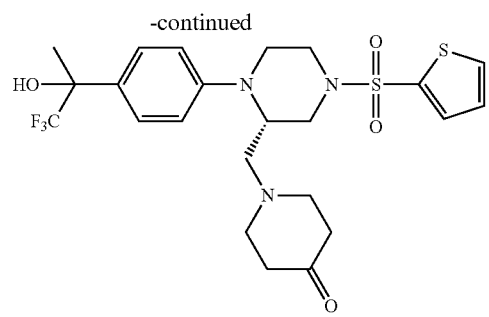

Step 1: 1-(((2S)-4-(2-thiophenylsulfonyl)-1-(4-(2,2,2-trifluoro-1-hydroxy-1-methylethyl)phenyl)-2-piperazinyl)methyl)-4-piperidinol This compound was synthesized following the procedure described for Example 143. The reaction of 4-piperidinol (Sigma-Aldrich, St. Louis, Mo.) and ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) delivered 1-(((2S)-4-(2-thiophenylsulfonyl)-1-(4-(2,2,2-trifluoro-1-hydroxy-1-methylethyl)phenyl)-2-piperazinyl)methyl)-4-piperidinol as a mixture of two isomers after column chromatography on silica gel (5 to 8% MeOH in CH$_2$Cl$_2$)

Step 2: 1-(((2S)-4-(2-thiophenylsulfonyl)-1-(4-(2,2,2-trifluoro-1-hydroxy-1-methylethyl)phenyl)-2-piperazinyl)methyl)-4-piperidinone A solution of 2.0 M solution of oxalyl chloride in CH$_2$Cl$_2$ (162 μL, 0.323 mmol, Sigma-Aldrich, St. Louis, Mo.) was diluted with CH$_2$Cl$_2$ and then chilled to −78° C. To this solution was added DMSO (45.9 μL, 0.647 mmol). The mixture was stirred for 30 min, and then a solution of 1-(((2S)-4-(2-thiophenylsulfonyl)-1-(4-(2,2,2-trifluoro-1-hydroxy-1-methylethyl)phenyl)-2-piperazinyl)methyl)-4-piperidinol (115 mg, 0.216 mmol) in CH$_2$Cl$_2$ was added to slowly to the mixture. The reaction was stirred for 1 h at −78° C. and then triethylamine (150 μl, 1.078 mmol) was added. Afterwards, the mixture was stirred for 15 min and allowed to slowly warm to room temperature and stirred for additional 4 h. Saturated aqueous NaHCO$_3$ was added and the mixture was concentrated. The crude material was absorbed onto silica gel and purified via column chromatography (40 g silica gel, 0 to 10% MeOH in CH$_2$Cl$_2$) to give 1-(((2S)-4-(2-thiophenylsulfonyl)-1-(4-(2,2,2-trifluoro-1-hydroxy-1-methylethyl)phenyl)-2-piperazinyl)methyl)-4-piperidinone (40 mg) as a mixture of two isomers.

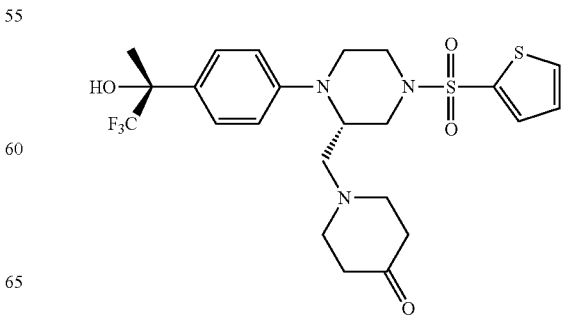

303

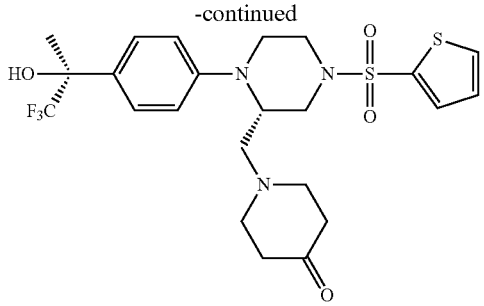

1-(((2S)-4-(2-thiophenylsulfonyl)-1-(4-((1R)-2,2,2-trifluoro-1-hydroxy-1-methylethyl)phenyl)-2-piperazinyl)methyl)-4-piperidinone and 1-(((2S)-4-(2-thiophenylsulfonyl)-1-(4-((1S)-2,2,2-trifluoro-1-hydroxy-1-methylethyl)phenyl)-2-piperazinyl)methyl)-4-piperidinone.

$^1$H NMR (400 MHz, CDCl$_3$) δ=7.65 (dd, J=0.8, 5.1 Hz, 1H), 7.59 (dd, J=0.9, 3.6 Hz, 1H), 7.43 (d, J=8.8 Hz, 2H), 7.18 (dd, J=4.1, 4.7 Hz, 1H), 6.83 (d, J=8.8 Hz, 2H), 4.10 (m, 1H), 4.00-3.93 (m, 1H), 3.86-3.80 (m, 1H), 3.42 (m, 1H), 3.28 (dd, J=3.4, 11.8 Hz, 1H), 2.94-2.86 (m, 1H), 2.83-2.68 (m, 4H), 2.61 (dt, J=3.6, 11.4 Hz, 1H), 2.50-2.43 (m, 1H), 2.38 (m, 1H), 2.35-2.30 (m, 4H), 1.74 (s, 3H). m/z (ESI, +ve ion) 532.6 (M+H)$^+$. GK-GKRP IC$_{50}$ (Binding)=0.564 μM; GK-GKRP EC$_{50}$ (LC MS/MS-2)=0.831 μM.

Example 145

(3S)-1-(((2S)-4-(2-thiophenylsulfonyl)-1-(4-(2,2,2-trifluoro-1-hydroxy-1-methylethyl)phenyl)-2-piperazinyl)methyl)-3-piperidinol

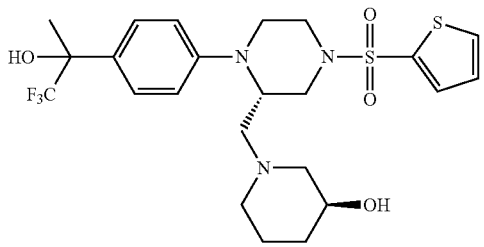 [SMILES: CC(O)(c1ccc(N2CCN(S(=O)(=O)c3cccs3)C[C@@H]2CN2CCC[C@H](O)C2)cc1)C(F)(F)F]

This compound was synthesized following the procedure described for Example 143. The reaction of 3(S)-3-piperidinol hydrochloride (Sigma-Aldrich, St. Louis, Mo.) and ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) delivered (3S)-1-(((2S)-4-(2-thiophenylsulfonyl)-1-(4-(2,2,2-trifluoro-1-hydroxy-1-methylethyl)phenyl)-2-piperazinyl)methyl)-3-piperidinol as a mixture of two isomers after column chromatography on silica gel (5 to 8% MeOH in CH$_2$Cl$_2$)

304

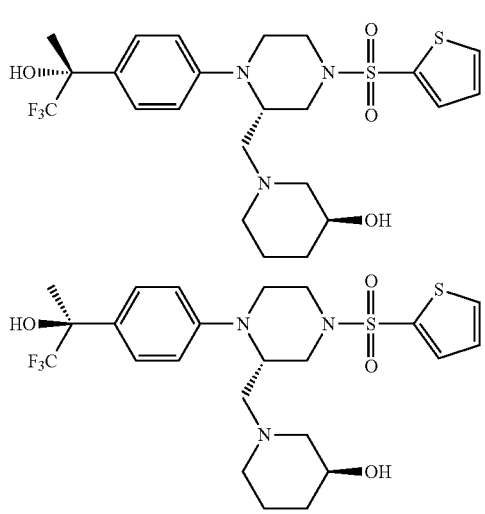

(3S)-1-(((2S)-4-(2-thiophenylsulfonyl)-1-(4-((1S)-2,2,2-trifluoro-1-hydroxy-1-methylethyl)phenyl)-2-piperazinyl)methyl)-3-piperidinol and (3S)-1-(((2S)-4-(2-thiophenylsulfonyl)-1-(4-((1R)-2,2,2-trifluoro-1-hydroxy-1-methylethyl)phenyl)-2-piperazinyl)methyl)-3-piperidinol.

$^1$H NMR (400 MHz, CDCl$_3$) δ=7.64 (d, J=5.1 Hz, 1H), 7.57 (d, J=3.7 Hz, 1H), 7.43 (d, J=8.4 Hz, 2H), 7.17 (t, J=4.3 Hz, 1H), 6.82 (d, J=8.8 Hz, 2H), 4.01 (m, 1H), 3.90 (d, J=11.2 Hz, 1H), 3.81 (d, J=11.3 Hz, 1H), 3.68 (m, 1H), 3.38 (m, 1H), 3.26 (dt, J=2.7, 11.8 Hz, 1H), 2.69 (m, 1H), 2.62-2.48 (m, 4H), 2.34 (m, 1H), 2.13 (m, 1H), 1.73 (s, 3H), 1.51 (m, 2H), 1.45-1.35 (m, 3H). m/z (ESI, +ve ion) 534.6 (M+H)$^+$. GK-GKRP IC$_{50}$ (Binding)=0.628 μM; GK-GKRP EC$_{50}$ (LC MS/MS-2)=0.880 μM.

Example 146

1,1,1,3,3,3-hexafluoro-2-(2-((2S)-2-methyl-4-(1,3-thiazol-2-ylsulfonyl)-1-piperazinyl)-5-pyrimidinyl)-2-propanol

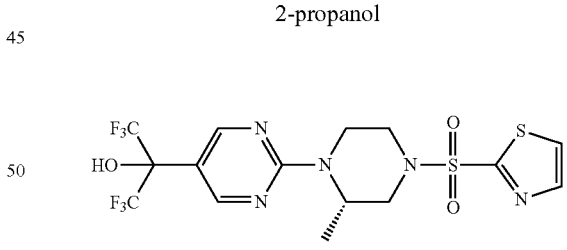

This compound was synthesized following the procedure described for Example 89, Step 3. Using that protocol, the reaction of thiazole-2-sulfonyl chloride (Bioorg. Med. Chem., 2006, 14, 6628) with 1,1,1,3,3,3-hexafluoro-2-(2-((2S)-2-methyl-1-piperazinyl)-5-pyrimidinyl)-2-propanol dihydrochloride (Example 89, Step 3) delivered 1,1,1,3,3,3-hexafluoro-2-(2-((2S)-2-methyl-4-(1,3-thiazol-2-ylsulfonyl)-1-piperazinyl)-5-pyrimidinyl)-2-propanol.

$^1$H NMR (400 MHz, CDCl$_3$) δ=8.55 (s, 2H), 7.97 (s, 1H), 7.64 (s, 1H), 5.13 (s, 1H), 4.75 (d, J=13.7 Hz, 1H), 3.98 (d, J=10.0 Hz, 1H), 3.83-3.65 (m, 1H), 3.45-3.30 (m, 1H), 2.99 (d, J=11.3 Hz, 1H), 2.91-2.77 (m, 1H), 1.37 (m, 3H). m/z (ESI, +ve ion) 492.4 (M+H)⁺. GK-GKRP IC$_{50}$ (Binding)=0.630 μM; GK-GKRP EC$_{50}$ (LC MS/MS-2)=0.867 μM.

Example 147

2-(2-((2S)-4-((2-amino-1,3-thiazol-5-yl)sulfonyl)-2-methyl-1-piperazinyl)-5-pyrimidinyl)-1,1,1,3,3,3-hexafluoro-2-propanol

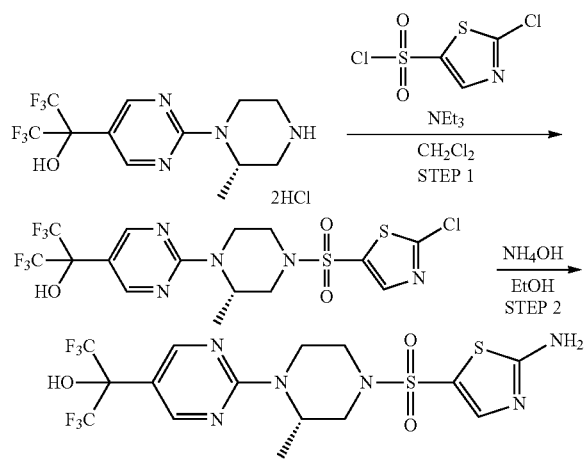

Step 1: 2-(2-((2S)-4-((2-chloro-1,3-thiazol-5-yl)sulfonyl)-2-methyl-1-piperazinyl)-5-pyrimidinyl)-1,1,1,3,3,3-hexafluoro-2-propanol This compound was synthesized following the procedure described for Example 89, Step 3. Using that protocol, the reaction of 2-chlorothiazole-5-sulfonyl chloride (Enamine Building Blocks, Kiev, Ukraine) with 1,1,1,3,3,3-hexafluoro-2-(2-((2S)-2-methyl-1-piperazinyl)-5-pyrimidinyl)-2-propanol dihydrochloride (Example 89, Step 3) delivered 2-(2-((2S)-4-((2-chloro-1,3-thiazol-5-yl)sulfonyl)-2-methyl-1-piperazinyl)-5-pyrimidinyl)-1,1,1,3,3,3-hexafluoro-2-propanol.

Step 2: 2-(2-((2S)-4-((2-amino-1,3-thiazol-5-yl)sulfonyl)-2-methyl-1-piperazinyl)-5-pyrimidinyl)-1,1,1,3,3,3-hexafluoro-2-propanol A mixture of 2-(2-((2S)-4-((2-chloro-1,3-thiazol-5-yl)sulfonyl)-2-methyl-1-piperazinyl)-5-pyrimidinyl)-1,1,1,3,3,3-hexafluoro-2-propanol (185 mg, 0.352 mmol) in 2 mL of EtOH and 2 mL of 30% NH$_4$OH was heated to 140° C. for 30 min. Afterwards, the solution was diluted with EtOAc (20 mL). The solution was transferred to a reparatory funnel and washed with water (10 mL) and brine (10 mL). The combined organics were dried over MgSO$_4$, filtered, and concentrated. The crude material was absorbed onto silica gel and purified via column chromatography (40 g silica gel, 0 to 10% MeOH in CH$_2$Cl$_2$) to give 2-(2-((2S)-4-((2-amino-1,3-thiazol-5-yl)sulfonyl)-2-methyl-1-piperazinyl)-5-pyrimidinyl)-1,1,1,3,3,3-hexafluoro-2-propanol (132 mg).

¹H NMR (400 MHz, CD$_3$OD) δ=8.46 (s, 2H), 7.35 (s, 1H), 5.01 (m, 1H), 4.63 (d, J=13.3 Hz, 1H), 3.64 (d, J=11.7 Hz, 1H), 3.48 (d, J=11.7 Hz, 1H), 3.25-3.17 (m, 1H), 2.61 (dd, J=3.8, 11.6 Hz, 1H), 2.45 (dt, J=3.5, 11.8 Hz, 1H), 1.21 (d, J=6.8 Hz, 3H). m/z (ESI, +ve ion) 507.5 (M+H)⁺. GK-GKRP IC$_{50}$ (Binding)=0.998 μM.

Example 148

1,1,1-trifluoro-2-(4-((2S)-2-(2-(3-oxetanylamino)propyl)-4-(2-thiophenylsulfonyl)-1-piperazinyl)phenyl)-2-propanol

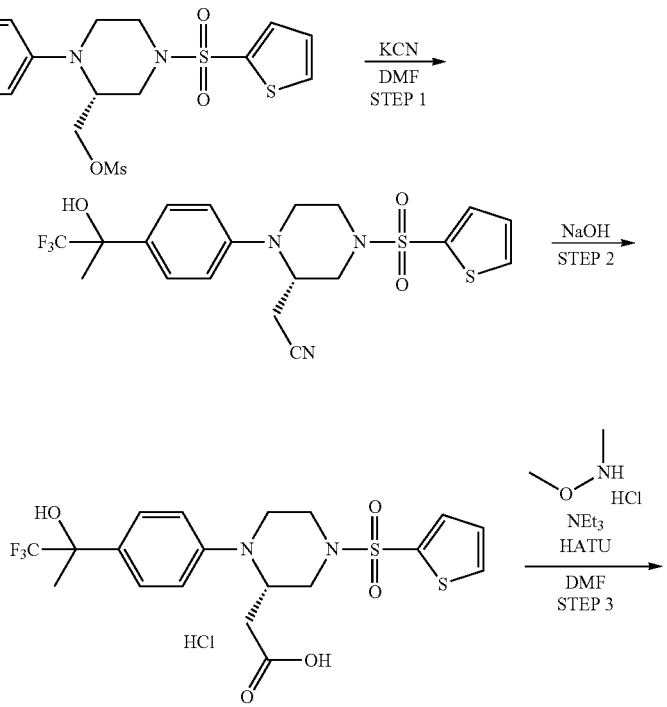

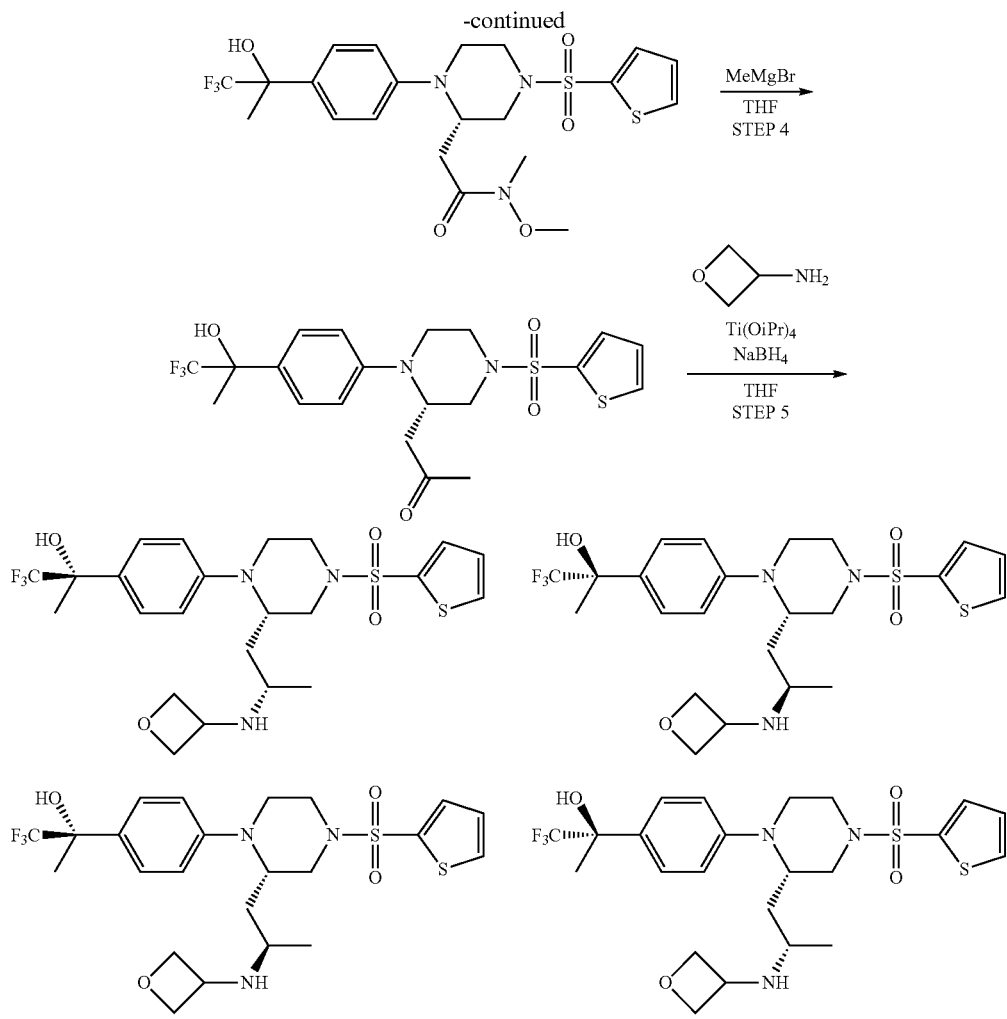

Step 1: ((2S)-4-(2-thiophenylsulfonyl)-1-(4-(2,2,2-trifluoro-1-hydroxy-1-methylethyl)phenyl)-2-piperazinyl)acetonitrile This compound was synthesized following the procedure described for Example 143. The reaction of potassium cyanide (Sigma-Aldrich, St. Louis, Mo.) and ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) (using and an extra equivalent of potassium carbonate) delivered ((2S)-4-(2-thiophenylsulfonyl)-1-(4-(2,2,2-trifluoro-1-hydroxy-1-methylethyl)phenyl)-2-piperazinyl)acetonitrile as a mixture of two isomers after column chromatography on silica gel (5 to 80% EtOAc in hexanes)

Step 2: ((2S)-4-(2-thiophenylsulfonyl)-1-(4-(2,2,2-trifluoro-1-hydroxy-1-methylethyl)phenyl)-2-piperazinyl)acetic acid hydrochloride A solution of 2-((2S)-4-(thiophen-2-ylsulfonyl)-1-(4-(1,1,1-trifluoro-2-hydroxypropan-2-yl)phenyl)piperazin-2-yl)acetonitrile (1.10 g, 2.40 mmol) and 5 M NaOH (3 mL) in 2:1 water-EtOH (10 mL) was heated to 150° C. and stirred for 1 h. Afterwards, the mixture was diluted with water (30 mL) and then neutralized with concentrated HCl to a pH of about 2 to 3. The aqueous solution was extracted with 3×EtOAc (20 mL). The organic layer was dried over is MgSO₄, filtered, and concentrated. The crude product was then dissolved in 1 N NaOH. The basic solution was extracted with 2×EtOAc. The basic aqueous solution was then neutralized with concentrated HCl and extracted with EtOAc. The combined organic extracts were dried over MgSO₄, filtered, and concentrated. The residue was dissolved in EtOAc (30 mL) and the solution was slowly acidified with 1 N HCl in diethyl ether. The resulting precipitate was collected and dried to give ((2S)-4-(2-thiophenylsulfonyl)-1-(4-(2,2,2-trifluoro-1-hydroxy-1-methylethyl)phenyl)-2-piperazinyl)acetic acid hydrochloride (0.655 g).

Step 3: N-methoxy-N-methyl-2-((2S)-4-(2-thiophenylsulfonyl)-1-(4-(2,2,2-trifluoro-1-hydroxy-1-methylethyl)phenyl)-2-piperazinyl)acetamide A solution of ((2S)-4-(2-thiophenylsulfonyl)-1-(4-(2,2,2-trifluoro-1-hydroxy-1-methylethyl)phenyl)-2-piperazinyl) acetic acid hydrochloride (1.55 g, 3.01 mmol), N,O-dimethylhydroxylamine hydrochloride (0.323 g, 3.31 mmol, Sigma-Aldrich, St. Louis, Mo.), and Hünig's base (1.05 mL, 6.02 mmol) in DMF (20 mL) was stirred at 0° C. To this mixture was added HATU (1.26 g, 3.31 mmol). The reaction was stirred for 3 h at room temperature and then diluted with EtOAc (30 mL) and water (20 mL). The organic layer was separated and then washed with water (2×20 mL) and brine (20 mL). The combined organic extracts were dried over MgSO₄, filtered, and concentrated. The crude material was absorbed onto silica gel and purified via column chromatography (80 g silica gel, 0 to 100% EtOAc in hexanes) to give N-methoxy-N-methyl-2-((2S)-4-(2-thiophenylsulfonyl)-1-(4-(2,2,2-trifluoro-1-hydroxy-1-methylethyl)phenyl)-2-piperazinyl)acetamide (1.48 g) as an orange oil.

Step 4: 1-((2S)-4-(2-thiophenylsulfonyl)-1-(4-(2,2,2-trifluoro-1-hydroxy-1-methylethyl)phenyl)-2-piperazinyl)-2-propanone A solution of N-methoxy-N-methyl-2-425)-4-(2-thiophenylsulfonyl)-1-(4-(2,2,2-trifluoro-1-hydroxy-1-methylethyl)phenyl)-2-piperazinyl)acetamide (1.05 g, 2.013 mmol) in THF was cooled to 0° C. To this was added a solution of methylmagnesium bromide (2.0 M in THF, 1.41 mL, 4.23 mmol, Sigma-Aldrich, St. Louis, Mo.). After addition was complete, the mixture was stirred at 0° C. for 30 min, and then quenched with saturated aqueous NH₄Cl. The solution was diluted with EtOAc (30 mL) and the organic layer was washed with water (20 mL) and brine (20 mL). The combined organic extracts were dried over MgSO₄, filtered, and concentrated. The crude material was absorbed onto silica gel and purified via column chromatography (80 g silica gel, 0 to 100% EtOAc in hexanes) to give 1-((2S)-4-(2-thiophenylsulfonyl)-1-(4-(2,2,2-trifluoro-1-hydroxy-1-methylethyl)phenyl)-2-piperazinyl)-2-propanone (0.653 g) as an orange oil.

Step 5: 1,1,1-trifluoro-2-(4-((2S)-2-(2-(3-oxetanylamino)propyl)-4-(2-thiophenylsulfonyl)-1-piperazinyl)phenyl)-2-propanol A solution of 1-((2S)-4-(2-thiophenylsulfonyl)-1-(4-(2,2,2-trifluoro-1-hydroxy-1-methylethyl)phenyl)-2-piperazinyl)-2-propanone (100 mg, 0.210 mmol) and oxetan-3-amine (18.41 mg, 0.252 mmol, J & W PharmLab, Levittown, Pa.) in THF (10 mL) was cooled to 0° C. To this mixture was added Ti(O-iPr)₄ (154 µL, 0.525 mmol, Sigma-Aldrich, St. Louis, Mo.). The mixture was stirred for 3 h and then a solution of sodium borohydride (11.91 mg, 0.315 mmol, Sigma-Aldrich, St. Louis, Mo.) in MeOH (1 mL) was added. The reaction mixture was stirred at ambient temperature for 4 h. Saturated aqueous NH₄Cl was added and the mixture was filtered. The filtrate was concentrated and purified via reverse-phase preparative HPLC using a Phenomenex Gemini C₁₈ column (150×30 mm, 10 µm) eluting with 0.1% TFA in MeCN/H₂O (5% to 100% over 15 min) to give 1,1,1-trifluoro-2-(4-((2S)-2-(2-(3-oxetanylamino)propyl)-4-(2-thiophenylsulfonyl)-1-piperazinyl)phenyl)-2-propanol (28 mg) as a mixture of four isomers

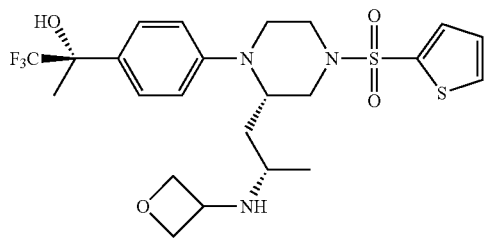

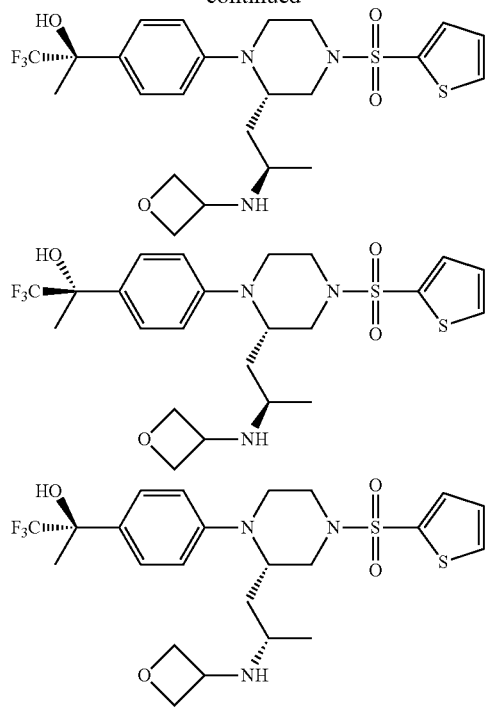

(2R)-1,1,1-trifluoro-2-(4-((2S)-2-((2S)-2-(3-oxetanylamino)propyl)-4-(2-thiophenylsulfonyl)-1-piperazinyl)phenyl)-2-propanol, (2S)-1,1,1-trifluoro-2-(4-((2S)-2-((2R)-2-(3-oxetanylamino)propyl)-4-(2-thiophenylsulfonyl)-1-piperazinyl)phenyl)-2-propanol, (2R)-1,1,1-trifluoro-2-(4-((2S)-2-((2S)-2-(3-oxetanylamino)propyl)-4-(2-thiophenylsulfonyl)-1-piperazinyl)phenyl)-2-propanol, and (2S)-1,1,1-trifluoro-2-(4-((2S)-2-((2S)-2-(3-oxetanylamino)propyl)-4-(2-thiophenylsulfonyl)-1-piperazinyl)phenyl)-2-propanol.

¹H NMR (400 MHz, CDCl₃) δ=7.64 (d, J=4.5 Hz, 1H), 7.58-7.53 (m, 1H), 7.44 (d, J=8.6 Hz, 2H), 7.19-7.14 (m, 1H), 6.88-6.81 (m, 2H), 4.78 (t, J=6.8 Hz, 2H), 4.46-4.33 (m, 2H), 4.27-4.05 (m, 1H), 4.02-3.84 (m, 1H), 3.81-3.67 (m, 2H), 3.46-3.38 (m, 1H), 3.36-3.22 (m, 1H), 2.76-2.64 (m, 2H), 2.62-2.52 (m, 2H), 1.96 (m, 1H), 1.80-1.69 (m, 3H), 0.99 (d, J=6.1 Hz, 3H). m/z (ESI, +ve ion) 534.2 (M+H)⁺. GK-GKRP IC₅₀ (Binding)=1.116 µM; GK-GKRP EC₅₀ (LC MS/MS-2)=0.529 µM.

Example 149

2-(4-((2S)-4-((5-amino-2-thiophenyl)sulfonyl)-2-methyl-1-piperazinyl)phenyl)-1,1,1,3,3,3-hexafluoro-2-propanol

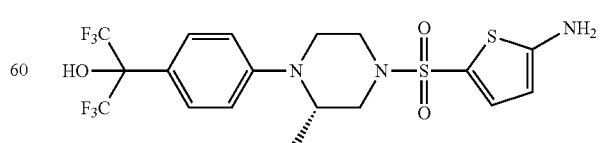

Following the procedure described for Example 88, the reaction of (S)-1,1,1,3,3,3-hexafluoro-2-(4-(2-methylpiperazin-1-yl)phenyl)-2-propanol (Example 11) delivered 2-(4-

((2S)-4-((5-amino-2-thiophenyl)sulfonyl)-2-methyl-1-piperazinyl)phenyl)-1,1,1,3,3,3-hexafluoro-2-propanol as a white solid. $^1$H NMR (400 MHz, CD$_3$OD) δ=7.45 (d, J=8.8 Hz, 2H), 7.10 (d, J=4.3 Hz, 1H), 6.88 (d, J=9.0 Hz, 2H), 5.95 (d, J=4.1 Hz, 1H), 4.16-3.95 (m, 1H), 3.52 (d, J=9.2 Hz, 1H), 3.43-3.29 (m, 2H), 3.15-3.00 (m, 1H), 2.71 (dd, J=3.3, 11.2 Hz, 1H), 2.55 (dt, J=3.4, 11.3 Hz, 1H), 1.03 (d, J=6.7 Hz, 3H). m/z (ESI, +ve ion) 504.0 (M+H)$^+$. GK-GKRP IC$_{50}$ (Binding)=0.450 μM; GK-GKRP EC$_{50}$ (LC MS/MS-2)=0.109 μM.

Example 150

4-(2-(4-(2-thiophenylsulfonyl)-1-piperazinyl)-5-(2,2,2-trifluoro-1-hydroxy-1-(trifluoromethyl)ethyl)phenyl)-3-butyn-1-ol

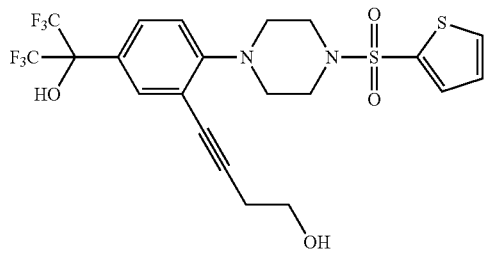 [SMILES: O=S(=O)(c1cccs1)N1CCN(c2ccc(C(O)(C(F)(F)F)C(F)(F)F)cc2C#CCCO)CC1]

2-(3-Bromo-4-(4-(thiophen-2-ylsulfonyl)piperazin-1-yl)phenyl)-1,1,1,3,3,3-hexafluoro-2-propanol (95 mg, 0.17 mmol, Example 69), potassium (4-(tert-butyldimethylsilyloxy)but-1-ynyl)trifluoroborate (75 mg, 0.26 mmol, ASDI, Newark, Del.), chloro(2-dicyclohexylphosphino-2',6'-di-i-propoxy-1,1'-biphenyl)[2-(2-aminoethylphenyl)]palladium(II), methyl-t-butylether adduct (14 mg, 0.02 mmol, Strem Chemical Inc, Newburyport, Mass.), and cesium carbonate (182 mg, 0.56 mmol) were combined in toluene (1.5 mL) and water (0.2 mL). The reaction mixture was purged with nitrogen gas for several minutes and then stirred and heated in an Emrys Optimizer microwave reactor (Personal Chemistry, Biotage AB, Inc., Uppsala, Sweden) at 135° C. for 30 min. The reaction mixture was filtered through a pad of Celite® (diatomaceous earth) eluting with CH$_2$Cl$_2$ and the filtrate was concentrated in vacuo. The residue was suspended in 1N HCl (5 mL) and stirred at room temperature for 30 min. The mixture was partitioned between CH$_2$Cl$_2$ (5 mL) and saturated aqueous sodium bicarbonate (5 mL). The layers were separated, the organic material was dried (Na$_2$SO$_4$), filtered, and concentrated. This crude material was subjected to reverse-phase preparative HPLC using a Phenomenex Gemini C$_{18}$ column (150×30 mm, 10 μm) eluting with 0.1% TFA in CH$_3$CN/H$_2$O (30% to 100% over 10 min) to provide 4-(2-(4-(2-thiophenylsulfonyl)-1-piperazinyl)-5-(2,2,2-trifluoro-1-hydroxy-1-(trifluoromethyl)ethyl)phenyl)-3-butyn-1-ol (22 mg) as an off-white solid. $^1$H NMR (400 MHz, DMSO-d$_6$) δ 8.67 (s, 1H), 8.11 (dd, J=1.27, 4.99 Hz, 1H), 7.71 (dd, J=1.37, 3.72 Hz, 1H), 7.55 (s, 1H), 7.52 (d, J=8.61 Hz, 1H), 7.35 (dd, J=3.81, 4.99 Hz, 1H), 7.08 (d, J=8.80 Hz, 1H), 4.88 (t, J=5.38 Hz, 1H), 3.50-3.59 (m, 2H), 3.27-3.32 (m, 4H), 3.08-3.15 (m, 4H) 2.56 (t, J=6.70 Hz, 2H); m/z (ESI, +ve ion) 543.1 (M+H)$^+$. GK-GKRP IC$_{50}$ (Binding)=0.656 μM. GK-GKRP EC$_{50}$ (LC MS/MS-2)=0.895 μM.

Example 151

4-(2-(4-(2-thiophenylsulfonyl)-1-piperazinyl)-5-(2,2,2-trifluoro-1-hydroxy-1-(trifluoromethyl)ethyl)phenyl)-3-butyn-2-ol

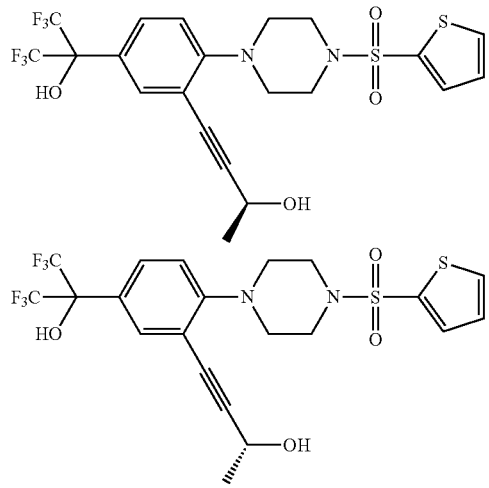

2-(3-Bromo-4-(4-(thiophen-2-ylsulfonyl)piperazin-1-yl)phenyl)-1,1,1,3,3,3-hexafluoro-2-propanol (102 mg, 0.18 mmol, Example 69), tert-butyldimethyl(4-(4,4,5,5-tetramethyl-1,3,2-dioxaborolan-2-yl)but-3-yn-2-yloxy)silane (86 mg, 0.28 mmol, Combi-Blocks, San Diego, Calif.), 1,1'-bis(diphenylphosphino)ferrocene-palladium(II) dichloride, dichloromethane complex (15 mg, 0.02 mmol, Sigma-Aldrich, St. Louis, Mo.), and cesium carbonate (180 mg, 0.55 mmol) were combined in DME (1.2 mL) and water (0.1 mL). The reaction mixture was purged with nitrogen for several minutes, and then stirred and heated in an Emrys Optimizer microwave reactor (Personal Chemistry, Biotage AB, Inc., Uppsala, Sweden) at 100° C. for 15 min and at 120° C. for 30 min. The reaction mixture was filtered through a pad of Celite® (diatomaceous earth) eluting with CH$_2$Cl$_2$ and the filtrate was concentrated in vacuo. The residue was suspended in 1N HCl (5 mL) and stirred at room temperature for 30 min. The mixture was partitioned between CH$_2$Cl$_2$ (5 mL) and saturated aqueous sodium bicarbonate (5 mL). The layers were separated, the organic material was dried (Na$_2$SO$_4$), filtered, and concentrated. The crude material was subjected to reverse-phase preparative HPLC using a Phenomenex Gemini C$_{18}$ column (150×30 mm, 10 μm) eluting with 0.1% TFA in CH$_3$CN/H$_2$O (30% to 100% over 10 min) to provide 4-(2-(4-(2-thiophenylsulfonyl)-1-piperazinyl)-5-(2,2,2-trifluoro-1-hydroxy-1-(trifluoromethyl)ethyl)phenyl)-3-butyn-2-ol (23 mg) as an off-white solid and a mixture of two enantiomers.

(2S)-4-(2-(4-(2-thiophenylsulfonyl)-1-piperazinyl)-5-(2,2,2-trifluoro-1-hydroxy-1-(trifluoromethyl)ethyl)phenyl)-3-butyn-2-ol; (2R)-4-(2-(4-(2-thiophenylsulfonyl)-1-piperazinyl)-5-(2,2,2-trifluoro-1-hydroxy-1-(trifluoromethyl)ethyl)phenyl)-3-butyn-2-ol $^1$H NMR (400 MHz, DMSO-d$_6$) δ 8.67 (s, 1H), 7.65 (d, J=2.15 Hz, 1H), 7.51 (br s, 2H), 7.23-7.36 (m, 1H), 7.06 (d, J=8.61 Hz, 1H), 5.31-5.49 (m, 1H), 4.53 (dd, J=6.26, 5.28 Hz, 1H), 3.25 (br s, 4H), 3.08 (br s, 4H), 1.26 (d, J=6.06 Hz, 3H); m/z (ESI, +ve ion) 543.2 (M+H)+. GK-GKRP IC$_{50}$ (Binding)=0.396 μM. GK-GKRP EC$_{50}$ (LC MS/MS-2)=0.994 μM.

Example 152

3-(2-(4-(2-thiophenylsulfonyl)-1-piperazinyl)-5-(2,2,2-trifluoro-1-hydroxy-1-(trifluoromethyl)ethyl)phenyl)-2-propyn-1-ol

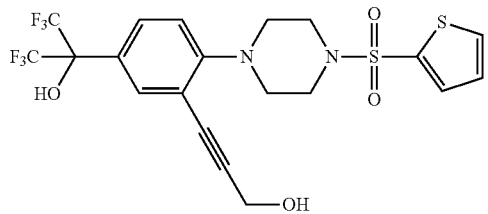

2-(3-Bromo-4-(4-(thiophen-2-ylsulfonyl)piperazin-1-yl)phenyl)-1,1,1,3,3,3-hexafluoro-2-propanol (117 mg, 0.21 mmol, Example 69), propargyl alcohol (25 μL, 0.42 mmol, Sigma-Aldrich, St. Louis, Mo.), diethylamine (44 μL, 0.42 mmol, Sigma-Aldrich, St. Louis, Mo.), bis(triphenylphosphine) palladium(II) dichloride (15 mg, 0.02 mmol, Strem Chemical Inc, Newburyport, Mass.), triphenylphosphine (11 mg, 0.04 mmol, Sigma-Aldrich, St. Louis, Mo.), and copper iodide (4 mg, 0.02 mmol, Strem Chemical Inc, Newburyport, Mass.) were combined in DMF (1 mL). The reaction mixture was purged with nitrogen for several minutes, and then stirred and heated in an Emrys Optimizer microwave reactor (Personal Chemistry, Biotage AB, Inc., Uppsala, Sweden) at 120° C. for 30 min. The reaction was diluted with CH$_2$Cl$_2$ (10 mL) and water (10 mL). The organic extracts were separated, washed with water (10 mL), dried (Na$_2$SO$_4$), filtered, and concentrated. Purification via column chromatography (12 g silica gel, 0 to 1% MeOH in CH$_2$Cl$_2$) afforded 3-(2-(4-(2-thiophenylsulfonyl)-1-piperazinyl)-5-(2,2,2-trifluoro-1-hydroxy-1-(trifluoromethyl)ethyl)phenyl)-2-propyn-1-ol (49 mg) as an off-white solid. $^1$H NMR (400 MHz, DMSO-d$_6$) δ 8.70 (s, 1H), 8.09 (br s, 1H), 7.45-7.75 (m, 3H), 7.33 (br s, 1H), 7.09 (d, J=7.63 Hz, 1H), 5.29 (br s, 1H), 4.27 (br s, 2H), 3.24-3.36 (m, 4H), 3.07-3.17 (m, 4H); m/z (ESI, +ve ion) 529.1 (M+H)+. GK-GKRP IC$_{50}$ (Binding)=0.712 μM. GK-GKRP EC$_{50}$ (LC MS/MS-2)=0.557 μM.

Example 153

1,1,1,3,3,3-hexafluoro-2-(3-(3-methoxyprop-1-YNYL)-4-(4-(thiophen-2-ylsulfonyl)piperazin-1-yl)phenyl)propan-2-ol

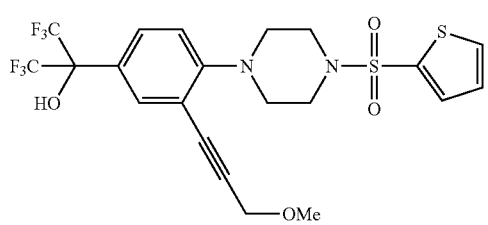 [SMILES: O=S(=O)(c1cccs1)N1CCN(c2ccc(C(O)(C(F)(F)F)C(F)(F)F)cc2C#CCO)CC1]

Following the procedure outlined for Example 152, 2-(3-Bromo-4-(4-(thiophen-2-ylsulfonyl)piperazin-1-yl)phenyl)-1,1,1,3,3,3-hexafluoro-2-propanol (Example 69) was coupled to methyl propargyl ether (Aldrich, St. Louis, Mo.) to afford 1,1,1,3,3,3-hexafluoro-2-(3-(3-methoxyprop-1-ynyl)-4-(4-(thiophen-2-ylsulfonyl)piperazin-1-yl)phenyl)propan-2-ol. $^1$H NMR (400 MHz, DMSO-d$_6$) δ 8.71 (s, 1H), 8.10 (dd, J=1.00, 4.90 Hz, 1H), 7.69 (dd, J=0.88, 3.62 Hz, 1H), 7.54-7.60 (m, 2H), 7.33 (dd, J=4.01, 4.79 Hz, 1H), 7.12 (d, J=8.80 Hz, 1H), 4.30 (s, 2H), 3.27-3.30 (m, J=5.10 Hz, 4H), 3.23 (s, 3H), 3.10 (d, J=4.30 Hz, 4H); m/z (ESI, +ve ion) 543.2 (M+H)+. GK-GKRP IC$_{50}$ (Binding)=0.363 μM. GK-GKRP EC$_{50}$ (LC MS/MS-2)=0.675 μM.

Example 154

1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol

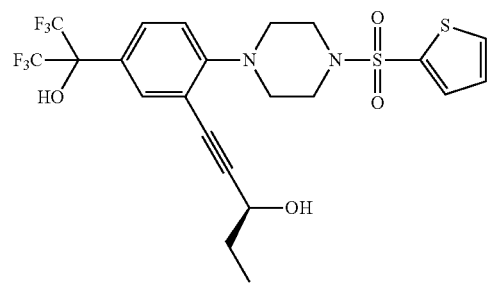

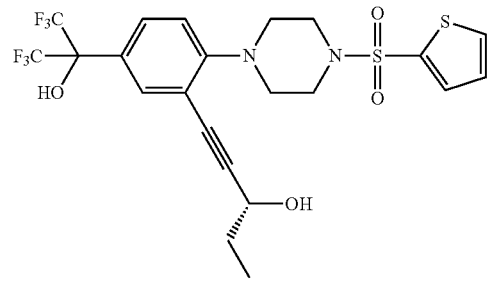

Following the procedure outlined for Example 152, 2-(3-bromo-4-(4-(thiophen-2-ylsulfonyl)piperazin-1-yl)phenyl)-1,1,1,3,3,3-hexafluoropropan-2-ol (Example 69) was coupled to 1-pentyn-3-ol (Aldrich, St. Louis, Mo.) to afford 1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol as a mixture of enantiomers.

(3S)-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol; (3R)-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol.

$^1$H NMR (400 MHz, DMSO-d$_6$) δ 8.71 (s, 1H), 8.13 (dd, J=1.27, 4.99 Hz, 1H), 7.70 (dd, J=1.27, 3.81 Hz, 1H), 7.52-7.62 (m, 2H), 7.35 (dd, J=3.81, 4.99 Hz, 1H), 7.12 (d, J=8.61 Hz, 1H), 5.41 (d, J=5.48 Hz, 1H), 4.37 (q, J=6.46 Hz, 1H), 3.27-3.32 (m, 4H), 3.02-3.17 (m, 4H), 1.49-1.66 (m, 2H),

Example 155

1,1,1,3,3,3-hexafluoro-2-(3-(3-methoxy-1-pentyn-1-yl)-4-(4-(2-thiophenylsulfonyl)-1-piperazinyl)phenyl)-2-propanol

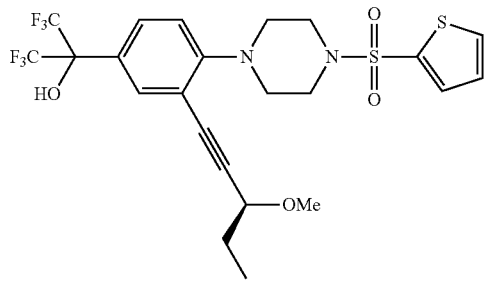

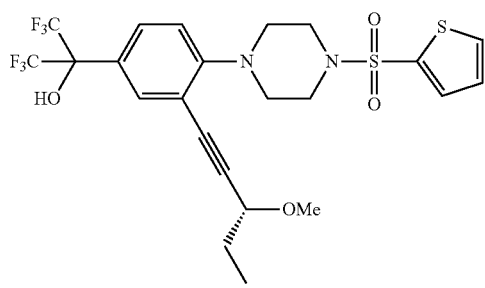

To a solution of 1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol (186 mg, 0.33 mmol, Example 154) in dry THF (5 mL) at room temperature was added sodium hydride (60% dispersion in mineral oil, 134 mg, 3.34 mmol). The reaction mixture was stirred at room temperature for 10 min then methyl iodide (0.21 mL, 3.34 mmol) was added. After stirring for an additional 2 h, the solvent was removed under reduced pressure. The crude material was absorbed onto a plug of silica gel and purified by column chromatography (12 g of silica gel, 10 to 30% ethyl acetate in hexanes), to provide 1,1,1,3,3,3-hexafluoro-2-(3-(3-methoxy-1-pentyn-1-yl)-4-(4-(2-thiophenylsulfonyl)-1-piperazinyl)phenyl)-2-propanol (156 mg) as an off-white solid.

(3S)-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol; (3R)-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol $^1$H NMR (400 MHz, DMSO-d$_6$) δ 8.73 (s, 1H), 8.12 (dd, J=4.99, 1.27 Hz, 1H), 7.69 (dd, J=3.72, 1.17 Hz, 1H), 7.54-7.62 (m, 2H), 7.34 (dd, J=4.99, 3.81 Hz, 1H), 7.14 (d, J=8.61 Hz, 1H), 4.16 (t, J=6.26 Hz, 1H), 3.27-3.31 (m, 4H), 3.25 (s, 3H), 2.99-3.16 (m, 4H), 1.54-1.74 (m, 2H), 0.86-0.93 (m, 3H); m/z (ESI, +ve ion) 571.1 (M+H)$^+$. GK-GKRP IC$_{50}$ (Binding)=0.145 μM. GK-GKRP EC$_{50}$ (LC MS/MS-2)=0.112 μM.

Example 156

4-methyl-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol

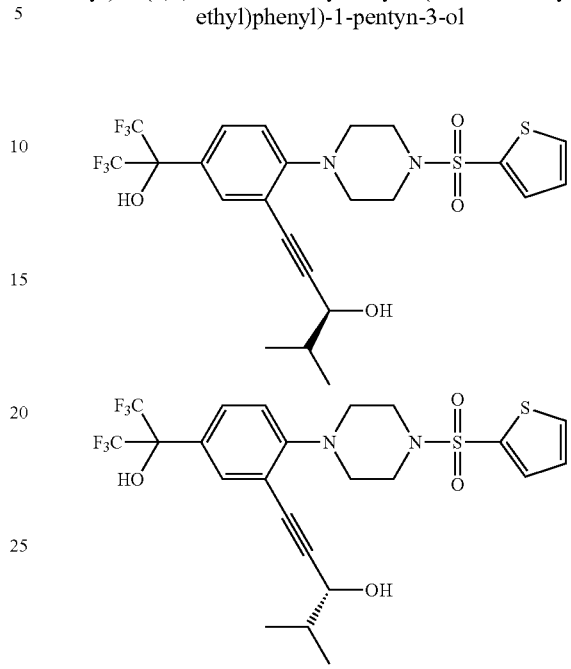

Following the procedure outlined for Example 152, 2-(3-bromo-4-(4-(2-thiophenylsulfonyl)-1-piperazinyl)phenyl)-1,1,1,3,3,3-hexafluoro-2-propanol (Example 69) was coupled to 4-methyl-1-pentyn-3-ol (Aldrich, St. Louis, Mo.) to afford 4-methyl-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol as a mixture of enantiomers.

(3R)-4-methyl-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol; (3S)-4-methyl-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol $^1$H NMR (400 MHz, DMSO-d$_6$) δ 8.70 (s, 1H), 8.11 (dd, J=1.17, 4.89 Hz, 1H), 7.67 (dd, J=1.27, 3.81 Hz, 1H), 7.50-7.60 (m, 2H), 7.33 (dd, J=3.91, 4.89 Hz, 1H), 7.11 (d, J=8.80 Hz, 1H), 5.39 (d, J=5.28 Hz, 1H), 4.20 (t, J=5.67 Hz, 1H), 3.23-3.30 (m, 4H), 3.01-3.15 (m, 4H), 1.71 (qd, J=6.59, 12.91 Hz, 1H), 0.86 (dd, J=1.56, 6.85 Hz, 6H); m/z (ESI, +ve ion) 571.1 (M+H)$^+$. GK-GKRP IC$_{50}$ (Binding)=2.861 μM.

Example 157

1,1,1,3,3,3-hexafluoro-2-(3-(3-methoxy-4-methyl-1-pentyn-1-yl)-4-(4-(2-thiophenylsulfonyl)-1-piperazinyl)phenyl)-2-propanol

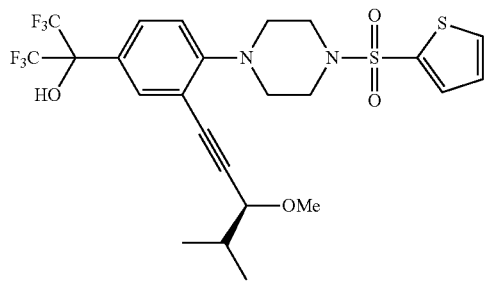

-continued

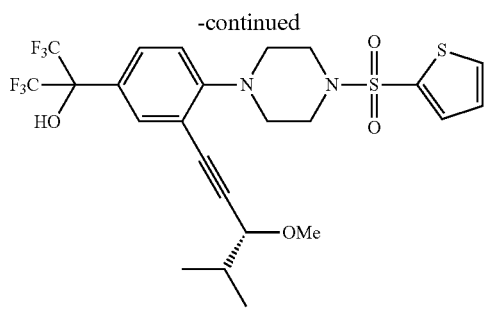

Following the procedure as outlined for Example 155, 4-methyl-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol (Example 156) was reacted with sodium hydride and methyl iodide to deliver 1,1,1,3,3,3-hexafluoro-2-(3-(3-methoxy-4-methyl-1-pentyn-1-yl)-4-(4-(2-thiophenylsulfonyl)-1-piperazinyl)phenyl)-2-propanol as a mixture of enantiomers.

1,1,1,3,3,3-hexafluoro-2-(3-((3S)-3-methoxy-4-methyl-1-pentyn-1-yl)-4-(4-(2-thiophenylsulfonyl)-1-piperazinyl)phenyl)-2-propanol; 1,1,1,3,3,3-hexafluoro-2-(3-((3R)-3-methoxy-4-methyl-1-pentyn-1-yl)-4-(4-(2-thiophenylsulfonyl)-1-piperazinyl)phenyl)-2-propanol.

$^1$H NMR (400 MHz, DMSO-d$_6$) δ 8.72 (s, 1H), 8.11 (dd, J=1.08, 4.99 Hz, 1H), 7.68 (dd, J=1.08, 3.81 Hz, 1H), 7.53-7.62 (m, 2H), 7.33 (dd, J=3.91, 4.89 Hz, 1H), 7.14 (d, J=8.80 Hz, 1H), 3.99 (d, J=5.48 Hz, 1H), 3.23-3.30 (m, 7H), 3.01-3.11 (m, 4H), 1.86 (qd, J=6.60, 12.86 Hz, 1H), 0.88 (dd, J=2.54, 6.65 Hz, 6H); m/z (ESI, +ve ion) 585.2 (M+H)$^+$. GK-GKRP IC$_{50}$ (Binding)=0.658 μM.

Example 158 tert-butyl (3-(2-(4-(2-thiophenylsulfonyl)-1-piperazinyl)-5-(2,2,2-trifluoro-1-hydroxy-1-(trifluoromethyl)ethyl)phenyl)-2-propyn-1-yl)carbamate

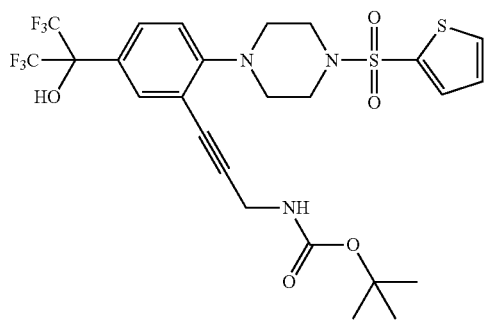 [SMILES: CC(C)(C)OC(=O)NCC#Cc1cc(C(O)(C(F)(F)F)C(F)(F)F)ccc1N1CCN(S(=O)(=O)c2cccs2)CC1]

Following the procedure outlined for Example 152, 2-(3-Bromo-4-(4-(thiophen-2-ylsulfonyl)piperazin-1-yl)phenyl)-1,1,1,3,3,3-hexafluoro-2-propanol (Example 69) was coupled to N-(tert-butoxycarbonyl)propargylamine (Aldrich, St. Louis, Mo.) to afford tert-butyl (3-(2-(4-(2-thiophenylsulfonyl)-1-piperazinyl)-5-(2,2,2-trifluoro-1-hydroxy-1-(trifluoromethyl)ethyl)phenyl)-2-propyn-1-yl)carbamate after purification via column chromatography on silica gel (10 to 40% EtOAc in hexanes). $^1$H NMR (400 MHz, DMSO-d$_6$) δ 8.68 (s, 1H), 8.08 (dd, J=1.00, 5.09 Hz, 1H), 7.69 (dd, J=0.98, 3.72 Hz, 1H), 7.51-7.56 (m, 2H), 7.32 (dd, J=3.91, 4.89 Hz, 2H), 7.07 (d, J=9.39 Hz, 1H), 3.94 (d, J=5.48 Hz, 2H), 3.26-3.29 (m, 4H), 3.12-3.18 (m, 4H), 1.40 (s, 9H); m/z (ESI, +ve ion) 628.1 (M+H)$^+$. GK-GKRP IC$_{50}$ (Binding)=0.695 μM.

Example 159

2-(3-(3-amino-1-propyn-1-yl)-4-(4-(2-thiophenylsulfonyl)-1-piperazinyl)phenyl)-1,1,1,3,3,3-hexafluoro-2-propanol trifluoroacetate

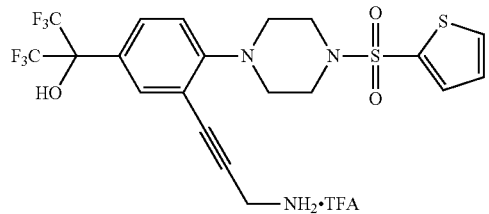

A solution of tert-butyl 3-(5-(1,1,1,3,3,3-hexafluoro-2-hydroxypropan-2-yl)-2-(4-(thiophen-2-ylsulfonyl)piperazin-1-yl)phenyl)prop-2-ynylcarbamate (698 mg, 1.11 mmol, Example 158) in 4 M HCl in dioxane (10 mL, 40 mmol) was stirred at room temperature for 30 min and then the solvent was removed under reduced pressure. The crude material was subjected to reverse-phase preparative HPLC using a Phenomenex Gemini C$_{18}$ column (150×30 mm, 10 μm) eluting with 0.1% TFA in CH$_3$CN/H$_2$O (10% to 100% over 15 min) to 2-(3-(3-amino-1-propyn-1-yl)-4-(4-(2-thiophenylsulfonyl)-1-piperazinyl)phenyl)-1,1,1,3,3,3-hexafluoro-2-propanol trifluoroacetate as a white solid. $^1$H NMR (400 MHz, DMSO-d$_6$) δ 8.77 (s, 1H), 8.24 (br s, 3H), 8.10 (d, J=4.89 Hz, 1H), 7.70 (d, J=3.33 Hz, 1H), 7.56-7.64 (m, 2H), 7.32 (t, J=4.40 Hz, 1H), 7.14 (d, J=8.61 Hz, 1H), 4.01 (s, 2H), 3.27-3.33 (m, 4H), 3.10-3.20 (m, 4H); m/z (ESI, +ve ion) 528.1 (M+H)$^+$. GK-GKRP IC$_{50}$ (Binding)=1.919 μM.

Example 160

N-(3-(2-(4-(2-thiophenylsulfonyl)-1-piperazinyl)-5-(2,2,2-trifluoro-1-hydroxy-1-(trifluoromethyl)ethyl)phenyl)-2-propyn-1-yl)methanesulfonamide

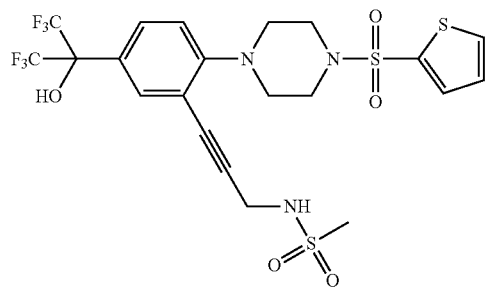 [SMILES: CS(=O)(=O)NCC#Cc1cc(C(O)(C(F)(F)F)C(F)(F)F)ccc1N1CCN(S(=O)(=O)c2cccs2)CC1]

To a solution of 2-(3-(3-amino-1-propyn-1-yl)-4-(4-(2-thiophenylsulfonyl)-1-piperazinyl)phenyl)-1,1,1,3,3,3-hexafluoro-2-propanol trifluoroacetate (102 mg, 0.17 mmol, Example 159) in CH$_2$Cl$_2$ (4 mL) was added diisopropylethylamine (89 μL, 0.51 mmol) and methanesulfonyl chloride (14 μL, 0.19 mmol). The reaction mixture was stirred at room temperature for 20 min and then partitioned between CH$_2$Cl$_2$ (5 mL) and saturated aqueous sodium bicarbonate (5 mL). The layers were separated, the organic material was separated, washed with saturated aqueous sodium bicarbonate (5 mL), dried (Na$_2$SO$_4$), filtered, and concentrated. The crude material was absorbed onto a plug of silica gel and purified by column chromatography (12 g of silica gel, 10% to 50% EtOAc in hexanes) to provide N-(3-(2-(4-(2-thiophenylsulfonyl)-1-piperazinyl)-5-(2,2,2-trifluoro-1-hydroxy-1-(trifluoromethyl)ethyl)phenyl)-2-propyn-1-yl)methanesulfonamide (57 mg) as white solid. $^1$H NMR (400 MHz, DMSO-d$_6$) δ 8.72 (br s, 1H), 8.09 (br s, 1H), 7.48-7.78 (m, 4H), 7.32 (br s, 1H), 7.11 (d, J=7.63 Hz, 1H), 4.07 (br s, 2H), 3.41-3.32 (m., 4H), 3.21-3.05 (m, 4H), 2.93 (s, 3H); m/z (ESI, +ve ion) 606.0 (M+H)$^+$. GK-GKRP IC$_{50}$ (Binding)=0.783 μM. GK-GKRP EC$_{50}$ (LC MS/MS-2)=0.412 μM.

Example 161

2-(4'-((6-amino-3-pyridinyl)sulfonyl)-4-biphenylyl)-1,1,1-trifluoro-2-propanol

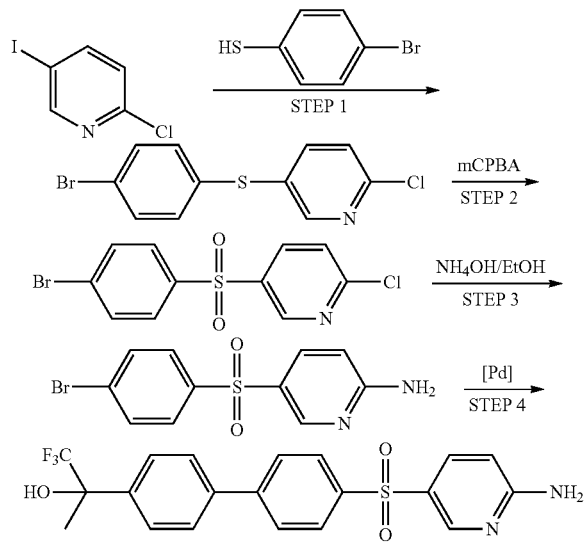

Step 1:
5-((4-bromophenyl)sulfanyl)-2-chloropyridine

2-Chloro-5-iodopyridine (1.11 g, 4.64 mmol, Sigma-Aldrich, St. Louis, Mo.), 4-bromothiophenol (0.88 g, 4.64 mmol, Sigma-Aldrich, St. Louis, Mo.), copper iodide (44 mg, 0.23 mmol, Strem Chemical Inc, Newburyport, Mass.), potassium carbonate (1.28 g, 9.29 mmol), ethylene glycol (0.52 mL, 9.29 mmol), and iPrOH (10 mL) were added to a reaction vial. The vial was closed, purged with nitrogen for several minutes, and heated at 80° C. for 16 h. After cooling to room temperature, the reaction mixture was diluted with water (10 mL) and extracted with CH$_2$Cl$_2$ (20 mL) and then EtOAc (20 mL). The combined organic extracts were combined and the solvents were removed under reduced pressure. The residue was absorbed onto a plug of silica gel and purified by column chromatography (24 g of silica gel, 0 to 10% EtOAc in hexanes), to provide 5-((4-bromophenyl)sulfanyl)-2-chloropyridine (1.17 g) as white solid. $^1$H NMR (400 MHz, DMSO-d$_6$) δ 8.41 (d, J=2.54 Hz, 1H), 7.81 (dd, J=2.54, 8.41 Hz, 1H), 7.57-7.61 (m, 2H), 7.54 (d, J=8.41 Hz, 1H), 7.30-7.35 (m, 2H); m/z (ESI, +ve ion) 300.0 (M+H)$^+$.

Step 2:
5-((4-bromophenyl)sulfonyl)-2-chloropyridine 5-((4-bromophenyl)sulfanyl)-2-chloropyridine (274 mg, 0.91 mmol) and mCPBA (409 mg, 1.82 mmol, 77% by weight, Sigma-Aldrich, St. Louis, Mo.) in CH$_2$Cl$_2$ (5 mL) were stirred at room temperature for 2 h. The mixture was partitioned between CH$_2$Cl$_2$ (10 mL) and saturated aqueous sodium bicarbonate (10 mL) and the layers were separated. The organic material was washed sequentially with saturated aqueous sodium bicarbonate (10 mL) and brine (10 mL), dried (Na$_2$SO$_4$), filtered, and concentrated in vacuo. The crude material was absorbed onto a plug of silica gel and purified by column chromatography (0 to 20% EtOAc in hexanes), to provide 5-((4-bromophenyl)sulfonyl)-2-chloropyridine (100 mg) as white solid. $^1$H NMR (400 MHz, DMSO-d$_6$) δ 9.02 (d, J=2.54 Hz, 1H), 8.40 (dd, J=2.64, 8.51 Hz, 1H), 7.93-8.02 (m, 2H), 7.84-7.91 (m, 2H), 7.79 (d, J=8.41 Hz, 1H); m/z (ESI, +ve ion) 332.0 (M+H)$^+$.

Step 3: 5-((4-bromophenyl)sulfonyl)-2-pyridinamine 5-((4-Bromophenyl)sulfonyl)-2-chloropyridine (98 mg, 0.29 mmol), concentrated NH$_4$OH (3 mL), and EtOH (3 mL) were added to a high-pressure reaction vessel. The vessel was sealed and heated at 120° C. for 18 h. After cooling to room temperature, the solvent was partially removed under vacuum. The white precipitate obtained was filtered, washed with ether, and dried under vacuum to provide 5-((4-bromophenyl)sulfonyl)-2-pyridinamine (75 mg) as a white solid.

Step 4: 2-(4'-((6-amino-3-pyridinyl)sulfonyl)-4-biphenylyl)-1,1,1-trifluoro-2-propanol A 10 mL vial was charged with 5-((4-bromophenyl)sulfonyl)-2-pyridinamine (71 mg, 0.23 mmol), 1,1,1-trifluoro-2-(4-(4,4,5,5-tetramethyl-1,3,2-dioxaborolan-2-yl)phenyl)propan-2-ol (86 mg, 0.27 mmol, synthesized in manner analogous to Example 21 using 2-(4-bromophenyl)-1,1,1-trifluoro-2-propanol (example 27)), 1,1'-bis(diphenylphosphino)ferrocene-palladium(II) dichloride, dichloromethane complex (18 mg, 0.02 mmol, Sigma-Aldrich, St. Louis, Mo.), and cesium carbonate (222 mg, 0.68 mmol) were combined in DME (1.2 mL) and water (0.1 mL). The reaction mixture was purged with nitrogen for several minutes, and then stirred and heated in an Emrys Optimizer microwave reactor (Personal Chemistry, Biotage AB, Inc., Uppsala, Sweden) at 100° C. for 30 min. The organic layer was taken and the solvent was removed under reduced pressure. The crude material was absorbed onto a plug of silica gel and purified by column chromatography (12 g of silica gel, 0 to 3% 2M NH$_3$ in MeOH/CH$_2$Cl$_2$) to provide 2-(4'-((6-amino-3-pyridinyl)sulfonyl)-4-biphenylyl)-1,1,1-trifluoro-2-propanol (83 mg) as an off-white solid.

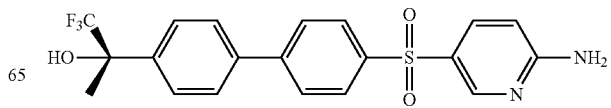

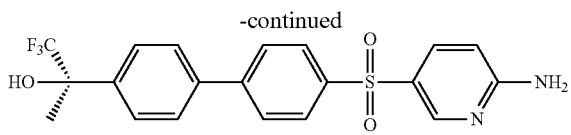

(2S)-2-(4'-((6-amino-3-pyridinyl)sulfonyl)-4-biphenylyl)-1,1,1-trifluoro-2-propanol; (2S)-2-(4'-((6-amino-3-pyridinyl)sulfonyl)-4-biphenylyl)-1,1,1-trifluoro-2-propanol.

$^1$H NMR (400 MHz, DMSO-$d_6$) δ 8.47 (d, J=2.54 Hz, 1H), 7.94-8.02 (m, 2H), 7.90 (d, J=8.61 Hz, 2H), 7.81 (dd, J=2.54, 9.00 Hz, 1H), 7.73 (q, J=8.61 Hz, 4H), 7.10 (br s, 2H), 6.67 (s, 1H), 6.51 (d, J=9.00 Hz, 1H), 1.72 (s, 3H); m/z (ESI, +ve ion) 423.0 (M+H)$^+$. GK-GKRP IC$_{50}$ (Binding)=1.01 μM.

Example 162

1-(2-(4-(phenylsulfonyl)-1-piperidinyl)-5-(2,2,2-trifluoro-1-hydroxy-1-(trifluoromethyl)ethyl)phenyl)-1-pentyn-3-ol

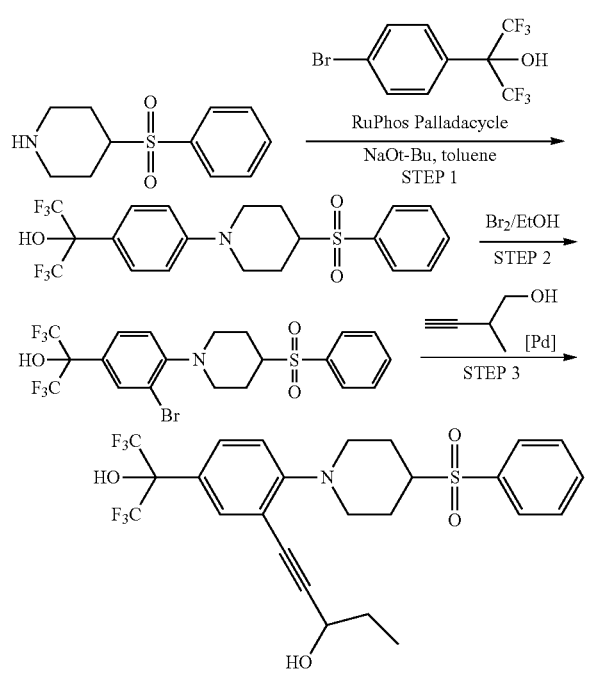

Step 1: 1,1,1,3,3,3-hexafluoro-2-(4-(4-(phenylsulfonyl)piperidin-1-yl)phenyl)-2-propanol A 15-mL reaction vial was charged with 4-(phenylsulfonyl)piperidine (1.05 g, 4.66 mmol, BetaPharma, Brandford, Conn.), sodium t-butoxide (0.98 g, 10.24 mmol), 2-(4-bromophenyl)-1,1,1,3,3,3-hexafluoro-2-propanol (1.50 g, 4.66 mmol, Bioorg. Med. Chem. Lett. 2002, 12, 3009), chloro(2-dicyclohexylphosphino-2',6'-di-i-propoxy-1,1'-biphenyl)[2-(2-aminoethylphenyl)]palladium(II), methyl-t-butylether adduct (RuPhos Palladacycle) (0.170 g, 0.233 mmol, Strem Chemicals, Inc, Newburyport, Mass.), and toluene (10 mL). The vial was closed and purged with nitrogen for several minutes. The reaction mixture was heated at 100° C. for 2.5 h and allowed to cool to room temperature. The reaction mixture was diluted with water (5 mL) and extracted with EtOAc (10 mL). The organic extract was washed with water (5 mL) and dried over Na$_2$SO$_4$. The solution was filtered and concentrated and then absorbed onto a plug of silica gel and purified by column chromatography (40 g of silica gel, 10 to 30% EtOAc in hexanes) to provide 1,1,1,3,3,3-hexafluoro-2-(4-(4-(phenylsulfonyl)piperidin-1-yl)phenyl)-2-propanol (1.94 g) as white solid Step 2: 2-(3-bromo-4-(4-(phenylsulfonyl)piperidin-1-yl)phenyl)-1,1,1,3,3,3-hexafluoro-2-propanol To a solution of 1,1,1,3,3,3-hexafluoro-2-(4-(4-(phenylsulfonyl)piperidin-1-yl)phenyl)-2-propanol (699 mg, 1.49 mmol) in EtOH (10 mL) was added bromine (77 μL, 1.49 mmol) and the reaction mixture was stirred at room temperature for 15 min. The reaction mixture was diluted with a saturated aqueous sodium thiosulfate (10 mL) and extracted with EtOAc (15 mL). The organic layer was separated and washed with water (10 mL), brine (10 mL), dried (Na$_2$SO$_4$), filtered, and concentrated in vacuo. The crude material was absorbed onto a plug of silica gel and purified by column chromatography (12 g of silica gel, 10 to 25% EtOAc in hexanes) to provide 2-(3-bromo-4-(4-(phenylsulfonyl)piperidin-1-yl)phenyl)-1,1,1,3,3,3-hexafluoro-2-propanol (567 mg) as a mixture of two enantiomers.

Step 3: 1-(5-(1,1,1,3,3,3-hexafluoro-2-hydroxypropan-2-yl)-2-(4-(phenylsulfonyl)piperidin-1-yl)phenyl)pent-1-yn-3-ol Following the procedure described for Example 152, 2-(3-bromo-4-(4-(phenylsulfonyl)piperidin-1-yl)phenyl)-1,1,1,3,3,3-hexafluoro-2-propanol was coupled to 1-pentyn-3-ol (Aldrich, St. Louis, Mo.) to afford 1-(5-(1,1,1,3,3,3-hexafluoro-2-hydroxypropan-2-yl)-2-(4-(phenylsulfonyl)piperidin-1-yl)phenyl)pent-1-yn-3-ol as a light yellow solid and a mixture of enantiomers.

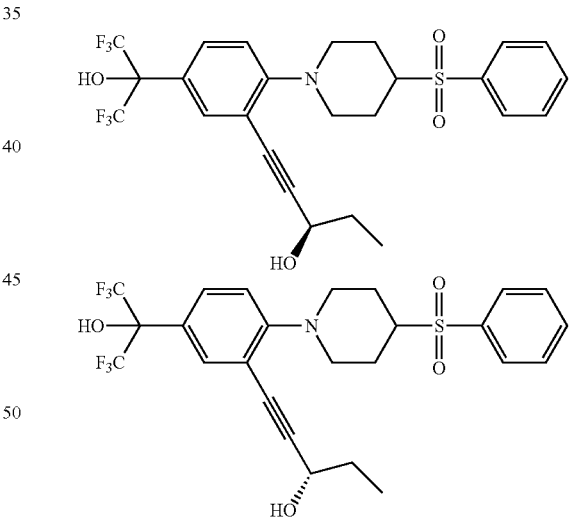

(3R)-1-(2-(4-(phenylsulfonyl)-1-piperidinyl)-5-(2,2,2-trifluoro-1-hydroxy-1-(trifluoromethyl)ethyl)phenyl)-1-pentyn-3-ol; (3S)-1-(2-(4-(phenylsulfonyl)-1-piperidinyl)-5-(2,2,2-trifluoro-1-hydroxy-1-(trifluoromethyl)ethyl)phenyl)-1-pentyn-3-ol $^1$H NMR (400 MHz, DMSO-$d_6$) δ 8.69 (s, 1H), 7.88 (d, J=7.24 Hz, 2H), 7.81 (t, J=7.80 Hz, 1H), 7.67-7.75 (m, 2H), 7.57-7.61 (m, 1H), 7.54 (d, J=8.80 Hz, 1H), 7.08 (d, J=8.80 Hz, 1H), 4.20 (t, J=6.36 Hz, 1H), 3.70 (d, J=11.74 Hz, 2H), 3.48 (dd, J=0.59, 3.72 Hz, 1H), 3.33 (s, 3H), 2.72 (t, J=11.44 Hz, 2H), 1.96 (d, J=11.15 Hz, 2H), 1.60-1.78 (m, 4H), 0.97 (t, J=7.43 Hz, 3H); m/z (ESI, +ve ion) 550.1 (M+H)$^+$. GK-GKRP IC$_{50}$ (Binding)=5.184 μM.

Example 163

1,1,1,3,3,3-hexafluoro-2-(3-(3-methoxypent-1-ynyl)-4-(4-(phenylsulfonyl)piperidin-1-yl)phenyl)-2-propanol

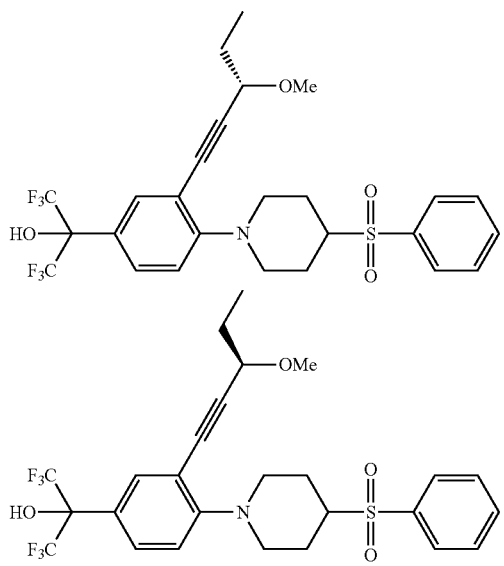

Following the procedure described for Example 155, -(5-(1,1,1,3,3,3-hexafluoro-2-hydroxypropan-2-yl)-2-(4-(phenylsulfonyl)piperidin-1-yl)phenyl)pent-1-yn-3-ol (Example 162) was reacted with sodium hydride and methyl iodide to afford 1,1,1,3,3,3-hexafluoro-2-(3-(3-methoxypent-1-ynyl)-4-(4-(phenylsulfonyl)piperidin-1-yl)phenyl)-2-propanol as a mixture of enantiomers.

1,1,1,3,3,3-hexafluoro-2-((3S)-3-methoxy-1-pentyn-1-yl)-4-(4-(phenylsulfonyl)-1-piperidinyl)phenyl)-2-propanol; 1,1,1,3,3,3-hexafluoro-2-(3-((3S)-3-methoxy-1-pentyn-1-yl)-4-(4-(phenylsulfonyl)-1-piperidinyl)phenyl)-2-propanol.

$^1$H NMR (400 MHz, DMSO-d$_6$) δ 8.69 (s, 1H), 7.88 (d, J=7.24 Hz, 2H), 7.81 (t, J=7.80 Hz, 1H), 7.67-7.75 (m, 2H), 7.57-7.61 (m, 1H), 7.54 (d, J=8.80 Hz, 1H), 7.08 (d, J=8.80 Hz, 1H), 4.20 (t, J=6.36 Hz, 1H), 3.70 (d, J=11.74 Hz, 2H), 3.48 (dd, J=0.59, 3.72 Hz, 1H), 3.33 (s, 3H), 2.72 (t, J=11.44 Hz, 2H), 1.96 (d, J=11.15 Hz, 2H), 1.60-1.78 (m, 4H), 0.97 (t, J=7.43 Hz, 3H); m/z (ESI, +ve ion) 564.2 (M+H)$^+$. GK-GKRP IC$_{50}$ (Binding)=0.602 µM. GK-GKRP EC$_{50}$ (LC MS/MS-2)=0.807 µM.

Example 164

2-(4-(4-(6-aminopyridazin-3-ylsulfonyl)piperazin-1-yl)phenyl)-1,1,1,3,3,3-hexafluoro-2-propanol

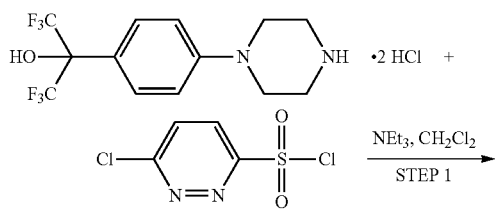

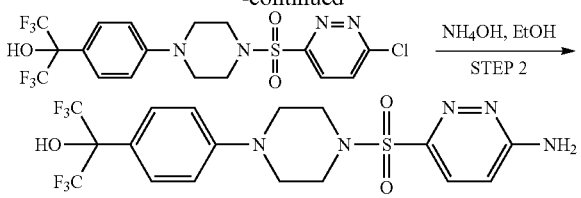

Step 1: 2-(4-(4-((6-chloro-3-pyridazinyl)sulfonyl)-1-piperazinyl)phenyl)-1,1,1,3,3,3-hexafluoro-2-propanol To a 20 mL vial was added 1,1,1,3,3,3-hexafluoro-2-(4-(1-piperazinyl)phenyl)-2-propanol dihydrochloride (0.35 g, 0.87 mmol, Example 91), 6-chloropyridazine-3-sulfonyl chloride (0.20 g, 0.96 mmol, Archiv der Pharmazie and Berichte der Deutschen Pharmazeutischen Gesellschaft 1966, 229, 646), CH$_2$Cl$_2$ (10 mL) and triethylamine (0.61 mL, 4.4 mmol). After 24 h at room temperature, an additional 100 mg of 6-chloropyridazine-3-sulfonyl chloride was added and the solution was stirred for an additional hour. The reaction was diluted with saturated aqueous sodium bicarbonate and CH$_2$Cl$_2$. This was stirred for 5 min and then the solution was transferred onto a phase separation cartridge (Radleys Discovery Technologies, Essex, UK) with the organic phase being collected and passed through a plug of Na$_2$SO$_4$. The collected solution was purified by silica gel chromatography (0 to 70% EtOAc in hexanes). The resulting oil was dissolved in EtOAc/heptanes, concentrated and dried under reduced pressure to afford 2-(4-(4-((6-chloropyridazin-3-yl)sulfonyl)piperazin-1-yl)phenyl)-1,1,1,3,3,3-hexafluoro-2-propanol (0.15 g) as a yellow solid.

Step 2: 2-(4-(4-((6-aminopyridazin-3-yl)sulfonyl)piperazin-1-yl)phenyl)-1,1,1,3,3,3-hexafluoro-2-propanol To a 2 mL microwave vial was added 2-(4-(4-((6-chloropyridazin-3-yl)sulfonyl)piperazin-1-yl)phenyl)-1,1,1,3,3,3-hexafluoropropan-2-ol (50 mg, 0.099 mmol), EtOH (1.0 mL) and ammonium hydroxide (2.0 mL, 51 mmol). The solution was heated in an Emrys Optimizer microwave reactor (Personal Chemistry, Biotage AB, Inc., Uppsala, Sweden) at 110° C. for 1 h and then concentrated. The resulting material was purified by silica gel chromatography (0 to 4% MeOH in CH$_2$Cl$_2$) to afford 2-(4-(4-((6-aminopyridazin-3-yl)sulfonyl)piperazin-1-yl)phenyl)-1,1,1,3,3,3-hexafluoro-2-propanol (29 mg) as a white solid. $^1$H NMR (400 MHz, DMSO-d$_6$) δ 8.40 (s, 1H), 7.67 (d, J=9.4 Hz, 1H), 7.47 (d, J=8.6 Hz, 2H), 7.28 (s, 2H), 7.02 (d, J=9.0 Hz, 2H), 6.89 (d, J=9.2 Hz, 1H), 3.29-3.33 (m, 4H), 3.22-3.28 (m, 4H). m/z (ESI, +ve ion) 485.9 (M+H)$^+$. GK-GKRP IC$_{50}$ (Binding)=0.285 µM; GK-GKRP EC$_{50}$ (LC MS/MS-2)=0.302 µM.

Example 165

2-(4-(4-(2-aminophenylsulfonyl)piperazin-1-yl)phenyl)-1,1,1,3,3,3-hexafluoro-2-propanol

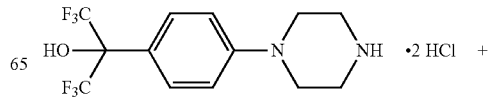

-continued

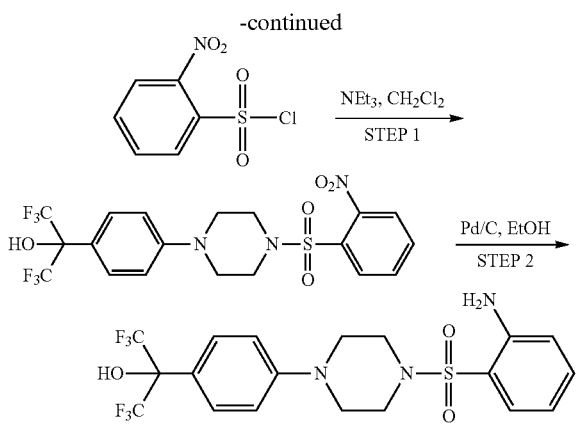

Step 1: 1,1,1,3,3,3-hexafluoro-2-(4-(4-(2-nitrophenylsulfonyl)piperazin-1-yl)phenyl)-2-propanol To a 15 mL round-bottomed flask was added 1,1,1,3,3,3-hexafluoro-2-(4-(1-piperazinyl)phenyl)-2-propanol dihydrochloride (0.25 g, 0.62 mmol, Example 91), triethylamine (0.26 mL, 1.9 mmol) and CH$_2$Cl$_2$ (6 mL). To this solution at room temperature was added 2-nitrobenzenesulfonyl chloride (0.14 g, 0.62 mmol, Sigma-Aldrich, St. Louis, Mo.). The mixture was stirred for 20 min and then was concentrated onto silica gel. Purification by silica gel chromatography (0 to 6% MeOH in CH$_2$Cl$_2$) afforded 1,1,1,3,3,3-hexafluoro-2-(4-(4-(2-nitrophenylsulfonyl)piperazin-1-yl)phenyl)-2-propanol (0.13 g) as a yellow solid.

Step 2: 2-(4-(4-(2-aminophenylsulfonyl)piperazin-1-yl)phenyl)-1,1,1,3,3,3-hexafluoro-2-propanol To a solution of 1,1,1,3,3,3-hexafluoro-2-(4-(4-(2-nitrophenylsulfonyl)piperazin-1-yl)phenyl)-2-propanol (0.13 g, 0.25 mmol) in EtOH (5 mL) was added 10% palladium on carbon (10 wt % (dry basis) on activated carbon, wet (water about 50%)) (0.026 g, 0.24 mmol). The reaction vessel stirred under a hydrogen atmosphere (1 atm). After 4 hours at room temperature, the reaction vessel was carefully evacuated and backfilled with N$_2$. The solution was filtered through Celite® (diatomaceous earth) and the filtrate was concentrated onto silica. Purification by silica gel chromatography (0 to 6% MeOH in CH$_2$Cl$_2$) afforded 2-(4-(4-(2-aminophenylsulfonyl)piperazin-1-yl)phenyl)-1,1,1,3,3,3-hexafluoro-2-propanol (79 mg) as a white solid. $^1$H NMR (400 MHz, DMSO-d$_6$) δ 8.40 (s, 1H), 7.45 (d, J=8.8 Hz, 2H), 7.41 (dd, J=1.2, 8.0 Hz, 1H), 7.28-7.35 (m, 1H), 7.00 (d, J=9.0 Hz, 2H), 6.87 (d, J=8.0 Hz, 1H), 6.66 (t, J=7.2 Hz, 1H), 6.09 (s, 2H), 3.22-3.29 (m, 4H), 3.06-3.14 (m, 4H). m/z (ESI, +ve ion) 483.8 (M+H)$^+$. GK-GKRP IC$_{50}$ (Binding)=0.298 μM; GK-GKRP EC$_{50}$ (LC MS/MS-2)=0.552 μM.

Example 166

2-(4-(4-(2,6-diaminopyridin-3-ylsulfonyl)piperazin-1-yl)phenyl)-1,1,1,3,3,3-hexafluoro-2-propanol

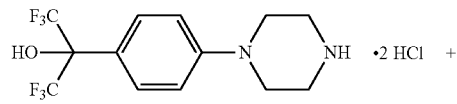

-continued

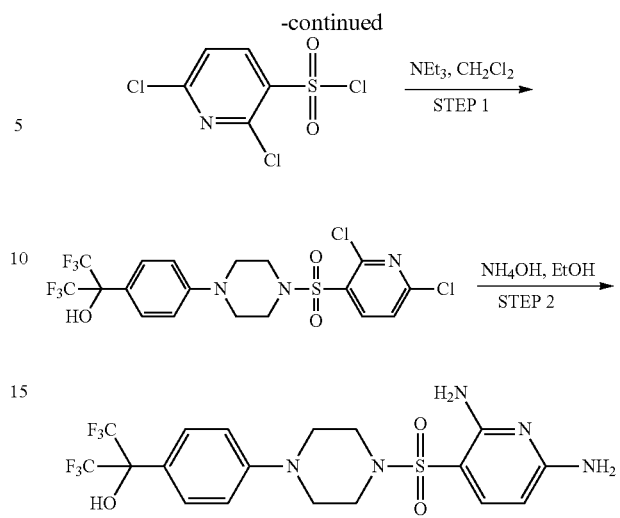

Step 1: 2-(4-(4-(2,6-dichloropyridin-3-ylsulfonyl)piperazin-1-yl)phenyl)-1,1,1,3,3,3-hexafluoro-2-propanol To a 20-mL vial was added 1,1,1,3,3,3-hexafluoro-2-(4-(1-piperazinyl)phenyl)-2-propanol dihydrochloride (0.40 g, 1.0 mmol, Example 91), CH$_2$Cl$_2$ (8 mL), and triethylamine (0.70 mL, 5.0 mmol). To this solution was added 2,6-dichloropyridine-3-sulfonyl chloride (0.30 g, 1.2 mmol, *Organic Process Research and Development* 2009, 875). After stirring overnight at room temperature, saturated aqueous sodium bicarbonate and CH$_2$Cl$_2$ were added to the reaction mixture. After stirring for 5 min, the solution was transferred onto a phase separation cartridge (Radleys Discovery Technologies, Essex, UK) with the organic phase being collected and passed through a plug of Na$_2$SO$_4$. The collected solution was purified by silica gel chromatography (0 to 70% EtOAc in hexanes) to afford 2-(4-(4-((2,6-dichloropyridin-3-yl)sulfonyl)piperazin-1-yl)phenyl)-1,1,1,3,3,3-hexafluoro-2-propanol (0.43 g) as an off-white solid.

Step 2: 2-(4-(4-(2,6-diaminopyridin-3-ylsulfonyl)piperazin-1-yl)phenyl)-1,1,1,3,3,3-hexafluoro-2-propanol To a 5-mL microwave vial was added 2-(4-(4-((2,6-dichloropyridin-3-yl)sulfonyl)piperazin-1-yl)phenyl)-1,1,1,3,3,3-hexafluoro-2-propanol (0.10 g, 0.19 mmol), EtOH (1.0 mL) and aqueous ammonium hydroxide (2.0 mL, 51 mmol). The vial was sealed and the solution was heated in an Emrys Optimizer microwave reactor (Personal Chemistry, Biotage AB, Inc., Uppsala, Sweden) at 110° C. for 5 h and then concentrated. Purification by silica gel chromatography (0 to 4% MeOH in CH$_2$Cl$_2$) afforded 2-(4-(4-((2,6-diaminopyridin-3-yl)sulfonyl)piperazin-1-yl)phenyl)-1,1,1,3,3,3-hexafluoro-2-propanol (38 mg) as a white solid. $^1$H NMR (400 MHz, DMSO-d$_6$) δ 8.40 (s, 1H), 7.47 (d, J=8.8 Hz, 2H), 7.37 (d, J=8.6 Hz, 1H), 7.02 (d, J=9.0 Hz, 2H), 6.52 (br s, 2H), 6.23 (br s, 2H), 5.81 (d, J=8.6 Hz, 1H), 3.23-3.30 (m, 4H), 2.99-3.10 (m, 4H). m/z (ESI, +ve ion) 499.9 (M+H)$^+$. GK-GKRP IC$_{50}$ (Binding)=0.299 μM; GK-GKRP EC$_{50}$ (LC MS/MS-2)=0.262 μM.

Example 167

(S)-2-(2-(4-(2-aminophenylsulfonyl)-2-methylpiperazin-1-yl)pyrimidin-5-yl)-1,1,1,3,3,3-hexafluoro-2-propanol

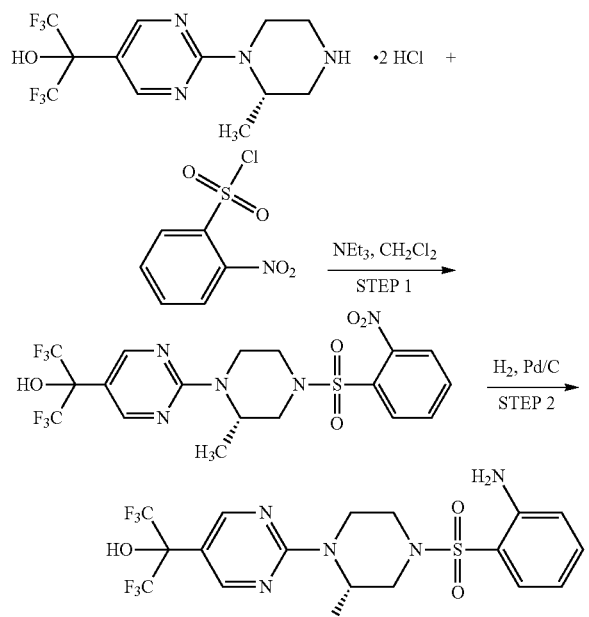

Step 1: (S)-1,1,1,3,3,3-hexafluoro-2-(2-(2-methyl-4-(2-nitrophenylsulfonyl)piperazin-1-yl)pyrimidin-5-yl)-2-propanol To a 15 mL round-bottomed flask was added 1,1,1,3,3,3-hexafluoro-2-(2-((2S)-2-methyl-1-piperazinyl)-5-pyrimidinyl)-2-propanol dihydrochloride (0.28 g, 0.66 mmol, Example 89, Step 2), triethylamine (0.28 mL, 2.0 mmol) and $CH_2Cl_2$ (6 mL). To this solution at room temperature was added 2-nitrobenzenesulfonyl chloride (0.15 g, 0.66 mmol, Sigma-Aldrich, St. Louis, Mo.). The mixture was stirred at room temperature for 3 h and then saturated aqueous sodium bicarbonate was added. This was stirred for an additional 5 min and then the solution was transferred onto a phase separation cartridge (Radleys Discovery Technologies, Essex, UK) with the organic phase being collected. The collected solution was purified by silica gel chromatography (0 to 75% EtOAc in hexanes) to afford (S)-1,1,1,3,3,3-hexafluoro-2-(2-(2-methyl-4-(2-nitrophenylsulfonyl)piperazin-1-yl)pyrimidin-5-yl)-2-propanol (0.24 g) as a white solid.

Step 2: (S)-2-(2-(4-(2-aminophenylsulfonyl)-2-methylpiperazin-1-yl)pyrimidin-5-yl)-1,1,1,3,3,3-hexafluoro-2-propanol Using a new 10% Pd/C CatCart cartridge (30 mm), a H-Cube/Gilson (Thalesnano Technology, Budapest, Hungary) system was purged with 1:1 0.5 M AcOH in EtOAc:EtOH. The CatCart was pre-saturated with $H_2$ for 10 min (using the pre-saturate setting in the autosampler software program) at 0.5 mL/min. A solution of ((S)-1,1,1,3,3,3-hexafluoro-2-(2-(2-methyl-4-(2-nitrophenylsulfonyl)piperazin-1-yl)pyrimidin-5-yl)-2-propanol (0.21 g, 0.40 mmol) in 4.0 mL 1:1 0.5 M AcOH in EtOAc:EtOH was prepared. Three injections set at 1.5 mL were made, 30 mm 10% Pd/C Cat-Cart, flow rate 0.5 mL/min, "1 bar" i.e., setting at "Full $H_2$" on H-cube; temp 40° C.; 10 mL volume collected for each injection. The collected solution was concentrated and then dissolved in $CH_2Cl_2$. The solution was treated with saturated aqueous sodium bicarbonate then passed through a phase separation cartridge (Radleys Discovery Technologies, Essex, UK) dried ($Na_2SO_4$), and then concentrated. The residue was then purification by silica gel chromatography (0 to 70% EtOAc/hexane) to afford (S)-2-(2-(4-(2-aminophenylsulfonyl)-2-methylpiperazin-1-yl)pyrimidin-5-yl)-1,1,1,3,3,3-hexafluoro-2-propanol (92 mg) as a white solid. $^1$H NMR (400 MHz, DMSO-$d_6$) δ 8.87 (s, 1H), 8.53 (s, 2H), 7.40 (dd, J=1.4, 8.2 Hz, 1H), 7.25-7.34 (m, 1H), 6.85 (d, J=7.8 Hz, 1H), 6.63 (t, J=7.1 Hz, 1H), 6.06 (s, 2H), 4.94 (br s, 1H), 4.57 (d, J=13.7 Hz, 1H), 3.75 (d, J=11.5 Hz, 1H), 3.51 (d, J=11.9 Hz, 1H), 3.10-3.27 (m, 1H), 2.60 (dd, J=3.7, 11.9 Hz, 1H), 2.38-2.47 (m, 1H), 1.10-1.22 (m, 3H). m/z (ESI, +ve ion) 499.9 (M+H)$^+$. GK-GKRP IC$_{50}$ (Binding)=0.508 μM; GK-GKRP EC$_{50}$ (LC MS/MS-2)=0.516 μM.

Example 168

(2-(4-((2S)-4-((2-aminophenyl)sulfonyl)-2-methyl-1-piperazinyl)phenyl)-1,1,1,3,3,3-hexafluoro-2-propanol

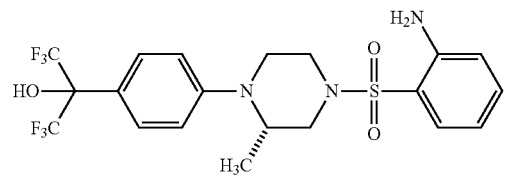 [SMILES: C[C@H]1CN(S(=O)(=O)c2ccccc2N)CCN1c1ccc(C(O)(C(F)(F)F)C(F)(F)F)cc1]

Following the procedure reported for Example 167, (S)-1,1,1,3,3,3-hexafluoro-2-(4-(2-methylpiperazin-1-yl)phenyl)-2-propanol dihydrochloride (Example 91) delivered 2-(4-((2S)-4-((2-aminophenyl)sulfonyl)-2-methyl-1-piperazinyl)phenyl)-1,1,1,3,3,3-hexafluoro-2-propanol (0.18 g) as a white solid. $^1$H NMR (400 MHz, DMSO-$d_6$) δ 8.36 (s, 1H), 7.45 (d, J=8.6 Hz, 2H), 7.41 (d, J=7.1 Hz, 1H), 7.32 (t, J=7.6 Hz, 1H), 6.95 (d, J=9.0 Hz, 2H), 6.87 (d, J=8.2 Hz, 1H), 6.66 (t, J=7.5 Hz, 1H), 6.08 (s, 2H), 4.10-4.26 (m, 1H), 3.67 (d, J=10.6 Hz, 1H), 3.52 (d, J=12.3 Hz, 1H), 3.44 (d, J=11.5 Hz, 1H), 3.05 (dt, J=3.3, 12.0 Hz, 1H), 2.67 (dd, J=3.2, 11.4 Hz, 1H), 2.52-2.58 (m, 1H), 1.01 (d, J=6.5 Hz, 3H). m/z (ESI, +ve ion) 497.7 (M+H)$^+$. GK-GKRP IC$_{50}$ (Binding)=0.660 μM; GK-GKRP EC$_{50}$ (LC MS/MS-2)=0.533 μM.

Example 169

2-(4-(4-(4-bromothiophen-3-ylsulfonyl)piperazin-1-yl)phenyl)-1,1,1,3,3,3-hexafluoro-2-propanol

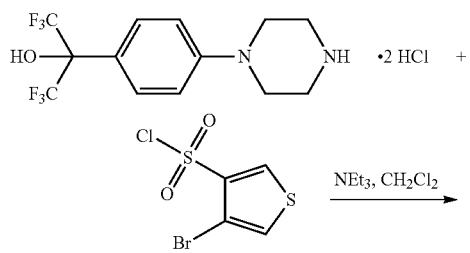

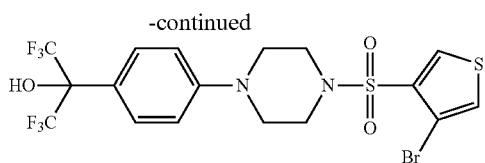

To a 20 mL vial containing 4-bromothiophene-3-sulfonyl chloride (0.20 g, 0.77 mmol, ASDI, Newark, Del.) was added a solution of 1,1,1,3,3,3-hexafluoro-2-(4-(piperazin-1-yl)phenyl)-2-propanol dihydrochloride (0.31 g, 0.77 mmol, Example 91) and triethylamine (0.53 mL, 3.8 mmol) in $CH_2Cl_2$ (7 mL). The solution was stirred at room temperature for 16 h. To the vial was added saturated aqueous sodium bicarbonate (4 mL) and the solution was stirred for 15 min. The solution was transferred onto a phase separation cartridge (Radleys Discovery Technologies, Essex, UK) with the organic phase being collected and passed through a plug of $Na_2SO_4$. The resulting solution was concentrated and purified by Prep-HPLC (Instrumentation: MS—Waters SQ; UV—Waters 2487 or Waters PD, Waters, Milford, Mass. Solvents: A: Water w/0.1% $NH_4OH$ B: Acetonitrile w/0.1% $NH_4OH$. Column: Phenomenex Gemini-NX $C_{18}$ 110 Å 5 µm 21×100. Flow Rate: 44 mL/min. 10 min Method, variable gradient over 8 min. Mass spectral data were acquired from 100-850 amu in electrospray positive mode) to afford 2-(4-(4-(4-bromothiophen-3-ylsulfonyl)piperazin-1-yl)phenyl)-1,1,1,3,3,3-hexafluoro-2-propanol (81 mg) as a white solid.
$^1$H NMR (400 MHz, DMSO-$d_6$) δ 8.43 (br s, 1H), 8.08 (d, J=5.1 Hz, 1H), 7.47 (d, J=9.0 Hz, 2H), 7.37 (d, J=5.1 Hz, 1H), 7.02 (d, J=9.0 Hz, 2H), 3.31-3.35 (m, 4H), 3.26-3.29 (m, 4H). m/z (ESI, +ve ion) 552.8 (M+H)$^+$. GK-GKRP IC$_{50}$ (Binding)=0.816 µM.

Example 170

2-(4-((S)-2-((1H-imidazol-1-yl)methyl)-4-(thiophen-2-yl sulfonyl)piperazin-1-yl)phenyl)-1,1,1-trifluoro-2-propanol

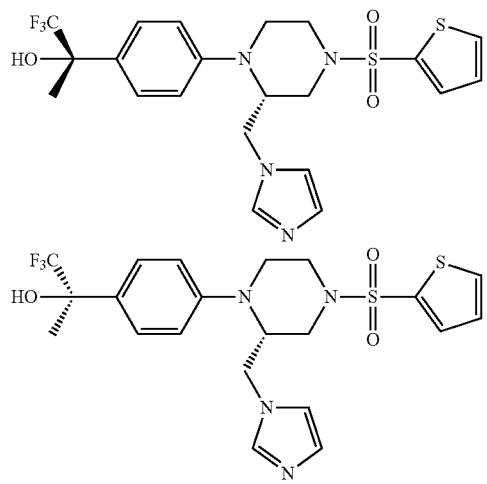

To a 50-mL round-bottomed flask was added ((2R)-4-(thiophen-2-ylsulfonyl)-1-(4-(1,1,1-trifluoro-2-hydroxypropan-2-yl)phenyl)piperazin-2-yl)methyl methanesulfonate (38 mg, 0.072 mmol, Intermediate B), imidazole (7 mg, 0.11 mmol, Aldrich, St. Louis, Mo.) and cesium carbonate (46 mg, 0.14 mmol) in acetonitrile (2 mL). The reaction mixture was stirred at 80° C. for 18 h. The reaction mixture was diluted with water (10 mL) and extracted with $CH_2Cl_2$ (2×40 mL). The organic extracts were washed with saturated NaCl (10 mL) and dried over $Na_2SO_4$. The solution was filtered and concentrated in vacuo to give the crude material as an off-white glass. The crude product was purified by silica gel chromatography, eluting with 5% MeOH in EtOAc to give 2-(4-((S)-2-((1H-imidazol-1-yl)methyl)-4-(thiophen-2-ylsulfonyl)piperazin-1-yl)phenyl)-1,1,1-trifluoro-2-propanol (28 mg) as a white solid.

(2S)-1,1,1-trifluoro-2-(4-((2S)-2-(1H-imidazol-1-ylmethyl)-4-(2-thiophenylsulfonyl)-1-piperazinyl)phenyl)-2-propanol; (2R)-1,1,1-trifluoro-2-(4-((2S)-2-(1H-imidazol-1-ylmethyl)-4-(2-thiophenylsulfonyl)-1-piperazinyl)phenyl)-2-propanol
$^1$H NMR (300 MHz, CDCl$_3$) δ 1.76 (s, 3H) 2.57-2.71 (m, 2H) 3.28-3.41 (m, 1H) 3.45-3.55 (m, 1H) 3.63-3.72 (m, 1H) 3.85-3.99 (m, 2H) 4.04-4.09 (m, 1H) 4.40 (dd, J=13.59, 9.35 Hz, 3H) 6.85 (d, J=8.62 Hz, 2H) 6.96 (s, 1H) 7.03 (s, 1H) 7.17 (dd, J=5.12, 3.80 Hz, 1H) 7.46 (s, 1H) 7.51 (d, J=8.77 Hz, 2H) 7.57 (dd, J=3.80, 1.32 Hz, 1H) 7.66 (dd, J=4.97, 1.32 Hz, 1H). m/z (ESI, +ve ion) 500.9 (M+H)$^+$. GK-GKRP EC$_{50}$ (NADPH-coupled)=0.762 µM; GK-GKRP EC$_{50}$ (LC MS/MS-2)=0.942 µM.

Example 171

2-(4-((S)-2-((5H-pyrrolo[2,3-b]pyrazin-5-yl)methyl)-4-(thiophen-2-ylsulfonyl)piperazin-1-yl)phenyl)-1,1,1-trifluoro-2-propanol

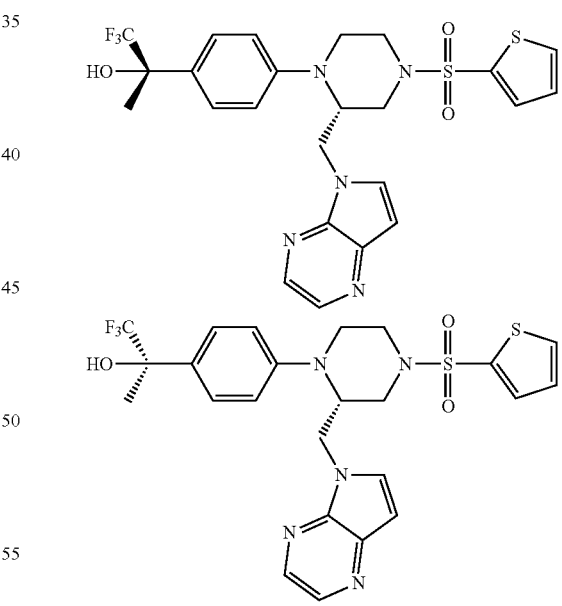

To a 50-mL round-bottomed flask was added ((2R)-4-(thiophen-2-ylsulfonyl)-1-(4-(1,1,1-trifluoro-2-hydroxypropan-2-yl)phenyl)piperazin-2-yl)methyl methanesulfonate (50 mg, 0.095 mmol, Intermediate B), 5H-pyrrolo[2,3-b]pyrazine (17 mg, 0.142 mmol, ARK Pharm., Libertyville, Ill.) and cesium carbonate (62 mg, 0.19 mmol) in acetonitrile (2 mL). The reaction mixture was stirred at 80° C. for 18 h. The mixture was allowed to cool to room temperature. The reaction mixture was diluted with water (10 mL) and extracted with EtOAc (2×40 mL). The organic extract was washed with saturated NaCl (10 mL) and dried over Na₂SO₄. The solution was filtered and concentrated in vacuo to give the crude material as an off-white glass. The crude product was purified by silica gel chromatography, eluting with 100% EtOAc to give 2-(4-((S)-2-((5H-pyrrolo[2,3-b]pyrazin-5-yl)methyl)-4-(thiophen-2-ylsulfonyl)piperazin-1-yl)phenyl)-1,1,1-trifluoro-2-propanol (38 mg) as a white solid.

(2S)-1,1,1-trifluoro-2-(4-((2S)-2-(5H-pyrrolo[2,3-b]pyrazin-5-ylmethyl)-4-(2-thiophenylsulfonyl)-1-piperazinyl)phenyl)-2-propanol; (2R)-1,1,1-trifluoro-2-(4-((2S)-2-(5H-pyrrolo[2,3-b]pyrazin-5-ylmethyl)-4-(2-thiophenylsulfonyl)-1-piperazinyl)phenyl)-2-propanol ¹H NMR (300 MHz, CDCl₃) δ 1.71 (s, 3H) 2.51-2.77 (m, 3H) 3.45-3.70 (m, 3H) 3.85-3.99 (m, 1H) 4.37-4.53 (m, 1H) 4.60-4.72 (m, 2H) 6.56 (dd, J=3.73, 0.95 Hz, 2H) 6.80-6.93 (m, 2H) 7.15 (dd, J=5.04, 3.73 Hz, 1H) 7.31 (dd, J=8.92, 2.34 Hz, 2H) 7.51-7.57 (m, 2H) 7.64 (dd, J=5.04, 1.24 Hz, 1H) 8.24 (d, J=2.48 Hz, 1H) 8.39 (dd, J=2.63, 1.02 Hz, 1H). m/z (ESI, +ve ion) 551.8 (M+H)⁺. GK-GKRP EC₅₀ (NADPH-coupled)=0.649 µM; GK-GKRP EC₅₀ (LC MS/MS-2)=0.801 µM.

Example 172

2-(4-((S)-2-((1H-pyrrolo[2,3-b]pyridin-1-yl)methyl)-4-(thiophen-2-yl sulfonyl)piperazin-1-yl)phenyl)-1,1,1-trifluoro-2-propanol as a white solid. Purification by silica gel chromatography, eluting with 50% EtOAc in hexanes gave 2-(4-((S)-2-((1H-pyrrolo[2,3-b]pyridin-1-yl)methyl)-4-(thiophen-2-ylsulfonyl)piperazin-1-yl)phenyl)-1,1,1-trifluoro-2-propanol (28 mg) as a mixture of two isomers.

(2S)-1,1,1-trifluoro-2-(4-((2S)-2-(1H-pyrrolo[2,3-b]pyridin-1-ylmethyl)-4-(2-thiophenylsulfonyl)-1-piperazinyl)phenyl)-2-propanol; (2R)-1,1,1-trifluoro-2-(4-((2S)-2-(1H-pyrrolo[2,3-b]pyridin-1-ylmethyl)-4-(2-thiophenylsulfonyl)-1-piperazinyl)phenyl)-2-propanol.

¹H NMR (300 MHz, CDCl₃) δ 1.71 (s, 3H) 2.29 (d, J=1.46 Hz, 1H) 2.50-2.66 (m, 2H) 3.47-3.72 (m, 3H) 3.83-3.98 (m, 1H) 4.45 (dd, J=13.30, 8.48 Hz, 1H) 4.61-4.79 (m, 2H) 6.35 (d, J=3.51 Hz, 1H) 6.96-7.02 (m, 2H) 7.05 (dd, J=7.89, 4.68 Hz, 1H) 7.14 (dd, J=4.97, 3.65 Hz, 1H); 7.26 (d, J=3.36 Hz, 1H, 7.33 (d, J=8.77 Hz, 2H) 7.53 (dd, J=3.80, 1.32 Hz, 1H) 7.62 (dd, J=4.97, 1.17 Hz, 1H) 7.82 (dd, J=7.75, 1.32 Hz, 1H) 8.32 (dd, J=4.68, 1.46 Hz, 1H). m/z (ESI, +ve ion) 550.8 (M+H)⁺. GK-GKRP EC₅₀ (NADPH-coupled)=0.253 µM; GK-GKRP EC₅₀ (LC MS/MS-2)=0.249 µM.

Example 173

1,1,1,3,3,3-hexafluoro-2-(4-(2-(3-methoxybenzyl)-4-(thiophen-2-ylsulfonyl)piperazin-1-yl)phenyl)-2-propanol

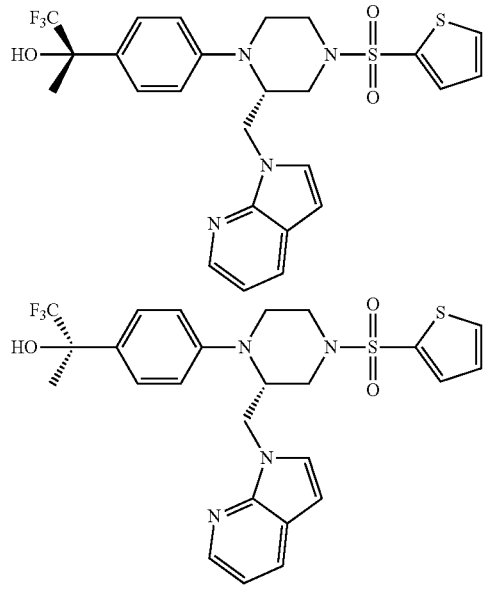

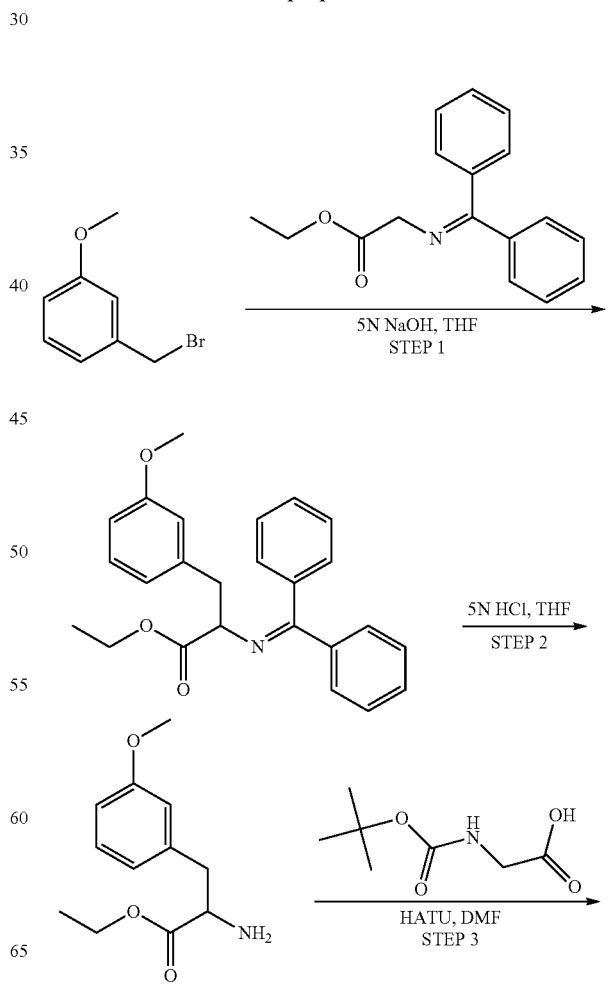

To a 50-mL round-bottomed flask was added ((2R)-4-(thiophen-2-ylsulfonyl)-1-(4-(1,1,1-trifluoro-2-hydroxypropan-2-yl)phenyl)piperazin-2-yl)methyl methanesulfonate (50 mg, 0.095 mmol, Intermediate B), 7-azaindole (16.76 mg, 0.142 mmol, Alfa Aesar, Ward Hill, Mass.) and cesium carbonate (62 mg, 0.19 mmol) in acetonitrile (2 mL). The reaction mixture was stirred at 80° C. for 18 h. The mixture was allowed to cool to room temperature. The reaction mixture was diluted with water (10 mL) and extracted with CH₂Cl₂ (2×30 mL). The organic extract was washed with saturated NaCl (10 mL) and dried over Na₂SO₄. The solution was filtered and concentrated in vacuo to give the crude material 333
-continued

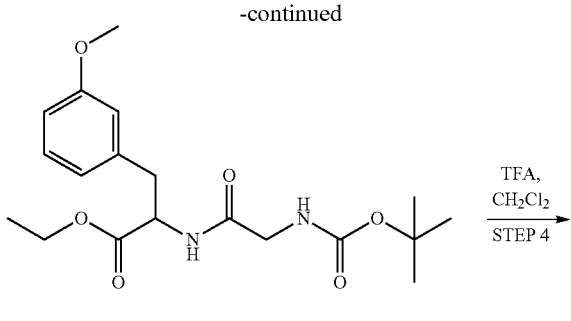

TFA, CH₂Cl₂
STEP 4

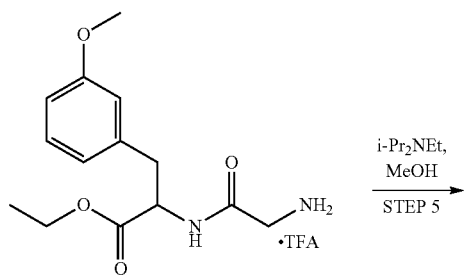

i-Pr₂NEt, MeOH
STEP 5

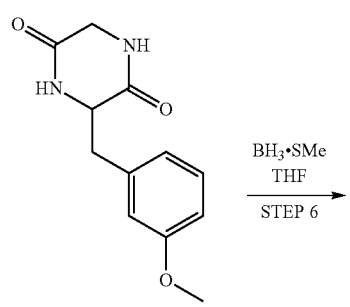

BH₃·SMe
THF
STEP 6

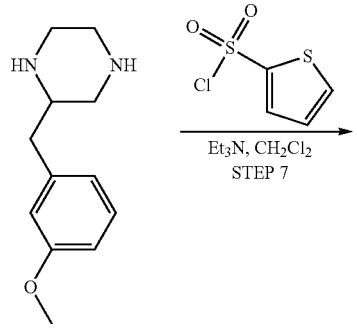

Et₃N, CH₂Cl₂
STEP 7

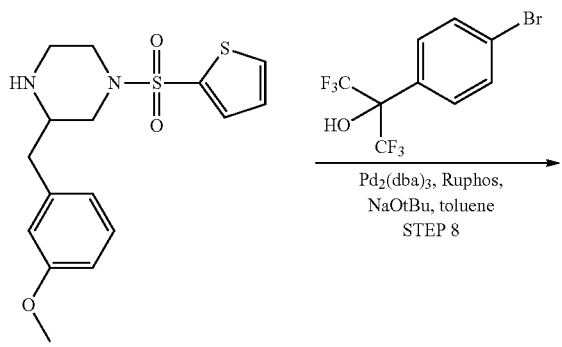

Pd₂(dba)₃, Ruphos, NaOtBu, toluene
STEP 8

334
-continued

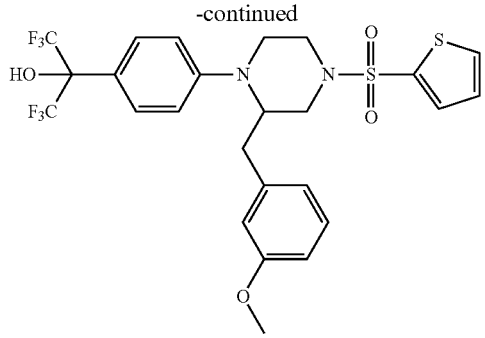

Step 1: ethyl N-(diphenylmethylidene)-3-methoxyphenylalaninate

To a 100-mL round-bottomed flask was added 3-methoxybenzyl bromide (0.73 mL, 5.22 mmol, Sigma-Aldrich, St. Louis, Mo.), ethyl N-(diphenylmethylene)glycinate (1.40 g, 5.22 mmol, Acros, Pittsburgh, Pa.), 5 M sodium hydroxide (5.22 mL, 26.1 mmol) and THF (20 mL). The reaction mixture was stirred at room temperature for 2 d. After that time, the mixture was diluted with water (30 mL) and extracted with EtOAc (2×60 mL). The organic extracts were washed with saturated NaCl (30 mL) and dried over Na₂SO₄. The solution was filtered and concentrated in vacuo to give the crude material as light-yellow oil. Purification by silica gel chromatography, eluting with 20% EtOAc in hexanes gave ethyl N-(diphenylmethylidene)-3-methoxyphenylalaninate (1.56 g).

Step 2: ethyl 3-methoxyphenylalaninate

To a 100-mL round-bottomed flask was added ethyl N-(diphenylmethylidene)-3-methoxyphenylalaninate (912 mg, 2.35 mmol), 5 M hydrochloric acid (0.471 mL, 2.35 mmol) and THF (20 mL). The reaction mixture was stirred at room temperature for 1 h. The solvent was removed in vacuo to give the crude product, ethyl 3-methoxyphenylalaninate which was used without further purification.

Step 3: ethyl N-(tert-butoxycarbonyl)glycyl-3-methoxyphenylalaninate

To a 100-mL round-bottomed flask was added ethyl 3-methoxyphenylalaninate (526 mg, 2.35 mmol), 2-(tert-butoxycarbonylamino)acetic acid (454 mg, 2.59 mmol, Sigma-Aldrich, St. Louis, Mo.), HATU (1.07 g, 2.82 mmol, Sigma-Aldrich, St. Louis, Mo.), Hünig's base (0.819 mL, 4.71 mmol) and DMF (5 mL). The reaction mixture was stirred at room temperature for 2 h then diluted with water (30 mL) and extracted with EtOAc (2×50 mL). The organic extract was washed with saturated aqueous NaCl (30 mL) and dried over Na₂SO₄. The solution was filtered and concentrated in vacuo to give the crude material as light-yellow oil. The crude product was purified by silica gel chromatography, eluting with 60% EtOAc in hexanes to give ethyl N-(tert-butoxycarbonyl)glycyl-3-methoxyphenylalaninate (822 mg).

Step 4: ethyl glycyl-3-methoxyphenylalaninate trifluoroacetate

To a 100-mL round-bottomed flask was added ethyl N-(tert-butoxycarbonyl)glycyl-3-methoxyphenylalaninate (812 mg, 2.13 mmol) and trifluoroacetic acid (5 mL, 67.3 mmol) in dichloromethane (5 mL). The reaction mixture was stirred at room temperature for 30 min. The solvent was removed in vacuo to give crude ethyl glycyl-3-methoxyphenylalaninate trifluoroacetate as a viscous oil which was used without purification.

Step 5: 3-(3-methoxybenzyl)-2,5-piperazinedione

To a 100-mL round-bottomed flask was added ethyl glycyl-3-methoxyphenylalaninate trifluoroacetate (598 mg, 2.13 mmol), Hünig's base (0.371 mL, 2.13 mmol), and MeOH (20 mL). The reaction mixture was stirred at 75° C. for 24 h. The mixture was allowed to cool to room temperature. The solid formed was collected by filtration and washed with MeOH to give 3-(3-methoxybenzyl)-2,5-piperazinedione (423 mg).

Step 6: 2-(3-methoxybenzyl)piperazine

To a 100-mL round-bottomed flask was added 3-(3-methoxybenzyl)-2,5-piperazinedione (201 mg, 0.858 mmol), 5 mL of THF and $BH_3$.DMS (0.326 mL, 3.43 mmol, Aldrich, St. Louis, Mo.). The reaction mixture was stirred at 70° C. for 18 h and then diluted with 1N NaOH (12 mL) and extracted with $CH_2Cl_2$ (2×50 mL). The organic extracts were washed with saturated aqueous NaCl (5 mL) and dried over $Na_2SO_4$. The solution was filtered and concentrated in vacuo to give the crude 2-(3-methoxybenzyl)piperazine (152 mg) as a colorless tar.

Step 7: 3-(3-methoxybenzyl)-1-(2-thiophenylsulfonyl)piperazine

To a 100-mL round-bottomed flask was added 2-(3-methoxybenzyl)piperazine (128 mg, 0.62 mmol), 5 mL of $CH_2Cl_2$, triethylamine (0.129 mL, 0.93 mmol) and 2-thiophenesulfonyl chloride (0.113 mL, 0.62 mmol, Aldrich, St. Louis, Mo.). The reaction mixture was stirred at 0° C. for 1 h and then diluted with aqueous saturated $NaHCO_3$ (5 mL) and extracted with EtOAc (2×30 mL). The organic extracts were washed with saturated NaCl (10 mL) and dried over $Na_2SO_4$. The solution was filtered and concentrated in vacuo to give the crude material as a light-yellow oil. The crude product was purified by silica gel chromatography, eluting with 5% MeOH in EtOAc to give 3-(3-methoxybenzyl)-1-(thiophen-2-ylsulfonyl)piperazine as a colorless oil (162 mg).

Step 8: 1,1,1,3,3,3-hexafluoro-2-(4-(2-(3-methoxybenzyl)-4-(thiophen-2-ylsulfonyl)piperazin-1-yl)phenyl)-2-propanol To a 50-mL round-bottomed flask was added 3-(3-methoxybenzyl)-1-(thiophen-2-ylsulfonyl)piperazine (48 mg, 0.14 mmol), tris(dibenzylideneacetone)dipalladium (0) (6 mg, 6.81 µmol, Strem, Newburyport, Mass.), dicyclohexyl(2',4',6'-triisopropyl-[1,1'-biphenyl]-2-yl)phosphine (RuPhos) (13 mg, 0.027 mmol, Strem Chemicals, Newburyport, Mass.), sodium tert-butoxide (33 mg, 0.34 mmol) and 2-(4-bromophenyl)-1,1,1,3,3,3-hexafluoro-2-propanol (53 mg, 0.16 mmol, Bioorg. Med. Chem. Lett. 2002, 12, 3009) in toluene (2 mL). The reaction mixture was stirred at 100° C. for 18 h. The mixture was cooled to room temperature and then diluted with saturated aqueous $NH_4Cl$ (10 mL) and extracted with EtOAc (2×30 mL). The organic extract was washed with saturated NaCl (10 mL) and dried over $Na_2SO_4$. The solution was filtered and concentrated in vacuo to give the crude material as light-yellow oil. The crude product was purified by silica gel chromatography, eluting with 20% EtOAc in hexanes to give 1,1,1,3,3,3-hexafluoro-2-(4-(2-(3-methoxybenzyl)-4-(thiophen-2-ylsulfonyl)piperazin-1-yl)phenyl)-2-propanol (41 mg) (racemic mixture) as a colorless tar.

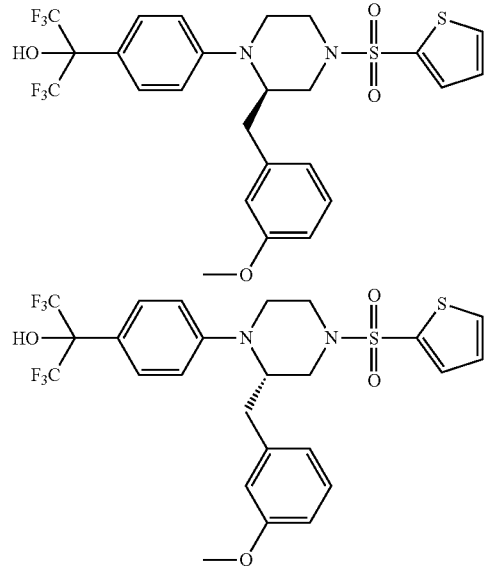

1,1,1,3,3,3-hexafluoro-2-(4-((2S)-2-(3-methoxybenzyl)-4-(2-thiophenylsulfonyl)-1-piperazinyl)phenyl)-2-propanol; 1,1,1,3,3,3-hexafluoro-2-(4-((2R)-2-(3-methoxybenzyl)-4-(2-thiophenylsulfonyl)-1-piperazinyl)phenyl)-2-propanol.

$^1$H NMR (300 MHz, $CDCl_3$) δ 2.40-2.70 (m, 3H) 3.19 (dd, J=13.01, 10.67 Hz, 1H) 3.32-3.62 (m, 3H) 3.74-3.82 (m, 1H) 3.84 (s, 3H) 3.86-3.95 (m, 1H) 3.99-4.07 (m, 1H) 6.75-6.98 (m, 5H) 7.14 (dd, J=4.97, 3.80 Hz, 1H) 7.24 (d, J=8.04 Hz, 1H) 7.54 (dd, J=3.80, 1.32 Hz, 1H) 7.57-7.65 (m, 3H). m/z (ESI, +ve ion) 594.8 (M+H)$^+$. GK-GKRP IC$_{50}$ (Binding)=0.542 µM.

Example 174

1,1,1,3,3,3-hexafluoro-2-(4-(2-(2-methoxybenzyl)-4-(thiophen-2-ylsulfonyl)piperazin-1-yl)phenyl)-2-propanol

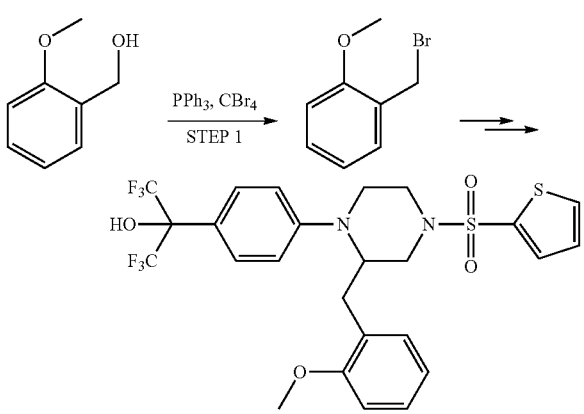

Step 1: 1-(bromomethyl)-2-methoxybenzene

To a 100-mL round-bottomed flask was added 2-methoxybenzyl alcohol (1.33 mL, 9.99 mmol, Aldrich, St. Louis, Mo.), triphenylphosphine (2.62 g, 9.99 mmol, Aldrich, St. Louis, Mo.) and carbon tetrabromide (0.969 mL, 9.99 mmol, Aldrich, St. Louis, Mo.) in dichloromethane (20 mL). The reaction mixture was stirred at room temperature for 4 h and then the solvent was removed in vacuo and the residue was purified by silica gel chromatography, eluting with 10% EtOAc in hexanes to give 1-(bromomethyl)-2-methoxybenzene (1.78 g) as a white solid.

Following to scheme described for Example 173, 1-(bromomethyl)-2-methoxybenzene delivered 1,1,1,3,3,3-hexafluoro-2-(4-(2-(2-methoxybenzyl)-4-(thiophen-2-ylsulfonyl)piperazin-1-yl)phenyl)-2-propanol as a mixture of two isomers.

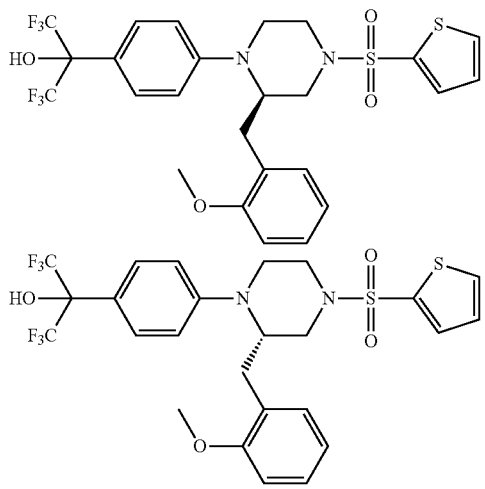

1,1,1,3,3,3-hexafluoro-2-(4-((2R)-2-(2-methoxybenzyl)-4-(2-thiophenylsulfonyl)-1-piperazinyl)phenyl)-2-propanol; 1,1,1,3,3,3-hexafluoro-2-(4-((2S)-2-(2-methoxybenzyl)-4-(2-thiophenylsulfonyl)-1-piperazinyl)phenyl)-2-propanol ¹H NMR (300 MHz, CDCl₃) δ 2.42-2.61 (m, 2H) 2.89 (dd, J=12.72, 3.65 Hz, 1H) 3.09 (dd, J=12.86, 10.38 Hz, 1H) 3.33 (s, 1H) 3.40-3.59 (m, 2H) 3.65-3.73 (m, 1H) 3.78 (s, 3H) 3.84-3.94 (m, 1H) 4.17-4.27 (m, 1H) 6.80 (d, J=7.89 Hz, 1H) 6.88-7.02 (m, 3H) 7.13 (dd, J=4.97, 3.95 Hz, 1H) 7.10-7.33 (m, 2H) 7.48-7.57 (m, 3H) 7.61 (dd, J=4.97, 1.46 Hz, 1H). m/z (ESI, +ve ion) 594.8 (M+H)⁺. GK-GKRP IC₅₀ (Binding)=0.167 µM; GK-GKRP EC₅₀ (LC MS/MS-2)=0.114 µM.

Example 175

1,1,1,3,3,3-hexafluoro-2-(4-(2-(4-methoxybenzyl)-4-(thiophen-2-ylsulfonyl)piperazin-1-yl)phenyl)-2-propanol

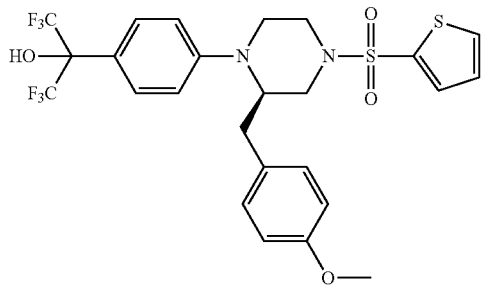

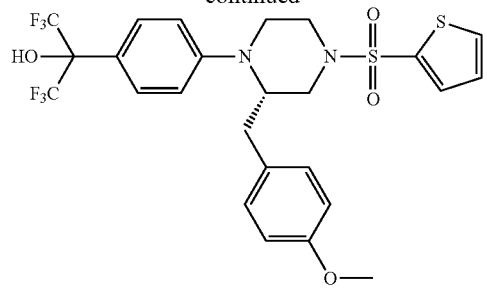

Following the scheme described for Example 173 using 1-(bromomethyl)-4-methoxybenzene (Sigma-Aldrich, St. Louis, Mo.) delivered 1,1,1,3,3,3-hexafluoro-2-(4-(2-(4-methoxybenzyl)-4-(thiophen-2-ylsulfonyl)piperazin-1-yl)phenyl)-2-propanol as a mixture of two isomers.

1,1,1,3,3,3-hexafluoro-2-(4-((2R)-2-(4-methoxybenzyl)-4-(2-thiophenylsulfonyl)-1-piperazinyl)phenyl)-2-propanol; 1,1,1,3,3,3-hexafluoro-2-(4-((2S)-2-(4-methoxybenzyl)-4-(2-thiophenylsulfonyl)-1-piperazinyl)phenyl)-2-propanol ¹H NMR (300 MHz, CDCl₃) δ 2.35-2.66 (m, 3H) 3.08-3.22 (m, 1H) 3.33-3.46 (m, 2H) 3.48-3.60 (m, 1H) 3.80 (s, 3H) 3.71-3.79 (m, 1H) 3.84-4.06 (m, 2H) 6.84-6.96 (m, 4H) 7.11-7.21 (m, 3H) 7.53 (dd, J=3.80, 1.32 Hz, 1H) 7.56-7.65 (m, 3H). m/z (ESI, +ve ion) 594.8 (M+H)⁺. GK-GKRP IC₅₀ (Binding)=2.87 µM.

Example 176

3-((1-(4-(1,1,1,3,3,3-hexafluoro-2-hydroxypropan-2-yl)phenyl)-4-(thiophen-2-ylsulfonyl)piperazin-2-yl)methyl)phenol

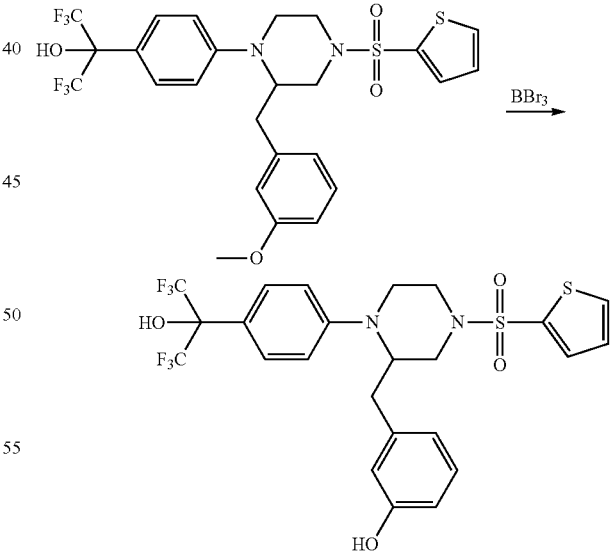

To a 50-mL round-bottomed flask was added 1,1,1,3,3,3-hexafluoro-2-(4-(2-(3-methoxybenzyl)-4-(thiophen-2-ylsulfonyl)piperazin-1-yl)phenyl)propan-2-ol (38 mg, 0.064 mmol, Example 175) and BBr₃ (0.025 mL, 0.256 mmol, Aldrich, St. Louis, Mo.) in DCE (3 mL). The reaction mixture was stirred at 80° C. for 2 h and then diluted with saturated NaHCO₃ (20 mL) and extracted with EtOAc (2×30 mL). The organic extracts were washed with saturated aqueous NaCl (10 mL) and dried over Na₂SO₄. The solution was filtered and concentrated in vacuo to give the crude material as a light-yellow glass. The crude product was purified by silica gel chromatography, eluting with 40% EtOAc in hexanes to give 3-((1-(4-(1,1,1,3,3,3-hexafluoro-2-hydroxypropan-2-yl)phenyl)-4-(thiophen-2-ylsulfonyl)piperazin-2-yl)methyl)phenol (32 mg) (racemic mixture) as a light-yellow tar.

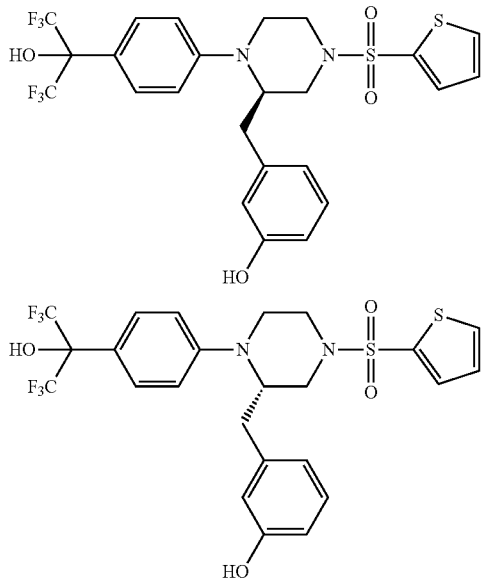

3-(((2R)-4-(2-thiophenylsulfonyl)-1-(4-(2,2,2-trifluoro-1-hydroxy-1-(trifluoromethyl)ethyl)phenyl)-2-piperazinyl)methyl)phenol; 3-(((2S)-4-(2-thiophenylsulfonyl)-1-(4-(2,2,2-trifluoro-1-hydroxy-1-(trifluoromethyl)ethyl)phenyl)-2-piperazinyl)methyl)phenol.

¹H NMR (300 MHz, CDCl₃) δ 2.41-2.66 (m, 3H) 3.08-3.20 (m, 1H) 3.32-3.60 (m, 4H) 3.71-4.08 (m, 3H) 5.56 (s, 1H) 6.68-6.84 (m, 3H) 6.92 (d, J=9.21 Hz, 2H) 7.11-7.24 (m, 2H) 7.51-7.68 (m, 4H). m/z (ESI, +ve ion) 580.7 (M+H)⁺. GK-GKRP EC₅₀ (NADPH-coupled)=1.81 μM.

Example 177

4-((1-(4-(1,1,1,3,3,3-hexafluoro-2-hydroxypropan-2-yl)phenyl)-4-(thiophen-2-ylsulfonyl)piperazin-2-yl)methyl)phenol

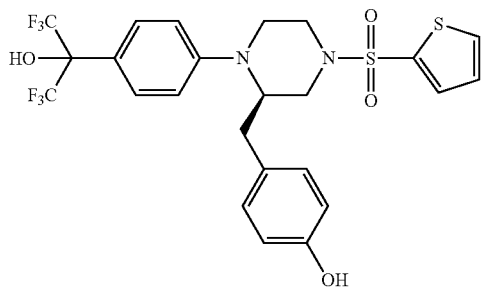

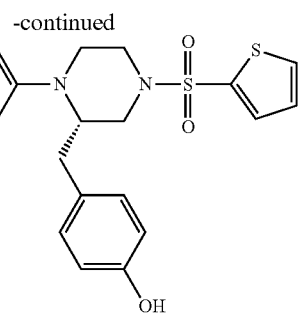

Following the procedure described for Example 176 using 1,1,1,3,3,3-hexafluoro-2-(4-(2-(4-methoxybenzyl)-4-(thiophen-2-ylsulfonyl)piperazin-1-yl)phenyl)-2-propanol (Example 176) gave 4-((1-(4-(1,1,1,3,3,3-hexafluoro-2-hydroxypropan-2-yl)phenyl)-4-(thiophen-2-ylsulfonyl)piperazin-2-yl)methyl)phenol (racemic mixture) as a viscous colorless oil.

3-(((2R)-4-(2-thiophenylsulfonyl)-1-(4-(2,2,2-trifluoro-1-hydroxy-1-(trifluoromethyl)ethyl)phenyl)-2-piperazinyl)methyl)phenol; 3-(((2S)-4-(2-thiophenylsulfonyl)-1-(4-(2,2,2-trifluoro-1-hydroxy-1-(trifluoromethyl)ethyl)phenyl)-2-piperazinyl)methyl)phenol.

¹H NMR (300 MHz, CDCl₃) δ 2.42-2.65 (m, 3H) 3.13 (dd, J=13.01, 10.67 Hz, 1H) 3.32-3.58 (m, 4H) 3.70-3.80 (m, 1H) 3.85-4.05 (m, 2H) 4.86 (s, 1H) 6.79 (d, J=8.48 Hz, 2H) 6.91 (d, J=9.21 Hz, 2H) 7.08-7.18 (m, 3H) 7.51-7.66 (m, 4H). m/z (ESI, +ve ion) 580.8 (M+H)⁺. GK-GKRP IC₅₀ (Binding)=0.786 μM;

Example 178

2-((1-(4-(1,1,1,3,3,3-hexafluoro-2-hydroxypropan-2-yl)phenyl)-4-(thiophen-2-ylsulfonyl)piperazin-2-yl)methyl)phenol

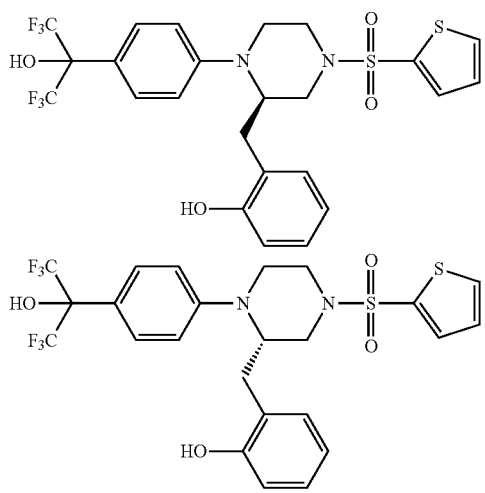

Following the procedure described for Example 176, 1,1,1,3,3,3-hexafluoro-2-(4-(2-(2-methoxybenzyl)-4-(thiophen-2-ylsulfonyl)piperazin-1-yl)phenyl)-2-propanol (Example 177) delivered 2-((1-(4-(1,1,1,3,3,3-hexafluoro-2-hydroxypropan-2-yl)phenyl)-4-(thiophen-2-ylsulfonyl)piperazin-2-yl)methyl)phenol (racemic mixture) as a light-yellow tar.

2-(((2R)-4-(2-thiophenylsulfonyl)-1-(4-(2,2,2-trifluoro-1-hydroxy-1-(trifluoromethyl)ethyl)phenyl)-2-piperazinyl)methyl)phenol; 2-(((2S)-4-(2-thiophenylsulfonyl)-1-(4-(2,2,2-trifluoro-1-hydroxy-1-(trifluoromethyl)ethyl)phenyl)-2-piperazinyl)methyl)phenol $^1$H NMR (300 MHz, CDCl$_3$) δ 2.46-2.68 (m, 2H) 2.86 (dd, J=13.45, 3.65 Hz, 1H) 3.17 (dd, J=13.45, 10.82 Hz, 1H) 3.33-3.71 (m, 4H) 3.82-3.93 (m, 1H) 4.19-4.33 (m, 1H) 5.12 (s, 1H) 6.68-6.79 (m, 1H) 6.87-7.24 (m, 6H) 7.49-7.68 (m, 4H). m/z (ESI, +ve ion) 580.7 (M+H)$^+$. GK-GKRP IC$_{50}$ (Binding)=0.17 µM; GK-GKRP EC$_{50}$ (LC MS/MS-2)=0.084 µM.

Example 179

4-(((2S)-4-(2-thiophensulfonyl)-1-(4-(2,2,2-trifluoro-1-hydroxy-1-methylethyl)phenyl)-2-piperazinyl)methyl)-2-piperazinone

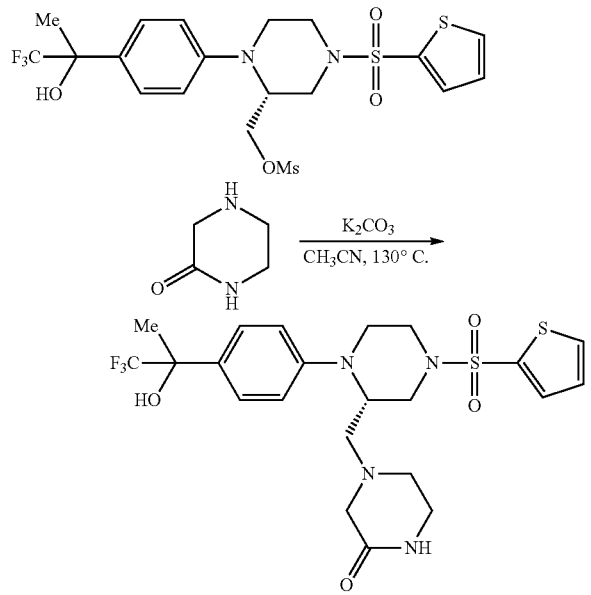

((2R)-4-(2-thiophenylsulfonyl)-1-(4-(2,2,2-trifluoro-1-hydroxy-1-methylethyl)phenyl)-2-piperazinyl)methyl methanesulfonate (100 mg, 0.189 mmol, Intermediate B) was combined with piperazin-2-one (18.9 mg, 0.189 mmol, Alfa-Aesar) and potassium carbonate (78 mg, 0.57 mmol, Sigma-Aldrich, St. Louis, Mo.) in acetonitrile (1.89 mL) and heated at 130° C. for 30 min. After the reaction was allowed to cool to room temperature, the mixture was diluted with EtOAc and the solids were removed by filtering through a 0.2 µm millipore Millex-FG filter (Millipore, Billerica, Mass.). After concentration of the filtrate, the crude residue was purified by silica gel chromatography (0 to 7% MeOH in CH$_2$Cl$_2$) followed by purification via reverse-phase HPLC (Phenomenex Gemini-NX 10µ, 110 Å, AXIA packed column, 100×50 mm, 60 mL/min, 10-95% CH$_3$CN/H$_2$O, 0.1% TFA, 10 min gradient). The collected fractions were partitioned between CH$_2$Cl$_2$ and saturated aqueous NaHCO$_3$ and then the organic extracts were dried (Na$_2$SO$_4$), filtered and concentrated. The residue was taken up in MeOH and was passed through an AccuBond SPE SCX cartridge eluting with 2M ammonia in MeOH to give the title compound (45 mg) as a mixture of two isomers.

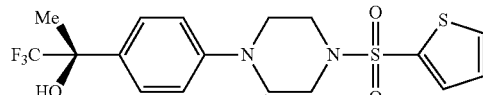
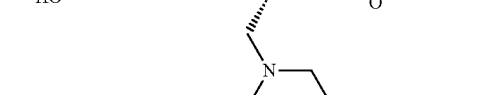

4-(((2S)-4-(2-thiophenylsulfonyl)-1-(4-((1S)-2,2,2-trifluoro-1-hydroxy-1-methylethyl)phenyl)-2-piperazinyl)methyl)-2-piperazinone; 4-(((2S)-4-(2-thiophenylsulfonyl)-1-(4-((1R)-2,2,2-trifluoro-1-hydroxy-1-methylethyl)phenyl)-2-piperazinyl)methyl)-2-piperazinone.

$^1$H NMR (400 MHz, CDCl$_3$) δ=1.74 (br. s., 3H), 2.37 (d, J=11.54 Hz, 1H), 2.54-2.70 (m, 3H), 2.77 (br. s., 1H), 2.87-3.05 (m, 2H), 3.12-3.46 (m, 5H), 3.73-4.17 (m, 3H), 6.03 (br. s., 1H), 6.82 (d, J=7.82 Hz, 2H), 7.18 (br. s., 1H), 7.44 (d, J=7.04 Hz, 2H), 7.58 (br. s., 1H), 7.66 (br. s., 1H). m/z (ESI, +ve ion) 532.8 (M)$^+$. GK-GKRP IC$_{50}$ (Binding)=0.542 µM; GK-GKRP EC$_{50}$ (LC MS/MS-2)=0.832 µM.

Example 180

3,3-dimethyl-4-(((2S)-4-(2-thiophenylsulfonyl)-1-(4-(2,2,2-trifluoro-1-hydroxy-1-methylethyl)phenyl)-2-piperazinyl)methyl)-2-piperazinone

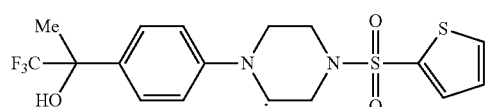

Following the procedure reported for Example 179, the reaction of ((2R)-4-(2-thiophenylsulfonyl)-1-(4-(2,2,2-trifluoro-1-hydroxy-1-methylethyl)phenyl)-2-piperazinyl)methyl methanesulfonate (102 mg, 0.193 mmol, Intermediate B), 3,3-dimethylpiperazin-2-one (26.0 mg, 0.203 mmol, ChemBridge, San Diego, Calif.), and potassium carbonate (80 mg, 0.579 mmol, Sigma-Aldrich, St. Louis, Mo.) in acetonitrile (1.286 mL). Purification by silica gel chromatography (1.5 to 7% MeOH in CH$_2$Cl$_2$ gradient) delivered the title compound as a mixture of two isomers.

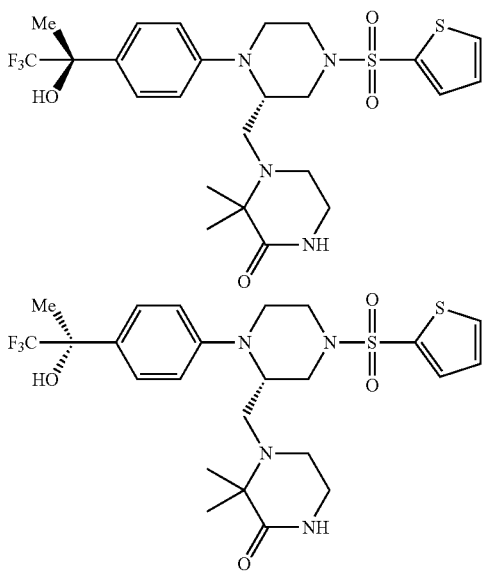

3,3-dimethyl-4-(((2S)-4-(2-thiophenylsulfonyl)-1-(4-((1R)-2,2,2-trifluoro-1-hydroxy-1-methylethyl)phenyl)-2-piperazinyl)methyl)-2-piperazinone; 3,3-dimethyl-4-((2S)-4-(2-thiophenylsulfonyl)-1-(4-((1S)-2,2,2-trifluoro-1-hydroxy-1-methylethyl)phenyl)-2-piperazinyl)methyl)-2-piperazinone ¹H NMR (400 MHz, CDCl₃) δ=1.27 (s, 3H), 1.34 (s, 3H), 1.76 (s, 3H), 2.37-2.46 (m, 2H), 2.53 (td, J=11.20, 3.62 Hz, 1H), 2.64 (d, J=8.22 Hz, 1H), 2.78-2.84 (m, 2H), 3.20 (br. s., 2H), 3.26-3.35 (m, 1H), 3.39-3.44 (m, 1H), 3.79 (d, J=9.39 Hz, 1H), 3.86 (br. s., 1H), 4.06 (d, J=10.95 Hz, 1H), 5.62 (br. s., 1H), 6.82 (d, J=8.80 Hz, 2H), 7.19 (dd, J=4.89, 3.72 Hz, 1H), 7.44 (d, J=8.61 Hz, 2H), 7.58-7.61 (m, 1H), 7.67 (dd, J=5.09, 1.17 Hz, 1H). m/z (ESI, +ve ion) 582.8 (M+Na)⁺. GK-GKRP IC$_{50}$ (Binding)=0.022 µM; GK-GKRP EC$_{50}$ (LC MS/MS-2)=0.051 µM.

The individual isomers were isolated via preparative SFC (Chiralpak® OZ-H (250×21 mm, 5 µm)) eluting with 70:30 liquid CO₂ in methanol:ethanol:isopropanol (1:1:1) (0.2% DEA) at a flow rate of 70 mL/min (40° C.), to give the two isomers in >99% diastereomeric excess and >99% purity:

First-Eluting Peak (Peak #1)

¹H NMR (400 MHz, CDCl₃)=1.26 (s, 3H), 1.34 (s, 3H), 1.76 (s, 3H), 2.41 (br s, 2H), 2.48-2.57 (m, 1H), 2.63 (d, J=8.41 Hz, 1H), 2.81 (br. s., 2H), 3.20 (br. s., 2H), 3.26-3.36 (m, 1H), 3.38-3.45 (m, 1H), 3.79 (d, J=10.76 Hz, 1H), 3.86 (br. s., 1H), 4.01-4.09 (m, 1H), 5.62 (br. s., 1H), 6.82 (d, J=8.61 Hz, 2H), 7.19 (t, J=4.21 Hz, 1H), 7.44 (d, J=8.41 Hz, 2H), 7.59 (d, J=3.13 Hz, 1H), 7.67 (d, J=5.09 Hz, 1H). m/z (ESI, +ve ion) 582.7 (M+Na)⁺. GK-GKRP IC$_{50}$ (Binding)=0.011 µM; GK-GKRP EC$_{50}$ (LC MS/MS-2)=0.040 µM.

Second Eluting Peak (Peak #2)

¹H NMR (400 MHz, CDCl₃) δ 1.26 (s, 3H), 1.34 (s, 3H), 1.76 (s, 3H), 2.42 (dd, J=13.79, 4.01 Hz, 1H), 2.46 (s, 1H), 2.53 (td, J=11.15, 3.33 Hz, 1H), 2.61-2.67 (m, 1H), 2.81 (t, J=5.09 Hz, 2H), 3.19 (br. s., 2H), 3.26-3.35 (m, 1H), 3.38-3.45 (m, 1H), 3.79 (d, J=10.17 Hz, 1H), 3.87 (d, J=8.02 Hz, 1H), 4.05 (d, J=11.35 Hz, 1H), 5.65 (br. s., 1H), 6.82 (d, J=8.61 Hz, 2H), 7.19 (t, J=4.40 Hz, 1H), 7.44 (d, J=8.41 Hz, 2H), 7.59 (d, J=3.52 Hz, 1H), 7.67 (d, J=5.09 Hz, 1H). m/z (ESI, +ve ion) 582.8 (M+Na)⁺. GK-GKRP IC$_{50}$ (Binding)=0.008 µM; GK-GKRP EC$_{50}$ (LC MS/MS-2)=0.042 µM.

Example 181

3-(1-methylethyl)-4-(((2S)-4-(2-thiophenylsulfonyl)-1-(4-(2,2,2-trifluoro-1-hydroxy-1-methylethyl)phenyl)-2-piperazinyl)methyl)-2-piperazinone

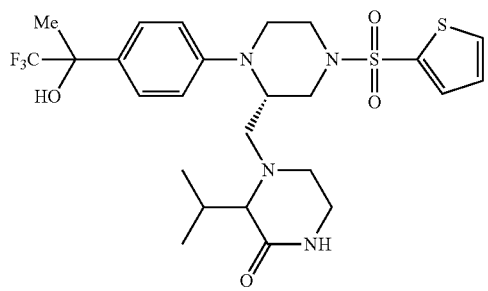

((2R)-4-(2-thiophenylsulfonyl)-1-(4-(2,2,2-trifluoro-1-hydroxy-1-methylethyl)phenyl)-2-piperazinyl)methyl methanesulfonate (250 mg, 0.473 mmol, Intermediate B), 3-isopropylpiperazin-2-one (67.3 mg, 0.473 mmol, ChemBridge, San Diego, Calif.), and potassium carbonate (196 mg, 1.419 mmol, Sigma-Aldrich, St. Louis, Mo.) in acetonitrile (3.15 mL) was heated to 120° C. for 30 min After the reaction was allowed to cool to room temperature, the mixture was diluted with EtOAc and the solids were removed by filtering through a 0.2 µm millipore Millex-FG filter (Millipore, Billerica, Mass.). After concentration of the filtrate, the crude residue was purified by reverse-phase HPLC, (Phenomenex Gemini-NX 10µ, 110 Å, AXIA packed column, 100×50 mm, 60 mL/min, 10-95% CH₃CN/H₂O, 0.1% TFA, 10 min gradient), two peaks were collected and each was partitioned between CH₂Cl₂ and saturated aqueous NaHCO₃, the organic layers were dried (Na₂SO₄), filtered and concentrated to give 4 isomeric products

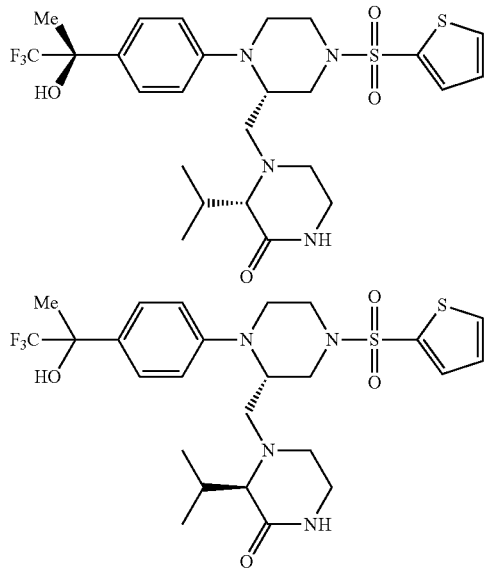

-continued

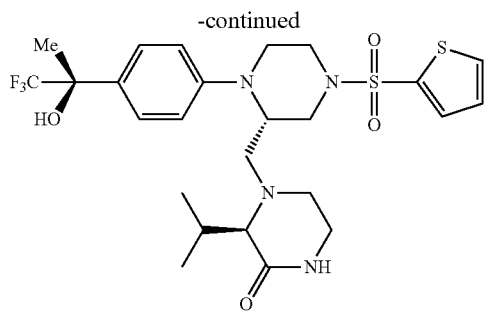

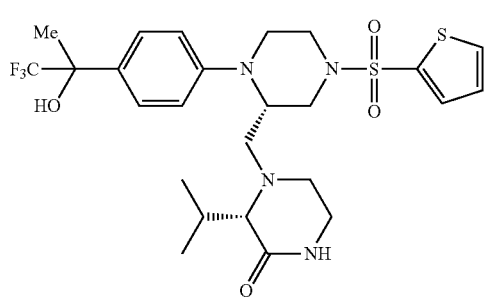 [SMILES: CC(C)C1C(=O)NCCN1C[C@H]1CN(S(=O)(=O)c2cccs2)CCN1c1ccc(C(C)(O)C(F)(F)F)cc1]

(3S)-3-(1-methylethyl)-4-(((2S)-4-(2-thiophenylsulfonyl)-1-(4-((1S)-2,2,2-trifluoro-1-hydroxy-1-methylethyl)phenyl)-2-piperazinyl)methyl)-2-piperazinone; (3S)-3-(1-methylethyl)-4-(((2 S)-4-(2-thiophenylsulfonyl)-1-(4-((1R)-2,2,2-trifluoro-1-hydroxy-1-methylethyl)phenyl)-2-piperazinyl) methyl)-2-piperazinone; (3R)-3-(1-methylethyl)-4-(((2S)-4-(2-thiophenylsulfonyl)-1-(4-((1R)-2,2,2-trifluoro-1-hydroxy-1-methylethyl)phenyl)-2-piperazinyl)methyl)-2-piperazinone; (3R)-3-(1-methylethyl)-4-(((2S)-4-(2-thiophenylsulfonyl)-1-(4-((1S)-2,2,2-trifluoro-1-hydroxy-1-methylethyl)phenyl)-2-piperazinyl)methyl)-2-piperazinone First Eluting Peak (Peak #1) (Mixture of Two Isomers)

¹H NMR (400 MHz, CDCl₃) δ=1.06 (d, J=6.65 Hz, 3H), 1.14 (d, J=6.85 Hz, 3H), 1.76 (s, 3H), 2.04-2.14 (m, 1H), 2.41-2.53 (m, 2H), 2.56-2.65 (m, 1H), 2.71 (dd, J=10.76, 2.74 Hz, 1H), 2.79 (br. s., 1H), 2.94-3.07 (m, 2H), 3.23 (td, J=11.74, 3.33 Hz, 3H), 3.39 (d, J=12.32 Hz, 1H), 3.76 (d, J=9.39 Hz, 1H), 3.84-3.91 (m, 1H), 3.94 (d, J=11.15 Hz, 1H), 5.73 (br. s., 2H), 6.84 (d, J=8.80 Hz, 2H), 7.18 (dd, J=4.99, 3.81 Hz, 1H), 7.45 (d, J=8.61 Hz, 2H), 7.59 (dd, J=3.72, 1.17 Hz, 1H), 7.66 (dd, J=5.09, 1.17 Hz, 1H). m/z (ESI, +ve ion) 596.9 (M+Na)⁺. GK-GKRP IC₅₀ (Binding)=0.043 μM; GK-GKRP EC₅₀ (LC MS/MS-2)=0.063 μM.

Second Eluting Peak (Peak #2) (Mixture of Two Isomers)

¹H NMR (400 MHz, CDCl₃) δ=1.06 (dd, J=8.90, 6.94 Hz, 6H), 1.75 (s, 3H), 2.03-2.12 (m, 1H), 2.46-2.58 (m, 2H), 2.59-2.67 (m, 1H), 2.70 (d, J=5.67 Hz, 1H), 2.83 (d, J=13.50 Hz, 1H), 2.99-3.07 (m, 1H), 3.16 (d, J=10.17 Hz, 1H), 3.19-3.30 (m, 2H), 3.39-3.47 (m, 2H), 3.80-3.90 (m, 2H), 4.11-4.18 (m, 1H), 5.77 (br. s., 1H), 6.79 (d, J=8.80 Hz, 2H), 7.20 (dd, J=4.89, 3.72 Hz, 1H), 7.44 (d, J=8.80 Hz, 2H), 7.60 (dd, J=3.72, 1.37 Hz, 1H), 7.67 (dd, J=4.89, 1.17 Hz, 1H). m/z (ESI, +ve ion) 596.8 (M+Na)⁺. GK-GKRP IC₅₀ (Binding)=0.001 μM; GK-GKRP EC₅₀ (LC MS/MS-2)=0.014 μM.

Example 182

(3S)-3-methyl-4-(((2S)-4-(2-thiophenylsulfonyl)-1-(4-(2,2,2-trifluoro-1-hydroxy-1-methylethyl)phenyl)-2-piperazinyl)methyl)-2-piperazinone

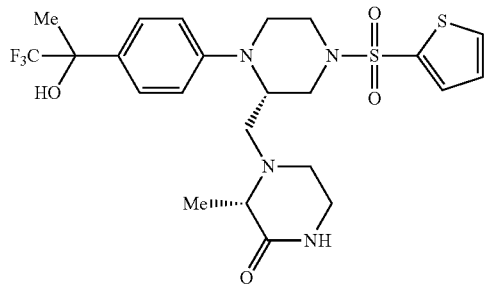 [SMILES: C[C@H]1C(=O)NCCN1C[C@H]1CN(S(=O)(=O)c2cccs2)CCN1c1ccc(C(C)(O)C(F)(F)F)cc1]

((2R)-4-(2-thiophenylsulfonyl)-1-(4-(2,2,2-trifluoro-1-hydroxy-1-methylethyl)phenyl)-2-piperazinyl)methyl methanesulfonate (100 mg, 0.189 mmol, Intermediate B) was combined with (S)-3-methylpiperazin-2-one (21.59 mg, 0.189 mmol, Fluka, St. Louis, Mo.) potassium carbonate (78 mg, 0.568 mmol, Sigma-Aldrich, St. Louis, Mo., St. Louis, Mo.) and acetonitrile (1.26 mL). This mixture was heated at 130° C. for 30 min. After the reaction was allowed to cool to room temperature, the mixture was diluted with EtOAc and the solids were removed by filtering through a 0.2 μm millipore Millex-FG filter (Millipore, Billerica, Mass.). The filtrate was concentrated and purified by silica gel chromatography (10-100% EtOAc in hexanes) and then by reverse-phase HPLC purification (Phenomenex Gemini-NX 10μ, 110 Å, AXIA packed column, 100×50 mm, 60 mL/min, 10-95% CH₃CN/H₂O, 0.1% TFA, 10 min gradient). The collected fractions were partitioned between CH₂Cl₂ and saturated aqueous NaHCO₃, the organic layer was dried (Na₂SO₄), filtered and concentrated. The residue was taken up in MeOH and was passed through an AccuBond SPE SCX cartridge eluting with 2M ammonia/MeOH, to give (3S)-3-methyl-4-(((2S)-4-(thiophen-2-ylsulfonyl)-1-(4-(1,1,1-trifluoro-2-hydroxypropan-2-yl)phenyl)piperazin-2-yl)methyl)-2-piperazinone as a mixture of two diastereomers.

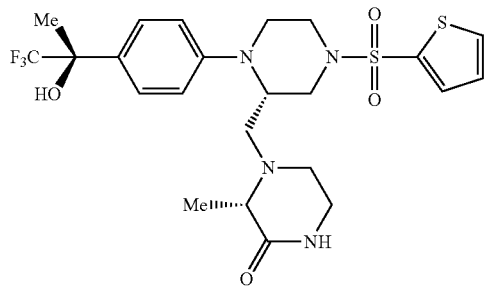

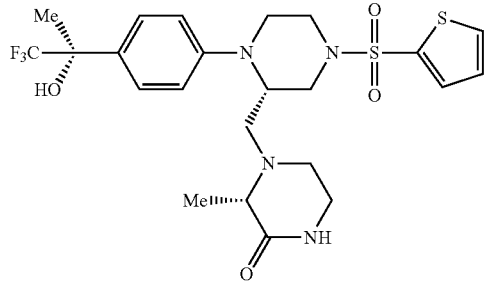

(3S)-3-methyl-4-(((2S)-4-(2-thiophenylsulfonyl)-1-(4-((1S)-2,2,2-trifluoro-1-hydroxy-1-methylethyl)phenyl)-2-piperazinyl)methyl)-2-piperazinone; (3S)-3-methyl-4-(((2S)-4-(2-thiophenylsulfonyl)-1-(4-((1R)-2,2,2-trifluoro-1-hydroxy-1-methylethyl)phenyl)-2-piperazinyl)methyl)-2-piperazinone ¹H NMR (400 MHz, CDCl₃) δ=1.33 (dd, J=6.94, 2.25 Hz, 3H), 1.75 (s, 3H), 2.42 (dt, J=13.01, 4.55 Hz, 1H), 2.48-2.62 (m, 2H), 2.67 (dd, J=10.95, 3.13 Hz, 1H), 2.93-3.07 (m, 2H), 3.14-3.30 (m, 4H), 3.37-3.44 (m, 1H), 3.81 (d, J=10.95 Hz, 1H), 3.87-3.94 (m, 1H), 4.02 (d, J=11.15 Hz, 1H), 5.70 (br. s., 1H), 6.83 (d, J=8.80 Hz, 2H), 7.19 (dd, J=4.99, 3.81 Hz, 1H), 7.44 (d, J=8.61 Hz, 2H), 7.59 (dd, J=3.72, 1.17 Hz, 1H), 7.66 (dd, J=4.99, 1.27 Hz, 1 H). m/z (ESI, +ve ion) 568.8 (M+Na)₊. GK-GKRP IC₅₀ (Binding)=0.046 μM; GK-GKRP EC₅₀ (LC MS/MS-2)=0.069 μM.

Example 183

5-methyl-4-(((2S)-4-(2-thiophenylsulfonyl)-1-(4-(2,2,2-trifluoro-1-hydroxy-1-methylethyl)phenyl)-2-piperazinyl)methyl)-2-piperazinone

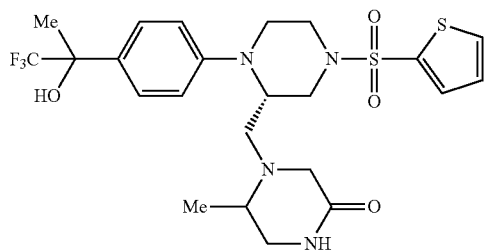 [SMILES: CC1CNC(=O)CN1C[C@H]1CN(S(=O)(=O)c2cccs2)CCN1c1ccc(C(C)(O)C(F)(F)F)cc1]

((2R)-4-(2-thiophenylsulfonyl)-1-(4-(2,2,2-trifluoro-1-hydroxy-1-methylethyl)phenyl)-2-piperazinyl)methyl methanesulfonate (350 mg, 0.662 mmol, Intermediate B) was combined with 5-methylpiperazin-2-one (79 mg, 0.695 mmol, Anichem, North Brunswick, N.J.), potassium carbonate (275 mg, 1.99 mmol, Sigma-Aldrich, St. Louis, Mo.) in acetonitrile (4.41 mL) was heated at 120° C. for 30 min. After the reaction was allowed to cool to room temperature, the mixture was diluted with EtOAc and the solids were removed by filtering through a 0.2 μm millipore Millex-FG filter (Millipore, Billerica, Mass.). The filtrate was concentrated and purified by reverse-phase HPLC (Phenomenex Gemini-NX 10μ, 110 Å, AXIA packed column, 100×50 mm, 60 mL/min, 10-95% CH₃CN/H₂O, 0.1% TFA, 10 min gradient). The collected fractions were partitioned between CH₂Cl₂ and saturated aqueous NaHCO₃, the organic layer was dried (Na₂SO₄), filtered and concentrated. The residue was taken up in MeOH and was passed through an AccuBond SPE SCX cartridge eluting with 2M ammonia/MeOH, to give the title compound (28 mg) as a mixture of four diastereomers.

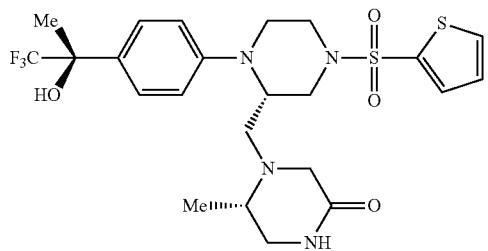

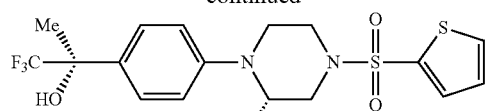

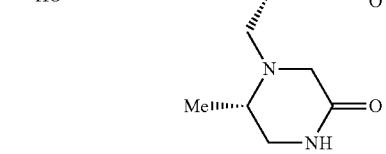

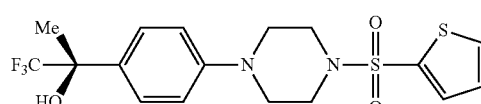

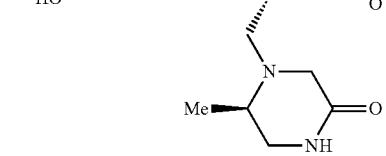

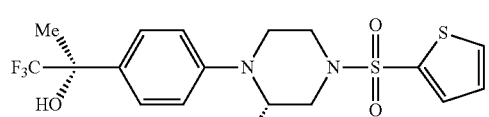

(5R)-5-methyl-4-(((2S)-4-(2-thiophenylsulfonyl)-1-(4-((1S)-2,2,2-trifluoro-1-hydroxy-1-methylethyl)phenyl)-2-piperazinyl)methyl)-2-piperazinone; (5R)-5-methyl-4-(((2S)-4-(2-thiophenylsulfonyl)-1-(4-((1R)-2,2,2-trifluoro-1-hydroxy-1-methylethyl)phenyl)-2-piperazinyl)methyl)-2-piperazinone; (5S)-5-methyl-4-(((2S)-4-(2-thiophenylsulfonyl)-1-(4-((1R)-2,2,2-trifluoro-1-hydroxy-1-methylethyl)phenyl)-2-piperazinyl)methyl)-2-piperazinone; (5S)-5-methyl-4-(((2S)-4-(2-thiophenylsulfonyl)-1-(4-((1R)-2,2,2-trifluoro-1-hydroxy-1-methylethyl)phenyl)-2-piperazinyl)methyl)-2-piperazinone.

¹H NMR (400 MHz, CDCl₃) δ=1.05-1.22 (m, 3H), 1.75 (s, 3H), 2.11 (d, J=12.72 Hz, 1H), 2.52-2.63 (m, 2H), 2.76 (d, J=3.72 Hz, 1H), 2.87-3.04 (m, 1H), 3.06-3.56 (m, 6H), 3.82 (d, J=11.35 Hz, 1H), 3.87-3.97 (m, 1H), 4.08 (t, J=10.47 Hz, 1H), 5.84 (d, J=18.00 Hz, 1H), 6.81 (t, J=7.43 Hz, 2H), 7.19 (t, J=4.21 Hz, 1H), 7.45 (d, J=8.41 Hz, 2H), 7.58 (br. s., 1H), 7.66 (d, J=4.89 Hz, 1H). m/z (ESI, +ve ion) 568.8 (M+Na)⁺. GK-GKRP IC₅₀ (Binding)=0.171 μM; GK-GKRP EC₅₀ (LC MS/MS-2)=0.287 μM

Example 184

4-(((S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone

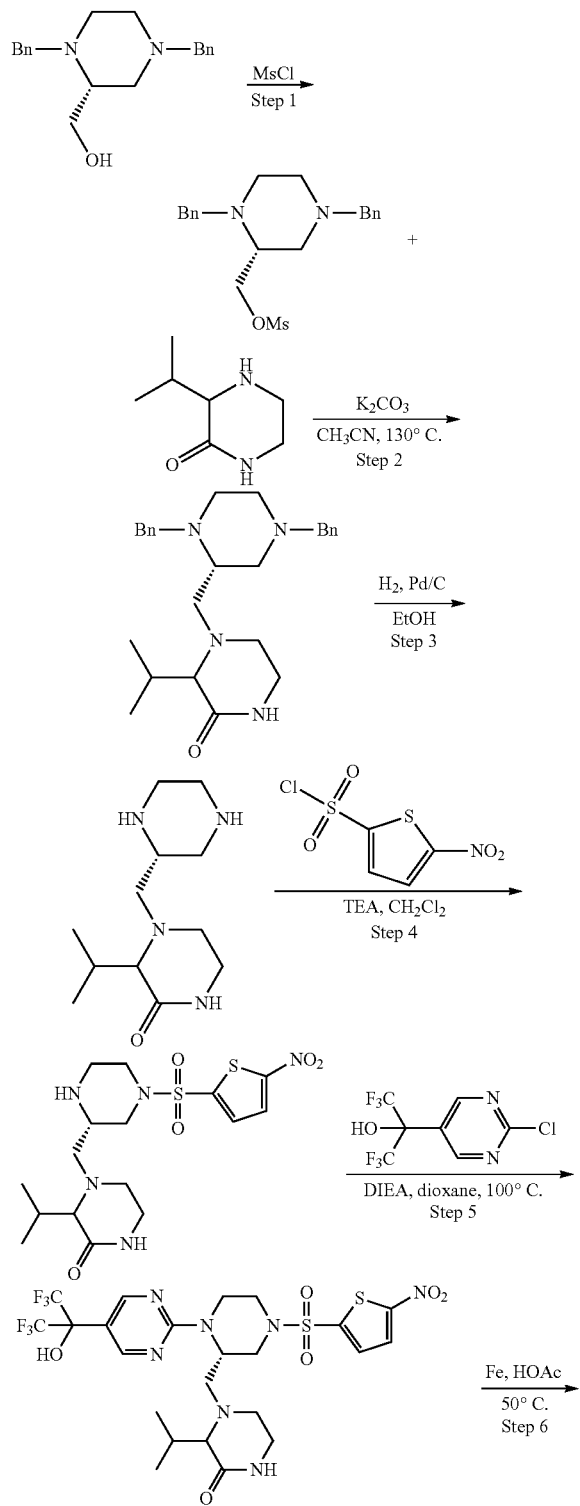

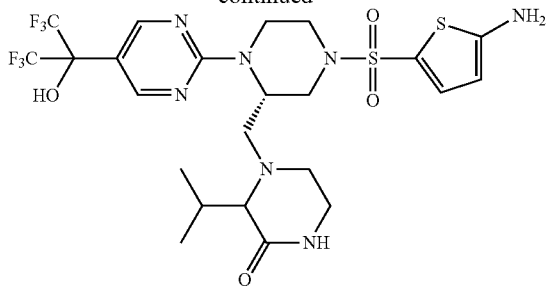

Step 1: ((2R)-1,4-dibenzyl-2-piperazinyl)methyl methanesulfonate

A mixture of (R)-(1,4-dibenzylpiperazin-2-yl)methanol (4.00 g, 13.49 mmol, US2007/0088039) and Hünig's base (2.35 mL, 13.49 mmol) in $CH_2Cl_2$ (27 mL) was stirred at 0° C. and methanesulfonyl chloride (1.04 mL, 13.49 mmol) was added drop-wise. The reaction mixture was filtered through a short pad of silica gel, using 19:1 $CH_2Cl_2/Et_2O$ (1000 mL) to rinse. The filtrate was concentrated in vacuo while maintaining the temperature below 25° C. Diethyl ether was added to the residue, the resulting slurry was placed in a sonicator for 1 min, filtered through a fitted funnel and the filtrate was concentrated to give a white solid ((2R)-1,4-dibenzyl-2-piperazinyl)methyl methanesulfonate (4.42 g).

Step 2: 4-(((2R)-1,4-dibenzyl-2-piperazinyl)methyl)-3-(1-methylethyl)-2-piperazinone ((2R)-1,4-dibenzyl-2-piperazinyl)methyl methanesulfonate (0.450 g, 1.202 mmol) was combined with 3-isopropylpiperazin-2-one (0.179 g, 1.262 mmol, ChemBridge, San Diego, Calif.) and potassium carbonate (0.498 g, 3.60 mmol, Sigma-Aldrich, St. Louis, Mo.) in acetonitrile (5.46 mL) and heated at 130° C. After 1 h, the mixture was diluted with EtOAc and the solids were removed by filtering through a 0.2 μm millipore Millex-FG filter (Millipore, Billerica, Mass.). After concentration, the crude residue was purified by silica gel chromatography (2.5-8.5% MeOH in $CH_2Cl_2$) to give 4-(((2R)-1,4-dibenzyl-2-piperazinyl)methyl)-3-(1-methylethyl)-2-piperazinone (212 mg).

Step 3: 3-(1-methylethyl)-4-((2R)-2-piperazinylmethyl)-2-piperazinone

A solution of 4-(((2R)-1,4-dibenzyl-2-piperazinyl)methyl)-3-(1-methylethyl)-2-piperazinone (0.414 g, 0.984 mmol) in ethanol (4.92 mL) was placed under an atmosphere of $N_2$ and charged with 10% palladium on carbon (10% wt. (dry basis) on activated carbon, wet, Degussa type (0.314 g, 0.295 mmol, Sigma-Aldrich, St. Louis, Mo.)). The mixture was purged with hydrogen gas and stirred at room temperature under a hydrogen atmosphere (1 atm) for 72 h. The solids were then removed by filtering through a pad of Celite® (diatomaceous earth), rinsing with EtOH, the filtrate was concentrated, and the product was carried forward without further purification (238 mg).

Step 4: 3-(1-methylethyl)-4-(((2S)-4-((5-nitro-2-thiophenyl)sulfonyl)-2-piperazinyl)methyl)-2-piperazinone To a stirred solution of 3-(1-methylethyl)-4-((2R)-2-piperazinylmethyl)-2-piperazinone (186 mg, 0.774 mmol) and triethylamine (324 µL, 2.32 mmol) in CH$_2$Cl$_2$ (5.00 mL) was added a solution of 5-nitrothiophene-2-sulfonyl chloride (190 mg, 0.836 mmol, Enamine, Kiev, Ukraine) in CH$_2$Cl$_2$ (1 mL) drop-wise at room temperature. The solution was stirred for 30 min and then the mixture was concentrated. The residue was dissolved in CH$_2$Cl$_2$, the organics were washed with water followed by brine. The combined organic extracts were dried (Na$_2$SO$_4$), filtered and concentrated. The residue was taken up in MeOH and was passed through an AccuBond SPE SCX cartridge eluting with 2M ammonia/MeOH to give 3-(1-methylethyl)-4-(((2S)-4-((5-nitro-2-thiophenyl)sulfonyl)-2-piperazinyl)methyl)-2-piperazinone (263 mg).

Step 5: 3-(1-methylethyl)-4-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-2-piperazinone To a 20-mL vial, 3-(1-methylethyl)-4-(((2S)-4-((5-nitro-2-thiophenyl)sulfonyl)-2-piperazinyl)methyl)-2-piperazinone (262 mg, 0.607 mmol), 2-(2-chloropyrimidin-5-yl)-1,1,1,3,3,3-hexafluoropropan-2-ol (170 mg, 0.607 mmol, Intermediate D) and Hünig's base (323 µL, 1.852 mmol) were dissolved into dioxane (3.77 mL). The vial was sealed and the reaction mixture was stirred at 100° C. for 12 h. After cooling to room temperature, the mixture was partitioned between water and EtOAc. The aqueous phase was extracted with EtOAc, and the combined organic phases were washed with brine. The organic phase was dried (Na$_2$SO$_4$), filtered and concentrated in vacuo. The crude residue was purified by silica gel chromatography (40 to 100% EtOAc in hexanes gradient) to give the title compound (228 mg).

Step 6: 4-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone 3-(1-methylethyl)-4-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-2-piperazinone (228 mg, 0.337 mmol) and iron filings (94 mg, 1.69 mmol, Sigma-Aldrich, St. Louis, Mo.) were combined in acetic acid (7.18 mL). The reaction mixture was stirred at 50° C. for 1.5 h. The mixture was allowed to cool to room temperature and saturated aqueous NaHCO$_3$ was slowly added. After partitioning with EtOAc, the aqueous phase was extracted with EtOAc (×3). The combined organic extracts were dried (Na$_2$SO$_4$), filtered and concentrated in vacuo to give a light brown oil. The crude product was purified by silica gel chromatography (25 to 75% EtOAc in hexanes gradient) to give a mixture of diastereomers which were separated via preparative SFC (Chrialpak® ASH (21×250 mm, 5 µm)), eluting with liquid CO$_2$ in 30% methanol with 20 mM NH$_3$, at a flow rate of 65 mL/min (40° C.), to give two products in >95% diastereomeric excess and >98% purity:

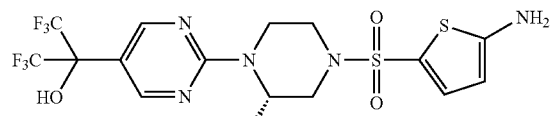

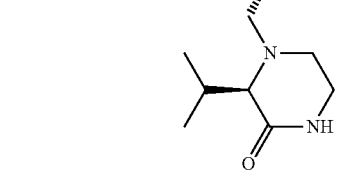

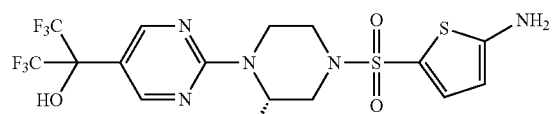

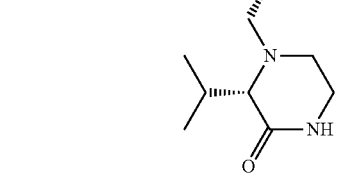

(3R)-4-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone; (3S)-4-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone First Eluting Peak (Peak #1)

$^1$H NMR (400 MHz, CD$_3$OD) δ=0.90 (d, J=6.65 Hz, 3H), 1.03 (d, J=6.85 Hz, 3H), 2.06 (dq, J=12.94, 6.64 Hz, 1H), 2.49 (td, J=11.83, 3.52 Hz, 1H), 2.58 (dd, J=11.54, 3.72 Hz, 1H), 2.67-2.80 (m, 2H), 2.86-2.96 (m, 2H), 3.04 (dt, J=12.32, 4.50 Hz, 1H), 3.16-3.30 (m, 2H), 3.35-3.42 (m, 1H), 3.73 (d, J=11.54 Hz, 1H), 3.91 (d, J=11.74 Hz, 1H), 4.70 (d, J=13.11 Hz, 1H), 4.97 (d, J=2.74 Hz, 1H), 6.04 (d, J=4.11 Hz, 1H), 7.21 (d, J=4.11 Hz, 1H), 8.56 (s, 2H). m/z (ESI, +ve ion) 667.8 (M+Na)$^+$. GK-GKRP IC$_{50}$ (Binding)=0.001 µM; GK-GKRP EC$_{50}$ (LC MS/MS-2)=0.012 µM.

Second Eluting Peak (Peak #2)

$^1$H NMR (400 MHz, CD$_3$OD) δ ppm 1.02 (d, J=6.65 Hz, 3H), 1.07 (d, J=6.85 Hz, 3H), 1.15 (d, J=6.06 Hz, 2H), 2.08-2.19 (m, 1H), 2.35-2.53 (m, 3H), 2.57-2.69 (m, 1H), 2.79 (d, J=4.89 Hz, 1H), 3.03-3.22 (m, 2H), 3.33-3.40 (m, 1H), 3.68 (d, J=11.35 Hz, 1H), 3.94 (d, J=11.93 Hz, 1H), 4.73 (d, J=13.69 Hz, 1H), 4.94 (d, J=9.78 Hz, 1H), 6.03 (d, J=4.11 Hz, 1H), 7.18 (d, J=4.11 Hz, 1H), 8.56 (s, 2H). m/z (ESI, +ve ion) 667.8 (M+Na)$^+$. GK-GKRP IC$_{50}$ (Binding)=0.001 µM; GK-GKRP EC$_{50}$ (LC MS/MS-2)=0.025 µM.

Example 185

3-(1-methylethyl)-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone

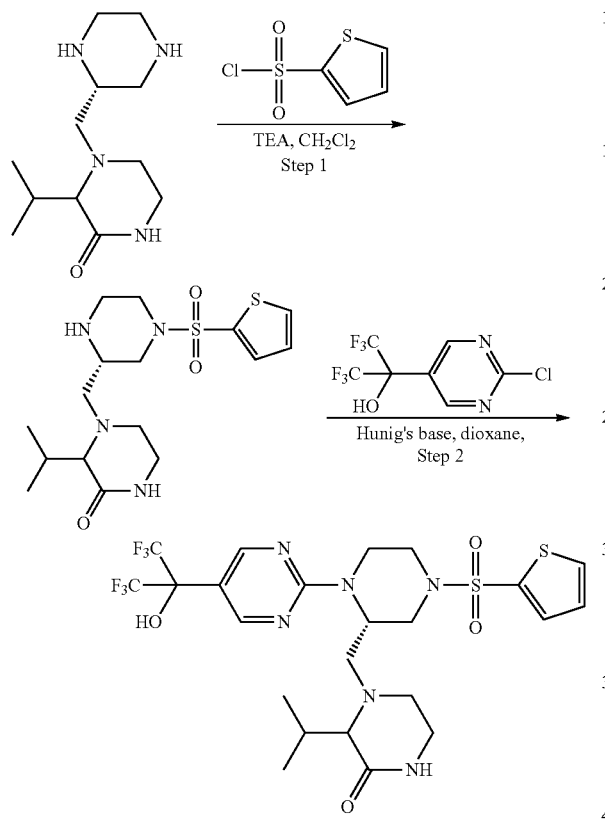

Step 1: 3-(1-methylethyl)-4-(((2S)-4-(2-thiophenylsulfonyl)-2-piperazinyl)methyl)-2-piperazinone To a stirred solution of 3-(1-methylethyl)-4-((2R)-2-piperazinylmethyl)-2-piperazinone (0.161 g, 0.670 mmol, Example 184) and triethylamine (0.290 mL, 2.083 mmol) in dichloromethane (5.82 mL) was added a solution of 2-thiophenesulfonyl chloride (0.138 g, 0.756 mmol, Sigma-Aldrich, St. Louis, Mo.) in $CH_2Cl_2$ (1 mL) drop-wise at room temperature. The solution was stirred for 30 min and then the mixture was concentrated. The residue was re-dissolved in $CH_2Cl_2$ and washed with water followed by brine. The organic layer was dried ($Na_2SO_4$), filtered, and concentrated to give 3-(1-methylethyl)-4-(((2S)-4-(2-thiophenylsulfonyl)-2-piperazinyl)methyl)-2-piperazinone (242 mg).

Step 2: 3-(1-methylethyl)-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone To a 20-mL vial were added 3-(1-methylethyl)-4-(425)-4-(2-thiophenylsulfonyl)-2-piperazinyl)methyl)-2-piperazinone (0.24 g, 0.62 mmol), 2-(2-chloropyrimidin-5-yl)-1,1,1,3,3,3-hexafluoro-2-propanol (0.26 g, 0.91 mmol, Intermediate D), Hünig's base (0.33 mL, 1.88 mmol) and dioxane (3.8 mL). The vial was sealed and the reaction mixture was stirred at 100° C. for 72 h. The reaction mixture was cooled to room temperature then partitioned between water and EtOAc. The aqueous phase was extracted with EtOAc (×3). The combined organic phases were washed with brine, dried ($Na_2SO_4$), filtered and concentrated in vacuo. The crude residue was purified by reverse-phase chromatography (Phenomenex Gemini-NX 10μ, 110 Å, AXIA packed column, 100×50 mm, 60 mL/min, 10 to 95% $CH_3CN/H_2O$, 0.1% TFA, 10 min gradient). The collected fractions were partitioned between $CH_2Cl_2$ and saturated aqueous $NaHCO_3$, the organic layer was dried ($Na_2SO_4$), filtered and concentrated to give the title compound (0.017 g), as a mixture of two isomers.

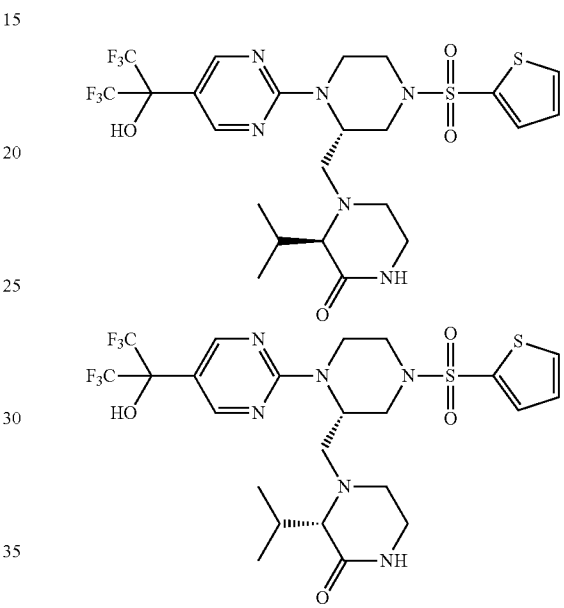

(3R)-3-(1-methylethyl)-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone; (3S)-3-(1-methylethyl)-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone.

$^1$H NMR (400 MHz, CDCl$_3$) δ=1.00 (d, J=6.65 Hz, 3H) 1.06 (d, J=6.65 Hz, 3H) 2.13 (dq, J=13.30, 6.65 Hz, 1H) 2.41-2.56 (m, 2H) 2.64 (dd, J=12.91, 4.69 Hz, 1H) 2.84 (d, J=13.69 Hz, 1H) 3.01-3.10 (m, 2H) 3.13-3.36 (m, 3H) 3.42-3.54 (m, 1H) 3.85 (d, J=11.35 Hz, 1H) 4.11 (d, J=11.54 Hz, 1H) 4.73 (d, J=13.30 Hz, 1H) 4.84-4.91 (m, 1H) 5.97 (br. s., 1H) 7.17 (dd, J=4.79, 4.01 Hz, 1H) 7.56-7.61 (m, 1H) 7.65 (dd, J=5.09, 0.78 Hz, 1H) 8.56 (s, 2H). m/z (ESI, +ve ion) 652.7 (M+Na)$^+$. GK-GKRP IC$_{50}$ (Binding)=0.001 μM; GK-GKRP EC$_{50}$ (LC MS/MS-2)=0.016 μM.

Example 186

1,1,1-trifluoro-2-(4-((2R)-2-((phenylsulfanyl)methyl)-4-(2-thiophenylsulfonyl)-1-piperazinyl)phenyl)-2-propanol

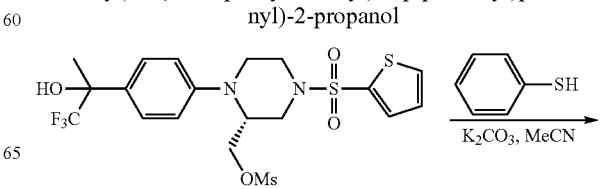

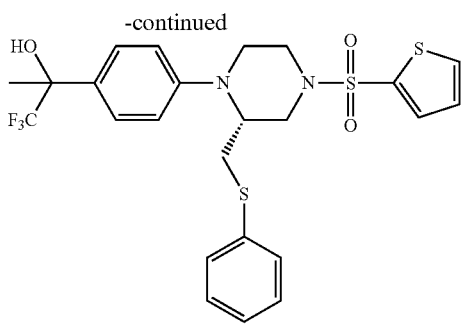

To a 5-mL microwave vial was added ((2R)-4-(thiophen-2-ylsulfonyl)-1-(4-(1,1,1-trifluoro-2-hydroxypropan-2-yl)phenyl)piperazin-2-yl)methyl methanesulfonate (0.200 g, 0.378 mmol, Intermediate B), potassium carbonate (0.105 g, 0.757 mmol), thiophenol (0.076 mL, 0.76 mmol, Aldrich, St. Louis, Mo.), and acetonitrile (3.0 mL). The vial was sealed and heated in an Initiator microwave reactor (Biotage AB, Inc., Uppsala, Sweden) at 140° C. for 40 min. The reaction mixture was filtered and the filtrate was concentrated. The crude product was purified by column chromatography (40 g of silica, 10 to 40% acetone in hexanes) to afford 1,1,1-trifluoro-2-(4-((2R)-2-((phenylsulfanyl)methyl)-4-(2-thiophenylsulfonyl)-1-piperazinyl)phenyl)-2-propanol (0.160 g) as a mixture of two isomers:

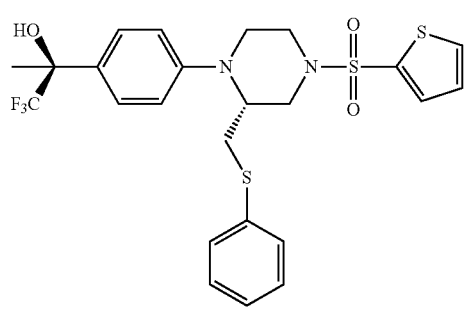

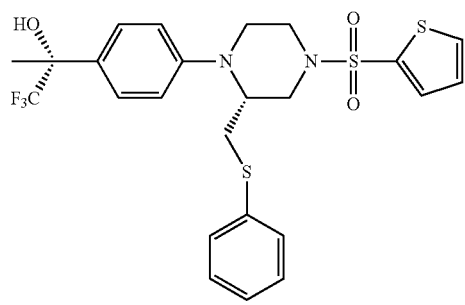

(2S)-1,1,1-trifluoro-2-(4-((2R)-2-((phenylsulfanyl)methyl)-4-(2-thiophenylsulfonyl)-1-piperazinyl)phenyl)-2-propanol, (2R)-1,1,1-trifluoro-2-(4-((2R)-2-((phenylsulfanyl)methyl)-4-(2-thiophenylsulfonyl)-1-piperazinyl)phenyl)-2-propanol.

$^1$H NMR (300 MHz, CDCl$_3$) δ=7.65 (dd, J=1.3, 5.1 Hz, 1H), 7.61 (dd, J=1.2, 3.7 Hz, 1H), 7.35 (d, J=8.6 Hz, 2H), 7.25 (s, 5H), 7.17 (dd, J=3.7, 5.0 Hz, 1H), 6.60 (d, J=8.9 Hz, 2H), 4.19 (d, J=11.7 Hz, 1H), 3.90-3.75 (m, 2H), 3.47-3.35 (m, 1H), 3.34-3.16 (m, 2H), 2.90 (d, J=13.4 Hz, 1H), 2.74-2.56 (m, 2H), 2.29 (d, J=2.3 Hz, 1H), 1.75 (d, J=2.6 Hz, 3H). m/z (ESI, +ve ion) 543.0 (M+H)$^+$. GK-GKRP IC$_{50}$ (Binding)=0.014 µM; GK-GKRP EC$_{50}$ (LC MS/MS-2)=0.024 µM Example 187

1,1,1-trifluoro-2-(4-((2R)-2-((phenylsulfonyl)methyl)-4-(2-thiophenylsulfonyl)-1-piperazinyl)phenyl)-2-propanol

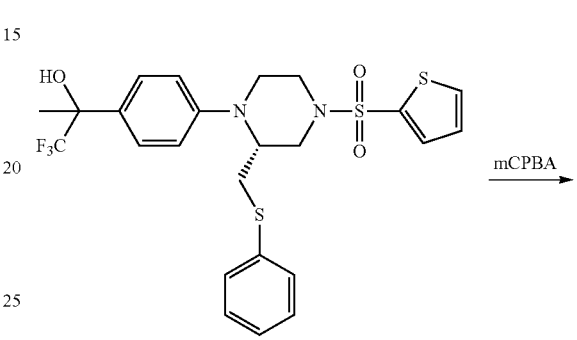

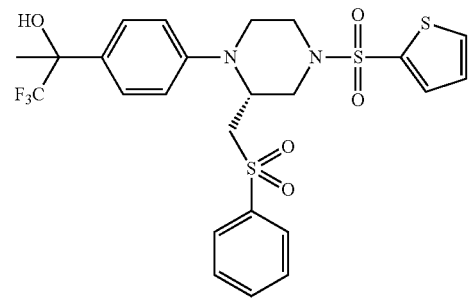

To a solution of 1,1,1-trifluoro-2-(4-((2R)-2-((phenylsulfanyl)methyl)-4-(2-thiophenylsulfonyl)-1-piperazinyl)phenyl)-2-propanol (0.150 g, 0.276 mmol, Example 186) in CH$_2$Cl$_2$ (3.0 mL) in 20-mL scintillation vial was added mCPBA (0.093 g, 0.420 mmol, Aldrich, St. Louis, Mo.). The resulting mixture was stirred at room temperature for 1 h, then partitioned between water (10 mL) and CH$_2$Cl$_2$ (30 mL). The aqueous layer was extracted with CH$_2$Cl$_2$ (2×10 mL). The combined organic extracts were dried over MgSO$_4$ and concentrated. The crude product was purified by column chromatography (40 g of silica, 10-20% EtOAc in hexanes) to afford 1,1,1-trifluoro-2-(4-((2R)-2-((phenylsulfonyl)methyl)-4-(2-thiophenylsulfonyl)-1-piperazinyl)phenyl)-2-propanol (0.080 g) as a mixture of two isomers. The individual isomers were separated using preparative SFC. The method used was as follows: (Chiralpak®AD-H column (250 mm×21 mm, 5 µm) eluting with 65% liquid CO$_2$ in 35% methanol with 20 mM ammonia at a flow rate of 70 mL/min). This method delivered two compounds with enantiomeric excesses >99%.

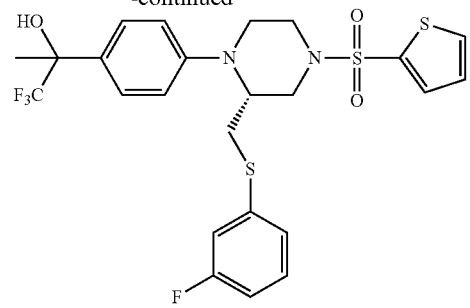

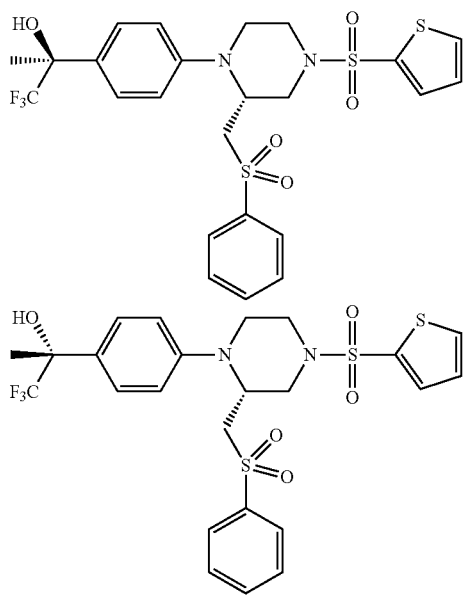

(2S)-1,1,1-trifluoro-2-(4-((2R)-2-((phenylsulfonyl)methyl)-4-(2-thiophenylsulfonyl)-1-piperazinyl)phenyl)-2-propanol;
(2R)-1,1,1-trifluoro-2-(4-((2R)-2-((phenylsulfonyl)methyl)-4-(2-thiophenylsulfonyl)-1-piperazinyl)phenyl)-2-propanol.

First Eluting Peak (Peak#1)

$^1$H NMR (300 MHz, CDCl$_3$) δ=7.91-7.82 (m, 2H), 7.72-7.63 (m, 2H), 7.61 (dd, J=1.2, 3.7 Hz, 1H), 7.59-7.50 (m, 2H), 7.40 (d, J=8.6 Hz, 2H), 7.19 (dd, J=3.8, 5.0 Hz, 1H), 6.79 (d, J=9.1 Hz, 2H), 4.52 (d, J=8.6 Hz, 1H), 4.21-4.10 (m, 1H), 3.90-3.70 (m, 2H), 3.46 (d, J=12.3 Hz, 1H), 3.09-2.94 (m, 2H), 2.78 (dd, J=1.5, 11.7 Hz, 1H), 2.63 (dt, J=3.4, 11.5 Hz, 1H), 2.32 (s, 1H), 1.75 (s, 3H). m/z (ESI, +ve ion) 575.0 (M+H)$^+$. GK-GKRP IC$_{50}$ (Binding)=0.041 μM; GK-GKRP EC$_{50}$ (LC MS/MS-2)=0.049 μM.

Second Eluting Peak (Peak#2)

$^1$H NMR (300 MHz, CDCl$_3$) δ=7.92-7.84 (m, 2H), 7.72-7.64 (m, 2H), 7.61 (dd, J=1.3, 3.8 Hz, 1H), 7.59-7.50 (m, 2H), 7.41 (d, J=8.8 Hz, 2H), 7.19 (dd, J=3.7, 5.0 Hz, 1H), 6.80 (d, J=9.1 Hz, 2H), 4.53 (d, J=9.1 Hz, 1H), 4.15 (d, J=11.8 Hz, 1H), 3.91-3.68 (m, 2H), 3.45 (d, J=12.6 Hz, 1H), 3.10-2.92 (m, 2H), 2.85-2.73 (m, 1H), 2.63 (dt, J=3.4, 11.5 Hz, 1H), 2.33 (br. s., 1H), 1.75 (s, 3H). m/z (ESI, +ve ion) 575.0 (M+H)$^+$. GK-GKRP IC$_{50}$ (Binding)=0.059 μM; GK-GKRP EC$_{50}$ (LC MS/MS-2)=0.052 μM.

Example 188

1,1,1-trifluoro-2-(4-((2R)-2-(((3-fluorophenyl)sulfanyl)methyl)-4-(2-thiophenylsulfonyl)-1-piperazinyl)phenyl)-2-propanol

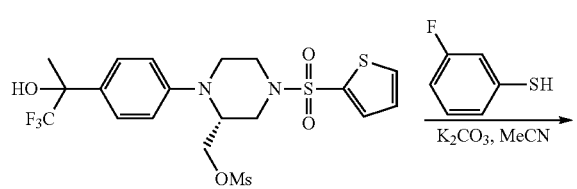

Following the procedure reported for Example 186, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and 3-fluorothiophenol (Aldrich, St. Louis, Mo.) delivered 1,1,1-trifluoro-2-(4-((2R)-2-(((3-fluorophenyl)sulfanyl)methyl)-4-(2-thiophenylsulfonyl)-1-piperazinyl)phenyl)-2-propanol as a mixture of two isomers:

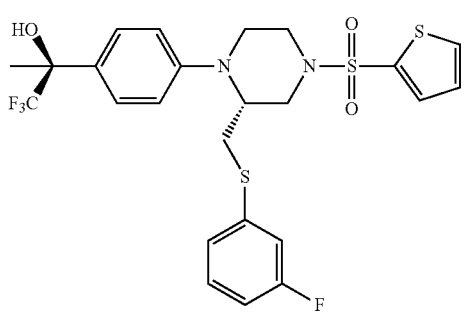

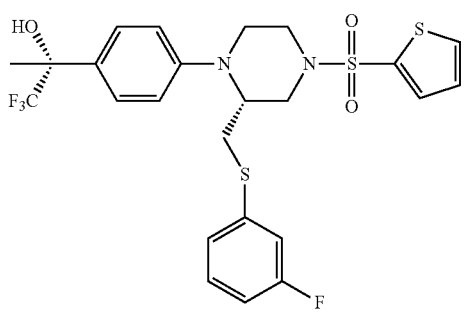

(2S)-1,1,1-trifluoro-2-(4-((2R)-2-(((3-fluorophenyl)sulfanyl)methyl)-4-(2-thiophenylsulfonyl)-1-piperazinyl)phenyl)-2-propanol; (2R)-1,1,1-trifluoro-2-(4-((2R)-2-(((3-fluorophenyl)sulfanyl)methyl)-4-(2-thiophenylsulfonyl)-1-piperazinyl)phenyl)-2-propanol.

$^1$H NMR (300 MHz, CDCl$_3$) δ=7.66 (dd, J=1.3, 5.0 Hz, 1H), 7.61 (dd, J=1.2, 3.7 Hz, 1H), 7.41 (d, J=8.9 Hz, 2H), 7.25-7.14 (m, 2H), 7.03-6.80 (m, 3H), 6.67 (d, J=9.1 Hz, 2H), 4.15 (dd, J=1.7, 11.5 Hz, 1H), 3.84 (t, J=8.8 Hz, 2H), 3.44-3.18 (m, 3H), 2.91 (d, J=14.2 Hz, 1H), 2.78-2.54 (m, 2H), 2.31 (s, 1H), 1.76 (d, J=1.0 Hz, 3H). m/z (ESI, +ve ion) 560.9

(M+H)+. GK-GKRP IC$_{50}$ (Binding)=0.112 μM; GK-GKRP EC$_{50}$ (LC MS/MS-2)=0.043 μM

Example 189

1,1,1-trifluoro-2-(4-((2R)-2-(((3-fluorophenyl)sulfonyl)methyl)-4-(2-thiophenylsulfonyl)-1-piperazinyl)phenyl)-2-propanol and 1,1,1-trifluoro-2-(4-((2R)-2-(((3-fluorophenyl)sulfinyl)methyl)-4-(2-thiophenylsulfonyl)-1-piperazinyl)phenyl)-2-propanol

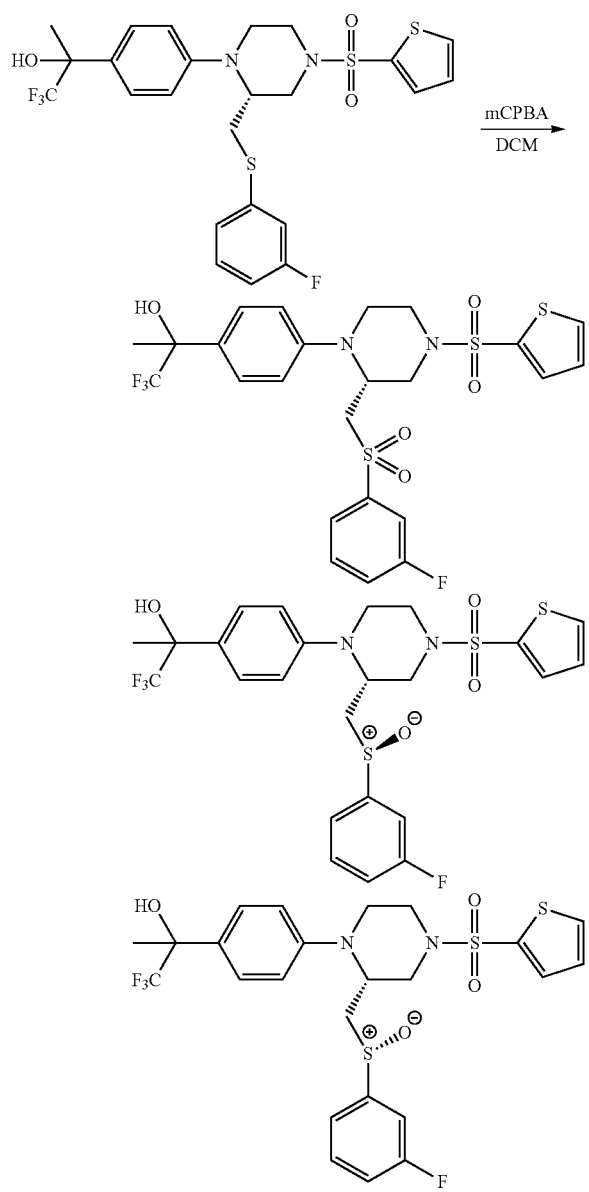

To a solution of 1,1,1-trifluoro-2-(4-((2R)-2-(((3-fluorophenyl)sulfanyl)methyl)-4-(2-thiophenylsulfonyl)-1-piperazinyl)phenyl)-2-propanol (0.330 g, 0.589 mmol, Example 188) in CH$_2$Cl$_2$ (3.0 mL) in 20 mL scintillation vial was added 3-chloroperoxybenzoic acid (0.066 g, 0.31 mmol, Aldrich, St. Louis, Mo.). The resulting mixture was stirred at room temperature for 15 h. The reaction mixture was partitioned between EtOAc (20 mL) and water (10 mL) and the aqueous layer was extracted with EtOAc (2×10 mL). The combined organic layers were dried over MgSO$_4$, filtered, and concentrated. The crude product was purified by column chromatography (40 g of silica gel, 15 to 40% EtOAc in hexanes) to separate the mixture into three peaks.

First Eluting Peak (Peak#1): 1,1,1-trifluoro-2-(4-((2R)-2-(((3-fluorophenyl)sulfonyl)methyl)-4-(2-thiophenylsulfonyl)-1-piperazinyl)phenyl)-2-propanol

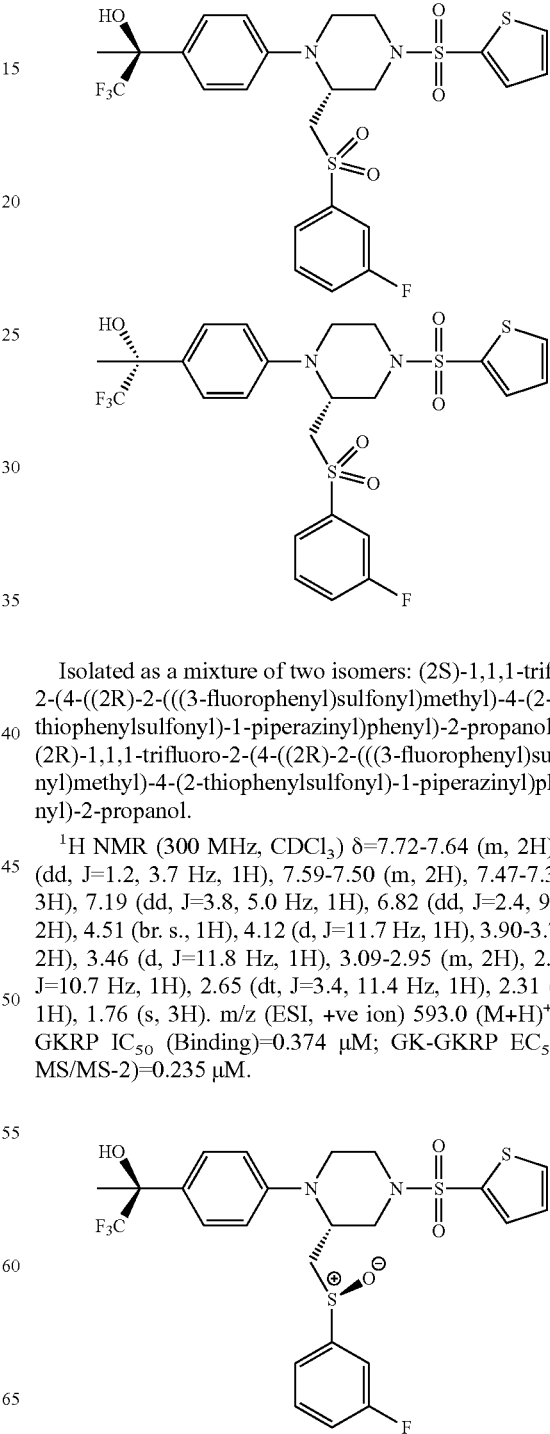

Isolated as a mixture of two isomers: (2S)-1,1,1-trifluoro-2-(4-((2R)-2-(((3-fluorophenyl)sulfonyl)methyl)-4-(2-thiophenylsulfonyl)-1-piperazinyl)phenyl)-2-propanol; (2R)-1,1,1-trifluoro-2-(4-((2R)-2-(((3-fluorophenyl)sulfonyl)methyl)-4-(2-thiophenylsulfonyl)-1-piperazinyl)phenyl)-2-propanol.

$^1$H NMR (300 MHz, CDCl$_3$) δ=7.72-7.64 (m, 2H), 7.61 (dd, J=1.2, 3.7 Hz, 1H), 7.59-7.50 (m, 2H), 7.47-7.32 (m, 3H), 7.19 (dd, J=3.8, 5.0 Hz, 1H), 6.82 (dd, J=2.4, 9.0 Hz, 2H), 4.51 (br. s., 1H), 4.12 (d, J=11.7 Hz, 1H), 3.90-3.73 (m, 2H), 3.46 (d, J=11.8 Hz, 1H), 3.09-2.95 (m, 2H), 2.82 (d, J=10.7 Hz, 1H), 2.65 (dt, J=3.4, 11.4 Hz, 1H), 2.31 (br. s., 1H), 1.76 (s, 3H). m/z (ESI, +ve ion) 593.0 (M+H)+. GK-GKRP IC$_{50}$ (Binding)=0.374 μM; GK-GKRP EC$_{50}$ (LC MS/MS-2)=0.235 μM.

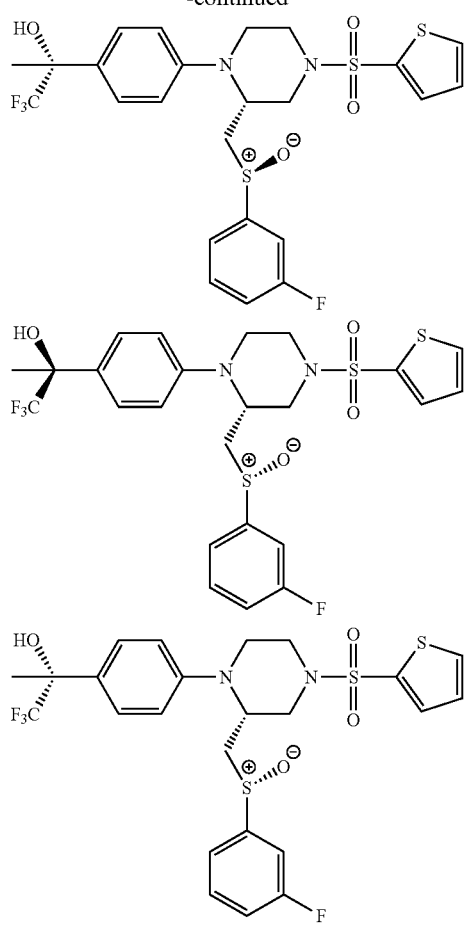

(2S)-1,1,1-trifluoro-2-(4-((2R)-2-(((3-fluorophenyl)-(S)-sulfinyl)methyl)-4-(2-thiophenylsulfonyl)-1-piperazinyl)phenyl)-2-propanol; (2S)-1,1,1-trifluoro-2-(4-((2R)-2-(((3-fluorophenyl)-(R)-sulfinyl)methyl)-4-(2-thiophenylsulfonyl)-1-piperazinyl)phenyl)-2-propanol; (2R)-1,1,1-trifluoro-2-(4-((2R)-2-(((3-fluorophenyl)-(S)-sulfinyl)methyl)-4-(2-thiophenylsulfonyl)-1-piperazinyl)phenyl)-2-propanol; (2R)-1,1,1-trifluoro-2-(4-((2R)-2-(((3-fluorophenyl)-(R)-sulfinyl)methyl)-4-(2-thiophenylsulfonyl)-1-piperazinyl)phenyl)-2-propanol.

Second Eluting Peak (Peak#2) (Mixture of Two Sulfoxide Isomers)

$^1$H NMR (300 MHz, CDCl$_3$) δ=7.70 (dd, J=1.2, 5.0 Hz, 1H), 7.64 (dd, J=1.2, 3.7 Hz, 1H), 7.52-7.39 (m, 3H), 7.38-7.29 (m, 2H), 7.24-7.10 (m, 2H), 6.86-6.75 (m, 2H), 4.51 (d, J=11.1 Hz, 1H), 4.21 (dd, J=2.0, 11.9 Hz, 1H), 3.88 (d, J=12.4 Hz, 1H), 3.56-3.38 (m, 2H), 3.15 (dt, J=3.4, 11.9 Hz, 1H), 2.91 (d, J=11.8 Hz, 1H), 2.78-2.61 (m, 2H), 2.36 (d, J=5.4 Hz, 1H), 1.75 (s, 3H). m/z (ESI, +ve ion) 577.0 (M+H)$^+$. GK-GKRP IC$_{50}$ (Binding)=0.717 μM Third Eluting Peak (Peak#3) (Mixture of Two Sulfoxide Isomers)

$^1$H NMR (300 MHz, CDCl$_3$) δ=7.64 (dd, J=1.2, 5.0 Hz, 1H), 7.60-7.53 (m, 1H), 7.53-7.45 (m, 3H), 7.43-7.32 (m, 2H), 7.25-7.19 (m, 1H), 7.15 (dd, J=3.8, 5.0 Hz, 1H), 7.00 (d, J=8.5 Hz, 2H), 4.56 (br. s., 1H), 3.77 (d, J=10.5 Hz, 1H), 3.63 (d, J=13.6 Hz, 1H), 3.44-3.28 (m, 2H), 3.19 (d, J=6.0 Hz, 2H), 2.79-2.57 (m, 2H), 2.37 (br. s., 1H), 1.76 (s, 3H). m/z (ESI, +ve ion) 577.2 (M+H)$^+$. GK-GKRP IC$_{50}$ (Binding)=0.535 μM.

Example 190

1,1,1-trifluoro-2-(4-((2R)-2-(((4-fluorophenyl)sulfanyl)methyl)-4-(2-thiophenylsulfonyl)-1-piperazinyl)phenyl)-2-propanol

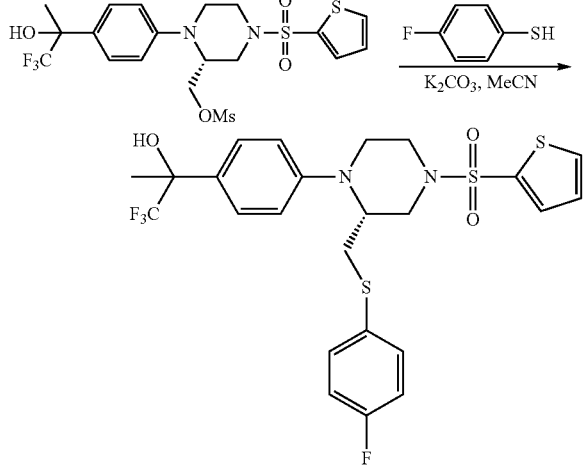

Following the procedure reported for Example 186, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and 4-fluorothiophenol (Aldrich, St. Louis, Mo.) delivered 1,1,1-trifluoro-2-(4-((2R)-2-(((4-fluorophenyl)sulfanyl)methyl)-4-(2-thiophenylsulfonyl)-1-piperazinyl)phenyl)-2-propanol as a mixture of two isomers.

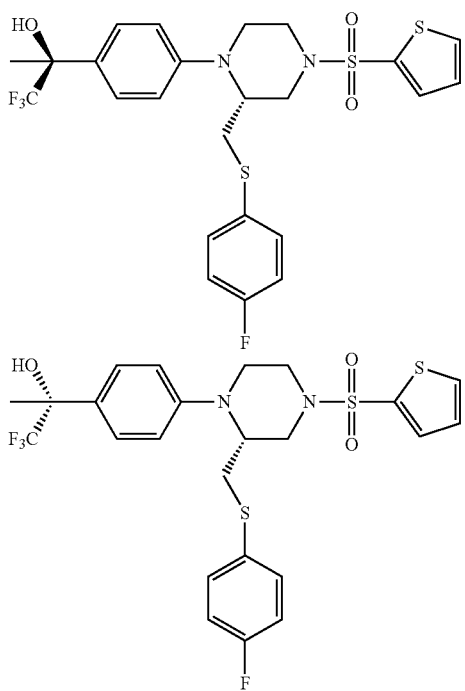

363

(2S)-1,1,1-trifluoro-2-(4-((2R)-2-(((4-fluorophenyl)sulfanyl)methyl)-4-(2-thiophenylsulfonyl)-1-piperazinyl)phenyl)-2-propanol; (2R)-1,1,1-trifluoro-2-(4-((2R)-2-(((4-fluorophenyl)sulfanyl)methyl)-4-(2-thiophenylsulfonyl)-1-piperazinyl)phenyl)-2-propanol.

$^1$H NMR (300 MHz, CDCl$_3$) δ=7.66 (dd, J=1.3, 5.0 Hz, 1H), 7.61 (dd, J=1.3, 3.8 Hz, 1H), 7.35 (d, J=8.8 Hz, 2H), 7.28 (d, J=1.6 Hz, 1H), 7.26-7.22 (m, 1H), 7.18 (dd, J=3.7, 5.0 Hz, 1H), 7.02-6.91 (m, 2H), 6.57 (d, J=9.1 Hz, 2H), 4.17 (d, J=11.3 Hz, 1H), 3.89-3.71 (m, 2H), 3.43-3.34 (m, 1H), 3.32-3.15 (m, 2H), 2.84 (d, J=13.3 Hz, 1H), 2.75-2.55 (m, 2H), 2.30 (d, J=1.9 Hz, 1H), 1.75 (d, J=1.8 Hz, 3H). m/z (ESI, +ve ion) 561.1 (M+H)$^+$. GK-GKRP IC$_{50}$ (Binding)=0.030 μM; GK-GKRP EC$_{50}$ (LC MS/MS-2)=0.015 μM.

Example 191

1,1,1-trifluoro-2-(4-((2R)-2-(((4-fluorophenyl)sulfonyl)methyl)-4-(2-thiophenylsulfonyl)-1-piperazinyl)phenyl)-2-propanol and 1,1,1-trifluoro-2-(4-((2R)-2-(((4-fluorophenyl)sulfinyl)methyl)-4-(2-thiophenylsulfonyl)-1-piperazinyl)phenyl)-2-propanol

364

-continued

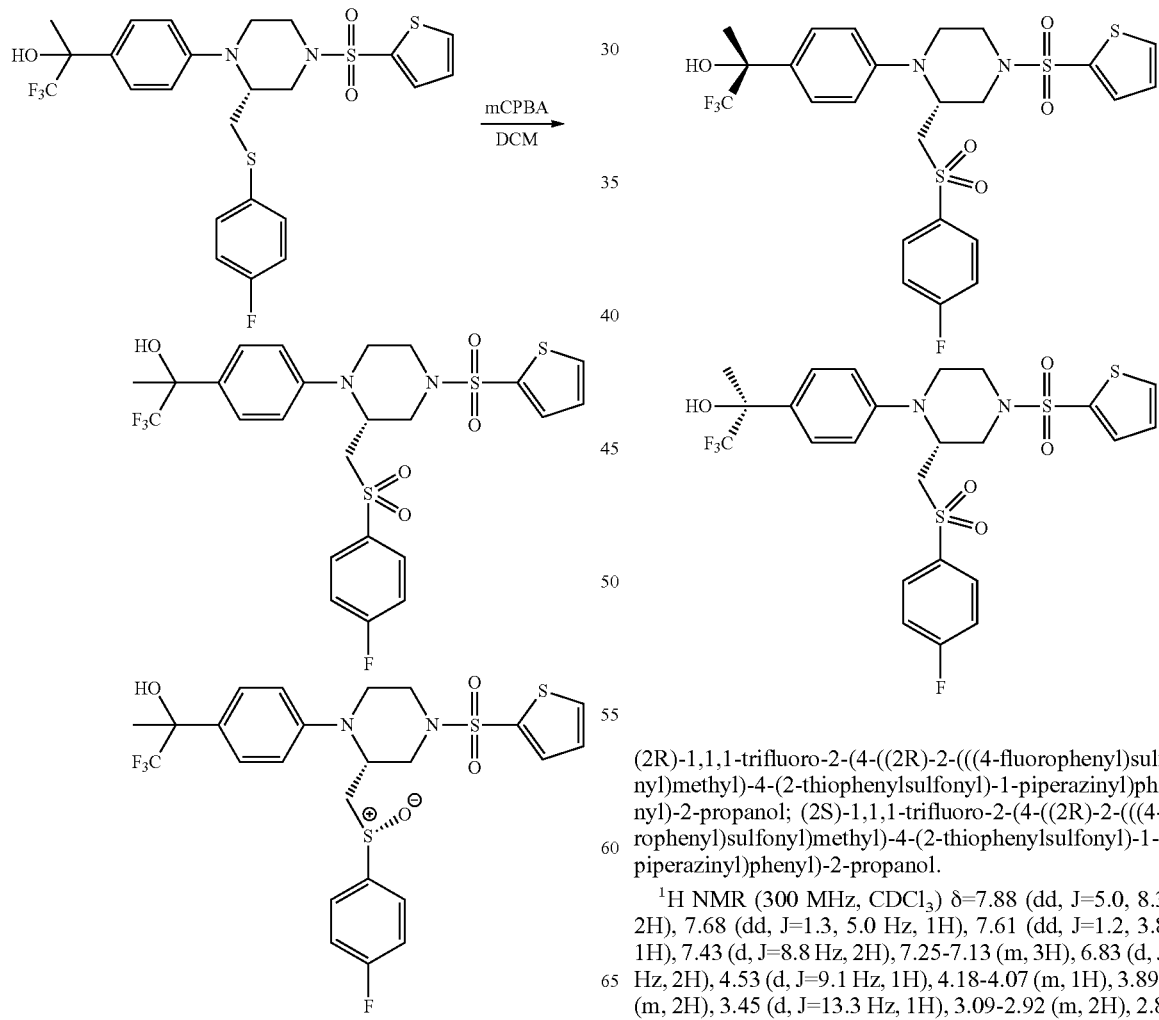

Following the procedure reported for Example 189, the reaction of 1,1,1-trifluoro-2-(4-((2R)-2-(((4-fluorophenyl)sulfanyl)methyl)-4-(2-thiophenylsulfonyl)-1-piperazinyl)phenyl)-2-propanol (Example 190) and 3-chloroperoxybenzoic acid (Aldrich, St. Louis, Mo.) delivered a mixture of sulfone (mixture of two isomers) and sulfoxides (mixture of four isomers).

First Eluting Peak (Peak#1): 1,1,1-trifluoro-2-(4-((2R)-2-(((4-fluorophenyl)sulfonyl)methyl)-4-(2-thiophenylsulfonyl)-1-piperazinyl)phenyl)-2-propanol (2R)-1,1,1-trifluoro-2-(4-((2R)-2-(((4-fluorophenyl)sulfonyl)methyl)-4-(2-thiophenylsulfonyl)-1-piperazinyl)phenyl)-2-propanol; (2S)-1,1,1-trifluoro-2-(4-((2R)-2-(((4-fluorophenyl)sulfonyl)methyl)-4-(2-thiophenylsulfonyl)-1-piperazinyl)phenyl)-2-propanol.

$^1$H NMR (300 MHz, CDCl$_3$) δ=7.88 (dd, J=5.0, 8.3 Hz, 2H), 7.68 (dd, J=1.3, 5.0 Hz, 1H), 7.61 (dd, J=1.2, 3.8 Hz, 1H), 7.43 (d, J=8.8 Hz, 2H), 7.25-7.13 (m, 3H), 6.83 (d, J=8.0 Hz, 2H), 4.53 (d, J=9.1 Hz, 1H), 4.18-4.07 (m, 1H), 3.89-3.72 (m, 2H), 3.45 (d, J=13.3 Hz, 1H), 3.09-2.92 (m, 2H), 2.80 (d, J=10.2 Hz, 1H), 2.64 (dt, J=3.5, 11.6 Hz, 1H), 2.31 (s, 1H), 1.76 (s, 3H). m/z (ESI, +ve ion) 593.1 (M+H)+. GK-GKRP IC$_{50}$ (Binding)=0.177 µM; GK-GKRP EC$_{50}$ (LC MS/MS-2)=0.166 µM.

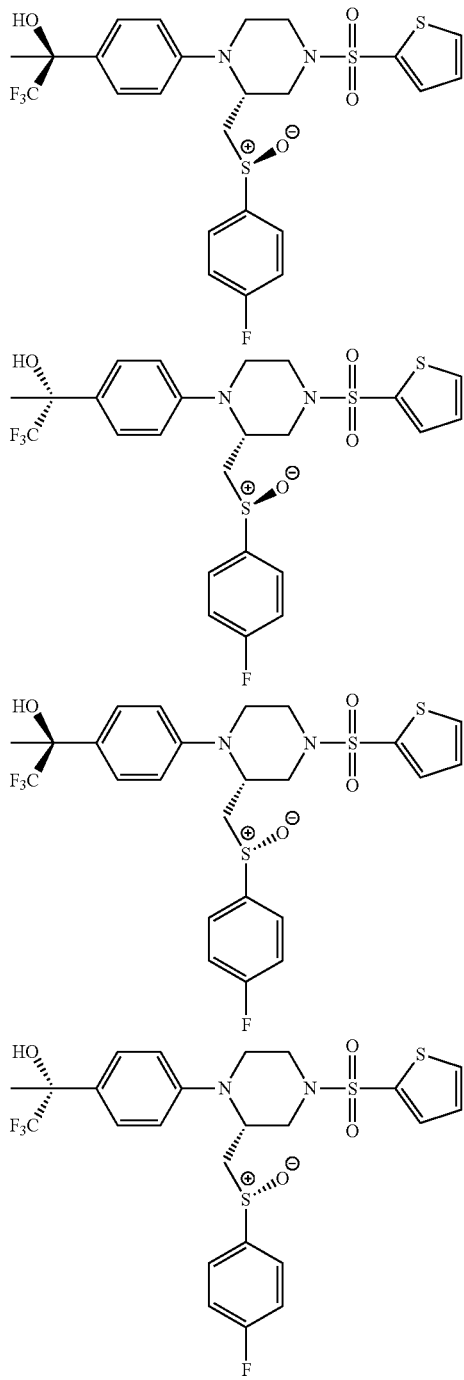

(2S)-1,1,1-trifluoro-2-(4-((2R)-2-(((4-fluorophenyl)-(S)-sulfinyl)methyl)-4-(2-thiophenylsulfonyl)-1-piperazinyl)phenyl)-2-propanol; (2S)-1,1,1-trifluoro-2-(4-((2R)-2-(((4-fluorophenyl)-(R)-sulfinyl)methyl)-4-(2-thiophenylsulfonyl)-1-piperazinyl)phenyl)-2-propanol; (2R)-1,1,1-trifluoro-2-(4-((2R)-2-(((4-fluorophenyl)-(S)-sulfinyl)methyl)-4-(2-thiophenylsulfonyl)-1-piperazinyl)phenyl)-2-propanol; (2R)-1,1,1-trifluoro-2-(4-((2R)-2-(((4-fluorophenyl)-(R)-sulfinyl)methyl)-4-(2-thiophenylsulfonyl)-1-piperazinyl)phenyl)-2-propanol.

Second Eluting Peak (Peak#2) (Mixture of Two Sulfoxide isomers)

$^1$H NMR (300 MHz, CDCl$_3$) δ=7.70 (dd, J=1.2, 5.0 Hz, 1H), 7.64 (dd, J=1.2, 3.7 Hz, 1H), 7.61-7.53 (m, 2H), 7.43 (d, J=8.8 Hz, 2H), 7.24-7.13 (m, 3H), 6.84 (d, J=8.9 Hz, 2H), 4.51 (d, J=8.8 Hz, 1H), 4.20 (d, J=12.0 Hz, 1H), 3.87 (d, J=10.7 Hz, 1H), 3.49 (d, J=12.1 Hz, 1H), 3.41 (dd, J=11.0, 12.9 Hz, 1H), 3.15 (dt, J=3.4, 11.9 Hz, 1H), 2.91 (d, J=11.5 Hz, 1H), 2.79-2.60 (m, 2H), 2.40 (br. s., 1H), 1.75 (s, 3H). m/z (ESI, +ve ion) 577.0 (M+H)+. GK-GKRP IC$_{50}$ (Binding)=0.425 µM; GK-GKRP EC$_{50}$ (LC MS/MS-2)=0.252 µM.

Third Eluting Peak (Peak#3) (Mixture of Two Sulfoxide isomers)

$^1$H NMR (300 MHz, CDCl$_3$) δ=7.68-7.57 (m, 3H), 7.53-7.43 (m, 3H), 7.31-7.28 (m, 1H), 7.26-7.23 (m, 1H), 7.16 (dd, J=3.7, 5.0 Hz, 1H), 6.99 (d, J=8.6 Hz, 2H), 4.53 (br. s., 1H), 3.77 (d, J=11.0 Hz, 1H), 3.61 (d, J=13.2 Hz, 1H), 3.43 (d, J=11.4 Hz, 1H), 3.38-3.25 (m, 1H), 3.24-3.06 (m, 2H), 2.77-2.56 (m, 2H), 2.39 (br. s., 1H), 1.76 (s, 3H). m/z (ESI, +ve ion) 577.3 (M+H)+. GK-GKRP IC$_{50}$ (Binding)=0.259 µM; GK-GKRP EC$_{50}$ (LC MS/MS-2)=0.262 µM.

Example 192

N-(((2S)-4-(2-thiophenylsulfonyl)-1-(4-(2,2,2-trifluoro-1-hydroxy-1-methylethyl)phenyl)-2-piperazinyl)methyl)-3-pyridinesulfonamide

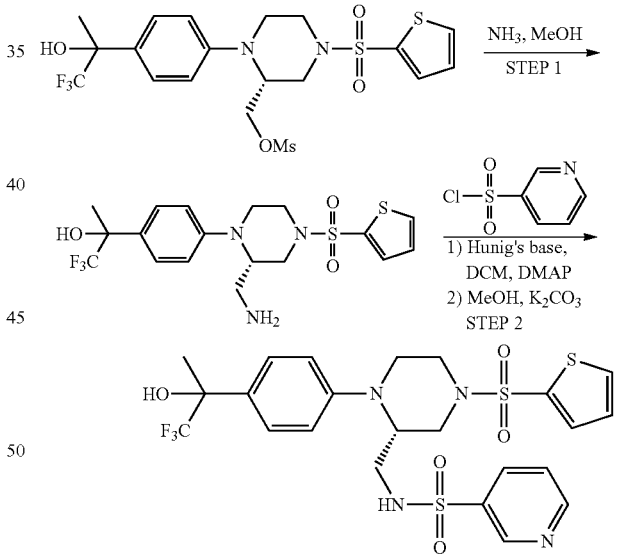

Step 1: 2-(4-((2S)-2-(aminomethyl)-4-(2-thiophenylsulfonyl)-1-piperazinyl)phenyl)-1,1,1-trifluoro-2-propanol To a 20 mL of microwave vial was added ((2R)-4-(thiophen-2-ylsulfonyl)-1-(4-(1,1,1-trifluoro-2-hydroxypropan-2-yl)phenyl)piperazin-2-yl)methyl methanesulfonate (1.0 g, 1.9 mmol, Intermediate B) and ammonia, 2M solution in methanol (9.5 mL, 19 mmol, Aldrich, St. Louis, Mo.). The vial was sealed and heated in an Initiator microwave reactor (Biotage AB, Inc., Uppsala, Sweden) at 140° C. for 30 min.

The reaction mixture was concentrated and the crude product was purified by column chromatography (80 g of silica gel, 100% $CH_2Cl_2$ first then 2 to 5% 2M $NH_3$ in $CH_2Cl_2$) to afford 2-(4-((2S)-2-(aminomethyl)-4-(2-thiophenylsulfonyl)-1-piperazinyl)phenyl)-1,1,1-trifluoro-2-propanol (0.540 g) as a white foam.

Step 2: N-(((2S)-4-(2-thiophenylsulfonyl)-1-(4-(2,2,2-trifluoro-1-hydroxy-1-methylethyl)phenyl)-2-piperazinyl)methyl)-3-pyridinesulfonamide To a solution of 2-(4-((2S)-2-(aminomethyl)-4-(2-thiophenylsulfonyl)-1-piperazinyl)phenyl)-1,1,1-trifluoro-2-propanol (0.130 g, 0.289 mmol) in $CH_2Cl_2$ (5.0 mL) was added 4-dimethylaminopyridine (7.0 mg, 0.062 mmol, Aldrich, St. Louis, Mo.), 3-pyridinesulfonyl chloride (0.077 g, 0.43 mmol, WAKO, Richmond, Va.), and diisopropylethylamine (0.50 mL, 2.9 mmol). The reaction mixture was heated at 60° C. for 30 min. The solvent was then removed in vacuo, The residue was dissolved in MeOH (5.0 mL) then potassium carbonate (0.240 g, 1.74 mmol) was added. The reaction mixture was heated at 60° C. for 1 h. Then the solvent was removed in vacuo. The residue was partitioned between water (20 mL) and $CH_2Cl_2$ (40 mL). The aqueous layer was extracted with $CH_2Cl_2$ (2×20 mL). The combined organic extracts were dried over $MgSO_4$, filtered, and concentrated. The crude product was purified by column chromatography (24 g of silica gel, 100% first then 5% to 8% 2M $NH_3$ in MeOH in $CH_2Cl_2$) to afford N-(((2S)-4-(2-thiophenylsulfonyl)-1-(4-(2,2,2-trifluoro-1-hydroxy-1-methylethyl)phenyl)-2-piperazinyl)methyl)-3-pyridinesulfonamide (0.120 g) as a mixture of two isomers:

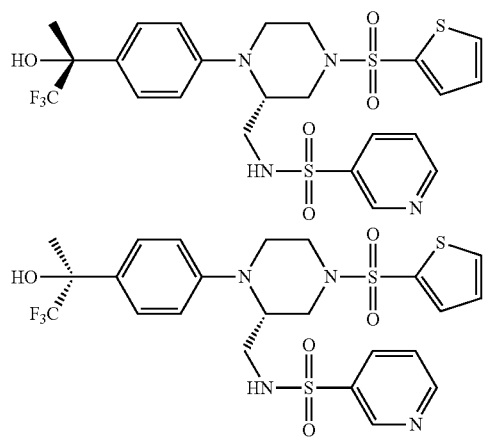

N-(((2S)-4-(2-thiophenylsulfonyl)-1-(4-((1R)-2,2,2-trifluoro-1-hydroxy-1-methylethyl)phenyl)-2-piperazinyl)methyl)-3-pyridinesulfonamide; N-(((2S)-4-(2-thiophenylsulfonyl)-1-(4-((1S)-2,2,2-trifluoro-1-hydroxy-1-methylethyl)phenyl)-2-piperazinyl)methyl)-3-pyridinesulfonamide.

$^1$H NMR (300 MHz, $CDCl_3$) δ=8.71 (d, J=4.4 Hz, 1H), 8.58 (d, J=13.2 Hz, 1H), 8.04 (dd, J=1.7, 8.0 Hz, 1H), 7.69 (dd, J=1.2, 5.0 Hz, 1H), 7.60 (dd, J=1.2, 3.7 Hz, 1H), 7.54 (dd, J=3.1, 8.8 Hz, 2H), 7.42 (dd, J=4.9, 8.0 Hz, 1H), 7.20 (dd, J=3.8, 5.0 Hz, 1H), 6.96 (d, J=7.2 Hz, 2H), 5.19 (br. s., 1H), 4.27-4.13 (m, 1H), 3.81 (t, J=9.4 Hz, 1H), 3.68 (br. s., 1H), 3.42-3.31 (m, 1H), 3.30-3.08 (m, 2H), 2.71-2.71 (m, 1H), 3.01-2.65 (m, 3H), 1.79 (s, 3H). m/z (ESI, +ve ion) 591.2 $(M+H)^+$. GK-GKRP $IC_{50}$ (Binding)=0.103 μM; GK-GKRP $EC_{50}$ (LC MS/MS-2)=0.126 μM.

Example 193

N-(((2S)-4-(2-thiophenylsulfonyl)-1-(4-(2,2,2-trifluoro-1-hydroxy-1-methylethyl)phenyl)-2-piperazinyl)methyl)benzenesulfonamide

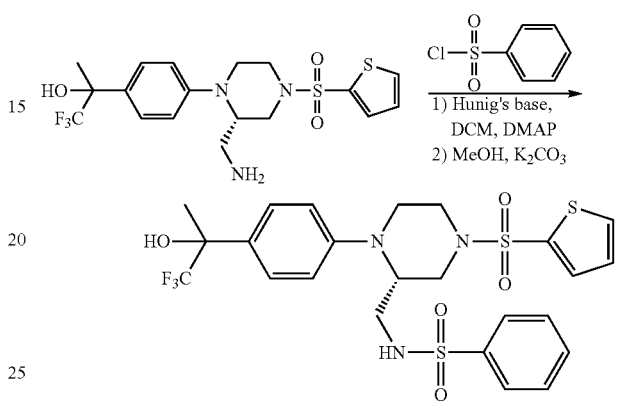

Following the procedure described for Example 192, Step 2 the reaction of 2-(4-((2S)-2-(aminomethyl)-4-(2-thiophenylsulfonyl)-1-piperazinyl)phenyl)-1,1,1-trifluoro-2-propanol (Example 192 [Step 1]) and benzenesulfonyl chloride (Aldrich, St. Louis, Mo.) delivered N-(((2S)-4-(2-thiophenylsulfonyl)-1-(4-(2,2,2-trifluoro-1-hydroxy-1-methylethyl)phenyl)-2-piperazinyl)methyl)benzenesulfonamide as a mixture of two isomers after purification by column chromatography on silica gel (24 g, 10 to 40% acetone in hexanes).

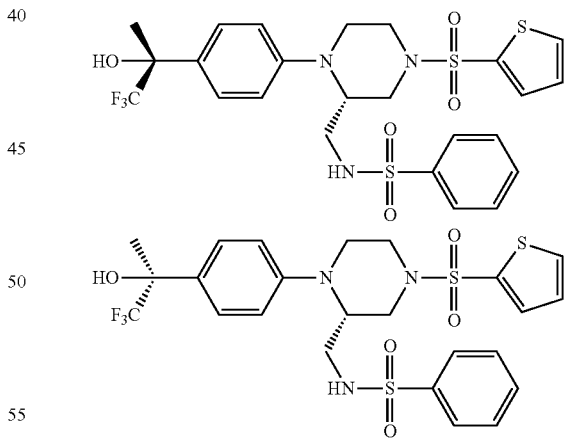

N-(((2S)-4-(2-thiophenylsulfonyl)-1-(4-((1R)-2,2,2-trifluoro-1-hydroxy-1-methylethyl)phenyl)-2-piperazinyl)methyl)benzenesulfonamide; N-(((2S)-4-(2-thiophenylsulfonyl)-1-(4-((1S)-2,2,2-trifluoro-1-hydroxy-1-methylethyl)phenyl)-2-piperazinyl)methyl)benzenesulfonamide.

$^1$H NMR (300 MHz, DMSO-$d_6$) δ=8.08 (dd, J=1.2, 5.0 Hz, 1H), 7.93 (br. s., 1H), 7.77-7.66 (m, 3H), 7.65-7.56 (m, 1H), 7.55-7.45 (m, 2H), 7.36 (d, J=8.6 Hz, 2H), 7.31 (dd, J=3.8, 5.0 Hz, 1H), 6.83 (d, J=8.3 Hz, 2H), 6.34 (d, J=1.2 Hz, 1H), 4.08 (d, J=7.3 Hz, 1H), 3.79 (d, J=11.3 Hz, 1H), 3.63-3.44 (m, 2H), 3.19-2.95 (m, 2H), 2.55 (br. s., 1H), 2.45-2.31 (m, 1H), 1.62 (s, 3H). m/z (ESI, +ve ion) 590.2 (M+H)$^+$. GK-GKRP IC$_{50}$ (Binding)=0.284 μM; GK-GKRP EC$_{50}$ (LC MS/MS-2)=0.374 μM.

Example 194

2-(4-((2S)-2-((bis(1-methylethyl)amino)methyl)-4-(2-thiophenylsulfonyl)-1-piperazinyl)phenyl)-1,1,1-trifluoro-2-propanol

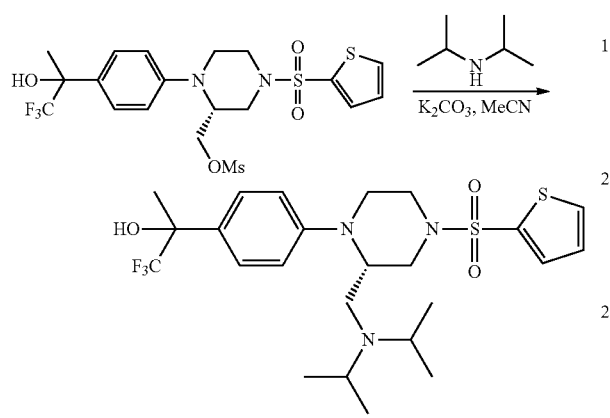

A 5-mL microwave vial was charged with ((2R)-4-(thiophen-2-ylsulfonyl)-1-(4-(1,1,1-trifluoro-2-hydroxypropan-2-yl)phenyl)piperazin-2-yl)methyl methanesulfonate (0.200 g, 0.378 mmol, Intermediate B) diisopropylamine (0.077 g, 0.757 mmol), potassium carbonate (0.105 g, 0.757 mmol), in 3 mL of MeCN. The vial was sealed and heated in an Initiator microwave reactor (Biotage AB, Inc., Uppsala, Sweden) at 140° C. for 30 min. The reaction mixture was filtered and the filtrate was concentrated. The crude product was purified by column chromatography on silica gel (40 g of silica gel, 10 to 40% EtOAc in hexanes) to afford 2-(4-((2S)-2-((bis(1-methylethyl)amino)methyl)-4-(2-thiophenylsulfonyl)-1-piperazinyl)phenyl)-1,1,1-trifluoro-2-propanol (0.130 g) as a mixture of two isomers.

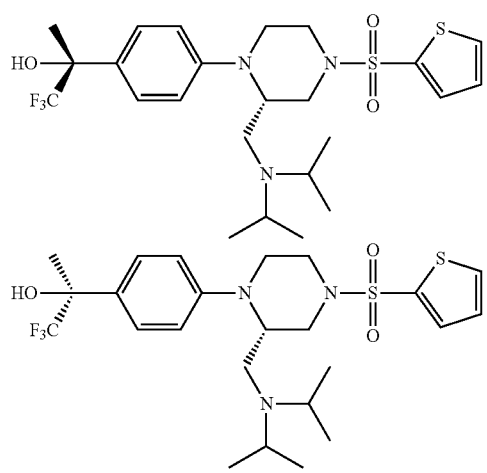

(2R)-2-(4-((2S)-2-((bis(1-methylethyl)amino)methyl)-4-(2-thiophenylsulfonyl)-1-piperazinyl)phenyl)-1,1,1-trifluoro-2-propanol; (2S)-2-(4-((2S)-2-((bis(1-methylethyl)amino)methyl)-4-(2-thiophenylsulfonyl)-1-piperazinyl)phenyl)-1,1,1-trifluoro-2-propanol.

$^1$H NMR (300 MHz, DMSO-d$_6$) δ=8.08 (dd, J=1.3, 5.0 Hz, 1H), 7.68 (dd, J=1.3, 3.8 Hz, 1H), 7.37 (d, J=8.6 Hz, 2H), 7.31 (dd, J=3.8, 5.0 Hz, 1H), 6.86 (d, J=8.8 Hz, 2H), 6.32 (s, 1H), 3.93 (d, J=9.9 Hz, 1H), 3.86 (d, J=10.7 Hz, 1H), 3.61 (d, J=11.4 Hz, 1H), 3.46 (d, J=13.3 Hz, 1H), 3.23-3.09 (m, 1H), 2.98 (quin, J=6.6 Hz, 2H), 2.83-2.70 (m, 1H), 2.43 (d, J=8.9 Hz, 1H), 2.38-2.28 (m, 1H), 2.22 (d, J=11.1 Hz, 1H), 1.61 (s, 3H), 1.03-0.92 (m, 6H), 0.88-0.77 (m, 6H). m/z (ESI, +ve ion) 534.2 (M+H)$^+$. GK-GKRP IC$_{50}$ (Binding)=0.205 μM; GK-GKRP EC$_{50}$ (LC MS/MS-2)=0.179 μM.

Example 195

N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide

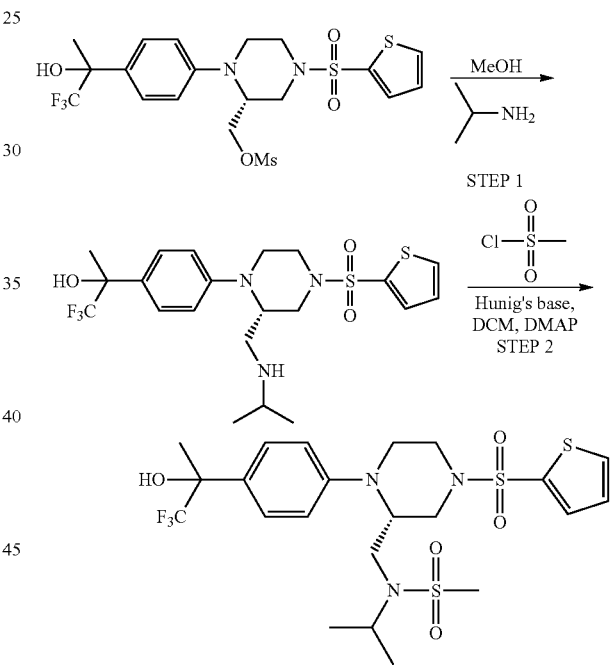

Step 1: 1,1,1-trifluoro-2-(4-((2S)-2-(((1-methylethyl)amino)methyl)-4-(2-thiophenylsulfonyl)-1-piperazinyl)phenyl)-2-propanol To a 20 mL of microwave vial was added ((2R)-4-(thiophen-2-ylsulfonyl)-1-(4-(1,1,1-trifluoro-2-hydroxypropan-2-yl)phenyl)piperazin-2-yl)methyl methanesulfonate (1.0 g, 1.9 mmol, Intermediate B), isopropylamine (2.5 mL, 28 mmol, Aldrich, St. Louis, Mo.), and MeOH (10.0 mL). The vial was sealed and heated in an Initiator microwave reactor (Biotage AB, Inc., Uppsala, Sweden) at 140° C. for 30 min. After cooling to room temperature, the reaction mixture was concentrated and the crude product was purified by column chromatography (80 g of silica gel, 100% CH$_2$Cl$_2$ first then 2 to 5% 2M NH$_3$ in MeOH/CH$_2$Cl$_2$) to afford 1,1,1-trifluoro- 2-(4-((2S)-2-(((1-methylethyl)amino)methyl)-4-(2-thiophenylsulfonyl)-1-piperazinyl)phenyl)-2-propanol (0.720 g) as a white foam.

Step 2: N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide To a solution of 1,1,1-trifluoro-2-(4-((2S)-2-(((1-methylethyl)amino)methyl)-4-(2-thiophenylsulfonyl)-1-piperazinyl)phenyl)-2-propanol (0.150 g, 0.305 mmol) in CH$_2$Cl$_2$ (5.0 mL) was added 4-dimethylaminopyridine (7.5 mg, 0.062 mmol), methanesulfonyl chloride (0.05 mL, 0.61 mmol, Aldrich, St. Louis, Mo.), and Hünig's base (0.2 mL, 0.9 mmol). The reaction mixture was stirred at room 20 min and then the solvent was removed in vacuo. The crude product was purified by column chromatography (40 g of silica, 10% to 30% acetone in hexanes) to afford N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide (0.110 g) as a mixture of two isomers:

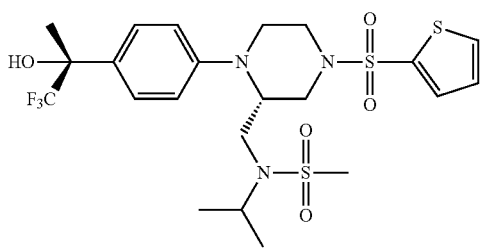

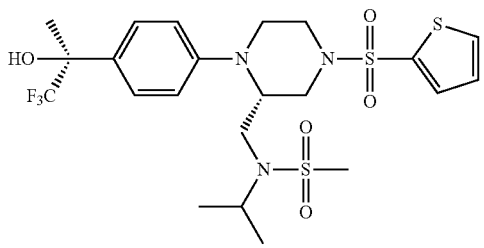

N-(1-methylethyl)-N-(((2R)-4-(2-thiophenylsulfonyl)-1-(4-((1R)-2,2,2-trifluoro-1-hydroxy-1-methylethyl)phenyl)-2-piperazinyl)methyl)methanesulfonamide; N-(1-methylethyl)-N-(((2R)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, DMSO-d$_6$) δ=8.08 (dd, J=1.3, 5.0 Hz, 1H), 7.69 (dd, J=1.2, 3.7 Hz, 1H), 7.36 (d, J=8.8 Hz, 2H), 7.30 (dd, J=3.8, 5.0 Hz, 1H), 6.90 (d, J=8.9 Hz, 2H), 6.32 (d, J=1.6 Hz, 1H), 4.38 (br. s., 1H), 3.82 (quin, J=6.7 Hz, 1H), 3.75-3.47 (m, 3H), 3.44-3.32 (m, 1H), 3.19-3.03 (m, 1H), 2.91 (s, 3H), 2.54 (d, J=3.8 Hz, 1H), 2.35 (dt, J=3.1, 11.1 Hz, 1H), 1.60 (s, 3H), 1.21 (d, J=6.7 Hz, 3H), 1.16-1.03 (m, 3H). m/z (ESI, +ve ion) 570.1 (M+H)$^+$. GK-GKRP IC$_{50}$ (Binding)=0.028 µM; GK-GKRP EC$_{50}$ (LC MS/MS-2)=0.057 µM.

Example 196

N-(1-methylethyl)-N-(((2S)-4-(2-thiophenylsulfonyl)-1-(4-(2,2,2-trifluoro-1-hydroxy-1-methylethyl)phenyl)-2-piperazinyl)methyl)acetamide

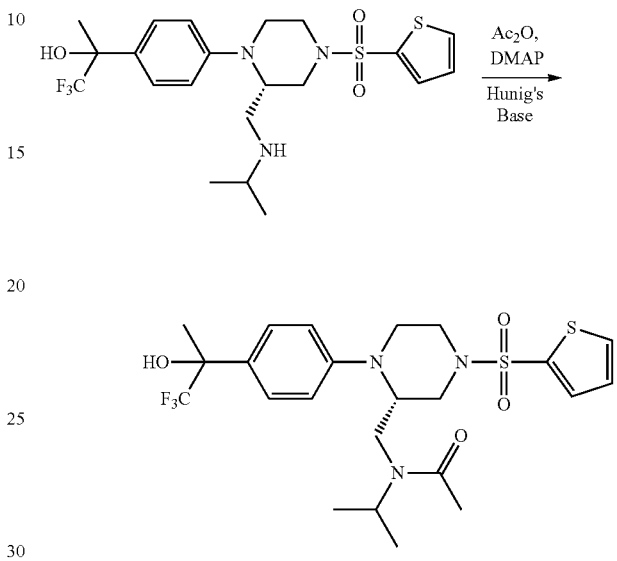

To a solution of 1,1,1-trifluoro-2-(4-((2S)-2-(((1-methylethyl)amino)methyl)-4-(2-thiophenylsulfonyl)-1-piperazinyl)phenyl)-2-propanol (0.150 g, 0.305 mmol, Example 195, Step 1) in CH$_2$Cl$_2$ (5.0 mL) was added 4-dimethylaminopyridine (7.46 mg, 0.061 mmol), acetyl chloride (0.043 mL, 0.610 mmol), Hünig's base (0.159 mL, 0.915 mmol). The resulting mixture was stirred at room temperature. After 20 min, the solvent was concentrated and the crude product was purified by column chromatography (24 g of silica, 10 to 40% acetone in hexanes) to afford N-(1-methylethyl)-N-(((2S)-4-(2-thiophenylsulfonyl)-1-(4-(2,2,2-trifluoro-1-hydroxy-1-methylethyl)phenyl)-2-piperazinyl)methyl)acetamide as a mixture of two isomers.

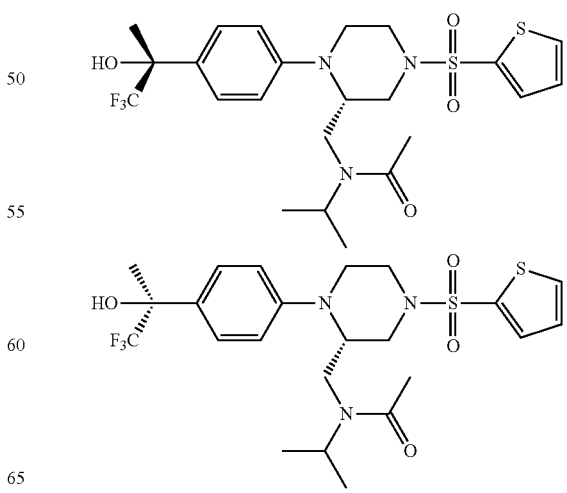

N-(1-methylethyl)-N-(((2S)-4-(2-thiophenylsulfonyl)-1-(4-((1R)-2,2,2-trifluoro-1-hydroxy-1-methylethyl)phenyl)-2-piperazinyl)methyl)acetamide; N-(1-methylethyl)-N-(((2S)-4-(2-thiophenylsulfonyl)-1-(4-((1S)-2,2,2-trifluoro-1-hydroxy-1-methylethyl)phenyl)-2-piperazinyl)methyl) acetamide.

$^1$H NMR (300 MHz, CDCl$_3$) δ=7.72-7.62 (m, 1H), 7.56 (dd, J=1.2, 3.8 Hz, 1H), 7.43 (d, J=8.0 Hz, 2H), 7.18 (dd, J=3.9, 4.9 Hz, 1H), 6.99 (br. s., 2H), 4.86 (br. s., 1H), 3.96 (td, J=6.7, 13.4 Hz, 1H), 3.74 (d, J=11.0 Hz, 2H), 3.63-3.54 (m, 1H), 3.48-3.38 (m, 2H), 3.28 (dd, J=8.1, 13.7 Hz, 1H), 2.57 (br. s., 2H), 2.36 (br. s., 1H), 2.08 (s, 3H), 1.73 (s, 3H), 1.33 (d, J=6.4 Hz, 3H), 1.08 (d, J=6.7 Hz, 3H). m/z (ESI, +ve ion) 534.1 (M+H)$^+$. GK-GKRP IC$_{50}$ (Binding)=0.466 μM; GK-GKRP EC$_{50}$ (LC MS/MS-2)=0.391 μM.

Example 197

N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)benzenesulfonamide

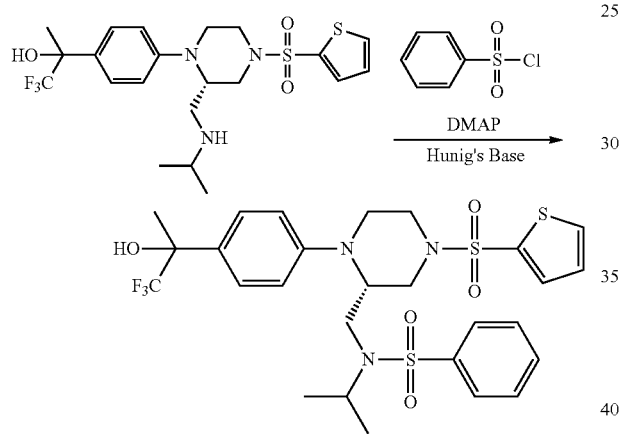

To a solution of 1,1,1-trifluoro-2-(4-((2S)-2-(((1-methylethyl)amino)methyl)-4-(2-thiophenylsulfonyl)-1-piperazinyl)phenyl)-2-propanol (0.150 g, 0.305 mmol, Example 195, Step 1) in CH$_2$Cl$_2$ (5.0 mL) was added 4-dimethylaminopyridine (0.0075 g, 0.061 mmol), benzenesulfonyl chloride (0.108 g, 0.610 mmol), and Hünig's base (0.159 mL, 0.915 mmol). The resulting mixture was stirred at room temperature. After 2 h, the mixture was concentrated and the crude product was purified by column chromatography (40 g of silica, 10 to 40% acetone in hexanes) to give N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)benzenesulfonamide (0.176 g) as a mixture of two isomers.

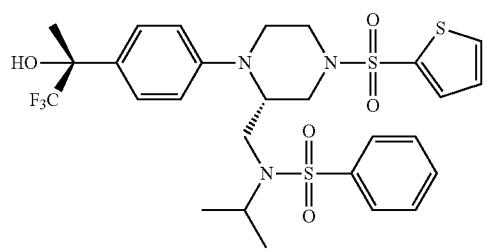

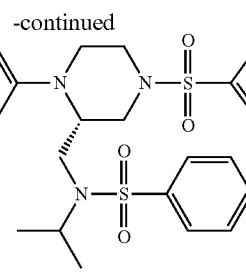

N-(1-methylethyl)-N-(((2R)-4-(2-thiophenylsulfonyl)-1-(4-((1R)-2,2,2-trifluoro-1-hydroxy-1-methylethyl)phenyl)-2-piperazinyl)methyl)benzenesulfonamide; N-(1-methylethyl)-N-(((2R)-4-(2-thiophenylsulfonyl)-1-(4-((1S)-2,2,2-trifluoro-1-hydroxy-1-methylethyl)phenyl)-2-piperazinyl)methyl)benzenesulfonamide.

$^1$H NMR (300 MHz, CDCl$_3$) δ=7.69 (dd, J=1.2, 5.0 Hz, 1H), 7.64-7.45 (m, 6H), 7.43-7.33 (m, 2H), 7.21 (dd, J=3.8, 5.1 Hz, 1H), 7.11 (br. s., 2H), 4.86 (d, J=5.6 Hz, 1H), 4.20-3.93 (m, 2H), 3.77 (d, J=11.1 Hz, 1H), 3.47 (d, J=12.4 Hz, 1H), 3.39-3.17 (m, 2H), 2.89-2.78 (m, 1H), 2.74 (dd, J=3.2, 6.9 Hz, 1H), 2.65-2.47 (m, 1H), 2.36 (d, J=2.5 Hz, 1H), 1.80 (s, 3H), 1.25 (dd, J=1.4, 6.8 Hz, 3H), 0.67 (dd, J=1.5, 6.7 Hz, 3H). m/z (ESI, +ve ion) 632.0 (M+H)$^+$. GK-GKRP IC$_{50}$ (Binding)=0.215 μM; GK-GKRP EC$_{50}$ (LC MS/MS-2)=0.080 μM.

Example 198

N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)-3-pyridinesulfonamide

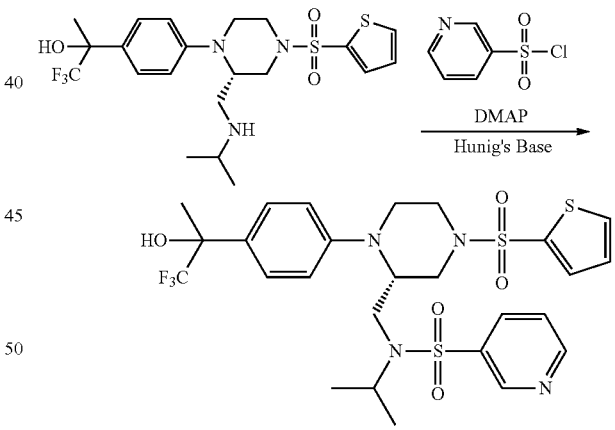

To a solution of 1,1,1-trifluoro-2-(4-((2S)-2-(((1-methylethyl)amino)methyl)-4-(2-thiophenylsulfonyl)-1-piperazinyl)phenyl)-2-propanol (0.100 g, 0.203 mmol, Example 195, Step 1) in CH$_2$Cl$_2$ (5.0 mL) was added 4-dimethylaminopyridine (0.005 g, 0.061 mmol), pyridine-3-sulfonyl chloride (0.072 g, 0.407 mmol, WAKO, Richmond, Va.) and Hünig's base (0.106 mL, 0.610 mmol). After 2 h at room temperature, the solvent was removed and the crude product was purified by column chromatography (40 g of silica, 20 to 40% acetone in hexanes) to give N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)-3-pyridinesulfonamide (0.120 g) as a mixture of two isomers.

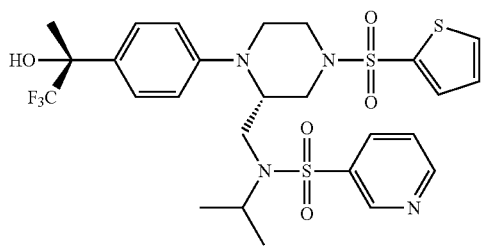

N-(1-methylethyl)-N-(((2R)-4-(2-thiophenylsulfonyl)-1-(4-((1R)-2,2,2-trifluoro-1-hydroxy-1-methylethyl)phenyl)-2-piperazinyl)methyl)-3-pyridinesulfonamide; N-(1-methylethyl)-N-(((2R)-4-(2-thiophenylsulfonyl)-1-(4-((1S)-2,2,2-trifluoro-1-hydroxy-1-methylethyl)phenyl)-2-piperazinyl)methyl)-3-pyridinesulfonamide.

$^1$H NMR (300 MHz, CDCl$_3$) δ=8.71-8.60 (m, 1H), 8.25 (br. s., 1H), 7.95 (s, 1H), 7.93-7.84 (m, 1H), 7.71 (d, J=5.0 Hz, 1H), 7.68-7.54 (m, 3H), 7.42-7.31 (m, 1H), 7.25-7.18 (m, 1H), 7.08 (br. s., 2H), 4.74 (t, J=10.4 Hz, 1H), 4.28-4.11 (m, 1H), 3.98 (d, J=11.0 Hz, 1H), 3.80 (d, J=10.8 Hz, 1H), 3.41-3.15 (m, 3H), 2.82 (br. s., 1H), 2.72-2.46 (m, 2H), 1.80 (s, 3H), 1.32 (dd, J=2.8, 6.9 Hz, 3H), 0.80 (dd, J=2.9, 6.7 Hz, 3H). m/z (ESI, +ve ion) 633.1 (M+H)$^+$. GK-GKRP IC$_{50}$ (Binding)=0.108 μM; GK-GKRP EC$_{50}$ (LC MS/MS-2)=0.177 μM.

Example 199

2-(4-((2S)-2-((cyclopropylamino)methyl)-4-(2-thiophenylsulfonyl)-1-piperazinyl)phenyl)-1,1,1-trifluoro-2-propanol

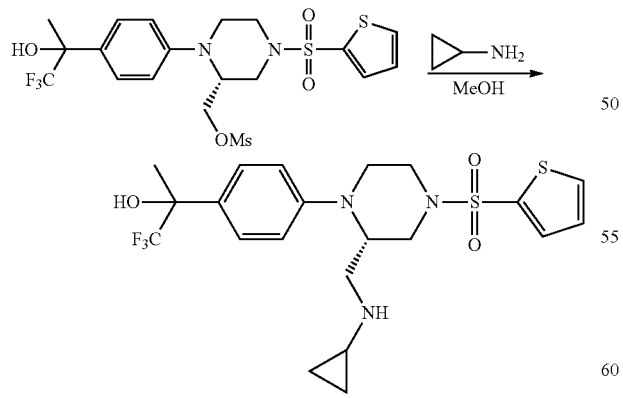

A 20-mL microwave vial was charged with ((2R)-4-(thiophen-2-ylsulfonyl)-1-(4-(1,1,1-trifluoro-2-hydroxypropan-2-yl)phenyl)piperazin-2-yl)methyl methanesulfonate (1.0 g, 1.9 mmol, Intermediate B), cyclopropylamine (4.0 mL, 57 mmol, Alfa Aesar, Ward Hill, Mass.) and MeOH (10.0 mL). The vial was sealed and heated in an Initiator microwave reactor (Biotage AB, Inc., Uppsala, Sweden) at 140° C. for 30 min. After cooling to room temperature, the reaction mixture was concentrated and the crude product was purified by column chromatography (120 g of silica, 2 to 8% 2M NH$_3$ in MeOH/CH$_2$Cl$_2$) to afford 2-(4-((2S)-2-((cyclopropylamino)methyl)-4-(2-thiophenylsulfonyl)-1-piperazinyl)phenyl)-1,1,1-trifluoro-2-propanol (0.613 g) as mixture of two isomers.

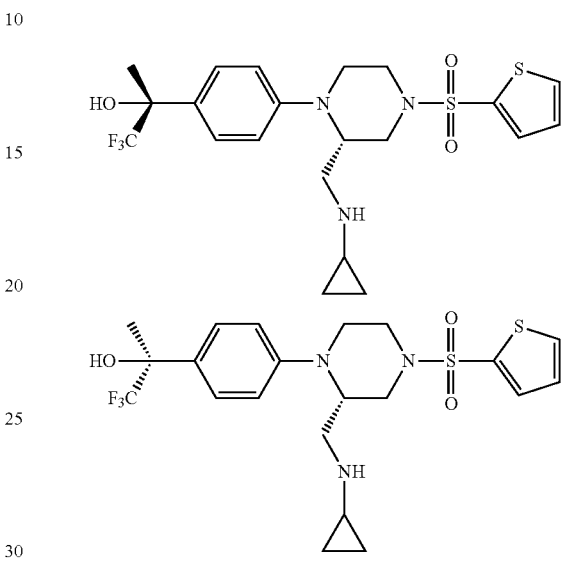

(2R)-2-(4-((2S)-2-((cyclopropylamino)methyl)-4-(2-thiophenylsulfonyl)-1-piperazinyl)phenyl)-1,1,1-trifluoro-2-propanol; (2S)-2-(4-((2S)-2-((cyclopropylamino)methyl)-4-(2-thiophenylsulfonyl)-1-piperazinyl)phenyl)-1,1,1-trifluoro-2-propanol.

$^1$H NMR (300 MHz, CDCl$_3$) δ=7.64 (dd, J=1.2, 5.0 Hz, 1H), 7.57 (dd, J=1.2, 3.7 Hz, 1H), 7.43 (d, J=8.6 Hz, 2H), 7.17 (dd, J=3.8, 5.0 Hz, 1H), 6.86 (d, J=8.9 Hz, 2H), 3.97-3.84 (m, 2H), 3.76 (d, J=11.3 Hz, 1H), 3.55-3.41 (m, 1H), 3.30 (dt, J=3.4, 12.0 Hz, 1H), 3.11 (dd, J=9.5, 12.3 Hz, 1H), 2.78 (dd, J=3.9, 12.4 Hz, 1H), 2.70-2.51 (m, 2H), 2.43-2.23 (m, 1H), 2.16-2.07 (m, 1H), 1.75 (s, 3H), 0.43 (q, J=5.7 Hz, 2H), 0.38-0.23 (m, 2H). m/z (ESI, +ve ion) 490.0 (M+H)$^+$. GK-GKRP IC$_{50}$ (Binding)=0.713 μM.

Example 200

N-cyclopropyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide

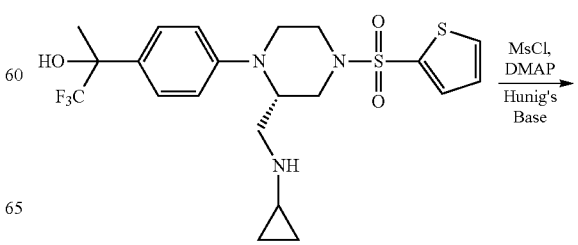

-continued

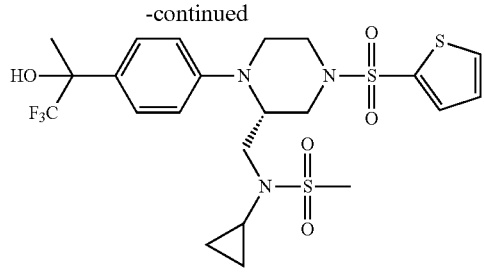

To a solution of 2-(4-((2S)-2-((cyclopropylamino)methyl)-4-(2-thiophenylsulfonyl)-1-piperazinyl)phenyl)-1,1,1-trifluoro-2-propanol (0.130 g, 0.258 mmol, Example 199) in CH$_2$Cl$_2$ (5.0 mL) was added 4-dimethylaminopyridine (0.006 g, 0.052 mmol), methanesulfonyl chloride (0.059 g, 0.516 mmol) and Hünig's base (0.135 mL, 0.774 mmol). After 20 min at room temperature, the solvent was concentrated and the crude product was purified by column chromatography (40 g of silica gel, 10 to 30% acetone in hexanes) to give N-cyclopropyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide (0.100 g) as a mixture of two isomers.

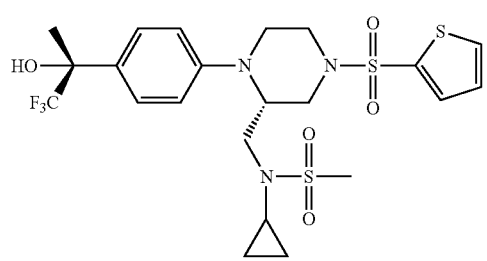

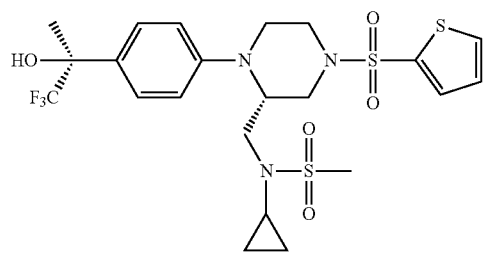

N-cyclopropyl-N-(((2R)-4-(2-thiophenylsulfonyl)-1-(4-((1R)-2,2,2-trifluoro-1-hydroxy-1-methylethyl)phenyl)-2-piperazinyl)methyl)methanesulfonamide; N-cyclopropyl-N-(((2R)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=7.67 (dd, J=1.3, 5.0 Hz, 1H), 7.58 (dd, J=1.2, 3.7 Hz, 1H), 7.45 (d, J=8.8 Hz, 2H), 7.19 (dd, J=3.8, 5.0 Hz, 1H), 6.95 (d, J=8.0 Hz, 2H), 4.56 (br. s., 1H), 3.88 (d, J=11.7 Hz, 1H), 3.78 (d, J=11.0 Hz, 1H), 3.63-3.51 (m, 1H), 3.51-3.28 (m, 3H), 2.85 (s, 3H), 2.73-2.49 (m, 2H), 2.42 (tt, J=3.7, 6.9 Hz, 1H), 2.30 (s, 1H), 1.74 (s, 3H), 1.04 (dd, J=3.9, 6.2 Hz, 1H), 0.99-0.67 (m, 3H). m/z (ESI, +ve ion) 568.0 (M+H)$^+$. GK-GKRP IC$_{50}$ (Binding)=0.026 µM; GK-GKRP EC$_{50}$ (LC MS/MS-2)=0.039 µM.

Example 201

N-(2-methylpropyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide This compound was synthesized following the scheme described for Example 195. The reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and isobutyl amine (Aldrich, St. Louis, Mo.), followed by sulfonamide formation (using MsCl) delivered 1,1,1-trifluoro-2-(4-((2S)-2-(((2-methylpropyl)amino)methyl)-4-(2-thiophenylsulfonyl)-1-piperazinyl)phenyl)-2-propanol as a mixture of two isomers.

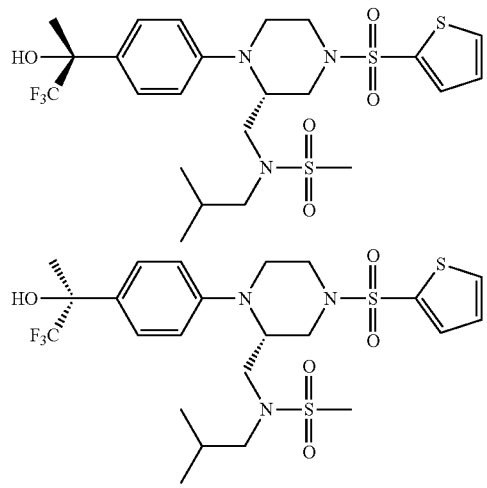

N-(2-methylpropyl)-N-(((2S)-4-(2-thiophenylsulfonyl)-1-(4-((1R)-2,2,2-trifluoro-1-hydroxy-1-methylethyl)phenyl)-2-piperazinyl)methyl)methanesulfonamide; N-(2-methylpropyl)-N-(((2S)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=7.68 (dd, J=1.3, 5.0 Hz, 1H), 7.59 (dd, J=1.3, 3.8 Hz, 1H), 7.47 (d, J=8.8 Hz, 2H), 7.20 (dd, J=3.8, 5.0 Hz, 1H), 6.98 (d, J=8.2 Hz, 2H), 4.45 (d, J=4.4 Hz, 1H), 3.89 (d, J=11.4 Hz, 1H), 3.79 (d, J=11.0 Hz, 1H), 3.62-3.51 (m, 1H), 3.50-3.18 (m, 3H), 3.16-3.00 (m, 2H), 2.82 (s, 3H), 2.71 (br. s., 1H), 2.66-2.52 (m, 1H), 2.31 (s, 1H), 1.93 (td, J=6.7, 13.9 Hz, 1H), 1.75 (s, 3H), 0.96 (d, J=6.6 Hz, 3H), 0.88 (d, J=6.6 Hz, 3H). m/z (ESI, +ve ion) 584.2 (M+H)$^+$. GK-GKRP IC$_{50}$ (Binding)=0.004 µM; GK-GKRP EC$_{50}$ (LC MS/MS-2)=0.014 µM.

Example 202

N-(cyclopropylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide This compound was synthesized following the scheme described for Example 195. The reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and cyclopropyl methylamine (Alfa Aesar, Ward Hill, Mass.), followed by sulfonamide formation (using MsCl) delivered 2-(4-((2S)-2-(((cyclopropylmethyl)amino) methyl)-4-(2-thiophenylsulfonyl)-1-piperazinyl)phenyl)-1,1,1-trifluoro-2-propanol as a mixture of two isomers.

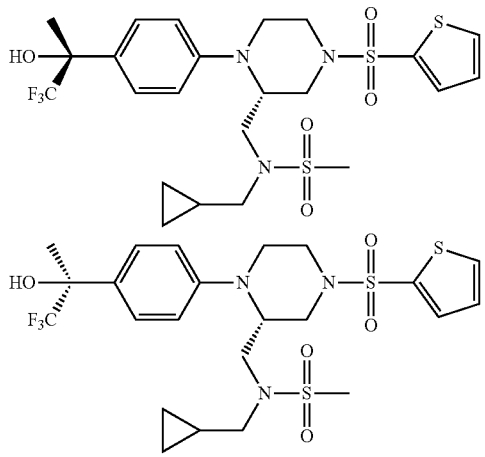

N-(cyclopropylmethyl)-N-(((2S)-4-(2-thiophenylsulfonyl)-1-(4-((1R)-2,2,2-trifluoro-1-hydroxy-1-methylethyl)phenyl)-2-piperazinyl)methyl)methanesulfonamide; N-(cyclopropylmethyl)-N-(((2S)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=7.68 (dd, J=1.2, 5.0 Hz, 1H), 7.59 (dd, J=1.2, 3.7 Hz, 1H), 7.46 (d, J=8.8 Hz, 2H), 7.20 (dd, J=3.8, 5.0 Hz, 1H), 6.95 (d, J=8.8 Hz, 2H), 4.45 (d, J=8.6 Hz, 1H), 3.95 (d, J=11.5 Hz, 1H), 3.82 (d, J=10.8 Hz, 1H), 3.56 (dd, J=10.0, 14.5 Hz, 2H), 3.40-3.20 (m, 4H), 2.91 (s, 3H), 2.68-2.48 (m, 2H), 2.29 (s, 1H), 1.75 (s, 3H), 0.93-0.85 (m, 1H), 0.68-0.49 (m, 2H), 0.42-0.21 (m, 2H). m/z (ESI, +ve ion) 582.1 (M+H)$^+$. GK-GKRP IC$_{50}$ (Binding)=0.026 μM; GK-GKRP EC$_{50}$ (LC MS/MS-2)=0.039 μM.

Example 203

1,1,1-trifluoro-2-(4-((2S)-2-((phenylamino)methyl)-4-(2-thiophenylsulfonyl)-1-piperazinyl)phenyl)-2-propanol

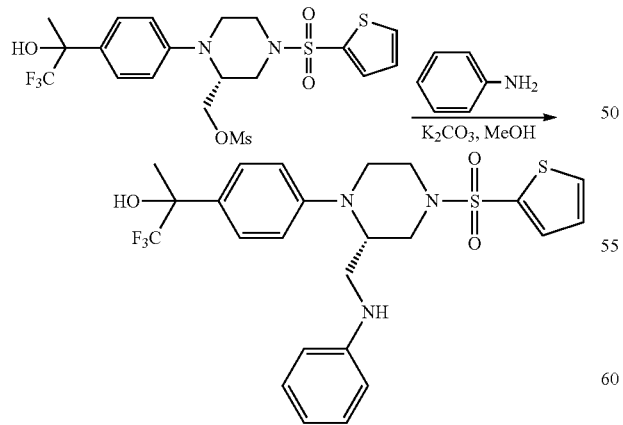

A 20-mL microwave vial was charged with ((2R)-4-(thiophen-2-ylsulfonyl)-1-(4-(1,1,1-trifluoro-2-hydroxypropan-2-yl)phenyl)piperazin-2-yl)methyl methanesulfonate (0.500 g, 0.946 mmol, Intermediate B), aniline (0.884 g, 9.46 mmol), and MeOH (8.0 mL). The vial was sealed and heated in an Initiator microwave reactor (Biotage AB, Inc., Uppsala, Sweden) at 140° C. for 30 min. After cooling to room temperature, the reaction mixture was concentrated and the crude product was purified by column chromatography (80 g, 2 to 5% 2M NH$_3$ in MeOH/CH$_2$Cl$_2$) to afford 1,1,1-trifluoro-2-(4-((2S)-2-((phenylamino)methyl)-4-(2-thiophenylsulfonyl)-1-piperazinyl)phenyl)-2-propanol (0.285 g) as a mixture of two isomers.

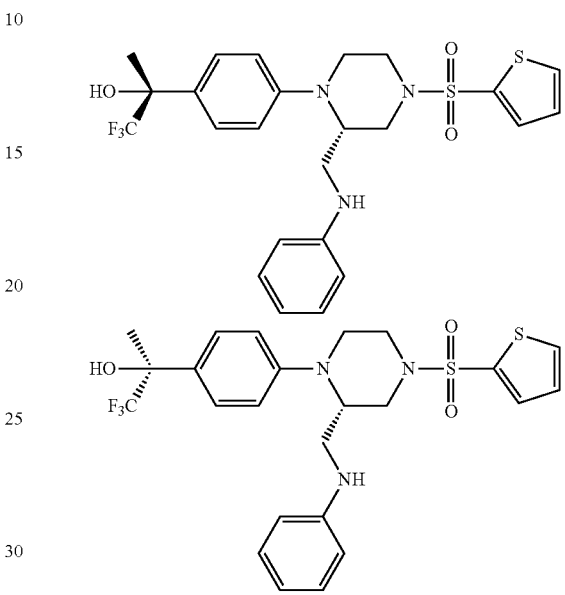

(2R)-1,1,1-trifluoro-2-(4-((2S)-2-((phenylamino)methyl)-4-(2-thiophenylsulfonyl)-1-piperazinyl)phenyl)-2-propanol, (2S)-1,1,1-trifluoro-2-(4-((2S)-2-((phenylamino)methyl)-4-(2-thiophenylsulfonyl)-1-piperazinyl)phenyl)-2-propanol.

$^1$H NMR (300 MHz, CDCl$_3$) δ=7.65 (dd, J=1.3, 5.0 Hz, 1H), 7.58 (dd, J=1.3, 3.7 Hz, 1H), 7.48 (d, J=8.6 Hz, 2H), 7.22-7.07 (m, 3H), 6.90 (d, J=8.9 Hz, 2H), 6.71 (t, J=7.4 Hz, 1H), 6.50 (d, J=7.9 Hz, 2H), 4.12 (d, J=3.2 Hz, 1H), 3.93-3.75 (m, 2H), 3.63-3.49 (m, 1H), 3.48-3.24 (m, 3H), 2.79-2.58 (m, 2H), 2.32 (s, 1H), 1.78 (s, 3H). m/z (ESI, +ve ion) 526.3 (M+H)$^+$. GK-GKRP IC$_{50}$ (Binding)=0.278 μM; GK-GKRP EC$_{50}$ (LC MS/MS-2)=0.146 μM.

Example 204

N-phenyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide

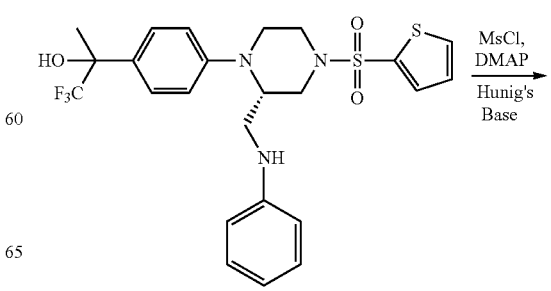

-continued

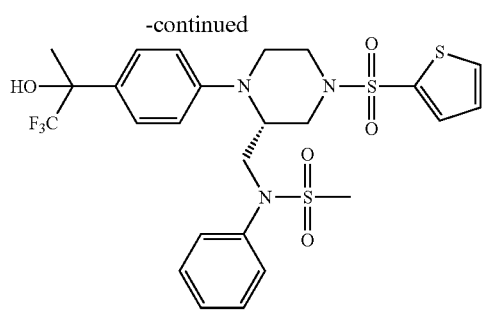

To a solution of 1,1,1-trifluoro-2-(4-((2S)-2-((phenylamino)methyl)-4-(2-thiophenylsulfonyl)-1-piperazinyl)phenyl)-2-propanol (0.100 g, 0.190 mmol, Example 203) in CH$_2$Cl$_2$ (3.0 mL) was added 4-dimethylaminopyridine (0.0046 g, 0.038 mmol), methanesulfonyl chloride (0.044 g, 0.381 mmol) and Hünig's base (0.135 mL, 0.774 mmol). After 15 h at room temperature, the solvent was removed and the crude product was purified by column chromatography (24 g of silica gel, 10 to 40% acetone in hexanes) to give N-phenyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide (0.034 g) as a mixture of two isomers.

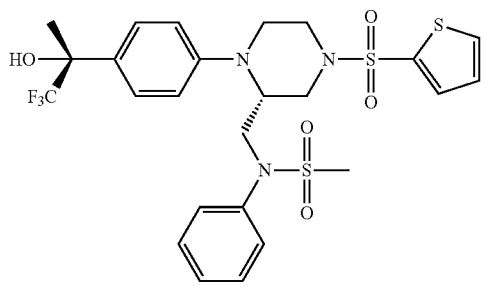

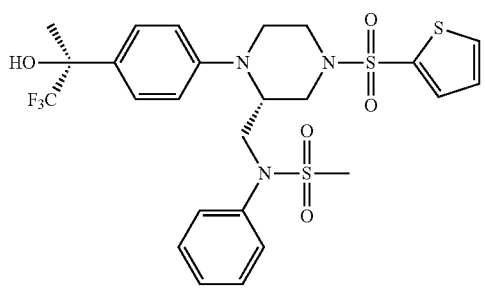

N-phenyl-N-(((2R)-4-(2-thiophenylsulfonyl)-1-(4-((1R)-2,2,2-trifluoro-1-hydroxy-1-methylethyl)phenyl)-2-piperazinyl)methyl)methanesulfonamide, N-phenyl-N-(((2R)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=7.65 (dd, J=1.3, 5.0 Hz, 1H), 7.55 (dd, J=1.2, 3.7 Hz, 1H), 7.43-7.30 (m, 5H), 7.17 (dd, J=3.7, 5.0 Hz, 1H), 7.12-7.05 (m, 2H), 6.72 (d, J=8.9 Hz, 2H), 4.15 (br. s., 1H), 4.04-3.89 (m, 2H), 3.83 (d, J=11.7 Hz, 1H), 3.71 (d, J=12.0 Hz, 1H), 3.48-3.38 (m, 1H), 3.37-3.23 (m, 1H), 2.85 (s, 3H), 2.70 (d, J=10.1 Hz, 1H), 2.61-2.48 (m, 1H), 2.30 (br. s., 1H), 1.76 (d, J=1.3 Hz, 3H). m/z (ESI, +ve ion) 604.1 (M+H)$^+$. GK-GKRP IC$_{50}$ (Binding)=0.004 µM; GK-GKRP EC$_{50}$ (LC MS/MS-2)=0.032 µM.

Example 205

2-(4-((2S)-2-((di-3-oxetanylamino)methyl)-4-(2-thiophenylsulfonyl)-1-piperazinyl)phenyl)-1,1,1-trifluoro-2-propanol

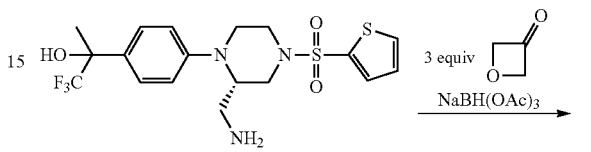

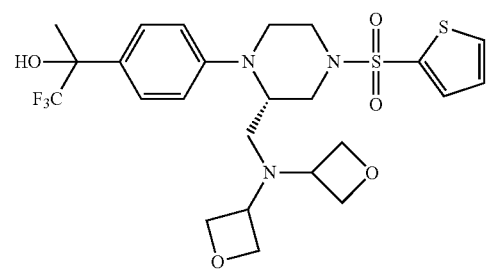

To a solution of 2-(4-((2S)-2-(aminomethyl)-4-(2-thiophenylsulfonyl)-1-piperazinyl)phenyl)-1,1,1-trifluoro-2-propanol (0.380 g, 0.845 mmol, Example 192, Step 1) in CH$_2$Cl$_2$ (8.0 mL) was added 3-oxetanone (0.20 mL, 2.5 mmol, Aldrich, St. Louis, Mo.), 4 Å molecular sieves (75 mg), acetic acid (0.015 mL, 0.17 mmol) and sodium triacetoxyborohydride (0.717 g, 3.38 mmol). The resulting mixture was stirred at room temperature for 15 h. The reaction mixture was partitioned between saturated aqueous NaHCO$_3$ (20 mL) and CH$_2$Cl$_2$ (40 mL). The aqueous layer was extracted with CH$_2$Cl$_2$ (2×15 mL) and the combined organic extracts were dried over MgSO$_4$ and concentrated. The crude product was purified by column chromatography (80 g of silica gel, 2 to 5% MeOH in CH$_2$Cl$_2$) to afford 2-(4-((2S)-2-((di-3-oxetanylamino)methyl)-4-(2-thiophenylsulfonyl)-1-piperazinyl)phenyl)-1,1,1-trifluoro-2-propanol (0.116 g) as a mixture of two isomers:

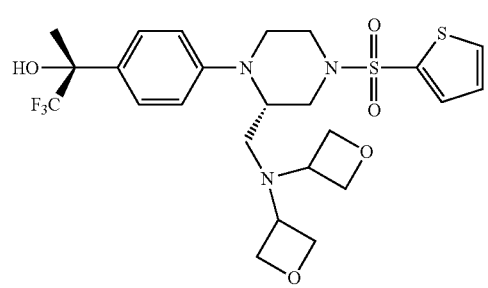

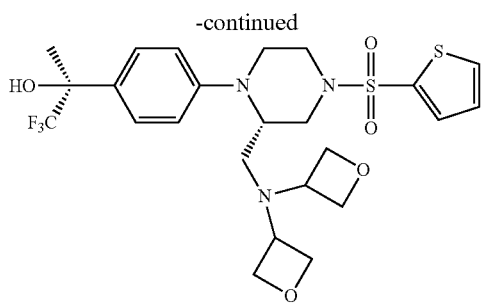

(2R)-2-(4-((2S)-2-((di-3-oxetanylamino)methyl)-4-(2-thiophenylsulfonyl)-1-piperazinyl)phenyl)-1,1,1-trifluoro-2-propanol; (2S)-2-(4-((2S)-2-((di-3-oxetanylamino)methyl)-4-(2-thiophenylsulfonyl)-1-piperazinyl)phenyl)-1,1,1-trifluoro-2-propanol.

$^1$H NMR (300 MHz, CDCl$_3$) δ=7.67 (dd, J=1.2, 5.0 Hz, 1H), 7.59 (dd, J=1.3, 3.8 Hz, 1H), 7.47 (d, J=8.8 Hz, 2H), 7.20 (dd, J=3.8, 5.0 Hz, 1H), 6.82 (d, J=8.9 Hz, 2H), 4.81-4.66 (m, 4H), 4.63-4.54 (m, 2H), 4.48 (t, J=6.6 Hz, 2H), 4.32-4.16 (m, 2H), 4.03 (d, J=11.3 Hz, 1H), 3.91-3.74 (m, 2H), 3.50-3.24 (m, 3H), 2.65-2.47 (m, 2H), 2.42-2.28 (m, 2H), 1.76 (s, 3H). m/z (ESI, +ve ion) 562.1 (M+H)$^+$. GK-GKRP IC$_{50}$ (Binding)=0.435 µM; GK-GKRP EC$_{50}$ (LC MS/MS-2)=0.480 µM.

Example 206

1,1,1-trifluoro-2-(4-((2S)-2-((3-oxetanylamino)methyl)-4-(2-thiophenylsulfonyl)-1-piperazinyl)phenyl)-2-propanol

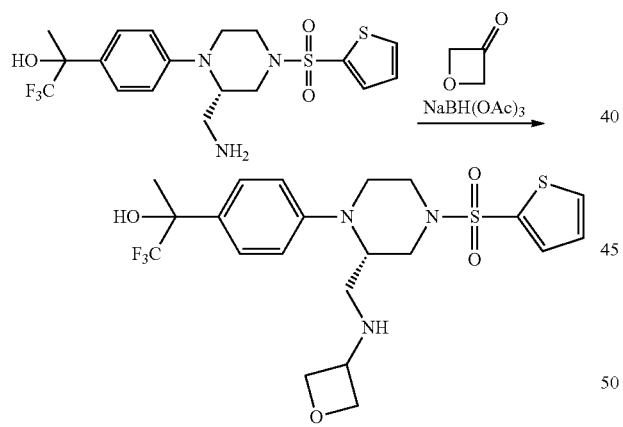

To a solution of 2-(4-((2S)-2-(aminomethyl)-4-(2-thiophenylsulfonyl)-1-piperazinyl)phenyl)-1,1,1-trifluoro-2-propanol (0.300 g, 0.667 mmol, Example 192, Step 1) in CH$_2$Cl$_2$ (5.0 mL) was added 3-oxetanone (0.050 mL, 0.67 mmol, Aldrich, St. Louis, Mo.), 4 Å molecular sieves (75 mg), and acetic acid (0.01 mL, 0.1 mmol). After stirred for 30 min, sodium triacetoxyborohydride (0.425 g, 2.01 mmol) was added and the reaction mixture was continued to stir at room temperature for 1 h. The reaction mixture was partitioned between saturated aqueous NaHCO$_3$ (20 mL) and CH$_2$Cl$_2$ (40 mL). The aqueous layer was extracted with CH$_2$Cl$_2$ (2×15 mL) and the combined organic layers were dried over MgSO$_4$ and concentrated. The crude product was purified by column chromatography (80 g of silica gel, 2 to 5% 2M NH$_3$ in MeOH/CH$_2$Cl$_2$) to afford 1,1,1-trifluoro-2-(4-((2S)-2-((3-oxetanylamino)methyl)-4-(2-thiophenylsulfonyl)-1-piperazinyl)phenyl)-2-propanol (0.235 g) as a mixture of two isomers:

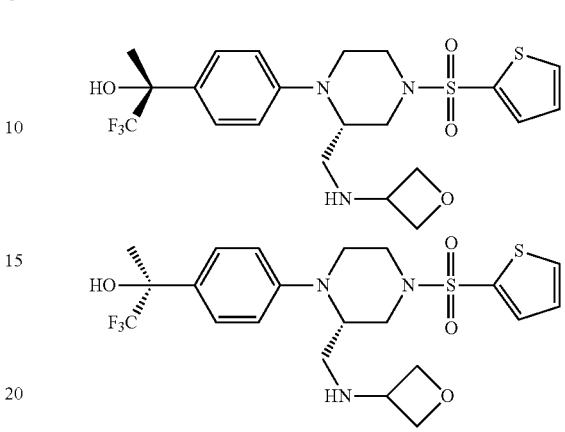

(2R)-1,1,1-trifluoro-2-(4-((2S)-2-((3-oxetanylamino)methyl)-4-(2-thiophenylsulfonyl)-1-piperazinyl)phenyl)-2-propanol; (2S)-1,1,1-trifluoro-2-(4-((2S)-2-((3-oxetanylamino)methyl)-4-(2-thiophenylsulfonyl)-1-piperazinyl)phenyl)-2-propanol.

$^1$H NMR (300 MHz, CDCl$_3$) δ=7.64 (dd, J=1.2, 5.0 Hz, 1H), 7.57 (dd, J=1.2, 3.7 Hz, 1H), 7.44 (d, J=8.8 Hz, 2H), 7.17 (dd, J=3.8, 5.1 Hz, 1H), 6.84 (d, J=9.1 Hz, 1H), 4.75 (td, J=6.7, 9.3 Hz, 2H), 4.31-4.31 (m, 1H), 4.43-4.27 (m, 2H), 3.99-3.83 (m, 3H), 3.75 (d, J=11.4 Hz, 1H), 3.46 (d, J=12.7 Hz, 1H), 3.27 (dt, J=3.7, 11.9 Hz, 1H), 2.94 (dd, J=9.0, 12.2 Hz, 1H), 2.75-2.56 (m, 3H), 2.35 (br. s., 1H), 1.74 (s, 3H). m/z (ESI, +ve ion) 506.1 (M+H)$^+$. GK-GKRP IC$_{50}$ (Binding)=0.248 µM; GK-GKRP EC$_{50}$ (LC MS/MS-2)=0.343 µM.

Example 207

N-3-oxetanyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide

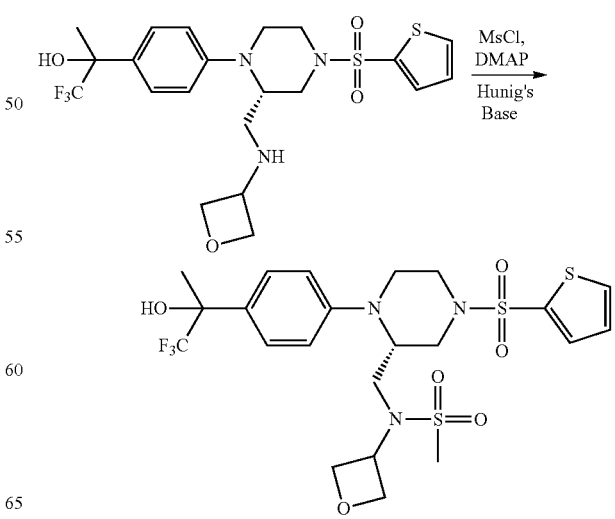

Following the procedure reported for Example 204, the reaction of 1,1,1-trifluoro-2-(4-((2S)-2-((3-oxetanylamino)methyl)-4-(2-thiophenylsulfonyl)-1-piperazinyl)phenyl)-2-propanol (Example 206) and methanesulfonyl chloride (Aldrich, St. Louis, Mo.) delivered N-3-oxetanyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide as a mixture of two isomers:

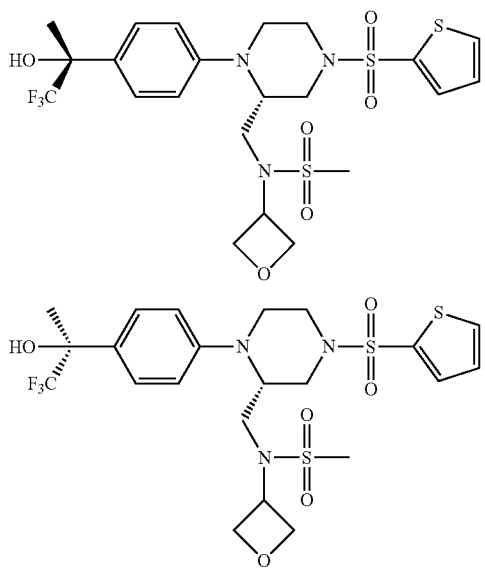

N-3-oxetanyl-N-(((2R)-4-(2-thiophenylsulfonyl)-1-(4-((1R)-2,2,2-trifluoro-1-hydroxy-1-methylethyl)phenyl)-2-piperazinyl)methyl)methanesulfonamide; N-3-oxetanyl-N-(((2R)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=7.69 (dd, J=1.2, 5.0 Hz, 1H), 7.59 (dd, J=1.2, 3.7 Hz, 1H), 7.47 (d, J=8.8 Hz, 2H), 7.20 (dd, J=3.8, 5.0 Hz, 1H), 6.95 (d, J=8.9 Hz, 2H), 5.12-5.01 (m, 1H), 4.97-4.85 (m, 2H), 4.80-4.61 (m, 3H), 4.00 (d, J=12.1 Hz, 1H), 3.83 (d, J=10.2 Hz, 1H), 3.77-3.55 (m, 2H), 3.41 (dt, J=3.4, 12.2 Hz, 1H), 3.27 (dd, J=4.8, 14.6 Hz, 1H), 2.73 (s, 3H), 2.66-2.45 (m, 2H), 2.32 (s, 1H), 1.75 (s, 3H). m/z (ESI, +ve ion) 584.0 (M+H)$^+$. GK-GKRP IC$_{50}$ (Binding) =0.241 μM; GK-GKRP EC$_{50}$ (LC MS/MS-2)=0.257 μM.

Example 208

N-methyl-N-(((2S)-4-(2-thiophenylsulfonyl)-1-(4-(2,2,2-trifluoro-1-hydroxy-1-methylethyl)phenyl)-2-piperazinyl)methyl)methanesulfonamide

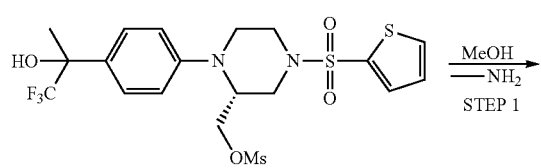

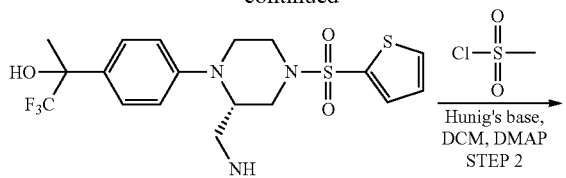

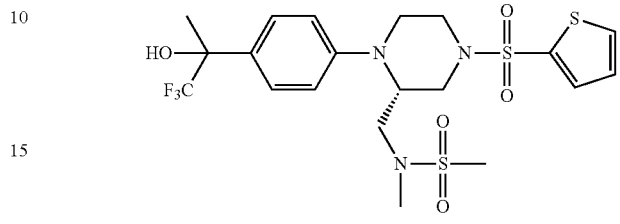

Step 1: 1,1,1-trifluoro-2-(4-((2S)-2-((methylamino)methyl)-4-(2-thiophenylsulfonyl)-1-piperazinyl)phenyl)-2-propanol Following the procedure reported for Example 199, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and methylamine, 2.0 M solution in THF (Aldrich, St. Louis, Mo.) delivered 1,1,1-trifluoro-2-(4-((2S)-2-((methylamino)methyl)-4-(2-thiophenylsulfonyl)-1-piperazinyl)phenyl)-2-propanol.

Step 2: N-methyl-N-(((2S)-4-(2-thiophenylsulfonyl)-1-(4-(2,2,2-trifluoro-1-hydroxy-1-methylethyl)phenyl)-2-piperazinyl)methyl)methanesulfonamide Following the procedure reported for Example 204, the reaction of 1,1,1-trifluoro-2-(4-((2S)-2-((methylamino)methyl)-4-(2-thiophenylsulfonyl)-1-piperazinyl)phenyl)-2-propanol and methanesulfonyl chloride (Aldrich, St. Louis, Mo.) delivered N-methyl-N-(((2S)-4-(2-thiophenylsulfonyl)-1-(4-(2,2,2-trifluoro-1-hydroxy-1-methylethyl)phenyl)-2-piperazinyl)methyl)methane sulfonamide as a mixture of two isomers:

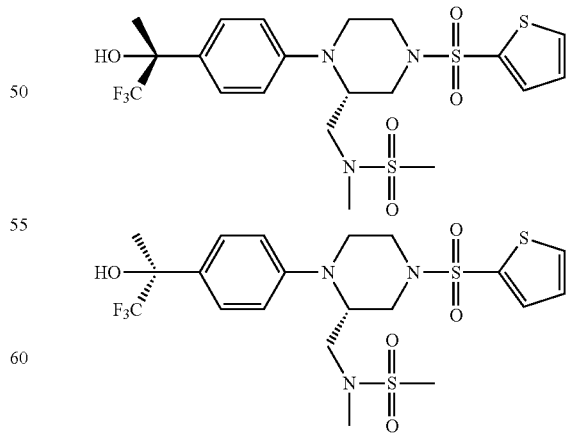

N-methyl-N-(((2S)-4-(2-thiophenylsulfonyl)-1-(4-((1R)-2,2,2-trifluoro-1-hydroxy-1-methylethyl)phenyl)-2-piperazinyl)methyl)methanesulfonamide; N-methyl-N-(((2S)-4-(2- thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=7.69 (dd, J=1.2, 5.0 Hz, 1H), 7.60 (dd, J=1.2, 3.7 Hz, 1H), 7.46 (d, J=8.8 Hz, 2H), 7.20 (dd, J=3.7, 5.0 Hz, 1H), 6.94 (d, J=8.8 Hz, 2H), 4.33 (br. s., 1H), 4.01 (d, J=11.7 Hz, 1H), 3.83 (d, J=11.1 Hz, 1H), 3.59 (d, J=12.4 Hz, 1H), 3.40-3.28 (m, 2H), 3.28-3.14 (m, 1H), 2.99 (s, 3H), 2.77 (s, 3H), 2.70-2.50 (m, 2H), 2.30 (s, 1H), 1.75 (s, 3H). m/z (ESI, +ve ion) 542.0 (M+H)$^+$. GK-GKRP IC$_{50}$ (Binding)=0.112 µM; GK-GKRP EC$_{50}$ (LC MS/MS-2)=0.234 µM Example 209

N,N-dimethyl-N'-(1-methylethyl)-N'-(((2R)-4-(2-thiophenylsulfonyl)-1-(4-(2,2,2-trifluoro-1-hydroxy-1-methylethyl)phenyl)-2-piperazinyl)methyl)sulfamide

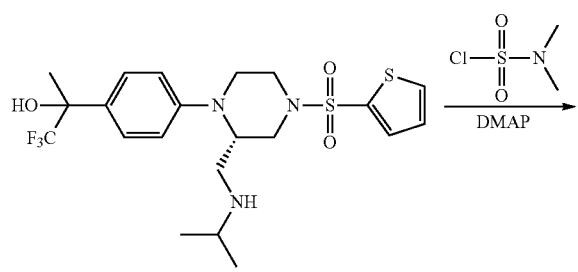

To a solution of 1,1,1-trifluoro-2-(4-((2S)-2-(((1-methylethyl)amino)methyl)-4-(2-thiophenylsulfonyl)-1-piperazinyl)phenyl)-2-propanol (0.100 g, 0.203 mmol, Example 195, Step 1) in pyridine (3.0 mL) was added 4-dimethylaminopyridine (5.0 mg, 0.040 mmol), Hünig's base (0.1 mL, 0.6 mmol), and dimethylsulfamoyl chloride (0.05 mL, 0.4 mmol, Aldrich, St. Louis, Mo.). The resulting mixture was heated at 80° C. for 6 h. The reaction mixture was allowed to cool to room temperature and then partitioned between EtOAc (30 mL) and water (20 mL). The aqueous layer was extracted with EtOAc (2×20 mL) and the combined organic extracts were dried over MgSO$_4$, filtered, and concentrated. The crude product was purified by column chromatography (24 g of silica, 10% to 40% EtOAc in hexanes) to afford N,N-dimethyl-N'-(1-methylethyl)-N'-(((2R)-4-(2-thiophenylsulfonyl)-1-(4-(2,2,2-trifluoro-1-hydroxy-1-methylethyl)phenyl)-2-piperazinyl)methyl)sulfamide (0.010 g) as a mixture of two isomers:

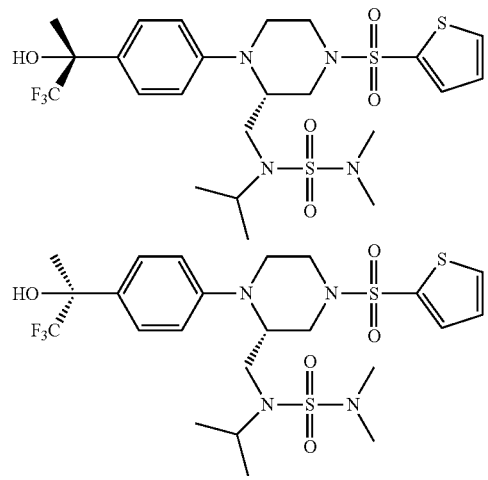

N,N-dimethyl-N'-(1-methylethyl)-N'-(((2R)-4-(2-thiophenylsulfonyl)-1-(4-((1R)-2,2,2-trifluoro-1-hydroxy-1-methylethyl)phenyl)-2-piperazinyl)methyl)sulfamide; N,N-dimethyl-N'-(1-methylethyl)-N'-(((2R)-4-(2-thiophenylsulfonyl)-1-(4-((1S)-2,2,2-trifluoro-1-hydroxy-1-methylethyl)phenyl)-2-piperazinyl)methyl)sulfamide.

$^1$H NMR (300 MHz, CDCl$_3$) δ=7.67 (dd, J=1.2, 5.0 Hz, 1H), 7.57 (dd, J=1.3, 3.8 Hz, 1H), 7.43 (d, J=8.8 Hz, 2H), 7.19 (dd, J=3.7, 5.0 Hz, 1H), 6.94 (d, J=8.8 Hz, 2H), 4.55 (d, J=6.4 Hz, 1H), 3.95-3.65 (m, 3H), 3.61-3.47 (m, 1H), 3.44-3.26 (m, 2H), 3.24-3.08 (m, 1H), 2.79 (d, J=1.9 Hz, 6H), 2.67 (d, J=8.6 Hz, 1H), 2.60-2.46 (m, 1H), 2.32 (s, 1H), 1.74 (s, 3H), 1.32 (d, J=6.7 Hz, 3H), 1.17 (d, J=6.7 Hz, 3H). m/z (ESI, +ve ion) 599.2 (M+H)$^+$. GK-GKRP IC$_{50}$ (Binding)=0.007 µM; GK-GKRP EC$_{50}$ (LC MS/MS-2)=0.023 µM.

Example 210

2-methyl-N-(((2S)-4-(2-thiophenylsulfonyl)-1-(4-(2,2,2-trifluoro-1-hydroxy-1-methylethyl)phenyl)-2-piperazinyl)methyl)-1-propanesulfonamide

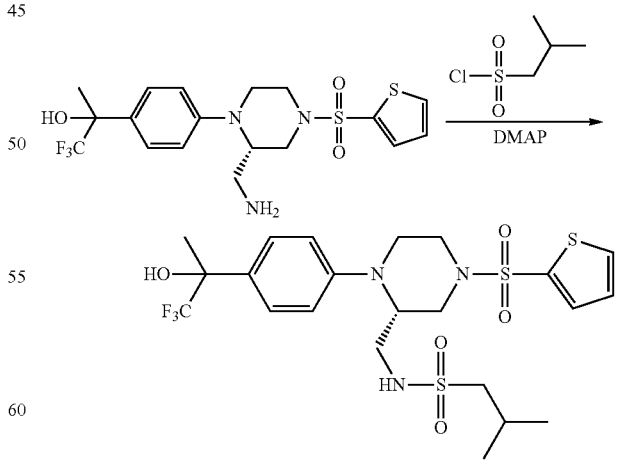

Following the procedure reported for Example 204, the reaction of 2-(4-((2S)-2-(aminomethyl)-4-(2-thiophenylsulfonyl)-1-piperazinyl)phenyl)-1,1,1-trifluoro-2-propanol (Example 192, Step 1) and isobutanesulfonyl chloride (Aldrich, St. Louis, Mo.) delivered 2-methyl-N-(((2S)-4-(2-thiophenylsulfonyl)-1-(4-(2,2,2-trifluoro-1-hydroxy-1-methylethyl)phenyl)-2-piperazinyl)methyl)-1-propanesulfonamide as a mixture of two isomers:

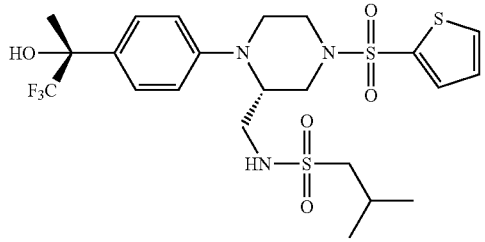

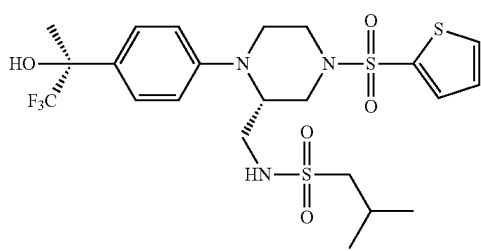

2-methyl-N-(((2S)-4-(2-thiophenylsulfonyl)-1-(4-((1R)-2,2,2-trifluoro-1-hydroxy-1-methylethyl)phenyl)-2-piperazinyl)methyl)-1-propanesulfonamide; 2-methyl-N-(((2S)-4-(2-thiophenylsulfonyl)-1-(4-((1S)-2,2,2-trifluoro-1-hydroxy-1-methylethyl)phenyl)-2-piperazinyl)methyl)-1-propanesulfonamide.

$^1$H NMR (300 MHz, CDCl$_3$) δ=7.67 (dd, J=1.2, 5.0 Hz, 1H), 7.59 (dd, J=1.3, 3.7 Hz, 1H), 7.47 (d, J=8.8 Hz, 2H), 7.19 (dd, J=3.7, 5.0 Hz, 1H), 6.93 (d, J=8.9 Hz, 2H), 4.50 (t, J=6.6 Hz, 1H), 4.18 (d, J=3.4 Hz, 1H), 3.92 (d, J=12.0 Hz, 1H), 3.80 (d, J=10.1 Hz, 1H), 3.55 (d, J=12.6 Hz, 1H), 3.48-3.16 (m, 3H), 2.99-2.82 (m, 2H), 2.79-2.62 (m, 2H), 2.32 (s, 1H), 2.22 (td, J=6.7, 13.3 Hz, 1H), 1.75 (s, 3H), 1.15-1.01 (m, 6H). m/z (ESI, +ve ion) 570.2 (M+H)$^+$. GK-GKRP IC$_{50}$ (Binding)=0.507 μM; GK-GKRP EC$_{50}$ (LC MS/MS-2)=0.249 μM.

Example 211

2-methyl-N-phenyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide

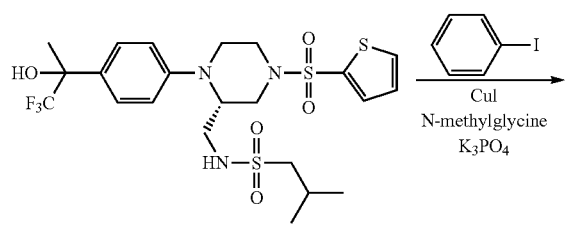

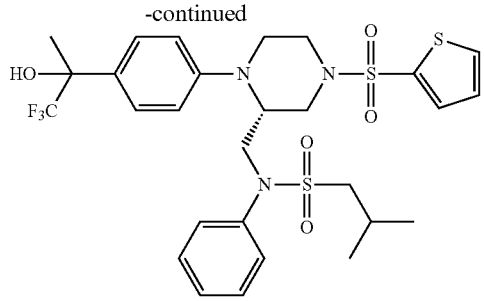

To a flame-dry 50-mL round-bottomed flask was added 2-methyl-N-(((2S)-4-(2-thiophenylsulfonyl)-1-(4-(2,2,2-trifluoro-1-hydroxy-1-methylethyl)phenyl)-2-piperazinyl)methyl)-1-propanesulfonamide (0.100 g, 0.176 mmol, Example 210), N-methylglycine (3.0 mg, 0.040 mmol, Aldrich, St. Louis, Mo.), CuI (0.02 g, 0.09 mmol, Aldrich, St. Louis, Mo.), and potassium phosphate (0.08 g, 0.37 mmol, Aldrich, St. Louis, Mo.). After the mixture was stirred for 10 min, iodobenzene (0.030 g, 0.14 mmol, Aldrich, St. Louis, Mo.) and DMF (3.0 mL) were added. The resulting mixture was heated at 110° C. for 24 h. Additional CuI was added (7.0 mg, 0.035 mmol) and the reaction was heated at 110° C. for an additional 6 d. The reaction mixture was allowed to cool to room temperature and filtered through a pad of Celite® (diatomaceous earth). The filtrate was concentrated and the crude product was purified by column chromatography (24 g of silica gel, 20 to 40% EtOAc in hexanes) to afford 2-methyl-N-phenyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide (0.032 g) as a mixture of two isomers:

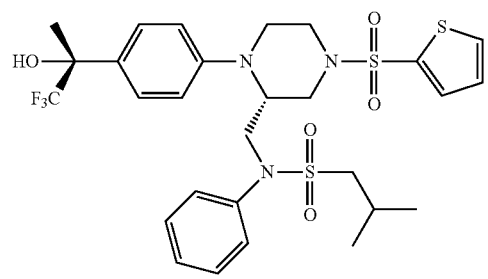

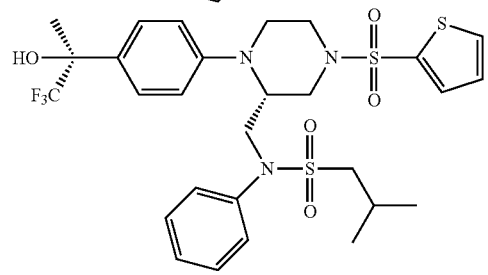

2-methyl-N-phenyl-N-(((2R)-4-(2-thiophenylsulfonyl)-1-(4-((1R)-2,2,2-trifluoro-1-hydroxy-1-methylethyl)phenyl)-2-piperazinyl)methyl)-1-propanesulfonamide; 2-methyl-N-phenyl-N-(((2R)-4-(2-thiophenylsulfonyl)-1-(4-((1S)-2,2,2-trifluoro-1-hydroxy-1-methylethyl)phenyl)-2-piperazinyl)methyl)-1-propanesulfonamide.

$^1$H NMR (300 MHz, CDCl$_3$) δ=7.64 (dd, J=1.2, 5.0 Hz, 1H), 7.55 (dd, J=1.3, 3.8 Hz, 1H), 7.37 (d, J=8.8 Hz, 2H), 7.34-7.28 (m, 3H), 7.16 (dd, J=3.8, 5.0 Hz, 1H), 7.09-7.02 (m,

2H), 6.70 (d, J=8.6 Hz, 2H), 4.13 (br. s., 1H), 4.09-3.99 (m, 1H), 3.98-3.87 (m, 1H), 3.80 (d, J=11.5 Hz, 1H), 3.70 (d, J=11.1 Hz, 1H), 3.46-3.24 (m, 2H), 2.94-2.74 (m, 2H), 2.69 (d, J=11.0 Hz, 1H), 2.60-2.44 (m, 1H), 2.35-2.19 (m, 2H), 1.76 (d, J=1.8 Hz, 3H), 1.06 (dd, J=2.6, 6.7 Hz, 6H). m/z (ESI, +ve ion) 646.0 (M+H)+. GK-GKRP IC$_{50}$ (Binding)=0.006 µM; GK-GKRP EC$_{50}$ (LC MS/MS-2)=0.020 µM.

Example 212

N-cyclobutyl-N-(((2R)-4-(2-thiophenylsulfonyl)-1-(4-(2,2,2-trifluoro-1-hydroxy-1-methylethyl)phenyl)-2-piperazinyl)methyl) methanesulfonamide

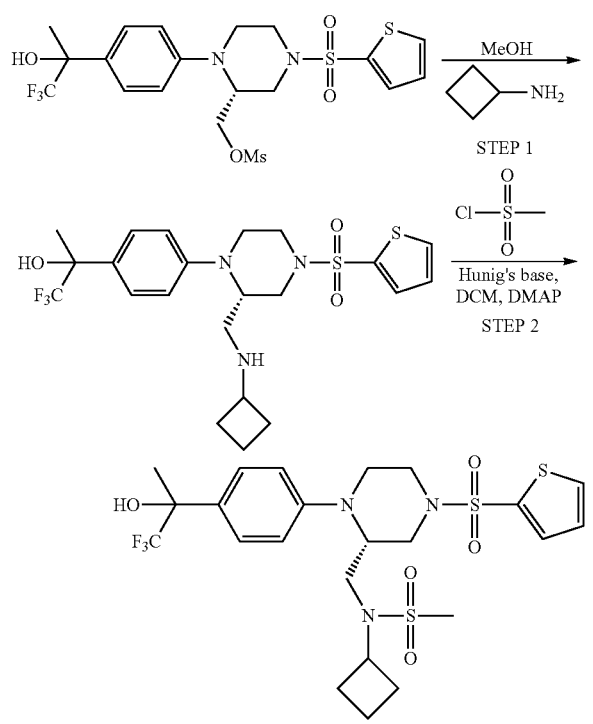

Step 1: 2-(4-((2S)-2-((cyclobutylamino)methyl)-4-(2-thiophenylsulfonyl)-1-piperazinyl)phenyl)-1,1,1-trifluoro-2-propanol Following the procedure reported for Example 199, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and cyclobutylamine (Aldrich, St. Louis, Mo.) delivered 2-(4-((2S)-2-((cyclobutylamino)methyl)-4-(2-thiophenylsulfonyl)-1-piperazinyl)phenyl)-1,1,1-trifluoro-2-propanol.

Step 2: N-cyclobutyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide Following the procedure reported for Example 204, the reaction of 2-(4-((2S)-2-((cyclobutylamino)methyl)-4-(2-thiophenylsulfonyl)-1-piperazinyl)phenyl)-1,1,1-trifluoro-2-propanol and methanesulfonyl chloride (0.031 mL, 0.40 mmol, Aldrich, St. Louis, Mo.) delivered N-cyclobutyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide as a mixture of two isomers:

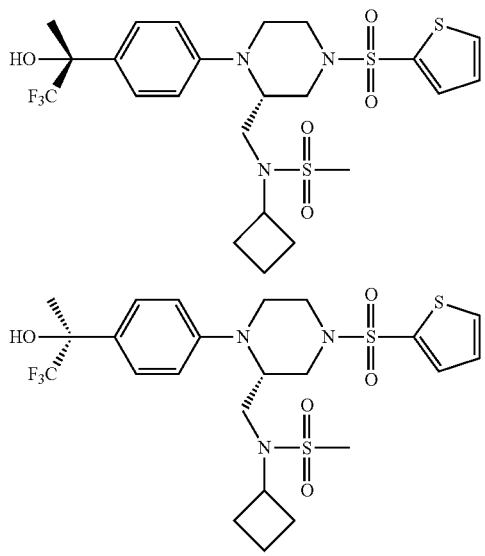

N-cyclobutyl-N-(((2R)-4-(2-thiophenylsulfonyl)-1-(4-((1R)-2,2,2-trifluoro-1-hydroxy-1-methylethyl)phenyl)-2-piperazinyl)methyl)methanesulfonamide; N-cyclobutyl-N-(((2R)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=7.67 (dd, J=1.3, 5.0 Hz, 1H), 7.58 (dd, J=1.2, 3.7 Hz, 1H), 7.45 (d, J=8.8 Hz, 2H), 7.19 (dd, J=3.7, 5.0 Hz, 1H), 6.94 (d, J=8.6 Hz, 2H), 4.57 (br. s., 1H), 4.24-4.07 (m, 1H), 3.98 (d, J=11.7 Hz, 1H), 3.79 (d, J=11.1 Hz, 1H), 3.60 (d, J=12.7 Hz, 1H), 3.51-3.28 (m, 2H), 3.16-3.06 (m, 1H), 2.72 (s, 2H), 2.67-2.45 (m, 2H), 2.43-2.24 (m, 3H), 2.19-2.03 (m, 2H), 1.80-1.71 (m, 4H), 1.71-1.57 (m, 1H). m/z (ESI, +ve ion) 582.2 (M+H)+. GK-GKRP IC$_{50}$ (Binding)=0.068 µM; GK-GKRP EC$_{50}$ (LC MS/MS-2)=0.092 µM.

Example 213

N-cyclobutyl-N-(((2R)-4-(2-thiophenylsulfonyl)-1-(4-(2,2,2-trifluoro-1-hydroxy-1-methylethyl)phenyl)-2-piperazinyl)methyl)-3-pyridinesulfonamide

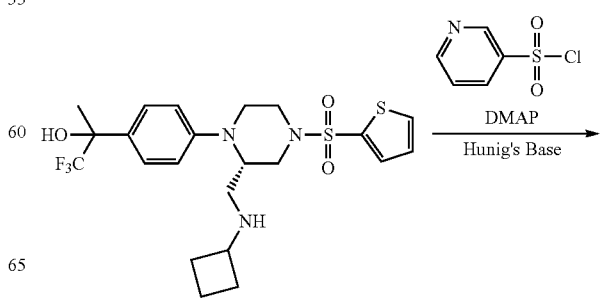

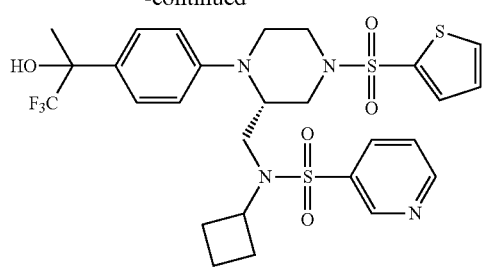

Following the procedure reported for Example 198, the reaction of 2-(4-(((2S)-2-((cyclobutylamino)methyl)-4-(2-thiophenylsulfonyl)-1-piperazinyl)phenyl)-1,1,1-trifluoro-2-propanol (Example 212 [Step 1]) and pyridine-3-sulfonyl chloride (WAKO, Richmond, Va.) delivered N-cyclobutyl-N-(((2R)-4-(2-thiophenylsulfonyl)-1-(4-(2,2,2-trifluoro-1-hydroxy-1-methylethyl)phenyl)-2-piperazinyl)methyl)-3-pyridinesulfonamide as a mixture of two isomers.

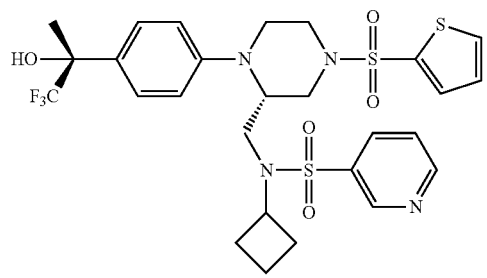

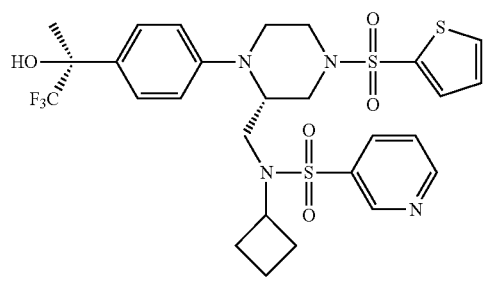

N-cyclobutyl-N-(((2R)-4-(2-thiophenylsulfonyl)-1-(4-((1R)-2,2,2-trifluoro-1-hydroxy-1-methylethyl)phenyl)-2-piperazinyl)methyl)-3-pyridinesulfonamide; N-cyclobutyl-N-(((2R)-4-(2-thiophenylsulfonyl)-1-(4-((1S)-2,2,2-trifluoro-1-hydroxy-1-methylethyl)phenyl)-2-piperazinyl)methyl)-3-pyridinesulfonamide.

$^1$H NMR (300 MHz, DMSO-$d_6$) δ=8.85-8.70 (m, 2H), 8.11 (dd, J=1.3, 5.0 Hz, 1H), 7.92 (td, J=1.9, 8.1 Hz, 1H), 7.73 (dd, J=1.1, 3.7 Hz, 1H), 7.54-7.40 (m, 3H), 7.33 (dd, J=3.8, 5.0 Hz, 1H), 6.97 (d, J=8.9 Hz, 2H), 6.39 (s, 1H), 4.53 (br. s., 1H), 4.20-4.00 (m, 1H), 3.80 (d, J=11.7 Hz, 1H), 3.61 (d, J=11.5 Hz, 1H), 3.50 (d, J=12.4 Hz, 1H), 3.45-3.33 (m, 1H), 2.78-2.65 (m, 1H), 2.58 (dd, J=3.5, 11.5 Hz, 1H), 2.41-2.29 (m, 1H), 2.28-2.16 (m, 1H), 2.09 (d, J=9.5 Hz, 1H), 1.94-1.76 (m, 1H), 1.66 (s, 3H), 1.56-1.40 (m, 2H), 1.25 (dd, J=4.5, 6.3 Hz, 2H). m/z (ESI, +ve ion) 645.1 (M+H)$^+$. GK-GKRP IC$_{50}$ (Binding)=0.928 μM.

Example 214

2,2,2-trifluoro-N-(2-methylpropyl)-N-(((2S)-4-(2-thiophenylsulfonyl)-1-(4-(2,2,2-trifluoro-1-hydroxy-1-methylethyl)phenyl)-2-piperazinyl)methyl) ethanesulfonamide

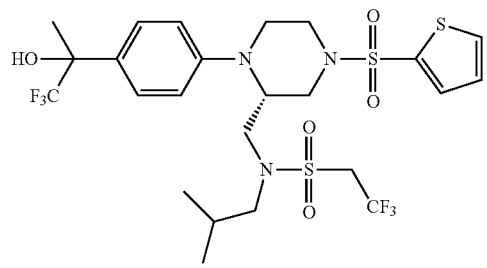 [SMILES: CC(C)CN(C[C@H]1CN(S(=O)(=O)c2cccs2)CCN1c1ccc(C(C)(O)C(F)(F)F)cc1)S(=O)(=O)CC(F)(F)F]

Following the procedure reported for Example 204, the reaction of 1,1,1-trifluoro-2-(4-((2S)-2-(((2-methylpropyl)amino)methyl)-4-(2-thiophenylsulfonyl)-1-piperazinyl)phenyl)-2-propanol (Example 201, Step 1) and 2,2,2-trifluoroethanesulfonyl chloride (Aldrich, St. Louis, Mo.) delivered 2,2,2-trifluoro-N-(2-methylpropyl)-N-(((2S)-4-(2-thiophenylsulfonyl)-1-(4-(2,2,2-trifluoro-1-hydroxy-1-methylethyl)phenyl)-2-piperazinyl)methyl)ethanesulfonamide as a mixture of two isomers.

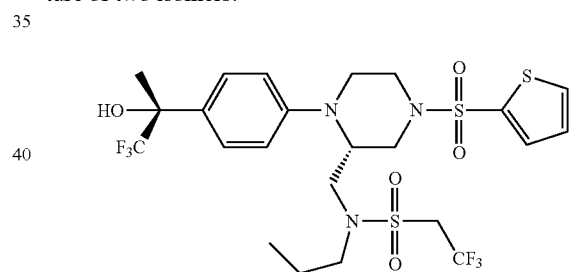

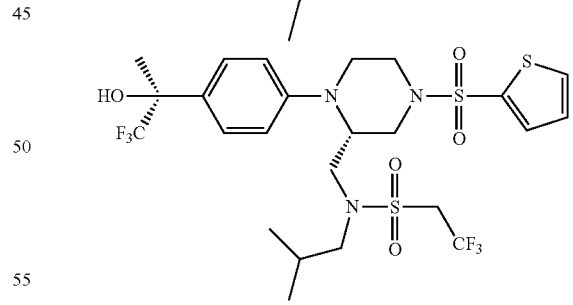

2,2,2-trifluoro-N-(2-methylpropyl)-N-(((2S)-4-(2-thiophenylsulfonyl)-1-(4-((1R)-2,2,2-trifluoro-1-hydroxy-1-methylethyl)phenyl)-2-piperazinyl)methyl)ethanesulfonamide; 2,2,2-trifluoro-N-(2-methylpropyl)-N-(((2S)-4-(2-thiophenylsulfonyl)-1-(4-((1S)-2,2,2-trifluoro-1-hydroxy-1-methylethyl)phenyl)-2-piperazinyl)methyl)ethanesulfonamide.

$^1$H NMR (300 MHz, CDCl$_3$) δ=7.68 (dd, J=1.2, 5.0 Hz, 1H), 7.59 (dd, J=1.3, 3.7 Hz, 1H), 7.47 (d, J=8.8 Hz, 2H), 7.20 (dd, J=3.8, 5.0 Hz, 1H), 6.92 (d, J=8.8 Hz, 2H), 4.37 (br. s., 1H), 3.80 (t, J=11.1 Hz, 2H), 3.75-3.62 (m, 2H), 3.62-3.47

(m, 2H), 3.44-3.30 (m, 2H), 3.12 (d, J=7.6 Hz, 2H), 2.73 (d, J=10.8 Hz, 1H), 2.59 (t, J=10.2 Hz, 1H), 2.30 (s, 1H), 1.87 (td, J=7.0, 13.7 Hz, 1H), 1.75 (s, 3H), 0.91 (dd, J=6.7, 16.2 Hz, 6H). m/z (ESI, +ve ion) 652.0 (M+H)+. GK-GKRP IC$_{50}$ (Binding)=0.238 μM; GK-GKRP EC$_{50}$ (LC MS/MS-2)=0.247 μM.

Example 215

N,N-dimethyl-N'-(2-methylpropyl)-N'-(((2R)-4-(2-thiophenylsulfonyl)-1-(4-(2,2,2-trifluoro-1-hydroxy-1-methylethyl)phenyl)-2-piperazinyl)methyl)sulfamide

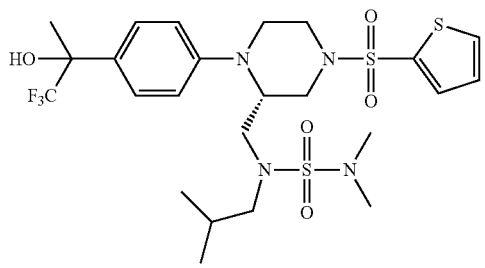 [SMILES: CC(C)CN(C[C@H]1CN(S(=O)(=O)c2cccs2)CCN1c1ccc(C(C)(O)C(F)(F)F)cc1)S(=O)(=O)N(C)C]

Following the procedure reported for Example 209, the reaction of 1,1,1-trifluoro-2-(4-((2S)-2-(((2-methylpropyl)amino)methyl)-4-(2-thiophenylsulfonyl)-1-piperazinyl)phenyl)-2-propanol (Example 201, Step 1) and dimethylsulfamoyl chloride (Aldrich, St. Louis, Mo.) delivered N,N-dimethyl-N'-(2-methylpropyl)-N'-(((2R)-4-(2-thiophenylsulfonyl)-1-(4-(2,2,2-trifluoro-1-hydroxy-1-methylethyl)phenyl)-2-piperazinyl)methyl)sulfamide as a mixture of two isomers.

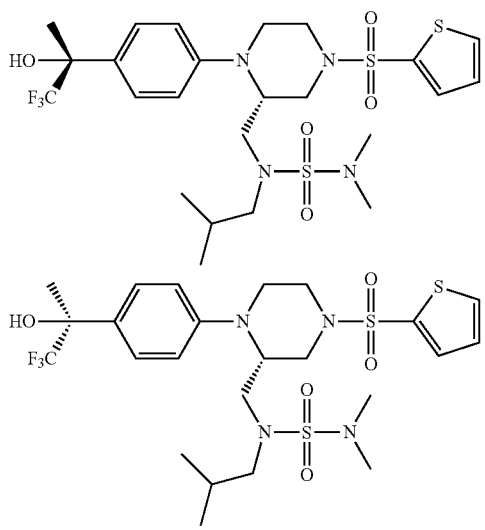

N,N-dimethyl-N'-(2-methylpropyl)-N'-(((2R)-4-(2-thiophenylsulfonyl)-1-(4-((1R)-2,2,2-trifluoro-1-hydroxy-1-methylethyl)phenyl)-2-piperazinyl)methyl)sulfamide; N,N-dimethyl-N'-(2-methylpropyl)-N'-(((2R)-4-(2-thiophenylsulfonyl)-1-(4-((1S)-2,2,2-trifluoro-1-hydroxy-1-methylethyl)phenyl)-2-piperazinyl)methyl)sulfamide.

$^1$H NMR (300 MHz, CDCl$_3$) δ=7.67 (dd, J=1.2, 5.0 Hz, 1H), 7.59 (dd, J=1.2, 3.7 Hz, 1H), 7.45 (d, J=8.8 Hz, 2H), 7.19 (dd, J=3.8, 5.0 Hz, 1H), 6.92 (d, J=8.8 Hz, 2H), 4.42 (d, J=6.9 Hz, 1H), 3.90 (d, J=11.5 Hz, 1H), 3.77 (d, J=8.9 Hz, 1H), 3.57-3.42 (m, 2H), 3.36-3.18 (m, 2H), 3.04 (dd, J=2.6, 7.3 Hz, 2H), 2.76 (d, J=1.2 Hz, 6H), 2.67 (d, J=12.3 Hz, 1H), 2.60-2.46 (m, 1H), 2.29 (s, 1H), 1.98-1.82 (m, 1H), 1.74 (s, 3H), 0.94 (d, J=6.6 Hz, 3H), 0.89-0.79 (m, 3H). m/z (ESI, +ve ion) 613.1 (M+H)+. GK-GKRP IC$_{50}$ (Binding)=0.07 μM; GK-GKRP EC$_{50}$ (LC MS/MS-2)=0.07 μM.

Example 216

N-((3-methyl-3-oxetanyl)methyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide

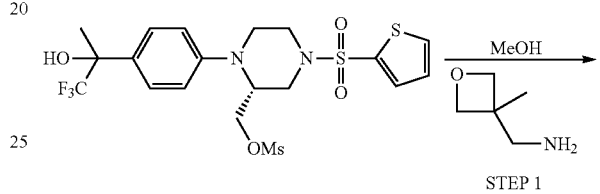

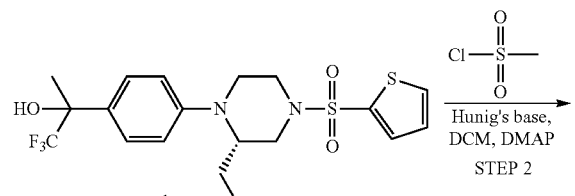

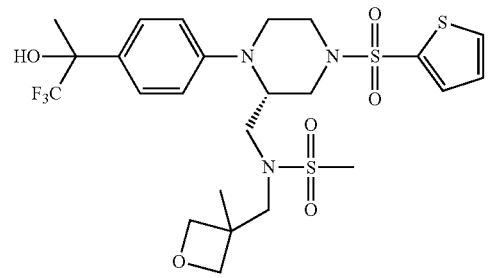

Step 1: 1,1,1-trifluoro-2-(4-((2S)-2-((((3-methyl-3-oxetanyl)methyl)amino)methyl)-4-(2-thiophenylsulfonyl)-1-piperazinyl)phenyl)-2-propanol Following the procedure reported for Example 199, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and 3-aminomethyl-3-methyloxetane (Advance Chemblocks, Burlingame, Calif.)

delivered 1,1,1-trifluoro-2-(4-((2S)-2-((((3-methyl-3-oxetanyl)methyl)amino)methyl)-4-(2-thiophenylsulfonyl)-1-piperazinyl)phenyl)-2-propanol.

Step 2: N-((3-methyl-3-oxetanyl)methyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide

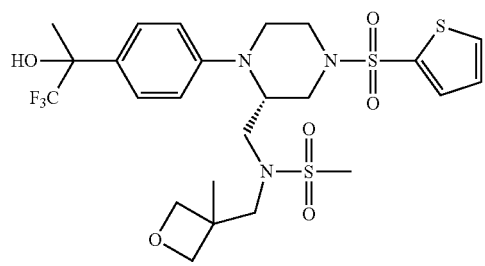 [SMILES: CC1(CN(C[C@H]2CN(S(=O)(=O)c3cccs3)CCN2c2ccc(C(C)(O)C(F)(F)F)cc2)S(C)(=O)=O)COC1]

Following the procedure reported for Example 204, the reaction of 1,1,1-trifluoro-2-(4-((2S)-2-((((3-methyl-3-oxetanyl)methyl)amino)methyl)-4-(2-thiophenylsulfonyl)-1-piperazinyl)phenyl)-2-propanol and methanesulfonyl chloride (Aldrich, St. Louis, Mo.) delivered N-((3-methyl-3-oxetanyl)methyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide as a mixture of two isomers.

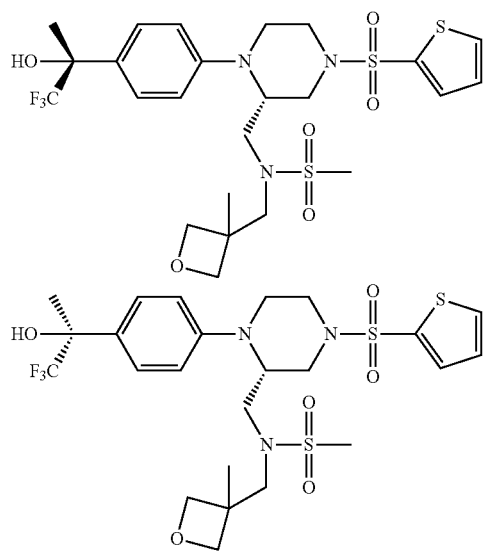

N-((3-methyl-3-oxetanyl)methyl)-N-(((2S)-4-(2-thiophenylsulfonyl)-1-(4-((1R)-2,2,2-trifluoro-1-hydroxy-1-methylethyl)phenyl)-2-piperazinyl)methyl)methanesulfonamide; N-((3-methyl-3-oxetanyl)methyl)-N-(((2S)-4-(2-thiophenylsulfonyl)-1-(4-((1S)-2,2,2-trifluoro-1-hydroxy-1-methylethyl)phenyl)-2-piperazinyl)methyl)methanesulfonamide.
$^1$H NMR (300 MHz, CDCl$_3$) δ=7.69 (dd, J=1.3, 5.0 Hz, 1H), 7.60 (dd, J=1.3, 3.8 Hz, 1H), 7.47 (d, J=8.8 Hz, 2H), 7.20 (dd, J=3.8, 5.0 Hz, 1H), 6.93 (d, J=8.9 Hz, 2H), 4.63-4.49 (m, 2H), 4.45 (br. s., 1H), 4.32 (d, J=6.1 Hz, 2H), 3.91 (d, J=12.0 Hz, 1H), 3.80 (d, J=10.5 Hz, 1H), 3.70-3.46 (m, 3H), 3.36-3.21 (m, 3H), 2.85 (s, 3H), 2.74-2.51 (m, 2H), 2.40 (d, J=3.8 Hz, 1H), 1.75 (s, 3H), 1.49-1.39 (m, 3H). m/z (ESI, +ve ion) 612.3 (M+H)$^+$. GK-GKRP IC$_{50}$ (Binding)=0.172 μM; GK-GKRP EC$_{50}$ (LC MS/MS-2)=0.194 μM.

Example 217

N-methyl-N-(((2S)-4-(2-thiophenylsulfonyl)-1-(4-(2,2,2-trifluoro-1-hydroxy-1-methylethyl)phenyl)-2-piperazinyl)methyl)-3-pyridinesulfonamide Following the procedure reported for Example 198, the reaction of 1,1,1-trifluoro-2-(4-((2S)-2-((methylamino)methyl)-4-(2-thiophenylsulfonyl)-1-piperazinyl)phenyl)-2-propanol (Example 208 [Step 1]) and pyridine-3-sulfonyl chloride (Astatech, Bristol, Pa.) delivered N-methyl-N-(((2S)-4-(2-thiophenylsulfonyl)-1-(4-(2,2,2-trifluoro-1-hydroxy-1-methylethyl)phenyl)-2-piperazinyl)methyl)-3-pyridinesulfonamide as a mixture of two isomers.

N-methyl-N-(((2S)-4-(2-thiophenylsulfonyl)-1-(4-((1R)-2,2,2-trifluoro-1-hydroxy-1-methylethyl)phenyl)-2-piperazinyl)methyl)-3-pyridinesulfonamide; N-methyl-N-(((2S)-4-(2-thiophenylsulfonyl)-1-(4-((1S)-2,2,2-trifluoro-1-hydroxy-1-methylethyl)phenyl)-2-piperazinyl)methyl)-3-pyridinesulfonamide.
$^1$H NMR (300 MHz, CDCl$_3$) δ=8.90-8.42 (m, 2H), 7.88 (d, J=7.2 Hz, 1H), 7.70 (dd, J=1.3, 5.0 Hz, 1H), 7.62 (dd, J=1.2, 3.7 Hz, 1H), 7.56 (dd, J=3.9, 8.6 Hz, 2H), 7.41 (br. s., 1H), 7.22 (dd, J=3.7, 5.0 Hz, 1H), 7.06-6.91 (m, 2H), 4.48 (br. s., 1H), 4.05 (dd, J=2.1, 11.8 Hz, 1H), 3.84 (d, J=8.9 Hz, 1H), 3.47-3.32 (m, 1H), 3.20 (dt, J=3.0, 11.9 Hz, 1H), 3.08-2.87 (m, 5H), 2.80-2.68 (m, 1H), 2.66-2.53 (m, 1H), 1.80 (d, J=1.6 Hz, 3H). m/z (ESI, +ve ion) 605.0 (M+H)$^+$. GK-GKRP IC$_{50}$ (Binding)=0.407 μM; GK-GKRP EC$_{50}$ (LC MS/MS-2)=0.752 μM.

Example 218

N-(cyclobutylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide

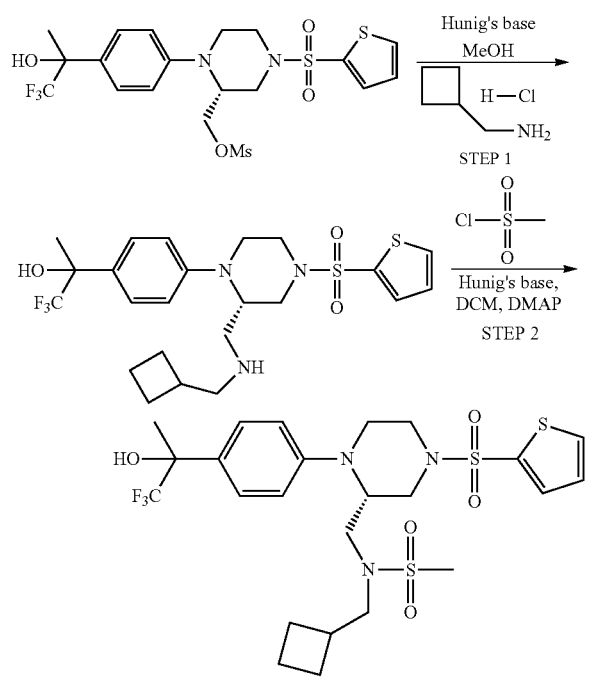

Step 1: 2-(4-((2S)-2-(((cyclobutylmethyl)amino)methyl)-4-(2-thiophenylsulfonyl)-1-piperazinyl)phenyl)-1,1,1-trifluoro-2-propanol To a 20-mL of microwave vial was added ((2R)-4-(thiophen-2-ylsulfonyl)-1-(4-(1,1,1-trifluoro-2-hydroxypropan-2-yl)phenyl)piperazin-2-yl)methyl methanesulfonate (1.0 g, 1.9 mmol, Intermediate B), cyclobutylmethanamine hydrochloride (0.097 g, 0.795 mmol, PharmaBlock, Ward Hill, Mass.), Hünig's base (0.367 g, 2.04 mmol), and MeOH (10.0 mL). The vial was sealed and heated in an Initiator microwave reactor (Biotage AB, Inc., Uppsala, Sweden) at 140° C. for 30 min. The reaction mixture was concentrated and the crude product was purified by column chromatography (120 g of silica, 2% to 8% 2M NH$_3$ in MeOH in CH$_2$Cl$_2$) to afford 2-(4-(((2S)-2-(((cyclobutylmethyl)amino)methyl)-4-(2-thiophenylsulfonyl)-1-piperazinyl)phenyl)-1,1,1-trifluoro-2-propanol (0.110 g).

Step 2: N-(cyclobutylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide Following the procedure reported for Example 204, the reaction of 2-(4-((2S)-2-(((cyclobutylmethyl)amino)methyl)-4-(2-thiophenylsulfonyl)-1-piperazinyl)phenyl)-1,1,1-trifluoro-2-propanol and methanesulfonyl chloride (Aldrich, St. Louis, Mo.) delivered N-(cyclobutylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide as a mixture of two isomers.

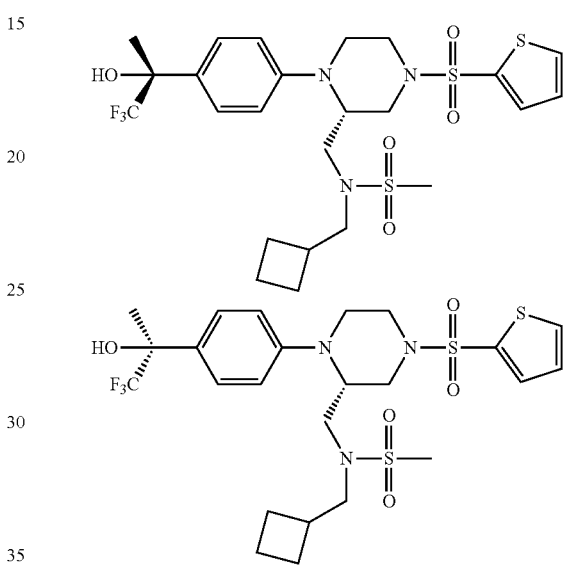

N-(cyclobutylmethyl)-N-(((2S)-4-(2-thiophenylsulfonyl)-1-(4-((1R)-2,2,2-trifluoro-1-hydroxy-1-methylethyl)phenyl)-2-piperazinyl)methyl)methanesulfonamide; N-(cyclobutylmethyl)-N-(((2S)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=7.68 (dd, J=1.2, 5.0 Hz, 1H), 7.60 (dd, J=1.3, 3.8 Hz, 1H), 7.46 (d, J=8.8 Hz, 2H), 7.20 (dd, J=3.8, 5.0 Hz, 1H), 6.93 (d, J=8.8 Hz, 2H), 4.41 (br. s., 1H), 3.90 (d, J=11.5 Hz, 1H), 3.80 (d, J=10.2 Hz, 1H), 3.56 (d, J=12.9 Hz, 1H), 3.45-3.32 (m, 3H), 3.32-3.13 (m, 2H), 2.81 (s, 3H), 2.59 (dt, J=7.6, 14.8 Hz, 3H), 2.30 (s, 1H), 2.18-1.95 (m, 2H), 1.94-1.78 (m, 3H), 1.78-1.67 (m, 4H). m/z (ESI, +ve ion) 596.1 (M+H)$^+$. GK-GKRP IC$_{50}$ (Binding)=0.024 μM; GK-GKRP EC$_{50}$ (LC MS/MS-2)=0.017 μM.

Example 219

1,1,1-trifluoro-2-(4-((2R)-2-(((2-fluorophenyl)sulfanyl)methyl)-4-(2-thiophenylsulfonyl)-1-piperazinyl)phenyl)-2-propanol

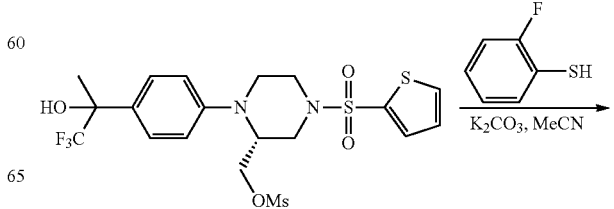

-continued

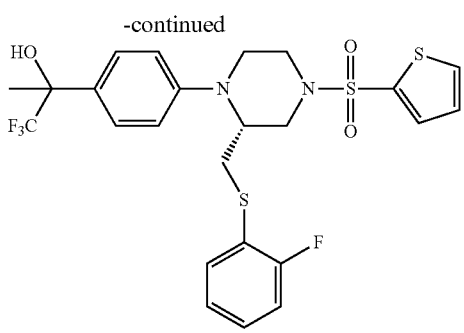

Following the procedure reported for Example 186, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and 2-fluorothiophenol (Aldrich, St. Louis, Mo.) delivered 1,1,1-trifluoro-2-(4-((2R)-2-(((2-fluorophenyl)sulfanyl)methyl)-4-(2-thiophenylsulfonyl)-1-piperazinyl)phenyl)-2-propanol as a mixture of two isomers.

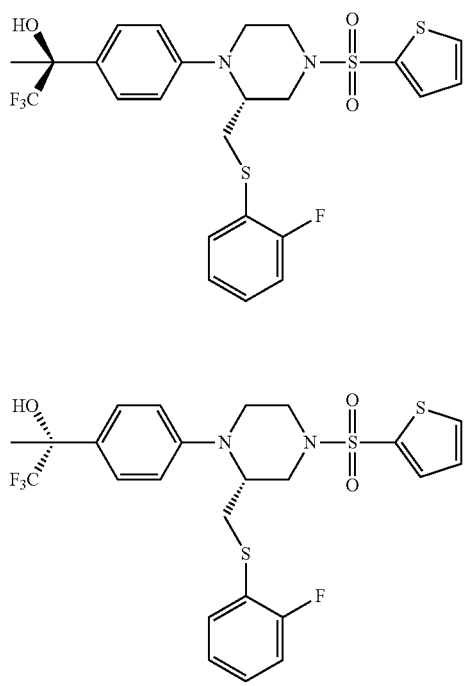

(2S)-1,1,1-trifluoro-2-(4-((2R)-2-(((2-fluorophenyl)sulfanyl)methyl)-4-(2-thiophenylsulfonyl)-1-piperazinyl)phenyl)-2-propanol; (2R)-1,1,1-trifluoro-2-(4-((2R)-2-(((2-fluorophenyl)sulfanyl)methyl)-4-(2-thiophenylsulfonyl)-1-piperazinyl)phenyl)-2-propanol.

$^1$H NMR (300 MHz, CDCl$_3$) δ=7.66 (dd, J=1.3, 5.1 Hz, 1H), 7.61 (dd, J=1.3, 3.8 Hz, 1H), 7.38-7.28 (m, 4H), 7.18 (dd, J=3.7, 5.0 Hz, 1H), 7.10-6.99 (m, 2H), 6.61 (br. s., 2H), 4.15 (d, J=11.5 Hz, 1H), 3.89-3.72 (m, 2H), 3.46-3.36 (m, 1H), 3.34-3.14 (m, 2H), 2.90 (d, J=13.7 Hz, 1H), 2.84-2.58 (m, 2H), 2.28 (br. s., 1H), 1.74 (d, J=1.9 Hz, 3H). m/z (ESI, +ve ion) 561.2 (M+H)$^+$. GK-GKRP IC$_{50}$ (Binding)=0.014 µM; GK-GKRP EC$_{50}$ (LC MS/MS-2)=0.025 µM.

Example 220

N-benzyl-N-(((2S)-4-(2-thiophenylsulfonyl)-1-(4-(2,2,2-trifluoro-1-hydroxy-1-methylethyl)phenyl)-2-piperazinyl)methyl)methanesulfonamide

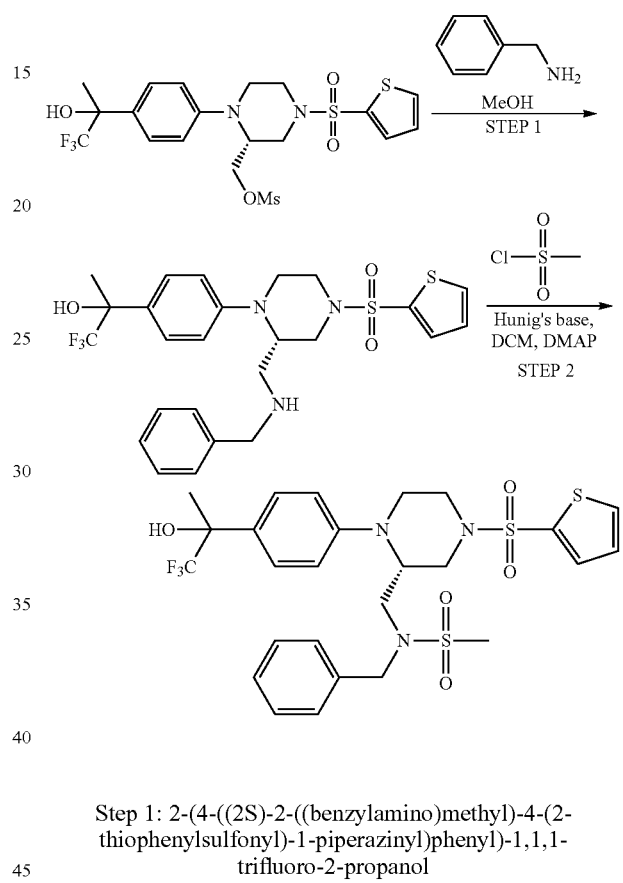

Step 1: 2-(4-((2S)-2-((benzylamino)methyl)-4-(2-thiophenylsulfonyl)-1-piperazinyl)phenyl)-1,1,1-trifluoro-2-propanol Following the procedure reported for Example 199, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and benzylamine (Aldrich, St. Louis, Mo.) delivered 2-(4-((2S)-2-((benzylamino)methyl)-4-(2-thiophenylsulfonyl)-1-piperazinyl)phenyl)-1,1,1-trifluoro-2-propanol as mixture of two isomers.

Step 2: N-benzyl-N-(((2S)-4-(2-thiophenylsulfonyl)-1-(4-(2,2,2-trifluoro-1-hydroxy-1-methylethyl)phenyl)-2-piperazinyl)methyl)methanesulfonamide Following the procedure reported for Example 204, the reaction of 2-(4-((2S)-2-((benzylamino)methyl)-4-(2-thiophenylsulfonyl)-1-piperazinyl)phenyl)-1,1,1-trifluoro-2-propanol and methanesulfonyl chloride (Aldrich, St. Louis, Mo.) delivered N-benzyl-N-(((2S)-4-(2-thiophenylsulfonyl)-1-(4-(2,2,2-trifluoro-1-hydroxy-1-methylethyl)phenyl)-2-piperazinyl)methyl)methanesulfonamide as a mixture of two isomers.

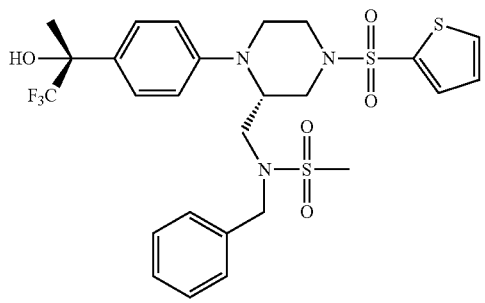

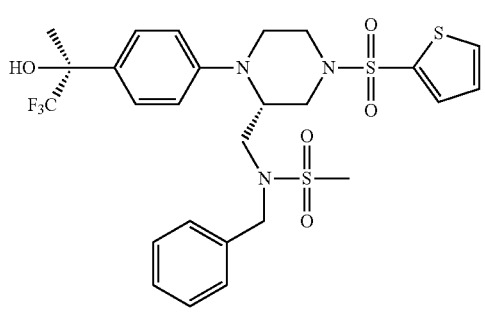

N-benzyl-N-(((2S)-4-(2-thiophenylsulfonyl)-1-(4-((1R)-2,2,2-trifluoro-1-hydroxy-1-methylethyl)phenyl)-2-piperazinyl)methyl)methanesulfonamide; N-benzyl-N-(((2S)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=7.68 (dd, J=1.2, 5.0 Hz, 1H), 7.60 (dd, J=1.3, 3.8 Hz, 1H), 7.48-7.40 (m, 2H), 7.38-7.29 (m, 5H), 7.20 (dd, J=3.8, 5.0 Hz, 1H), 6.94-6.82 (m, 2H), 4.70-4.58 (m, 1H), 4.50-4.41 (m, 1H), 4.37 (br. s., 1H), 4.00-3.87 (m, 1H), 3.77 (d, J=12.7 Hz, 1H), 3.61-3.42 (m, 2H), 3.34-3.18 (m, 2H), 2.67 (s, 5H), 2.33-2.22 (m, 1H), 1.74 (s, 3H). m/z (ESI, +ve ion) 618.2 (M+H)$^+$. GK-GKRP IC$_{50}$ (Binding)=0.003 µM; GK-GKRP EC$_{50}$ (LC MS/MS-2)=0.015 µM.

Example 221

N-(3-pyridinylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide

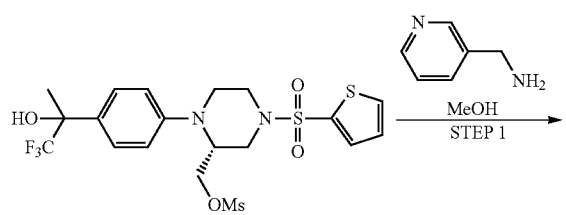

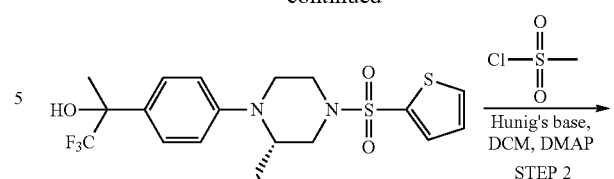

Step 1: 1,1,1-trifluoro-2-(4-((2S)-2-(((3-pyridinylmethyl)amino)methyl)-4-(2-thiophenylsulfonyl)-1-piperazinyl)phenyl)-2-propanol Following the procedure reported for Example 199, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and 3-(aminomethyl)pyridine (Aldrich, St. Louis, Mo.) delivered 1,1,1-trifluoro-2-(4-((2S)-2-(((3-pyridinylmethyl)amino)methyl)-4-(2-thiophenylsulfonyl)-1-piperazinyl)phenyl)-2-propanol.

Step 2: N-(3-pyridinylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide Following the procedure reported for Example 204, the reaction of 1,1,1-trifluoro-2-(4-((2S)-2-(((3-pyridinylmethyl)amino)methyl)-4-(2-thiophenylsulfonyl)-1-piperazinyl)phenyl)-2-propanol and methanesulfonyl chloride (Aldrich, St. Louis, Mo.) delivered N-(3-pyridinylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide as a mixture of two isomers.

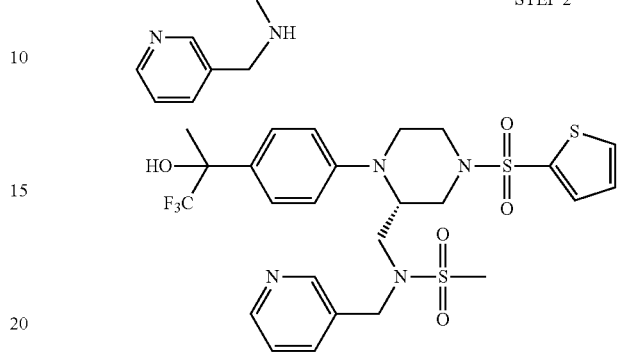

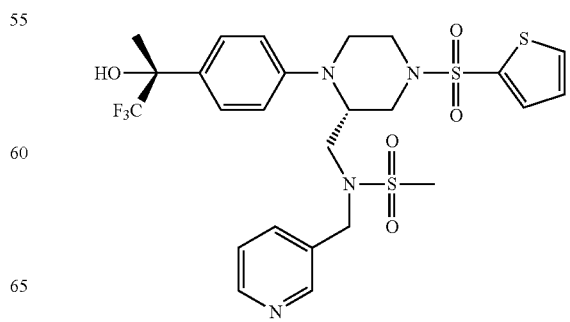

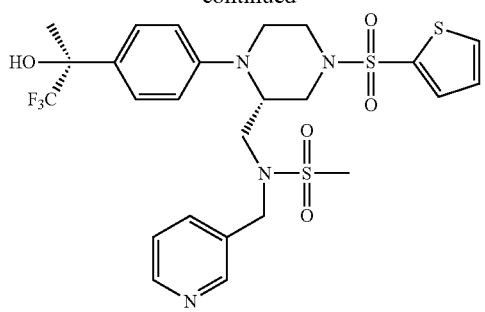

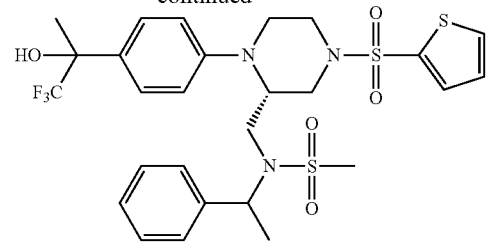

N-(3-pyridinylmethyl)-N-(((2S)-4-(2-thiophenylsulfonyl)-1-(4-((1R)-2,2,2-trifluoro-1-hydroxy-1-methylethyl)phenyl)-2-piperazinyl)methyl)methanesulfonamide; N-(3-pyridinylmethyl)-N-(((2S)-4-(2-thiophenylsulfonyl)-1-(4-((1S)-2,2,2-trifluoro-1-hydroxy-1-methylethyl)phenyl)-2-piperazinyl)methyl)methanesulfonamide.

$^1$H NMR (300 MHz, CDCl$_3$) δ=8.53-8.41 (m, 1H), 8.11-7.94 (m, 1H), 7.87-7.78 (m, 1H), 7.70 (dd, J=1.2, 5.0 Hz, 1H), 7.60 (dd, J=1.2, 3.7 Hz, 1H), 7.48 (d, J=7.5 Hz, 2H), 7.30 (d, J=4.7 Hz, 1H), 7.21 (dd, J=3.8, 5.0 Hz, 1H), 6.84 (dd, J=2.7, 9.0 Hz, 2H), 4.60 (d, J=15.9 Hz, 1H), 4.32 (d, J=15.8 Hz, 1H), 4.15 (br. s., 1H), 3.88 (d, J=12.7 Hz, 1H), 3.76 (d, J=12.3 Hz, 1H), 3.62 (dd, J=9.2, 14.6 Hz, 1H), 3.42-3.15 (m, 3H), 3.04 (d, J=14.8 Hz, 1H), 2.89 (d, J=3.5 Hz, 3H), 2.77 (dd, J=3.4, 11.8 Hz, 1H), 2.59 (dt, J=3.9, 11.0 Hz, 1H), 1.75 (s, 3H). m/z (ESI, +ve ion) 619.1 (M+H)$^+$. GK-GKRP IC$_{50}$ (Binding)=0.013 μM; GK-GKRP EC$_{50}$ (LC MS/MS-2)=0.041 μM.

Example 222

N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide

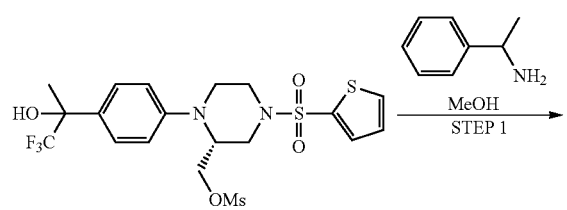

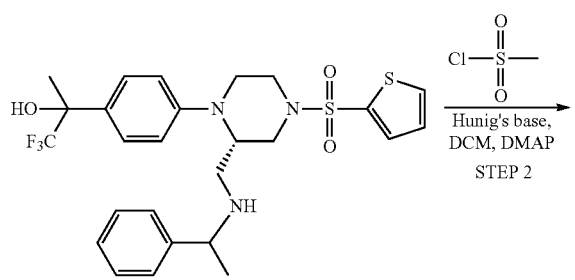

Step 1: 1,1,1-trifluoro-2-(4-((2S)-2-(((1-phenylethyl)amino)methyl)-4-(2-thiophenylsulfonyl)-1-piperazinyl)phenyl)-2-propanol Following the procedure reported for Example 199, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and racemic alpha-methylbenzylamine (Aldrich, St. Louis, Mo.) delivered 1,1,1-trifluoro-2-(4-((2S)-2-(((1-phenylethyl)amino)methyl)-4-(2-thiophenylsulfonyl)-1-piperazinyl)phenyl)-2-propanol.

Step 2: N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide Following the procedure reported for Example 204, the reaction of 1,1,1-trifluoro-2-(4-((2S)-2-(((1-phenylethyl)amino)methyl)-4-(2-thiophenylsulfonyl)-1-piperazinyl)phenyl)-2-propanol and methanesulfonyl chloride (Aldrich, St. Louis, Mo.) delivered N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide as a mixture of two isomers.

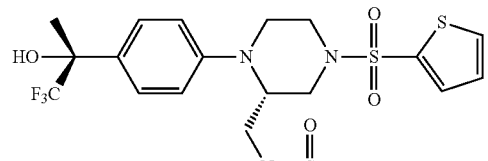

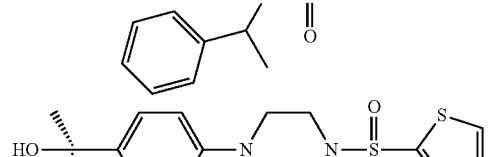

N-(1-phenylethyl)-N-(((2R)-4-(2-thiophenylsulfonyl)-1-(4-((1R)-2,2,2-trifluoro-1-hydroxy-1-methylethyl)phenyl)-2-piperazinyl)methyl)methane sulfonamide; N-(1-phenylethyl)-N-(((2R)-4-(2-thiophenylsulfonyl)-1-(4-((1S)-2,2,2-trifluoro-1-hydroxy-1-methylethyl)phenyl)-2-piperazinyl)methyl)methanesulfonamide.

¹H NMR (300 MHz, CDCl₃) δ=7.71-7.62 (m, 1H), 7.60-7.51 (m, 1H), 7.48-7.29 (m, 7H), 7.23-7.13 (m, 1H), 6.80 (d, J=7.7 Hz, 2H), 5.14 (q, J=7.1 Hz, 1H), 4.32 (br. s., 1H), 3.81 (d, J=12.0 Hz, 1H), 3.71-3.44 (m, 3H), 3.41-3.24 (m, 1H), 3.15-2.89 (m, 2H), 2.62 (s, 3H), 2.49 (s, 1H), 2.39-2.28 (m, 1H), 1.74 (s, 3H), 1.68 (d, J=7.2 Hz, 3H). m/z (ESI, +ve ion) 632.2 (M+H)⁺. GK-GKRP IC$_{50}$ (Binding)=0.671 μM;

Example 223

2-methyl-N-3-pyridinyl-N-(((2R)-4-(2-thiophenyl-sulfonyl)-1-(4-(2,2,2-trifluoro-1-hydroxy-1-methylethyl)phenyl)-2-piperazinyl)methyl)-1-propanesulfonamide

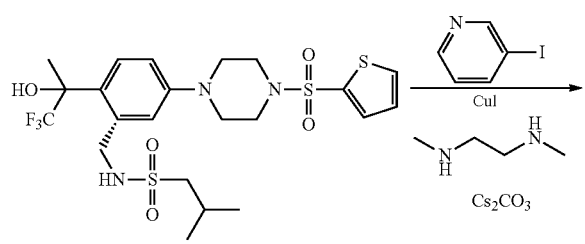

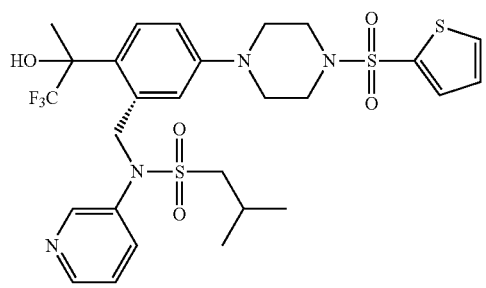

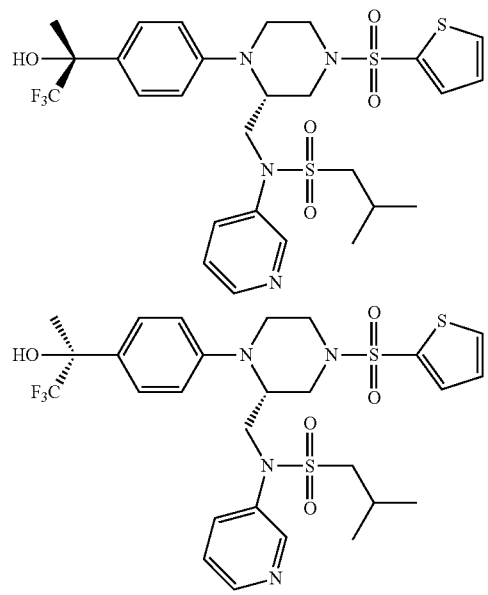

2-methyl-N-3-pyridinyl-N-(((2R)-4-(2-thiophenylsulfonyl)-1-(4-((1R)-2,2,2-trifluoro-1-hydroxy-1-methylethyl)phenyl)-2-piperazinyl)methyl)-1-propanesulfonamide; 2-methyl-N-3-pyridinyl-N-(((2R)-4-(2-thiophenylsulfonyl)-1-(4-((1S)-2,2,2-trifluoro-1-hydroxy-1-methylethyl)phenyl)-2-piperazinyl)methyl)-1-propanesulfonamide.

¹H NMR (600 MHz, DMSO-d₆) δ=8.48 (td, J=1.3, 4.7 Hz, 1H), 8.44 (dd, J=2.3, 17.5 Hz, 1H), 8.02 (d, J=5.0 Hz, 1H), 7.63 (td, J=1.1, 3.6 Hz, 1H), 7.56 (dtd, J=1.5, 2.8, 8.1 Hz, 1H), 7.34-7.26 (m, 4H), 6.64 (dd, J=3.5, 9.0 Hz, 2H), 6.15 (s, 1H), 4.09-4.04 (m, 1H), 4.00 (dd, J=7.3, 14.5 Hz, 1H), 3.94 (ddd, J=3.4, 6.5, 14.3 Hz, 1H), 3.68 (d, J=11.5 Hz, 1H), 3.59-3.47 (m, 2H), 3.25-3.18 (m, 1H), 3.03 (dd, J=6.7, 13.9 Hz, 1H), 2.98 (ddd, J=5.3, 6.5, 13.9 Hz, 1H), 2.60 (td, J=2.9, 11.7 Hz, 1H), 2.42 (dt, J=3.0, 11.4 Hz, 1H), 2.10 (quind, J=6.7, 13.3 Hz, 1H), 1.63 (d, J=4.6 Hz, 3H), 0.99 (d, J=6.9 Hz, 3H), 0.99 (d, J=6.9 Hz, 3H). m/z (ESI, +ve ion) 647.2 (M+H)⁺. GK-GKRP IC$_{50}$ (Binding)=0.035 μM; GK-GKRP EC$_{50}$ (LC MS/MS-2)=0.086 μM.

To a solution of 2-methyl-N-(((2S)-4-(2-thiophenylsulfonyl)-1-(4-(2,2,2-trifluoro-1-hydroxy-1-methylethyl)phenyl)-2-piperazinyl)methyl)-1-propanesulfonamide (0.130 g, 0.228 mmol, Example 210) in DMF (3.0 mL) was added 3-iodopyridine (0.094 g, 0.46 mmol, Aldrich, St. Louis, Mo.), N,N'-dimethylethylenediamine (0.020 mL, 0.18 mmol, Aldrich, St. Louis, Mo.), CuI (0.015 mg, 0.21 mmol, Aldrich, St. Louis, Mo.), cesium carbonate (0.22 g, 0.69 mmol), and water (0.30 mL). The resulting mixture was heated at 120° C. for 14 d, with additional aliquots of 3-iodopyridine (50 mg, 0.23 mmol) being added on 2$^{nd}$ and 5$^{th}$ day. The reaction mixture was then filtered and the filtrate was concentrated. The crude product was purified by column chromatography (24 g of silica gel, 1 to 5% 2M NH₃ in MeOH in CH₂Cl₂) to afford 2-methyl-N-3-pyridinyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide (0.015 mg) as a mixture of two isomers.

Example 224

N-phenyl-N-(((2S)-4-(2-thiophenylsulfonyl)-1-(4-(2,2,2-trifluoro-1-hydroxy-1-methylethyl)phenyl)-2-piperazinyl)methyl)acetamide

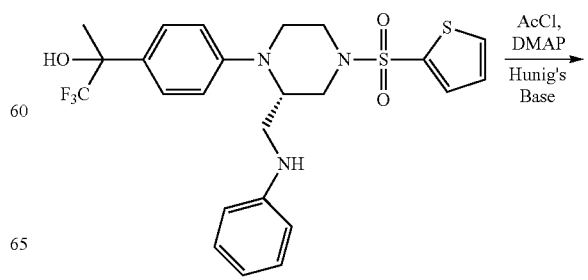

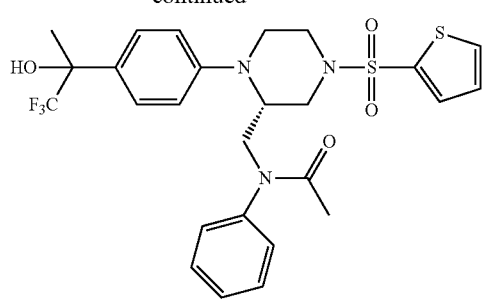

To a solution of 1,1,1-trifluoro-2-(4-((2S)-2-((phenylamino)methyl)-4-(2-thiophenylsulfonyl)-1-piperazinyl)phenyl)-2-propanol (0.130 g, 0.247 mmol, Example 203) in CH$_2$Cl$_2$ (3.0 mL) was added 4-dimethylaminopyridine (6.1 mg, 0.049 mmol), Hünig's base (0.129 mL, 0.742 mmol), and acetyl chloride (0.035 mL, 0.49 mmol, Aldrich, St. Louis, Mo.). The resulting mixture was stirred at room temperature for 30 min and then the solvent was removed in vacuo. The residue was purified by column chromatography (24 g of silica gel, 10% to 40% EtOAc in hexanes) to afford N-phenyl-N-(((2S)-4-(2-thiophenylsulfonyl)-1-(4-(2,2,2-trifluoro-1-hydroxy-1-methylethyl)phenyl)-2-piperazinyl)methyl)acetamide (0.032 g) as a mixture of two isomers:

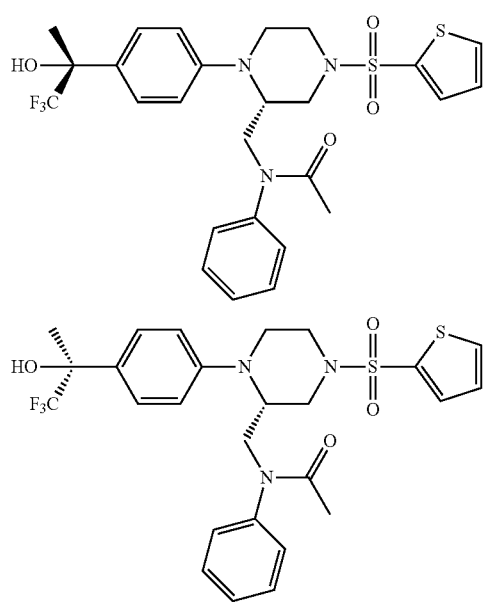

N-phenyl-N-(((2S)-4-(2-thiophenylsulfonyl)-1-(4-((1R)-2,2,2-trifluoro-1-hydroxy-1-methylethyl)phenyl)-2-piperazinyl)methyl)acetamide, N-phenyl-N-(((2S)-4-(2-thiophenylsulfonyl)-1-(4-((1S)-2,2,2-trifluoro-1-hydroxy-1-methylethyl)phenyl)-2-piperazinyl)methyl)acetamide.

$^1$H NMR (300 MHz, CDCl$_3$) δ=7.63 (d, J=4.8 Hz, 1H), 7.53 (d, J=3.1 Hz, 1H), 7.43 (d, J=8.2 Hz, 2H), 7.37-7.29 (m, 3H), 7.26-7.20 (m, 1H), 7.15 (t, J=4.3 Hz, 1H), 6.87 (br. s., 3H), 4.62 (br. s., 1H), 4.30-4.16 (m, 1H), 3.86 (d, J=13.9 Hz, 1H), 3.73 (d, J=11.4 Hz, 1H), 3.65 (d, J=10.7 Hz, 1H), 3.49-3.35 (m, 1H), 3.33-3.17 (m, 1H), 2.72 (br. s., 1H), 2.53 (br. s., 1H), 2.34 (s, 1H), 1.76 (s, 3H), 1.71 (s, 3H). m/z (ESI, +ve ion) 568.2 (M+H)$^+$. GK-GKRP IC$_{50}$ (Binding)=0.008 μM; GK-GKRP EC$_{50}$ (LC MS/MS-2)=0.027 μM.

Example 225

2-(4-((2S)-4-((5-amino-2-thiophenyl)sulfonyl)-2-(((3S)-3-methyl-4-morpholinyl)methyl)-1-piperazinyl)phenyl)-1,1,1,3,3,3-hexafluoro-2-propanol

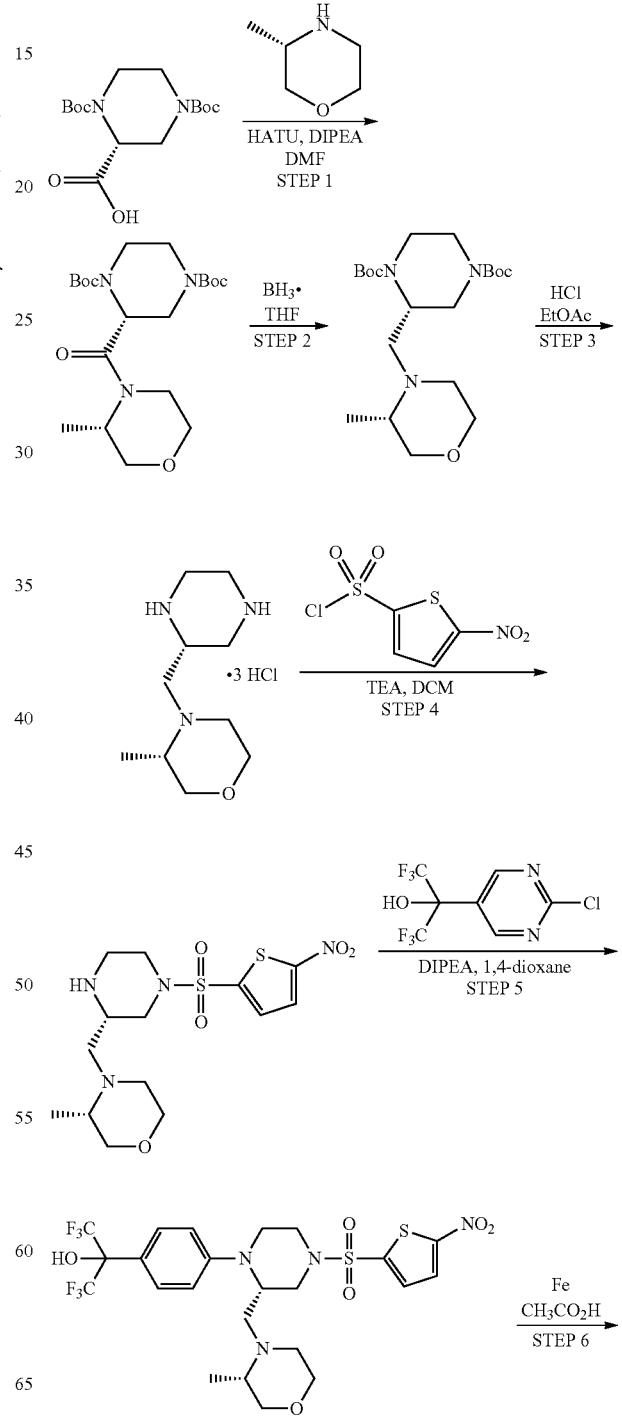

-continued

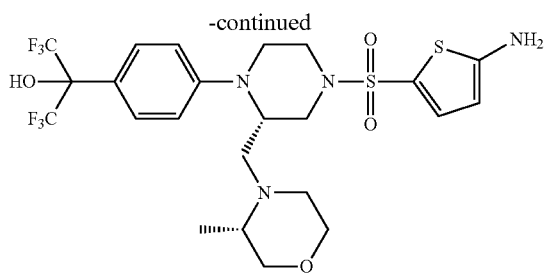

Step 1: di-tert-butyl (2R)-2-(((3S)-3-methyl-4-morpholinyl)carbonyl)-1,4-piperazinedicarboxylate A 100-mL round-bottomed flask was charged with (R)-1,4-bis(tert-butoxycarbonyl)piperazine-2-carboxylic acid (2.04 g, 6.17 mmol, ASW MedChem. Inc., New Brunswick, N.J.), (S)-3-methylmorpholine (0.657 g, 6.50 mmol, Synthetech Inc., Albany, Oreg.), HATU (2.83 g, 7.45 mmol, ChemImpex International Inc., Wood Dale, Ill.), DIPEA (2.20 mL, 12.6 mmol) and DMF (12 mL). The reaction mixture was stirred at room temperature for 1 h. After this time, additional HATU (0.475 g) was added and the stirring at room temperature was resumed for 2 days. The reaction mixture was partitioned between water (120 mL) and EtOAc (50 mL). The aqueous phase was extracted with EtOAc (2×40 mL). The combined organic phases were washed with water (50 mL), saturated aqueous NaHCO$_3$ (50 mL), water (50 mL) and saturated aqueous NaCl (50 mL). The organic phase was dried over sodium sulfate, filtered and concentrated in vacuo to afford di-tert-butyl (2R)-2-(((3S)-3-methyl-4-morpholinyl)carbonyl)-1,4-piperazinedicarboxylate (2.71 g) as a light-brown solid.

Step 2: di-tert-butyl (2S)-2-(((3S)-3-methyl-4-morpholinyl)methyl)-1,4-piperazinedicarboxylate A 250-mL round-bottomed flask was charged with di-tert-butyl (2R)-2-(((3S)-3-methyl-4-morpholinyl)carbonyl)-1,4-piperazinedicarboxylate (2.55 g, 6.17 mmol, step 1), BH$_3$.THF (1.0 M in THF, 19.0 mL, 19.0 mmol, Sigma-Aldrich, St. Louis, Mo.) and THF (100 mL). The mixture was stirred at 50° C. for 15 h. The mixture was allowed to cool to room temperature and then additional BH$_3$.THF complex (1.0 M in THF, 5.0 mL, 5.0 mmol) was added. The reaction mixture was heated at 50° C. for 1 h. The mixture was allowed to cool to room temperature and then MeOH was added slowly until bubbling ceased. The reaction mixture was concentrated to give di-tert-butyl (2S)-2-(((3S)-3-methyl-4-morpholinyl)methyl)-1,4-piperazinedicarboxylate (2.5 g) as a white solid.

Step 3: (3S)-3-methyl-4-((2R)-2-piperazinylmethyl)morpholine trihydrochloride A 250-mL round-bottomed flask was charged with di-tert-butyl (2S)-2-(((3S)-3-methyl-4-morpholinyl)methyl)-1,4-piperazinedicarboxylate (2.46 g, 6.16 mmol, step 2), HCl (4.0 M solution in 1,4-dioxane, 4.62 mL, 18.5 mmol, Sigma-Aldrich, St. Louis, Mo.) and EtOAc (100 mL). The reaction mixture was heated at 70° C. for 3 h. At this time, additional HCl (4.0 M solution in 1,4-dioxane, 5.00 mL, 20.0 mmol) was added and heating at 70° C. was resumed for an additional 3 h. The reaction mixture was cooled to room temperature and the resulting white solid was collected, washed with EtOAc and dried overnight under reduced pressure to afford (3S)-3-methyl-4-((2R)-2-piperazinylmethyl)morpholine trihydrochloride (2.05 g) as a white powder.

Step 4: (3S)-4-(((2S)-4-((5-nitro-2-thiophenyl)sulfonyl)-2-piperazinyl)methyl)-3-methylmorpholine A 150-mL round-bottomed flask was charged with (3S)-3-methyl-4-((2R)-2-piperazinylmethyl)morpholine trihydrochloride (0.750 g, 2.43 mmol, step 3), TEA (2.03 mL, 14.6 mmol) and CH$_2$Cl$_2$ (10 mL). To this was added a solution of 5-nitrothiophene-2-sulfonyl chloride (0.560 g, 2.46 mmol, Enamine LLC, Monmouth Jct., NJ) in CH$_2$Cl$_2$ (5 mL). The reaction mixture was stirred at room temperature for 20 min. The reaction mixture was partitioned between water (20 mL) and CH$_2$Cl$_2$ (20 mL). The aqueous phase was extracted with CH$_2$Cl$_2$ (2×20 mL). The combined organic phases were washed with water (40 mL) and saturated aqueous NaCl (40 mL). The organic phase was dried over sodium sulfate, filtered and concentrated in vacuo. The crude product was purified by column chromatography (50 g of silica gel, 0 to 12.5% iPrOH (with 10% NH$_4$OH) in CHCl$_3$) to afford (3S)-4-(((2S)-4-((5-nitro-2-thiophenyl)sulfonyl)-2-piperazinyl)methyl)-3-methylmorpholine (0.797 g) as a light orange glass.

Step 5: 2-(4-((2S)-4-((5-nitro-2-thiophenyl)sulfonyl)-2-(((3S)-3-methyl-4-morpholinyl)methyl)-1-piperazinyl)phenyl)-1,1,1,3,3,3-hexafluoro-2-propanol A 20-mL vial was charged with (3S)-4-(((2S)-4-((5-nitro-2-thiophenyl)sulfonyl)-2-piperazinyl)methyl)-3-methylmorpholine (0.797 g, 2.04 mmol, step 4), (2-chloro-5-pyrimidinyl)-1,1,1,3,3,3-hexafluoro-2-propanol (0.859 g, 3.06 mmol, Intermediate D), DIPEA (1.10 mL, 6.30 mmol) and 1,4-dioxane (10 mL). The vial was sealed and heated at 100° C. for 12 h. The reaction mixture was allowed to cool to room temperature and then partitioned between water (30 mL) and EtOAc (20 mL). The aqueous phase was extracted with EtOAc (40 mL). The combined organic phases were washed with saturated aqueous NaCl (50 mL). The organic phase was dried over sodium sulfate, filtered and concentrated in vacuo. The crude product was purified by column chromatography (50 g of silica gel, 0 to 50% EtOAc in hexanes) to afford 2-(4-((2S)-4-((5-nitro-2-thiophenyl)sulfonyl)-2-(((3S)-3-methyl-4-morpholinyl)methyl)-1-piperazinyl)phenyl)-1,1,1,3,3,3-hexafluoro-2-propanol (0.936 g) as a tan solid.

Step 6: 2-(4-((2S)-4-((5-amino-2-thiophenyl)sulfonyl)-2-(((3S)-3-methyl-4-morpholinyl)methyl)-1-piperazinyl)phenyl)-1,1,1,3,3,3-hexafluoro-2-propanol A 5-mL vial was charged with 2-(4-((2S)-4-((5-nitro-2-thiophenyl)sulfonyl)-2-(((3S)-3-methyl-4-morpholinyl)methyl)-1-piperazinyl)phenyl)-1,1,1,3,3,3-hexafluoro-2-propanol (0.060 g, 0.094 mmol, step 5), iron filings (0.0282 g, 0.505 mmol, Sigma-Aldrich, St. Louis, Mo.) and acetic acid (2 mL). The mixture was stirred at 50° C. for 40 min. Saturated aqueous NaHCO$_3$ (20 mL) was added slowly and then the aqueous phase was extracted with EtOAc (2×20 mL). The combined organic extracts were dried over sodium sulfate, filtered and concentrated in vacuo. The crude product was purified by column chromatography (twice, 25 g of silica gel, 30 to 90% EtOAc in hexanes then 10 g of silica gel, 30 to 90% EtOAc in hexanes) to afford 2-(4-((2S)-4-((5-amino-2- thiophenyl)sulfonyl)-2-(((3S)-3-methyl-4-morpholinyl)me-thyl)-1-piperazinyl)phenyl)-1,1,1,3,3,3-hexafluoro-2-propanol (0.0386 g) as a white solid.

$^1$H NMR (400 MHz, CDCl$_3$) δ=8.52 (s, 2H), 7.19 (d, J=3.9 Hz, 1H), 6.11 (d, J=4.1 Hz, 1H), 4.89 (d, J=9.6 Hz, 1H), 4.75 (br. s., 1H), 4.24 (s, 2H), 4.04 (d, J=11.5 Hz, 1H), 3.72 (d, J=11.5 Hz, 2H), 3.62 (d, J=10.6 Hz, 2H), 3.51 (s, 1H), 3.37 (t, J=11.2 Hz, 1H), 3.30-3.14 (m, 2H), 3.02 (d, J=11.9 Hz, 1H), 2.51-2.39 (m, 3H), 2.38-2.29 (m, 1H), 1.99 (d, J=11.0 Hz, 1H), 1.07 (d, J=6.3 Hz, 3H). MS (ESI, pos. ion) m/z: 604.8 [M+1]. GK-GKRP IC$_{50}$ (Binding)=0.007 μM; GK-GKRP EC$_{50}$ (LC MS/MS-2)=0.019 μM.

Example 226

3,3-dimethyl-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone

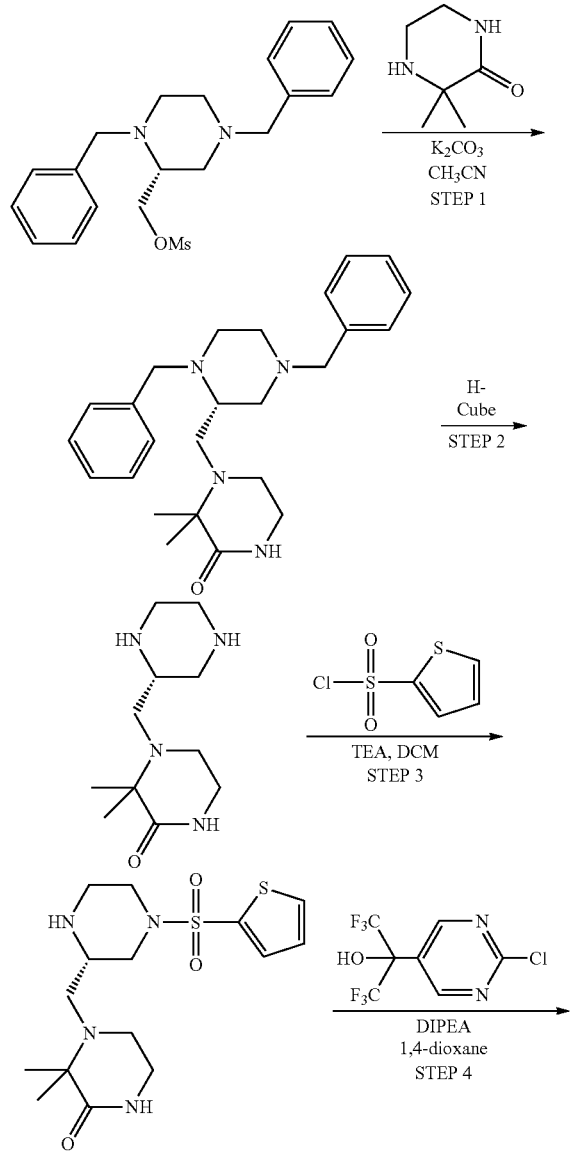

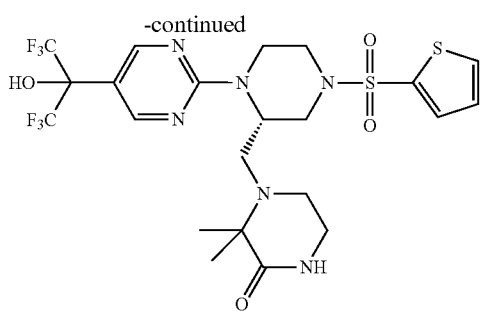

Step 1: 4-(((2R)-1,4-dibenzyl-2-piperazinyl)methyl)-3,3-dimethyl-2-piperazinone

A 20 ml, microwave vial was charged with ((2R)-1,4-dibenzyl-2-piperazinyl)methyl methanesulfonate (0.817 g, 2.18 mmol, Example 184, Step 1), 3,3-dimethylpiperazin-2-one (0.297 g, 2.32 mmol, ChemBridge, San Diego, Calif.), potassium carbonate (0.910 g, 6.58 mmol) and acetonitrile (10 mL). The vial was sealed and the reaction mixture was stirred at 130° C. for 30 min. The reaction was allowed to cool to room temperature then saturated aqueous NH$_4$Cl/water (1:1) (100 mL) and 10% iPrOH in chloroform (100 mL) were added. The aqueous phase was extracted with 10% iPrOH in chloroform (2×50 mL). The combined organic phases were washed with saturated aqueous NaCl (200 mL), dried over sodium sulfate, filtered and concentrated in vacuo. The crude product was purified by column chromatography (50 g of silica gel, 0 to 10% iPrOH (with 10% NH$_4$OH) in CHCl$_3$) to afford 4-(((2R)-1,4-dibenzyl-2-piperazinyl)methyl)-3,3-dimethyl-2-piperazinone (0.53 g) as a white foam.

Step 2: 3,3-dimethyl-4-((2R)-2-piperazinylmethyl)-2-piperazinone 4-(((2R)-1,4-dibenzyl-2-piperazinyl)methyl)-3,3-dimethyl-2-piperazinone (0.500 g, 1.23 mmol) was dissolved in MeOH (25 mL). This solution was passed through an H-Cube™ flow hydrogenator (ThalesNano Technology, Budapest, Hungary) via the solvent inlet using a 10% Pd/C CatCart™ (30 mm cartridge length, source ThalesNano, pre-washed and hydrogenated at full H2 mode for 10 min at 1 mL/min) at 1 mL/min flow rate in full H$_2$ mode at 60° C. The solution collected was concentrated in vacuo to give 3,3-dimethyl-4-((2R)-2-piperazinylmethyl)-2-piperazinone (0.27 g) as a colorless solid.

Step 3: 3,3-dimethyl-4-(((2S)-4-(2-thiophenylsulfo-nyl)-2-piperazinyl)methyl)-2-piperazinone A 20-mL vial was charged with 3,3-dimethyl-4-((2R)-2-piperazinylmethyl)-2-piperazinone (0.104 g, 0.461 mmol), triethylamine (0.200 mL, 1.44 mmol), and CH$_2$Cl$_2$ (3 mL). To this mixture thiophene-2-sulfonyl chloride (0.0951 g, 0.521 mmol, Sigma-Aldrich, St. Louis, Mo.) in CH$_2$Cl$_2$ (1 mL) was added drop wise at room temperature. The clear solution was stirred at room temperature for 30 min and then the mixture was concentrated and dissolved in CH$_2$Cl$_2$ (20 mL). The organic phase was washed with water (2×20 mL) and saturated aqueous NaCl (20 mL). The combined organic extracts were dried over sodium sulfate, filtered, and concentrated in vacuo to afford 3,3-dimethyl-4-(((2S)-4-(2-thiophenylsulfo-nyl)-2-piperazinyl)methyl)-2-piperazinone (0.166 g) as an off-white foam.

Step 4: 3,3-dimethyl-4-((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone A 5-mL vial was charged with 3,3-dimethyl-4-((2S)-4-(2-thiophenylsulfonyl)-2-piperazinyl)methyl)-2-piperazinone (0.166 g, 0.446 mmol, step 1), 2-(2-chloropyrimidin-5-yl)-1,1,1,3,3,3-hexafluoropropan-2-ol (0.185 g, 0.658 mmol, Intermediate D), DIPEA (0.24 mL, 1.4 mmol) and 1,4-dioxane (2 mL). The vial was sealed and the reaction mixture was stirred at 100° C. for 12 h. The reaction mixture was allowed to cool to room temperature then partitioned between water (30 mL) and EtOAc (30 mL). The aqueous phase was extracted with EtOAc (30 mL) then with 10% IPA in $CHCl_3$ with 1% $NH_4OH$ (3×30 mL). The combined organic extracts were combined and dried over sodium sulfate, filtered and concentrated in vacuo. The crude product was purified by silica gel chromatography (50 g of silica gel, 40 to 100% EtOAc in hexanes) to afford a white solid. This solid was taken into small amount of MeOH and then water was added drop wise. The resulting white precipitate was collected via filtration and dried under reduced pressure to afford 3,3-dimethyl-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone (0.101 g) as a white solid.

$^1$H NMR (400 MHz, $CDCl_3$) δ=8.57 (s, 2H), 7.65 (d, J=5.1 Hz, 1H), 7.59 (d, J=3.1 Hz, 1H), 7.21-7.14 (m, J=4.7 Hz, 1H), 5.70 (br. s., 1H), 4.97-4.72 (m, 2H), 4.70-4.41 (m, 1H), 4.14 (br. s., 1H), 3.88-3.78 (m, 1H), 3.28 (d, J=14.3 Hz, 3H), 3.20-2.89 (m, 3H), 2.63-2.34 (m, 3H), 1.40 (br. s., 6H). MS (ESI, pos. ion) m/z: 617.0 [M+1]. GK-GKRP $IC_{50}$ (Binding)=0.006 µM; GK-GKRP $EC_{50}$ (LC MS/MS-2)=0.014 µM.

Example 227

(S)-4-((4-((5-aminothiophen-2-yl)sulfonyl)-1-(5-(1,1,1,3,3,3-hexafluoro-2-hydroxypropan-2-yl)pyrimidin-2-yl)piperazin-2-yl)methyl)-3,3-dimethylpiperazin-2-one

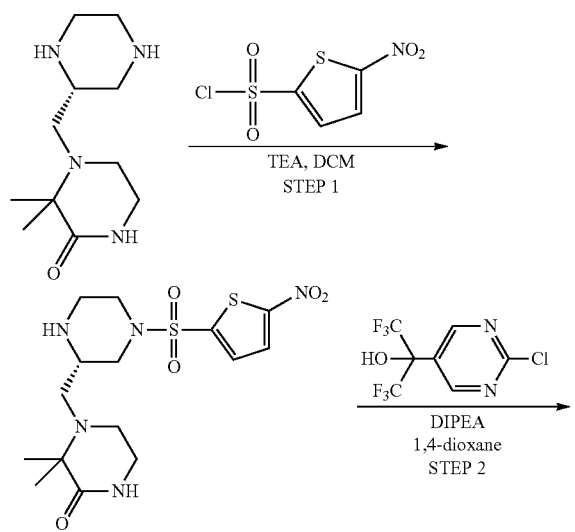

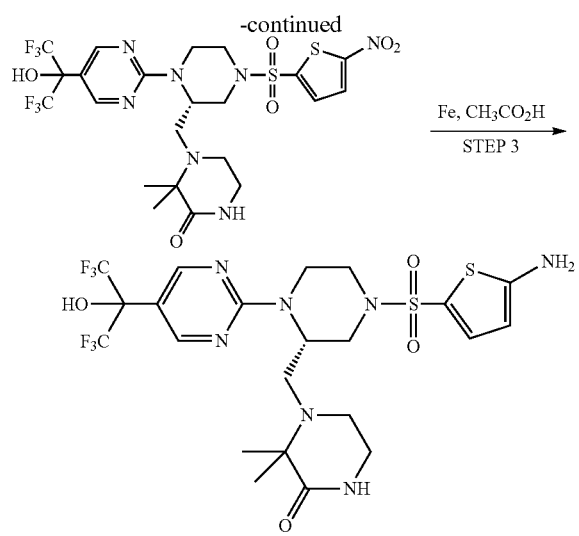

Step 1: 4-(((2S)-4-((5-nitro-2-thiophenyl)sulfonyl)-2-piperazinyl)methyl)-3,3-dimethyl-2-piperazinone Following the procedure reported for Example 226, Step 3, the reaction of 3,3-dimethyl-4-((2R)-2-piperazinylmethyl)-2-piperazinone (Example 226, Step 2) coupled with 5-nitrothiophene-2-sulfonyl chloride (Enamine LLC, Monmouth Jct., NJ) delivered 4-(((2S)-4-((5-nitro-2-thiophenyl)sulfonyl)-2-piperazinyl)methyl)-3,3-dimethyl-2-piperazinone.

Step 2: 4-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone Following the procedure reported for Example 226, Step 4, the coupling of 4-(((2S)-4-((5-nitro-2-thiophenyl)sulfonyl)-2-piperazinyl)methyl)-3,3-dimethyl-2-piperazinone with 2-(2-chloropyrimidin-5-yl)-1,1,1,3,3,3-hexafluoropropan-2-ol (Intermediate D) delivered 4-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone.

Step 3: 4-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone A 250-mL round-bottomed flask was charged with 4-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone (0.314 g, 0.475 mmol, step 2), iron filings (0.136 g, 2.43 mmol) and AcOH (10 mL). The reaction mixture was heated at 50° C. for 3 h. An additional 0.052 g of iron filing was added and the heating at 50° C. was continued for 30 min. The mixture was allowed to cool to room temperature and then saturated aqueous $NaHCO_3$ (300 mL) was slowly added. The aqueous phase was extracted with EtOAc (3×100 mL). The combined organic phases were dried over sodium sulfate, filtered and concentrated in vacuo. The crude product was purified by preparative HPLC (Phenomenex 5 µm, $C_{18}$ column, 150×30 mm) eluting with 10 to 90% ACN with 0.1% TFA in $H_2O$ with 0.1% TFA in 15 min. The fractions were concentrated and basified with saturated aqueous NaHCO₃. The resulting solid was collected (0.130 g). The aqueous phase was extracted with 10% iPrOH in CHCl₃ containing 1% NH₄OH. The combined organic extracts were dried over sodium sulfate, filtered and concentrated to obtain an additional 0.265 g. The combined material was purified by column chromatography (25 g of silica gel, 0 to 10% (2M NH₃ in MeOH) in CH₂Cl₂ to afford 4-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone (0.084 g) as an off-white solid.

¹H NMR (400 MHz, DMSO-d₆) δ=8.91 (s, 1H), 8.54 (s, 2H), 7.53 (s, 1H), 7.17 (d, J=4.1 Hz, 1H), 6.70 (s, 2H), 5.94 (d, J=4.1 Hz, 1H), 4.78 (br. s., 1H), 4.62 (d, J=13.1 Hz, 1H), 3.83 (d, J=11.3 Hz, 1H), 3.60 (d, J=10.6 Hz, 1H), 3.25-3.04 (m, 2H), 2.99-2.85 (m, 3H), 2.79-2.65 (m, 1H), 2.39 (dd, J=3.6, 11.2 Hz, 1H), 2.35-2.29 (m, 1H), 2.28-2.21 (m, 1H), 1.24 (s, 3H), 1.12 (s, 3H). MS (ESI, pos. ion) m/z: 632.0 [M+1]. GK-GKRP IC₅₀ (Binding)=0.002 μM; GK-GKRP EC₅₀ (LC-MS/MS-2)=0.021 μM.

Example 228

5,5-dimethyl-1-(((2S)-4-(2-thiophenylsulfonyl)-1-(4-(2,2,2-trifluoro-1-hydroxy-1-methylethyl)phenyl)-2-piperazinyl)methyl)-2,4-imidazolidinedione

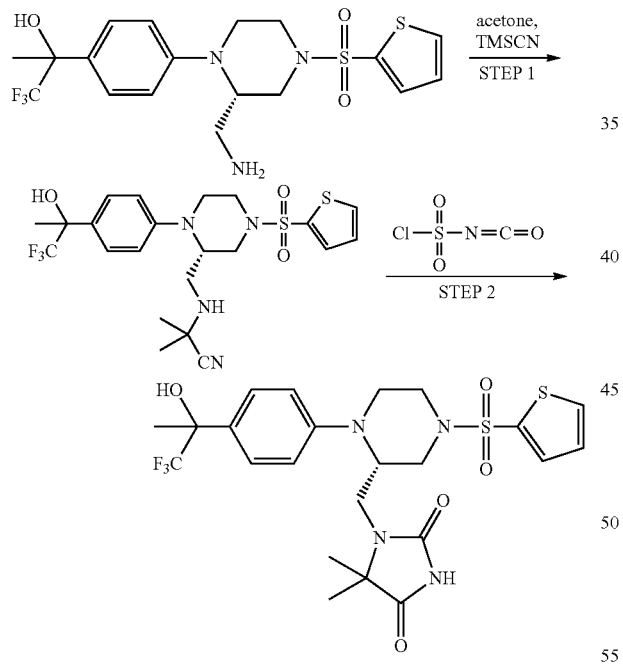

Step 1: 2-methyl-2-((((2S)-4-(2-thiophenylsulfonyl)-1-(4-(2,2,2-trifluoro-1-hydroxy-1-methylethyl)phenyl)-2-piperazinyl)methyl)amino)propanenitrile A 5-mL vial was charged with 2-(4-((2S)-2-(aminomethyl)-4-(2-thiophenylsulfonyl)-1-piperazinyl)phenyl)-1,1,1-trifluoro-2-propanol (0.0521 g, 0.116 mmol, Example 192, Step 2), acetone (10 μL, 0.14 mmol) and EtOH (1 mL). The reaction mixture was cooled to 0° C. and stirred for 35 min. Trimethylsilyl cyanide (46.3 μL, 0.348 mmol, Sigma-Aldrich, St. Louis, Mo.) was added drop wise at 0° C. The mixture was slowly allowed to warm up to room temperature and stirred for 12 h. The solvent was removed and the remaining white residue was dissolved into EtOAc and passed through a pad of silica gel rinsing with EtOAc as eluent. The solvent was removed and the crude product was purified by column chromatography (10 g of silica gel, 50 to 100% EtOAc in hexanes) to afford 2-methyl-2-((((2S)-4-(2-thiophenylsulfonyl)-1-(4-(2,2,2-trifluoro-1-hydroxy-1-methylethyl)phenyl)-2-piperazinyl)methyl)amino)propanenitrile (0.0312 g) as an off-white solid.

Step 2: 5,5-dimethyl-1-(((2S)-4-(2-thiophenylsulfonyl)-1-(4-(2,2,2-trifluoro-1-hydroxy-1-methylethyl)phenyl)-2-piperazinyl)methyl)-2,4-imidazolidinedione A 100-mL round-bottomed flask was charged with 2-methyl-2-((((2S)-4-(2-thiophenylsulfonyl)-1-(4-(2,2,2-trifluoro-1-hydroxy-1-methylethyl)phenyl)-2-piperazinyl)methyl)amino)propanenitrile (0.031 g, 0.060 mmol) and CH₂Cl₂ (2 mL). The mixture was cooled to 0° C. and chlorosulfonyl isocyanate (5.75 μL, 0.066 mmol, Sigma-Aldrich, St. Louis, Mo.) was added drop wise. The mixture was stirred at 0° C. for 30 min then concentrated in vacuo. The white residue was dissolved in water (2 mL) and heated at 100° C. for 12 h. 1N HCl (1 mL) was added and the stirring at 100° C. resumed for an additional hour. The reaction mixture was then allowed to cool to room temperature and then saturated aqueous NaHCO₃ was slowly added. The aqueous phase was extracted with EtOAc (2×10 mL). The combined organic extracts were washed with saturated aqueous NaCl (20 mL), dried over sodium sulfate, filtered and concentrated in vacuo. The crude product was purified by column chromatography (10 g of silica, 20 to 80% EtOAc in hexanes) to afford 5,5-dimethyl-1-(((2S)-4-(2-thiophenylsulfonyl)-1-(4-(2,2,2-trifluoro-1-hydroxy-1-methylethyl)phenyl)-2-piperazinyl)methyl)-2,4-imidazolidinedione (0.019 g) as a mixture of two isomers.

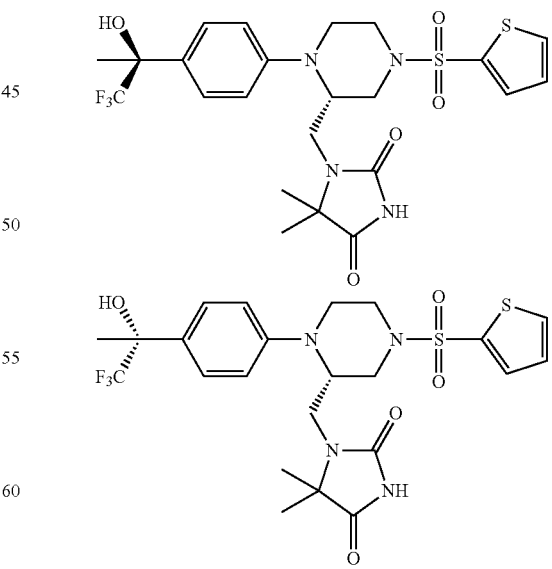

5,5-dimethyl-1-(((2S)-4-(2-thiophenylsulfonyl)-1-(4-((1S)-2,2,2-trifluoro-1-hydroxy-1-methylethyl)phenyl)-2-piperazinyl)methyl)-2,4-imidazolidinedione; 5,5-dimethyl-

1-(((2S)-4-(2-thiophenylsulfonyl)-1-(4-((1R)-2,2,2-trifluoro-1-hydroxy-1-methylethyl)phenyl)-2-piperazinyl)methyl)-2,4-imidazolidinedione $^1$H NMR (400 MHz, CDCl$_3$) δ=8.24-8.08 (m, 1H), 7.67 (d, J=5.1 Hz, 1H), 7.57 (d, J=3.5 Hz, 1H), 7.45 (d, J=8.4 Hz, 2H), 7.18 (t, J=4.3 Hz, 1H), 6.98 (d, J=8.4 Hz, 2H), 4.87 (br. s., 1H), 3.84-3.72 (m, 2H), 3.56 (br. s., 1H), 3.42-3.27 (m, 3H), 2.69 (d, J=16.2 Hz, 2H), 2.60-2.47 (m, 1H), 1.72 (d, J=3.1 Hz, 3H), 1.49 (s, 3H), 1.30 (s, 3H). MS (ESI, pos. ion) m/z: 561.0 [M+1]. GK-GKRP IC$_{50}$ (Binding)=0.151 µM; GK-GKRP EC$_{50}$ (LC MS/MS-2)=0.312 µM.

Example 229

N-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide

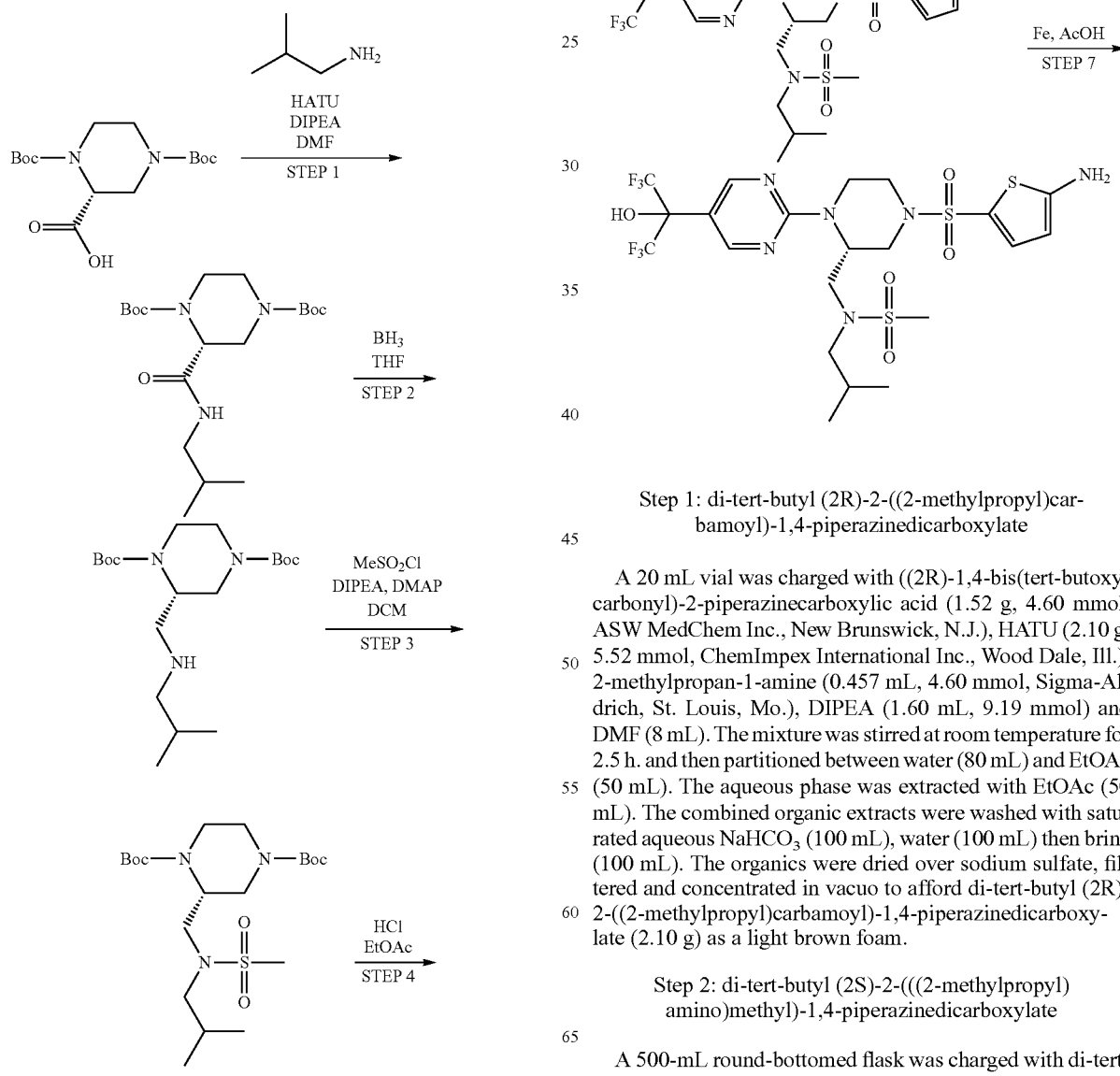

Step 1: di-tert-butyl (2R)-2-((2-methylpropyl)carbamoyl)-1,4-piperazinedicarboxylate A 20 mL vial was charged with ((2R)-1,4-bis(tert-butoxycarbonyl)-2-piperazinecarboxylic acid (1.52 g, 4.60 mmol, ASW MedChem Inc., New Brunswick, N.J.), HATU (2.10 g, 5.52 mmol, ChemImpex International Inc., Wood Dale, Ill.), 2-methylpropan-1-amine (0.457 mL, 4.60 mmol, Sigma-Aldrich, St. Louis, Mo.), DIPEA (1.60 mL, 9.19 mmol) and DMF (8 mL). The mixture was stirred at room temperature for 2.5 h. and then partitioned between water (80 mL) and EtOAc (50 mL). The aqueous phase was extracted with EtOAc (50 mL). The combined organic extracts were washed with saturated aqueous NaHCO$_3$ (100 mL), water (100 mL) then brine (100 mL). The organics were dried over sodium sulfate, filtered and concentrated in vacuo to afford di-tert-butyl (2R)-2-((2-methylpropyl)carbamoyl)-1,4-piperazinedicarboxylate (2.10 g) as a light brown foam.

Step 2: di-tert-butyl (2S)-2-(((2-methylpropyl)amino)methyl)-1,4-piperazinedicarboxylate A 500-mL round-bottomed flask was charged with di-tert-butyl (2R)-2-((2-methylpropyl)carbamoyl)-1,4-piperazinedicarboxylate (1.77 g, 4.60 mmol), BH$_3$.THF (1.0 M in THF, 13.8 mL, 13.8 mmol, Sigma-Aldrich, St. Louis, Mo.) and THF (60 mL). The reaction mixture was heated at 50° C. for 12 h. The mixture was allowed to cool to room temperature and then MeOH was added until the bubbling ceased. The reaction mixture was concentrated and the crude product was purified by silica gel chromatography (100 g of silica gel, 0 to 10% iPrOH (with 10% NH$_4$OH) in CHCl$_3$) to obtain di-tert-butyl (2S)-2-(((2-methylpropyl)amino)methyl)-1,4-piperazinedicarboxylate (0.939 g) as a clear oil which solidified upon standing.

Step 3: di-tert-butyl (2R)-2-(((2-methylpropyl)(methylsulfonyl)amino)methyl)-1,4-piperazinedicarboxylate A 250-mL round-bottomed flask was charged with di-tert-butyl (2S)-2-(((2-methylpropyl)amino)methyl)-1,4-piperazinedicarboxylate (0.77 g, 2.1 mmol), DMAP (0.0287 g, 0.235 mmol) and DIPEA (1.45 mL, 8.29 mmol) and CH$_2$Cl$_2$ (10 mL). Methanesulfonyl chloride (0.321 mL, 4.15 mmol) was added drop wise at room temperature. The mixture was stirred for 30 min and partitioned between water (30 mL) and CH$_2$Cl$_2$ (20 mL). The aqueous phase was extracted with CH$_2$Cl$_2$ (30 mL) and the combined organic phases were washed with saturated aqueous NaCl (50 mL). The organic phase was dried over sodium sulfate, filtered and concentrated in vacuo. The crude product was purified by column chromatography (50 g of silica gel, 10 to 70% EtOAc in hexanes) to afford di-tert-butyl (2R)-2-(((2-methylpropyl)(methylsulfonyl)amino)methyl)-1,4-piperazinedicarboxylate (0.842 g) as a white solid.

Step 4: N-(2-methylpropyl)-N-((2R)-2-piperazinylmethyl)methanesulfonamide dihydrochloride A 250-mL round-bottomed flask was charged with di-tert-butyl (2R)-2-(((2-methylpropyl)(methylsulfonyl)amino)methyl)-1,4-piperazinedicarboxylate (0.840 g, 1.87 mmol), HCl (4.0 M in 1,4-dioxane, 2.4 mL, 9.6 mmol, Sigma-Aldrich, St. Louis, Mo.) and EtOAc (20 mL). The reaction mixture was heated at 70° C. for 24 h and then was allowed to cool to room temperature. The resulting white solid was collected via filtration and washed with EtOAc to give N-(2-methylpropyl)-N-((2R)-2-piperazinylmethyl)methanesulfonamide dihydrochloride (0.633 g) as a white solid.

Step 5: N-(((2S)-4-((5-nitro-2-thiophenyl)sulfonyl)-2-piperazinyl)methyl)-N-(2-methylpropyl)methanesulfonamide A 5-mL vial was charged with N-(2-methylpropyl)-N-((2R)-2-piperazinylmethyl)methanesulfonamide dihydrochloride (0.144 g, 0.446 mmol) and CH$_2$Cl$_2$ (2 mL). To this was added triethylamine (0.650 mL, 4.66 mmol) in potions at room temperature followed by drop wise addition of 5-nitrothiophene-2-sulfonyl chloride (0.120 g, 0.525 mmol, Enamine LLC, Monmouth Jct. NJ) in CH$_2$Cl$_2$ (1 mL). The mixture was stirred at room temperature for 15 min and then the reaction mixture was partitioned between water (20 mL) and CH$_2$Cl$_2$ (20 mL). The aqueous phase was extracted with CH$_2$Cl$_2$ (2×20 mL) and the combined organic extracts were washed with saturated aqueous NaCl (50 mL), dried over sodium sulfate, filtered and concentrated in vacuo. The crude product was purified by column chromatography (25 g of silica gel, 0 to 10% (2 M NH$_3$ in MeOH) in CH$_2$Cl$_2$) to afford N-(((2S)-4-((5-nitro-2-thiophenyl)sulfonyl)-2-piperazinyl)methyl)-N-(2-methylpropyl)methanesulfonamide (0.173 g) as a light-brown foam.

Step 6: N-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide A 5-mL vial was charged with N-(((2S)-4-((5-nitro-2-thiophenyl)sulfonyl)-2-piperazinyl)methyl)-N-(2-methylpropyl)methanesulfonamide (0.170 g, 0.386 mmol), 2-(2-chloropyrimidin-5-yl)-1,1,1,3,3,3-hexafluoropropan-2-ol (0.124 g, 0.442 mmol, Intermediate D), DIPEA (0.202 mL, 1.16 mmol), and 1,4-dioxane (2 mL). The vial was sealed and stirred at 100° C. for 21 h. The reaction mixture was allowed to cool to room temperature and partitioned between water (20 mL) and EtOAc (20 mL). The aqueous phase was extracted with EtOAc (20 mL) and the combined organic extracts were washed with saturated aqueous NaCl (40 mL), dried over sodium sulfate, filtered and concentrated in vacuo. The crude product was purified by column chromatography (25 g of silica gel, 40 to 100% EtOAc in hexanes followed by 0-10% (2M NH$_3$ in MeOH) in CH$_2$Cl$_2$) to afford N-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide (0.0454 g) as a brown solid.

Step 7: N-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide A 20-mL vial was charged with N-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide (0.0916 g, 0.134 mmol), iron filings (0.0455 g, 0.815 mmol) and acetic acid (2 mL). The reaction mixture was heated at 50° C. for 20 min., then allowed to cool iii to room temperature. Saturated aqueous NaHCO$_3$ (40 mL) was carefully added and the aqueous phase was extracted with EtOAc (2×20 mL). The combined organic extracts were washed with water (2×40 mL) and saturated aqueous NaCl (40 mL), dried over sodium sulfate, filtered and concentrated in vacuo. The crude product was purified by column chromatography (10 g of silica gel, 30 to 100% EtOAc in hexanes) to afford N-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide (0.0668 g) as a yellow foam.

$^1$H NMR (400 MHz, CDCl$_3$) δ=8.55 (s, 2H), 7.18 (d, J=3.9 Hz, 1H), 6.11 (d, J=3.9 Hz, 1H), 5.37 (br. s., 1H), 4.86 (d, J=13.7 Hz, 1H), 3.83-3.67 (m, 3H), 3.58-3.36 (m, 3H), 3.09 (t, J=6.5 Hz, 2H), 2.83 (s, 3H), 2.59 (dd, J=3.8, 11.8 Hz, 1H), 2.51-2.38 (m, 1H), 2.07-1.92 (m, 1H), 1.00-0.82 (m, 6H). MS (ESI, pos. ion) m/z: 655.0 [M+1]. GK-GKRP IC$_{50}$ (Binding)=0.001 μM; GK-GKRP EC$_{50}$ (LC MS/MS-2)=0.013 μM.

Example 230

N-(((2S)-4-((6-amino-3-pyridinyl)sulfonyl)-1-(5-(2, 2,2-trifluoro-1-hydroxy-1-(trifluoromethyl)ethyl)-2-pyrimidinyl)-2-piperazinyl)methyl)-N-(2-methylpropyl)methanesulfonamide and N-(((2S)-4-((2-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide

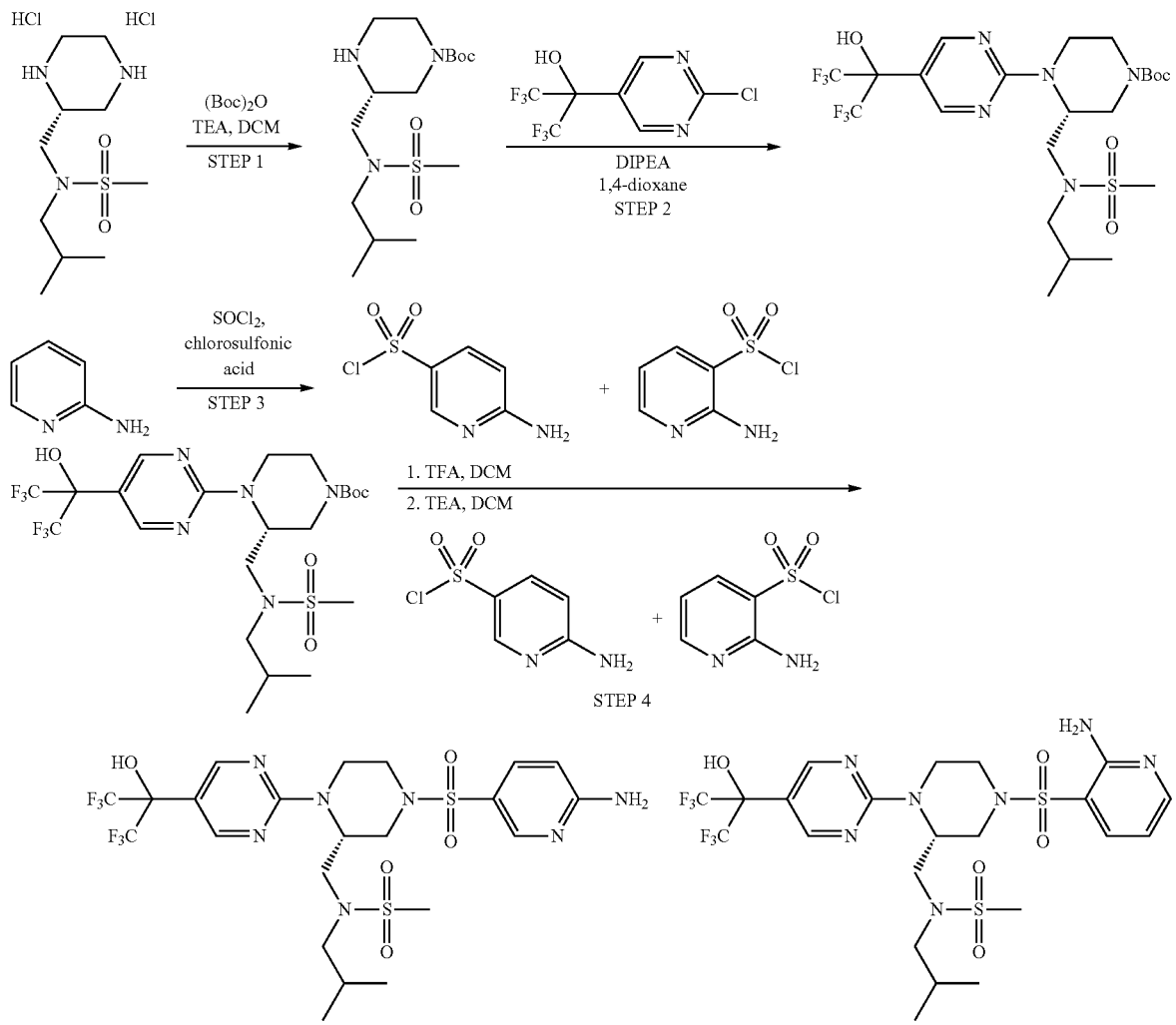

Step 1: tert-butyl (3R)-3-(((2-methylpropyl)(methylsulfonyl)amino)methyl)-1-piperazinecarboxylate A 20-mL vial was charged with N-(2-methylpropyl)-N-((2R)-2-piperazinylmethyl)methanesulfonamide dihydrochloride (0.462 g, 0.945 mmol, Example 229, Step 4), triethylamine (1.00 mL, 7.17 mmol) and $CH_2Cl_2$ (8 mL). The mixture was stirred at room temperature for 15 min and then was cooled to 0° C. To this solution was added $Boc_2O$ (0.333 g, 1.53 mmol, Sigma-Aldrich, St. Louis, Mo.). After 30 min at 0° C., the reaction mixture was partitioned between water (10 mL) and $CH_2Cl_2$ (10 mL). The aqueous phase was extracted with $CH_2Cl_2$ (2×10 mL). The combined organic extracts were washed with water (30 mL), saturated aqueous NaCl (30 mL), dried over sodium sulfate, filtered and concentrated in vacuo to afford tert-butyl (3R)-3-(((2-methylpropyl)(methylsulfonyl)amino)methyl)-1-piperazinecarboxylate (0.498 g) as a white solid.

Step 2: tert-butyl (3R)-3-(((2-methylpropyl)(methylsulfonyl)amino)methyl)-4-(5-(2,2,2-trifluoro-1-hydroxy-1-(trifluoromethyl)ethyl)-2-pyrimidinyl)-1-piperazinecarboxylate A 20-mL vial was charged with tert-butyl (3R)-3-(((2-methylpropyl)(methylsulfonyl)amino)methyl)-1-piperazinecarboxylate (0.498 g, 1.42 mmol, step 1), 2-(2-chloropyrimidin-5-yl)-1,1,1,3,3,3-hexafluoropropan-2-ol (0.479 g, 1.71 mmol, Intermediate D), DIPEA (0.75 mL, 4.3 mmol) and 1,4-dioxane (5 mL). The mixture was heated at 100° C. for 12 h and then cooled to room temperature and partitioned between water (50 mL) and EtOAc (40 mL). The aqueous phase was extracted with EtOAc (40 mL) and the combined organic extracts were washed with saturated aqueous NaCl (60 mL) dried over sodium sulfate, filtered and concentrated in vacuo. The crude product was purified by column chromatography (50 g of silica gel, 0 to 50% EtOAc in hexanes) to afford tert-butyl (3R)-3-(((2-methylpropyl)(methylsulfonyl)amino)methyl)-4-(5-(2,2,2-trifluoro-1-hydroxy-1-(trifluoromethyl)ethyl)-2-pyrimidinyl)-1-piperazinecarboxylate (0.655 g) as a light-yellow foam.

Step 3: 6-amino-3-pyridinesulfonyl chloride and 2-amino-3-pyridinesulfonyl chloride To chlorosulfonic acid (6.50 mL, 98 mmol) in a 75-mL pressure tube at 0° C., was slowly added 2-aminopyridine (0.898 g, 9.54 mmol) while streaming argon gas into the reaction. After the addition was complete, thionyl chloride (2.80 mL, 38.4 mmol) was then added drop wise at 0° C. The tube was then sealed and heated at 80° C. for 2.5 h., and then temperature was raised to 150° C. and heating was continued for an additional 12 h. The reaction mixture was allowed to cool to room temperature and then poured carefully onto ice (about 300 g). The mixture was extracted with EtOAc (3×80 mL) and the combined organic extracts were washed with saturated aqueous NaCl (150 mL), dried over sodium sulfate, filtered and concentrated in vacuo to afford a mixture of 6-amino-3-pyridinesulfonyl chloride and 2-amino-3-pyridinesulfonyl chloride (0.0651 g) as a light-brown solid.

Step 4: N-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide and N-(((2S)-4-((2-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide A 5-mL vial was charged with tert-butyl (3R)-3-(((2-methylpropyl)(methylsulfonyl)amino)methyl)-4-(5-(2,2,2-trifluoro-1-hydroxy-1-(trifluoromethyl)ethyl)-2-pyrimidinyl)-1-piperazinecarboxylate (0.106 g, 0.178 mmol), TFA (1.00 mL, 13.0 mmol) and $CH_2Cl_2$ (2 mL). The mixture was stirred at room temperature for 15 min and then the volatiles were removed in vacuo. The residue was taken into $CH_2Cl_2$ (1 mL) and treated with triethylamine (0.30 mL, 2.15 mmol) and stirred at room temperature for 5 min. This mixture was added to a solution of a mixture of 6-amino-3-pyridinesulfonyl chloride and 2-amino-3-pyridinesulfonyl chloride (0.034 g, 0.18 mmol) in $CH_2Cl_2$ (1 mL). The reaction mixture was stirred at room temperature for 5 min and then concentrated and purified by column chromatography (twice, 25 g of silica gel, EtOAc in hexanes 30 to 100% then (10 g of silica gel (2 M $NH_3$ in MeOH) in $CH_2Cl_2$ 0 to 10%). Purification by preparative HPLC (Phenomenex $C_{18}$ Gemini NX column, (5 μm, 150×30 mm) eluting with 10 to 90% MeCN with 0.1% TFA in water with 0.1% TFA in 10 min at a flow rate of 40 mL/min to afford the following two products.

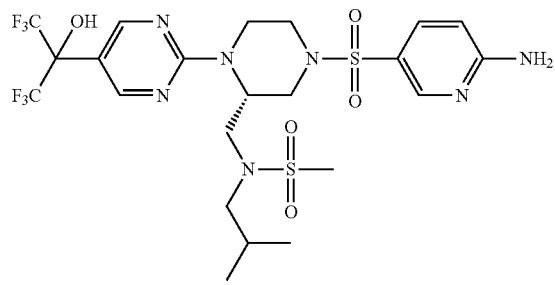 [SMILES: CC(C)CN(C[C@H]1CN(S(=O)(=O)c2ccc(N)nc2)CCN1c1ncc(C(O)(C(F)(F)F)C(F)(F)F)cn1)S(C)(=O)=O]

N-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide (0.0434 g) as a white solid.

$^1$H NMR (400 MHz, CDCl$_3$) δ=8.47 (s, 2H), 8.32 (d, J=2.0 Hz, 1H), 7.66 (dd, J=2.2, 8.8 Hz, 1H), 6.47 (d, J=8.8 Hz, 1H), 5.27 (br. s., 1H), 5.03 (br. s., 2H), 4.78 (d, J=13.9 Hz, 1H), 3.98 (br. s., 1H), 3.78-3.58 (m, 3H), 3.47-3.28 (m, 2H), 3.09-2.95 (m, 2H), 2.76 (s, 3H), 2.42 (dd, J=3.9, 11.7 Hz, 1H), 2.28 (dt, J=3.3, 11.6 Hz, 1H), 1.93 (td, J=7.1, 13.8 Hz, 1H), 0.94-0.78 (m, 6H). MS (ESI, pos. ion) m/z: 650.0 [M+1]. GK-GKRP IC$_{50}$ (Binding)=0.001 μM; GK-GKRP EC$_{50}$ (LC MS/MS-2)=0.011 μM.

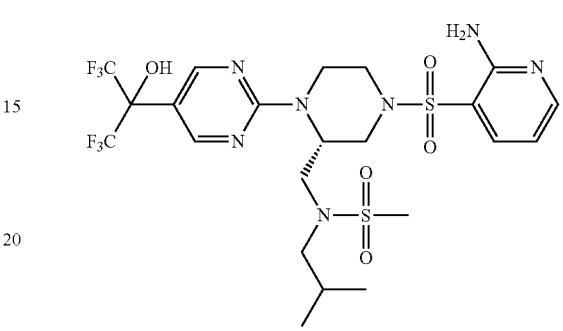

N-(((2S)-4-((2-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide (0.020 g) as a off-white solid.

$^1$H NMR (400 MHz, CDCl$_3$) δ=8.54 (s, 2H), 8.20 (dd, J=1.5, 4.8 Hz, 1H), 7.85 (dd, J=1.7, 7.7 Hz, 1H), 6.73 (dd, J=4.9, 7.8 Hz, 1H), 5.87 (br. s., 2H), 5.32 (br. s., 1H), 4.84 (d, J=13.5 Hz, 1H), 4.71-4.02 (m, 1H), 3.85 (d, J=12.1 Hz, 1H), 3.73 (d, J=11.3 Hz, 1H), 3.66-3.57 (m, 1H), 3.49 (dd, J=6.7, 13.8 Hz, 1H), 3.42-3.31 (m, 1H), 3.13-3.02 (m, 2H), 2.80 (s, 3H), 2.71 (dd, J=4.0, 12.0 Hz, 1H), 2.57 (dt, J=3.5, 11.8 Hz, 1H), 2.05-1.92 (m, J=7.0, 7.0, 13.6 Hz, 1H), 0.99-0.84 (m, 6H). MS (ESI, pos. ion) m/z: 650.0 [M+1]. GK-GKRP IC$_{50}$ (Binding)=0.064 μM; GK-GKRP EC$_{50}$ (LC MS/MS-2) =0.095 μM.

Example 231

N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide

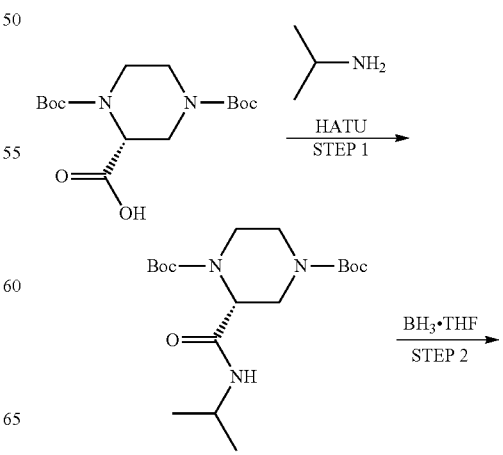

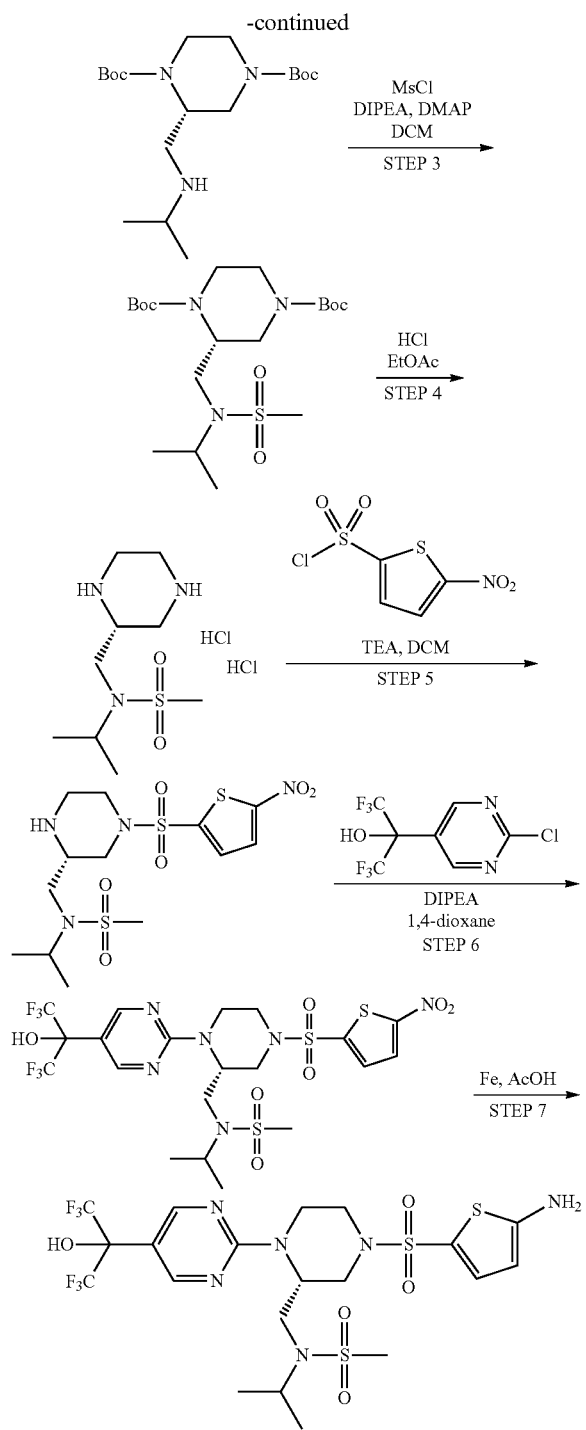

EtOAc (50 mL). The aqueous phase was extracted with EtOAc (50 mL). and the combined organic phases were washed with saturated aqueous $NaHCO_3$ (100 mL), water (100 mL), then brine (100 mL), dried over sodium sulfate, filtered, and concentrated in vacuo to afford di-tert-butyl (2R)-2-((1-methylethyl)carbamoyl)-1,4-piperazinedicarboxylate (2.30 g) as a light-brown foam.

Step 2: di-tert-butyl (2S)-2-(((1-methylethyl)amino) methyl)-1,4-piperazinedicarboxylate A 500-mL round-bottomed flask was charged with di-tert-butyl (2R)-2-((1-methylethyl)carbamoyl)-1,4-piperazinedicarboxylate (1.77 g, 4.76 mmol, step 1), $BH_3$.THF (1.0 M in THF, 15.0 mL, 15.0 mmol) and THF (60 mL). The mixture was heated at 50° C. for 12 h. After allowing the reaction to cool to room temperature, additional $BH_3$.THF (1.0 M in THF, 5.0 mL, 5.0 mmol) was added. The mixture was then heated at 50° C. for 1.5 h. The reaction mixture was allowed to cool to room temperature and MeOH (20 mL) was slowly added. The solvent was removed in vacuo and the crude product was purified by column chromatography (100 g of silica gel, 0 to 10% iPrOH (with 10% $NH_4OH$) in $CHCl_3$) to afford di-tert-butyl (2S)-2-(((1-methylethyl)amino)methyl)-1,4-piperazinedicarboxylate (0.69 g) as a clear oil.

Step 3: di-tert-butyl (2R)-2-(((1-methylethyl)(methylsulfonyl)amino)methyl)-1,4-piperazinedicarboxylate A 500-mL round-bottomed flask was charged with di-tert-butyl (2S)-2-(((1-methylethyl)amino)methyl)-1,4-piperazinedicarboxylate (0.69 g, 1.9 mmol), DMAP (0.0358 g, 0.293 mmol), DIPEA (1.40 mL, 8.05 mmol) and $CH_2Cl_2$ (8 mL). To this mixture was added methanesulfonyl chloride (0.299 mL, 3.86 mmol) at room temperature. After 20 min at room temperature additional methanesulfonyl chloride (0.10 mL, 1.3 mmol) was added and stirring was continued at room temperature for an additional 1 h. The reaction mixture was partitioned between water (30 mL) and $CH_2Cl_2$ (20 mL). The aqueous phase was extracted with $CH_2Cl_2$ (30 mL) and the combined organic extracts were washed with saturated aqueous NaCl (50 mL), dried over sodium sulfate, filtered and concentrated in vacuo. The crude product was purified by column chromatography (50 g of silica gel, 0 to 50% EtOAc in hexanes) to afford di-tert-butyl (2R)-2-(((1-methylethyl) (methylsulfonyl)amino)methyl)-1,4-piperazinedicarboxylate (0.617 g) as a white solid.

Step 4: N-(1-methylethyl)-N-((2R)-2-piperazinylmethyl) methanesulfonamide dihydrochloride A 150-mL round-bottomed flask was charged with di-tert-butyl (2R)-2-(((1-methylethyl)(methylsulfonyl)amino)methyl)-1,4-piperazinedicarboxylate (0.617 g, 1.42 mmol), HCl (4.0 M in 1,4-dioxane, 2.80 mL, 11.2 mmol) and EtOAc (20 mL). The mixture was heated at 70° C. for 18 h. The reaction mixture was allowed to cool to room temperature and the resulting white solid was collected by filtration. The solid was washed with EtOAc and to obtain N-(1-methylethyl)-N-((2R)-2-piperazinylmethyl)methanesulfonamide dihydrochloride (0.421 g) as a white solid.

Step 5: N-(((2R)-4-((5-nitro-2-thiophenyl)sulfonyl)-2-piperazinyl)methyl)-N-(1-methylethyl)methanesulfonamide Following the procedure reported for Example 229, Step 5, the reaction of N-(1-methylethyl)-N-((2R)-2-piperazinylm- Step 1: di-tert-butyl (2R)-2-((1-methylethyl)carbamoyl)-1,4-piperazinedicarboxylate A 20-mL vial was charged with ((2R)-1,4-bis(tert-butoxycarbonyl)-2-piperazinecarboxylic acid (1.57 g, 4.76 mmol, ASW MedChem Inc., New Brunswick, N.J.), HATU (2.17 g, 5.72 mmol, ChemImpex International Inc., Wood Dale, Ill.), propan-2-amine (0.450 mL, 5.28 mmol, Sigma-Aldrich, St. Louis, Mo.), DIPEA (1.70 mL, 9.76 mmol) and DMF (8 mL). The mixture was stirred at room temperature for 2.5 h. The reaction mixture was partitioned between water (80 mL) and ethyl)methanesulfonamide dihydrochloride with 5-nitrothiophene-2-sulfonyl chloride (Enamine LLC, Monmouth Jct. NJ) delivered N-(((2R)-4-((5-nitro-2-thiophenyl)sulfonyl)-2-piperazinyl)methyl)-N-(1-methylethyl)methanesulfonamide.

Step 6: N-(((2R)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide Following the procedure reported for Example 229, Step 6, the reaction of N-(((2R)-4-((5-nitro-2-thiophenyl)sulfonyl)-2-piperazinyl)methyl)-N-(1-methylethyl)methanesulfonamide with 2-(2-chloropyrimidin-5-yl)-1,1,1,3,3,3-hexafluoropropan-2-ol (Intermediate D) delivered N-(((2R)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide.

Step 7: N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide Following the procedure reported for Example 229, Step 7, the reaction of N-(((2R)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide with iron delivered N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide.

$^1$H NMR (400 MHz, CDCl$_3$) δ=8.55 (s, 2H), 7.18 (d, J=4.3 Hz, 1H), 6.11 (d, J=3.7 Hz, 1H), 5.46 (br. s., 1H), 4.88 (d, J=15.3 Hz, 1H), 4.01-3.81 (m, 2H), 3.74 (br. s., 1H), 3.65-3.31 (m, 5H), 2.84 (s, 3H), 2.58 (dd, J=4.0, 11.8 Hz, 1H), 2.50-2.38 (m, J=3.5 Hz, 1H), 1.34 (d, J=6.7 Hz, 3H), 1.24-1.11 (m, 4H). MS (ESI, pos. ion) m/z: 641.0 [M+1]. GK-GKRP IC$_{50}$ (Binding)=0.007 μM; GK-GKRP EC$_{50}$ (LC MS/MS-2)=0.020 μM.

Example 232

N-(((2R)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide

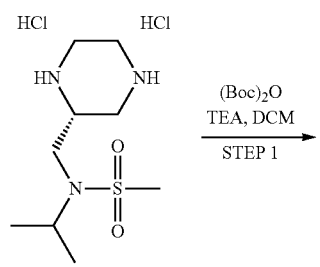

Step 1: tert-butyl (3R)-3-(((1-methylethyl)(methylsulfonyl)amino)methyl)-1-piperazinecarboxylate Following the procedure reported for Example 230, Step 1, N-(1-methylethyl)-N-((2R)-2-piperazinylmethyl)methanesulfonamide dihydrochloride (Example 231, Step 4), the reaction delivered tert-butyl (3R)-3-(((1-methylethyl)(methylsulfonyl)amino)methyl)-1-piperazinecarboxylate.

Step 2: tert-butyl (3R)-3-(((1-methylethyl)(methylsulfonyl) amino)methyl)-4-(5-(2,2,2-trifluoro-1-hydroxy-1-(trifluoromethyl)ethyl)-2-pyrimidinyl)-1-piperazinecarboxylate A 20-mL vial was charged with tert-butyl (3R)-3-(((1-methylethyl)(methylsulfonyl)amino)methyl)-1-piperazinecarboxylate (0.315 g, 0.939 mmol, step 1), 2-(2-chloropyrimidin-5-yl)-1,1,1,3,3,3-hexafluoropropan-2-ol (0.287 g, 1.02 mmol, Intermediate D), DIPEA (0.492 mL, 2.82 mmol) and 1,4-dioxane (5 mL). The vial was sealed and heated at 100° C. for 12 h. The reaction mixture was allowed to cool to room temperature and additional 2-(2-chloropyrimidin-5-yl)-1,1,1,3,3,3-hexafluoropropan-2-ol (0.082 g, 0.29 mmol, Intermediate D) was added. The mixture was heated at 100° C. for an additional 12 h. After allowing the reaction to cool to room temperature, the mixture was partitioned between water (50 mL) and EtOAc (40 mL). The aqueous phase was extracted with EtOAc (40 mL). The combined organic extracts was washed with saturated aqueous NaCl (60 mL), dried over sodium sulfate, filtered and concentrated in vacuo. The crude product was purified by column chromatography (50 g of silica gel, 0 to 50% EtOAc in hexanes) to afford tert-butyl (3R)-3-(((1-methylethyl)(methylsulfonyl)amino) methyl)-4-(5-(2,2,2-trifluoro-1-hydroxy-1-(trifluoromethyl) ethyl)-2-pyrimidinyl)-1-piperazinecarboxylate (0.455 g) as a light yellow foam.

Step 3: N-(((2R)-4-((6-chloro-3-pyridinyl)sulfonyl)-1-(5-(2,2,2-trifluoro-1-hydroxy-1-(trifluoromethyl) ethyl)-2-pyrimidinyl)-2-piperazinyl)methyl)-N-(1-methylethyl)methanesulfonamide A 5-mL vial was charged with tert-butyl (3R)-3-(((1-methylethyl)(methylsulfonyl)amino)methyl)-4-(5-(2,2,2-trifluoro-1-hydroxy-1-(trifluoromethyl)ethyl)-2-pyrimidinyl)-1-piperazinecarboxylate (0.150 g, 0.259 mmol, step 2), TFA (1.0 mL, 13 mmol) and $CH_2Cl_2$ (2 mL). The reaction mixture was stirred at room temperature for 30 min and then the volatiles were removed in vacuo. To the resulting residue was added $CH_2Cl_2$ (2 mL) followed by TEA (0.40 mL, 2.9 mmol). The mixture was stirred at room temperature for 10 min and then 6-chloropyridine-3-sulfonyl chloride (0.0627 g, 0.296 mmol, *Organic Process Research & Development* 2009, 13, 875) was added. After 10 min at room temperature, the mixture was concentrated and the crude product was purified by column chromatography (25 g of silica gel, 0 to 50% EtOAc in hexanes) to afford N-(((2R)-4-((6-chloro-3-pyridinyl)sulfonyl)-1-(5-(2,2,2-trifluoro-1-hydroxy-1-(trifluoromethyl) ethyl)-2-pyrimidinyl)-2-piperazinyl)methyl)-N-(1-methylethyl)methanesulfonamide (0.163 g) as a light-yellow solid.

Step 4: N-(((2R)-4-((6-amino-3-pyridinyl)sulfonyl)-1-(5-(2,2,2-trifluoro-1-hydroxy-1-(trifluoromethyl) ethyl)-2-pyrimidinyl)-2-piperazinyl)methyl)-N-(1-methylethyl)methanesulfonamide A 5-mL microwave reaction vial charged with N-(((2R)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide (0.161 g, 0.246 mmol), concentrated ammonium hydroxide (0.65 mL, 5.0 mmol) and EtOH (2 mL). The vial was heated in an Initiator microwave reactor (Biotage AB, Inc., Uppsala, Sweden) at 140° C. for 2.5 h. The mixture was allowed to cool to room temperature and then concentrated in vacuo. The crude product was purified by column chromatography (25 g of silica gel, 30 to 100% EtOAc in hexanes) to afford N-(((2R)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide (0.0873 g) as a white solid.

$^1$H NMR (400 MHz, $CDCl_3$) δ=8.49 (s, 2H), 8.35 (d, J=2.0 Hz, 1H), 7.71 (dd, J=2.2, 8.7 Hz, 1H), 6.51 (d, J=8.8 Hz, 1H), 5.41-5.32 (m, J=3.5 Hz, 1H), 5.16 (br. s., 2H), 4.82 (d, J=12.9 Hz, 1H), 3.97-3.62 (m, 4H), 3.55-3.31 (m, 3H), 2.80 (s, 3H), 2.45 (dd, J=4.1, 11.9 Hz, 1H), 2.32 (dt, J=3.6, 11.8 Hz, 1H), 1.31 (d, J=6.8 Hz, 3H), 1.14 (d, J=6.7 Hz, 3H). MS (ESI, pos. ion) m/z: 636.0 [M+1]. GK-GKRP $IC_{50}$ (Binding)=0.035 µM; GK-GKRP $EC_{50}$ (LC MS/MS-2)=0.063 µM.

Example 233

N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-phenyl-methanesulfonamide

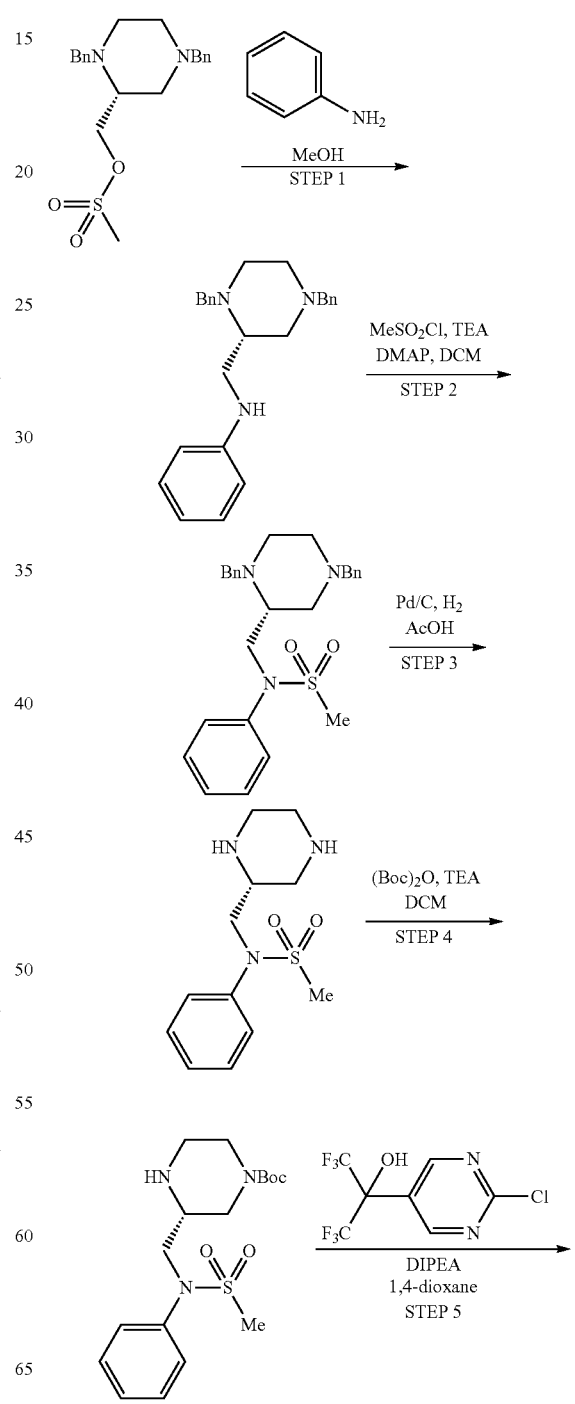

-continued

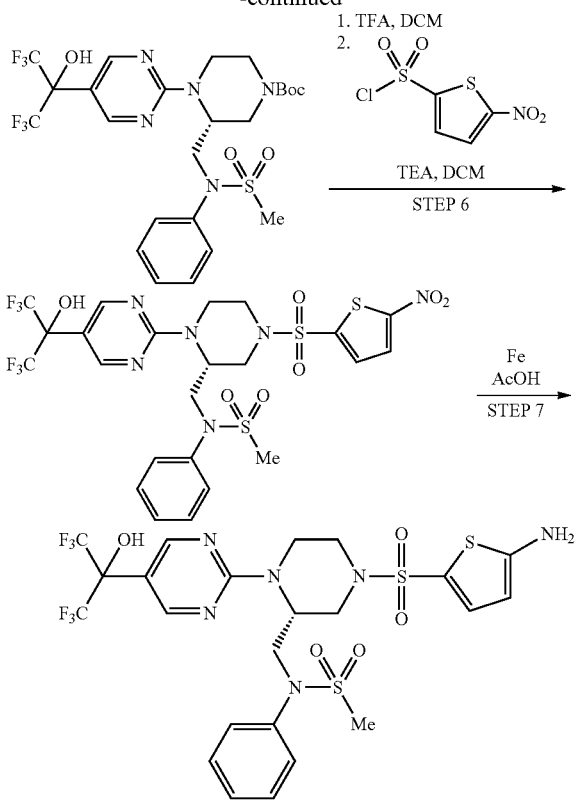

Step 1: N-(((2S)-1,4-dibenzyl-2-piperazinyl)methyl) aniline

A 20-mL vial was charged ((2R)-1,4-dibenzyl-2-piperazinyl)methyl methanesulfonate (1.01 g, 2.70 mmol, Example 184, Step 1), aniline (1.30 mL, 14.3 mmol, Alfa Aesar, Ward Hill, Mass.) and MeOH (12 mL). The reaction mixture was sealed and heated at 140° C. for 30 min in an Initiator microwave reactor (Biotage AB, Inc., Uppsala, Sweden). The mixture was allowed to cool to room temperature and then concentrated in vacuo. The crude product was purified by column chromatography (50 g of silica gel, (2 M $NH_3$ in MeOH) in $CH_2Cl_2$ 0 to 5%) to afford N-(((2S)-1,4-dibenzyl-2-piperazinyl)methyl)aniline (0.734 g) as an orange oil.

Step 2: N-(((2R)-1,4-dibenzyl-2-piperazinyl)methyl)-N-phenylmethanesulfonamide A 250-mL round-bottomed flask was charged with N-(((2S)-1,4-dibenzyl-2-piperazinyl)methyl)aniline (0.734 g, 1.98 mmol), DMAP (0.027 g, 0.22 mmol), triethylamine (0.85 mL, 6.1 mmol) and $CH_2Cl_2$ (8 mL). Methanesulfonyl chloride (0.23 mL, 3.0 mmol) was added drop wise at room temperature and the mixture was stirred at room temperature for 2 h. Additional methanesulfonyl chloride (0.20 mL, 2.6 mmol) and triethylamine (1.0 mL, 7.2 mmol) were added. The mixture was stirred at room temperature for another 1.5 h and then the mixture was concentrated to half the original volume and partitioned between water (40 mL) and EtOAc (40 mL). The aqueous phase was extracted with EtOAc (30 mL). The combined organic phases were washed with saturated aqueous NaCl (50 mL), dried over sodium sulfate, filtered and concentrated in vacuo. The crude product was purified by column chromatography (25 g of silica gel, 0 to 60% EtOAc in hexanes) to afford N-(((2R)-1,4-dibenzyl-2-piperazinyl)methyl)-N-phenylmethanesulfonamide (0.528 g) as a light yellow solid.

Step 3: N-phenyl-N-((2R)-2-piperazinylmethyl) methanesulfonamide

A 150-mL round-bottomed flask was charged with N-(((2R)-1,4-dibenzyl-2-piperazinyl)methyl)-N-phenyl-methanesulfonamide (0.527 g, 1.172 mmol, step 2), AcOH (0.10 mL, 1.7 mmol), Pd (10 wt. % (dry basis) on activated carbon, wet, Degussa type, 0.528 g), EtOH (10 mL) and EtOAc (2 mL). The reaction mixture was evacuated under vacuum and refilled with hydrogen. The mixture was stirred under an atmosphere of hydrogen at room temperature for 4.5 h then at 50° C. for 12 h. The reaction mixture was filtered and the filtrate was concentrated and re-subjected to the reaction condition (Pd/C 0.683 g and EtOH 10 mL). The reaction mixture was evacuated under vacuum and refilled with hydrogen. The mixture was stirred under an atmosphere of hydrogen at 50° C. for 12 h. The reaction mixture was filtered through a pad of filter agent. The filtrate was concentrated to give N-phenyl-N-((2R)-2-piperazinylmethyl)methanesulfonamide (0.378 g) as a clear oil.

Step 4: tert-butyl (3R)-3-(((methylsulfonyl)(phenyl)amino)methyl)-1-piperazinecarboxylate A 250-mL round-bottomed flask was charged with N-phenyl-N-((2R)-2-piperazinylmethyl)methanesulfonamide (0.315 g, 1.17 mmol), triethylamine (0.49 mL, 3.5 mmol) and $CH_2Cl_2$ (10 mL). The mixture was cooled to 0° C. then $Boc_2O$ (0.273 g, 1.25 mmol) was added in potions. The reaction was stirred at 0° C. for 30 min and then the reaction mixture was partitioned between water (20 mL) and $CH_2Cl_2$ (10 mL). The aqueous phase was extracted with $CH_2Cl_2$ (2×20 mL). The combined organic extracts were washed with water (30 mL) and saturated aqueous NaCl (30 mL), dried over sodium sulfate, filtered and concentrated in vacuo to afford tert-butyl (3R)-3-(((methylsulfonyl)(phenyl)amino)methyl)-1-piperazinecarboxylate (0.427 g) as a white solid.

Step 5: tert-butyl (3R)-3-(((methylsulfonyl)(phenyl)amino)methyl)-4-(5-(2,2,2-trifluoro-1-hydroxy-1-(trifluoromethyl)ethyl)-2-pyrimidinyl)-1-piperazinecarboxylate A 20-mL vial was charged with tert-butyl (3R)-3-(((methylsulfonyl)(phenyl)amino)methyl)-1-piperazinecarboxylate (0.425 g, 1.15 mmol, step 4), 2-(2-chloropyrimidin-5-yl)-1,1,1,3,3,3-hexafluoropropan-2-ol (0.411 g, 1.47 mmol, Intermediate D), DIPEA (0.602 mL, 3.45 mmol) and 1,4-dioxane (5 mL). The vial was sealed and the reaction mixture was heated at 100° C. for 20 h. The reaction mixture was allowed to cool to room temperature and partitioned between water (30 mL) and EtOAc (30 mL). The aqueous phase was extracted with EtOAc (2×30 mL). The combined organic phases were washed with saturated aqueous NaCl (50 mL), dried over sodium sulfate, filtered and concentrated in vacuo. The crude product was purified by column chromatography (50 g of silica gel, 0 to 50% EtOAc in hexanes) to afford tert-butyl (3R)-3-(((methylsulfonyl)(phenyl)amino)methyl)-4-(5-(2,2,2-trifluoro-1-hydroxy-1-(trifluoromethyl)ethyl)-2-pyrimidinyl)-1-piperazinecarboxylate (0.464 g) as a light-brown solid.

Step 6: N-(((2R)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide A 5-mL vial was charged with tert-butyl (3R)-3-(((methylsulfonyl)(phenyl)amino)methyl)-4-(5-(2,2,2-trifluoro-1-hydroxy-1-(trifluoromethyl)ethyl)-2-pyrimidinyl)-1-piperazinecarboxylate (0.229 g, 0.373 mmol), TFA (1.0 mL, 13 mmol) and CH$_2$Cl$_2$ (2 mL). The mixture was stirred at room temperature for 35 min and then concentrated. CH$_2$Cl$_2$ (1 mL) was added to the residue followed by triethylamine (0.60 mL, 4.3 mmol). The mixture was stirred at room temperature for 10 min and then a solution of 5-nitrothiophene-2-sulfonyl chloride (0.104 g, 0.456 mmol, Enamine LLC, Monmouth Jct. NJ) in CH$_2$Cl$_2$ (1 mL) was added drop wise. After stirring at room temperature for 40 min, the mixture was concentrated and purified by column chromatography (50 g of silica gel, 0 to 60% EtOAc in hexanes) to afford N-(((2R)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide (0.131 g) as a light-brown foam.

Step 7: N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide A 20-mL vial was charged with N-(((2R)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide (0.131 g, 0.186 mmol, step 1), iron filings (0.052 g, 0.93 mmol) and acetic acid (2 mL). The reaction mixture was heated at 50° C. for 40 min and then allowed to cool to room temperature. Saturated aqueous NaHCO$_3$ (20 mL) was then added slowly. The aqueous phase was extracted with EtOAc (2×20 mL) and the combined organic phases were washed with saturated aqueous NaCl (30 mL), dried over sodium sulfate, filtered and concentrated in vacuo. The crude product was purified by column chromatography (25 g of silica gel, 20 to 80% EtOAc in hexanes) to afford N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide (0.0912 g) as a light-yellow solid.

$^1$H NMR (400 MHz, CDCl$_3$) δ=8.48 (s, 2H), 7.35-7.28 (m, 3H), 7.19-7.07 (m, 3H), 6.10 (d, J=4.1 Hz, 1H), 5.33 (d, J=4.3 Hz, 1H), 4.71 (d, J=14.7 Hz, 1H), 4.36 (dd, J=9.5, 14.4 Hz, 1H), 3.94 (dd, J=5.2, 14.2 Hz, 1H), 3.77-3.65 (m, 2H), 3.58 (br. s., 1H), 3.30-3.17 (m, 1H), 2.87 (s, 3H), 2.56 (dd, J=3.8, 11.8 Hz, 1H), 2.42 (dt, J=3.5, 11.8 Hz, 1H). MS (ESI, pos. ion) m/z: 674.9 [M+1]. GK-GKRP IC$_{50}$ (Binding)<0.001 μM; GK-GKRP EC$_{50}$ (LC MS/MS-2)=0.008 μM.

Example 234

N-(((2R)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide

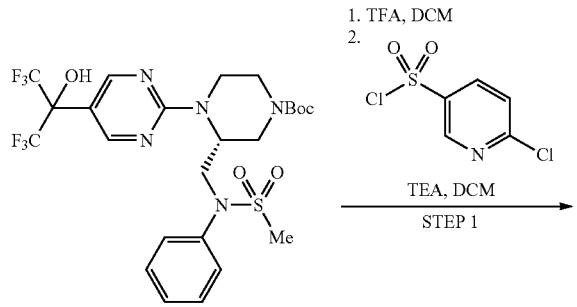

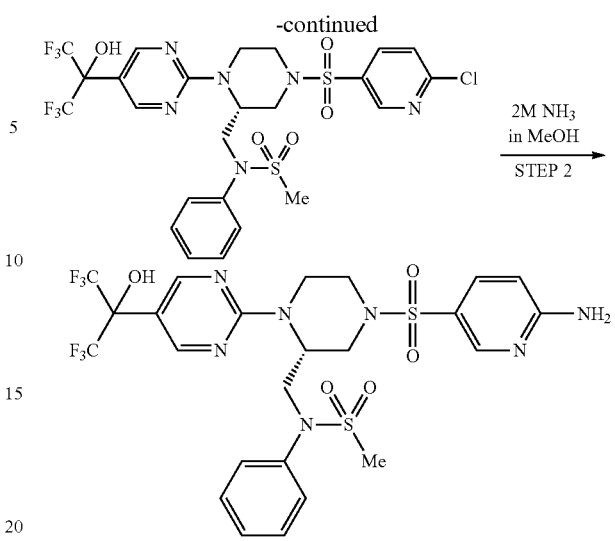

Step 1: N-(((2R)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide A 5-mL vial was charged with (R)-tert-butyl 4-(5-(1,1,1,3,3,3-hexafluoro-2-hydroxypropan-2-yl)pyrimidin-2-yl)-3-((N-phenylmethylsulfonamido)methyl)piperazine-1-carboxylate (0.214 g, 0.348 mmol, Example 233, Step 5), TFA (1.0 mL, 13 mmol) and CH$_2$Cl$_2$ (2 mL). The mixture was stirred at room temperature for 35 min and then concentrated. CH$_2$Cl$_2$ (2 mL) and triethylamine (0.50 mL, 3.6 mmol) were added and the mixture was stirred at room temperature for 10 min. 6-chloropyridine-3-sulfonyl chloride (0.0910 g, 0.429 mmol, *Organic Process Research & Development* 2009, 13, 875) was then added in potions and the mixture was stirred at room temperature for 1.5 h. The mixture was concentrated and purified by column chromatography (50 g of silica gel, 0 to 60% EtOAc in hexanes) to afford N-(((2R)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide (0.134 g) as a white solid.

Step 2: N-(((2R)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide A 5-mL microwave vial was charged with N-(((2R)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide (0.134 g, 0.194 mmol, step 1) and 2M NH$_3$ in MeOH (2 mL). The reaction mixture was heated in an Initiator microwave reactor (Biotage AB, Inc., Uppsala, Sweden) at 140° C. for 3 h. Then the mixture was then heated at 130° C. (thermal) for 12 h. The solvent was removed and the crude product was purified by column chromatography (25 g of silica gel, 10 to 90% EtOAc in hexanes) to afford N-(((2R)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide (0.0385 g) as a white solid.

$^1$H NMR (400 MHz, CDCl$_3$) δ=8.46 (s, 2H), 8.38 (d, J=2.0 Hz, 1H), 7.76-7.68 (m, 1H), 7.37-7.29 (m, 3H), 7.19-7.09 (m,

2H), 6.54 (d, J=8.8 Hz, 1H), 5.33-5.23 (m, J=14.7 Hz, 1H), 5.13 (br. s., 2H), 4.70 (d, J=15.5 Hz, 1H), 4.32 (dd, J=9.0, 14.1 Hz, 1H), 4.01-3.93 (m, 1H), 3.88 (br. s., 1H), 3.80-3.66 (m, 2H), 3.29-3.15 (m, 1H), 2.87 (s, 3H), 2.51-2.43 (m, 1H), 2.34 (dt, J=3.7, 11.7 Hz, 1H). MS (ESI, pos. ion) m/z: 670.1 [M+1]. GK-GKRP IC$_{50}$ (Binding)=0.004 μM; GK-GKRP EC$_{50}$ (LC MS/MS-2)=0.017 μM.

Example 235

4-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone

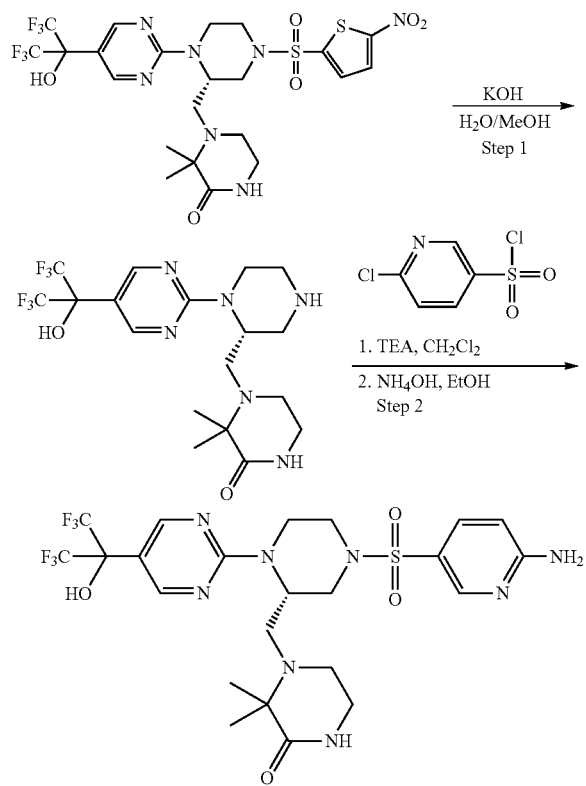

Step 1: 3,3-dimethyl-4-(((2R)-1-(5-(2,2,2-trifluoro-1-hydroxy-1-(trifluoromethyl)ethyl)-2-pyrimidinyl)-2-piperazinyl)methyl)-2-piperazinone A 20-mL vial was charged with 3,3-dimethyl-4-(((2S)-4-((5-nitro-2-thiophenyl)sulfonyl)-1-(5-(2,2,2-trifluoro-1-hydroxy-1-(trifluoromethyl)ethyl)-2-pyrimidinyl)-2-piperazinyl)methyl)-2-piperazinone (0.187 g, 0.282 mmol, Example 227, Step 2), a solution of potassium hydroxide (0.528 g, 9.40 mmol) in water (5.2 mL) and MeOH (2 mL). The reaction mixture was stirred at room temperature for 12 h and then was partitioned between water (10 mL) and EtOAc (10 mL). The aqueous phase was lyophilized and the residue was dissolved in MeOH. The solid was removed via filtration and the filtrate was concentrated and then dissolved into CH$_2$Cl$_2$. The resulting solid was removed by filtration and the filtrate was concentrated for a second time. The crude product was purified by preparative HPLC (Phenomenex, Gemini NX, 5 μm, C18 150×30 mm column) eluting with 10 to 90% CH$_3$CN with 0.1% TFA in H$_2$O over 10 min. The product fractions were combined and volatiles were removed. Lyophilizing the aqueous phase afforded 3,3-dimethyl-4-(((2R)-1-(5-(2,2,2-trifluoro-1-hydroxy-1-(trifluoromethyl)ethyl)-2-pyrimidinyl)-2-piperazinyl)methyl)-2-piperazinone as the TFA salt (0.057 g).

Step 2: 4-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone A solution of 3,3-dimethyl-4-(((2R)-1-(5-(2,2,2-trifluoro-1-hydroxy-1-(trifluoromethyl)ethyl)-2-pyrimidinyl)-2-piperazinyl)methyl)-2-piperazinone trifluoroacetate (56 mg, 0.096 mmol) and triethylamine (40.1 μL, 0.287 mmol) in CH$_2$Cl$_2$ (618 μL) was cooled to 0° C. and 6-chloropyridine-3-sulfonyl chloride (21.94 mg, 0.103 mmol, Organic Process Research & Development 2009, 13, 875) was added. Following complete consumption of the starting material, water was added to the mixture and the mixture was diluted with CH$_2$Cl$_2$. The layers were separated, and the organic layer was dried (MgSO$_4$), filtered and concentrated to give the crude pyridyl chloride intermediate. To this was added 1.5 mL EtOH and 1.5 mL concentrated NH$_4$OH. The mixture was heated in a sealed microwave vial at 100° C. for 12 h. After allowing the mixture to cool to room temperature, it was diluted with EtOAc and the organics were washed with water, dried over MgSO$_4$, filtered and concentrated. The crude residue was purified by silica gel chromatography (0.5 to 10% MeOH in CH$_2$Cl$_2$). The collected fractions were concentrated and the residue was taken up in MeOH and passed through an AccuBond SPE SCX cartridge, eluting with 2M ammonia in MeOH to give 4-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone (19.0 mg). $^1$H NMR (400 MHz, CD$_3$OD) δ=1.20 (s, 3H) 1.29 (s, 3H) 2.26 (td, J=11.79, 3.42 Hz, 1H) 2.30-2.43 (m, 2H) 2.79-2.94 (m, 2H) 2.96-3.08 (m, 2H) 3.10-3.19 (m, 2H) 3.68 (d, J=11.15 Hz, 1H) 3.94 (d, J=11.54 Hz, 1H) 4.64 (d, J=13.50 Hz, 1H) 6.53 (d, J=8.80 Hz, 1H) 7.64 (dd, J=8.90, 2.45 Hz, 1H) 8.21 (d, J=2.15 Hz, 1H) 8.46 (s, 2H). m/z (ESI, +ve ion) 648.8 (M+Na)$^+$. GK-GKRP IC$_{50}$ (Binding)=0.008 μM; GK-GKRP EC$_{50}$ (LC MS/MS-2)=0.013 μM.

Alternatively, this compound can be made by the following scheme.

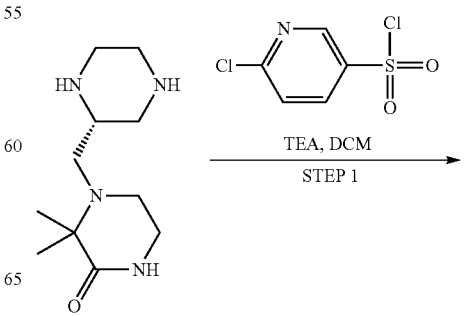

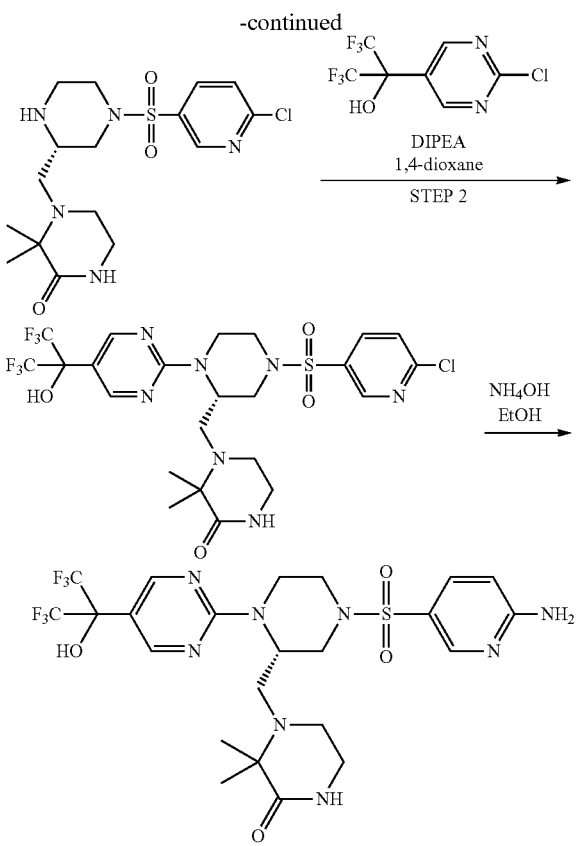

pyrimidinyl)-2-piperazinyl)methyl)-3,3-dimethyl-2-piperazinone would deliver 4-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone.

Example 236

5-(((2S)-4-(2-thiophenylsulfonyl)-1-(4-(2,2,2-trifluoro-1-hydroxy-1-methylethyl)phenyl)-2-piperazinyl)methyl)-5,7-diazaspiro[3.4]octane-6,8-dione

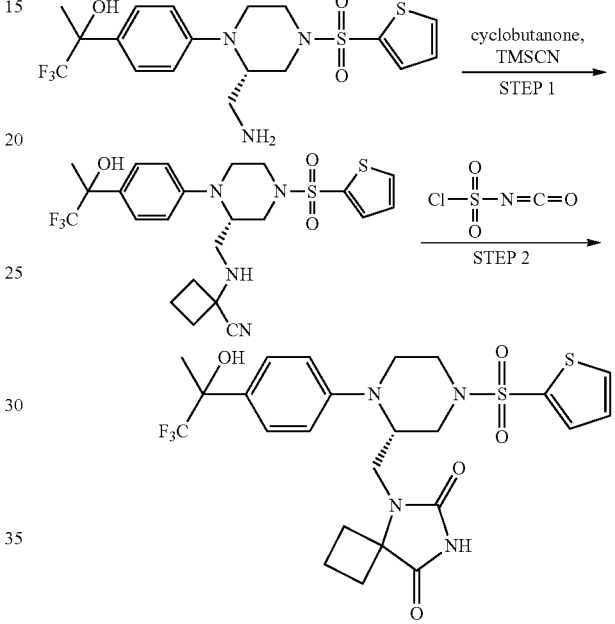

Step 1: 1-((((2S)-4-(2-thiophenylsulfonyl)-1-(4-(2,2,2-trifluoro-1-hydroxy-1-methylethyl)phenyl)-2-piperazinyl)methyl)amino)cyclobutanecarbonitrile Step 1: 4-(((2S)-4-((6-chloro-3-pyridinyl)sulfonyl)-2-piperazinyl)methyl)-3,3-dimethyl-2-piperazinone Following the procedure reported for Example 226, Step 3, the reaction of 3,3-dimethyl-4-((2R)-2-piperazinylmethyl)-2-piperazinone (Example 226, Step 2) and 6-chloropyridine-3-sulfonyl chloride (*Organic Process Research & Development* 2009, 13, 875) would deliver 4-(((2S)-4-((6-chloro-3-pyridinyl)sulfonyl)-2-piperazinyl)methyl)-3,3-dimethyl-2-piperazinone.

Step 2: 4-(((2S)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone Following the procedure reported for Example 226, Step 4, the reaction of 4-(((2S)-4-((6-chloro-3-pyridinyl)sulfonyl)-2-piperazinyl)methyl)-3,3-dimethyl-2-piperazinone and 2-(2-chloropyrimidin-5-yl)-1,1,1,3,3,3-hexafluoropropan-2-ol (Intermediate D) would deliver 4-(((2S)-4-((6-chloro-3-pyridinyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone.

Step 3: 4-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone Following the procedure reported for Example 232, step 4, the reaction of 4-(((2S)-4-((6-chloro-3-pyridinyl)sulfonyl)-1-(5-(2,2,2-trifluoro-1-hydroxy-1-(trifluoromethyl)ethyl)-2-

A 5-mL vial was charged with 2-(4-((2S)-2-(aminomethyl)-4-(2-thiophenylsulfonyl)-1-piperazinyl)phenyl)-1,1,1-trifluoro-2-propanol (0.202 g, 0.448 mmol, Example 192, Step 2), cyclobutanone (0.0364 g, 0.519 mmol, Alfa Aesar, Ward Hill, Mass.) and 1,2-dichloroethane (2.5 mL). The solution was stirred at room temperature for 20 min then trimethylsilanecarbonitrile (0.120 mL, 0.959 mmol, Sigma-Aldrich, St. Louis, Mo.) was added. After stirring at room temperature for 12 h, the material was purified by column chromatography (10 g of silica, 20 to 70% EtOAc in hexanes) to afford 1-(((((2S)-4-(2-thiophenylsulfonyl)-1-(4-(2,2,2-trifluoro-1-hydroxy-1-methylethyl)phenyl)-2-piperazinyl)methyl)amino)cyclobutanecarbonitrile (0.198 g) as a white solid.

Step 2: 5-(((2S)-4-(2-thiophenylsulfonyl)-1-(4-(2,2,2-trifluoro-1-hydroxy-1-methylethyl)phenyl)-2-piperazinyl)methyl)-5,7-diazaspiro[3.4]octane-6,8-dione A 100-mL round-bottomed flask was charged with 1-(((((2S)-4-(thiophen-2-ylsulfonyl)-1-(4-(1,1,1-trifluoro-2-hydroxypropan-2-yl)phenyl)piperazin-2-yl)methyl)amino)cyclobutanecarbonitrile (0.195 g, 0.369 mmol) and $CH_2Cl_2$ (2 mL). After cooling to 0° C., chlorosulfonyl isocyanate (0.035 mL, 0.406 mmol, Aldrich) was added drop wise. The mixture was stirred at 0° C. for 30 min. and the mixture was allowed to warm to room temperature. The solvent was removed under reduced pressure and water (2.0 mL) was added. The mixture was heated at 100° C. for 12 h. After the reaction mixture was allowed to cool to room temperature, water (10 mL) and EtOAc (10 mL) were added. The aqueous phase was extracted with EtOAc (10 mL). The combined organic extracts were washed with saturated aqueous NaCl (20 mL), dried over sodium sulfate, filtered and concentrated in vacuo. The crude product was purified by column chromatography (25 g of silica gel, 20 to 90% EtOAc in hexanes). The compound was then purified by preparative HPLC (Phenomenex, Gemni NX, 5 μm, C18, 150×30 mm column) eluting with 30 to 95% $CH_3CN$ with 0.1% TFA in $H_2O$ with 0.1% TFA in 10 min at flow rate of 40 mL/min. The product fractions were combined and acetonitrile was evaporated. The aqueous phase was basified by adding saturated aqueous $NaHCO_3$. The mixture was extracted with EtOAc and the organic phase was washed with brine, dried over sodium sulfate, filtered and concentrated in vacuo to afford 5-(((2S)-4-(2-thiophenylsulfonyl)-1-(4-(2,2,2-trifluoro-1-hydroxy-1-methylethyl)phenyl)-2-piperazinyl)methyl)-5,7-diazaspiro[3.4]octane-6,8-dione (0.0889 g) as a mixture of two isomers:

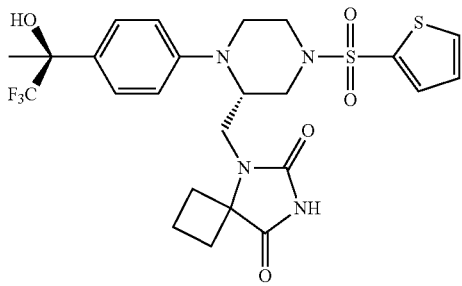

5-(((2S)-4-(2-thiophenylsulfonyl)-1-(4-((1S)-2,2,2-trifluoro-1-hydroxy-1-methylethyl)phenyl)-2-piperazinyl)methyl)-5,7-diazaspiro[3.4]octane-6,8-dione; 5-(((2S)-4-(2-thiophenylsulfonyl)-1-(4-((1R)-2,2,2-trifluoro-1-hydroxy-1-methylethyl)phenyl)-2-piperazinyl)methyl)-5,7-diazaspiro[3.4]octane-6,8-dione.

$^1H$ NMR (400 MHz, $CDCl_3$) δ=7.69 (d, J=4.9 Hz, 1H), 7.59 (d, J=3.7 Hz, 1H), 7.50-7.36 (m, 3H), 7.20 (t, J=4.1 Hz, 1H), 7.01 (br. s., 2H), 4.89 (br. s., 1H), 3.88-3.75 (m, 2H), 3.64-3.42 (m, 4H), 2.80-2.08 (m, 8H), 1.85 (br. s., 1H), 1.73 (s, 3H). MS (ESI, pos. ion) m/z: 573.0 [M+1]. GK-GKRP $IC_{50}$ (Binding)=0.379 μM; GK-GKRP $EC_{50}$ (LC MS/MS-2)=0.363 μM.

Example 237

N-(((2S)-4-(thiophen-2-ylsulfonyl)-1-(4-(1,1,1-trifluoro-2-hydroxypropan-2-yl)phenyl)piperazin-2-yl)methyl)propane-2-sulfonamide

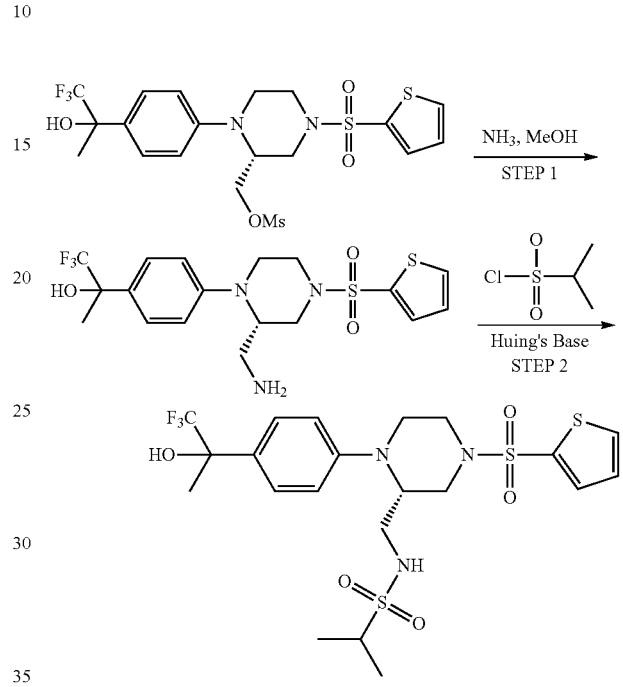

Step 1: 2-(4-(((2S)-2-(aminomethyl)-4-(2-thiophenylsulfonyl)-1-piperazinyl)phenyl)-1,1,1-trifluoro-2-propanol A mixture of ((2R)-4-(thiophen-2-ylsulfonyl)-1-(4-(1,1,1-trifluoro-2-hydroxypropan-2-yl)phenyl)piperazin-2-yl)methyl methanesulfonate (0.9 g, 1.70 mmol, Intermediate B) in 2 M $NH_3$ in MeOH (10 mL, 20.0 mmol) was heated in an Initiator microwave reactor (Biotage AB, Inc., Uppsala, Sweden) at 140° C. for 30 min. The mixture was concentrated and purified on silica gel [2% MeOH in $CH_2Cl_2$ to 2% (2 N $NH_3$-MeOH) in $CH_2Cl_2$) to give 2-(4-((2S)-2-(aminomethyl)-4-(2-thiophenylsulfonyl)-1-piperazinyl)phenyl)-1,1,1-trifluoro-2-propanol as a white foam (500 mg).

Step 2: N-(((2S)-4-(2-thiophenylsulfonyl)-1-(4-(2,2,2-trifluoro-1-hydroxy-1-methylethyl)phenyl)-2-piperazinyl)methyl)-2-propanesulfonamide To a solution of 2-(4-((2S)-2-(aminomethyl)-4-(2-thiophenylsulfonyl)-1-piperazinyl)phenyl)-1,1,1-trifluoro-2-propanol (108 mg, 0.240 mmol) in $CH_2Cl_2$ (3 mL) was added pyridine (50 μL, 0.618 mmol, Sigma-Aldrich, St. Louis, Mo.) followed by isopropylsulfonyl chloride (27.0 μL, 0.240 mmol, Sigma-Aldrich, St. Louis, Mo.). After stirring at room temperature for 12 h, Hünig's base (0.5 mL) and more isopropylsulfonyl chloride (27.0 μL, 0.240 mmol) were added. The mixture was then heated at 60° C. for 12 h. MeOH (2 mL) was added and the mixture was concentrated. The residue was partitioned between $CH_2Cl_2$ and saturated aqueous $NH_4Cl$.

The organic layer was concentrated and purified on silica gel (1 to 4% MeOH in CH$_2$Cl$_2$) then by preparative TLC (1 to 4% MeOH in CH$_2$Cl$_2$) to give N-(((2S)-4-(2-thiophenylsulfonyl)-1-(4-(2,2,2-trifluoro-1-hydroxy-1-methylethyl)phenyl)-2-piperazinyl)methyl)-2-propanesulfonamide (10 mg) as a mixture of two isomers.

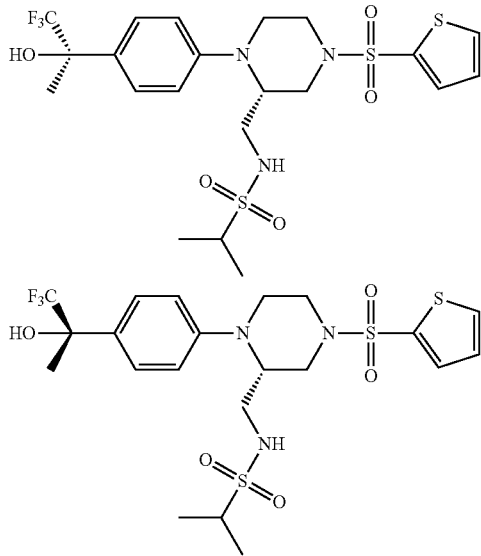

N-(((2S)-4-(2-thiophenylsulfonyl)-1-(4-((1R)-2,2,2-trifluoro-1-hydroxy-1-methylethyl)phenyl)-2-piperazinyl)methyl)-2-propanesulfonamide; N-(((2S)-4-(2-thiophenylsulfonyl)-1-(4-((1S)-2,2,2-trifluoro-1-hydroxy-1-methylethyl)phenyl)-2-piperazinyl)methyl)-2-propanesulfonamide.

$^1$H NMR (400 MHz, CDCl$_3$) δ=7.66 (dd, J=4.89, 1.17 Hz, 1H), 7.58 (dd, J=3.72, 1.17 Hz, 1H), 7.46 (d, J=8.80 Hz, 2H), 7.18 (dd, J=4.89, 3.91 Hz, 1H), 4.13-4.20 (m, 1H), 3.90 (d, J=12.13 Hz, 1H), 3.78 (d, J=11.74 Hz, 1H), 3.54 (d, J=12.72 Hz, 1H), 3.36-3.45 (m, 11.34 (dd, J=12.91, 6.85 Hz, 6H), 6.92 (d, J=9.00 Hz, 2H), 4.40 (t, J=6.46 Hz, 1H), 3.24-3.35 (m, 2H), H), 3.15 (quin, J=6.85 Hz, 1H), 2.65-2.78 (m, 2H), 1.74 (s, 3H), 2.35 (bs, 1H). m/z (ESI, +ve ion) 556.1 (M+H)$^+$. GK-GKRP IC$_{50}$ (Binding)=0.335 µM; GK-GKRP EC$_{50}$ (LC MS/MS-2)=0.632 µM.

Example 238

N-(((2S)-4-(2-thiophenylsulfonyl)-1-(4-(2,2,2-trifluoro-1-hydroxy-1-methylethyl)phenyl)-2-piperazinyl)methyl)-2-butanesulfonamide

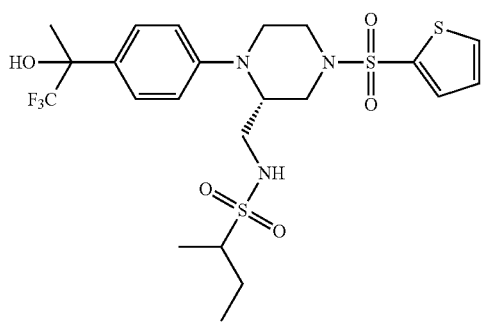 [SMILES: CCC(C)S(=O)(=O)NC[C@H]1CN(S(=O)(=O)c2cccs2)CCN1c1ccc(C(C)(O)C(F)(F)F)cc1]

According to the procedure for Example 237, the reaction of 2-(4-((2S)-2-(aminomethyl)-4-(2-thiophenylsulfonyl)-1-piperazinyl)phenyl)-1,1,1-trifluoro-2-propanol (Example 237, Step 2) and butane-2-sulfonyl chloride (Sigma-Aldrich, St. Louis, Mo.) gave N-(((2S)-4-(2-thiophenylsulfonyl)-1-(4-(2,2,2-trifluoro-1-hydroxy-1-methylethyl)phenyl)-2-piperazinyl)methyl)-2-butanesulfonamide as a mixture of 4 compounds.

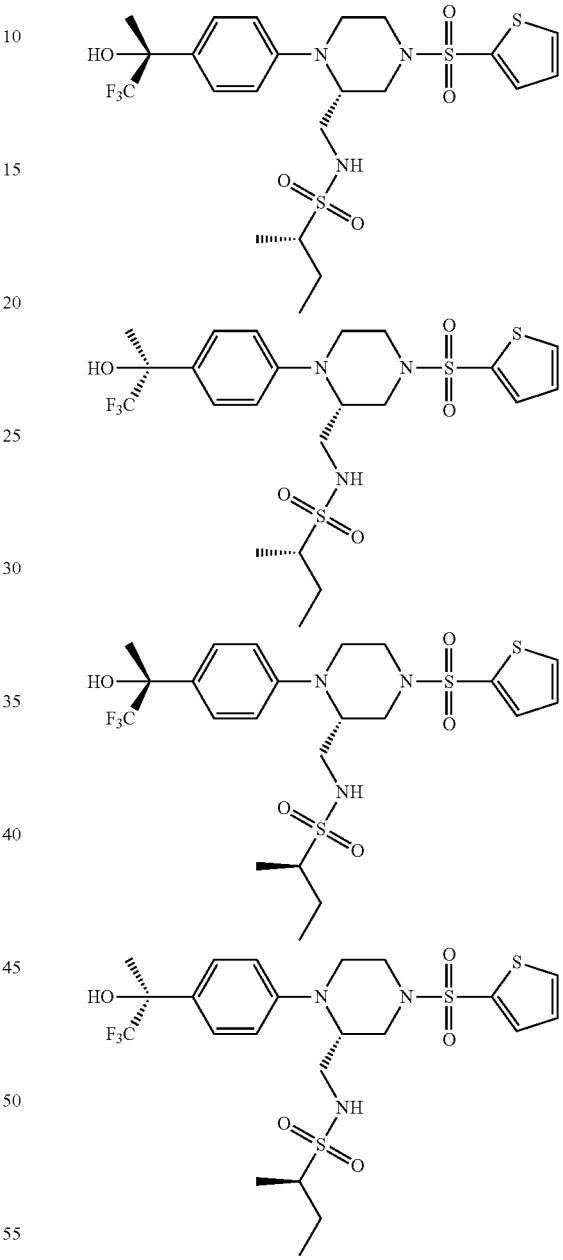

(2S)—N-(((2S)-4-(2-thiophenylsulfonyl)-1-(4-((1R)-2,2,2-trifluoro-1-hydroxy-1-methylethyl)phenyl)-2-piperazinyl)methyl)-2-butanesulfonamide; (2S)—N-(((2S)-4-(2-thiophenylsulfonyl)-1-(4-((1S)-2,2,2-trifluoro-1-hydroxy-1-methylethyl)phenyl)-2-piperazinyl)methyl)-2-butanesulfonamide; (2R)—N-(((2S)-4-(2-thiophenylsulfonyl)-1-(4-((1R)-2,2,2-trifluoro-1-hydroxy-1-methylethyl)phenyl)-2-piperazinyl)methyl)-2-butanesulfonamide; (2R)—N-(((2S)-4-(2-thiophenylsulfonyl)-1-(4-((1S)-2,2,2-trifluoro-1-hydroxy-1-methylethyl)phenyl)-2-piperazinyl)methyl)-2-butanesulfonamide.

$^1$H NMR (400 MHz, CDCl$_3$) δ=7.66 (d, J=4.89 Hz, 1H), 7.58 (d, J=3.52 Hz, 1H), 7.46 (d, J=8.80 Hz, 2H), 7.17 (t, J=4.30 Hz, 1H), 6.92 (d, J=9.00 Hz, 2H), 4.42-4.51 (m, 1H), 4.16 (d, J=2.93 Hz, 1H), 3.89 (d, J=12.13 Hz, 1H), 3.78 (d, J=10.95 Hz, 1H), 3.54 (d, J=10.76 Hz, 1H), 3.20-3.45 (m, 3H), 2.83-2.97 (m, 1H), 2.64-2.77 (m, 2H), 2.42 (br. s., 1H), 1.88-2.10 (m, 1H), 1.74 (s, 3H), 1.42-1.60 (m, 1H), 1.31 (dd, J=13.30, 6.85 Hz, 3H), 1.00 (q, J=7.24 Hz, 3H). m/z (ESI, +ve ion) 570.0 (M+H)$^+$. GK-GKRP IC$_{50}$ (Binding)=0.204 μM; GK-GKRP EC$_{50}$ (LC MS/MS-2)=0.27 μM.

Example 239

1,1,1-trifluoro-2-(2-(2-(prop-1-yn-1-yl)-4-(thiophen-2-ylsulfonyl)piperazin-1-yl)pyrimidin-5-yl)propan-2-ol

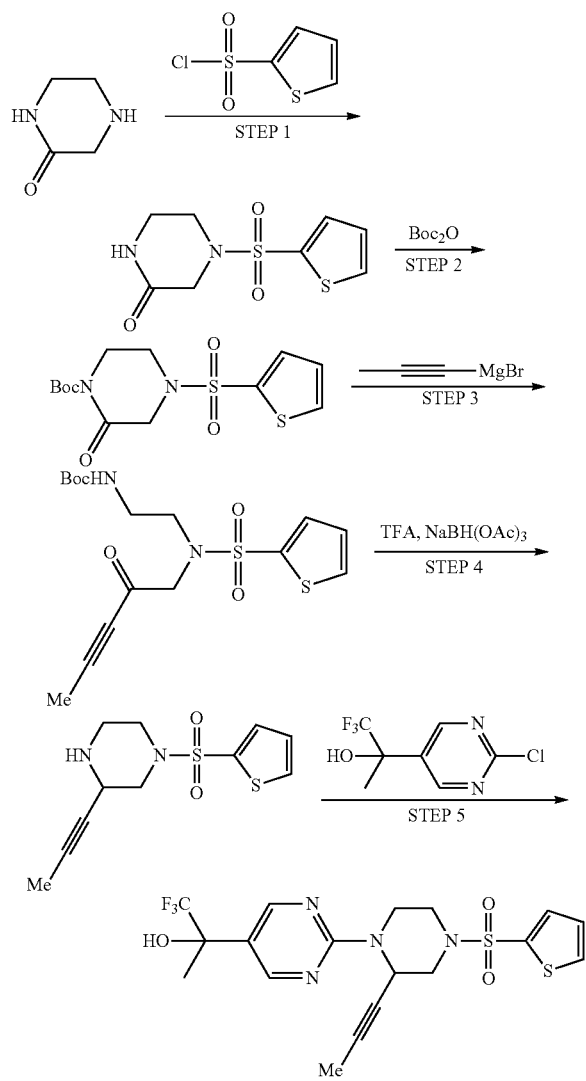

Step 1: 4-(2-thiophenylsulfonyl)-2-piperazinone

To a mixture of 2-piperazinone (0.98 g, 9.79 mmol, Sigma-Aldrich, St. Louis, Mo.) and triethylamine (Aldrich, 2.0 mL, 14.35 mmol) in CH$_2$Cl$_2$ (20 mL) at 0° C. was added a solution of 2-thiophenesulfonyl chloride (1.79 g, 9.79 mmol, Sigma-Aldrich, St. Louis, Mo.) in CH$_2$Cl$_2$ (10 mL). After 30 min, the mixture was diluted with saturated aqueous NaHCO$_3$ (10 mL) and stirred at room temperature for 3 d. The slurry was filtered and washed with water (3×5 mL) to give 4-(2-thiophenylsulfonyl)-2-piperazinone as a white powder (2.1 g).

Step 2: tert-butyl 2-oxo-4-(2-thiophenylsulfonyl)-1-piperazinecarboxylate

To a mixture of 4-(thiophen-2-ylsulfonyl)piperazin-2-one (2.1 g, 8.53 mmol), DMAP (1.04 g, 8.53 mmol, Sigma-Aldrich, St. Louis, Mo.), and triethylamine (1.19 mL, 8.53 mmol) in CH$_2$Cl$_2$ (30 mL) was added Boc$_2$O (3.94 mL, 16.95 mmol, Sigma-Aldrich, St. Louis, Mo.). After 26 h at room is temperature, the mixture was diluted with EtOAc (40 mL) and washed with 1 N HCl (10 mL), water (2×10 mL), and saturated aqueous NaHCO$_3$ (30 mL). The organic extracts were dried over Na$_2$SO$_4$, filtered, and concentrated. The solid was purified by chromatography on silica gel using (5 to 50% EtOAc in hexane) to give tert-butyl 2-oxo-4-(2-thiophenylsulfonyl)-1-piperazinecarboxylate (2.31 g) as a white powder.

Step 3: tert-butyl (2-((2-oxo-3-pentyn-1-yl)(2-thiophenylsulfonyl)amino)ethyl)carbamate A solution of tert-butyl 2-oxo-4-(2-thiophenylsulfonyl)-1-piperazinecarboxylate (600 mg, 1.73 mmol) in THF (8 mL) at 0° C. was added to a solution of 1-propynylmagnesium bromide (0.5 M in THF, 5.0 mL, 2.50 mmol, Sigma-Aldrich, St. Louis, Mo.). After 1.5 h at 0° C., additional 1-propynylmagnesium bromide (3.0 mL, 1.50 mmol) was added. After an additional 50 min, the mixture was quenched with ice (20 g) and saturated aqueous NH$_4$Cl (15 mL). EtOAc (20 mL) was added and the aqueous layer was further extracted with EtOAc (2×10 mL). The combined organic extracts were dried over Na$_2$SO$_4$, filtered, and concentrated. The residue was purified by chromatography on silica gel using (10 to 50% EtOAc in hexane) to give tert-butyl (2-((2-oxo-3-pentyn-1-yl)(2-thiophenylsulfonyl)amino)ethyl)carbamate as yellow oil (540 mg).

Step 4: 3-(1-propyn-1-yl)-1-(2-thiophenylsulfonyl)piperazine

To a solution of tert-butyl (2-((2-oxo-3-pentyn-1-yl)(2-thiophenylsulfonyl)amino)ethyl)carbamate (330 mg, 0.854 mmol) in CH$_2$Cl$_2$ (10 mL) was added sodium triacetoxyborohydride (1.0 g, 4.72 mmol, Sigma-Aldrich, St. Louis, Mo.) followed by TFA (2.5 mL, 32.4 mmol). The mixture was stirred at room temperature for 1 h and then concentrated to half the original volume. MeOH (5 mL) was added and the solution was concentrated by one-third and then partitioned between NaOH (0.5 N, 20 mL) and CHCl$_3$ (containing 10% i-PrOH) (20 mL). The aqueous layer was extracted twice with CHCl$_3$ (containing 10% i-PrOH) and the combined organic extracts were dried over Na$_2$SO$_4$, filtered, and concentrated to orange oil. The residue was purified by chromatography on silica gel using (1 to 5% MeOH in EtOAc) to give 3-(1-propyn-1-yl)-1-(2-thiophenylsulfonyl)piperazine as a light-yellow film (150 mg).

Step 5: 1,1,1-trifluoro-2-(2-(2-(1-propyn-1-yl)-4-(2-thiophenylsulfonyl)-1-piperazinyl)-5-pyrimidinyl)-2-propanol A mixture of 3-(1-propyn-1-yl)-1-(2-thiophenylsulfonyl)piperazine (55 mg, 0.203 mmol), 2-(2-chloro-5-pyrimidinyl)-1,1,1-trifluoro-2-propanol (100 mg, 0.441 mmol, Intermediate E), Hünig's base (100 μL, 0.573 mmol), and dioxane (2 mL) was heated in an Emrys Optimizer microwave reactor (Personal Chemistry, Biotage AB, Inc., Uppsala, Sweden) at 140° C. for 1 h and then at 160° C. for 3 h. The resulting red mixture was purified via silica gel chromatography (10-50% EtOAc in hexanes) to give 1,1,1-trifluoro-2-(2-(2-(1-propyn-1-yl)-4-(2-thiophenylsulfonyl)-1-piperazinyl)-5-pyrimidinyl)-2-propanol (18 mg) as a mixture of 4 isomers.

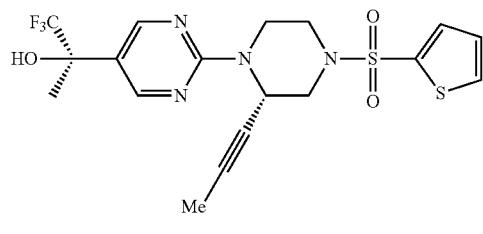
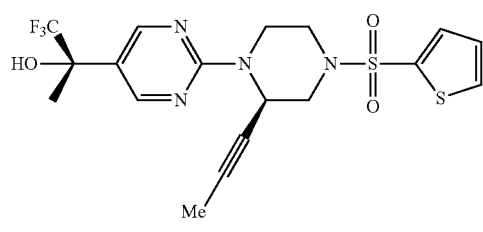
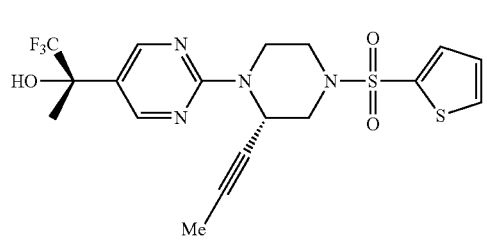
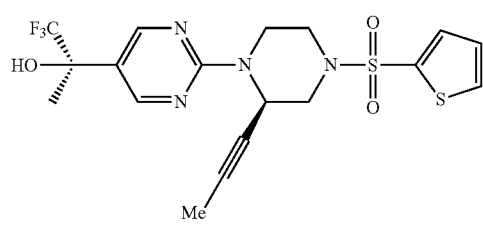

(2R)-1,1,1-trifluoro-2-(2-((2S)-2-(1-propyn-1-yl)-4-(2-thiophenylsulfonyl)-1-piperazinyl)-5-pyrimidinyl)-2-propanol; (2S)-1,1,1-trifluoro-2-(2-((2R)-2-(1-propyn-1-yl)-4-(2-thiophenylsulfonyl)-1-piperazinyl)-5-pyrimidinyl)-2-propanol; (2S)-1,1,1-trifluoro-2-(2-((2S)-2-(1-propyn-1-yl)-4-(2-thiophenylsulfonyl)-1-piperazinyl)-5-pyrimidinyl)-2-propanol; (2R)-1,1,1-trifluoro-2-(2-((2R)-2-(1-propyn-1-yl)-4-(2-thiophenylsulfonyl)-1-piperazinyl)-5-pyrimidinyl)-2-propanol.

$^1$H NMR (400 MHz, CDCl$_3$) δ=8.50 (s, 2H), 7.61 (d, J=4.50 Hz, 1H), 7.56 (d, J=3.72 Hz, 1H), 7.09-7.17 (m, 1H), 5.74 (br. s., 1H), 4.67 (d, J=13.50 Hz, 1H), 3.87 (dd, J=17.80, 11.54 Hz, 2H), 3.51 (td, J=12.81, 3.13 Hz, 1H), 2.62 (dd, J=11.25, 3.62 Hz, 1H2.48 (td, J=11.79, 3.23 Hz, 1H)), 1.82 (d, J=1.56 Hz, 3H), 1.74 (s, 3H). m/z (ESI, +ve ion) 461.0 (M+H)$^+$. GK-GKRP IC$_{50}$ (Binding)=0.019 μM; GK-GKRP EC$_{50}$ (LC MS/MS-2)=0.050 μM.

Example 240

2-(2-(4-((6-amino-3-pyridinyl)sulfonyl)-2-(1-propyn-1-yl)-1-piperazinyl)-5-pyrimidinyl)-1,1,1,3,3,3-hexafluoro-2-propanol

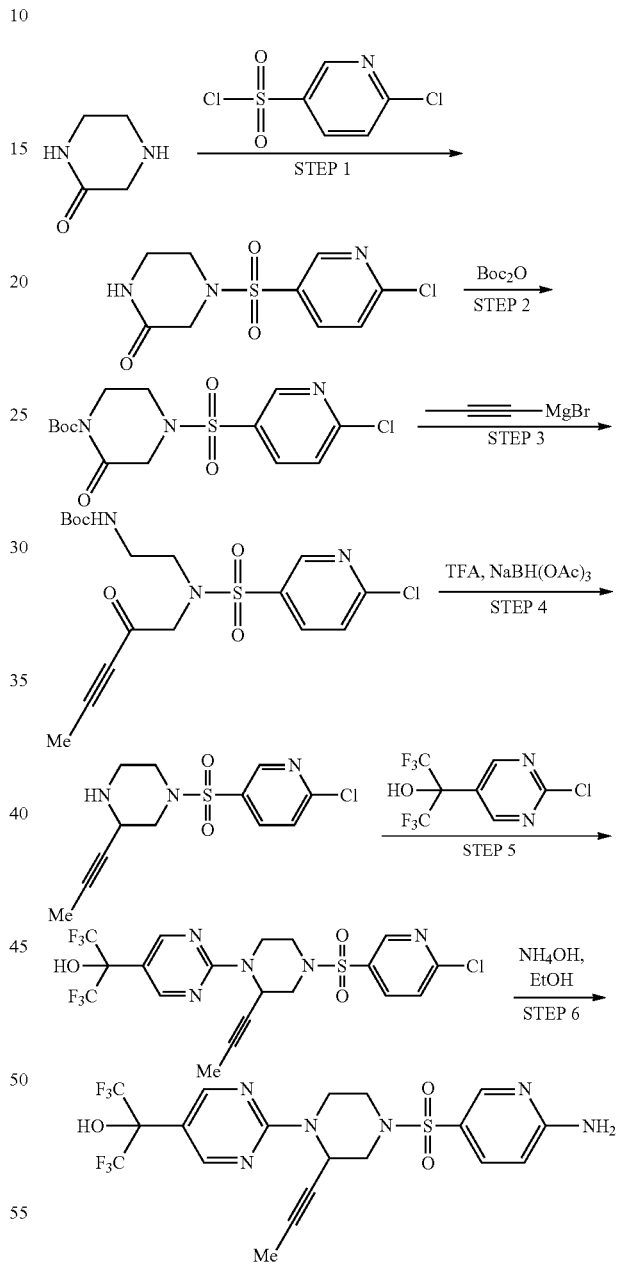

Step 1:
4-((6-chloro-3-pyridinyl)sulfonyl)-2-piperazinone

To a mixture of 2-piperazinone (0.46 g, 4.59 mmol, Sigma-Aldrich, St. Louis, Mo.) and triethylamine (1.5 mL, 10.76 mmol) in CH$_2$Cl$_2$ (20 mL) at 0° C. was added 6-chloropyridine-3-sulfonyl chloride (0.974 g, 4.59 mmol, *Organic Process Research & Development* 2009, 13, 875). The resulting slurry was stirred at room temperature for 30 min and then was concentrated. The residue was mixed with saturated aqueous NaHCO$_3$ (10 mL) and was stirred at room temperature for 1 d. The slurry was filtered, washed with water (3×5 mL), and dried under reduced pressure to give 4-((6-chloro-3-pyridinyl)sulfonyl)-2-piperazinone as a white solid (1.12 g).

Step 2: tert-butyl 4-((6-chloro-3-pyridinyl)sulfonyl)-2-oxo-1-piperazinecarboxylate To a mixture of 4-((6-chloro-3-pyridinyl)sulfonyl)-2-piperazinone (1.12 g, 4.06 mmol), DMAP (0.50 g, 4.09 mmol), and triethylamine (0.60 mL, 4.30 mmol) in CH$_2$Cl$_2$ (10 mL) was added Boc$_2$O (1.81 mL, 7.79 mmol, Sigma-Aldrich, St. Louis, Mo.). After 19 h, the mixture was concentrated and the residue was suspended in EtOAc (40 mL). The mixture was washed with aqueous 0.1 M HCl (1.0 mmol, 10 mL), water (10 mL), and then saturated aqueous NH$_4$Cl (10 mL). The organic layer was dried over Na$_2$SO$_4$, filtered, and concentrated. The resulting solid was agitated in hot CH$_2$Cl$_2$-hexane (1:1, 20 mL) and then collected by filtration to give tert-butyl 4-((6-chloro-3-pyridinyl)sulfonyl)-2-oxo-1-piperazinecarboxylate (1.17 g).

Step 3: tert-butyl (2-(((6-chloro-3-pyridinyl)sulfonyl)(2-oxo-3-pentyn-1-yl)amino)ethyl)carbamate To a slurry of tert-butyl 4-((6-chloro-3-pyridinyl)sulfonyl)-2-oxo-1-piperazinecarboxylate (1.16 g, 3.09 mmol) in THF (5.0 mL) at 0° C. was added a solution of prop-1-yn-1-ylmagnesium bromide (0.5 M in THF, 13 mL, 6.50 mmol, Sigma-Aldrich, St. Louis, Mo.). After 1.5 h at 0° C., additional prop-1-yn-1-ylmagnesium bromide (4 mL, 2.0 mmol) was added. After an additional 2.5 h at 0° C., the mixture was quenched with saturated aqueous NH$_4$Cl (25 mL). EtOAc (40 mL) was added, the layers were separated, and the aqueous layer was extracted with EtOAc (10 mL). The combined organic extracts were dried over Na$_2$SO$_4$, filtered, and concentrated. The residue was purified by chromatography on silica gel using (30 to 90% EtOAc in hexanes) to give tert-butyl (2-(((6-chloro-3-pyridinyl)sulfonyl)(2-oxo-3-pentyn-1-yl)amino)ethyl)carbamate as a yellow powder (1.05 g)

Step 4: 1-((6-chloro-3-pyridinyl)sulfonyl)-3-(1-propyn-1-yl)piperazine

To a solution of tert-butyl (2-(((6-chloro-3-pyridinyl)sulfonyl)(2-oxo-3-pentyn-1-yl)amino)ethyl)carbamate (1.0 g, 2.40 mmol) in CH$_2$Cl$_2$ (40 mL) at 0° C. was added TFA (4.0 mL, 51.9 mmol). After 20 min, additional TFA (4.0 mL, 51.9 mmol) was added and the cooling bath was removed. After 50 min at room temperature, solid sodium triacetoxyborohydride (2.1 g, 9.91 mmol) was added. The mixture was stirred at room temperature for 20 min then MeOH (5 mL) was added. The mixture was concentrated to about ⅕ its original volume and then saturated aqueous NaHCO$_3$ (20 mL) was added. The pH of the aqueous layer was adjusted to about 8 with NaOH (1 N) and then the mixture was extracted with CHCl$_3$ (containing 10% iPrOH) (3×10 mL). The combined organic extracts were dried with Na$_2$SO$_4$, filtered, and concentrated. The resulting orange oil was purified by chromatography on silica gel using (1 to 5% MeOH in EtOAc) to give 1-((6-chloro-3-pyridinyl)sulfonyl)-3-(1-propyn-1-yl)piperazine as a light-yellow solid (0.39 g)

Step 5: 2-(2-(4-((6-chloro-3-pyridinyl)sulfonyl)-2-(1-propyn-1-yl)-1-piperazinyl)-5-pyrimidinyl)-1,1,1,3,3,3-hexafluoro-2-propanol A mixture of 2-(2-chloropyrimidin-5-yl)-1,1,1,3,3,3-hexafluoropropan-2-ol (490 mg, 1.747 mmol, Intermediate D), 1-((6-chloropyridin-3-yl)sulfonyl)-3-(prop-1-yn-1-yl)piperazine (325 mg, 1.08 mmol), Hünig's base (1.0 mL, 5.73 mmol) and dioxane (5.0 mL) was heated at 120° C. for 15 h. The temperature was increased to 130° C. and stirring was continued for 24 h. The dark mixture was allowed to cool to room temperature and was then purified by silica gel chromatography (80 g silica gel, 10-50% EtOAc in hexane) to give 2-(2-(4-((6-chloro-3-pyridinyl)sulfonyl)-2-(1-propyn-1-yl)-1-piperazinyl)-5-pyrimidinyl)-1,1,1,3,3,3-hexafluoro-2-propanol as a white foam (0.664 g).

Step 6: 2-(2-(4-((6-amino-3-pyridinyl)sulfonyl)-2-(1-propyn-1-yl)-1-piperazinyl)-5-pyrimidinyl)-1,1,1,3,3,3-hexafluoro-2-propanol A 20-mL microwave vial was charged with 2-(2-(4-((6-chloro-3-pyridinyl)sulfonyl)-2-(1-propyn-1-yl)-1-piperazinyl)-5-pyrimidinyl)-1,1,1,3,3,3-hexafluoro-2-propanol (440 mg, 0.809 mmol), EtOH (4 mL) and concentrated ammonium hydroxide (5.0 mL, 36.0 mmol). The vial was sealed and heated in an Initiator microwave reactor (Biotage AB, Inc., Uppsala, Sweden) at 140° C. for 4 h. The mixture was then allowed to let stand over for 2 d. Saturated aqueous NH$_4$Cl (6 mL) and CHCl$_3$ (containing 10% iPrOH) (20 mL) were added and the aqueous layer was extracted with CHCl$_3$ (containing 10% iPrOH) (3×5 mL). The combined organic extracts were dried over Na$_2$SO$_4$, filtered and concentrated. Chromatography was performed on silica gel using EtOAc to give an oil.

To this oil was added MeOH (10 mL) and NaBH$_4$ (50 mg, 1.322 mmol). After 10 min at room temperature, the mixture was concentrated and partitioned between saturated aqueous NH$_4$Cl (10 mL) and CHCl$_3$ (containing 10% iPrOH) (20 mL). The aqueous layer was further extracted with CHCl$_3$ (containing 10% iPrOH) (2×5 mL). The combined organic extracts were dried with Na$_2$SO$_4$, filtered and concentrated. Chromatography on silica gel using (20 to 80% EtOAc in CH$_2$Cl$_2$) afforded 2-(2-(4-((6-amino-3-pyridinyl)sulfonyl)-2-(1-propyn-1-yl)-1-piperazinyl)-5-pyrimidinyl)-1,1,1,3,3,3-hexafluoro-2-propanol as white foam (90 mg). $^1$H NMR (400 MHz, CDCl$_3$) δ=8.58 (s, 2H), 8.55 (s, 0.5H, OH), 8.45 (s, 1H), 7.77 (dd, J=8.80, 1.96 Hz, 1H), 6.52 (d, J=8.80 Hz, 1H), 5.75 (br. s., 1H), 5.04 (br. s., 2H, NH$_2$), 4.69 (d, J=13.30 Hz, 1H), 3.74-3.91 (m, 2H), 3.42-3.57 (m, 1H), 2.63 (dd, J=11.25, 3.23 Hz, 1H), 2.40-2.56 (m, 1H), 1.82 (d, J=1.76 Hz, 3H). m/z (ESI, +ve ion) 525.0 (M+H)$^+$. GK-GKRP IC$_{50}$ (Binding)=0.026 µM; GK-GKRP EC$_{50}$ (LC MS/MS-2)=0.058 µM.

The individual isomers were isolated using preparative SFC. The method used was as follows; Chiralpak® AD-H column (150 mm×4.6 mm, 5 µm) eluting with 80% liquid CO$_2$ in 20% MeOH at a flow rate of 4.0 mL/min, 40° C.). This method delivered two products in >99% enantiomeric excess and >99% purity.

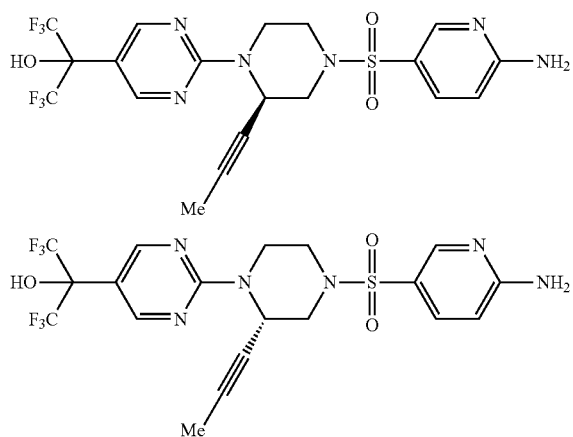

2-(2-((2R)-4-((6-amino-3-pyridinyl)sulfonyl)-2-(1-propyn-1-yl)-1-piperazinyl)-5-pyrimidinyl)-1,1,1,3,3,3-hexafluoro-2-propanol; 2-(2-((2S)-4-((6-amino-3-pyridinyl)sulfonyl)-2-(1-propyn-1-yl)-1-piperazinyl)-5-pyrimidinyl)-1,1,1,3,3,3-hexafluoro-2-propanol.

First Eluting Peak (Peak #1)

$^1$H NMR (400 MHz, CDCl$_3$) δ=8.59 (s, 2H), 8.43 (d, J=2.15 Hz, 1H), 7.77 (dd, J=8.71, 2.25 Hz, 1H), 6.54 (d, J=8.80 Hz, 1H), 5.75 (br. s., 1H), 5.10 (br. s., 2H), 4.69 (d, J=13.30 Hz, 1H), 3.75-3.89 (m, 2H), 3.49-3.55 (m, 1H), 2.63 (dd, J=11.15, 3.72 Hz, 1H), 2.49 (td, J=11.69, 3.03 Hz, 1H), 1.82 (d, J=2.15 Hz, 3H). m/z (ESI, +ve ion) 525.0 (M+H)$^+$. GK-GKRP IC$_{50}$ (Binding)=0.010 μM; GK-GKRP EC$_{50}$ (LC MS/MS-2)=0.015 μM.

Second Eluting Peak (Peak #2)

$^1$H NMR (400 MHz, CDCl$_3$) δ=8.59 (s, 2H), 8.44 (d, J=2.15 Hz, 1H), 7.77 (dd, J=8.71, 2.25 Hz, 1H), 6.54 (d, J=8.80 Hz, 1H), 5.75 (br. s., 1H), 5.12 (br. s., 2H), 4.69 (d, J=13.50 Hz, 1H), 3.74-3.89 (m, 2H), 3.50-3.54 (m, 1H), 2.63 (dd, J=11.44, 3.42 Hz, 1H), 2.49 (td, J=11.74, 3.33 Hz, 1H), 1.82 (d, J=2.15 Hz, 3H). m/z (ESI, +ve ion) 525.0 (M+H)$^+$. GK-GKRP IC$_{50}$ (Binding)=4.382 μM.

Example 241

2-(4-(4-((6-amino-3-pyridinyl)sulfonyl)-2-(1-propyn-1-yl)-1-piperazinyl)phenyl)-1,1,1,3,3,3-hexafluoro-2-propanol

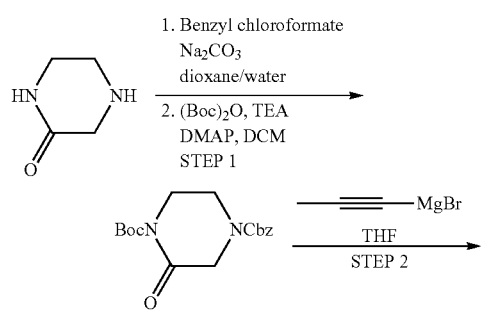

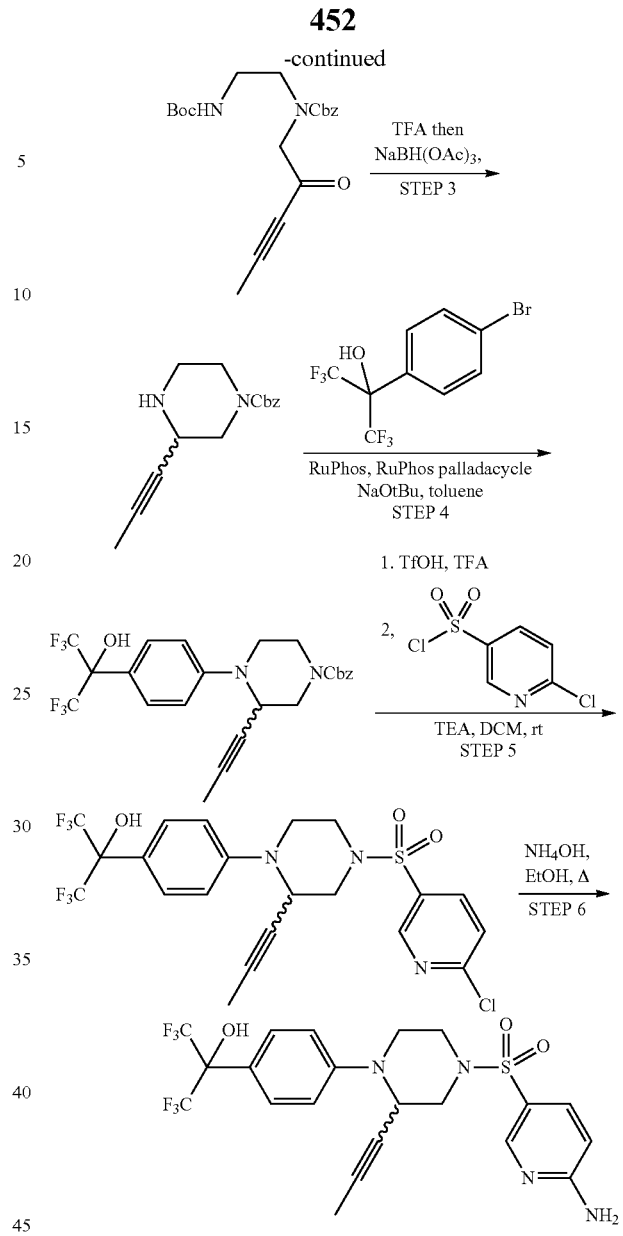

Step 1: 4-benzyl 1-tert-butyl 2-oxo-1,4-piperazinedicarboxylate

A 2-L Erlenmeyer flask was charged with 2-piperazinone (36.5 g, 364 mmol, Sigma-Aldrich, St. Louis, Mo.), sodium carbonate (116 g, 1093 mmol), 600 mL of dioxane, and 150 mL of water. To this was slowly added benzyl chloroformate (62.1 g, 364 mmol, Sigma-Aldrich, St. Louis, Mo.) at room temperature over 20 min. After the addition was complete, the mixture was stirred for 2 h and then diluted with water and extracted with EtOAc (2 L). The combined organic extracts were dried (MgSO$_4$), filtered, and concentrated to give a white solid. To this solid was added 500 mL of DCM, triethylamine (128 mL, 911 mmol), DMAP (4.45 g, 36.4 mmol), and di-tert-butyl dicarbonate (119 g, 546 mmol, Sigma-Aldrich, St. Louis, Mo.). After 1 h at room temperature, the mixture was diluted with water and the organics were separated. The organics were dried (MgSO$_4$), filtered, and concentrated to give a brown oil. To this oil was added 100 mL of DCM followed by 1 L of hexane. The resulting white solid was collected by filtration to give 4-benzyl 1-tert-butyl 2-oxo-1, 4-piperazinedicarboxylate (101 g).

Step 2: benzyl (2-((tert-butoxycarbonyl)amino)ethyl) (2-oxo-3-pentyn-1-yl)carbamate A 150-mL round-bottomed flask was charged with 4-benzyl 1-tert-butyl 2-oxo-1,4-piperazinedicarboxylate (1.41 g, 4.22 mmol) and THF (5 mL). 1-Propynylmagnesium bromide (0.5 M in THF, 20.0 mL, 10.0 mmol, Sigma-Aldrich, St. Louis, Mo.) was added at 0° C. slowly. The mixture was stirred at 0° C. for 2 h. Saturated aqueous $NH_4Cl$ (40 mL) was added and the aqueous phase was extracted with EtOAc (200 mL, then 2×100 mL). The combined organic phases were dried over sodium sulfate, filtered and concentrated in vacuo. The crude product was purified by column chromatography (50 g of silica, 0 to 50% EtOAc in hexanes) to afford benzyl (2-((tert-butoxycarbonyl)amino)ethyl)(2-oxo-3-pentyn-1-yl)carbamate (1.55 g) as a clear oil.

Step 3: benzyl 3-(1-propyn-1-yl)-1-piperazinecarboxylate

A 3-L round-bottomed flask was charged with 2-((tert-butoxycarbonyl)amino)ethyl)(2-oxo-3-pentyn-1-yl)carbamate (82.2 g, 219 mmol) and 300 ml of DCM. After cooling to −10° C., TFA (169 mL, 2195 mmol) was added and the resulting dark solution was stirred at room temperature for 15 min. Sodium triacetoxyborohydride (186 g, 878 mmol, Sigma-Aldrich, St. Louis, Mo.) was then added portion-wise over 10 min. After 2 h, the mixture was concentrated, diluted with EtOAc (1 L), and neutralized with 5 N NaOH. The layers were separated and the organic extracts were washed with brine, dried ($MgSO_4$), filtered and concentrated. The resulting orange oil was purified via column chromatography (750 g of silica gel, 0 to 4.5% MeOH/DCM) to give benzyl 3-(1-propyn-1-yl)-1-piperazinecarboxylate (43.7 g) as a brown foam.

Step 4: benzyl 3-(1-propyn-1-yl)-4-(4-(2,2,2-trifluoro-1-hydroxy-1-(trifluoromethyl)ethyl)phenyl)-1-piperazinecarboxylate A 150-mL reaction vessel was charged with benzyl 3-(prop-1-yn-1-yl)piperazine-1-carboxylate (2.88 g, 11.2 mmol), 2-(4-bromophenyl)-1,1,1,3,3,3-hexafluoropropan-2-ol (4.36 g, 13.5 mmol, Bioorg. Med. Chem. Lett. 2002, 12, 3009), dicyclohexyl(2',6'-diisopropoxy-[1,1'-biphenyl]-2-yl)phosphine, RuPhos (0.530 g, 1.14 mmol, Sigma-Aldrich, St. Louis, Mo.), RuPhos Palladacycle (0.417 g, 0.572 mmol, Strem Chemical Inc, Newburyport, Mass.), sodium tert-butoxide (2.73 g, 28.4 mmol, Strem Chemical Inc, Newburyport, Mass.) and toluene (35 mL). The mixture was degassed by bubbling Ar through the solution for 10 min. The vessel was sealed and heated at 100° C. for 1.5 h. The reaction mixture was cooled to room temperature and water (100 mL) was added. The aqueous phase was extracted with EtOAc (3×100 mL) and the combined organic phases were washed with saturated aqueous sodium chloride (150 mL). The organic extracts were dried over sodium sulfate, filtered and concentrated in vacuo. The crude product was purified by column chromatography (100 g of silica, 0 to 50% EtOAc in hexanes) to afford benzyl 3-(1-propyn-1-yl)-4-(4-(2,2,2-trifluoro-1-hydroxy-1-(trifluoromethyl)ethyl)phenyl)-1-piperazinecarboxylate as a yellow solid.

Step 5: 2-(4-(4-((6-chloro-3-pyridinyl)sulfonyl)-2-(1-propyn-1-yl)-1-piperazinyl)phenyl)-1,1,1,3,3,3-hexafluoro-2-propanol A 500-mL round-bottomed flask was charged with benzyl 3-(1-propyn-1-yl)-4-(4-(2,2,2-trifluoro-1-hydroxy-1-(trifluoromethyl)ethyl)phenyl)-1-piperazinecarboxylate (3.13 g, 6.25 mmol) and TFA (40 mL). Trifluoromethanesulfonic acid (1.25 mL, 14.1 mmol, Acros/Fisher Scientific, Waltham, Mass.) was added dropwise at room temperature. After 5 min, additional TfOH (0.45 mL, 5.1 mmol) was added. After an additional 10 min, solid $NaHCO_3$ was carefully added in potions. Saturated aqueous $NaHCO_3$ (250 mL) was added slowly to bring pH to approximately 7. The aqueous phase was extracted with EtOAc (100 mL). At this time, more solid $NaHCO_3$ was added to the aqueous phase and extracted again with EtOAc (100 mL). The combined organic phases were washed with water (200 mL) and saturated aqueous sodium chloride (200 mL). The combined organic extracts were dried over sodium sulfate, filtered and concentrated in vacuo to afford 3.10 g of tan solid.

A 500-mL round-bottomed flask was charged with this material, triethylamine (5.00 mL, 35.9 mmol) and $CH_2Cl_2$ (30 mL). 6-Chloropyridine-3-sulfonyl chloride (1.58 g, 7.43 mmol, Organic Process Research & Development 2009, 13, 875) was added in potions at 0° C. The brown mixture was stirred at 0° C. for 10 min. The volume of the reaction mixture was reduced to approximately 10 mL in vacuo then the mixture was purified twice by column chromatography (100 g of silica, 0 to 50% EtOAc in hexanes) to afford 2-(4-(4-((6-chloro-3-pyridinyl)sulfonyl)-2-(1-propyn-1-yl)-1-piperazinyl)phenyl)-1,1,1,3,3,3-hexafluoro-2-propanol (3.46 g) as an off-white solid.

Step 6: 2-(4-(4-((6-amino-3-pyridinyl)sulfonyl)-2-(1-propyn-1-yl)-1-piperazinyl)phenyl)-1,1,1,3,3,3-hexafluoro-2-propanol A 20-mL sealed tube was charged with 2-(4-(4-((6-chloro-3-pyridinyl)sulfonyl)-2-(1-propyn-1-yl)-1-piperazinyl)phenyl)-1,1,1,3,3,3-hexafluoro-2-propanol (0.340 g, 0.627 mmol), concentrated ammonium hydroxide (5.00 mL, 38.5 mmol) and EtOH (5 mL). The reaction mixture was heated in an Initiator (Biotage, AB, Uppsala, Sweden) at 120° C. for 1 h. The reaction mixture was further heated in a heating block at 110° C. for 5 h. The reaction mixture was concentrated and purified by column chromatography (25 g of silica, 30 to 80% EtOAc in hexanes) to afford 2-(4-(4-((6-amino-3-pyridinyl)sulfonyl)-2-(1-propyn-1-yl)-1-piperazinyl)phenyl)-1,1,1,3,3,3-hexafluoro-2-propanol (0.289 g) as a mixture of two enantiomers.

$^1$H NMR (400 MHz, $CDCl_3$) δ ppm 8.49 (br. s., 1H), 7.80 (dd, J=2.3, 8.8 Hz, 1H), 7.59 (d, J=8.8 Hz, 2H), 6.97 (d, J=9.0 Hz, 2H), 6.55 (d, J=8.8 Hz, 1H), 5.05 (s, 2H), 4.46 (br. s., 1H), 3.85-3.72 (m, 2H), 3.54 (br. s., 1H), 3.50-3.34 (m, 2H), 2.83 (dd, J=3.3, 11.0 Hz, 1H), 2.69 (dt, J=3.4, 11.0 Hz, 1H), 1.80 (s, 3H). m/z (ESI, +ve ion) 523.1 (M+H)$^+$. GK-GKRP $IC_{50}$ (Binding)=0.003 μM The individual enantiomers were isolated using chiral SFC. The method used was as follows: Chiralpak® ADH column (21×250 mm, 5 μm) using 35% methanol in supercritical $CO_2$ (total flow was 70 mL/min). This produced the two is enantiomers with enantiomeric excesses greater than 98%.

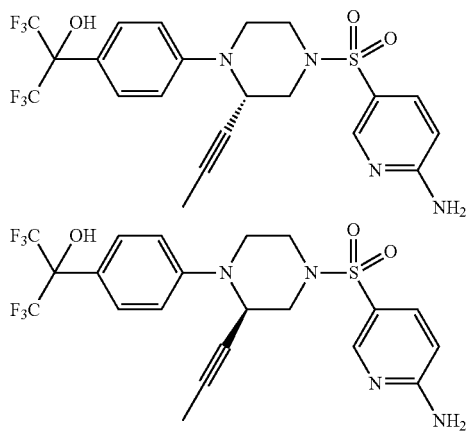

2-(4-((2S)-4-((6-amino-3-pyridinyl)sulfonyl)-2-(1-propyn-1-yl)-1-piperazinyl)phenyl)-1,1,1,3,3,3-hexafluoro-2-propanol and 2-(4-((2R)-4-((6-amino-3-pyridinyl)sulfonyl)-2-(1-propyn-1-yl)-1-piperazinyl)phenyl)-1,1,1,3,3,3-hexafluoro-2-propanol.

First Eluting Peak (Peak #1)

$^1$H NMR (400 MHz, CDCl$_3$) δ 8.48 (d, J=2.3 Hz, 1H), 7.77 (dd, J=2.5, 8.8 Hz, 1H), 7.57 (d, J=8.8 Hz, 2H), 6.95 (d, J=9.2 Hz, 2H), 6.52 (d, J=8.8 Hz, 1H), 4.94 (s, 2H), 4.44 (br. s., 1H), 3.82-3.71 (m, 2H), 3.58-3.33 (m, 3H), 2.81 (dd, J=3.2, 11.1 Hz, 1H), 2.67 (dt, J=3.9, 11.0 Hz, 1H), 1.78 (d, J=2.2 Hz, 3H). m/z (ESI, +ve ion) 523.2 (M+H)$^+$. GK-GKRP IC$_{50}$ (Binding)=0.002 μM.

Second Eluting Peak (Peak #2)

$^1$H NMR (400 MHz, CDCl$_3$) δ 8.49 (d, J=1.8 Hz, 1H), 7.78 (dd, J=2.3, 8.8 Hz, 1H), 7.59 (d, J=8.6 Hz, 2H), 6.97 (d, J=9.0 Hz, 2H), 6.54 (d, J=8.8 Hz, 1H), 4.97 (s, 2H), 4.46 (br. s., 1H), 3.77 (t, J=11.7 Hz, 2H), 3.67 (br. s., 1H), 3.51-3.33 (m, 2H), 2.82 (dd, J=3.3, 11.0 Hz, 1H), 2.68 (dt, J=3.9, 11.1 Hz, 1H), 1.79 (d, J=2.0 Hz, 3H). m/z (ESI, +ve ion) 523.2 (M+H)$^+$. GK-GKRP IC$_{50}$ (Binding)=0.342 μM.

Alternative Procedure Starting after Step 4.

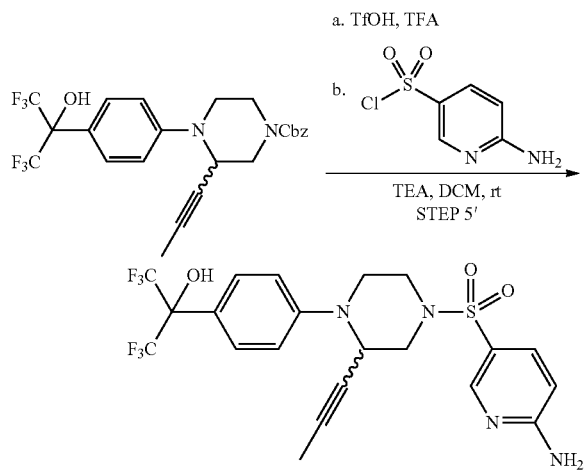

Step 5': 2-(4-(4-((6-amino-3-pyridinyl)sulfonyl)-2-(1-propyn-1-yl)-1-piperazinyl)phenyl)-1,1,1,3,3,3-hexafluoro-2-propanol Alternatively, 2-(4-(4-((6-amino-3-pyridinyl)sulfonyl)-2-(1-propyn-1-yl)-1-piperazinyl)phenyl)-1,1,1,3,3,3-hexafluoro-2-propanol was synthesized from benzyl 3-(1-propyn-1-yl)-4-(4-(2,2,2-trifluoro-1-hydroxy-1-(trifluoromethyl)ethyl)phenyl)-1-piperazinecarboxylate as follows.

A 2-L round-bottomed flask was charged with benzyl 3-(1-propyn-1-yl)-4-(4-(2,2,2-trifluoro-1-hydroxy-1-(trifluoromethyl)ethyl)phenyl)-1-piperazinecarboxylate (21.8 g, 43.5 mmol, step 5) and TFA (130 mL). Trifluoromethanesulfonic acid (11.6 mL, 131 mmol, Acros/Fisher Scientific, Waltham, Mass.) was added slowly at rt resulting orange cloudy mixture. After stirring at rt for 10 min, the volume of the reaction mixture was reduced to half in vacuo. Solid NaHCO$_3$ was added in potions until the mixture became sludge. Saturated aqueous NaHCO$_3$ (800 mL) was added slowly until the pH was about 8. The aqueous phase was extracted with EtOAc (3×250 mL). The combined organic phases were washed with water (500 mL) and saturated aqueous NaCl (500 mL). The organic phase was dried over sodium sulfate, filtered and concentrated in vacuo. This material was dissolved into DCM (200 mL) and triethylamine (31.0 mL, 222 mmol) was added. Then 6-aminopyridine-3-sulfonyl chloride (9.40 g, 48.8 mmol, published PCT patent application no. WO 2009/140309) was added in potions over 10 min period. The brown mixture was stirred at room temperature for 10 min. The reaction mixture was washed with water (300 mL) and saturated aqueous NaCl (300 mL). The organic phase was dried over sodium sulfate, filtered and concentrated in vacuo. The crude product was purified by column chromatography (780 g of total silica, 30 to 90% EtOAc in hexanes) to afford 2-(4-(4-((6-amino-3-pyridinyl)sulfonyl)-2-(1-propyn-1-yl)-1-piperazinyl)phenyl)-1,1,1,3,3,3-hexafluoro-2-propanol (19.4 g) as a mixture of two enantiomers.

Example 242

5,5-dimethyl-3-(1-methylethyl)-1-(((2S)-4-(2-thiophenylsulfonyl)-1-(4-(2,2,2-trifluoro-1-hydroxy-1-methylethyl)phenyl)-2-piperazinyl)methyl)-2,4-imidazolidinedione

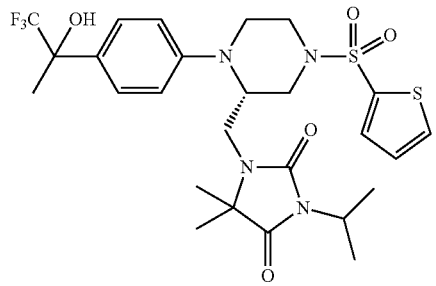 [SMILES: CC(C)N1C(=O)N(C[C@H]2CN(S(=O)(=O)c3cccs3)CCN2c2ccc(C(C)(O)C(F)(F)F)cc2)C(C)(C)C1=O]

To a stirred mixture of sodium hydride (0.0203 g, 0.508 mmol, Sigma-Aldrich, St. Louis, Mo.) in DMF (1 mL) in a 5 mL vial, 5,5-dimethyl-1-(((2s)-4-(2-thiophenylsulfonyl)-1-(4-(2,2,2-trifluoro-1-hydroxy-1-methylethyl)phenyl)-2-piperazinyl)methyl)-2,4-imidazolidinedione (0.090 g, 0.161 mmol, Example 228) in DMF (total 1.5 mL) was added dropwise at 0° C. The mixture was stirred at 0° C. for 15 min and 2-iodopropane (0.020 mL, 0.20 mmol, Sigma-Aldrich, St. Louis, Mo.) was added dropwise. The cold bath was removed and the mixture was stirred at room temperature for 12 h. The reaction mixture was partitioned between water (20 mL) and EtOAc (20 mL). The aqueous phase was extracted with EtOAc (20 mL). Saturated aqueous NaCl (20 mL) was added and the aqueous phase was extracted with EtOAc (2×20 mL). The combined organic extracts were washed with saturated aqueous NaCl (80 mL). The organic phase was dried over sodium sulfate, filtered and concentrated. The crude product was purified by silica gel chromatography (25 g of silica, 0 to 80% EtOAc in hexanes) to afford 5,5-dimethyl-3-(1-methylethyl)-1-(((2S)-4-(2-thiophenylsulfonyl)-1-(4-(2,2,2-trifluoro-1-hydroxy-1-methylethyl)phenyl)-2-piperazinyl)methyl)-2,4-imidazolidinedione (0.021 g) as a mixture of two isomers.

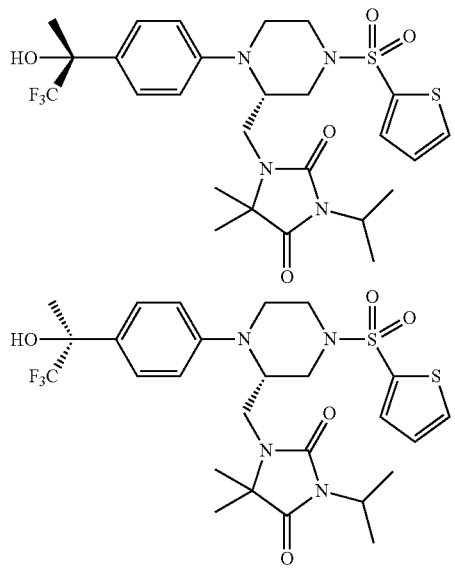

5,5-dimethyl-3-(1-methylethyl)-1-(((2S)-4-(2-thiophenylsulfonyl)-1-(4-((1R)-2,2,2-trifluoro-1-hydroxy-1-methylethyl)phenyl)-2-piperazinyl)methyl)-2,4-imidazolidinedione and 5,5-dimethyl-3-(1-methylethyl)-1-(((2S)-4-(2-thiophenylsulfonyl)-1-(4-((1S)-2,2,2-trifluoro-1-hydroxy-1-methylethyl)phenyl)-2-piperazinyl)methyl)-2,4-imidazolidinedione.

$^1$H NMR (400 MHz, CDCl$_3$) δ 7.66 (dd, J=1.17, 5.09 Hz, 1H), 7.56 (dd, J=1.17, 3.72 Hz, 1H), 7.41 (d, J=8.80 Hz, 2H), 7.17 (dd, J=3.72, 4.89 Hz, 1H), 6.95 (d, J=8.80 Hz, 2H), 4.90 (br. s., 1H), 4.25 (quin, J=6.90 Hz, 1H), 3.72-3.84 (m, 2H), 3.57 (d, J=12.72 Hz, 1H), 3.38-3.48 (m, 2H), 3.28-3.37 (m, 1H), 2.64 (dd, J=3.42, 11.64 Hz, 1H), 2.44-2.55 (m, 1H), 2.28 (s, 1H), 1.71 (s, 3H), 1.32-1.43 (m, 9H), 1.20 (s, 3H). m/z (ESI, +ve ion) 603.2 (M+H)$^+$. GK-GKRP IC$_{50}$ (Binding)=0.019 µM; GK-GKRP EC$_{50}$ (LC MS/MS-2)=0.029 µM.

Example 243

2-(4-(4-((6-amino-3-pyridinyl)sulfonyl)-2-(1-propyn-1-yl)-1-piperazinyl)phenyl)-1,1,1-trifluoro-2-propanol

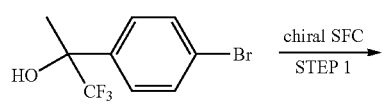

Step 1: (2R)-2-(4-bromophenyl)-1,1,1-trifluoro-2-propanol and (2S)-2-(4-bromophenyl)-1,1,1-trifluoro-2-propanol The racemic mixture (Example 27, Step 1) was separated using the following chiral SFC method: Chiralcel® OJH column (250×30 mm) using 5% isopropanol in supercritical CO$_2$ (total flow was 120 mL/min). This produced two products with enantiomeric excesses over 95%. The absolute stereochemistry was assigned based on vibrational circular dichroism (VCD) methodology (*Chirality* 2008, 20, 643)

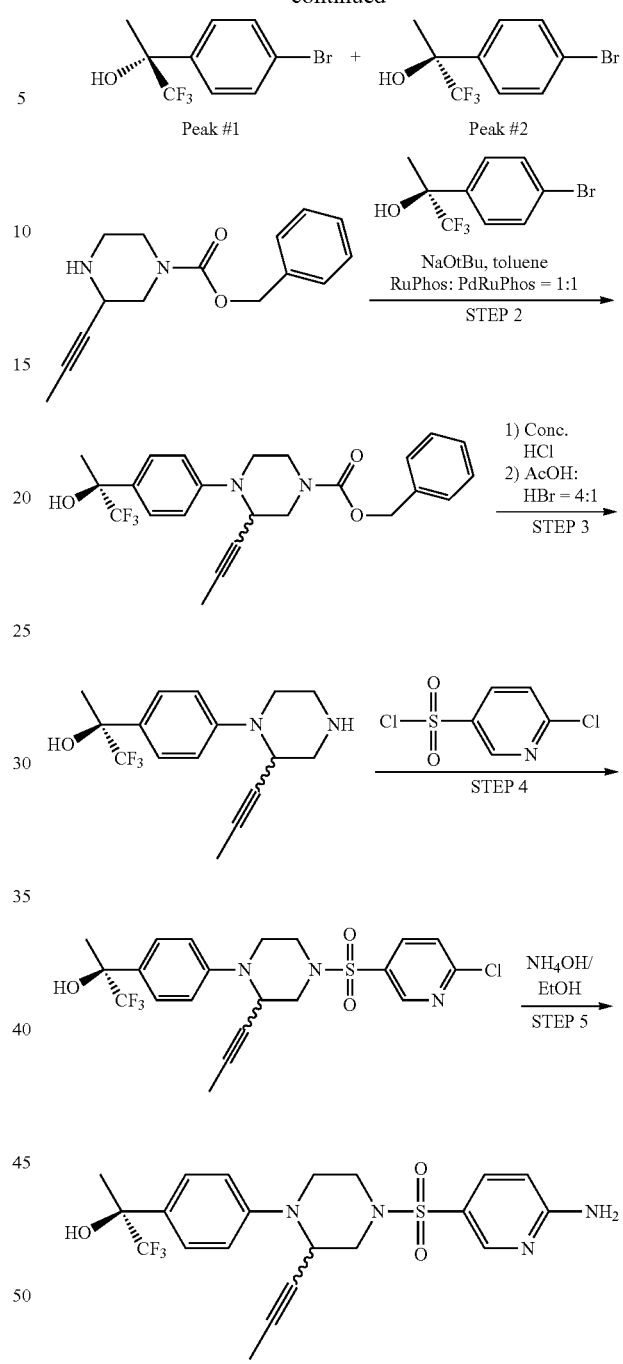

which furnished an assignment consistent with that assumed in a literature example (*Org. Lett.* 2007, 9(18), 3707).

Step 2: benzyl 3-(1-propyn-1-yl)-4-(4-((1S)-2,2,2-trifluoro-1-hydroxy-1-methylethyl)phenyl)-1-piperazine carboxylate

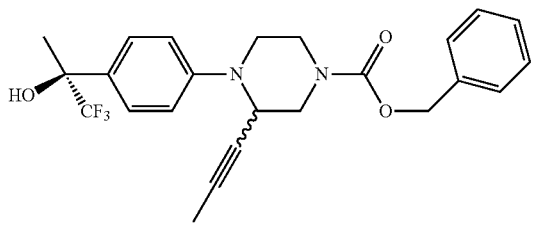 [SMILES: CC#CC1CN(C(=O)OCc2ccccc2)CCN1c1ccc([C@](C)(O)C(F)(F)F)cc1]

To a 20 mL vial was added benzyl 3-(1-propyn-1-yl)-1-piperazinecarboxylate (0.700 g, 2.71 mmol, Example 241, Step 3), sodium tert-butoxide (0.650 g, 6.80 mmol, Sigma-Aldrich, St. Louis, Mo.), ((2',6'-bis(1-methylethoxy)-2-biphenylyl)(dicyclohexyl)phosphane):(2',6'-bis(1-methylethoxy)-2-biphenylyl)(dicyclohexyl)phosphane-(2-(2-aminoethyl)phenyl)(chloro)palladium(1:1)) (0.35 g, 0.30 mmol, Strem Chemical, Newburyport, Mass.), (2S)-2-(4-bromophenyl)-1,1,1-trifluoro-2-propanol (0.875 g, 3.25 mmol, Peak #2, Step 1), and toluene (8.0 mL). The resulting mixture was degassed by bubbling N₂ for 10 min. The vial was sealed and heated at 100° C. for 7 h. The reaction mixture was cooled to room temperature and partitioned between EtOAc (40 mL) and water (30 mL). The aqueous layer was extracted with EtOAc (2×20 mL). The combined organic extracts were dried over MgSO₄, filtered and concentrated. The residue was purified by column chromatography (120 g of silica, 10 to 40% EtOAc in hexanes then 5 to 10% MeOH in EtOAc) to afford bernzyl 3-(1-propyn-1-yl)-4-(4-((1S)-2,2,2-trifluoro-1-hydroxy-1-methylethyl)phenyl)-1-piperazinecarboxylate (0.400 g) as a yellow foam.

Step 3: (2S)-1,1,1-trifluoro-2-(4-(2-(1-propyn-1-yl)-1-piperazinyl)phenyl)-2-propanol

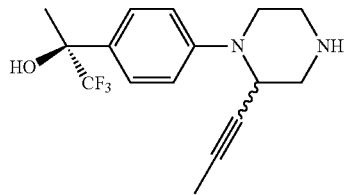 [SMILES: CC#CC1CNCCN1c1ccc([C@](C)(O)C(F)(F)F)cc1]

To a 20-mL scintillation vial was added benzyl 3-(1-propyn-1-yl)-4-(4-((1S)-2,2,2-trifluoro-1-hydroxy-1-methylethyl)phenyl)-1-piperazinecarboxylate (0.400 g, 0.896 mmol) and hydrochloric acid (6.5 mL, 78 mmol, Aldrich, St. Louis, Mo.). The resulting suspension was capped and stirred for 24 h. The solution and the solid in the reaction mixture were then separated. The solution was concentrated to afford the crude product as a light brown solid (0.280 g). The solid that was separated from the solution was redissolved in AcOH (4 mL) and HBr (1 mL) mixture and heated at 60° C. for 3 h then concentrated to give a brown solid (0.110 g). Both solids were combined and dissolved in EtOAc (75 mL). The organic layer was washed with saturated aqueous NaHCO₃ (30 mL) and extracted with EtOAc (2×30 mL). The combined organic extracts were dried over MgSO₄, filtered and concentrated. The crude product was purified by column chromatography (40 g of silica, 1 to 8% 2M NH₃MeOH in DCM) to afford (2S)-1,1,1-trifluoro-2-(4-(2-(1-propyn-1-yl)-1-piperazinyl)phenyl)-2-propanol (0.200 g) as a light brown foam.

Step 4: (2S)-2-(4-(4-((6-chloro-3-pyridinyl)sulfonyl)-2-(1-propyn-1-yl)-1-piperazinyl)phenyl)-1,1,1-trifluoro-2-propanol

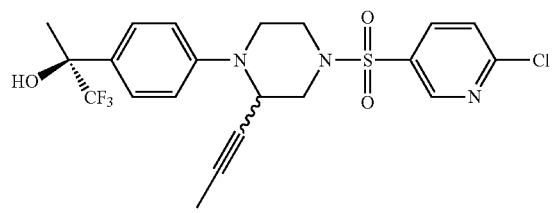 [SMILES: CC#CC1CN(S(=O)(=O)c2ccc(Cl)nc2)CCN1c1ccc([C@](C)(O)C(F)(F)F)cc1]

To a solution of (2S)-1,1,1-trifluoro-2-(4-(2-(1-propyn-1-yl)-1-piperazinyl)phenyl)-2-propanol (0.190 g, 0.608 mmol) in DCM (5.0 mL) was added triethylamine (0.254 mL, 1.83 mmol, Aldrich, St. Louis, Mo.). The reaction mixture was cooled to 0° C. and 6-chloropyridine-3-sulfonyl chloride (0.155 g, 0.730 mmol, *Organic Process Research & Development* 2009, 13, 875) was added in one portion. After the addition, the resulting mixture was stirred at 0° C. for 15 min. The reaction mixture was concentrated and the crude product was purified by column chromatography (40 g of silica, 10 to 30% acetone in hexanes) to afford (2S)-2-(4-(4-((6-chloro-3-pyridinyl)sulfonyl)-2-(1-propyn-1-yl)-1-piperazinyl)phenyl)-1,1,1-trifluoro-2-propanol (0.240 g) as a white foam.

Step 5: (2S)-2-(4-(4-((6-amino-3-pyridinyl)sulfonyl)-2-(1-propyn-1-yl)-1-piperazinyl)phenyl)-1,1,1-trifluoro-2-propanol

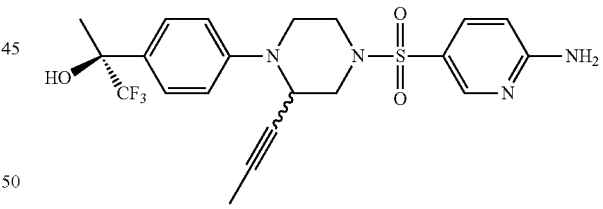

To a 20-mL vial was added (2S)-2-(4-(4-((6-chloro-3-pyridinyl)sulfonyl)-2-(1-propyn-1-yl)-1-piperazinyl)phenyl)-1,1,1-trifluoro-2-propanol (0.235 g, 0.482 mmol), EtOH (3.0 mL), and ammonium hydroxide (30%, 3.0 mL, 23 mmol, J. T. Baker, Philipsburg, N.J.). The vial was sealed and heated at 110° C. for 20 h. The reaction mixture was cooled to rt and the solvent was removed in vacuo. The residue was partitioned between water (20 mL) and DCM (40 mL). The aqueous layer was extracted with DCM (2×20 mL). The combined organic extracts were dried over MgSO₄, filtered, and concentrated. The crude product was purified by column chromatography (40 g of silica, 10 to 30% acetone in hexanes) to afford (2S)-2-(4-(4-((6-amino-3-pyridinyl)sulfonyl)-2-(1-propyn-1-yl)-1-piperazinyl)phenyl)-1,1,1-trifluoro-2-propanol (0.180 g) as a mixture of two isomers.

$^1$H NMR (300 MHz, CDCl$_3$) δ=8.50 (d, J=2.0 Hz, 1H), 7.79 (dd, J=2.5, 8.8 Hz, 1H), 7.47 (d, J=8.6 Hz, 2H), 6.94 (d, J=8.9 Hz, 2H), 6.55 (d, J=8.8 Hz, 1H), 5.07 (s, 2H), 4.42 (d, J=2.2 Hz, 1H), 3.83-3.66 (m, 2H), 3.38 (dd, J=2.8, 7.3 Hz, 2H), 2.86 (dd, J=3.4, 11.1 Hz, 1H), 2.71 (td, J=7.2, 11.3 Hz, 1H), 2.42 (br. s., 1H), 1.79 (d, J=1.9 Hz, 3H), 1.76 (s, 3H). m/z (ESI, +ve ion) 469.2 (M+H)$^+$. GK-GKRP IC$_{50}$ (Binding)=0.011 μM.

This mixture was resolved using preparative SFC (Chiralpak® AD-H column (4.6×150 mm, 5 um) eluting with 60% liquid CO$_2$ in 40% methanol with 40 mM ammonia at a flow rate of 60 mL/min) to give two products in greater than 99% diastereomeric excess.

First Eluting Peak—(2S)-2-(4-((2S)-4-((6-amino-3-pyridinyl)sulfonyl)-2-(1-propyn-1-yl)-1-piperazinyl)phenyl)-1,1,1-trifluoro-2-propanol

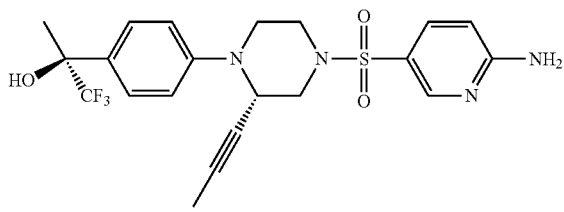 [SMILES: CC#CC1CN(S(=O)(=O)c2ccc(N)nc2)CCN1c1ccc([C@](C)(O)C(F)(F)F)cc1]

$^1$H NMR (300 MHz, CDCl$_3$) δ=8.50 (s, 1H), 7.83-7.74 (m, 1H), 7.47 (d, J=8.6 Hz, 2H), 6.94 (d, J=8.8 Hz, 2H), 6.54 (d, J=8.6 Hz, 1H), 5.01 (s, 2H), 4.42 (br. s., 1H), 3.74 (t, J=10.2 Hz, 2H), 3.44-3.31 (m, 2H), 2.86 (dd, J=3.1, 11.2 Hz, 1H), 2.78-2.60 (m, 1H), 2.38 (br. s., 1H), 1.79 (d, J=1.9 Hz, 3H), 1.76 (s, 3H). m/z (ESI, +ve ion) 469.2 (M+H)$^+$. GK-GKRP IC$_{50}$ (Binding)=0.003 μM.

Second Eluting Peak—(2S)-2-(4-((2R)-4-((6-amino-3-pyridinyl)sulfonyl)-2-(1-propyn-1-yl)-1-piperazinyl)phenyl)-1,1,1-trifluoro-2-propanol

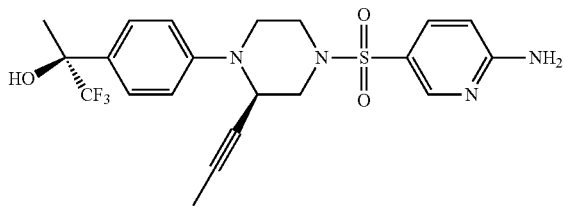

$^1$H NMR (300 MHz, CDCl$_3$) δ=8.50 (d, J=2.0 Hz, 1H), 7.79 (dd, J=2.3, 8.8 Hz, 1H), 7.47 (d, J=8.6 Hz, 2H), 6.99-6.87 (m, 2H), 6.54 (d, J=8.8 Hz, 1H), 5.01 (s, 2H), 4.42 (d, J=1.8 Hz, 1H), 3.74 (t, J=10.1 Hz, 2H), 3.43-3.34 (m, 2H), 2.86 (dd, J=3.3, 11.0 Hz, 1H), 2.77-2.60 (m, 1H), 2.39 (br. s., 1H), 1.78 (d, J=2.0 Hz, 3H), 1.76 (s, 3H). m/z (ESI, +ve ion) 469.1 (M+H)$^+$. GK-GKRP IC$_{50}$ (Binding)=6.35 μM.

This sequence of reactions was also conducted with (2R)-2-(4-bromophenyl)-1,1,1-trifluoro-2-propanol from step 1. This delivered two products as a mixture of isomers.

$^1$H NMR (300 MHz, CDCl$_3$) δ=8.50 (d, J=1.9 Hz, 1H), 7.79 (dd, J=2.5, 8.8 Hz, 1H), 7.47 (d, J=8.6 Hz, 2H), 7.03-6.84 (m, 2H), 6.55 (d, J=8.8 Hz, 1H), 5.06 (s, 2H), 4.42 (d, J=2.0 Hz, 1H), 3.84-3.66 (m, 2H), 3.38 (dd, J=2.8, 7.3 Hz, 2H), 2.86 (dd, J=3.4, 11.1 Hz, 1H), 2.71 (td, J=7.3, 11.4 Hz, 1H), 2.40 (br. s., 1H), 1.79 (d, J=1.9 Hz, 3H), 1.76 (s, 3H). m/z (ESI, +ve ion) 469.2 (M+H)$^+$. GK-GKRP IC$_{50}$ (Binding)=0.021 μM.

This mixture was separated using preparative SFC (Chiralpak® AD-H column (21×150 mm, 5 um) eluting with 50% liquid CO$_2$ in 50% methanol with 20 mM ammonia at a flow rate of 70 mL/min) to give two products in greater than 99% diastereomeric excess.

First Eluting Peak—(2R)-2-(4-((2S)-4-((6-amino-3-pyridinyl)sulfonyl)-2-(1-propyn-1-yl)-1-piperazinyl)phenyl)-1,1,1-trifluoro-2-propanol

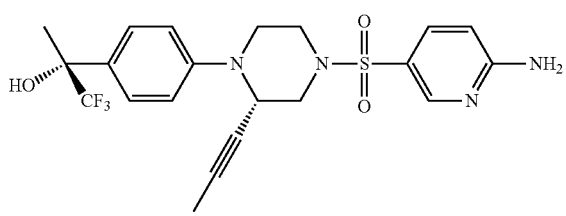 [SMILES: CC#C[C@H]1CN(S(=O)(=O)c2ccc(N)nc2)CCN1c1ccc([C@@](C)(O)C(F)(F)F)cc1]

$^1$H NMR (300 MHz, CDCl$_3$) δ=8.49 (s, 1H), 7.78 (dd, J=2.3, 8.8 Hz, 1H), 7.46 (d, J=8.6 Hz, 2H), 7.00-6.87 (m, 2H), 6.60-6.47 (m, 1H), 4.99 (s, 2H), 4.41 (d, J=2.3 Hz, 1H), 3.82-3.65 (m, 2H), 3.37 (dd, J=2.8, 7.3 Hz, 2H), 2.85 (dd, J=3.4, 11.1 Hz, 1H), 2.70 (td, J=7.3, 11.4 Hz, 1H), 2.39 (s, 1H), 1.77 (d, J=2.0 Hz, 3H), 1.75 (d, J=0.7 Hz, 3H). m/z (ESI, +ve ion) 469.0 (M+H)$^+$. GK-GKRP IC$_{50}$ (Binding)=0.007 μM.

Second Eluting Peak—(2R)-2-(4-((2R)-4-((6-amino-3-pyridinyl)sulfonyl)-2-(1-propyn-1-yl)-1-piperazinyl)phenyl)-1,1,1-trifluoro-2-propanol

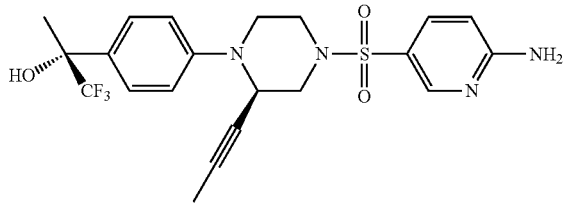 [SMILES: CC#C[C@@H]1CN(S(=O)(=O)c2ccc(N)nc2)CCN1c1ccc([C@@](C)(O)C(F)(F)F)cc1]

$^1$H NMR (300 MHz, CDCl$_3$) δ=8.50 (d, J=2.2 Hz, 1H), 7.79 (dd, J=2.4, 8.7 Hz, 1H), 7.47 (d, J=8.8 Hz, 2H), 6.94 (d, J=8.9 Hz, 2H), 6.54 (d, J=8.8 Hz, 1H), 4.98 (s, 2H), 4.42 (d, J=2.2 Hz, 1H), 3.74 (t, J=10.3 Hz, 2H), 3.39 (dd, J=2.7, 7.2 Hz, 2H), 2.85 (dd, J=3.3, 11.0 Hz, 1H), 2.70 (td, J=7.2, 11.3 Hz, 1H), 2.41 (br. s., 1H), 1.79 (d, J=2.0 Hz, 3H), 1.76 (s, 3H). m/z (ESI, +ve ion) 469.1 (M+H)$^+$. GK-GKRP IC$_{50}$ (Binding) =25.2 μM.

Example 244

2-(2-(4-((6-amino-3-pyridinyl)sulfonyl)-2-(2-hydroxypropyl)-1-piperazinyl)-5-pyrimidinyl)-1,1,1,3,3,3-hexafluoro-2-propanol

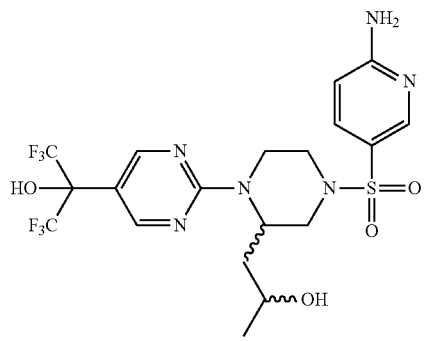 [SMILES: CC(O)CC1CN(S(=O)(=O)c2ccc(N)nc2)CCN1c1ncc(C(O)(C(F)(F)F)C(F)(F)F)cn1]

This material was isolated as a side-product from Step 6 in Example 240.

¹H NMR (400 MHz, DMSO-d₆)=8.50 (d, J=2.15 Hz, 2H), 8.13-8.24 (m, 1H), 7.59 (d, J=8.80 Hz, 1H), 6.96 (d, J=4.69 Hz, 2H, NH₂), 6.49 (dd, J=8.80, 3.91 Hz, 1H), 4.95-5.15 (m, 1H, OH), 4.66 (t, J=10.66 Hz, 1H), 4.36-4.57 (2d, J=4.5, 4.7 Hz, 1H), 3.48-3.70 (m, 3H), 2.13-2.43 (m, 2H) 3.19 (m, 1H), 1.48-1.94 (m, 2H), 1.08 (dd, J=6.36 Hz, 3H). m/z (ESI, +ve ion) 545.2 (M+H)⁺. GK-GKRP IC₅₀ (Binding)=0.743 μM.

Example 245

2-(2-(4-((6-amino-3-pyridinyl)sulfonyl)-2-(²H₃)-1-propyn-1-yl-1-piperazinyl)-5-pyrimidinyl)-1,1,1,3,3,3-hexafluoro-2-propanol

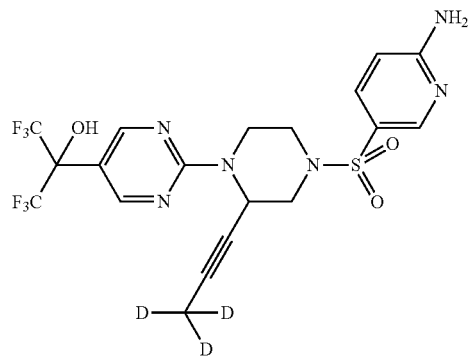 [SMILES: [2H]C([2H])([2H])C#CC1CN(S(=O)(=O)c2ccc(N)nc2)CCN1c1ncc(C(O)(C(F)(F)F)C(F)(F)F)cn1]

Prepared via the method described for Example 240 substituting ²H₃-prop-1-yn-1-ylmagnesium bromide, generated from (3,3,3-²H₃)-1-propyne (Sigma-Aldrich, St. Louis, Mo.) and isopropylmagnesium bromide (Sigma-Aldrich, St. Louis, Mo.), in place of prop-1-yn-1-ylmagnesium chloride.
¹H NMR (300 MHz, CDCl₃) δ=8.58 (s, 2H), 8.45 (d, J=2.2 Hz, 1H), 7.76 (dd, J=2.3, 8.8 Hz, 1H), 6.52 (d, J=8.6 Hz, 1H), 5.74 (br. s., 1H), 5.01 (s, 2H, NH2), 4.69 (d, J=13.0 Hz, 1H), 3.90-3.76 (m, 2H), 3.58-3.42 (m, 1H), 2.62 (dd, J=3.6, 11.3 Hz, 1H), 2.48 (dt, J=3.1, 11.7 Hz, 1H). m/z (ESI, +ve ion) 528.2 (M+H)⁺. GK-GKRP IC₅₀ (Binding)=0.027 μM.

Example 246

2-(2-(4-((6-amino-3-pyridinyl)sulfonyl)-2-(cyclopropylethynyl)-1-piperazinyl)-5-pyrimidinyl)-1,1,1,3,3,3-hexafluoro-2-propanol

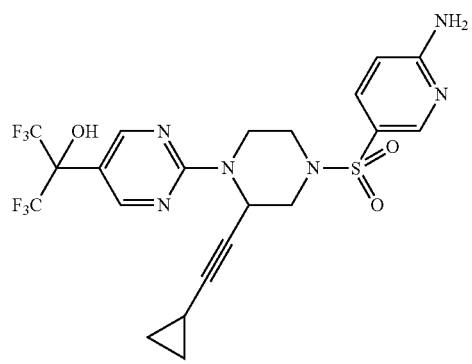 [SMILES: Nc1ccc(S(=O)(=O)N2CCN(c3ncc(C(O)(C(F)(F)F)C(F)(F)F)cn3)C(C#CC3CC3)C2)cn1]

Prepared via the method described for Example 240 substituting (cyclopropylethynyl)magnesium chloride (*Org. Lett.*, 2007, 9, 1335) for isopropylmagnesium bromide.

¹H NMR (400 MHz, CD₃OD) δ=8.61 (s, 2H), 8.31 (d, J=2.3 Hz, 1H), 7.74 (dd, J=2.4, 8.9 Hz, 1H), 6.62 (d, J=9.0 Hz, 1H), 5.73 (br. s., 1H), 4.66 (d, J=13.1 Hz, 1H), 3.78 (d, J=11.5 Hz, 2H), 3.42-3.36 (m, 1H), 2.65 (dd, J=3.5, 11.7 Hz, 1H), 2.48 (dt, J=3.2, 11.9 Hz, 1H), 1.30-1.21 (m, 1H), 0.82-0.71 (m, 2H), 0.66-0.54 (m, 2H). m/z (ESI, +ve ion) 551.0 (M+H)⁺. GK-GKRP IC₅₀ (Binding)=0.191 μM; GK-GKRP EC₅₀ (LC MS/MS-2)=0.314 μM.

Example 247

1,1,1,3,3,3-hexafluoro-2-(4-((2S)-4-(phenylsulfonyl)-2-(1-propyn-1-yl)-1-piperazinyl)phenyl)-2-propanol

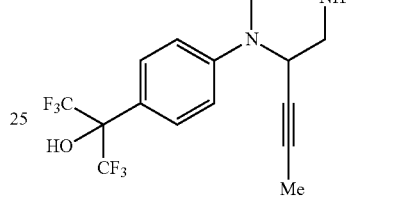

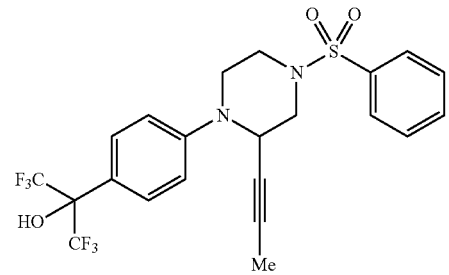

To a stirred solution of 1,1,1,3,3,3-hexafluoro-2-(4-(2-(1-propyn-1-yl)-1-piperazinyl)phenyl)-2-propanol (155 mg, 0.423 mmol, Example 241, Step 3) and triethylamine (302 μL, 2.17 mmol, Sigma-Aldrich, St. Louis, Mo.) in DCM (3.2 mL) was added benzenesulfonyl chloride (63.5 μL, 0.504 mmol, Sigma-Aldrich, St. Louis, Mo.) drop-wise at 0° C. The solution was stirred for 30 min and then diluted with DCM and washed with water followed by brine. The organic phase was dried over Na₂SO₄, filtered and concentrated. The crude residue was purified by silica gel chromatography (0 to 50% EtOAc in hexanes) to give 1,1,1,3,3,3-hexafluoro-2-(4-((2S)-4-(phenylsulfonyl)-2-(1-propyn-1-yl)-1-piperazinyl)phenyl)-2-propanol as a mixture of enantiomers.

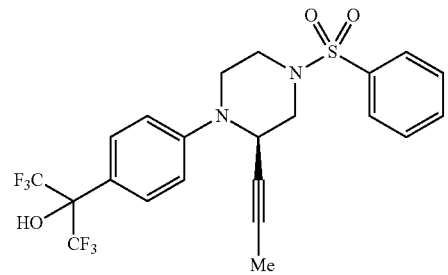

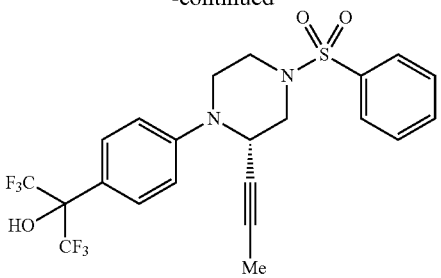

1,1,1,3,3,3-hexafluoro-2-(4-((2S)-4-(phenylsulfonyl)-2-(1-propyn-1-yl)-1-piperazinyl)phenyl)-2-propanol; and 1,1,1,3,3,3-hexafluoro-2-(4-((2R)-4-(phenylsulfonyl)-2-(1-propyn-1-yl)-1-piperazinyl)phenyl)-2-propanol $^1$H NMR (400 MHz, DMSO-$d_6$) δ ppm 1.76 (d, J=1.96 Hz, 3H) 2.36 (td, J=11.59, 3.03 Hz, 1H) 2.52-2.57 (m, 1H) 3.12 (td, J=11.98, 3.03 Hz, 1H) 3.60 (d, J=12.52 Hz, 1H) 3.65-3.74 (m, 2H) 4.82 (br. s., 1H) 7.03 (d, J=9.19 Hz, 2H) 7.48 (d, J=8.80 Hz, 2H) 7.64-7.70 (m, 2H) 7.72-7.82 (m, 3H) 8.43 (s, 1H). m/z (ESI, +ve ion) 506.9 (M)$^+$. GK-GKRP IC$_{50}$ (binding)=0.021 μM.

Example 248

2-(4-(4-((5-amino-1,3,4-thiadiazol-2-yl)sulfonyl)-2-(1-propyn-1-yl)-1-piperazinyl)phenyl)-1,1,1,3,3,3-hexafluoro-2-propanol

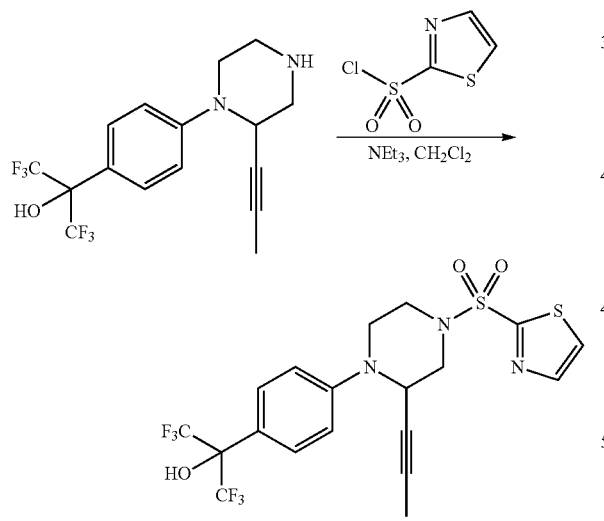

To 25-mL round-bottomed flask at 0° C. charged with 1,1,1,3,3,3-hexafluoro-2-(4-(2-(1-propyn-1-yl)-1-piperazinyl)phenyl)-2-propanol (300 mg, 0.819 mmol, Example 241, Step 3) and CH$_2$Cl$_2$ (15 mL) was added triethylamine (0.23 mL, 1.64 mmol) followed by 1,3-thiazole-2-sulfonyl chloride (2.46 mL, 1.23 mmol, *Bioorganic & Medicinal Chemistry,* 2006, 14(19), 6628) as a solution in CH$_2$Cl$_2$ (5 mL). After 10 min, o an additional equivalent of the sulfonyl chloride was added. After a further 10 min the reaction was diluted with water (50 mL) and extracted with CH$_2$Cl$_2$ (3×50 mL). The combined organics were dried (Na$_2$SO$_4$), filtered, and concentrated to give an oil. Purification via silica gel column chromatography (0 to 100% EtOAc in hexanes) gave 2-(4-(4-((5-amino-1,3,4-thiadiazol-2-yl)sulfonyl)-2-(1-propyn-1-yl)-1-piperazinyl)phenyl)-1,1,1,3,3,3-hexafluoro-2-propanol (250 mg) as a white solid that was a mixture of two isomers.

$^1$H NMR (400 MHz, CD$_3$OD) δ=8.06 (d, J=3.1 Hz, 1H), 7.98 (d, J=2.9 Hz, 1H), 7.57 (d, J=8.6 Hz, 2H), 7.05 (d, J=9.0 Hz, 2H), 4.70 (br. s., 1H), 3.92 (d, J=11.7 Hz, 2H), 3.60-3.50 (m, 1H), 3.38-3.33 (m, 1H), 3.18-3.05 (m, 1H), 3.02-2.85 (m, 1H), 1.76 (s, 3H). m/z (ESI, +ve ion) 514.1 (M+H)$^+$. GK-GKRP IC$_{50}$ (Binding)=0.015 μM.

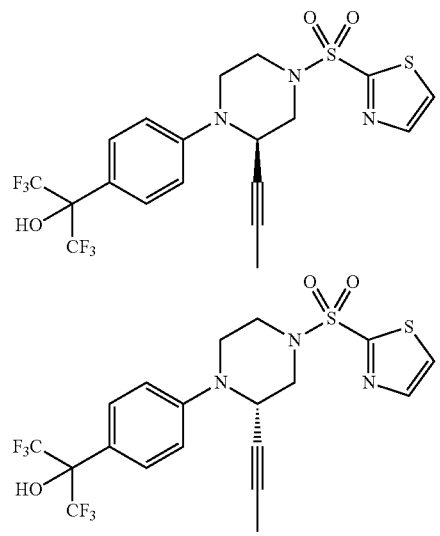

1,1,1,3,3,3-hexafluoro-2-(4-((2R)-2-(1-propyn-1-yl)-4-(1,3-thiazol-2-ylsulfonyl)-1-piperazinyl)phenyl)-2-propanol; and 1,1,1,3,3,3-hexafluoro-2-(4-((2S)-2-(1-propyn-1-yl)-4-(1,3-thiazol-2-ylsulfonyl)-1-piperazinyl)phenyl)-2-propanol.

Example 249

2-(4-(4-((5-amino-1,3,4-thiadiazol-2-yl)sulfonyl)-2-(1-propyn-1-yl)-1-piperazinyl)phenyl)-1,1,1,3,3,3-hexafluoro-2-propanol

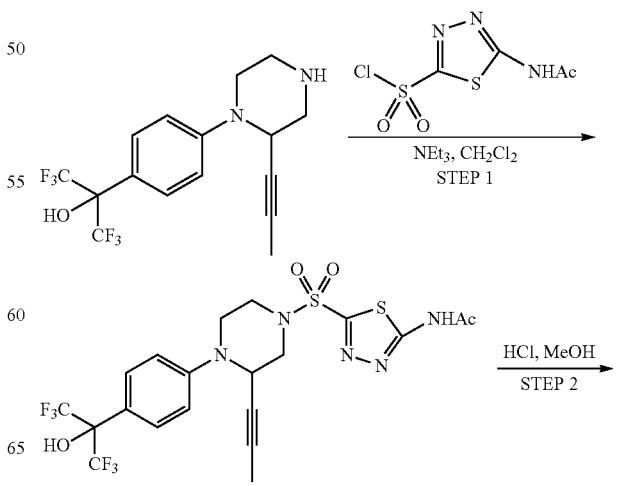

467

-continued

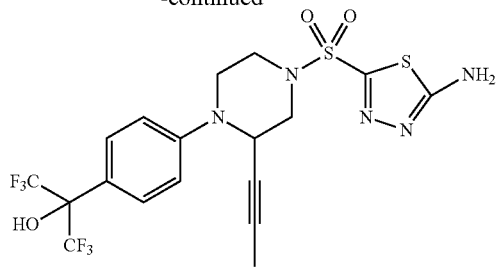

Step 1: N-(5-((3-(1-propyn-1-yl)-4-(4-(2,2,2-trifluoro-1-hydroxy-1-(trifluoromethyl)ethyl)phenyl)-1-piperazinyl)sulfonyl)-1,3,4-thiadiazol-2-yl)acetamide Following the general procedure reported for Example 248, using a single equivalent of 5-(acetylamino)-1,3,4-thiadiazole-2-sulfonyl chloride (See, *European Journal of Medicinal Chemistry*, 2006, 41(8), 918) and 1,1,1,3,3,3-hexafluoro-2-(4-(2-(1-propyn-1-yl)-1-piperazinyl)phenyl)-2-propanol (Example 241, Step 3) delivered N-(5-((3-(1-propyn-1-yl)-4-(4-(2,2,2-trifluoro-1-hydroxy-1-(trifluoromethyl)ethyl)phenyl)-1-piperazinyl)sulfonyl)-1,3,4-thiadiazol-2-yl)acetamide as a mixture of two isomers that was purified via column chromatography on silica gel (0 to 10% MeOH in CH$_2$Cl$_2$).

Step 2: 2-(4-(4-((5-amino-1,3,4-thiadiazol-2-yl)sulfonyl)-2-(1-propyn-1-yl)-1-piperazinyl)phenyl)-1,1,1,3,3,3-hexafluoro-2-propanol A 20-mL microwave vial was charged with N-(5-((3-(1-propyn-1-yl)-4-(4-(2,2,2-trifluoro-1-hydroxy-1-(trifluoromethyl)ethyl)phenyl)-1-piperazinyl)sulfonyl)-1,3,4-thiadiazol-2-yl)acetamide (370 mg, 0.647 mmol), MeOH (2 mL), 1N aq. HCl (3 mL, 3.00 mmol) and 4N HCl in dioxane (3 mL, 12.00 mmol). The reaction vessel was sealed and the mixture heated to 100° C. for 4 h. The reaction was concentrated onto silica and purified via column chromatography on silica gel (0 to 10% MeOH in CH$_2$Cl$_2$) to give 2-(4-(4-((5-amino-1,3,4-thiadiazol-2-yl)sulfonyl)-2-(1-propyn-1-yl)-1-piperazinyl)phenyl)-1,1,1,3,3,3-hexafluoro-2-propanol (160 mg) as a mixture of two isomers.

$^1$H NMR (400 MHz, CD$_3$OD) δ=7.58 (d, J=8.6 Hz, 2H), 7.06 (d, J=9.0 Hz, 2H), 4.76-4.67 (m, 1H), 3.97-3.80 (m, 2H), 3.61-3.52 (m, 1H), 3.36-3.33 (m, 1H), 3.26-3.19 (m, 1H), 3.11-2.97 (m, 1H), 1.76 (s, 3H). m/z (ESI, +ve ion) 530.2 (M+H)$^+$. GK-GKRP IC$_{50}$ (Binding)=0.112 μM;

468

-continued

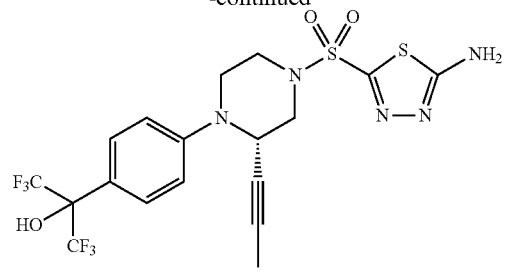

2-(4-((2R)-4-((5-amino-1,3,4-thiadiazol-2-yl)sulfonyl)-2-(1-propyn-1-yl)-1-piperazinyl)phenyl)-1,1,1,3,3,3-hexafluoro-2-propanol; 2-(4-((2S)-4-((5-amino-1,3,4-thiadiazol-2-yl)sulfonyl)-2-(1-propyn-1-yl)-1-piperazinyl)phenyl)-1,1,1,3,3,3-hexafluoro-2-propanol.

Example 250

2-(4-(4-((6-amino-5-fluoro-3-pyridinyl)sulfonyl)-2-(1-propyn-1-yl)-1-piperazinyl)phenyl)-1,1,1,3,3,3-hexafluoro-2-propanol

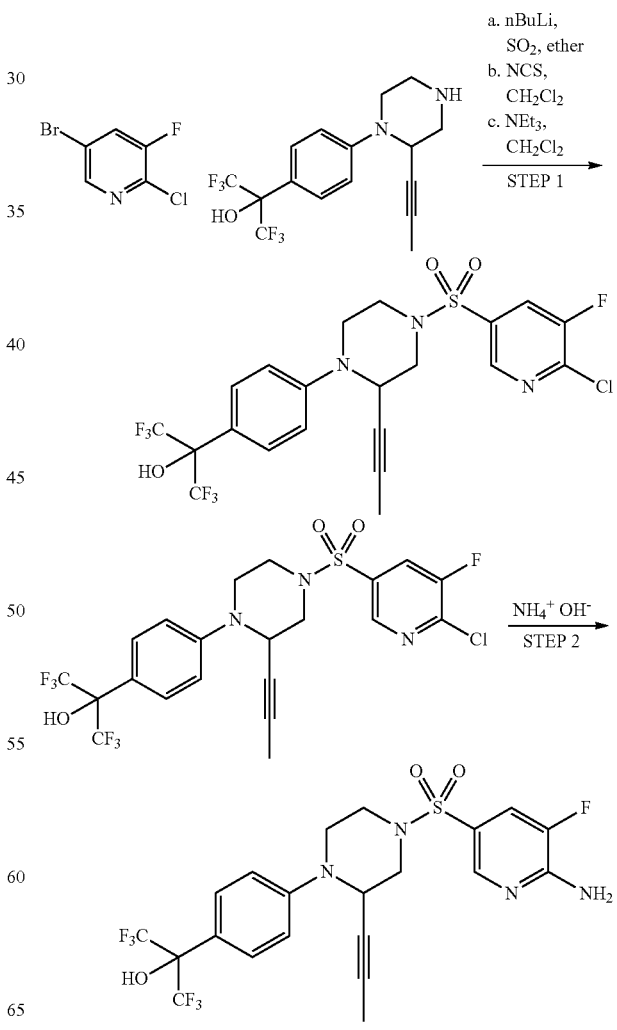

Step 1: 2-(4-(4-(((6-chloro-5-fluoro-3-pyridinyl)sulfonyl)-2-(1-propyn-1-yl)-1-piperazinyl)phenyl)-1,1,1,3,3,3-hexafluoro-2-propanol A 50-mL round-bottomed flask solution was cooled to −78° C. and charged with 5-bromo-2-chloro-3-fluoropyridine (259 mg, 1.23 mmol, Asymchem Laboratories, Inc., Morrisville, N.C.) and diethylether (10 mL). n-BuLi (0.49 mL, 2.5M solution in hexanes, 1.23 mmol) was added and after 5 min. Sulfur dioxide (52.5 mg, 0.819 mmol, Sigma-Aldrich, St. Louis, Mo.) was then bubbled through the cold solution for 1 min. The mixture was then allowed to warm to room temperature and concentrated. To this was solid was added $CH_2Cl_2$ (10 mL) and NCS (152 mg, 1.15 mmol, Alfa Aesar, Ward Hill, Mass.) added. After 20 min, 1,1,1,3,3,3-hexafluoro-2-(4-(2-(1-propyn-1-yl)-1-piperazinyl)phenyl)-2-propanol (300 mg, 0.819 mmol, Example 241, Step 3) and triethylamine (0.457 mL, 3.28 mmol) were added to the reaction mixture. After a further 10 min at room temperature, the reaction was quenched with water (50 mL) and extracted with EtOAc (3×100 mL). The combined organics were dried ($Na_2SO_4$), filtered, and concentrated to give an oil that was purified via column chromatography on silica gel (0 to 100% EtOAc in hexanes) to give 2-(4-(4-(((6-chloro-5-fluoro-3-pyridinyl)sulfonyl)-2-(1-propyn-1-yl)-1-piperazinyl)phenyl)-1,1,1,3,3,3-hexafluoro-2-propanol (165 mg) as a mixture of two isomers

Step 2: 2-(4-(4-(((6-amino-5-fluoro-3-pyridinyl)sulfonyl)-2-(1-propyn-1-yl)-1-piperazinyl)phenyl)-1,1,1,3,3,3-hexafluoro-2-propanol A 20-mL microwave vial was charged with 2-(4-(4-(((6-chloro-5-fluoro-3-pyridinyl)sulfonyl)-2-(1-propyn-1-yl)-1-piperazinyl)phenyl)-1,1,1,3,3,3-hexafluoro-2-propanol (165 mg, 0.30 mmol), aq. ammonium hydroxide (3 mL, 30% solution, 15.4 mmol, J. T. Baker, Phillipsburg, N.J.) and EtOH (3 mL). The is reaction vessel was sealed and the mixture heated to 150° C. overnight. The reaction was diluted with water (50 mL) and extracted with EtOAc (3×100 mL). The combined organics were dried ($Na_2SO_4$), filtered, and concentrated to give an oil that was purified via column chromatography on silica gel (0-10% MeOH in $CH_2Cl_2$) to give 2-(4-(4-(((6-amino-5-fluoro-3-pyridinyl)sulfonyl)-2-(1-propyn-1-yl)-1-piperazinyl)phenyl)-1,1,1,3,3,3-hexafluoro-2-propanol (60 mg) as a mixture of two isomers.

$^1H$ NMR (400 MHz, $CD_3OD$) δ=8.19 (s, 1H), 7.67-7.60 (m, 1H), 7.54 (d, J=8.4 Hz, 2H), 7.01 (d, J=9.4 Hz, 2H), 4.71-4.59 (m, 1H), 3.76 (d, J=11.2 Hz, 2H), 3.58-3.50 (m, 1H), 3.29-3.21 (m, 1H), 2.85-2.74 (m, 1H), 2.72-2.57 (m, 1H), 1.76 (s, 3H). m/z (ESI, +ve ion) 541.1 (M+H)+. GK-GKRP $IC_{50}$ (Binding)=0.015 μM.

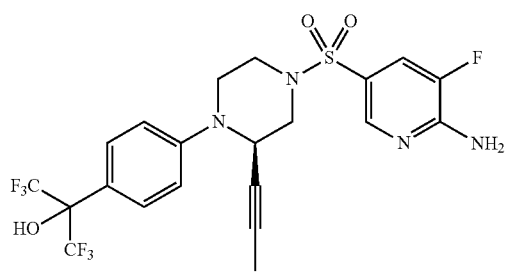

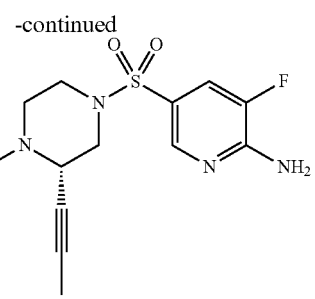

2-(4-((2R)-4-(((6-amino-5-fluoro-3-pyridinyl)sulfonyl)-2-(1-propyn-1-yl)-1-piperazinyl)phenyl)-1,1,1,3,3,3-hexafluoro-2-propanol; and 2-(4-((2S)-4-(((6-amino-5-fluoro-3-pyridinyl)sulfonyl)-2-(1-propyn-1-yl)-1-piperazinyl)phenyl)-1,1,1,3,3,3-hexafluoro-2-propanol.

Example 251

2-(2-(4-(((6-amino-3-pyridinyl)sulfonyl)-2-(1-propyn-1-yl)-1-piperazinyl)-5-pyrimidinyl)-1,1,1-trifluoro-2-propanol

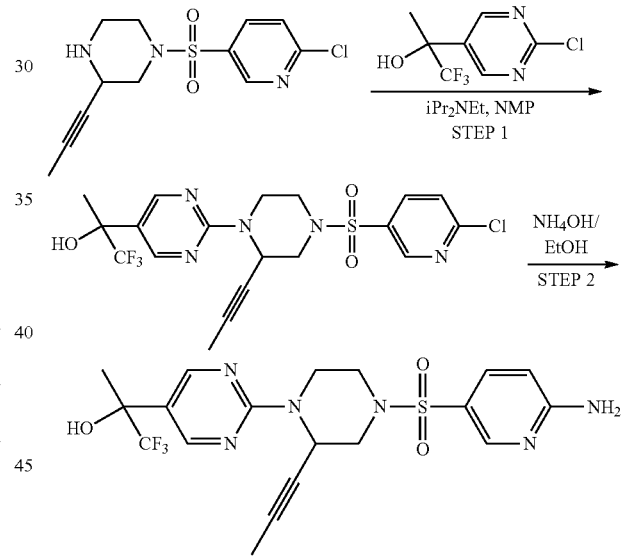

Step 1: 2-(2-(4-(((6-chloro-3-pyridinyl)sulfonyl)-2-(1-propyn-1-yl)-1-piperazinyl)-5-pyrimidinyl)-1,1,1-trifluoro-2-propanol To a 20 mL vial was added 1-(((6-chloro-3-pyridinyl)sulfonyl)-3-(1-propyn-1-yl)piperazine (1.70 g, 7.47 mmol, Example 240, Step 4), diisopropylethylamine (4.20 mL, 24.2 mmol), and NMP (8.0 mL), and 2-(2-chloro-5-pyrimidinyl)-1,1,1-trifluoro-2-propanol (1.4 g, 6.37 mmol, Intermediate E). The vial was sealed and heated at 140° C. for 9 h. The reaction mixture was cooled to rt and partitioned between EtOAc (200 mL) and water (100 mL). The aqueous layer was extracted with EtOAc (2×75 mL). The combined organic extracts were dried over $MgSO_4$, filtered, and concentrated. The crude product was purified by column chromatography (120 g of silica, 10 to 50% EtOAc in hexanes) to afford 2-(2-(4-(((6-chloro-3-pyridinyl)sulfonyl)-2-(1-propyn-1-yl)-1-piperazinyl)-5-pyrimidinyl)-1,1,1-trifluoro-2-propanol (1.5 g) as a light yellow solid.

Step 2: 2-(2-(4-(((6-amino-3-pyridinyl)sulfonyl)-2-(1-propyn-1-yl)-1-piperazinyl)-5-pyrimidinyl)-1,1,1-trifluoro-2-propanol To a 330-mL pressure vessel was added 2-(2-(4-(((6-chloro-3-pyridinyl)sulfonyl)-2-(1-propyn-1-yl)-1-piperazinyl)-5-pyrimidinyl)-1,1,1-trifluoro-2-propanol (6.50 g, 13.3 mmol), EtOH (80 mL), and ammonium hydroxide (30%, 80.0 mL, 616 mmol, J. T. Baker, Philipsburg, N.J.). The tube was sealed and heated at 120° C. for 10 h and then the solvent was removed in vacuo. The residue was partitioned between water (100 mL) and DCM (200 mL). The aqueous layer was extracted with DCM (2×100 mL) and the combined organic extracts were dried over $MgSO_4$, filtered, and concentrated. The crude product was purified by column chromatography (330 g of silica, 1 to 5% 2 M $NH_3$ in MeOH in DCM) to afford 2-(2-(4-(((6-amino-3-pyridinyl)sulfonyl)-2-(1-propyn-1-yl)-1-piperazinyl)-5-pyrimidinyl)-1,1,1-trifluoro-2-propanol (5.0 g) as a mixture of four isomers.

$^1$H NMR (300 MHz, $CDCl_3$) δ=8.56-8.42 (m, 3H), 7.77 (dd, J=2.5, 8.8 Hz, 1H), 6.51 (d, J=8.8 Hz, 1H), 5.72 (br. s., 1H), 4.95 (s, 2H), 4.65 (d, J=13.2 Hz, 1H), 3.90-3.70 (m, 2H), 3.56-3.32 (m, 1H), 2.62 (dd, J=3.7, 11.3 Hz, 1H), 2.56-2.39 (m, 2H), 1.82 (d, J=2.0 Hz, 3H), 1.75 (s, 3H). m/z (ESI, +ve ion) 471.1 $(M+H)^+$. GK-GKRP $IC_{50}$ (Binding)=0.036 μM.

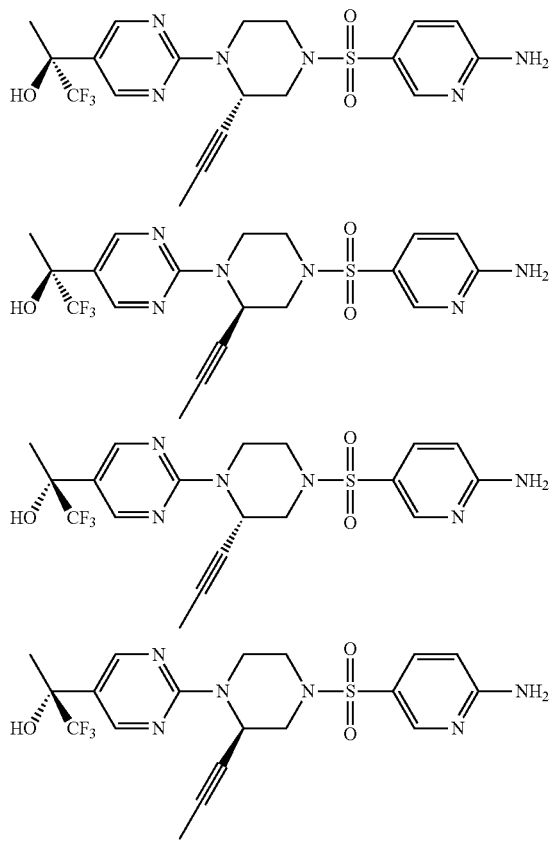

(2S)-2-(2-((2S)-4-((6-amino-3-pyridinyl)sulfonyl)-2-(1-propyn-1-yl)-1-piperazinyl)-5-pyrimidinyl)-1,1,1-trifluoro-2-propanol; (2R)-2-(2-((2S)-4-((6-amino-3-pyridinyl)sulfonyl)-2-(1-propyn-1-yl)-1-piperazinyl)-5-pyrimidinyl)-1,1,1-trifluoro-2-propanol; (2S)-2-(2-((2R)-4-((6-amino-3-pyridinyl)sulfonyl)-2-(1-propyn-1-yl)-1-piperazinyl)-5-pyrimidinyl)-1,1,1-trifluoro-2-propanol; and (2R)-2-(2-((2R)-4-((6-amino-3-pyridinyl)sulfonyl)-2-(1-propyn-1-yl)-1-piperazinyl)-5-pyrimidinyl)-1,1,1-trifluoro-2-propanol.

This mixture of four isomers was first resolved using preparative SFC (Chiralpak® AD-H column (21×150 mm, 5 um) eluting with 40% liquid $CO_2$ in 60% methanol with 0.2% diethylamine at a flow rate of 70 mL/min) to separate the mixture of four isomers into two sets of compounds (both containing two isomers each: set one and set two)

The first eluting set of two isomers (set one) was further resolved using SFC (Chiralpak® AS-H column (21×250 mm, 5 um) eluting with 82% liquid $CO_2$ in 18% methanol with 0.2% diethylamine at a flow rate of 75 mL/min) to give two products in greater than 99% diastereomeric and enantiomeric excess.

The latter eluting set of two isomers (set two) (from above) was further resolved using SFC (Chiralpak® AS-H column (21×250 mm, 5 um) eluting with 80% liquid $CO_2$ in 20% ethanol with 20 mM ammonia at a flow rate of 75 mL/min) to give two products in greater than 99% diastereomeric excess.

First Eluting Peak from Set One Pair of Isomers $^1$H NMR (400 MHz, $CDCl_3$) δ=8.57-8.42 (m, 3H), 7.76 (dd, J=2.3, 8.8 Hz, 1H), 6.51 (d, J=8.6 Hz, 1H), 5.72 (br. s., 1H), 4.95 (s, 2H), 4.65 (d, J=13.3 Hz, 1H), 3.91-3.74 (m, 2H), 3.47 (dt, J=3.3, 12.7 Hz, 1H), 2.75 (q, J=7.1 Hz, 1H), 2.62 (dd, J=3.6, 11.2 Hz, 1H), 2.48 (dt, J=3.1, 11.7 Hz, 1H), 1.82 (d, J=2.0 Hz, 3H), 1.75 (s, 3H). m/z (ESI, +ve ion) 471.1 $(M+H)^+$. GK-GKRP $IC_{50}$ (Binding)=0.015 μM Second Eluting Peak from Set One Pair of Isomers $^1$H NMR (400 MHz, $CDCl_3$) δ=8.56-8.44 (m, 3H), 7.76 (dd, J=2.2, 8.7 Hz, 1H), 6.51 (d, J=8.6 Hz, 1H), 5.71 (br. s., 1H), 4.95 (s, 2H), 4.65 (d, J=13.3 Hz, 1H), 3.92-3.73 (m, 2H), 3.47 (dt, J=3.1, 12.7 Hz, 1H), 2.78 (q, J=7.2 Hz, 1 H), 2.62 (dd, J=3.5, 11.2 Hz, 1H), 2.48 (dt, J=3.0, 11.7 Hz, 1H), 1.82 (d, J=1.8 Hz, 3H), 1.75 (s, 3H). m/z (ESI, +ve ion) 471.2 $(M+H)^+$. GK-GKRP $IC_{50}$ (Binding)=0.009 μM First Eluting Peak from Set Two Pair of Isomers $^1$H NMR (300 MHz, $CDCl_3$) δ=8.59-8.41 (m, 3H), 7.77 (dd, J=2.4, 8.7 Hz, 1H), 6.52 (d, J=8.8 Hz, 1H), 5.72 (br. s., 1H), 5.01 (s, 2H), 4.65 (d, J=13.4 Hz, 1H), 3.91-3.73 (m, 2H), 3.54-3.35 (m, 1H), 2.63 (dd, J=3.6, 11.3 Hz, 1H), 2.57-2.37 (m, 2H), 1.82 (d, J=2.2 Hz, 3H), 1.75 (s, 3H). m/z (ESI, +ve ion) 471.1 $(M+H)^+$. GK-GKRP $IC_{50}$ (Binding)=11.3 μM Second Eluting Peak from Set Two Pair of Isomers $^1$H NMR (300 MHz, $CDCl_3$) δ=8.55-8.42 (m, 3H), 7.78 (dd, J=2.3, 8.8 Hz, 1H), 6.53 (d, J=8.8 Hz, 1H), 5.72 (br. s., 1H), 5.05 (s, 2H), 4.65 (d, J=13.3 Hz, 1H), 3.91-3.72 (m, 2H), 3.56-3.35 (m, 1H), 2.63 (dd, J=3.7, 11.3 Hz, 1H), 2.49 (dt, J=3.4, 11.7 Hz, 2H), 1.82 (d, J=2.2 Hz, 3H), 1.75 (s, 3H). m/z (ESI, +ve ion) 471.0 $(M+H)^+$. GK-GKRP $IC_{50}$ (Binding)=15.3 μM

Example 252

N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide

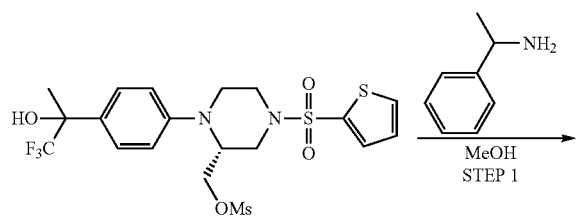

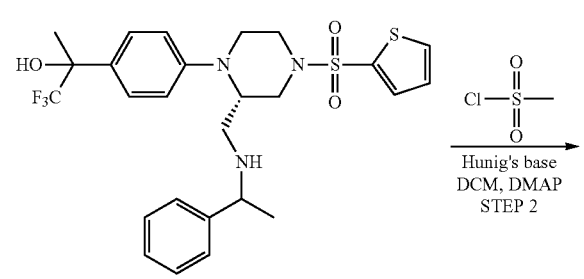

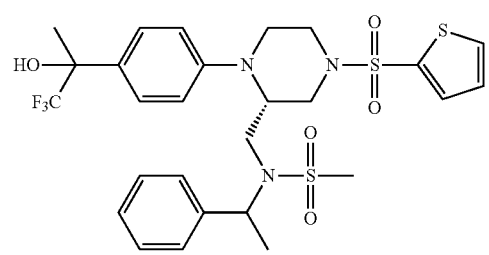

Step 1: 1,1,1-trifluoro-2-(4-((2S)-2-(((1-phenylethyl)amino)methyl)-4-(2-thiophenylsulfonyl)-1-piperazinyl)phenyl)-2-propanol

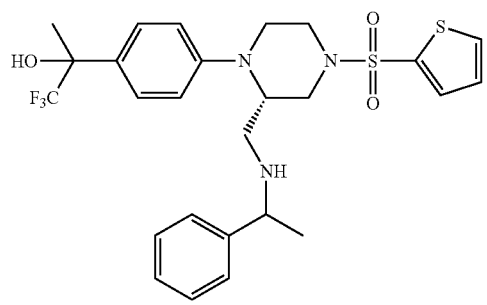 [SMILES: CC(NC[C@H]1CN(S(=O)(=O)c2cccs2)CCN1c1ccc(C(C)(O)C(F)(F)F)cc1)c1ccccc1]

Following the procedure of Example 195, Step 1, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and 1-phenylethanamine (Acros Organics, N.J.) delivered 1,1,1-trifluoro-2-(4-((2S)-2-(((1-phenylethyl)amino)methyl)-4-(2-thiophenylsulfonyl)-1-piperazinyl)phenyl)-2-propanol.

Step 2: N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide

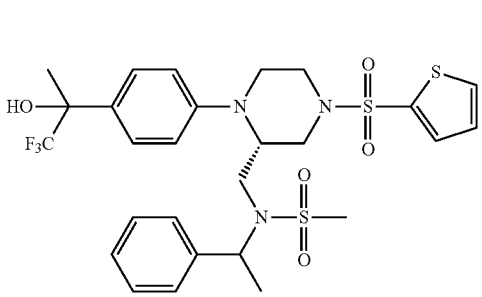 [SMILES: CC(c1ccccc1)N(C[C@H]1CN(S(=O)(=O)c2cccs2)CCN1c1ccc(C(C)(O)C(F)(F)F)cc1)S(C)(=O)=O]

Following the procedure of Example 195, Step 2, the reaction of 1,1,1-trifluoro-2-(4-((2S)-2-(((1-phenylethyl)amino)methyl)-4-(2-thiophenylsulfonyl)-1-piperazinyl)phenyl)-2-propanol and methanesulfonyl chloride (Sigma-Aldrich, St. Louis, Mo.) delivered N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide as a mixture of 4 isomers.

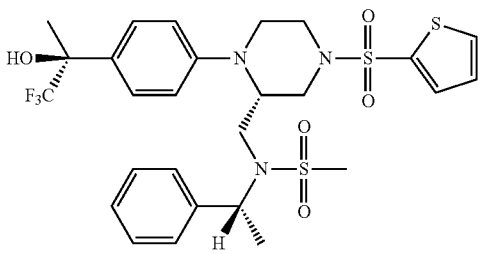

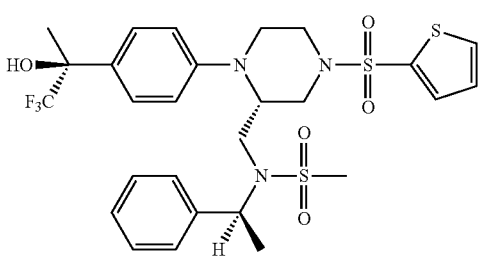

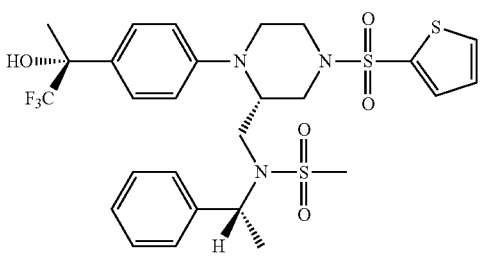

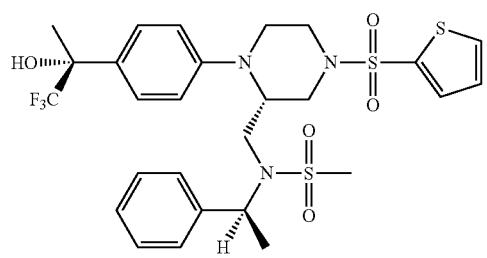

N-((1R)-1-phenylethyl)-N-(((2R)-4-(2-thiophenylsulfonyl)-1-(4-((1S)-2,2,2-trifluoro-1-hydroxy-1-methylethyl)phenyl)-2-piperazinyl)methyl)methanesulfonamide; N-((1S)-1-phenylethyl)-N-(((2R)-4-(2-thiophenylsulfonyl)-1-(4-((1S)-2,2,2-trifluoro-1-hydroxy-1-methylethyl)phenyl)-2-piperazinyl)methyl)methanesulfonamide; N-((1R)-1-phenylethyl)-N-(((2R)-4-(2-thiophenylsulfonyl)-1-(4-((1R)-2,2,2-trifluoro-1-hydroxy-1-methylethyl)phenyl)-2-piperazinyl)methyl)methanesulfonamide; and N-((1S)-1-phenylethyl)-N-(((2R)-4-(2-thiophenylsulfonyl)-1-(4-((1R)-2,2,2-trifluoro-1-hydroxy-1-methylethyl)phenyl)-2-piperazinyl)methyl)methanesulfonamide $^1$H NMR (300 MHz, CDCl$_3$) δ=7.71-7.62 (m, 1H), 7.60-7.51 (m, 1H), 7.48-7.29 (m, 7H), 7.23-7.13 (m, 1H), 6.80 (d, J=7.7 Hz, 2H), 5.14 (q, J=7.1 Hz, 1H), 4.32 (br. s., 1H), 3.81 (d, J=12.0 Hz, 1H), 3.71-3.44 (m, 3H), 3.41-3.24 (m, 1H), 3.15-2.89 (m, 2H), 2.62 (s, 3H), 2.49 (s, 1H), 2.39-2.28 (m, 1H), 1.74 (s, 3H), 1.68 (d, J=7.2 Hz, 3H). m/z (ESI, +ve ion) 632.2 (M+H)$^+$. GK-GKRP IC$_{50}$ (Binding)=0.671 μM.

Example 253

2-methyl-N-3-pyridinyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide

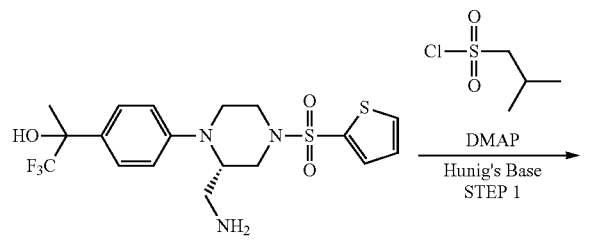

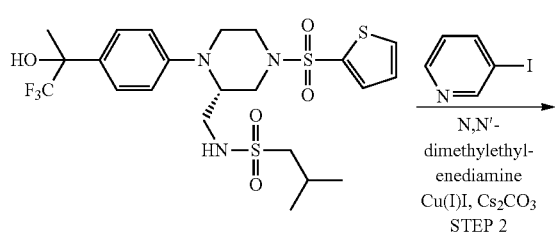

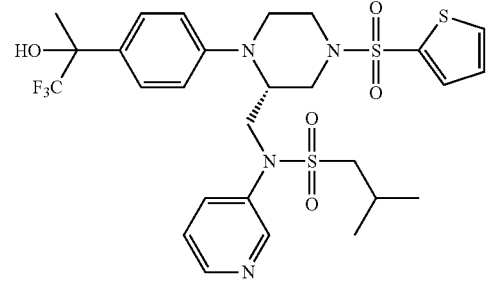 [SMILES: CC(C)CS(=O)(=O)N(C[C@H]1CN(S(=O)(=O)c2cccs2)CCN1c1ccc(C(C)(O)C(F)(F)F)cc1)c1cccnc1]

Step 1: 2-methyl-N-(((2S)-4-(2-thiophenylsulfonyl)-1-(4-(2,2,2-trifluoro-1-hydroxy-1-methylethyl)phenyl)-2-piperazinyl)methyl)-1-propanesulfonamide

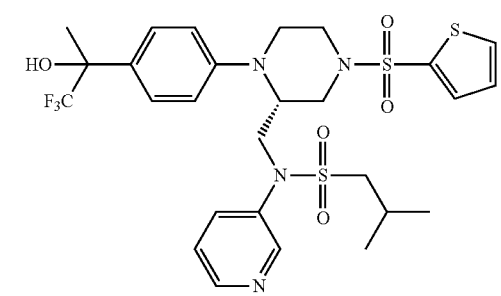

Following the general procedure of Example 195, Step 2, the reaction of 2-(4-((2S)-2-(aminomethyl)-4-(2-thiophenylsulfonyl)-1-piperazinyl)phenyl)-1,1,1-trifluoro-2-propanol (Example 192, Step 1) and 2-methyl-1-propanesulfonyl chloride (Sigma-Aldrich, St. Louis, Mo.) delivered 2-methyl-N-(((2S)-4-(2-thiophenylsulfonyl)-1-(4-(2,2,2-trifluoro-1-hydroxy-1-methylethyl)phenyl)-2-piperazinyl)methyl)-1-propanesulfonamide.

Step 2: 2-methyl-N-3-pyridinyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide To a solution of 2-methyl-N-(((2S)-4-(2-thiophenylsulfonyl)-1-(4-(2,2,2-trifluoro-1-hydroxy-1-methylethyl)phenyl)-2-piperazinyl)methyl)-1-propanesulfonamide (0.130 g, 0.228 mmol) in DMF (3.0 mL) was added 3-iodopyridine (0.094 g, 0.46 mmol, Sigma-Aldrich, St. Louis, Mo.), N,N'-dimethylethylenediamine (0.020 mL, 0.18 mmol, Sigma-Aldrich, St. Louis, Mo.), copper(i) iodide (0.022 g, 0.11 mmol, Sigma-Aldrich, St. Louis, Mo.), cesium carbonate (0.223 g, 0.685 mmol, Sigma-Aldrich, St. Louis, Mo.), and water (0.300 mL). The resulting mixture was heated at 120° C. under N₂ for 5 days. The reaction mixture was filtered through the Celite® (diatomaceous earth) and the filtrate was concentrated. The residue was purified by column chromatography (24 g of silica, 1% to 5% (2M NH₃ in MeOH) in DCM) to afford 2-methyl-N-3-pyridinyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide (15 mg) as a mixture of 2 isomers.

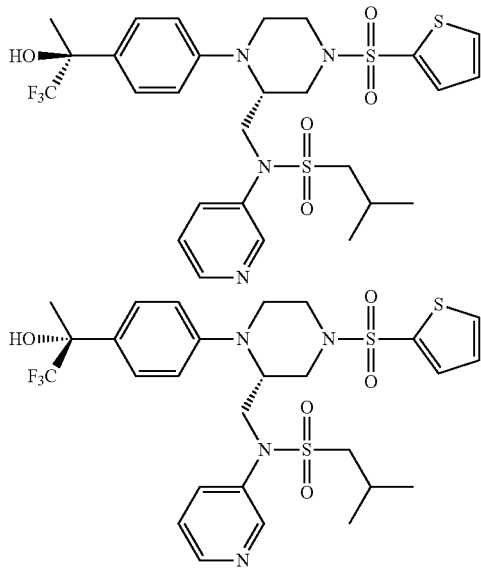

2-methyl-N-3-pyridinyl-N-(((2R)-4-(2-thiophenylsulfonyl)-1-(4-((1S)-2,2,2-trifluoro-1-hydroxy-1-methylethyl)phenyl)-2-piperazinyl)methyl)-1-propanesulfonamide; and 2-methyl-N-3-pyridinyl-N-(((2R)-4-(2-thiophenylsulfonyl)-1-(4-((1R)-2,2,2-trifluoro-1-hydroxy-1-methylethyl)phenyl)-2-piperazinyl)methyl)-1-propanesulfonamide.

¹H NMR (600 MHz, DMSO-d₆) δ=8.48 (td, J=1.3, 4.7 Hz, 1H), 8.44 (dd, J=2.3, 17.5 Hz, 1H), 8.02 (d, J=5.0 Hz, 1H), 7.63 (td, J=1.1, 3.6 Hz, 1H), 7.56 (dtd, J=1.5, 2.8, 8.1 Hz, 1H), 7.34-7.26 (m, 4H), 6.64 (dd, J=3.5, 9.0 Hz, 2H), 6.15 (s, 1H), 4.09-4.04 (m, 1H), 4.00 (dd, J=7.3, 14.5 Hz, 1H), 3.94 (ddd, J=3.4, 6.5, 14.3 Hz, 1H), 3.68 (d, J=11.5 Hz, 1H), 3.59-3.47 (m, 2H), 3.25-3.18 (m, 1H), 3.03 (dd, J=6.7, 13.9 Hz, 1H), 2.98 (ddd, J=5.3, 6.5, 13.9 Hz, 1H), 2.60 (td, J=2.9, 11.7 Hz, 1H), 2.42 (dt, J=3.0, 11.4 Hz, 1H), 2.10 (quind, J=6.7, 13.3 Hz, 1H), 1.63 (d, J=4.6 Hz, 3H), 0.99 (d, J=6.9 Hz, 3H), 0.99 (d, J=6.9 Hz, 3H). m/z (ESI, +ve ion) 647.2 (M+H)⁺. GK-GKRP IC₅₀ (Binding)=0.035 µM.

Example 254

4-fluoro-N-(((2S)-4-(2-thiophenylsulfonyl)-1-(4-(2,2,2-trifluoro-1-hydroxy-1-methylethyl)phenyl)-2-piperazinyl)methyl)benzenesulfonamide

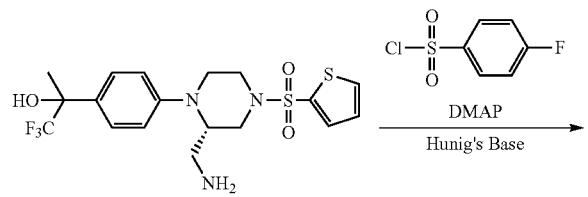

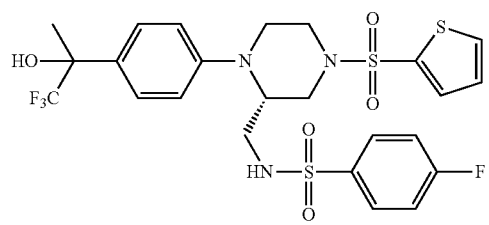

Following the procedure of Example 204, the reaction of 2-(4-((2S)-2-(aminomethyl)-4-(2-thiophenylsulfonyl)-1-piperazinyl)phenyl)-1,1,1-trifluoro-2-propanol (Example 192, Step 1) and 4-fluorobenzenesulfonyl chloride (Sigma-Aldrich, St. Louis, Mo.) delivered 4-fluoro-N-(((2S)-4-(2-thiophenylsulfonyl)-1-(4-(2,2,2-trifluoro-1-hydroxy-1-methylethyl)phenyl)-2-piperazinyl)methyl)benzenesulfonamide as a mixture of two isomers.

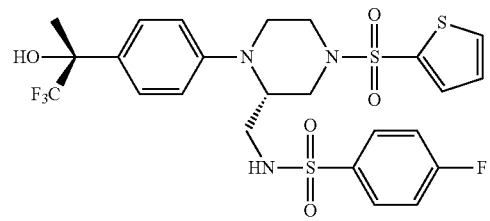

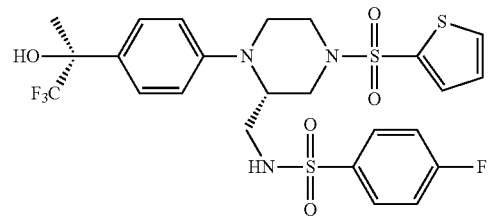

4-fluoro-N-(((2S)-4-(2-thiophenylsulfonyl)-1-(4-((1R)-2,2,2-trifluoro-1-hydroxy-1-methylethyl)phenyl)-2-piperazinyl)methyl)benzenesulfonamide; and 4-fluoro-N-(((2S)-4-(2-thiophenylsulfonyl)-1-(4-((1S)-2,2,2-trifluoro-1-hydroxy-1-methylethyl)phenyl)-2-piperazinyl)methyl)benzenesulfonamide.

¹H NMR (300 MHz, CDCl₃) δ=7.73 (dd, J=5.0, 8.6 Hz, 2H), 7.68 (dd, J=1.3, 5.1 Hz, 1H), 7.59 (dd, J=1.2, 3.7 Hz, 1H), 7.50 (d, J=8.8 Hz, 2H), 7.19 (dd, J=3.8, 5.0 Hz, 1H), 7.16-7.05 (m, 2H), 6.95 (d, J=8.8 Hz, 2H), 4.88 (br. s., 1H), 4.22 (br. s., 1H), 3.92 (d, J=12.4 Hz, 1H), 3.76 (d, J=11.0 Hz, 1H), 3.46 (d, J=12.3 Hz, 1H), 3.30-3.10 (m, 2H), 3.02-2.89

(m, 1H), 2.86-2.65 (m, 2H), 2.36 (d, J=2.6 Hz, 1H), 1.78 (s, 3H). m/z (ESI, +ve ion) 608.0 (M+H)⁺. GK-GKRP IC$_{50}$ (Binding)=0.323 µM.

Example 255

N-(4-fluorophenyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide

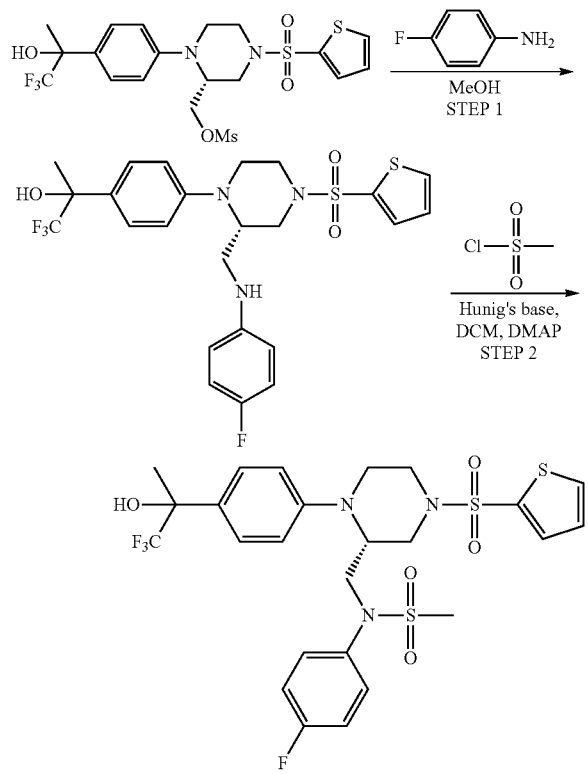

Step 1: 1,1,1-trifluoro-2-(4-((2S)-2-(((4-fluorophenyl)amino)methyl)-4-(2-thiophenylsulfonyl)-1-piperazinyl)phenyl)-2-propanol Following the procedure of Example 195, Step 1, the reaction of ((2R)-4-(thiophen-2-ylsulfonyl)-1-(4-(1,1,1-trifluoro-2-hydroxypropan-2-yl)phenyl)piperazin-2-yl)methyl methanesulfonate (Intermediate B) and 4-fluoroaniline (Sigma-Aldrich, St. Louis, Mo.) delivered 1,1,1-trifluoro-2-(4-((2S)-2-(((4-fluorophenyl)amino)methyl)-4-(2-thiophenylsulfonyl)-1-piperazinyl)phenyl)-2-propanol.

Step 2: N-(4-fluorophenyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide Following the procedure of Example 195, Step 2, the reaction of 1,1,1-trifluoro-2-(4-((2S)-2-(((4-fluorophenyl)amino)methyl)-4-(2-thiophenylsulfonyl)-1-piperazinyl)phenyl)-2-propanol and methanesulfonyl chloride (Sigma-Aldrich, St. Louis, Mo.) delivered N-(4-fluorophenyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide as a mixture of two isomers.

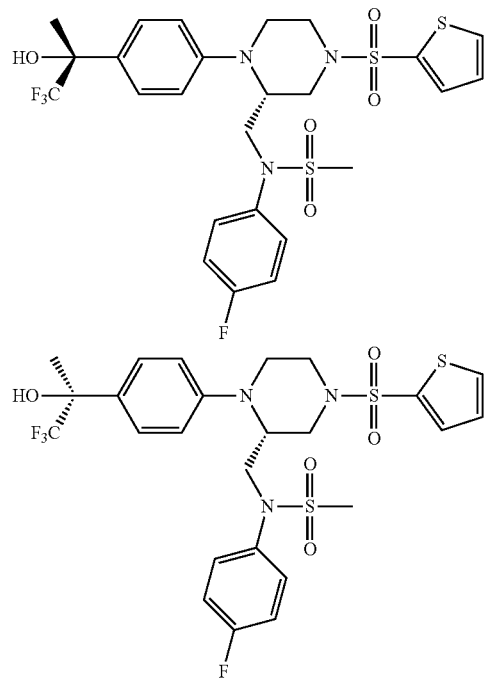

N-(4-fluorophenyl)-N-(((2R)-4-(2-thiophenylsulfonyl)-1-(4-((1R)-2,2,2-trifluoro-1-hydroxy-1-methylethyl)phenyl)-2-piperazinyl)methyl)methanesulfonamide; and N-(4-fluorophenyl)-N-(((2R)-4-(2-thiophenylsulfonyl)-1-(4-((1S)-2,2,2-trifluoro-1-hydroxy-1-methylethyl)phenyl)-2-piperazinyl)methyl)methanesulfonamide.

¹H NMR (300 MHz, CDCl₃) δ=7.65 (d, J=4.2 Hz, 1H), 7.56 (d, J=3.8 Hz, 1H), 7.39 (d, J=8.9 Hz, 2H), 7.22-7.12 (m, 1H), 7.07-6.94 (m, 4H), 6.72 (d, J=8.9 Hz, 2H), 4.18 (br. s., 1H), 4.06-3.94 (m, 1H), 3.93-3.78 (m, 2H), 3.72 (d, J=11.4 Hz, 1H), 3.48-3.22 (m, 2H), 2.85 (s, 3H), 2.73-2.61 (m, 1H), 2.52 (dt, J=3.9, 11.4 Hz, 1H), 2.32 (br. s., 1H), 1.76 (s, 3H). m/z (ESI, +ve ion) 622.2 (M+H)⁺. GK-GKRP IC$_{50}$ (Binding)=0.002 µM.

Example 256

N-(4-fluorophenyl)-N-(((2S)-4-(2-thiophenylsulfonyl)-1-(4-(2,2,2-trifluoro-1-hydroxy-1-methylethyl)phenyl)-2-piperazinyl)methyl)acetamide

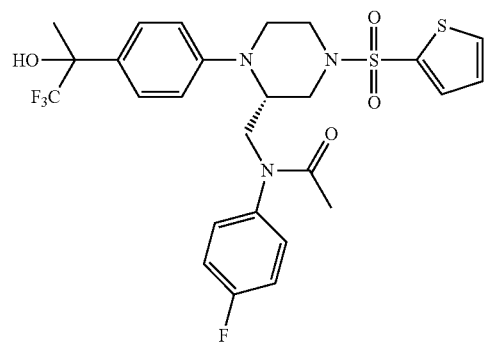 [SMILES: CC(=O)N(C[C@H]1CN(S(=O)(=O)c2cccs2)CCN1c1ccc(C(C)(O)C(F)(F)F)cc1)c1ccc(F)cc1]

Following the procedure of Example 196, the reaction of 1,1,1-trifluoro-2-(4-((2S)-2-(((4-fluorophenyl)amino)methyl)-4-(2-thiophenylsulfonyl)-1-piperazinyl)phenyl)-2-propanol and acetyl chloride (Sigma-Aldrich, St. Louis, Mo.) delivered N-(4-fluorophenyl)-N-(((2S)-4-(2-thiophenylsulfonyl)-1-(4-(2,2,2-trifluoro-1-hydroxy-1-methylethyl)phenyl)-2-piperazinyl)methyl)acetamide as a mixture of two isomers.

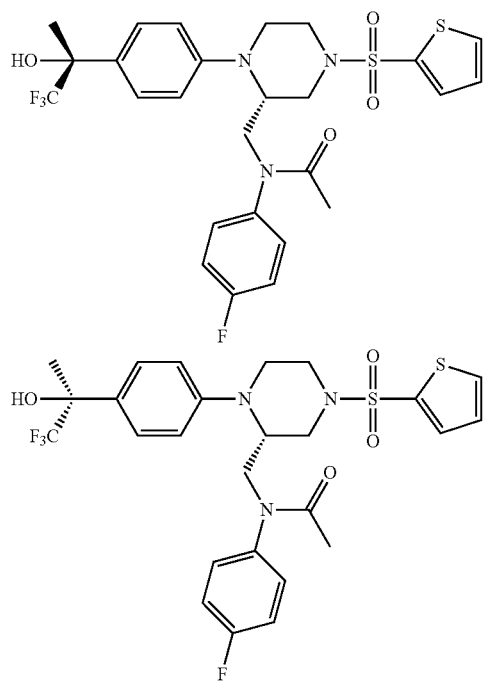

N-(4-fluorophenyl)-N-(((2S)-4-(2-thiophenylsulfonyl)-1-(4-((1R)-2,2,2-trifluoro-1-hydroxy-1-methylethyl)phenyl)-2-piperazinyl)methyl)acetamide; and N-(4-fluorophenyl)-N-(((2S)-4-(2-thiophenylsulfonyl)-1-(4-((1S)-2,2,2-trifluoro-1-hydroxy-1-methylethyl)phenyl)-2-piperazinyl)methyl)acetamide.

$^1$H NMR (300 MHz, CDCl$_3$) δ=7.64 (dd, J=1.2, 5.0 Hz, 1H), 7.54 (dd, J=1.2, 3.7 Hz, 1H), 7.43 (d, J=8.8 Hz, 2H), 7.16 (dd, J=3.8, 5.0 Hz, 1H), 7.07-6.95 (m, 2H), 6.91-6.70 (m, 4H), 4.64 (br. s., 1H), 4.20 (ddd, J=2.6, 8.5, 13.9 Hz, 1H), 3.88-3.58 (m, 3H), 3.50-3.37 (m, 1H), 3.34-3.16 (m, 1H), 2.68 (d, J=8.8 Hz, 1H), 2.59-2.43 (m, 1H), 2.38 (s, 1H), 1.76 (s, 3H), 1.70 (s, 3H). m/z (ESI, +ve ion) 586.2 (M+H)$^+$. GK-GKRP IC$_{50}$ (Binding)=0.023 μM.

Example 257

1,1,1,3,3,3-hexafluoro-2-(4-(2-((2-methoxy-3-pyridinyl)methyl)-4-(2-thiophenylsulfonyl)-1-piperazinyl)phenyl)-2-propanol

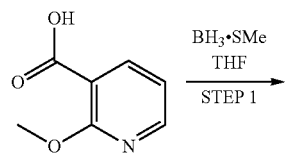

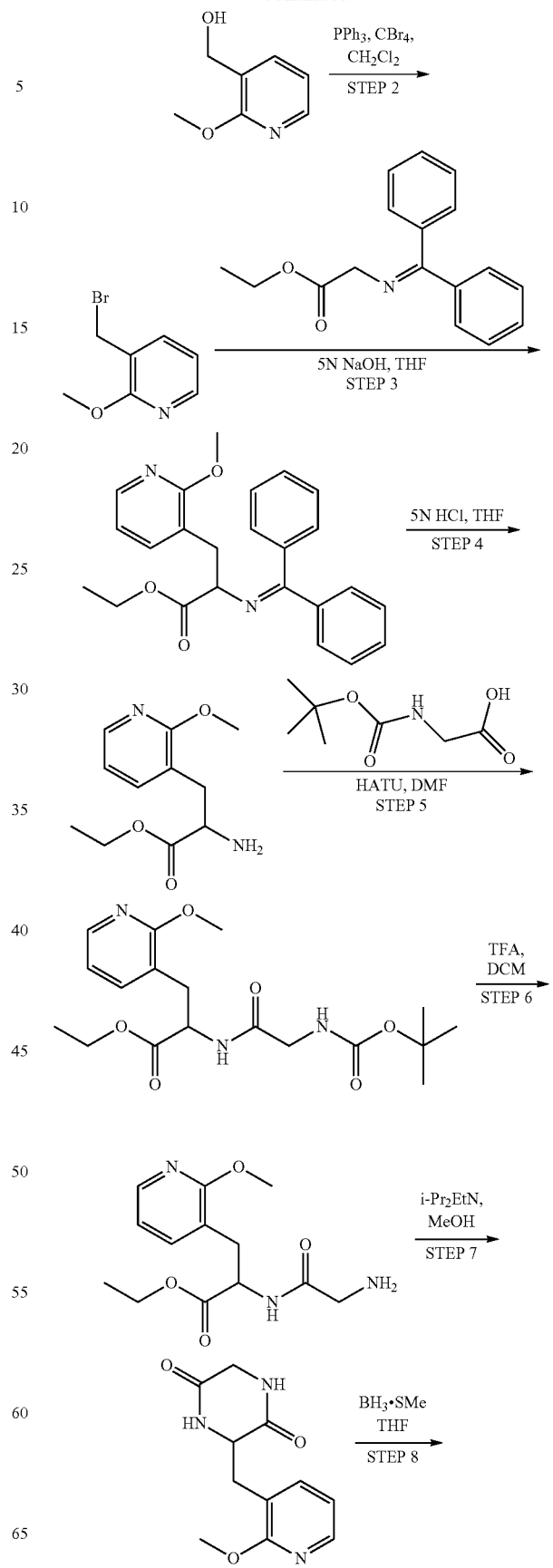

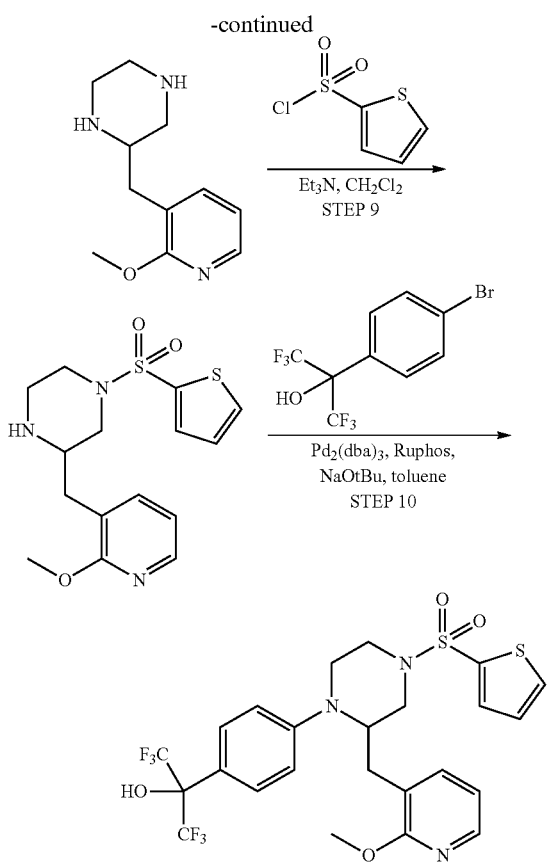

Step 1: (2-methoxy-3-pyridinyl)methanol

To a 100-mL round-bottomed flask was added 2-methoxynicotinic acid (1.52 g, 9.93 mmol, Aldrich, St. Louis, Mo.) and borane methyl sulfide complex (3.77 mL, 39.7 mmol, Aldrich, St. Louis, Mo.) in tetrahydrofuran (30 mL). The reaction mixture was stirred at 70° C. for 16 h. The mixture was cooled to 0° C. and MeOH (10 mL) was added dropwise. After the addition was completed, the reaction mixture was stirred for further 20 min. The solvent was removed in vacuo and the residue was purified by silica gel chromatography, eluting with 60% EtOAc/hexanes to give (2-methoxy-3-pyridinyl)methanol (1.15 g) as a white solid.

Step 2: 3-(bromomethyl)-2-methoxypyridine

To a 100-mL round-bottomed flask was added (2-methoxy-3-pyridinyl)methanol (1.12 g, 8.05 mmol), triphenylphosphine (2.32 g, 8.85 mmol, Aldrich, St. Louis, Mo.) and carbon tetrabromide (0.86 mL, 8.85 mmol, Aldrich, St. Louis, Mo.) in DCM (20 mL). The reaction mixture was stirred at room temperature for 3 h. The solvent was removed in vacuo and the residue was purified by silica gel chromatography, eluting with 20% EtOAc/hexanes to give 3-(bromomethyl)-2-methoxypyridine (1.10 g) as a colorless oil.

Step 3: ethyl N-(diphenylmethylidene)-3-(2-methoxy-3-pyridinyl)alaninate

To a 100-mL round-bottomed flask were added 3-(bromomethyl)-2-methoxypyridine (1.10 g, 5.44 mmol), ethyl N-(diphenylmethylene)glycinate (1.46 g, 5.44 mmol, Acros, N.J.) and 5N sodium hydroxide (5.44 mL, 27.2 mmol) in tetrahydrofuran (30 mL). The reaction mixture was stirred at room temperature for 24 h. The reaction mixture was diluted with water (30 mL) and extracted with EtOAc (2×50 mL). The organic extract was washed with saturated NaCl (20 mL) and dried over $Na_2SO_4$. The solution was filtered and concentrated in vacuo to give the crude material as light-yellow oil. The crude product was purified by silica gel chromatography, eluting with 20% EtOAc/hexanes to give ethyl N-(diphenylmethylidene)-3-(2-methoxy-3-pyridinyl)alaninate (1.52 g) as viscous oil.

Step 4: ethyl 3-(2-methoxy-3-pyridinyl)alaninate

To a 100-mL round-bottomed flask was added ethyl N-(diphenylmethylidene)-3-(2-methoxy-3-pyridinyl)alaninate (1.52 g, 3.91 mmol) and 5N hydrochloric acid (1.72 mL, 8.61 mmol) in tetrahydrofuran (20 mL). The reaction mixture was stirred at 0° C. for 1 h. The solvent was removed in vacuo to give crude ethyl 3-(2-methoxy-3-pyridinyl)alaninate as a white tar, which was used without purification.

Step 5: ethyl N-(tert-butoxycarbonyl)glycyl-3-(2-methoxy-3-pyridinyl)alaninate

To a 100-mL round-bottomed flask was added ethyl 3-(2-methoxy-3-pyridinyl)alaninate (0.877 g, 3.91 mmol), N-α-t-Boc-glycine (0.753 g, 4.30 mmol, Aldrich, St. Louis, Mo.), HATU (1.784 g, 4.69 mmol, Aldrich, St. Louis, Mo.) and N,N-diisopropylethylamine (2.05 mL, 11.73 mmol, Aldrich, St. Louis, Mo.) in DMF (8 mL). The reaction mixture was stirred at room temperature for 16 h. The reaction mixture was diluted with water (30 mL) and extracted with EtOAc (2×50 mL). The organic extract was washed with saturated NaCl (20 mL) and dried over $Na_2SO_4$. The solution was filtered and concentrated in vacuo to give the crude material as a light-yellow oil. The crude product was purified by silica gel chromatography, eluting with 60% EtOAc/hexanes to give ethyl N-(tert-butoxy carbonyl)glycyl-3-(2-methoxy-3-pyridinyl)alaninate (1.38 g) as a colorless oil.

Step 6: ethyl glycyl-3-(2-methoxy-3-pyridinyl)alaninate

To a 100-mL round-bottomed flask was added ethyl N-(tert-butoxycarbonyl)glycyl-3-(2-methoxy-3-pyridinyl)alaninate (1.38 g, 3.62 mmol) and trifluoroacetic acid (5 mL, 67.3 mmol) in DCM (5 mL). The reaction mixture was stirred at room temperature for 2 h. The solvent was removed in vacuo to give the crude ethyl glycyl-3-(2-methoxy-3-pyridinyl)alaninate as a colorless oil, which was used without purification.

Step 7: 3-((2-methoxy-3-pyridinyl)methyl)-2,5-piperazinedione

To a 100-mL round-bottomed flask was added ethyl glycyl-3-(2-methoxy-3-pyridinyl)alaninate (1.018 g, 3.62 mmol) and N,N-diisopropylethylamine (0.63 mL, 3.62 mmol) in MeOH (20 mL). The reaction mixture was stirred at 70° C. for 36 h. The solvent was partially removed under a vacuum and the solid formed was filtered, washed with MeOH and dried to give 3-((2-methoxy-3-pyridinyl)methyl)-2,5-piperazinedione (0.732 g) as a white solid.

Step 8: 2-((2-methoxy-3-pyridinyl)methyl)piperazine

To a 100-mL round-bottomed flask was added 3-((2-methoxy-3-pyridinyl)methyl)-2,5-piperazinedione (398 mg, 1.69 mmol) and borane methyl sulfide, complex (0.64 mL, 6.77 mmol, Aldrich, St. Louis, Mo.) in THF (10 mL). The reaction mixture was stirred at 70° C. for 2 h. The mixture was cooled to room temperature, diluted with MeOH (1 mL), followed by 1N NaOH (12 mL), and extracted with DCM (2×50 mL). The organic extract was washed with saturated NaCl (20 mL) and dried over $Na_2SO_4$. The solution was filtered and concentrated in vacuo to give the crude 2-((2-methoxy-3-pyridinyl)methyl)piperazine as colorless viscous oil, which was used without purification.

Step 9: 3-((2-methoxy-3-pyridinyl)methyl)-1-(2-thiophenylsulfonyl)piperazine

To a 100-mL round-bottomed flask was added 2-((2-methoxy-3-pyridinyl)methyl)piperazine (350 mg, 1.69 mmol), triethylamine (0.353 mL, 2.54 mmol), and 2-thiophenesulfonyl chloride (0.34 mL, 1.86 mmol, Aldrich, St. Louis, Mo.) in DCM (5 mL). The reaction mixture was stirred at 0° C. for 1 h. The reaction mixture was diluted with saturated $NaHCO_3$ (5 mL) and extracted with EtOAc (2×30 mL). The organic extract was washed with saturated NaCl (5 mL) and dried over $Na_2SO_4$. The solution was filtered and concentrated in vacuo to give the crude material as a yellow glass. The crude product was purified by silica gel chromatography, eluting with 10% MeOH/EtOAc to give 3-((2-methoxy-3-pyridinyl)methyl)-1-(2-thiophenylsulfonyl)piperazine (202 mg) as a white solid.

Step 10: 1,1,1,3,3,3-hexafluoro-2-(4-(2-((2-methoxy-3-pyridinyl)methyl)-4-(2-thiophenylsulfonyl)-1-piperazinyl)phenyl)-2-propanol To a 50-mL round-bottomed flask was added 3-((2-methoxy-3-pyridinyl)methyl)-1-(2-thiophenylsulfonyl)piperazine (202 mg, 0.571 mmol), dicyclohexyl(2',4',6'-triisopropyl-[1',1'-biphenyl]-2-yl)phosphine (RuPhos) (109 mg, 0.23 mmol, Strem, Newburyport, Mass.), tris(dibenzylideneacetone)dipalladium (52 mg, 0.057 mmol, Strem, Newburyport, Mass.), 2-(4-bromophenyl)-1,1,1,3,3,3-hexafluoropropan-2-ol (222 mg, 0.69 mmol, Bioorg. Med. Chem. Lett. 2002, 12, 3009), and sodium tert-butoxide (165 mg, 1.71 mmol, Aldrich, St. Louis, Mo.) in toluene (5 mL). The reaction mixture was stirred at 100° C. for 18 h and then allowed to cool to room temperature. The reaction mixture was diluted with saturated $NH_4Cl$ (5 mL) and extracted with EtOAc (2×40 mL). The organic extract was washed with saturated NaCl (5 mL) and dried over $Na_2SO_4$. The solution was filtered and concentrated in vacuo to give the crude material as a light-yellow oil. The crude product was purified by silica gel chromatography, eluting with 40% EtOAc/hexanes to give 1,1,1,3,3,3-hexafluoro-2-(4-(2-((2-methoxy-3-pyridinyl)methyl)-4-(2-thiophenylsulfonyl)-1-piperazinyl)phenyl)-2-propanol (226 mg) as a colorless oil (mixture of enantiomers).

$^1$H NMR (300 MHz, $CDCl_3$) δ 8.04 (dd, J=1.75, 5.12 Hz, 1H), 7.62 (dd, J=1.17, 5.12 Hz, 1H), 7.50-7.59 (m, 3H), 7.15 (dd, J=3.80, 5.12 Hz, 1H), 6.99-7.01 (m, 1H), 6.94-7.02 (m, 2H), 6.86 (dd, J=5.12, 7.02 Hz, 1H), 4.21-4.31 (m, 1H), 3.94 (s, 3H), 3.85-3.93 (m, 1H), 3.51-3.67 (m, 1H), 3.39-3.51 (m, 1H), 3.36 (s, 1H), 3.05 (dd, J=10.23, 12.86 Hz, 1H), 2.86 (dd, J=3.65, 12.72 Hz, 1H), 2.44-2.63 (m, 2H); m/z (ESI, +ve ion) 595.8 (M+H)$^+$. GK-GKRP $IC_{50}$ (Binding)=0.177 μM.

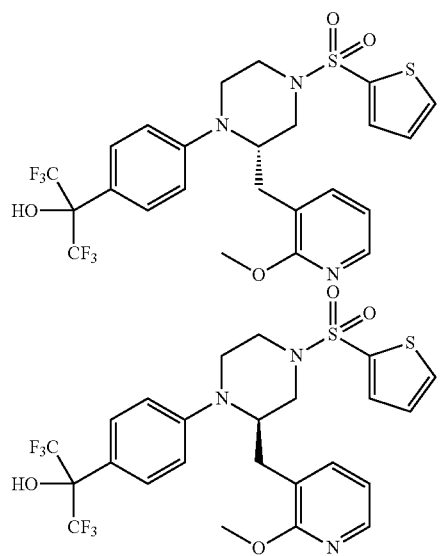

1,1,1,3,3,3-hexafluoro-2-(4-((2S)-2-((2-methoxy-3-pyridinyl)methyl)-4-(2-thiophenylsulfonyl)-1-piperazinyl)phenyl)-2-propanol; and 1,1,1,3,3,3-hexafluoro-2-(4-((2R)-2-((2-methoxy-3-pyridinyl)methyl)-4-(2-thiophenylsulfonyl)-1-piperazinyl)phenyl)-2-propanol.

Example 258

1,1,1,3,3,3-hexafluoro-2-(4-(2-((6-methoxy-2-pyridinyl)methyl)-4-(2-thiophenylsulfonyl)-1-piperazinyl)phenyl)-2-propanol

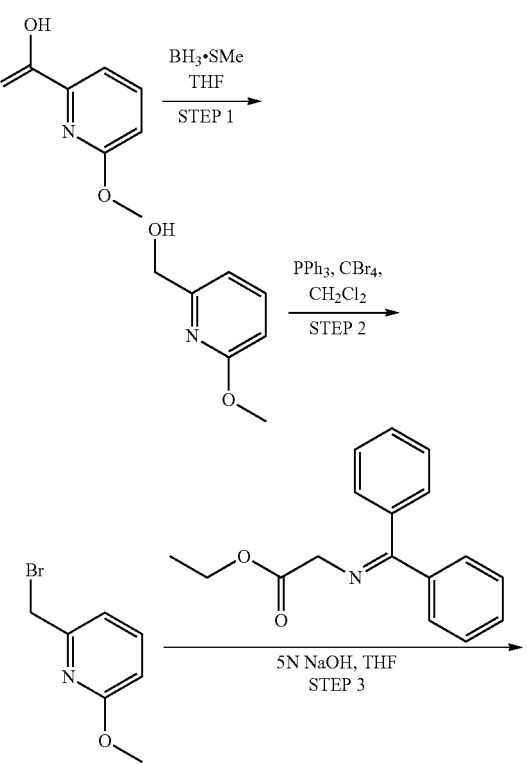

487
-continued

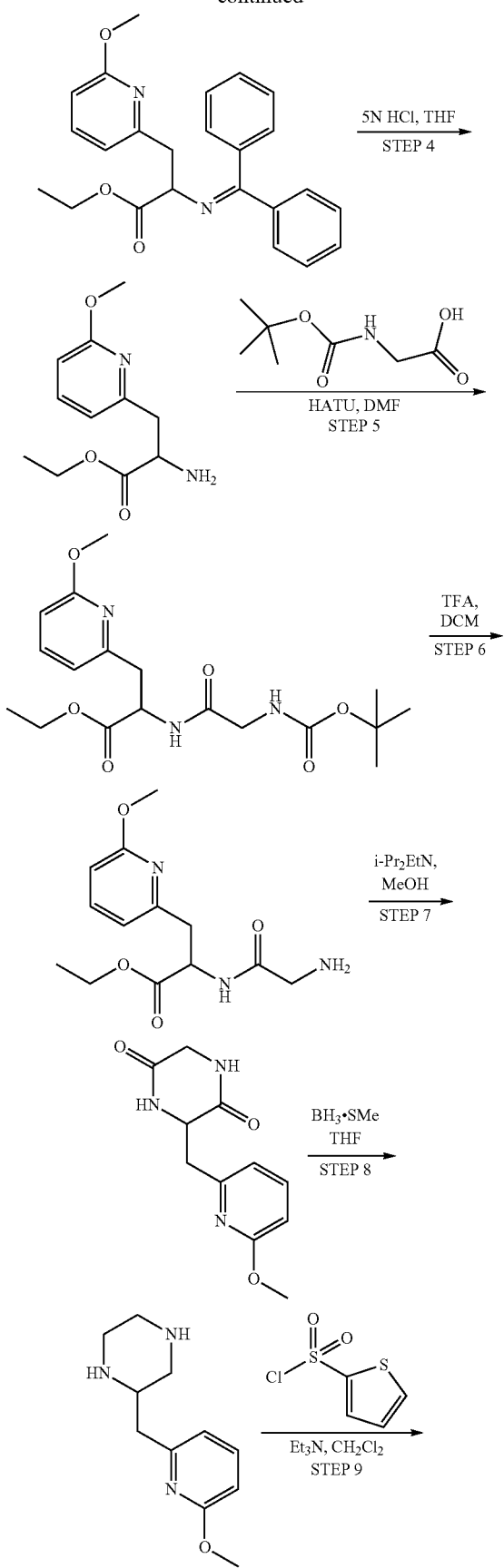

488
-continued

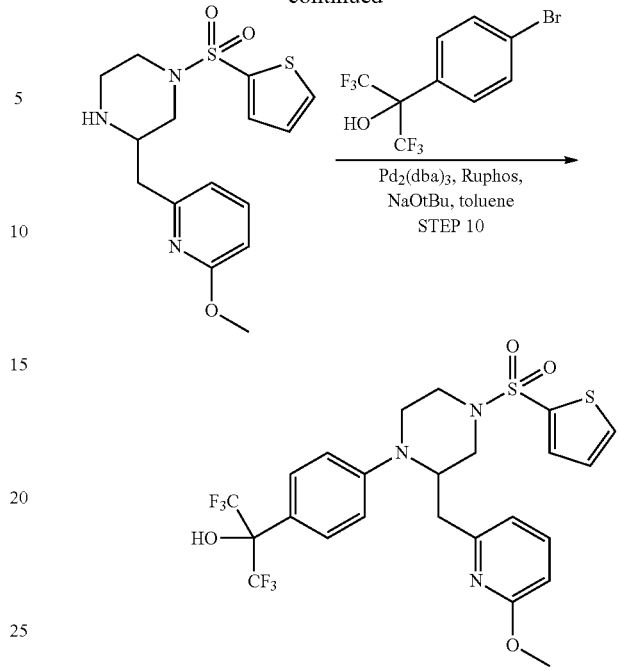

Step 1: 6-methoxy-2-pyridinyl)methanol

To a 100-mL round-bottomed flask was added 6-methoxypyridine-2-m carboxylic acid (1.5 g, 9.80 mmol, Aldrich, St. Louis, Mo.) and borane methyl sulfide complex (3.72 mL, 39.2 mmol, Aldrich, St. Louis, Mo.) in THF (20 mL). The reaction mixture was stirred at 70° C. for 18 h, cooled to 0° C., and then carefully quenched by the addition of MeOH (10 mL). After the addition was completed, the reaction mixture was stirred for an additional 20 min at rt. The solvent was removed in vacuo and the residue was purified by silica gel chromatography, eluting with 60% EtOAc/hexanes to give 6-methoxy-2-pyridinyl)methanol (1.09 g) as a white solid.

Step 2: 2-(bromomethyl)-6-methoxypyridine

To a 100-mL round-bottomed flask was added 6-methoxy-2-pyridinyl)methanol (1.1 g, 7.91 mmol), triphenylphosphine (2.28 g, 8.70 mmol, Aldrich, St. Louis, Mo.) and tetrabromomethane (0.84 mL, 8.70 mmol, Aldrich, St. Louis, Mo.) in DCM (20 mL). The reaction mixture was stirred at 0° C. for 2 h. The solvent was removed in vacuo and the residue was purified by silica gel chromatography, eluting with 10% EtOAc/hexanes to give 2-(bromomethyl)-6-methoxypyridine (1.33 g) as a colorless oil.

Step 3: ethyl N-(diphenylmethylidene)-3-(6-methoxy-2-pyridinyl)alaninate

To a 100-mL round-bottomed flask was added 2-(bromomethyl)-6-methoxypyridine (1.33 g, 6.58 mmol), 2-(bromomethyl)-6-methoxypyridine (1.33 g, 6.58 mmol), ethyl N-(diphenylmethylene)glycinate (1.76 g, 6.58 mmol, Acros, N.J.) and 5N sodium hydroxide (6.58 mL, 32.9 mmol) in THF (30 mL). The reaction mixture was stirred at room temperature for 24 h. The reaction mixture was diluted with water (30 mL) and extracted with EtOAc (2×50 mL). The organic extract was washed with saturated NaCl (30 mL) and dried over Na$_2$SO$_4$. The solution was filtered and concentrated in vacuo to give the crude material as a light-yellow oil. The crude product was purified by silica gel chromatography, eluting with 10% EtOAc/hexanes to give ethyl N-(diphenylmethylidene)-3-(6-methoxy-2-pyridinyl)alaninate (1.86 g) as a colorless oil.

Step 4: ethyl 3-(6-methoxy-2-pyridinyl)alaninate

To a 100-mL round-bottomed flask was added ethyl N-(diphenylmethylidene)-3-(6-methoxy-2-pyridinyl)alaninate (1.81 g, 4.66 mmol) and 5N hydrochloric acid (1.86 mL, 9.32 mmol), and THF (20 mL). The reaction mixture was stirred at room temperature for 30 min. The solvent was removed in vacuo to give crude ethyl 3-(6-methoxy-2-pyridinyl)alaninate as a light-yellow tar, which was used without purification.

Step 5: ethyl N-(tert-butoxycarbonyl)glycyl-3-(6-methoxy-2-pyridinyl)alaninate

To a 100-mL round-bottomed flask was added ethyl 3-(6-methoxy-2-pyridinyl)alaninate (1.045 g, 4.66 mmol), N-bocglycine (0.898 g, 5.13 mmol, Aldrich, St. Louis, Mo.), HATU (2.126 g, 5.59 mmol, Aldrich, St. Louis, Mo.), and N,N-diisopropylethylamine (2.43 mL, 13.98 mmol, Aldrich, St. Louis, Mo.) in DMF (5 mL). The reaction mixture was stirred at room temperature for 3 h. The reaction mixture was diluted with water (40 mL) and extracted with EtOAc (2×50 mL). The organic extract was washed with saturated NaCl (30 mL) and dried over Na$_2$SO$_4$. The solution was filtered and concentrated in vacuo to give the crude material as light-yellow oil. The crude product was purified by silica gel chromatography, eluting with 70% EtOAc/hexanes to give ethyl N-(tert-butoxycarbonyl)glycyl-3-(6-methoxy-2-pyridinyl)alaninate (1.29 g) as a colorless oil.

Step 6: ethyl glycyl-3-(6-methoxy-2-pyridinyl)alaninate

To a 100-mL round-bottomed flask was added ethyl N-(tert-butoxycarbonyl)glycyl-3-(6-methoxy-2-pyridinyl)alaninate (1.28 g, 3.36 mmol) and trifluoroacetic acid (5 mL, 67.3 mmol) in DCM (5 mL). The reaction mixture was stirred at room temperature for 3 h. The solvent was removed in vacuo to give the crude ethyl glycyl-3-(6-methoxy-2-pyridinyl)alaninate as a colorless viscous oil, which was used without purification.

Step 7: 3-((6-methoxy-2-pyridinyl)methyl)-2,5-piperazinedione

To a 100-mL round-bottomed flask was added ethyl glycyl-3-(6-methoxy-2-pyridinyl)alaninate (945 mg, 3.36 mmol) and N,N-diisopropylethylamine (0.58 mL, 3.36 mmol) in MeOH (20 mL). The reaction mixture was stirred at 70° C. for two days. The mixture was allowed to cool to room temperature. The solid that formed was collected by filtration, washed with MeOH, and dried to give 3-((6-methoxy-2-pyridinyl)methyl)-2,5-piperazinedione (426 mg) as a white solid.

Step 8: 2-((6-methoxy-2-pyridinyl)methyl)piperazine

To a 50-mL round-bottomed flask was added 3-((6-methoxy-2-pyridinyl)methyl)-2,5-piperazinedione (423 mg, 1.80 mmol), borane methyl sulfide, complex (0.68 mL, 7.19 mmol, Aldrich, St. Louis, Mo.), and THF (6 mL). The reaction mixture was stirred at 70° C. for 2 h and allowed to cool to room temperature. The reaction mixture was diluted with MeOH (1 mL), followed by 1N NaOH (12 mL), and extracted with DCM (2×50 mL). The organic extracts were washed with saturated NaCl (10 mL) and dried over Na$_2$SO$_4$. The solution was filtered and concentrated in vacuo to give the crude 2-((6-methoxy-2-pyridinyl)methyl)piperazine as light-yellow viscous oil, which was used without purification.

Step 9: 3-((6-methoxy-2-pyridinyl)methyl)-1-(2-thiophenylsulfonyl)piperazine

To a 100-mL round-bottomed flask were added 2-((6-methoxy-2-pyridinyl)methyl)piperazine (373 mg, 1.80 mmol), triethylamine (0.375 mL, 2.70 mmol), 2-thiophenesulfonyl chloride (0.328 mL, 1.80 mmol, Aldrich, St. Louis, Mo., and DCM (5 mL). The reaction mixture was stirred at 0° C. for 1 h. The reaction mixture was diluted with saturated NaHCO$_3$ (5 mL) and extracted with EtOAc (2×30 mL). The organic extract was washed with saturated NaCl (5 mL) and dried over Na$_2$SO$_4$. The solution was filtered and concentrated in vacuo to give the crude material as light-yellow oil. The crude product was purified by silica gel chromatography, eluting with 10% MeOH/EtOAc to give 3-((6-methoxy-2-pyridinyl)methyl)-1-(2-thiophenylsulfonyl)piperazine (135 mg) as viscous oil.

Step 10: 1,1,1,3,3,3-hexafluoro-2-(4-(2-((6-methoxy-2-pyridinyl)methyl)-4-(2-thiophenylsulfonyl)-1-piperazinyl)phenyl)-2-propanol To a 50-mL round-bottomed flask was added 3-((6-methoxy-2-pyridinyl)methyl)-1-(2-thiophenylsulfonyl)piperazine (115 mg, 0.325 mmol), 2-(4-bromophenyl)-1,1,1,3,3,3-hexafluoropropan-2-ol (126 mg, 0.390 mmol, Bioorg. Med. Chem. Lett. 2002, 12, 3009), dicyclohexyl(2',4',6'-triisopropyl-[1',1'-biphenyl]-2-yl)phosphine (RuPhos)(62 mg, 0.13 mmol, Strem, Newburyport, Mass.), tris(dibenzylideneacetone)dipalladium (30 mg, 0.033 mmol, Strem, Newburyport, Mass.) and sodium tert-butoxide (94 mg, 0.98 mmol, Aldrich, St. Louis, Mo.) in toluene (5 mL). The reaction mixture was stirred at 100° C. for 18 h and then allowed to cool to room temperature and then diluted with saturated NH$_4$Cl (5 mL) and extracted with EtOAc (2×40 mL). The organic extract was washed with saturated NaCl (5 mL) and dried over Na$_2$SO$_4$. The solution was filtered and concentrated in vacuo to give the crude material as a light-yellow oil. The crude product was purified by silica gel chromatography, eluting with 30% EtOAc/hexanes to give 1,1,1,3,3,3-hexafluoro-2-(4-(2-((6-methoxy-2-pyridinyl)methyl)-4-(2-thiophenylsulfonyl)-1-piperazinyl)phenyl)-2-propanol (146 mg) as a light-yellow tar (mixture of enantiomers).

$^1$H NMR (300 MHz, CDCl$_3$) δ 7.62 (dd, J=1.17, 4.97 Hz, 1H), 7.51-7.58 (m, 3H), 7.48 (dd, J=7.23, 8.26 Hz, 1H), 7.14 (dd, J=3.80, 4.97 Hz, 1H), 7.08 (d, J=9.21 Hz, 2H), 6.80 (d, J=7.16 Hz, 1H), 6.58 (d, J=8.18 Hz, 1H), 4.44-4.54 (m, 1H), 3.98 (s, 3H), 3.86-3.95 (m, 1H), 3.60-3.71 (m, 2H), 3.32-3.44 (m, 2H), 3.26 (dd, J=10.08, 13.45 Hz, 1H), 2.76-2.86 (m, 1H), 2.53-2.68 (m, 2H); m/z (ESI, +ve ion) 595.7 (M+H)$^+$. GK-GKRP IC$_{50}$ (Binding)=0.281 μM.

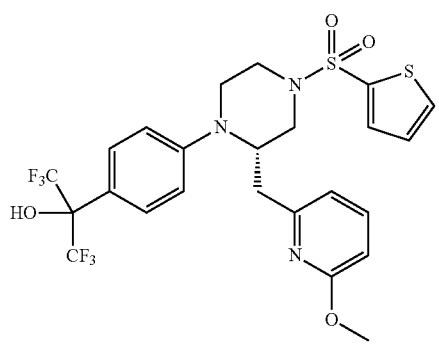
1,1,1,3,3,3-hexafluoro-2-(4-((2S)-2-((6-methoxy-2-pyridinyl)methyl)-4-(2-thiophenylsulfonyl)-1-piperazinyl)phenyl)-2-propanol; and 1,1,1,3,3,3-hexafluoro-2-(4-((2R)-2-((6-methoxy-2-pyridinyl)methyl)-4-(2-thiophenylsulfonyl)-1-piperazinyl)phenyl)-2-propanol.
Example 259
4-((4-(2-thiophenylsulfonyl)-1-(4-(2,2,2-trifluoro-1-hydroxy-1-(trifluoromethyl)ethyl)phenyl)-2-piperazinyl)methyl)-2(1H)-pyridinone
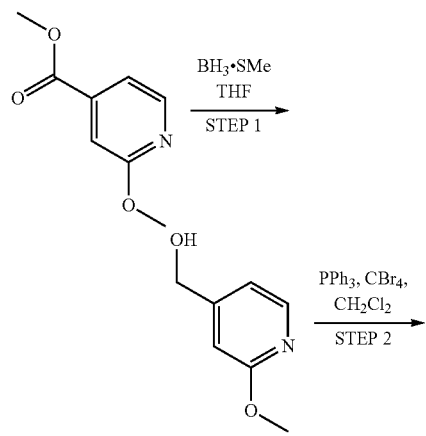
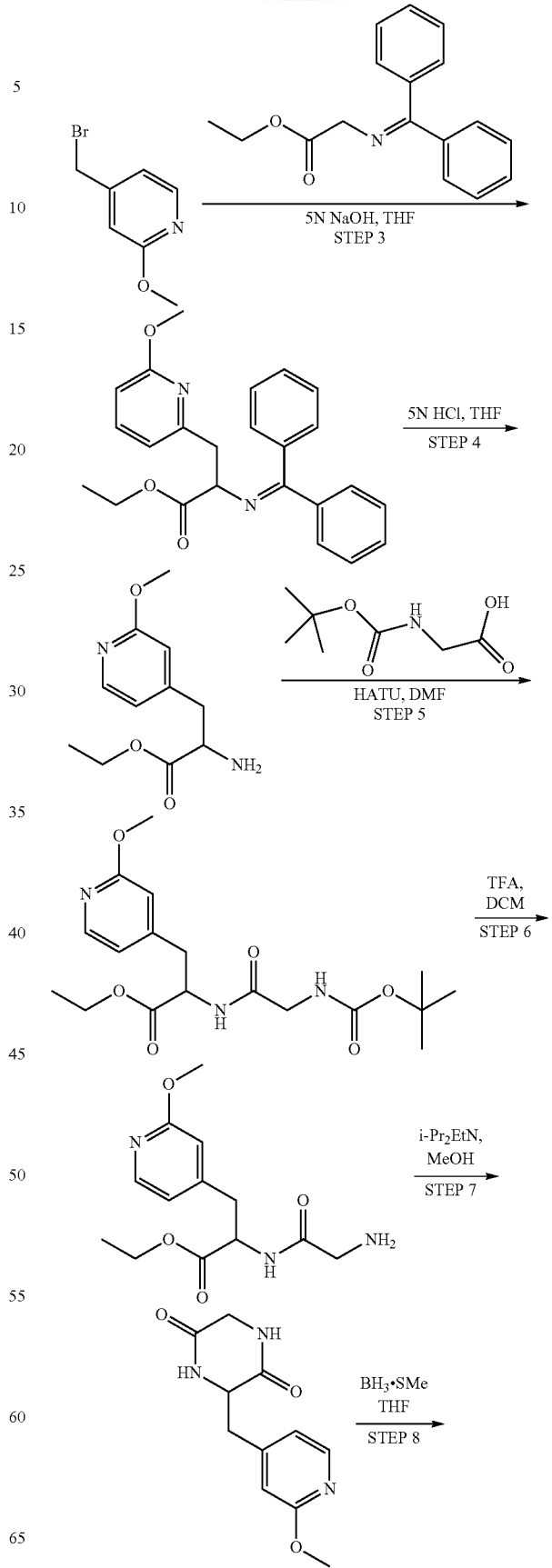

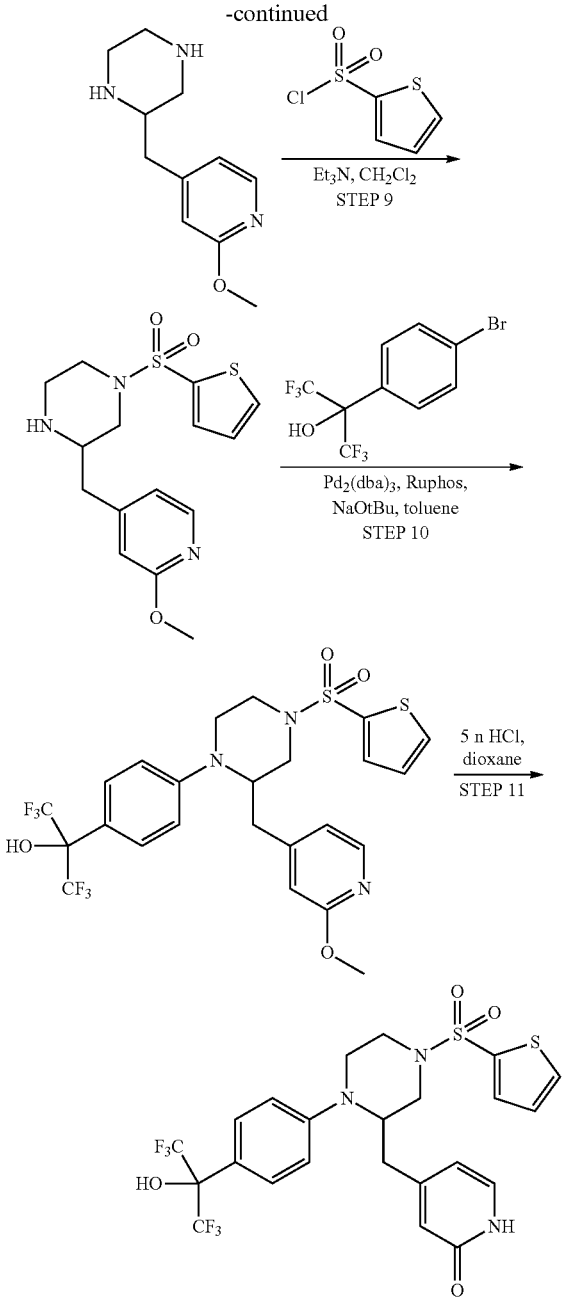

Step 2: 4-(bromomethyl)-2-methoxypyridine

To a 100-mL round-bottomed flask was added (2-methoxy-4-pyridinyl)methanol (1.52 g, 10.92 mmol), triphenylphosphine (3.15 g, 12.02 mmol, Aldrich, St. Louis, Mo.), and carbon tetrabromide (1.165 mL, 12.02 mmol, Aldrich, St. Louis, Mo.) in DCM (20 mL). The reaction mixture was stirred at 0° C. for 2 h. The solvent was removed in vacuo and the residue was purified by silica gel chromatography, eluting with 20% EtOAc/hexanes to give 4-(bromomethyl)-2-methoxypyridine (1.98 g) as a colorless oil.

Step 3: ethyl N-(diphenylmethylidene)-3-(6-methoxy-2-pyridinyl)alaninate

To a 100-mL round-bottomed flask were added 4-(bromomethyl)-2-methoxypyridine (1.98 g, 9.80 mmol), ethyl N-(diphenylmethylene)glycinate (2.62 g, 9.80 mmol, Acros, N.J.) and 5N sodium hydroxide (9.80 mL, 49.0 mmol) in THF (20 mL). The reaction mixture was stirred at room temperature for 24 h, diluted with water (30 mL), and extracted with EtOAc (2×50 mL). The organic extract was washed with saturated NaCl (30 mL) and dried over $Na_2SO_4$. The solution was filtered and concentrated in vacuo to give the crude material as a light-yellow oil. The crude product was purified by silica gel chromatography, eluting with 20% EtOAc/hexanes to give ethyl N-(diphenylmethylidene)-3-(6-methoxy-2-pyridinyl)alaninate (2.58 g) as a light-yellow oil.

Step 4: ethyl 3-(2-methoxy-4-pyridinyl)alaninate

To a 100-mL round-bottomed flask was added ethyl N-(diphenylmethylidene)-3-(6-methoxy-2-pyridinyl)alaninate (2.55 g, 6.56 mmol) and 5N hydrochloric acid (2.89 mL, 14.44 mmol) in THF (20 mL). The reaction mixture was stirred at 0° C. for 2 h. The solvent was removed in vacuo to give crude ethyl 3-(2-methoxy-4-pyridinyl)alaninate as a white solid, which was used without purification.

Step 5: ethyl N-(tert-butoxycarbonyl)glycyl-3-(2-methoxy-4-pyridinyl)alaninate

To a 100-mL round-bottomed flask was added ethyl 3-(2-methoxy-4-pyridinyl)alaninate (1.47 g, 6.56 mmol), N-α-t-boc-glycine (1.26 g, 7.22 mmol, Aldrich, St. Louis, Mo.), HATU (2.99 g, 7.87 mmol, Aldrich, St. Louis, Mo.) and N,N-diisopropylethylamine (3.42 mL, 19.68 mmol, Aldrich, St. Louis, Mo.) in DMF (6 mL). The reaction mixture was stirred room temperature for 18 h, diluted with water (50 mL), and extracted with EtOAc (2×20 mL). The organic extract was washed with saturated NaCl (30 mL) and dried over $Na_2SO_4$. The solution was filtered and concentrated in vacuo to give the crude material as a light-yellow oil. The crude product was purified by silica gel chromatography, eluting with 60% EtOAc/hexanes to give ethyl N-(tert-butoxycarbonyl)glycyl-3-(2-methoxy-4-pyridinyl)alaninate (2.31 g) as a colorless oil.

Step 6: ethyl glycyl-3-(2-methoxy-4-pyridinyl)alaninate

To a 100-mL round-bottomed flask was added ethyl N-(tert-butoxycarbonyl)glycyl-3-(2-methoxy-4-pyridinyl) alaninate (2.3 g, 6.03 mmol) and trifluoroacetic acid (8 mL, 108 mmol) in DCM (8 mL). The reaction mixture was stirred at 0° C. for 2 h. The solvent was removed in vacuo to give Step 1: (2-methoxy-4-pyridinyl)methanol To a 100-mL round-bottomed flask was added methyl 2-methoxyisonicotinate (2.04 mL, 14.12 mmol, Aldrich, St. Louis, Mo.) and borane methyl sulfide complex (4.02 mL, 42.4 mmol, Aldrich, St. Louis, Mo.) in THF (30 mL). The reaction mixture was stirred at 70° C. for 18 h, cooled to 0° C. and quenched by the addition of MeOH (5 mL), followed by 1N NaOH (20 mL). The reaction mixture was extracted with EtOAc (2×50 mL), the organic extract was washed with saturated NaCl (20 mL) and dried over $Na_2SO_4$. The solution was filtered and concentrated in vacuo to give the crude material as a light-yellow oil. The crude product was purified by silica gel chromatography, eluting with 60% EtOAc/hexanes to give (2-methoxy-4-pyridinyl)methanol (1.56 g) as colorless oil.

crude ethyl glycyl-3-(2-methoxy-4-pyridinyl)alaninate as a colorless tar, which was used without further purification.

Step 7: 3-((2-methoxy-4-pyridinyl)methyl)-2,5-piperazinedione

To a 100-mL round-bottomed flask was added ethyl glycyl-3-(2-methoxy-4-pyridinyl)alaninate (1.70 g, 6.03 mmol) and N,N-diisopropylethylamine (1.05 mL, 6.03 mmol) in MeOH (20 mL). The reaction mixture was stirred at 70° C. for 18 h and allowed to cool to room temperature. The solid formed was filtered and washed with MeOH to give 3-((2-methoxy-4-pyridinyl)methyl)-2,5-piperazinedione (1.32 g) as a white solid.

Step 8: 2-((2-methoxy-4-pyridinyl)methyl)piperazine

To a 100-mL round-bottomed flask was added 3-((2-methoxy-4-pyridinyl)methyl)-2,5-piperazinedione (398 mg, 1.69 mmol) and borane methyl sulfide complex (0.64 mL, 6.77 mmol, Aldrich, St. Louis, Mo.) in THF (10 mL). The reaction mixture was stirred at 70° C. for 2 h and allowed to cool to room temperature. The reaction mixture was diluted with MeOH (1 mL), followed by 1N NaOH (12 mL), and extracted with DCM (2×50 mL). The organic extract was washed with saturated NaCl (10 mL) and dried over Na$_2$SO$_4$. The solution was filtered and concentrated in vacuo to give the 2-((2-methoxy-4-pyridinyl)methyl)piperazine as a colorless viscous oil, which was used without further purification.

Step 9: 3-((2-methoxy-4-pyridinyl)methyl)-1-(2-thiophenylsulfonyl)piperazine

To a 100-mL round-bottomed flask was added 2-((2-methoxy-4-pyridinyl)methyl)piperazine (350 mg, 1.69 mmol), triethylamine (0.353 mL, 2.54 mmol), and 2-thiophenesulfonyl chloride (0.34 mL, 1.86 mmol, Aldrich, St. Louis, Mo.) in DCM (5 mL). The reaction mixture was stirred at 0° C. for 30 min. The reaction mixture was diluted with saturated NaHCO$_3$ (10 mL) and extracted with EtOAc (2×40 mL). The organic extract was washed with saturated NaCl (5 mL) and dried over Na$_2$SO$_4$. The solution was filtered and concentrated in vacuo to give the crude material as light-yellow oil. The crude product was purified by silica gel chromatography, eluting with 10% MeOH/EtOAc to give 3-((2-methoxy-4-pyridinyl)methyl)-1-(2-thiophenylsulfonyl)piperazine (198 mg) as colorless glass.

Step 10: 1,1,1,3,3,3-hexafluoro-2-(4-(2-((2-methoxy-4-pyridinyl)methyl)-4-(2-thiophenylsulfonyl)-1-piperazinyl)phenyl)-2-propanol To a 50-mL round-bottomed flask was added 3-((2-methoxy-4-pyridinyl)methyl)-1-(2-thiophenylsulfonyl)piperazine (168 mg, 0.47 mmol), 2-(4-bromophenyl)-1,1,1,3,3,3-hexafluoropropan-2-ol (184 mg, 0.57 mmol, Bioorg. Med. Chem. Lett. 2002, 12, 3009), dicyclohexyl(2',4',6'-triisopropyl-[1',1'-biphenyl]-2-yl)phosphine (91 mg, 0.19 mmol, Strem, Newburyport, Mass.), tris(dibenzylideneacetone)dipalladium (43 mg, 0.05 mmol, Strem, Newburyport, Mass.), sodium tert-butoxide (137 mg, 1.43 mmol, Aldrich, St. Louis, Mo.), and toluene (5 mL). The reaction mixture was stirred at 100° C. for 18 h and allowed to cool to room temperature. The reaction mixture was diluted with saturated NH$_4$Cl (20 mL) and extracted with EtOAc (2×30 mL). The organic extract was washed with saturated NaCl (5 mL) and dried over Na$_2$SO$_4$. The solution was filtered and concentrated in vacuo to give the crude material as a yellow oil. The crude product was purified by silica gel chromatography, eluting with 40% EtOAc/hexanes to give 1,1,1,3,3,3-hexafluoro-2-(4-(2-((2-methoxy-4-pyridinyl)methyl)-4-(2-thiophenylsulfonyl)-1-piperazinyl)phenyl)-2-propanol (121 mg) as a colorless oil.

Step 11: 4-((4-(2-thiophenylsulfonyl)-1-(4-(2,2,2-trifluoro-1-hydroxy-1-(trifluoromethyl)ethyl)phenyl)-2-piperazinyl)methyl)-2(1H)-pyridinone To a 100-mL round-bottomed flask was added 1,1,1,3,3,3-hexafluoro-2-(4-(2-((2-methoxy-4-pyridinyl)methyl)-4-(2-thiophenylsulfonyl)-1-piperazinyl)phenyl)-2-propanol (72 mg, 0.12 mmol), 5N hydrochloric acid (0.121 mL, 0.60 mmol), and dioxane (3 mL). The reaction mixture was stirred at 100° C. for 16 h and allowed to cool to room temperature. The reaction mixture was diluted with saturated NaHCO$_3$ (20 mL) and extracted with EtOAc (2×40 mL). The organic extract was washed with saturated NaCl (5 mL) and dried over Na$_2$SO$_4$. The solution was filtered and concentrated in vacuo to give the crude material as an off-white solid. The crude product was purified by silica gel chromatography, eluting with 5% MeOH/EtOAc to give 4-((4-(2-thiophenylsulfonyl)-1-(4-(2,2,2-trifluoro-1-hydroxy-1-(trifluoromethyl)ethyl)phenyl)-2-piperazinyl)methyl)-2(1H)-pyridinone (58 mg) as a white solid.

$^1$H NMR (300 MHz, CD$_3$OD) δ 7.89 (d, J=5.12 Hz, 1H), 7.65 (d, J=3.95 Hz, 1H), 7.58 (d, J=8.92 Hz, 2H), 7.33 (d, J=6.43 Hz, 1H), 7.25 (dd, J=3.80, 5.12 Hz, 1H), 7.03 (d, J=8.77 Hz, 2H), 6.43-6.44 (m, 1H), 6.44 (s, 1H), 6.29-6.39 (m, 1H), 4.48-4.66 (m, 1H), 4.26-4.41 (m, 1H), 3.80-3.94 (m, 1H), 3.53-3.75 (m, 2H), 3.38-3.47 (m, 1H), 2.96-3.11 (m, 1H), 2.52-2.73 (m, 2H); m/z (ESI, +ve ion) 581.7 (M+H)$^+$. GK-GKRP IC$_{50}$ (Binding)=0.842 μM.

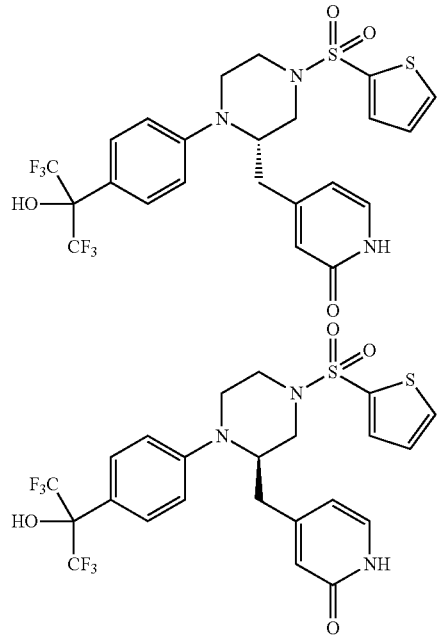

4-(((2S)-4-(2-thiophenylsulfonyl)-1-(4-(2,2,2-trifluoro-1-hydroxy-1-(trifluoromethyl)ethyl)phenyl)-2-piperazinyl)methyl)-2(1H)-pyridinone; and 4-(((2R)-4-(2-thiophenylsulfonyl)-1-(4-(2,2,2-trifluoro-1-hydroxy-1-(trifluoromethyl)ethyl)phenyl)-2-piperazinyl)methyl)-2(1H)-pyridinone.

Example 260

2-(4-(4-((4-amino-3-pyridinyl)sulfonyl)-1-piperazinyl)phenyl)-1,1,1,3,3,3-hexafluoro-2-propanol

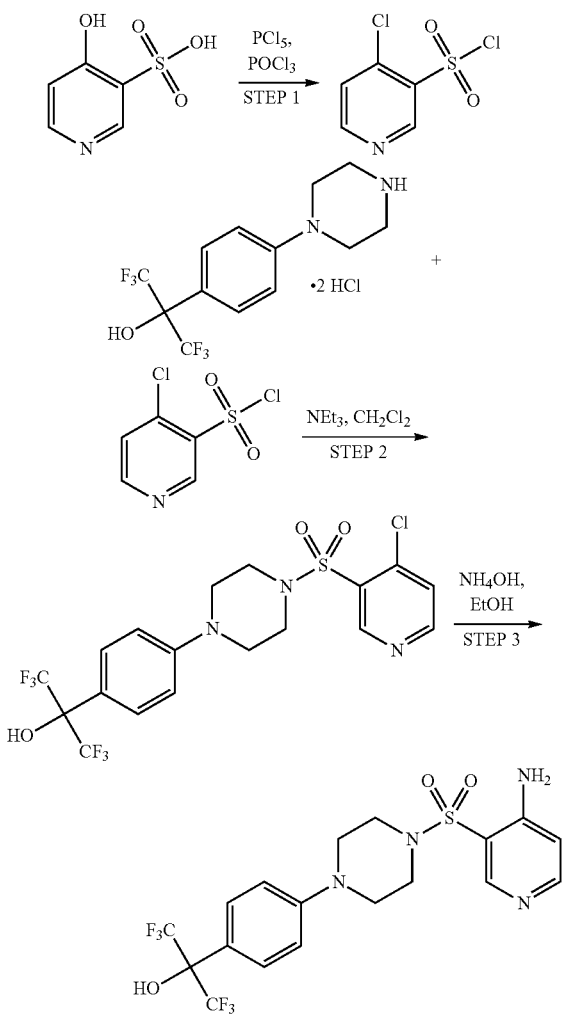

Step 1: 4-chloro-3-pyridinesulfonyl chloride (Annales Pharmaceutiques Francaises 1975, 33, 10, 487-494). To a 25 mL round-bottomed flask was added 4-hydroxy-3-pyridinesulfonic acid (1.7 g, 9.4 mmol, TCI America, Portland, Oreg.), PCl$_5$ (6.9 g, 33 mmol) and POCl$_3$ (1.8 ml, 19 mmol). The mixture was stirred at 125° C. for 1 h. The solution was allowed to cool to room temperature and then concentrated to remove excess POCl$_3$. The residue was dissolved in 50 mL diethylether and then poured onto ice. The solution was stirred for 5 min and then was neutralized with solid NaHCO$_3$. The mixture was extracted with diethylether (3×50 mL) and the combined extracts were dried (Na$_2$SO$_4$) and concentrated to afford 4-chloro-3-pyridinesulfonyl chloride (1.8 g) as a white solid.

Step 2: 2-(4-(4-((4-chloro-3-pyridinyl)sulfonyl)-1-piperazinyl)phenyl)-1,1,1,3,3,3-hexafluoro-2-propanol To a 20 mL resealable vial was added 1,1,1,3,3,3-hexafluoro-2-(4-(1-piperazinyl)phenyl)-2-propanol dihydrochloride (0.26 g, 0.64 mmol, Example 91, Step 1), DCM (6 mL), triethylamine (0.44 mL, 3.2 mmol) and 4-chloro-3-pyridinesulfonyl chloride (0.16 g, 0.76 mmol). The mixture was stirred at room temperature for 15 min. To the reaction mixture was added saturated aqueous NaHCO$_3$. The mixture was stirred for 5 min and then the solution was transferred onto a phase separation cartridge (Radleys Discovery Technologies) with the organic phase being collected and passed through a plug of Na$_2$SO$_4$. The collected solution was concentrated and purified by silica gel chromatography (0 to 70% EtOAc/hexane) to afford 2-(4-(4-((4-chloro-3-pyridinyl)sulfonyl)-1-piperazinyl)phenyl)-1,1,1,3,3,3-hexafluoro-2-propanol as a white solid.

Step 3: 2-(4-(4-((4-amino-3-pyridinyl)sulfonyl)-1-piperazinyl)phenyl)-1,1,1,3,3,3-hexafluoro-2-propanol To a 2-mL microwave vial was added 2-(4-(4-((4-chloro-3-pyridinyl)sulfonyl)-1-piperazinyl)phenyl)-1,1,1,3,3,3-hexafluoro-2-propanol (90 mg, 0.18 mmol), ethanol (1.5 mL) and aqueous ammonium hydroxide (1.5 mL, 39 mmol). The solution was then heated in the microwave at 110° C. for 2 h and then concentrated. The residue was diluted with saturated aqueous NaHCO$_3$ and DCM. The solution was stirred for 5 min and then transferred onto a phase separation cartridge (Radleys Discovery Technologies) with the organic phase being collected and passed through a plug of Na$_2$SO$_4$. The collected solution was concentrated and purified by silica gel chromatography (0 to 5.0% MeOH/DCM) afforded 2-(4-(4-((4-amino-3-pyridinyl)sulfonyl)-1-piperazinyl)phenyl)-1,1,1,3,3,3-hexafluoro-2-propanol (63 mg) as a white solid.

$^1$H NMR (400 MHz, DMSO-d$_6$) δ 8.44 (s, 1H), 8.36 (s, 1H), 8.14 (d, J=5.9 Hz, 1H), 7.46 (d, J=8.6 Hz, 2H), 7.02 (d, J=9.0 Hz, 2H), 6.76 (d, J=5.9 Hz, 1H), 3.24-3.32 (m, 4H), 3.08-3.19 (m, 4H). m/z (ESI, +ve ion) 484.8 (M+H)$^+$. GK-GKRP IC$_{50}$ (Binding)=0.591 µM.

Example 261

2-(4-(4-((2,4-diaminophenyl)sulfonyl)-1-piperazinyl)phenyl)-1,1,1,3,3,3-hexafluoro-2-propanol

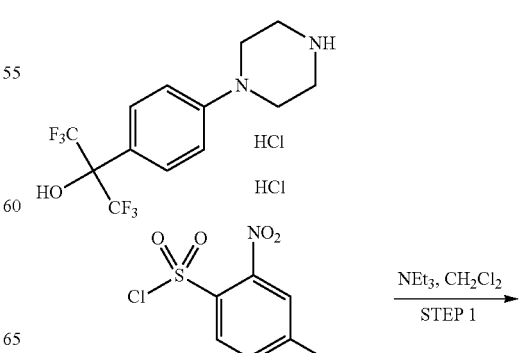

-continued

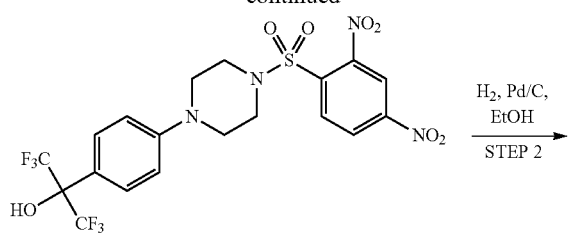

Step 1: 2-(4-(4-((2,4-dinitrophenyl)sulfonyl)-1-piperazinyl)phenyl)-1,1,1,3,3,3-hexafluoro-2-propanol To a 20 mL resealable vial was added 1,1,1,3,3,3-hexafluoro-2-(4-(1-piperazinyl)phenyl)-2-propanol dihydrochloride (0.27 g, 0.67 mmol, Example 91, Step 1), DCM (6 mL), triethylamine (0.47 mL, 3.4 mmol) and finally 2,4-dinitrobenzenesulfonyl chloride (0.22 g, 0.81 mmol). The mixture was stirred at room temperature for 15 min. To the reaction mixture was added saturated aqueous NaHCO$_3$. This was stirred for 5 min and then the solution was transferred onto a phase separation cartridge (Radleys Discovery Technologies) with the organic phase being collected and passed through a plug of Na$_2$SO$_4$. The collected solution was concentrated and purified by silica gel chromatography (0 to 70% EtOAc/hexane) afforded 2-(4-(4-((2,4-dinitrophenyl)sulfonyl)-1-piperazinyl)phenyl)-1,1,1,3,3,3-hexafluoro-2-propanol (0.31 g) as a white solid.

Step 2: 2-(4-(4-((2,4-diaminophenyl)sulfonyl)-1-piperazinyl)phenyl)-1,1,1,3,3,3-hexafluoro-2-propanol To a solution of 2-(4-(4-((2,4-dinitrophenyl)sulfonyl)-1-piperazinyl)phenyl)-1,1,1,3,3,3-hexafluoro-2-propanol (0.13 g, 0.22 mmol) in EtOH (5 mL) was added palladium, 10 wt % (dry basis) on activated carbon, wet, Degussa type E101 NE/W, water about 50% (26 mg, 0.24 mmol, Sigma-Aldrich, St. Louis, Mo.). The reaction vessel was carefully evacuated and backfilled with hydrogen. This was repeated twice and then the solution was left under an atmosphere of hydrogen (1 atm; 101.3 kpascal) for 18 h. The reaction vessel was then carefully evacuated and backfilled with N$_2$. The solution was filtered through a syringe filter and the filtrate was concentrated onto silica. Purification by silica gel chromatography (0 to 6% MeOH/DCM) afforded 2-(4-(4-((2,4-diaminophenyl)sulfonyl)-1-piperazinyl)phenyl)-1,1,1,3,3,3-hexafluoro-2-propanol (96 mg) as an off-white solid.

$^1$H NMR (400 MHz, DMSO-d$_6$) δ 8.39 (s, 1H), 7.46 (d, J=8.6 Hz, 2H), 7.08 (d, J=8.6 Hz, 1H), 7.01 (d, J=9.0 Hz, 2H), 5.86-5.94 (m, 2H), 5.67-5.78 (m, 4H), 3.22-3.29 (m, 4H), 2.97-3.05 (m, 4H). m/z (ESI, +ve ion) 499.0 (M+H)$^+$. GK-GKRP IC$_{50}$ (Binding)=0.277 μM.

Example 262

1,1,1,3,3,3-hexafluoro-2-(3-(1-propyn-1-yl)-4-(4-(2-thiophenylsulfonyl)-1-piperazinyl)phenyl)-2-propanol

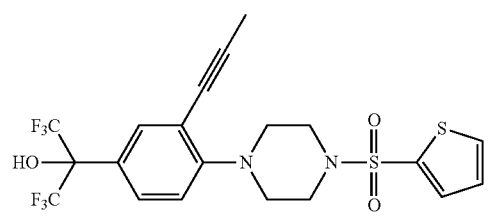 [SMILES: CC#Cc1cc(C(O)(C(F)(F)F)C(F)(F)F)ccc1N1CCN(S(=O)(=O)c2cccs2)CC1]

A glass microwave reaction vessel was charged with 2-(3-bromo-4-(4-(thiophen-2-ylsulfonyl)piperazin-1-yl)phenyl)-1,1,1,3,3,3-hexafluoropropan-2-ol (128 mg, 0.23 mmol, Example 69, step 2), 1-(trimethylsilyl)-1-propyne (0.173 mL, 1.16 mmol, Sigma-Aldrich, St. Louis, Mo.), diethylamine (48 μL, 0.46 mmol, Sigma-Aldrich, St. Louis, Mo.), bis(triphenylphosphine) palladium(II) dichloride (15 mg, 0.02 mmol, Strem Chemical Inc, Newburyport, Mass.), triphenylphosphine (12 mg, 0.05 mmol, Sigma-Aldrich, St. Louis, Mo.), copper iodide (9 mg, 0.05 mmol, Strem Chemical Inc, Newburyport, Mass.), and DMF (1 mL). The reaction mixture was purged with nitrogen for several minutes, and then stirred and heated in an Emrys Optmizer microwave reactor (Personal Chemistry, Biotage AB, Inc., Upssala, Sweden) at 120° C. for 30 min. The reaction was diluted with EtOAc (about 10 mL) and water (about 10 mL). The organic layer was separated and washed with water (10 mL), dried (Na$_2$SO$_4$), concentrated and purified column chromatography (12 g silica, 0 to 20% EtOAc in hexanes to afford 1,1,1,3,3,3-hexafluoro-2-(3-(1-propyn-1-yl)-4-(4-(2-thiophenylsulfonyl)-1-piperazinyl)phenyl)-2-propanol (28 mg) as a white solid.

$^1$H NMR (400 MHz, DMSO-d$_6$) δ 8.64 (s, 1H), 8.09 (d, J=4.89 Hz, 1H), 7.70 (d, J=2.74 Hz, 1H), 7.45-7.56 (m, 2H), 7.29-7.36 (m, 1H), 7.06 (d, J=8.61 Hz, 1H), 3.24-3.29 (m, 4H), 3.04-3.15 (m, 4H), 2.02 (s, 3H); m/z (ESI, +ve ion) 513.2 (M+H)$^+$. GK-GKRP IC$_{50}$ (Binding)=0.834 μM.

Example 263

1,1,1,3,3,3-hexafluoro-2-(2-(4-(phenylsulfonyl)phenyl)-5-pyrimidinyl)-2-propanol

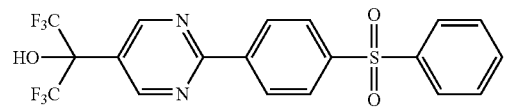 [SMILES: O=S(=O)(c1ccccc1)c1ccc(-c2ncc(C(O)(C(F)(F)F)C(F)(F)F)cn2)cc1]

A glass microwave reaction vessel was charged with 4,4,5,5-tetramethyl-2-(4-(phenylsulfonyl)phenyl)-1,3,2-dioxaborolane (196 mg, 0.57 mmol, Example 17, Step 2), 2-(2-chloropyrimidin-5-yl)-1,1,1,3,3,3-hexafluoropropan-2-ol (145 mg, 0.52 mmol, Intermediate D), (1,1'-bis(diphenylphosphino)ferrocene)dichloropalladium (24 mg, 0.03 mmol, Strem Chemical Inc, Newburyport, Mass.), cesium carbonate (0.51 g, 1.56 mmol, Sigma-Aldrich, St. Louis, Mo.), DME (1 mL), and water (0.1 mL). The reaction mixture was purged with nitrogen for several minutes, and then stirred and heated in an Emrys Optmizer microwave reactor (Personal Chemistry, Biotage AB, Inc., Upssala, Sweden) at 100° C. for 30 min. The reaction was diluted with EtOAc (about 10 mL) and water (about 10 mL). The organic layer was taken and the solvent was removed under vacuum. The crude material was absorbed onto a plug of silica gel and purified by chromatography through a silica gel column (12 g), eluting with a gradient of 10% to 20% EtOAc in hexane, to provide 1,1,1,3,3,3-hexafluoro-2-(2-(4-(phenylsulfonyl)phenyl)-5-pyrimidinyl)-2-propanol (171 mg) as an off-white solid. $^1$H NMR (400 MHz, DMSO-$d_6$) δ 9.58 (s, 1H), 9.28 (s, 2H), 8.69 (d, J=8.61 Hz, 2H), 8.22 (d, J=8.61 Hz, 2H), 8.04-8.10 (m, 2H), 7.68-7.82 (m, 4H); m/z (ESI, +ve ion) 463.1 (M+H)$^+$. GK-GKRP IC$_{50}$ (Binding)=0.484 μM. GKRP EC$_{50}$ (LC MS/MS-2)=0.478 μM.

Example 264

2-(2-(4-((6-amino-3-pyridinyl)sulfonyl)phenyl)-5-pyrimidinyl)-1,1,1,3,3,3-hexafluoro-2-propanol

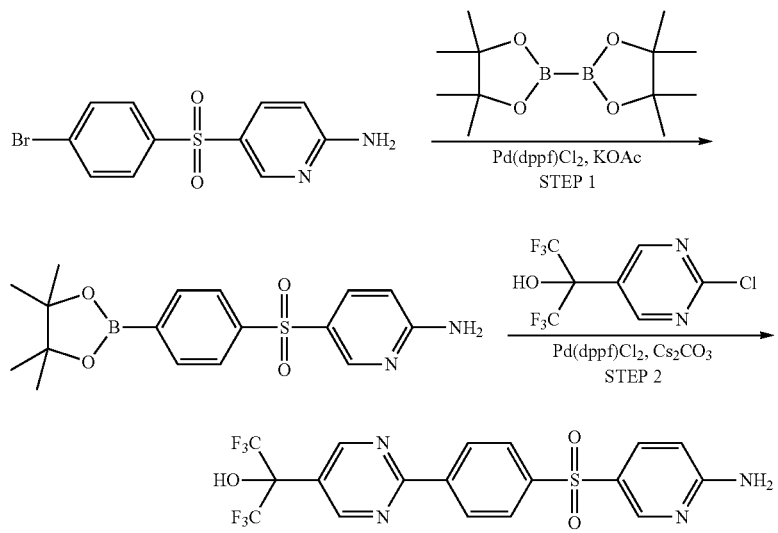

Step 1: 5-((4-(4,4,5,5-tetramethyl-1,3,2-dioxaborolan-2-yl)phenyl)sulfonyl)-2-pyridinamine 5-((4-Bromophenyl)sulfonyl)-2-pyridinamine (0.53 g, 1.69 mmol, Example 161, Step 3), bis(pinacolato)diboron (0.43 g, 1.69 mmol, Sigma-Aldrich, St. Louis, Mo.), (1,1'-bis(diphenylphosphino)ferrocene)dichloropalladium (69 mg, 0.08 mmol, Strem Chemical Inc, Newburyport, Mass.), potassium acetate (0.50 g, 5.1 mmol, Sigma-Aldrich, St. Louis, Mo.), and dioxane (8 mL) were added to a reaction vial. The vial was closed, purged with nitrogen for several minutes, and heated at 100° C. for 18 h. After cooling to room temperature, the reaction mixture was filtered through a pad of Celite® (diatomaceous earth) eluting with DCM. The filtrate was concentrated to yield 5-((4-(4,4,5,5-tetramethyl-1,3,2-dioxaborolan-2-yl)phenyl)sulfonyl)-2-pyridinamine as a brown solid that was used without further purification. m/z (ESI, +ve ion) 279.2 (M)$^+$.

Step 2: 2-(2-(4-((6-amino-3-pyridinyl)sulfonyl)phenyl)-5-pyrimidinyl)-1,1,1,3,3,3-hexafluoro-2-propanol A glass microwave reaction vessel was charged with 5-((4-(4,4,5,5-tetramethyl-1,3,2-dioxaborolan-2-yl)phenyl)sulfonyl)-2-pyridinamine (262 mg, 0.73 mmol), 2-(2-chloropyrimidin-5-yl)-1,1,1,3,3,3-hexafluoropropan-2-ol (102 mg, 0.36 mmol, Example X, Intermediate D), (1,1'-bis(diphenylphosphino)ferrocene)dichloropalladium (15 mg, 0.02 mmol, Strem Chemical Inc, Newburyport, Mass.), cesium carbonate (355 mg, 1.1 mmol, Sigma-Aldrich, St. Louis, Mo.), DME (2 mL), and water (0.2 mL). The reaction mixture was purged with nitrogen for several minutes, and then stirred and heated in an Emrys Optmizer microwave reactor (Personal Chemistry, Biotage AB, Inc., Upssala, Sweden) at 100° C. for 30 min. The organic layer was taken and the solvent was removed under vacuum. The crude material was absorbed onto a plug of silica gel and purified by chromatography through a silica gel column (12 g), eluting with a gradient of DCM to 3% 2M NH$_3$/MeOH in DCM, to provide 2-(2-(4-((6-amino-3-pyridinyl)sulfonyl)phenyl)-5-pyrimidinyl)-1,1,1,3,3-hexafluoro-2-propanol (56 mg) as a tan solid.

$^1$H NMR (400 MHz, DMSO-$d_6$) δ 9.33 (br s, 1H), 9.04 (s, 2H), 8.42 (d, J=8.41 Hz, 2H), 8.31 (d, J=2.74 Hz, 1H), 7.91 (d, J=8.61 Hz, 2H), 7.63 (dd, J=2.54, 9.00 Hz, 1H), 6.96 (s, 2H), 6.35 (s, 1H); m/z (ESI, +ve ion) 479.1 (M+H)$^+$. GK-GKRP IC$_{50}$ (Binding)=0.063 μM.

Example 265

2-(2-(4-((6-amino-3-pyridinyl)sulfonyl)phenyl)-5-pyrimidinyl)-1,1,1-trifluoro-2-propanol

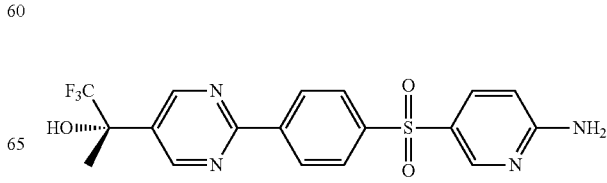

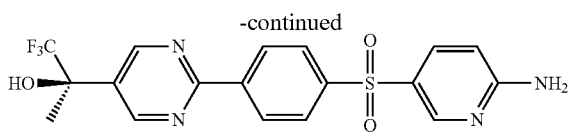

A glass microwave reaction vessel was charged with 5-((4-(4,4,5,5-tetramethyl-1,3,2-dioxaborolan-2-yl)phenyl)sulfonyl)-2-pyridinamine (318 mg, 0.88 mmol), 2-(2-chloro-5-pyrimidinyl)-1,1,1-trifluoro-2-propanol (100 mg, 0.44 mmol, Intermediate E), (1,1'-bis(diphenylphosphino)ferrocene)dichloropalladium (18 mg, 0.02 mmol, Strem Chemical Inc, Newburyport, Mass.), cesium carbonate (431 mg, 1.32 mmol, Sigma-Aldrich, St. Louis, Mo.), DME (1.5 mL), and water (0.2 mL). The reaction mixture was purged with nitrogen for several minutes, and then stirred and heated in an Emrys Optmizer microwave reactor (Personal Chemistry, Biotage AB, Inc., Upssala, Sweden) at 100° C. for 45 min. The organic layer was taken and the solvent was removed under vacuum. The crude material was absorbed onto a plug of silica gel and purified by chromatography through a silica gel column (12 g), eluting with a gradient of DCM to 3% 2M $NH_3$.MeOH in DCM, to provide 2-(2-(4-((6-amino-3-pyridinyl)sulfonyl)phenyl)-5-pyrimidinyl)-1,1,1-trifluoro-2-propanol (70 mg) as an off-white solid and a mixture of enantiomers.

$^1$H NMR (400 MHz, DMSO-$d_6$) δ 9.06 (s, 2H), 8.50 (d, J=8.41 Hz, 2H), 8.40 (d, J=1.96 Hz, 1H), 7.98 (d, J=8.22 Hz, 2H), 7.73 (dd, J=2.15, 8.80 Hz, 1H), 7.00-7.10 (m, 3H), 6.43 (d, J=8.80 Hz, 1H), 1.73 (s, 3H); m/z (ESI, +ve ion) 425.1 (M+H)$^+$. GK-GKRP IC$_{50}$ (Binding)=0.229 µM.

Example 266

2-(6-(4-((6-amino-3-pyridinyl)sulfonyl)phenyl)-3-pyridinyl)-1,1,1,3,3,3-hexafluoro-2-propanol

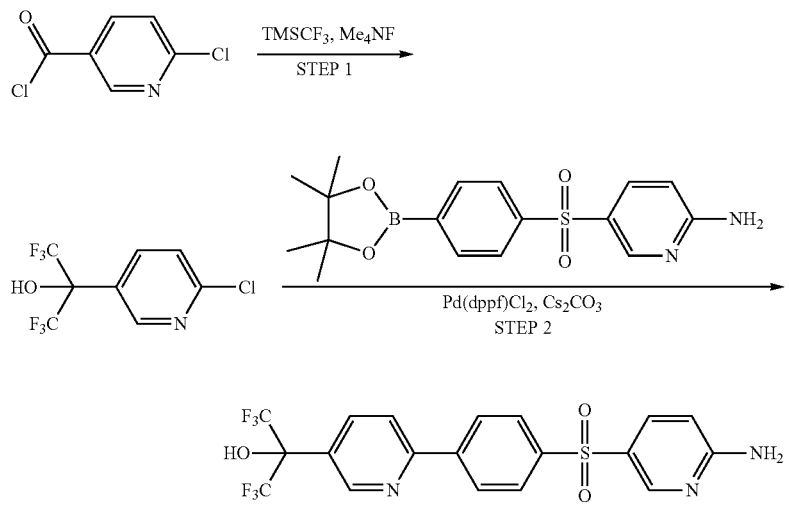

Step 1: 2-(6-chloro-3-pyridinyl)-1,1,1,3,3,3-hexafluoro-2-propanol

To a 50-mL round-bottomed flask was added 6-chloronicotinyl chloride (500 mg, 2.84 mmol, Alfa Aesar, Ward Hill, Mass.) and DME (16 mL). The flask was closed and purged with nitrogen for several minutes. The reaction mixture was cooled to −78° C. and added tetramethylammonium fluoride (794 mg, 8.52 mmol, Sigma-Aldrich, St. Louis, Mo.) and trifluoromethyltrimethylsilane (1.26 mL, 8.52 mmol, TCI America, Portland, Oreg.). The resulting mixture was gradually warmed to room temperature and stirred for 16 h. The reaction mixture was diluted with water (5 mL), 1N HCl (5 mL), and extracted with EtOAc (15 mL). The organic extract was washed with saturated aqueous NaCl (10 mL) and dried over $Na_2SO_4$. The solution was filtered and concentrated in vacuo to give 2-(6-chloro-3-pyridinyl)-1,1,1,3,3,3-hexafluoro-2-propanol (794 mg) as an off-white solid that was used without further purification. m/z (ESI, +ve ion) 280.1 (M+H)$^+$.

Step 2: 2-(6-(4-((6-amino-3-pyridinyl)sulfonyl)phenyl)-3-pyridinyl)-1,1,1,3,3,3-hexafluoro-2-propanol A glass microwave reaction vessel was charged with 5-((4-(4,4,5,5-tetramethyl-1,3,2-dioxaborolan-2-yl)phenyl)sulfonyl)-2-pyridinamine (381 mg, 1.06 mmol, Example 264, step 1), 2-(6-chloro-3-pyridinyl)-1,1,1,3,3,3-hexafluoro-2-propanol (148 mg, 0.53 mmol), (1,1'-bis(diphenylphosphino)ferrocene)dichloropalladium (22 mg, 0.03 mmol, Strem Chemical Inc, Newburyport, Mass.), cesium carbonate (517 mg, 1.59 mmol, Sigma-Aldrich, St. Louis, Mo.), DME (1.5 mL), and water (0.15 mL). The reaction mixture was purged with nitrogen for several minutes, and then stirred and heated in an Emrys Optmizer microwave reactor (Personal Chemistry, Biotage AB, Inc., Upssala, Sweden) at 100° C. for 30 min. The organic layer was taken and the solvent was removed under vacuum. The crude material was absorbed onto a plug of silica gel and purified by chromatography through a silica gel column (12 g), eluting with a gradient of DCM to 3% 2M $NH_3$/MeOH in DCM, to provide 2-(6-(4-((6-amino-3-pyridinyl)sulfonyl)phenyl)-3-pyridinyl)-1,1,1,3,3,3-hexafluoro-2-propanol (99 mg) as a white solid.

$^1$H NMR (400 MHz, DMSO-$d_6$) δ 9.00 (s, 1H), 8.79 (s, 1H), 8.29 (d, J=2.35 Hz, 1H), 8.13 (d, J=8.80 Hz, 2H), 7.99-8.05 (m, 2H), 7.85 (d, J=8.61 Hz, 2H), 7.62 (dd, J=2.64, 8.90 Hz, 1H), 6.92 (s, 2H), 6.32 (d, J=8.80 Hz, 1H); m/z (ESI, +ve ion) 478.1 (M+H)$^+$. GK-GKRP IC$_{50}$ (Binding)=0.253 µM.

Example 267

2-(2-(6-((6-amino-3-pyridinyl)sulfonyl)-3-pyridinyl)-5-pyrimidinyl)-1,1,1,3,3,3-hexafluoro-2-propanol

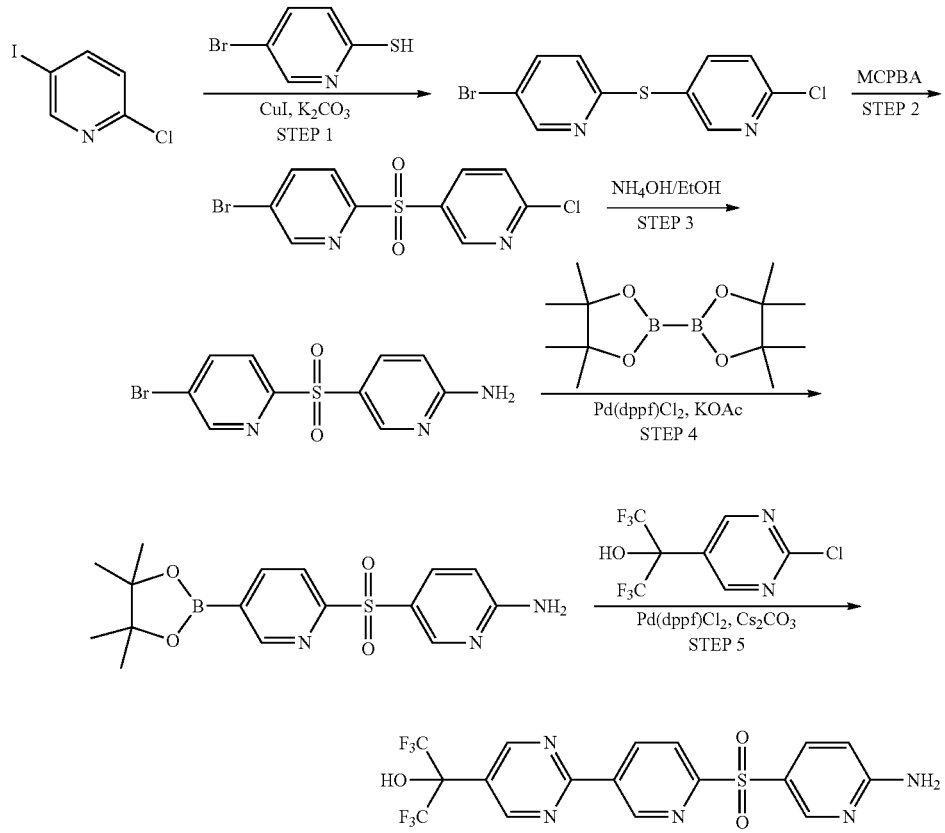

Step 1:
5-bromo-2-((6-chloro-3-pyridinyl)sulfanyl)pyridine

5-Bromo-2-pyridinethiol (633 mg, 3.33 mmol, Combi-Blocks, Inc., San Diego, Calif.), 2-chloro-5-iodopyridine (798 mg, 3.33 mmol, Sigma-Aldrich, St. Louis, Mo.), copper iodide (32 mg, 0.17 mmol, Strem Chemical Inc, Newburyport, Mass.), potassium carbonate (921 mg, 6.67 mmol), ethylene glycol (0.37 mL, 6.67 mmol), and 2-propanol (8 mL) were added to a reaction vial. The vial was sealed, purged with nitrogen for several minutes, and heated at 80° C. for 16 h. After cooling to room temperature, the solvents were removed under vacuum. The residue was absorbed onto a plug of silica gel and purified by chromatography through a silica gel column (40 g), eluting with a gradient of 0% to 10% EtOAc in hexanes, to provide 5-bromo-2-((6-chloro-3-pyridinyl)sulfanyl)pyridine (318 mg) as a white solid.

$^1$H NMR (400 MHz, DMSO-$d_6$) δ 8.44 (dd, J=2.45, 10.86 Hz, 2H), 7.96 (dd, J=2.54, 8.41 Hz, 1H), 7.83 (dd, J=2.45, 8.51 Hz, 1H), 7.54 (d, J=8.41 Hz, 1H), 7.13 (d, J=8.61 Hz, 1H); m/z (ESI, +ve ion) 301.0 (M+H)$^+$.

Step 2:
5-bromo-2-((6-chloro-3-pyridinyl)sulfonyl)pyridine

5-Bromo-2-((6-chloro-3-pyridinyl)sulfanyl)pyridine (295 mg, 0.98 mmol) and 3-chloroperoxybenzoic acid (438 mg, 1.96 mmol, 77% by weight, Sigma-Aldrich, St. Louis, Mo.) in DCM (5 mL) were stirred at room temperature for 2 h. The mixture was partitioned between DCM (about 10 mL) and saturated aqueous sodium bicarbonate (about 10 mL) and the layers were separated. The organic layer was taken and was washed sequentially with saturated aqueous sodium bicarbonate (about 10 mL) and brine (about 10 mL), dried (Na$_2$SO$_4$), filtered, and concentrated in vacuum to yield 5-bromo-2-((6-chloro-3-pyridinyl)sulfonyl)pyridine (326 mg) as a white solid that was used without further purification. m/z (ESI, +ve ion) 333.0 (M+H)$^+$.

Step 3:
5-((5-bromo-2-pyridinyl)sulfonyl)-2-pyridinamine

5-Bromo-2-((6-chloro-3-pyridinyl)sulfonyl)pyridine (298 mg, 0.89 mmol), NH$_4$OH (aqueous, 3 mL), and EtOH (3 mL) were added to a high-pressure reaction vessel. The vessel was sealed and heated at 120° C. for 2 h. After cooling to room temperature, the solvent was partially removed under vacuum. The white precipitate obtained was filtered, washed with ether, and dried under vacuum to provide 5-((5-bromo-2-pyridinyl)sulfonyl)-2-pyridinamine (280 mg) as a white solid that was used without further purification.

Step 4: 5-((5-(4,4,5,5-tetramethyl-1,3,2-dioxaborolan-2-yl)-2-pyridinyl)sulfonyl)-2-pyridinamine 5-((5-Bromo-2-pyridinyl)sulfonyl)-2-pyridinamine (154 mg, 0.49 mmol), bis(pinacolato)diboron (124 mg, 0.49 mmol, Sigma-Aldrich, St. Louis, Mo.), (1,1'-bis(diphenylphosphino)ferrocene)dichloropalladium (20 mg, 0.02 mmol, Strem Chemical Inc, Newburyport, Mass.), potassium acetate (144 mg, 1.47 mmol, Sigma-Aldrich, St. Louis, Mo.), and dioxane (3 mL) were added to a reaction vial. The vial was closed, purged with nitrogen for several minutes, and heated at 100° C. for 18 h. After cooling to room temperature, the reaction mixture was filtered through a pad of Celite® (diatomaceous earth) eluting with DCM. The filtrate was concentrated to yield 5-((5-(4,4,5,5-tetramethyl-1,3,2-dioxaborolan-2-yl)-2-pyridinyl)sulfonyl)-2-pyridinamine (177 mg) as a tan solid that was used without further purification.

Step 5: 2-(2-(6-((6-amino-3-pyridinyl)sulfonyl)-3-pyridinyl)-5-pyrimidinyl)-1,1,1,3,3,3-hexafluoro-2-propanol A glass microwave reaction vessel was charged with 5-((4-(4,4,5,5-tetramethyl-1,3,2-dioxaborolan-2-yl)phenyl)sulfonyl)-2-pyridinamine (164 mg, 0.45 mmol), 2-(2-chloropyrimidin-5-yl)-1,1,1,3,3,3-hexafluoropropan-2-ol (85 mg, 0.30 mmol, Intermediate D), (1,1'-bis(diphenylphosphino)ferrocene)dichloropalladium (12 mg, 0.015 mmol, Strem Chemical Inc, Newburyport, Mass.), cesium carbonate (296 mg, 0.91 mmol, Sigma-Aldrich, St. Louis, Mo.), DME (1.5 mL), and water (0.1 mL). The reaction mixture was purged with nitrogen for several minutes, and then stirred and heated in an Emrys Optmizer microwave reactor (Personal Chemistry, Biotage AB, Inc., Upssala, Sweden) at 100° C. for 30 min. The organic layer was taken and the solvent was removed under vacuum. The crude material was absorbed onto a plug of silica gel and purified by chromatography through a silica gel column (12 g), eluting with a gradient of DCM to 3% 2M $NH_3$/MeOH in DCM, to provide 2-(2-(6-((6-amino-3-pyridinyl)sulfonyl)-3-pyridinyl)-5-pyrimidinyl)-1,1,1,3,3,3-hexafluoro-2-propanol (56 mg) as a tan solid. $^1$H NMR (400 MHz, DMSO-$d_6$) 9.57 (d, J=1.37 Hz, 1H), 9.52 (br s, 1H), 9.25 (s, 2H), 8.97 (dd, J=2.15, 8.22 Hz, 1H), 8.46 (d, J=2.54 Hz, 1H), 8.31 (d, J=8.22 Hz, 1H), 7.82 (dd, J=2.54, 9.00 Hz, 1H), 7.20 (br. s, 2H), 6.53 (d, J=9.00 Hz, 1H); m/z (ESI, +ve ion) 480.1 (M+H)$^+$. GK-GKRP IC$_{50}$ (Binding)=0.103 µM. GKRP EC$_{50}$ (LC MS/MS-2)=0.113 µM.

Example 268

2-(2-(4-((6-amino-3-pyridinyl)sulfonyl)-2-methylphenyl)-5-pyrimidinyl)-1,1,3,3,3-hexafluoro-2-propanol

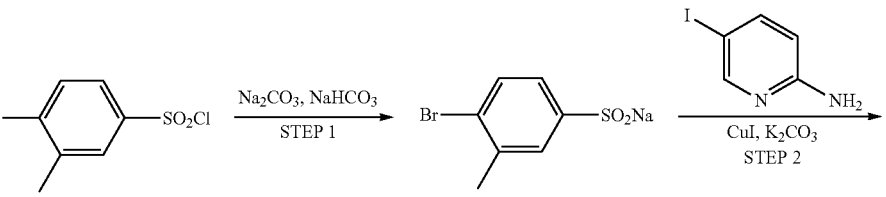

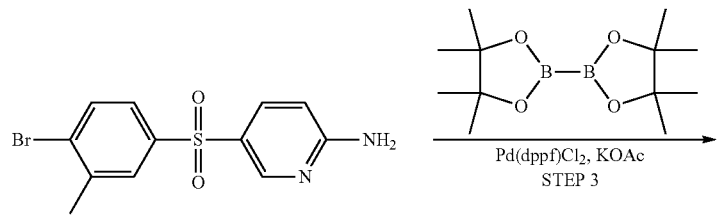

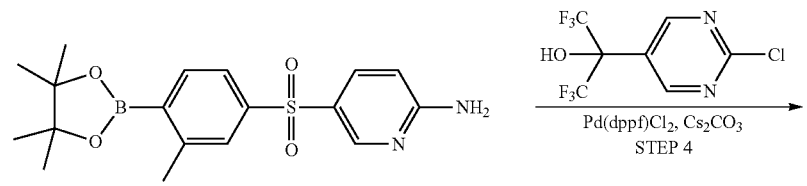

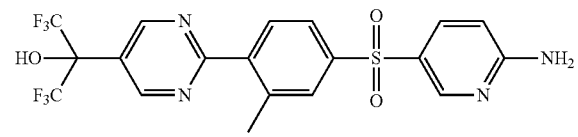

Step 1: sodium 4-bromo-3-methylbenzenesulfinate

To a 100-mL round-bottomed flask was added sodium bicarbonate (1.18 g, 14 mmol, Sigma-Aldrich, St. Louis, Mo.), sodium sulfite (1.77 g, 14 mmol, Sigma-Aldrich, St. Louis, Mo.) and water (15 mL). The reaction mixture was heated at 80° C. and 4-bromo-3-methylbenzenesulfonyl chloride (3.15 g, 11.69 mmol, Sigma-Aldrich, St. Louis, Mo.) was added portion-wise. When the addition was completed the reaction mixture was heated at 90° C. for 3 h and allowed to cool to room temperature. The solvent was partially removed under vacuum and the white precipitate obtained was filtered and dried in vacuo to provide sodium 4-bromo-3-methylbenzenesulfinate (2.94 g) that was used without further purification.

Step 2: 5-((4-bromo-3-methylphenyl)sulfonyl)-2-pyridinamine

Sodium 4-bromo-3-methylbenzenesulfinate (2.92 mg, 11.36 mmol), 2-amino-5-iodopyridine (1.25 g, 5.68 mmol, Alfa Aesar, Ward Hill, Mass.), copper iodide (216 mg, 1.14 mmol, Strem Chemical Inc, Newburyport, Mass.), potassium carbonate (785 mg, 5.68 mmol), N,N-dimethylethylenediamine (0.25 mL, 2.27 mmol, Alfa Aesar, Ward Hill, Mass.), and DMSO (15 mL) were added to a reaction vial. The vial was closed, purged with nitrogen for several minutes, and heated at 100° C. for 16 h. After cooling to room temperature, the reaction mixture was diluted with water (20 mL) and extracted with EtOAc (20 mL×3). The combined organic extracts were dried over $Na_2SO_4$. The solution was filtered and concentrated in vacuo to give the crude material. The crude material was absorbed onto a plug of silica gel and purified by chromatography through a Redi-Sep pre-packed silica gel column (40 g), eluting with a gradient of 20% to 50% EtOAc in hexane, to provide 5-((4-bromo-3-methylphenyl)sulfonyl)-2-pyridinamine (377 mg) as a white solid.

Step 3: 5-((3-methyl-4-(4,4,5,5-tetramethyl-1,3,2-dioxaborolan-2-yl)phenyl)sulfonyl)-2-pyridinamine 5-((4-Bromo-3-methylphenyl)sulfonyl)-2-pyridinamine (377 mg, 1.15 mmol), bis(pinacolato)diboron (410 mg, 1.61 mmol, Sigma-Aldrich, St. Louis, Mo.), (1,1'-bis(diphenylphosphino)ferrocene)dichloropalladium (47 mg, 0.06 mmol, Strem Chemical Inc, Newburyport, Mass.), potassium acetate (339 mg, 3.46 mmol, Sigma-Aldrich, St. Louis, Mo.), and DMF (6 mL) were added to a reaction vial. The vial was closed, purged with nitrogen for several minutes, and heated at 80° C. for 16 h. After cooling to room temperature, the reaction mixture was diluted with water (10 mL) and extracted with EtOAc (20 mL). The organic extract was washed with saturated NaCl (5 mL) and dried over $Na_2SO_4$. The solution was filtered and concentrated in vacuo to give the crude material. This material was filtered though a short silica pad eluting with EtOAc to provide 5-((3-methyl-4-(4,4,5,5-tetramethyl-1,3,2-dioxaborolan-2-yl)phenyl)sulfonyl)-2-pyridinamine (450 mg) as a tan solid that was used without further purification.

Step 4: 2-(2-(4-((6-amino-3-pyridinyl)sulfonyl)-2-methylphenyl)-5-pyrimidinyl)-1,1,1,3,3,3-hexafluoro-2-propanol A glass microwave reaction vessel was charged with 5-((3-methyl-4-(4,4,5,5-tetramethyl-1,3,2-dioxaborolan-2-yl)phenyl)sulfonyl)-2-pyridinamine (278 mg, 0.74 mmol), 2-(2-chloropyrimidin-5-yl)-1,1,1,3,3,3-hexafluoropropan-2-ol (139 mg, 0.49 mmol, Intermediate D), (1,1'-bis(diphenylphosphino)ferrocene)dichloropalladium (20 mg, 0.025 mmol, Strem Chemical Inc, Newburyport, Mass.), cesium carbonate (484 mg, 1.49 mmol, Sigma-Aldrich, St. Louis, Mo.), DME (1.2 mL), and water (0.1 mL). The reaction mixture was purged with nitrogen for several minutes, and then stirred and heated in an Emrys Optmizer microwave reactor (Personal Chemistry, Biotage AB, Inc., Upssala, Sweden) at 100° C. for 45 min. The organic layer was taken and the solvent was removed under the vacuum. The crude material was absorbed onto a plug of silica gel and purified by chromatography through a silica gel column (12 g), eluting with a gradient of DCM to 2% 2M $NH_3$.MeOH in DCM, to provide 2-(2-(4-((6-amino-3-pyridinyl)sulfonyl)-2-methylphenyl)-5-pyrimidinyl)-1,1,1,3,3,3-hexafluoro-2-propanol (61 mg) as an off-white solid.

$^1$H NMR (400 MHz, DMSO-d$_6$) δ 9.50 (br s, 1H), 9.21 (s, 2H), 8.48 (d, J=2.35 Hz, 1H), 8.04 (d, J=8.22 Hz, 1H), 7.90 (s, 1H), 7.86 (d, J=8.22 Hz, 1H), 7.81 (dd, J=2.45, 8.90 Hz, 1H), 7.11 (s, 2H), 6.51 (d, J=9.00 Hz, 1H), 2.58 (s, 3H); m/z (ESI, +ve ion) 493.1 (M+H)$^+$. GK-GKRP IC$_{50}$ (Binding)=0.103 μM. GKRP EC$_{50}$ (LC MS/MS-2)=0.232 μM.

Example 269

1,1,1,3,3,3-hexafluoro-2-(2-(2-(1-propyn-1-yl)-4-(2-thiophenylsulfonyl)-1-piperazinyl)-5-pyrimidinyl)-2-propanol

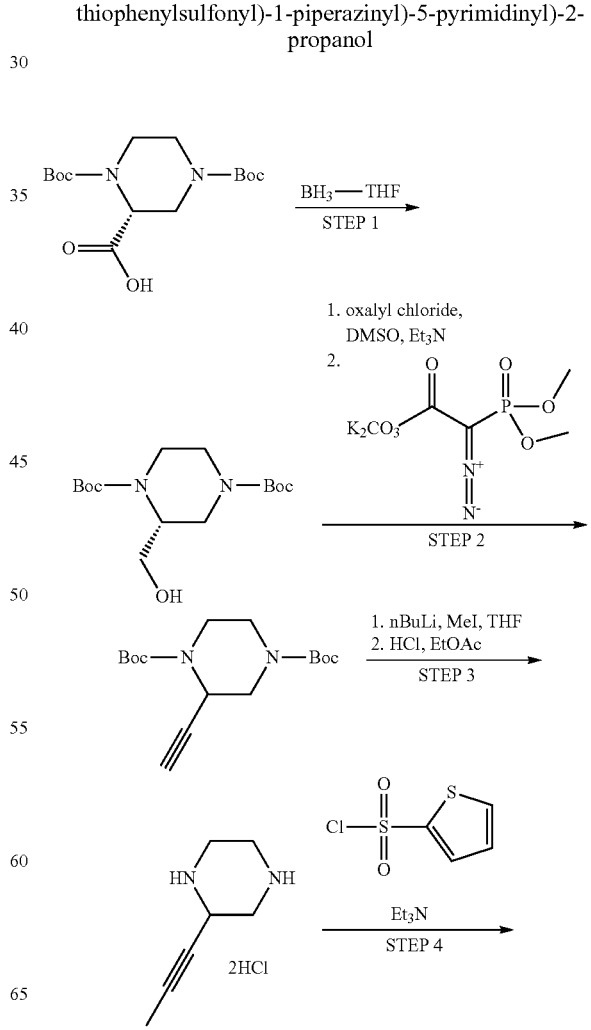

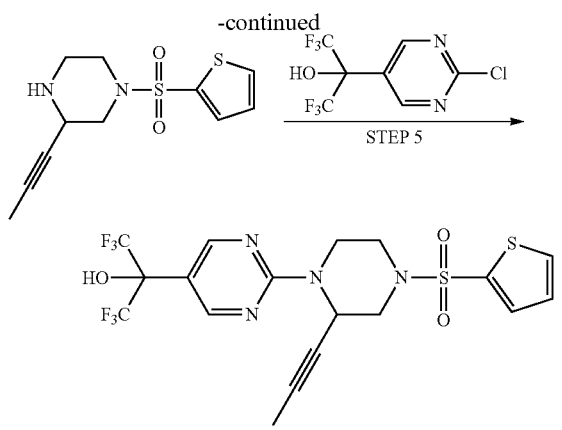

Step 1: di-tert-butyl (2R)-2-(hydroxymethyl)-1,4-piperazinedicarboxylate

A 250-mL round bottom flask was charged with (2R)-1,4-bis(tert-butoxycarbonyl)-2-piperazinecarboxylic acid (10.5 g, 31.8 mmol, ASW Medchem, New Brunswick, N.J.) under nitrogen. THF (20 mL) was added and the mixture was cooled in an ice bath. A solution of $BH_3$·THF (1M in THF, 65 mL, 65.0 mmol, Sigma-Aldrich) was added over 10 min. The ice bath was removed and after 15 min, the flask was equipped with a reflux condenser and was the reaction was heated at 60° C. After 1.5 h, the mixture was cooled in an ice bath and was then quenched with MeOH (10 mL, 247 mmol) over 20 min. The mixture was concentrated, treated with MeOH (20 mL), and concentrated a second time to give di-tert-butyl (2R)-2-(hydroxymethyl)-1,4-piperazinedicarboxylate as a white solid (10 g).

Step 2: di-tert-butyl 2-ethynyl-1,4-piperazinedicarboxylate

A 150-mL round-bottomed flask containing $CH_2Cl_2$ (30 mL) was cooled to −78° C. The flask was charged with oxalyl dichloride (2 M in $CH_2Cl_2$, 8.34 ml, 20.86 mmol, Sigma-Aldrich, St. Louis, Mo.) followed by DMSO (2.96 ml, 41.7 mmol). It was stirred at −78° C. for 20 min, then a solution of di-tert-butyl (2R)-2-(hydroxymethyl)-1,4-piperazinedicarboxylate (6.00 g, 18.96 mmol) in $CH_2Cl_2$ (30 mL) was added slowly drop-wise to the reaction mixture. After 30 min, the mixture was treated with triethylamine (10.57 mL, 76 mmol) and stirred at −78° C. for 10 min then at 0° C. for 30 min. The reaction was quenched by the addition of water and was extracted with $CH_2Cl_2$ (2×50 mL). The combined organic extracts were dried over $MgSO_4$, filtered, and concentrated affording the crude aldehyde intermediate.

A solution of dimethyl (1-diazo-2-oxopropyl)phosphonate (3.64 g, 18.96 mmol, TCI America, Portland, Oreg.) and potassium carbonate (2.62 g, 18.96 mmol) in MeOH (30 mL) was stirred at room temp for 20 min. The crude aldehyde in 5 mL of MeOH was added to this solution, and the reaction mixture was stirred for 16 h. The mixture was concentrated and absorbed onto silica gel. The crude material was purified via column chromatography (about 80 g of silica gel, 5% to 90% EtOAc in hexanes) to give racemic di-tert-butyl 2-ethynyl-1,4-piperazinedicarboxylate (3.25 g) as a white solid.

Step 3: 2-(1-propyn-1-yl)piperazine bis(trifluoroacetate)

A 50-mL round-bottomed flask containing a solution of di-tert-butyl 2-ethynyl-1,4-piperazinedicarboxylate (165 mg, 0.532 mmol) in THF was cooled to −78° C. To this was added n-butyllithium (2.5 M in hexanes, 234 μL, 0.585 mmol, Sigma-Aldrich, St. Louis, Mo.) slowly. The mixture was stirred at −78° C. for 15 min, 0° C. for 30 min, and then cooled back to −78° C. A solution of iodomethane (83 mg, 0.585 mmol) in THF (1 mL) was then added to the mixture. The reaction was slowly warmed to room temperature and stirred for 6 h. The mixture was quenched with saturated aqueous $NH_4Cl$ and then concentrated. The crude material was filtered through a plug of silica gel and the filtrate was concentrated. The crude product was dissolved in a 1:2 TFA-DCM solution and stirred at room temperature for 3 h. Afterwards, the mixture was concentrated to give 2-(1-propyn-1-yl)piperazine bis(trifluoroacetate) (125 mg) as a viscous oil.

Step 4: 3-(1-propyn-1-yl)-1-(2-thiophenylsulfonyl)piperazine

The 2-(1-propyn-1-yl)piperazine bis(trifluoroacetate (110 mg, 0.312 mmol) was dissolved in $CH_2Cl_2$ in a 50 mL round-bottomed flask and was then cooled to 0° C. To this solution was added an excess of triethylamine (152 μL, 1.093 mmol) followed by thiophene-2-sulfonyl chloride (57.0 mg, 0.312 mmol, Sigma-Aldrich, St. Louis, Mo.). The mixture was warmed slowly to room temperature and stirred for 2 h. Afterwards, the mixture was concentrated and absorbed onto silica gel. The crude material was purified via column chromatography (about 40 g silica gel, 0% to 10% MeOH in $CH_2Cl_2$) to give 3-(1-propyn-1-yl)-1-(2-thiophenylsulfonyl)piperazine (42 mg) as a foamy solid.

Step 5: 1,1,1,3,3,3-hexafluoro-2-(2-(2-(1-propyn-1-yl)-4-(2-thiophenylsulfonyl)-1-piperazinyl)-5-pyrimidinyl)-2-propanol In a 50-mL sealed vial, a mixture of (S)-3-(prop-1-yn-1-yl)-1-(thiophen-2-ylsulfonyl)piperazine (40 mg, 0.148 mmol), 2-(2-chloropyrimidin-5-yl)-1,1,1,3,3,3-hexafluoropropan-2-ol (41.5 mg, 0.148 mmol), and triethylamine (30.9 μl, 0.222 mmol) in dioxane was heated to 100° C. for 16 h. Afterwards, the mixture was concentrated and the crude material was purified via column chromatography (about 40 g silica gel, 0% to 10% MeOH in $CH_2Cl_2$) to give the racemate of 1,1,1,3,3,3-hexafluoro-2-(2-((2S)-2-(1-propyn-1-yl)-4-(2-thiophenylsulfonyl)-1-piperazinyl)-5-pyrimidinyl)-2-propanol (18 mg) and 1,1,1,3,3,3-hexafluoro-2-(2-((2R)-2-(1-propyn-1-yl)-4-(2-thiophenylsulfonyl)-1-piperazinyl)-5-pyrimidinyl)-2-propanol (18 mg).

$^1$H NMR (400 MHz, MeOD) δ=8.62 (s, 2H), 7.87 (dd, J=1.3, 5.0 Hz, 1H), 7.70-7.61 (m, 1H), 7.25 (dd, J=3.8, 5.0 Hz, 1H), 5.79 (m, 1H), 4.71 (d, J=13.3 Hz, 1H), 3.90-3.81 (m, 2H), 3.46 (dt, J=3.3, 12.8 Hz, 1H), 2.66 (m, 1H), 2.49 (dt, J=3.3, 11.9 Hz, 1H), 1.85 (d, J=2.2 Hz, 3H). m/z (ESI, +ve ion) 515.5 (M+H)$^+$. GK-GKRP IC$_{50}$ (Binding)=0.024 μM.

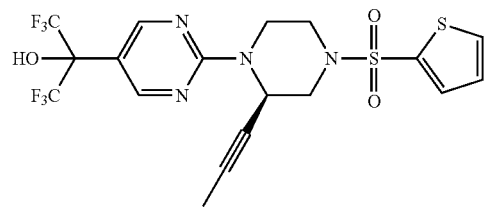

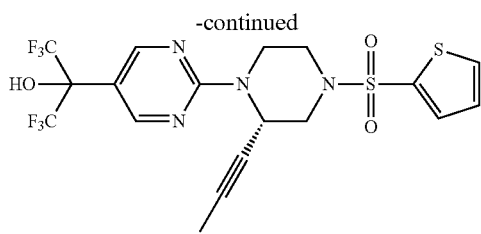

1,1,1,3,3,3-hexafluoro-2-(2-((2R)-2-(1-propyn-1-yl)-4-(2-thiophenylsulfonyl)-1-piperazinyl)-5-pyrimidinyl)-2-propanol; and 1,1,1,3,3,3-hexafluoro-2-(2-((2S)-2-(1-propyn-1-yl)-4-(2-thiophenylsulfonyl)-1-piperazinyl)-5-pyrimidinyl)-2-propanol Example 270

1,1,1-trifluoro-2-(4-((2S)-4-(2-thiophenylsulfonyl)-2-((3-(trifluoromethyl)-1-piperazinyl)methyl)-1-piperazinyl)phenyl)-2-propanol

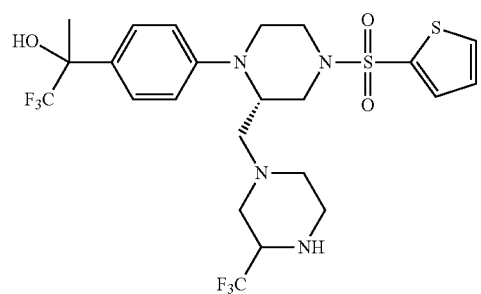

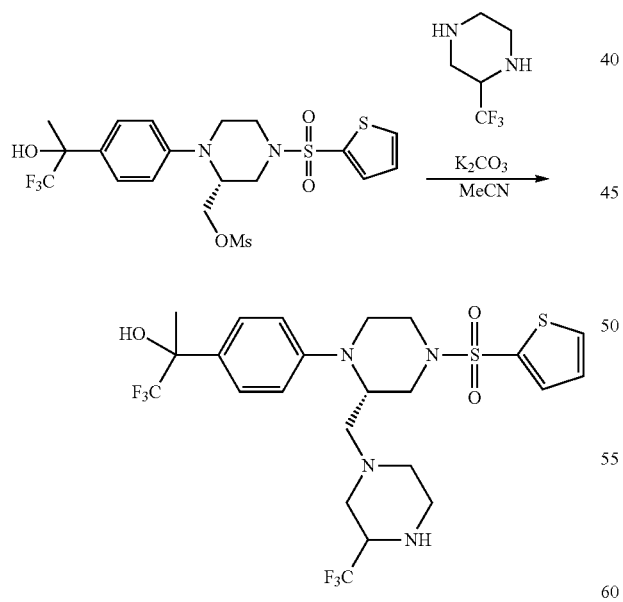

This compound was synthesized following the procedure described for Example 143. The reaction of 2-(trifluoromethyl)piperazine (109 mg, 0.709 mmol, Oakwood Products, West Columbia, S.C.) and ((2R)-4-(2-thiophenylsulfonyl)-1-(4-(2,2,2-trifluoro-1-hydroxy-1-methylethyl)phenyl)-2-piperazinyl)methyl methanesulfonate (Intermediate B) delivered 1,1,1-trifluoro-2-(4-((2S)-4-(2-thiophenylsulfonyl)-2-((3-(trifluoromethyl)-1-piperazinyl)methyl)-1-piperazinyl)phenyl)-2-propanol as a mixture of four isomers after column chromatography on silica gel (0% to 8% MeOH in CH$_2$Cl$_2$). Further purification by reverse phase HPLC (Phenomenex Gemini-NX C$_{18}$ column, 21×100 mm, 5 μm eluting with A: Water w/0.1% NH$_4$OH B: Acetonitrile w/0.1% NH$_4$OH) yielded two peaks, each comprised of a pair of isomers.

First Eluting Peak (Peak 1):

$^1$H NMR (400 MHz, MeOD) δ=7.90 (dd, J=1.3, 5.0 Hz, 1H), 7.69-7.64 (m, 1H), 7.50-7.44 (m, 2H), 7.31-7.25 (m, 1H), 6.94 (d, J=8.6 Hz, 2H), 4.20-4.11 (m, 1H), 3.98-3.90 (m, 1H), 3.81 (m, 1H), 3.45 (m, 1H), 3.26 (m, 1H), 3.08-2.86 (m, 3H), 2.81 (d, J=11.0 Hz, 1H), 2.74-2.56 (m, 4H), 2.53-2.41 (m, 1H), 2.16-2.00 (m, 2H), 1.70 (s, 3H). m/z (ESI, +ve ion) 587.6 (M+H)$^+$. GK-GKRP IC$_{50}$ (Binding)=0.251 μM.

Second Eluting Peak (Peak 2):

$^1$H NMR (400 MHz, MeOD) δ=7.90 (dd, J=1.3, 5.0 Hz, 1H), 7.69-7.64 (m, 1H), 7.47 (d, J=8.6 Hz, 2H), 7.28 (dd, J=3.7, 5.1 Hz, 1H), 6.99-6.91 (m, 2H), 4.11 (m, 1H), 3.98-3.91 (m, 1H), 3.83-3.75 (m, 1H), 3.48-3.41 (m, 1H), 3.31-3.19 (m, 2H), 3.00-2.93 (m, 1H), 2.89 (m, 1H), 2.84-2.76 (m, 1H), 2.75-2.55 (m, 4H), 2.36 (m, 1H), 2.24-2.15 (m, 1H), 1.99 (m, 1H), 1.70 (s, 3H). m/z (ESI, +ve ion) 587.6 (M+H)$^+$. GK-GKRP IC$_{50}$ (Binding)=0.463 μM.

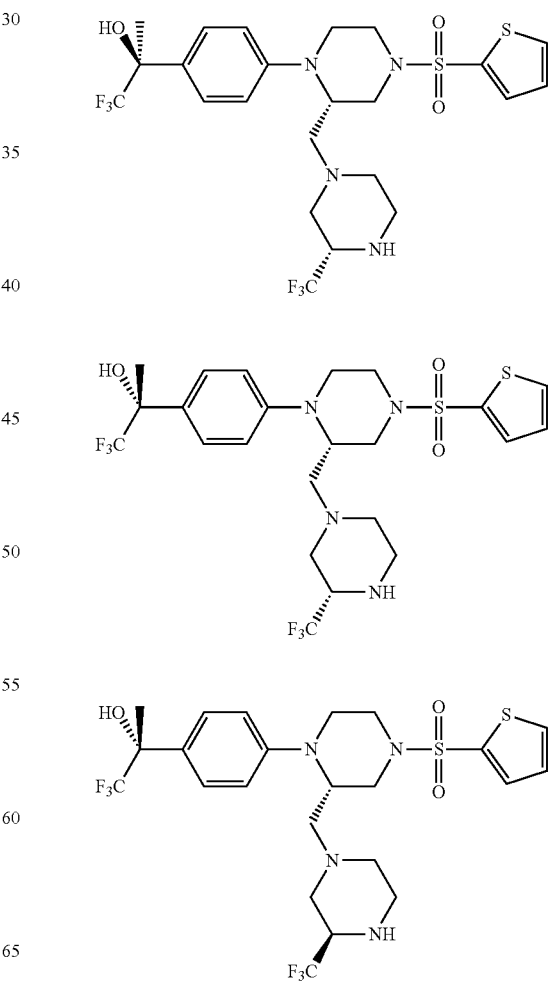

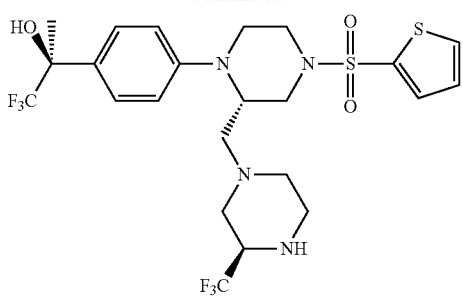

(2S)-1,1,1-trifluoro-2-(4-((2S)-4-(2-thiophenylsulfonyl)-2-(((3S)-3-(trifluoromethyl)-1-piperazinyl)methyl)-1-piperazinyl)phenyl)-2-propanol; (2R)-1,1,1-trifluoro-2-(4-((2S)-4-(2-thiophenylsulfonyl)-2-(((3S)-3-(trifluoromethyl)-1-piperazinyl)methyl)-1-piperazinyl)phenyl)-2-propanol; (2S)-1,1,1-trifluoro-2-(4-((2S)-4-(2-thiophenylsulfonyl)-2-(((3R)-3-(trifluoromethyl)-1-piperazinyl)methyl)-1-piperazinyl)phenyl)-2-propanol; and (2R)-1,1,1-trifluoro-2-(4-((2S)-4-(2-thiophenylsulfonyl)-2-(((3R)-3-(trifluoromethyl)-1-piperazinyl)methyl)-1-piperazinyl)phenyl)-2-propanol.

Example 271

2-(2-((2S)-4-((6-amino-3-pyridinyl)sulfonyl)-2-(3-oxa-8-azabicyclo[3.2.1]oct-8-ylmethyl)-1-piperazinyl)-5-pyrimidinyl)-1,1,1,3,3,3-hexafluoro-2-propanol

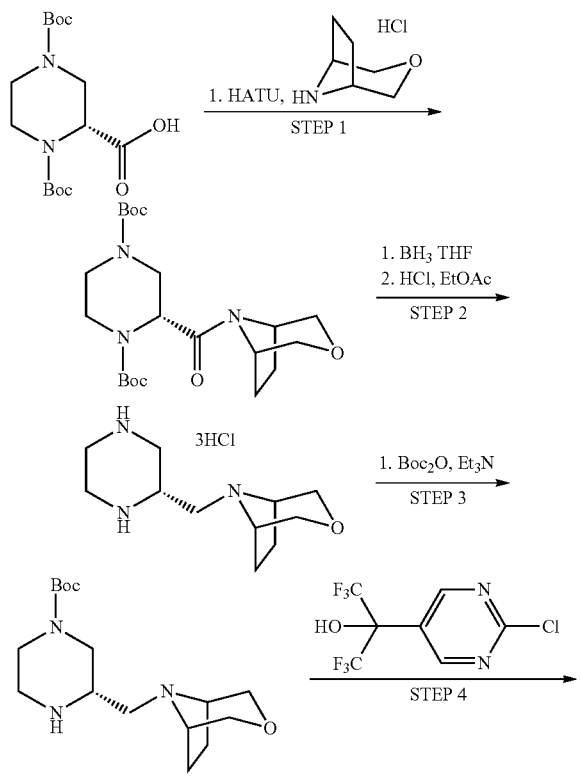

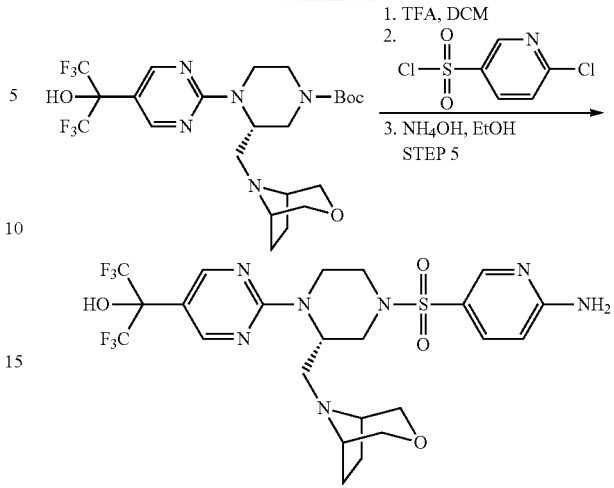

Step 1: di-tert-butyl (2R)-2-(3-oxa-8-azabicyclo[3.2.1]oct-8-ylcarbonyl)-1,4-piperazinedicarboxylate In a 250-mL round-bottomed flask, a solution of (R)-1,4-bis(tert-butoxycarbonyl)piperazine-2-carboxylic acid (1.51 g, 4.57 mmol, ASW Medchem, New Brunswick, N.J.), 3-oxa-8-azabicyclo[3.2.1]octane hydrochloride (0.684 g, 4.57 mmol, Advanced Chemblocks, Burlingame, Calif.), and Hünig's base (1.76 mL, 10.06 mmol) in 15 mL of DMF was stirred at 0° C. To this mixture was added HATU (1.912 g, 5.03 mmol, Oakwood Products, West Columbia, S.C.). The reaction was stirred for 3 h at room temperature. The mixture was then diluted with EtOAc (25 mL) and water (25 mL). The organic solution was then extracted with water (2×25 mL) and brine (25 mL). The organic layer was dried over $MgSO_4$, filtered, and concentrated. The crude material was purified via column chromatography (about 40 g silica gel, 5% to 80% of EtOAc in hexanes) to give (R)-di-tert-butyl 2-((1R,5S)-3-oxa-8-azabicyclo[3.2.1]octane-8-carbonyl)piperazine-1,4-dicarboxylate (1.78 g) as a colorless oil.

Step 2: 8-((2R)-2-piperazinylmethyl)-3-oxa-8-azabicyclo[3.2.1]octane trihydrochloride A 150-mL round-bottomed flask was charged with di-tert-butyl 2-((1R,5S)-3-oxa-8-azabicyclo[3.2.1]octane-8-carbonyl)piperazine-1,4-dicarboxylate (1.90 g, 4.47 mmol), and 100 mL of THF. To this was added $BH_3$.THF (1M in THF, 22.33 ml, 22.33 mmol, Sigma-Aldrich, St. Louis, Mo.). The mixture was heated at 60° C. for 2 h and then cooled to 0° C. and slowly quenched with 100 mL of MeOH. The mixture was concentrated in vacuo and then diluted with 200 mL of EtOAc. To this was added 100 mL of 4N HCl in dioxane. The mixture was heated at 70° C. for 16 h and the resulting white precipitate was collected by filtration to give 8-((2R)-2-piperazinylmethyl)-3-oxa-8-azabicyclo[3.2.1]octane trihydrochloride (1.38 g).

Step 3: (3S)-3-(3-oxa-8-azabicyclo[3.2.1]oct-8-ylmethyl)-1-piperazinecarboxylate A mixture of 8-((2R)-2-piperazinylmethyl)-3-oxa-8-azabicyclo[3.2.1]octane trihydrochloride (1.39 g, 4.33 mmol) suspended in $CH_2Cl_2$ was chilled to 0° C. To this mixture was added triethylamine (2.42 mL, 17.34 mmol)

followed by di-tert-butyl dicarbonate (1.00 mL, 4.33 mmol, Sigma-Aldrich, St. Louis, Mo.). The reaction was gradually allowed to warm to room temperature and stirred for 3 h. Afterwards, the mixture was concentrated. The crude material was purified by via column chromatography (about 40 g silica gel, 0% to 10% of MeOH in $CH_2Cl_2$) to give (3S)-3-(3-oxa-8-azabicyclo[3.2.1]oct-8-ylmethyl)-1-piperazinecarboxylate (0.995 g) as a colorless oil.

Step 4 and Step 5: 2-(2-((2S)-4-((6-amino-3-pyridinyl)sulfonyl)-2-(3-oxa-8-azabicyclo[3.2.1]oct-8-ylmethyl)-1-piperazinyl)-5-pyrimidinyl)-1,1,1,3,3,3-hexafluoro-2-propanol Following the procedure outlined in Example 128, starting with (3S)-3-(3-oxa-8-azabicyclo[3.2.1]oct-8-ylmethyl)-1-piperazinecarboxylate gave 2-(2-((2S)-4-((6-amino-3-pyridinyl)sulfonyl)-2-(3-oxa-8-azabicyclo[3.2.1]oct-8-ylmethyl)-1-piperazinyl)-5-pyrimidinyl)-1,1,1,3,3,3-hexafluoro-2-propanol.

$^1$H NMR (400 MHz, $CDCl_3$) δ=8.53 (s, 2H), 8.44 (s, 1H), 7.76 (d, J=8.8 Hz, 1H), 6.53 (d, J=8.8 Hz, 1H), 5.00 (s, 2H), 4.86 (m, 1H), 4.72 (m, 1H), 4.11 (d, J=11.3 Hz, 1H), 3.79 (d, J=11.0 Hz, 1H), 3.57 (m, 1H), 3.52-3.38 (m, 2H), 3.25-3.04 (m, 4H), 2.65 (t, J=10.2 Hz, 1H), 2.51-2.32 (m, 3H), 1.83 (br. s., 4H). m/z (ESI, +ve ion) 612.2 $(M+H)^+$. GK-GKRP $IC_{50}$ (Binding)=0.003 µM.

Example 272

(S)-5-methyl-4-(((S)-4-(tiophen-2-yl sulfonyl)-1-(4-((S)-1,1,1-trifluoro-2-hydroxypropan-2-yl)phenyl)piperazin-2-yl)methyl)morpholin-3-one

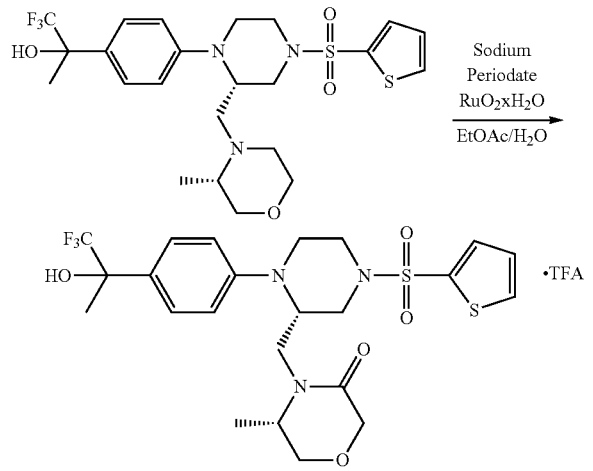

A solution of (2S)-1,1,1-trifluoro-2-(4-(2-(((R)-3-methylmorpholino)methyl)-4-(thiophen-2-ylsulfonyl)piperazin-1-yl)phenyl)propan-2-ol (50 mg, 0.094 mmol, Example 45, peak 2) in EtOAc (1 mL) was added to a mixture of dioxoruthenium hydrate (1.42 mg, 9.37 µmol, Sigma Aldrich, St. Louis, Mo.) and 10% aqueous sodium periodate (30.1 mg, 0.141 mmol, Sigma Aldrich, St. Louis, Mo.) in water (1.5 mL). The solution was stirred vigorously for 48 hours at room temperature. The reaction mixture was then concentrated in a GeneVac HT-12 (GeneVac Technologies, IPS Technologies, UK), re-dissolved in MeOH (1.5 mL), filtered through syringe filters (Pall Life Sciences, Acrodic®, 25 mm Syringe Filter w/0.45 µm HT Tuffryn® Membrane) and purified on Prep HPLC (Method: 10 min, 10 to 90% ACN, Water, 0.1% TFA, 254 nm; Column: Phenomenex, Gemini-NX, 5µ, $C_{18}$, 150×30.00 mm) to afford (S)-5-methyl-4-(((S)-4-(thiophen-2-ylsulfonyl)-1-(4-((S)-1,1,1-trifluoro-2-hydroxypropan-2-yl)phenyl)piperazin-2-yl)methyl)morpholin-3-one (12.6 mg).

$^1$H NMR (300 MHz, MeOD) δ ppm 7.86-7.91 (m, 1H), 7.63-7.68 (m, 1H), 7.39-7.47 (m, 2H), 7.22-7.29 (m, 1H), 6.83-6.91 (m, 2H), 4.86-4.89 (m, 1H), 3.85-3.88 (m, 1H), 3.80-3.84 (m, 1H), 3.75-3.79 (m, 1H), 3.70-3.74 (m, 1H), 3.53 (m, 1H) 3.47-3.50 (m, 1H), 3.43-3.47 (m, 1H), 3.40-3.43 (m, 1H), 3.34-3.39 (m, 1H), 3.21-3.28 (m, 1H), 2.97-3.08 (m, 1H), 2.64-2.73 (m, 1H), 2.43-2.55 (m, 1H), 2.30-2.39 (m, 1H), 1.67 (s, 3H), 1.16-1.24 (m, 3H). m/z (ESI, +ve ion) 548.0. $(M+H)^+$. GK-GKRP $IC_{50}$ (Binding)=0.217 µM.

Example 273

2-(4-((2R)-4-((6-amino-3-pyridinyl)sulfonyl)-2-((phenylsulfonyl)methyl)-1-piperazinyl)phenyl)-1,1,1,3,3,3-hexafluoro-2-propanol

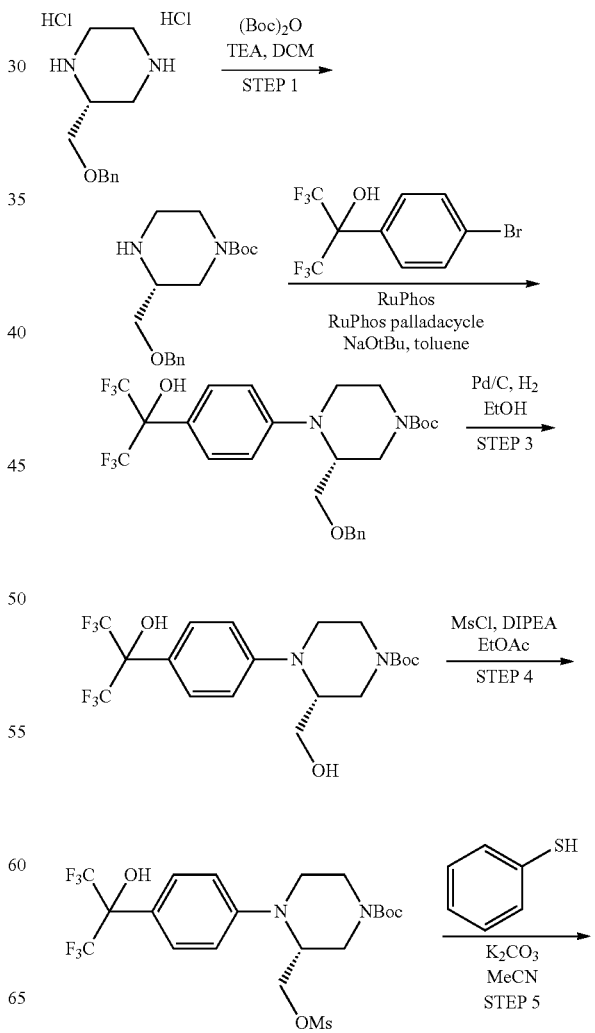

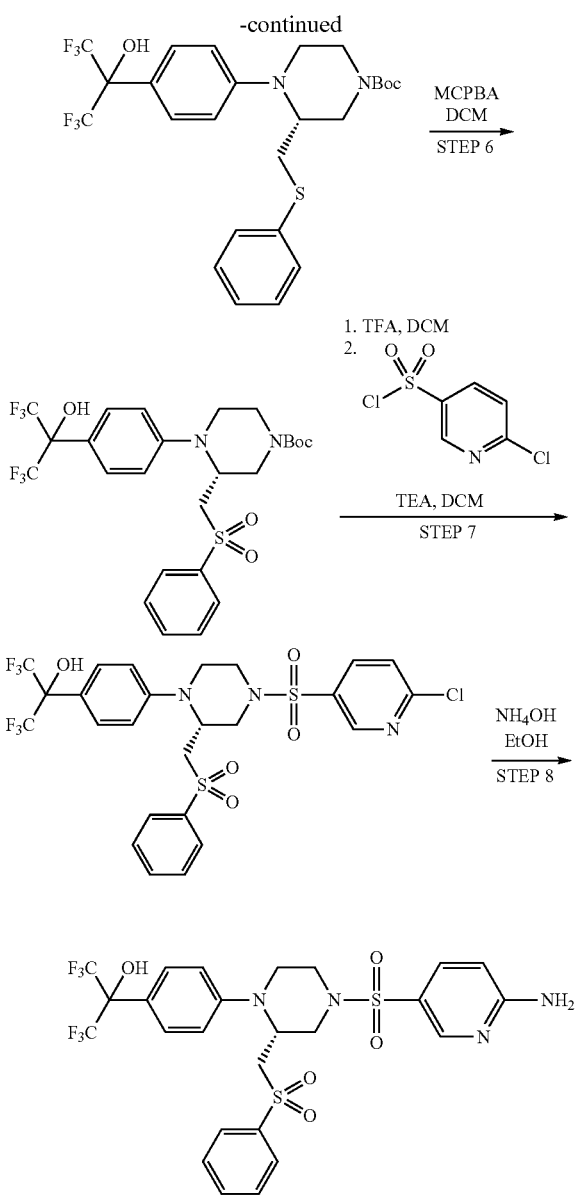

Step 1: tert-butyl (3R)-3-((benzyloxy)methyl)-1-piperazinecarboxylate

A 150-mL round-bottomed flask was charged with (2R)-2-((benzyloxy)methyl)piperazine dihydrochloride (2.60 g, 9.30 mmol, Intermediate B, step 2), TEA (6.50 mL, 46.6 mmol) and DCM (30 mL). The reaction mixture was stirred at rt for 30 min then cooled to 0° C. Di-tert-butyl dicarbonate (2.07 g, 9.47 mmol, Sigma-Aldrich, St. Louis, Mo.) was added and the mixture was stirred at 0° C. for 1 h. Water (75 mL) was added and the aqueous phase was extracted with DCM (2×50 mL). The combined organic phases were washed with water (100 mL) and saturated aqueous NaCl (100 mL). The organic phase was dried over sodium sulfate, filtered and concentrated in vacuo. The crude product was purified by column chromatography (50 g of silica, 1-8% MeOH in DCM) to afford tert-butyl (3R)-3-((benzyloxy)methyl)-1-piperazinecarboxylate (1.55 g) as a light brown oil.

Step 2: tert-butyl (3R)-3-((benzyloxy)methyl)-4-(4-(2,2,2-trifluoro-1-hydroxy-1-(trifluoromethyl)ethyl)phenyl)-1-piperazinecarboxylate A 20 mL vial was charged with tert-butyl (3R)-3-((benzyloxy)methyl)-1-piperazinecarboxylate (1.19 g, 3.88 mmol), 2-(4-bromophenyl)-1,1,1,3,3,3-hexafluoro-2-propanol (1.39 g, 4.31 mmol, Bioorg. Med. Chem. Lett. 2002, 12, 3009), RuPhos Palladacycle (0.047 g, 0.039 mmol, Strem Chemical Inc, Newburyport, Mass.), NaOtBu (0.938 g, 9.76 mmol, Sigma-Aldrich, St. Louis, Mo.) and toluene (12 mL). The mixture was degassed by bubbling Ar through the solution for 10 min. The vial was sealed and the mixture was heated at 100° C. for 3 h. Water (100 mL) was added and the aqueous phase was extracted with EtOAc (2×60 mL). The combined organic phases were dried over sodium sulfate, filtered and concentrated in vacuo. The crude product was purified by column chromatography (100 g of silica, 0-30% EtOAc in hexanes) to afford tert-butyl (3R)-3-((benzyloxy)methyl)-4-(4-(2,2,2-trifluoro-1-hydroxy-1-(trifluoromethyl)ethyl)phenyl)-1-piperazinecarboxylate (1.78 g) as an off-white foam.

Step 3: tert-butyl (3R)-3-(hydroxymethyl)-4-(4-(2,2,2-trifluoro-1-hydroxy-1-(trifluoromethyl)ethyl)phenyl)-1-piperazinecarboxylate A 150-mL round-bottomed flask was charged with tert-butyl (3R)-3-((benzyloxy)methyl)-4-(4-(2,2,2-trifluoro-1-hydroxy-1-(trifluoromethyl)ethyl)phenyl)-1-piperazinecarboxylate (0.917 g, 1.67 mmol), palladium on activated carbon (10 wt %, wet, degussa type, 1.34 g, 0.632 mmol, Sigma-Aldrich, St. Louis, Mo.) and EtOH (15 mL). The reaction mixture was evacuated under vacuum and refilled with hydrogen (5 times). The mixture was hydrogenated under balloon pressure of hydrogen at 60° C. for 2 h. The catalyst was removed via filtration through a pad of filter agent. The filter cake was covered with sand and washed with EtOH. The filtrate was concentrated to give tert-butyl (3R)-3-(hydroxymethyl)-4-(4-(2,2,2-trifluoro-1-hydroxy-1-(trifluoromethyl)ethyl)phenyl)-1-piperazinecarboxylate (0.767 g) as a white solid.

Step 4: tert-butyl (3R)-3-(((methylsulfonyl)oxy)methyl)-4-(4-(2,2,2-trifluoro-1-hydroxy-1-(trifluoromethyl)ethyl)phenyl)-1-piperazinecarboxylate A 150-mL round-bottomed flask was charged with tert-butyl (3R)-3-(hydroxymethyl)-4-(4-(2,2,2-trifluoro-1-hydroxy-1-(trifluoromethyl)ethyl)phenyl)-1-piperazinecarboxylate (0.393 g, 0.857 mmol), DIPEA (0.450 mL, 2.58 mmol) and EtOAc (5 mL). The reaction mixture was cooled to 0° C. and methanesulfonyl chloride (0.095 mL, 1.2 mmol, Sigma-Aldrich, St. Louis, Mo.) was added dropwise. The mixture was stirred at 0° C. for 1 h. At that time, 4 drops of methanesulfonyl chloride was added and stirring at 0° C. resumed for 10 min. The material was directly purified by column chromatography (25 g of silica, 0 to 50% EtOAc in hexanes) to afford tert-butyl (3R)-3-(((methylsulfonyl)oxy)methyl)-4-(4-(2,2,2-trifluoro-1-hydroxy-1-(trifluoromethyl)ethyl)phenyl)-1-piperazinecarboxylate (0.311 g) as a white foam.

Step 5: tert-butyl (3R)-3-((phenylsulfanyl)methyl)-4-(4-(2,2,2-trifluoro-1-hydroxy-1-(trifluoromethyl)ethyl)phenyl)-1-piperazinecarboxylate A 5 mL vial was charged with (3R)-3-(((methylsulfonyl)oxy)methyl)-4-(4-(2,2,2-trifluoro-1-hydroxy-1-(trifluoromethyl)ethyl)phenyl)-1-piperazinecarboxylate (0.300 g, 0.559 mmol), potassium carbonate (0.190 g, 1.38 mmol), benzenethiol (0.070 mL, 0.69 mmol, Sigma-Aldrich, St. Louis, Mo.) and acetonitrile (2 mL). The reaction mixture was heated in an Initiator microwave reactor (Biotage AB, Inc., Uppsala, Sweden) at 120° C. for 30 min. The reaction mixture was partitioned between water (20 mL) and EtOAc (20 mL). The aqueous phase was extracted with EtOAc (20 mL). The combined organic phases were washed with saturated aqueous NaCl (40 mL). The organic phase was dried over sodium sulfate, filtered and concentrated in vacuo. The crude product was purified by column chromatography (25 g of silica, 0-30% EtOAc in hexanes) to afford tert-butyl (3R)-3-((phenylsulfanyl)methyl)-4-(4-(2,2,2-trifluoro-1-hydroxy-1-(trifluoromethyl)ethyl)phenyl)-1-piperazinecarboxylate (0.189 g) as a white solid.

Step 6: tert-butyl (3R)-3-((phenylsulfonyl)methyl)-4-(4-(2,2,2-trifluoro-1-hydroxy-1-(trifluoromethyl)ethyl)phenyl)-1-piperazinecarboxylate A 150-mL round-bottomed flask was charged with tert-butyl (3R)-3-((phenylsulfanyl)methyl)-4-(4-(2,2,2-trifluoro-1-hydroxy-1-(trifluoromethyl)ethyl)phenyl)-1-piperazinecarboxylate (0.189 g, 0.343 mmol), mCPBA (0.179 g, 0.726 mmol, Sigma-Aldrich, St. Louis, Mo.) and DCM (5 mL). The solution was stirred at rt for 20 min. The mixture was concentrated and the crude product was purified by column chromatography (25 g of silica, 0-50% EtOAc in hexanes) to afford tert-butyl (3R)-3-((phenylsulfonyl)methyl)-4-(4-(2,2,2-trifluoro-1-hydroxy-1-(trifluoromethyl)ethyl)phenyl)-1-piperazinecarboxylate (0.0385 g) as a white solid.

Step 7: 2-(4-((2R)-4-((6-chloro-3-pyridinyl)sulfonyl)-2-((phenylsulfonyl)methyl)-1-piperazinyl)phenyl)-1,1,1,3,3,3-hexafluoro-2-propanol A 20 mL vial was charged with tert-butyl (3R)-3-((phenylsulfonyl)methyl)-4-(4-(2,2,2-trifluoro-1-hydroxy-1-(trifluoromethyl)ethyl)phenyl)-1-piperazinecarboxylate (0.038 g, 0.065 mmol), TFA (0.50 mL, 6.5 mmol, Sigma-Aldrich, St. Louis, Mo.) and DCM (1 mL). The mixture was stirred at rt for 10 min. The volatile was removed and the residue was taken into DCM (1 mL). TEA (0.10 mL, 0.78 mmol) was added and the mixture was stirred at rt for 5 min. At this time, 6-chloropyridine-3-sulfonyl chloride (0.016 g, 0.073 mmol, *Organic Process Research & Development* 2009, 13, 875) was added and the mixture was stirred at rt for 10 min. The reaction mixture was directly purified by column chromatography (10 g of silica, 0 to 50% EtOAc in hexanes) to afford 2-(4-((2R)-4-((6-chloro-3-pyridinyl)sulfonyl)-2-((phenylsulfonyl)methyl)-1-piperazinyl)phenyl)-1,1,1,3,3,3-hexafluoro-2-propanol (0.026 g) as a white solid.

Step 8: 2-(4-((2R)-4-((6-amino-3-pyridinyl)sulfonyl)-2-((phenylsulfonyl)methyl)-1-piperazinyl)phenyl)-1,1,1,3,3,3-hexafluoro-2-propanol A 2-mL vial was charged with 2-(4-((2R)-4-((6-chloro-3-pyridinyl)sulfonyl)-2-((phenylsulfonyl)methyl)-1-piperazinyl)phenyl)-1,1,1,3,3,3-hexafluoro-2-propanol (0.026 g, 0.039 mmol) and ammonium hydroxide (30 wt %, 0.50 mL, 3.9 mmol) and EtOH (0.5 mL). The vial was sealed and the reaction mixture was stirred at 110° C. for 5 h. The reaction mixture was concentrated and purified by column chromatography (10 g of silica, 0-5% (2 M NH$_3$ in MeOH) in DCM) to afford 2-(4-((2R)-4-((6-amino-3-pyridinyl)sulfonyl)-2-((phenylsulfonyl)methyl)-1-piperazinyl)phenyl)-1,1,1,3,3,3-hexafluoro-2-propanol (0.0057 g) as a white solid.

$^1$H NMR (400 MHz, CD$_3$OD) δ=8.30 (d, J=2.0 Hz, 1H), 7.83 (d, J=7.6 Hz, 2H), 7.76-7.69 (m, 2H), 7.62-7.54 (m, 2H), 7.40 (d, J=8.8 Hz, 2H), 6.72 (d, J=9.0 Hz, 2H), 6.63 (d, J=9.0 Hz, 1H), 4.43 (d, J=8.8 Hz, 1H), 3.99 (d, J=11.5 Hz, 1H), 3.82-3.71 (m, 2H), 3.47 (d, J=12.3 Hz, 1H), 3.10 (d, J=14.3 Hz, 1H), 3.00 (dt, J=3.2, 12.3 Hz, 1H), 2.71 (d, J=10.6 Hz, 1H), 2.58-2.48 (m, 1H). m/z (ESI, +ve ion) 639.1 (M+H)$^+$. GK-GKRP IC$_{50}$ (Binding)=0.049 μM.

What is claimed is:

1. A compound of Formula I, or a pharmaceutically acceptable salt thereof,

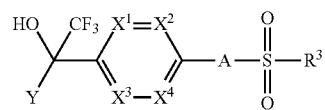

wherein:
Y is —CF$_3$, —CHF$_2$, —CFH$_2$, —C$_{1-6}$alkyl, —OC$_{1-6}$alkyl, —(CR$^c$R$^c$)$_n$OR$^c$, or C$_{3-6}$cycloalkyl;
A is

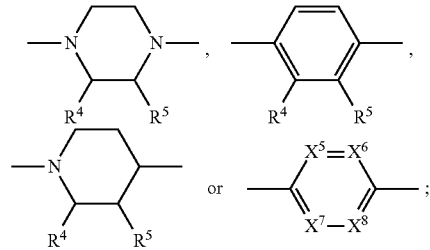

R$^3$ is a five or six membered aryl ring or five or six membered heteroaryl ring containing from 1 to 3 heteroatoms independently selected from N, O or S, which aryl or heteroaryl ring can be optionally substituted with from one to four substituents independently selected from C$_{1-6}$alkyl,
—OC$_{1-6}$alkyl, —NR$^c$R$^c$, —CF$_3$, —CN, —OH, —NO$_2$ or halo;
each R$^b$ is independently hydrogen,
C$_{1-6}$alkyl,
—S(=O)$_2$C$_{1-6}$alkyl,
—C(=O)C$_{1-6}$alkyl,
—CD$_3$,
—(CR$^c$R$^c$)$_n$CFH$_2$,
—(CR$^c$R$^c$)$_n$CF$_2$H,
—(CR$^c$R$^c$)$_n$CF$_3$,
—(CR$^c$R$^c$)$_n$ 5 to 10 membered aryl,
—(CR$^c$R$^c$)$_n$ 5 to 10 membered substituted aryl,
—(CR$^c$R$^c$)$_n$ 5 to 10 membered heteroaryl containing from 1 to 3 heteroatoms independently selected from N, O or S,
—(CR$^c$R$^c$)$_n$ 5 to 10 membered substituted heteroaryl containing from 1 to 3 heteroatoms independently selected from N, O or S,
—(CR$^c$R$^c$)$_n$ 3 to 10 membered cycloalkyl,
—(CR$^c$R$^c$)$_n$ 3 to 10 membered substituted cycloalkyl,
—(CR$^c$R$^c$)$_n$ 3 to 10 membered heterocycloalkyl containing from 1 to 3 heteroatoms independently selected from N, O or S, or —(CR$^c$R$^c$)$_n$ 3 to 10 membered substituted heterocycloalkyl containing from 1 to 3 heteroatoms independently selected from N, O or S, wherein substituted groups can have from one to four substitutents independently selected from —C$_{1-6}$alkyl,
—OC$_{1-6}$alkyl, —NR$^c$R$^c$, —CF$_3$, —CN, —(CR$^c$R$^c$)$_n$OR$^c$, —C$_{3-6}$cycloalkyl, halo,
—(CR$^c$R$^c$)$_n$NR$^c$S(=O)$_2$R$^c$, —(CR$^c$R$^c$)$_n$C(=O)OR$^c$, —(CR$^c$R$^c$)$_n$C(=O)NR$^c$R$^c$, 5 to 10 membered aryl, or 5 to 10 membered aryl substituted with from one to four substitutents independently selected from —C$_{1-6}$alkyl,
—OC$_{1-6}$alkyl, —NR$^c$R$^c$, —CF$_3$, —CN, —(CR$^c$R$^c$)$_n$OR$^c$, C$_{3-6}$cycloalkyl, halo,
—(CR$^c$R$^c$)$_n$NR$^c$S(=O)$_2$R$^c$, —(CR$^c$R$^c$)$_n$C(=O)OR$^c$, —(CR$^c$R$^c$)$_n$C(=O)NR$^c$R$^c$;

each R$^c$ is independently hydrogen or C$_{1-6}$alkyl;

X$^1$, X$^2$, X$^3$ and X$^4$ are each independently selected from CR$^a$ or N;

X$^5$ and X$^6$ are independently selected from N or CR$^a$;

X$^7$ is N or CR$^4$;

X$^8$ is N or CR$^5$;

each R$^a$, R$^4$ and R$^5$ are independently selected from hydrogen,
C$_{1-6}$alkyl,
halo,
—C≡CCF$_2$CH$_3$,
—C≡CCF$_2$CF$_3$,
—OC$_{1-6}$alkyl,
—(CR$^b$R$^b$)$_n$NR$^c$R$^c$,
—(CR$^b$R$^b$)$_n$CF$_3$,
—(CR$^b$R$^b$)$_n$OR$^c$,
—(CR$^b$R$^b$)$_n$CN,
—(CR$^b$R$^b$)$_n$NR$^b$(CR$^b$R$^b$)$_n$OR$^c$,
—(CR$^b$R$^b$)$_n$NR$^b$(CR$^b$R$^b$)$_n$ 5 to 10 membered aryl,
—(CR$^b$R$^b$)$_n$NR$^b$(CR$^b$R$^b$)$_n$ 5 to 10 membered substituted aryl,
—(CR$^b$R$^b$)$_n$O(CR$^b$R$^b$)$_n$ 5 to 10 membered aryl,
—(CR$^b$R$^b$)$_n$O(CR$^b$R$^b$)$_n$ 5 to 10 membered substituted aryl,
—(CR$^b$R$^b$)$_n$O(CR$^b$R$^b$)$_n$ 5 to 10 membered heteroaryl,
—(CR$^b$R$^b$)$_n$O(CR$^b$R$^b$)$_n$ 5 to 10 membered substituted heteroaryl,
—(CR$^b$R$^b$)$_n$NR$^b$(CR$^b$R$^b$)$_n$ 5 to 10 membered heteroaryl,
—(CR$^b$R$^b$)$_n$NR$^b$(CR$^b$R$^b$)$_n$ 5 to 10 membered substituted heteroaryl,
—(CR$^b$R$^b$)$_n$ 5 to 10 membered aryl,
—(CR$^b$R$^b$)$_n$ 5 to 10 membered substituted aryl,
—(CR$^b$R$^b$)$_n$ 5 to 10 membered heteroaryl,
—(CR$^b$R$^b$)$_n$ 5 to 10 membered substituted heteroaryl,
—(CR$^b$R$^b$)$_n$ 3 to 10 membered cycloalkyl,
—(CR$^b$R$^b$)$_n$ 3 to 10 membered substituted cycloalkyl,
—(CR$^b$R$^b$)$_n$ 5 to 10 membered heterocycloalkyl,
—(CR$^b$R$^b$)$_n$ 5 to 10 membered substituted heterocycloalkyl,
—C≡C—R$^b$,
—C≡C—(CR$^b$R$^b$)$_n$OR$^c$,
—C≡C—(CR$^b$R$^b$)$_n$ 3 to 10 membered heterocycloalkyl,
—C≡C—(CR$^b$R$^b$)$_n$ 3 to 10 membered substituted heterocycloalkyl,
—(CR$^b$R$^b$)$_n$ 3 to 10 membered heterocycloalkyl,
—(CR$^b$R$^b$)$_n$ 3 to 10 membered substituted heterocycloalkyl,
—(CR$^b$R$^b$)$_n$O(CR$^b$R$^b$)$_n$ 3 to 10 membered cycloalkyl,
—(CR$^b$R$^b$)$_n$O(CR$^b$R$^b$)$_n$ 3 to 10 membered substituted cycloalkyl,
—(CR$^b$R$^b$)$_n$O(CR$^b$R$^b$)$_n$ 3 to 10 membered heterocycloalkyl,
—(CR$^b$R$^b$)$_n$O(CR$^b$R$^b$)$_n$ 3 to 10 membered substituted heterocycloalkyl,
—(CR$^b$R$^b$)$_n$NR$^b$(CR$^b$R$^b$)$_n$ 3 to 10 membered heterocycloalkyl,
—(CR$^b$R$^b$)$_n$NR$^b$(CR$^b$R$^b$)$_n$ 3 to 10 membered substituted heterocycloalkyl,
—C≡C—(CR$^b$R$^b$)$_n$NR$^b$C(=O)OR$^b$,
—C≡C—(CR$^b$R$^b$)$_n$—NR$^b$R$^b$,
—C≡C—(CR$^b$R$^b$)$_n$NR$^b$—S(=O)$_2$R$^b$,
—(CR$^b$R$^b$)$_n$S(CR$^b$R$^b$)$_n$ 5 to 10 membered aryl,
—(CR$^b$R$^b$)$_n$S(CR$^b$R$^b$)$_n$ 5 to 10 membered substituted aryl,
—(CR$^b$R$^b$)$_n$S(CR$^b$R$^b$)$_n$ 5 to 10 membered heteroaryl,
—(CR$^b$R$^b$)$_n$S(CR$^b$R$^b$)$_n$ 5 to 10 membered substituted heteroaryl,
—(CR$^b$R$^b$)$_n$S(=O)$_2$(CR$^b$R$^b$)$_n$ 5 to 10 membered aryl,
—(CR$^b$R$^b$)$_n$S(=O)$_2$(CR$^b$R$^b$)$_n$ 5 to 10 membered substituted aryl,
—(CR$^b$R$^b$)$_n$S(=O)$_2$(CR$^b$R$^b$)$_n$ 5 to 10 membered heteroaryl,
—(CR$^b$R$^b$)$_n$S(=O)$_2$(CR$^b$R$^b$)$_n$ 5 to 10 membered substituted heteroaryl,
—(CR$^b$R$^b$)$_n$S(=O)(CR$^b$R$^b$)$_n$ 5 to 10 membered aryl,
—(CR$^b$R$^b$)$_n$S(=O)(CR$^b$R$^b$)$_n$ 5 to 10 membered substituted aryl,
—(CR$^b$R$^b$)$_n$NR$^b$S(=O)$_2$(CR$^b$R$^b$)$_n$ 5 to 10 membered aryl,
—(CR$^b$R$^b$)$_n$NR$^b$S(=O)$_2$(CR$^b$R$^b$)$_n$ 5 to 10 membered substituted aryl,
—(CR$^b$R$^b$)$_n$NR$^b$S(=O)$_2$(CR$^b$R$^b$)$_n$ 5 to 10 membered heteroaryl,
—(CR$^b$R$^b$)$_n$NR$^b$S(=O)$_2$(CR$^b$R$^b$)$_n$ 5 to 10 membered substituted heteroaryl,
—(CR$^b$R$^b$)$_n$NR$^b$—S(=O)$_2$R$^b$,
—(CR$^b$R$^b$)$_n$NR$^b$—C(=O)R$^b$, or
—(CR$^b$R$^b$)$_n$NR$^b$—S(=O)$_2$NR$^b$R$^b$, wherein the heteroaryl or heterocycloalkyl groups can have from 1 to 3 heteroatoms independently selected from O, N or S, and wherein substituted groups can have from one to four substitutents independently selected from —C$_{1-6}$alkyl, —OC$_{1-6}$alkyl, —NR$^c$R$^c$, —CF$_3$, —CN, —(CR$^c$R$^c$)$_n$OR$^c$, C$_{3-6}$cycloalkyl, halo,
—(CR$^c$R$^c$)$_n$NR$^c$S(=O)$_2$R$^c$, —(CR$^c$R$^c$)$_n$C(=O)OR$^c$, —(CR$^c$R$^c$)$_n$C(=O)NR$^c$R$^c$, 5 to 10 membered aryl, or 5 to 10 membered aryl substituted with from one to four substitutents independently selected from —C$_{1-6}$alkyl, —OC$_{1-6}$alkyl, —NR$^c$R$^c$, —CF$_3$, —CN, —(CR$^c$R$^c$)$_n$OR$^c$, C$_{3-6}$cycloalkyl, halo, —(CR$^c$R$^c$)$_n$NR$^c$S(=O)$_2$R$^c$,
—(CR$^c$R$^c$)$_n$C(=O)OR$^c$, —(CR$^c$R$^c$)$_n$C(=O)NR$^c$R$^c$, or one or more carbon atoms in any ring group may be replaced with —C(=O)— or —S(=O)$_2$—; and each n is independently 0, 1 or 2, provided that the compound is not 1,1,1,3,3,3-hexafluoro-2-(4-(4-(2-thiophenylsulfonyl)-1-piperazinyl)phenyl)-2-propanol; 1,1,1,3,3,3-hexafluoro-2-(4-(4-(phenylsulfonyl)-1-piperazinyl)phenyl)-2-propanol; 1,1,1,3,3,3-hexafluoro-2-(4-(4-((2-fluorophenyl)sulfonyl)-1-piperazinyl)phenyl)-2-propanol; 2-(4-(4-(3-chlorophenylsulfonyl)piperazin-1-yl)phenyl)-1,1,1,3,3,3-hexafluoro-2-propanol; or 2-(4-(4-((2-chlorophenyl)sulfonyl)-1-piperazinyl)phenyl)-1,1,1,3,3,3-hexafluoro-2-propanol.

2. A compound of Formula I, or a pharmaceutically acceptable salt thereof,

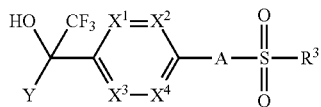

wherein:
Y is —CF$_3$, —CHF$_2$, —C$_{1-6}$alkyl, —OC$_{1-6}$alkyl, —CH$_2$OH, or C$_{3-6}$cycloalkyl;
A is

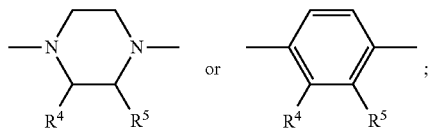

R$^3$ is a five or six membered aryl ring or five or six membered heteroaryl ring containing from 1 to 3 heteroatoms independently selected from N, O or S, which aryl or heteroaryl ring can be optionally substituted with from one to four substituents independently selected from C$_{1-6}$alkyl,
—OC$_{1-6}$alkyl, —NR$^b$R$^b$, —CF$_3$, —CN or halo;
each R$^b$ is independently hydrogen or C$_{1-6}$alkyl;
X$^1$, X$^2$, X$^3$ and X$^4$ are each independently selected from CR$^a$ or N;
each R$^a$, R$^4$ and R$^5$ are independently selected from hydrogen, C$_{1-6}$ alkyl,
—OC$_{1-6}$alkyl, —NR$^b$R$^b$, —CF$_3$, halo, —(CR$^b$R$^b$)$_n$OH, —(CR$^b$R$^b$)$_n$CN,
—(CR$^b$R$^b$)$_n$NR$^b$(CR$^b$R$^b$)$_n$OH,
—(CR$^b$R$^b$)$_n$NR$^b$(CR$^b$R$^b$)$_n$ 5 to 6 membered aryl,
—(CR$^b$R$^b$)$_n$NR$^b$(CR$^b$R$^b$)$_n$ 5 to 6 membered substituted aryl,
—(CR$^b$R$^b$)$_n$O(CR$^b$R$^b$)$_n$ 5 to 6 membered aryl,
—(CR$^b$R$^b$)$_n$O(CR$^b$R$^b$)$_n$ 5 to 6 membered substituted aryl,
—(CR$^b$R$^b$)$_n$O(CR$^b$R$^b$)$_n$ 5 to 6 membered heteroaryl,
—(CR$^b$R$^b$)$_n$O(CR$^b$R$^b$)$_n$ 5 to 6 membered substituted heteroaryl,
—(CR$^b$R$^b$)$_n$NR$^b$(CR$^b$R$^b$)$_n$ 5 to 6 membered heteroaryl,
—(CR$^b$R$^b$)$_n$NR$^b$(CR$^b$R$^b$)$_n$ 5 to 6 membered substituted heteroaryl,
—(CR$^b$R$^b$)$_n$ 5 to 6 membered aryl, —(CR$^b$R$^b$)$_n$ 5 to 6 membered substituted aryl,
—(CR$^b$R$^b$)$_n$ 5 to 6 membered heteroaryl,
—(CR$^b$R$^b$)$_n$ 5 to 6 membered substituted heteroaryl,
—(CR$^b$R$^b$)$_n$C$_{3-6}$cycloalkyl,
—(CR$^b$R$^b$)$_n$ substituted C$_{3-6}$cycloalkyl;
—C≡C—CR$^b$R$^b$OH, —C≡C— 3 to 8 membered heterocycloalkyl,
—C≡C— 3 to 8 membered substituted heterocycloalkyl,
—(CR$^b$R$^b$)$_n$ 3 to 8 membered heterocycloalkyl,
—(CR$^b$R$^b$)$_n$ 3 to 8 membered substituted heterocycloalkyl, wherein the heteroaryl or heterocycloalkyl groups can have from 1 to 3 heteroatoms independently selected from O, N or S, and wherein substituted groups can have from one to four substitutents independently selected from —C$_{1-6}$ alkyl, —OC$_{1-6}$alkyl, —NR$^b$R$^b$, —CF$_3$, —CN, —OH or halo; and
each n is independently 0, 1 or 2, provided that the compound is not 1,1,1,3,3,3-hexafluoro-2-(4-(4-(2-thiophenylsulfonyl)-1-piperazinyl)phenyl)-2-propanol; 1,1,1,3,3,3-hexafluoro-2-(4-(4-(phenylsulfonyl)-1-piperazinyl)phenyl)-2-propanol; 1,1,1,3,3,3-hexafluoro-2-(4-(4-((2-fluorophenyl)sulfonyl)-1-piperazinyl)phenyl)-2-propanol; 2-(4-(4-(3-chlorophenylsulfonyl)piperazin-1-yl)phenyl)-1,1,1,3,3,3-hexafluoro-2-propanol; or 2-(4-(4-((2-chlorophenyl)sulfonyl)-1-piperazinyl)phenyl)-1,1,1,3,3,3-hexafluoro-2-propanol.

3. A compound of Formula I, or a pharmaceutically acceptable salt thereof,

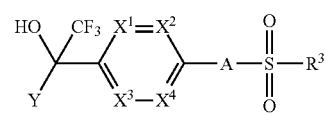

wherein:
Y is —CF$_3$, —CHF$_2$, —C$_{1-6}$alkyl, —OC$_{1-6}$alkyl, —CH$_2$OH, or C$_{3-6}$cycloalkyl;
A is

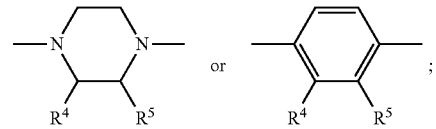

R$^3$ is a five or six membered aryl ring or five or six membered heteroaryl ring containing from 1 to 3 heteroatoms independently selected from N, O or S, which aryl or heteroaryl ring can be optionally substituted with from one to four substituents independently selected from C$_{1-6}$alkyl,
—OC$_{1-6}$alkyl, —NR$^b$R$^b$, —CF$_3$, —CN, —OH, —NO$_2$ or halo;
each R$^b$ is independently hydrogen,
C$_{1-6}$alkyl,
—(CR$^c$R$^c$)$_n$CF$_3$,
—(CR$^c$R$^c$)$_n$ 5 to 10 membered aryl,
—(CR$^c$R$^c$)$_n$ 5 to 10 membered substituted aryl,
—(CR$^c$R$^c$)$_n$ 5 to 10 membered heteroaryl containing from 1 to 3 heteroatoms independently selected from N, O or S,
—(CR$^c$R$^c$)$_n$ 5 to 10 membered substituted heteroaryl containing from 1 to 3 heteroatoms independently selected from N, O or S,
—(CR$^c$R$^c$)$_n$ 3 to 10 membered cycloalkyl,
—(CR$^c$R$^c$)$_n$ 3 to 10 membered substituted cycloalkyl,
—(CR$^c$R$^c$)$_n$ 3 to 10 membered heterocycloalkyl containing from 1 to 3 heteroatoms independently selected from N, O or S, or
—(CR$^c$R$^c$)$_n$ 3 to 10 membered substituted heterocycloalkyl containing from 1 to 3 heteroatoms independently selected from N, O or S, wherein substituted groups can have from one to four substitutents independently selected from —C$_{1-6}$alkyl,
—OC$_{1-6}$alkyl, —NR$^b$R$^b$, —CF$_3$, —CN, —(CR$^b$R$^b$)$_n$OH, C$_{3-6}$cycloalkyl, halo,
—(CR$^b$R$^b$)$_n$NR$^b$S(═O)$_2$R$^b$, —(CR$^b$R$^b$)$_n$C(═O)OR$^b$, —(CR$^b$R$^b$)$_n$C(═O)NR$^b$R$^b$, 5 to 10 membered aryl, or 5 to 10 membered substituted aryl;

each $R^c$ is independently hydrogen or $C_{1-6}$alkyl;
$X^1$, $X^2$, $X^3$ and $X^4$ are each independently selected from $CR^a$ or N;
each $R^a$, $R^4$ and $R^5$ are independently selected from hydrogen,
$C_{1-6}$alkyl,
halo,
—$OC_{1-6}$alkyl,
—$(CR^bR^b)_nNR^bR^b$,
—$(CR^bR^b)_nCF_3$,
—$(CR^bR^b)_nOH$,
—$(CR^bR^b)_nCN$,
—$(CR^bR^b)_nNR^b(CR^bR^b)_nOH$,
—$(CR^bR^b)_nNR^b(CR^bR^b)_n$ 5 to 10 membered aryl,
—$(CR^bR^b)_nNR^b(CR^bR^b)_n$ 5 to 10 membered substituted aryl,
—$(CR^bR^b)_nO(CR^bR^b)_n$ 5 to 10 membered aryl,
—$(CR^bR^b)_nO(CR^bR^b)_n$ 5 to 10 membered substituted aryl,
—$(CR^bR^b)_nO(CR^bR^b)_n$ 5 to 10 membered heteroaryl,
—$(CR^bR^b)_nO(CR^bR^b)_n$ 5 to 10 membered substituted heteroaryl,
—$(CR^bR^b)_nNR^b(CR^bR^b)_n$ 5 to 10 membered heteroaryl,
—$(CR^bR^b)_nNR^b(CR^bR^b)_n$ 5 to 10 membered substituted heteroaryl,
—$(CR^bR^b)_n$ 5 to 10 membered aryl,
—$(CR^bR^b)_n$ 5 to 10 membered substituted aryl,
—$(CR^bR^b)_n$ 5 to 10 membered heteroaryl,
—$(CR^bR^b)_n$ 5 to 10 membered substituted heteroaryl,
—$(CR^bR^b)_n$ 3 to 10 membered cycloalkyl,
—$(CR^bR^b)_n$ 3 to 10 membered substituted cycloalkyl,
—C≡C—$R^b$,
—C≡C—$(CR^bR^b)_nOR^b$,
—C≡C— 3 to 10 membered heterocycloalkyl,
—C≡C— 3 to 10 membered substituted heterocycloalkyl,
—$(CR^bR^b)_n$ 3 to 10 membered heterocycloalkyl,
—$(CR^bR^b)_n$ 3 to 10 membered substituted heterocycloalkyl,
—$(CR^bR^b)_nO(CR^bR^b)_n$ 3 to 10 membered cycloalkyl,
—$(CR^bR^b)_nO(CR^bR^b)_n$ 3 to 10 membered substituted cycloalkyl,
—$(CR^bR^b)_nO(CR^bR^b)_n$ 3 to 10 membered heterocycloalkyl,
—$(CR^bR^b)_nO(CR^bR^b)_n$ 3 to 10 membered substituted heterocycloalkyl,
—$(CR^bR^b)_nNR^b(CR^bR^b)_n$ 3 to 10 membered heterocycloalkyl,
—$(CR^bR^b)_nNR^b(CR^bR^b)_n$ 3 to 10 membered substituted heterocycloalkyl,
—C≡C—$(CR^bR^b)_nNR^bC(=O)OR^b$,
—C≡C—$(CR^bR^b)_nNR^bR^b$,
—C≡C—$(CR^bR^b)_nNR^b$—S(=O)$_2R^b$,
—$(CR^bR^b)_nS(CR^bR^b)_n$ 5 to 10 membered aryl,
—$(CR^bR^b)_nS(CR^bR^b)_n$ 5 to 10 membered substituted aryl,
—$(CR^bR^b)_nS(CR^bR^b)_n$ 5 to 10 membered heteroaryl,
—$(CR^bR^b)_nS(CR^bR^b)_n$ 5 to 10 membered substituted heteroaryl,
—$(CR^bR^b)_nS(=O)_2(CR^bR^b)_n$ 5 to 10 membered aryl,
—$(CR^bR^b)_nS(=O)_2(CR^bR^b)_n$ 5 to 10 membered substituted aryl,
—$(CR^bR^b)_nS(=O)_2(CR^bR^b)_n$ 5 to 10 membered heteroaryl,
—$(CR^bR^b)_nS(=O)_2(CR^bR^b)_n$ 5 to 10 membered substituted heteroaryl,
—$(CR^bR^b)_nS(=O)(CR^bR^b)_n$ 5 to 10 membered aryl,
—$(CR^bR^b)_nS(=O)(CR^bR^b)_n$ 5 to 10 membered substituted aryl,
—$(CR^bR^b)_nNR^bS(=O)_2(CR^bR^b)_n$ 5 to 10 membered aryl,
—$(CR^bR^b)_nNR^bS(=O)_2(CR^bR^b)_n$ 5 to 10 membered substituted aryl,
—$(CR^bR^b)_nNR^bS(=O)_2(CR^bR^b)_n$ 5 to 10 membered heteroaryl,
—$(CR^bR^b)_nNR^bS(=O)_2(CR^bR^b)_n$ 5 to 10 membered substituted heteroaryl,
—$(CR^bR^b)_nNR^b$—S(=O)$_2R^b$,
—$(CR^bR^b)_nNR^b$—C(=O)$R^b$, or
—$(CR^bR^b)_nNR^b$—S(=O)$_2NR^bR^b$, wherein the heteroaryl or heterocycloalkyl groups can have from 1 to 3 heteroatoms independently selected from O, N or S, and wherein substituted groups can have from one to four substitutents independently selected from —$C_{1-6}$alkyl, —$OC_{1-6}$alkyl, —$NR^bR^b$, —$CF_3$, —CN, —$(CR^bR^b)_nOH$, $C_{3-6}$cycloalkyl, halo,
—$(CR^bR^b)_nNR^bS(=O)_2R^b$, —$(CR^bR^b)_nC(=O)OR^b$, —$(CR^bR^b)_nC(=O)NR^bR^b$, 5 to 10 membered aryl, or 5 to 10 membered substituted aryl, or a carbon atom in any ring group may be replaced with —C(=O)— or —S(=O)$_2$—; and each n is independently 0, 1 or 2, provided that the compound is not 1,1,1,3,3,3-hexafluoro-2-(4-(4-(2-thiophenylsulfonyl)-1-piperazinyl)phenyl)-2-propanol; 1,1,1,3,3,3-hexafluoro-2-(4-(4-(phenylsulfonyl)-1-piperazinyl)phenyl)-2-propanol; 1,1,1,3,3,3-hexafluoro-2-(4-(4-((2-fluorophenyl)sulfonyl)-1-piperazinyl)phenyl)-2-propanol; 2-(4-(4-(3-chlorophenylsulfonyl)piperazin-1-yl)phenyl)-1,1,1,3,3,3-hexafluoro-2-propanol; or 2-(4-(4-((2-chlorophenyl)sulfonyl)-1-piperazinyl)phenyl)-1,1,1,3,3,3-hexafluoro-2-propanol.

4. A compound in accordance with claim 1, or a pharmaceutically acceptable salt thereof, wherein $R^3$ is thienyl.

5. A compound in accordance with claim 1, or a pharmaceutically acceptable salt thereof, wherein A is

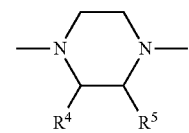

6. A compound in accordance with claim 1, or a pharmaceutically acceptable salt thereof, wherein A is

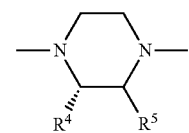

7. A compound in accordance with claim 1, or a pharmaceutically acceptable salt thereof, wherein A is

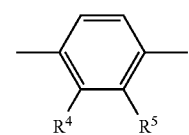

8. A compound in accordance with claim 1, or a pharmaceutically acceptable salt thereof, wherein $R^3$ is thienyl, phenyl, pyridyl, pyrazolyl, imidazolyl, furyl, thiazolyl or thiadiazolyl, which can be optionally substituted with from one to four substituents independently selected from $C_{1-6}$alkyl, $-OC_{1-6}$alkyl, $-NR^cR^c$, $-CF_3$, $-CN$ or halo.

9. A compound in accordance with claim 1, or a pharmaceutically acceptable salt thereof, wherein Y is $-CH_2OH$, $-CF_3$, $-CH_3$ or cyclopropyl.

10. A compound in accordance with claim 1, or a pharmaceutically acceptable salt thereof, wherein Y is $-CF_3$.

11. A compound in accordance with claim 1, or a pharmaceutically acceptable salt thereof, wherein Y is $-CH_3$.

12. A compound in accordance with claim 1, or a pharmaceutically acceptable salt thereof, wherein
A is

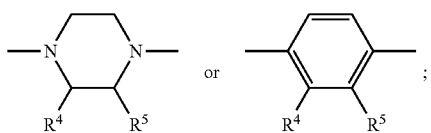

and $R^4$ and $R^5$ are hydrogen.

13. A compound in accordance with claim 1, or a pharmaceutically acceptable salt thereof, wherein $X^1$, $X^2$, $X^3$ and $X^4$ are $CR^a$.

14. A compound in accordance with claim 1, or a pharmaceutically acceptable salt thereof, wherein $X^1$, $X^2$, $X^3$ and $X^4$ are CH.

15. A compound in accordance with claim 1, or a pharmaceutically acceptable salt thereof, wherein $X^1$ and $X^3$ are $CR^a$ and $X^2$ and $X^4$ are N.

16. A compound in accordance with claim 1, or a pharmaceutically acceptable salt thereof, wherein at least one of $X^1$, $X^2$, $X^3$ or $X^4$ is N.

17. A compound in accordance with claim 1, or a pharmaceutically acceptable salt thereof, wherein
A is

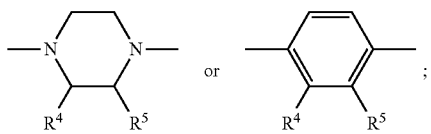

and $R^4$ and $R^5$ are independently hydrogen, halo or $-CH_3$.

18. A compound in accordance with claim 1, or a pharmaceutically acceptable salt thereof, wherein
A is

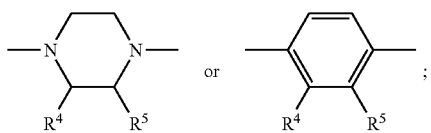

and $R^4$ is hydrogen and $R^5$ is $-CH_3$.

19. A compound in accordance with claim 1, or a pharmaceutically acceptable salt thereof, wherein
A is

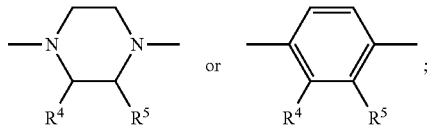

and $R^4$ is hydrogen and $R^5$ is $-CH_2$-morpholino.

20. A compound in accordance with claim 1, or a pharmaceutically acceptable salt thereof, wherein
$R^3$ is thienyl, phenyl, pyridyl, pyrazolyl, imidazolyl, furyl, thiazolyl or thiadiazolyl, which can be optionally substituted with from one to four substituents independently selected from $C_{1-6}$alkyl, $-OC_{1-6}$alkyl, $-NR^cR^c$, $-CF_3$, $-CN$ or halo;
A is

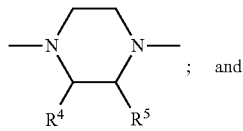 ; and

Y is $-CH_2OH$, $-CF_3$, $-CH_3$ or cyclopropyl.

21. A compound in accordance with claim 1, or a pharmaceutically acceptable salt thereof, wherein
$R^3$ is thienyl, phenyl, pyridyl, pyrazolyl, imidazolyl, furyl, thiazolyl or thiadiazolyl, which can be optionally substituted with from one to four substituents independently selected from $C_{1-6}$alkyl, $-OC_{1-6}$alkyl, $-NR^cR^c$, $-CF_3$, $-CN$ or halo;
A is

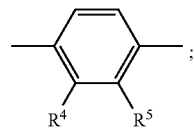

$X^2$ and $X^4$ are N; and
Y is $-CF_3$, $-CH_3$ or cyclopropyl.

22. A compound in accordance with claim 20 or 21, or a pharmaceutically acceptable salt thereof, wherein Y is $-CF_3$ or $-CH_3$.

23. A compound in accordance with claim 1, or a pharmaceutically acceptable salt thereof, wherein
$R^3$ is thienyl, phenyl, pyridyl, pyrazolyl, imidazolyl, furyl, thiazolyl or thiadiazolyl, which can be optionally substituted with from one to four substituents independently selected from $C_{1-6}$alkyl, $-OC_{1-6}$alkyl, $-NR^cR^c$, $-CF_3$, $-CN$ or halo;
A is

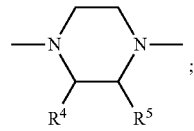

Y is —CF₃ or —CH₃; and
X¹, X², X³ and X⁴ are CH or X¹ and X² are CH, and X³ and X⁴ are N.

24. A compound in accordance with claim 1, or a pharmaceutically acceptable salt thereof, wherein R³ is

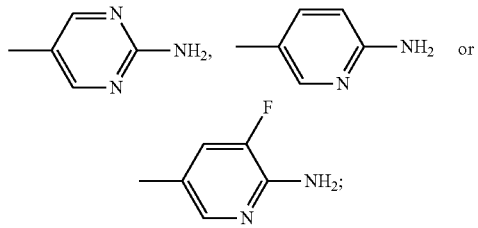

A is

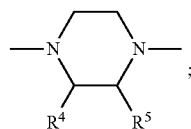

Y is —CF₃ or —CH₃; and
X¹, X², X³ and X⁴ are CH or X¹ and X² are CH, and X³ and X⁴ are N.

25. A compound in accordance with claim 1, or a pharmaceutically acceptable salt thereof, wherein R³ is

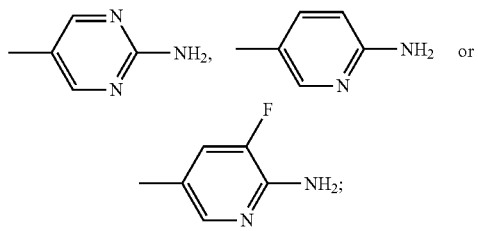

A is

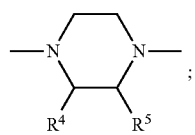

R⁴ is —C≡C—H or —C≡C—C₁₋₆alkyl;
R⁵ is hydrogen;
Y is —CF₃ or —CH₃; and
X¹, X², X³ and X⁴ are CH or X¹ and X² are CH, and X³ and X⁴ are N.

26. A compound in accordance with claim 1, or a pharmaceutically acceptable salt thereof, wherein
R³ is thienyl, or phenyl, pyridyl, pyrazolyl, imidazolyl, furyl, thiazolyl or thiadiazolyl, which can be optionally substituted with from one to four substituents independently selected from C₁₋₆alkyl, —OC₁₋₆alkyl, —NR$^c$R$^c$, —CF₃, —CN or halo;

A is

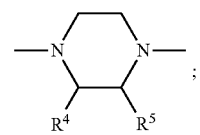

Y is —CF₃ or —CH₃; and
X¹, X², X³ and X⁴ are CH or —C—CH₃.

27. A compound in accordance with claim 1, or a pharmaceutically acceptable salt thereof, wherein R³ is

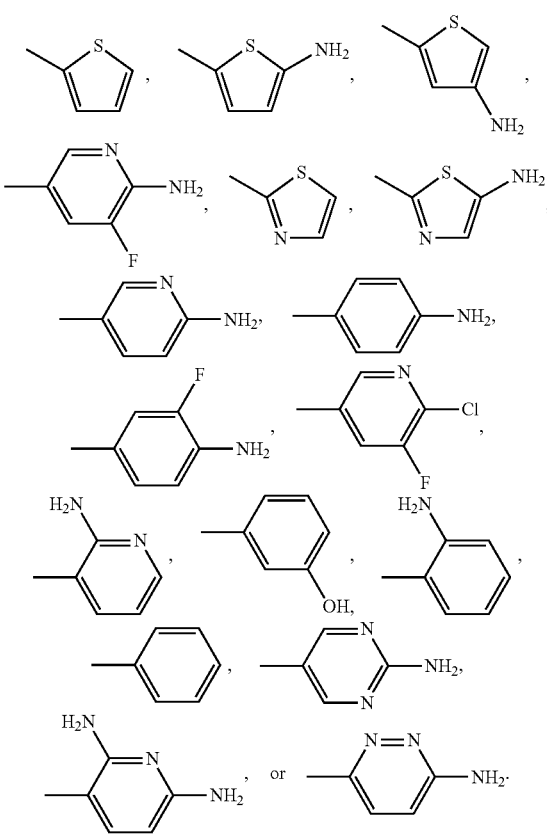

28. A compound in accordance with claim 1, or a pharmaceutically acceptable salt thereof, wherein R³ is

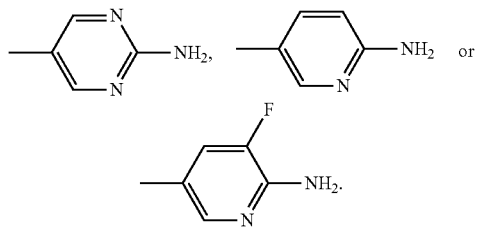

29. A compound, or a pharmaceutically acceptable salt thereof, selected from:
1,1,1,3,3,3-hexafluoro-2-(4-(4-(3-thiophenylsulfonyl)-1-piperazinyl)phenyl)-2-propanol;
1,1,1,3,3,3-hexafluoro-2-(4-(4-((2-methylphenyl)sulfonyl)-1-piperazinyl)phenyl)-2-propanol;

1,1,1,3,3,3-hexafluoro-2-(4-(4-((1-methyl-1h-pyrazol-3-yl)sulfonyl)-1-piperazinyl)phenyl)-2-propanol;
1,1,1,3,3,3-hexafluoro-2-(4-(4-(2-pyridinylsulfonyl)-1-piperazinyl)phenyl)-2-propanol;
1,1,1,3,3,3-hexafluoro-2-(4-(4-((5-methyl-2-thiophenyl)sulfonyl)-1-piperazinyl)phenyl)-2-propanol;
1,1,1,3,3,3-hexafluoro-2-(4-(4-((2S)-2-methyl-4-(2-thiophenylsulfonyl)-1-piperazinyl)phenyl)-2-propanol;
1,1,1,3,3,3-hexafluoro-2-(4-(4-((2S)-2-methyl-4-(phenylsulfonyl)-1-piperazinyl)phenyl)-2-propanol;
2-(4-(2-(2,5-dichlorophenyl)-4-(2-thiophenylsulfonyl)-1-piperazinyl)phenyl)-1,1,1-trifluoro-2-propanol;
2-(4-((3R)-3-cyclopropyl-4-(2-thiophenylsulfonyl)-1-piperazinyl)phenyl)-1,1,1,3,3,3-hexafluoro-2-propanol;
1-cyclopropyl-2,2,2-trifluoro-1-(4-(4-(phenylsulfonyl)-1-piperazinyl)phenyl)ethanol;
1,1,1-trifluoro-2-(2-((2S)-2-methyl-4-(2-thiophenylsulfonyl)-1-piperazinyl)-5-pyrimidinyl)-2-propanol;
(2S)-1,1,1-trifluoro-2-(2-((2S)-2-methyl-4-(2-thiophenylsulfonyl)-1-piperazinyl)-5-pyrimidinyl)-2-propanol;
(2R)-1,1,1-trifluoro-2-(2-((2S)-2-methyl-4-(2-thiophenylsulfonyl)-1-piperazinyl)-5-pyrimidinyl)-2-propanol;
1,1,1,3,3,3-hexafluoro-2-(6-(4-(phenylsulfonyl)phenyl)-3-pyridinyl)-2-propanol;
2-(6-(3-chloro-4-(phenylsulfonyl)phenyl)-3-pyridinyl)-1,1,1-trifluoro-2-propanol;
2-(3'-chloro-4'-(phenylsulfonyl)-4-biphenylyl)-1,1,1-trifluoro-2-propanol;
2-methyl-4-(4-(phenylsulfonyl)-4'-(2,2,2-trifluoro-1-hydroxy-1-methylethyl)-3-biphenylyl)-3-butyn-2-ol;
1,1,1,3,3,3-hexafluoro-2-(4'-(phenylsulfonyl)-4-biphenylyl)-2-propanol;
1,1,1,3,3,3-hexafluoro-2-(6-(4-(phenylsulfonyl)-1-piperazinyl)-3-pyridinyl)-2-propanol;
1,1,1,3,3,3-hexafluoro-2-(2-(4-(phenylsulfonyl)-1-piperazinyl)-5-pyrimidinyl)-2-propanol;
1,1,1-trifluoro-2-(4-(4-(phenylsulfonyl)-1-piperazinyl)phenyl)-2-propanol;
(2R)-1,1,1-trifluoro-2-(4-(4-(phenylsulfonyl)-1-piperazinyl)phenyl)-2-propanol;
(2S)-1,1,1-trifluoro-2-(4-(4-(phenylsulfonyl)-1-piperazinyl)phenyl)-2-propanol;
1,1,1,3,3,3-hexafluoro-2-(4-((3R)-3-methyl-4-(2-thiophenylsulfonyl)-1-piperazinyl)phenyl)-2-propanol;
1,1,1,3,3,3-hexafluoro-2-(4-((3S)-3-methyl-4-(2-thiophenylsulfonyl)-1-piperazinyl)phenyl)-2-propanol;
1,1,1-trifluoro-2-(4-((2S)-2-methyl-4-(2-thiophenylsulfonyl)-1-piperazinyl)phenyl)-2-propanol;
(2R)-1,1,1-trifluoro-2-(4-((2S)-2-methyl-4-(2-thiophenylsulfonyl)-1-piperazinyl)phenyl)-2-propanol;
(2S)-1,1,1-trifluoro-2-(4-((2S)-2-methyl-4-(2-thiophenylsulfonyl)-1-piperazinyl)phenyl)-2-propanol;
1,1,1-trifluoro-2-(4-((2S)-2-methyl-4-(phenylsulfonyl)-1-piperazinyl)phenyl)-2-propanol;
1,1,1-trifluoro-2-(4-(4-(2-thiophenylsulfonyl)-1-piperazinyl)phenyl)-2-propanol;
(2S)-1,1,1-trifluoro-2-(4-(4-(2-thiophenylsulfonyl)-1-piperazinyl)phenyl)-2-propanol;
(2R)-1,1,1-trifluoro-2-(4-(4-(2-thiophenylsulfonyl)-1-piperazinyl)phenyl)-2-propanol;
1,1,1-trifluoro-2-(4-((2S)-2-methyl-4-(3-furanylsulfonyl)phenyl)-2-propanol;
1,1,1,3,3,3-hexafluoro-2-(4-((2S)-2-methyl-4-(1,3-thiazol-2-ylsulfonyl)-1-piperazinyl)phenyl)-2-propanol;
1,1,1-trifluoro-2-(4-(4-(1,3-thiazol-2-ylsulfonyl)-1-piperazinyl)phenyl)-2-propanol;
1,1,1,3,3,3-hexafluoro-2-(4-(4-(1,3-thiazol-2-ylsulfonyl)-1-piperazinyl)phenyl)-2-propanol;
1,1,1-trifluoro-2-(4-((2S)-2-methyl-4-(1,3-thiazol-2-ylsulfonyl)-1-piperazinyl)phenyl)-2-propanol;
(2S)-1,1,1-trifluoro-2-(4-((2S)-2-methyl-4-(1,3-thiazol-2-ylsulfonyl)-1-piperazinyl)phenyl)-2-propanol;
(2R)-1,1,1-trifluoro-2-(4-((2S)-2-methyl-4-(1,3-thiazol-2-ylsulfonyl)-1-piperazinyl)phenyl)-2-propanol;
2-(4-((2S)-4-((5-amino-1,3,4-thiadiazol-2-yl)sulfonyl)-2-methyl-1-piperazinyl)phenyl)-1,1,1-trifluoro-2-propanol;
1,1,1,3,3,3-hexafluoro-2-(4-(2-(tetrahydro-2H-pyran-4-ylmethyl)-4-(2-thiophenylsulfonyl)-1-piperazinyl)phenyl)-2-propanol;
1,1,1-trifluoro-2-(4-(2-(tetrahydro-2H-pyran-4-ylmethyl)-4-(2-thiophenylsulfonyl)-1-piperazinyl)phenyl)-2-propanol;
(2R)-1,1,1-trifluoro-2-(4-((2R)-2-(tetrahydro-2H-pyran-4-ylmethyl)-4-(2-thiophenylsulfonyl)-1-piperazinyl)phenyl)-2-propanol;
(2R)-1,1,1-trifluoro-2-(4-((2S)-2-(tetrahydro-2H-pyran-4-ylmethyl)-4-(2-thiophenylsulfonyl)-1-piperazinyl)phenyl)-2-propanol;
(2S)-1,1,1-trifluoro-2-(4-((2S)-2-(tetrahydro-2H-pyran-4-ylmethyl)-4-(2-thiophenylsulfonyl)-1-piperazinyl)phenyl)-2-propanol;
(2S)-1,1,1-trifluoro-2-(4-((2R)-2-(tetrahydro-2H-pyran-4-ylmethyl)-4-(2-thiophenylsulfonyl)-1-piperazinyl)phenyl)-2-propanol;
1,1,1-trifluoro-2-(4-(2-(2-fluorobenzyl)-4-(2-thiophenylsulfonyl)-1-piperazinyl)phenyl)-2-propanol;
1,1,1-trifluoro-2-(4-(2-(3-fluorobenzyl)-4-(2-thiophenylsulfonyl)-1-piperazinyl)phenyl)-2-propanol;
1,1,1-trifluoro-2-(4-(2-(4-fluorobenzyl)-4-(2-thiophenylsulfonyl)-1-piperazinyl)phenyl)-2-propanol;
1,1,1-trifluoro-2-(4-(4-(phenylsulfonyl)-2-(tetrahydro-2H-pyran-4-ylmethyl)-1-piperazinyl)phenyl)-2-propanol;
1,1,1,3,3,3-hexafluoro-2-(4-(2-(3-methylbenzyl)-4-(2-thiophenylsulfonyl)-1-piperazinyl)phenyl)-2-propanol;
1,1,1,3,3,3-hexafluoro-2-(4-(2-(4-methylbenzyl)-4-(2-thiophenylsulfonyl)-1-piperazinyl)phenyl)-2-propanol;
1,1,1-trifluoro-2-(4-(2-(hydroxymethyl)-4-(2-thiophenylsulfonyl)-1-piperazinyl)phenyl)-2-propanol;
1,1,1-trifluoro-2-(4-(2-(((3S)-3-methyl-4-morpholinyl)methyl)-4-(2-thiophenylsulfonyl)-1-piperazinyl)phenyl)-2-propanol;
1,1,1-trifluoro-2-(4-(2-(8-oxa-3-azabicyclo[3.2.1]oct-3-ylmethyl)-4-(2-thiophenylsulfonyl)-1-piperazinyl)phenyl)-2-propanol;
2-(4-(2-((2,2-dimethyl-4-morpholinyl)methyl)-4-(2-thiophenylsulfonyl)-1-piperazinyl)phenyl)-1,1,1-trifluoro-2-propanol;
1,1,1-trifluoro-2-(4-(2-((3-(hydroxymethyl)-4-morpholinyl)methyl)-4-(2-thiophenylsulfonyl)-1-piperazinyl)phenyl)-2-propanol;
1,1,1-trifluoro-2-(4-(2-((2-methyl-4-morpholinyl)methyl)-4-(2-thiophenylsulfonyl)-1-piperazinyl)phenyl)-2-propanol;
1,1,1-trifluoro-2-(4-(2-((1R,4R)-2-oxa-5-azabicyclo[2.2.1]hept-5-ylmethyl)-4-(2-thiophenylsulfonyl)-1-piperazinyl)phenyl)-2-propanol;
2-(4-(2-((4,4-difluoro-1-piperidinyl)methyl)-4-(2-thiophenylsulfonyl)-1-piperazinyl)phenyl)-1,1,1-trifluoro-2-propanol;

1,1,1-trifluoro-2-(4-(2-((2-(hydroxymethyl)-4-morpholinyl)methyl)-4-(2-thiophenylsulfonyl)-1-piperazinyl)phenyl)-2-propanol;
1-((4-(2-thiophenylsulfonyl)-1-(4-(2,2,2-trifluoro-1-hydroxy-1-methylethyl)phenyl)-2-piperazinyl)methyl)-3-azetidinol;
2-methyl-2-(((4-(2-thiophenylsulfonyl)-1-(4-(2,2,2-trifluoro-1-hydroxy-1-methylethyl)phenyl)-2-piperazinyl)methyl)amino)-1-propanol;
(4-(2-thiophenylsulfonyl)-1-(4-(2,2,2-trifluoro-1-hydroxy-1-methylethyl)phenyl)-2-piperazinyl)acetonitrile;
(3R)-1-((4-(2-thiophenylsulfonyl)-1-(4-(2,2,2-trifluoro-1-hydroxy-1-methylethyl)phenyl)-2-piperazinyl)methyl)-3-pyrrolidinol;
1,1,1-trifluoro-2-(4-(2-(2-methylpropyl)-4-(2-thiophenylsulfonyl)-1-piperazinyl)phenyl)-2-propanol;
2-(4-(2-(cyclohexylmethyl)-4-(2-thiophenylsulfonyl)-1-piperazinyl)phenyl)-1,1,1-trifluoro-2-propanol;
1,1,1-trifluoro-2-(4-(2-((3-pyridinylmethoxy)methyl)-4-(2-thiophenylsulfonyl)-1-piperazinyl)phenyl)-2-propanol;
1,1,1,3,3,3-hexafluoro-2-(4-(4-(1H-imidazol-4-ylsulfonyl)-1-piperazinyl)phenyl)-2-propanol;
1,1,1-trifluoro-2-(4-(2-(4-morpholinylmethyl)-4-(2-thiophenylsulfonyl)-1-piperazinyl)phenyl)-2-propanol;
2-(4-(2-((benzyl(methyl)amino)methyl)-4-(2-thiophenylsulfonyl)-1-piperazinyl)phenyl)-1,1,1-trifluoro-2-propanol;
2-(4-((2S)-2-ethyl-4-(2-thiophenylsulfonyl)-1-piperazinyl)phenyl)-1,1,1,3,3,3-hexafluoro-2-propanol;
2-(4-((2S)-2-benzyl-4-(2-thiophenylsulfonyl)-1-piperazinyl)phenyl)-1,1,1,3,3,3-hexafluoro-2-propanol;
2-(4-((2S)-2-benzyl-4-(2-thiophenylsulfonyl)-1-piperazinyl)phenyl)-1,1,1-trifluoro-2-propanol;
(2S)-2-(4-((2S)-2-benzyl-4-(2-thiophenylsulfonyl)-1-piperazinyl)phenyl)-1,1,1-trifluoro-2-propanol;
(2R)-2-(4-((2S)-2-benzyl-4-(2-thiophenylsulfonyl)-1-piperazinyl)phenyl)-1,1,1-trifluoro-2-propanol;
3,3,3-trifluoro-2-(4-(4-(2-thiophenylsulfonyl)-1-piperazinyl)phenyl)-1,2-propanediol;
(2S)-3,3,3-trifluoro-2-(4-(4-(2-thiophenylsulfonyl)-1-piperazinyl)phenyl)-1,2-propanediol;
(2R)-3,3,3-trifluoro-2-(4-(4-(2-thiophenylsulfonyl)-1-piperazinyl)phenyl)-1,2-propanediol;
2-(4-((2S)-2-methyl-4-(2-thiophenylsulfonyl)-1-piperazinyl)phenyl)-3,3,3-trifluoro-1,2-propanediol;
2-(4-((2S)-2-benzyl-4-(2-thiophenylsulfonyl)-1-piperazinyl)phenyl)-3,3,3-trifluoro-1,2-propanediol;
1,1,1,3,3,3-hexafluoro-2-(6-(4-(2-thiophenylsulfonyl)-1-piperazinyl)-3-biphenylyl)-2-propanol;
1,1,1,3,3,3-hexafluoro-2-(3'-methoxy-6-(4-(2-thiophenylsulfonyl)-1-piperazinyl)-3-biphenylyl)-2-propanol;
1,1,1,3,3,3-hexafluoro-2-(3'-fluoro-6-(4-(2-thiophenylsulfonyl)-1-piperazinyl)-3-biphenylyl)-2-propanol;
1,1,1,3,3,3-hexafluoro-2-(3-(3-pyridinyl)-4-(4-(2-thiophenylsulfonyl)-1-piperazinyl)phenyl)-2-propanol;
1,1,1,3,3,3-hexafluoro-2-(3-(3-thiophenyl)-4-(4-(2-thiophenylsulfonyl)-1-piperazinyl)phenyl)-2-propanol;
2'-(4-(2-thiophenylsulfonyl)-1-piperazinyl)-5'-(2,2,2-trifluoro-1-hydroxy-1-(trifluoromethyl)ethyl)-4-biphenylol;
1,1,1-trifluoro-2-(3-((3-methyl-3-oxetanyl)ethynyl)-4-(4-(2-thiophenylsulfonyl)-1-piperazinyl)phenyl)-2-propanol; or
1,1,1-trifluoro-2-(4-(2-(4-pyridinylmethyl)-4-(2-thiophenylsulfonyl)-1-piperazinyl)phenyl)-2-propanol.

30. A compound, or a pharmaceutically acceptable salt thereof, selected from:
8-(((2S)-4-(2-thiophenylsulfonyl)-1-(4-(2,2,2-trifluoro-1-hydroxy-1-methylethyl)phenyl)-2-piperazinyl)methyl)-3-oxa-8-azabicyclo[3.2.1]octan-6-ol (endo);
(1R,5R,6R)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol;
(1R,5R,6R)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol;
(1S,5S,6S)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol;
(1S,5S,6S)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol;
8-(((2S)-4-(2-thiophenylsulfonyl)-1-(4-(2,2,2-trifluoro-1-hydroxy-1-methylethyl)phenyl)-2-piperazinyl)methyl)-3-oxa-8-azabicyclo[321]octan-6-ol (exo);
(1S,5S,6R)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol;
(1S,5S,6R)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol;
(1R,5R,6S)-8-(((2S)-4-(2-thiophenylsulfonyl)-1-(4-((1R)-2,2,2-trifluoro-1-hydroxy-1-methylethyl)phenyl)-2-piperazinyl)methyl)-3-oxa-8-azabicyclo[3.2.1]octan-6-ol;
(1R,5R,6S)-8-(((2S)-4-(2-thiophenylsulfonyl)-1-(4-((1S)-2,2,2-trifluoro-1-hydroxy-1-methylethyl)phenyl)-2-piperazinyl)methyl)-3-oxa-8-azabicyclo[3.2.1]octan-6-ol;
8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol;
(1R,5S,6S)-8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol;
(1R,5R,6R)-8-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[321]octan-6-ol;
8-(((2S)-4-(phenylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol;
8-(((2S)-4-(1,3-thiazol-2-ylsulfonyl)-1-(5-(2,2,2-trifluoro-1-hydroxy-1-(trifluoromethyl)ethyl)-2-pyrimidinyl)-2-piperazinyl)methyl)-3-oxa-8-azabicyclo[3.2.1]octan-6-ol;
1,1,1,3,3,3-hexafluoro-2-(2-((2S)-2-(((3S)-3-methyl-4-morpholinyl)methyl)-4-(2-thiophenylsulfonyl)-1-piperazinyl)-5-pyrimidinyl)-2-propanol;
3,3,3-trifluoro-2-(4-((2S)-2-(((3S)-3-methyl-4-morpholinyl)methyl)-4-(2-thiophenylsulfonyl)-1-piperazinyl)phenyl)-1,2-propanediol;

(2S)-3,3,3-trifluoro-2-(4-((2S)-2-(((3S)-3-methyl-4-morpholinyl)methyl)-4-(2-thiophenylsulfonyl)-1-piperazinyl)phenyl)-1,2-propanediol;
(2R)-3,3,3-trifluoro-2-(4-((2S)-2-(((3S)-3-methyl-4-morpholinyl)methyl)-4-(2-thiophenylsulfonyl)-1-piperazinyl)phenyl)-1,2-propanediol;
1,1,1-trifluoro-2-(4-((2S)-2-(2-oxa-6-azaspiro[3.3]hept-6-ylmethyl)-4-(2-thiophenylsulfonyl)-1-piperazinyl)phenyl)-2-propanol;
2-(4-((2S)-2-((1,1-dioxido-4-thiomorpholinyl)methyl)-4-(2-thiophenylsulfonyl)-1-piperazinyl)phenyl)-1,1,1-trifluoro-2-propanol;
1,1,1-trifluoro-2-(4-((2S)-2-((3-methyl-1,1-dioxido-4-thiomorpholinyl)methyl)-4-(2-thiophenylsulfonyl)-1-piperazinyl)phenyl)-2-propanol;
2-(4-((2S)-2-((3-cyclopropyl-1,1-dioxido-4-thiomorpholinyl)methyl)-4-(2-thiophenylsulfonyl)-1-piperazinyl)phenyl)-1,1,1-trifluoro-2-propanol;
2-(4-(4-((5-amino-2-thiophenyl)sulfonyl)-1-piperazinyl)phenyl)-1,1,1,3,3,3-hexafluoro-2-propanol;
2-(2-((2S)-4-((5-amino-2-thiophenyl)sulfonyl)-2-methyl-1-piperazinyl)-5-pyrimidinyl)-1,1,1,3,3,3-hexafluoro-2-propanol;
2-(4-(4-((5-amino-2-thiophenyl)sulfonyl)-1-piperazinyl)phenyl)-1,1,1-trifluoro-2-propanol;
2-(4-(4-((6-amino-3-pyridinyl)sulfonyl)-1-piperazinyl)phenyl)-1,1,1,3,3,3-hexafluoro-2-propanol;
2-(4-((2S)-4-((6-amino-3-pyridinyl)sulfonyl)-2-methyl-1-piperazinyl)phenyl)-1,1,1,3,3,3-hexafluoro-2-propanol;
2-(2-((2S)-4-((6-amino-3-pyridinyl)sulfonyl)-2-methyl-1-piperazinyl)-5-pyrimidinyl)-1,1,1,3,3,3-hexafluoro-2-propanol;
1,1,1,3,3,3-hexafluoro-2-(2-((2S)-2-methyl-4-(2-thiophenylsulfonyl)-1-piperazinyl)-5-pyrimidinyl)-2-propanol;
2-(4-(4-((6-amino-3-pyridinyl)sulfonyl)-1-piperazinyl)phenyl)-1,1,1-trifluoro-2-propanol;
2-(4-(4-((2-amino-5-pyrimidinyl)sulfonyl)-1-piperazinyl)phenyl)-1,1,1,3,3,3-hexafluoro-2-propanol;
2-(4-(4-((6-amino-5-fluoro-3-pyridinyl)sulfonyl)-1-piperazinyl)phenyl)-1,1,1,3,3,3-hexafluoro-2-propanol;
9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo);
9-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one;
9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-ol (endo);
9-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3-oxa-9-azabicyclo[3.3.1]nonan-7-one;
8-(((2S)-4-(2-thiophenylsulfonyl)-1-(5-(2,2,2-trifluoro-1-hydroxy-1-methylethyl)-2-pyrimidinyl)-2-piperazinyl)methyl)-3-oxa-8-azabicyclo[3.2.1]octan-6-ol (endo);
(1R,5R,6R)-8-(((2S)-4-(2-thiophenylsulfonyl)-1-(5-((1R)-2,2,2-trifluoro-1-hydroxy-1-methylethyl)-2-pyrimidinyl)-2-piperazinyl)methyl)-3-oxa-8-azabicyclo[3.2.1]octan-6-ol (endo);
(1R,5R,6R)-8-(((2S)-4-(2-thiophenylsulfonyl)-1-(5-((1S)-2,2,2-trifluoro-1-hydroxy-1-methylethyl)-2-pyrimidinyl)-2-piperazinyl)methyl)-3-oxa-8-azabicyclo[3.2.1]octan-6-ol (endo);
(1S,5S,6S)-8-(((2S)-4-(2-thiophenylsulfonyl)-1-(5-((1R)-2,2,2-trifluoro-1-hydroxy-1-methylethyl)-2-pyrimidinyl)-2-piperazinyl)methyl)-3-oxa-8-azabicyclo[3.2.1]octan-6-ol (endo);
(1S,5S,6S)-8-(((2S)-4-(2-thiophenylsulfonyl)-1-(5-((1S)-2,2,2-trifluoro-1-hydroxy-1-methylethyl)-2-pyrimidinyl)-2-piperazinyl)methyl)-3-oxa-8-azabicyclo[3.2.1]octan-6-ol (endo);
1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol;
(2R)-1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol;
(2S)-1,1,1-trifluoro-2-(2-((2S)-2-(((3S)-3-methyl-4-morpholinyl)methyl)-4-(2-thiophenylsulfonyl)-1-piperazinyl)-5-pyrimidinyl)-2-propanol;
1,1,1-trifluoro-2-(4-((2S)-2-(((3S)-3-methyl-4-morpholinyl)methyl)-4-(1,3-thiazol-2-ylsulfonyl)-1-piperazinyl)phenyl)-2-propanol;
2-(4-(4-((4-aminophenyl)sulfonyl)-1-piperazinyl)phenyl)-1,1,1,3,3,3-hexafluoro-2-propanol;
2-(4-(4-((4-amino-3-fluorophenyl)sulfonyl)-1-piperazinyl)phenyl)-1,1,1,3,3,3-hexafluoro-2-propanol;
3-((4-(4-(2,2,2-trifluoro-1-hydroxy-1-(trifluoromethyl)ethyl)phenyl)-1-piperazinyl)sulfonyl)phenol;
9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-one;
9-(((2S)-4-(2-thiophenylsulfonyl)-1-(4-((1R)-2,2,2-trifluoro-1-hydroxy-1-methylethyl)phenyl)-2-piperazinyl)methyl)-3-oxa-9-azabicyclo[3.3.1]nonan-7-one;
9-(((2S)-4-(2-thiophenylsulfonyl)-1-(4-((1S)-2,2,2-trifluoro-1-hydroxy-1-methylethyl)phenyl)-2-piperazinyl)methyl)-3-oxa-9-azabicyclo[3.3.1]nonan-7-one;
9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-ol (endo);
(1R,5S)-7-methyl-9-(((2S)-4-(2-thiophenylsulfonyl)-1-(4-(2,2,2-trifluoro-1-hydroxy-1-methylethyl)phenyl)-2-piperazinyl)methyl)-3-oxa-9-azabicyclo[3.3.1]nonan-7-ol (endo);
1,1,1-trifluoro-2-(4-((2S)-2-(((1R,5S)-7-methoxy-3-oxa-9-azabicyclo[3.3.1]non-9-yl)methyl)-4-(2-thiophenylsulfonyl)-1-piperazinyl)phenyl)-2-propanol (endo);
1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol;
(2R)-1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol;
(2S)-1,1,1-trifluoro-2-(4-((2S)-2-(((3R)-3-(hydroxymethyl)-4-morpholinyl)methyl)-4-(2-thiophenylsulfonyl)-1-piperazinyl)phenyl)-2-propanol;
1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol;
(2R)-1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol;
(2S)-1,1,1-trifluoro-2-(4-((2S)-2-(((3S)-3-(hydroxymethyl)-4-morpholinyl)methyl)-4-(2-thiophenylsulfonyl)-1-piperazinyl)phenyl)-2-propanol;

N-((4-(((2S)-4-(2-thiophenylsulfonyl)-1-(4-(2,2,2-trifluoro-1-hydroxy-1-methylethyl)phenyl)-2-piperazinyl)methyl)-3-morpholinyl)methyl)methanesulfonamide;
N-(((3R)-4-(((2S)-4-(2-thiophenylsulfonyl)-1-(4-((1Rr)-2,2,2-trifluoro-1-hydroxy-1-methylethyl)phenyl)-2-piperazinyl)methyl)-3-morpholinyl)methyl)methanesulfonamide;
N-(((3S)-4-(((2S)-4-(2-thiophenylsulfonyl)-1-(4-((1S)-2,2,2-trifluoro-1-hydroxy-1-methylethyl)phenyl)-2-piperazinyl)methyl)-3-morpholinyl)methyl)methanesulfonamide;
N-(((3R)-4-(((2S)-4-(2-thiophenylsulfonyl)-1-(4-((1S)-2,2,2-trifluoro-1-hydroxy-1-methylethyl)phenyl)-2-piperazinyl)methyl)-3-morpholinyl)methyl)methanesulfonamide;
N-(((3S)-4-(((2S)-4-(2-thiophenylsulfonyl)-1-(4-((1R)-2,2,2-trifluoro-1-hydroxy-1-methylethyl)phenyl)-2-piperazinyl)methyl)-3-morpholinyl)methyl)methanesulfonamide;
(4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetate;
N,N-dimethyl-2-(4-(((2S)-4-(2-thiophenylsulfonyl)-1-(4-(2,2,2-trifluoro-1-hydroxy-1-methylethyl)phenyl)-2-piperazinyl)methyl)-3-morpholinyl)acetamide;
1,1,1-trifluoro-2-(4-((2S)-2-(((3-(4-fluorophenyl)-4-morpholinyl)methyl)-4-(2-thiophenylsulfonyl)-1-piperazinyl)phenyl)-2-propanol;
(2R)-1,1,1-trifluoro-2-(4-((2S)-2-(((3R)-3-(4-fluorophenyl)-4-morpholinyl)methyl)-4-(2-thiophenylsulfonyl)-1-piperazinyl)phenyl)-2-propanol;
(2S)-1,1,1-trifluoro-2-(4-((2S)-2-(((3S)-3-(4-fluorophenyl)-4-morpholinyl)methyl)-4-(2-thiophenylsulfonyl)-1-piperazinyl)phenyl)-2-propanol;
(2R)-1,1,1-trifluoro-2-(4-((2S)-2-(((3S)-3-(4-fluorophenyl)-4-morpholinyl)methyl)-4-(2-thiophenylsulfonyl)-1-piperazinyl)phenyl)-2-propanol;
(2S)-1,1,1-trifluoro-2-(4-((2S)-2-(((3R)-3-(4-fluorophenyl)-4-morpholinyl)methyl)-4-(2-thiophenylsulfonyl)-1-piperazinyl)phenyl)-2-propanol;
1,1,1-trifluoro-2-(4-((2R)-2-((2-furanylmethoxy)methyl)-4-(2-thiophenylsulfonyl)-1-piperazinyl)phenyl)-2-propanol;
1,1,1-trifluoro-2-(4-((2R)-2-(((3-methyl-3-oxetanyl)methoxy)methyl)-4-(2-thiophenylsulfonyl)-1-piperazinyl)phenyl)-2-propanol;
1,1,1-trifluoro-2-(4-((2R)-2-((tetrahydro-2-furanylmethoxy)methyl)-4-(2-thiophenylsulfonyl)-1-piperazinyl)phenyl)-2-propanol;
1,1,1-trifluoro-2-(4-((2R)-2-(((1-methyl-1H-imidazol-4-yl)methoxy)methyl)-4-(2-thiophenylsulfonyl)-1-piperazinyl)phenyl)-2-propanol;
(2R)-1,1,1-trifluoro-2-(4-((2R)-2-(((1-methyl-1H-imidazol-4-yl)methoxy)methyl)-4-(2-thiophenylsulfonyl)-1-piperazinyl)phenyl)-2-propanol;
(2S)-1,1,1-trifluoro-2-(4-((2R)-2-(((1-methyl-1H-imidazol-4-yl)methoxy)methyl)-4-(2-thiophenylsulfonyl)-1-piperazinyl)phenyl)-2-propanol;
1,1,1-trifluoro-2-(4-((2R)-2-(((1-methyl-1H-imidazol-4-yl)methoxy)methyl)-4-(2-thiophenylsulfonyl)-1-piperazinyl)phenyl)-2-propanol;
1,1,1-trifluoro-2-(4-((2S)-2-((tetrahydro-2H-pyran-4-ylamino)methyl)-4-(2-thiophenylsulfonyl)-1-piperazinyl)phenyl)-2-propanol;
1,1,1-trifluoro-2-(4-((2S)-2-((methyl((1-methyl-1H-imidazol-4-yl)methyl)amino)methyl)-4-(2-thiophenylsulfonyl)-1-piperazinyl)phenyl)-2-propanol;
1,1,1-trifluoro-2-(4-((2S)-2-(cis-hexahydro-5H-furo[2,3-c]pyrrol-5-ylmethyl)-4-(2-thiophenylsulfonyl)-1-piperazinyl)phenyl)-2-propanol;
1,1,1-trifluoro-2-(4-((2S)-2-((3aR,6aS)-tetrahydro-1H-furo[3,4-c]pyrrol-5(3H)-ylmethyl)-4-(2-thiophenylsulfonyl)-1-piperazinyl)phenyl)-2-propanol;
2-(4-((2S)-4-((6-amino-3-pyridinyl)sulfonyl)-2-(((3S)-3-methyl-4-morpholinyl)methyl)-1-piperazinyl)phenyl)-1,1,1,3,3,3-hexafluoro-2-propanol;
125: 2-(4-((2S)-4-((6-amino-3-pyridinyl)sulfonyl)-2-(((3S)-3-methyl-4-morpholinyl)methyl)-1-piperazinyl)phenyl)-1,1,1-trifluoro-2-propanol;
(2S)-2-(4-((2S)-4-((6-amino-3-pyridinyl)sulfonyl)-2-(((3R)-3-methyl-4-morpholinyl)methyl)-1-piperazinyl)phenyl)-1,1,1-trifluoro-2-propanol;
(2R)-2-(4-((2S)-4-((6-amino-3-pyridinyl)sulfonyl)-2-(((3R)-3-methyl-4-morpholinyl)methyl)-1-piperazinyl)phenyl)-1,1,1-trifluoro-2-propanol;
2-(4-((2S)-4-((6-amino-3-pyridinyl)sulfonyl)-2-(tetrahydro-2H-pyran-4-ylmethyl)-1-piperazinyl)phenyl)-1,1,1,3,3,3-hexafluoro-2-propanol;
2-(4-((2S)-4-((6-amino-3-pyridinyl)sulfonyl)-2-(tetrahydro-2H-pyran-4-ylmethyl)-1-piperazinyl)phenyl)-1,1,1-trifluoro-2-propanol;
(2R)-2-(4-((2S)-4-((6-amino-3-pyridinyl)sulfonyl)-2-(tetrahydro-2H-pyran-4-ylmethyl)-1-piperazinyl)phenyl)-1,1,1-trifluoro-2-propanol;
(2S)-2-(4-((2S)-4-((6-amino-3-pyridinyl)sulfonyl)-2-(tetrahydro-2H-pyran-4-ylmethyl)-1-piperazinyl)phenyl)-1,1,1-trifluoro-2-propanol;
2-(2-((2S)-4-((6-amino-3-pyridinyl)sulfonyl)-2-(((3S)-3-methyl-4-morpholinyl)methyl)-1-piperazinyl)-5-pyrimidinyl)-1,1,1,3,3,3-hexafluoro-2-propanol;
2-(2-((2S)-4-((6-amino-3-pyridinyl)sulfonyl)-2-(((3S)-3-methyl-4-morpholinyl)methyl)-1-piperazinyl)-5-pyrimidinyl)-1,1,1-trifluoro-2-propanol;
2-(2-((2S)-4-((6-amino-3-pyridinyl)sulfonyl)-2-(tetrahydro-2H-pyran-4-ylmethyl)-1-piperazinyl)-5-pyrimidinyl)-1,1,1,3,3,3-hexafluoro-2-propanol;
2-(2-((2S)-4-((6-amino-3-pyridinyl)sulfonyl)-2-(tetrahydro-2H-pyran-4-ylmethyl)-1-piperazinyl)-5-pyrimidinyl)-1,1,1,3,3,3-hexafluoro-2-propanol;
1,1,1,3,3,3-hexafluoro-2-(4-((2S)-2-(((3S)-3-methyl-4-morpholinyl)methyl)-4-(2-thiophenylsulfonyl)-1-piperazinyl)phenyl)-2-propanol;
2-(2-((2S)-4-((5-amino-2-thiophenyl)sulfonyl)-2-(tetrahydro-2H-pyran-4-ylmethyl)-1-piperazinyl)-5-pyrimidinyl)-1,1,1,3,3,3-hexafluoro-2-propanol;
1,1,1,3,3,3-hexafluoro-2-(2-((2S)-2-(tetrahydro-2H-pyran-4-ylmethyl)-4-(2-thiophenylsulfonyl)-1-piperazinyl)-5-pyrimidinyl)-2-propanol;
2-(2-((2S)-4-((5-amino-2-thiophenyl)sulfonyl)-2-(tetrahydro-2H-pyran-4-ylmethyl)-1-piperazinyl)-5-pyrimidinyl)-1,1,1-trifluoro-2-propanol;
2-(4-((2S)-4-((5-amino-2-thiophenyl)sulfonyl)-2-benzyl-1-piperazinyl)phenyl)-1,1,1-trifluoro-2-propanol;
2-(2-((2S)-4-((5-amino-2-thiophenyl)sulfonyl)-2-methyl-1-piperazinyl)-5-pyrimidinyl)-1,1,1-trifluoro-2-propanol;
2-(4-(4-((4-amino-2-thiophenyl)sulfonyl)-1-piperazinyl)phenyl)-1,1,1,3,3,3-hexafluoro-2-propanol;
2-(4-((2S)-4-((5-amino-2-thiophenyl)sulfonyl)-2-methyl-1-piperazinyl)phenyl)-1,1,1-trifluoro-2-propanol;
9-(((2S)-4-(2-thiophenylsulfonyl)-1-(4-(2,2,2-trifluoro-1-hydroxy-1-methylethyl)phenyl)-2-piperazinyl)methyl)-9-azabicyclo[3.3.1]nonan-3-one;

9-(((2S)-4-(2-thiophenylsulfonyl)-1-(4-(2,2,2-trifluoro-1-hydroxy-1-methylethyl)phenyl)-2-piperazinyl)methyl)-9-azabicyclo[3.3.1]nonan-3-ol (endo);
3-fluoro-9-(((2S)-1-(4-(1,2,2,2-tetrafluoro-1-methylethyl)phenyl)-4-(2-thiophenylsulfonyl)-2-piperazinyl)methyl)-9-azabicyclo[3.3.1]nonane (exo);
2-(4-((2S)-2-((3-ethyl-4-morpholinyl)methyl)-4-(2-thiophenylsulfonyl)-1-piperazinyl)phenyl)-1,1,1-trifluoro-2-propanol;
1-(((2S)-4-(2-thiophenylsulfonyl)-1-(4-(2,2,2-trifluoro-1-hydroxy-1-methylethyl)phenyl)-2-piperazinyl)methyl)-4-piperidinone;
(3S)-1-(((2S)-4-(2-thiophenylsulfonyl)-1-(4-(2,2,2-trifluoro-1-hydroxy-1-methylethyl)phenyl)-2-piperazinyl)methyl)-3-piperidinol;
1,1,1,3,3,3-hexafluoro-2-(2-((2S)-2-methyl-4-(1,3-thiazol-2-ylsulfonyl)-1-piperazinyl)-5-pyrimidinyl)-2-propanol;
2-(2-((2S)-4-((2-amino-1,3-thiazol-5-yl)sulfonyl)-2-methyl-1-piperazinyl)-5-pyrimidinyl)-1,1,1,3,3,3-hexafluoro-2-propanol;
1,1,1-trifluoro-2-(4-((2S)-2-(2-(3-oxetanylamino)propyl)-4-(2-thiophenylsulfonyl)-1-piperazinyl)phenyl)-2-propanol;
2-(4-((2S)-4-((5-amino-2-thiophenyl)sulfonyl)-2-methyl-1-piperazinyl)phenyl)-1,1,1,3,3,3-hexafluoro-2-propanol;
4-(2-(4-(2-thiophenylsulfonyl)-1-piperazinyl)-5-(2,2,2-trifluoro-1-hydroxy-1-(trifluoromethyl)ethyl)phenyl)-3-butyn-1-ol;
4-(2-(4-(2-thiophenylsulfonyl)-1-piperazinyl)-5-(2,2,2-trifluoro-1-hydroxy-1-(trifluoromethyl)ethyl)phenyl)-3-butyn-2-ol;
3-(2-(4-(2-thiophenylsulfonyl)-1-piperazinyl)-5-(2,2,2-trifluoro-1-hydroxy-1-(trifluoromethyl)ethyl)phenyl)-2-propyn-1-ol;
1,1,1,3,3,3-hexafluoro-2-(3-(3-methoxyprop-1-ynyl)-4-(4-(thiophen-2-ylsulfonyl)piperazin-1-yl)phenyl)propan-2-ol;
1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol;
1,1,1,3,3,3-hexafluoro-2-(3-(3-methoxy-1-pentyn-1-yl)-4-(4-(2-thiophenylsulfonyl)-1-piperazinyl)phenyl)-2-propanol;
4-methyl-1-(2-(4-(2-thiophenylsulfonyl)-1-piperazinyl)-5-(2,2,2-trifluoro-1-hydroxy-1-(trifluoromethyl)ethyl)phenyl)-1-pentyn-3-ol;
1,1,1,3,3,3-hexafluoro-2-(3-(3-methoxy-4-methyl-1-pentyn-1-yl)-4-(4-(2-thiophenylsulfonyl)-1-piperazinyl)phenyl)-2-propanol;
tert-butyl (3-(2-(4-(2-thiophenylsulfonyl)-1-piperazinyl)-5-(2,2,2-trifluoro-1-hydroxy-1-(trifluoromethyl)ethyl)phenyl)-2-propyn-1-yl)carbamate;
2-(3-(3-amino-1-propyn-1-yl)-4-(4-(2-thiophenylsulfonyl)-1-piperazinyl)phenyl)-1,1,1,3,3,3-hexafluoro-2-propanol;
N-(3-(2-(4-(2-thiophenylsulfonyl)-1-piperazinyl)-5-(2,2,2-trifluoro-1-hydroxy-1-(trifluoromethyl)ethyl)phenyl)-2-propyn-1-yl)methanesulfonamide;
2-(4'-((6-amino-3-pyridinyl)sulfonyl)-4-biphenylyl)-1,1,1-trifluoro-2-propanol;
1-(2-(4-(phenylsulfonyl)-1-piperidinyl)-5-(2,2,2-trifluoro-1-hydroxy-1-(trifluoromethyl)ethyl)phenyl)-1-pentyn-3-ol;
1,1,1,3,3,3-hexafluoro-2-(3-(3-methoxypent-1-ynyl)-4-(4-(phenylsulfonyl)piperidin-1-yl)phenyl)-2-propanol;
2-(4-(4-(6-aminopyridazin-3-ylsulfonyl)piperazin-1-yl)phenyl)-1,1,1,3,3,3-hexafluoro-2-propanol;
2-(4-(4-(2-aminophenylsulfonyl)piperazin-1-yl)phenyl)-1,1,1,3,3,3-hexafluoro-2-propanol;
2-(4-(4-(2,6-diaminopyridin-3-ylsulfonyl)piperazin-1-yl)phenyl)-1,1,1,3,3,3-hexafluoro-2-propanol;
(S)-2-(2-(4-(2-aminophenylsulfonyl)-2-methylpiperazin-1-yl)pyrimidin-5-yl)-1,1,1,3,3,3-hexafluoro-2-propanol;
(2-(4-((2S)-4-((2-aminophenyl)sulfonyl)-2-methyl-1-piperazinyl)phenyl)-1,1,1,3,3,3-hexafluoro-2-propanol;
2-(4-(4-(4-bromothiophen-3-ylsulfonyl)piperazin-1-yl)phenyl)-1,1,1,3,3,3-hexafluoro-2-propanol;
2-(4-((S)-2-((1 h-imidazol-1-yl)methyl)-4-(thiophen-2-ylsulfonyl)piperazin-1-yl)phenyl)-1,1,1-trifluoro-2-propanol;
2-(4-((S)-2-((5H-pyrrolo[2,3-b]pyrazin-5-yl)methyl)-4-(thiophen-2-ylsulfonyl)piperazin-1-yl)phenyl)-1,1,1-trifluoro-2-propanol;
2-(4-((S)-2-((1H-pyrrolo[2,3-b]pyridin-1-yl)methyl)-4-(thiophen-2-ylsulfonyl)piperazin-1-yl)phenyl)-1,1,1-trifluoro-2-propanol;
1,1,1,3,3,3-hexafluoro-2-(4-(2-(3-methoxybenzyl)-4-(thiophen-2-ylsulfonyl)piperazin-1-yl)phenyl)-2-propanol;
1,1,1,3,3,3-hexafluoro-2-(4-(2-(2-methoxybenzyl)-4-(thiophen-2-ylsulfonyl)piperazin-1-yl)phenyl)-2-propanol;
1,1,1,3,3,3-hexafluoro-2-(4-(2-(4-methoxybenzyl)-4-(thiophen-2-ylsulfonyl)piperazin-1-yl)phenyl)-2-propanol;
3-((1-(4-(1,1,1,3,3,3-hexafluoro-2-hydroxypropan-2-yl)phenyl)-4-(thiophen-2-ylsulfonyl)piperazin-2-yl)methyl)phenol;
4-((1-(4-(1,1,1,3,3,3-hexafluoro-2-hydroxypropan-2-yl)phenyl)-4-(thiophen-2-ylsulfonyl)piperazin-2-yl)methyl)phenol;
2-((1-(4-(1,1,1,3,3,3-hexafluoro-2-hydroxypropan-2-yl)phenyl)-4-(thiophen-2-ylsulfonyl)piperazin-2-yl)methyl)phenol;
4-(((2S)-4-(2-thiophensulfonyl)-1-(4-(2,2,2-trifluoro-1-hydroxy-1-methylethyl)phenyl)-2-piperazinyl)methyl)-2-piperazinone;
3,3-dimethyl-4-((2S)-4-(2-thiophenylsulfonyl)-1-(4-(2,2,2-trifluoro-1-hydroxy-1-methylethyl)phenyl)-2-piperazinyl)methyl)-2-piperazinone;
3-(1-methylethyl)-4-(((2S)-4-(2-thiophenylsulfonyl)-1-(4-(2,2,2-trifluoro-1-hydroxy-1-methylethyl)phenyl)-2-piperazinyl)methyl)-2-piperazinone;
(3S-3-methyl-4-(((2S)-4-(2-thiophenylsulfonyl)-1-(4-(2,2,2-trifluoro-1-hydroxy-1-methylethyl)phenyl)-2-piperazinyl)methyl)-2-piperazinone;
5-methyl-4-(((2S)-4-(2-thiophenylsulfonyl)-1-(4-(2,2,2-trifluoro-1-hydroxy-1-methylethyl)phenyl)-2-piperazinyl)methyl)-2-piperazinone;
4-(((S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone;
(3R)-4-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone;
(3S)-4-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-3-(1-methylethyl)-2-piperazinone;

3-(1-methylethyl)-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone;

1,1,1-trifluoro-2-(4-((2R)-2-((phenylsulfanyl)methyl)-4-(2-thiophenylsulfonyl)-1-piperazinyl)phenyl)-2-propanol;

1,1,1-trifluoro-2-(4-((2R)-2-((phenylsulfonyl)methyl)-4-(2-thiophenylsulfonyl)-1-piperazinyl)phenyl)-2-propanol;

(2S)-1,1,1-trifluoro-2-(4-((2R)-2-((phenylsulfonyl)methyl)-4-(2-thiophenylsulfonyl)-1-piperazinyl)phenyl)-2-propanol;

(2R)-1,1,1-trifluoro-2-(4-((2R)-2-((phenylsulfonyl)methyl)-4-(2-thiophenylsulfonyl)-1-piperazinyl)phenyl)-2-propanol;

1,1,1-trifluoro-2-(4-((2R)-2-(((3-fluorophenyl)sulfanyl)methyl)-4-(2-thiophenylsulfonyl)-1-piperazinyl)phenyl)-2-propanol;

1,1,1-trifluoro-2-(4-((2R)-2-(((3-fluorophenyl)sulfonyl)methyl)-4-(2-thiophenylsulfonyl)-1-piperazinyl)phenyl)-2-propanol;

1,1,1-trifluoro-2-(4-((2R)-2-(((3-fluorophenyl)sulfinyl)methyl)-4-(2-thiophenylsulfonyl)-1-piperazinyl)phenyl)-2-propanol;

1,1,1-trifluoro-2-(4-((2R)-2-(((4-fluorophenyl)sulfanyl)methyl)-4-(2-thiophenylsulfonyl)-1-piperazinyl)phenyl)-2-propanol;

1,1,1-trifluoro-2-(4-((2R)-2-(((4-fluorophenyl)sulfonyl)methyl)-4-(2-thiophenylsulfonyl)-1-piperazinyl)phenyl)-2-propanol;

1,1,1-trifluoro-2-(4-((2R)-2-(((4-fluorophenyl)sulfinyl)methyl)-4-(2-thiophenylsulfonyl)-1-piperazinyl)phenyl)-2-propanol;

N-(((2S)-4-(2-thiophenylsulfonyl)-1-(4-(2,2,2-trifluoro-1-hydroxy-1-methylethyl)phenyl)-2-piperazinyl)methyl)-3-pyridinesulfonamide;

N-(((2S)-4-(2-thiophenylsulfonyl)-1-(4-(2,2,2-trifluoro-1-hydroxy-1-methylethyl)phenyl)-2-piperazinyl)methyl)benzenesulfonamide;

2-(4-((2S)-2-((bis(1-methylethyl)amino)methyl)-4-(2-thiophenylsulfonyl)-1-piperazinyl)phenyl)-1,1,1-trifluoro-2-propanol;

N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

N-(1-methylethyl)-N-(((2S)-4-(2-thiophenylsulfonyl)-1-(4-(2,2,2-trifluoro-1-hydroxy-1-methylethyl)phenyl)-2-piperazinyl)methyl)acetamide;

N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)benzenesulfonamide;

N-(1-methylethyl)-N-(((2R)-4-(2-thiophenylsulfonyl)-1-(4-(2,2,2-trifluoro-1-hydroxy-1-methylethyl)phenyl)-2-piperazinyl)methyl)-3-pyridinesulfonamide;

2-(4-((2S)-2-((cyclopropylamino)methyl)-4-(2-thiophenylsulfonyl)-1-piperazinyl)phenyl)-1,1,1-trifluoro-2-propanol;

N-cyclopropyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

N-(2-methylpropyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;

N-(cyclopropylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;

1,1,1-trifluoro-2-(4-((2S)-2-((phenylamino)methyl)-4-(2-thiophenylsulfonyl)-1-piperazinyl)phenyl)-2-propanol;

N-phenyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

2-(4-((2S)-2-((di-3-oxetanylamino)methyl)-4-(2-thiophenylsulfonyl)-1-piperazinyl)phenyl)-1,1,1-trifluoro-2-propanol;

1,1,1-trifluoro-2-(4-((2S)-2-((3-oxetanylamino)methyl)-4-(2-thiophenylsulfonyl)-1-piperazinyl)phenyl)-2-propanol;

N-3-oxetanyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

N-methyl-N-(((2S)-4-(2-thiophenylsulfonyl)-1-(4-(2,2,2-trifluoro-1-hydroxy-1-methylethyl)phenyl)-2-piperazinyl)methyl)methanesulfonamide;

N,N-dimethyl-N'-(1-methylethyl)-N'-(((2R)-4-(2-thiophenylsulfonyl)-1-(4-(2,2,2-trifluoro-1-hydroxy-1-methylethyl)phenyl)-2-piperazinyl)methyl)sulfamide;

2-methyl-N-(((2S)-4-(2-thiophenylsulfonyl)-1-(4-(2,2,2-trifluoro-1-hydroxy-1-methylethyl)phenyl)-2-piperazinyl)methyl)-1-propanesulfonamide;

2-methyl-N-phenyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide;

N-cyclobutyl-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

N-cyclobutyl-N-(((2R)-4-(2-thiophenylsulfonyl)-1-(4-(2,2,2-trifluoro-1-hydroxy-1-methylethyl)phenyl)-2-piperazinyl)methyl)-3-pyridinesulfonamide;

2,2,2-trifluoro-N-(2-methylpropyl)-N-(((2S)-4-(2-thiophenylsulfonyl)-1-(4-(2,2,2-trifluoro-1-hydroxy-1-methylethyl)phenyl)-2-piperazinyl)methyl)ethanesulfonamide;

N,N-dimethyl-N-(2-methylpropyl)-N-(((2R)-4-(2-thiophenylsulfonyl)-1-(4-(2,2,2-trifluoro-1-hydroxy-1-methylethyl)phenyl)-2-piperazinyl)methyl)sulfamide;

N-((3-methyl-3-oxetanyl)methyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;

N-methyl-N-(((2S)-4-(2-thiophenylsulfonyl)-1-(4-(2,2,2-trifluoro-1-hydroxy-1-methylethyl)phenyl)-2-piperazinyl)methyl)-3-pyridinesulfonamide;

N-(cyclobutylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;

1,1,1-trifluoro-2-(4-((2R)-2-(((2-fluorophenyl)sulfanyl)methyl)-4-(2-thiophenylsulfonyl)-1-piperazinyl)phenyl)-2-propanol;

N-benzyl-N-(((2S)-4-(2-thiophenylsulfonyl)-1-(4-(2,2,2-trifluoro-1-hydroxy-1-methylethyl)phenyl)-2-piperazinyl)methyl)methanesulfonamide;

N-(3-pyridinylmethyl)-N-(((2S)-4-(2-thiophenylsulfonyl)-1-(4-(2,2,2-trifluoro-1-hydroxy-1-methylethyl)phenyl)-2-piperazinyl)methyl)methanesulfonamide;

N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

2-methyl-N-3-pyridinyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide;

N-phenyl-N-(((2S)-4-(2-thiophenylsulfonyl)-1-(4-(2,2,2-trifluoro-1-hydroxy-1-methylethyl)phenyl)-2-piperazinyl)methyl)acetamide;

2-(4-((2S)-4-((5-amino-2-thiophenyl)sulfonyl)-2-(((3S)-3-methyl-4-morpholinyl)methyl)-1-piperazinyl)phenyl)-1,1,1,3,3,3-hexafluoro-2-propanol;

3,3-dimethyl-4-(((2S)-4-(2-thiophenylsulfonyl)-1-(5-(2,2,2-trifluoro-1-hydroxy-1-(trifluoromethyl)ethyl)-2-pyrimidinyl)-2-piperazinyl)methyl)-2-piperazinone;

(S)-4-((4-((5-aminothiophen-2-yl)sulfonyl)-1-(5-(1,1,1,3,3,3-hexafluoro-2-hydroxypropan-2-yl)pyrimidin-2-yl)piperazin-2-yl)methyl)-3,3-dimethylpiperazin-2-one;

5,5-dimethyl-1-(((2S)-4-(2-thiophenylsulfonyl)-1-(4-(2,2,2-trifluoro-1-hydroxy-1-methylethyl)phenyl)-2-piperazinyl)methyl)-2,4-imidazolidinedione;

N-(((2S)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-n-(2-methylpropyl)methanesulfonamide;

N-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide;

N-(((2S)-4-((2-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(2-methylpropyl)methanesulfonamide;

N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide;

N-(((2R)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-(1-methylethyl)methanesulfonamide;

N-(((2R)-4-((5-amino-2-thiophenyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide;

N-(((2R)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-N-phenylmethanesulfonamide;

4-(((2S)-4-((6-amino-3-pyridinyl)sulfonyl)-1-(5-(2,2,2-trifluoro-1-hydroxy-1-(trifluoromethyl)ethyl)-2-pyrimidinyl)-2-piperazinyl)methyl)-3,3-dimethyl-2-piperazinone;

5-(((2S)-4-(2-thiophenylsulfonyl)-1-(4-(2,2,2-trifluoro-1-hydroxy-1-methylethyl)phenyl)-2-piperazinyl)methyl)-5,7-diazaspiro[3.4]octane-6,8-dione;

N-(((2S)-4-(thiophen-2-ylsulfonyl)-1-(4-(1,1,1-trifluoro-2-hydroxypropan-2-yl)phenyl)piperazin-2-yl)methyl)propane-2-sulfonamide;

N-(((2S)-4-(2-thiophenylsulfonyl)-1-(4-(2,2,2-trifluoro-1-hydroxy-1-methylethyl)phenyl)-2-piperazinyl)methyl)-2-butanesulfonamide;

1,1,1-trifluoro-2-(2-(2-(prop-1-yn-1-yl)-4-(thiophen-2-ylsulfonyl)piperazin-1-yl)pyrimidin-5-yl)propan-2-ol;

2-(2-(4-((6-amino-3-pyridinyl)sulfonyl)-2-(1-propyn-1-yl)-1-piperazinyl)-5-pyrimidinyl)-1,1,1,3,3,3-hexafluoro-2-propanol;

2-(2-((2R)-4-((6-amino-3-pyridinyl)sulfonyl)-2-(1-propyn-1-yl)-1-piperazinyl)-5-pyrimidinyl)-1,1,1,3,3,3-hexafluoro-2-propanol; or 2-(2-((2S)-4-((6-amino-3-pyridinyl)sulfonyl)-2-(1-propyn-1-yl)-1-piperazinyl)-5-pyrimidinyl)-1,1,1,3,3,3-hexafluoro-2-propanol.

31. A compound, or a pharmaceutically acceptable salt thereof, selected from:

2-(4-(4-((6-amino-3-pyridinyl)sulfonyl)-2-(1-propyn-1-yl)-1-piperazinyl)phenyl)-1,1,1,3,3,3-hexafluoro-2-propanol;

2-(4-((2S)-4-((6-amino-3-pyridinyl)sulfonyl)-2-(1-propyn-1-yl)-1-piperazinyl)phenyl)-1,1,1,3,3,3-hexafluoro-2-propanol;

2-(4-((2R)-4-((6-amino-3-pyridinyl)sulfonyl)-2-(1-propyn-1-yl)-1-piperazinyl)phenyl)-1,1,1,3,3,3-hexafluoro-2-propanol;

5,5-dimethyl-3-(1-methylethyl)-1-(((2S)-4-(2-thiophenylsulfonyl)-1-(4-(2,2,2-trifluoro-1-hydroxy-1-methylethyl)phenyl)-2-piperazinyl)methyl)-2,4-imidazolidinedione;

2-(4-(4-((6-amino-3-pyridinyl)sulfonyl)-2-(1-propyn-1-yl)-1-piperazinyl)phenyl)-1,1,1-trifluoro-2-propanol;

(2S)-2-(4-((2S)-4-((6-amino-3-pyridinyl)sulfonyl)-2-(1-propyn-1-yl)-1-piperazinyl)phenyl)-1,1,1-trifluoro-2-propanol;

(2S)-2-(4-((2R)-4-((6-amino-3-pyridinyl)sulfonyl)-2-(1-propyn-1-yl)-1-piperazinyl)phenyl)-1,1,1-trifluoro-2-propanol;

(2R)-2-(4-((2S)-4-((6-amino-3-pyridinyl)sulfonyl)-2-(1-propyn-1-yl)-1-piperazinyl)phenyl)-1,1,1-trifluoro-2-propanol;

(2R)-2-(4-((2R)-4-((6-amino-3-pyridinyl)sulfonyl)-2-(1-propyn-1-yl)-1-piperazinyl)phenyl)-1,1,1-trifluoro-2-propanol;

2-(2-(4-((6-amino-3-pyridinyl)sulfonyl)-2-(2-hydroxypropyl)-1-piperazinyl)-5-pyrimidinyl)-1,1,1,3,3,3-hexafluoro-2-propanol;

2-(2-(4-((6-amino-3-pyridinyl)sulfonyl)-2-($^2H_3$)-1-propyn-1-yl-1-piperazinyl)-5-pyrimidinyl)-1,1,1,3,3,3-hexafluoro-2-propanol;

2-(2-(4-((6-amino-3-pyridinyl)sulfonyl)-2-(cyclopropylethynyl)-1-piperazinyl)-5-pyrimidinyl)-1,1,1,3,3,3-hexafluoro-2-propanol;

1,1,1,3,3,3-hexafluoro-2-(4-((2S)-4-(phenylsulfonyl)-2-(1-propyn-1-yl)-1-piperazinyl)phenyl)-2-propanol;

2-(4-(4-((5-amino-1,3,4-thiadiazol-2-yl)sulfonyl)-2-(1-propyn-1-yl)-1-piperazinyl)phenyl)-1,1,1,3,3,3-hexafluoro-2-propanol;

2-(4-(4-((5-amino-1,3,4-thiadiazol-2-yl)sulfonyl)-2-(1-propyn-1-yl)-1-piperazinyl)phenyl)-1,1,1,3,3,3-hexafluoro-2-propanol;

2-(4-(4-((6-amino-5-fluoro-3-pyridinyl)sulfonyl)-2-(1-propyn-1-yl)-1-piperazinyl)phenyl)-1,1,1,3,3,3-hexafluoro-2-propanol;

2-(2-(4-((6-amino-3-pyridinyl)sulfonyl)-2-(1-propyn-1-yl)-1-piperazinyl)-5-pyrimidinyl)-1,1,1-trifluoro-2-propanol;

(2S)-2-(2-((2S)-4-((6-amino-3-pyridinyl)sulfonyl)-2-(1-propyn-1-yl)-1-piperazinyl)-5-pyrimidinyl)-1,1,1-trifluoro-2-propanol;

(2R)-2-(2-((2S)-4-((6-amino-3-pyridinyl)sulfonyl)-2-(1-propyn-1-yl)-1-piperazinyl)-5-pyrimidinyl)-1,1,1-trifluoro-2-propanol;

(2S)-2-(2-((2R)-4-((6-amino-3-pyridinyl)sulfonyl)-2-(1-propyn-1-yl)-1-piperazinyl)-5-pyrimidinyl)-1,1,1-trifluoro-2-propanol;

(2R)-2-(2-((2R)-4-((6-amino-3-pyridinyl)sulfonyl)-2-(1-propyn-1-yl)-1-piperazinyl)-5-pyrimidinyl)-1,1,1-trifluoro-2-propanol;

N-(1-phenylethyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

2-methyl-N-3-pyridinyl-N-(((2R)-4-(2-thiophenylsulfonyl)-1-(4-(2,2,2-trifluoro-1-hydroxy-1-methylethyl)phenyl)-2-piperazinyl)methyl)-1-propanesulfonamide;

4-fluoro-N-(((2S)-4-(2-thiophenylsulfonyl)-1-(4-(2,2,2-trifluoro-1-hydroxy-1-methylethyl)phenyl)-2-piperazinyl)methyl)benzenesulfonamide;

N-(4-fluorophenyl)-N-(((2R)-4-(2-thiophenylsulfonyl)-1-(4-(2,2,2-trifluoro-1-hydroxy-1-methylethyl)phenyl)-2-piperazinyl)methyl)methanesulfonamide;

N-(4-fluorophenyl)-N-(((2S)-4-(2-thiophenylsulfonyl)-1-(4-(2,2,2-trifluoro-1-hydroxy-1-methylethyl)phenyl)-2-piperazinyl)methyl)acetamide;

1,1,1,3,3,3-hexafluoro-2-(4-(2-((2-methoxy-3-pyridinyl)methyl)-4-(2-thiophenylsulfonyl)-1-piperazinyl)phenyl)-2-propanol;

1,1,1,3,3,3-hexafluoro-2-(4-(2-((6-methoxy-2-pyridinyl)methyl)-4-(2-thiophenylsulfonyl)-1-piperazinyl)phenyl)-2-propanol;

4-((4-(2-thiophenylsulfonyl)-1-(4-(2,2,2-trifluoro-1-hydroxy-1-(trifluoromethyl)ethyl)phenyl)-2-piperazinyl)methyl)-2(1H)-pyridinone;

2-(4-(4-((4-amino-3-pyridinyl)sulfonyl)-1-piperazinyl)phenyl)-1,1,1,3,3,3-hexafluoro-2-propanol;

2-(4-(4-((2,4-diaminophenyl)sulfonyl)-1-piperazinyl)phenyl)-1,1,1,3,3,3-hexafluoro-2-propanol;

1,1,1,3,3,3-hexafluoro-2-(3-(1-propyn-1-yl)-4-(2-thiophenylsulfonyl)-1-piperazinyl)phenyl)-2-propanol;

1,1,1,3,3,3-hexafluoro-2-(2-(4-(phenylsulfonyl)phenyl)-5-pyrimidinyl)-2-propanol;

2-(2-(4-((6-amino-3-pyridinyl)sulfonyl)phenyl)-5-pyrimidinyl)-1,1,1,3,3,3-hexafluoro-2-propanol;

2-(2-(4-((6-amino-3-pyridinyl)sulfonyl)phenyl)-5-pyrimidinyl)-1,1,1-trifluoro-2-propanol;

2-(6-(4-((6-amino-3-pyridinyl)sulfonyl)phenyl)-3-pyridinyl)-1,1,1,3,3,3-hexafluoro-2-propanol;

2-(2-(6-((6-amino-3-pyridinyl)sulfonyl)-3-pyridinyl)-5-pyrimidinyl)-1,1,1,3,3,3-hexafluoro-2-propanol;

2-(2-(4-((6-amino-3-pyridinyl)sulfonyl)-2-methylphenyl)-5-pyrimidinyl)-1,1,1,3,3,3-hexafluoro-2-propanol;

1,1,1,3,3,3-hexafluoro-2-(2-(2-(1-propyn-1-yl)-4-(2-thiophenylsulfonyl)-1-piperazinyl)-5-pyrimidinyl)-2-propanol;

1,1,1-trifluoro-2-(4-((2S)-4-(2-thiophenylsulfonyl)-2-((3-(trifluoromethyl)-1-piperazinyl)methyl)-1-piperazinyl)phenyl)-2-propanol;

2-(2-((2S)-4-((6-amino-3-pyridinyl)sulfonyl)-2-(3-oxa-8-azabicyclo[3.2.1]oct-8-ylmethyl)-1-piperazinyl)-5-pyrimidinyl)-1,1,1,3,3,3-hexafluoro-2-propanol;

(S)-5-methyl-4-(4S)-4-(tiophen-2-ylsulfonyl)-1-(4-((S)-1,1,1-trifluoro-2-hydroxypropan-2-yl)phenyl)piperazin-2-yl)methyl)morpholin-3-one; or 2-(4-((2R)-4-((6-amino-3-pyridinyl)sulfonyl)-2-((phenylsulfonyl)methyl)-1-piperazinyl)phenyl)-1,1,1,3,3,3-hexafluoro-2-propanol.

32. A method of treating type 2 diabetes, hyperglycemia, impaired glucose tolerance, insulin resistance, retinopathy, nephropathy, neuropathy, cataracts, glaucoma, Syndrome X, or polycystic ovarian syndrome, the method comprising administering to a patient in need thereof a therapeutically effective amount of a compound in accordance with claim 1, or a pharmaceutically acceptable salt thereof.

33. The method of claim 32 wherein the treatment is for type 2 diabetes.

34. A pharmaceutical composition comprising a compound in accordance with claim 1, or a pharmaceutically acceptable salt thereof, and a pharmaceutically acceptable excipient.

* * * * *